(12) United States Patent
Oka et al.

(10) Patent No.: US 7,977,331 B1
(45) Date of Patent: Jul. 12, 2011

(54) TETRACYCLIC FUSED HETEROCYCLIC COMPOUND AND USE THEREOF AS HCV POLYMERASE INHIBITOR

(75) Inventors: Takahiro Oka, Takatsuki (JP); Kazutaka Ikegashira, Takatsuki (JP); Shintaro Hirashima, Takatsuki (JP); Hiroshi Yamanaka, Takatsuki (JP); Satoru Noji, Takatsuki (JP); Yasushi Niwa, Takatsuki (JP); Yoko Matsumoto, Takatsuki (JP); Toshihiro Sato, Takatsuki (JP); Izuru Ando, Takatsuki (JP); Yukihiro Nomura, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 11/962,622

(22) Filed: Dec. 21, 2007

Related U.S. Application Data

(63) Continuation of application No. 11/064,319, filed on Feb. 23, 2005, now abandoned.

(60) Provisional application No. 60/623,822, filed on Oct. 29, 2004.

(30) Foreign Application Priority Data

| Feb. 24, 2004 | (JP) | ................. | 2004-048815 |
| Jun. 7, 2004 | (JP) | ................. | 2004-169190 |
| Oct. 8, 2004 | (JP) | ................. | 2004-296390 |

(51) Int. Cl.
| | |
|---|---|
| *A61K 31/53* | (2006.01) |
| *A61K 31/495* | (2006.01) |
| *A61K 31/519* | (2006.01) |
| *A61K 31/44* | (2006.01) |
| *A61K 31/415* | (2006.01) |
| *A61K 31/40* | (2006.01) |
| *C07D 253/00* | (2006.01) |
| *C07D 487/00* | (2006.01) |
| *C07D 239/02* | (2006.01) |
| *C07D 471/02* | (2006.01) |
| *C07D 209/80* | (2006.01) |

(52) U.S. Cl. ..... 514/243; 514/248; 514/249; 514/265.1; 514/300; 514/406; 514/410; 544/182; 544/236; 544/280; 544/330; 546/113; 548/420

(58) Field of Classification Search .................. 514/243, 514/248, 249, 265.1, 300, 406, 410; 544/182, 544/236, 280, 330; 546/113; 548/420
See application file for complete search history.

(56) References Cited

U.S. PATENT DOCUMENTS

| 5,620,973 | A | 4/1997 | Goto et al. |
| 5,633,388 | A | 5/1997 | Diana et al. |
| 5,814,642 | A | 9/1998 | Goto et al. |
| 5,830,905 | A | 11/1998 | Diana et al. |
| 5,866,684 | A | 2/1999 | Attwood et al. |
| 5,932,743 | A | 8/1999 | Collini et al. |
| 5,990,276 | A | 11/1999 | Zhang et al. |
| 6,127,384 | A | 10/2000 | Diana et al. |
| 6,387,938 | B1 | 5/2002 | Mizuguchi et al. |
| 6,727,267 | B2 | 4/2004 | Jaen et al. |
| 6,770,666 | B2 | 8/2004 | Hashimoto et al. |
| 6,809,101 | B2 | 10/2004 | Fujishita et al. |
| 6,867,284 | B1 | 3/2005 | Matassa et al. |
| 7,091,209 | B2 | 8/2006 | Gardelli et al. |
| 7,153,848 | B2 | 12/2006 | Hudyma et al. |
| 7,285,551 | B2 | 10/2007 | Hashimoto et al. |
| 7,348,425 | B2 | 3/2008 | Hudyma et al. |
| 7,399,758 | B2 | 7/2008 | Meanwell et al. |
| 7,452,876 | B2 | 11/2008 | Yeung et al. |
| 7,456,166 | B2 | 11/2008 | Bender et al. |
| 7,456,167 | B2 | 11/2008 | Bergstrom |
| 7,485,633 | B2 | 2/2009 | Meanwell et al. |
| 2003/0108862 | A1 | 6/2003 | Kukolj et al. |
| 2004/0082635 | A1 | 4/2004 | Hashimoto et al. |
| 2004/0097438 | A1 | 5/2004 | Hashimoto et al. |
| 2006/0046983 | A1 | 3/2006 | Hudyma et al. |
| 2006/0100262 | A1 | 5/2006 | Conte et al. |

(Continued)

FOREIGN PATENT DOCUMENTS

EP 0 145 095 A2 6/1985

(Continued)

OTHER PUBLICATIONS

Dörwald, F. Zaragoza, *Side Reactions in Organic Synthesis: A Guide to Successful Synthesis Design*, Weinheim: Wiley-VCH Verlag GmbH & Co. KGaA, 2005, Preface.
Jordan, Nature Reviews: Drug Discovery, 2: 205-213 (2003).
Shvedov et al., Chemistry of Heterocyclic Compounds, 1133-1136 (1976).
Shvedov et al., American Chemical Society, CA Database Accession No. 84: 43903 [*Khimya Geterotsiklicheskikh Soedinenii*, 1975 (10): 1324-1327 (1975)].
Battistuzzi et al., *Organic Letters*, 4(8): 1355-1358 (2002).

(Continued)

*Primary Examiner* — Joseph R Kosack
(74) *Attorney, Agent, or Firm* — Leydig, Voit & Mayer, Ltd.

(57) ABSTRACT

The present invention relates to a tetracyclic fused heterocyclic compound represented by the following formula [I]

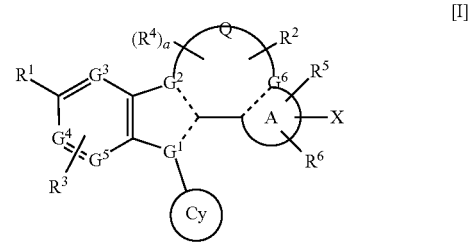

[I]

wherein each symbol is as defined in the specification, or a pharmaceutically acceptable a salt thereof, and a hepatitis C virus (HCV) polymerase inhibitor and a therapeutic agent for hepatitis C containing this compound. The compound of the present invention shows an anti-HCV activity based on the HCV polymerase inhibitory activity, and useful as an agent for the prophylaxis or treatment of hepatitis C.

11 Claims, No Drawings

U.S. PATENT DOCUMENTS

| | | |
|---|---|---|
| 2006/0167246 A1 | 7/2006 | Mizojiri et al. |
| 2007/0049593 A1 | 3/2007 | Oka et al. |
| 2007/0185083 A1 | 8/2007 | Bergstrom et al. |
| 2007/0270406 A1 | 11/2007 | Gentles et al. |
| 2007/0275930 A1 | 11/2007 | Gentles et al. |
| 2008/0045498 A1 | 2/2008 | Griffith et al. |
| 2008/0146537 A1 | 6/2008 | Bender et al. |
| 2008/0153895 A1 | 6/2008 | Stansfield et al. |
| 2008/0171015 A1 | 7/2008 | Bender et al. |
| 2008/0188458 A1 | 8/2008 | Yeung et al. |
| 2008/0214522 A1 | 9/2008 | Stansfield et al. |
| 2008/0221090 A1 | 9/2008 | Yeung et al. |
| 2008/0226590 A1 | 9/2008 | Bender et al. |
| 2008/0226591 A1 | 9/2008 | Gentles et al. |
| 2008/0226592 A1 | 9/2008 | Miojiri et al. |
| 2008/0226593 A1 | 9/2008 | Hewawasam et al. |
| 2008/0227769 A1 | 9/2008 | Gentles et al. |
| 2009/0036444 A1 | 2/2009 | Mizojiri et al. |
| 2009/0042860 A1 | 2/2009 | Bergstrom et al. |
| 2009/0074715 A1 | 3/2009 | Martin et al. |

FOREIGN PATENT DOCUMENTS

| | | |
|---|---|---|
| EP | 0 226 508 A1 | 6/1987 |
| EP | 0 407 898 A1 | 1/1991 |
| EP | 0 906 097 | 4/1999 |
| EP | 0 932 617 B1 | 8/1999 |
| EP | 1 162 196 A1 | 12/2001 |
| EP | 1 688 420 A1 | 8/2006 |
| JP | 57-123175 A | 7/1982 |
| JP | 61-275271 A | 12/1986 |
| JP | 04-329547 A | 11/1992 |
| JP | 07-069899 A | 3/1995 |
| JP | 07-309835 A | 11/1995 |
| JP | 08-268890 A | 10/1996 |
| JP | 10-101591 A | 4/1998 |
| JP | 10-298151 A | 11/1998 |
| JP | 11-127861 A | 5/1999 |
| JP | 11-180981 | 7/1999 |
| JP | 11-292840 A | 10/1999 |
| JP | 2000-511899 A | 9/2000 |
| JP | 2001-103993 A | 4/2001 |
| JP | 2001-247550 A | 9/2001 |
| JP | 2003-212846 A | 7/2003 |
| WO | WO 93/15730 A1 | 8/1993 |
| WO | WO 97/25041 A1 | 7/1997 |
| WO | WO 97/36554 A1 | 10/1997 |
| WO | WO 97/36866 A1 | 10/1997 |
| WO | WO 97/43310 A1 | 11/1997 |
| WO | WO 97/46237 A1 | 12/1997 |
| WO | WO 98/17679 A1 | 4/1998 |
| WO | WO 98/22496 A2 | 5/1998 |
| WO | WO 98/46597 A1 | 10/1998 |
| WO | WO 98/46630 A1 | 10/1998 |
| WO | WO 99/07733 A2 | 2/1999 |
| WO | WO 99/07734 A2 | 2/1999 |
| WO | WO 99/09007 A1 | 2/1999 |
| WO | WO 99/50230 A1 | 10/1999 |
| WO | WO 99/51619 A1 | 10/1999 |
| WO | WO 99/61613 A2 | 12/1999 |
| WO | WO 99/64442 A1 | 12/1999 |
| WO | WO 00/04141 A2 | 1/2000 |
| WO | WO 00/06529 A1 | 2/2000 |
| WO | WO 00/09543 A2 | 2/2000 |
| WO | WO 00/09558 A1 | 2/2000 |
| WO | WO 00/10573 A1 | 3/2000 |
| WO | WO 00/13708 A1 | 3/2000 |
| WO | WO 00/18231 A1 | 4/2000 |
| WO | WO 00/20400 A1 | 4/2000 |
| WO | WO 00/24725 A1 | 5/2000 |
| WO | WO 00/31129 A1 | 6/2000 |
| WO | WO 00/59929 A1 | 10/2000 |
| WO | WO 01/07027 A2 | 2/2001 |
| WO | WO 01/07027 A3 | 2/2001 |
| WO | WO 01/07407 A1 | 2/2001 |
| WO | WO 01/12214 A2 | 2/2001 |
| WO | WO 01/16379 A1 | 3/2001 |
| WO | WO 01/32153 A2 | 5/2001 |
| WO | WO 01/32691 A1 | 5/2001 |
| WO | WO 01/40262 A1 | 6/2001 |
| WO | WO 01/47883 A1 | 7/2001 |
| WO | WO 01/58877 A1 | 8/2001 |
| WO | WO 01/58929 A1 | 8/2001 |
| WO | WO 01/60315 A2 | 8/2001 |
| WO | WO 01/64678 A2 | 9/2001 |
| WO | WO 01/74768 A2 | 10/2001 |
| WO | WO 01/77091 A2 | 10/2001 |
| WO | WO 01/77113 A2 | 10/2001 |
| WO | WO 02/04425 A2 | 1/2002 |
| WO | WO 02/06246 A1 | 1/2002 |
| WO | WO 02/07761 A1 | 1/2002 |
| WO | WO 02/08187 A2 | 1/2002 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/20497 A1 | 3/2002 |
| WO | WO 03/000254 A1 | 1/2003 |
| WO | WO 03/007945 A1 | 1/2003 |
| WO | WO 03/010140 A2 | 2/2003 |
| WO | WO 03/010141 A2 | 2/2003 |
| WO | WO 03/026587 A2 | 4/2003 |
| WO | WO 03/099824 A1 | 12/2003 |
| WO | WO 2004/064925 A1 | 8/2004 |
| WO | WO 2004/065367 A1 | 8/2004 |
| WO | WO 2004/087714 A1 | 10/2004 |
| WO | WO 2005/023819 A1 | 3/2005 |
| WO | WO 2005/049622 A1 | 6/2005 |
| WO | WO 2005/080399 A1 | 9/2005 |
| WO | WO 2006/008556 A1 | 1/2006 |
| WO | WO 2006/020082 A1 | 2/2006 |
| WO | WO 2006/046030 A2 | 5/2006 |
| WO | WO 2006/046039 A2 | 5/2006 |
| WO | WO 2006/052013 A1 | 5/2006 |
| WO | WO 2006/119975 A1 | 11/2006 |
| WO | WO 2007/029029 A2 | 3/2007 |
| WO | WO 2007/029029 A3 | 3/2007 |
| WO | WO 2007/033032 A1 | 3/2007 |
| WO | WO 2007/033175 A1 | 3/2007 |
| WO | WO 2007/054741 A1 | 5/2007 |
| WO | WO 2007/092000 A1 | 8/2007 |
| WO | WO 2007/129119 A1 | 11/2007 |
| WO | WO 2007/136982 A1 | 11/2007 |
| WO | WO 2007/140109 A1 | 12/2007 |
| WO | WO 2007/140200 A2 | 12/2007 |
| WO | WO 2007/140200 A3 | 12/2007 |
| WO | WO 2007/140254 A2 | 12/2007 |
| WO | WO 2007/140254 A3 | 12/2007 |
| WO | WO 2007/143521 A1 | 12/2007 |
| WO | WO 2008/008907 A2 | 1/2008 |
| WO | WO 2008/008912 A1 | 1/2008 |
| WO | WO 2008/011521 A2 | 1/2008 |
| WO | WO 2008/011521 A3 | 1/2008 |
| WO | WO 2008/075103 A1 | 6/2008 |
| WO | WO 2008/089027 A1 | 7/2008 |
| WO | WO 2008/097796 A1 | 8/2008 |
| WO | WO 2008/109584 A1 | 9/2008 |
| WO | WO 2008/111978 A1 | 9/2008 |
| WO | WO 2008/112473 A1 | 9/2008 |
| WO | WO 2008/112841 A1 | 9/2008 |
| WO | WO 2008/112848 A1 | 9/2008 |
| WO | WO 2008/112851 A1 | 9/2008 |
| WO | WO 2008/112863 A1 | 9/2008 |
| WO | WO 2009/023487 A2 | 2/2009 |
| WO | WO 2009/029384 A2 | 3/2009 |
| WO | WO 2009/120745 A1 | 10/2009 |
| WO | WO 2009/137454 A1 | 11/2009 |
| WO | WO 2010/082050 A1 | 7/2010 |
| WO | WO 2010/093359 A1 | 8/2010 |
| WO | WO 2010/099159 A1 | 9/2010 |

OTHER PUBLICATIONS

Behrens et al., *EMBO Journal*, 15(1):12-22 (1996).
Buscemi et al., *Journal of Organic Chemistry*, 61(24): 8397-8401 (1996).
Campo et al., *Journal of the American Chemical Society*, 125(38): 11506-11507 (2003).

Chen et al., *Journal of Organic Chemistry*, 61(19): 6639-6645 (1996).
De Koning et al., *Tetrahedron Letters*, 39: 8725-8728 (1998).
Foye et al., *Journal of Organic Chemistry*, 31: 2417-2418 (Jul. 1966).
Gatta et al., *Bollettino Chimico Farmaceutico*, 120(2): 102-107 (1981).
Greig et al., *Tetrahedron Letters*, 23 (51): 5453-5354 (1982).
Heubach, *Liebigs Annalen der Chemie*, 9: 1376-1383 (1980).
Hiremath et al., *Journal of Heterocyclic Chemistry*, 30(3): 603-609 (May-Jun. 1993).
Höft et al, *Journal für Praktische Chemie*, 314(1): 145-156 (1972).
Kauffman, *Journal of Organic Chemistry*, 39(16): 2472-2473 (1974).
Kohara et al., *Journal of Medicinal Chemistry*, 39(26): 5228-5235 (1996).
Kozikowski et al, *Tetrahedron Letters*, 32(28): 3317-3320 (1991).
Michel et al., *Helvetica Chimica Acta*, 48(8): 1973-1983 (1965).
Minami et al., *Japanese Journal of Dermatology*, 111(7): 1075-1081 (2001).
Roesch et al., *Journal of Organic Chemistry*, 66(2): 412-420 (2001).
Sauer et al., *Tetrahedron Letters*, 3: 319-324 (1968).
Sheehan et al., *Journal of the American Chemical Society*, 73: 4752-4755 (Oct. 1951).
Sohda et al., *Chem Pharm Bull*, 30(10): 3563-3573 (1982).
Stempel et al., *Journal of Organic Chemistry*, 20: 412-418 (Apr. 1955).
Takamizawa et al., *Journal of Virology*, 65(3): 1105-1113 (Mar. 1991).
Thiel et al., *Journal für Praktische Chemie*, 332(1): 55-64 (1990).
Unangst et al., *Journal of Medicinal Chemistry*, 35(20): 3691-3698 (1992).
Wolthuis et al., *Journal of Organic Chemistry*, 31(6): 2009-2011 (Jun. 1966).
Zou et al., *Heterocycles*, 43(1): 49-52 (1996).
Ikegashira et al., *Journal of Medicinal Chemistry*, 49: 6950-6953 (2006).

TETRACYCLIC FUSED HETEROCYCLIC COMPOUND AND USE THEREOF AS HCV POLYMERASE INHIBITOR

CROSS-REFERENCE TO RELATED APPLICATIONS

This application is a continuation of copending U.S. patent application Ser. No. 11/064,319, filed Feb. 23, 2005, which claims the benefit of U.S. Provisional Patent Application No. 60/623,822, filed Oct. 29, 2004, which is incorporated by reference.

TECHNICAL FIELD

The present invention relates to a tetracyclic fused heterocyclic compound or a pharmaceutically acceptable salt thereof, which shows anti-hepatitis C virus (HCV) activity, particularly anti-HCV activity based on an RNA-dependent RNA polymerase inhibitory activity. In addition, the present invention relates to a hepatitis C virus polymerase inhibitor, an anti-hepatitis C virus agent and a therapeutic agent for hepatitis C containing said tetracyclic fused heterocyclic compound or a pharmaceutically acceptable salt thereof.

BACKGROUND ART

In 1989, a main causative virus of non-A non-B posttransfusion hepatitis was found and named hepatitis C virus (HCV). Since then, several types of hepatitis viruses have been found besides type A, type B and type C, wherein hepatitis caused by HCV is called hepatitis C.

The patients infected with HCV are considered to involve several percent of the world population, and the infection with HCV characteristically becomes chronic.

HCV is an envelope RNA virus, wherein the genome is a single strand plus-strand RNA, and belongs to the genus Hepacivirus of Flavivirus (from The International Committee on Taxonomy of Viruses, International Union of Microbiological Societies). Of the same hepatitis viruses, for example, hepatitis B virus (HBV), which is a DNA virus, is eliminated by the immune system and the infection with this virus ends in an acute infection except for neonates and infants having yet immature immunological competence. In contrast, HCV somehow avoids the immune system of the host due to an unknown mechanism. Once infected with this virus, even an adult having a mature immune system frequently develops persistent infection. When chronic hepatitis is associated with the persistent infection with HCV, it advances to cirrhosis or hepatic cancer in a high rate. Enucleation of tumor by operation does not help much, because the patient often develops recurrent hepatic cancer due to the sequela inflammation in non-cancerous parts. In addition, there is a report on the involvement of HCV infection in dermatosis such as chronic urticaria, lichen planus, cryoglobulinemic purpura and the like (The Japanese Journal of Dermatology, Vol. 111, No. 7, pages 1075-1081, 2001).

Thus, an effective therapeutic method of hepatitis C is desired. Apart from the symptomatic therapy to suppress inflammation with an anti-inflammatory agent, the development of a therapeutic agent that reduces HCV to a low level free from inflammation and that eradicates HCV has been strongly demanded.

At present, a treatment with interferon is the only effective method known for the eradication of HCV. However, interferon can eradicate the virus only in about one-third of the patient population. For the rest of the patients, it has no effect or provides only a temporary effect. In recent years, polyethylene glycolated interferon has been put to practical use, and enhanced effects and reduced side effects have been achieved. However, complete response rate still remains at a low level, and therefore, an anti-HCV drug to be used in the place of or concurrently with interferon is awaited in great expectation.

In recent years, Ribavirin (1-β-D-ribofuranosyl-1H-1,2,4-triazole-3-carboxamide) has become commercially available as a therapeutic agent for hepatitis C, which is to be used concurrently with interferon. It enhances the efficacy of interferon but only to a low efficacy rate, and a different novel therapeutic agent for hepatitis C is desired.

Also, an attempt has been made to potentiate the immunocompetence of the patient with an interferon agonist, an interleukin-12 agonist and the like, thereby to eradicate the virus, but an effective pharmaceutical agent has not been found yet.

In addition, the inhibition of HCV growth, wherein HCV-specific protein is targeted, has been drawing attention these days.

The gene of HCV encodes a protein such as serine protease, RNA helicase, RNA-dependent RNA polymerase and the like. These proteins function as a specific protein essential for the growth of HCV.

One of the specific proteins, RNA-dependent RNA polymerase (hereinafter to be also briefly referred to as an HCV polymerase), is an enzyme essential for the growth of the virus. The gene replication of HCV having a plus-strand RNA gene is considered to involve synthesis of a complementary minus-strand RNA by the use of the plus-strand RNA as a template and using the obtained minus-strand RNA as a template, amplifying the plus-strand RNA. The portion called NS5B of a protein precursor, that HCV codes for, has been found to show an RNA-dependent RNA polymerase activity (EMBO J., Vol, 15, pages 12-22, 1996), and is considered to play a central role in the HCV gene replication.

Therefore, an HCV polymerase inhibitor can be a target in the development of an anti-HCV drug, and the development thereof is eagerly awaited. However, an effective HCV polymerase inhibitor has not been developed yet, like in other attempts to develop an anti-HCV drug based on other action mechanisms. As the situation stands, no pharmaceutical agent can treat hepatitis C satisfactorily.

The following describes known compounds comparatively similar to the present invention.

WO03/099824 discloses the following compound a etc. as anti-HCV agents, and teaches that this compound shows an HCV polymerase inhibitory action (WO03/099824, Example 4 (page 32, line 10-page 35), Table 1 (page 20)).

compound a

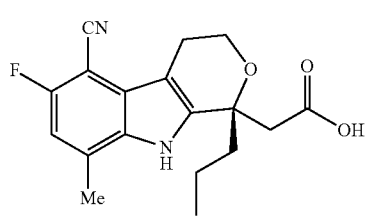

However, the compound of the present invention is not disclosed therein and no description suggestive thereof is found in the specification.

On the other hand, as known tetracyclic fused heterocyclic compounds, whose pharmaceutical use is known, the following can be mentioned.

EP226508 discloses that the following compound b etc. show an anticancerous action (EP226508, Example 2 (page 4, last line—page 6, line 2), formula VII of claim 5 (page 31)).

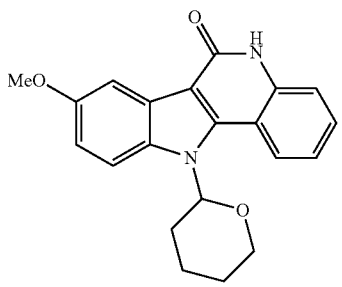

compound b

Other reference describes following compound c etc. and synthetic methods of compounds usable as central nervous system agents (Bollettino Chimico Farmaceutico, Vol. 120, No. 2, pages 102-107, 1981).

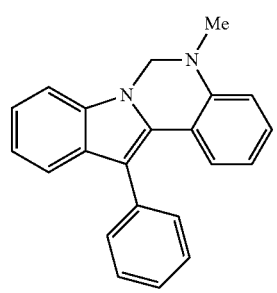

compound c

However, none of these references discloses the compound of the present invention, not to mention disclosure of use of the compounds of these references as antiviral agents or description suggestive thereof.

As the compounds comparatively similar to the compound of the present invention, relating to use other than a pharmaceutical agent, the following can be mentioned.

JP-A-4-329547 discloses the following compound d known as an electronic photographic-sensitized material (JP-A-4-329547, formula 52 (page 7, lower right column)).

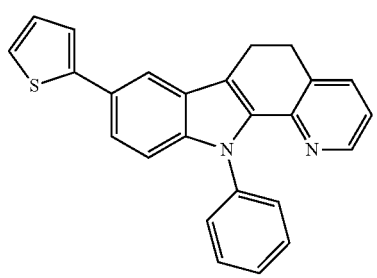

compound d

A different reference discloses the following compound e etc., wherein its synthetic method is described (J. Org. Chem., Vol. 66, No. 2, pages 412-420, 2001, Table 3 No. 19 (page 415)).

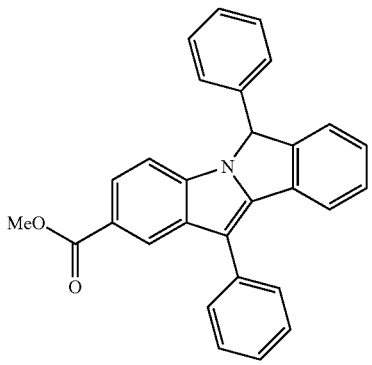

compound e

A yet different reference discloses the following compound f etc., wherein its synthetic method is described (Organic Letters, Vol. 4, No. 8, pages 1355-1358, 2002, Table 1 No. 17 (page 1357), Scheme 4 (page 1356)).

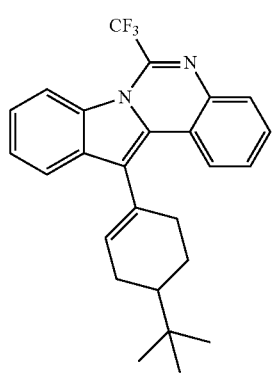

compound f

Another different reference discloses the following compound g etc., wherein its synthetic method is described (J. Org. Chem., Vol. 31, No. 6, pages 2009-2011, 1966, Scheme 1 (page 2010)).

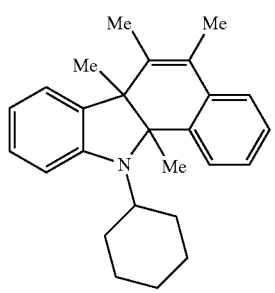

compound g

However, none of these references discloses the compound of the present invention, not to mention disclosure of use of the compounds of these references as an antiviral agents or description suggestive thereof.

As a therapeutic agent for hepatitis C having an indole skeleton, WO03/010140 is known (WO03/010140, Example Nos. 1 (page 41), 10 (page 51), 14 (page 57), 18 (page 60), 20 (page 63), 22 (page 64), compound No. 149 (page 79)).

In this publication, as an anti-HCV agent having a polymerase inhibitory activity, the following indole compounds A, B, C, D etc. are described.

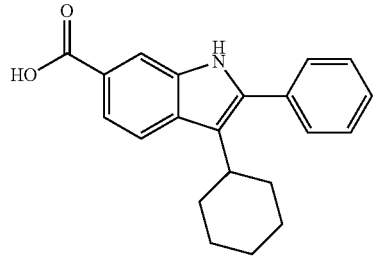

compound A (Ex. 1)

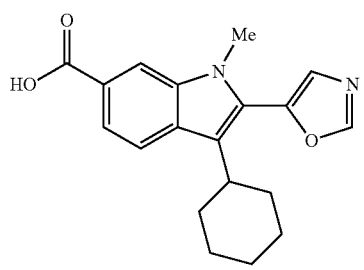

compound B (Ex. 14)

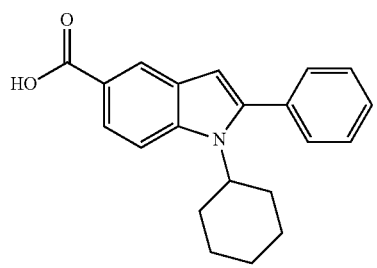

compound C (Ex. 10)

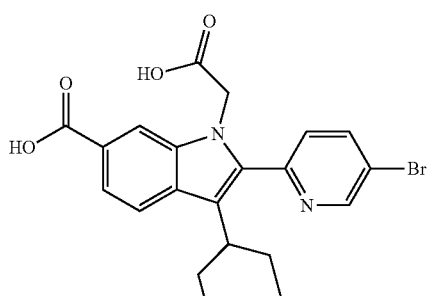

compound D
(Compound# 149)

wherein Ex. means Example No. in the publication.

In this publication, as compounds having other skeleton, the following compounds E, F, G etc. are described.

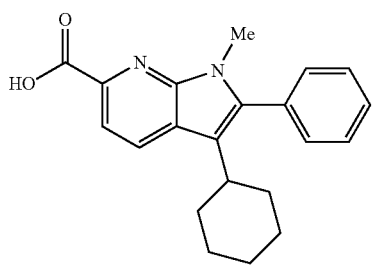

compound E (Ex. 22)

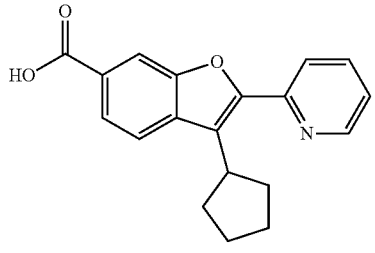

compound F (Ex. 18)

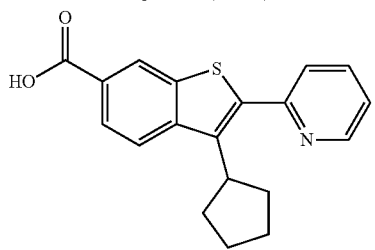

compound G (Ex. 20)

In WO03/010141, as a synthetic intermediate for an anti-HCV agent having a polymerase inhibitory activity, the above-mentioned compounds etc. are described (WO03/010141, page 92, page 101, page 108, page 112, page 115, page 116).

Furthermore, JP-A-2001-247550 (WO01/47883, EP1162196A1, US2003/0050320) and WO03/000254 (US2003/0050320) describe, as an anti-HCV agent having a polymerase inhibitory activity, the following indole compound H etc., benzimidazole compound I etc. (JP-A-2001-247550, Example compound Nos. 502 (page 206), 701 (page 417), 1198 (page 315); WO03/000254, Example compound Nos. 502 (page 206), 701 (page 417), 1198 (page 315), 371 (page 468), 405 (page 479), 407 (page 480), 423, 424 (page 485)).

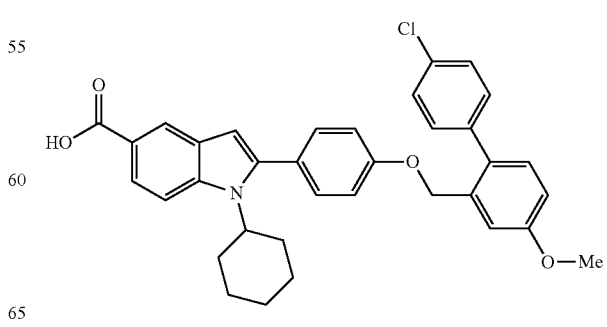

compound H (Ex. 502)

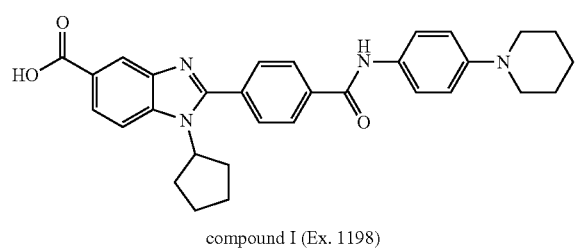

compound I (Ex. 1198)

This publication also describes the following compound J etc. as compounds having other skeletons.

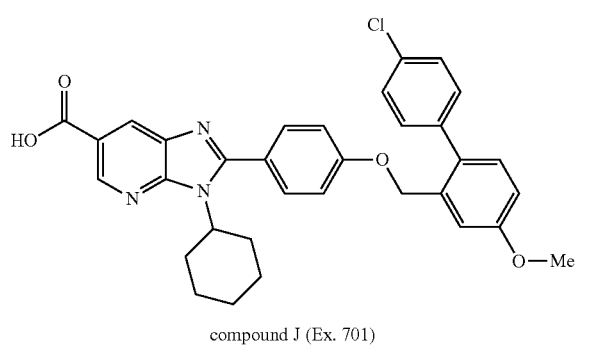

compound J (Ex. 701)

The above-mentioned WO03/000254 further describes the following benzimidazole compounds K, L, M, N, O etc.

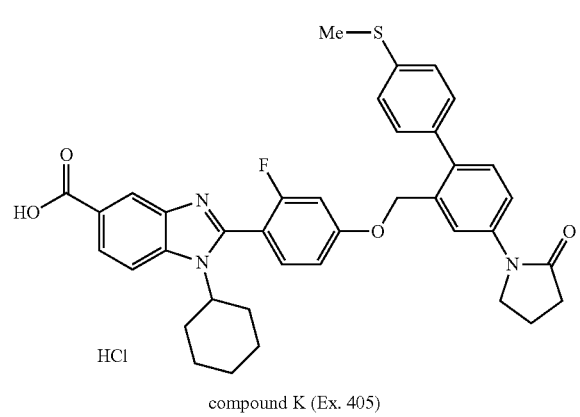

compound K (Ex. 405)

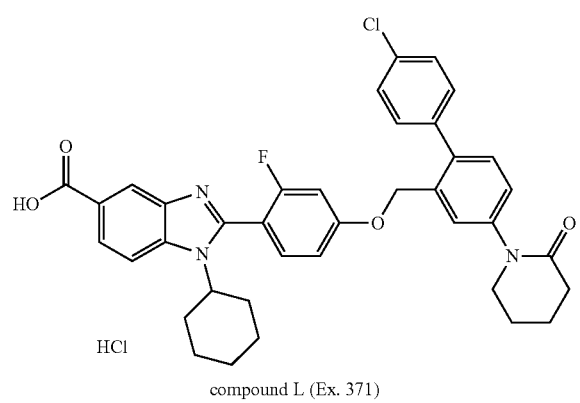

compound L (Ex. 371)

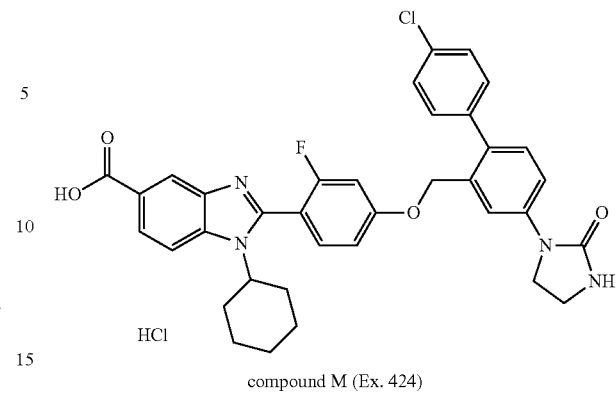

compound M (Ex. 424)

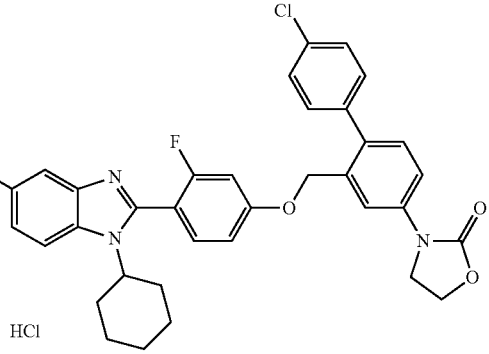

compound N (Ex. 423)

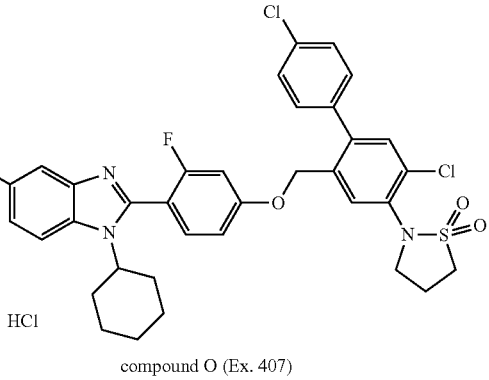

compound O (Ex. 407)

In addition, WO02/04425 describes the following benzimidazole compound P etc. as anti-HCV agents having a polymerase inhibitory activity (WO02/04425, entry No. 7005 (page 228), Example Nos. 28 (page 84), 148 (page 163)).

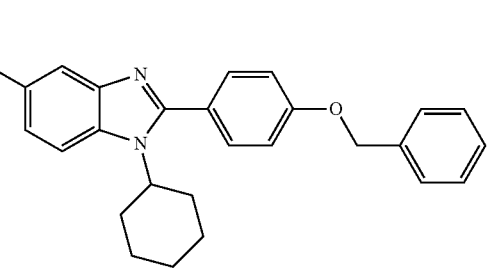

compound P (Entry# 7005)

In this publication, the following compounds Q, R etc. are described as compounds having other skeletons.

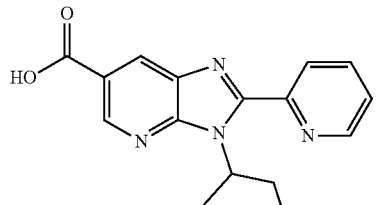

compound Q (Ex. 28)

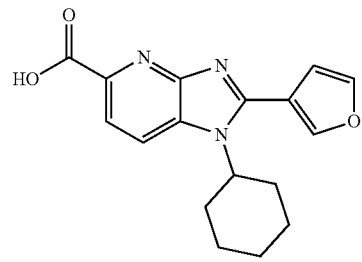

compound R (Ex. 148)

WO03/026587 also discloses the following compounds S, T etc. as anti-HCV agents having a polymerase inhibitory activity (WO03/026587, Example Nos. 12 (page 56), 65 (page 65)).

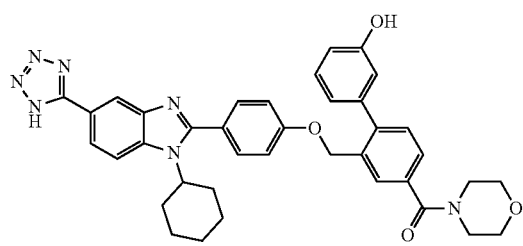

compound S (Ex. 65)

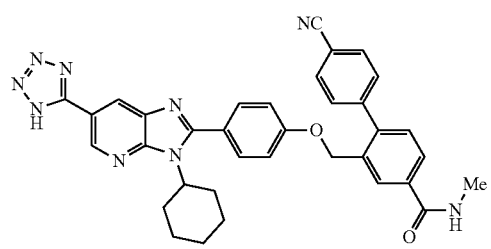

compound T (Ex. 12)

As therapeutic agents for hepatitis C having a benzimidazole skeleton, the compounds described in WO97/36866, JP-T-2000-511899 (EP906097) and WO99/51619 are also known.

WO03/007945 also describes benzimidazole compound etc. as synthetic intermediates for anti-HCV agents having a polymerase inhibitory activity.

Furthermore, WO99/09007 and U.S. Pat. No. 5,932,743 describe the following indole compound U etc. as chemical library compounds that can be used for screening of pharmaceutical products (see WO99/09007, Example 12 (page 25); U.S. Pat. No. 5,932,743).

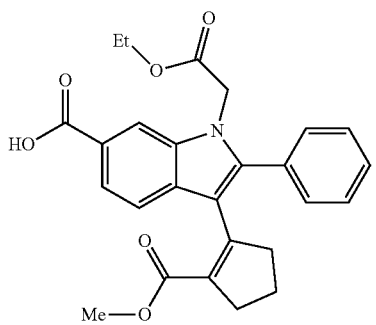

compound U (Ex. 12)

DISCLOSURE OF INVENTION

Based on the findings from the preceding studies, it has been elucidated that a pharmaceutical agent having an anti-HCV activity is effective for the prophylaxis and treatment of hepatitis C, and particularly an anti-HCV agent having an inhibitory activity on RNA-dependent RNA polymerase of HCV can be a prophylactic and therapeutic agent effective against hepatitis C and a prophylactic and therapeutic agent for the disease caused by hepatitis C.

Accordingly, the present invention provides a compound having an anti-HCV activity, particularly a compound having an RNA-dependent RNA polymerase inhibitory activity.

The present inventors have made an in-depth study of compounds having an anti-HCV activity, particularly RNA-dependent RNA polymerase inhibitory activity, and completed the present invention.

Thus, the present invention provides the following [1] to [70].

[1] A compound represented by the following formula [I] or a pharmaceutically acceptable salt thereof:

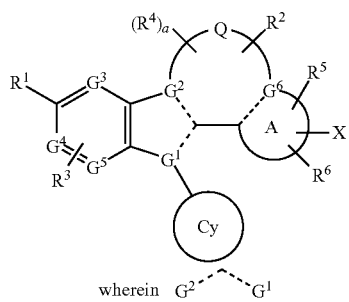

[I]

wherein $G^2 \cdots G^1$ is C=C—N or N—C=C, $G^3$, $G^4$ and $G^5$ are each independently a carbon atom or a nitrogen atom, when at least one of $G^3$, $G^4$ and $G^5$ is a carbon atom, said carbon atom is optionally substituted by $R^3$, Q is
(1) —(CH$_2$)$_b$— or
(2) —(CH$_2$)$_c$-Q$^1$-(CH$_2$)$_d$—
(wherein b is an integer of 1 to 4,
c and d are each independently 0 or an integer of 1 to 4,
Q$^1$ is
(1') —O—,
(2') —NH—,
(3') —S—,
(4') —OCO—,
(5') —OCONH—,
(6') —CO—,
(7') —SO—,
(8') —SO$_2$—,
(9') —NHCO—,
(10') —NHSO$_2$—,
(11') —NHCOO—,
(12') —COO—,
(13') —CONH—,
(14') —SO$_2$NH—,
(15') —NHCONH—,
(16') —NHSO$_2$NH—,
(17') —CH═CH—,
(18') —CH═N— or
(19') —N═CH—),
ring A is
(1) benzene,
(2) cyclopentane or cyclohexane,
(3) cyclopentane or cyclohexane or
(4) a 5- or 6-membered heterocycle comprising 1 to 4 heteroatoms selected from oxygen atom, nitrogen atom and sulfur atom,
G$^6$ is a carbon atom or a nitrogen atom, a broken line in ring A shows a single bond or a double bond,
R$^1$ is
(1) a carboxyl group,
(2) a carboxylic acid equivalent,
(3) —CONR$^{11}$R$^{12}$
(wherein R$^{11}$ and R$^{12}$ are each independently
(1') a hydrogen atom,
(2') a C$_{1-6}$ alkyl group optionally substituted by 1 to 3 substituents selected from the following group E,
(3') a C$_{2-6}$ alkenyl group optionally substituted by 1 to 3 substituents selected from the following group E,
(4') a C$_{6-14}$ aryl group optionally substituted by 1 to 5 substituents selected from the following group E,
(5') a heterocyclic group optionally substituted by 1 to 5 substituents selected from the following group E
(wherein said heterocyclic group comprises 1 to 4 heteroatoms selected from oxygen atom, nitrogen atom and sulfur atom),
(6') a C$_{3-10}$ cycloalkyl group optionally substituted by 1 to 5 substituents selected from the following group E,
(7') —NR$^{131}$R$^{132}$,
(8') —NHCOOR$^{133}$,
(9') —NHCOR$^{134}$
(wherein R$^{131}$, R$^{132}$, R$^{133}$ and R$^{134}$ are each independently a hydrogen atom or a group selected from the following group F),
(10') —CR$^{135}$R$^{136}$-L$^{100}$-R$^{137}$,
(11') —CR$^{135}$R$^{136}$-L$^{101}$-CONR$^{140}$—R$^{137}$, (12')

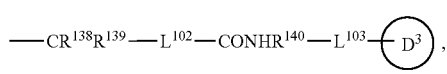

-continued

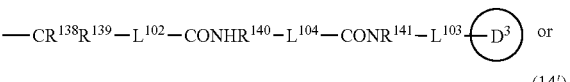 (13')

or

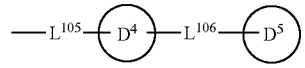 (14')

(wherein R$^{135}$, R$^{136}$, R$^{138}$ and R$^{139}$ are each independently
(1″) a hydrogen atom or
(2″) a group selected from the following group G,
group G:
(1‴) cyano group,
(2‴) —COOR$^{142}$
(wherein R$^{142}$ is a hydrogen atom or a group selected from the following group F)
(3‴) —CONR$^{143}$R$^{144}$
(wherein R$^{143}$ and R$^{144}$ are each independently a hydrogen atom, a C$_{1-6}$ alkoxy group or a group selected from the following group F)
(4‴) a C$_{1-6}$ alkyl group optionally substituted by 1 to 3 substituents selected from the following group A,
(5‴) a C$_{2-6}$ alkenyl group optionally substituted by 1 to 3 substituents selected from the following group A,
(6‴) a C$_{6-14}$ aryl group optionally substituted by 1 to 5 substituents selected from the following group B,
(7‴) a heterocyclic group optionally substituted by 1 to 5 substituents selected from the following group B
(wherein said heterocyclic group comprises 1 to 4 heteroatoms selected from oxygen atom, nitrogen atom and sulfur atom),
(8‴) a C$_{3-10}$ cycloalkyl group optionally substituted by 1 to 5 substituents selected from the following group B,
(9‴) a C$_{6-14}$ aryl C$_{1-6}$ alkyl group optionally substituted by 1 to 5 substituents selected from the following group B,
(10‴) a heterocycle C$_{1-6}$ alkyl group optionally substituted by 1 to 5 substituents selected from the following group B and
(11‴) a C$_{3-10}$ cycloalkyl C$_{1-6}$ alkyl group optionally substituted by 1 to 5 substituents selected from the following group B; or
R$^{135}$ and R$^{136}$, or, R$^{138}$ and R$^{139}$ are bonded to each other, and optionally form, together with the carbon atom bonded thereto,
(1″) a C$_{3-10}$ cycloalkyl group optionally substituted by 1 to 5 substituents selected from the following group B or
(2″) a heterocyclic group optionally substituted by 1 to 5 substituents selected from the following group B
(wherein said heterocyclic group comprises 1 to 4 heteroatoms selected from oxygen atom, nitrogen atom and sulfur atom),
R$^{137}$ is
(1″) a hydrogen atom,
(2″) a carboxyl group,
(3″) a C$_{1-6}$ alkyl group optionally substituted by 1 to 3 substituents selected from the following group E,
(4″) a C$_{2-6}$ alkenyl group optionally substituted by 1 to 3 substituents selected from the following group E,
(5″) a C$_{6-14}$ aryl group optionally substituted by 1 to 5 substituents selected from the following group E,
(6″) a heterocyclic group optionally substituted by 1 to 5 substituents selected from the following group E
(wherein said heterocyclic group comprises 1 to 4 heteroatoms selected from oxygen atom, nitrogen atom and sulfur atom) or (7") a $C_{3-10}$ cycloalkyl group optionally substituted by 1 to 5 substituents selected from the following group E, $R^{140}$ and $R^{141}$ are each independently
(1") a hydrogen atom or
(2") a $C_{1-6}$ alkyl group, $L^{100}$ is
(1") a bond,
(2") —CO—,
(3") —$CH_2O$—,
(4") —$CH_2NH$—,
(5") —$CH_2NHCO$—,
(6") a $C_{1-6}$ alkylene optionally substituted by hydroxyl group or
(7") a $C_{2-6}$ alkenylene, $L^{101}$ and $L^{102}$ are each independently
(1") a bond,
(2") —CO—,
(3") a $C_{1-6}$ alkylene optionally substituted by hydroxyl group or
(4") a $C_{2-6}$ alkenylene, $L^{103}$ is
(1") a bond or
(2") a $C_{1-6}$ alkylene, $L^{104}$ is a $C_{1-6}$ alkylene, $L^{105}$ is
(1") a bond or
(2") a $C_{1-6}$ alkylene, $L^{106}$ is
(1") a bond,
(2") a $C_{1-6}$ alkylene,
(3") —NH—,
(4") —NH—$CH_2$— or
(5") —$CH_2$—CONH—, ring $D^3$, ring $D^4$ and ring $D^5$ are each independently
(1") a $C_{6-14}$ aryl group optionally substituted by 1 to 5 substituents selected from the following group E,
(2") a $C_{3-10}$ cycloalkyl group optionally substituted by 1 to 5 substituents selected from the following group E or
(3") a heterocyclic group optionally substituted by 1 to 5 substituents selected from the following group E
(wherein said heterocyclic group comprises 1 to 4 heteroatoms selected from oxygen atom, nitrogen atom and sulfur atom))),
(4) —$COOR^{103}$
(wherein $R^{103}$ is a group selected from the following group C or a glucuronic acid residue), (5)

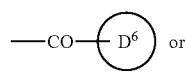

(6)

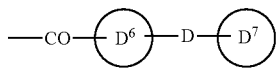

(wherein ring $D^6$ is a heterocyclic group optionally, substituted by 1 to 5 substituents selected from the following group E (wherein said heterocyclic group comprises 1 to 4 heteroatoms selected from oxygen atom, nitrogen atom and sulfur atom), ring $D^7$ is a $C_{6-14}$ aryl group optionally substituted by 1 to 5 substituents selected from the following group E), $R^2$ may substitute at a substitutable position on carbon atom or nitrogen atom constituting Q and is
(1) a hydrogen atom,
(2) a group selected from the following group E,
(3) a $C_{1-6}$ alkyl group optionally substituted by 1 to 3 substituents selected from the following group E,
(4) a $C_{2-6}$ alkenyl group optionally substituted by 1 to 3 substituents selected from the following group E, (5)

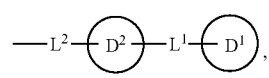

(6)

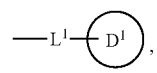

(7)

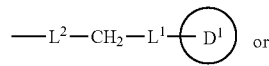 or (8)

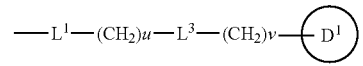

{wherein $L^1$ and $L^2$ are each independently
(1) a bond,
(2') $C_{1-6}$ alkylene,
(3') $C_{2-6}$ alkenylene,
(4') —$(CH_2)_{u1}$—O—$(CH_2)_{v1}$—,
(5') —$(CH_2)_{u1}$—S—$(CH_2)_{v1}$—,
(6') —$(CH_2)_{u1}$—$NR^{L1}$—$(CH_2)_{v1}$—,
(7') —$(CH_2)_{u1}$—CO—$(CH_2)_{v1}$—,
(8') —$(CH_2)_{u1}$—$CONR^{L2}$—$(CH_2)_{v1}$—,
(9') —$(CH_2)_{u1}$—$NR^{L2}CO_2$—$(CH_2)_{v1}$—,
(10') —$(CH_2)_{u1}$—$NR^{L2}CONR^{L3}$—$(CH_2)_{v1}$—,
(11') —$(CH_2)_{u1}$—$NR^{L2}CO$—$(CH_2)_{v1}$—,
(12') —$(CH_2)_{u1}$—$NR^{L2}SO_2$—$(CH_2)_{v1}$—,
(13') —$(CH_2)_{u1}$—$SO_2$—$(CH_2)_{v1}$—,
(14') —$(CH_2)_{u1}$—$SO_2NR^{L2}$—$(CH_2)_{v1}$— or
(15') —$(CH_2)_{u1}$—$N^+R^{L2}R^{L2'}$—$(CH_2)_{v1}$—,
(wherein u, v, u1 and v1 are each independently 0 or an integer of 1 to 6, $R^{L1}$ is
(1") a hydrogen atom,
(2") a group selected from the following group C,
(3") —$COR^{L11}$,
(4") —$CONR^{L11}R^{L12}$,
(5") —$COOR^{L11}$ or
(6") —$SO_2R^{L13}$
(wherein $R^{L11}$ and $R^{L12}$ are each independently a hydrogen atom or a group selected from the following group C, and $R^{L13}$ is a group selected from the following group C), $R^{L2}$, $R^{L2'}$ and $R^{L3}$ are each independently
(1") a hydrogen atom,
(2") a group selected from the following group C,
(3") —$COR^{L11}$ or
(4") —$SO_2R^{L13}$
(wherein $R^{L11}$ and $R^{L13}$ are as defined above)), $L^3$ is
(1') —$CHR^{L14}$— or
(2') —$NR^{L14}$—
(wherein $R^{L14}$ is a group selected from the following group F), ring $D^1$ and ring $D^2$ are each independently
(1') a $C_{6-14}$ aryl group optionally substituted by 1 to 5 substituents selected from the following group E,
(2') a $C_{3-10}$ cycloalkyl group optionally substituted by 1 to 5 substituents selected from the following group E or (3') a heterocyclic group optionally substituted by 1 to 5 substituents selected from the following group E
(wherein said heterocyclic group comprises 1 to 4 heteroatoms selected from oxygen atom, nitrogen atom and sulfur atom)},
$R^3$ is
(1) a hydrogen atom,
(2) a halogen atom,
(3) a $C_{1-6}$ alkanoyl group,
(4) a carboxyl group,
(5) a cyano group,
(6) a nitro group,
(7) a $C_{1-6}$ alkyl group optionally substituted by 1 to 3 substituents selected from the following group A,
(8) —$OR^{101}$
(wherein $R^{101}$ is a hydrogen atom or a group selected from the following group C),
(9) —$NR^{102}R^{119}$
(wherein $R^{102}$ and $R^{119}$ are each independently a hydrogen atom, a $C_{1-6}$ alkanoyl group or a $C_{1-6}$ alkylsulfonyl group),
(10) —$COOR^{103}$
(wherein $R^{103}$ is a group selected from the following group C or a glucuronic acid residue),
(11) —$CONR^{104}R^{105}$
(wherein $R^{104}$ and $R^{105}$ are each independently a hydrogen atom, a hydroxyl group, a cyano group, a $C_{1-6}$ alkoxy group or a $C_{1-6}$ alkyl group optionally substituted by 1 to 3 substituents selected from the following group A),
(12) —$SO_2R^{106}$
(wherein $R^{106}$ is a hydroxyl group, an amino group, a $C_{1-6}$ alkyl group or a $C_{1-6}$ alkylamino group),
(13) —$NRCOR^{107}$
(wherein $R^{107}$ is an amino group or a $C_{1-6}$ alkylamino group),
(14) —$C(=NR^{108})$—$NH_2$
(wherein $R^{108}$ is a hydrogen atom, a $C_{1-6}$ alkyl group optionally substituted by 1 to 3 substituents selected from the following group A, a hydroxyl group or a $C_{1-6}$ alkoxy group),
(15) —$P(=O)(OR^{109})_2$
(wherein $R^{109}$ are each independently a hydrogen atom or a group selected from the following group C),
(16) —$P(=O)(OR^{110})NR^{111}R^{112}$
(wherein $R^{110}$, $R^{111}$ and $R^{112}$ are each independently a hydrogen atom or a group selected from the following group C),
(17) —$CONHCO$—$R^{113}$
(wherein $R^{113}$ is a group selected from the following group C),
(18) —$CONHSO_2$—$R^{114}$
(wherein $R^{114}$ is a group selected from the following group C),
(19) —$SO_2NHCO$—$R^{115}$
(wherein $R^{115}$ is a group selected from the following group C) or
(20) a heterocyclic group optionally substituted by 1 to 5 substituents selected from the following group B
(wherein said heterocyclic group comprises 1 to 4 heteroatoms selected from oxygen atom, nitrogen atom and sulfur atom),
$R^4$ may substitute at a substitutable position on carbon atom or nitrogen atom constituting Q and each is independently
(1) a halogen atom,
(2) a $C_{1-6}$ alkyl group optionally substituted by 1 to 3 substituents selected from the following group A,
(3) —$OR^{116}$
(wherein $R^{116}$ is a hydrogen atom or a group selected from the following group C), (4) —$NR^{117}R^{118}$
(wherein $R^{117}$ and $R^{118}$ are each independently a hydrogen atom, a $C_{1-6}$ alkanoyl group or a group selected from the following group C),
(5) a $C_{6-14}$ aryl group optionally substituted by 1 to 5 substituents selected from the following group B or
(6) a heterocyclic group optionally substituted by 1 to 5 substituents selected from the following group B
(wherein said heterocyclic group comprises 1 to 4 heteroatoms selected from oxygen atom, nitrogen atom and sulfur atom),
a is 0, 1 or 2,
$R^5$ and $R^6$ are each independently
(1) a hydrogen atom,
(2) a halogen atom,
(3) a $C_{1-6}$ alkyl group optionally substituted by 1 to 3 substituents selected from the following group A,
(4) —$OR^{120}$
(wherein $R^{120}$ is a hydrogen atom or a group selected from the following group C) or
(5) —$NR^{121}R^{122}$
(wherein $R^{121}$ and $R^{122}$ are each independently a hydrogen atom, a $C_{1-6}$ alkanoyl group or a group selected from the following group C),
ring Cy is
(1) a $C_{3-10}$ cycloalkyl group optionally substituted by 1 to 5 substituents selected from the following group B,
(2) a $C_{3-10}$ cycloalkenyl group optionally substituted by 1 to 5 substituents selected from the following group B or
(3) a heterocyclic group optionally substituted by 1 to 5 substituents selected from the following group B
(wherein said heterocyclic group comprises 1 to 4 heteroatoms selected from oxygen atom, nitrogen atom and sulfur atom),
X is
(1) a group selected from the following group D,
(2) a $C_{2-6}$ alkenyl group optionally substituted by 1 to 3 substituents selected from the following group A or

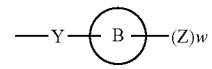

(3)

wherein ring B is
(1') a $C_{6-14}$ aryl group,
(2') a $C_{3-10}$ cycloalkyl group or
(3') a heterocyclic group comprising 1 to 4 heteroatoms selected from oxygen atom, nitrogen atom and sulfur atom,
each Z is independently
(1') a group selected from the following group D,
(2') a $C_{6-14}$ aryl group optionally substituted by 1 to 5 substituents selected from the following group D,
(3') a $C_{3-10}$ cycloalkyl group optionally substituted by 1 to 5 substituents selected from the following group D,
(4') a $C_{6-14}$ aryl $C_{1-6}$ alkyl group optionally substituted by 1 to 5 substituents selected from the following group D,
(5') a heterocyclic group optionally substituted by 1 to 5 substituents selected from the following group D
(wherein said heterocyclic group comprises 1 to 4 heteroatoms selected from oxygen atom, nitrogen atom and sulfur atom) or
(6') a heterocycle $C_{1-6}$ alkyl group optionally substituted by 1 to 5 substituents selected from the following group D
(wherein said heterocycle $C_{1-6}$ alkyl group is a $C_{1-6}$ alkyl group substituted by "a heterocyclic group optionally substituted by 1 to 5 substituents selected from group D" as defined above),
w is an integer of 1 to 3, Y is
(a) $C_{1-6}$ alkylene,
(b) $C_{2-6}$ alkenylene or
(c) —$Y^1$—$(CH_2)_m$—$Y^2$—$(CH_2)_n$—
(wherein m and n are each independently 0 or an integer of 1 to 6,
$Y^1$ and $Y^2$ are each independently
(1') a bond,
(2') —O—,
(3') —$NR^{y1}$—,
(4') —S—,
(5') —CO—,
(6') —SO—,
(7') —$SO_2$—,
(8') —$CO_2$—,
(9') —OCO—,
(10') —$CONR^{y2}$—,
(11') —$NR^{y2}CO$—,
(12') —$SO_2NR^{y2}$—,
(13') —$NR^{y2}SO_2$—,
(14') —$NR^{y2}CO_2$—,
(15') —$OCONR^{y2}$—,
(16') —$NR^{y2}CONR^{y3}$—,
(17') —$CR^{y4}R^{y5}$— or
(18') —CH=CH—
(wherein $R^{y1}$ is
(1") a hydrogen atom,
(2") a group selected from the following group C,
(3''') —$(CH_2)_s$—$COOR^{y11}$,
(4") —$(CH_2)_s$—$CONR^{y11}R^{y12}$,
(5") —$(CH_2)_s$—$COR^{y11}$ or
(6") —$(CH_2)_s$—$SO_2R^{y13}$
(wherein s is 0 or an integer of 1 to 6, $R^{y11}$ and $R^{y12}$ are each independently a hydrogen atom or a group selected from the following group C, $R^{y13}$ is a group selected from the following group C),
$R^{y2}$ and $R^{y3}$ are each independently
(1") a hydrogen atom,
(2") a group selected from the following group C,
(3") —$COR^{y11}$ or
(4") —$SO_2R^{y13}$ (wherein $R^{y13}$ and $R^{y13}$ are as defined above),
$R^{y4}$ and $R^{y5}$ are each independently
(1") a hydrogen atom,
(2") a carboxyl group,
(3") a group selected from group F,
(4") —$OR^{y14}$ or
(5") —$NHR^{y15}$
(wherein $R^{y14}$ is a group selected from the following group C, $R^{y15}$ is a hydrogen atom, a $C_{1-6}$ alkyl group, a $C_{1-6}$ alkanoyl group, a $C_{6-14}$ aryl $C_{1-6}$ alkyloxycarbonyl group or a $C_{1-6}$ alkoxycarbonyl group)))
group A:
(1) a halogen atom,
(2) a $C_{1-6}$ alkoxy $C_{1-6}$ alkoxy group,
(3) a cyano group,
(4) —$OR^{a1}$,
(5) —$SR^{a1}$,
(6) —$NR^{a1}R^{a2}$,
(7) —$COOR^{a1}$,
(8) —$CONR^{a1}R^{a2}$,
(9) —$SO_3H$,
(10) —$SO_2NR^{a1}R^{a2}$,
(11) —$NHCOR^{a1}$,
(12) —$NHSO_2R^{a3}$,
(13) —$NHCO_2R^{a4}$,
(14) —$COR^{a1}$ and
(15) —$N^+R^{a1}R^{a2}R^{a3}$
(wherein $R^{a1}$ and $R^{a2}$ are each a hydrogen atom, a $C_{1-6}$ alkyl group or a benzyl group, $R^{a3}$ is a $C_{1-6}$ alkyl group and $R^{a4}$ is a $C_{1-6}$ alkyl group)
group B:
(1) a halogen atom,
(2) a cyano group,
(3) a nitro group,
(4) a $C_{1-6}$ alkyl group,
(5) a $C_{2-6}$ alkenyl group optionally substituted by carboxyl group,
(6) a halogenated $C_{1-6}$ alkyl group,
(7) —$(CH_2)_r$—$OR^{b1}$,
(8) —$(CH_2)_r$—$SR^{b1}$,
(9) —$(CH_2)_r$—$NR^{b1}R^{b2}$,
(10) —$(CH_2)_r$—$COOR^{b1}$,
(11) —$(CH_2)_r$—$CONR^{b1}R^{b2}$,
(12) —$(CH_2)_r$—$COR^{b1}$,
(13) —$(CH_2)_r$—$NR^{b1}$—$COR^{b2}$,
(14) —$(CH_2)_r$—$NR^{b1}$—$SO_2R^{b3}$,
(15) —$(CH_2)_r$—$SO_2R^{b3}$,
(16) —$(CH_2)_r$—$SO_2NR^{b1}R^{b2}$,
(17) —$(CH_2)_r$—$CONR^{b1}$—$SO_2R^{b3}$,
(18) —$(CH_2)_r$—$SO_2NR^{b1}$—$COR^{b2}$,
(19) —$(CH_2)_r$—$NR^{b1}$—$COOR^{b3}$,
(20) —$(CH_2)_r$—$NR^{b1}$—$CONR^{b2}R^{b4}$,
(21) —O—$(CH_2)_r$—$COOR^{b1}$ and
(22) —CO—$(CH_2)_r$—$R^{b5}$
(wherein $R^{b1}$, $R^{b2}$ and $R^{b4}$ are each independently a hydrogen atom or a $C_{1-6}$ alkyl group, $R^{b3}$ is a $C_{1-6}$ alkyl group, $R^{b5}$ is a heterocyclic group and r is 0 or an integer of 1 to 6)
group C:
(1) a $C_{1-6}$ alkyl group optionally substituted by 1 to 3 substituents selected from the aforementioned group A,
(2) a $C_{6-14}$ aryl group optionally substituted by 1 to 5 substituents selected from the aforementioned group B,
(3) a $C_{6-14}$ aryl $C_{1-6}$ alkyl group optionally substituted by 1 to 5 substituents selected from the aforementioned group B,
(4) a heterocyclic group optionally substituted by 1 to 5 substituents selected from the aforementioned group B and
(5) a heterocycle $C_{1-6}$ alkyl group optionally substituted by 1 to 5 substituents selected from the aforementioned group B
group D:
(a) a hydrogen atom,
(b) a halogen atom,
(c) a cyano group,
(d) a nitro group,
(e) a $C_{1-6}$ alkyl group optionally substituted by 1 to 3 substituents selected from the aforementioned group A,
(f) —$(CH_2)_t$—$OR^{d1}$,
wherein $R^{d1}$ is
(1) a hydrogen atom,
(2) a group selected from the following group F,
(3) a $C_{2-6}$ alkenyl group optionally substituted by 1 to 3 substituents selected from the aforementioned group A or
(4) a $C_{2-6}$ alkynyl group optionally substituted by 1 to 3 substituents selected from the aforementioned group A, hereinafter each t is independently 0 or an integer of 1 to 6,
(g) —$(CH_2)_t$—$S(O)_q$—$R^{d2}$,
wherein $R^{d2}$ is
(1) a hydrogen atom or
(2) a group selected from the following group F,
q is 0, 1, 2 or 3,
(h) —$(CH_2)_t$—$NR^{d3}R^{d4}$, wherein $R^{d3}$ and $R^{d4}$ are each independently
  (1) a hydrogen atom or
  (2) a group selected from the following group F,
(i) —(CH$_2$)$_t$—COOR$^{d5}$,
wherein $R^{d5}$ is
  (1) a hydrogen atom or
  (2) a group selected from the following group F,
(j) —(CH$_2$)$_t$—CONR$^{d6}$R$^{d7}$,
wherein $R^{d6}$ and $R^{d7}$ are each independently
  (1) a hydrogen atom,
  (2) a hydroxyl group,
  (3) a group selected from the following group F or
  (4) a $C_{1-6}$ alkoxy group,
(k) —(CH$_2$)$_t$—COR$^{d8}$,
wherein $R^{d8}$ is
  (1) a hydrogen atom or
  (2) a group selected from the following group F,
(l) —(CH$_2$)$_t$—NR$^{d9}$CO—R$^{d10}$,
wherein $R^{d9}$ is
  (1) a hydrogen atom,
  (2) a $C_{1-6}$ alkyl group optionally substituted by 1 to 3 substituents selected from the aforementioned group A or
  (3) a $C_{1-6}$ alkanoyl group,
$R^{d10}$ is
  (1) an amino group,
  (2) a $C_{1-6}$ alkylamino group or
  (3) a group selected from the following group F,
(m) —(CH$_2$)$_t$—NR$^{d11}$SO$_2$—R$^{d12}$,
wherein $R^{d11}$ is
  (1) a hydrogen atom,
  (2) a $C_{1-6}$ alkyl group optionally substituted by 1 to 3 substituents selected from the aforementioned group A or
  (3) a $C_{1-6}$ alkanoyl group,
$R^{d12}$ is
  (1) a hydrogen atom or
  (2) a group selected from the following group F,
(n) —(CH$_2$)$_t$—SO$_2$—NR$^{d13}$R$^{d14}$,
wherein $R^{d13}$ and $R^{d14}$ are each independently
  (1) a hydrogen atom or
  (2) a group selected from the following group F,
(o) —(CH$_2$)$_t$—CONR$^{d15}$—SO$_2$R$^{d16}$,
wherein $R^{d15}$ and $R^{d16}$ are each independently
  (1) a hydrogen atom or
  (2) a group selected from the following group F,
(p) —(CH$_2$)$_t$—SO$_2$NR$^{d17}$—COR$^{d18}$,
wherein $R^{d17}$ is
  (1) a hydrogen atom or
  (2) a group selected from the following group F,
$R^{d18}$ is a group selected from the following group F,
(q) —(CH$_2$)$_t$—NR$^{d19}$—COOR$^{d20}$,
wherein $R^{d19}$ and $R^{d20}$ are each independently
  (1) a hydrogen atom or
  (2) a group selected from the following group F,
(r) —(CH$_2$)$_t$—NR$^{d21}$—CONR$^{d22}$R$^{d23}$,
wherein $R^{d21}$, $R^{d22}$ and $R^{d23}$ are each independently
  (1) a hydrogen atom or
  (2) a group selected from the following group F,
(s) —(CH$_2$)$_t$—C(=NR$^{d24}$)NH$_2$,
wherein $R^{d24}$ is
  (1) a hydrogen atom,
  (2) a hydroxyl group,
  (3) a $C_{1-6}$ alkyl group optionally substituted by 1 to 3 substituents selected from the aforementioned group A or
  (4) $C_{1-6}$ alkoxy group,
(t) —(CH$_2$)$_t$—O—(CH$_2$)$_p$—COR$^{d25}$,
wherein $R^{d25}$ is
  (1) an amino group,
  (2) a $C_{1-6}$ alkylamino group or
  (3) a heterocyclic group optionally substituted by 1 to 5 substituents selected from the aforementioned group B,
p is 0 or an integer of 1 to 6,
(u) —(CH$_2$)$_t$—O—(CH$_2$)$_p$—NR$^{d26}$R$^{d27}$,
wherein $R^{d26}$ and $R^{d27}$ are each independently
  (1) a hydrogen atom or
  (2) a $C_{1-6}$ alkyl group optionally substituted by 1 to 3 substituents selected from the aforementioned group A,
p is 0 or an integer of 1 to 6,
(v) —(CH$_2$)$_t$—O—COOR$^{d28}$,
wherein $R^{d28}$ is
  (1) a hydrogen atom or
  (2) a group selected from the following group F, and
(w) a heterocyclic group optionally substituted by 1 to 5 substituents selected from the aforementioned group B (wherein said heterocyclic group comprises 1 to 4 heteroatoms selected from oxygen atom, nitrogen atom and sulfur atom)
  group E:
(a) a halogen atom,
(b) a cyano group,
(c) a nitro group,
(d) an azido group,
(e) —OP(=O)(OH)$_2$,
(f) —OR$^{e1}$,
wherein $R^{e1}$ is
  (1) a hydrogen atom,
  (2) a group selected from the following group F,
  (3) a $C_{2-6}$ alkenyl group optionally substituted by 1 to 3 substituents selected from the aforementioned group A or
  (4) a $C_{2-6}$ alkynyl group optionally substituted by 1 to 3 substituents selected from the aforementioned group A,
(g) —S(O)$_q$—R$^{e2}$,
wherein $R^{e2}$ is
  (1) a hydrogen atom or
  (2) a group selected from the following group F,
q is 0, 1, 2 or 3,
(h) —NR$^{e3}$R$^{e4}$,
wherein $R^{e3}$ and $R^{e4}$ are each independently
  (1) a hydrogen atom,
  (2) a cyano group or
  (3) a group selected from the following group F,
(i) —COOR$^{e5}$,
wherein $R^{e5}$ is
  (1) a hydrogen atom or
  (2) a group selected from the following group F,
(j) —CONR$^{e6}$R$^{e7}$,
wherein $R^{e6}$ and $R^{e7}$ are each independently
  (1) a hydrogen atom,
  (2) a hydroxyl group,
  (3) a group selected from the following group F or
  (4) a $C_{1-6}$ alkoxy group,
(k) —COR$^{e8}$,
wherein $R^{e8}$ is a group selected from the following group F,
(l) —NR$^{e9}$CO—R$^{e10}$,
wherein $R^{e9}$ is
  (1) a hydrogen atom,
  (2) a $C_{1-6}$ alkyl group or
  (3) a $C_{1-6}$ alkanoyl group,
$R^{e10}$ is
  (1) a hydrogen atom,
  (2) an amino group,
  (3) a $C_{1-6}$ alkylamino group,
  (4) a $C_{2-6}$ alkenyl group optionally substituted by 1 to 3 substituents selected from the aforementioned group A or
  (5) a group selected from the following group F,
(m) —NR$^{e11}$SO$_2$—R$^{e12}$, wherein $R^{e11}$ is
(1) a hydrogen atom,
(2) a $C_{1-6}$ alkyl group or
(3) a $C_{1-6}$ alkanoyl group,
$R^{e12}$ is
(1) a hydrogen atom or
(2) a group selected from the following group F,
(n) —$SO_2$—$NR^{e13}R^{e14}$,
wherein $R^{e13}$ and $R^{e14}$ are each independently
(1) a hydrogen atom or
(2) a group selected from the following group F,
(o) —$CONR^{e15}$—$SO_2R^{e16}$,
wherein $R^{e15}$ and $R^{e16}$ are each independently
(1) a hydrogen atom or
(2) a group selected from the following group F,
(p) —$SO_2NR^{e17}$—$COR^{e18}$,
wherein $R^{e17}$ is
(1) a hydrogen atom or
(2) a group selected from the following group F,
$R^{e18}$ is a group selected from the following group F,
(q) —$NR^{e19}$—$COOR^{e20}$,
wherein $R^{e19}$ and $R^{e20}$ are each independently
(1) a hydrogen atom or
(2) a group selected from the following group F,
(r) —$NR^{e21}$—$CONR^{e22}R^{e23}$
wherein $R^{e21}$, $R^{e22}$ and $R^{e23}$ are each independently
(1) a hydrogen atom or
(2) a group selected from the following group F,
(s) —NHCO—$COOR^{e24}$
wherein $R^{e24}$ is
(1) a hydrogen atom or
(2) a group selected from the following group F,
(t) —NHCO—$CONR^{e25}R^{e26}$
wherein $R^{e25}$ and $R^{e26}$ are each independently
(1) a hydrogen atom,
(2) a hydroxyl group or
(3) a group selected from the following group F,
(u) —CONH—COOH, (v) 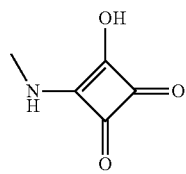

(w) 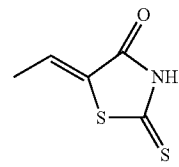

(x) 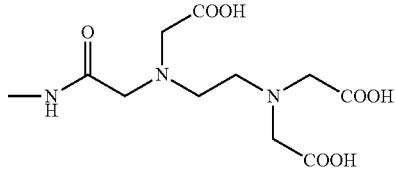

(y) a $C_{6-14}$ aryl group optionally substituted by 1 to 5 substituents selected from the aforementioned group B,
(z) a $C_{3-10}$ cycloalkyl group optionally substituted by 1 to 5 substituents selected from the aforementioned group B, (aa) a heterocyclic group optionally substituted by 1 to 5 substituents selected from the aforementioned group B (wherein said heterocyclic group comprises 1 to 4 heteroatoms selected from oxygen atom, nitrogen atom and sulfur atom),
(bb) a $C_{3-10}$ cycloalkylidene group optionally substituted by 1 to 5 substituents selected from the aforementioned group B, and
(cc) a heterocycle ylidene group optionally substituted by 1 to 5 substituents selected from the aforementioned group B (wherein said heterocycle ylidene group comprises 1 to 4 heteroatoms selected from oxygen atom, nitrogen atom and sulfur atom), when group E is a substituent on a $C_{6-14}$ aryl group, a $C_{3-10}$ cycloalkyl group or a heterocyclic group, it may be
(dd) a $C_{1-6}$ alkyl group optionally substituted by 1 to 3 substituents selected from the aforementioned group A,
(ee) a $C_{2-6}$ alkenyl group optionally substituted by 1 to 3 substituents selected from the aforementioned group A,
(ff) a $C_{2-6}$ alkynyl group optionally substituted by 1 to 3 substituents selected from the aforementioned group A,
(gg) $C_{1-6}$ alkylidene group optionally substituted by 1 to 3 substituents selected from the aforementioned group A,
(hh) a $C_{6-14}$ aryl $C_{1-6}$ alkyl group optionally substituted by 1 to 5 substituents selected from the aforementioned group B,
(ii) a $C_{3-10}$ cycloalkyl $C_{1-6}$ alkyl group optionally substituted by 1 to 5 substituents selected from the aforementioned group B, or
(jj) a heterocycle $C_{1-6}$ alkyl group optionally substituted by 1 to 5 substituents selected from the aforementioned group B group F:
(1) a $C_{1-6}$ alkyl group optionally substituted by 1 to 3 substituents selected from the aforementioned group A,
(2) a $C_{6-14}$ aryl group optionally substituted by 1 to 5 substituents selected from the aforementioned group B,
(3) a heterocyclic group optionally substituted by 1 to 5 substituents selected from the aforementioned group B (wherein said heterocyclic group comprises 1 to 4 heteroatoms selected from oxygen atom, nitrogen atom and sulfur atom),
(4) a $C_{3-10}$ cycloalkyl group optionally substituted by 1 to 5 substituents selected from the aforementioned group B,
(5) a $C_{6-14}$ aryl $C_{1-6}$ alkyl group optionally substituted by 1 to 5 substituents selected from the aforementioned group B,
(6) a heterocycle $C_{1-6}$ alkyl group optionally substituted by 1 to 5 substituents selected from the aforementioned group B (wherein said heterocycle $C_{1-6}$ alkyl group is a $C_{1-6}$ alkyl group substituted by "a heterocyclic group optionally substituted by 1 to 5 substituents selected from group B" as defined above) and
(7) a $C_{3-10}$ cycloalkyl $C_{1-6}$ alkyl group optionally substituted by 1 to 5 substituents selected from the aforementioned group B.

[2] The compound of [1], wherein, in the formula [I],

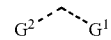

is N—C=C, or a pharmaceutically acceptable salt thereof.

[3] The compound of [1], wherein, in the formula [I], the moiety
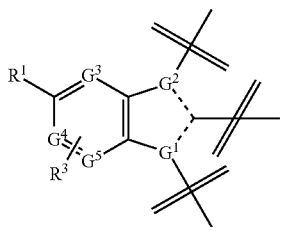
is a fused ring selected from the group consisting of
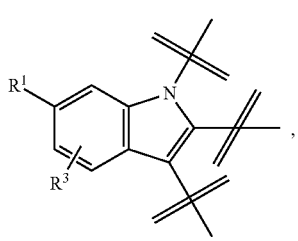

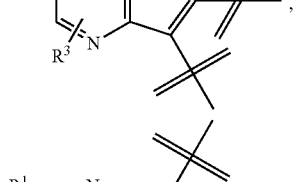
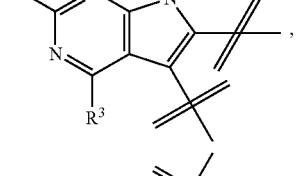
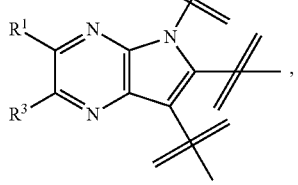
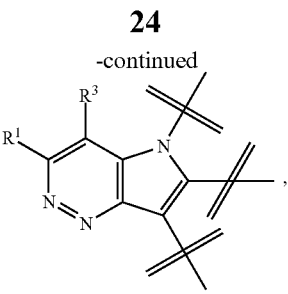
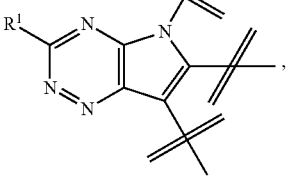
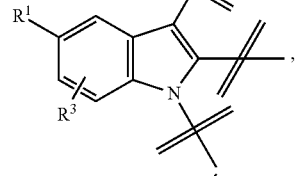
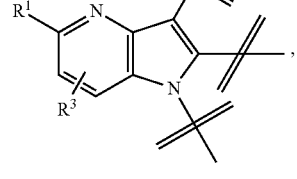
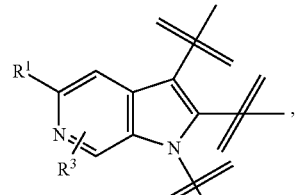
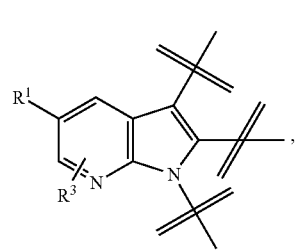
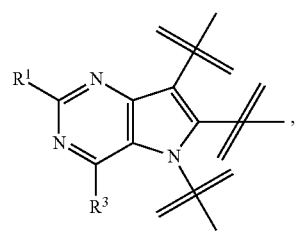

-continued

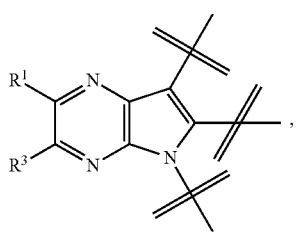

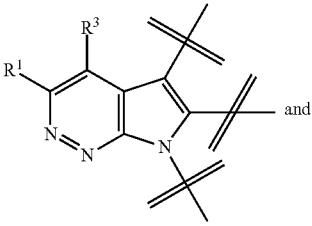

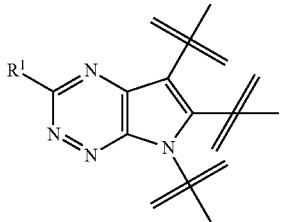

or a pharmaceutically acceptable salt thereof.

[4] The compound of [3], wherein, in the formula [I], the moiety

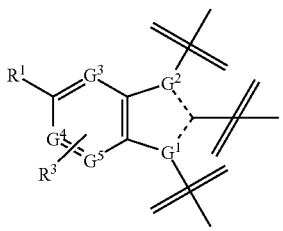

is a fused ring selected from the group consisting of

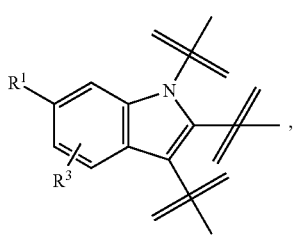

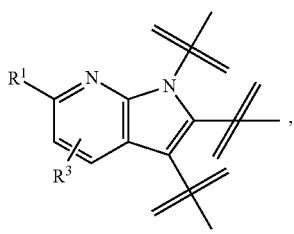

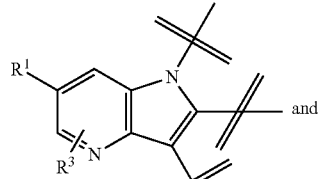

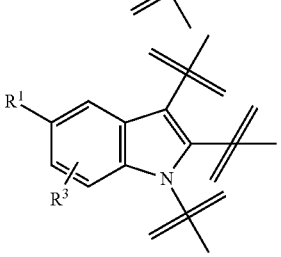

or a pharmaceutically acceptable salt thereof.

[5] The compound of [4], wherein, in the formula [I], the moiety

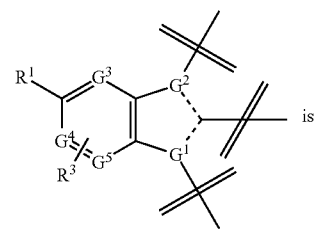

is

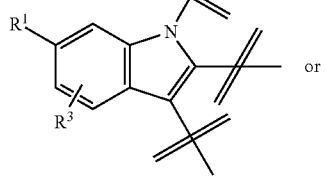

or

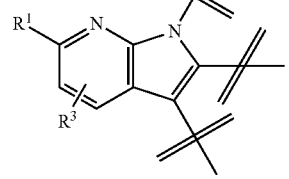

or a pharmaceutically acceptable salt thereof.

[6] The compound of [5], wherein, in the formula [I], the moiety

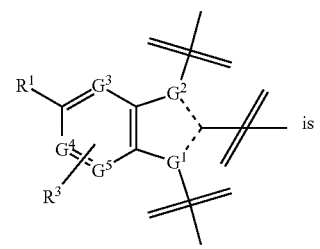

is

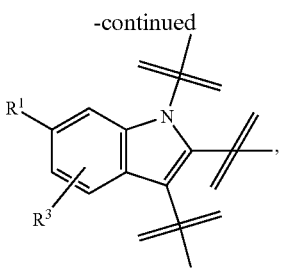

or a pharmaceutically acceptable salt thereof.

[7] The compound of [1], wherein $G^3$, $G^4$ and $G^5$ are carbon atoms, or a pharmaceutically acceptable salt thereof.

[8] The compound of [1], wherein $Q^1$ is —O—, —NH—, —S— or —CONH—, or a pharmaceutically acceptable salt thereof.

[9] The compound of [8], wherein $Q^1$ is —NH—, or a pharmaceutically acceptable salt thereof.

[10] The compound of [8], wherein b is an integer of 1 to 3, c is an integer of 1 to 3 and d is 0, or a pharmaceutically acceptable salt thereof.

[11] The compound of [1], wherein Q is —(CH$_2$)$_2$—O— or —(CH$_2$)$_2$—NH—, or a pharmaceutically acceptable salt thereof.

[12] The compound of [1], wherein $R^1$ is a carboxyl group or —CONR$^{11}$R$^{12}$, or a pharmaceutically acceptable salt thereof.

[13] The compound of [12], wherein $R^1$ is a carboxyl group, or a pharmaceutically acceptable salt thereof.

[14] The compound of [12], wherein $R^1$ is —CONR$^{11}$R$^{12}$, or a pharmaceutically acceptable salt thereof.

[15] The compound of [14], wherein $R^{11}$ is a hydrogen atom, and $R^{12}$ is
—CR$^{135}$R$^{136}$-L$^{100}$-R$^{137}$,
—CR$^{135}$R$^{136}$-L$^{101}$-CONR$^{140}$—R$^{137}$,

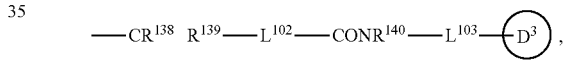 or

or a pharmaceutically acceptable salt thereof.

[16] The compound of [15], wherein $R^{12}$ is —CR$^{135}$R$^{136}$-L$^{100}$-R$^{137}$, or a pharmaceutically acceptable salt thereof.

[17] The compound of [16], wherein L$^{100}$ is a bond, and R$^{137}$ is a C$_{6-14}$ aryl group optionally substituted by 1 to 5 substituents selected from group E or
a heterocyclic group optionally substituted by 1 to 5 substituents selected from group E
(wherein said heterocyclic group comprises 1 to 4 heteroatoms selected from oxygen atom, nitrogen atom and sulfur atom), or a pharmaceutically acceptable salt thereof.

[18] The compound of [17], wherein R$^{135}$ and R$^{136}$ are each independently a group selected from group G, or, R$^{135}$ and R$^{136}$ are bonded to each other, and form, together with the carbon atom bonded thereto, a C$_{3-10}$ cycloalkyl group optionally substituted by 1 to 5 substituents selected from group B, or a heterocyclic group optionally substituted by 1 to 5 substituents selected from group B, or a pharmaceutically acceptable salt thereof.

[19] The compound of [16], wherein L$^{100}$ is methylene, and R$^{137}$ is a C$_{6-14}$ aryl group optionally substituted by 1 to 5 substituents selected from group E or a heterocyclic group optionally substituted by 1 to 5 substituents selected from group E
(wherein said heterocyclic group comprises 1 to 4 heteroatoms selected from oxygen atom, nitrogen atom and sulfur atom),
or a pharmaceutically acceptable salt thereof.

[20] The compound of [19], wherein R$^{135}$ is a group selected from group G, and R$^{136}$ is a hydrogen atom, or a pharmaceutically acceptable salt thereof.

[21] The compound of [15], wherein $R^{12}$ is —CR$^{135}$R$^{136}$-L$^{101}$-CONR$^{140}$—R$^{137}$, or a pharmaceutically acceptable salt thereof.

[22] The compound of [21], wherein L$^{101}$ is a bond, or a pharmaceutically acceptable salt thereof.

[23] The compound of [22], wherein R$^{135}$ and R$^{136}$ are each independently a group selected from group G, or, R$^{135}$ and R$^{136}$ are bonded to each other, and form, together with the carbon atom bonded thereto, a C$_{3-10}$ cycloalkyl group optionally substituted by 1 to 5 substituents selected from group B, or a heterocyclic group optionally substituted by 1 to 5 substituents selected from group B, or a pharmaceutically acceptable salt thereof.

[24] The compound of [23], wherein R$^{140}$ is a hydrogen atom, and R$^{137}$ is a C$_{6-14}$ aryl group optionally substituted by 1 to 5 substituents selected from group E or
a heterocyclic group optionally substituted by 1 to 5 substituents selected from group E
(wherein said heterocyclic group comprises 1 to 4 heteroatoms selected from oxygen atom, nitrogen atom and sulfur atom), or a pharmaceutically acceptable salt thereof.

[25] The compound of [15], wherein $R^{12}$ is

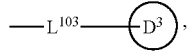, or a pharmaceutically acceptable salt thereof.

[26] The compound of [15], wherein $R^{12}$ is

—CR$^{138}$ R$^{139}$—L$^{102}$—CONR$^{140}$—L$^{104}$—CONR$^{141}$—
—L$^{103}$—(D$^3$), or a pharmaceutically acceptable salt thereof.

[27] The compound of [25] or [26], wherein L$^{102}$ is a bond, or a pharmaceutically acceptable salt thereof.

[28] The compound of [27], wherein R$^{138}$ and R$^{139}$ are each independently a group selected from group G, or, R$^{138}$ and R$^{139}$ are bonded to each other, and form, together with the carbon atom bonded thereto, a C$_{3-10}$ cycloalkyl group optionally substituted by 1 to 5 substituents selected from group B, or a heterocyclic group optionally substituted by 1 to 5 substituents selected from group B, or a pharmaceutically acceptable salt thereof.

[29] The compound of [28], wherein L$^{103}$ is a bond, ring D$^3$ is a C$_{6-14}$ aryl group optionally substituted by 1 to 5 substituents selected from group E or
a heterocyclic group optionally substituted by 1 to 5 substituents selected from group E
(wherein said heterocyclic group comprises 1 to 4 heteroatoms selected from oxygen atom, nitrogen atom and sulfur atom), and R$^{140}$ and R$^{141}$ are each independently a hydrogen atom, or a pharmaceutically acceptable salt thereof.

[30] The compound of [1], wherein $R^2$ is a hydrogen atom, a group selected from group E, a $C_{1-6}$ alkyl group optionally substituted by 1 to 3 substituents selected from group E,

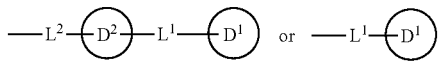

wherein each symbol is as defined in [1], or a pharmaceutically acceptable salt thereof.

[31] The compound of [30], wherein $R^2$ is a $C_{1-6}$ alkyl group optionally substituted by 1 to 3 substituents selected from group E or

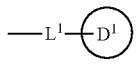

wherein each symbol is as defined in [1], or a pharmaceutically acceptable salt thereof.

[32] The compound of [31], wherein $R^2$ is

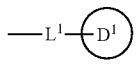

wherein each symbol is as defined in [1], or a pharmaceutically, acceptable salt thereof.

[33] The compound of [30], wherein $L^1$ and $L^2$ are each independently a bond, $C_{1-6}$ alkylene, $-(CH_2)_{u1}-NR^{L1}-(CH_2)_{v1}-$, $-(CH_2)_{u1}-(CH_2)_{v1}-$ or $-(CH_2)_{u1}-CONR^{L2}-(CH_2)_{v1}-$, or a pharmaceutically acceptable salt thereof.

[34] The compound of [33], wherein $L^1$ and $L^2$ are each independently $C_{1-6}$ alkylene, or a pharmaceutically acceptable salt thereof.

[35] The compound of [33], wherein u1 and v1 are each independently 0 or an integer of 1 to 3, or a pharmaceutically acceptable salt thereof.

[36] The compound of [30], wherein ring $D^1$ and ring $D^2$ are each independently a $C_{6-14}$ aryl group optionally substituted by 1 to 5 substituents selected from group E or a heterocyclic group optionally substituted by 1 to 5 substituents selected from group E, or a pharmaceutically acceptable salt thereof.

[37] The compound of [1], wherein $R^3$ is a hydrogen atom, a halogen atom, a alkyl group optionally substituted by 1 to 3 substituents selected from group A or $-OR^{101}$ (wherein $R^{101}$ is a hydrogen atom or a group selected from group C), or a pharmaceutically acceptable salt thereof.

[38] The compound of [1], wherein $R^5$ and $R^6$ are each independently a hydrogen atom, a halogen atom, a $C_{1-6}$ alkyl group optionally substituted by 1 to 3 substituents selected from group A or $-OR^{120}$ (wherein $R^{120}$ is a hydrogen atom or a group selected from group C), or a pharmaceutically acceptable salt thereof.

[39] The compound of [1], wherein ring A is benzene or a 5- or 6-membered heterocycle comprising 1 to 4 heteroatoms selected from oxygen atom, nitrogen atom and sulfur atom, or a pharmaceutically acceptable salt thereof.

[40] The compound of [39], wherein ring A is benzene, or a pharmaceutically acceptable salt thereof.

[41] The compound of [1], wherein ring Cy is a $C_{3-10}$ cycloalkyl group or a $C_{3-10}$ cycloalkenyl group, or a pharmaceutically acceptable salt thereof.

[42] The compound of [41], wherein ring Cy is a cyclohexyl group, or a pharmaceutically acceptable salt thereof.

[43] The compound of [1], wherein X is a hydrogen atom, a halogen atom, a $C_{1-6}$ alkyl group optionally substituted by 1 to 3 substituents selected from group A, $-(CH_2)_t-OR^{d1}$, $-(CH_2)_t-S(O)_q-R^{d2}$, $-(CH_2)_t-NR^{d3}R^{d4}$ or

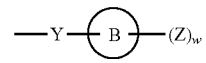

wherein each symbol is as defined in [1], or a pharmaceutically acceptable salt thereof.

[44] The compound of [43], wherein Y is $-(CH_2)_m-O-(CH_2)_n-$ or $-NR^{y1}-(CH_2)_m-Y^2-$ wherein each symbol is as defined in [1], or a pharmaceutically acceptable salt thereof.

[45] The compound of [43], wherein Y is $-O-CH_2-$ or $-O-$, or a pharmaceutically acceptable salt thereof.

[46] The compound of [43], wherein Y is $-NR^{y1}-CH_2-CO-$ or $-NR^{y1}-(CH_2)_2-$, or a pharmaceutically acceptable salt thereof.

[47] The compound of [43], wherein ring B is a $C_{6-14}$ aryl group or a heterocyclic group comprising 1 to 4 heteroatoms selected from oxygen atom, nitrogen atom and sulfur atom, or a pharmaceutically acceptable salt thereof.

[48] The compound of [47], wherein ring B is a phenyl group, a pyridyl group, a piperidyl group, pyrrolidinyl group, piperazinyl group, morpholinyl group, azepanyl group, 1,4-oxazepanyl group, isoxazolyl group, thiazolyl group or 2-oxooxazolidinyl group, or a pharmaceutically acceptable salt thereof.

[49] The compound of [43], wherein Z is 1 to 3 substituents selected from (1) a hydrogen atom, (2) a halogen atom, (3) a nitro group, (4) a $C_{6-14}$ aryl group optionally substituted by 1 to 5 substituents selected from group D, (5) a $C_{3-10}$ cycloalkyl group optionally substituted by 1 to 5 substituents selected from group D, (6) a heterocyclic group optionally substituted by 1 to 5 substituents selected from group D, (7) a $C_{1-6}$ alkyl group optionally substituted by 1 to 3 substituents selected from the aforementioned group A, (8) $-(CH_2)_t-OR^{d1}$, (9) $-(CH_2)_t-S(O)_q-R^{d2}$,

(10) $-(CH_2)_t-NR^{d3}R^{d4}$,

(11) $-(CH_2)_t-COOR^{d5}$,

(12) $-(CH_2)_t-CONR^{d6}R^{d7}$,

(13) $-(CH_2)_t-COR^{d8}$,

(14) $-(CH_2)_t-NR^{d9}CO-R^{d10}$,

(15) $-(CH_2)_t-NR^{d11}SO_2-R^{d12}$ and

(16) $-(CH_2)_t-NR^{d19}-COOR^{d20}$ wherein each symbol is as defined in [1], or a pharmaceutically acceptable salt thereof.

[50] The compound of [1], which is represented by the following formula [I-A], or a pharmaceutically acceptable salt thereof:

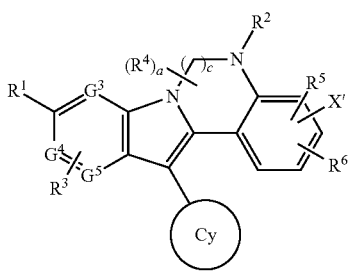

wherein X' is a hydrogen atom, a halogen atom, a $C_{1-6}$ alkyl group optionally substituted by 1 to 3 substituents selected from group A or $-OR^{d1}$, and other symbols are as defined in [1].

[51] The compound of [1], which is represented by the following formula [I-B], or a pharmaceutically acceptable salt thereof:

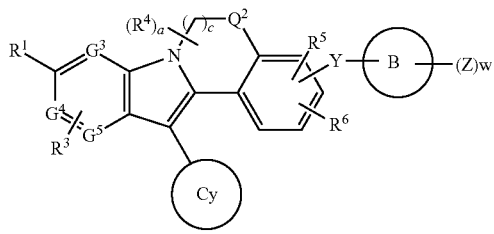

wherein $Q^2$ is —O— or —NH—, and other symbols are as defined in [1].

[52] The compound of [1], which is represented by the following formula [I-C], or a pharmaceutically acceptable salt thereof:

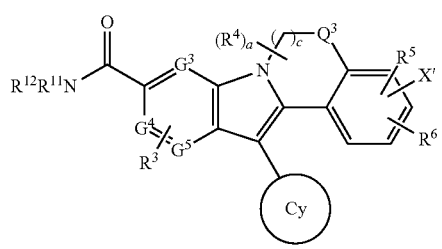

wherein $Q^3$ is —O— or —NR$^2$—, X' is a hydrogen atom, a halogen atom, a $C_{1-6}$ alkyl group optionally substituted by 1 to 3 substituents selected from group A or $-OR^{d1}$, and other symbols are as defined in [1].

[53] A pharmaceutical composition comprising a compound of any of [1] to [52], or a pharmaceutically acceptable salt thereof, and a pharmaceutically acceptable carrier.

[54] A hepatitis C virus polymerase inhibitor comprising a compound of any of [1] to [52] or a pharmaceutically acceptable salt thereof as an active ingredient.

[55] An anti-hepatitis C virus agent comprising a compound of any of [1] to [52] or a pharmaceutically acceptable salt thereof as an active ingredient.

[56] A therapeutic agent for hepatitis C, which comprises a compound of any of [1] to [52] or a pharmaceutically acceptable salt thereof as an active ingredient.

[57] A therapeutic agent for hepatitis C, which comprises (a) a hepatitis C virus polymerase inhibitor of [54] and (b) at least one pharmaceutical agent selected from the group consisting of a different antiviral agent, an antiinflammatory agent and an immunostimulant.

[58] A therapeutic agent for hepatitis C, which comprises (a) a hepatitis C virus polymerase inhibitor of [54] and (b) interferon.

[59] An anti-hepatitis C virus agent, which comprises (a) an anti-hepatitis C virus agent of [55] and (b) at least one pharmaceutical agent selected from the group consisting of a different antiviral agent, an antiinflammatory agent and an immunostimulant.

[60] An anti-hepatitis C virus agent comprising (a) an anti-hepatitis C virus agent of [55] and (b) interferon.

[61] A pharmaceutical composition comprising (a) a compound of any of [1] to [52] or a pharmaceutically acceptable salt thereof, and (b) at least one pharmaceutical agent selected from the group consisting of a different antiviral agent, an antiinflammatory agent and an immunostimulant.

[62] A pharmaceutical composition comprising (a) a compound of any of [1] to [52] or a pharmaceutically acceptable salt thereof, and (b) interferon.

[63] Use of a compound of any of [1] to [52] or a pharmaceutically acceptable salt thereof for the production of a pharmaceutical agent for treating hepatitis C.

[64] Use of a compound of any of [1] to [52] or a pharmaceutically acceptable salt thereof for the production of a hepatitis C virus polymerase inhibitor.

[65] A method for treating hepatitis C, which comprises administering an effective amount of a compound of any of [1] to [52] or a pharmaceutically acceptable salt thereof to a mammal.

[66] The method of [65], further comprising administering an effective amount of at least one pharmaceutical agent selected from the group consisting of a different antiviral agent, an antiinflammatory agent and an immunostimulant to the mammal.

[67] The method of [65], further comprising administering an effective amount of interferon to the mammal.

[68] A method for inhibiting hepatitis C virus polymerase, which comprises administering an effective amount of a compound of any of [1] to [52] or a pharmaceutically acceptable salt thereof to a mammal.

[69] The method of [68], further comprising administering an effective amount of at least one pharmaceutical agent selected from the group consisting of a different antiviral agent, an antiinflammatory agent and an immunostimulant to the mammal.

[70] The method of [68], further comprising administering an effective amount of interferon to the mammal.

DETAILED DESCRIPTION OF THE INVENTION

The definitions of respective substituents and moieties used in the present specification are as follows.

The "halogen atom" is a fluorine atom, chlorine atom, bromine atom or iodine atom, preferably fluorine atom, chlorine atom or bromine atom.

The "$C_{1-6}$ alkyl group" is a linear or branched chain alkyl group having 1 to 6 carbon atoms, preferably a linear or branched chain alkyl group having 1 to 4 carbon atoms. Specifically, methyl group, ethyl group, propyl group, isopropyl group, butyl group, isobutyl group, sec-butyl group, tert-butyl group, pentyl group, isopentyl group, tert-pentyl group, hexyl group and the like can be mentioned.

The "$C_{2-6}$ alkenyl group" is a linear or branched chain alkenyl group having 2 to 6 carbon atoms. Specifically, vinyl group, allyl group, 1-propenyl group, isopropenyl group, 1-butenyl group, 2-butenyl group, 1,3-butadienyl group, 2-isopentenyl group, 3-isohexenyl group, 4-methyl-3-pentenyl group and the like can be mentioned.

The "$C_{2-6}$ alkynyl group" is a linear or branched chain alkynyl group having 2 to 6 carbon atoms. Specifically, ethynyl group, 1-propynyl group, 2-propynyl group, 3-butynyl group and the like can be mentioned.

The "halogenated $C_{1-6}$ alkyl group" is the above-defined "$C_{1-6}$ alkyl group" substituted by the above-defined "halogen atom", which is preferably a halogenated alkyl group wherein the alkyl moiety is a linear or branched chain alkyl group having 1 to 4 carbon atoms. Specifically, fluoromethyl group, difluoromethyl group, trifluoromethyl group, bromomethyl group, chloromethyl group, 1,2-dichloroethyl group, 2,2-dichloroethyl group, 2,2,2-trifluoroethyl group and the like can be mentioned.

The "$C_{1-6}$ alkylene" is a straight chain alkylene having 1 to 6 carbon atoms, and methylene, ethylene, trimethylene, tetramethylene, pentamethylene, hexamethylene and the like can be mentioned.

The "$C_{2-6}$ alkenylene" is a straight chain alkenylene having 2 to 6 carbon atoms, and vinylene, propenylene, 1-butenylene, 1,3-butadienylene and the like can be mentioned.

The "$C_{1-6}$ alkoxy group" is an alkyl-oxy group wherein the alkyl moiety is the above-defined "$C_{1-6}$ alkyl group", preferably an alkoxy group wherein the alkyl moiety is a linear or branched chain alkyl group having 1 to 4 carbon atoms. Specifically, methoxy group, ethoxy group, propoxy group, isopropyloxy group, butoxy group, isobutyloxy group, tert-butyloxy group, pentyloxy group, hexyloxy group and the like can be mentioned.

The "$C_{1-6}$ alkoxy $C_{1-6}$ alkoxy group" is an alkyl-oxy-alkyl-oxy group wherein the above-defined "$C_{1-6}$ alkoxy group" is substituted by the above-defined "$C_{1-6}$ alkoxy group", preferably that wherein the alkyl moiety is a linear or branched chain alkyl group having 1 to 4 carbon atoms. Specifically, methoxymethoxy group, ethoxymethoxy group, 1-(methoxy)ethoxy group, 2-(methoxy)ethoxy group, methoxypropoxy group, isopropyloxyethoxy group and the like can be mentioned.

The "$C_{1-6}$ alkanoyl group" is an alkyl-carbonyl group wherein the alkyl moiety is the above-defined "$C_{1-6}$ alkyl group", preferably an alkyl-carbonyl group wherein the alkyl moiety is a linear or branched chain alkyl group having 1 to 4 carbon atoms. Specifically, acetyl group, propionyl group, butyryl group, isobutyryl group, pivaloyl group and the like can be mentioned.

The "$C_{1-6}$ alkoxycarbonyl group" is an alkyl-oxy-carbonyl group wherein the alkoxy moiety is the above-defined "$C_{1-6}$ alkoxy group", preferably an alkyl-oxy-carbonyl group wherein the alkyl moiety is a linear or branched chain alkyl group having 1 to 4 carbon atoms. Specifically, methoxycarbonyl group, ethoxycarbonyl group, propoxycarbonyl group, isopropyloxycarbonyl group, butoxycarbonyl group, isobutyloxycarbonyl group, tert-butyloxycarbonyl group, pentyloxycarbonyl group, hexyloxycarbonyl group and the like can be mentioned.

The "$C_{1-6}$ alkylamino group" is an alkyl-amino group or a dialkyl-amino group wherein the alkyl moiety is the above-defined "$C_{1-6}$ alkyl group", preferably an alkyl-amino group or a dialkyl-amino group wherein the alkyl moiety is a linear or branched chain alkyl group having 1 to 4 carbon atoms. Specifically, methylamino group, ethylamino group, propylamino group, isopropylamino group, butylamino group, isobutylamino group, tert-butylamino group, pentylamino group, hexylamino group, dimethylamino group, diethylamino group, N-ethyl-N-methylamino group, N-isobutyl-N-isopropylamino group and the like can be mentioned.

The "$C_{1-6}$ alkanoylamino group" is an alkyl-carbonyl-amino group wherein the alkanoyl moiety is the above-defined "$C_{1-6}$ alkanoyl group", preferably an alkyl-carbonyl-amino group wherein the alkyl moiety is a linear or branched chain alkyl group having 1 to 4 carbon atoms. Specifically, acetylamino group, propionylamino group, butyrylamino group, isobutyrylamino group, pivaloylamino group and the like can be mentioned.

The "$C_{1-6}$ alkylsulfonyl group" is an alkyl-sulfonyl group wherein the alkyl moiety is the above-defined "$C_{1-6}$ alkyl group", preferably an alkyl-sulfonyl group wherein the alkyl moiety is a linear or branched chain alkyl group having 1 to 4 carbon atoms. Specifically, methanesulfonyl group, ethylsulfonyl group, propylsulfonyl group, isopropylsulfonyl group, butylsulfonyl group, isobutylsulfonyl group, tert-butylsulfonyl group, pentylsulfonyl group, hexylsulfonyl group and the like can be mentioned.

The "$C_{6-14}$ aryl group" is an aromatic hydrocarbon group having 6 to 14 carbon atoms. Specifically, phenyl group, naphthyl group, anthryl group, indenyl group, azulenyl group, fluorenyl group, phenanthryl group and the like can be mentioned, with preference given to phenyl group.

The "$C_{3-10}$ cycloalkyl group" is a saturated cycloalkyl group having 3 to 10, preferably 3 to 8, more preferably 5 to 7, carbon atoms, and includes monocycle and fused ring. Specifically, cyclopropyl group, cyclobutyl group, cyclopentyl group, cyclohexyl group, cycloheptyl group, cyclooctyl group, adamantyl group and the like can be mentioned.

The "$C_{3-10}$ cycloalkenyl group" is a cycloalkenyl group having 3 to 10, preferably 3 to 8, more preferably 5 to 7, carbon atoms, and includes at least one, preferably 1 or 2, double bonds. Specifically, cyclopropenyl group, cyclobutenyl group, cyclopentenyl group, cyclopentadienyl group, cyclohexenyl group, 2,4-cyclohexadien-1-yl group, 2,5-cyclohexadien-1-yl group, cycloheptenyl group, cyclooctenyl group and the like can be mentioned. It does not include aryl group such as phenyl group and completely saturated cycloalkyl group.

The "$C_{6-14}$ aryl $C_{1-6}$ alkyloxycarbonyl group" is an aryl-alkyl-oxy-carbonyl group wherein the alkyl moiety is the above-defined "$C_{1-6}$ alkyl group", and the aryl moiety is the above-defined "$C_{6-14}$ aryl group". Preferred is an aryl-alkyl-oxy-carbonyl group wherein the alkyl moiety is a straight or branched chain alkyl group having 1 to 4 carbon atoms and the aryl moiety is a phenyl group. Specifically, benzyloxycarbonyl group, phenethyloxycarbonyl group, 3-phenylpropyloxycarbonyl group, 2-phenylpropyloxycarbonyl group, 4-phenylbutyloxycarbonyl group and the like can be mentioned.

The "bond" means a direct connection. For example, when $L^1$ is a "bond" in —O-$L^1$-Ph, it means —O-Ph.

The "glucuronic acid residue" is a group remaining after removing any hydroxyl group from glucuronic acid, and preferably substitutes at the 1-position of β-D-glucuronic acid.

The "heterocyclic group" and "heterocyclic group comprising 1 to 4 heteroatoms selected from oxygen atom, nitrogen atom and sulfur atom" has, as a ring-constituting atom, 1 to 4 heteroatoms selected from oxygen atom, nitrogen atom and sulfur atom besides carbon atom, wherein the number of atom constituting the ring is 3 to 14, includes saturated ring and unsaturated ring, monocycle and fused ring, and may be a spiro ring.

As the monocyclic heterocyclic group, specifically, pyridyl group, pyrazinyl group, pyrimidinyl group, pyridazinyl group, 1,3,5-triazinyl group, pyrrolyl group, pyrazolyl group, imidazolyl group, triazolyl group (1,2,3-triazolyl group, 1,2,4-triazolyl group), tetrazolyl group, thienyl group, furyl group, oxazolyl group, isoxazolyl group, triazolyl group, isothiazolyl group, oxadiazolyl group (1,2,4-oxadiazolyl group, 1,3,4-oxadiazolyl group, 1,2,5-oxadiazolyl group), thiadiazolyl group (1,2,4-thiadiazolyl group, 1,3,4-thiadiazolyl group, 1,2,5-thiadiazolyl group), pyrrolinyl group (1-pyrrolinyl group, 2-pyrrolinyl group, 3-pyrrolinyl group), pyrrolidinyl group, 4,5-dihydro-1H-imidazolyl group, 4,5-dihydro-1H-oxazolyl group, 4,5-dihydro-1H-thiazolyl group, imidazolidinyl group, azetidinyl group, piperidyl group, piperazinyl group, 1,2,3,6-tetrahydropyridyl group, morpholinyl group, thiomorpholinyl group, 3,6-dihydro-2H-pyranyl group, tetrahydropyranyl group, tetrahydrofuranyl group, azepanyl group (e.g., azepan-1-yl group), azocanyl group (e.g., azocan-1-yl group), azonanyl group (e.g., azonan-1-yl group), 1,4-diazepanyl group (e.g., 1,4-diazepan-1-yl group), 1,4-oxazepanyl group (e.g., 1,4-oxazepan-4-yl group) and the like can be mentioned.

This heterocyclic group includes the groups represented by the following formulas.

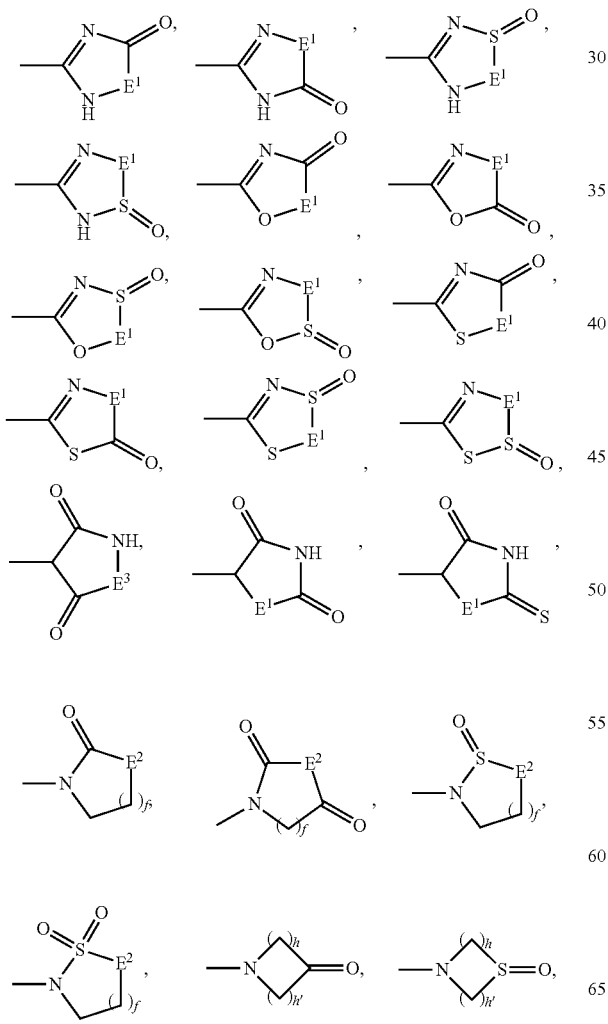

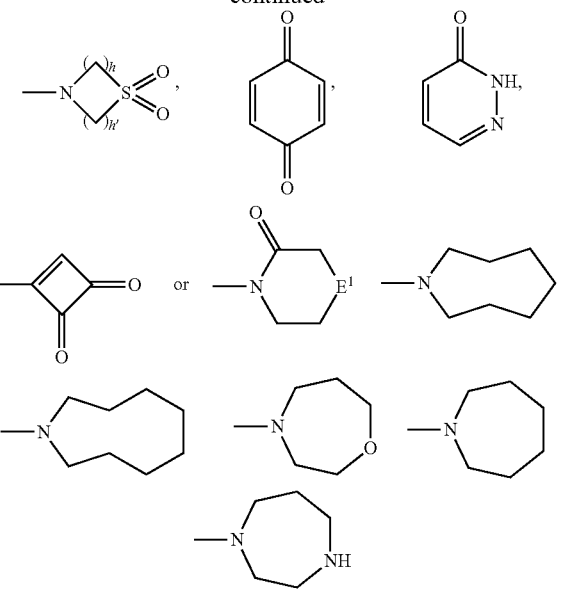

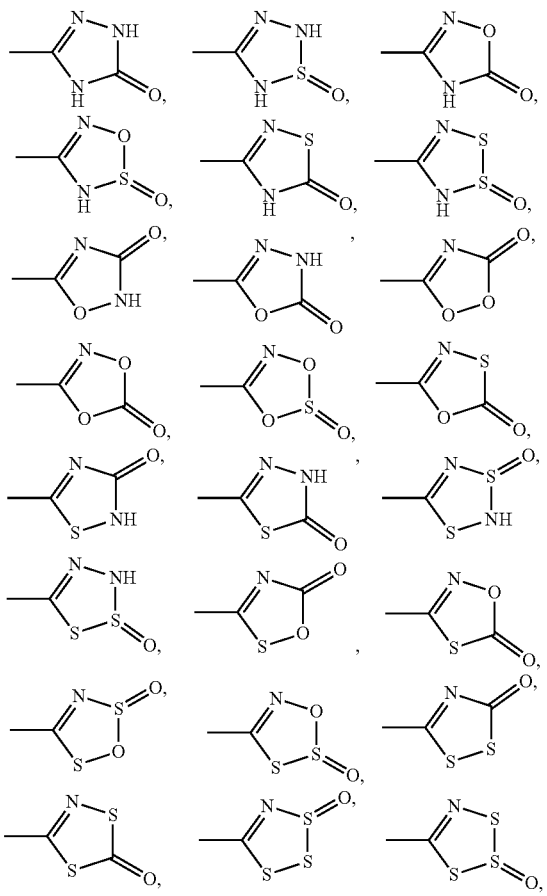

wherein $E^1$ is an oxygen atom, a sulfur atom or NH, $E^2$ is an oxygen atom, $CH_2$ or NH, $E^3$ is an oxygen atom or a sulfur atom, wherein f is an integer of 1 to 3, h and h' are the same or different and each is an integer of 1 to 3.

Specifically,

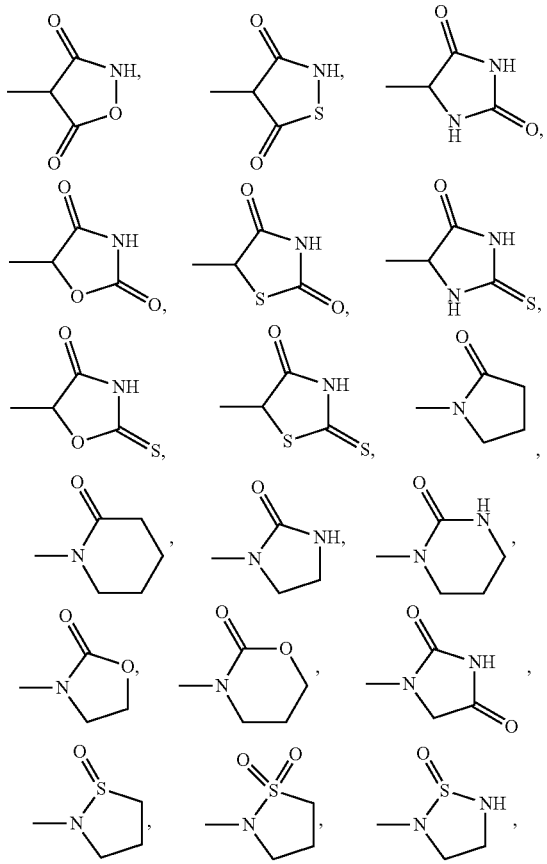

and the like can be mentioned.

As a fused heterocyclic group, specifically, quinolyl group, isoquinolyl group, quinazolinyl group, quinoxalinyl group, phthalazinyl group, cinnolinyl group, naphthyridinyl group, 1,2,3,4-tetrahydroquinolyl group, 5,6,7,8-tetrahydroquinolyl group, 1,2,3,4-tetrahydroisoquinolyl group, 5,6,7,8-tetrahydroisoquinolyl group, indolyl group, benzimidazolyl group, 2,3-dihydrobenzimidazolyl group, 2,3-dihydro-2-oxobenzimidazolyl group, indolinyl group, isoindolinyl group, octahydroindolyl group, octahydroisoindolyl group, benzofuranyl group, benzothienyl group, benzoxazolyl group, benzothiazolyl group, 3,4-dihydro-2H-benzo[1,4]oxazinyl group, 3-oxo-3,4-dihydro-2H-benzo[1,4]oxazinyl group, octahydrocyclopenta[c]pyrrolyl group, 2-oxo-2H-chromenyl group, benzo[1,3]dioxolanyl group, 4-oxo-1H-quinolinyl group, 2-oxohexahydrothieno[3,4-d]imidazolyl group, 7-azabicyclo[2.2.1]heptyl group,

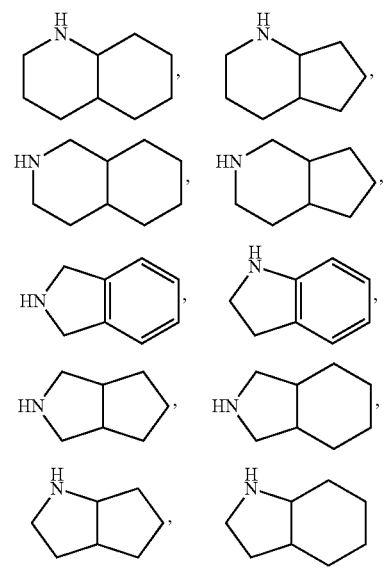

and the like can be mentioned.

As a spiro heterocyclic group, specifically,

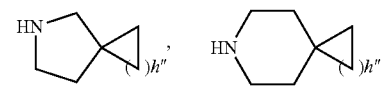

wherein h" is an integer of 1 to 6 and the like can be mentioned.

The "5- or 6-membered heterocycle comprising 1 to 4 heteroatoms selected from oxygen atom, nitrogen atom and sulfur atom" is a 5-membered or 6-membered saturated or unsaturated ring containing $G^6$, which contains, besides carbon atom, 1 to 4 heteroatoms selected from oxygen atom, nitrogen atom and sulfur atom, wherein $G^6$ is a nitrogen atom or a carbon atom, and a broken line in ring A is a single bond or a double bond.

Preferably, it is a heterocycle containing 1 or 2, more preferably 1, heteroatom selected from oxygen atom, nitrogen atom and sulfur atom, besides carbon atom, wherein the heteroatom is preferably a nitrogen atom.

As the ring A, specifically, benzene, cyclopentane, cyclohexane, cyclopentane, cyclohexene, pyridine, pyrazine, pyrimidine, pyridazine, 1,3,5-triazine, pyrrole, pyrazole, imidazole, 1,2,3-triazole, 1,2,4-triazole, tetrazole, thiophene, furan, oxazole, isoxazole, thiazole, isothiazole, 1,2,4-thiadiazole, 1,2,5-thiadiazole, 1,3,4-thiadiazole, 2,3-dihydro-1H-pyrrole, 2,5-dihydro-1H-pyrrole, pyrrolidine, imidazolidine, piperidine, piperazine, morpholine, thiomorpholine, tetrahydropyran, oxazolidine, 1,2,3,4-tetrahydropyridine, 1,2,3,6-tetrahydropyridine,

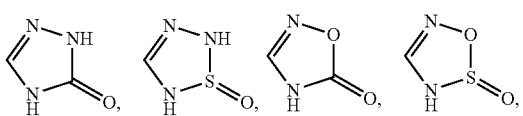

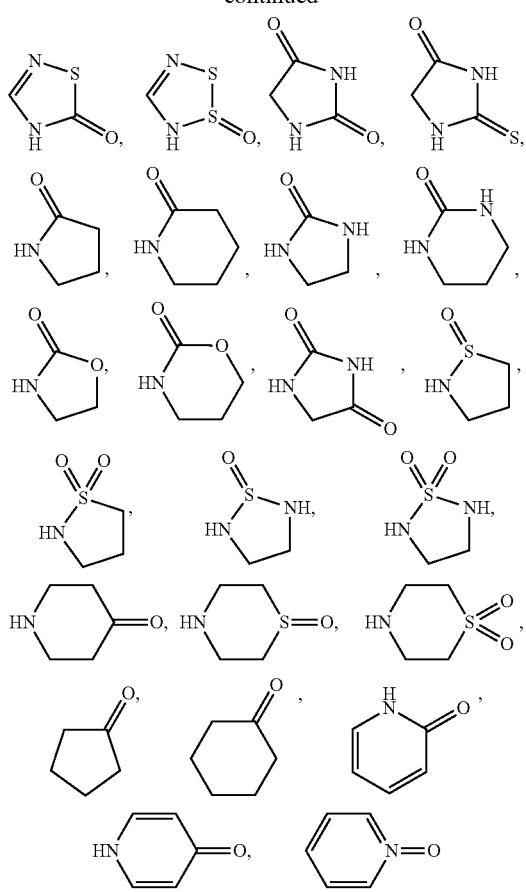

and the like can be mentioned.

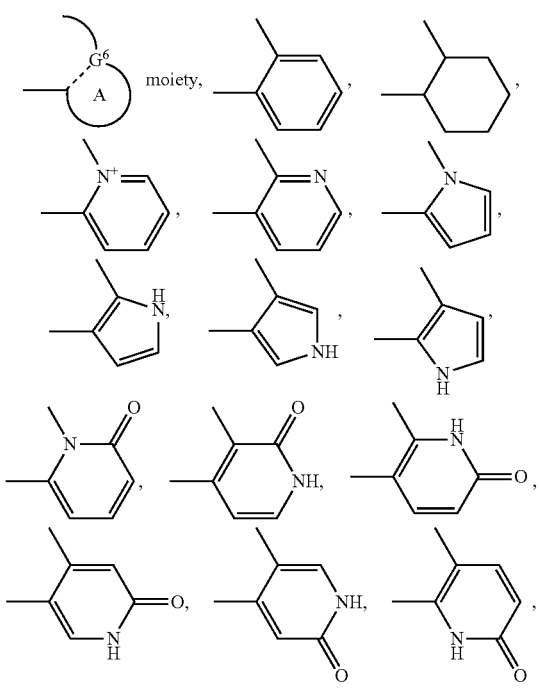

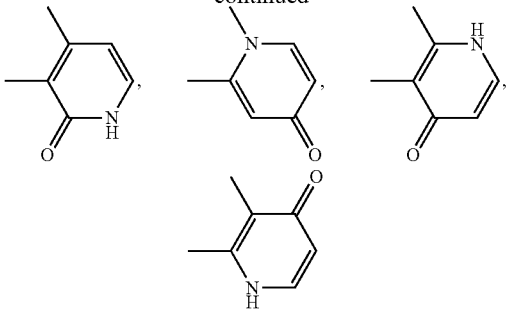

and the like can be mentioned.

The "group A" means the substituent groups of the following (1) to (15).

($R^{a1}$ and $R^{a2}$ are each independently a hydrogen atom, the above-defined "$C_{1-6}$ alkyl group" or a benzyl group, $R^{a3}$ is the above-defined "$C_{1-6}$ alkyl group" and $R^{a4}$ is the above-defined "$C_{1-6}$ alkyl group")

(1) the above-defined "halogen atom",
(2) the above-defined "$C_{1-6}$ alkoxy $C_{1-6}$ alkoxy group",
(3) a cyano group,
(4) —$OR^{a1}$ (e.g., hydroxyl group, methoxy group, ethoxy group, isopropyloxy group, tert-butyloxy group, benzyloxy group etc.),
(5) —$SR^{a1}$ (e.g., mercapto group, methylsulfanyl group etc.),
(6) —$NR^{a1}R^{a2}$ (e.g., amino group, methylamino group, ethylamino group, isopropylamino group, dimethylamino group, diethylamino group, diisopropylamino group, di-tert-butylamino group, N-ethyl-N-methylamino group etc.),
(7) —$COOR^{a1}$ (e.g., carboxyl group, methoxycarbonyl group, ethoxycarbonyl group, isopropyloxycarbonyl group, tert-butoxycarbonyl group etc.),
(8) —$CONR^{a1}R^{a2}$ (e.g., carbamoyl group, methylcarbamoyl group, ethylcarbamoyl group, isopropylcarbamoyl group, dimethylcarbamoyl group, diethylcarbamoyl group, diisopropylcarbamoyl group, di-tert-butylcarbamoyl group, N-ethyl-N-methylcarbamoyl group etc.),
(9) —$SO_3H$,
(10) —$SO_2NR^{a1}R^{a2}$ (e.g., sulfamoyl group, methylsulfamoyl group, ethylsulfamoyl group, isoptopylsulfamoyl group, dimethylsulfamoyl group, diethylsulfamoyl group, diisopropylsulfamoyl group, di-tert-butylsulfamoyl group, N-ethyl-N-methylsulfamoyl group etc.),
(11) —$NHCOR^{a1}$ (e.g., formylamino group, acetylamino group, propionylamino group, isobutyrylamino group, pivaloylamino group etc.),
(12) —$NHSO_2R^{a3}$ (e.g., methanesulfonylamino group, ethylsulfonylamino group, isopropylsulfonylamino group, tert-butylsulfonylamino group etc.),
(13) —$NHCO_2R^{a4}$ (e.g., tert-butoxycarbonylamino group etc.),
(14) —$COR^{a1}$ (e.g., formyl group, acetyl group, propionyl group, isobutyryl group, pivaloyl group etc.) and
(15) —$N^+R^{a1}R^{a2}R^{a3}$ (e.g., trimethylammonio group, triethylammonio group etc.).

The "group B" means the substituent groups of the following (1) to (22).

(the following $R^{b1}$, $R^{b2}$ and $R^{b4}$ are each independently a hydrogen atom or the above-defined "$C_{1-6}$ alkyl group", $R^{b3}$ is the above-defined "$C_{1-6}$ alkyl group", $R^{b5}$ is the above-defined "heterocyclic group" and r is 0 or an integer of 1 to 6)

(1) the above-defined "halogen atom",
(2) a cyano group, (3) a nitro group,
(4) the above-defined "$C_{1-6}$ alkyl group",
(5) the above-defined "$C_{2-6}$ alkenyl group" optionally substituted by carboxyl group (e.g., vinyl group, allyl group, 1-propenyl group, isopropenyl group, 1-butenyl group, 2-butenyl group, 1,3-butadienyl group, 2-isopentenyl group, 3-isohexenyl group, 4-methyl-3-pentenyl group, 2-carboxyethenyl group etc.)
(6) the above-defined "halogenated $C_{1-6}$ alkyl group",
(7) —$(CH_2)_r$—$OR^{b1}$ (e.g., hydroxyl group, methoxy group, ethoxy group, isopropyloxy group, tert-butyloxy group, hydroxymethyl group, methoxymethyl group, 2-(methoxy)ethyl group etc.),
(8) —$(CH_2)_r$—$SR^{b1}$ (e.g., mercapto group, methylsulfanyl group, mercaptomethyl group, 2-(methylsulfanyl)ethyl group etc.),
(9) —$(CH_2)_r$—$NR^{b1}R^{b2}$ (e.g., amino group, methylamino group, ethylamino group, isopropylamino group, dimethylamino group, diethylamino group, diisopropylamino group, di-tert-butylamino group, N-ethyl-N-methylamino group, aminomethyl group, 2-(methylamino) ethyl group etc.),
(10) —$(CH_2)_r$—$COOR^{b1}$ (e.g., carboxyl group, methoxycarbonyl group, ethoxycarbonyl group, isopropyloxycarbonyl group, tert-butoxycarbonyl group, carboxymethyl group, 2-(carboxy)ethyl group etc.),
(11) —$(CH_2)_r$—$CONR^{b1}R^{b2}$ (e.g., carbamoyl group, methylcarbamoyl group, ethylcarbarnoyl group, isopropylcarbamoyl group, dimethylcarbamoyl group, diethylcarbamoyl group, diisopropylcarbamoyl group, di-tert-butylcarbamoyl group, N-ethyl-N-methylcarbamoyl group, carbamoylmethyl group, dimethylcarbamoylmethyl group, 2-(methylcarbamoyl)ethyl group etc.),
(12) —$(CH_2)_r$—$COR^{b1}$ (e.g., formyl group, acetyl group, propionyl group, isobutyryl group, pivaloyl group, acetylmethyl group, 2-pivaloylethyl group etc.),
(13) —$(CH_2)_r$—$NR^{b1}$—$COR^{b2}$ (e.g., formylamino group, acetylamino group, propionylamino group, isobutyrylamino group, pivaloylamino group, N-acetyl-N-methylamino group, acetylaminomethyl group, 2-(isobutyrylamino)ethyl group etc.),
(14) —$(CH_2)_r$—$NR^{b1}$—$SO_2R^{b3}$ (e.g., methanesulfonylamino group, ethylsulfonylamino group, isopropylsulfonylamino group, tert-butylsulfonylamino group, N-methyl-N-(methanesulfonyl)amino group, methanesulfonylaminomethyl group, 2-(tert-butylsulfonylamino)ethyl group etc.),
(15) —$(CH_2)_r$—$SO_2R^{b3}$ (e.g., rnethanesulfonyl group, ethylsulfonyl group, isopropylsulfonyl group, tert-butylsulfonyl group, methanesulfonylmethyl group, 2-(ethylsulfonyl)ethyl group etc.),
(16) —$(CH_2)_r$—$SO_2NR^{b1}R^{b2}$ (e.g., sulfamoyl group, methylsulfamoyl group, ethylsulfamoyl group, isopropylsulfamoyl group, dimethylsulfamoyl group, diethylsulfamoyl group, diisopropylsulfamoyl group, di-tert-butylsulfamoyl group, N-ethyl-N-methylsulfamoyl group, sulfamoylmethyl group, 2-(methylsulfamoyl)ethyl group etc.),
(17) —$(CH_2)_r$—$CONR^{b1}$—$SO_2R^{b3}$ (e.g., methanesulfonylcarbamoyl group, ethylsulfonylcarbamoyl group, isopropylsulfonylcarbamoyl group, tert-butylsulfonylcarbamoyl group, N-methyl-N-(methanesulfonyl)carbamoyl group, methanesulfonylcarbamoylmethyl group, 2-(ethylsulfonylcarbamoyl)ethyl group etc.),
(18) —$(CH_2)_r$—$SO_2NR^{b1}$—$COR^{b2}$ (e.g., acetylsulfamoyl group, propionylsulfamoyl group, isobutyrylsulfamoyl group, pivaloylsulfamoyl group, N-acetyl-N-methylsulfamoyl group, acetylsulfamoylmethyl group, 2-(pivaloylsulfamoyl)ethyl group etc.),
(19) —$(CH_2)_r$—$NR^{b1}$—$COOR^{b3}$ (e.g., methoxycarbonylamino group, ethoxycarbonylamino group, isopropyloxycarbonylamino group, tert-butoxycarbonylamino group, methoxycarbonylaminomethyl group, 2-(tert-butoxycarbonylamino)ethyl group etc.),
(20) —$(CH_2)_r$—$NR^{b1}$—$CONR^{b2}R^{b4}$ (e.g., ureido group, 3-methylureido group, 3-ethylureido group, 3-isopropylureido group, 3,3-dimethylureido group, 3,3-diethylureido group, 3,3-diisopropylureido group, 3,3-di-tert-butylureido group, 3-ethyl-3-methylureido group, 1,3-dimethylureido group, trimethylureido group, ureidomethyl group, 2-(3,3-dimethylureido) ethyl group),
(21) —O—$(CH_2)_r$—$COOR^{b1}$ (e.g., carboxymethoxy group, 2-carboxyethoxy group, 3-carboxypropoxy group, 4-carboxybutoxy group, 5-carboxypentyloxy group, methoxycarbonylmethoxy group, 2-ethoxycarbonylethoxy group etc.) and
(22) —CO—$(CH_2)_r$—$R^{b5}$ (e.g., 1-oxo-5-(2-oxohexahydrothieno[3,4-d]imidazol-6-yl)pentyl group etc.).

The "$C_{1-6}$ alkyl group optionally substituted by 1 to 3 substituents selected from group A" is a group wherein the above-defined "$C_{1-6}$ alkyl group" is optionally substituted by 1 to 3 substituents selected from the above-defined "group A", which includes non-substituted alkyl group.

Specifically, methyl group, ethyl group, propyl group, isopropyl group, butyl group, isobutyl group, sec-butyl group, tert-butyl group, pentyl group, isopentyl group, tert-pentyl group, neopentyl group, 1-ethylpropyl group, hexyl group, trifluoromethyl group, hydroxymethyl group, 2-hydroxyethyl group, 3-hydroxypropyl group, 4-hydroxybutyl group, 1-hydroxy-1-methylethyl group, 1-hydroxypropan-2-yl group, 1,3-dihydroxypropan-2-yl group, 1-hydroxy-2-methylpropan-2-yl group, carboxymethyl group, ethoxycarbonylmethyl group, 2-carboxyethyl group, methoxymethyl group, methoxyethyl group, methoxyethoxyethyl group, ethoxycarbonylmethyl group, 2-ethoxycarbonylethyl group, 2-dimethylaminoethyl group, carbamoylmethyl group, methylcarbamoylmethyl group, sulfomethyl group, sulfamoylmethyl group, 2-sulfamoylethyl group, methylsulfamoylmethyl group and the like can be mentioned.

The "$C_{2-6}$ alkenyl group optionally substituted by 1 to 3 substituents selected from group A" is the above-defined "$C_{2-6}$ alkenyl group" optionally substituted by 1 to 3 substituents selected from the above-defined "group A", which includes non-substituted alkenyl group.

Specifically, vinyl group, allyl group, 1-propenyl group, isopropenyl group, 1-butenyl group, 2-butenyl group, 1,3-butadienyl group, 2-isopentenyl group, 3-isohexenyl group, 4-methyl-3-pentenyl group, 2-carboxyethenyl group and the like can be mentioned.

The "$C_{2-6}$ alkynyl group optionally substituted by 1 to 3 substituents selected from group A" is the above-defined "$C_{2-6}$ alkynyl group" optionally substituted by 1 to 3 substituents selected from the above-defined "group A", which includes non-substituted alkynyl group.

Specifically, ethynyl group, 1-propynyl group, 2-propynyl group, 3-butynyl group and the like can be mentioned.

The "$C_{6-14}$ aryl group optionally substituted by 1 to 5 substituents selected from group B" is the above-defined "$C_{6-14}$ aryl group" optionally substituted by 1 to 5 substituents selected from the above-defined "group B", which includes non-substituted aryl group.

Specifically, phenyl group, naphthyl group, anthryl group, indenyl group, azulenyl group, fluorenyl group, phenanthryl group, 3-fluorophenyl group, 4-fluorophenyl group, 3-chlorophenyl group, 4-chlorophenyl group, 2,4-dichlorophenyl group, 3,5-dichlorophenyl group, pentafluorophenyl group, 4-tolyl group, 4-tert-butylphenyl group, 2-trifluoromethylphenyl group, 4-trifluoromethylphenyl group, 4-nitrophenyl group, 4-cyanophenyl group, 4-acetylphenyl group, 4-carboxyphenyl group, 4-carbamoylphenyl group, 4-aminophenyl group, 4-dimethylaminophenyl group, 4-acetylaminophenyl group, 4-(methylsulfonylamino)phenyl group, 4-methoxyphenyl group, 3,4,5-trimethoxyphenyl group, 4-methylthiophenyl group, 4-methylsulfonylphenyl group, 4-aminosulfonylphenyl group, 3-nitro-4-methoxyphenyl group and 4-nitro-3-methoxyphenyl group can be mentioned.

The "$C_{3-10}$ cycloalkyl group optionally substituted by 1 to 5 substituents selected from group B" is the above-defined "$C_{3-10}$ cycloalkyl group" optionally substituted by 1 to 5 substituents selected from the above-defined "group B", which includes non-substituted cycloalkyl group.

Specifically, cyclopropyl group, cyclobutyl group, cyclopentyl group, cyclohexyl group, cycloheptyl group, 1-adamantyl group, 4-fluorocyclohexyl group, 2-methylcyclopentyl group, 3-methylcyclohexyl group, 4-methylcyclohexyl group, 4,4-dimethylcyclohexyl group, 3,5-dimethylcyclohexyl group, 4-tert-butylcyclohexyl group, 4-hydroxycyclohexyl group, 4-methoxycyclohexyl group and 2,3,4,5,6-pentafluorocyclohexyl group can be mentioned.

The "$C_{3-10}$ cycloalkenyl group optionally substituted by 1 to 5 substituents selected from group B" is the above-defined "$C_{3-10}$ cycloalkenyl group" optionally substituted by 1 to 5 substituents selected from the above-defined "group B", which includes non-substituted cycloalkenyl group.

Specifically, cyclopropenyl group, cyclobutenyl group, cyclopentenyl group, cyclopentadienyl group, cyclohexenyl group (cyclohex-1-enyl group, cyclohex-2-enyl group, cyclohex-3-enyl group), 5-methylcyclohex-3-enyl group, 5-methoxycyclohex-3-enyl group, 5-acetylcyclohex-3-enyl group, 2,4-cyclohexadien-1-yl group, 2,5-cyclohexadien-1-yl group, cycloheptenyl group and cyclooctenyl group and the like can be mentioned.

The "heterocyclic group optionally substituted by 1 to 5 substituents selected from group B" is the above-defined "heterocyclic group" optionally substituted by 1 to 5 substituents selected from the above-defined "group B", which includes non-substituted heterocyclic group.

Specifically, 2-pyridyl group, 3-pyridyl group, 4-pyridyl group, 3-fluoropyridin-4-yl group, 3-chloropyridin-4-yl group, 4-chloropyridin-3-yl group, pyrazinyl group, pyrimidinyl group, pyridazinyl group, 1,3,5-triazinyl group, pyrrolyl group, pyrazolyl group, imidazolyl group, 1,2,4-triazolyl group, tetrazolyl group, 2-thienyl group, 3-thienyl group, furyl group, oxazolyl group, 2-methyloxazol-4-yl group, isoxazolyl group, thiazolyl group, 2-methylthiazol-4-yl group, 2,5-dimethylthiazol-4-yl group, 2,4-dimethylthiazol-5-yl group, isothiazolyl group, thiadiazolyl group, pyrrolinyl group, pyrrolidinyl group, 3-hydroxypyrrolidinyl group, imidazolidinyl group, azetidinyl group, piperidyl group, 3-hydroxypiperidino group, 4-hydroxypiperidino group 3,4-dihydroxypiperidino group, 4-methoxypiperidino group, 4-carboxypiperidino group, 4-(hydroxymethyl)piperidino group, 2,2,6,6-tetramethylpiperidino group, 2,2,6,6-tetramethyl-4-hydroxypiperidino group, N-methylpiperidin-4-yl group, N-(tert-butoxycarbonyl)piperidin-4-yl group, N-acetylpiperidin-4-yl group, N-methylsulfonylpiperidin-4-yl group, piperazinyl group, 4-methylpiperazinyl group, 4-methylsulfonylpiperazinyl group, morpholinyl group, thiomorpholinyl group, 1-oxothiomorpholin-4-yl group, 1,1-dioxothiomorpholin-4-yl group, tetrahydropyranyl group, tetrahydrofuranyl group, azepanyl group, azocanyl group, azonanyl group, 1,4-diazepanyl group, 1,4-oxazepanyl group, quinolyl group, isoquinolyl group, quinazolinyl group, quinoxalinyl group, phthalazinyl group, cinnolinyl group, naphthyridinyl group, 1,2,3,4-tetrahydroquinolyl group, 5,6,7,8-tetrahydroquinolyl group, 1,2,3,4-tetrahydroisoquinolyl group, 5,6,7,8-tetrahydroisoquinolyl group, indolyl group, benzimidazolyl group, indolinyl group, isoindolinyl group, octahydroindolyl group, octahydroisoindolyl group, benzofuranyl group, benzothienyl group, benzoxazolyl group, benzothiazolyl group, octahydrocyclopenta[c]pyrrolyl group,

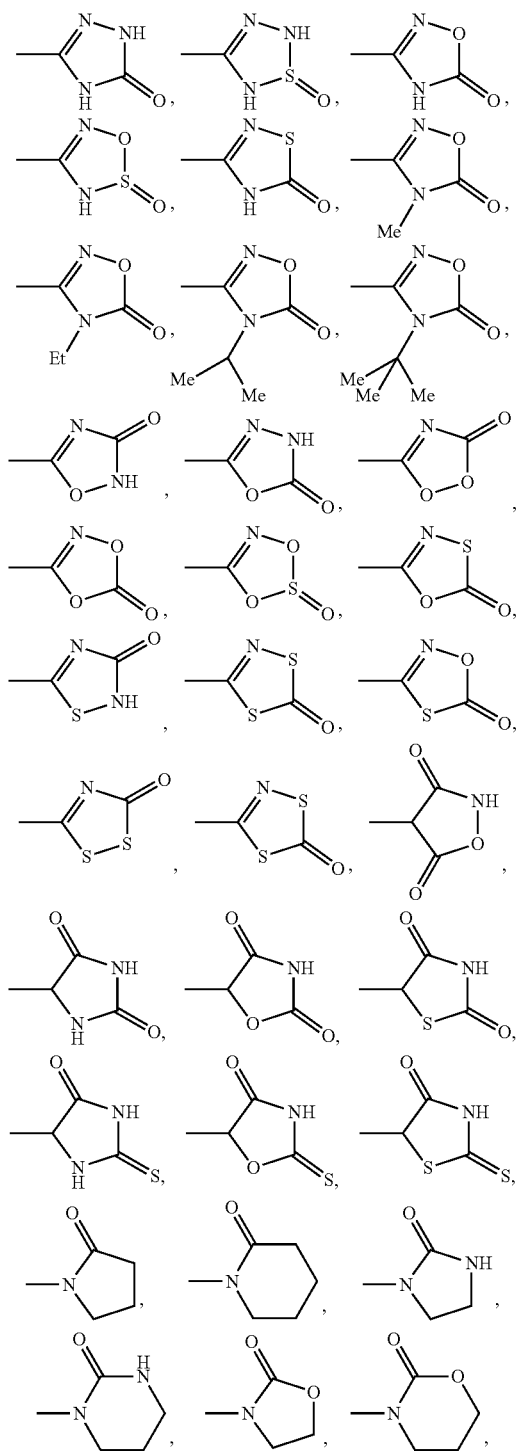

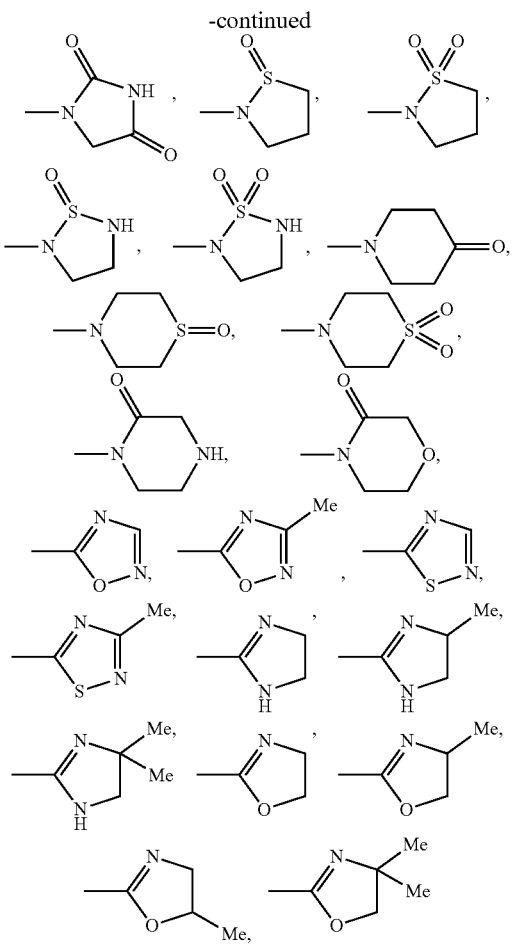

and the like can be mentioned.

For ring Cy, preferable "heterocyclic group optionally substituted by 1 to 5 substituents selected from group B" is

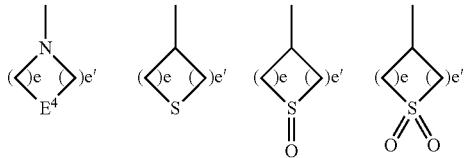

wherein $E^4$ is an oxygen atom, a sulfur atom, $CH_2$ or $N(-R^{Cy1})$, wherein $R^{Cy1}$ is a hydrogen atom or a $C_{1-6}$ alkyl group, and e and e' are each independently an integer of 1 to 3.

Specifically, pyrrolidinyl group, imidazolidinyl group, piperidyl group, piperazinyl group, morpholinyl group, thiomorpholinyl group, tetrahydropyranyl group, tetrahydrothiopyranyl group, 1-oxotetrahydrothiopyranyl group, 1,1-dioxotetrahydrothiopyranyl group and the like can be mentioned.

The "$C_{6-14}$ aryl $C_{1-6}$ alkyl group optionally substituted by 1 to 5 substituents selected from group B" is the above-defined "$C_{1-6}$ alkyl group" substituted by the above-defined "$C_{6-14}$ aryl group optionally substituted by 1 to 5 substituents selected from group B".

Specifically, benzyl group, 1-naphthylmethyl group, 2-naphthylmethyl group, phenethyl group, 3-phenylpropyl group, 2-phenylpropyl group, 3-fluorobenzyl group, 4-fluorobenzyl group, 3-chlorobenzyl group, 4-chlorobenzyl group, 2,4-dichlorobenzyl group, 3,5-dichlorobenzyl group, pentafluorobenzyl group, 4-methylbenzyl group, 4-tert-butylbenzyl group, 2-trifluoromethylbenzyl group, 4-trifluoromethylbenzyl group, 4-nitrobenzyl group, 4-cyanobenzyl group, 4-acetylbenzyl group, 4-carboxybenzyl group, 4-carbamoylbenzyl group, 4-aminobenzyl group, 4-dimethylaminobenzyl group, 4-acetylaminobenzyl group, 4-(methylsulfonylamino)benzyl group, 4-methoxybenzyl group, 3,4,5-trimethoxybenzyl group, 4-methylthiobenzyl group, 4-methylsulfonylbenzyl group, 4-aminosulfonylbenzyl group, 3-nitro-4-methoxybenzyl group, 4-nitro-3-methoxybenzyl group and the like can be mentioned.

The "heterocycle $C_{1-6}$ alkyl group optionally substituted by 1 to 5 substituents selected from group B" is the above-defined "$C_{1-6}$ alkyl group" substituted by the above-defined "heterocyclic group optionally substituted by 1 to 5 substituents selected from group B".

Specifically, 2-pyridylmethyl group, 3-pyridylmethyl group, 2-chloropyridin-4-ylmethyl group, 4-pyridylmethyl group, pyrrolylmethyl group, imidazolylmethyl group, 2-thienylmethyl group, 3-thienylmethyl group, 2-furylmethyl group, 2-oxazolylmethyl group, 5-isothiazolylmethyl group, 2-methyloxazol-4-ylmethyl group, 2-thiazolylmethyl group, 4-thiazolylmethyl group, 5-thiazolylmethyl group, 2-methylthiazol-4-ylmethyl group, 2-methylthiazol-5-ylmethyl group, 2,5-dimethylthiazol-4-ylmethyl group, 4-methylthiazol-2-ylmethyl group, 2,4-dimethylthiazol-5-ylmethyl group, 2-isothiazolylmethyl group, 2-pyrrolinylmethyl group, pyrrolidinylmethyl group, piperidylmethyl group, 4-piperidylmethyl group, 1-methylpiperidin-4-ylmethyl group, 4-hydroxypiperidinomethyl group, 3-hydroxypyrrolidinylmethyl group, 2-(4-hydroxypiperidino)ethyl group, 1-(tert-butoxycarbonyl)piperidin-4-ylmethyl group, 1-acetylpiperidin-4-ylmethyl group, 1-methylsulfonylpiperidin-4-ylmethyl group, piperazinylmethyl group, morpholinomethyl group, thiomorpholinylmethyl group, 1-tetrahydropyranylmethyl group, 2-quinolylmethyl group, 1-isoquinolylmethyl group and the like can be mentioned.

The "$C_{3-10}$ cycloalkyl $C_{1-6}$ alkyl group optionally substituted by 1 to 5 substituents selected from group B" is the above-defined "$C_{1-6}$ alkyl group" substituted by the above-defined "$C_{3-10}$ cycloalkyl group optionally substituted by 1 to 5 substituents selected from group B".

Specifically, cyclopropylmethyl group, cyclobutylmethyl group, cyclopentylmethyl group, cyclohexylmethyl group, 2-(cyclopentyl)ethyl group, 2-(cyclohexyl)ethyl group, cycloheptylmethyl group, 4-fluorocyclohexylmethyl group, 2-methylcyclopentylmethyl group, 3-methylcyclohexylmethyl group, 4-methylcyclohexylmethyl group, 4,4-dimethylcyclohexylmethyl group, 3,5-dimethylcyclohexylmethyl group, 4-tert-butylcyclohexylmethyl group, 4-hydroxycyclohexylmethyl group, 4-methoxycyclohexylmethyl group, 2,3,4,5,6-pentafluorocyclohexylmethyl group, 1-adamantylmethyl group and the like can be mentioned.

The "$C_{3-10}$ cycloalkylidene group optionally substituted by 1 to 5 substituents selected from group B" is such group wherein $C_{3-10}$ cycloalkylidene group is optionally substituted by 1 to 5 substituents selected from the above-defined "group B", which includes non-substituted cycloalkylidene group.

Specifically, cyclopropylidene group, cyclobutylidene group, cyclopentylidene group, cyclohexylidene group, cycloheptylidene group, 4-fluorocyclohexylidene group, 2-methylcyclopentylidene group, 3-methylcyclohexylidene group, 4-methylcyclohexylidene group, 4-ethylcyclohexylidene group, 4,4-dimethylcyclohexylidene group, 3,5-dimethylcyclohexylidene group, 4-tert-butylcyclohexylidene group, 4-hydroxycyclohexylidene group, 4-methoxycyclohexylidene group, 4-methoxycarbonylcyclohexylidene group, 2,3,4,5,6-pentafluorocyclohexylidene group and the like can be mentioned.

In addition, a group wherein the cyclopentylidene group or cyclohexylidene group is substituted by fluorine atom, chlorine atom, bromine atom, nitro group, methyl group, ethyl group, isopropyl group, tert-butyl group, carboxyl group, methoxycarbonyl group, acetyl group, trifluoromethyl group, hydroxymethyl group, methoxymethyl group, 2-carboxyethyl group, methoxy group, carbamoyl group, methylthio group, dimethylaminocarbonyl group, methylsulfonyl group or acetylamino group can be mentioned.

For group E for $R^2$, it is preferably a cyclohexylidene group.

The "heterocycle ylidene group optionally substituted by 1 to 5 substituents selected from group B" is such group wherein the heterocycle ylidene group is optionally substituted by 1 to 5 substituents selected from the above-defined "group B", which includes non-substituted heterocycle ylidene group.

The heterocycle ylidene group contains, as ring-constituting atom, 1 to 4 heteroatoms selected from oxygen atom, nitrogen atom and sulfur atom besides carbon atom, wherein the number of atom constituting the ring is 3 to 14, which includes saturated ring and unsaturated ring, monocycle and fused ring.

As the "heterocycle ylidene group optionally substituted by 1 to 5 substituents selected from group B", specifically, dihydrofuran-3-ylidene group, pyrrolidin-3-ylidene group, tetrahydropyran-4-ylidene group, piperidin-3-ylidene group, piperidin-4-ylidene group, 1-methylpiperidin-4-ylidene group, 1-ethylpiperidin-4-ylidene group, 1-isopropylpiperidin-4-ylidene group, 1-tert-butylpiperidin-4-ylidene group, 1-acetylpiperidin-4-ylidene group, 1-methanesulfonylpiperidin-4-ylidene group, 1-methoxycarbonylpiperidin-4-ylidene group, tetrahydrothiopyran-4-ylidene group, pyran-4-ylidene group, 1H-pyridin-4-ylidene group, 2,3-dihydro-1H-quinolin-4-ylidene group, 4-oxocyclohexylidene group and the like can be mentioned.

For group E for $R^2$, it is preferably 1-methylpiperidin-4-ylidene group, 1-ethylpiperidin-4-ylidene group, 1-acetylpiperidin-4-ylidene group, 1-methanesulfonylpiperidin-4-ylidene group, 1-methoxypiperidin-4-ylidene group or 1-methoxycarbonylpiperidin-4-ylidene group.

The "$C_{1-6}$ alkylidene group optionally substituted by 1 to 3 substituents selected from group A" is such group wherein a linear or branched chain having 1 to 6 carbon atoms, preferably having 1 to 4 carbon atoms, preferably a branched chain alkylidene group, is optionally substituted by 1 to 3 substituents selected from the above-defined "group A", which includes non-substituted alkylidene group.

Specifically, methylidene group, ethylidene group, propylidene group, isopropylidene group, butylidene group, pentylidene group, dimethylaminomethylidene group, methoxycarbonylmethylidene group, 2-methoxyethylidene group, diaminomethylidene group and the like can be mentioned.

For group E for $R^2$, it is preferably an isopropylidene group.

The "group C" means the substituent groups of the following (1) to (5).
(1) the above-defined "$C_{1-6}$ alkyl group optionally substituted by 1 to 3 substituents selected from group A",
(2) the above-defined "$C_{6-14}$ aryl group optionally substituted by 1 to 5 substituents selected from group B",
(3) the above-defined "$C_{6-4}$ aryl $C_{1-6}$ alkyl group optionally substituted by 1 to 5 substituents selected from group B",
(4) the above-defined "heterocyclic group optionally substituted by 1 to 5 substituents selected from group B" and
(5) the above-defined "heterocycle $C_{1-6}$ alkyl group optionally substituted by 1 to 5 substituents selected from group B".

The "group F" means the substituent groups of the following (1) to (7).
(1) the above-defined "$C_{1-6}$ alkyl group optionally substituted by 1 to 3 substituents selected from group A",
(2) the above-defined "$C_{6-14}$ aryl group optionally substituted by 1 to 5 substituents selected from group B",
(3) the above-defined "heterocyclic group optionally substituted by 1 to 5 substituents selected from group B",
(4) the above-defined "$C_{3-10}$ cycloalkyl group optionally substituted by 1 to 5 substituents selected from group B",
(5) the above-defined "$C_{6-14}$ aryl $C_{1-6}$ alkyl group optionally substituted by 1 to 5 substituents selected from group B",
(6) the above-defined "heterocycle $C_{1-6}$ alkyl group optionally substituted by 1 to 5 substituents selected from group B" and
(7) the above-defined "$C_{3-10}$ cycloalkyl $C_{1-6}$ alkyl group optionally substituted by 1 to 5 substituents selected from group B".

The "group D" means the substituent groups of the following (a) to (w).
(in the following, each t independently means 0 or an integer of 1 to 6)
(a) a hydrogen atom,
(b) the above-defined "halogen atom",
(c) a cyano group,
(d) a nitro group,
(e) the above-defined "$C_{1-6}$ alkyl group optionally substituted by 1 to 3 substituents selected from group A",
(f) —$(CH_2)_t$—$OR^{d1}$,
  wherein $R^{d1}$ is
  (1) a hydrogen atom,
  (2) the above-defined "group selected from group F",
  (3) the above-defined "$C_{2-6}$ alkenyl group optionally substituted by 1 to 3 substituents selected from group A" or
  (4) the above-defined "$C_{2-6}$ alkynyl group optionally substituted by 1 to 3 substituents selected from group A",
  (e.g., substituent exemplified for "—$(CH_2)_r$—$OR^{b1}$" in group B, trifluoromethyloxy group, methoxymethoxy group, phenoxy group, benzyloxy group, 4-pyridylmethoxy group, 4-carboxybenzyloxy group, vinyloxy group, ethynyloxy group etc.)
(g) —$(CH_2)_t$—$S(O)_q$—$R^{d2}$,
  wherein $R^{d2}$ is
  (1) a hydrogen atom or
  (2) the above-defined "group selected from group F",
  q is 0, 1, 2 or 3
  (e.g., substituent exemplified for "—$(CH_2)_r$—$SR^{b1}$" and "—$(CH_2)_r$—$SO_2R^{b3}$" in group B, methylsulfinyl group, sulfa group, trifluoromethanesulfonyl group, 2-(methylamino)ethylsulfonyl group, 2-(dimethylamino)ethylsulfonyl group, 3-(dimethylamino)propylsulfonyl group, phenylsulfonyl group, 4-tolylsulfonyl group, benzylsulfonyl group etc.)
(h) —$(CH_2)_t$—$NR^{d3}R^{d4}$,
  wherein $R^{d3}$ and $R^{d4}$ are each independently
  (1) a hydrogen atom or
  (2) the above-defined "group selected from group F",
  (e.g., substituent exemplified for "—$(CH_2)_r$—$NR^{b1}R^{b2}$" in group B, phenylamino group, benzyloxyamino group, methoxymethylamino group, N-ethyl-N-(carbamoylmethyl)amino group, N-ethyl-N-[2-(acetylamino)ethyl]amino group, N-[2-amino-2-(dimethylcarbamoyl)ethyl]-N-ethylamino group, N,N-bis(aminomethyl)amino group etc.)
(i) —$(CH_2)_r$—$COOR^{d5}$,
wherein $R^{d5}$ is
(1) a hydrogen atom or
(2) the above-defined "group selected from group F",
(e.g., substituent exemplified for "—$(CH_2)_r$—$COOR^{b1}$" in group B, trifluoromethyloxycarbonyl group, phenoxycarbonyl group, benzyloxycarbonyl group, 2-morpholinoethoxycarbonyl group, 2-(dimethylamino)ethoxycarbonyl group etc.)
(j) —$(CH_2)_r$—$CONR^{d6}R^{d7}$,
wherein $R^{d6}$ and $R^{d7}$ are each independently
(1) a hydrogen atom,
(2) a hydroxyl group,
(3) the above-defined "group selected from group F" or
(4) the above-defined "$C_{1-6}$ alkoxy group",
(e.g., substituent exemplified for "—$(CH_2)_r$—$CONR^{b1}R^{b2}$" in group B, hydroxycarbamoyl group, methoxycarbamoyl group, phenylcarbamoyl group, benzylcarbamoyl group, 2-morpholinoethylcarbamoyl group, 2-(dimethylamino)ethylcarbamoyl group, methoxymethylcarbamoyl group etc.)
(k) —$(CH_2)_r$—$COR^{d8}$
wherein $R^{d8}$ is the above-defined "group selected from group F",
(e.g., substituent exemplified for "—$(CH_2)_r$—$COR^{b1}$" in group B, trifluoroacetyl group, methoxyacetyl group, carboxyacetyl group, benzoyl group, phenylacetyl group, 3-(dimethylamino)propionyl group, 3-morpholinopropionyl group etc.)
(l) —$(CH_2)_r$—$NR^{d9}CO$—$R^{d10}$,
wherein $R^{d9}$ is
(1) a hydrogen atom,
(2) the above-defined "$C_{1-6}$ alkyl group optionally substituted by 1 to 3 substituents selected from group A" or
(3) the above-defined "$C_{1-6}$ alkanoyl group",
$R^{d10}$ is
(1) an amino group,
(2) the above-defined "$C_{1-6}$ alkylamino group" or
(3) the above-defined "group selected from group F",
(e.g., substituent exemplified for "—$(CH_2)_r$—$NR^{b1}$—$COR^{b2}$" in group B, ureido group, 3-methylureido group, 3-ethylureido group, 3-isopropylureido group, 3,3-dimethylureido group, 3,3-diethylureido group, 3,3-diisopropylureido group, 3,3-di-tert-butylureido group, 3-ethyl-3-methylureido group, 1,3-dimethylureido group, trimethylureido group, ureidomethyl group, 2-(3,3-dimethylureido)ethyl group, benzoylamino group, phenylacetylamino group, trifluoroacetylamino group, methylaminoacetylamino group, N-acetyl-N-methylamino group, N-isopropyl-N-pivaloylamino group, dimethylaminoacetylamino group, N-(dimethylaminoacetyl)-N-methylamino group, morpholinoacetylamino group, N-methyl-N-(morpholinoacetyl)amino group etc.)
(m) —$(CH_2)_r$—$NR^{d11}SO_2$—$R^{d12}$,
wherein $R^{d11}$ is
(1) a hydrogen atom,
(2) the above-defined "$C_{1-6}$ alkyl group optionally substituted by 1 to 3 substituents selected from group A" or
(3) the above-defined "$C_{1-6}$ alkanoyl group",
$R^{d12}$ is
(1) a hydrogen atom or
(2) the above-defined "group selected from group F",
(e.g., substituent exemplified for "—$(CH_2)_r$—$NR^{b1}$—$SO_2R^{b3}$" in group B, trifluoromethylsulfonylamino group, phenylsulfonylamino group, benzylsulfonylamino group, 2-(dimethylamino)ethylsulfonylamino group, 2-morpholinoethylsulfonylamino group, N-acetyl-N-methanesulfonylamino group, N-benzyl-N-methanesulfonylamino group etc.)
(n) —$(CH_2)_r$—$SO_2$—$NR^{d13}R^{d14}$,
wherein $R^{d13}$ and $R^{d14}$ are each independently
(1) a hydrogen atom or
(2) the above-defined "group selected from group F",
(e.g., substituent exemplified for "—$(CH_2)_r$—$SO_2NR^{b1}R^{b2}$" in group B, trifluoromethylsulfamoyl group, 2-(dimethylamino)ethylsulfamoyl group, phenylsulfamoyl group, benzylsulfamoyl group, 2-morpholinoethylsulfamoyl group etc.)
(o) —$(CH_2)_r$—$CONR^{d15}$—$SO_2R^{d16}$,
wherein $R^{d15}$ and $R^{d16}$ are each independently
(1) a hydrogen atom or
(2) the above-defined "group selected from group F", (e.g., substituent exemplified for "—$(CH_2)_r$—$CONR^{b1}$—$SO_2R^{b3}$" in group B, trifluoromethylsulfonylcarbamoyl group, 2-(dimethylamino)ethylsulfonylcarbamoyl group, phenylsulfonylcarbamoyl group, benzylsulfonylcarbamoyl group, 2-morpholinoethylsulfonylcarbamoyl group, N-benzyl-N-(methanesulfonyl)carbamoyl group etc.)
(p) —$(CH_2)_r$—$SO_2NR^{d17}$—$COR^{d18}$,
wherein $R^{d17}$ is
(1) a hydrogen atom or
(2) the above-defined "group selected from group F",
$R^{d18}$ is the above-defined "group selected from group F",
(e.g., substituent exemplified for "—$(CH_2)_r$—$SO_2NR^{b1}$—$COR^{b2}$" in group B, trifluoroacetylsulfamoyl group, 2-(dimethylamino)ethylcarbonylsulfamoyl group, benzoylsulfamoyl group, phenylacetylsulfamoyl group, 3-morpholinopropionylsulfamoyl group, N-acetyl-N-benzylsulfamoyl group etc.)
(q) —$(CH_2)_r$—$NR^{d19}$—$COOR^{d20}$,
wherein $R^{d19}$ and $R^{d20}$ are each independently
(1) a hydrogen atom or
(2) the above-defined "group selected from group F",
(e.g., substituent exemplified for "—$(CH_2)_r$—$NR^{b1}$—$COOR^{b3}$" in group B, trifluoromethyloxycarbonylamino group, 2-(dimethylamino)ethoxycarbonylamino group, phenoxycarbonylamino group, benzyloxycarbonylamino group, 2-morpholinoethoxycarbonylamino group, N-ethoxycarbonyl-N-benzylamino group etc.)
(r) —$(CH_2)_r$—$NR^{d21}$—$CONR^{d22}R^{d23}$,
wherein $R^{d21}$, $R^{d22}$ and $R^{d23}$ are each independently
(1) a hydrogen atom or
(2) the above-defined "group selected from group F",
(e.g., substituent exemplified for "—$(CH_2)_r$—$NR^{b1}$—$CONR^{b2}R^{b4}$" in group B etc.)
(s) —$(CH_2)_r$—$C(=NR^{d24})NH_2$,
wherein $R^{d24}$ is
(1) a hydrogen atom,
(2) a hydroxyl group,
(3) the above-defined "$C_{1-6}$ alkyl group optionally substituted by 1 to 3 substituents selected from group A" or
(4) the above-defined "$C_{1-6}$ alkoxy group",
(e.g., carbamimidoyl group, N-hydroxycarbamimidoyl group, N-methylcarbamimidoyl group, N-methoxycarbamimidoyl group, N-(2-methoxyethyl)carbamimidoyl group etc.)
(t) —$(CH_2)_t$—O—$(CH_2)_p$—$COR^{d25}$, wherein $R^{d25}$ is
(1) an amino group,
(2) the above-defined "$C_{1-6}$ alkylamino group" or
(3) the above-defined "heterocyclic group optionally substituted by 1 to 5 substituents selected from group B",
p is 0 or an integer of 1 to 6
(e.g., carbamoylmethoxy group, methylcarbamoylmethoxy group, 2-(dimethylcarbamoyl)ethoxy group, 2-(pyridin-2-yl)-2-oxoethoxy group, 2-piperidin-1-yl-2-oxoethoxy group, 2-piperazin-1-yl-2-oxoethoxy group, 2-pyrrolidin-1-yl-2-oxoethoxy group, 2-morpholin-4-yl-2-oxoethoxy group etc.)
(u) —$(CH_2)_t$—O—$(CH_2)_p$—$NR^{d26}R^{d27}$,
wherein $R^{d26}$ and $R^{d27}$ are each independently
(1) a hydrogen atom or
(2) the above-defined "$C_{1-6}$ alkyl group optionally substituted by 1 to 3 substituents selected from the aforementioned group A",
p is 0 or an integer of 1 to 6,
(e.g., 2-(2-hydroxyethylamino)ethoxy group, 2-(2-aminoethylamino)ethoxy group etc.)
(v) —$(CH_2)_t$—O—$COOR^{d28}$,
wherein $R^{d28}$ is
(1) a hydrogen atom or
(2) the above-defined "group selected from group F",
(e.g., methoxycarbonyloxy group, ethoxycarbonyloxy group, tert-butoxycarbonyloxy group, benzyloxycarbonyloxy group etc.) and
(w) the above-defined "heterocyclic group optionally substituted by 1 to 5 substituents selected from group B".

The "group E" means the substituent groups of the following (a) to (jj).
(a) the above-defined "halogen atom",
(b) a cyano group,
(c) a nitro group,
(d) an azido group,
(e) —OP(=O)(OH)$_2$,
(f) —$OR^{e1}$,
wherein $R^{e1}$ is
(1) a hydrogen atom,
(2) the above-defined "group selected from group F",
(3) the above-defined "$C_{2-6}$ alkenyl group optionally substituted by 1 to 3 substituents selected from group A" or
(4) the above-defined "$C_{2-6}$ alkynyl group optionally substituted by 1 to 3 substituents selected from group A",
(e.g., hydroxyl group, methoxy group, ethoxy group, isopropyloxy group, tert-butyloxy group, trifluoromethyloxy group, methoxymethoxy group, phenoxy group, benzyloxy group, 4-pyridylmethoxy group, 4-carboxybenzyloxy group, vinyloxy group, ethynyloxy group etc.)
(g) —$S(O)_q$—$R^{e2}$,
wherein $R^{e2}$ is
(1) a hydrogen atom or
(2) the above-defined "group selected from group F",
q is 0, 1, 2 or 3
(e.g., mercapto group, methylsulfanyl group, methanesulfonyl group, ethylsulfonyl group, isopropylsulfonyl group, tert-butylsulfonyl group, methylsulfinyl group, sulfo group, trifluoromethanesulfonyl group, 2-(methylamino)ethylsulfonyl group, 2-(dimethylamino)ethylsulfonyl group, 3-(dimethylamino)propylsulfonyl group, phenylsulfonyl group, 4-tolylsulfonyl group, benzylsulfonyl group etc.)
(h) —$NR^{e3}R^{e4}$,
wherein $R^{e3}$ and $R^{e4}$ are each independently
(1) a hydrogen atom,
(2) a cyano group or
(3) the above-defined "group selected from group F",
(e.g., amino group, methylamino group, ethylamino group, isopropylamino group, dimethylamino group, diethylamino group, diisopropylamino group, di-tert-butylamino group, N-ethyl-N-methylamino group, phenylamino group, benzyloxyamino group, methoxymethylamino group, N-ethyl-N-(carbamoylmethyl)amino group, N-ethyl-N-[2-(acetylamino)ethyl]amino group, N-[2-amino-2-(dimethylcarbamoyl)ethyl]-N-ethylamino group, N,N-bis(aminomethyl)amino group etc.)
(i) —$COOR^{e5}$
wherein $R^{e5}$ is
(1) a hydrogen atom or
(2) the above-defined "group selected from group F",
(e.g., carboxyl group, methoxycarbonyl group, ethoxycarbonyl group, isopropyloxycarbonyl group, tert-butoxycarbonyl group, trifluoromethyloxycarbonyl group, phenoxycarbonyl group, benzyloxycarbonyl group, 2-morpholinoethoxycarbonyl group, 2-(dimethylamino)ethoxycarbonyl group etc.)
(j) —$CONR^{e6}R^{e7}$,
wherein $R^{e6}$ and $R^{e7}$ are each independently
(1) a hydrogen atom,
(2) a hydroxyl group,
(3) the above-defined "group selected from group F" or
(4) the above-defined "$C_{1-6}$ alkoxy group",
(e.g., carbamoyl group, methylcarbamoyl group, ethylcarbamoyl group, isopropylcarbamayl group, dimethylcarbamoyl group, diethylcarbamoyl group, diisopropylcarbamoyl group, di-tert-butylcarbamoyl group, N-ethyl-N-methylcarbamayl group, hydroxycarbamoyl group, methoxycarbamoyl group, phenylcarbamoyl group, benzylcarbamoyl group, 2-morpholinoethylcarbamoyl group, 2-(dimethylamino)ethylcarbamoyl group, methoxymethylcarbamoyl group etc.)
(k) —$COR^{e8}$
wherein $R^{e8}$ is the above-defined "group selected from group F",
(e.g., formyl group, acetyl group, propionyl group, isobutyryl group, pivaloyl group, trifluoroacetyl group, methoxyacetyl group, carboxyacetyl group, benzoyl group, phenylacetyl group, 3-(dimethylamino)propionyl group, 3-morpholinopropionyl group etc.)
(l) —$NR^{e9}CO$—$R^{e10}$,
wherein $R^{e9}$ is
(1) a hydrogen atom,
(2) the above-defined "$C_{1-6}$ alkyl group" or
(3) the above-defined "$C_{1-6}$ alkanoyl group",
$R^{e10}$ is
(1) a hydrogen atom,
(2) an amino group,
(3) the above-defined "$C_{1-6}$ alkylamino group",
(4) the above-defined "$C_{2-6}$ alkenyl group optionally substituted by 1 to 3 substituents selected from group A" or
(5) the above-defined "group selected from group F",
(e.g., formylamino group, acetylamino group, propionylamino group, isobutyrylamino group, pivaloylamino group, N-acetyl-N-methylamino group, ureido group, 3-methylureido group, 3-ethylureido group, 3-isopropylureido group, 3,3-dimethylureido group, 3,3-diethylureido group, 3,3-diisopropylureido group, 3,3-di-tert-butylureido group, 3-ethyl-3-methylureido group, 1,3-dimethylureido group, trimethylureido group, benzoylamino group, phenylacetylamino group, trifluoroacetylamino group, methylaminoacetylamino group, N-acetyl-N-methylamino group, N-isopropyl-N-pivaloylamino group, 3-carboxy-3-butenoylamino group etc.)
(m) —$NR^{e11}SO_2$—$R^{e12}$,
wherein $R^{e11}$ is
(1) a hydrogen atom,
(2) the above-defined "$C_{1-6}$ alkyl group" or
(3) the above-defined "$C_{1-6}$ alkanoyl group", $R^{e12}$ is
(1) a hydrogen atom or
(2) the above-defined "group selected from group F",
(e.g., methanesulfonylamino group, ethylsulfonylamino group, isopropylsulfonylamino group, tert-butylsulfonylamino group, N-methyl-N-(methanesulfonyl)amino group, trifluoromethylsulfonylamino group, phenylsulfonylamino group, benzylsulfonylamino group, 2-(dimethylamino)ethylsulfonylamino group, 2-morpholinoethylsulfonylamino group, N-acetyl-N-methanesulfonylamino group, N-benzyl-N-methanesulfonylamino group etc.)

(n) —$SO_2$—$NR^{e13}R^{e14}$,
wherein $R^{e13}$ and $R^{e14}$ are each independently
(1) a hydrogen atom or
(2) the above-defined "group selected from group F",
(e.g., sulfamoyl group, methylsulfamoyl group, ethylsulfamoyl group, isopropylsulfamoyl group, dimethylsulfamoyl group, diethylsulfamoyl group, diisopropylsulfamoyl group, di-tert-butylsulfamoyl group, trifluoromethylsulfamoyl group, 2-(dimethylamino)ethylsulfamoyl group, phenylsulfamoyl group, benzylsulfamoyl group, 2-morpholinoethylsulfamoyl group etc.)

(o) —$CONR^{e15}$—$SO_2R^{e16}$,
wherein $R^{e15}$ and $R^{e16}$ are each independently
(1) a hydrogen atom or
(2) the above-defined "group selected from group F",
(e.g., methanesulfonylcarbamoyl group, ethylsulfonylcarbamoyl group, isopropylsulfonylcarbamoyl group, tert-butylsulfonylcarbamoyl group, N-methyl-N-(methanesulfonyl)carbamoyl group, trifluoromethylsulfonylcarbamoyl group, 2-(dimethylamino)ethylsulfonylcarbamoyl group, phenylsulfonylcarbamoyl group, benzylsulfonylcarbamoyl group, 2-morpholinoethylsulfonylcarbamoyl group, N-benzyl-N-(methanesulfonyl)carbamoyl group etc.)

(p) —$SO_2NR^{e17}$—$COR^{e18}$,
wherein $R^{e17}$ is
(1) a hydrogen atom or
(2) the above-defined "group selected from group F",
$R^{e18}$ is the above-defined "group selected from group F",
(e.g., acetylsulfamoyl group, propionylsulfamoyl group, isobutyrylsulfamoyl group, pivaloylsulfamoyl group, N-acetyl-N-methylsulfamoyl group, trifluoroacetylsulfamoyl group, 2-(dimethylamino)ethylsulfamoyl group, benzoylsulfamoyl group, phenylacetylsulfamoyl group, 3-morpholinopropionylsulfamoyl group, N-acetyl-N-benzylsulfamoyl group etc.)

(q) —$NR^{e19}$—$COOR^{e20}$,
wherein $R^{e19}$ and $R^{e20}$ are each independently
(1) a hydrogen atom or
(2) the above-defined "group selected from group F",
(e.g., methoxycarbonylamino group, ethoxycarbonylamino group, isopropyloxycarbonylamino group, tert-butoxycarbonylamino group, trifluoromethyloxycarbonylamino group, 2-(dimethylamino)ethyloxycarbonylamino group, phenoxycarbonylamino group, benzyloxycarbonylamino group, 2-morpholinoethoxycarbonylamino group, N-ethoxycarbonyl-N-benzylamino group etc.)

(r) —$NR^{e21}$—$CONR^{e22}R^{e23}$
wherein $R^{e21}$, $R^{e22}$ and $R^{e23}$ are each independently
(1) a hydrogen atom or
(2) the above-defined "group selected from group F",
(e.g., ureido group, 3-methylureido group, 3-ethylureido group, 3-isopropylureido group, 3,3-dimethylureido group, 3,3-diethylureido group, 3,3-diisopropylureido group, 3,3-di-tert-butylureido group, 3-ethyl-3-methylureido group, 1,3-dimethylureido group, trimethylureido group etc.)

(s) —NHCO—$COOR^{e24}$
wherein $R^{e24}$ is
(1) a hydrogen atom or
(2) the above-defined "group selected from group F",
(e.g., —NHCO—COOH etc.)
(t) —NHCO—$CONR^{e25}R^{e26}$
wherein $R^{e25}$ and $R^{e26}$ are each independently
(1) a hydrogen atom,
(2) a hydroxyl group or
(3) the above-defined "group selected from group F",
(e.g., —NHCO—$CONH_2$, —NHCO—$CONHCH_3$, —NHCO—CONHOH etc.)
(u) —CONH—COOH,

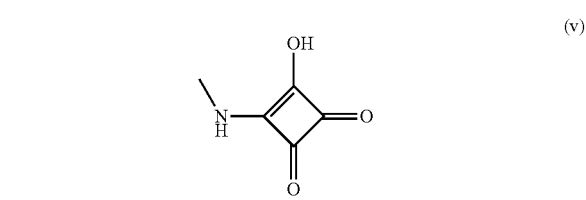

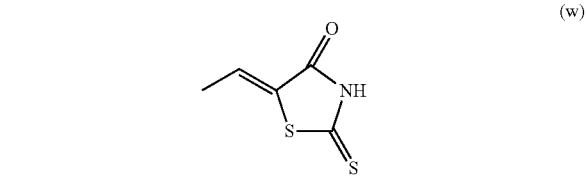

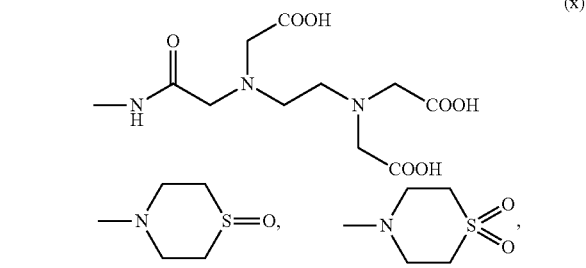

(y) the above-defined "$C_{6-14}$ aryl group optionally substituted by 1 to 5 substituents selected from group B",
(z) the above-defined "$C_{3-10}$ cycloalkyl group optionally substituted by 1 to 5 substituents selected from group B",
(aa) the above-defined "heterocyclic group optionally substituted by 1 to 5 substituents selected from group B",
(bb) the above-defined "$C_{3-10}$ cycloalkylidene group optionally substituted by 1 to 5 substituents selected from group B", and
(cc) the above-defined "heterocycle ylidene group optionally substituted by 1 to 5 substituents selected from group B", when group E is a substituent on a $C_{6-14}$ aryl group, a $C_{3-10}$ cycloalkyl group or a heterocyclic group, it may be
(dd) the above-defined "$C_{1-6}$ alkyl group optionally substituted by 1 to 3 substituents selected from group A",
(ee) the above-defined "$C_{2-6}$ alkenyl group optionally substituted by 1 to 3 substituents selected from group A",
(ff) the above-defined "$C_{2-6}$ alkynyl group optionally substituted by 1 to 3 substituents selected from group A",
(gg) the above-defined "$C_{1-6}$ alkylidene group optionally substituted by 1 to 3 substituents selected from group A",
(hh) the above-defined "$C_{6-14}$ aryl $C_{1-6}$ alkyl group optionally substituted by 1 to 5 substituents selected from group B",
(ii) the above-defined "$C_{3-10}$ cycloalkyl $C_{1-6}$ alkyl group optionally substituted by 1 to 5 substituents selected from group B", or (jj) the above-defined "heterocycle $C_{1-6}$ alkyl group optionally substituted by 1 to 5 substituents selected from group B".

The "$C_{6-14}$ aryl group optionally substituted by 1 to 5 substituents selected from group D" is the above-defined "$C_{6-14}$ aryl group" optionally substituted by 1 to 5 substituents selected from the above-defined "group D", which includes non-substituted aryl group.

Specifically, phenyl group, naphthyl group, anthryl group, indenyl group, azulenyl group, fluorenyl group, phenanthryl group, 3-fluorophenyl group, 4-fluorophenyl group, 3-chlorophenyl group, 4-chlorophenyl group, 2,4-dichlorophenyl group, 3,5-dichlorophenyl group, 4-bromophenyl group, 4-nitrophenyl group, pentafluorophenyl group, 4-methylphenyl group, 4-tert-butylphenyl group, 2-trifluoromethylphenyl group, 4-trifluoromethylphenyl group, 4-(hydroxymethyl) phenyl group, 4-(methoxymethyl)phenyl group, 4-(2-carboxyethyl)phenyl group, 3-carboxyphenyl group, 4-carboxyphenyl group, 4-methoxyphenyl group, 3,4,5-trimethoxyphenyl group, 4-carbamoylphenyl group, 4-methylthiophenyl group, 4-(dimethylaminocarbonyl)phenyl group, 4-methylsulfonylphenyl group, 4-acetylaminophenyl group, 4-cyanophenyl group, 4-acetylphenyl group, 4-aminophenyl group, 4-dimethylaminophenyl group, 4-(methylsulfonylamino)phenyl group, 4-methylsulfinylphenyl group, 4-aminosulfonylphenyl group, 3-nitro-4-methoxyphenyl group, 4-nitro-3-methoxyphenyl group, 4-(tetrazol-5-yl)phenyl group and the like can be mentioned.

The "$C_{3-10}$ cycloalkyl group optionally substituted by 1 to substituents selected from group D" is the above-defined "$C_{3-10}$ cycloalkyl group" optionally substituted by 1 to 5 substituents selected from the above-defined "group D", which includes non-substituted cycloalkyl group.

Specifically, cyclopropyl group, cyclobutyl group, cyclopentyl group, cyclohexyl group, cycloheptyl group, 4-fluorocyclohexyl group, 2-methylcyclopentyl group, 3-methylcyclohexyl group, 4-methylcyclohexyl group, 4,4-dimethylcyclohexyl group, 3,5-dimethylcyclohexyl group, 4-tert-butylcyclohexyl group, 4-hydroxycyclohexyl group, 4-methoxycyclohexyl group, 2,3,4,5,6-pentafluorocyclohexyl group, 1-adamantylmethyl group and the like can be mentioned.

In addition, such group wherein cyclopentyl group or cyclohexyl group is substituted by fluorine atom, chlorine atom, bromine atom, nitro group, methyl group, tert-butyl group, carboxyl group, trifluoromethyl group, hydroxymethyl group, methoxymethyl group, 2-carboxyethyl group, methoxy group, carbamoyl group, methylthio group, dimethylaminocarbonyl group, methylsulfonyl group or acetylamino group can be mentioned.

The "heterocyclic group optionally substituted by 1 to 5 substituents selected from group D" is the above-defined "heterocyclic group" optionally substituted by 1 to 5 substituents selected from the above-defined "group D", which includes non-substituted heterocyclic group.

Specifically, 2-pyridyl group, 3-pyridyl group, 4-pyridyl group, 3-fluoropyridin-4-yl group, 3-chloropyridin-4-yl group, 4-chloropyridin-3-yl group, pyrazinyl group, pyrimidinyl group, pyridazinyl group, 1,3,5-triazinyl group, pyrrolyl group, pyrazolyl group, imidazolyl group, 1,2,4-triazolyl group, tetrazolyl group, 2-thienyl group, 3-thienyl group, furyl group, oxazolyl group, 2-methyloxazol-4-yl group, isoxazolyl group, thiazolyl group, 2-methylthiazol-4-yl group, 2,5-dimethylthiazol-4-yl group, 2,4-dimethylthiazol-5-yl group, isothiazolyl group, thiadiazolyl group, pyrrolinyl group, pyrrolidinyl group, imidazolidinyl group, piperidyl group, N-methylpiperidin-4-yl group, N-(tert-butoxycarbonyl)piperidin-4-yl group, N-acetylpiperidin-4-yl group, N-methylsulfonylpiperidin-4-yl group, piperazinyl group, 4-ethylpiperazin-1-yl group, 4-methanesulfonylpiperazin-1-yl group, 4-dimethylcarbamoylmethylpiperazin-1-yl group, morpholinyl group, thiomorpholinyl group, tetrahydropyranyl group, quinolyl group, isoquinolyl group, quinazolinyl group, quinoxalinyl group, phthalazinyl group, cinnolinyl group, naphthyridinyl group, 5,6,7,8-tetrahydroquinolyl group, indolyl group, benzimidazolyl group, indolinyl group, benzofuranyl group, benzothienyl group, benzoxazolyl group, benzothiazolyl group,

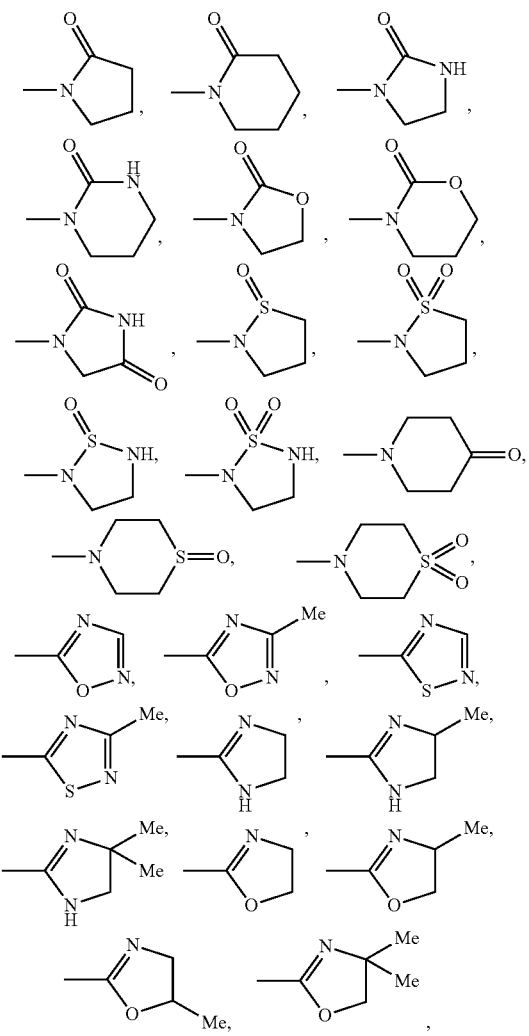

and the like can be mentioned.

In addition, such group wherein the 3, 4, 5 or 6-position of 2-pyridyl group, 2, 4, 5 or 6-position of 3-pyridyl group, 2, 3, 5 or 6-position of 4-pyridyl group, 3, 4 or 5-position of 2-thienyl group, and 2, 4 or 5-position of 3-thienyl group are substituted by fluorine atom, chlorine atom, bromine atom, nitro group, methyl group, tert-butyl group, carboxyl group, trifluoromethyl group, hydroxymethyl group, methoxymethyl group, 2-carboxyethyl group, methoxy group, carbamoyl group, methylthio group, dimethylaminocarbonyl group, methylsulfonyl group, amino group or acetylamino group can be mentioned.

The "$C_{6-14}$ aryl $C_{1-6}$ alkyl group optionally substituted by 1 to 5 substituents selected from group D" is the above-defined "C$_{1-6}$ alkyl group" substituted by the above-defined "C$_{6-14}$ aryl group optionally substituted by 1 to 5 substituents selected from group D".

Specifically, benzyl group, 1-naphthylmethyl group, 2-naphthylmethyl group, phenethyl group, 3-phenylpropyl group, 2-phenylpropyl group, 3-fluorobenzyl group, 4-fluorobenzyl group, 3-chlorobenzyl group, 4-chlorobenzyl group, 2,4-dichlorobenzyl group, 3,5-dichlorobenzyl group, 4-bromobenzyl group, 4-nitrobenzyl group, pentafluorobenzyl group, 4-methylbenzyl group, 4-tert-butylbenzyl group, 2-trifluoromethylbenzyl group, 4-trifluoromethylbenzyl group, 4-(hydroxymethyl)benzyl group, 4-(methoxymethyl)benzyl group, 4-(2-carboxyethyl)benzyl group, 3-carboxybenzyl group, 4-carboxybenzyl group, 4-methoxybenzyl group, 3,4,5-trimethoxybenzyl group, 4-carbamoylbenzyl group, 4-methylthiobenzyl group, 4-(dimethylaminocarbonyl)benzyl group, 4-methylsulfonylbenzyl group, 4-(acetylamino)benzyl group, 4-cyanobenzyl group, 4-acetylbenzyl group, 4-aminobenzyl group, 4-dimethylaminobenzyl group, 4-(methylsulfonylamino)benzyl group, 4-methylsulfinylbenzyl group, 4-aminosulfonylbenzyl group, (3-nitro-4-methoxyphenyl)methyl group, (4-nitro-3-methoxyphenyl)methyl group and the like can be mentioned.

The "heterocycle C$_{1-6}$ alkyl group optionally substituted by 1 to 5 substituents selected from group D" is the above-defined "C$_{1-6}$ alkyl group" substituted by the above-defined "heterocyclic group optionally substituted by 1 to 5 substituents selected from group D".

Specifically, 2-pyridylmethyl group, 3-pyridylmethyl group, 2-chloropyridin-4-ylmethyl group, 4-pyridylmethyl group, pyrrolylmethyl group, imidazolylmethyl group, 2-thienylmethyl group, 3-thienylmethyl group, 2-furylmethyl group, 2-oxazolylmethyl group, 5-isothiazolylmethyl group, 2-methyloxazol-4-ylmethyl group, 2-thiazolylmethyl group, 4-thiazolylmethyl group, 5-thiazolylmethyl group, 2-methylthiazol-4-ylmethyl group, 2-methylthiazol-5-ylmethyl group, 2,5-dimethylthiazol-4-ylmethyl group, 4-methylthiazol-2-ylmethyl group, 2,4-dimethylthiazol-5-ylmethyl group, 2-isothiazolylmethyl group, 2-pyrrolinylmethyl group, pyrrolidinylmethyl group, piperidylmethyl group, 4-piperidylmethyl group, 1-methylpiperidin-4-ylmethyl group, 4-hydroxypiperidinomethyl group, 2-(4-hydroxypiperidino)ethyl group, 1-(tert-butoxycarbonyl)piperidin-4-ylmethyl group, 1-acetylpiperidin-4-ylmethyl group, 1-methylsulfonylpiperidin-4-ylmethyl group, piperazinylmethyl group, morpholinomethyl group, thiomorpholinylmethyl group, 1-tetrahydropyranylmethyl group, 2-quinolylmethyl group, 1-isoquinolylmethyl group and the like can be mentioned.

The "C$_{1-6}$ alkyl group optionally substituted by 1 to 3 substituents selected from group E" is the above-defined "C$_{1-6}$ alkyl group" optionally substituted by 1 to 3 substituents selected from the above-defined "group E", which includes non-substituted alkyl group.

Specifically, methyl group, ethyl group, propyl group, isopropyl group, butyl group, isobutyl group, sec-butyl group, tert-butyl group, pentyl group, isopentyl group, tert-pentyl group, neopentyl group, 1-ethylpropyl group, hexyl group, trifluoromethyl group, hydroxymethyl group, 2-hydroxyethyl group, 3-hydroxypropyl group, 4-hydroxybutyl group, 1-hydroxy-1-methylethyl group, 1-hydroxypropan-2-yl group, 1,3-dihydroxypropan-2-yl group, 1-hydroxy-2-methylpropan-2-yl group, 1,1-dimethyl-2-hydroxyethyl group, carboxymethyl group, ethoxycarbonylmethyl group, 2-carboxyethyl group, methoxymethyl group, methoxyethyl group, methoxyethoxyethyl group, ethoxycarbonylethyl group, 2-ethoxycarbonylethyl group, 2-dimethylaminoethyl group, carbamoylmethyl group, methylcarbamoylmethyl group, sulfomethyl group, sulfamoylmethyl group, 2-sulfamoylethyl group, methylsulfamoylmethyl group and the like can be mentioned.

The "C$_{2-6}$ alkenyl group optionally substituted by 1 to 3 substituents selected from group E" is the above-defined "C$_{2-6}$ alkenyl group" optionally substituted by 1 to 3 substituents selected from the above-defined "group E", which includes non-substituted alkenyl group.

Specifically, vinyl group, allyl group, 1-propenyl group, isopropenyl group, 1-butenyl group, 2-butenyl group, 1,3-butadienyl group, 2-isopentenyl group, 3-isohexenyl group, 4-methyl-3-pentenyl group and the like can be mentioned.

The "C$_{6-14}$ aryl group optionally substituted by 1 to 5 substituents selected from group E" is the above-defined "C$_{6-14}$ aryl group" optionally substituted by 1 to 5 substituents selected from the above-defined "group E", which includes non-substituted aryl group.

Specifically, phenyl group, naphthyl group, anthryl group, indenyl group, azulenyl group, fluorenyl group, phenanthryl group, 3-fluorophenyl group, 4-fluorophenyl group, 3-chlorophenyl group, 4-chlorophenyl group, 2,4-dichlorophenyl group, 3,5-dichlorophenyl group, 4-bromophenyl group, 4-nitrophenyl group, pentafluorophenyl group, 4-methylphenyl group, 4-tert-butylphenyl group, 2-trifluoromethylphenyl group, 4-trifluoromethylphenyl group, 4-(hydroxymethyl)phenyl group, 4-(methoxymethyl)phenyl group, 4-(2-carboxyethyl)phenyl group, 3-carboxyphenyl group, 4-carboxyphenyl group, 4-methoxyphenyl group, 3,4,5-trimethoxyphenyl group, 4-carbamoylphenyl group, 4-methylthiophenyl group, 4-(dimethylaminocarbonyl)phenyl group, 4-methylsulfonylphenyl group, 4-acetylaminophenyl group, 4-cyanophenyl group, 4-acetylphenyl group, 4-aminophenyl group, 4-dimethylaminophenyl group, 4-(methylsulfonylamino)phenyl group, 4-methylsulfinylphenyl group, 4-aminosulfonylphenyl group, 3-nitro-4-methoxyphenyl group, 4-nitro-3-methoxyphenyl group, 4-(tetrazol-5-yl)phenyl group and the like can be mentioned.

The "C$_{3-10}$ cycloalkyl group optionally substituted by 1 to 5 substituents selected from group E" is the above-defined "C$_{3-10}$ cycloalkyl group" optionally substituted by 1 to 5 substituents selected from the above-defined "group E", which includes non-substituted cycloalkyl group.

Specifically, cyclopropyl group, cyclobutyl group, cyclopentyl group, cyclohexyl group, cycloheptyl group, 1-adamantyl group, 4-fluorocyclohexyl group, 2-methylcyclopentyl group, 3-methylcyclohexyl group, 4-methylcyclohexyl group, 4,4-dimethylcyclohexyl group, 3,5-dimethylcyclohexyl group, 4-tert-butylcyclohexyl group, 4-hydroxycyclohexyl group, 4-methoxycyclohexyl group, 2,3,4,5,6-pentafluorocyclohexyl group and the like can be mentioned.

In addition, such group wherein the cyclopentyl group or cyclohexyl group is substituted by fluorine atom, chlorine atom, bromine atom, nitro group, methyl group, tert-butyl group, carboxyl group, trifluoromethyl group, hydroxymethyl group, methoxymethyl group, 2-carboxyethyl group, methoxy group, carbamoyl group, methylthio group, dimethylaminocarbonyl group, methylsulfonyl group or acetylamino group can be mentioned.

The "heterocyclic group optionally substituted by 1 to 5 substituents selected from group E" is the above-defined "heterocyclic group" optionally substituted by 1 to 5 substituents selected from the above-defined "group E", which includes non-substituted heterocyclic group.

Specifically, 2-pyridyl group, 3-pyridyl group, 4-pyridyl group, 3-fluoropyridin-4-yl group, 3-chloropyridin-4-yl group, 4-chloropyridin-3-yl group, pyrazinyl group, pyrimidinyl group, pyridazinyl group, 1,3,5-triazinyl group, pyrrolyl group, pyrazolyl group, imidazolyl group, 2-methylimidazol-1-yl group, 1,2,4-triazolyl group, tetrazolyl group, 2-thienyl group, 3-thienyl group, furyl group, oxazolyl group, 2-methyloxazol-4-yl group, isoxazolyl group, thiazolyl group, 2-methylthiazol-4-yl group, 2,5-dimethylthiazol-4-yl group, 2,4-dimethylthiazol-5-yl group, 2-(dimethylamino)thiazol-4-yl group, isothiazolyl group, thiadiazolyl group, pyrrolinyl group, pyrrolidinyl group, 1-methylpyrrolidin-3-yl group, 1-acetylpyrrolidin-3-yl group, 1-methanesulfonylpyrrolidin-3-yl group, 1-methoxycarbonylpyrrolidin-3-yl group, imidazolidinyl group, piperidyl group, 4-methylpiperidin-1-yl group, 2-methylpiperidin-1-yl group, 3-methylpiperidin-1-yl group, 4-ethylpiperidin-1-yl group, 4-propylpiperidin-1-yl group, 4-isopropylpiperidin-1-yl group, 4,4-dimethylpiperidin-1-yl group, 2,2,6,6-tetramethylpiperidin-1-yl group, 4-trifluoromethylpiperidin-1-yl group, 4-hydroxypiperidin-1-yl group, 3-hydroxypiperidin-1-yl group, 4-methoxypiperidin-1-yl group, 3-methoxypiperidin-1-yl group, 4-(dimethylamino)piperidin-1-yl group, 4-methylenepiperidin-1-yl group, 4-ethylidenepiperidin-1-yl group, 4-isopropylidenepiperidin-1-yl group, 1-methylpiperidin-4-yl group, 1-ethylpiperidin-4-yl group, 1-methoxypiperidin-4-yl group, 1-methoxycarbonylpiperidin-4-yl group, 1-(tert-butoxycarbonyl)piperidin-4-yl group, 1-acetylpiperidin-4-yl group, 1-methanesulfonylpiperidin-4-yl group, 1-methylpiperidin-3-yl group, 1-ethylpiperidin-3-yl group, 1-acetylpiperidin-3-yl group, 1-methanesulfonylpiperidin-3-yl group, 1-methoxypiperidin-3-yl group, 1-methoxycarbonylpiperidin-3-yl group, 1-methylpiperidin-2-yl group, 1-ethylpiperidin-2-yl group, 1-acetylpiperidin-2-yl group, 1-methanesulfonylpiperidin-2-yl group, 1-methoxypiperidin-2-yl group, 1-methoxycarbonylpiperidin-2-yl group, piperazinyl group, 4-methylpiperazin-1-yl group, 4-ethylpiperazin-1-yl group, 4-isopropylpiperazin-1-yl group, 4-methoxypiperazin-1-yl group, 4-phenylpiperazin-1-yl group, 4-benzylpiperazin-1-yl group, 4-methoxycarbonylpiperazin-1-yl group, 4-ethoxycarbonylpiperazin-1-yl group, 4-(tert-butoxycarbonyl)piperazin-1-yl group, 4-cyclopentyloxycarbonylpiperazin-1-yl group, 4-acetylpiperazin-1-yl group, 4-isobutyrylpiperazin-1-yl group, 4-benzoylpiperazin-1-yl group, 4-(2-methoxyacetyl)piperazin-1-yl group, 4-methylcarbamoylpiperazin-1-yl group, 4-dimethylcarbamoylpiperazin-1-yl group, 4-methanesulfonylpiperazin-1-yl group, 1,2,3,6-tetrahydropyridyl group, morpholinyl group, thiomorpholinyl group, tetrahydropyranyl group, tetrahydrofuranyl group, azepanyl group, azocanyl group, azonanyl group, 1,4-diazepanyl group, 4-methyl-1,4-diazepan-4-yl group, 4-ethyl-1,4-diazepan-4-yl group, 1,4-oxazepanyl group, quinolyl group, isoquinolyl group, quinazolinyl group, quinoxalinyl group, phthalazinyl group, cinnolinyl group, naphthyridinyl group, 1,2,3,4-tetrahydroquinolyl group, 5,6,7,8-tetrahydroquinolyl group, 1,2,3,4-tetrahydroisoquinolyl group, 5,6,7,8-tetrahydroisoquinolyl group, indolyl group, benzimidazolyl group, indolinyl group, isoindolinyl group, octahydroindolyl group, octahydroisoindolyl group, benzofuranyl group, benzothienyl group, benzoxazolyl group, benzothiazolyl group, octahydrocyclopenta[c]pyrrolyl group,

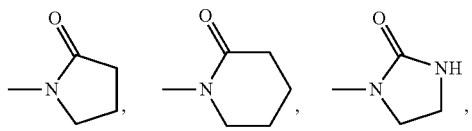

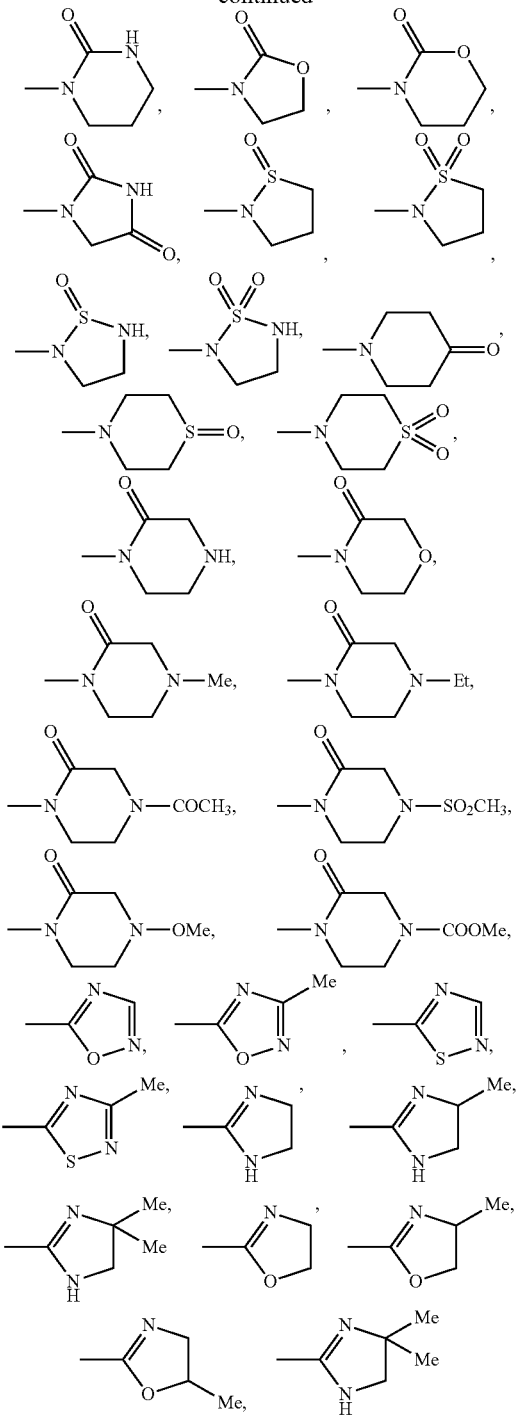

and the like can be mentioned.

In addition, such group wherein the 3, 4, 5 or 6-position of 2-pyridyl group, 2, 4, 5 or 6-position of 3-pyridyl group, 2, 3, 5 or 6-position of 4-pyridyl group, 3, 4 or 5-position of 2-thienyl group, and 2, 4 or 5-position of 3-thienyl group are substituted by fluorine atom, chlorine atom, bromine atom, nitro iv group, methyl group, tert-butyl group, carboxyl group, trifluoromethyl group, hydroxymethyl group, methoxymethyl group, 2-carboxyethyl group, methoxy group, carbamoyl group, methylthio group, dimethylaminocarbonyl group, methylsulfonyl group, amino group or acetylamino group can be mentioned.

The "carboxylic acid equivalent" means a bioisostere and may only be a substituent having a similar polar effect as carboxylic acid. Specifically, a chain substituent such as
—CONHR$^{105'}$,
(wherein R$^{105'}$ is a hydroxyl group, a cyano group, a C$_{1-6}$ alkoxy group or a C$_{6-14}$ aryloxy group),
—SO$_2$R$^{106'}$,
(wherein R$^{106'}$ is a hydroxyl group, an amino group or a C$_{1-6}$ alkylamino group),
—NHCOR$^{107'}$,
(wherein R$^{107'}$ is an amino group or a C$_{1-6}$ alkylamino group),
—P(=O)(OH)(OR$^{109}$)
(wherein R$^{109}$ is a hydrogen atom or a substituent selected from the above-mentioned group C),
—P(=O)(OH)NR$^{111}$R$^{112}$
(wherein R$^{111}$ and R$^{112}$ are each independently a hydrogen atom or a substituent selected from the above-mentioned group C),
—CONHCO—R$^{113}$
(wherein R$^{113}$ is a substituent selected from the above-mentioned group C),
—CONHSO$_2$—R$^{114}$,
(wherein R$^{114}$ is a substituent selected from the above-mentioned group C),
—SO$_2$NHCO—R$^{115}$
(wherein R$^{115}$ is a substituent selected from the above-mentioned group C) and the like, or a cyclic substituent such as a heterocyclic group having a hydrogen atom donor such as (wherein E$^{h1}$ is an oxygen atom, a sulfur atom or N(—R$^{h1}$) R$^{h1}$ is a hydrogen atom or a C$_{1-6}$ alkyl group, E$^{h3}$ is an oxygen atom or a sulfur atom, R$^{h2}$ is a C$_{1-6}$ alkyl group, R$^{h1}$ is an electron-withdrawing group such as a halogen atom, a cyano group, a C$_{1-6}$ alkyl group, a trifluoromethyl group, a formyl group, a chlorocarbonyl group, a nitro group, an acetyl group, an ethoxycarbonyl group, a carbamoyl group and the like) and the like, and said heterocyclic group substituted by an electron-withdrawing group and the like can be mentioned.

More specifically,
—CONHCN, —CONHOH, —CONHOMe,
—CONHOt-Bu, —CONHOBn,
—SO$_3$H, —SO$_2$NH$_2$, —SO$_2$NHMe,
—NHCONH$_2$, —NHCON(Me)$_2$,
—P(=O)(OH)$_2$, —P(=O)(OH) (OEt),
—P(=O)(OH)NH$_2$, —P(=O)(OH)NHMe, —CONHCOMe,
—CONHCOBn, —CONHSO$_2$Me, —CONHSO$_2$Pr,
—CONHSO$_2$Ph, —SO$_2$NHCOMe, —SO$_2$NHCOPh
wherein Me is a methyl group, Et is an ethyl group, Pr is a propyl group, t-Bu is a tert-butyl group, Ph is a phenyl group and Bn is a benzyl group, and

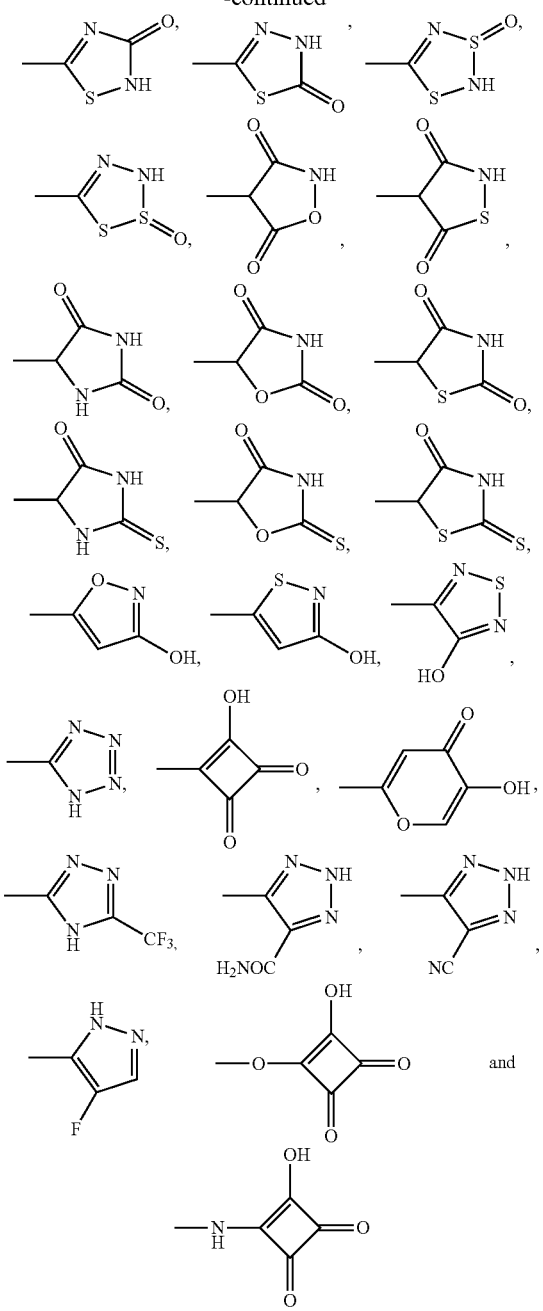
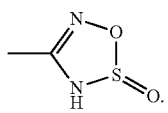
In the formula [I], as a
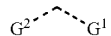
moiety, N—C=C is preferable, as a
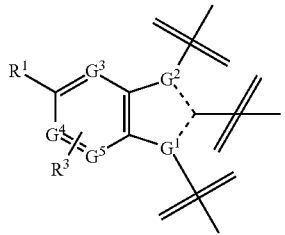
moiety, preferred is a fused ring selected from the group consisting of
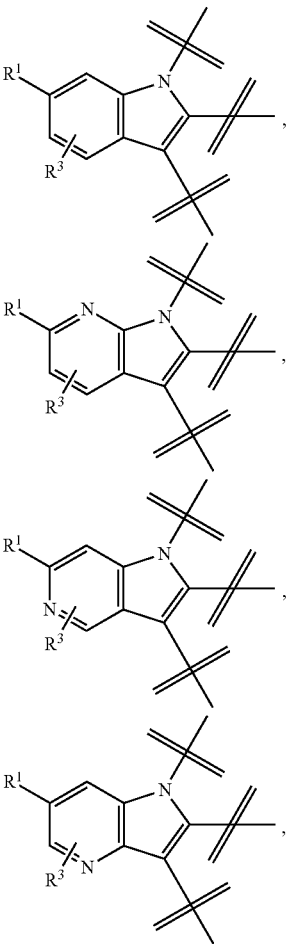
and the like can be mentioned.
As the carboxylic acid equivalent, preferred are —CONHOt-Bu, —CONHOBn, —SO$_3$H, —CONHSO$_2$Me, —CONHSO$_2$Pr, —CONHSO$_2$Ph,
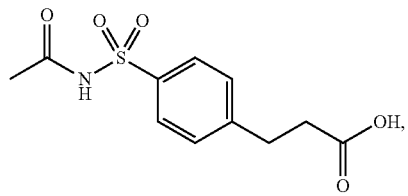
—SO$_2$NHCOMe, —SO$_2$NHCOPh, -continued
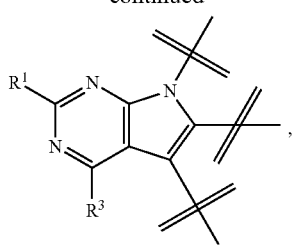,
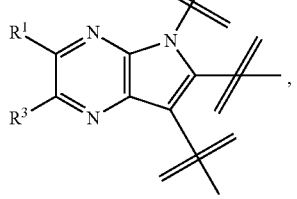,
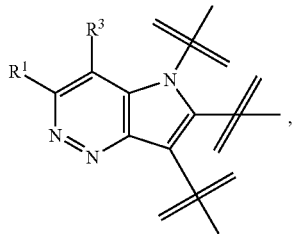,
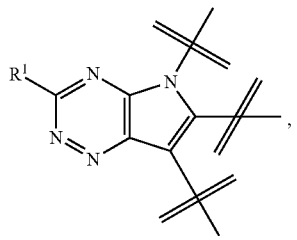,
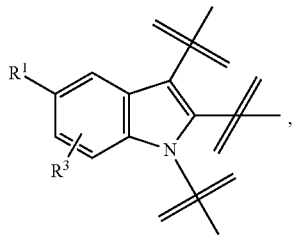,
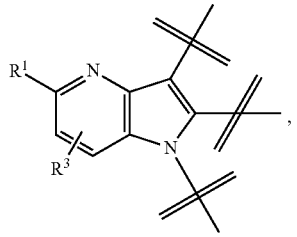,
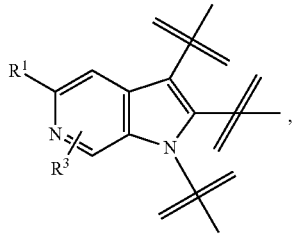,
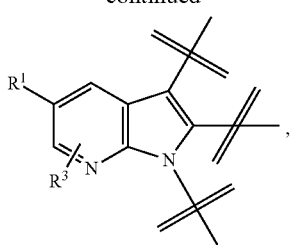,
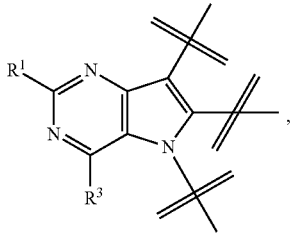,
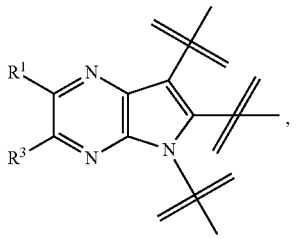,
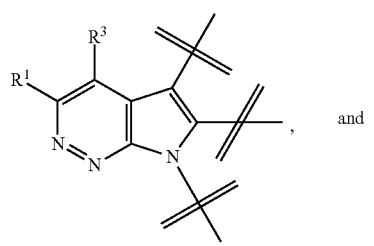, and
more preferably, a fused ring selected from the group consisting of
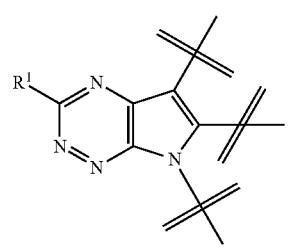,
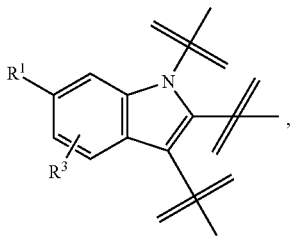, -continued

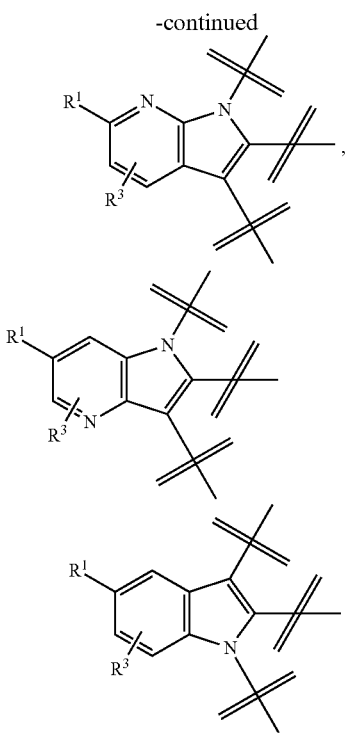

still more preferably,

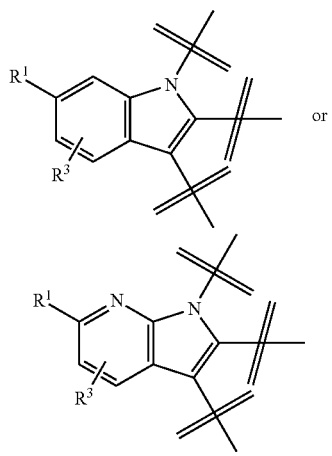

particularly preferably,

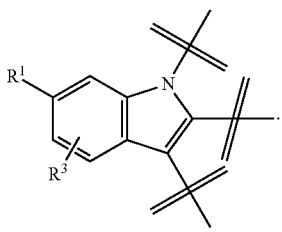

For $G^3$, $G^4$ or $G^5$, preferred is a carbon atom, when pharmacological activity is not markedly degraded, it may be a nitrogen atom, which may be substituted by $R^3$.

Q is —$(CH_2)_b$— or —$(CH_2)_c$-$Q^1$-$(CH_2)_d$—, wherein the bond on the left side is joined with $G^2$, and the bond on the right side is joined with $G^6$.

$Q^1$ is —O—, —NH—, —S—, —OCO—, —OCONH—, —CO—, —SO—, —$SO_2$—, —NHCO—, —$NHSO_2$—, —NHCOO—, —COO—, —CONH—, —$SO_2$NH—, —NHCONH—, —$NHSO_2$NH—, —CH=CH— or —CH=N—, wherein the bond on the left side is joined with —$(CH_2)_c$—, and the bond on the right side is joined with —$(CH_2)_d$—.

For $Q^1$, preferred are —O—, —NH—, —S— or —CONH—, more preferred are —O—, —NH— and —CONH—, particularly preferred is —NH—.

For b, preferred is an integer of 1 to 3, particularly preferably 1 or 3,

For c, preferred is an integer of 1 to 3, particularly preferred is 2,

For d, preferred is 0,

For Q, preferred are —$(CH_2)_2$—O— and —$(CH_2)_2$—NH—.

For $R^1$, preferred is a carboxyl group, —$CONR^{11}R^{12}$, —$COOR^{103}$,

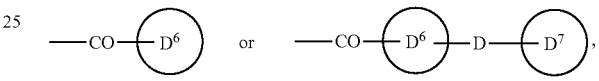

more preferably a carboxyl group or —$CONR^{11}R^{12}$.

For $R^{11}$, preferred is a hydrogen atom or a $C_{1-6}$ alkyl group.

For $R^{12}$, preferred is a hydrogen atom, "a $C_{1-6}$ alkyl group optionally substituted by 1 to 3 substituents selected from group E", "a $C_{6-14}$ aryl group optionally substituted by 1 to 5 substituents selected from group E", "a heterocyclic group optionally substituted by 1 to 5 substituents selected from group E", "a $C_{3-10}$ cycloalkyl group optionally substituted by 1 to 5 substituents selected from group E", —$NR^{131}R^{132}$, —$NHCOOR^{133}$, —$NHCOR^{134}$, —$CR^{135}R^{136}$-$L^{100}$-$R^{137}$,

—$CR^{138}R^{139}$——$L^{102}$——$CONR^{140}$——$L^{103}$——(D³),

—$CR^{138}R^{139}$-$L^{102}$-$CONR^{140}$-$L^{104}$-$CONR^{141}$-$L^{103}$-(D³) or

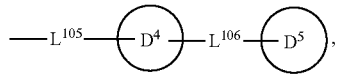

For $R^{103}$, preferred is "a $C_{1-6}$ alkyl group optionally substituted by 1 to 3 substituents selected from group A", "a $C_{6-14}$ aryl group optionally substituted by 1 to 5 substituents selected from group B" or "a $C_{6-14}$ aryl $C_{1-6}$ alkyl group optionally substituted by 1 to 5 substituents selected from group B".

As the "heterocyclic group" of "a heterocyclic group optionally substituted by 1 to 5 substituents selected from group E" for ring $D^6$, preferred is a pyrrolidinyl group, a piperidyl group, a piperazinyl group, a 2,6-dioxopiperazinyl group or a 2,3,4,9-tetrahydro-1H-β-carbolinyl group.

As the "$C_{6-14}$ aryl group" of "a $C_{6-14}$ aryl group optionally substituted by 1 to 5 substituents selected from group E" for ring $D^7$, preferred is a phenyl group.

For group E in ring $D^6$ and ring $D^7$, preferred is a hydroxyl group, a carboxyl group or a $C_{2-6}$ alkenyl group optionally substituted by carboxyl group.

For $R^{131}$, $R^{132}$, $R^{133}$ and $R^{134}$, preferred for each independently is a hydrogen atom, "a $C_{1-6}$ alkyl group optionally substituted by 1 to 3 substituents selected from group A", "a $C_{6-14}$ aryl group optionally substituted by 1 to 5 substituents selected from group B" or "a $C_{6-14}$ aryl $C_{1-6}$ alkyl group optionally substituted by 1 to 5 substituents selected from group B".

More preferably, $R^{131}$ and $R^{132}$ are each a $C_{1-6}$ alkyl group, $R^{133}$ is a $C_{6-14}$ aryl $C_{1-6}$ alkyl group, $R^{134}$ is a $C_{6-14}$ aryl group optionally substituted by carboxyl group.

For $R^{135}$ and $R^{136}$, preferred for each independently is a hydrogen atom, —$COOR^{142}$, —$CONR^{143}R^{144}$, "a $C_{1-6}$ alkyl group optionally substituted by 1 to 3 substituents selected from group A" or "a heterocyclic group optionally substituted by 1 to 5 substituents selected from group B", or $R^{135}$ and $R^{136}$ are bonded to each other, and form, together with the carbon atom bonded thereto, "a $C_{3-10}$ cycloalkyl group optionally substituted by 1 to 5 substituents selected from group B".

For $R^{142}$, preferred is a hydrogen atom or "a $C_{1-6}$ alkyl group optionally substituted by 1 to 3 substituents selected from group A". More preferably, $R^{142}$ is a hydrogen atom or a $C_{1-6}$ alkyl group.

For $R^{143}$ and $R^{144}$, preferred for each independently is a hydrogen atom, a $C_{1-6}$ alkoxy group, "a $C_{1-6}$ alkyl group optionally substituted by 1 to 3 substituents selected from group A", "a heterocyclic group optionally substituted by 1 to 5 substituents selected from group B" or "a heterocycle $C_{1-6}$ alkyl group optionally substituted by 1 to 5 substituents selected from group B". More preferably, $R^{143}$ is a hydrogen atom, $R^{144}$ is a hydrogen atom, "a $C_{1-6}$ alkyl group optionally substituted by 1 to 3 substituents selected from group A", "a heterocyclic group optionally substituted by 1 to 5 substituents selected from group B" or "a heterocycle $C_{1-6}$ alkyl group optionally substituted by 1 to 5 substituents selected from group B". For "a $C_{1-6}$ alkyl group optionally substituted by 1 to 3 substituents selected from group A" represented by $R^{144}$, preferred is a $C_{1-6}$ alkyl group optionally substituted by 1 to 3 substituents selected from a hydroxyl group and —$NR^{a1}R^{a2}$ (wherein $R^{a1}$ and $R^{a2}$ are each independently a hydrogen atom or a $C_{1-6}$ alkyl group). For the "heterocyclic group" of "a heterocyclic group optionally substituted by 1 to 5 substituents selected from group B" represented by $R^{144}$, preferred is a pyridyl group. For the "heterocycle" moiety of "a heterocycle $C_{1-6}$ alkyl group optionally substituted by 1 to 5 substituents selected from group B" represented by $R^{144}$, preferred is a morpholinyl group, pyrrolidinyl group or, a pyridyl group.

For the "heterocyclic group" of "a heterocyclic group optionally substituted by 1 to 5 substituents selected from group B" represented by $R^{135}$ and $R^{136}$, preferred is a thiazolyl group or a pyridyl group.

For the "$C_{3-10}$ cycloalkyl group" of "a $C_{3-10}$ cycloalkyl group optionally substituted by 1 to 5 substituents selected from group B" which is formed by $R^{135}$ and $R^{136}$ bonded to each other, together with the carbon atom bonded thereto, preferred is "a $C_{3-7}$ cycloalkyl group", more preferably a cyclopropyl group, a cyclobutyl group, a cyclopentyl group or a cyclohexyl group.

For $L^{100}$, preferred is a bond, —CO—, —$CH_2O$—, —$CH_2NH$—, —$CH_2NHCO$— or methylene, more preferably a bond or methylene.

For $L^{101}$, preferred is a bond or methylene.

For $R^{137}$, preferred is "a $C_{6-14}$ aryl group optionally substituted by 1 to 5 substituents selected from group E" or "a heterocyclic group optionally substituted by 1 to 5 substituents selected from group E".

For the "$C_{6-14}$ aryl group" of "a $C_{6-14}$ aryl group optionally substituted by 1 to 5 substituents selected from group E" represented by $R^{137}$, preferred is a phenyl group.

For the "heterocyclic group" of "a heterocyclic group optionally substituted by 1 to 5 substituents selected from group E" represented by $R^{137}$, preferred is an indolyl group, a 2-oxo-2H-chromenyl group, a benzo[1,3]dioxolanyl group, a benzimidazolyl group, a benzofuranyl group, a benzothienyl group, a benzothiazolyl group, a pyridyl group, a pyrimidinyl group, a pyrazolyl group, a 4-oxo-1H-quinolinyl group, a furyl group, a thienyl group, an oxazolyl group or a thiazolyl group, more preferably, an indolyl group, a benzimidazolyl group, a benzofuranyl group or a benzothienyl group, and particularly preferably, an indolyl group.

For $R^{138}$ and $R^{139}$, preferred for each independently is a hydrogen atom or "a $C_{1-6}$ alkyl group optionally substituted by 1 to 3 substituents selected from group A", or $R^{138}$ and $R^{139}$ are bonded to each other, and form, together with the carbon atom bonded thereto, "a $C_{3-10}$ cycloalkyl group optionally substituted by 1 to 5 substituents selected from group B" or "a heterocyclic group optionally substituted by 1 to 5 substituents selected from group B".

For the "$C_{3-10}$ cycloalkyl group" of "a $C_{3-10}$ cycloalkyl group optionally substituted by 1 to 5 substituents selected from group B", which is formed by $R^{138}$ and $R^{139}$ bonded to each other, together with the carbon atom bonded thereto, preferred is "a C3-7 cycloalkyl group", more preferred is a cyclopropyl group, a cyclobutyl group, a cyclopentyl group or a cyclohexyl group.

For the "heterocyclic group" of "a heterocyclic group optionally substituted by 1 to 5 substituents selected from group B", which is formed by $R^{138}$ and $R^{139}$ bonded to each other, together with the carbon atom bonded thereto, preferred is a "4-, 5- or 6-membered heterocyclic group comprising 1 to 3 heteroatoms selected from oxygen atom, nitrogen atom and sulfur atom", more preferably, a piperidyl group, a pyrrolidinyl group, a tetrahydropyranyl group or a tetrahydrothiopyranyl group.

Particularly preferably, $R^{138}$ and $R^{139}$ are each independently a hydrogen atom or a $C_{1-6}$ alkyl group, or $R^{138}$ and $R^{139}$ are bonded to each other, and form, together with the carbon atom bonded thereto, a cyclobutyl group or a cyclopentyl group.

For $R^{140}$ and $R^{142}$, preferred is a hydrogen atom.

For $L^{102}$, preferred is a bond or vinylene.

For $L^{103}$, preferred is a bond.

For $L^{104}$, preferred is propylene.

For ring $D^3$, preferred is "a $C_{6-14}$ aryl group optionally substituted by 1 to 5 substituents selected from group E" or "a heterocyclic group optionally substituted by 1 to 5 substituents selected from group E".

For the "$C_{6-14}$ aryl group" of "a $C_{6-14}$ aryl group optionally substituted by 1 to 5 substituents selected from group E" represented by ring $D^3$, preferred is a phenyl group.

For the "heterocyclic group" of "a heterocyclic group optionally substituted by 1 to 5 substituents selected from group E" represented by ring $D^3$, preferred is an indolyl group, a 2-oxo-2H-chromenyl group, a benzo[1,3]dioxolanyl group, a benzimidazolyl group, a benzofuranyl group, a benzothienyl group, a benzothiazolyl group, a pyridyl group, a pyrimidinyl group, a pyrazolyl group, a 4-oxo-1H-quinolinyl group, a furyl group, a thienyl group, an oxazolyl group or a thiazolyl group, more preferably, an indolyl group, a benzimidazolyl group, a benzofuranyl group or a benzothienyl group, particularly preferably, an indolyl group.

For ring $D^4$, preferred is "a $C_{3-10}$ cycloalkyl group optionally substituted by 1 to 5 substituents selected from group E" or "a heterocyclic group optionally substituted by 1 to 5 substituents selected from group E".

For ring $D^5$, preferred is "a $C_{6-14}$ aryl group optionally substituted by 1 to 5 substituents selected from group E".

For the "$C_{3-10}$ cycloalkyl group" of "a $C_{3-10}$ cycloalkyl group optionally substituted by 1 to 5 substituents selected from group E" represented by ring $D^4$ and ring $D^5$, preferred is a cyclohexyl group.

For the "heterocyclic group" of "a heterocyclic group optionally substituted by 1 to 5 substituents selected from group E" represented by ring $D^4$ and ring $D^5$, preferred is a piperidyl group or a pyrrolidinyl group.

For the "$C_{6-14}$ aryl group" of "a $C_{6-14}$ aryl group optionally substituted by 1 to 5 substituents selected from group E" represented by ring $D^4$ and ring $D^5$, preferred is a phenyl group.

For the group E in $R^{137}$, ring $D^3$, ring $D^4$ and ring $D^5$, preferred is a halogen atom, a cyano group, a nitro group, an azido group, —OP(=O)(OH)$_2$, —OR$^{e1}$, —S(O)$_q$—R$^{e2}$, —NR$^{e3}$R$^{e4}$, —COOR$^{e5}$, CONR$^{e6}$R$^{e7}$, —COR$^{e8}$, —NR$^{e9}$CO—R$^{e10}$, —NR$^{e11}$SO$_2$—R$^{e12}$, —NR$^{e21}$—CONR$^{e22}$R$^{e23}$, —NHCO—COOR$^{e24}$, —NHCO—CONR$^{e25}$R$^{e26}$, —CONH—COOH,

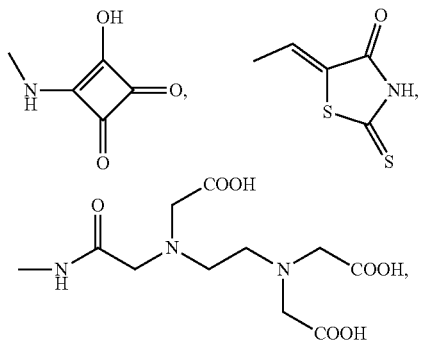

"a $C_{6-14}$ aryl group optionally substituted by 1 to 5 substituents selected from group B", "a $C_{3-10}$ cycloalkyl group optionally substituted by 1 to 5 substituents selected from group B", "a heterocyclic group optionally substituted by 1 to 5 substituents selected from group B", "a $C_{1-6}$ alkyl group optionally substituted by 1 to 3 substituents selected from group A", "a $C_{2-6}$ alkenyl group optionally substituted by 1 to 3 substituents selected from group A", "a $C_{2-6}$ alkynyl group optionally substituted by 1 to 3 substituents selected from group A" or "a $C_{6-14}$ aryl $C_{1-6}$ alkyl group optionally substituted by 1 to 5 substituents selected from group B", more preferably, a carboxyl group, —OR$^{e1}$ (wherein R$^{e1}$ is a hydrogen atom or a $C_{1-6}$ alkyl group substituted by carboxyl group), a $C_{1-6}$ alkyl group substituted by carboxyl group or a $C_{2-6}$ alkenyl group substituted by carboxyl group, particularly preferably, a carboxyl group, a hydroxyl group, —OCH$_2$COOH, —CH=CH—COOH or —CH$_2$CH$_2$COOH.

Preferably, $R^{12}$ is

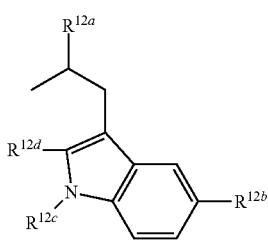

wherein $R^{12a}$ is preferably selected from a hydrogen atom, a 5- to 10-membered heterocyclic group comprising 1 to 4 heteroatoms selected from oxygen atom, nitrogen atom and sulfur atom (wherein the heterocyclic group is optionally substituted by 1 to 4 substituents selected from the group consisting of —CH$_3$, —CF$_3$, —OH, —CH$_2$COOH, —COOH, —NHCH(CH$_3$)$_2$, —NHCOCH$_3$, —NH$_2$, —NHCH$_3$ and —N(CH$_3$)$_2$), —COOH, —COO(C$_{1-6}$ alkyl), —CONH$_2$, —COCH$_3$, —(CH$_2$)$_{p1}$COOH (wherein p1 is an integer of 1 to 4), benzyloxy, —CH$_2$—(C$_{6-14}$ aryl)-COOH, pyridylcarbamoyl, pyridylmethylcarbamoyl and —CONH—(C$_{2-4}$ alkyl)-N(CH$_3$)$_2$.

More preferably, $R^{12a}$ is —COOR$^{12g}$, —CONHR$^{12f}$ or

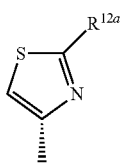

wherein, $R^{12e}$ is preferably a hydrogen atom, a $C_{1-6}$ alkyl group, an amino group, —NH(C$_{1-6}$ alkyl), —N(C$_{1-6}$ alkyl)$_2$ or —NHCO(C$_{1-6}$ alkyl).

Preferably, $R^{12f}$ is a hydrogen atom, a heterocycle $C_{1-6}$ alkyl group (wherein the heterocycle is selected from morpholinyl, pyrrolidinyl and N-methylpyrrolidinyl), —(C$_{1-6}$ alkyl)-N(CH$_3$)$_2$, —(C$_{1-6}$ alkyl)-OH, —CH(CH$_2$OH)$_2$ or —CH$_2$CH(OH)CH$_2$OH.

More preferably, $R^{12f}$ is a hydrogen atom.

Preferably, $R^{12g}$ is a hydrogen atom or a $C_{1-6}$ alkyl group. More preferably, $R^{12g}$ is a hydrogen atom or —CH$_3$.

Preferably, $R^{12b}$ is selected from a hydrogen atom, a hydroxyl group, an amino group, a 5- to 10-membered heterocyclic group comprising 1 to 4 heteroatoms selected from oxygen atom, nitrogen atom, sulfur atom (wherein the heterocyclic group is optionally substituted by hydroxyl group), —COOH, —CH$_3$, —CF$_3$, —CH$_2$COOH, —O(C$_{1-6}$ alkyl)-COOH, —NHCOCOOH, —NHSO$_2$CH$_3$, —NHSO$_2$CF$_3$,

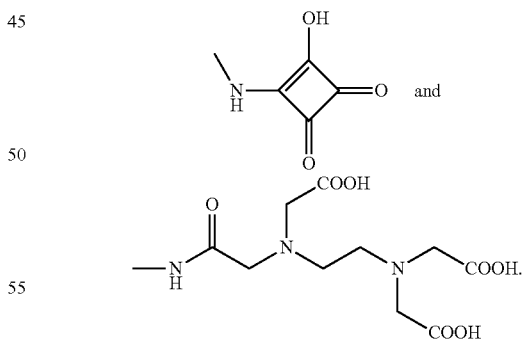

More preferably, $R^{12b}$ is —OCH$_2$COOH or a hydroxyl group.

Preferably, $R^{12c}$ is selected from a hydrogen atom, a $C_{1-6}$ alkyl group and —(CH$_2$)$_{p1}$COOH (wherein p1 is an integer of 1 to 4). More preferably, $R^{12c}$ is a hydrogen atom, —CH$_3$ or —CH$_2$COOH.

Preferably, $R^{12d}$ is a hydrogen atom or a $C_{1-6}$ alkyl group. More preferably, $R^{12d}$ is a hydrogen atom or —CH$_3$. Still more preferably, $R^{12d}$ is a hydrogen atom.

Alternatively, $R^{12}$ is preferably

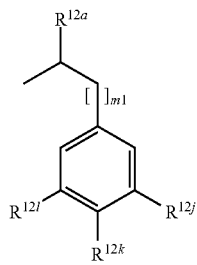

wherein $R^{12a}$ is as defined above.

Preferably, $R^{12j}$ is a $C_{1-6}$ alkoxy group, a hydroxyl group, —O($C_{1-6}$ alkyl)-COOH, a $C_{1-6}$ alkyl group, a halogen atom, —($C_{2-6}$ alkenyl)-COOH, —($C_{1-6}$ alkyl)-OH, —COOH or an azido group.

Preferably, $R^{12k}$ is a hydroxyl group, —$(CH_2)_{p1}$COOH (wherein p1 is an integer of 1 to 4), an amino group, a $C_{1-6}$ alkoxy group, —NHCOCOOH, —NH($C_{1-6}$ alkyl)-COOH, —O($C_{1-6}$ alkyl)-COOH, —COOH, a 5- or 6-membered heterocyclic group comprising 1 to 4 heteroatoms selected from oxygen atom, nitrogen atom and sulfur atom (wherein the 5- or 6-membered heterocyclic group is optionally substituted by 1 to 4 substituents selected from the group consisting of —$CH_3$, —$CF_3$, —OH, —$CH_2$COOH and —COOH), —O($C_{1-6}$ alkyl)-COOH,

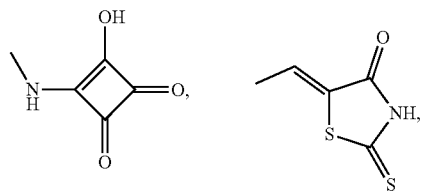

—NHCONH$_2$, —NHCN, —NHCHO, —NHSO$_2$CF$_3$, —NHCOCH$_3$, —NHSO$_2$CH$_3$, —CONH$_2$, —($C_{3-10}$ cycloalkyl)-COOH, —($C_{2-6}$ alkenyl)-COOH or —NHCOCH$_2$CH(OH)COOH.

Preferably, $R^{12l}$ is —O($C_{1-6}$ alkyl)-COOH, a $C_{1-6}$ alkyl group or a halogen atom.

Preferably, m1 is 0 or an integer of 1 to 4. More preferably, m1 is 1.

Alternatively, $R^{12}$ is preferably

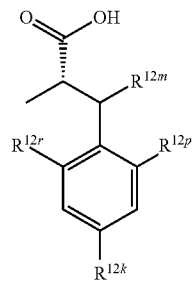

wherein $R^{12k}$ is as defined above.

Preferably, $R^{12m}$ is a hydrogen atom or a hydroxyl group.

Preferably, $R^{12p}$ is a hydrogen atom, a halogen atom or a $C_{1-6}$ alkyl group.

Preferably, $R^{12r}$ is a hydrogen atom, a halogen atom or a $C_{1-6}$ alkyl group.

Alternatively, $R^{12}$ is preferably

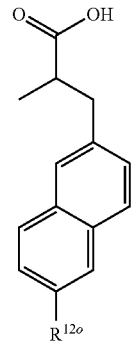

wherein $R^{12o}$ is preferably a hydroxyl group or —O($C_{1-6}$ alkyl)-COOH.

Alternatively, $R^{12}$ is preferably

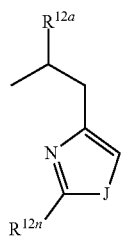

wherein $R^{12a}$ is as defined above.

Preferably, J is S or N($C_{1-6}$ alkyl). More preferably, J is S or N($CH_3$).

Preferably, $R^{12n}$ is a hydrogen atom or an amino group.

Alternatively, $R^{12}$ is more preferably

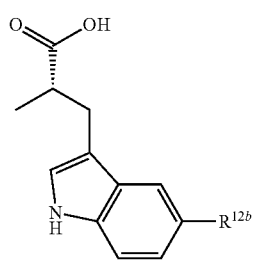

wherein $R^{12b}$ is as defined above.

Alternatively, $R^{12}$ is more preferably

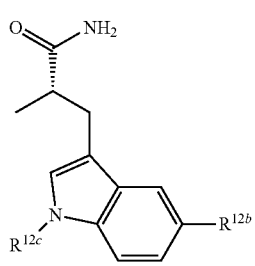

wherein $R^{12b}$ and $R^{12c}$ are as defined above.

Alternatively, $R^{12}$ is more preferably

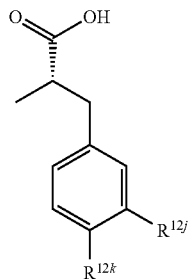

wherein $R^{12j}$ and $R^{12k}$ are as defined above.

Alternatively, $R^{12}$ is preferably

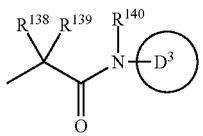

wherein $R^{138}$ and $R^{139}$ are each independently a hydrogen atom, "a $C_{1-6}$ alkyl group optionally substituted by 1 to 3 substituents selected from group A", "a $C_{3-10}$ cycloalkyl group optionally substituted by 1 to 5 substituents selected from group B", "a $C_{6-14}$ aryl group optionally substituted by 1 to 5 substituents selected from group B", "a heterocyclic group optionally substituted by 1 to 5 substituents selected from group B", "a $C_{6-14}$ aryl $C_{1-6}$ alkyl group optionally substituted by 1 to 5 substituents selected from group B", "a heterocycle $C_{1-6}$ alkyl group optionally substituted by 1 to 5 substituents selected from group B" or "a $C_{3-10}$ cycloalkyl $C_{1-6}$ alkyl group optionally substituted by 1 to 5 substituents selected from group B"; or $R^{138}$ and $R^{139}$ are bonded to each other and optionally form, together with the carbon atom bonded thereto, "a $C_{3-10}$ cycloalkyl group optionally substituted by 1 to 5 substituents selected from group B" or "a heterocyclic group optionally substituted by 1 to 5 substituents selected from group B".

Here, as the substituent selected from group A, preferred are 1 to 3 substituents selected from a halogen atom, $-OR^{a1}$, $-NR^{a1}R^{a2}$, $-COOR^{a1}$, $-CONR^{a1}R^{a2}$ and $-COR^{a1}$ (wherein $R^{a1}$ and $R^{a2}$ are each independently a hydrogen atom or a $C_{1-6}$ alkyl group), and as the substituent selected from group B, preferred are 1 to 5 substituents selected from a halogen atom, a $C_{1-6}$ alkyl group, a $C_{2-6}$ alkenyl group, $-OR^{b1}$, $-NR^{b1}R^{b2}$, $-COOR^{b1}$, $-CONR^{b1}R^{b2}$, $-COR^{b1}$ and $-SO_2R^{b3}$ (wherein $R^{b1}$ and $R^{b2}$ are each independently a hydrogen atom or a $C_{1-6}$ alkyl group and $R^{b3}$ is a $C_{1-6}$ alkyl group).

Preferably, $R^{140}$ is a hydrogen atom.

Preferably, ring $D^3$ is "a $C_{6-14}$ aryl group optionally substituted by 1 to 5 substituents selected from group E" or "a heterocyclic group optionally substituted by 1 to 5 substituents selected from group E".

Here, as the substituent selected from group E, preferred are 1 to 5 substituent selected from a halogen atom, a cyano group, a nitro group, an azido group, $-OR^{e1}$ (wherein $R^{e1}$ is a hydrogen atom or a $C_{1-6}$ alkyl group optionally substituted by carboxyl group), $-S(O)_q-R^{e2}$ (wherein $R^{e2}$ is a hydrogen atom or a $C_{1-6}$ alkyl group optionally substituted by carboxyl group and q is 0, 1, 2 or 3), $-NR^{e3}R^{e4}$ (wherein $R^{e3}$ and $R^{e4}$ is independently a hydrogen atom, a $C_{1-6}$ alkyl group or a heterocyclic group optionally substituted by 1 to 5 substituents selected from group B), $-COOR^{e5}$ (wherein $R^{e5}$ is a hydrogen atom or a $C_{1-6}$ alkyl group), $-CONR^{e6}R^{e7}$ (wherein $R^{e6}$ and $R^{e7}$ are each independently a hydrogen atom or a $C_{1-6}$ alkyl group optionally substituted by carboxyl group), $-NR^{e9}CO-R^{e10}$ (wherein $R^{e9}$ is a hydrogen atom or a $C_{1-6}$ alkyl group, and $R^{e10}$ is a hydrogen atom, an amino group, a $C_{1-6}$ alkylamino group or a $C_{1-6}$ alkyl group), $-SO_2-NR^{e13}R^{e14}$ (wherein $R^{e13}$ and $R^{e14}$ are each a hydrogen atom or a $C_{1-6}$ alkyl group), $-NR^{e21}-CONR^{e22}R^{e23}$ (wherein $R^{e21}$, $R^{e22}$ and $R^{e23}$ are each independently a hydrogen atom or a $C_{1-6}$ alkyl group), $-NHCO-COOR^{e24}$ (wherein $R^{e24}$ is a hydrogen atom or a $C_{1-6}$ alkyl group), $-NHCO-CONR^{e25}R^{e26}$ (wherein $R^{e25}$ and $R^{e26}$ are each a hydrogen atom, a hydroxyl group or a $C_{1-6}$ alkyl group), a $C_{6-14}$ aryl group optionally substituted by 1 to 5 substituents selected from group B, a $C_{3-10}$ cycloalkyl group optionally substituted by 1 to 5 substituents selected from group B, a heterocyclic group optionally substituted by 1 to 5 substituents selected from group B, a $C_{1-6}$ alkyl group optionally substituted by 1 to 3 substituents selected from group A, a $C_{2-6}$ alkenyl group optionally substituted by 1 to 3 substituents selected from group A, a $C_{2-6}$ alkynyl group optionally substituted by 1 to 3 substituents selected from group A, a $C_{6-14}$ aryl $C_{1-6}$ alkyl group optionally substituted by 1 to 5 substituents selected from group B, a $C_{3-10}$ cycloalkyl $C_{1-6}$ alkyl group optionally substituted by 1 to 5 substituents selected from group B, and a heterocycle $C_{1-6}$ alkyl group optionally substituted by 1 to 5 substituents selected from group B.

Here, as the substituent selected from group A, preferred are 1 to 3 substituents selected from a halogen atom, a cyano group, $-OR^{a1}$, $-NR^{a1}R^{a2}$, $-COOR^{a1}$, $-CONR^{a1}R^{a2}$, $-SO_2NR^{a1}R^{a2}$ and $-NHCOR^{a1}$ (wherein $R^{a1}$ and $R^{a2}$ are each independently a hydrogen atom or a $C_{1-6}$ alkyl group), and as the substituent selected from group B, preferred are 1 to 5 substituent selected from a halogen atom, a $C_{1-6}$ alkyl group, a halogenated $C_{1-6}$ alkyl group, $-(CH_2)_r-OR^{b1}$, $-(CH_2)_r-NR^{b1}R^{b2}$, $-(CH_2)_r-COOR^{b1}$, $-(CH_2)_r-CONR^{b1}R^{b2}$, $-(CH_2)_r-SO_2NR^{b1}R^{b2}$ and $-(CH_2)_r-NR^{b1}-COR^{b2}$ (wherein $R^{b1}$ and $R^{b2}$ are each independently a hydrogen atom or a $C_{1-6}$ alkyl group, and r is 0 or an integer of 1 to 6).

For $R^1$, preferred is $-CONR^{11}R^{12}$.

More preferably, $R^{11}$ is a hydrogen atom, and $R^{12}$ is
—$CR^{135}R^{136}$-$L^{100}$-$R^{137}$,
—$CR^{135}R^{136}$-$L^{101}$-$CONR^{140}$—$R^{137}$,

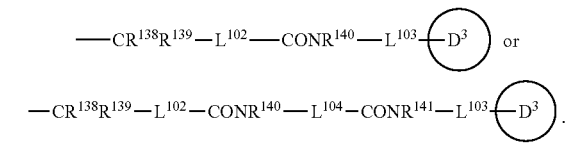

When $R^{12}$ is —$CR^{135}R^{136}$-$L^{100}$-$R^{137}$, preferably, $L^{100}$ is a bond, and $R^{137}$ is a $C_{6-14}$ aryl group optionally substituted by 1 to 5 substituents selected from group E or a heterocyclic group optionally substituted by 1 to 5 substituents selected from group E (wherein said heterocyclic group comprises 1 to 4 heteroatoms selected from oxygen atom, nitrogen atom and sulfur atom).

More preferably, $R^{135}$ and $R^{136}$ are each independently a group selected from group G, or $R^{135}$ and $R^{136}$ are bonded to each other, and form, together with the carbon atom bonded thereto, a $C_{3-10}$ cycloalkyl group optionally substituted by 1 to 5 substituents selected from group B, or a heterocyclic group optionally substituted by 1 to 5 substituents selected from group B.

In a different preferable embodiment wherein $R^{12}$ is —$CR^{135}R^{136}$-$L^{100}$-$R^{137}$, $L^{100}$ is methylene, and $R^{137}$ is a $C_{6-14}$ aryl group optionally substituted by 1 to 5 substituents selected from group E or a heterocyclic group optionally substituted by 1 to 5 substituents selected from group E (wherein said heterocyclic group comprises 1 to 4 heteroatoms selected from oxygen atom, nitrogen atom and sulfur atom).

More preferably, $R^{135}$ is a group selected from group G and $R^{136}$ is a hydrogen atom.

When $R^{12}$ is —$CR^{135}R^{136}$-$L^{101}$-$CONR^{140}$—$R^{137}$, $L^{101}$ is preferably a bond.

More preferably, $R^{135}$ and $R^{136}$ are each independently a group selected from group G, or $R^{135}$ and $R^{136}$ are bonded to each other, and form, together with the carbon atom bonded thereto, a $C_{3-10}$ cycloalkyl group optionally substituted by 1 to 5 substituents selected from group B, or a heterocyclic group optionally substituted by 1 to 5 substituents selected from group B.

Still more preferably, $R^{140}$ is a hydrogen atom and $R^{137}$ is a $C_{6-14}$ aryl group optionally substituted by 1 to 5 substituents selected from group E or a heterocyclic group optionally substituted by 1 to 5 substituents selected from group E (wherein said heterocyclic group comprises 1 to 4 heteroatoms selected from oxygen atom, nitrogen atom and sulfur atom).

When $R^{12}$ is

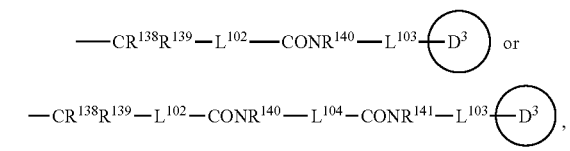

$L^{102}$ is preferably a bond.

More preferably, $R^{138}$ and $R^{139}$ are each independently a group selected from group G, or $R^{138}$ and $R^{139}$ are bonded to each other, and form, together with the carbon atom bonded thereto, a $C_{3-10}$ cycloalkyl group optionally substituted by 1 to 5 substituents selected from group B, or a heterocyclic group optionally substituted by 1 to 5 substituents selected from group B.

Still more preferably, $L^{103}$ is a bond, ring $D^3$ is a $C_{6-14}$ aryl group optionally substituted by 1 to 5 substituents selected from group E or a heterocyclic group optionally substituted by 1 to 5 substituents selected from group E (wherein said heterocyclic group comprises 1 to 4 heteroatoms selected from oxygen atom, nitrogen atom and sulfur atom), and $R^{140}$ and $R^{141}$ are each a hydrogen atom.

$R^1$ is specifically a carboxyl group, a methoxycarbonyl group, an ethoxycarbonyl group, a phenoxycarbonyl group, a benzyloxycarbonyl group, a carbamoyl group, a methylcarbamoyl group, a (2-hydroxyethyl)carbamoyl group, a (1,1-dimethyl-2-hydroxyethyl)carbamoyl group, a carboxymethylcarbamoyl group, an N-carboxymethyl-N-methylcarbamoyl group, a (1-carboxy-3-methylbutyl)carbamoyl group, a (1-carboxy-2-methoxyethyl)carbamoyl group, a (1-carboxy-2-methylthioethyl)carbamoyl group, a (1-carboxy-2-dimethylaminoethyl)carbamoyl group, a 5-carboxypentylcarbamoyl group, a (1-carboxy-1,3-dimethylbutyl)carbamoyl group, a (1-carboxy-2-methyl-2-methylthiopropyl)carbamoyl group, a (1-carboxy-2,2-dimethylpropyl)carbamoyl group, a [2-(2-hydroxyethoxy)ethyl]carbamoyl group or a tert-butylcarbamoyl group, particularly preferably a carboxyl group.

$R^1$ may be a "carboxylic acid equivalent" which is a substituent biologically equivalent to a carboxyl group, and as a specific "carboxylic acid equivalent", the aforementioned substituent and the like can be mentioned.

Moreover, an example of $R^1$ is a group represented by

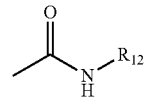

wherein $R^{12}$ is selected from the following formulas, can be mentioned.

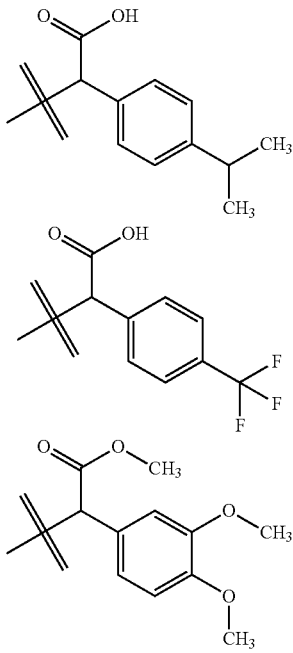

79
-continued
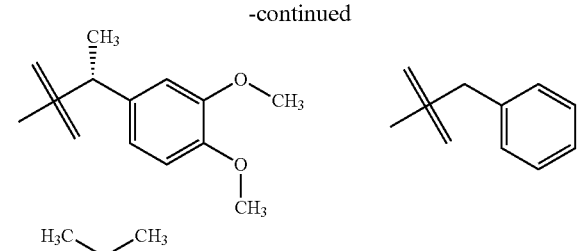
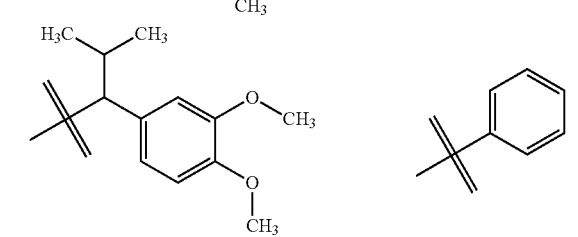
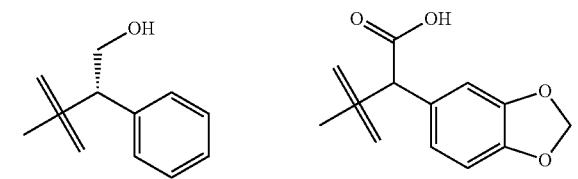
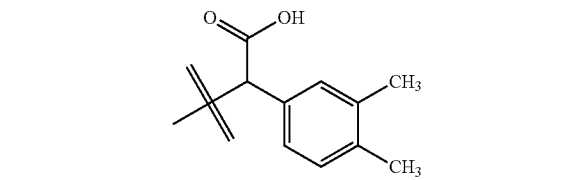
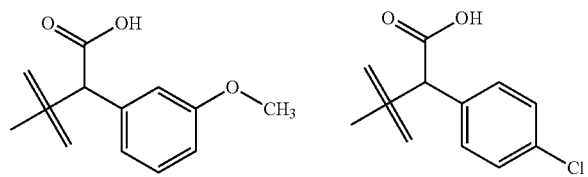
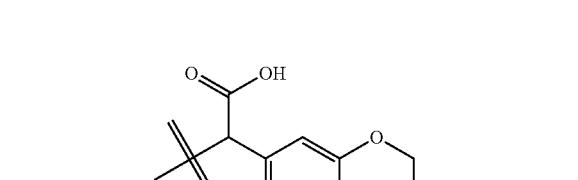
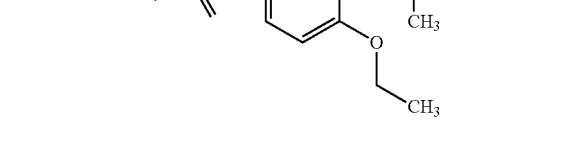
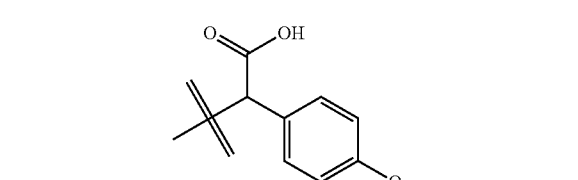
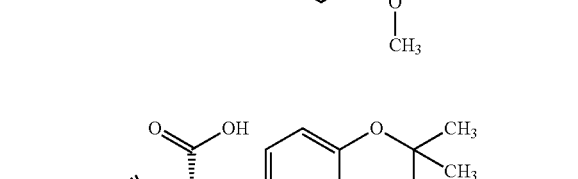
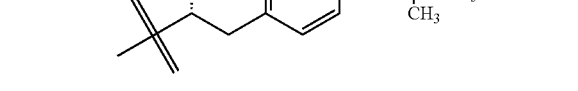
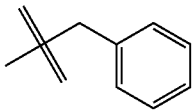
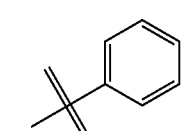
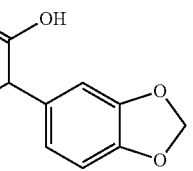
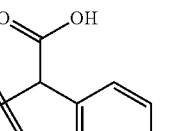
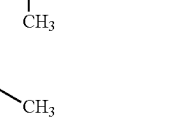
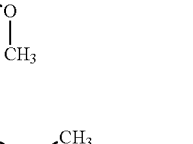
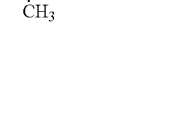
80
-continued
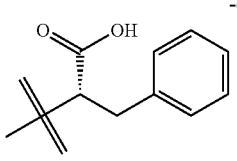
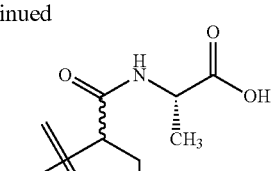
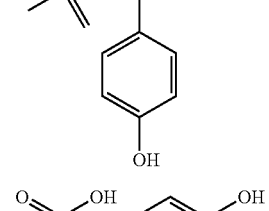
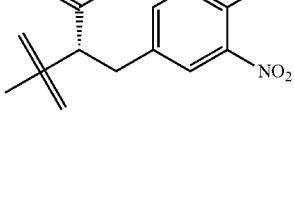
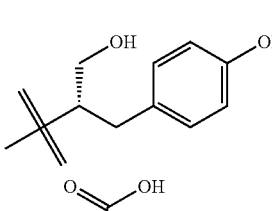
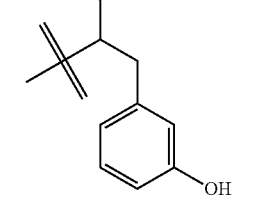
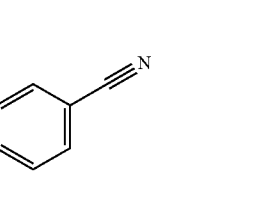
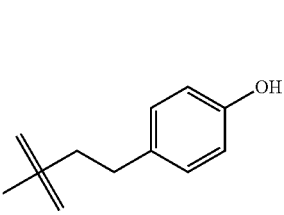
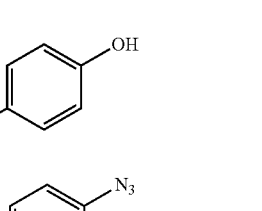
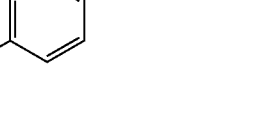

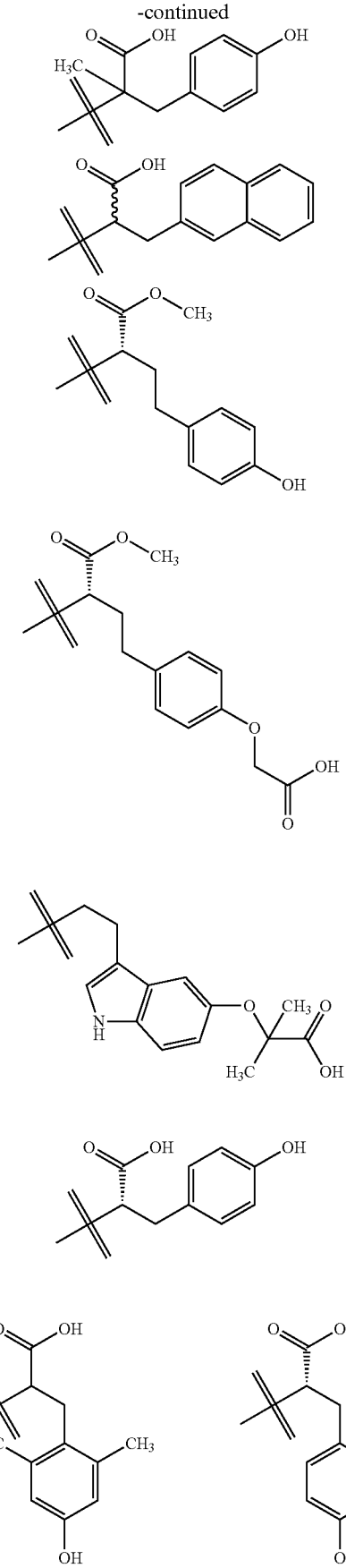
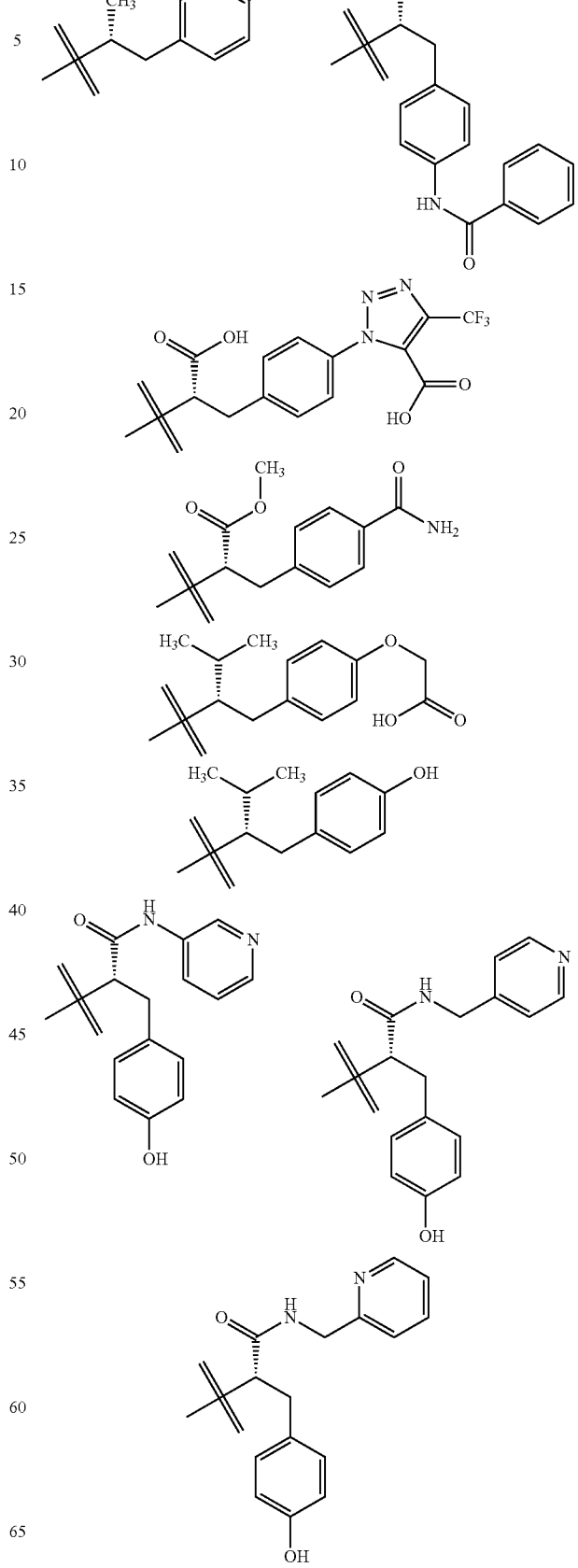

83
-continued
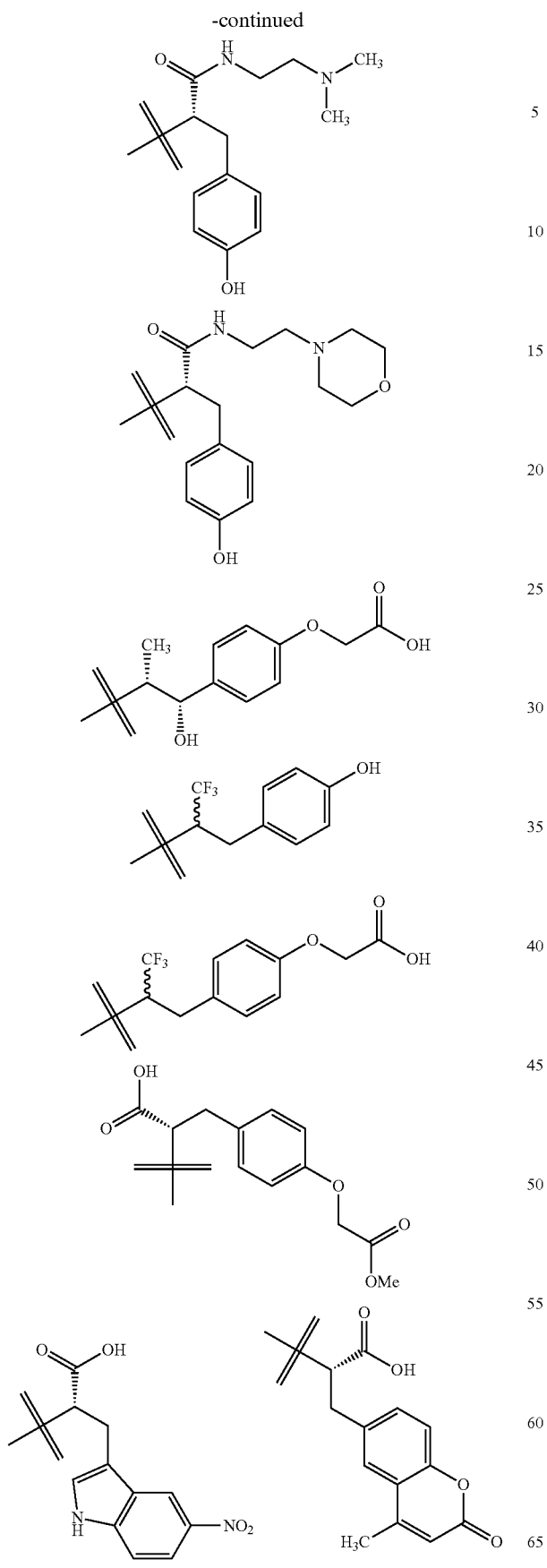
84
-continued
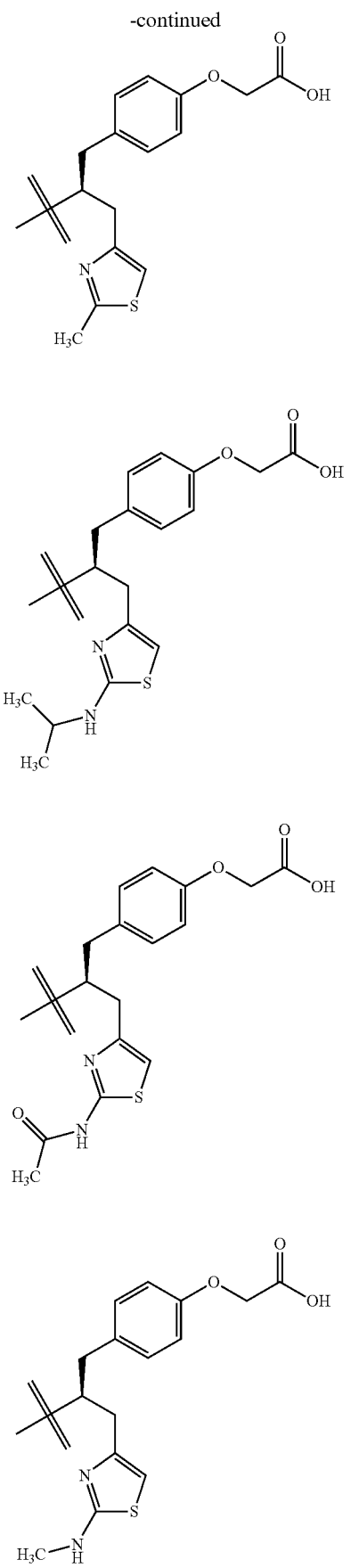

85
-continued
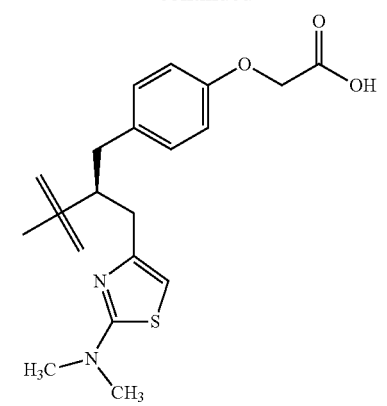
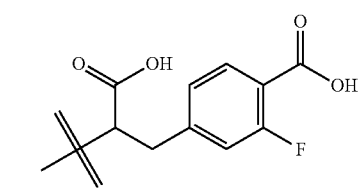
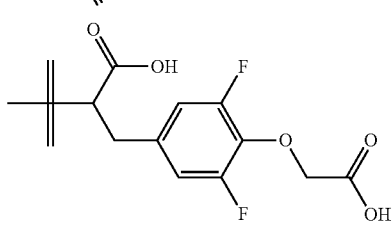
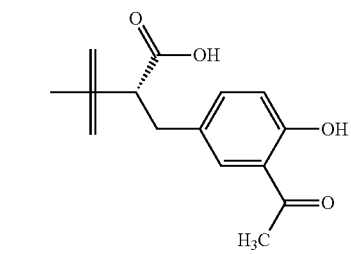
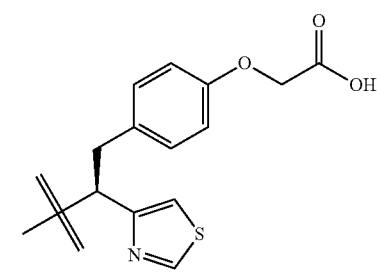
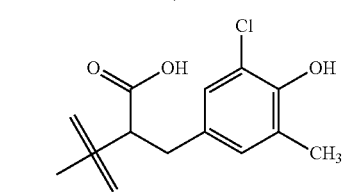
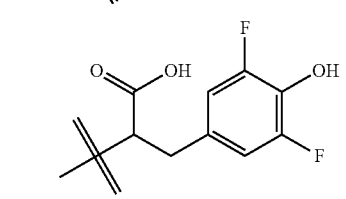
86
-continued
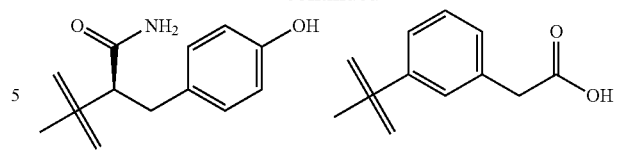
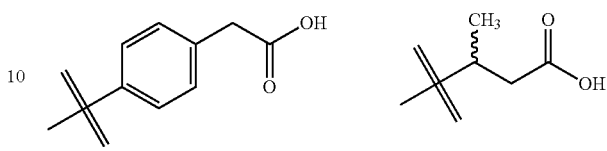
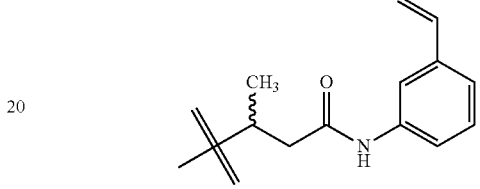
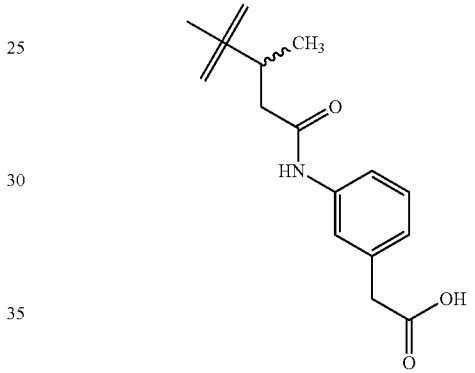
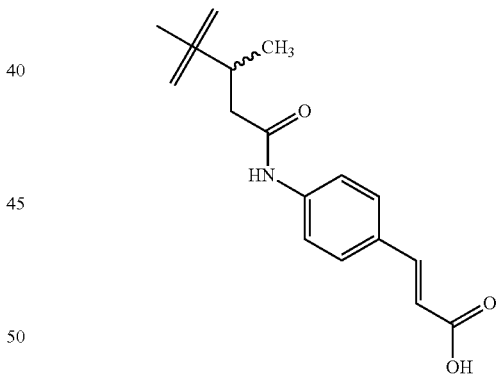
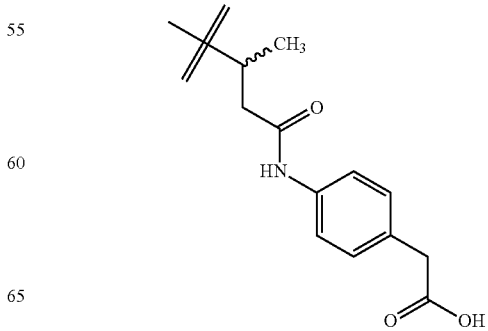

87
-continued
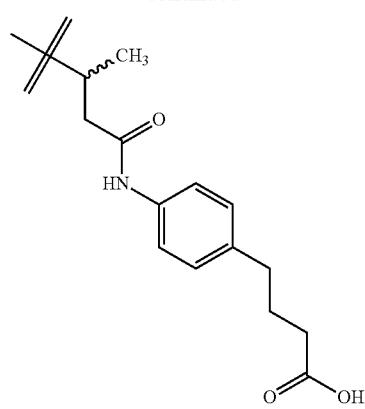
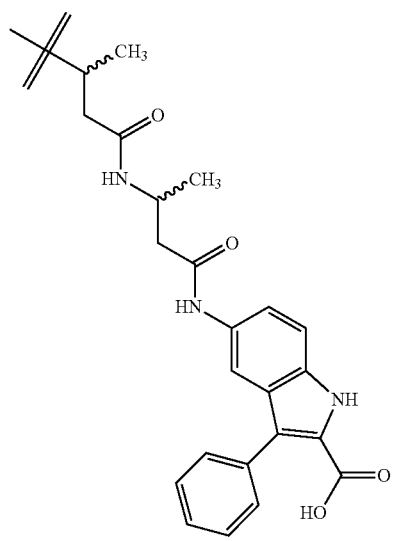
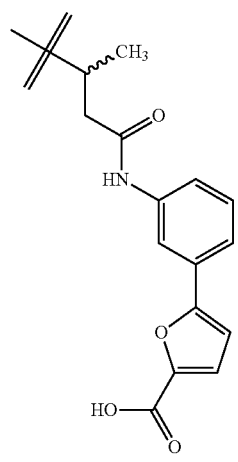
88
-continued
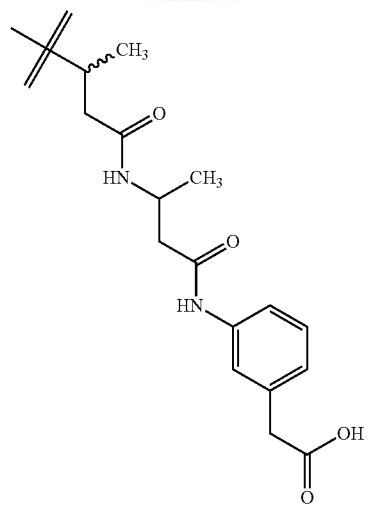
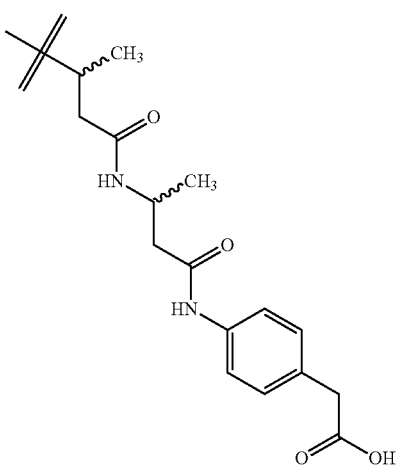
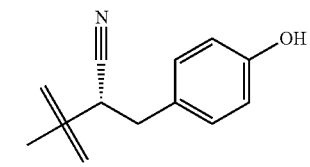
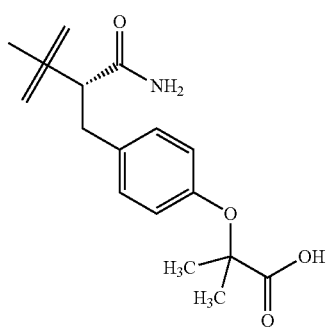

-continued
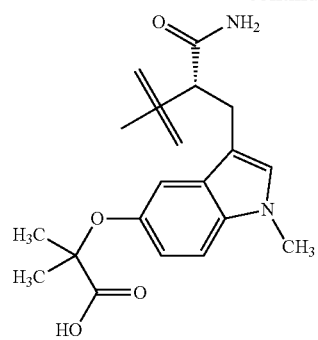
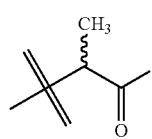
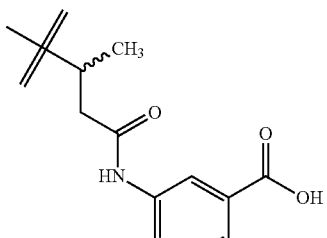
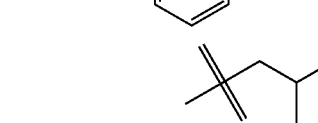
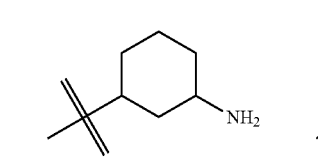
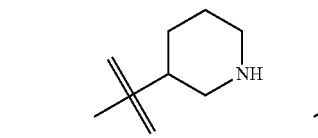
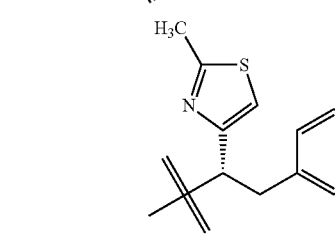
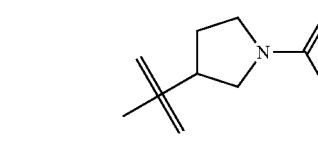
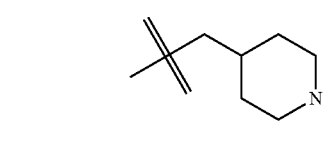
-continued
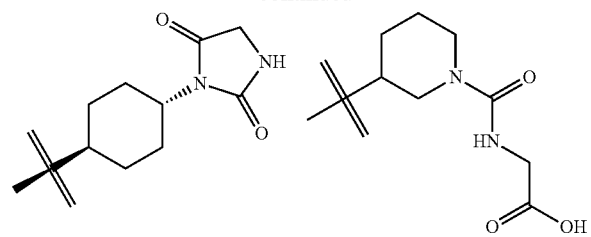
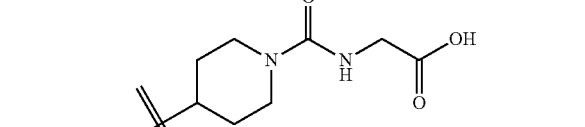
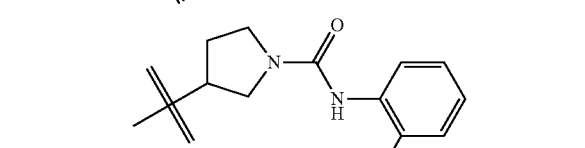
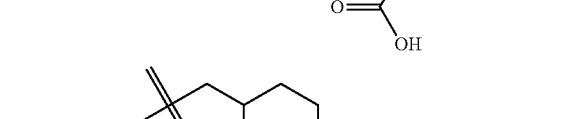
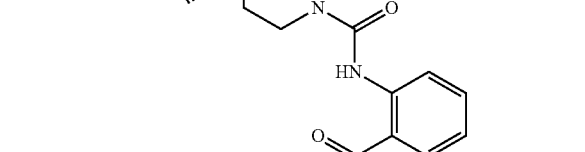
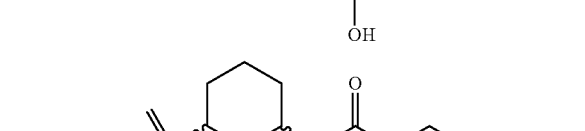
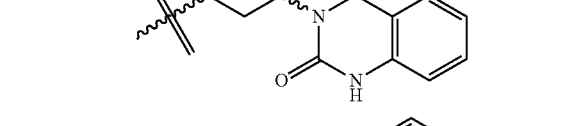
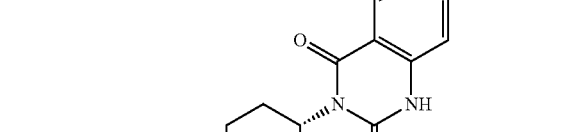
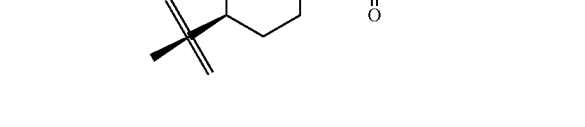
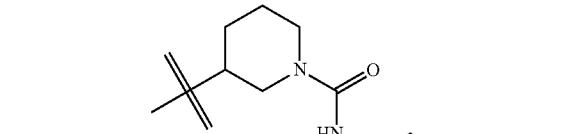
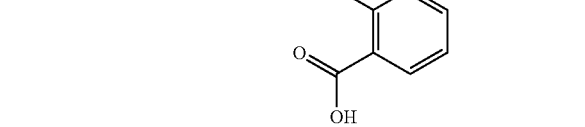

-continued
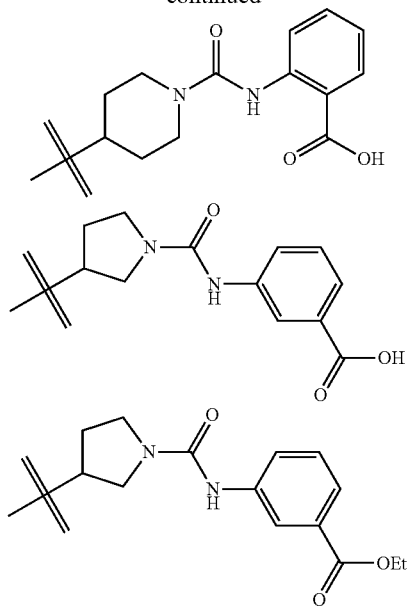
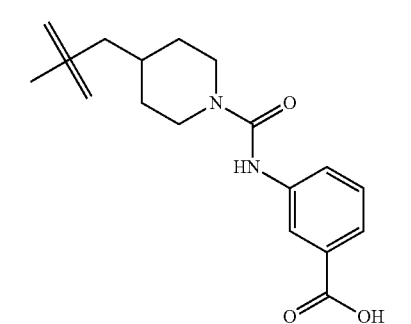
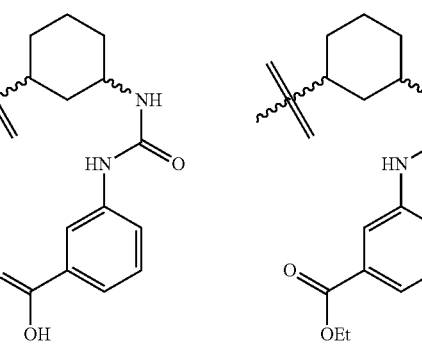
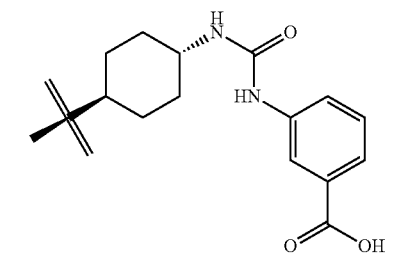
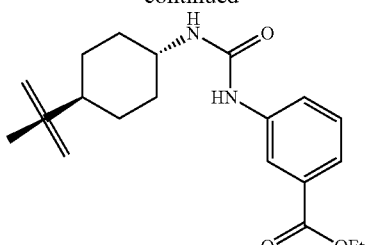
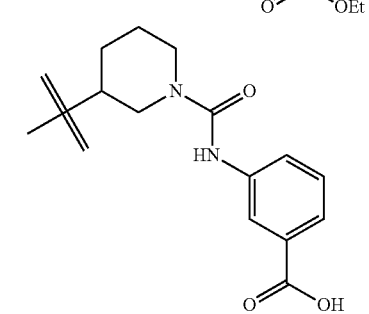
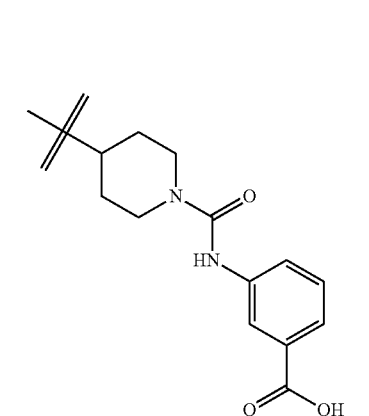
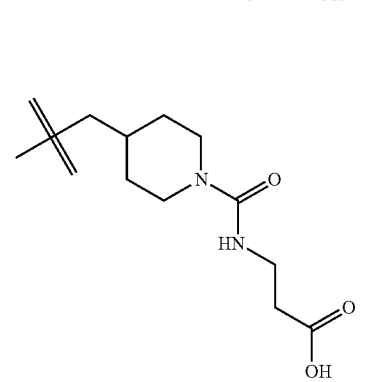
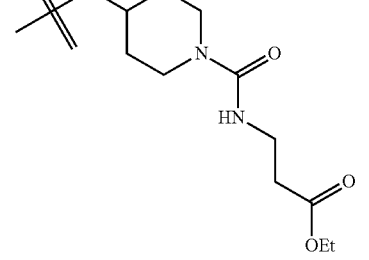

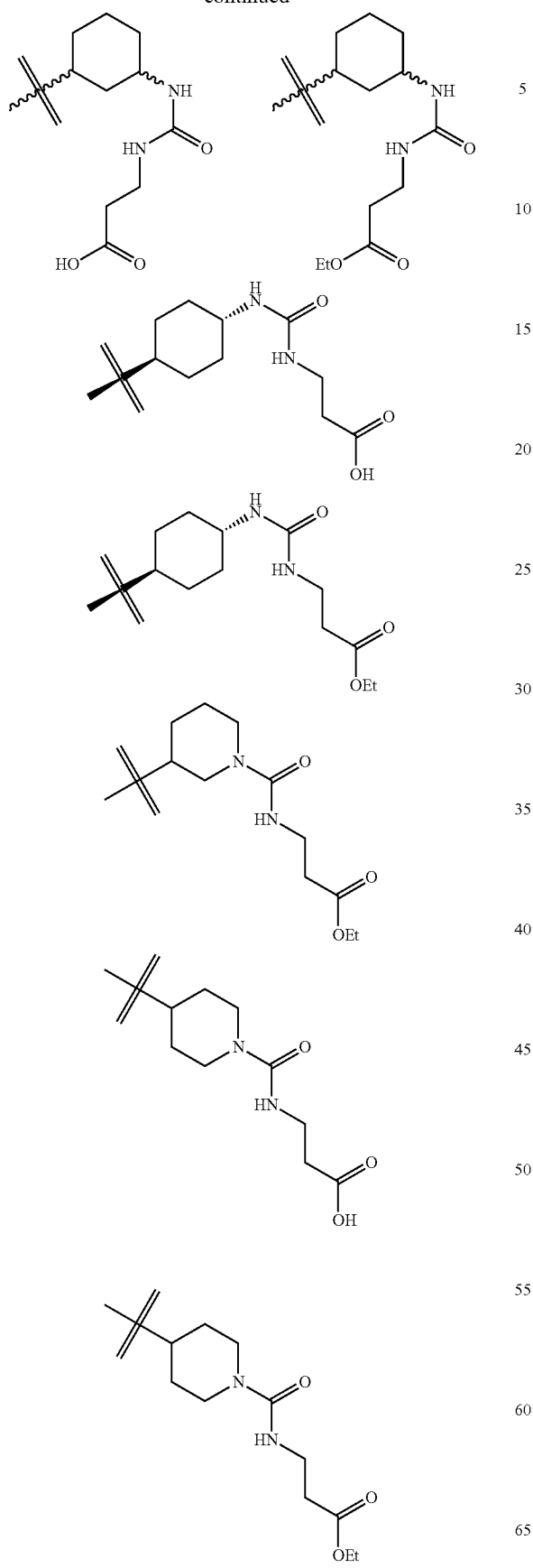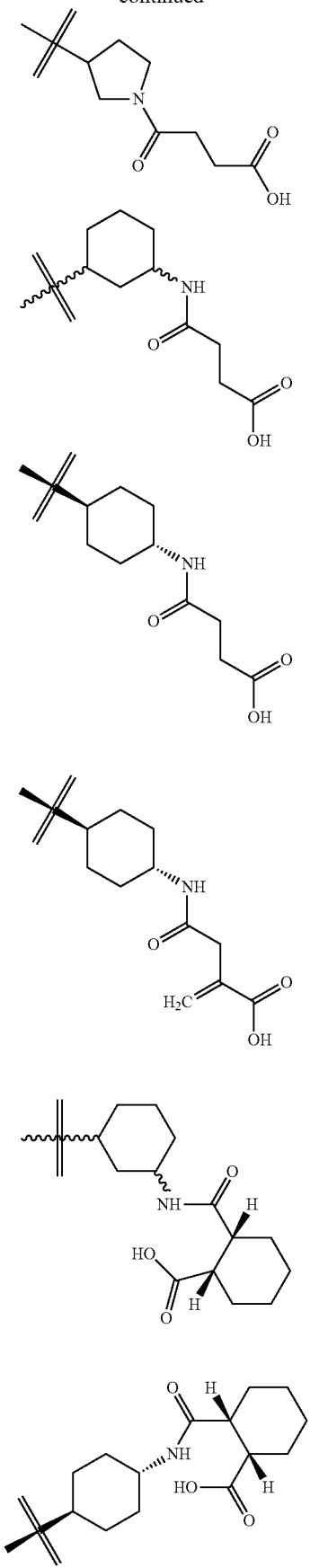

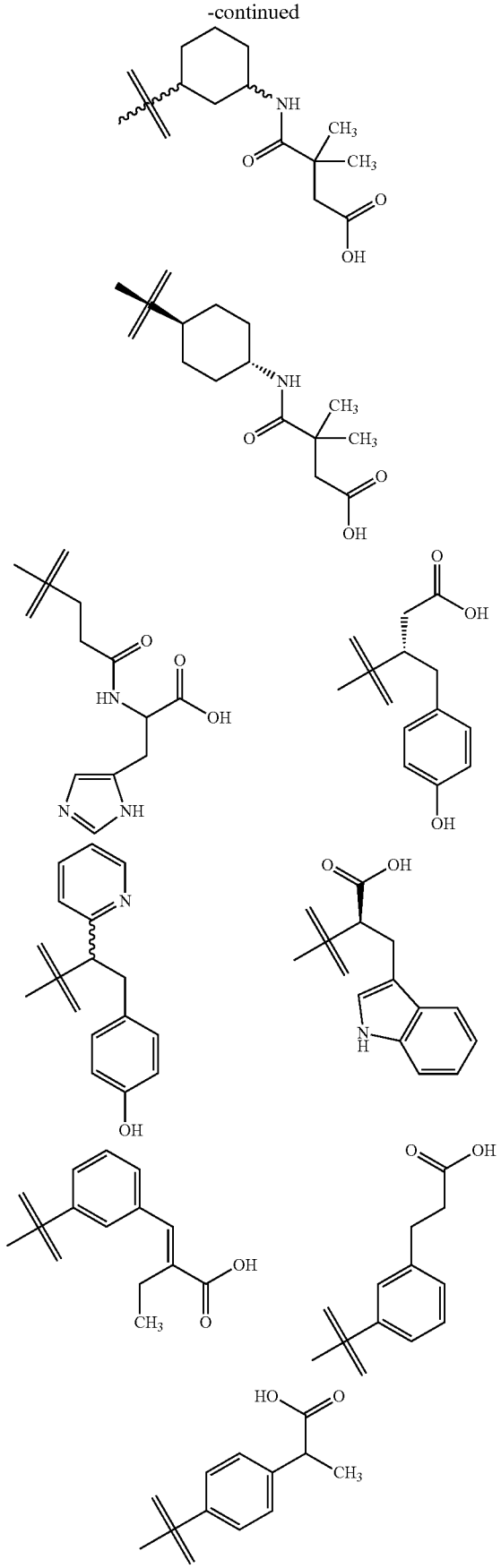
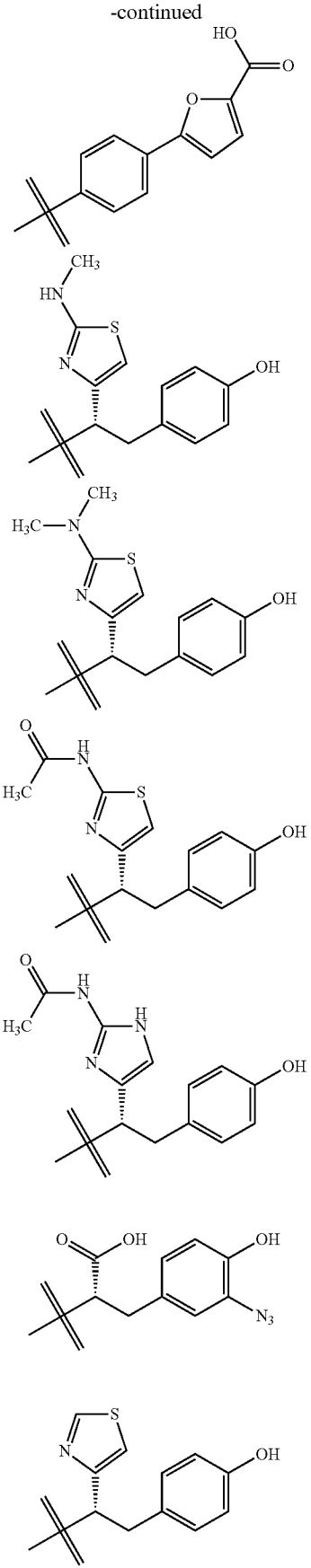

97
-continued
98
-continued
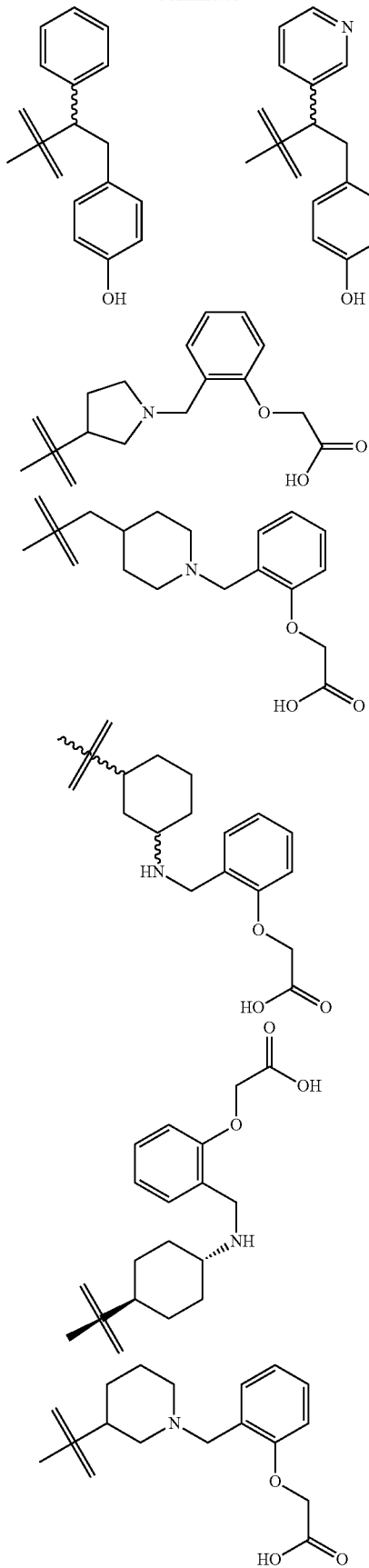
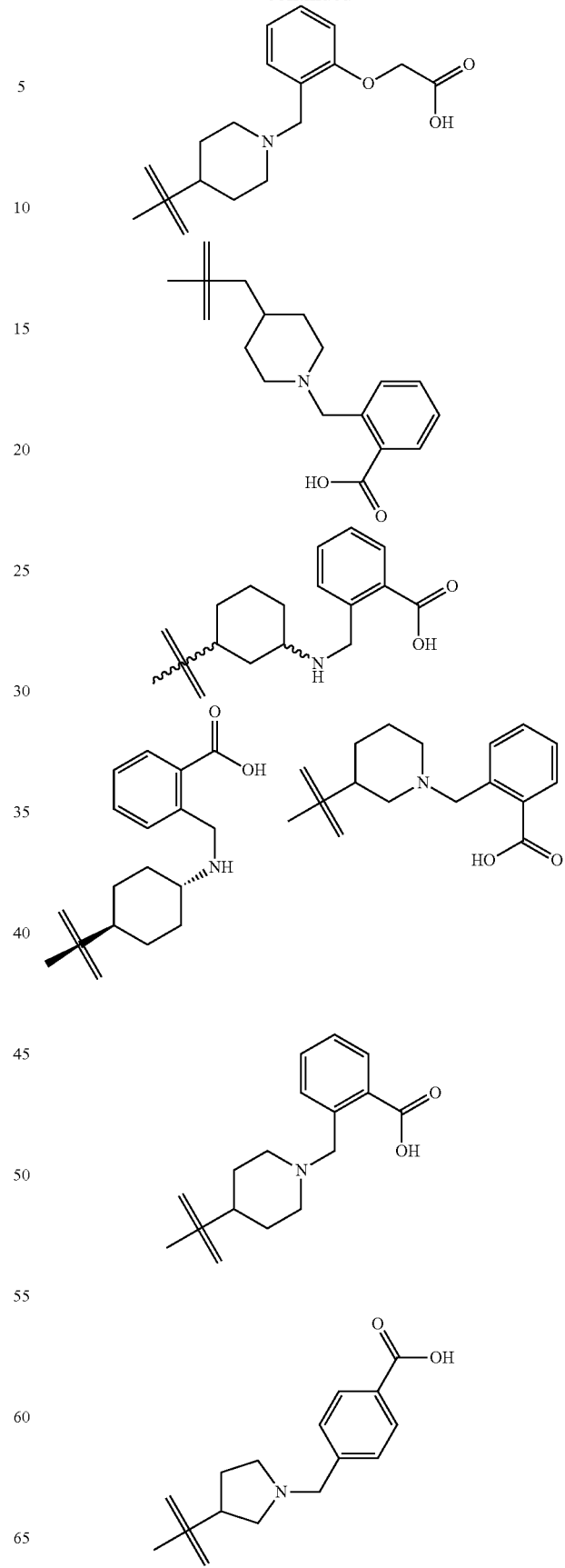

99
-continued
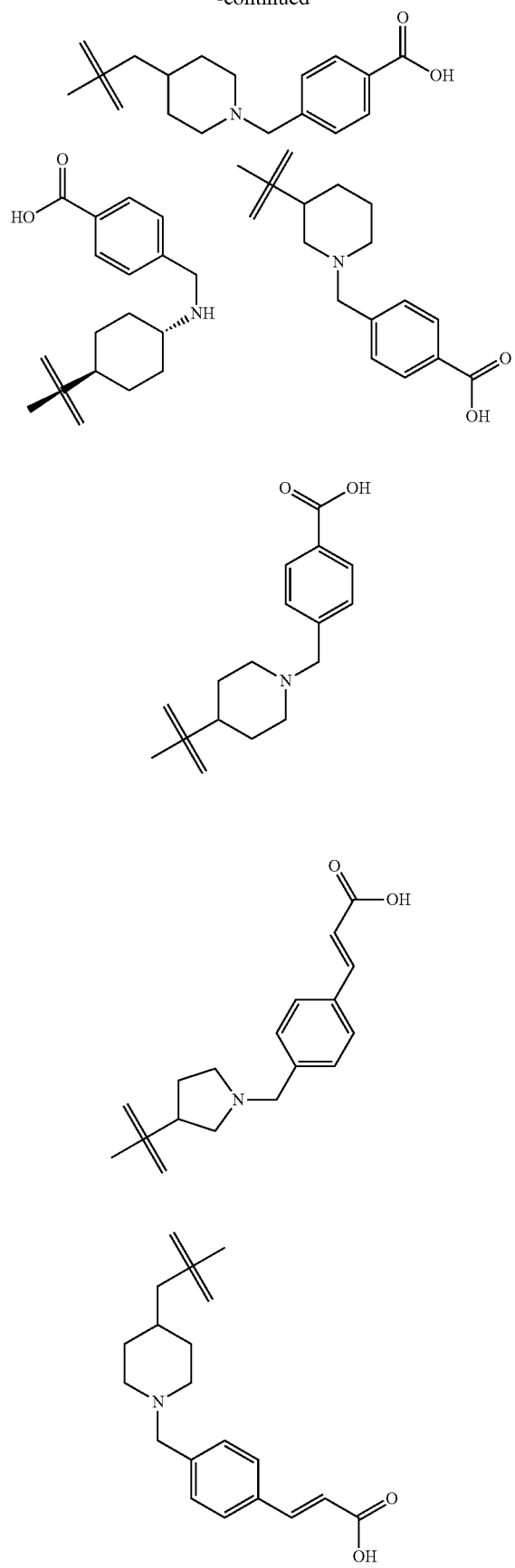
100
-continued
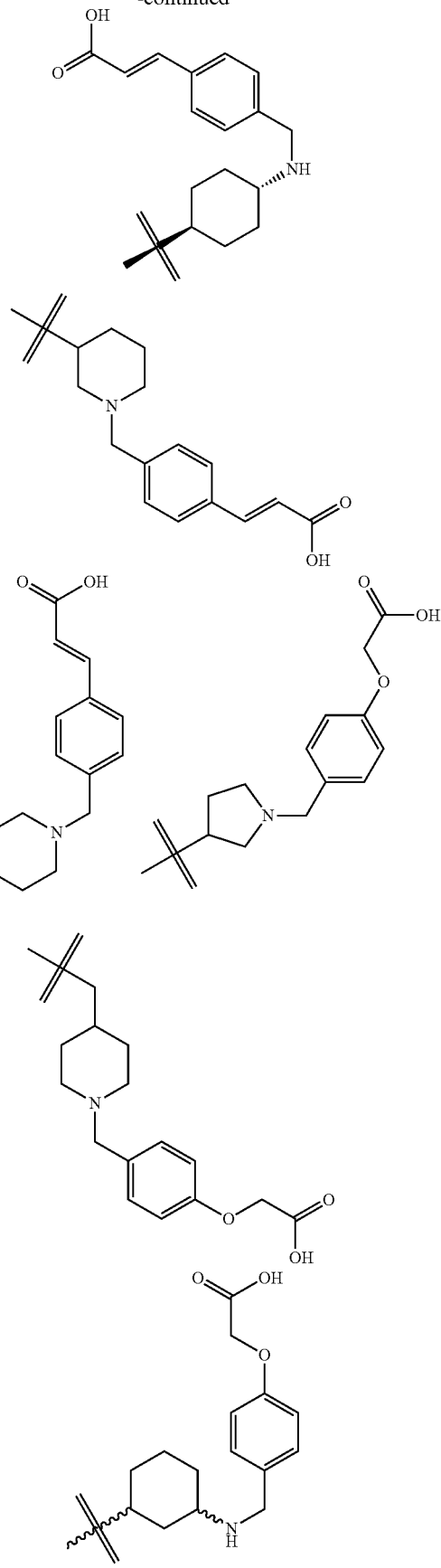

101
-continued
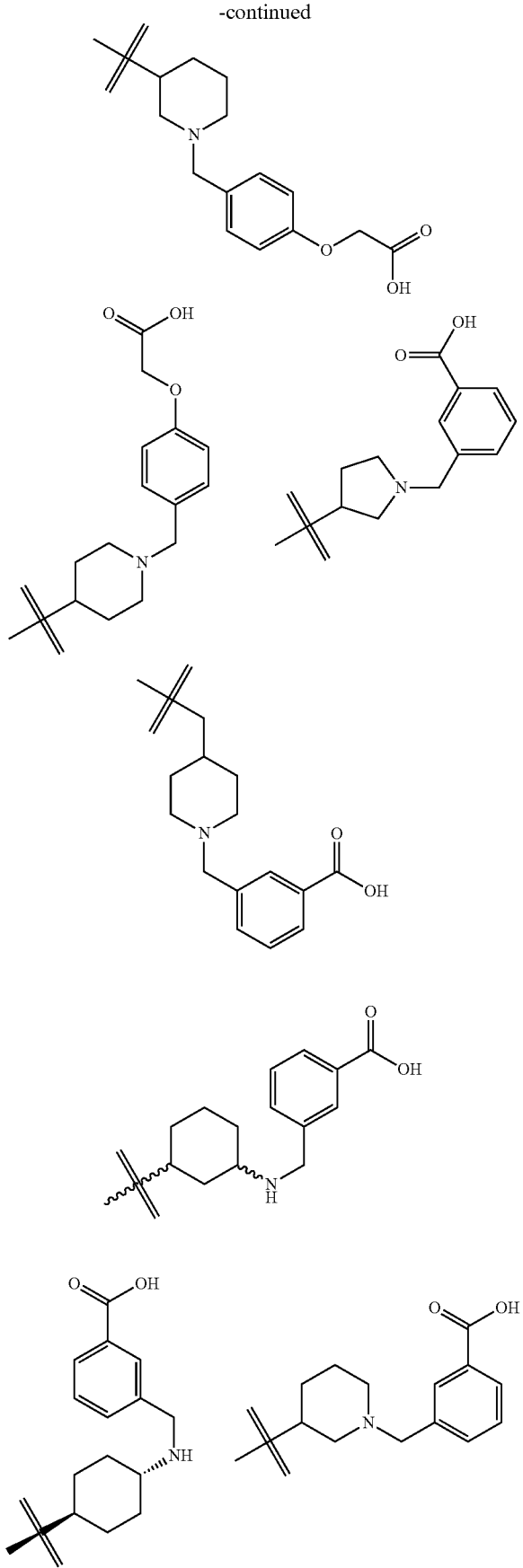
102
-continued
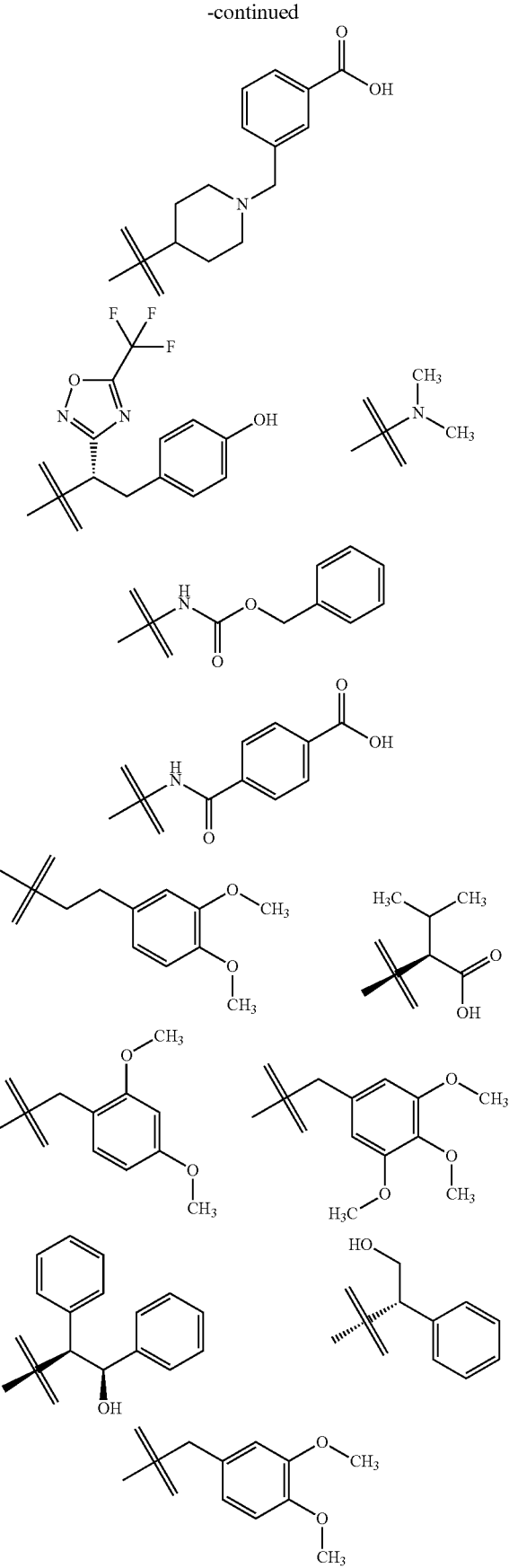

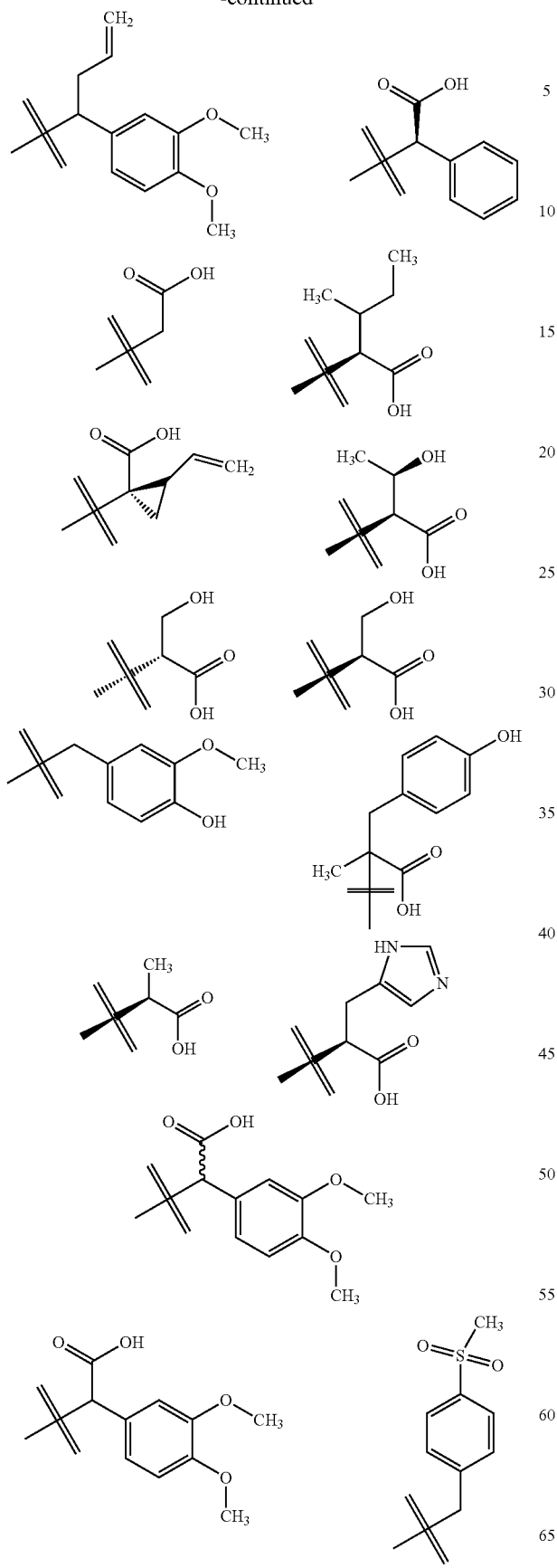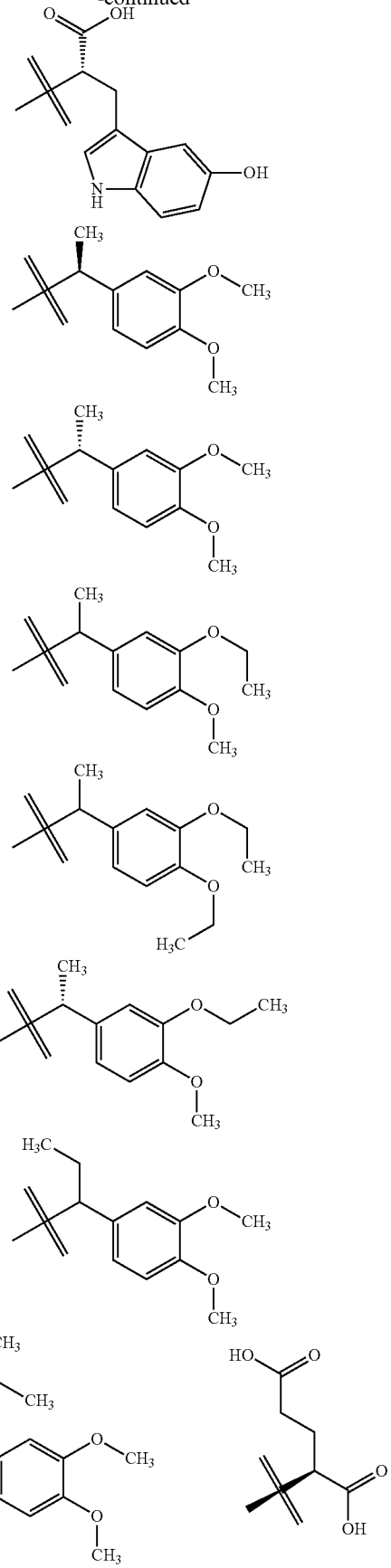

105
-continued
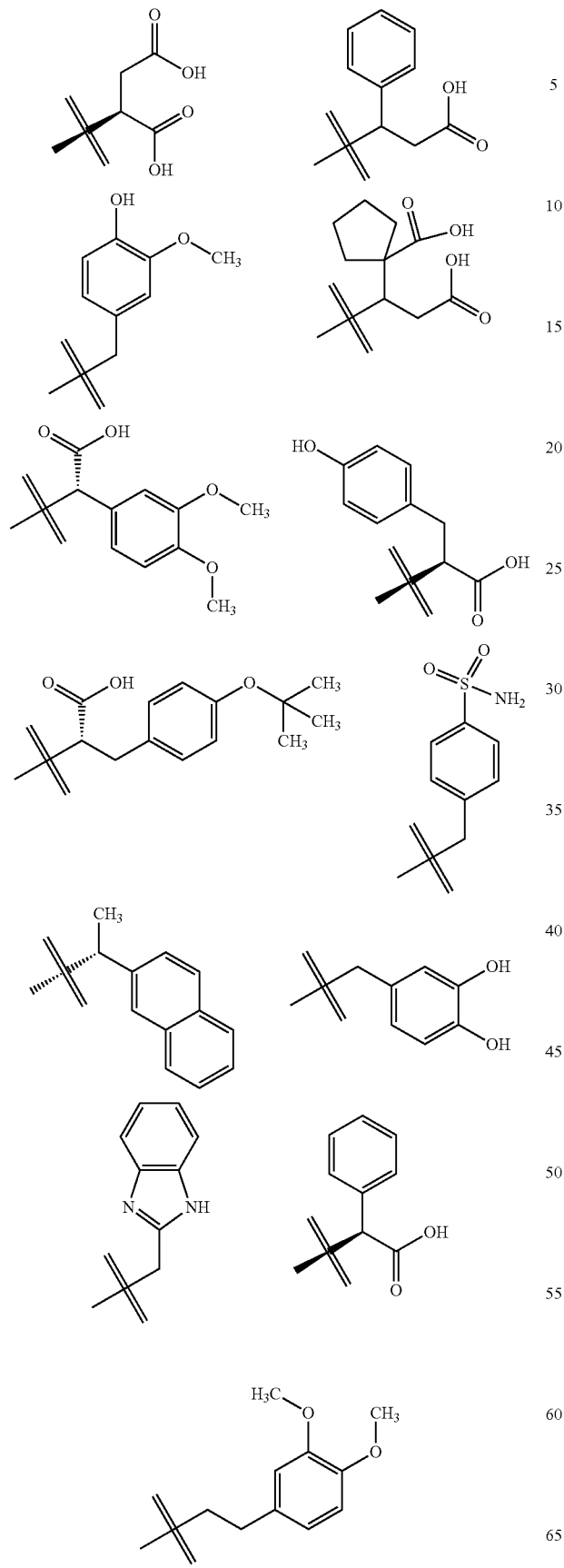
106
-continued
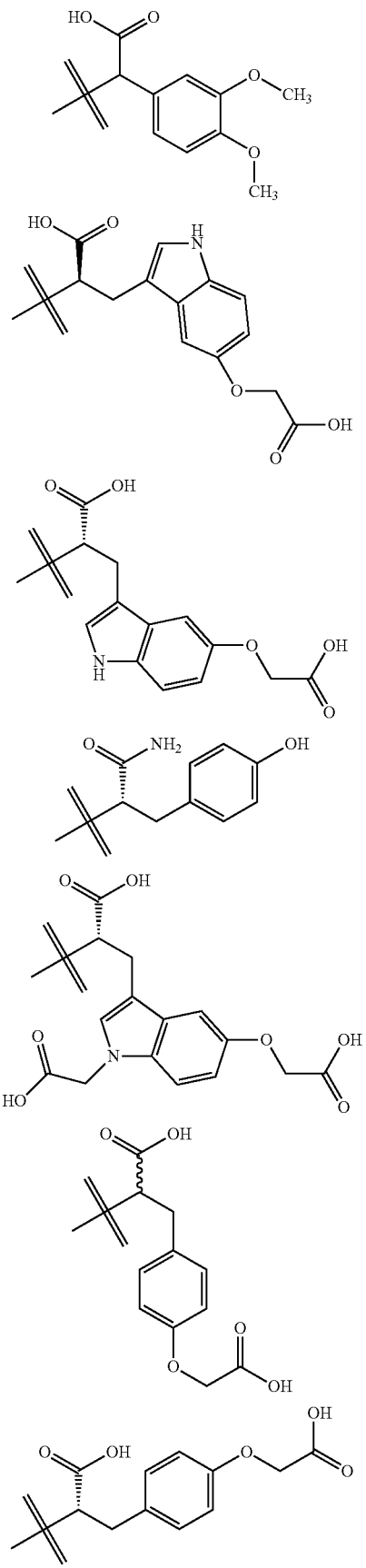

107
-continued
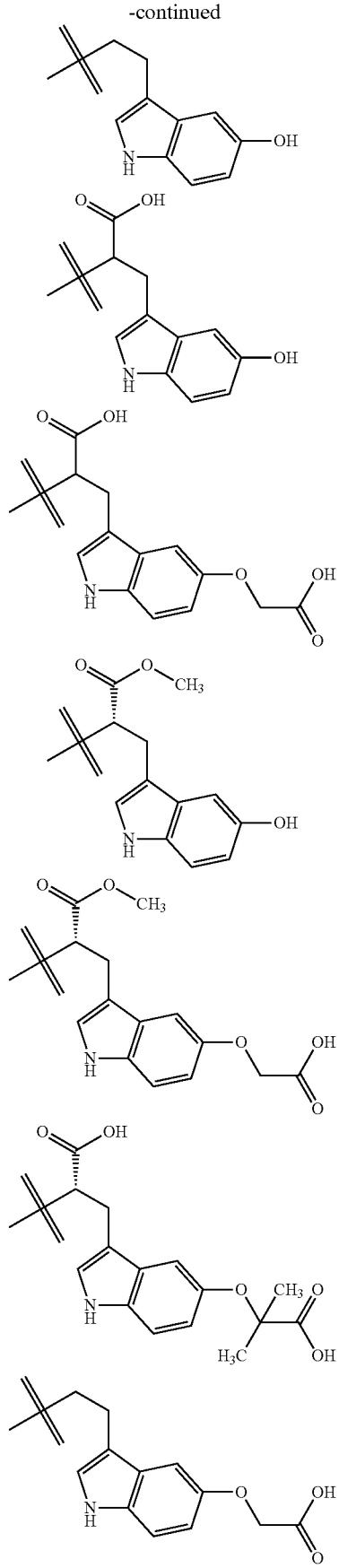
108
-continued
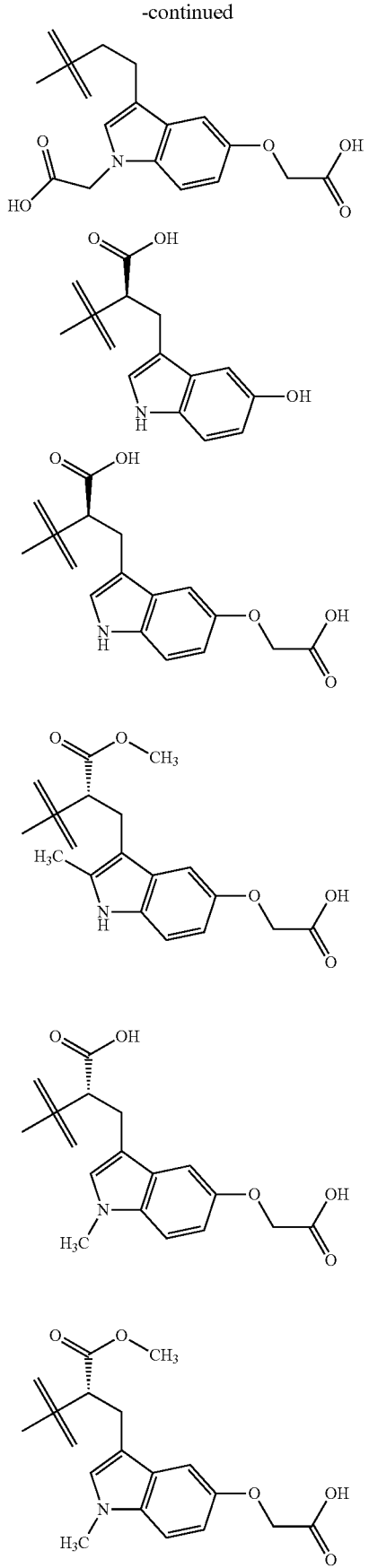

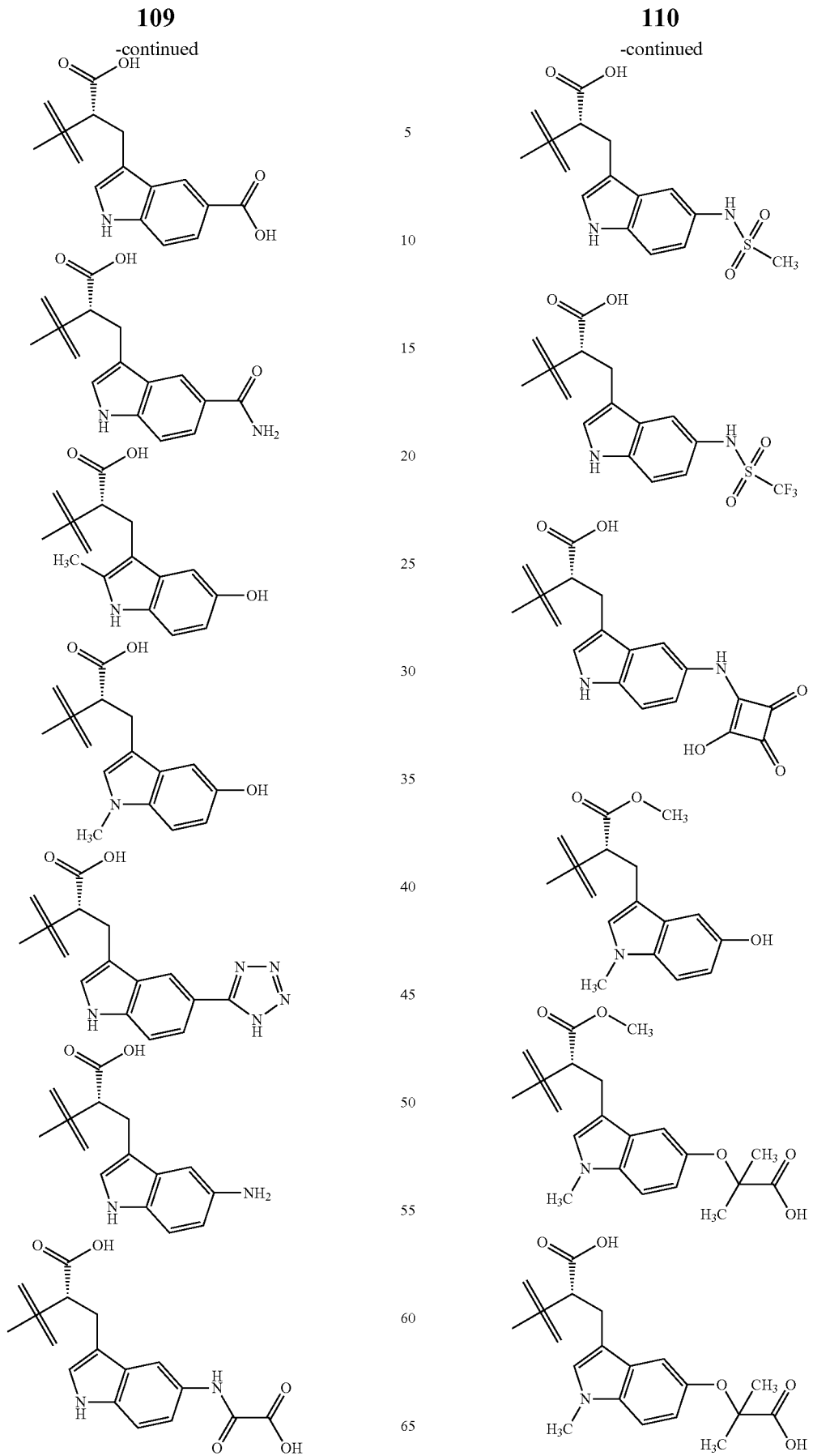

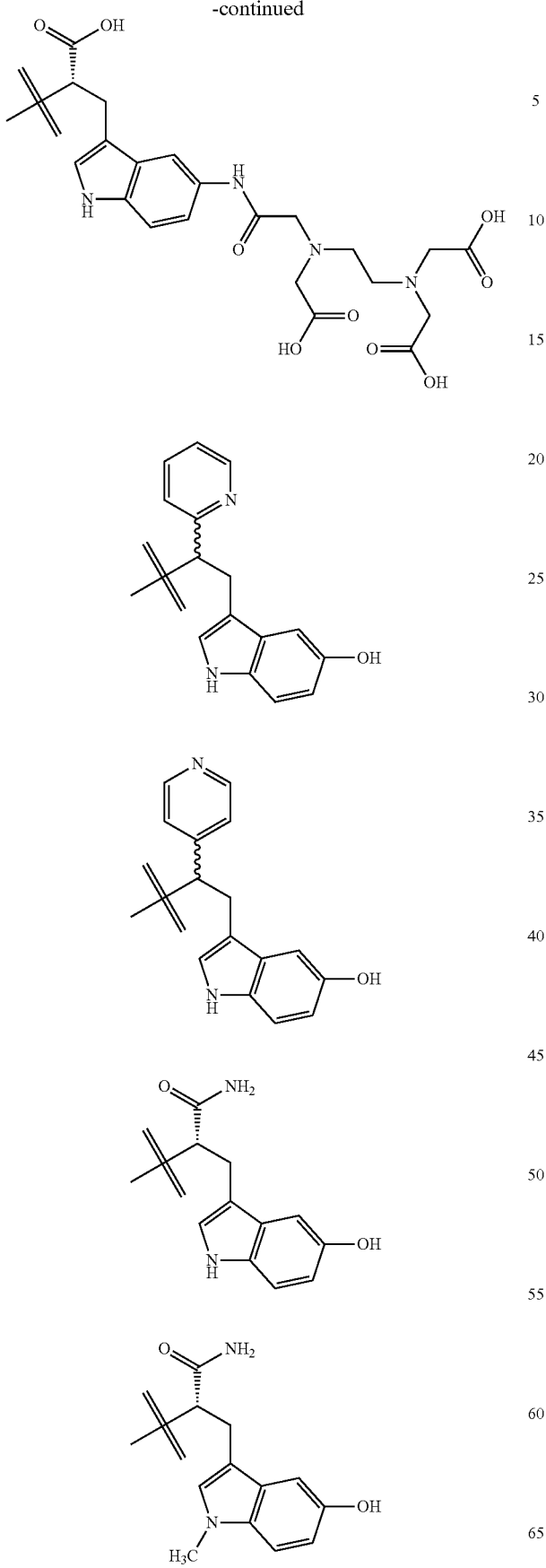
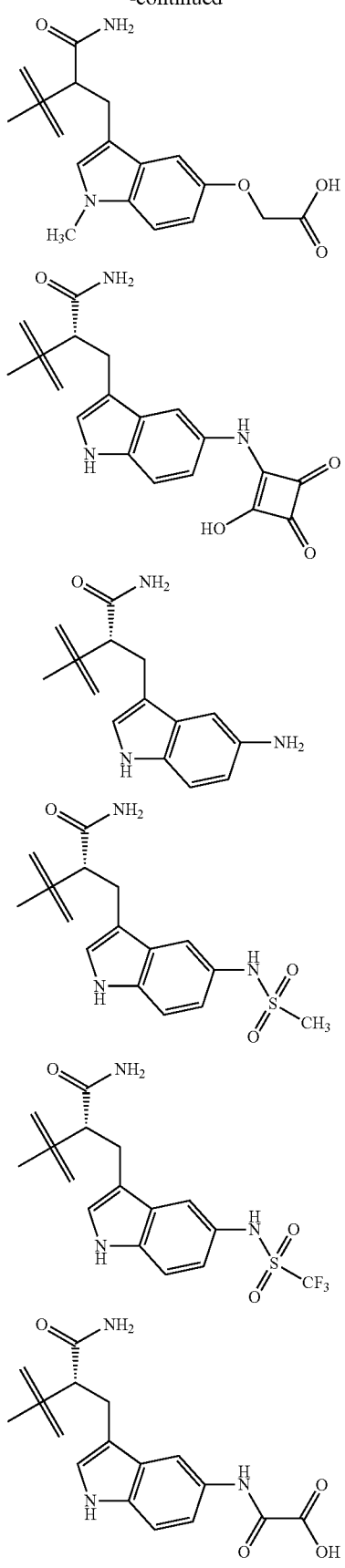

113 -continued
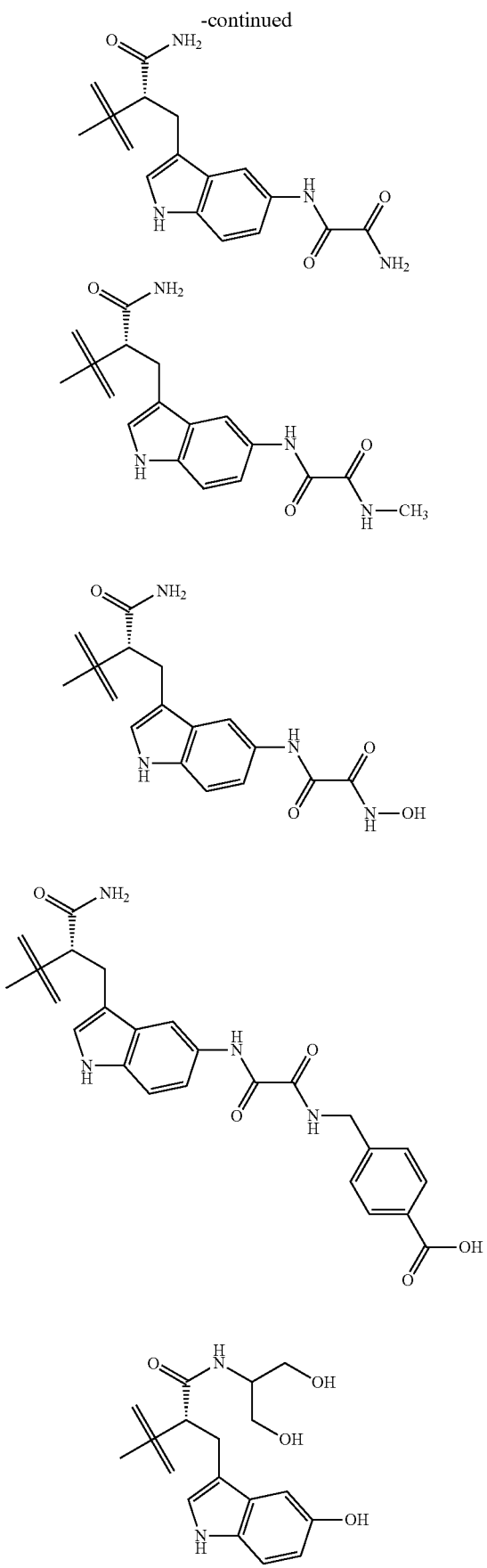
114 -continued
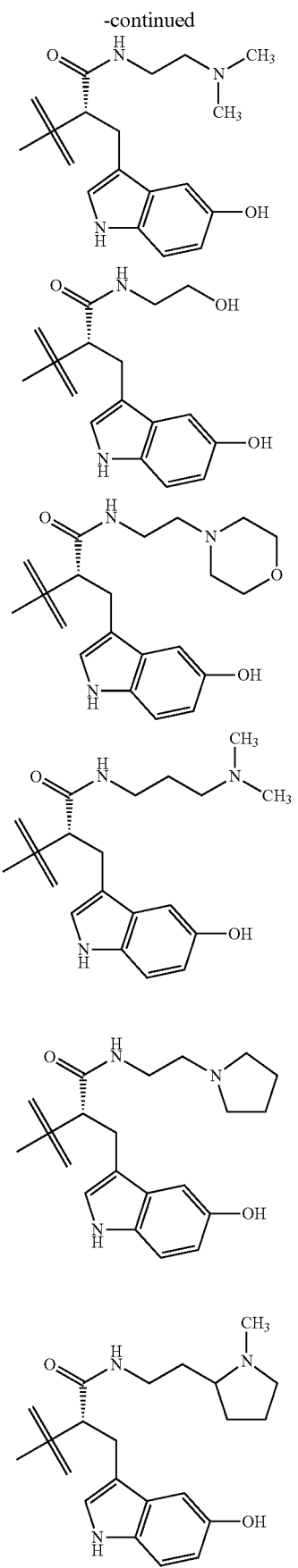

115
-continued
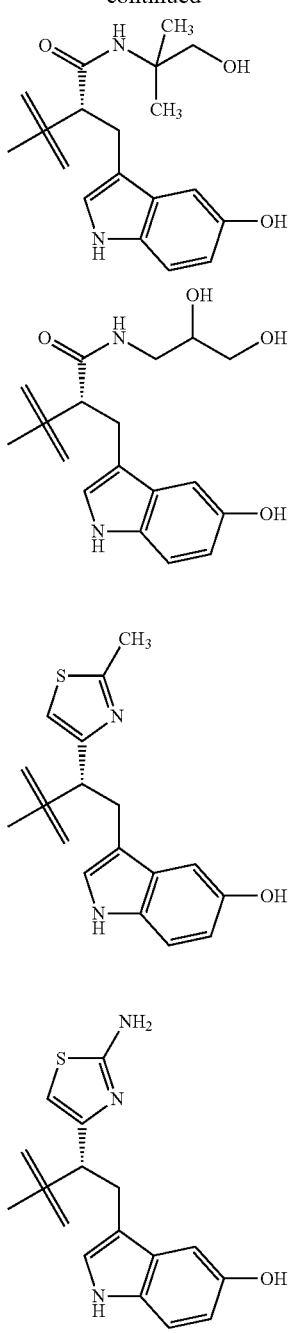
116
-continued
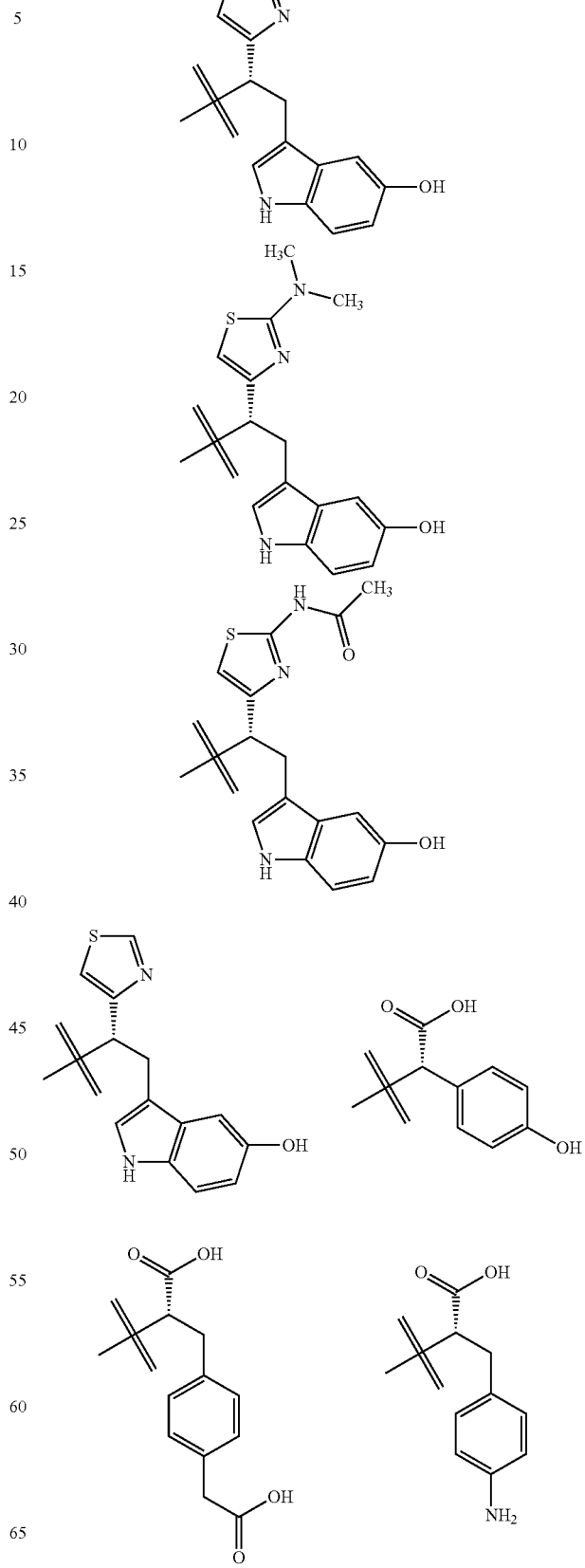

117
-continued
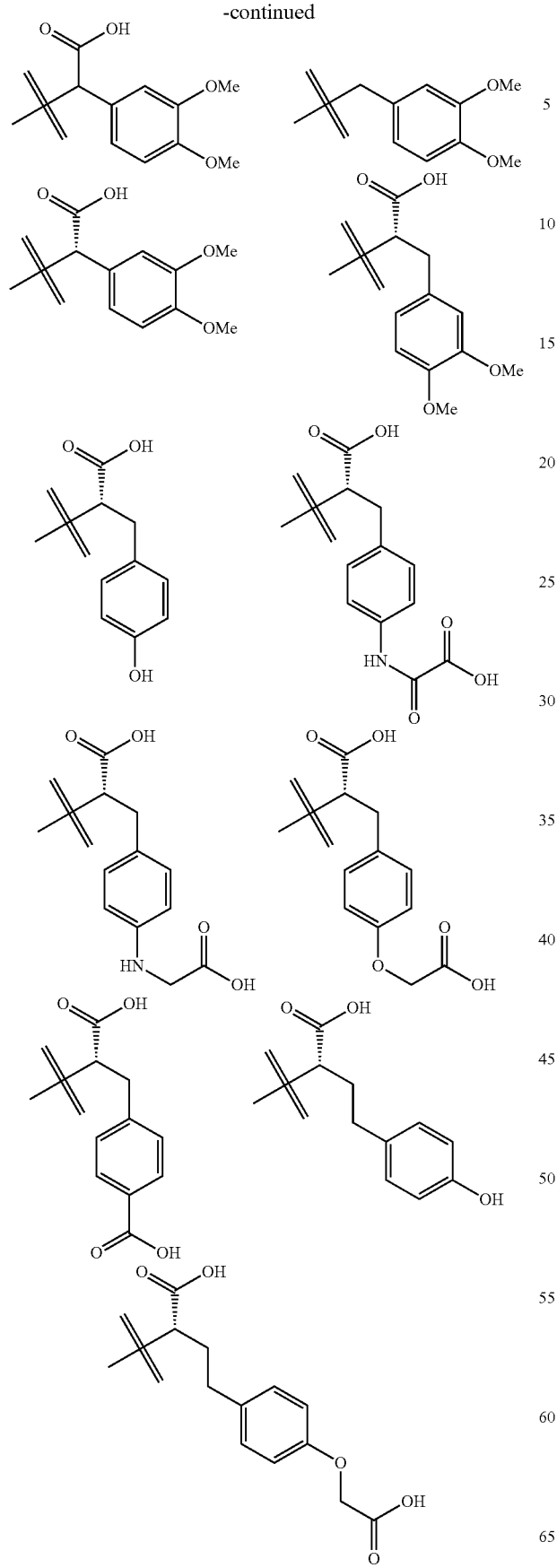
118
-continued
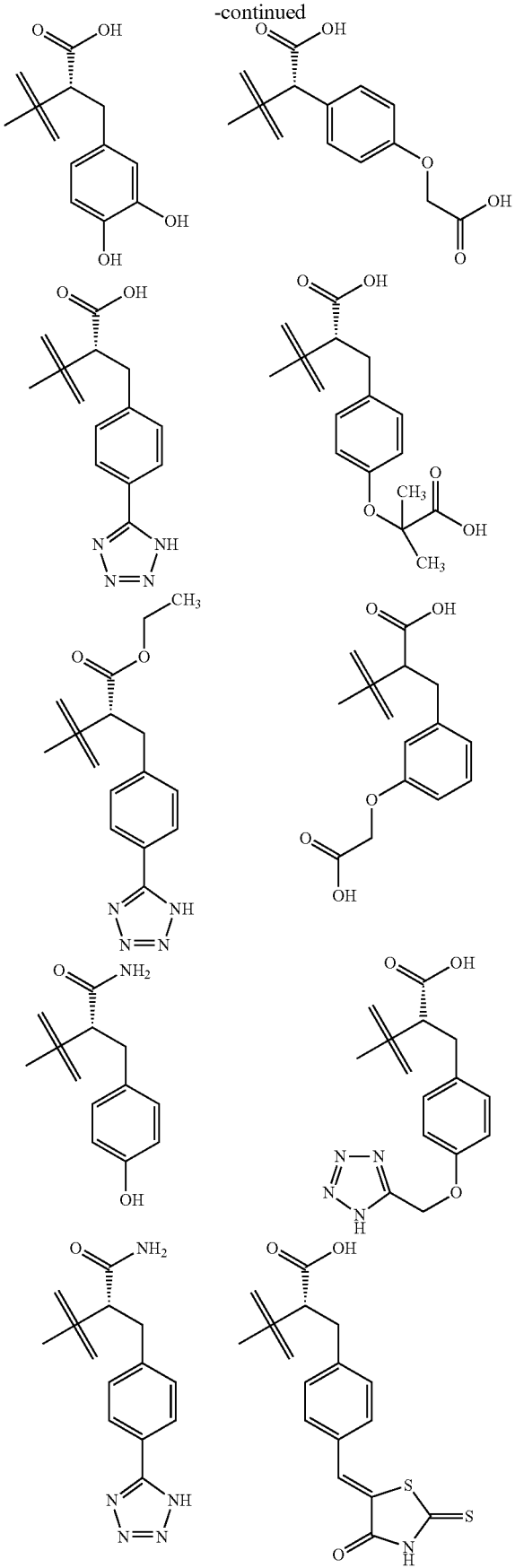

119
-continued
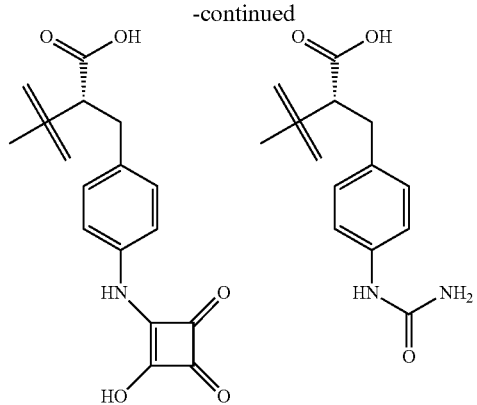
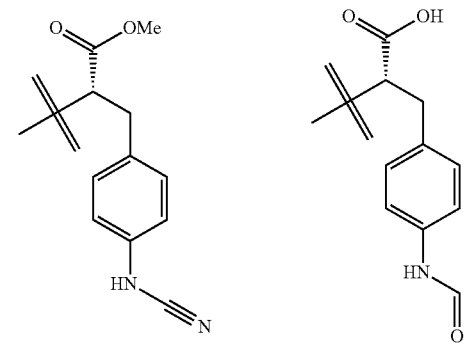
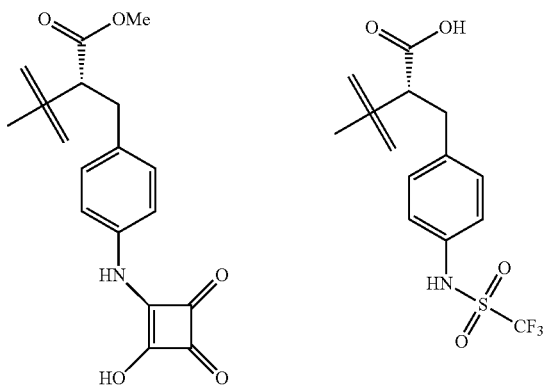
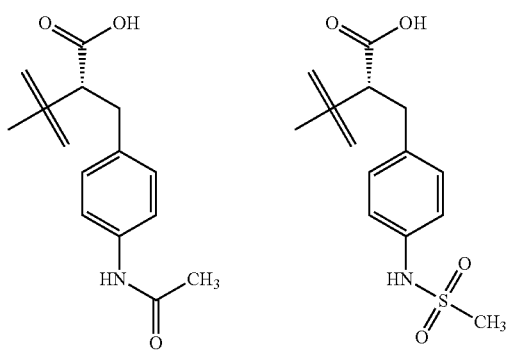
120
-continued
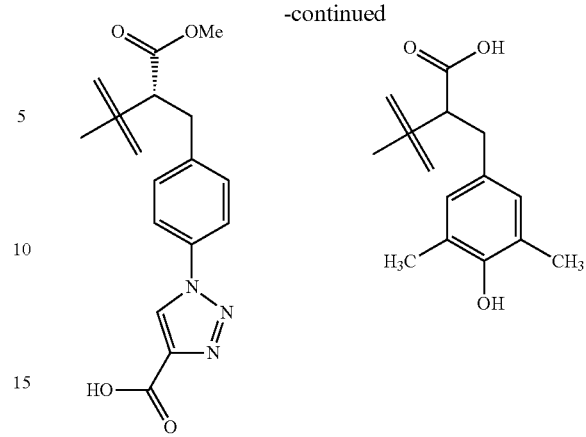
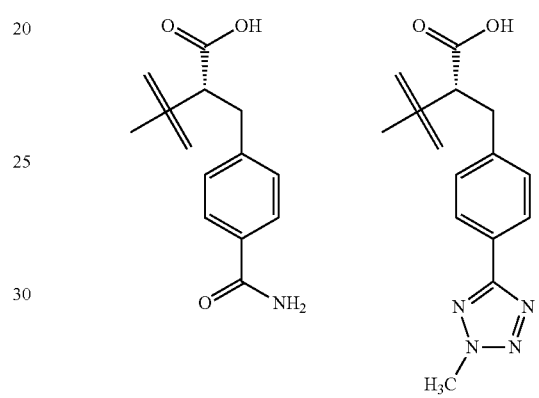
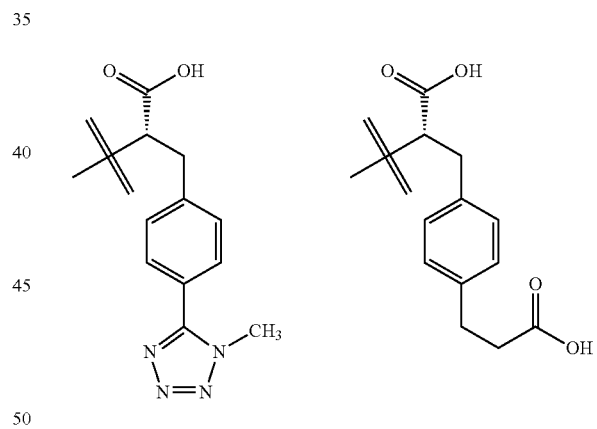
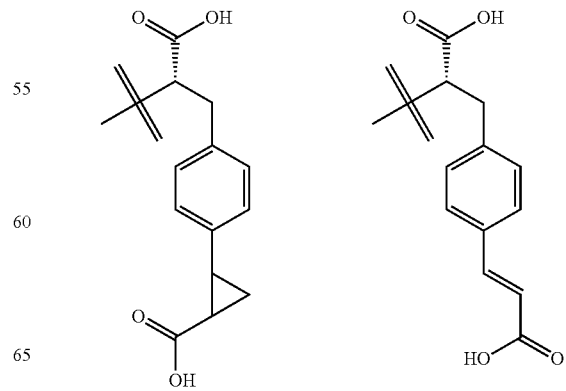

121
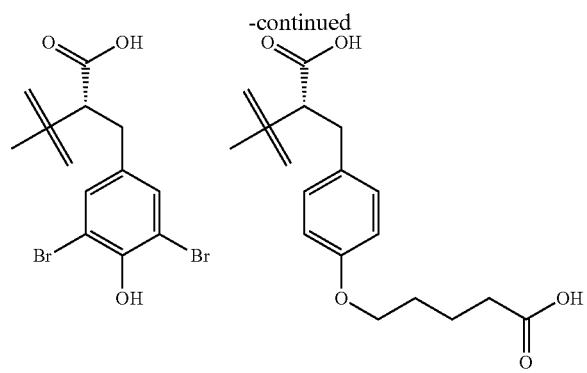
-continued
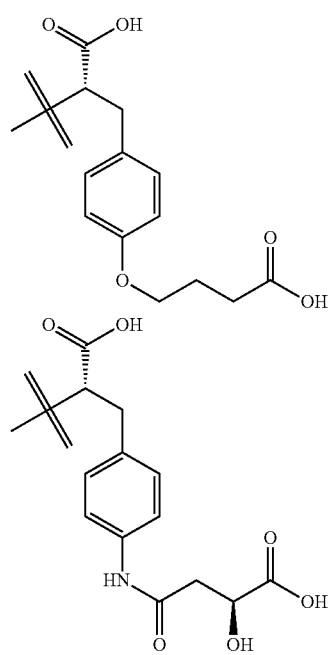
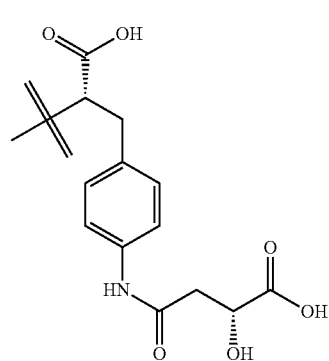
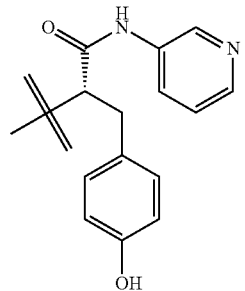
122
-continued
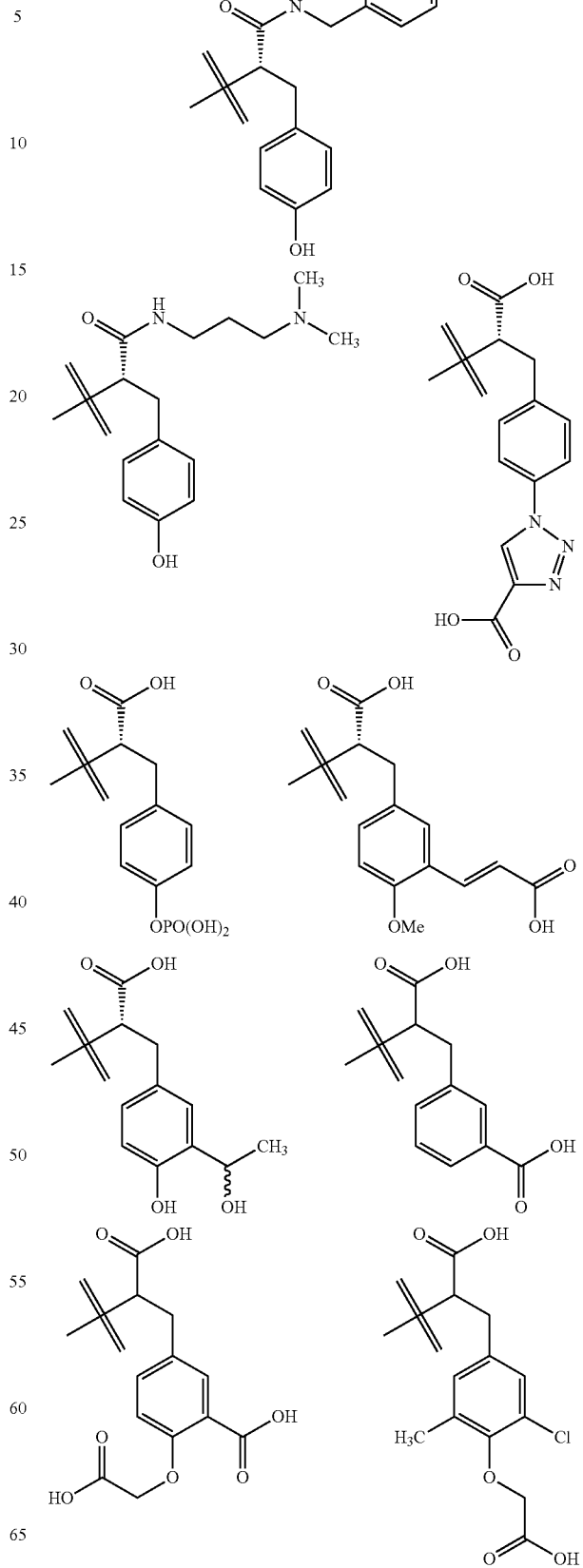

123
-continued
124
-continued
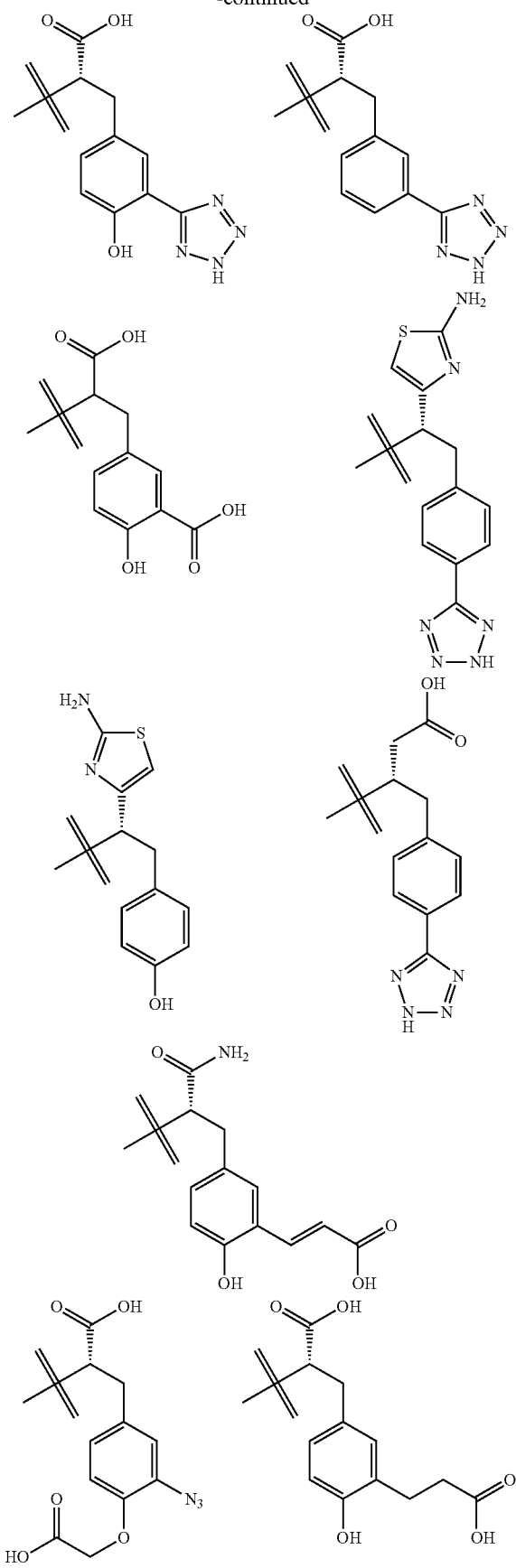
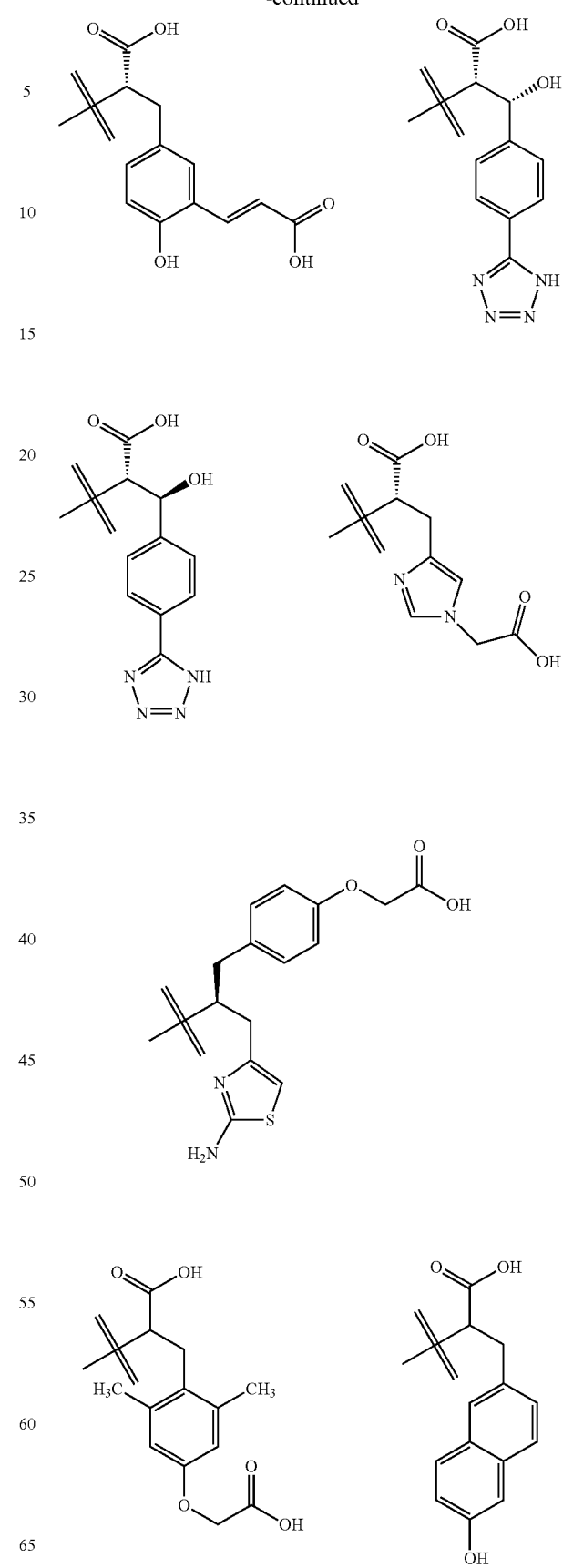

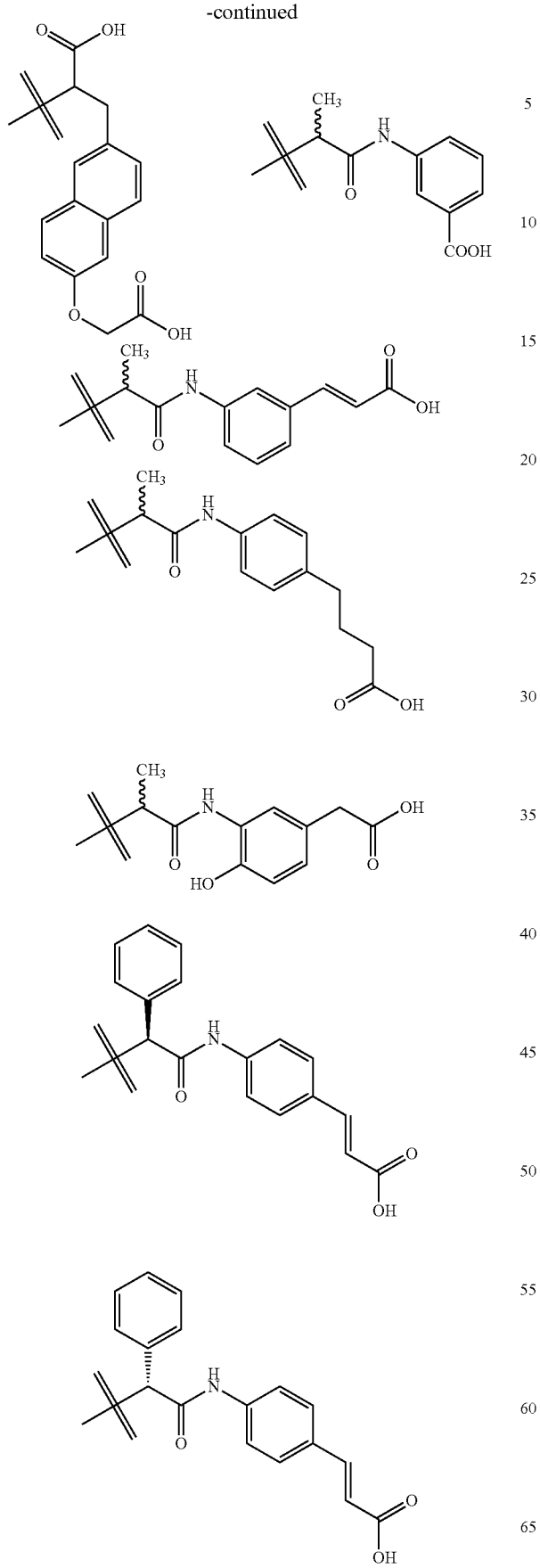
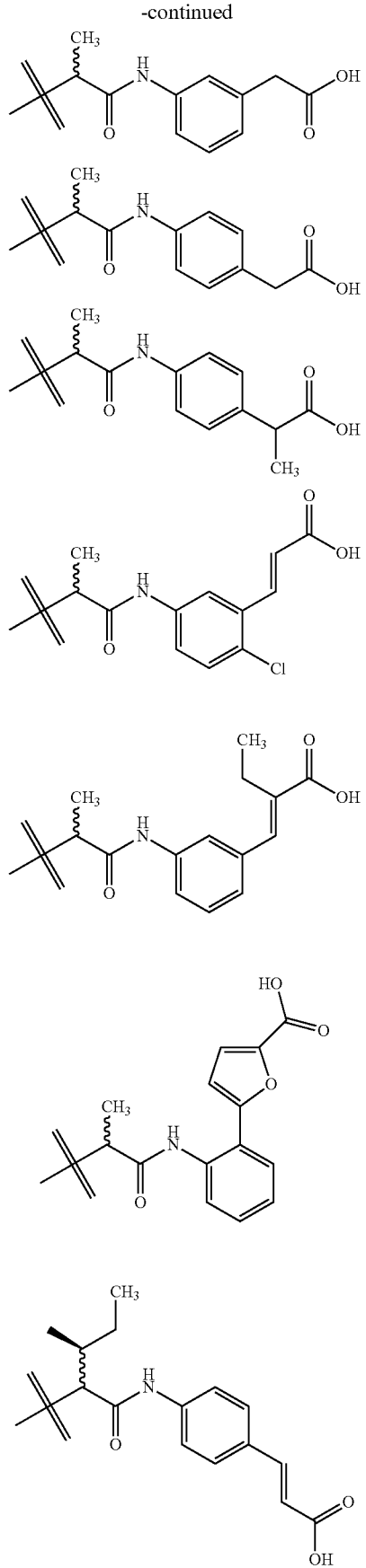

127
-continued
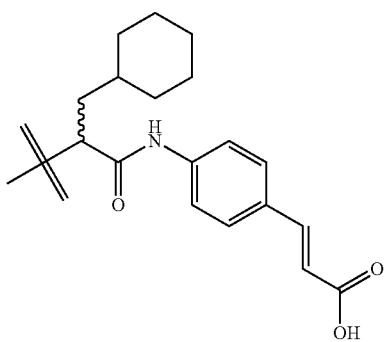
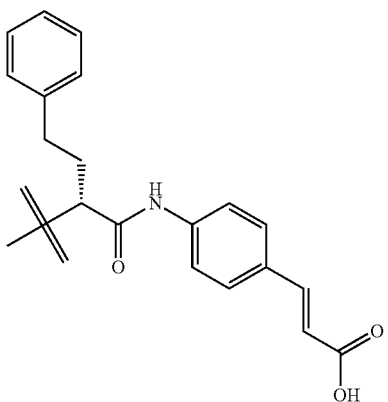
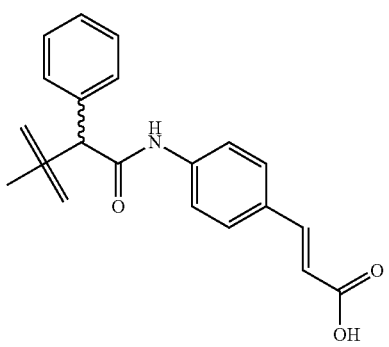
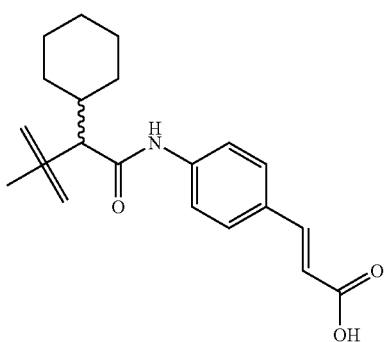
128
-continued
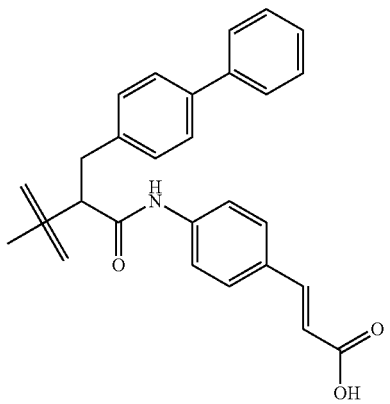
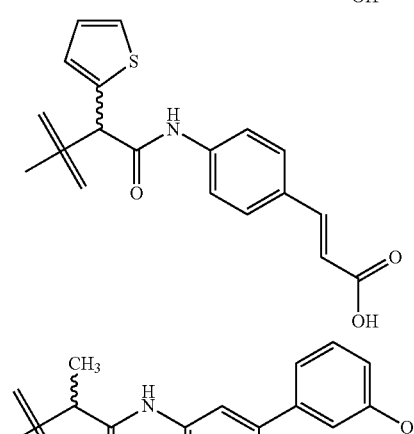
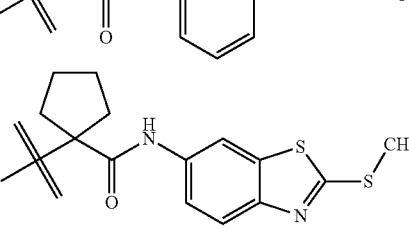
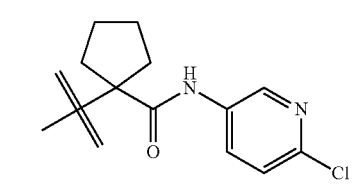
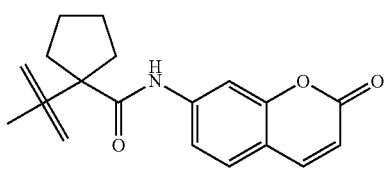
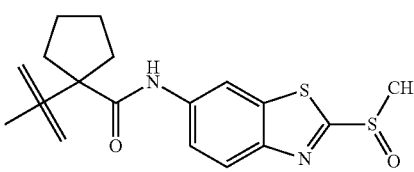

129
-continued
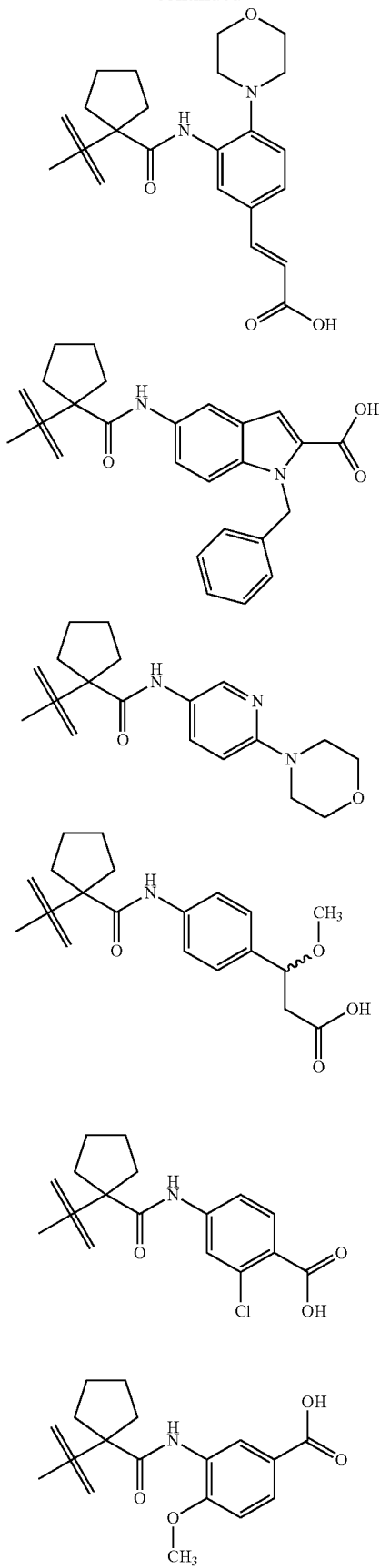
130
-continued
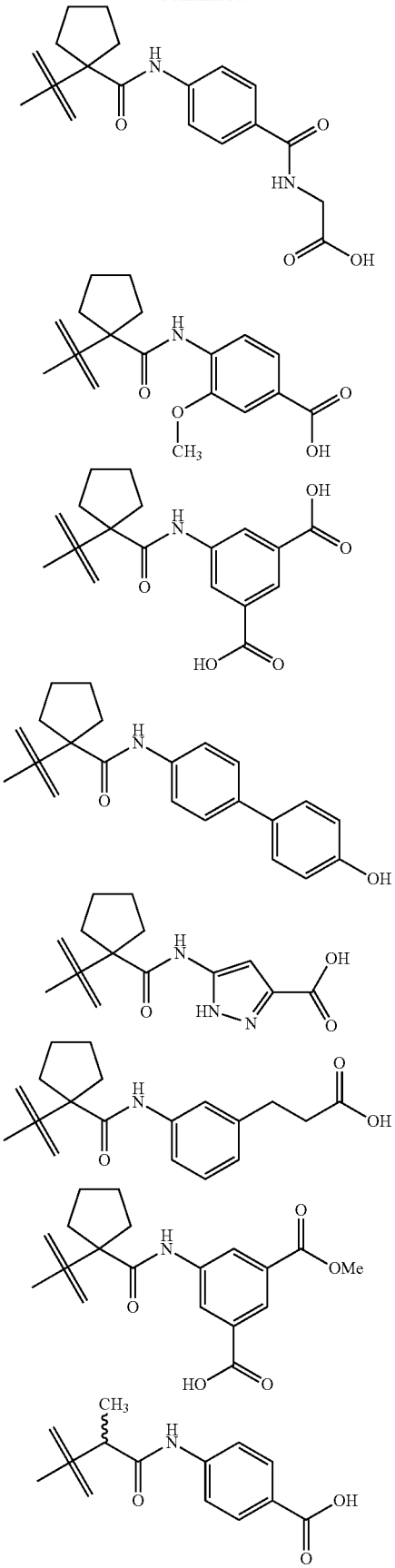

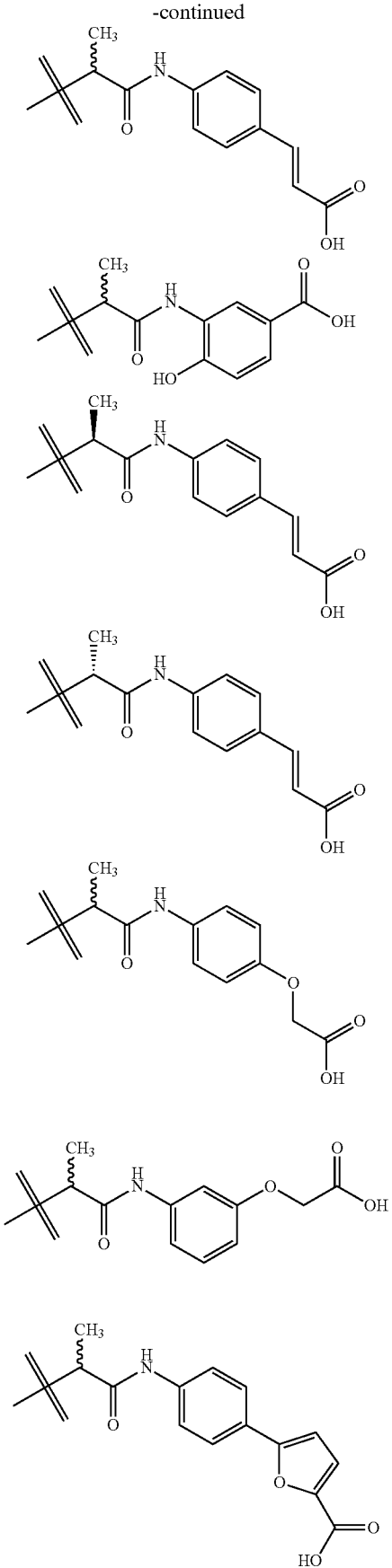
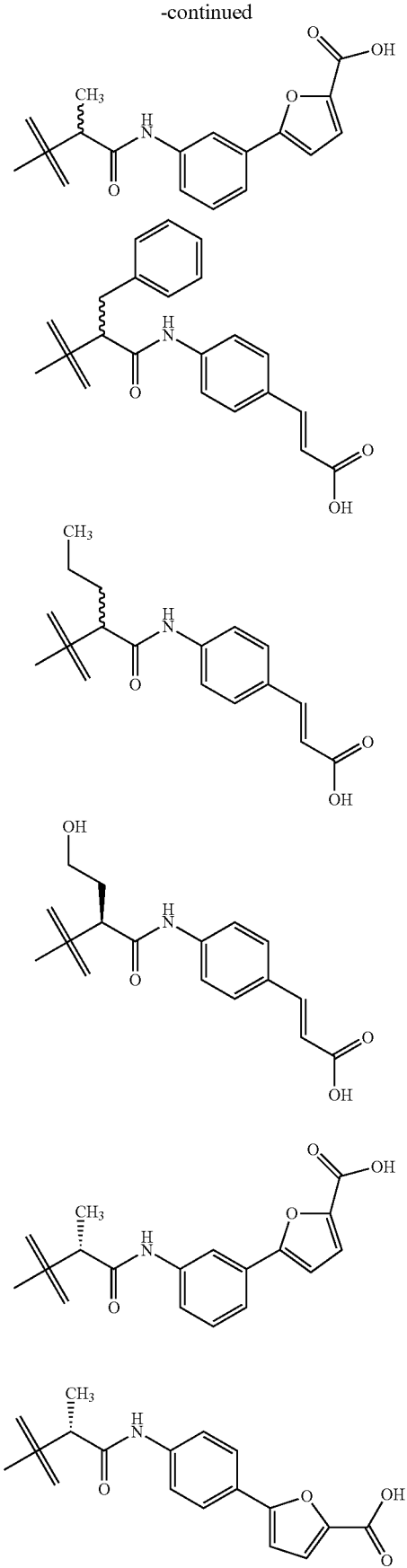

133
-continued
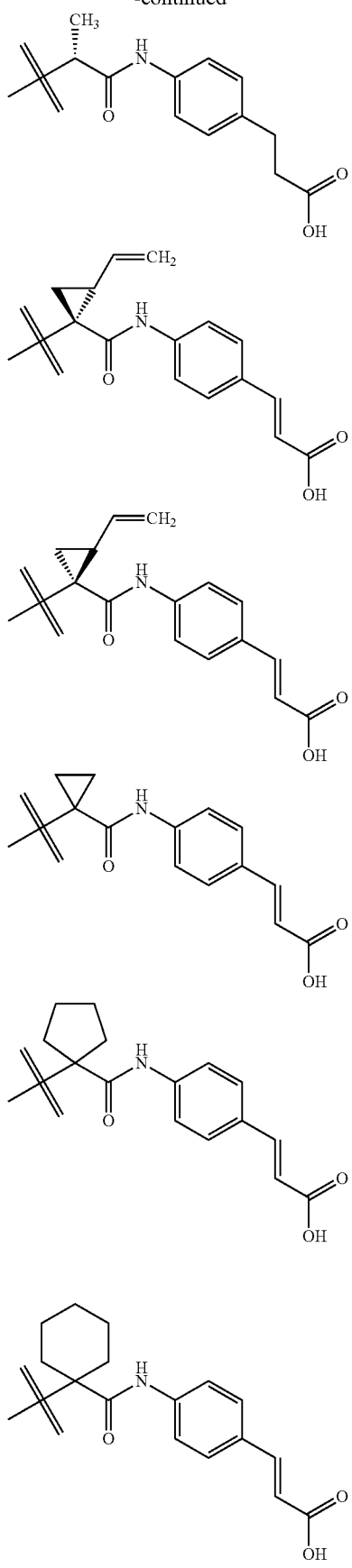
134
-continued
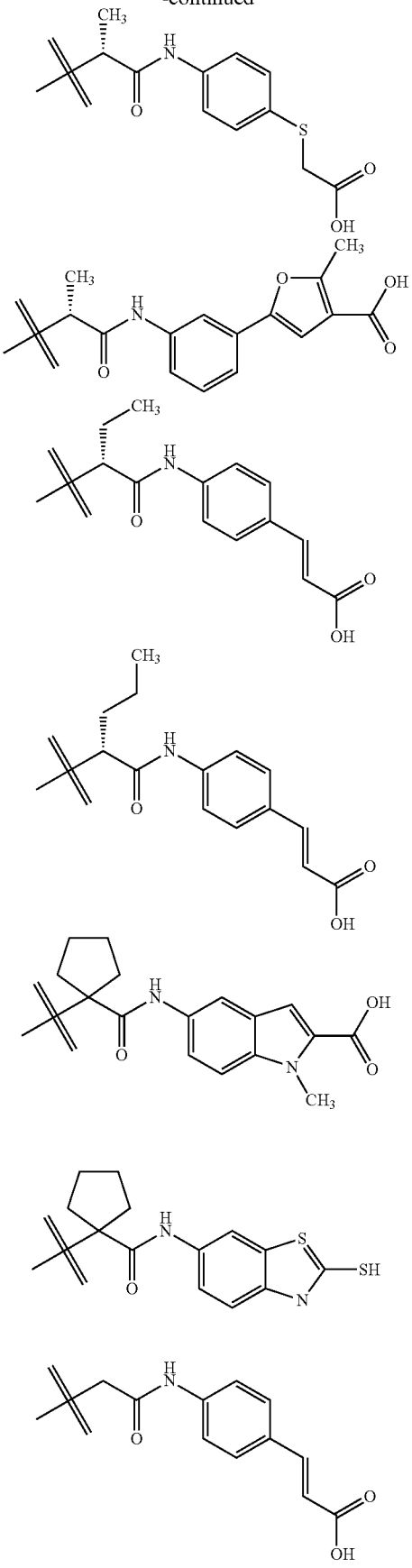

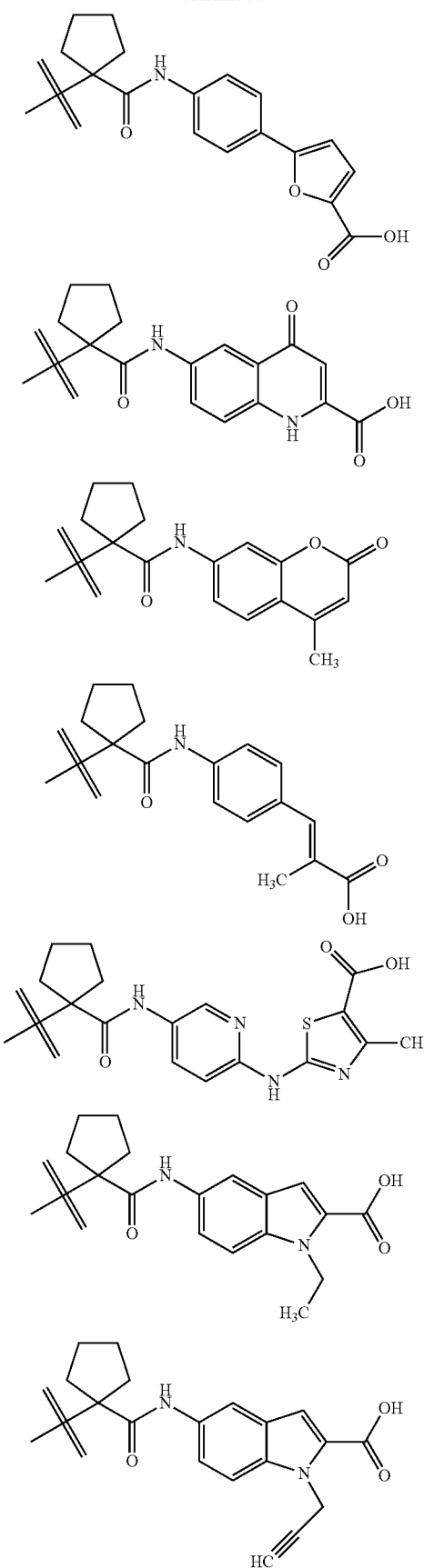
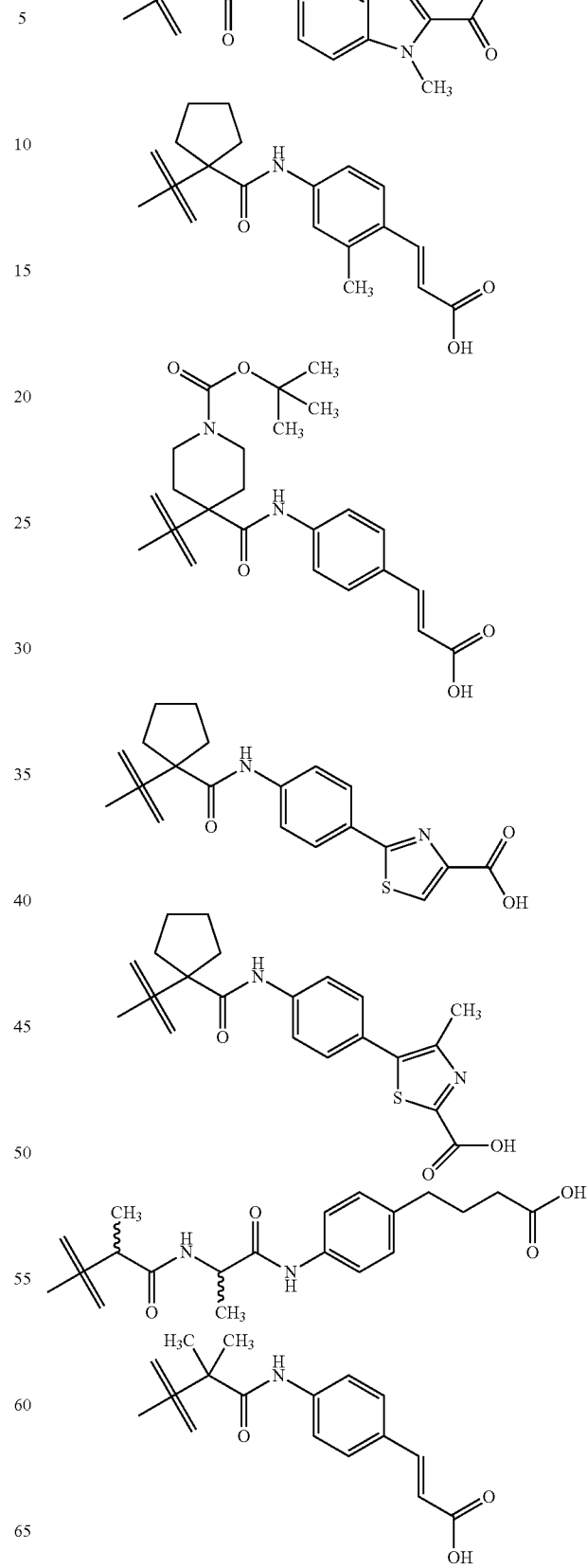

137
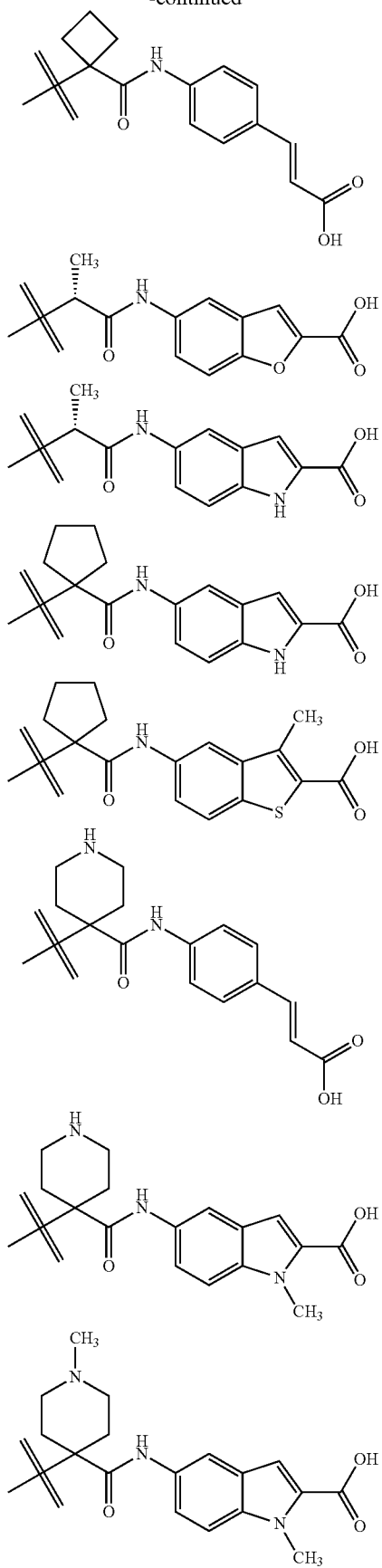
138
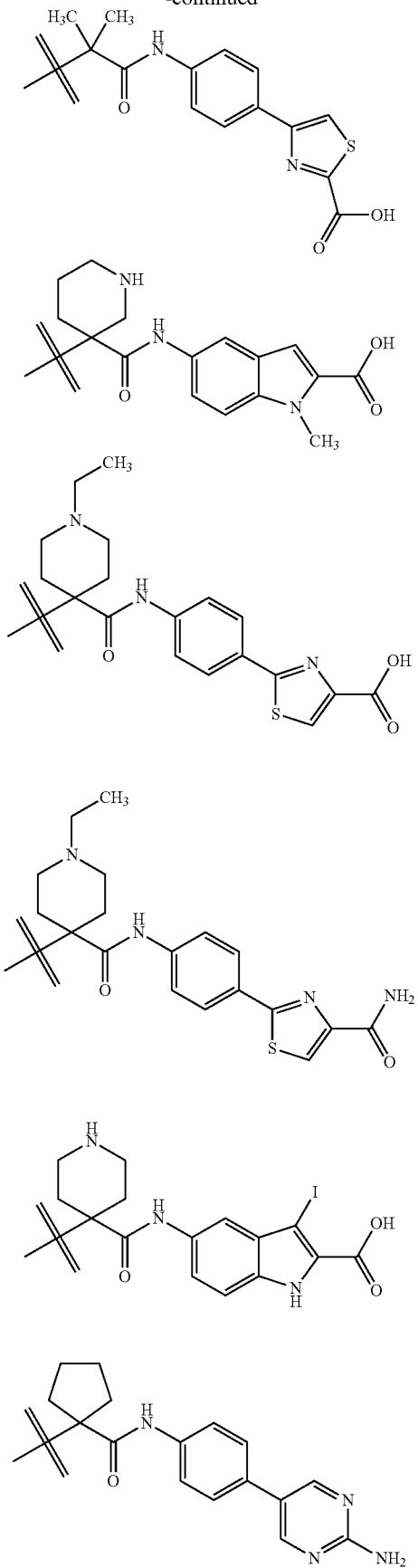

139
-continued
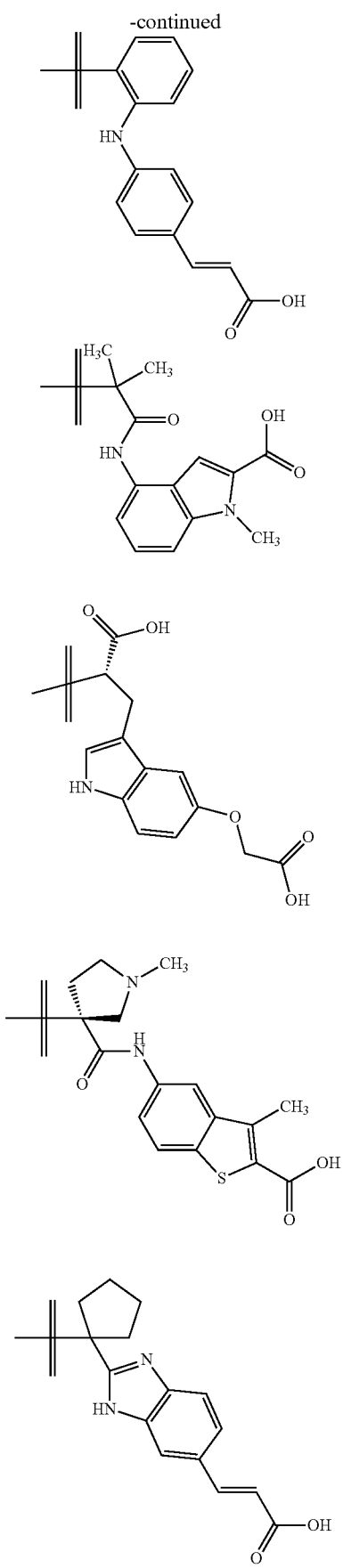
140
-continued
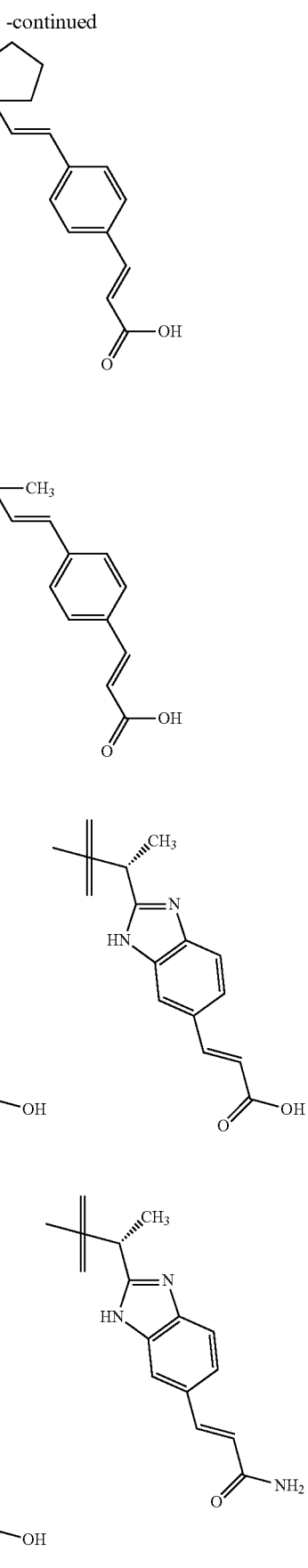

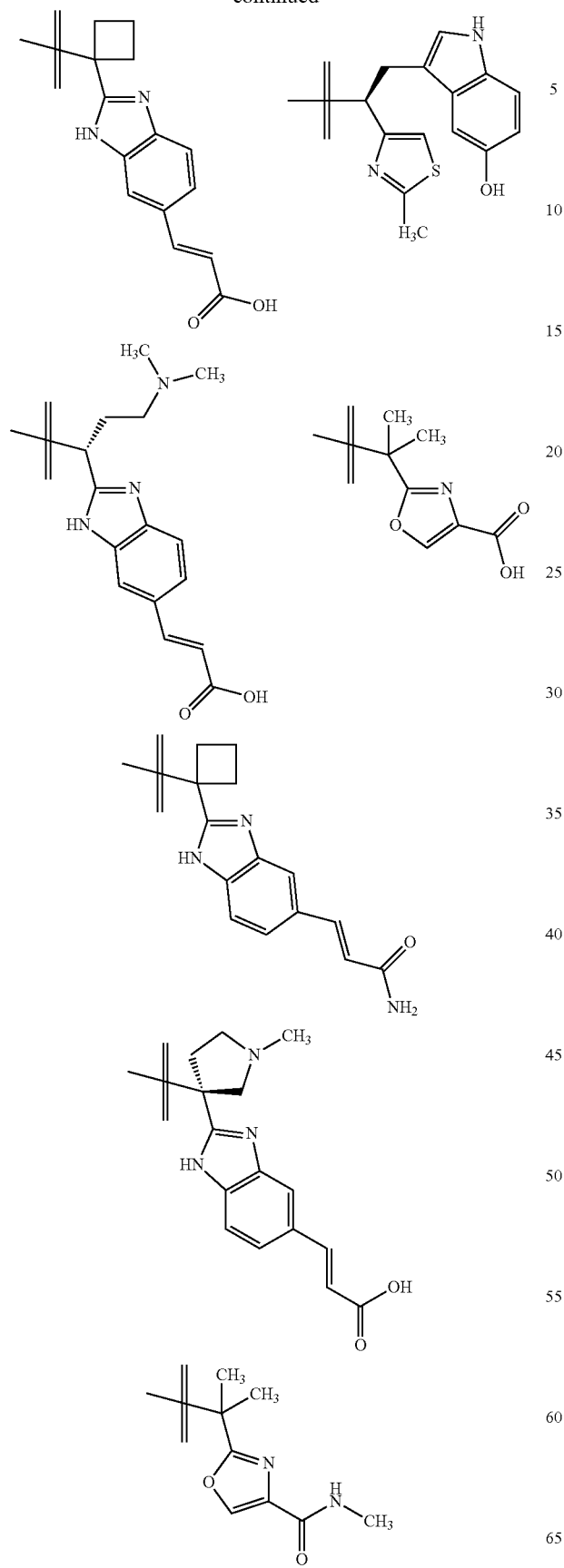
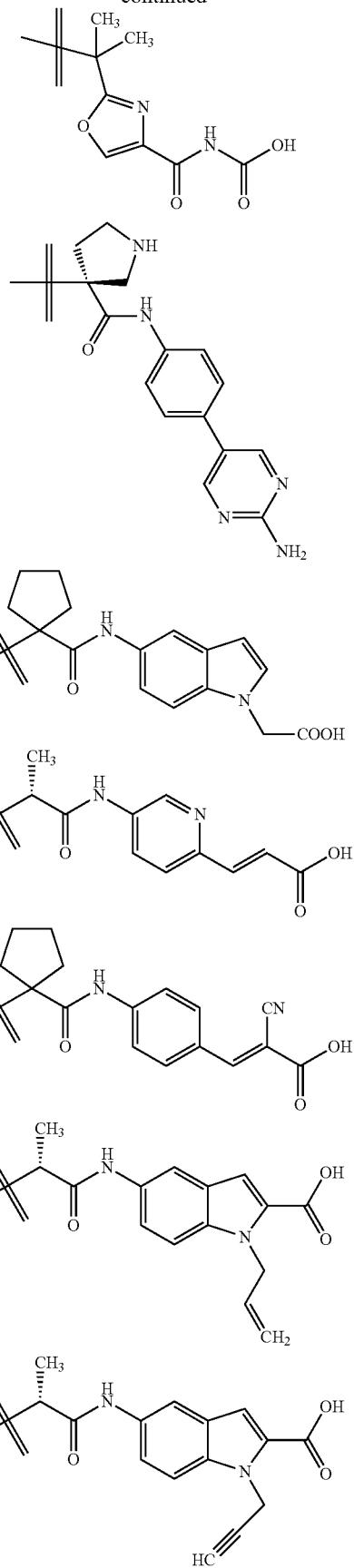

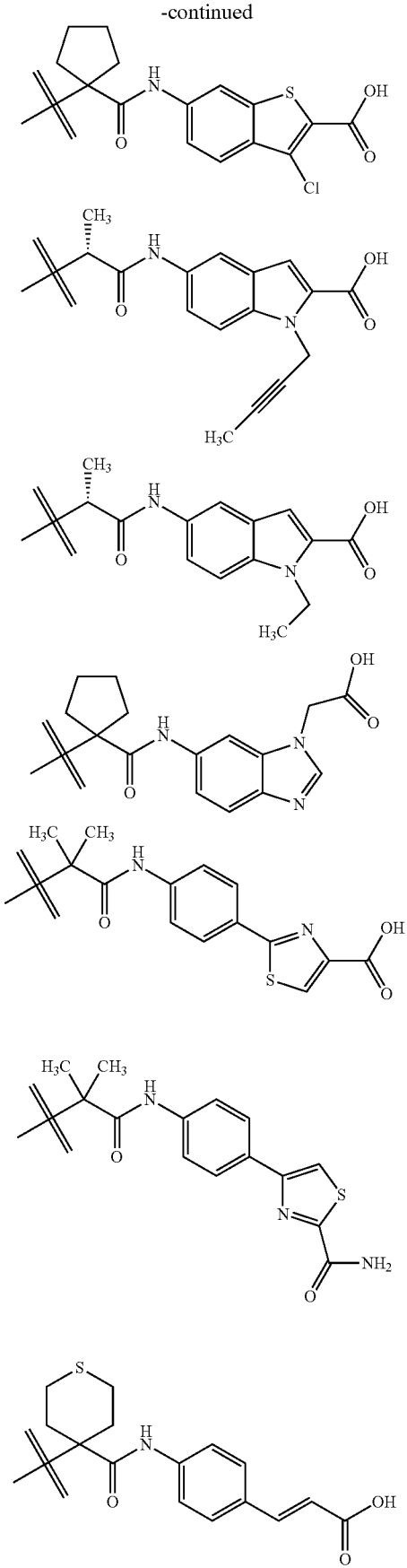
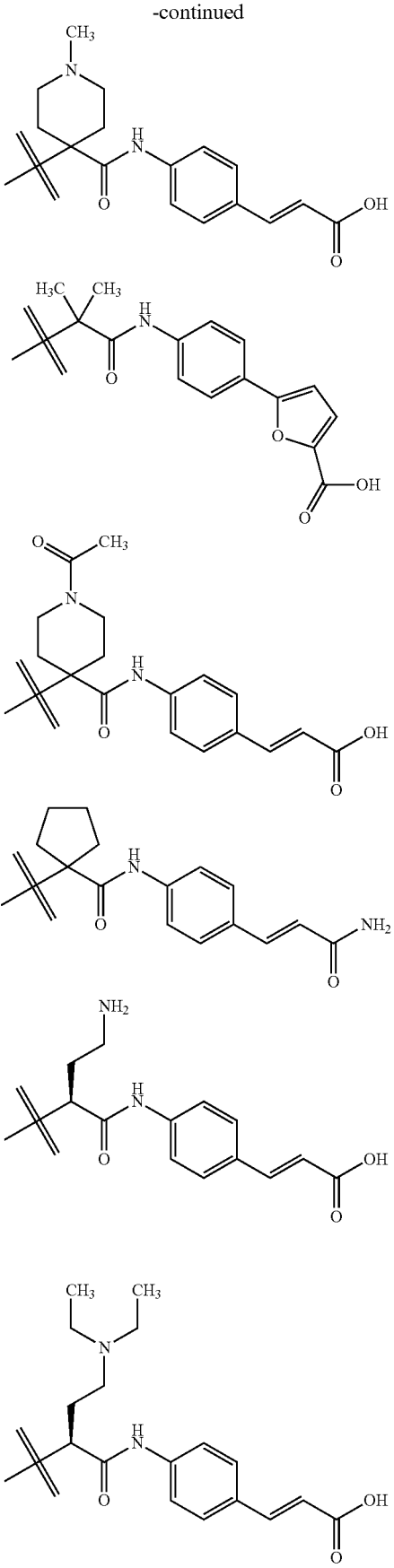

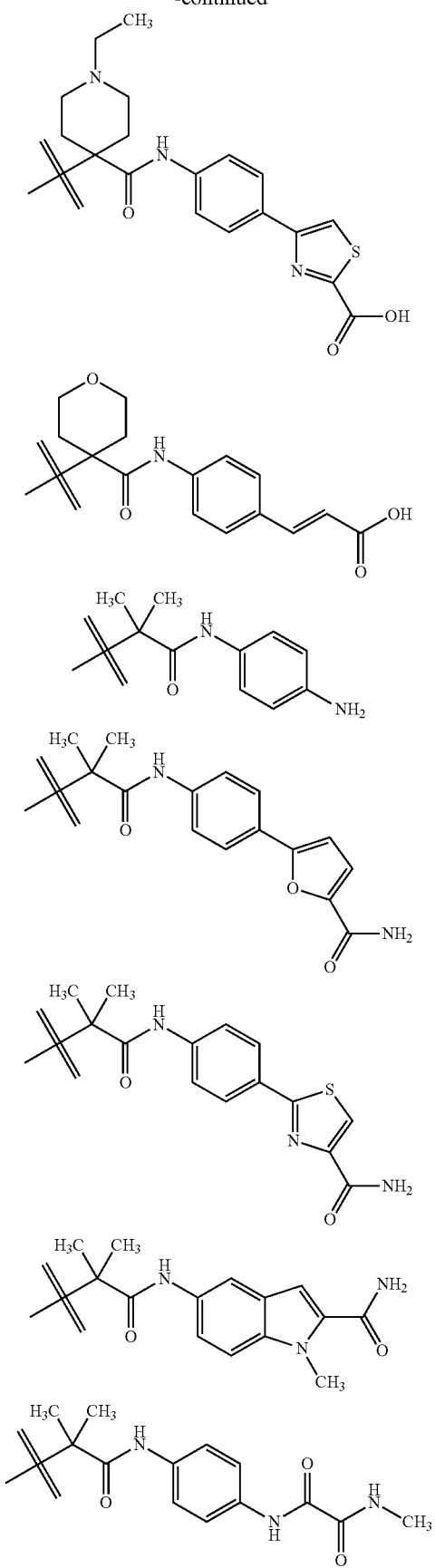
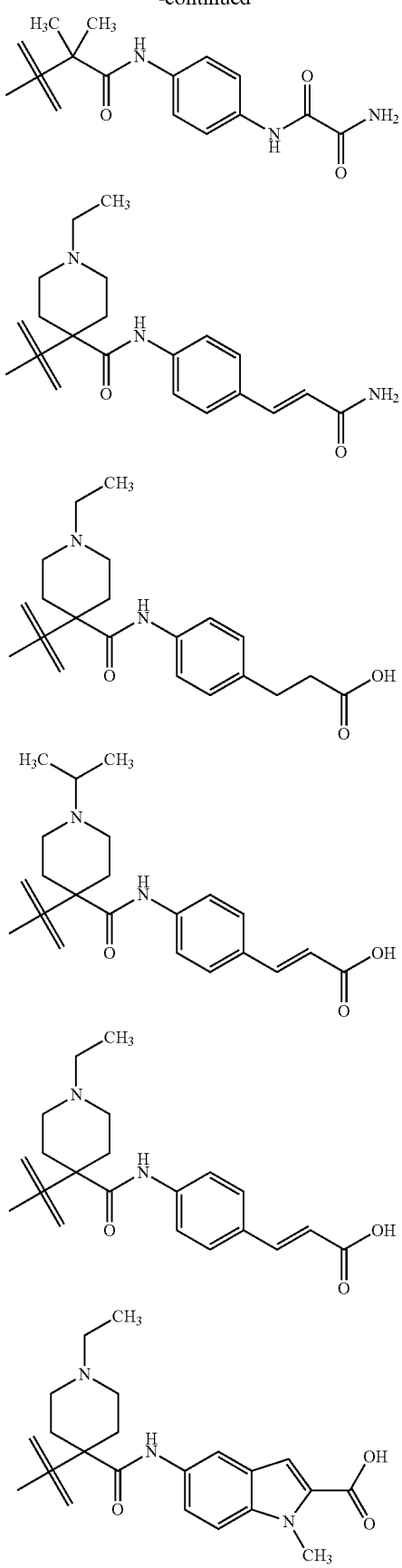

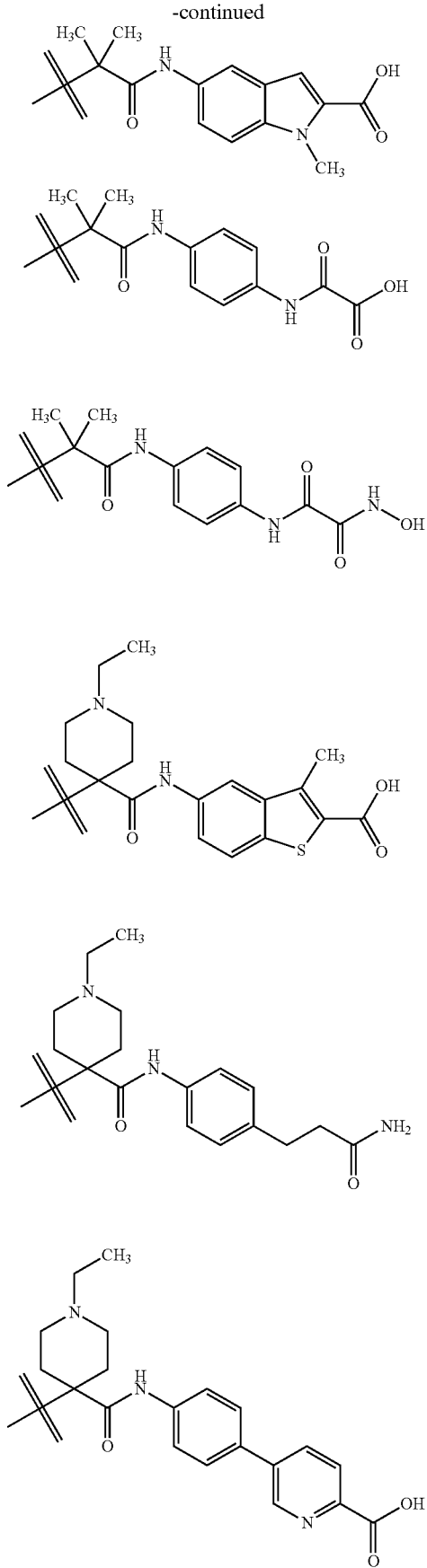
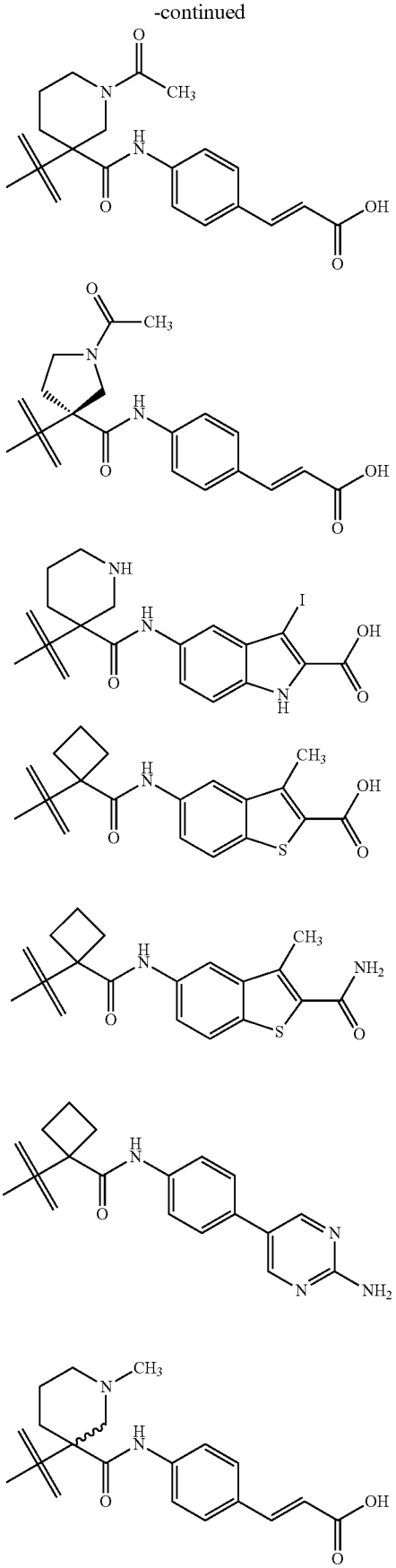

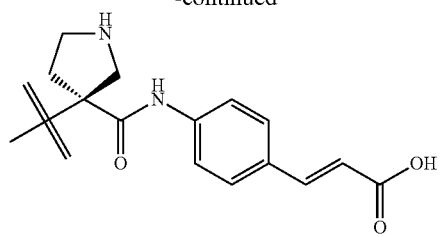
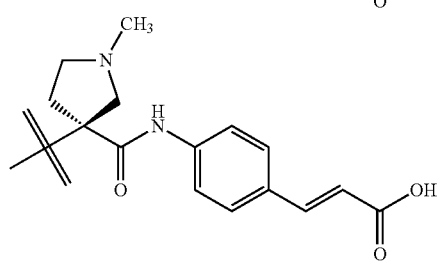
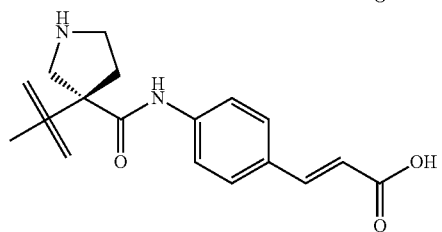
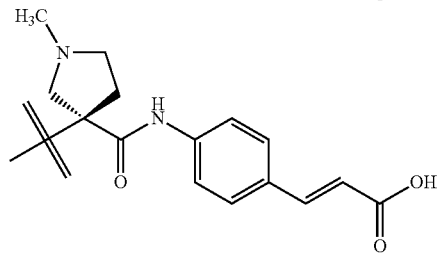
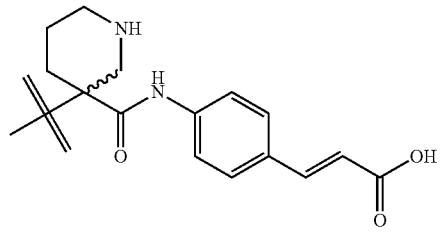
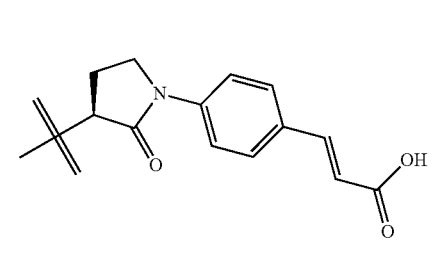
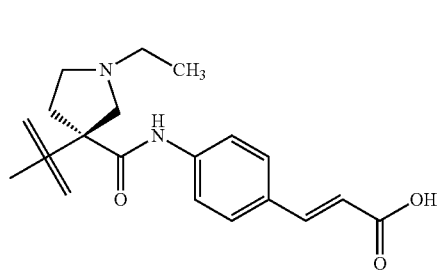
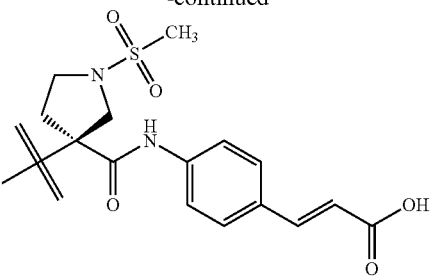
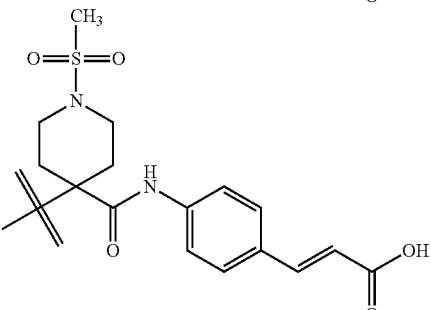
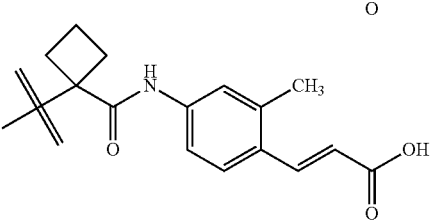
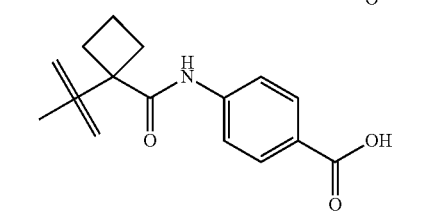
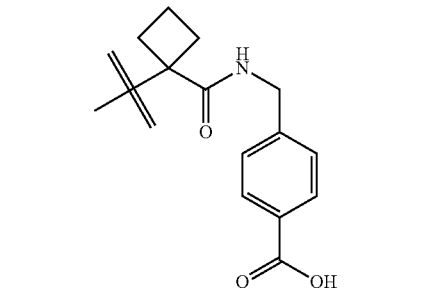
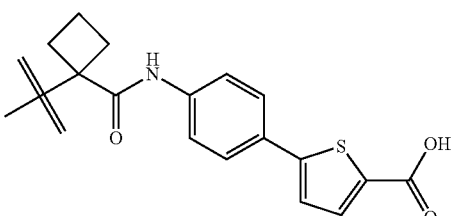
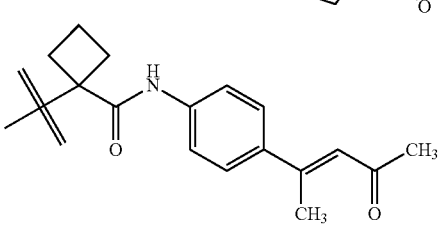

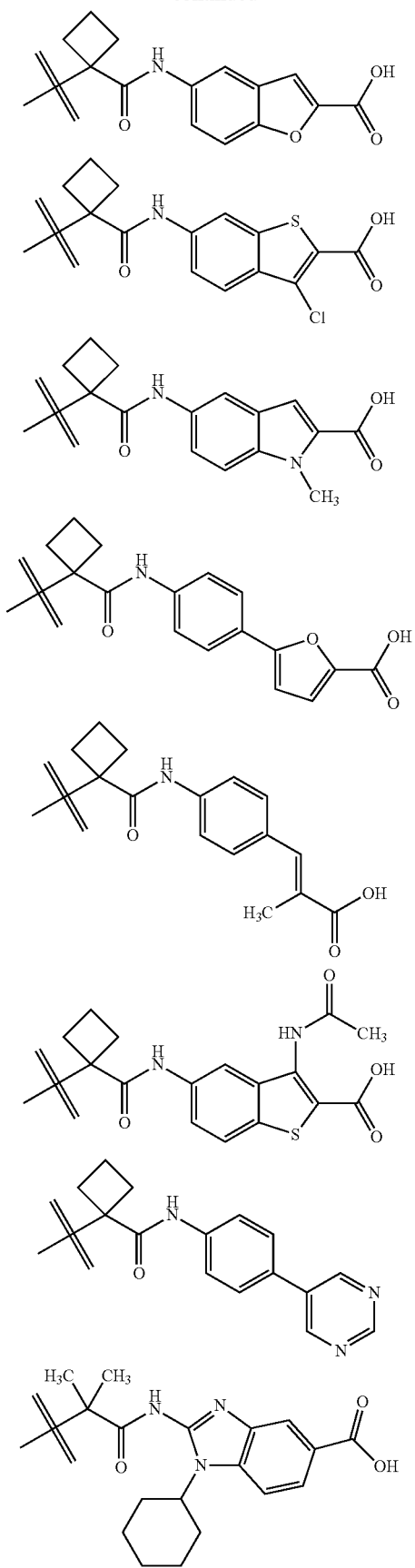
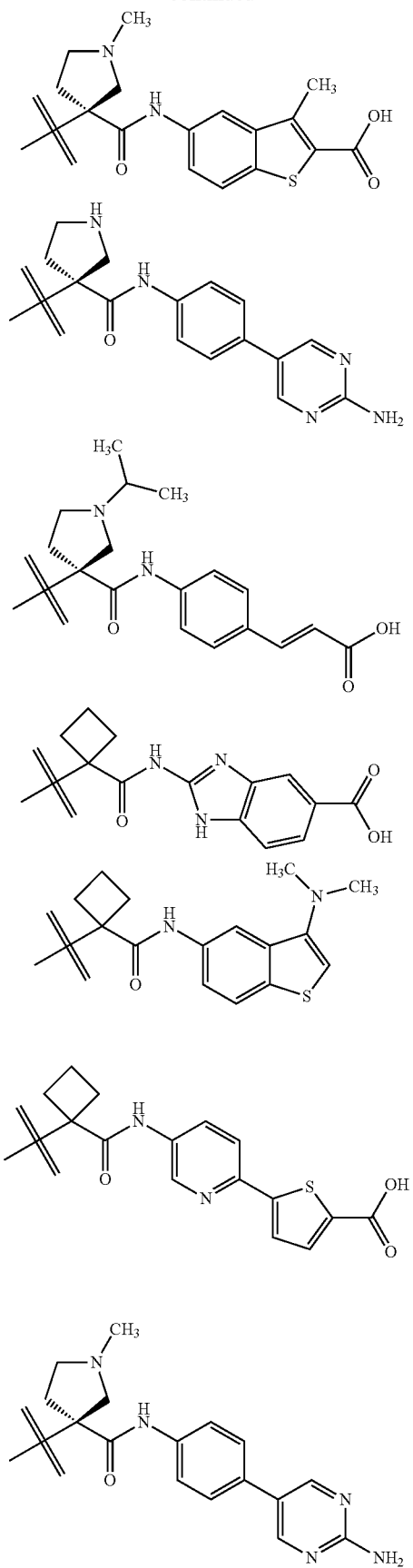

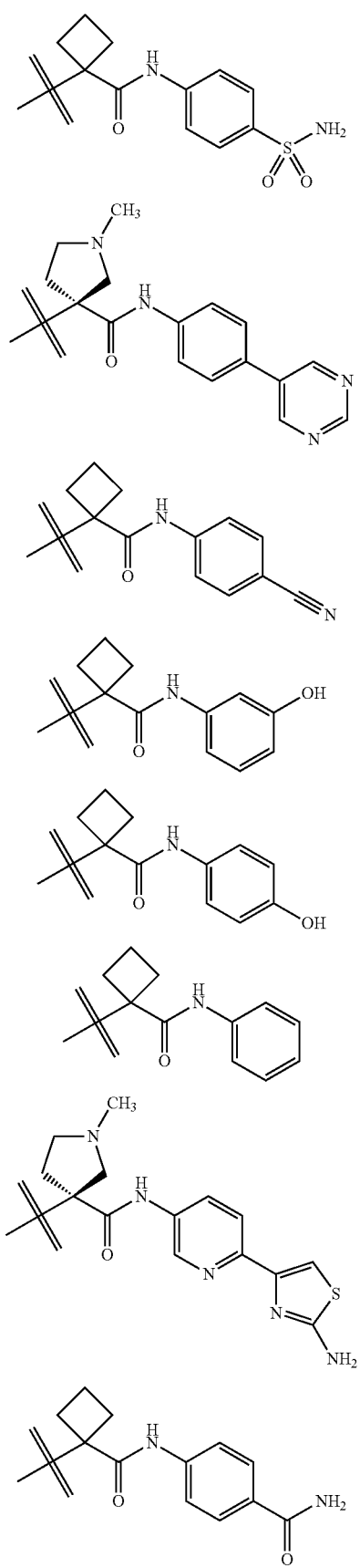
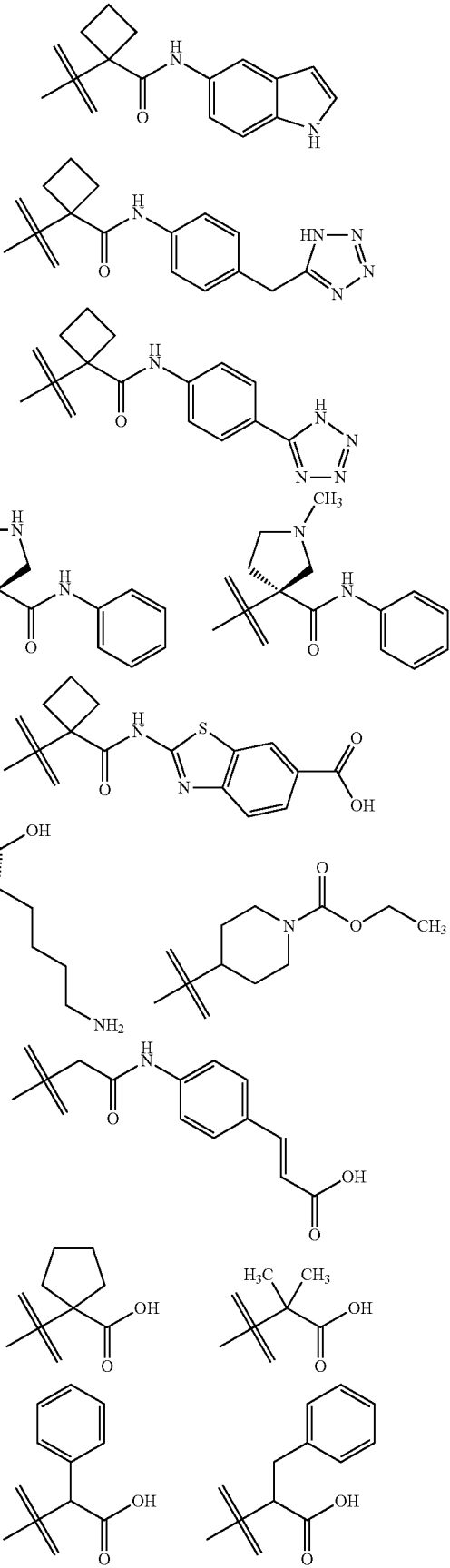

155
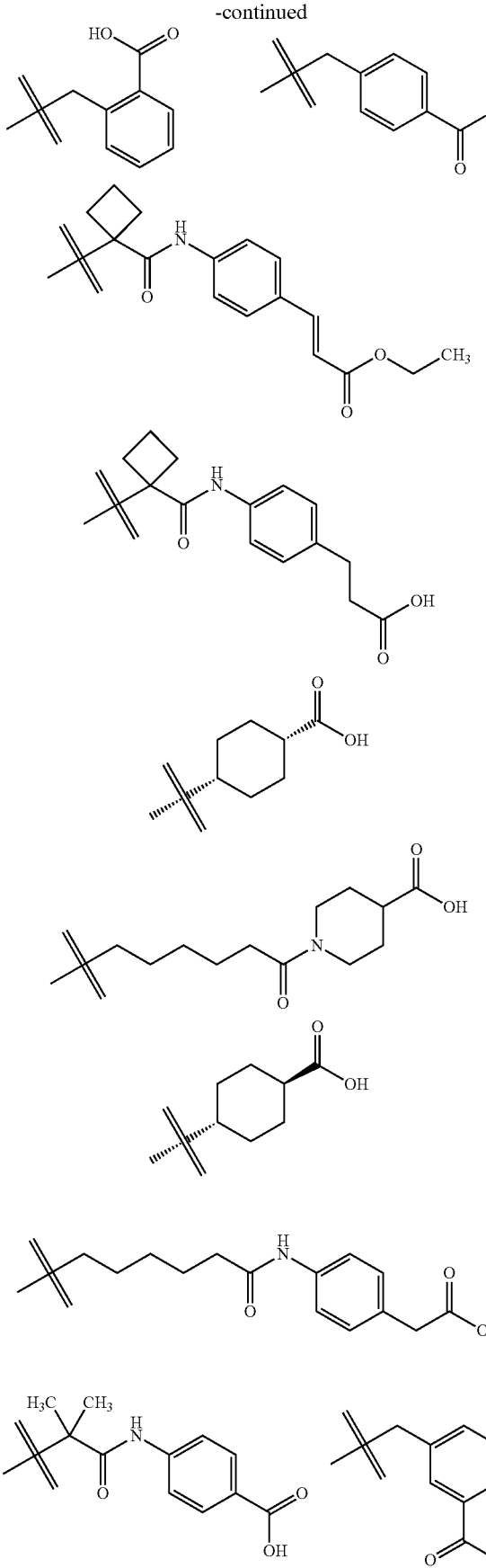
156
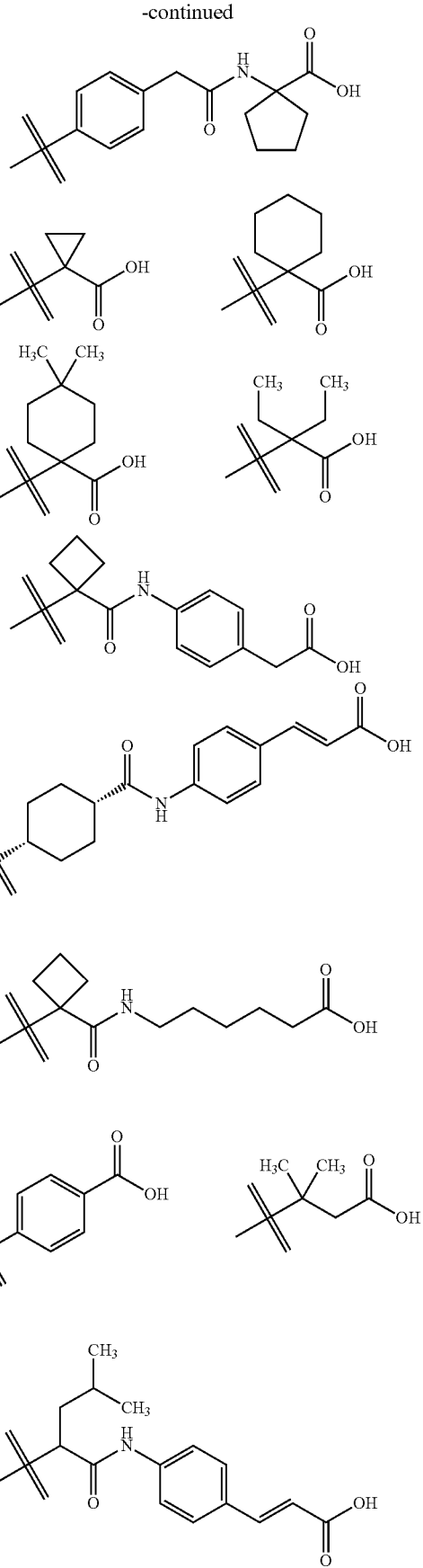

157
-continued
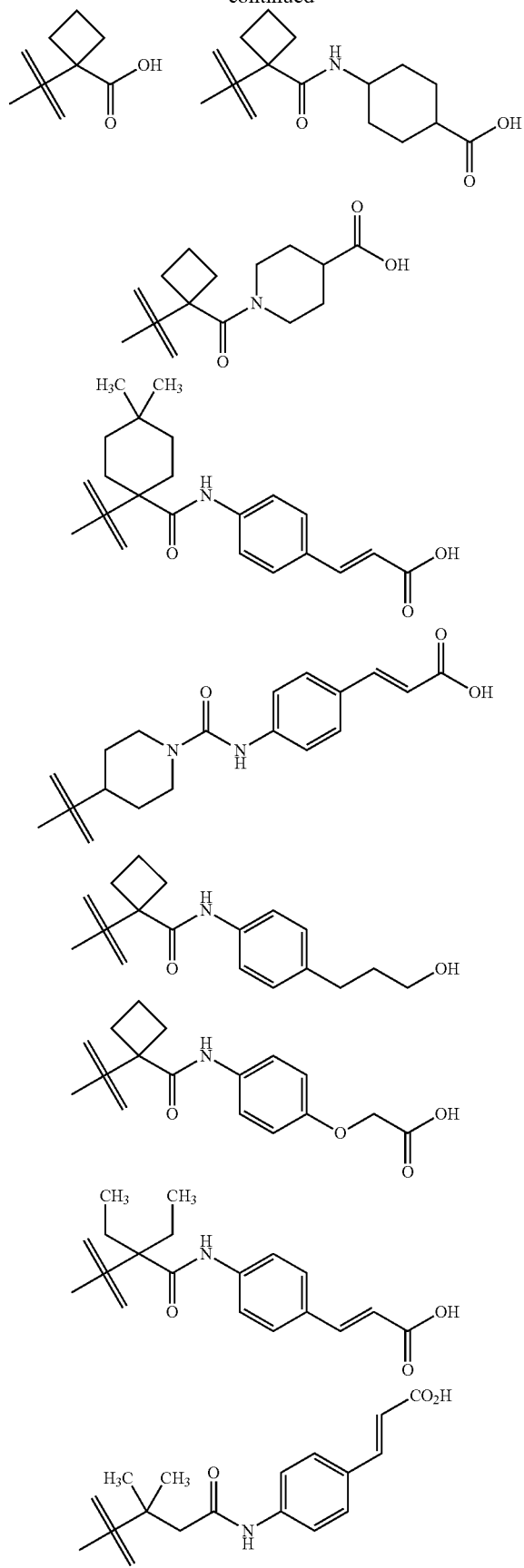
158
-continued
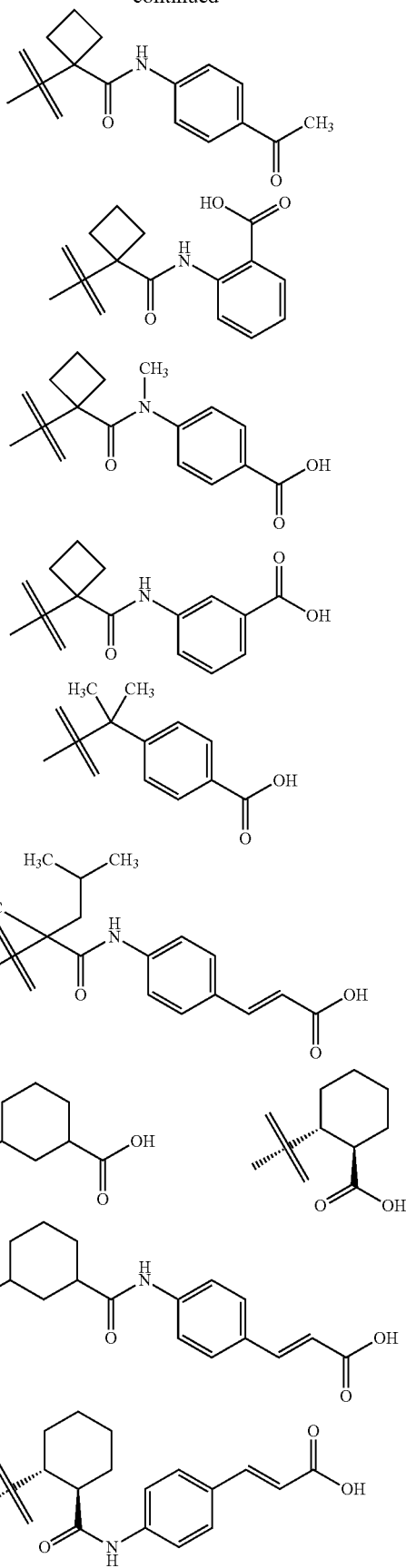

159
-continued
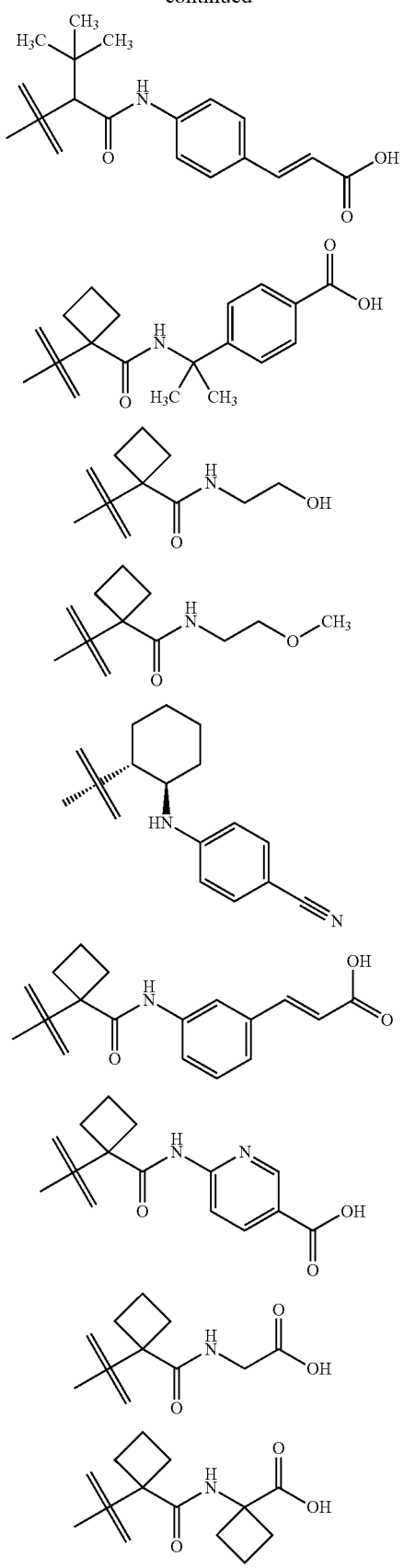
160
-continued
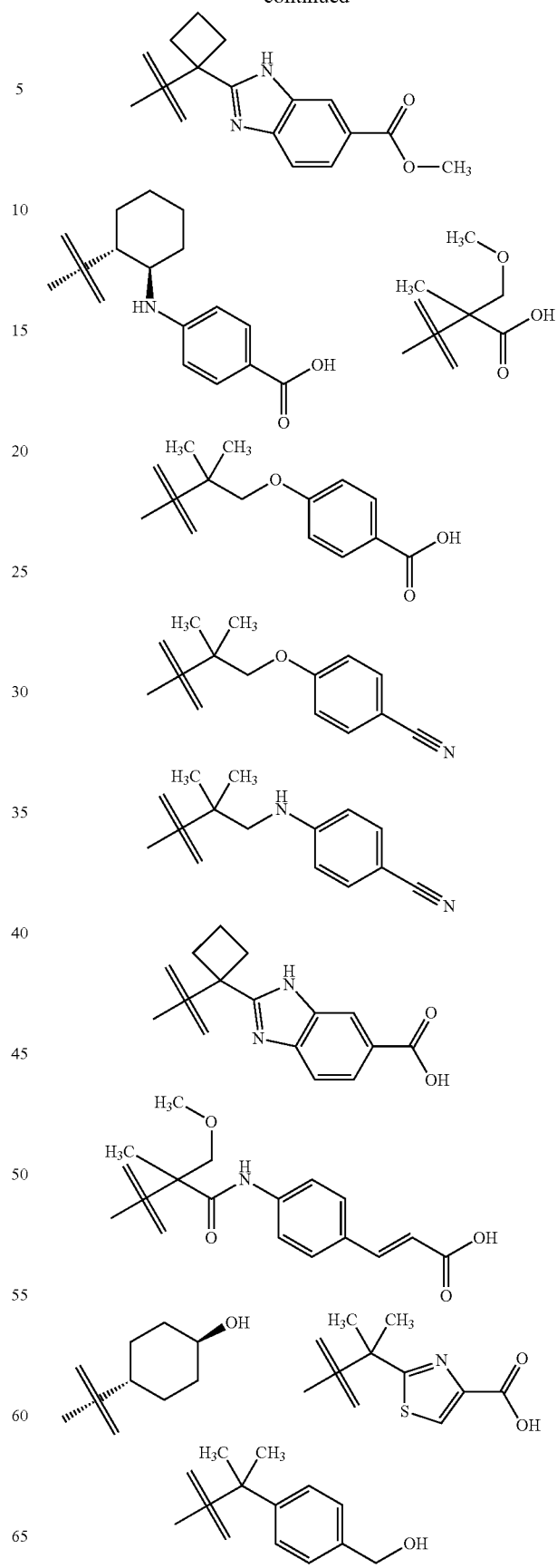

161
-continued
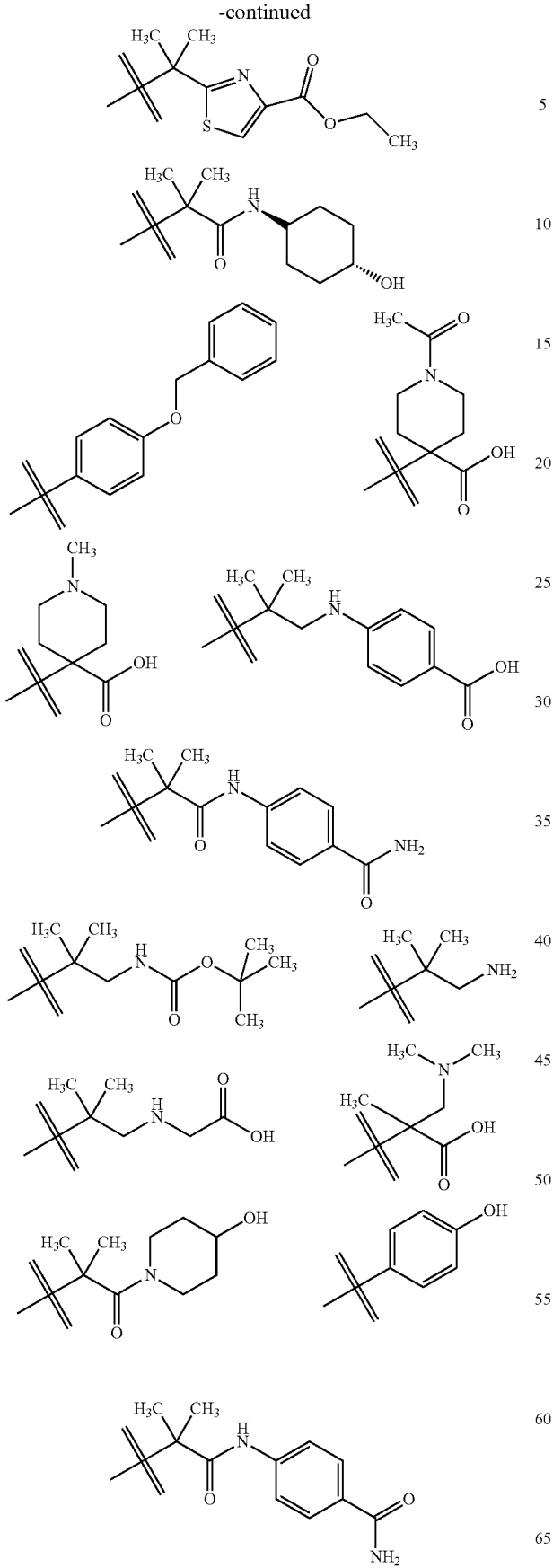
162
-continued
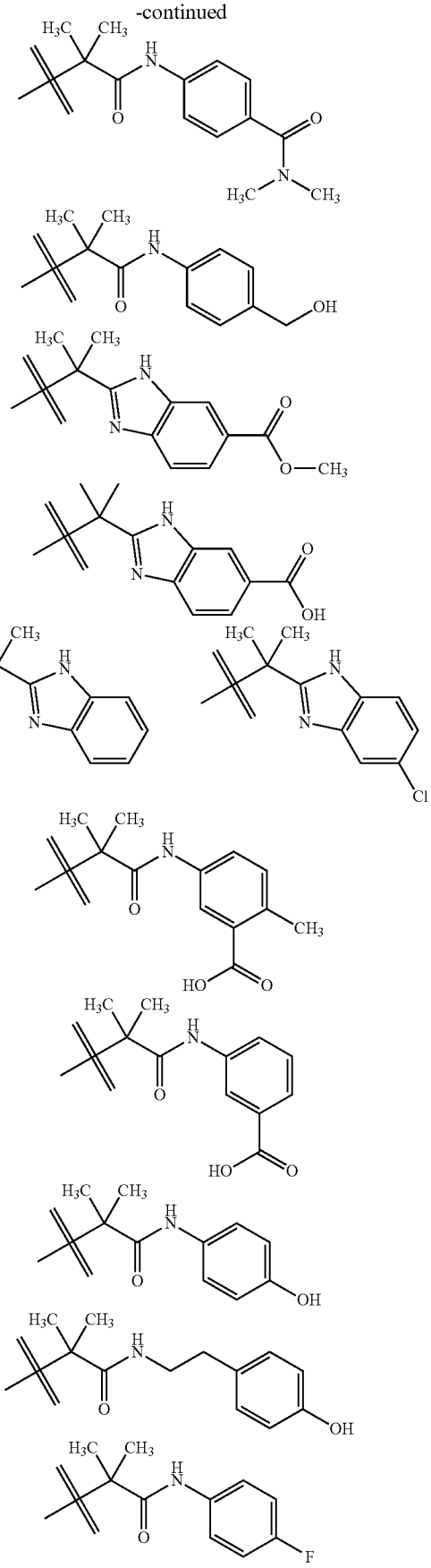

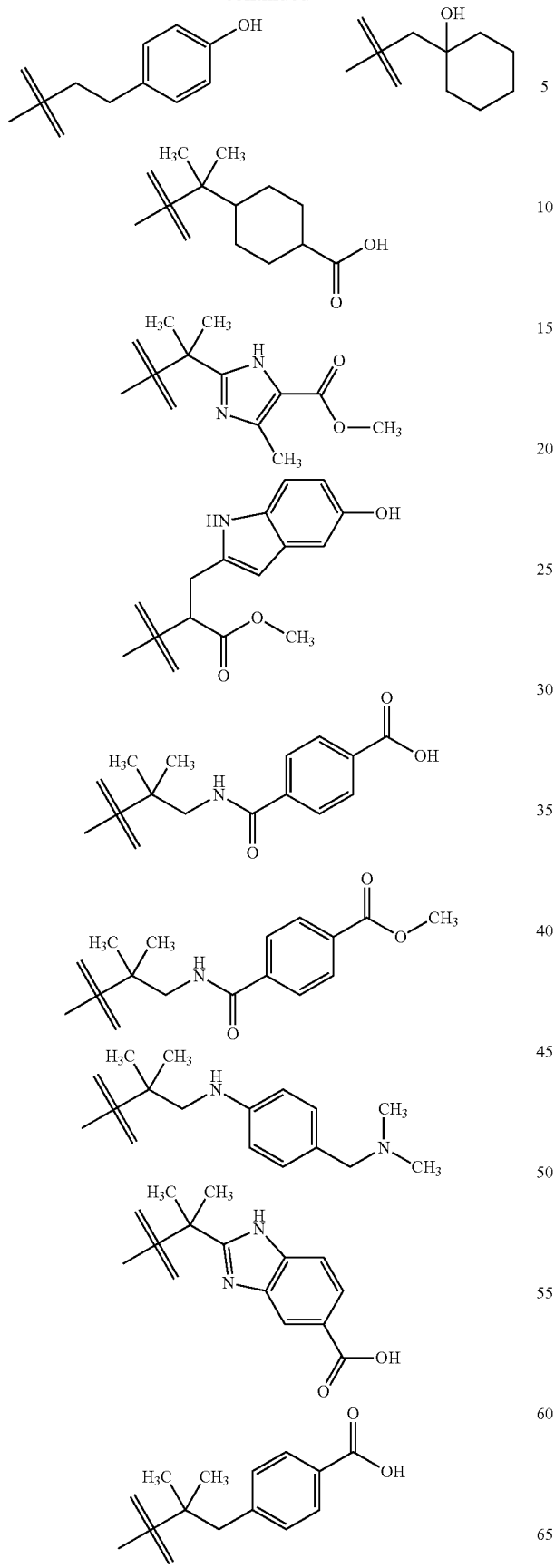
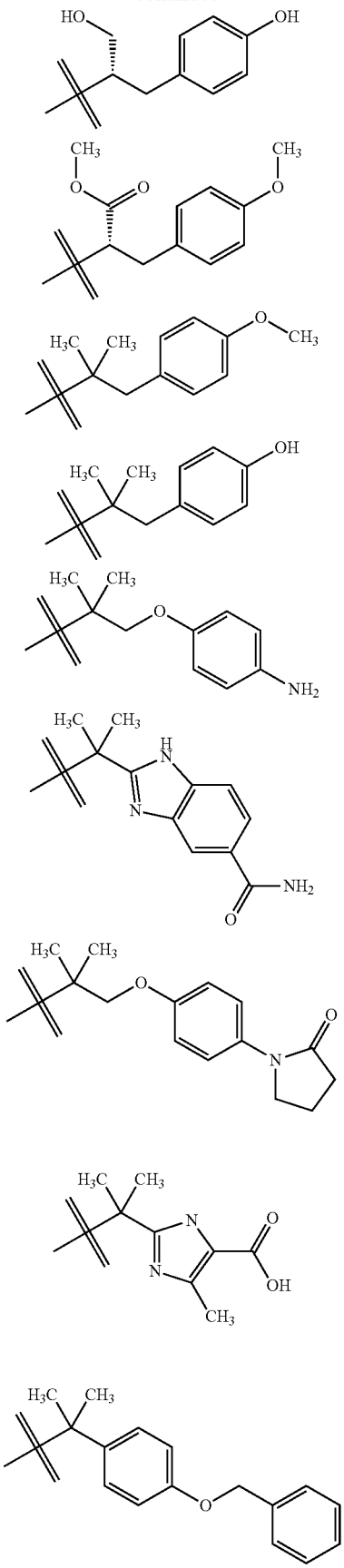

165
-continued
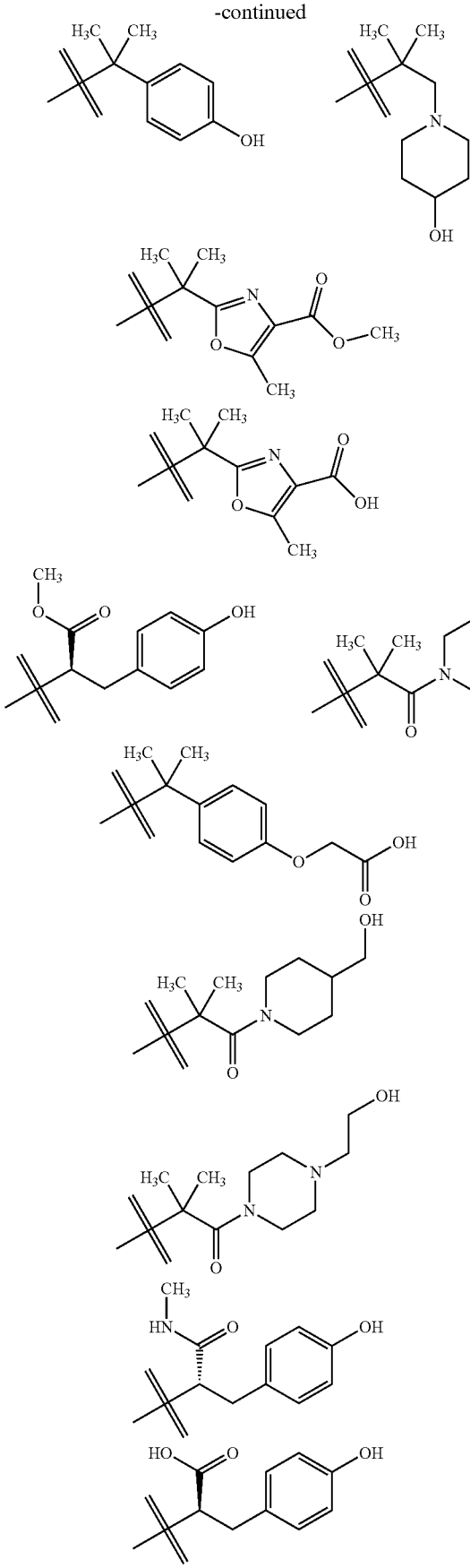
166
-continued
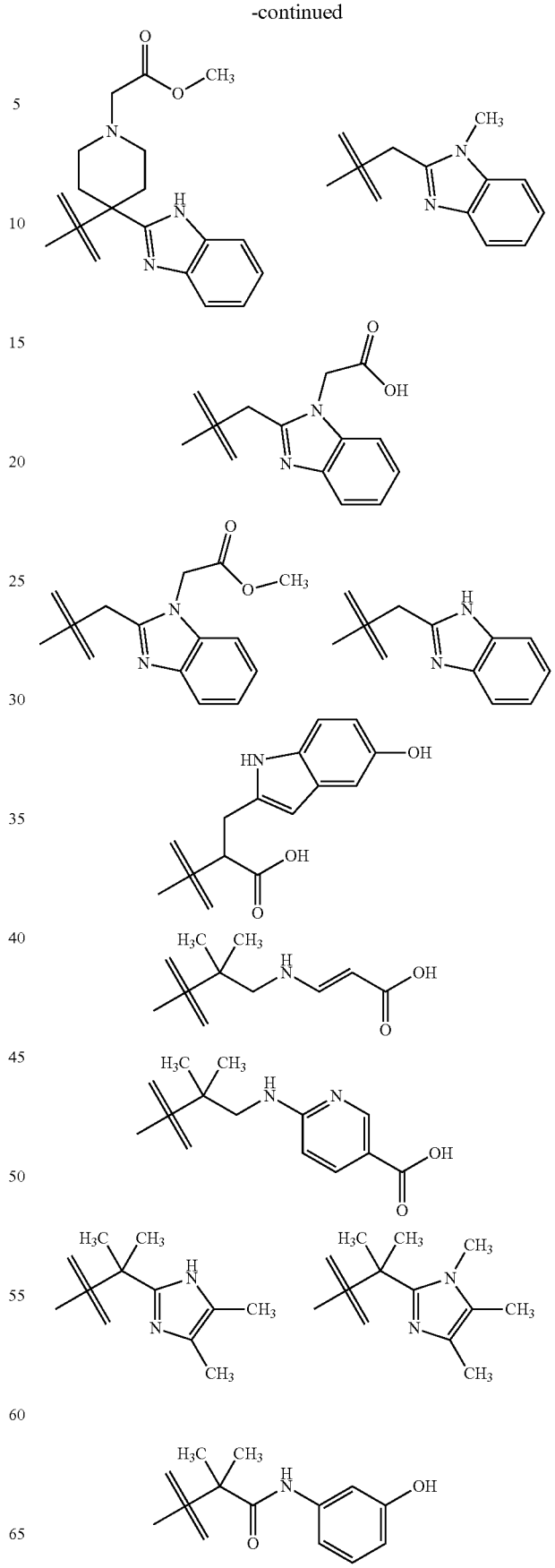

167
-continued
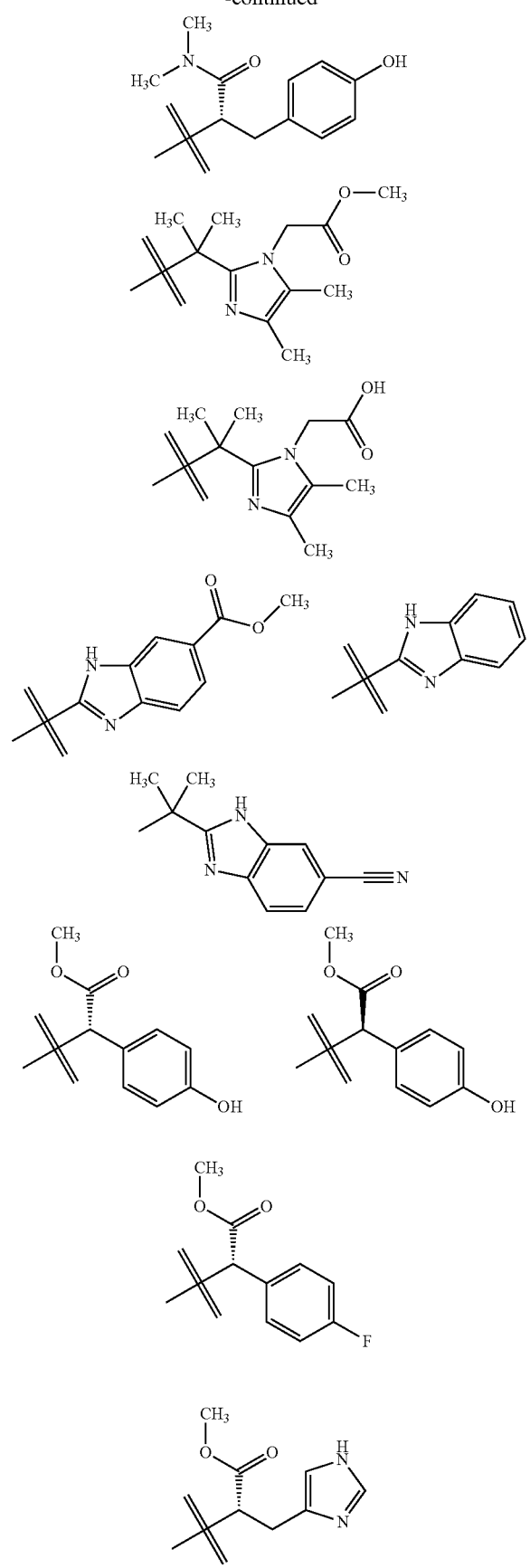
168
-continued
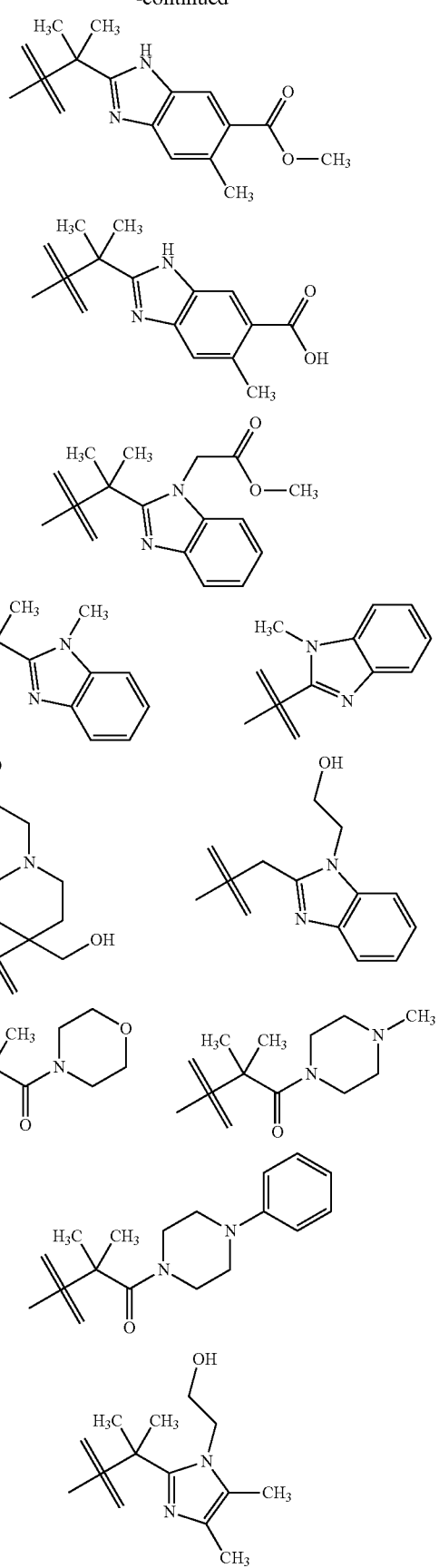

169
-continued
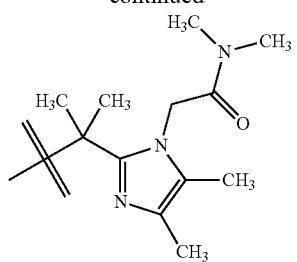
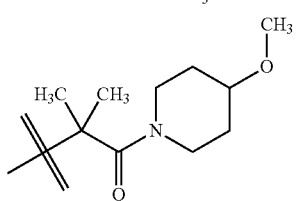
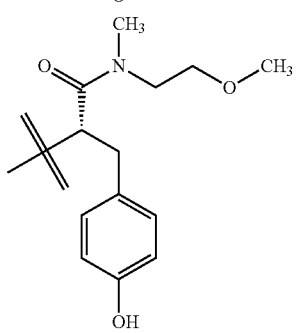
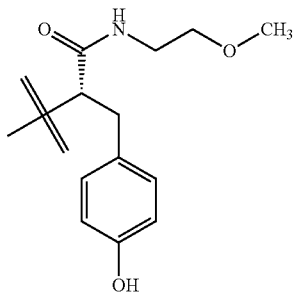
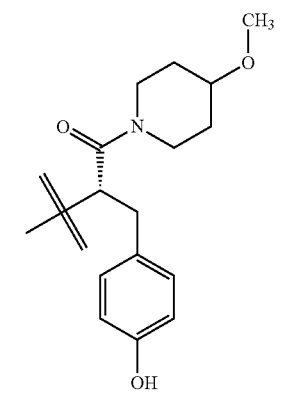
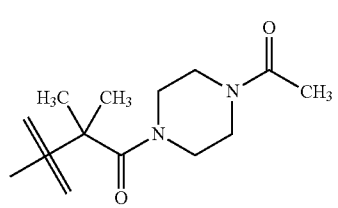
170
-continued
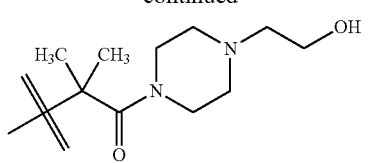
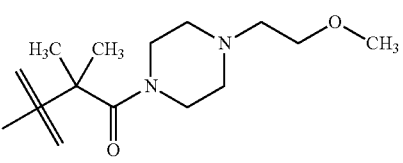
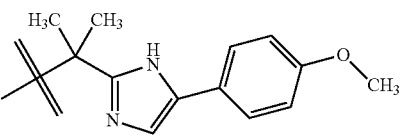
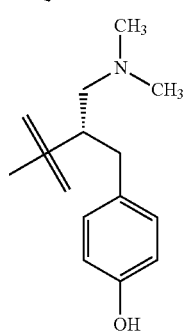
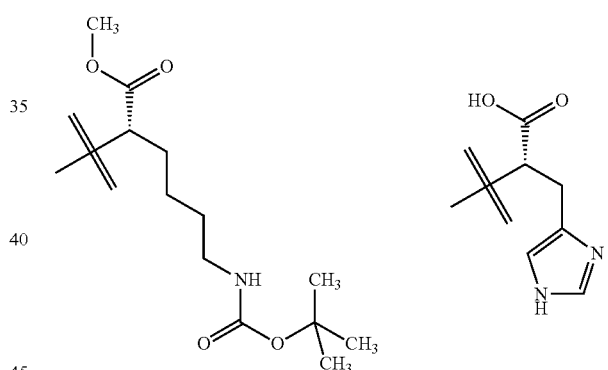
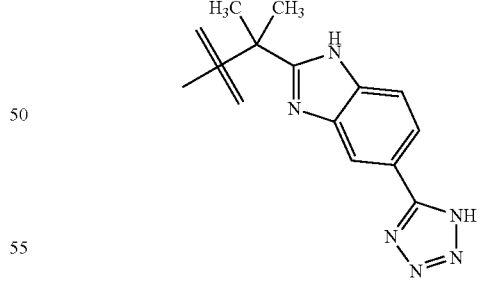
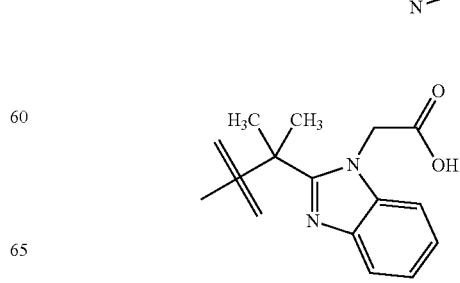

171
-continued
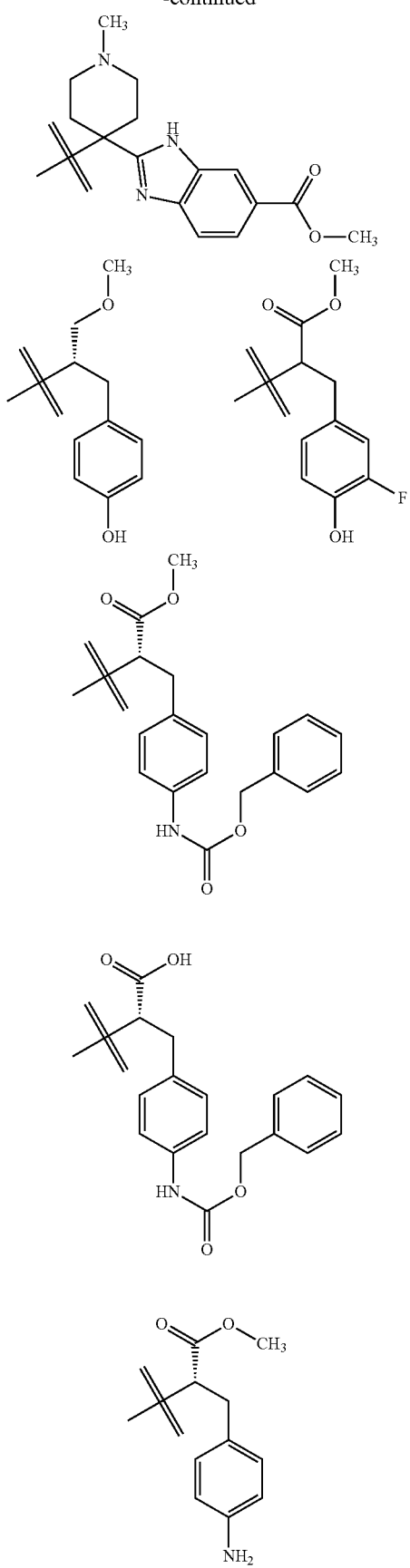
172
-continued
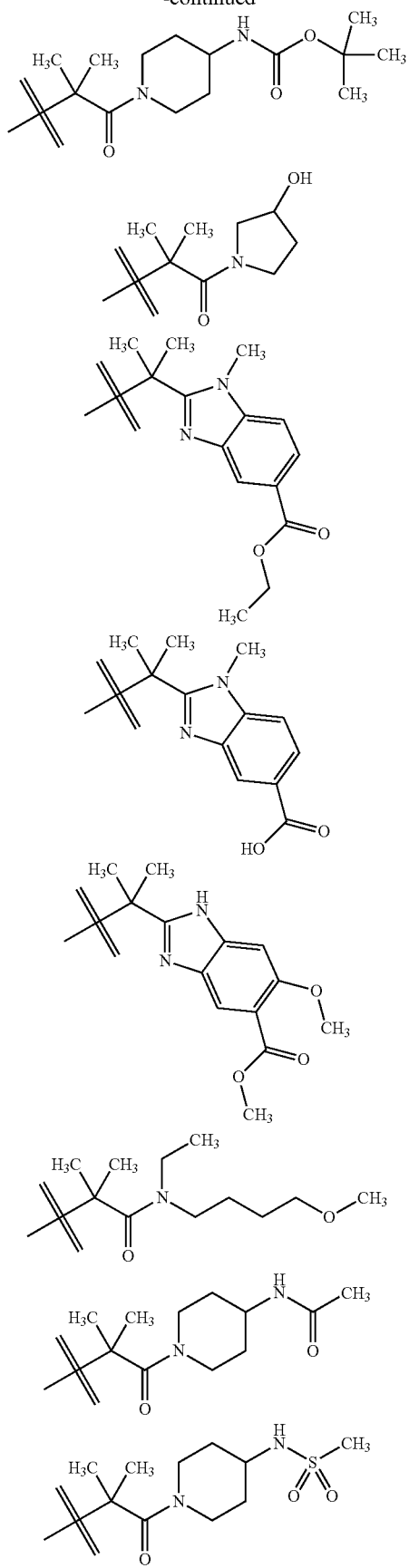

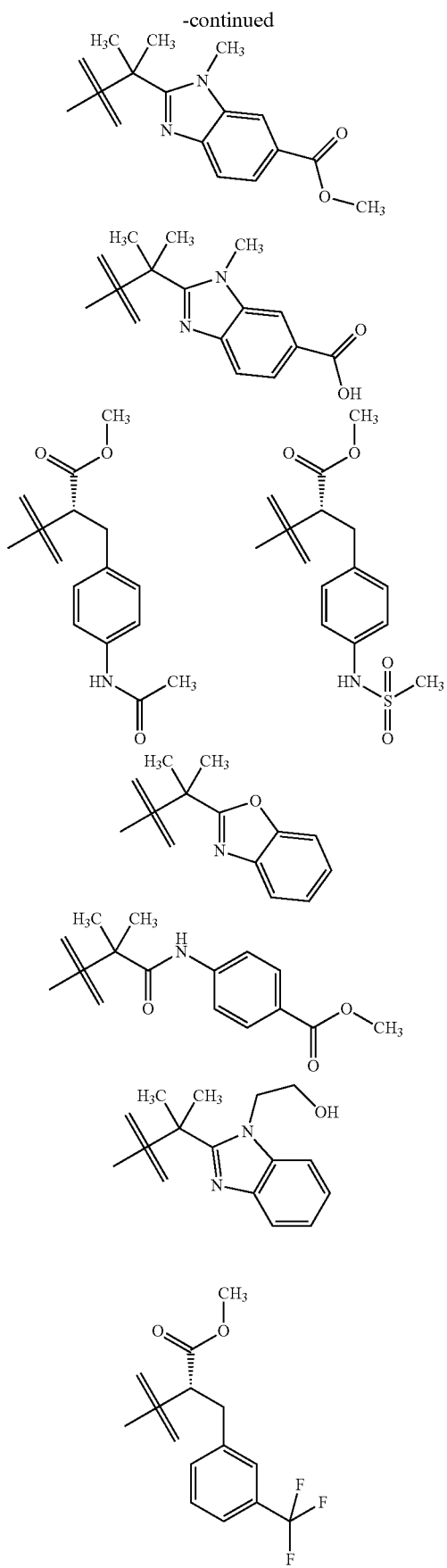
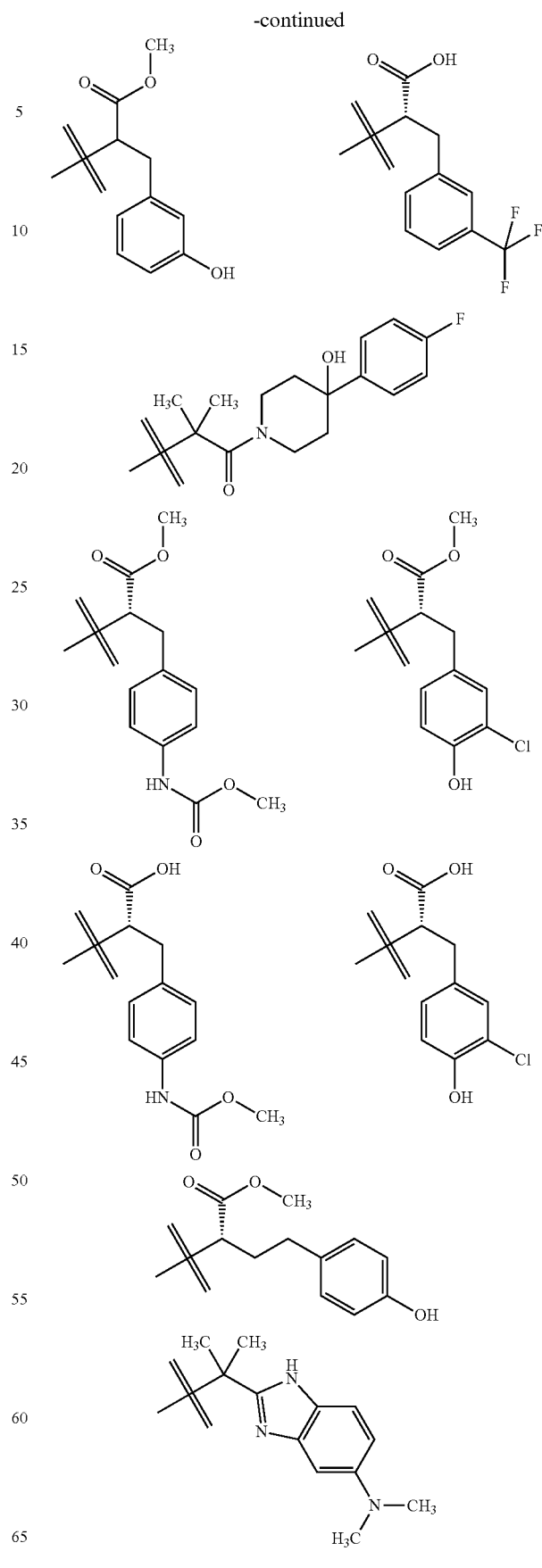

175
-continued
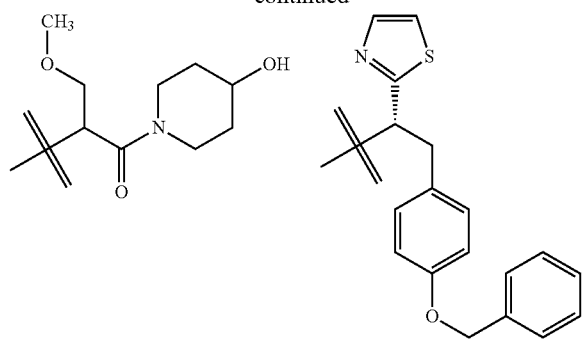
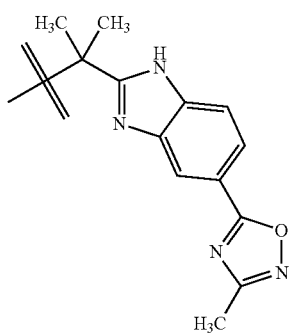
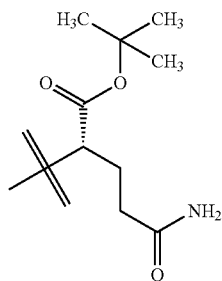 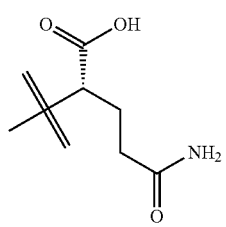
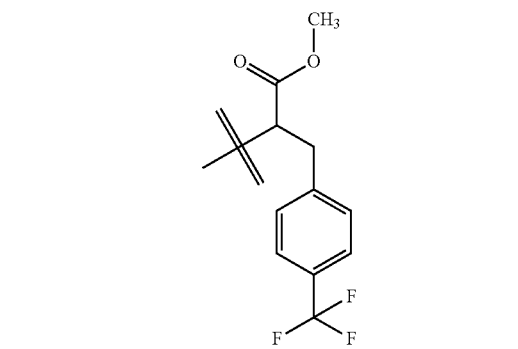
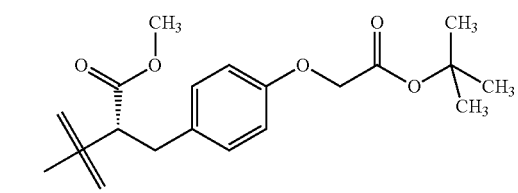
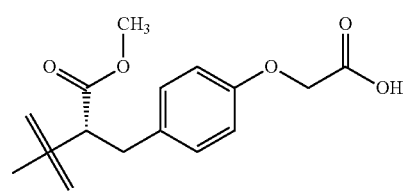
176
-continued
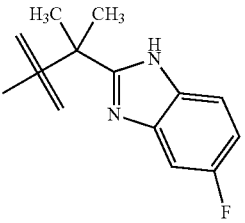
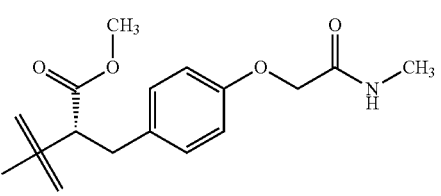
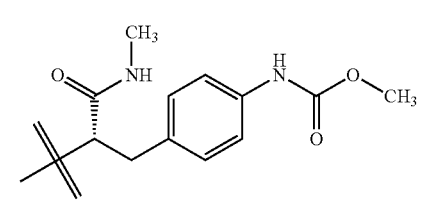
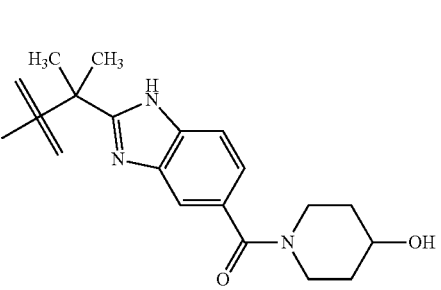

177
-continued
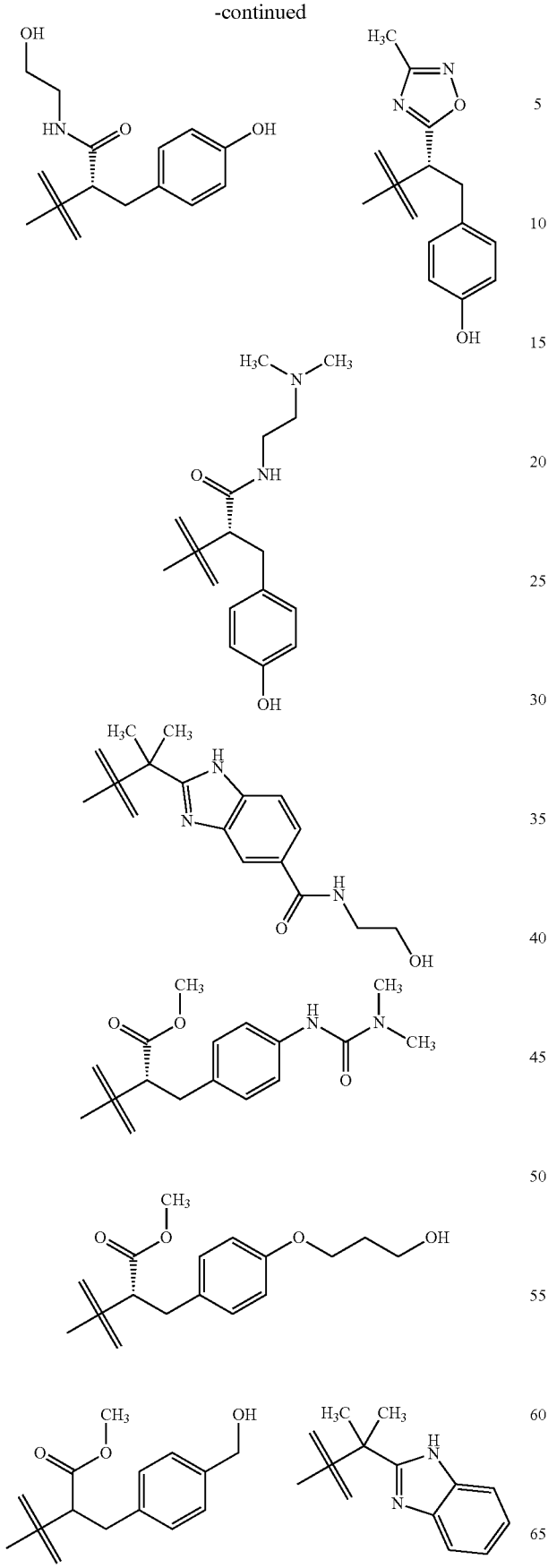
178
-continued
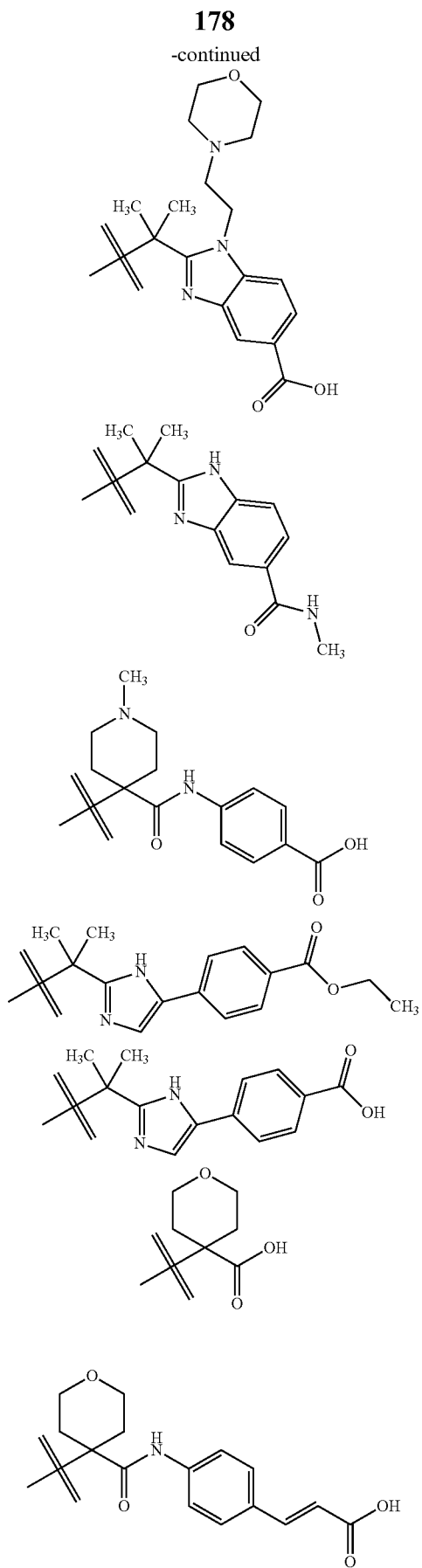

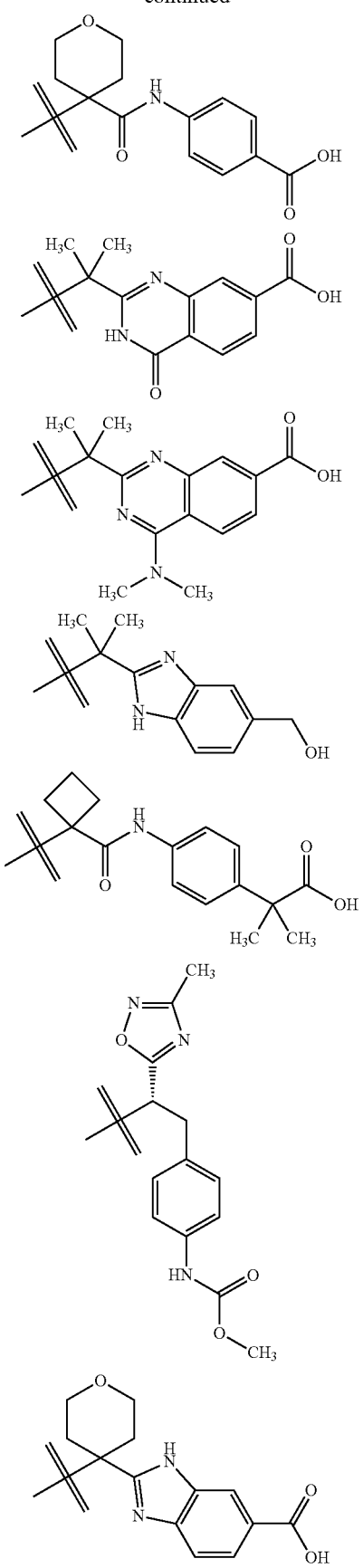
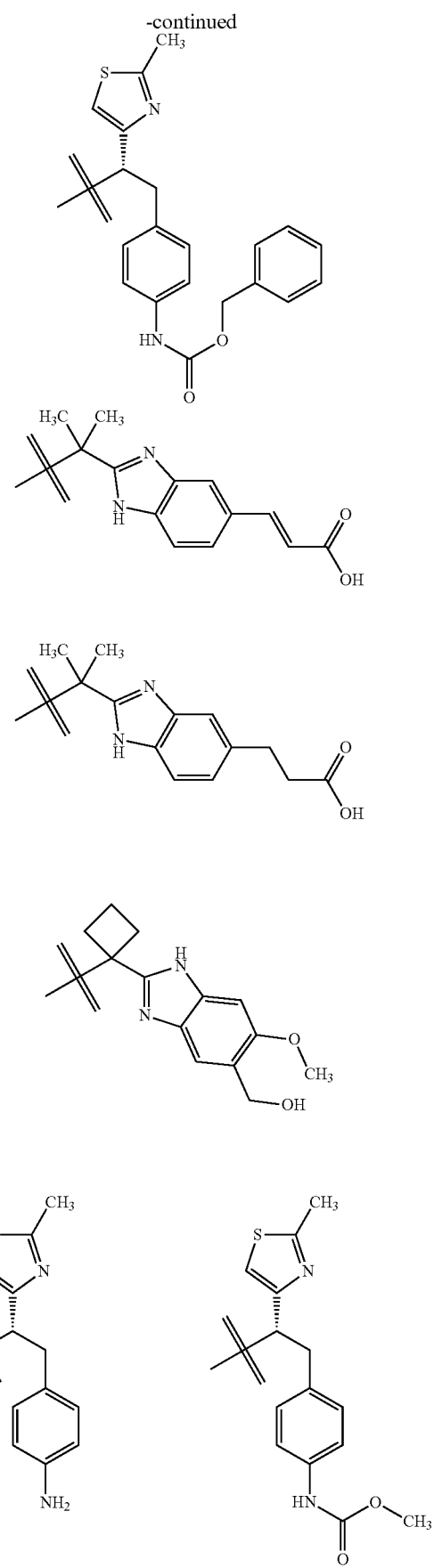

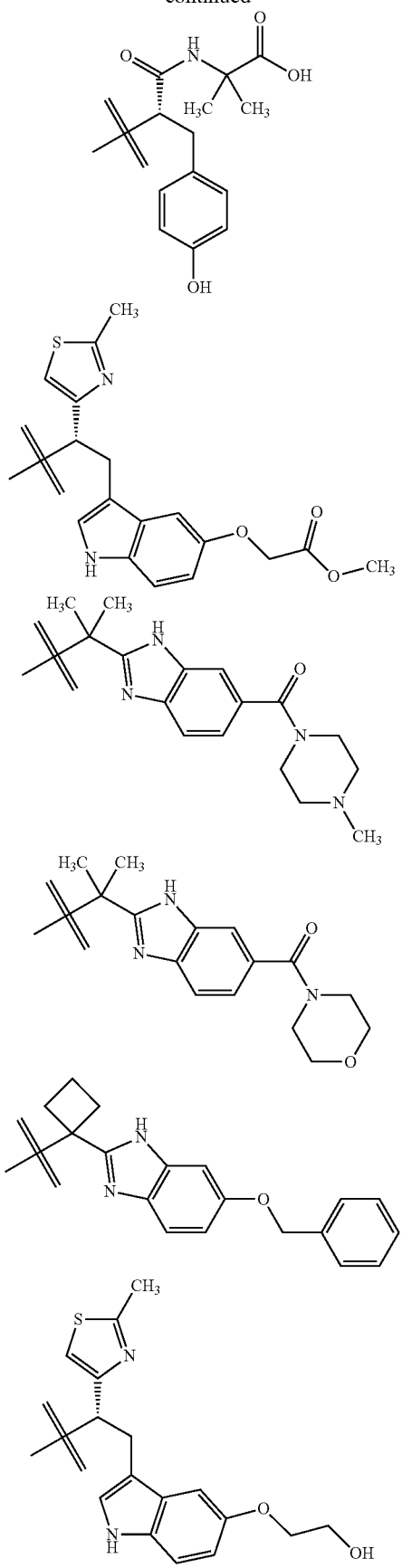
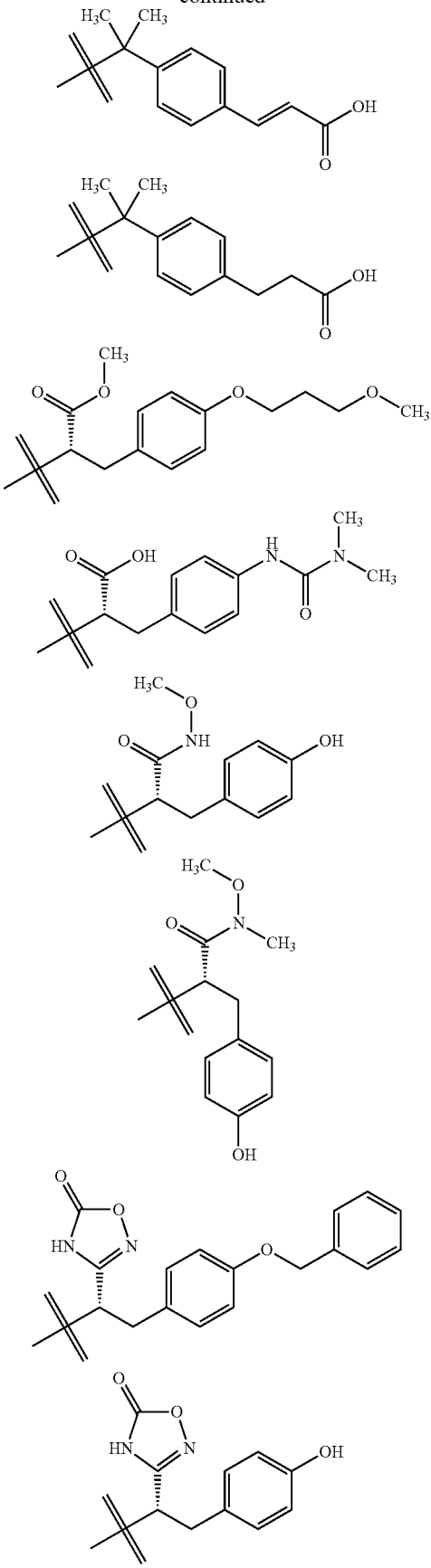

183
-continued
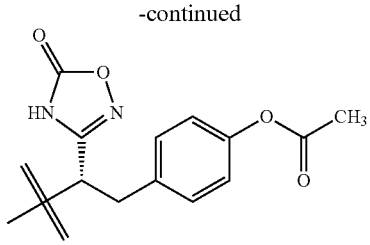
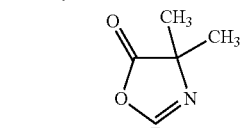
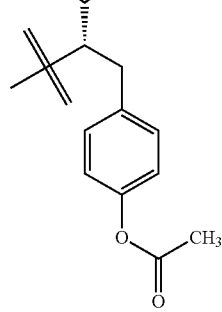
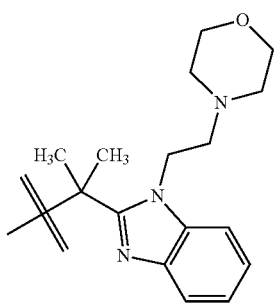
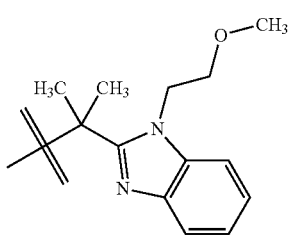
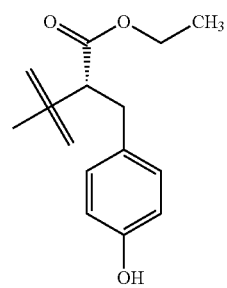
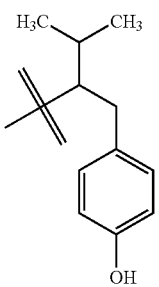
184
-continued
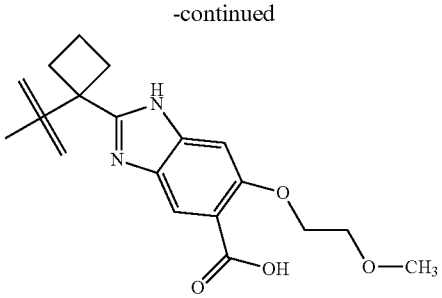
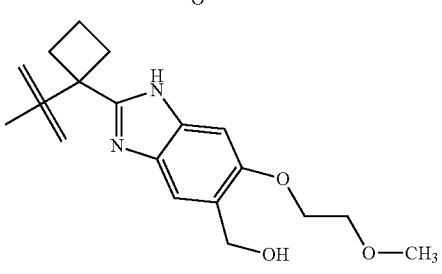
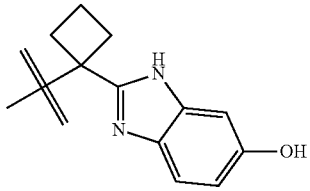
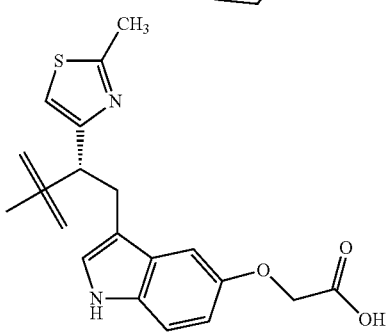
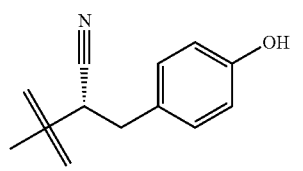
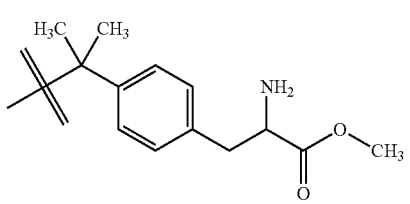
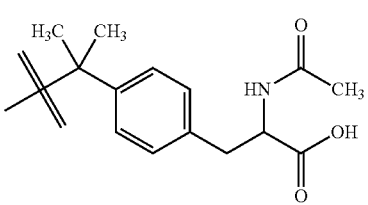

185
-continued
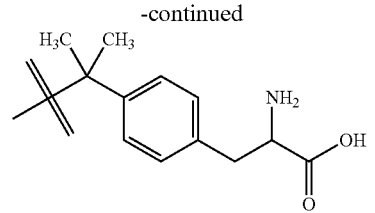
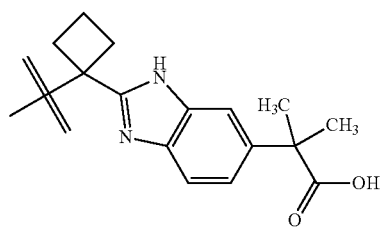
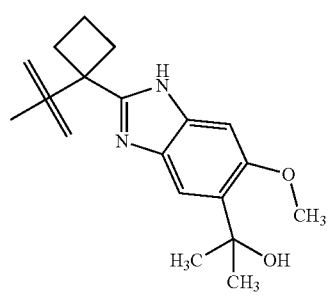
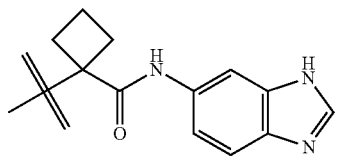
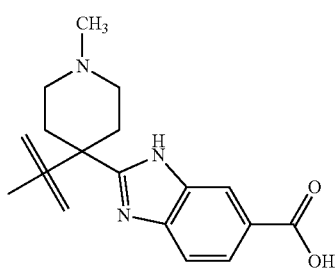
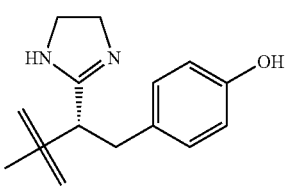
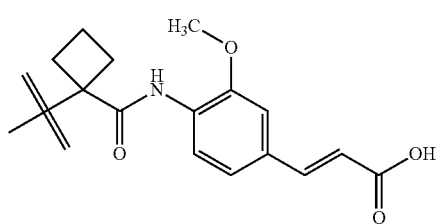
186
-continued
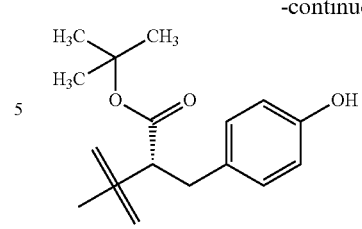
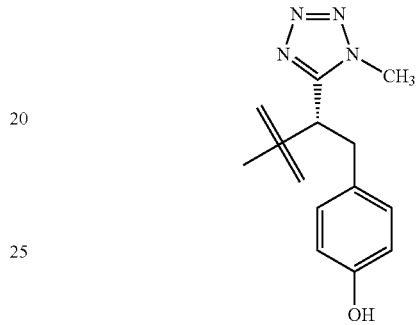
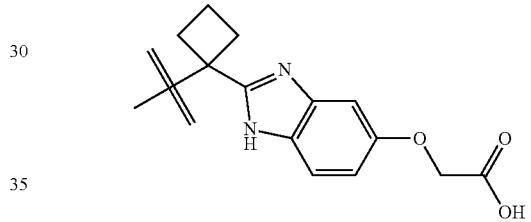
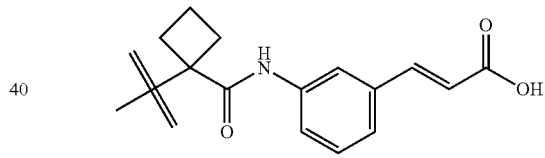
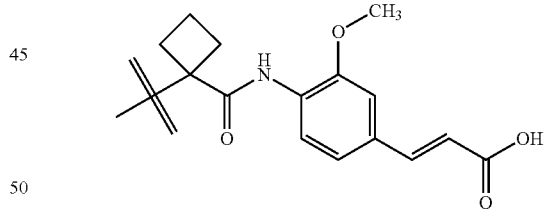
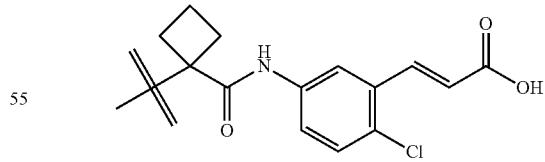
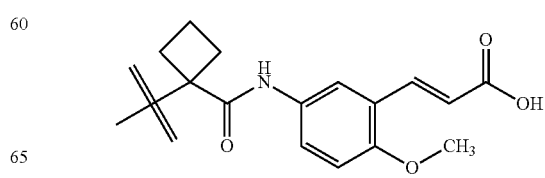

187
-continued
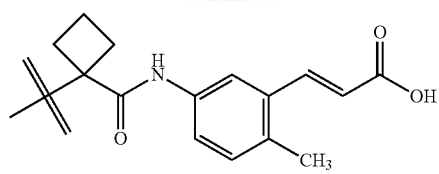
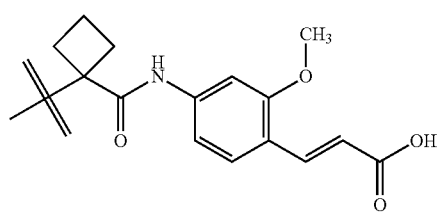
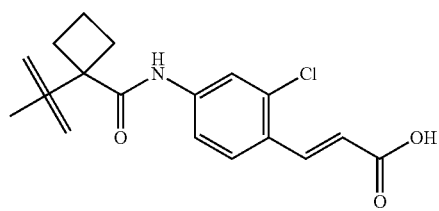
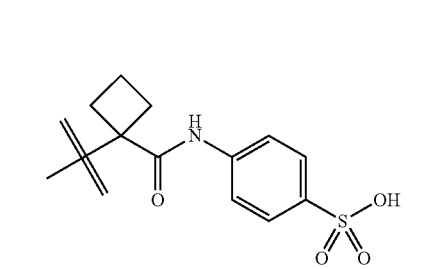
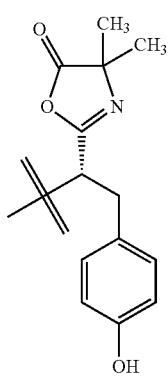
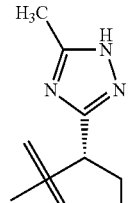
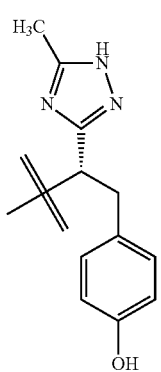
188
-continued
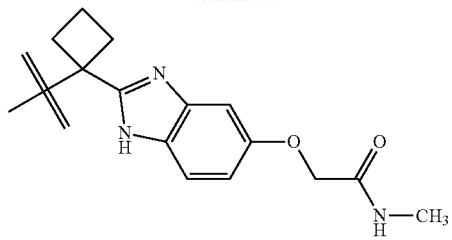
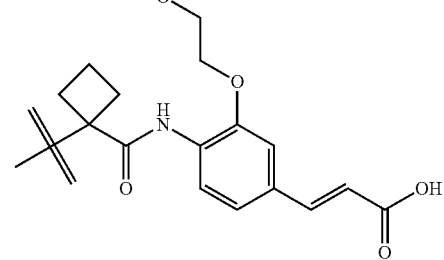
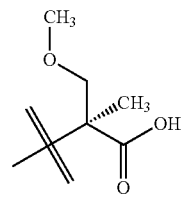
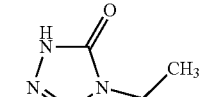
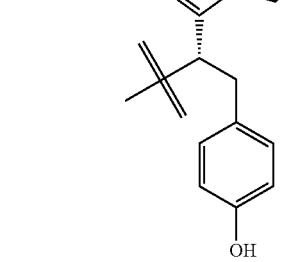
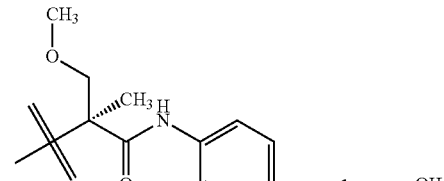
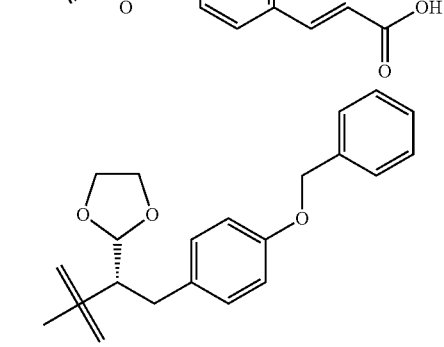

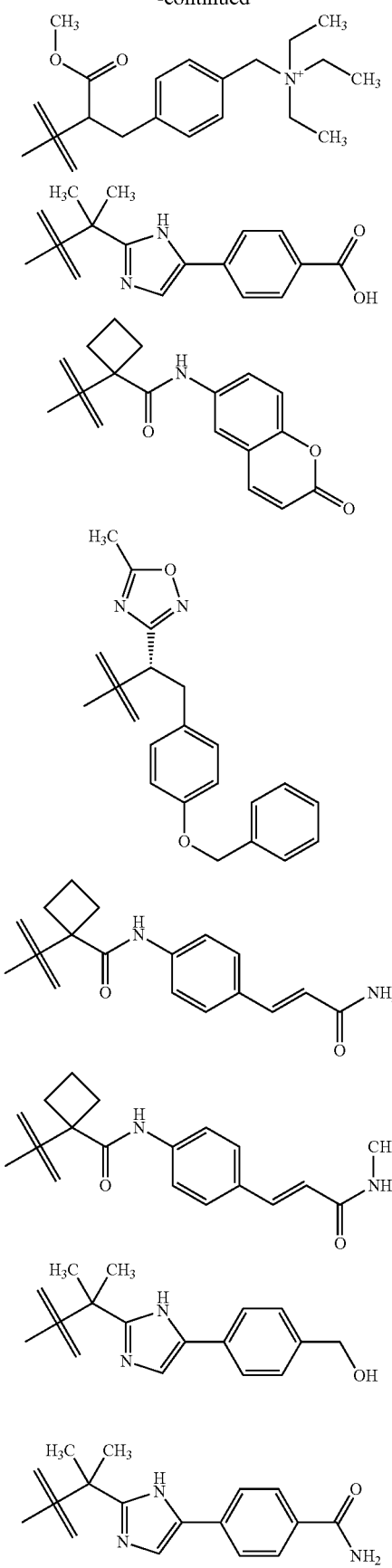
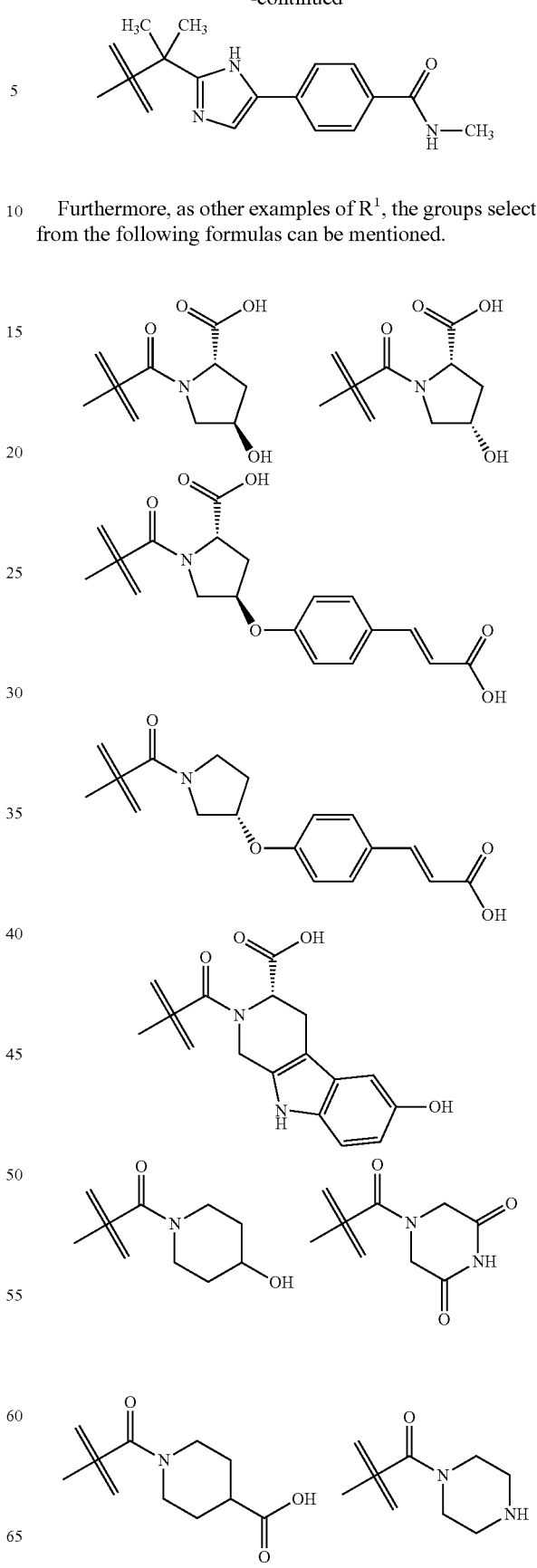
Furthermore, as other examples of $R^1$, the groups selected from the following formulas can be mentioned.

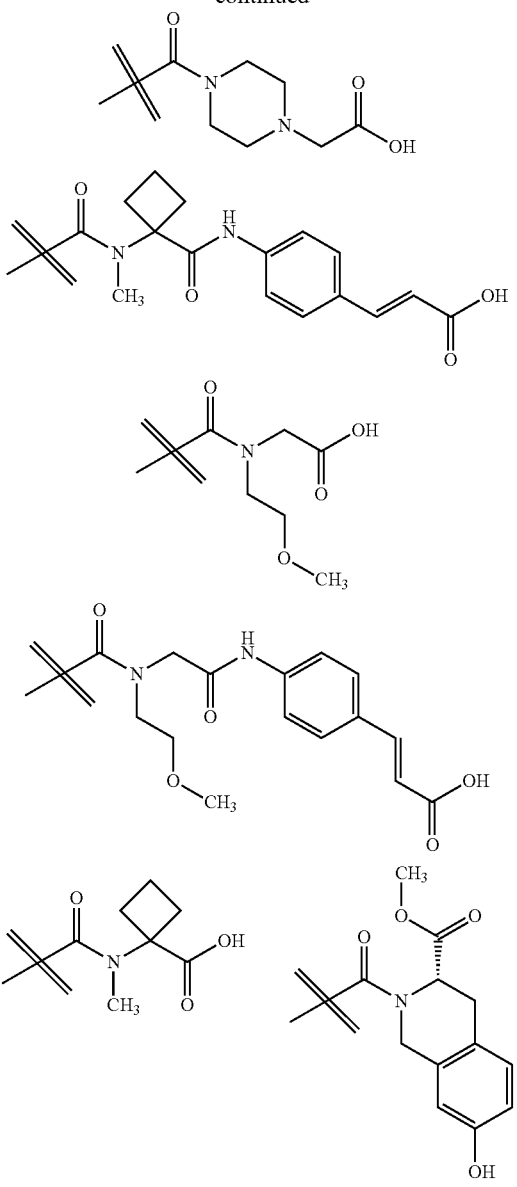

For R², preferred are a hydrogen atom, "a group selected from group E", "a C$_{1-6}$ alkyl group optionally substituted by 1 to 3 substituents selected from group E",

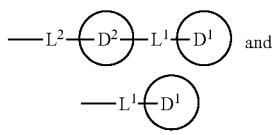

, more preferred are "a C$_{1-6}$ alkyl group optionally substituted by 1 to 3 substituents selected from group E" and

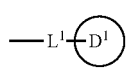

, particularly preferably,

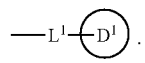

Preferably, L¹ and L² are each independently a bond, C$_{1-6}$ alkylene, —(CH$_2$)$_{u1}$—NR$^{L1}$—(CH$_2$)$_{v1}$—, —(CH$_2$)$_{u1}$—CO—(CH$_2$)$_{v1}$— or —(CH$_2$)$_{u1}$—CONR$^{L2}$—(CH$_2$)$_{v1}$—, more preferably C$_{1-6}$ alkylene.

Preferably, u, v, u1 and v1 are each independently 0 or an integer of 1 to 3, more preferably 0 or 1, particularly preferably 1.

For R$^{L1}$, preferred is a hydrogen atom, preferably, ring D¹ and ring D² are each independently "a C$_{6-14}$ aryl group optionally substituted by 1 to 5 substituents selected from group E" or "a heterocyclic group optionally substituted by 1 to 5 substituents selected from group E".

As the "C$_{6-14}$ aryl group" of "a C$_{6-14}$ aryl group optionally substituted by 1 to 5 substituents selected, from group E" for ring D¹ and ring D², preferred is a phenyl group.

As the "heterocyclic group" of the "heterocyclic group optionally substituted by 1 to 5 substituents selected from group E" for ring D¹ and ring D², preferred is a 5- to 10-membered saturated or unsaturated monocyclic or fused heterocyclic group having 1 or 2 nitrogen atoms and optionally further having an oxygen atom or a sulfur atom, such as pyrrolidinyl group, 2-oxopyrrolidinyl group, pyridyl group, piperidyl group, piperazinyl group, morpholinyl group, thiomorpholinyl group, 1,1-dioxomorpholinyl group, azepanyl, group, 4-oxoazepanyl group, 1,4-diazepanyl group, 5-oxo-1,4-diazepanyl group, 1,4-oxazepanyl group, azocanyl group, azonanyl group, thiazolyl group,

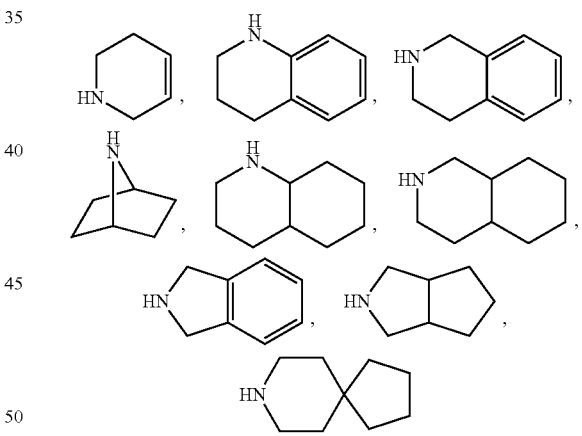

and the like. More preferred is a 5- to 7-membered saturated or unsaturated monocyclic heterocyclic group having 1 or 2 nitrogen atoms and optionally further having an oxygen atom or a sulfur atom, and particularly preferably, pyrrolidinyl group, 2-oxopyrrolidinyl group, pyridyl group, piperidyl group, piperazinyl group, morpholinyl group, thiomorpholinyl group, 1,1-dioxomorpholinyl group, azepanyl group, 1,4-diazepanyl group and 1,4-oxazepanyl group can be mentioned.

As the group E in R², preferred are "—OR$^{e1}$", "—S(O)$_q$—R$^{e2}$", "—NR$^{e3}$R$^{e4}$", "—COOR$^{e5}$", "—CONR$^{e6}$R$^{e7}$", "—COR$^{e8}$" and "a C$_{6-14}$ aryl group optionally substituted by 1 to 5 substituents selected from group B", when group E is a substituent on ring D¹ and ring D², it may be "a C$_{1-6}$ alkyl group optionally substituted by 1 to 3 substituents selected from group A".

As the "group selected from group E" represented by $R^2$, preferred are "—$CONR^{e6}R^{e7}$" and "—$COR^{e8}$".

As the "$C_{1-6}$ alkyl group optionally substituted by 1 to 3 substituents selected from group E" represented by $R^2$, preferred are a $C_{1-6}$ alkyl group optionally substituted by 1 to 3 substituents selected from "—$OR^{e1}$", "—$NR^{e3}R^{e4}$", "—$COOR^{e5}$", "—$CONR^{e6}R^{e7}$" and "—$COR^{e8}$".

With regard to group E in $R^2$,
preferred for $R^{e1}$ is a hydrogen atom or a $C_{1-6}$ alkyl group,
preferred for $R^{e2}$ is a hydrogen atom or a $C_{1-6}$ alkyl group,
preferably, $R^{e3}$ and $R^{e4}$ are each independently a hydrogen atom or a $C_{1-6}$ alkyl group,
preferred for $R^{e5}$ is a hydrogen atom or a $C_{1-6}$ alkyl group,
preferably, $R^{e6}$ and $R^{e7}$ are each independently a hydrogen atom, a hydroxyl group, a $C_{1-6}$ alkyl group optionally substituted by $C_{1-6}$ alkoxy group or $C_{1-6}$ alkoxy group,
preferred for $R^{e8}$ is a $C_{1-6}$ alkyl group or a $C_{6-14}$ aryl group,
preferred for "$C_{6-14}$ aryl group optionally substituted by 1 to 5 substituents selected from group B" is a $C_{6-14}$ aryl group,
when group E is a substituent on ring $D^1$ or ring $D^2$, "a $C_{1-6}$ alkyl group optionally substituted by 1 to 3 substituents selected from group A" is preferably a $C_{1-6}$ alkyl group.

For $R^2$, hydrogen atom, phenylsulfonyl group, benzyloxycarbonyl group, dimethylcarbamoyl group, acetyl group, allyl group, methyl group, ethyl group, propyl group, isopropyl group, butyl group, isobutyl group, sec-butyl group, tert-butyl group, cyclohexyl group, 2,2,2-trifluoroethyl group, cyanomethyl group, nitromethyl group, 2-(2-methoxyethoxy)ethyl group, pivaloylmethyl group, ethoxycarbonylmethyl group, 3-(3-methylureido)propyl group, 2-(methylcarbamoyloxy)ethyl group, 2-(methylsulfanyl)ethyl group, 2-(methanesulfonyl)ethyl group, 2-(methylsulfamoyl)ethyl group, 2-hydroxy-2-methylpropyl group, methanesulfonylcarbamoylmethyl group, 3-(dimethylamino)-2-hydroxypropyl group, carbamoylmethyl group, methylcarbamoylmethyl group, isopropylcarbamoylmethyl group, dimethylcarbamoylmethyl group, 2-(dimethylcarbamoyl)ethyl group, 3-(dimethylcarbamoyl)propyl group, isobutylcarbamoylmethyl group, (1-ethylpropyl)carbamoylmethyl group, tert-butylcarbamoylmethyl group, (2,2-dimethylpropyl)carbamoylmethyl group, (3,3-dimethylbutyl)carbamoylmethyl group, (2,2,2-trifluoroethyl)carbamoylmethyl group, methoxycarbamoylmethyl group, 2-methoxyethylcarbamoylmethyl group, 3-methoxypropylcarbamoylmethyl group, 2-(methylsulfanyl)ethylcarbamoylmethyl group, carboxymethylcarbamoylmethyl group, 2-carboxyethylcarbamoylmethyl group, 3-carboxypropylcarbamoylmethyl group, carbamoylmethylcarbamoylmethyl group, 2-(dimethylamino)ethylcarbamoylmethyl group, N-[2-(dimethylamino)ethyl]-N-methylcarbamoylmethyl group, N-(2-methoxyethyl)-N-methylcarbamoylmethyl group, 3-(dimethylamino)propylcarbamoylmethyl group, 2-(acetylamino)ethylcarbamoylmethyl group, 2-hydroxyethyl group, 3-hydroxypropyl group, 2-methoxyethyl group, 2-(dimethylamino)ethyl group, carboxymethyl group, 2-(acetylamino)ethyl group, 3-(acetylamino)propyl group, 2-(methanesulfonylamino)ethyl group, 3-(methanesulfonylamino) propyl group, 2-[N-(methanesulfonyl)-N-methylamino]ethyl group, 3-(acetylsulfamoyl)propyl group, 2-(3-methyl-2-butenyloxy)ethyl group, 2-(2-methoxyethoxy)ethylcarbamoylmethyl group, 2-(tetrahydropyran-2-yloxy)ethyl group, 2-(4-methylphenoxy)ethyl group, 3-(4-chlorophenylamino) propyl group, 2-(4-methylthiazol-2-ylamino)ethyl group, cyclopropylcarbamoylmethyl group, cyclobutylcarbamoylmethyl group, cyclopentylcarbamoylmethyl group, cyclohexylcarbamoylmethyl group, phenylcarbamoylmethyl group, benzylcarbamoylmethyl group, phenethylcarbamoylmethyl group, N-benzyl-N-methylcarbamoylmethyl group, 3-phenylpropylcarbamoylmethyl group, 4-phenylbutylcarbamoylmethyl group, 2-(3-chlorobenzyloxy)ethyl group, 3-(4-methylbenzylsulfanyl)propyl group, 2-(phenylacetylamino)ethyl group, 2-pyridylmethylcarbamoylmethyl group, 3-pyridylmethylcarbamoylmethyl group, 4-pyridylmethylcarbamoylmethyl group, 2-(pyridin-2-yl)ethylcarbamoylmethyl group, 2-(pyridin-3-yl)ethylcarbamoylmethyl group, 2-(pyridin-4-yl)ethylcarbamoylmethyl group, N-methyl-N-(pyridin-2-ylmethyl)carbamoylmethyl group, N-methyl-N-[2-(pyridin-2-yl)ethyl]carbamoylmethyl group, 3-(imidazol-1-yl)propylcarbamoylmethyl group, benzoylmethyl group, 2-(2,4-dimethylthiazol-5-yl)-2-oxoethyl group, 2-(3-methylisoxazol-4-yl)-2-oxoethyl group, 2-oxo-2-(pyrrolidin-1-yl)ethyl group, 2-(3-methoxypyrrolidin-1-yl)-2-oxoethyl group, 2-(2-carboxypyrrolidin-1-yl)-2-oxoethyl group, 2-(2-carbamoylpyrrolidin-1-yl)-2-oxoethyl group, 2-oxo-2-piperidinoethyl group, 2-morpholino-2-oxoethyl group, 2-(4-methylpiperidin-1-yl)-2-oxoethyl group, 2-(4-ethylpiperidin-1-yl)-2-oxoethyl group, 2-(3-methoxypiperidin-1-yl)-2-oxoethyl group, 2-(4-hydroxypiperidin-1-yl)-2-oxoethyl group, 2-(4-methoxypiperidin-1-yl)-2-oxoethyl group, 2-[4-(tert-butoxycarbonylamino)piperidin-1-yl]-2-oxoethyl group, 2-[4-(dimethylamino)piperidin-1-yl]-2-oxoethyl group, 2-oxo-2-(4-oxopiperidin-1-yl)ethyl group, 2-(4-methylpiperazin-1-yl)-2-oxoethyl group, 2-(4-ethylpiperazin-1-yl)-2-oxoethyl group, 2-(4-isopropylpiperazin-1-yl)-2-oxoethyl group, 2-(4-phenylpiperazin-1-yl)-2-oxoethyl group, 2-(4-acetylpiperazin-1-yl)-2-oxoethyl group, 2-(4-carboxypiperazin-1-yl)-2-oxoethyl group, 2-(4-ethoxycarbonylpiperazin-1-yl)-2-oxoethyl group, 2-(4-methanesulfonylpiperazin-1-yl)-2-oxoethyl group, 2-oxo-2-(thiomorpholin-4-yl)ethyl group, 2-oxo-2-(1-oxothiomorpholin-4-yl)ethyl group, 2-(1,1-dioxothiomorpholin-4-yl)-2-oxoethyl group, 2-(azepan-1-yl)-2-oxoethyl group, 2-(1,4-oxazepan-4-yl)-2-oxoethyl group, 2-(4-methyl-1,4-diazepan-1-yl)-2-oxoethyl group, 4-morpholino-4-oxobutyl group, 4-(4-ethylpiperazin-1-yl)-4-oxobutyl group, 2-(thiophen-2-ylcarbonylamino)ethyl group, 2-piperidinoethylcarbamoylmethyl group, 2-morpholinoethylcarbamoylmethyl group, 2-(1-methylpyrrolidin-2-yl)ethylcarbamoylmethyl group, 3-(2-oxopyrrolidin-1-yl)propylcarbamoylmethyl group and 2-(1-benzylpiperidin-4-yl)ethylcarbamoylmethyl group can be specifically mentioned.

For $R^2$, benzyl group, phenethyl group, 3-phenylpropyl group, 2-methoxybenzyl group, 2-(dimethylamino)benzyl group, 3-methoxybenzyl group, 3-(dimethylamino)benzyl group, 3-phenoxybenzyl group, 4-fluorobenzyl group, 4-chlorobenzyl group, 4-methylbenzyl group, 4-hydroxybenzyl group, 4-methoxybenzyl group, 4-cyanobenzyl group, 4-(dimethylamino)benzyl group, 4-(methylcarbamoyl)benzyl group, 4-methanesulfonylbenzyl group, 2-pyridylmethyl group, 3-pyridylmethyl group, 4-pyridylmethyl group, 6-aminopyridin-3-ylmethyl group, 6-acetylaminopyridin-3-ylmethyl group, 2-(pyrrolidin-1-yl)ethyl group, 2-(2-oxopyrrolidin-1-yl)ethyl group, 2-piperidinoethyl group, 2-(piperazin-1-yl)ethyl group, 2-(4-methylpiperidin-1-yl)ethyl group, 2-(4-ethylpiperidin-1-yl)ethyl group, 2-(1-ethylpiperidin-4-yl)ethyl group, 2-(4-hydroxypiperidin-1-yl)ethyl group, 2-(4-methoxypiperidin-1-yl)ethyl group, 2-(4-phenoxypiperidin-1-yl)ethyl group, 2-[4-(dimethylamino)piperidin-1-yl]ethyl group, 2-(1-acetylpiperidin-4-yl)ethyl group, 2-[1-(tert-butoxycarbonyl)piperidin-4-yl]ethyl group, 2-(1-methanesulfonylpiperidin-4-yl)ethyl group, 2-(4-methylpiperazin-1-yl)ethyl group, 2-(4-ethylpiperazin-1-yl)ethyl group, 2-(4-isopropylpiperazin-1-yl)ethyl group, 2-(4-phenylpiperazin-1-yl)ethyl group, 2-[4-(tert-butoxycarbonyl)piperazin-1-yl]ethyl group, 2-(4-benzoylpiperazin-1-yl)ethyl group, 2-(4-dimethylcarbamoylpiperazin-1-yl)ethyl group, 2-(4-methanesulfonylpiperazin-1-yl)ethyl group, 2-morpholinoethyl group, 2-(thiomorpholin-4-yl)ethyl group, 2-(azepan-1-yl)ethyl group, 2-(1,4-oxazepan-4-yl)ethyl group, 2-(4-methyl-1,4-diazepan-1-yl)ethyl group, 3-morpholinopropyl group, 4-morpholinobutyl group, 1-methylimidazol-2-ylmethyl group, 4-tert-butylthiazol-2-ylmethyl group, 2-methylthiazol-4-ylmethyl group, 3,5-dimethylisoxazol-4-ylmethyl group, 5-methylisoxazol-3-ylmethyl group, [1,2,4]oxadiazol-3-ylmethyl group, 4,4-dimethyl-4,5-dihydrooxazol-2-ylmethyl group, 4-methyl-4H-[1,2,4]triazol-3-ylmethyl group, 1-methyl-1H-tetrazol-5-ylmethyl group, 2-methylpyrimidin-5-ylmethyl group, 5-methylthiophen-2-ylmethyl group, 2,5-dimethyloxazol-4-ylmethyl group, 5-methyl-4-methylcarbamoyloxazol-2-ylmethyl group, 2-methoxymethyl-5-methyloxazol-4-ylmethyl group, 2-(2-dimethylaminothiazol-4-yl)ethyl group, 2-phenyl-4-methylthiazol-5-ylmethyl group, 5-(dimethylaminomethyl)-[1,2,4]oxadiazol-3-ylmethyl group, 5-(acetylaminomethyl)-[1,2,4]oxadiazol-3-ylmethyl group, 2-(dimethylcarbamoylmethyl)-2H-tetrazol-5-ylmethyl group, 1-methylindo-3-ylmethyl group, phenylpyridin-2-ylmethyl group, benzhydrylcarbamoylmethyl group, 4-styrylbenzyl group, 2-(2-morpholino-2-oxoethoxy)ethyl group, 2-oxo-2-[4-(piperidinoacetyl)piperazino]ethyl group, 2-oxo-2-[4-(pyrrolidin-1-yl)piperidin-1-yl]ethyl group, 2-(2-phenoxyethylamino)ethyl group, 4-(morpholinocarbonyl)benzyl group, 3-(3-morpholinophenyl)propyl group, 3-ethynyloxybenzyl group, 2-{N-[3-(dimethylaminoacetylamino)benzyl]-N-methylamino}ethyl group, 2-(dibenzylamino)ethylcarbamoylmethyl group, 4-(2-dibenzylaminomethyl)cyclohexylmethyl group, 2-(morpholinoacetylamino)ethoxycarbonylmethyl group, 3-{1-[2-(2-methoxyethoxy)phenylacetyl]piperidin-4-ylmethylcarbamoyl}benzyl group, 2-(2-morpholinoethoxy)-5-{N-methyl-N-[4-(4-nitrophenylsulfonyl)benzoyl]amino}benzyl group, 2-[N-(2-pyridylmethyl)amino]ethyl group and 2-[N-(2-methoxyethyl)-N-methylamino]ethyl group can be specifically mentioned.

In addition, for $R^2$,
3-oxo-3-piperidinopropyl group,
3-morpholino-3-oxopropyl group,
3-(4-methylpiperazin-1-yl)-3-oxopropyl group,
3-(4-ethylpiperazin-1-yl)-3-oxopropyl group,
3-(4-acetylpiperazin-1-yl)-3-oxopropyl group,
3-(4-methanesulfonylpiperazin-1-yl)-3-oxopropyl group,
3-(4-methoxypiperazin-1-yl)-3-oxopropyl group,
3-(4-methoxycarbonylpiperazin-1-yl)-3-oxopropyl group,
3-piperidinopropyl group,
3-(4-methylpiperazin-1-yl)propyl group,
3-(4-ethylpiperazin-1-yl)propyl group,
3-(4-acetylpiperazin-1-yl)propyl group,
3-(4-methanesulfonylpiperazin-1-yl)propyl group,
3-(4-methoxypiperazin-1-yl)propyl group,
3-(4-methoxycarbonylpiperazin-1-yl)propyl group,
(tetrahydropyran-4-yl)methyl group,
2-(tetrahydropyran-4-yl)ethyl group,
(1-methylpiperidin-4-yl)methyl group,
(1-ethylpiperidin-4-yl)methyl group,
(1-acetylpiperidin-4-yl)methyl group,
(1-methanesulfonylpiperidin-4-yl)methyl group,
(1-methoxypiperidin-4-yl)methyl group,
(1-methoxycarbonylpiperidin-4-yl)methyl group,
2-(tetrahydropyran-3-yl)ethyl group,
2-(1-methylpiperidin-3-yl)ethyl group,
2-(1-ethylpiperidin-3-yl)ethyl group,
2-(1-acetylpiperidin-3-yl)ethyl group,
2-(1-methanesulfonylpiperidin-3-yl)ethyl group,
2-(1-methoxypiperidin-3-yl)ethyl group,
2-(1-methoxycarbonylpiperidin-3-yl)ethyl group,
(tetrahydropyran-3-yl)methyl group,
(1-methylpiperidin-3-yl)methyl group,
(1-ethylpiperidin-3-yl)methyl group,
(1-acetylpiperidin-3-yl)methyl group,
(1-methanesulfonylpiperidin-3-yl)methyl group,
(1-methoxypiperidin-3-yl)methyl group,
(1-methoxycarbonylpiperidin-3-yl)methyl group,
2-(tetrahydropyran-2-yl)ethyl group,
2-(1-methylpiperidin-2-yl)ethyl group,
2-(1-ethylpiperidin-2-yl)ethyl group,
2-(1-acetylpiperidin-2-yl)ethyl group,
2-(1-methanesulfonylpiperidin-2-yl)ethyl group,
2-(1-methoxypiperidin-2-yl)ethyl group,
2-(1-methoxycarbonylpiperidin-2-yl)ethyl group,
(tetrahydropyran-2-yl)methyl group,
(1-methylpiperidin-2-yl)methyl group,
(1-ethylpiperidin-2-yl)methyl group,
(1-acetylpiperidin-2-yl)methyl group,
(1-methanesulfonylpiperidin-2-yl)methyl group,
(1-methoxypiperidin-2-yl)methyl group,
(1-methoxycarbonylpiperidin-2-yl)methyl group,
2-(2-oxopiperidin-1-yl)ethyl group,
2-(3-oxomorpholin-4-yl)ethyl group,
2-(4-methyl-2-oxopiperazin-1-yl)ethyl group,
2-(4-ethyl-2-oxopiperazin-1-yl)ethyl group,
2-(4-acetyl-2-oxopiperazin-1-yl)ethyl group,
2-(4-methanesulfonyl-2-oxopiperazin-1-yl)ethyl group,
2-(4-methoxy-2-oxopiperazin-1-yl)ethyl group,
3-(4-methoxycarbonyl-2-oxopiperazin-1-yl)ethyl group,
2-(4-ethylidenepiperidin-1-yl)ethyl group,
2-(4-methylenepiperidin-1-yl)ethyl group,
2-(4-isopropylidenepiperidin-1-yl)ethyl group,
2-(1-methylpiperidin-4-ylidene)ethyl group,
2-(1-ethylpiperidin-4-ylidene)ethyl group,
2-(1-acetylpiperidin-4-ylidene)ethyl group,
2-(1-methanesulfonylpiperidin-4-ylidene)ethyl group,
2-(1-methoxypiperidin-4-ylidene)ethyl group,
2-(1-methoxycarbonylpiperidin-4-ylidene)ethyl group,
2-cyclohexyloxyethyl group,
2-(tetrahydropyran-4-yloxy)ethyl group,
2-(1-methylpiperidin-4-yloxy)ethyl group,
2-(1-ethylpiperidin-4-yloxy)ethyl group,
2-(1-acetylpiperidin-4-yloxy)ethyl group,
2-(1-methanesulfonylpiperidin-4-yloxy)ethyl group,
2-(1-methoxypiperidin-4-yloxy)ethyl group,
2-(1-methoxycarbonylpiperidin-4-yloxy)ethyl group,
2-isopropoxyethyl group,
2-(2-thiazolyl)ethyl group,
2-(2-methylimidazol-1-yl)ethyl group,
2-(2-pyridyl)ethyl group,
2-(3-pyridyl)ethyl group,
2-(4-pyridyl)ethyl group,
2-(2-dimethylaminothiazol-4-yl)ethyl group,
(2-thiazolyl)methyl group,
(2-methylimidazol-1-yl)methyl group,
(2-pyridyl)methyl group,
(3-pyridyl)methyl group,
(4-pyridyl)methyl group,
2-dimethylaminothiazol-4-yl)methyl group,
2-(4-ethyl-1,4-diazepan-1-yl)-2-oxoethyl group,
2-(3-hydroxypiperidin-1-yl)-2-oxoethyl group, 2-(3-methoxypiperidin-1-yl)-2-oxoethyl group,
2-(3-methylpiperidin-1-yl)-2-oxoethyl group,
2-(azocan-1-yl)-2-oxoethyl group,
2-(azonan-1-yl)-2-oxoethyl group,
2-oxo-2-(1,2,3,4-tetrahydroquinolin-1-yl)ethyl group,
2-oxo-2-(1,2,3,4-tetrahydroisoquinolin-2-yl)ethyl group,
2-(octahydrocyclopenta[c]pyrrol-2-yl)-2-oxoethyl group,
2-oxo-2-(4-trifluoromethylpiperidin-1-yl)ethyl group,
2-oxo-2-(4-propylpiperidin-1-yl)ethyl group,
2-(4-isopropylpiperidin-1-yl)-2-oxoethyl group,
2-(4,4-dimethylpiperidin-1-yl)-2-oxoethyl group,
2-oxo-2-(2,2,6,6-tetramethylpiperidin-1-yl)ethyl group,
2-oxo-2-(1,2,3,6-tetrahydropyridin-1-yl)ethyl group,
2-(isoindolin-2-yl)-2-oxoethyl group,
2-(octahydroisoindol-2-yl)-2-oxoethyl group,
1-adamantylcarbamoylmethyl group,
2-(2-methylpiperidin-1-yl)-2-oxoethyl group,
diethylcarbamoylmethyl group,
diisopropylcarbamoylmethyl group,
2-(4-ethyl-1,4-diazepan-1-yl)ethyl group,
2-(3-hydroxypiperidin-1-yl)ethyl group,
2-(3-methoxypiperidin-1-yl)ethyl group,
2-(3-methylpiperidin-1-yl)ethyl group,
2-(azocan-1-yl)ethyl group,
2-(azonan-1-yl)ethyl group,
2-(1,2,3,4-tetrahydroquinolin-1-yl)ethyl group,
2-(1,2,3,4-tetrahydroisoquinolin-2-yl)ethyl group,
2-(octahydrocyclopenta[c]pyrrol-2-yl)ethyl group,
2-(4-trifluoromethylpiperidin-1-yl)ethyl group,
2-(4-propylpiperidin-1-yl)ethyl group,
2-(4-isopropylpiperidin-1-yl)ethyl group,
2-(4,4-dimethylpiperidin-1-yl)ethyl group,
2-(2,2,6,6-tetramethylpiperidin-1-yl)ethyl group,
2-(1,2,3,6-tetrahydropyridin-1-yl)ethyl group,
2-(isoindolin-2-yl)ethyl group,
2-(octahydroisoindol-2-yl)ethyl group,
2-(1-adamantylamino)ethyl group,
2-(2-methylpiperidin-1-yl)ethyl group,
2-(diethylamino)ethyl group,
2-(diisopropylamino)ethyl group,
2-(4-methoxycarbonylpiperazin-1-yl)-2-oxoethyl group,
2-(4-methylcarbamoylpiperazin-1-yl)-2-oxoethyl group,
2-[4-(2-methoxyacetyl)piperazin-1-yl]-2-oxoethyl group,
2-(4-cyclopentyloxycarbonylpiperazin-1-yl)-2-oxoethyl group,
2-(4-benzylpiperazin-1-yl)-2-oxoethyl group,
2-(4-isobutyrylpiperazin-1-yl)-2-oxoethyl group,
2-(4-methoxycarbonylpiperazin-1-yl)ethyl group,
2-(4-methylcarbamoylpiperazin-1-yl)ethyl group,
2-[4-(2-methoxyacetyl)piperazin-1-yl]ethyl group,
2-(4-cyclopentyloxycarbonylpiperazin-1-yl)ethyl group,
2-(4-benzylpiperazin-1-yl)ethyl group,
2-(4-isobutyrylpiperazin-1-yl)ethyl group,
methylcarbamoyl group,
tert-butylcarbamoyl group,
N-tert-butyl-N-methylcarbamoyl group,
cyclohexylcarbamoyl group,
(tetrahydropyran-4-yl)carbamoyl group,
(1-methylpiperidin-4-yl)carbamoyl group,
(1-acetylpiperidin-4-yl)carbamoyl group,
(1-methanesulfonylpiperidin-4-yl)carbamoyl group,
(1-methoxycarbonylpiperidin-4-yl)carbamoyl group,
cyclopentylcarbamoyl group,
(tetrahydrofuran-3-yl)carbamoyl group,
(1-methylpyrrolidin-3-yl)carbamoyl group,
(1-acetylpyrrolidin-3-yl)carbamoyl group,
(1-methanesulfonylpyrrolidin-3-yl)carbamoyl group,
(1-methoxycarbonylpyrrolidin-3-yl)carbamoyl group,
N-cyclohexyl-N-methylcarbamoyl group,
N-methyl-N-(tetrahydropyran-4-yl)carbamoyl group,
N-methyl-N-(1-methylpiperidin-4-yl)carbamoyl group,
N-(1-acetylpiperidin-4-yl)-N-methylcarbamoyl group,
N-(1-methanesulfonylpiperidin-4-yl)-N-methylcarbamoyl group,
N-(1-methoxycarbonylpiperidin-4-yl)-N-methylcarbamoyl group,
N-cyclopentyl-N-methylcarbamoyl group,
N-methyl-N-(tetrahydrofuran-3-yl)carbamoyl group,
N-methyl-N-(1-methylpyrrolidin-3-yl)carbamoyl group,
N-(1-acetylpyrrolidin-3-yl)-N-methylcarbamoyl group,
N-(1-methanesulfonylpyrrolidin-3-yl)-N-methylcarbamoyl group,
N-(1-methoxycarbonylpyrrolidin-3-yl)-N-methylcarbamoyl group,
2-(N-acetyl-N-methylamino)ethyl group,
2-(N-methyl-N-propionylamino)ethyl group,
2-(N-cyclohexanecarbonyl-N-methylamino)ethyl group,
2-[N-methyl-N-(tetrahydropyran-4-carbonyl)amino]ethyl group,
2-[N-methyl-N-(1-methylpiperidine-4-carbonyl)amino]ethyl group,
2-[N-(1-acetylpiperidine-4-carbonyl)-N-methylamino]ethyl group,
2-[N-(1-methanesulfonylpiperidine-4-carbonyl)-N-methylamino]ethyl group,
2-[N-(1-methoxycarbonylpiperidine-4-carbonyl)-N-methylamino]ethyl group,
2-(N-cyclopentanecarbonyl-N-methylamino)ethyl group,
2-[N-methyl-N-(tetrahydrofuran-3-carbonyl)amino]ethyl group,
2-[N-methyl-N-(1-methylpyrrolidine-3-carbonyl)amino]ethyl group,
2-[N-(1-acetylpyrrolidine-3-carbonyl)-N-methylamino]ethyl group,
2-[N-(1-methanesulfonylpyrrolidine-3-carbonyl)-N-methylamino]ethyl group,
2-[N-(1-methoxycarbonylpyrrolidine-3-carbonyl)-N-methylamino]ethyl group,
2-(N-methanesulfonyl-N-methylamino)ethyl group,
2-(N-methoxycarbonyl-N-methylamino)ethyl group,
2-(N-ethoxycarbonyl-N-methylamino)ethyl group,
2-(N-cyclohexyloxycarbonyl-N-methylamino)ethyl group,
2-[N-methyl-N-(tetrahydropyran-4-yloxycarbonyl)amino]ethyl group,
2-[(N-methyl-N-(1-methylpiperidin-4-yloxycarbonyl)amino]ethyl group,
2-[N-(1-acetylpiperidin-4-yloxycarbonyl)-N-methylamino]ethyl group,
2-[N-(1-methanesulfonylpiperidin-4-yloxycarbonyl)-N-methylamino]ethyl group,
2-[N-(1-methoxycarbonylpiperidin-4-yloxycarbonyl)-N-methylamino]ethyl group,
2-(N-cyclopentyloxycarbonyl-N-methylamino)ethyl group,
2-[N-methyl-N-(tetrahydrofuran-3-yloxycarbonyl)amino]ethyl group,
2-[N-methyl-N-(1-methylpyrrolidin-3-yloxycarbonyl)amino]ethyl group,
2-[N-(1-acetylpyrrolidin-3-yloxycarbonyl)-N-methylamino]ethyl group,
2-[N-(1-methanesulfonylpyrrolidin-3-yloxycarbonyl)-N-methylamino]ethyl group, and
2-[N-(1-methoxycarbonylpyrrolidin-3-yloxycarbonyl)-N-methylamino]ethyl group can be mentioned.

As specific examples of $R^2$, the following groups can be mentioned.

2-(4-acetylpiperazin-1-yl)ethyl group,
3-(tetrahydropyran-2-yloxy)propyl group,
2-(1-isopropylpiperidin-4-yl)ethyl group,
2-(3,6-dihydro-2H-pyridin-1-yl)-2-oxoethyl group,
2-(octahydroquinolin-1-yl)-2-oxoethyl group,
2-(1,3-dihydroisoindol-2-yl)-2-oxoethyl group,
2-(octahydroisoquinolin-2-yl)-2-oxoethyl group,
2-(octahydroquinolin-1-yl)ethyl group,
2-(1,3-dihydroisoindol-2-yl)ethyl group,
2-(octahydroisoquinolin-2-yl)ethyl group,
3-dimethylaminopropyl group,
1-tert-butoxycarbonylpiperidin-3-ylmethyl group
2-(1-cyclopentylpiperidin-4-yl)ethyl group,
2-(1-tert-butoxycarbonylpiperidin-2-yl)ethyl group,
2-(piperidin-3-yl)ethyl group,
2-(1-tert-butoxycarbonylpiperidin-3-yl)ethyl group,
2-(4,4-difluoropiperidin-1-yl)-2-oxoethyl group,
2-(1-propylpiperidin-4-yl)ethyl group,
2-(4,4-difluoropiperidin-1-yl)ethyl group,
2-(1-ethylpiperidin-4-ylidene)-2-fluoroethyl group,
cis-2-(octahydroisoindol-2-yl)ethyl group,
2-(8-azaspiro[4.5]decan-8-yl)ethyl],
2-(3,5-dimethylpiperidin-1-yl)-2-oxoethyl group,
2-(3-ethylpiperidin-1-yl)ethyl group,
2-(cis-2,6-dimethylpiperidin-1-yl)ethyl group,
3-(azepan-1-yl)propyl group,
2-(4-methoxymethylpiperidin-1-yl)ethyl group,
2-(N-methyl-N-propylamino)ethyl group,
2-(3-methoxymethylpiperidin-1-yl)ethyl group,
2-(1-isopropylpiperidin-3-yl)ethyl group,
2-(3,6-dihydro-2H-pyridin-1-yl)ethyl group,
2-((S)-2-methoxymethylpyrrolidin-1-yl)ethyl group,
2-(2-methylpyrrolidin-1-yl)ethyl group,
2-(N-isobutyl-N-methylamino)ethyl group,
2-(N-isopropyl-N-methylamino)ethyl group,
2-[N-(2-dimethylaminoethyl)-N-methylamino group,
2-(4-ethanesulfonylpiperazin-1-yl)ethyl group,
2-(4-propionylpiperazin-1-yl)ethyl group,
2-(4-isopropoxycarbonylpiperazin-1-yl)ethyl group,
2-(1-propylpiperidin-3-yl)ethyl group,
2-(N-cyclohexyl-N-methylamino)ethyl group,
2-(4-methanesulfonyl-1,4-diazepan-1-yl)ethyl group,
2-(4-methoxycarbonyl-1,4-diazepan-1-yl)ethyl group,
2-(3-methylpyrroidin-1-yl)ethyl group,
2-(3-methoxypyrrolidin-1-yl)ethyl group,
2-(piperidin-4-yl)ethyl group,
2-(1-methylpiperidin-4-yl)ethyl group,
2-[N-(1-methoxycarbonylpyrrolidin-3-yl)-N-methylamino] ethyl group,
2-[N-(1-acetylpyrrolidin-3-yl)-N-methylamino]ethyl group,
2-[N-(1-methanesulfonylpyrrolidin-3-yl)-N-methylamino] ethyl group,
2-(2-methylmorpholin-4-yl)ethyl group,
2-(2-ethylmorpholin-4-yl)ethyl group,
2-(3-ethylmorpholin-4-yl)ethyl group,
2-(1-isobutylpiperidin-3-yl)ethyl group,
2-(1-cyclopentylpiperidin-3-yl)ethyl group,
2-(3-propylpiperidin-1-yl)ethyl group,
3-(pyrrolidin-1-yl)propyl group,
3-(1,4-oxazepan-4-yl)propyl group,
2-(2-methoxymethylpiperidin-1-yl)ethyl group,
2-[N-(1-acetylpiperidin-4-yl)-N-methylamino]ethyl group,
2-[N-(1-methanesulfonylpiperidin-4-yl)-N-methylamino] ethyl group,
2-[N-(1-methoxycarbonylpiperidin-4-yl)-N-methylamino] ethyl group,
2-[N-methyl-N-(1-methylpiperidin-4-yl)amino]ethyl group,
2-[N-methyl-N-(tetrahydropyran-4-yl)amino]ethyl group,
2-[N-methyl-N-(1-methylpyrrolidin-3-yl)amino]ethyl group,
2-[N-methyl-N-(pyrrolidin-3-yl)amino]ethyl group,
3-diethylaminopropyl group,
2-[3-(2-methoxyethyl)piperidin-1-yl]ethyl group,
2-((R)-2-methoxymethylpyrrolidin-1-yl)ethyl group,
2-(1-isopropylpiperidin-4-yloxy)ethyl group,
2-(N-cyclopentyl-N-methylamino)ethyl group,
3-(3-methylpiperidin-1-yl)propyl group,
2-[N-methyl-N-(tetrahydrofuran-3-yl)amino]ethyl group,
3-(2-methylpiperidin-1-yl) propyl group,
2-(3-ethoxypiperidin-1-yl)ethyl group,
2-(2-ethylpiperidin-1-yl)ethyl group,
2-((S)-3-ethylpiperidin-1-yl)ethyl group,
2-((R)-3-ethylpiperidin-1-yl)ethyl group,
2-(1-cyclopropylpiperidin-3-yl)ethyl group,
2-[N,N-dimethyl-N-(5-methylisoxazol-3-ylmethyl)ammonio]ethyl group,
3-(3-methoxymethylpiperidin-1-yl)propyl group,
3-(2-ethylpiperidin-1-yl)propyl group,
3-(2-methoxymethylpiperidin-1-yl)propyl group,
2-(3-isopropylpiperidin-1-yl)ethyl group,
3-(2-methylpyrrolidin-1-yl)propyl group,
2-(1-isopropylpiperidin-3-yloxy)ethyl group,
3-(3-ethylpiperidin-1-yl)propyl group,
2-(1-cyclohexylpiperidin-3-yl)ethyl group,
2-(3-ethylpyrrolidin-1-yl)ethyl group,
2-[1-(1-ethylpropyl)piperidin-3-yl]ethyl group,
2-(3-ethoxymethylpiperidin-1-yl)ethyl group,
2-(3-isopropoxypiperidin-1-yl)ethyl group,
2-[(S)-3-(2-methoxyethyl)piperidin-1-yl]ethyl group,
2-[(R)-3-(2-methoxyethyl)piperidin-1-yl]ethyl group,
2-(1-ethylpiperidin-3-yloxy)ethyl group,
3-(N-ethyl-N-isopropylamino)propyl group,
2-((S)-1-cyclopentylpiperidin-3-yl)ethyl group,
2-(3-isopropoxymethylpiperidin-1-yl)ethyl group,
2-((R)-1-cyclopentylpiperidin-3-yl)ethyl group,
3-(1-ethylpiperidin-3-yl)propyl group,
3-(1-cyclopentylpiperidin-3-yl)propyl group,
4-(piperidin-1-yl)butyl group,
2-((R)-3-methoxymethylpiperidin-1-yl)ethyl group,
2-((S)-3-methoxymethylpiperidin-1-yl)ethyl group,
4-diethylaminobutyl group,
2-(1-methylpyrrolidin-2-yl)ethyl group,
3-(N-ethyl-N-propylamino)propyl group,
3-diisopropylaminopropyl group,
3-[N-ethyl-N-(2-methoxyethyl)amino]propyl group,
3-[N-ethyl-N-(3-methoxypropyl)amino]propyl group,
3-[N-(3-ethoxypropyl)-N-ethylamino]propyl group,
2-(3-hydroxymethylpiperidin-1-yl)ethyl group,
3-diethylamino-2,2-dimethylpropyl group,
2-(3,3-dimethylpiperidin-1-yl)ethyl group,
3-diethylamino-2-methoxypropyl group,
3-[N-ethyl-N-(2-hydroxyethyl)amino]propyl group,
2-(4-hydroxymethylpiperidin-1-yl)ethyl group,
2-[(S)-3-(2-phenoxyethyl)piperidin-1-yl]ethyl group,
2-((S)-3-phenoxymethylpiperidin-1-yl)ethyl group,
2-(7-benzyl-7-azabicyclo[2.2.1]hept-1-yl)ethyl group,
2-(7-azabicyclo[2.2.1]hept-1-yl)ethyl group,
2-(7-carboxymethyl-7-azabicyclo[2.2.1]hept-1-yl)ethyl group,
2-cyclohexylethyl group,
2-[(S)-3-(2-hydroxyethyl)piperidin-1-yl]ethyl group, 2-((R)-3-phenoxymethylpiperidin-1-yl)ethyl group,
2-[4-(2-methoxyethyl)piperidin-1-yl]ethyl group,
3-diethylamino-2-hydroxypropyl group,
2-(4-acetyl-1,4-diazepan-1-yl)ethyl group,
2-[(S)-3-(2-ethoxyethyl)piperidin-1-yl]ethyl group,
2-(5-oxo-1,4-diazepan-1-yl)ethyl group,
2-(4-methoxyazepan-1-yl)ethyl group,
2-(4-methyl-5-oxo-1,4-diazepan-1-yl)ethyl group,
2-[(S)-3-(dimethylcarbamoylmethyl)piperidin-1-yl]ethyl group,
2-[(R)-3-(2-methoxyethoxymethyl)piperidin-1-yl]ethyl group,
2-[(S)-3-(2-hydroxy-2-methylpropyl)piperidin-1-yl]ethyl group,
2-[N-ethyl-N-(3-methoxypropyl)amino]ethyl group,
2-(6-methyl-1,4-oxazepan-4-yl)ethyl group,
2-[(R)-3-(1-hydroxy-1-methylethyl)piperidin-1-yl]ethyl group,
2-[1-(2-methoxyethyl)piperidin-3-yl]ethyl group,
2-(4-oxoazepan-1-yl)ethyl group,
2-[(S)-3-(2-dimethylcarbamoylethyl)piperidin-1-yl]ethyl group,
2-(4-hydroxyazepan-1-yl)ethyl group,
2-[N-ethyl-N-(4-methoxybutyl)amino]ethyl group,
2-[(S)-3-(3-methoxypropyl)piperidin-1-yl]ethyl group,
2-[(R)-3-(1-methoxy-1-methylethyl)piperidin-1-yl]ethyl group,
2-(3-dimethylcarbamoylpiperidin-1-yl)ethyl group,
2-[(R)-3-(2-methoxyethoxy)piperidin-1-yl]ethyl group,
2-(3-methoxymethylazepan-1-yl)ethyl group,
2-{(S)-3-[2-(N-acetyl-N-methylamino)ethyl]piperidin-1-yl}ethyl group,
2-[(S)-3-(2-dimethylaminoethyl)piperidin-1-yl]ethyl group,
2-((S)-3-carboxymethylpiperidin-1-yl)ethyl group,
2-{(S)-3-[2-(N-tert-butoxycarbonyl-N-methylamino)ethyl]piperidin-1-yl}ethyl group,
1-benzyloxycarbonylpiperidin-4-yl group,
2-{(S)-3-[2-(trimethylureido)ethyl]piperidin-1-yl}ethyl group,
piperidin-4-yl group,
1-acetylpiperidin-4-yl group,
1-methylpiperidin-4-yl group,
2-{(S)-3-[2-(2-oxopyrrolidin-1-yl)ethyl]piperidin-1-yl}ethyl group,
2-[(S)-3-(2-methoxyethyl)piperidin-1-yl]-2-oxoethyl group,
2-(1-methoxycarbonylpiperidin-4-yl)ethyl group,
2-(4-fluorophenyl)ethyl group,
2-(4-methylthiazol-2-yl)ethyl group.

For $R^3$, preferred are hydrogen atom, halogen atom, "a $C_{1-6}$ alkyl group optionally substituted by 1 to 3 substituents selected from group A" or $-OR^{101}$ (wherein $R^{101}$ is a hydrogen atom or a group selected from group C), and specifically, a hydrogen atom, fluorine atom, chlorine atom, methyl group, methoxy group and the like can be specifically mentioned, particularly preferably hydrogen atom.

For $R^4$, preferred are a group that does not markedly degrade pharmacological activity, such as fluorine atom, chlorine atom, methyl group, methoxy group and the like can be mentioned.

For a, preferred is 0.

Preferably, $R^5$ and $R^6$ are each independently a hydrogen atom, "a halogen atom", "a $C_{1-6}$ alkyl group optionally substituted by 1 to 3 substituents selected from group A" or "$-OR^{120}$", which is specifically hydrogen atom, fluorine atom, methyl group, ethyl group or trifluoromethyl group, more preferably hydrogen atom.

For ring A, preferred are benzene or "a 5- or 6-membered heterocycle comprising 1 to 4 heteroatoms selected from oxygen atom, nitrogen atom and sulfur atom", more prepared are benzene and pyrrole, particularly preferred is benzene.

For ring Cy, preferred are a $C_{3-10}$ cycloalkyl group and a $C_{3-10}$ cycloalkenyl group, more preferred are cyclohexyl group and cyclohexenyl group, particularly preferred is cyclohexyl group.

For X, preferred are a hydrogen atom, a halogen atom, "a $C_{1-6}$ alkyl group optionally substituted by 1 to 3 substituents selected from group A", "$-(CH_2)_t-OR^{d1}$", "$-(CH_2)_t-S(O)_q-R^{d2}$", "$-(CH_2)_t-NR^{d3}R^{d4}$" and

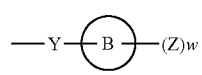

wherein each symbol is as defined above, more preferred are a hydrogen atom, a halogen atom, "a $C_{1-6}$ alkyl group optionally substituted by 1 to 3 substituents selected from group A", "$-(CH_2)_t-OR^{d1}$", "$-(CH_2)_t-S(O)_q-R^{d2}$" and

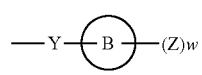

wherein each symbol is as defined above.

For Y, preferred is $-(CH_2)_m-O-(CH_2)_n-$ (wherein each symbol is as defined above), more preferred are $-O-CH_2-$ and $-O-$, still more preferred is $-O-CH_2-$.

Other preferable embodiment of Y is $-NR^{y1}-(CH_2)_m-Y^2-$, more preferably, $-NR^{y1}-CH_2-CO-$ or $-NR^{y1}-(CH_2)_2-$.

For $R^{y1}$, preferred is "a heterocycle $C_{1-6}$ alkyl group optionally substituted by 1 to 5 substituents selected from group B" or $-(CH_2)_s-COR^{y11}$. For $R^{y11}$, preferred is "a heterocyclic group optionally substituted by 1 to 5 substituents selected from group B".

For ring B, preferred are a $C_{6-14}$ aryl group and "a heterocyclic group comprising 1 to 4 heteroatoms selected from oxygen atom, nitrogen atom and sulfur atom", more preferred are phenyl group, pyridyl group, piperidyl group, pyrrolidinyl group, piperazinyl group, morpholinyl group, azepanyl group, 1,4-oxazepanyl group, isoxazolyl group, thiazolyl group and 2-oxooxazolidinyl group, more preferred are phenyl group, pyridyl group and piperidyl group, and still more preferred is phenyl group.

For Z, preferred are 1 to 3 substituents selected from
(1) a hydrogen atom,
(2) a halogen atom,
(3) a nitro group,
(4) a $C_{6-14}$ aryl group optionally substituted by 1 to 5 substituents selected from group D,
(5) a $C_{3-10}$ cycloalkyl group optionally substituted by 1 to 5 substituents selected from group D,
(6) a heterocyclic group optionally substituted by 1 to 5 substituents selected from group D,
(7) a $C_{1-6}$ alkyl group optionally substituted by 1 to 3 substituents selected from the aforementioned group A,
(8) $-(CH_2)_t-OR^{d1}$,
(9) $-(CH_2)_t-S(O)_q-R^{d2}$,
(10) $-(CH_2)_t-NR^{d3}R^{d4}$,
(11) $-(CH_2)_t-COOR^{d5}$,
(12) $-(CH_2)_t-CONR^{d6}R^{d7}$,

(13) —(CH$_2$)$_t$—COR$^{d8}$,
(14) —(CH$_2$)$_t$—NR$^{d9}$CO—R$^{d10}$,
(15) —(CH$_2$)$_t$—NR$^{d11}$SO$_2$—R$^{d12}$, and
(16) —(CH$_2$)$_t$—NR$^{d19}$—COOR$^{d20}$
(wherein each symbol is as defined above), more preferably, 1 to 3 substituents selected from
(1) a hydrogen atom,
(2) a halogen atom,
(3) a C$_{6-14}$ aryl group optionally substituted by 1 to 5 substituents selected from group D,
(4) a heterocyclic group optionally substituted by 1 to 5 substituents selected from group D,
(5) —(CH$_2$)$_t$—OR$^{d1}$,
(6) —(CH$_2$)$_t$—S(O)$_q$—R$^{d2}$,
(7) —(CH$_2$)$_t$—NR$^{d3}$R$^{d4}$,
(8) —(CH$_2$)$_t$—COOR$^{d5}$,
(9) —(CH$_2$)$_t$—NR$^{d9}$CO—R$^{d10}$, and
(10) —(CH$_2$)$_t$—NR$^{d11}$SO$_2$—R$^{d12}$
(wherein each symbol is as defined above).

The "C$_{6-14}$ aryl group" of the "C$_{6-14}$ aryl group optionally substituted by 1 to 5 substituents selected from group D" for Z is preferably a phenyl group.

The "heterocyclic group" of the "heterocyclic group optionally substituted by 1 to 5 substituents selected from group D" for Z is preferably a pyrrolidinyl group, a 2-oxopyrrolidinyl group, a piperidinyl group, a piperidinyl group or a morpholinyl group.

When Z is "a C$_{6-14}$ aryl group optionally substituted by 1 to 5 substituents selected from group D" or "a heterocyclic group optionally substituted by 1 to 5 substituents selected from group D", the group D is preferably a hydrogen atom, "C$_{1-6}$ alkyl group optionally substituted by 1 to 3 substituents selected from A", "—(CH$_2$)$_t$—S(O)$_q$—R$^{d2}$" or "—(CH$_2$)$_t$—CONR$^{d6}$R$^{d7}$".

With regard to group D in Z,
for R$^{d1}$, preferred are a hydrogen atom and a C$_{1-6}$ alkyl group,
for R$^{d2}$, preferred are a hydrogen atom and a C$_{1-6}$ alkyl group,
preferably, R$^{d3}$ and R$^{d4}$ are each independently a hydrogen atom or a C$_{1-6}$ alkyl group,
for R$^{d5}$, preferred are a hydrogen atom and a C$_{1-6}$ alkyl group,
for R$^{d9}$, preferred are a hydrogen atom, a C$_{1-6}$ alkyl group and a C$_{1-6}$ alkanoyl group,
for R$^{d10}$, preferred are a C$_{1-6}$ alkyl group optionally substituted by —NR$^{a1}$R$^{a2}$ and a heterocycle C$_{1-6}$ alkyl group (wherein the heterocycle C$_{1-6}$ alkyl group is preferably a morpholinomethyl group),
for R$^{d11}$, preferred are a hydrogen atom, a C$_{1-6}$ alkyl group and a C$_{1-6}$ alkanoyl group,
for R$^{d12}$, preferred are a hydrogen atom and a C$_{1-6}$ alkyl group, for the "C$_{1-6}$ alkyl group optionally substituted by 1 to 3 substituents selected from A", preferred is a C$_{1-6}$ alkyl group.

X is specifically hydrogen atom, methyl group, ethyl group, propyl group, isopropyl group, tert-butyl group, fluorine atom, chlorine atom, bromine atom, trifluoromethyl group, hydroxyl group, methoxy group, ethoxy group, isopropoxy group, methylsulfanyl group, trifluoromethoxy group, cyano group, nitro group, amino group, dimethylamino group, phenyl group, pyridyl group (2-pyridyl group, 3-pyridyl group, 4-pyridyl group), carbamoyl group, carboxyl group, 2-methoxyethoxy group, 2-(2-hydroxyethylamino)ethoxy group, 2-dimethylaminoethoxy group, carboxymethoxy group, methoxycarbonyloxy group and the like can be mentioned.

X is more specifically

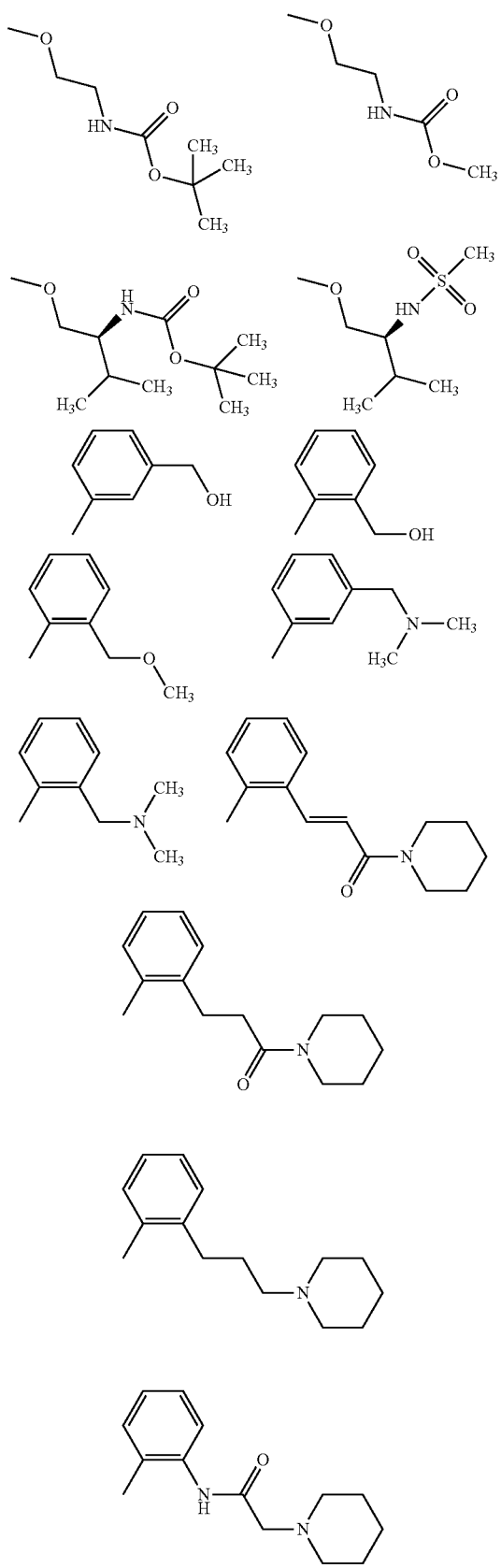

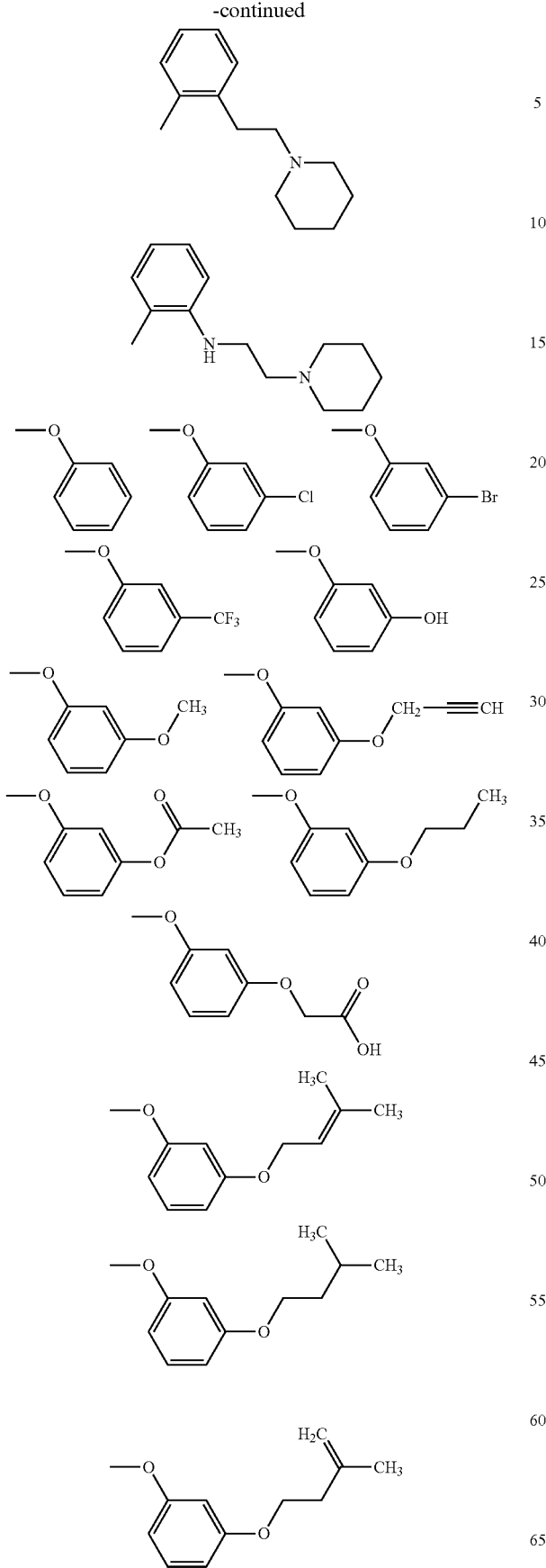
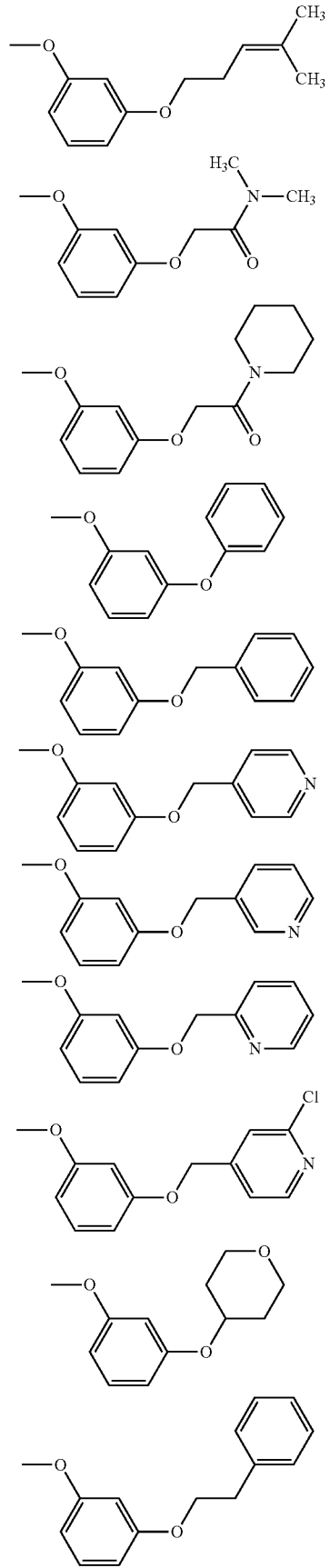

207
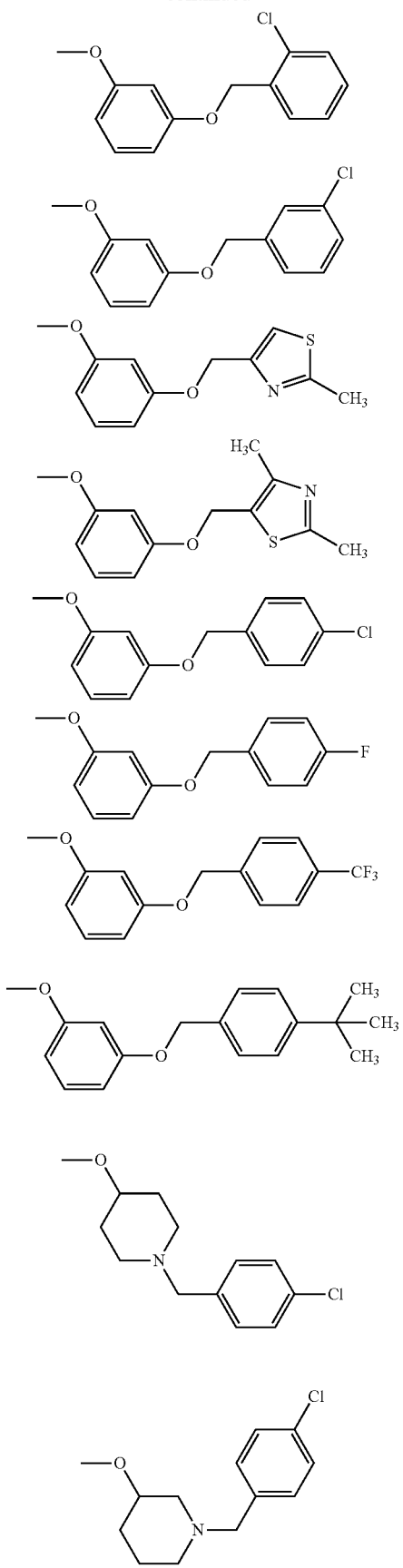
208
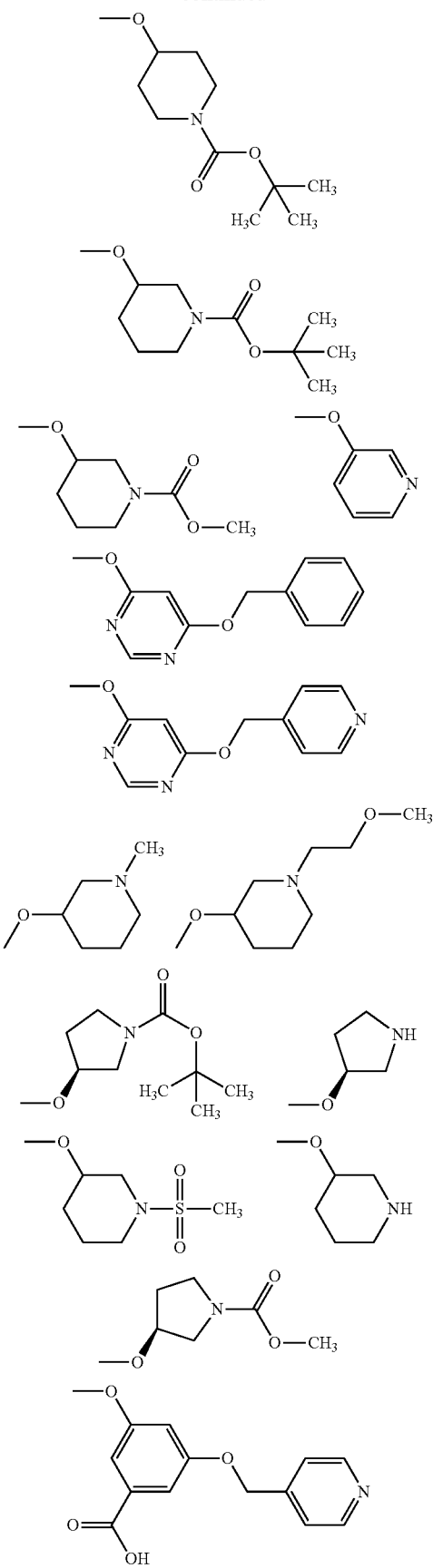

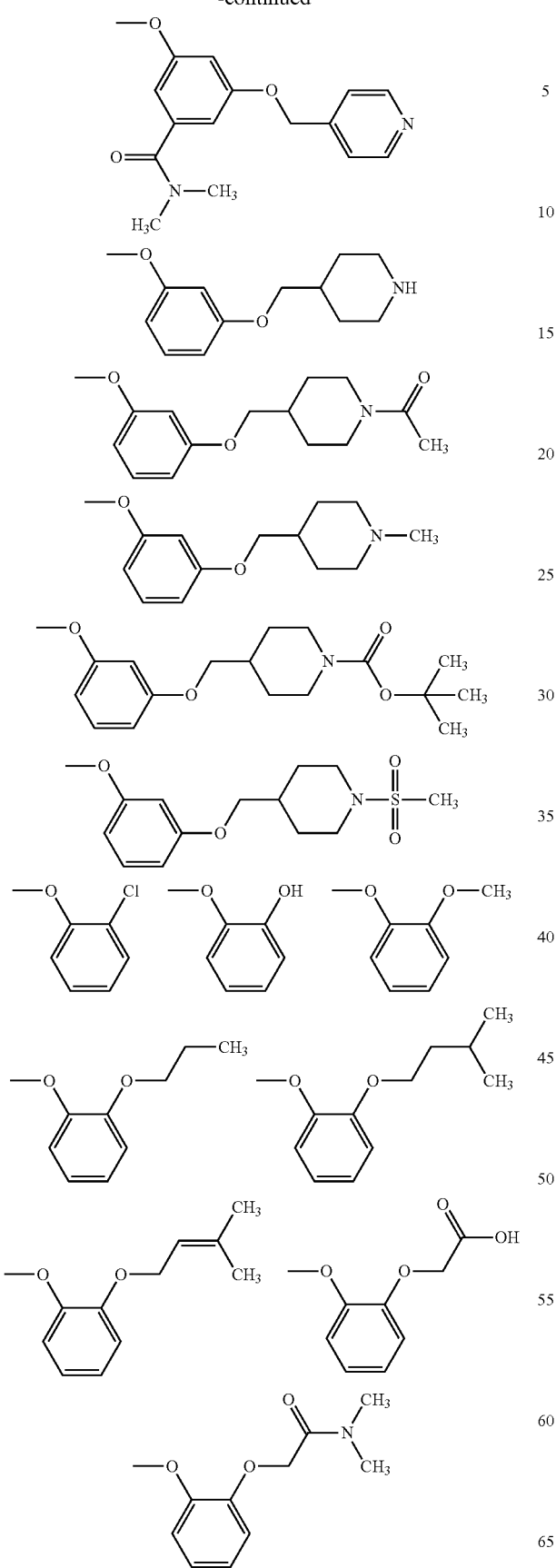
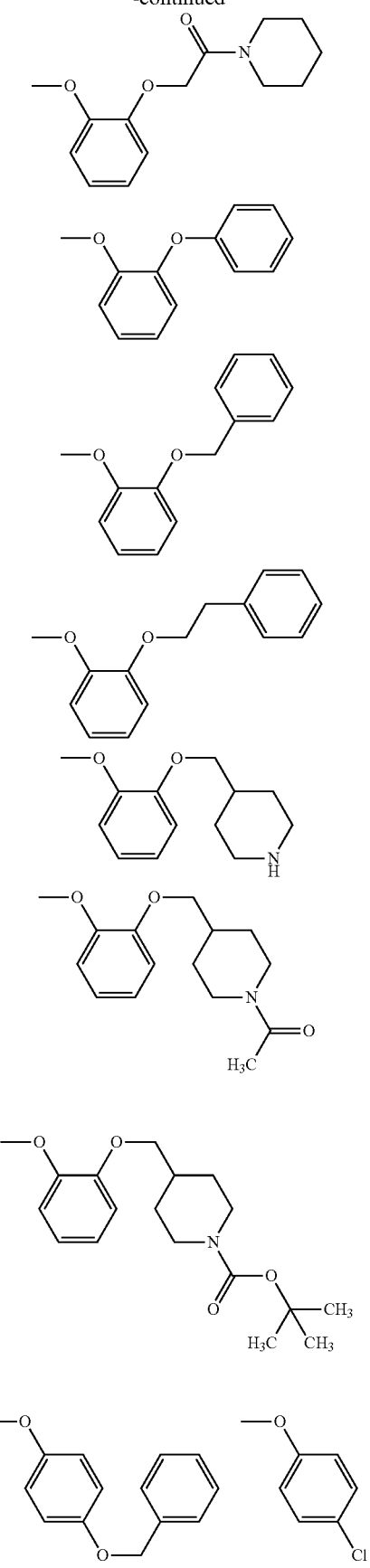

211
-continued
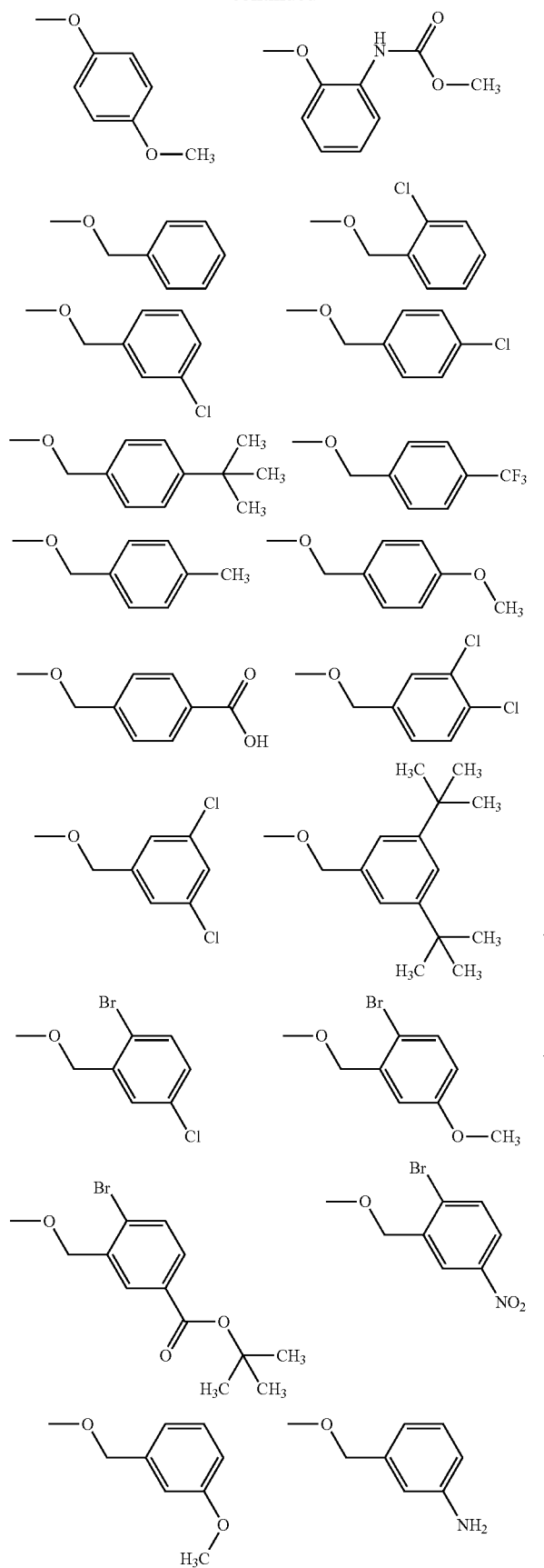
212
-continued
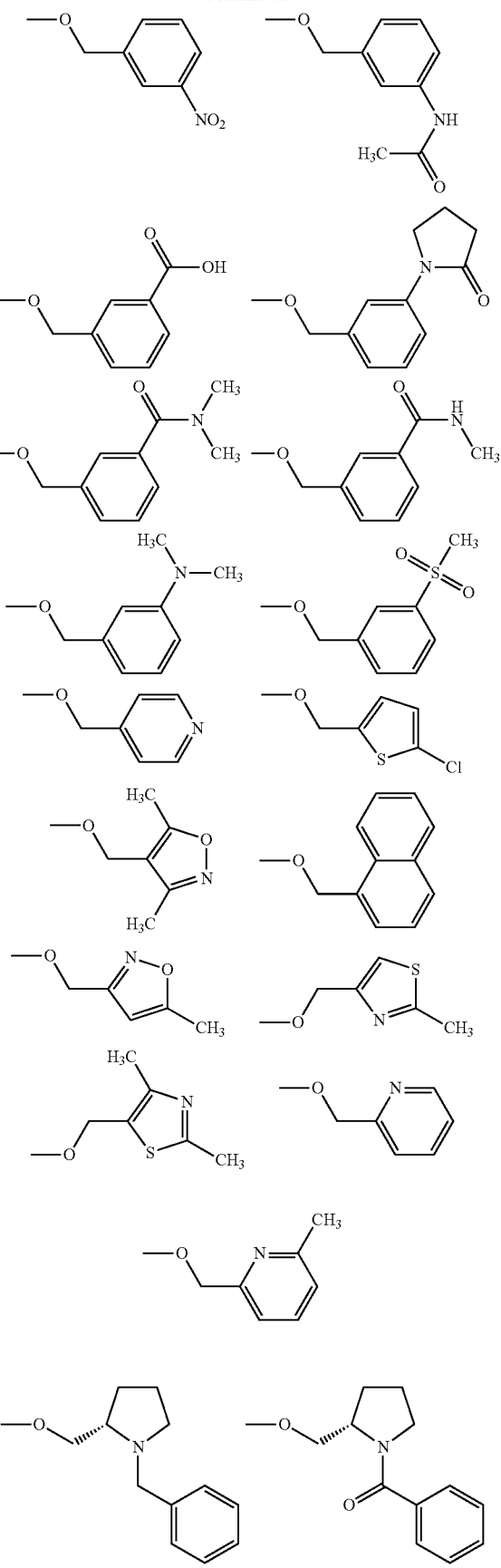

213
-continued
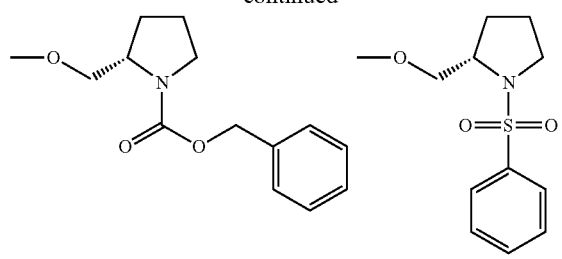
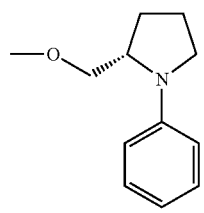
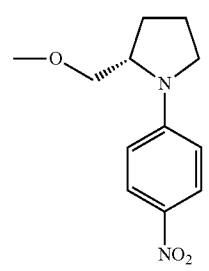
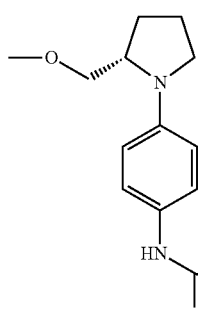
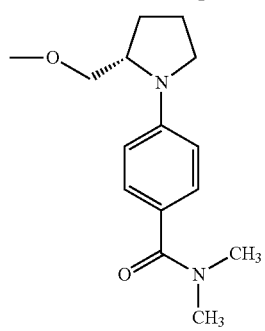
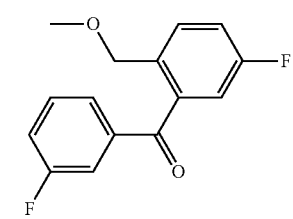
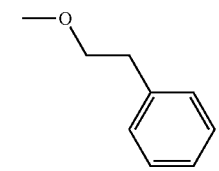
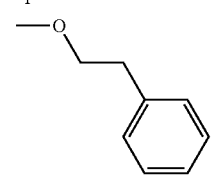
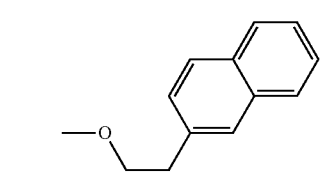
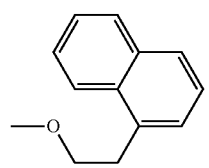
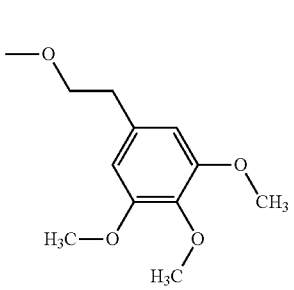
214
-continued
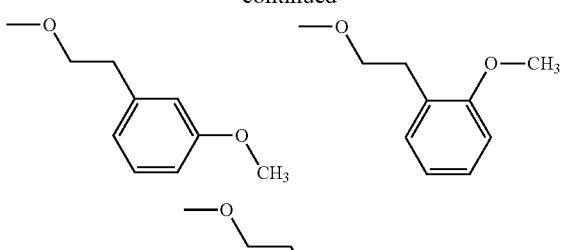
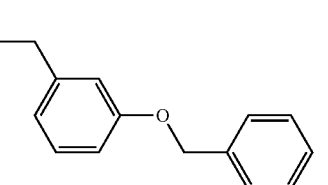
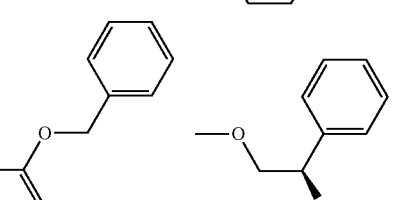
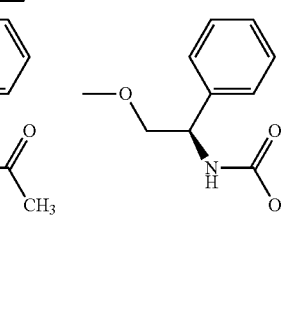
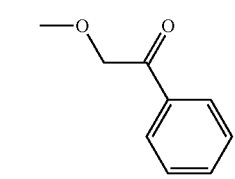
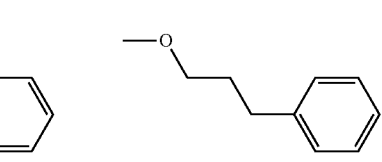
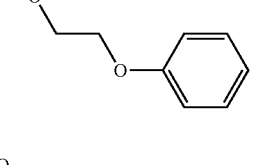
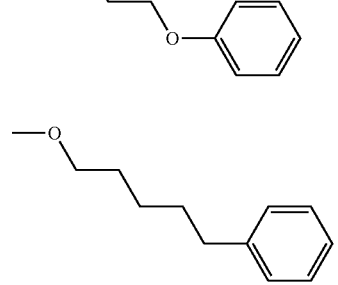

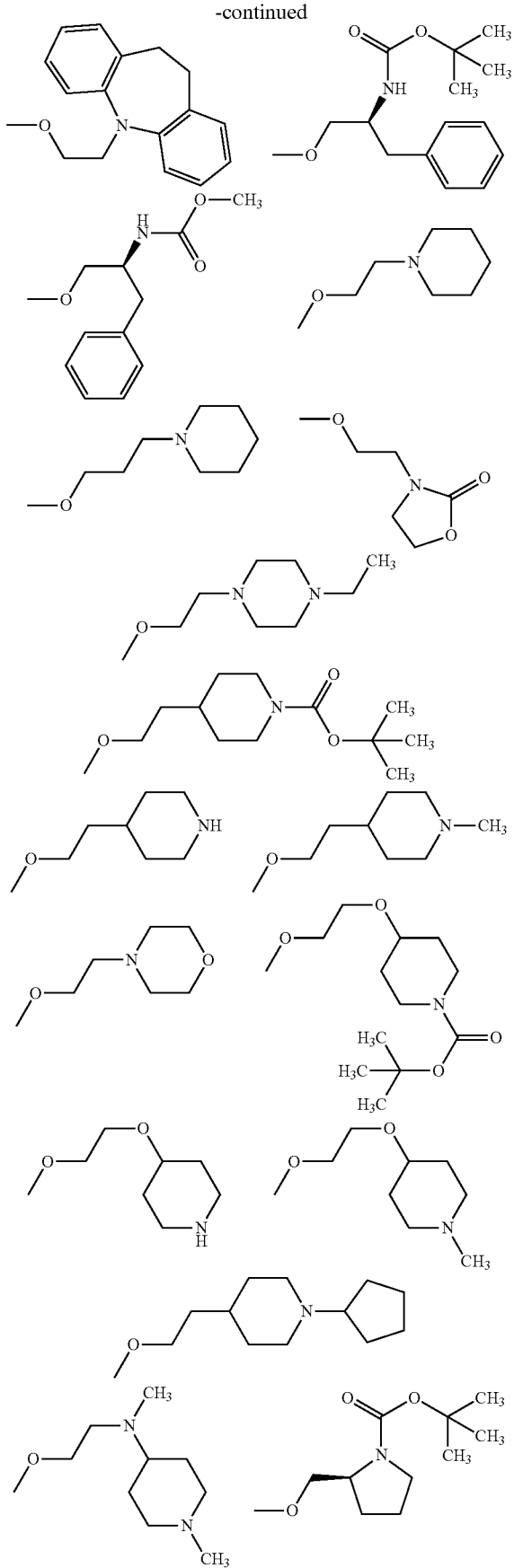
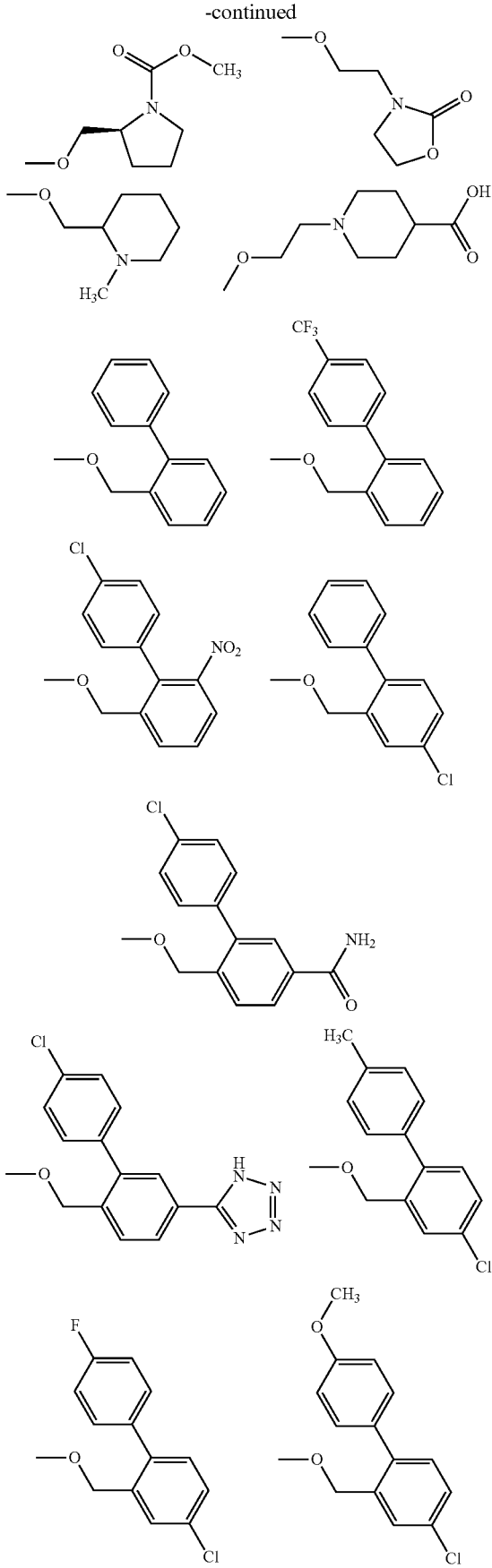

217
-continued
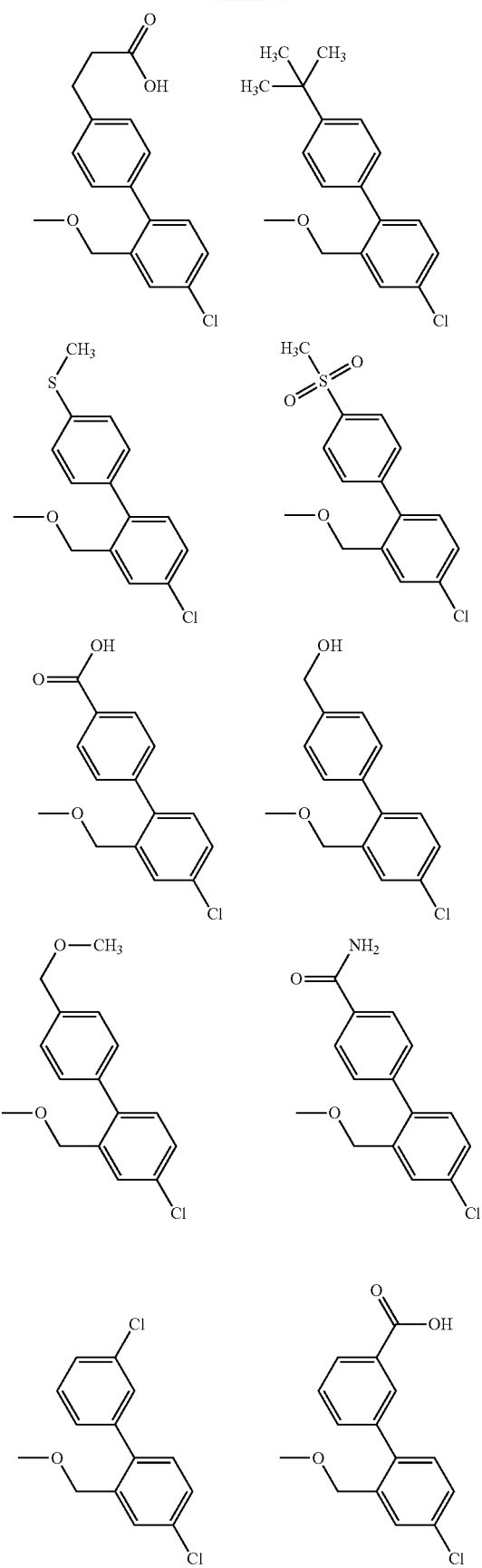
218
-continued
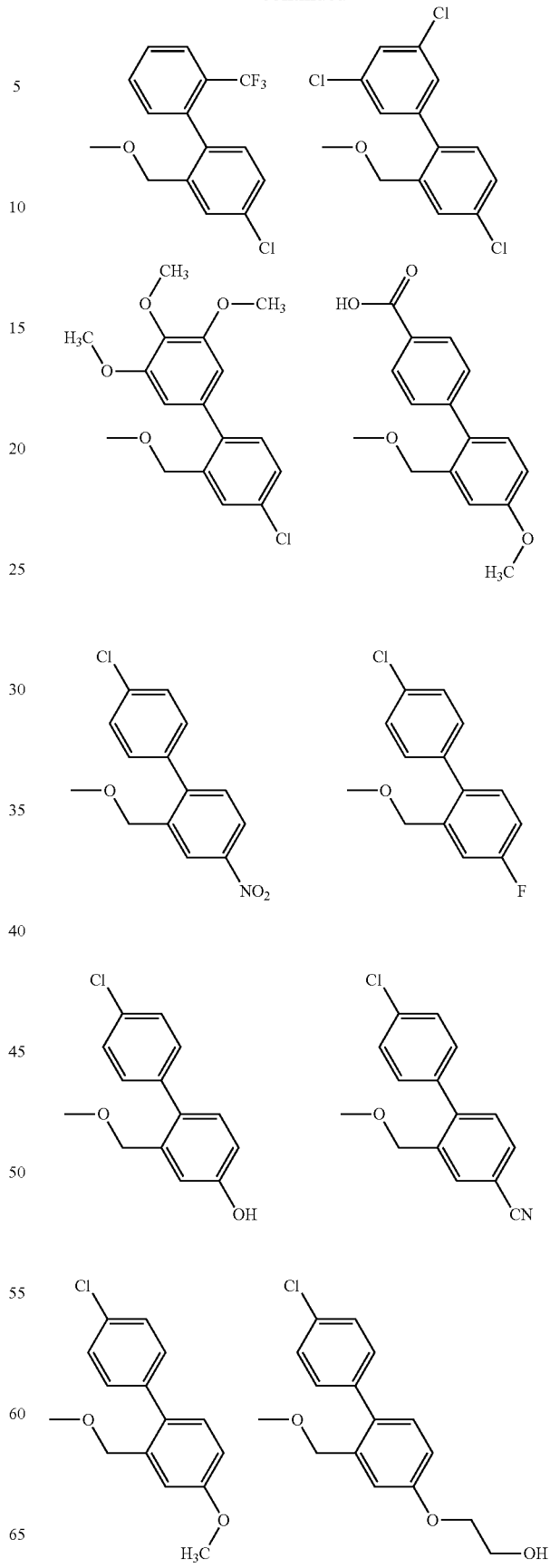

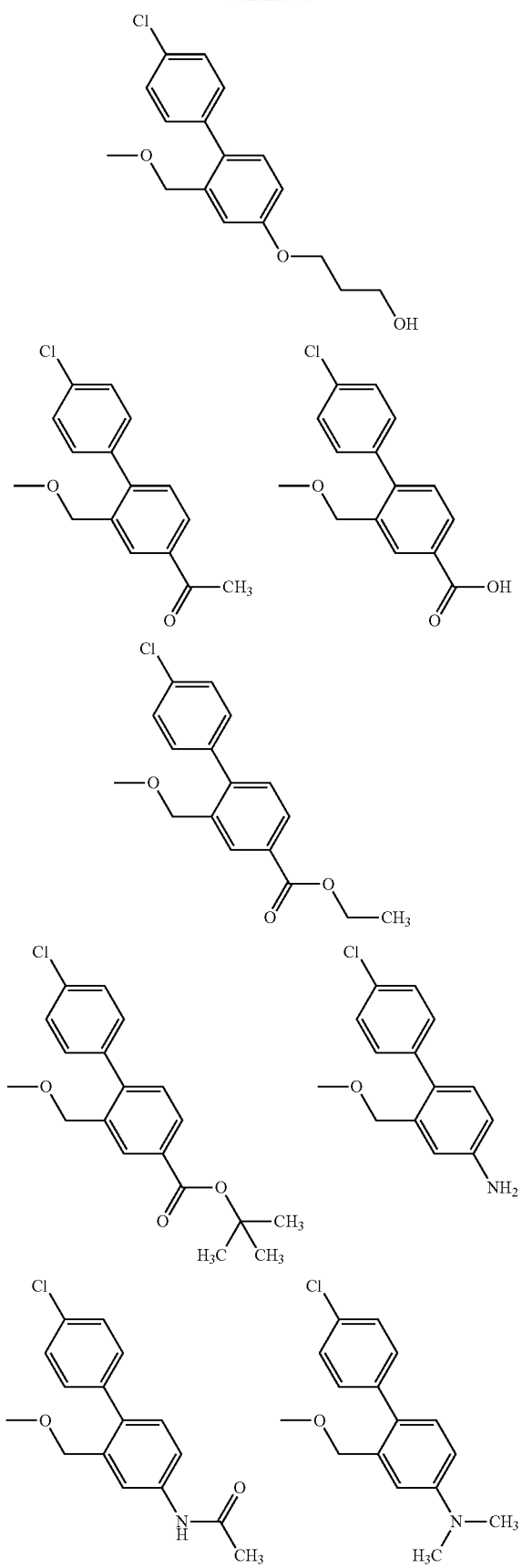
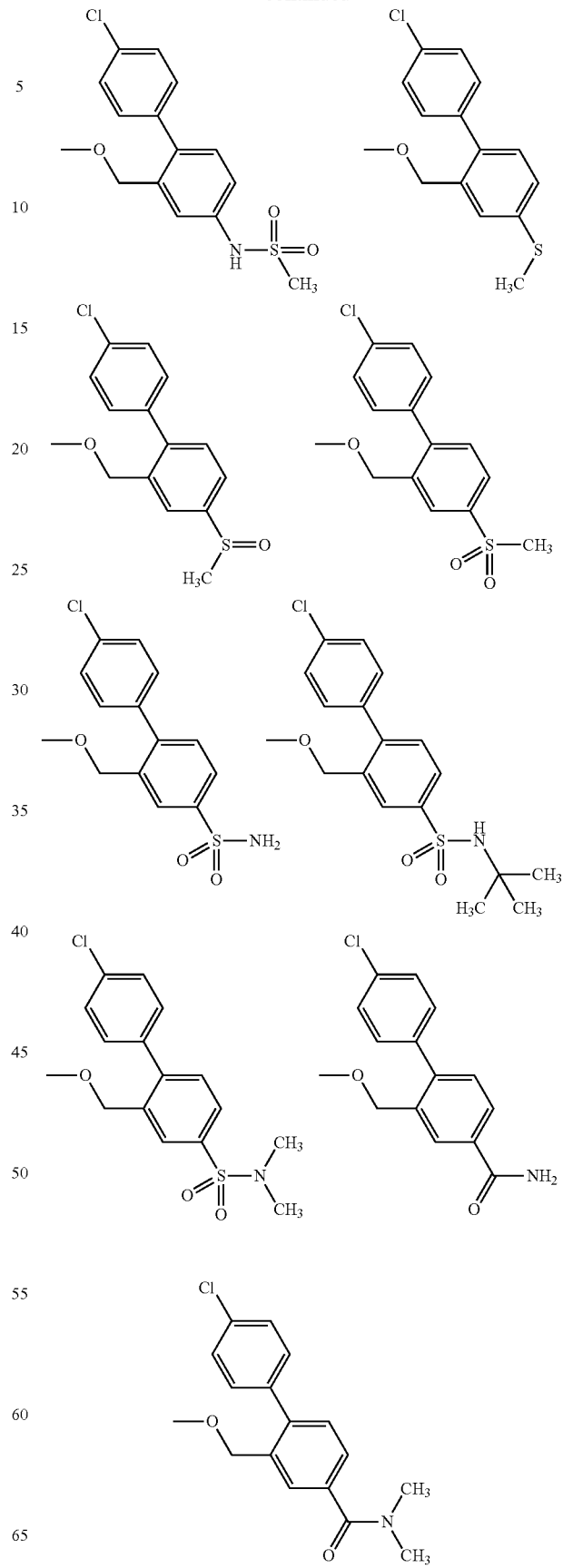

221
-continued
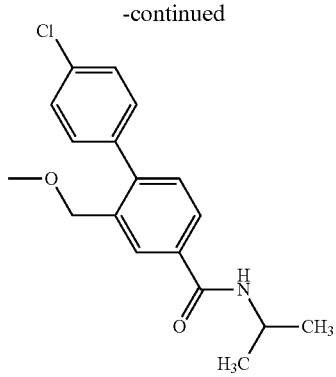
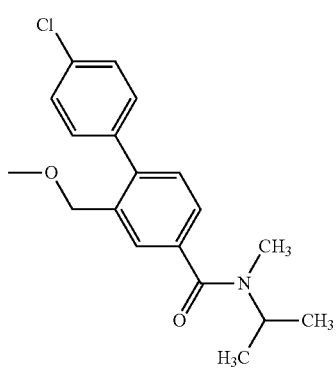
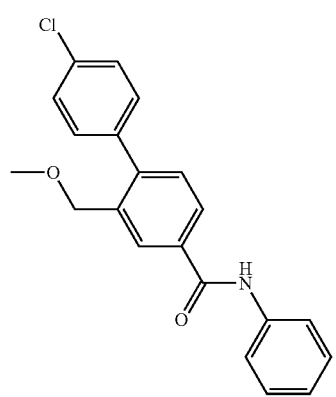
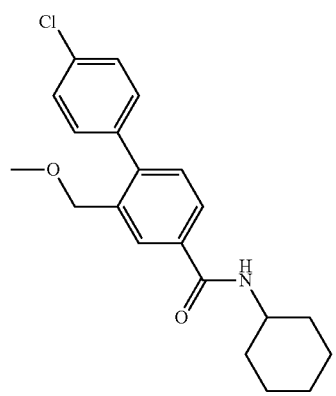
222
-continued
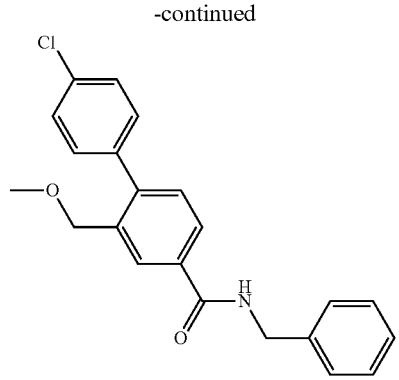
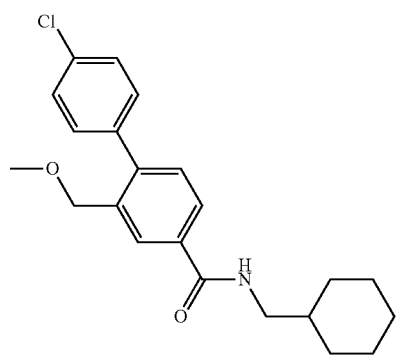
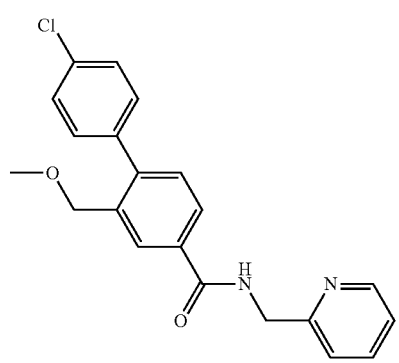
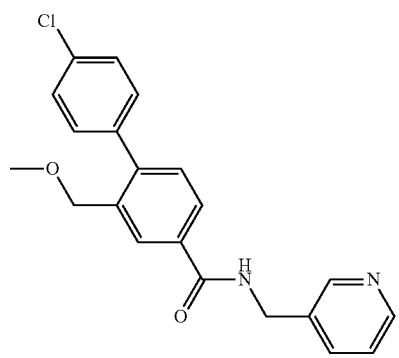

223
-continued
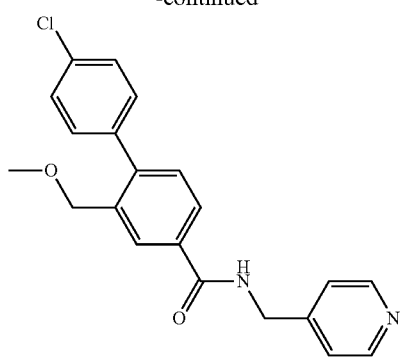
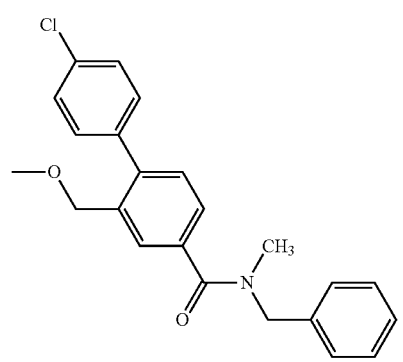
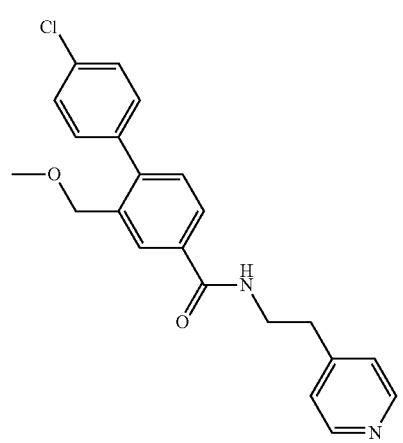
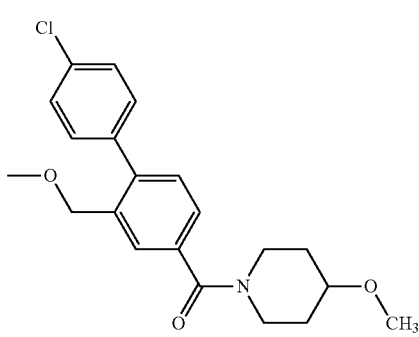
224
-continued
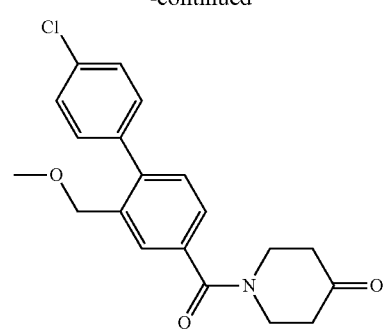
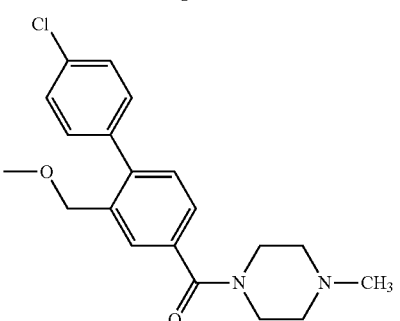
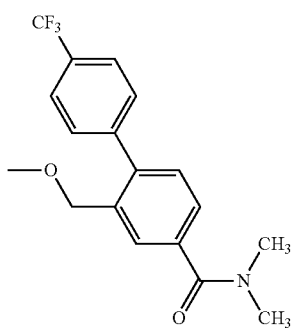
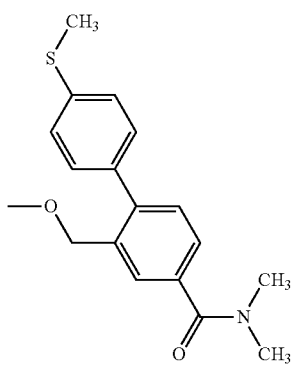
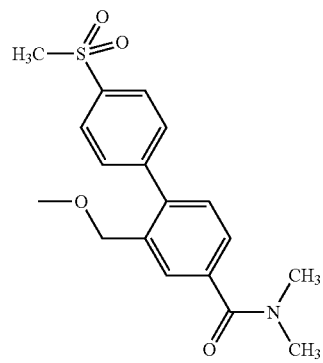

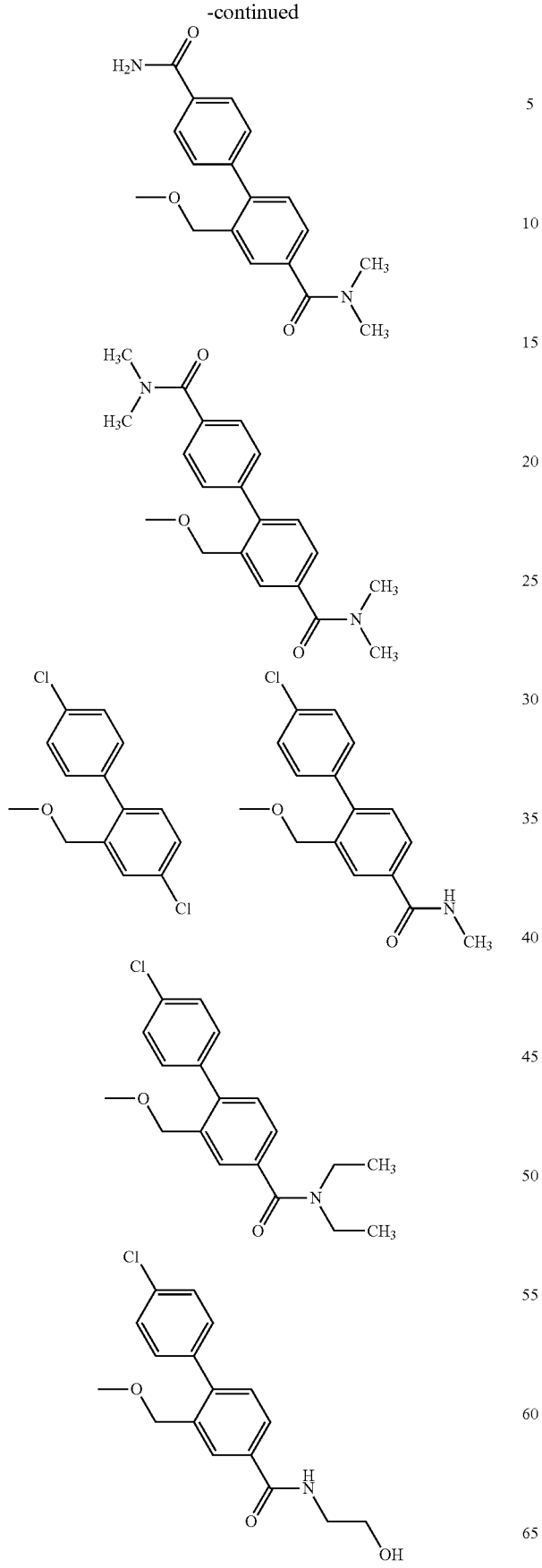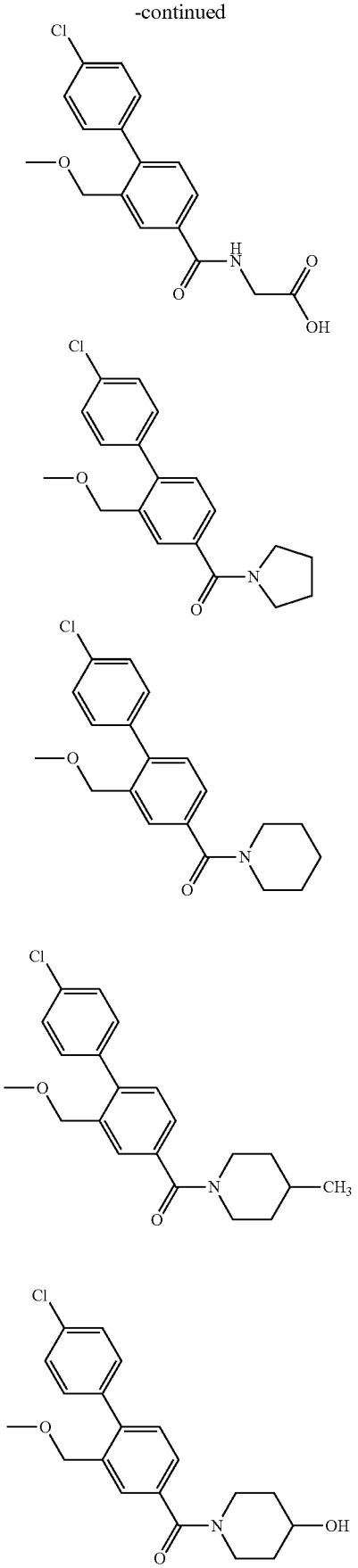

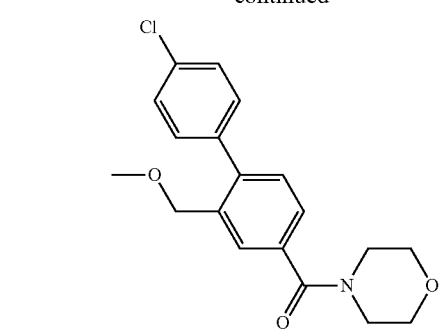
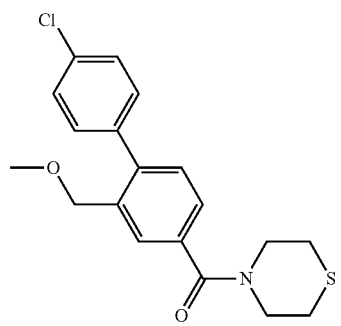
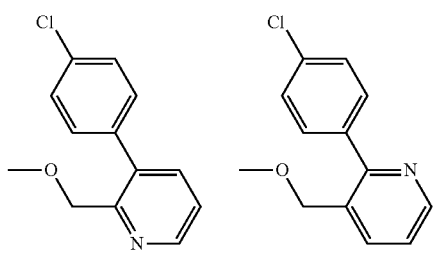
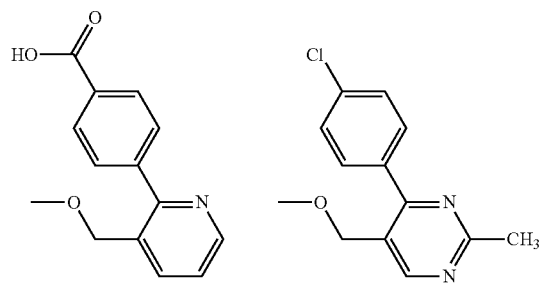
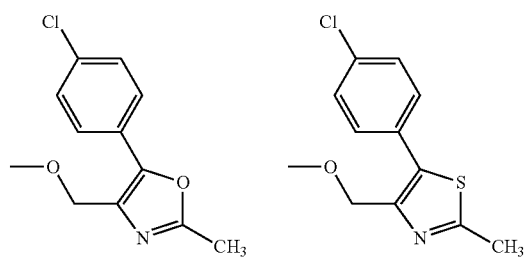
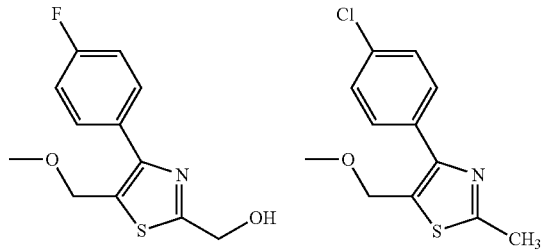
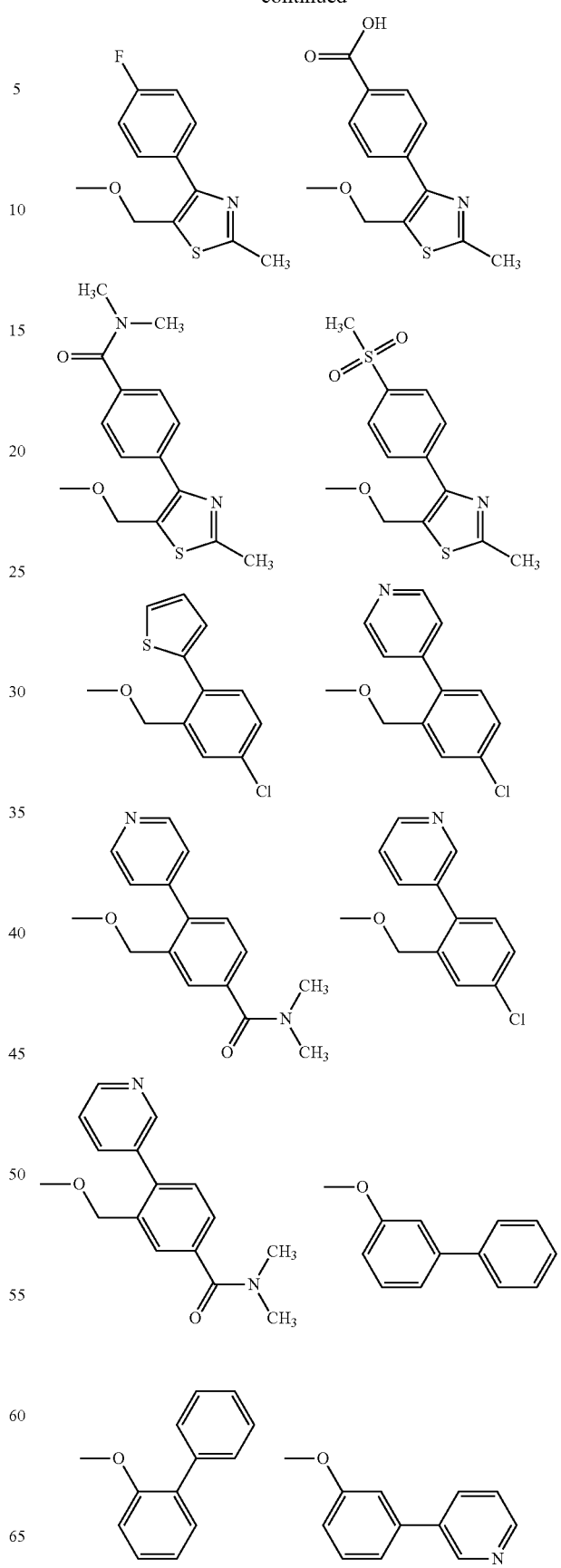

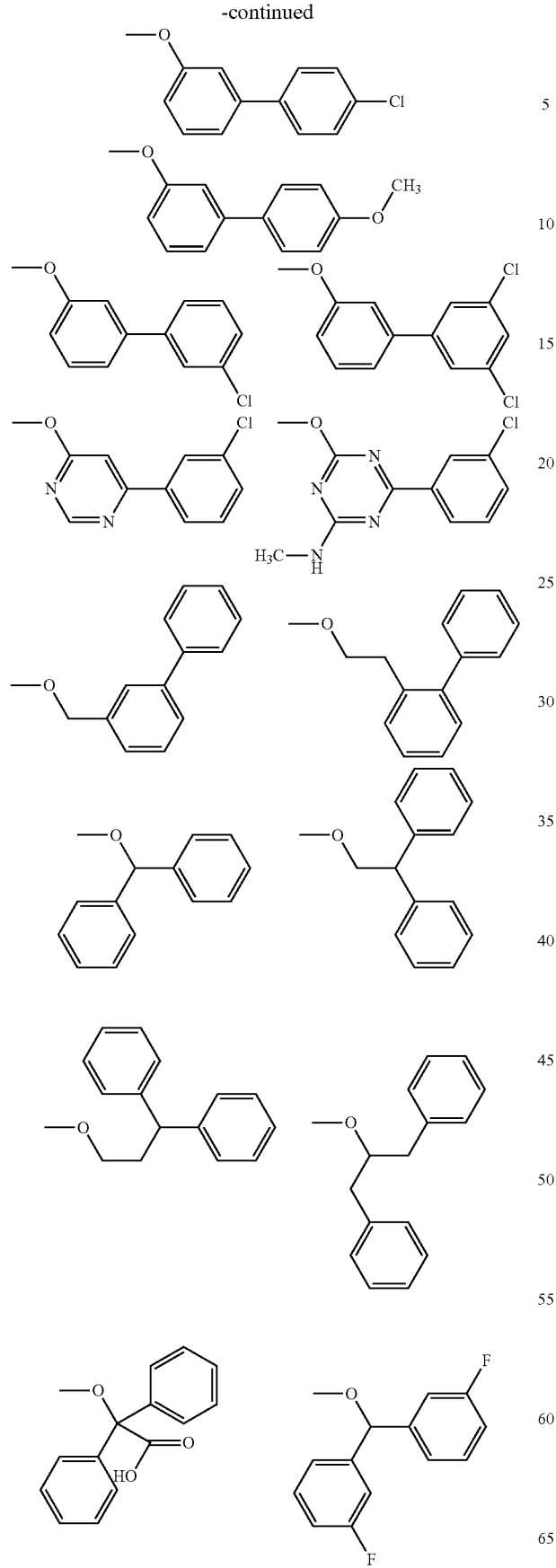
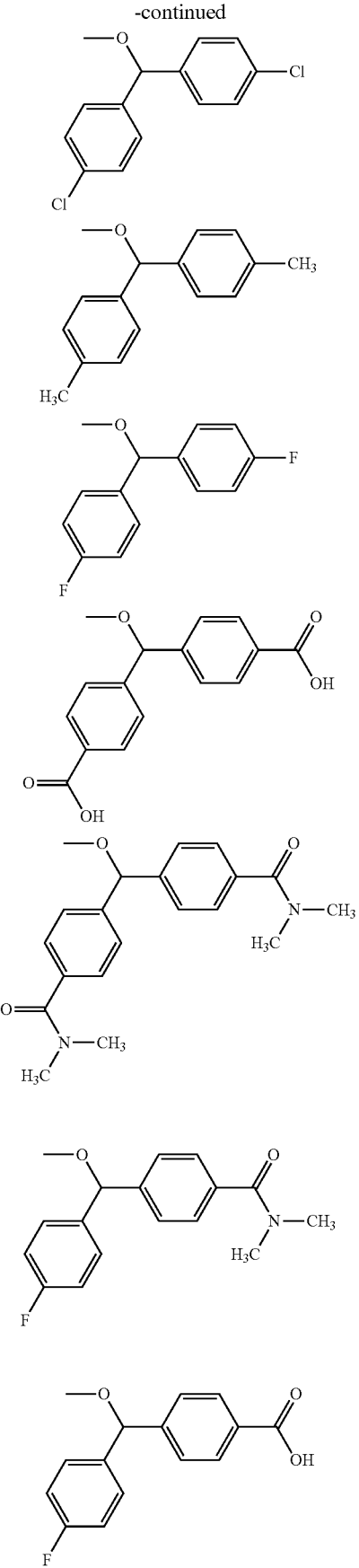

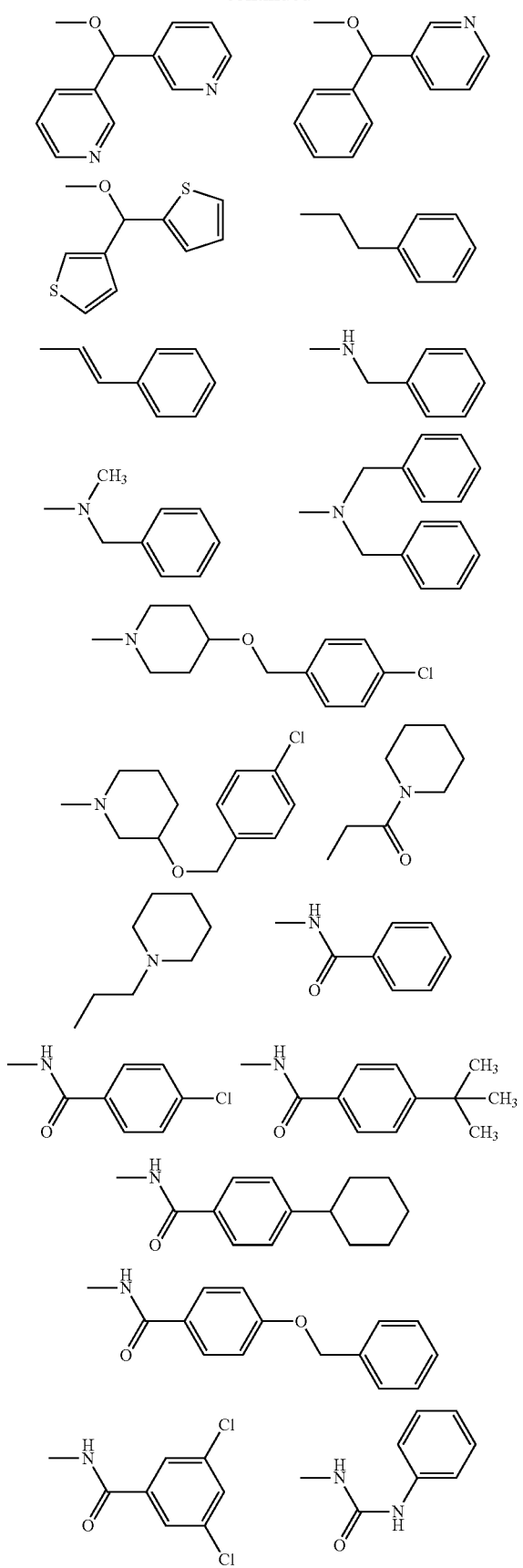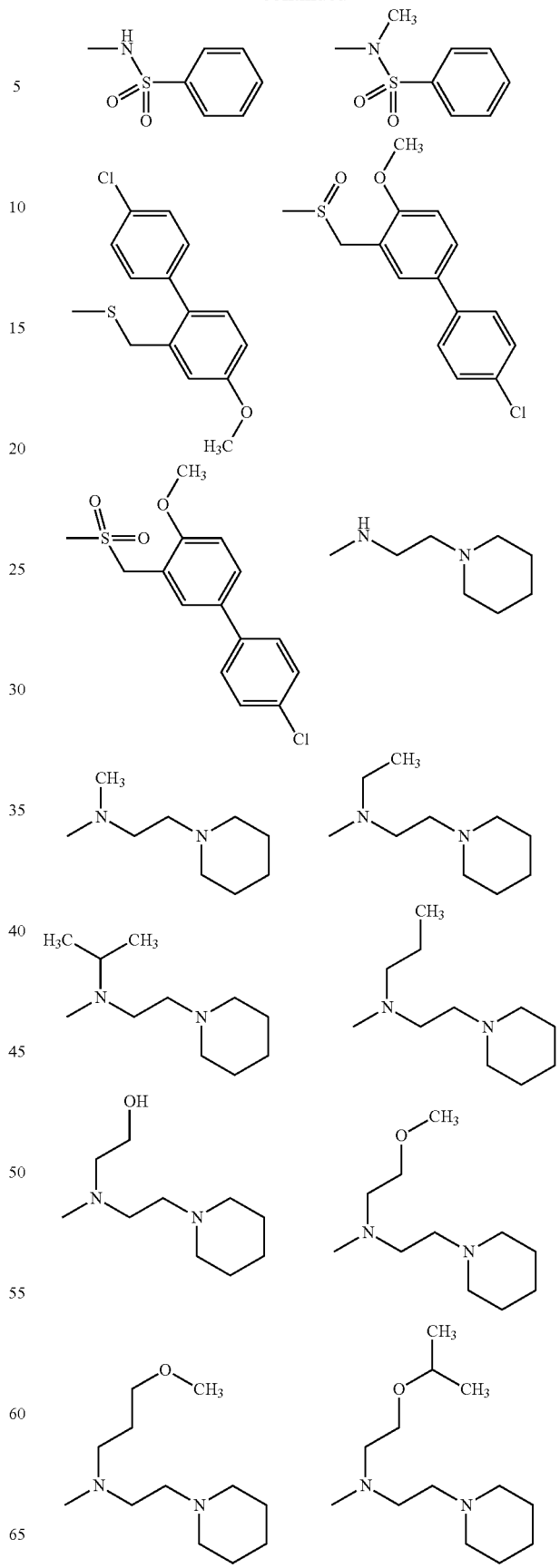

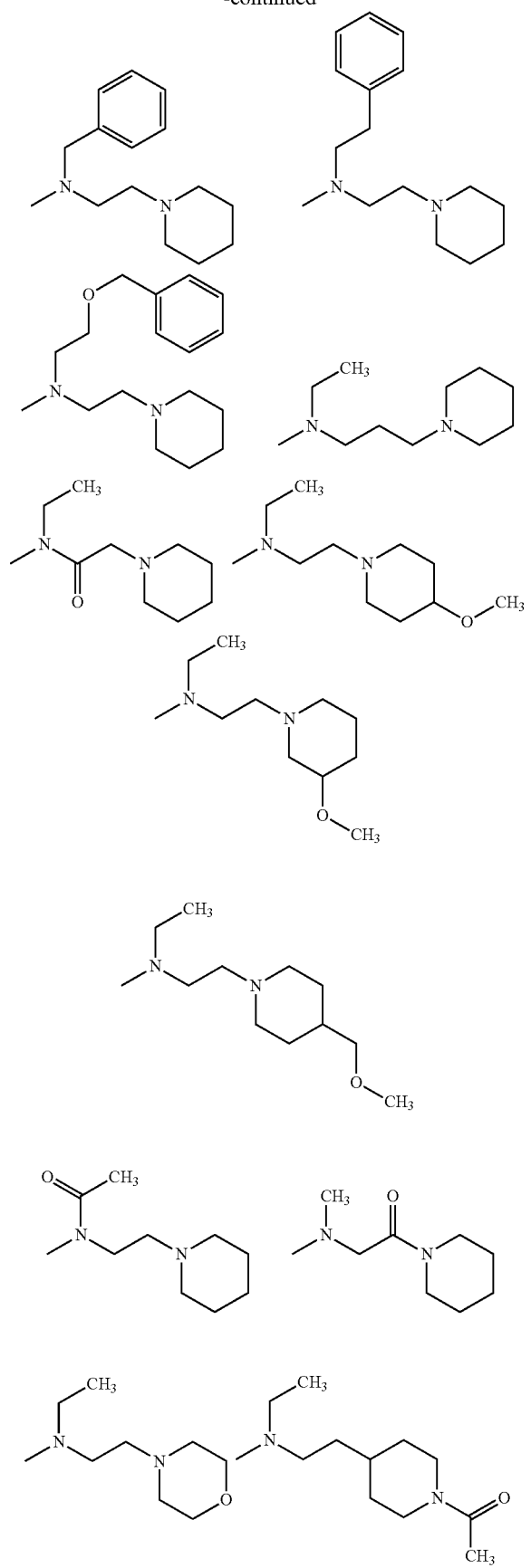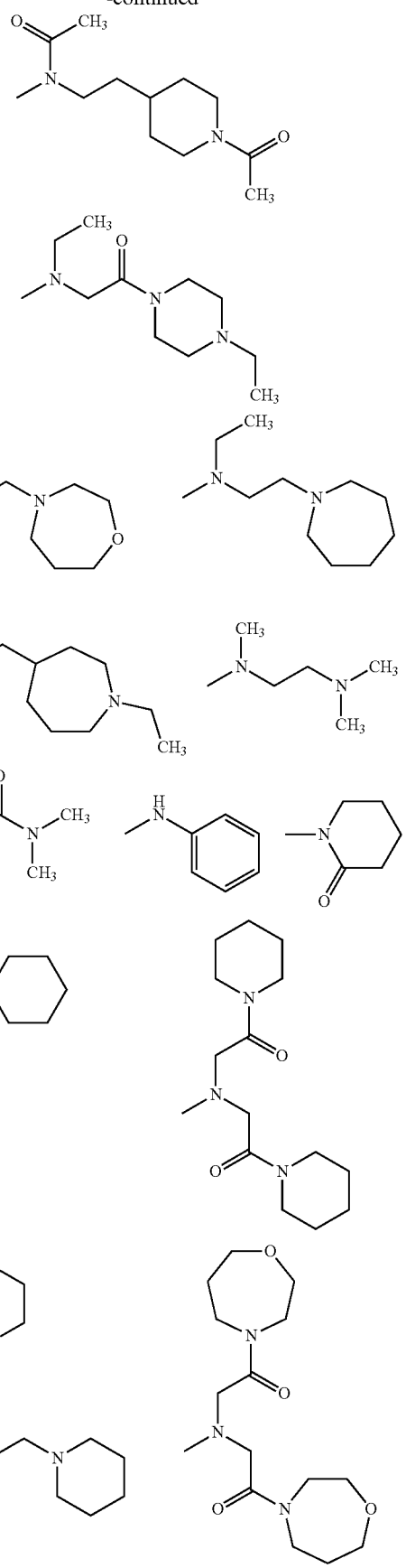

-continued
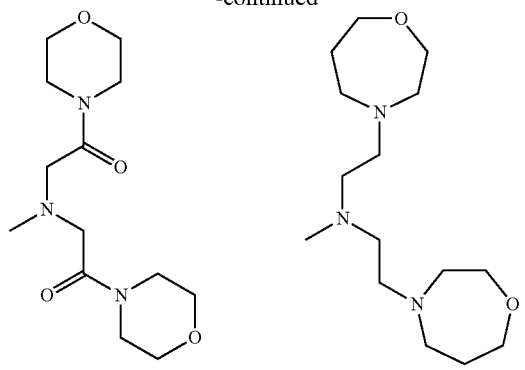
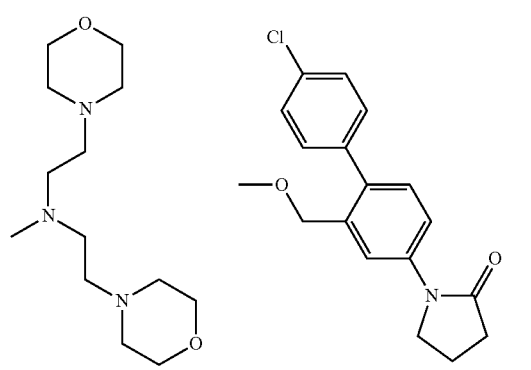
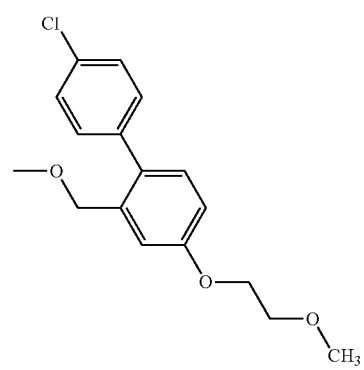
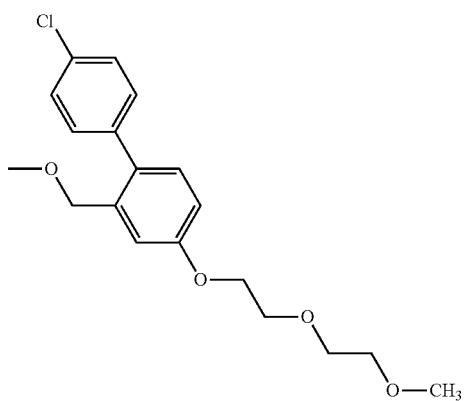
-continued
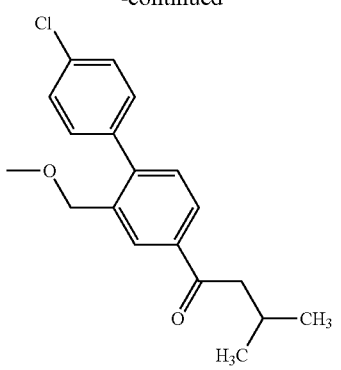
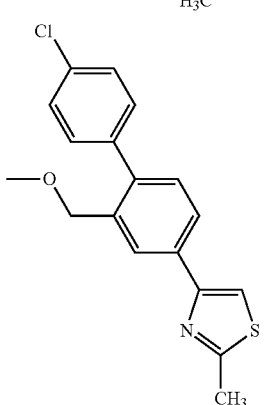
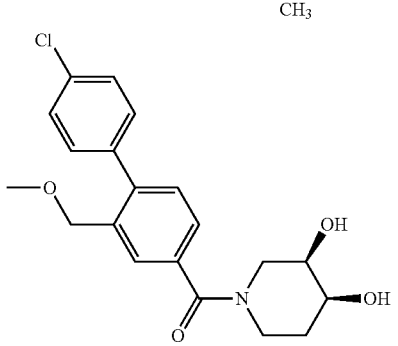
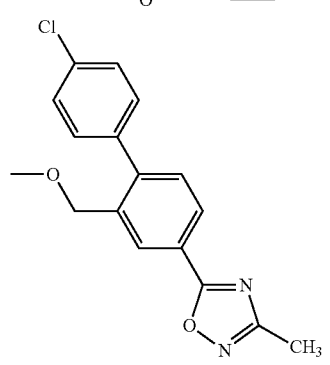
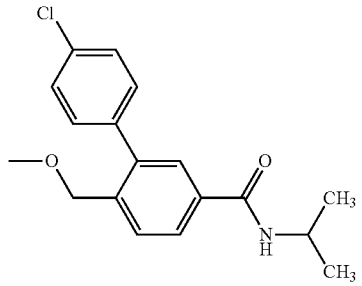

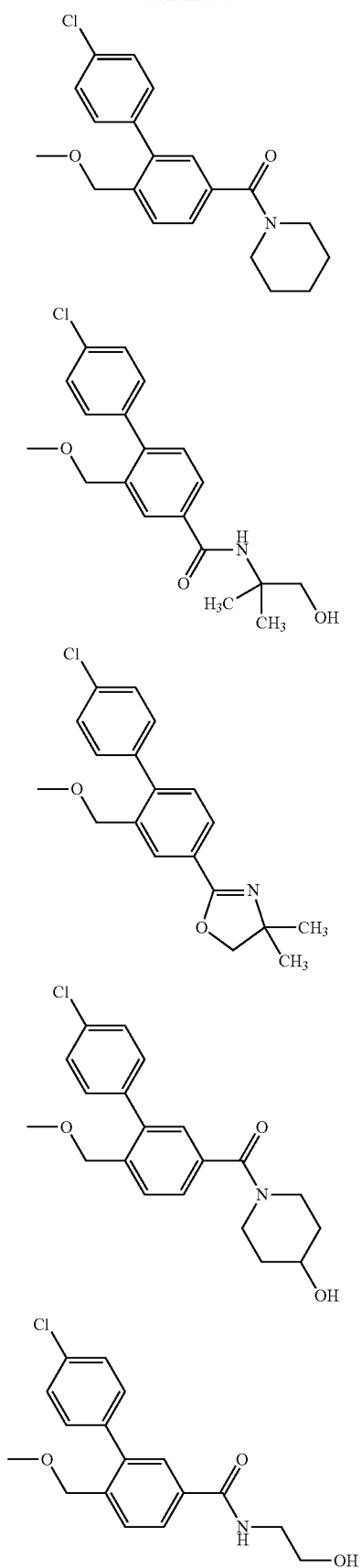
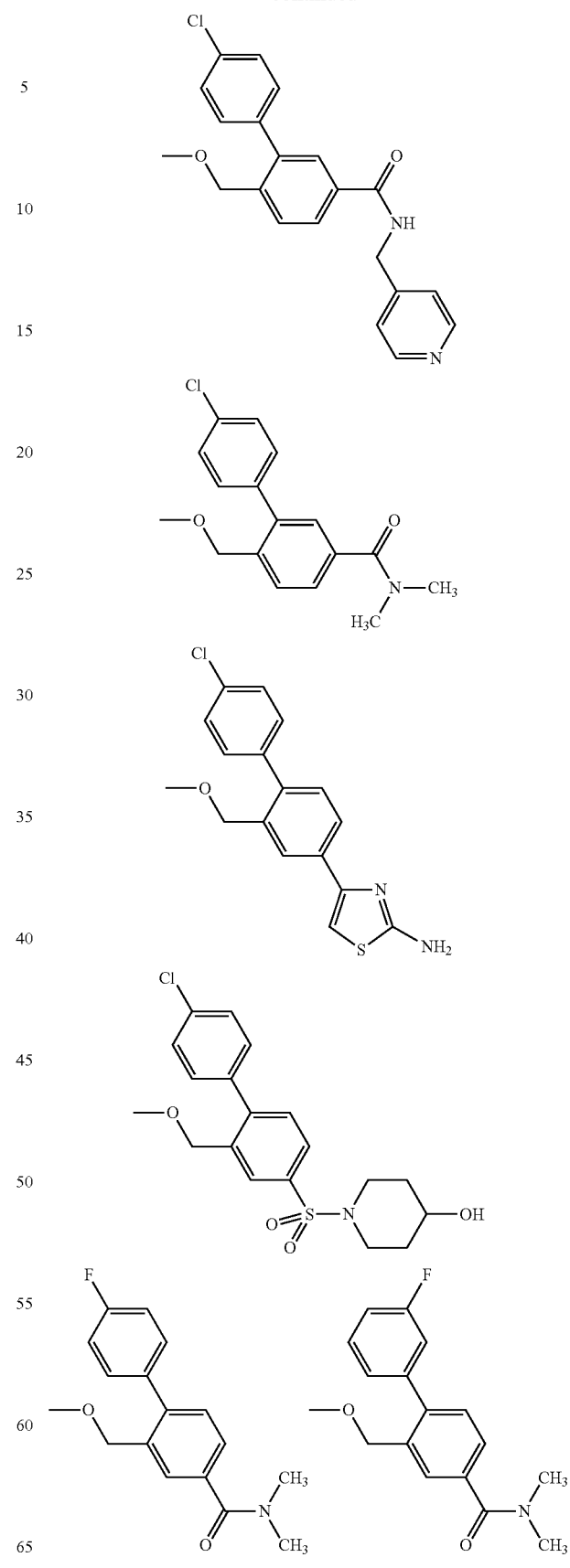

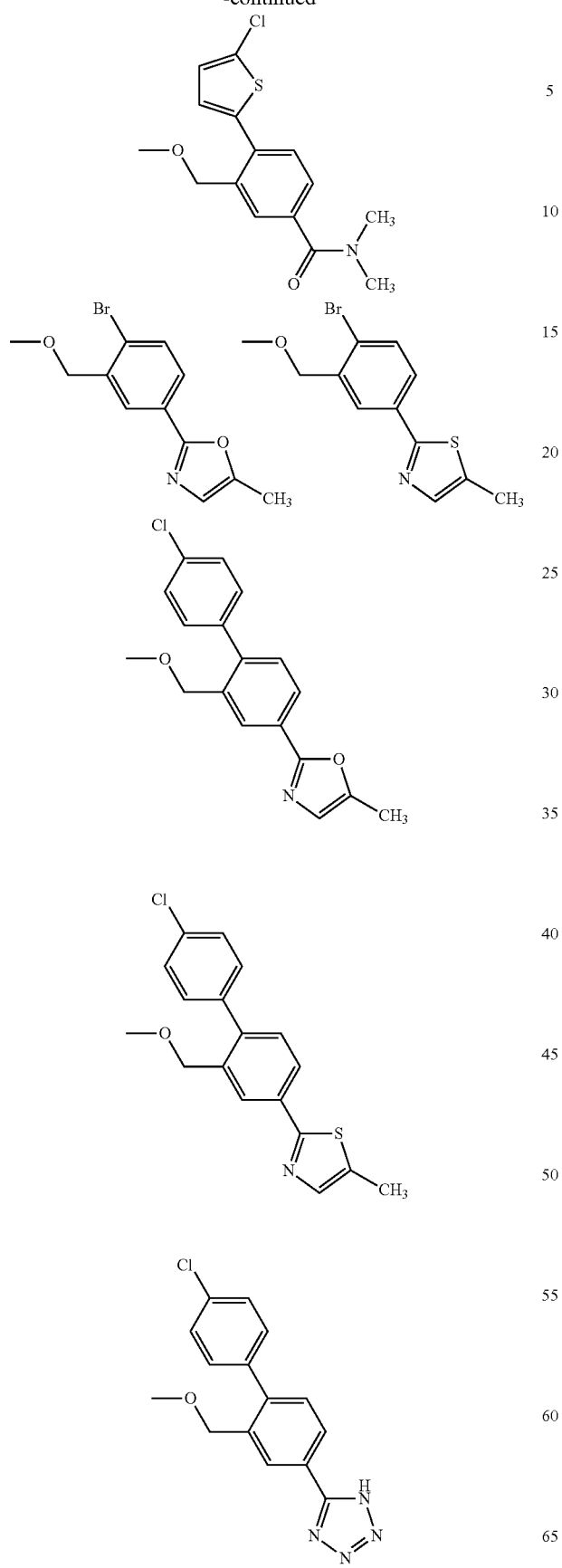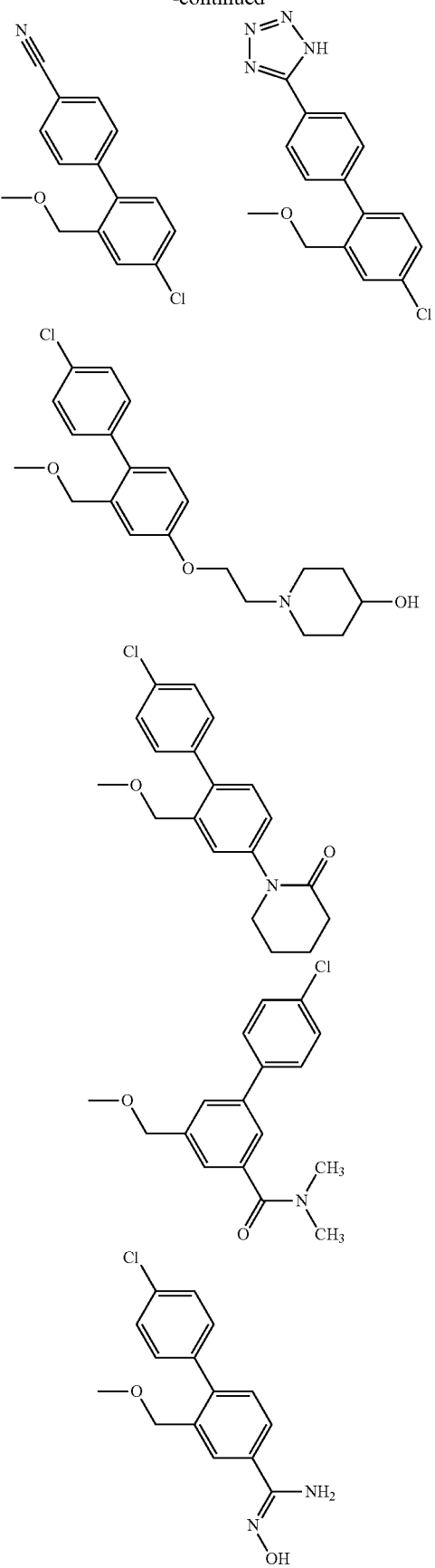

241
-continued
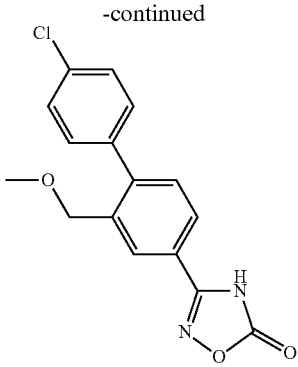
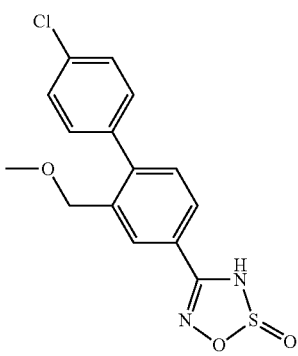
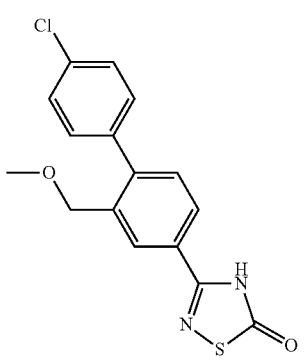
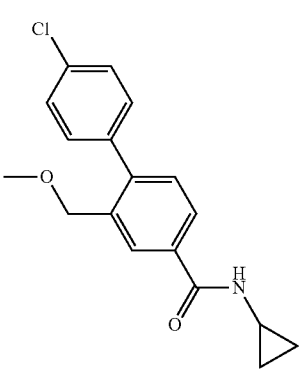
242
-continued
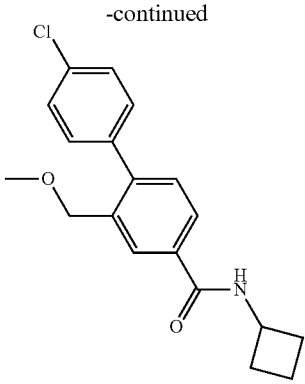
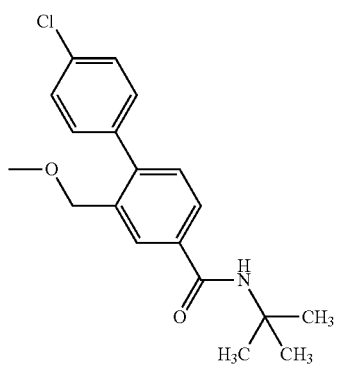
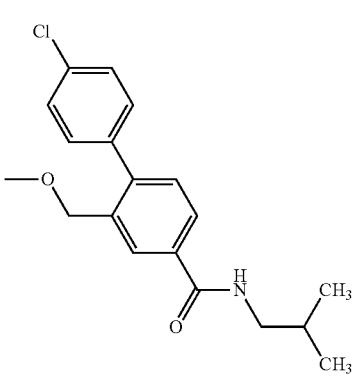
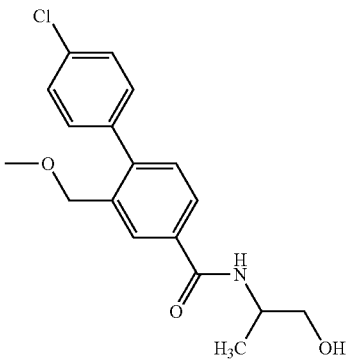

243
-continued
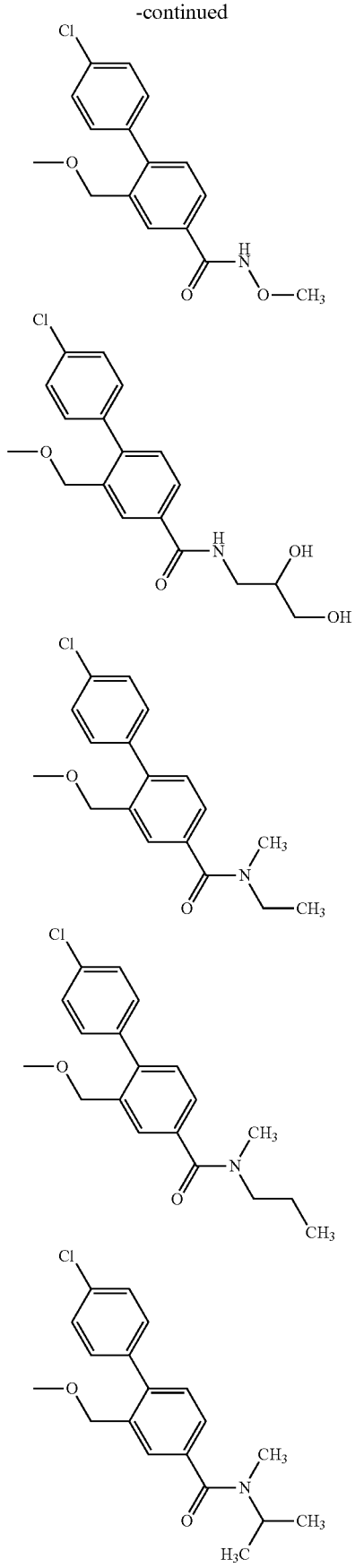
244
-continued
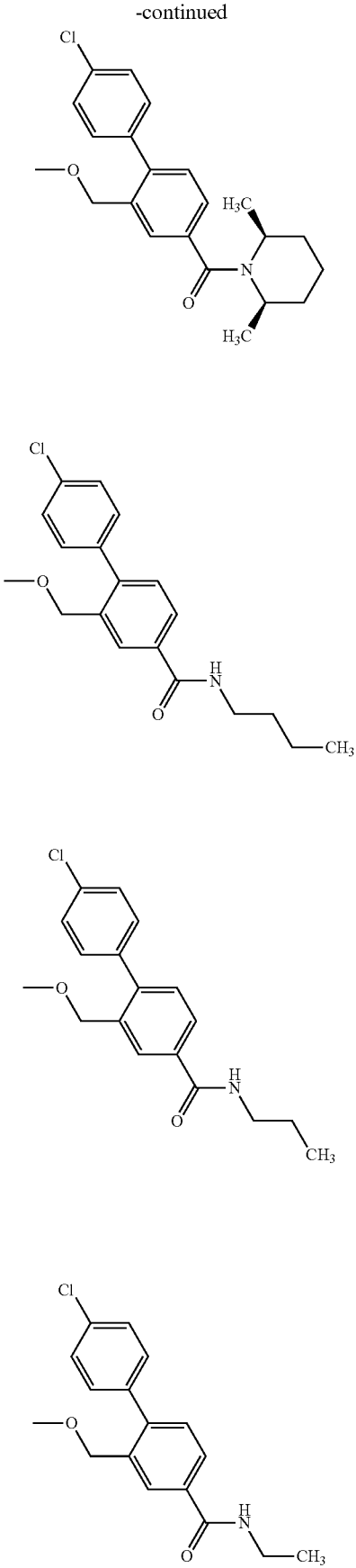

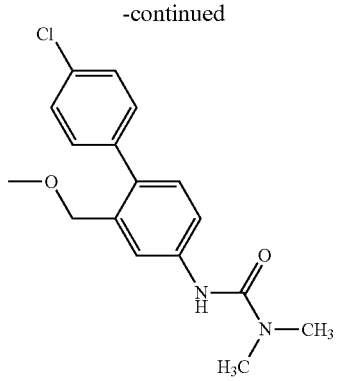
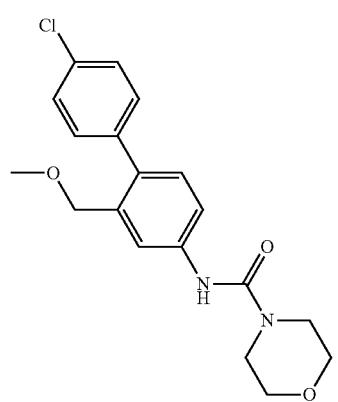
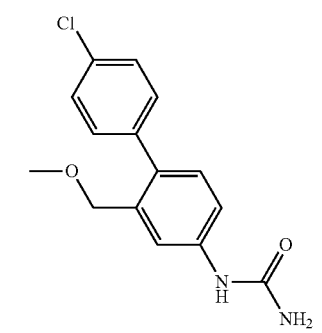
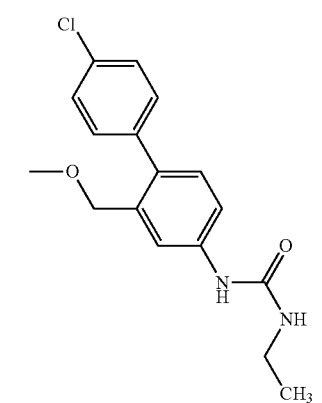
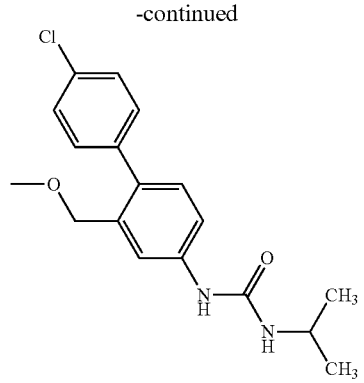
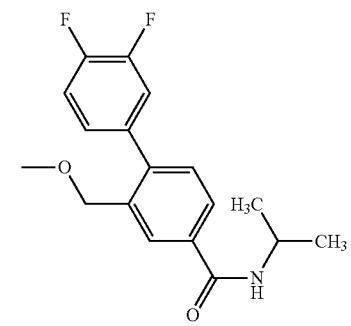
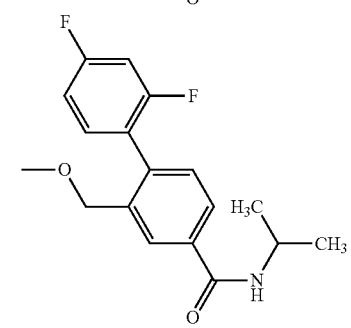
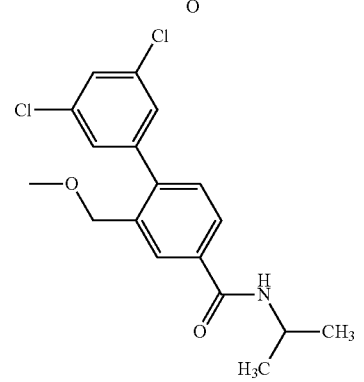
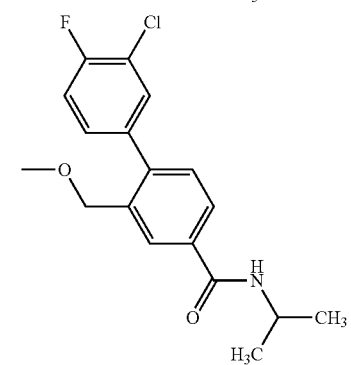

247
-continued
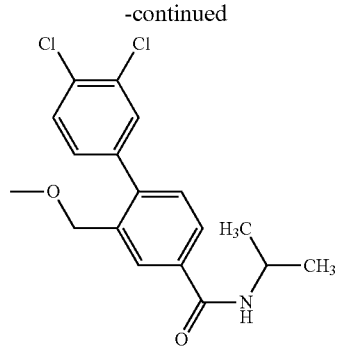
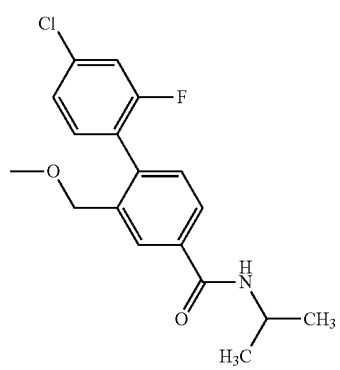
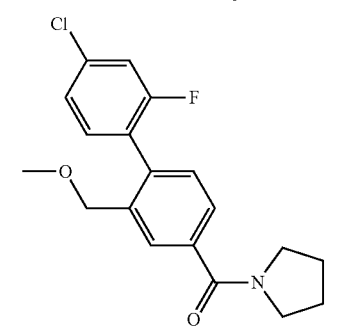
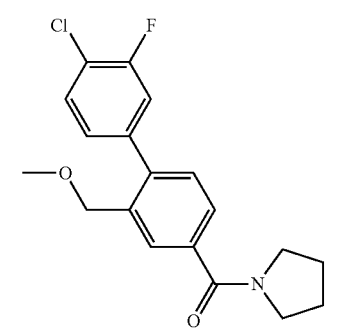
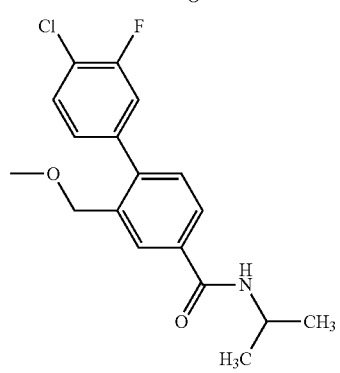
248
-continued
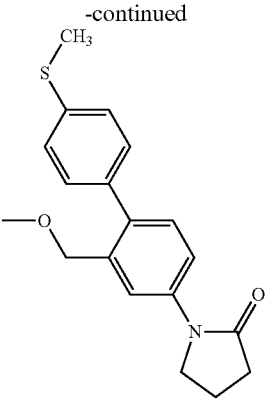
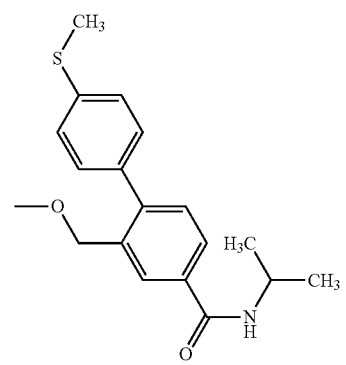
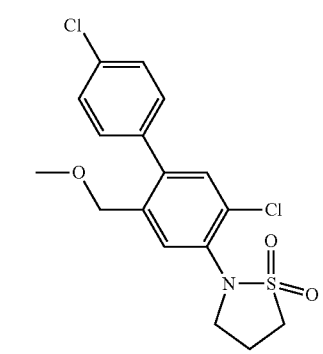
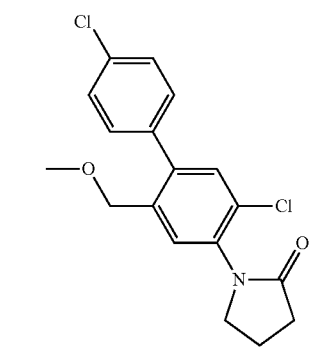

249
-continued
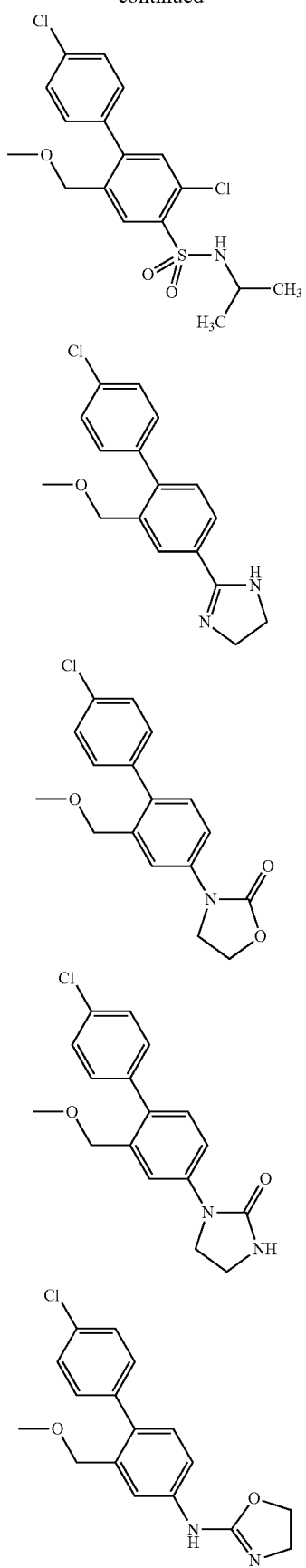
250
-continued
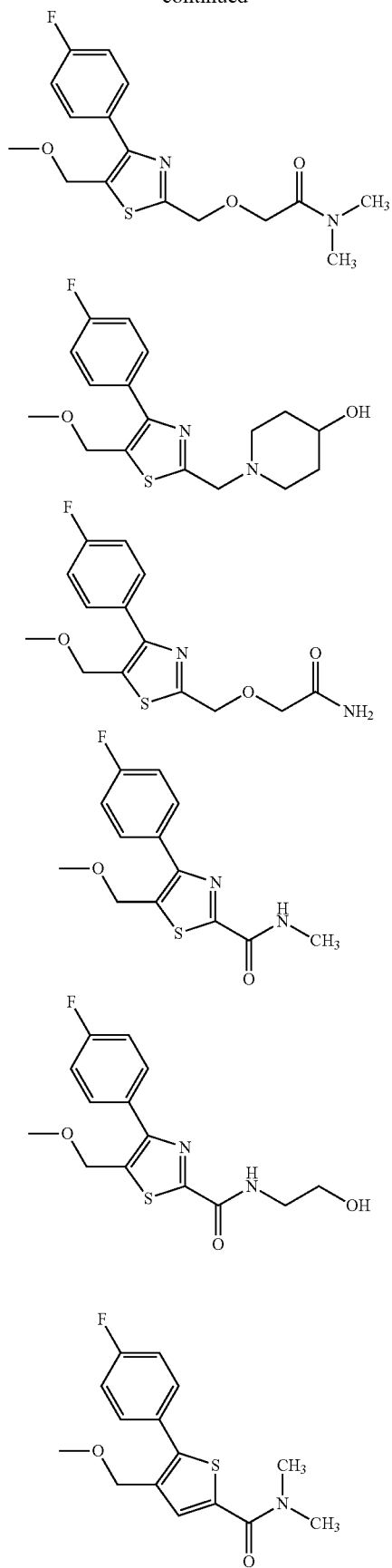

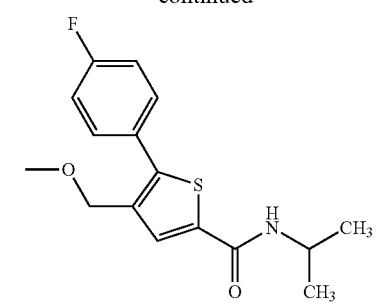
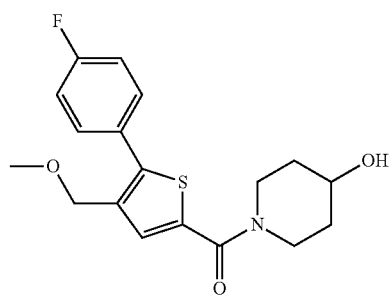
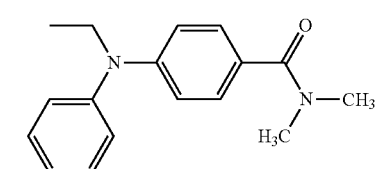
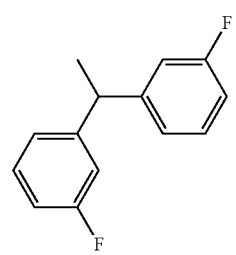
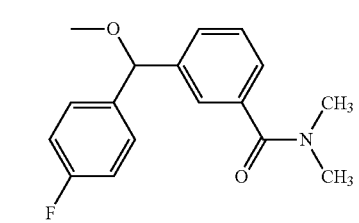
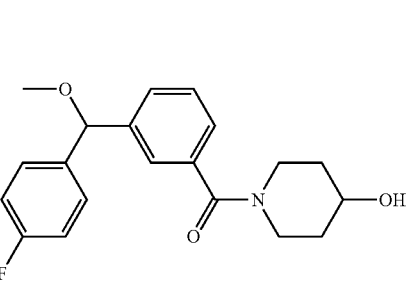
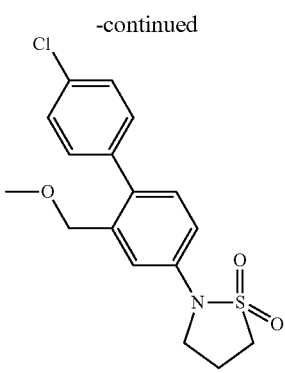
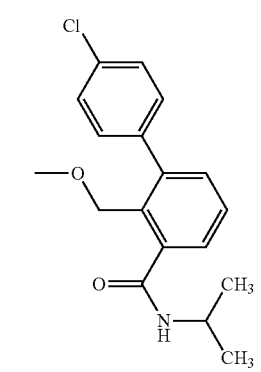
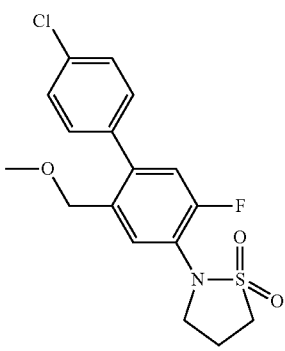
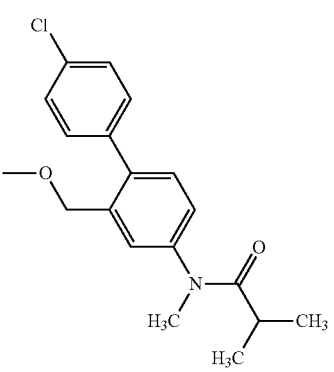

253
-continued
254
-continued
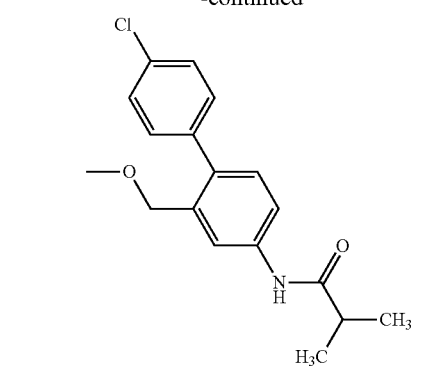
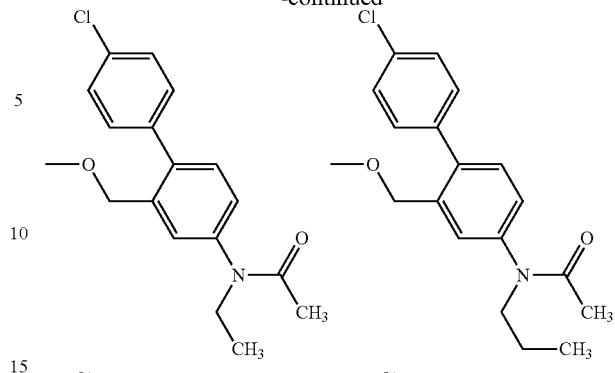
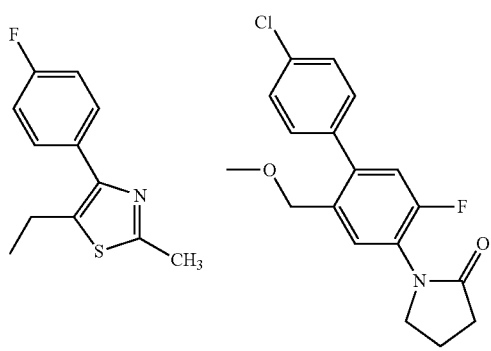
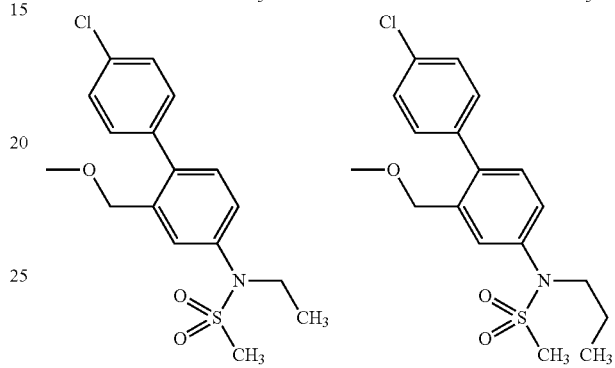
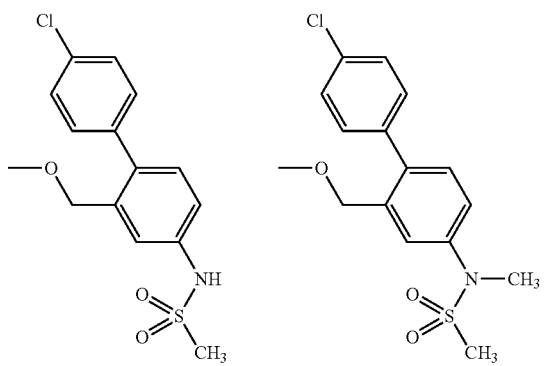
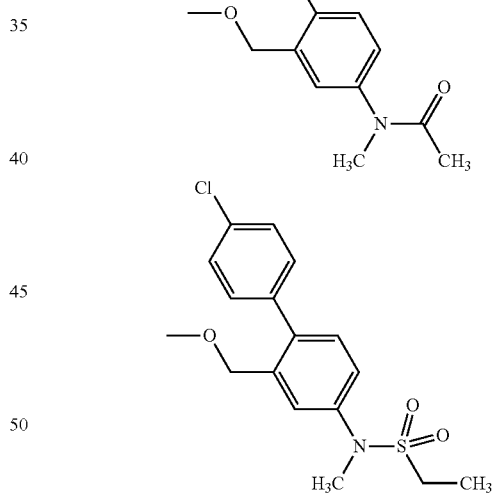
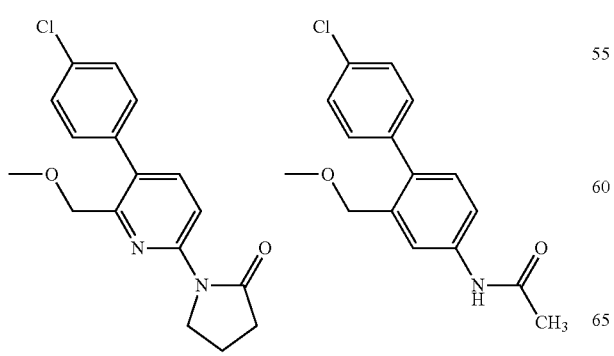
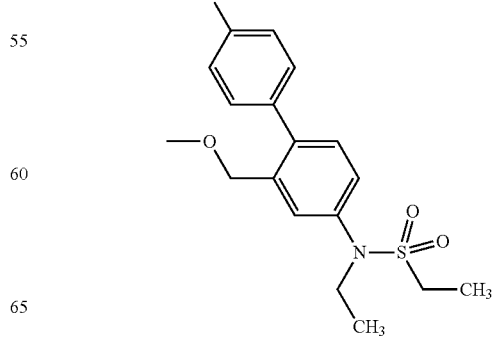

255
-continued
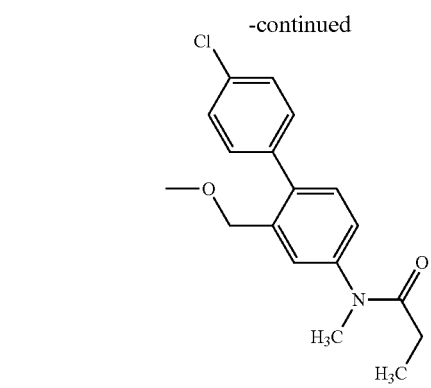
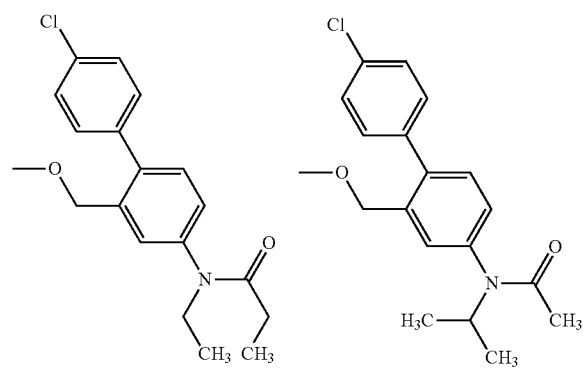
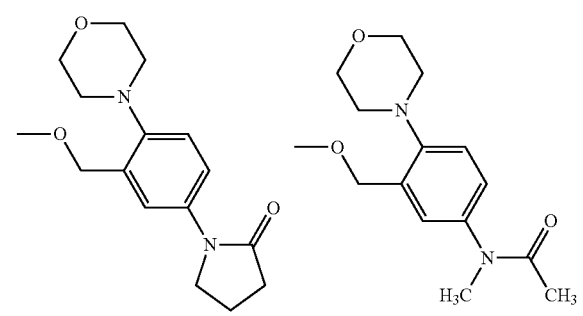
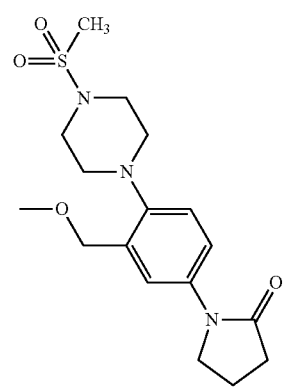
256
-continued
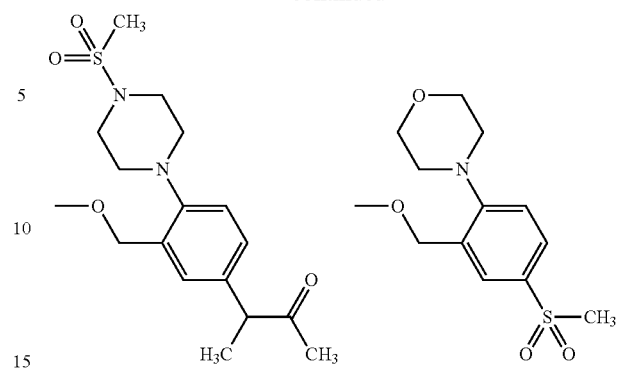
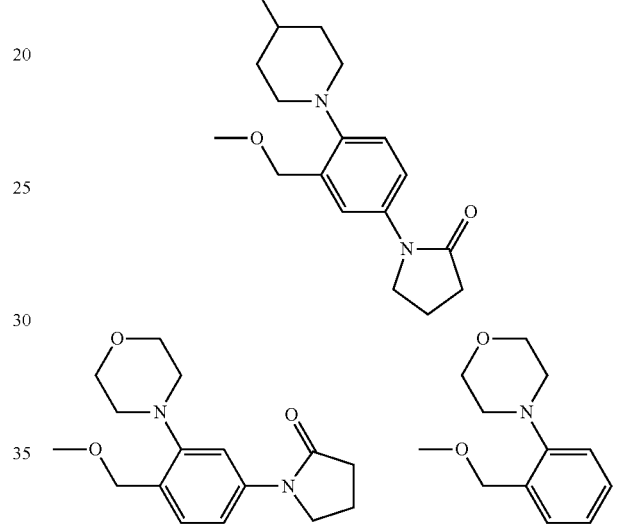
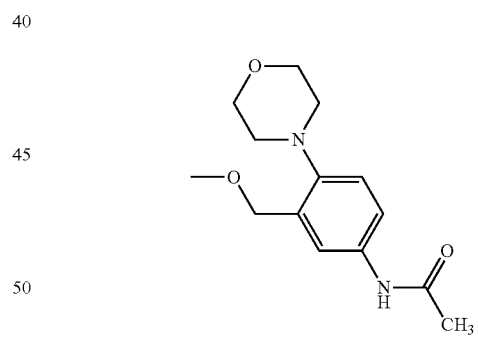
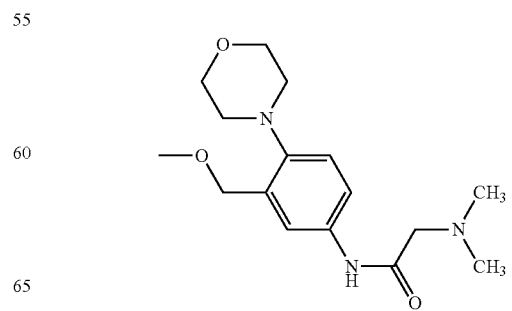

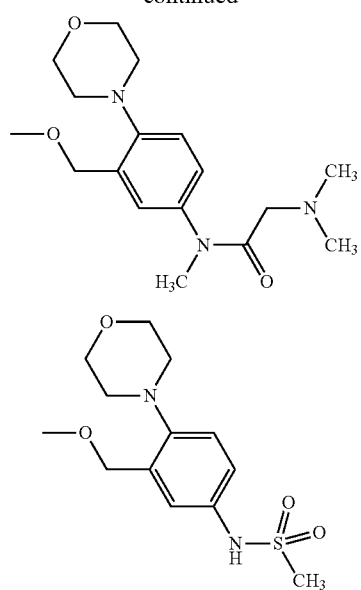
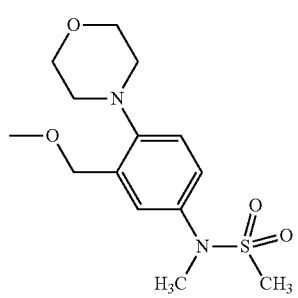
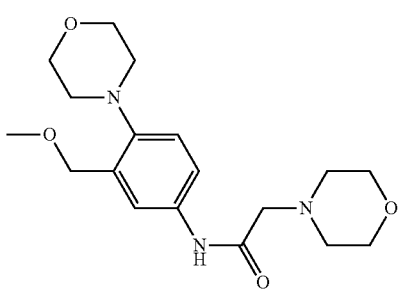
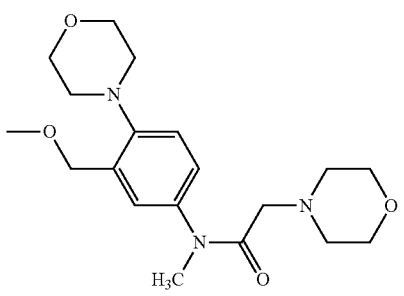

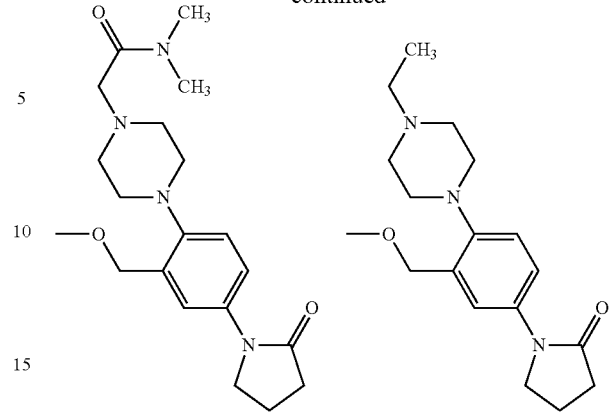

and the like can be mentioned.

In the formula [I], moreover, a compound represented by the following formula [I-A], [I-B] or [I-C] is particularly preferable.

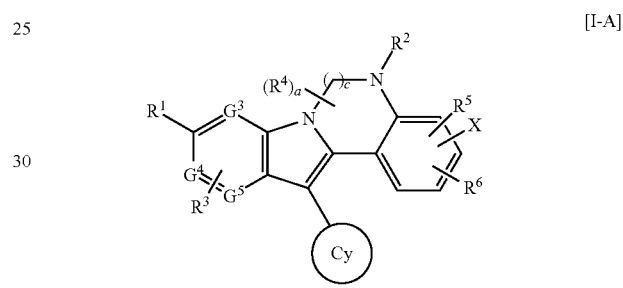

[I-A]

wherein X' is a hydrogen atom, a halogen atom, "a $C_{1-6}$ alkyl group optionally substituted by 1 to 3 substituents selected from group A" or "—$OR^{d1}$", and other symbols are as defined above.

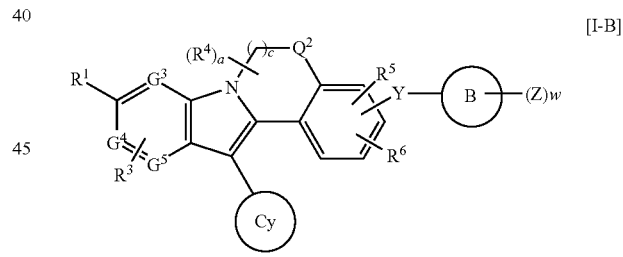

[I-B]

wherein $Q^2$ is —O— or —NH—, and other symbols are as defined above

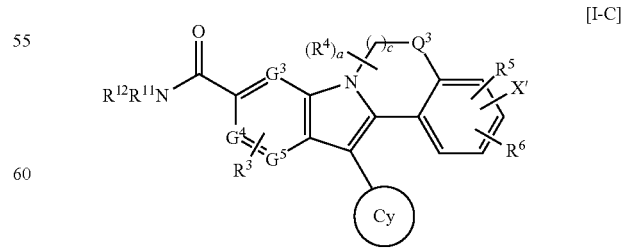

[I-C]

wherein $Q^3$ is —O— or —$NR^2$—, X' is a hydrogen atom, a halogen atom, a $C_{1-6}$ alkyl group optionally substituted by 1 to 3 substituents selected from group A or —$OR^{d1}$, and other symbols are as defined above.

The "carboxyl-protecting group" only needs to be suitable for reaction conditions, and is capable of protecting and deprotecting and may be, for example, methyl; substituted methyl group such as methoxymethyl, methylthiomethyl, 2-tetrahydropyranyl, methoxyethoxymethyl, benzyloxymethyl, phenacyl, diacylmethyl, phthalimidomethyl etc.; ethyl; substituted ethyl group such as 2,2,2-trichloroethyl, 2-chloroethyl, 2-(trimethylsilyl)ethyl, 2-methylthioethyl, 2-(p-toluenesulfonyl)ethyl, t-butyl etc.; benzyl; substituted benzyl group such as diphenylmethyl, triphenylmethyl, p-nitrobenzyl, 4-picolyl, p-methoxybenzyl, 2-(9,10-dioxo)anthrylmethyl etc.; silyl group such as trimethylsilyl, t-butyldimethylsilyl, phenyldimethylsilyl etc.; and the like.

The "pharmaceutically acceptable salt" may be any as long as it forms a non-toxic salt with a compound of the above-mentioned formula [I]. Such salt can be obtained by reacting the compound with an inorganic acid, such as hydrochloric acid, sulfuric acid, phosphoric acid, hydrobromic acid and the like; or an organic acid, such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid, meglumine acid and the like; or an inorganic base, such as sodium hydroxide, potassium hydroxide, calcium hydroxide, magnesium hydroxide, ammonium hydroxide and the like; or an organic base, such as methylamine, diethylamine, triethylamine, triethanolamine, ethylenediamine, tris(hydroxymethyl)methylamine, guanidine, choline, cinchonine and the like; with an amino acid, such as lysine, arginine, alanine and the like. The present invention encompasses water-retaining product, hydrate and solvate of each compound.

The compounds of the above-mentioned formula [I] have various isomers. For example, E compound and Z compound are present as geometric isomers, and when the compound has asymmetric carbon(s), an enantiomer and a diastereomer are present as a stereoisomer due to the asymmetric carbon(s). When an axial chirality exists, a stereoisomer based thereon exists. A tautomer may be also present. The present invention encompasses all of these isomers and mixtures thereof.

The present invention also encompasses a prodrug and a metabolite of each compound.

A "prodrug" means a derivative of the compound of the present invention, which is capable of chemical or metabolic decomposition, which shows inherent efficacy by reverting to the original compound after administration to a body, and which includes salts and complexes without a covalent bond.

A prodrug is utilized for, for example, improving absorption by oral administration, or targeting of a target site.

As the modification moiety, a functional group having high reactivity in the compound of the present invention can be mentioned such as hydroxyl group, carboxyl group, amino group, thiol group and the like.

As preferable embodiments of the compound of the present invention, a compound having fine pharmacological activity (e.g., a compound having strong polymerase inhibitory activity, a compound having strong inhibitory activity on enzyme complex comprising polymerase, a compound having strong HCV replicon-inhibitory activity, a compound having high anti-HCV activity in HCV infected cells and the like), a compound having fine bioavailability (e.g., a compound showing high oral absorbability, a compound having high cell-permeability, a compound stable to metabolic enzyme, a compound with low binding ability to protein and the like), a highly safe compound (e.g., a compound free of immunogenicity or showing low allergic response, a compound free of or low in increase in bilirubin value, a compound showing low P450 (CYP)-inhibitory activity and the like) and the like can be mentioned.

When the inventive compound is used as a pharmaceutical preparation, the inventive compound is generally admixed with pharmaceutically acceptable carriers, excipients, diluents, binders, disintegrators, stabilizers, preservatives, buffers, emulsifiers, aromatics, coloring agents, sweeteners, thickeners, correctives, solubilizers known per se, and other additives such as water, vegetable oil, alcohol such as ethanol, benzyl alcohol and the like, polyethylene glycol, glycerol triacetate, gelatin, lactose, carbohydrate such as starch and the like, magnesium stearate, talc, lanolin, petrolatum and the like, and prepared into a dosage form of tablets, pills, powders, granules, suppositories, injections, eye drops, liquids, capsules, troches, aerosols, elixirs, suspensions, emulsions, syrups and the like, which can be administered systemically or topically and orally or parenterally.

While the dose varies depending on the age, body weight, general condition, treatment effect, administration route and the like, it is from 0.01 mg to 3 g for an adult per dose, which is given one to several times a day.

The "prophylaxis of hepatitis C" means, for example, administration of a pharmaceutical agent to an individual found to carry an HCV by a test and the like but without a symptom of hepatitis C, or to an individual who shows an improved disease state of hepatitis after a treatment of hepatitis C, but who still carries an HCV and is associated with a risk of recurrence of hepatitis.

The therapeutic agent for hepatitis C of the present invention is expected to provide a synergistic effect when concurrently used with other antiviral agents, antiinflammatory agents or immunostimulants.

The medicaments with the prospect of synergistic effect include, for example, interferon-α, interferon-β, interferon-γ, interleukin-2, interleukin-8, interleukin-10, interleukin-12, TNFα, recombinant or modified products thereof, agonists, antibodies, vaccines, ribozymes, antisense nucleotides and the like.

As evidenced in the combination therapy of anti-HIV agents, which is also called a cocktail therapy, the combined use of various anti-virus agents against viruses showing frequent genetic mutations is expected to show effect for suppressing emergence and increase of drug tolerant viruses. For example, 2 or 3 agents from HCV-IRES inhibitors, HCV-NS3 protease inhibitors, HCV-NS2NS3 protease inhibitors, HCV-NS5A inhibitors and HCV polymerase inhibitor may be used in combination. Specifically, the combined use with Ribavirin(R), interferon-α (IFN-α, Roferon(R), Intron A(R), Sumiferon(R), MultiFeron(R), infergen(R), Omniferon(R), Pegasys(R), PEG-Intron A(R)), interferon-β (Frone(R), Rebif(R), AvoneX(R), IFNβMOCHIDA(R)), interferon-ω, 1-β-L-ribofuranosyl-1H-1,2,4-triazole-3-carboxamide, 16α-bromo-3β-hydroxy-5α-androstan-17-one, 1H-imidazole-4-ethanamide dihydrochloride, HCV ribozyme Heptazyme(R), polyclonal antibody Civacir(R), lactoferrin GPX-400, (1S, 2R,8R,8aR)-1,2,8-trihydroxyoctahydroindolizidinium chloride, HCV vaccine (MTH-68/B, Innivax C(R), Engerix B(R)), antisense oligonucleotide ISIS-14803, HCV-RNA transcriptase inhibitor VP-50406, tetrachlorodecaoxide (high concentration Oxoferin(R)), tetrahydrofuran-3-yl (S)—N-3-[3-(3-methoxy-4-oxazol-5-ylphenyl)ureido]benzylcarbamate, 4-amino-2-ethoxymethyl-α,α-dimethyl-1H-imidazo[4,5-c]quinoline-1-ethanol, interleukin-2 (Proleukin(R)), thymosin α1 and the like is exemplified, wherein (R) shows product names.

Furthermore, the combined use with the compounds disclosed in JP-A-08-268890, JP-A-10-101591, JP-A-07-069899, WO99/61613 and the like as HCV-IRES inhibitors; the compounds disclosed in WO98/22496, WO99/07733, WO99/07734, WO00/09543, WO00/09558, WO01/59929, WO98/17679, EP932617, WO99/50230, WO00/74768, WO97/43310, U.S. Pat. No. 5,990,276, WO01/58929, WO01/77113, WO02/8198, WO02/8187, WO02/8244, WO02/8256, WO01/07407, WO01/40262, WO01/64678, WO98/46630, JP-A-11-292840, JP-A-10-298151, JP-A-11-127861, JP-A-2001-103993, WO98/46597, WO99/64442, WO00/31129, WO01/32961, WO93/15730, U.S. Pat. No. 7,832,236, WO00/200400, WO02/8251, WO01/16379, WO02/7761 and the like as HCV protease inhibitors; the compounds disclosed in WO97/36554, U.S. Pat. No. 5,830, 905, WO97/36866, U.S. Pat. No. 5,633,388, WO01/07027, WO00/24725 and the like as HCV helicase inhibitors; the compounds disclosed in WO00/10573, WO00/13708, WO00/18231, WO00/06529, WO02/06246, WO01/32153, WO01/60315, WO01/77091, WO02/04425, WO02/20497, WO00/04141 and the like as HCV polymerase inhibitors; the compounds disclosed in WO01/58877, JP-A-11-180981, WO01/12214 and the like as interferon agonists or enhancers; and the like is also exemplified.

In the case of combined administration, the compound of the present invention can be administered simultaneously with a pharmaceutical agent to be used in combination (hereinafter combination drug) or administered at certain time intervals. In the case of combined administration, a pharmaceutical composition containing the compound of the present invention and a combination drug can be administered. Alternatively, a pharmaceutical composition containing the compound of the present invention and a pharmaceutical composition containing a combination drug may be administered separately. The is administration route of the compound of the present invention and that of the combination drug may be the same or different.

In the case of a combined administration, the compound of the present invention can be administered once a day or several times a day in a single dose of 0.1 mg to 1 g, or may be administered at a smaller dose. The combination drug can be administered at a dose generally used for the prevention or treatment of hepatitis C, for example, at a single dose of 0.2 mg to 0.8 mg. Alternatively, it may be administered at a smaller dose.

Inasmuch as HCV is known to be a virus associated with many genetic mutations, a compound effective for many genotypes is one of the preferable modes. If a compound ensures high blood concentration and sustention thereof when administered as a pharmaceutical agent to an animal infected with HCV, it is also one of the preferable modes. From these aspects, a compound having high inhibitory activity on both HCV type 1a and type 1b and high blood concentration is particularly preferable.

Examples of the Production Method of the compound to be used for the practice of the present invention are given in the following. However, the Production Method of the compound of the present invention is not limited to these examples.

Even if no directly corresponding disclosure is found in the following Production Methods, the steps may be modified for efficient production of the compound, such as introduction of a protecting group into a functional group with deprotection in a subsequent step, and changing the order of Production Methods and steps.

The treatment after reaction in each step may be conventional ones, for which typical methods, such as isolation and purification, crystallization, recrystallization, silica gel chromatography, preparative HPLC and the like, can be appropriately selected and combined.

Reference Example 1

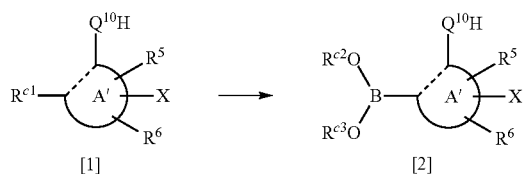

wherein $Q^{10}$ is, for example, O or NH, $R^{c1}$ is a leaving group such as bromine atom, iodine atom, —OTf (trifluoromethylsulfonyloxy group) and the like, —B(OR$^{c2}$)(OR$^{c3}$) is —B(OH)$_2$, 4,4,5,5-tetramethyl-1,3,2-dioxaborolan-2-yl group, ring A' is ring A wherein $G^6$ is carbon atom, and other symbols are as defined above.

Compound [2] can be obtained from commercially available compound [1] or compound [1] obtained by a conventional method and a boric acid ester.

As the boric acid ester, pinacolborane, bis(pinacolato)diboron and the like can be mentioned.

As a catalyst, palladium catalysts such as Pd(PPh$_3$)$_4$, Pd(dppb)Cl$_2$, PdCl$_2$(dppf)CH$_2$Cl$_2$, PdCl$_2$(PPh$_3$)$_2$, Pd(OAc)$_2$, PdCl$_2$, palladium black, palladium carbon and the like can be mentioned.

As a base, strong bases such as ethylenediamine, sodium carbonate, barium hydroxide, potassium phosphate, cesium carbonate, sodium hydrogen carbonate, sodium tert-butoxide, potassium tert-butoxide, triethylamine, potassium acetate and the like are generally preferable. As the ligand, triphenylphosphine, tri(2-tolyl)phosphine, (2-biphenyl)dicyclohexylphosphine and the like may be added.

In addition, compound [1] may be reacted with a boric acid ester such as triisopropyl borate, trimethyl borate and the like in the presence of n-butyllithium. Where necessary, a protecting group may be introduced into -Q$^{10}$H and the protected compound may be subjected to the reaction.

As a solvent, 1,4-dioxane, THF (tetrahydrofuran), toluene, dimethoxyethane, water and the like can be mentioned.

Reference Example 2

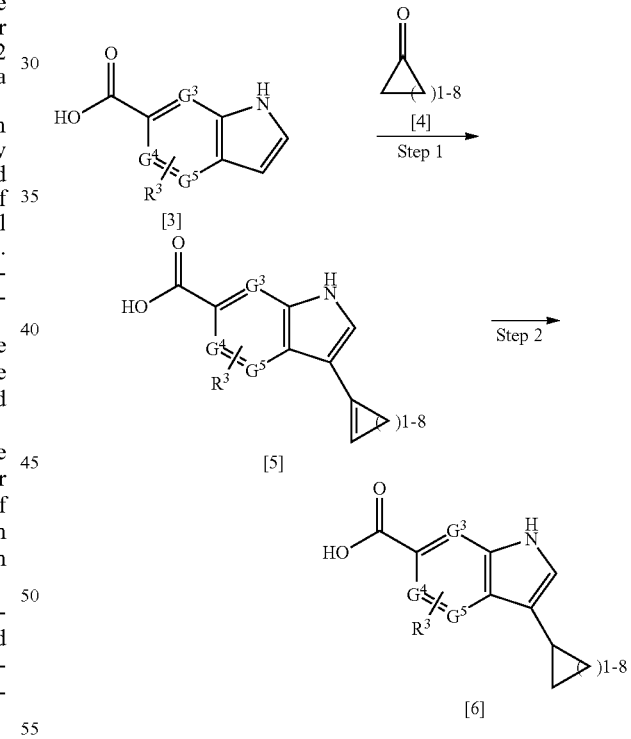

wherein compound [4] is, for example, a compound wherein cycloalkyl group having 3 to 10 carbon atoms is substituted by oxo group, such as cyclopentanone, cyclohexanone and the like.

Step 1

Compound [5] can be obtained by reacting commercially available compound [3] or compound [3] obtained by a conventional method with compound [4] in the presence of a base, or under aldol reaction conditions.

As a base, preferably, sodium methoxide, sodium ethoxide, lithium, diisopropylamide, sodium hydroxide, potassium hydroxide, sodium hydride and the like can be mentioned.

As a solvent, alcohol solvent such as methanol, ethanol and the like, THF, 1,4-dioxane, DMF (dimethylformamide), DMSO (dimethyl sulfoxide), DMA (dimethylacetamide), water and a mixed solvent thereof and the like can be mentioned.

As the reaction temperature, −20° C. to 120° C. is preferable.

In addition, for a reaction under acidic conditions, in a mixed solvent of acetic acid and phosphoric acid, they may be treated at a reaction temperature of from 15° C. to 120° C.

Step 2

Compound [6] can be obtained by hydrogenation of compound [5] in a solvent such as methanol, ethanol, THF, ethyl acetate, acetic acid, formic acid, water and the like, in the presence of a catalyst such as palladium carbon, palladium hydroxide, palladium hydroxide on carbon, platinum oxide, Raney-nickel and the like, at room temperature or under heating.

Reference Example 3

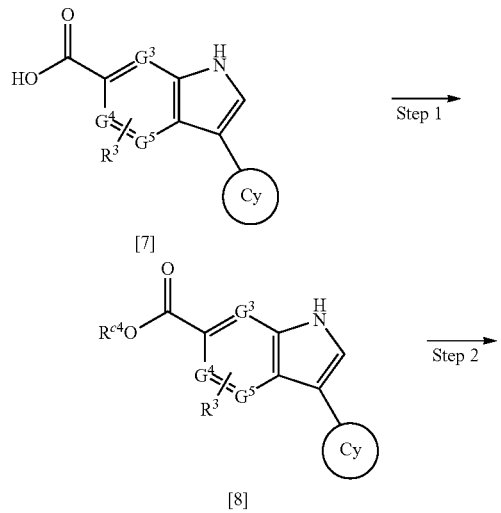

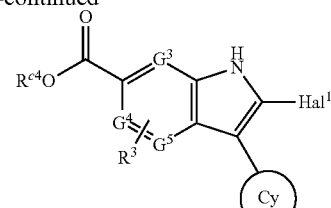

wherein $R^{c4}$ is carboxyl-protecting group such as methyl group, ethyl group, tert-butyl group, benzyl group and the like, $Hal^1$ is halogen atom such as bromine atom, iodine atom and the like, and other symbols are as defined above.

Step 1

Compound [8] can be obtained by introducing a protecting group into a carboxyl group of compound [7] obtained by a conventional method or in the same manner as in Reference Example 2.

Where necessary, a protecting group may be introduced into a nitrogen atom of indole.

Step 2

Compound [9] can be obtained by halogenating compound [8] with a halogenating agent.

As the halogenating agent, bromine, N-bromosuccinimide, pyridine tribromide, dibromohydantoin, pyridinium hydrobromide perbromide, an iodide thereof and the like can be mentioned.

As a solvent, halogen solvents (dichloromethane, chloroform, carbon tetrachloride etc.), hydrocarbon solvents (toluene etc.), ether solvents (1,4-dioxane, DME (1,2-dimethoxyethane), THF etc.), acetic acid, ethyl acetate, isopropyl alcohol or a mixed solvent thereof and the like can be mentioned.

As the reaction temperature, from −40° C. to 100° C. is preferable.

Production Method 1

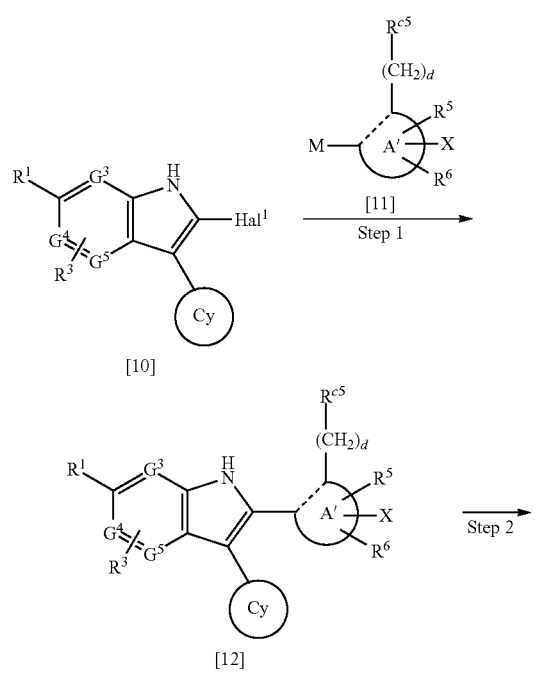

-continued
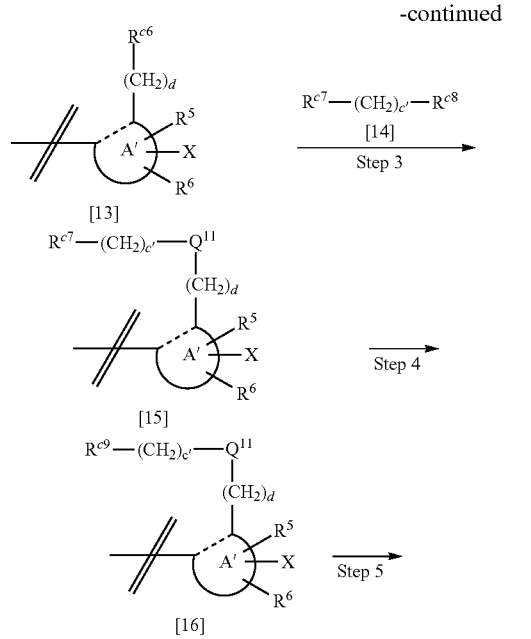
Step 3
[13] → [15]
Step 4
[15] → [16]
Step 5
[16] →
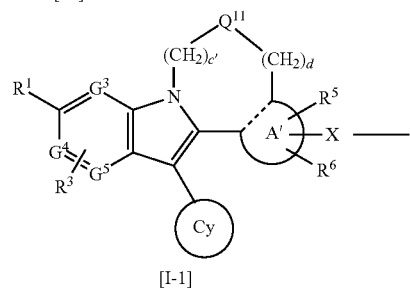
[I-1]
Step 6
when Q¹¹ is -CONH-
[I-2]
when Q¹¹ is -NHCO-
[I-3]
Step 7
when Q¹¹ is -S-
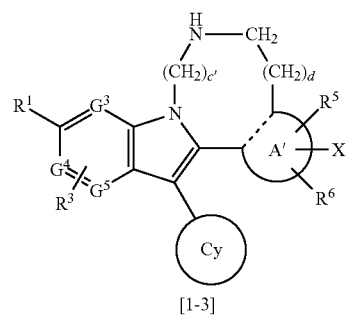
[I-4]
and
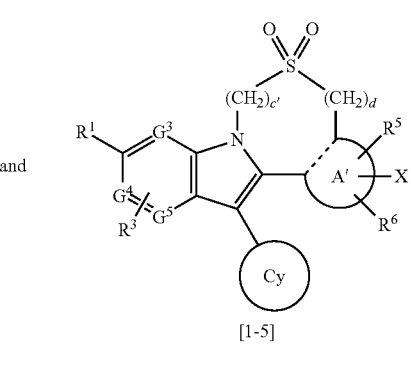
[I-5]

wherein c' is an integer of 1 to 4,
$Q^{11}$ is —O—, —S—, —OCO—, —OCONH—, —NHCO—, —NHSO$_2$—, —NHCOO—, —COO—, —CONH—, —SO$_2$NH—, —NHCONH—, —NHSO$_2$NH—, —CH=CH—, —CH=N— or —N=CH—, $R^{c5}$ is —OH, —SH, —NH$_2$, —COOH, —SO$_2$NH$_2$, a protected group thereof or —CHO,
$R^{c6}$ is —OH, —SH, —NH$_2$, —COOH, —SO$_2$NH$_2$ or —CHO,
$R^{c7}$ is a leaving group such as Hal$^2$ (wherein Hal$^2$ is halogen atom such as chlorine atom, bromine atom, iodine atom and the like), —OMs (mesyloxy group), —OTs (tosyloxy group), —OTf and the like or a protected OH group,
$R^{c8}$ is —OH, —NH$_2$, —COOH, —CHO, —COHal$^2$, —OCOHal$^2$, —SO$_2$Hal$^2$, —NHSO$_2$Hal$^2$, —OC(=NH)C(Hal)$_3$ (wherein Hal is halogen atom such as fluorine atom, chlorine atom and the like), —NCO, Hal$^2$ or —P$^+$(Ph)$_3$,
$R^{c9}$ is a leaving group such as Hal$^2$, —OMs or —OTs and the like, compound [11] is a metal compound, wherein the metal moiety M includes boron, zinc, tin, magnesium, lithium and the like, for example, phenylboronic acid derivative, and other symbols are as defined above.

Step 1
Compound [12] can be obtained by reacting compound [10] obtained by a conventional method or in the same manner as in Reference Example 3 with compound [11] obtained by a conventional method or in the same manner as in Reference Example 1.

Step 2
When $R^{c5}$ is a protected group, deprotection is conducted by a conventional method to give compound [13] from compound [12].

Step 3
Compound [15] can be obtained by reacting compound [13] with compound [14].
For example, when a desired $Q^{11}$ is —OCO—, Compound [15] can be obtained by esterification of compound [14] wherein $R^{c8}$ is —OH and compound [13] wherein $R^{c6}$ is HOOC— by a conventional method.

In the following, examples of reaction for each desired $Q^{11}$ are shown in the form of a Table.

TABLE 1-1

| Desired $Q^{11}$ | —$R^{c8}$ | $R^{c6}$— | Reaction |
|---|---|---|---|
| —OCO— | —OH | HOOC— | esterification or amidation by reaction in the presence of condensing agent, reaction as acid halide, Mitsunobu reaction and the like. |
| —COO— | —COOH | HO— | |
| —CONH— | —COHal$^2$ | H$_2$N— | |
| —NHCO— | —NH$_2$ | HOOC— | |
| —OCONH— | —OCOHal$^2$ | H$_2$N— | |
| —SO$_2$NH— | —SO$_2$Hal$^2$ | H$_2$N— | |
| —NHSO$_2$NH— | —NHSO$_2$Hal$^2$ | | |
| —NHCONH— | —NCO | H$_2$N— | urea formation or carbamation with isocyanate. |
| —NHCOO— | | HO— | |
| —NHSO$_2$— | —OC(=NH)C(Hal)$_3$ | H$_2$NO$_2$S— | reaction with imidoyloxy group in the presence of acid. |
| —O— | | HO— | |
| —S— | | HS— | |
| —CH=CH— | —P$^+$(Ph)$_3$ | HOC— | using Wittig reaction. |
| —CH=N— | —CHO | H$_2$N— | imine formation with amine and aldehyde. |
| —N=CH— | —NH$_2$ | HOC— | |

Step 4
When $R^{c7}$ is a protected OH group, deprotection is conducted by a conventional method, after which halogenation, mesylation or tosylation is conducted to give compound [16] from compound [15].

Step 5
Compound [I-1] can be obtained by condensation cyclization of compound [16] by a conventional method.

Step 6
When $Q^{11}$ is —CONH— or —NHCO—, compounds [I-2] and [I-3] can be respectively obtained by reduction of compound [I-1] by a conventional method.

Step 7
When $Q^{11}$ is —S—, compounds [I-4] and [I-5] can be obtained by oxidation of compound [I-1] by a conventional method.

Production Method 1-1

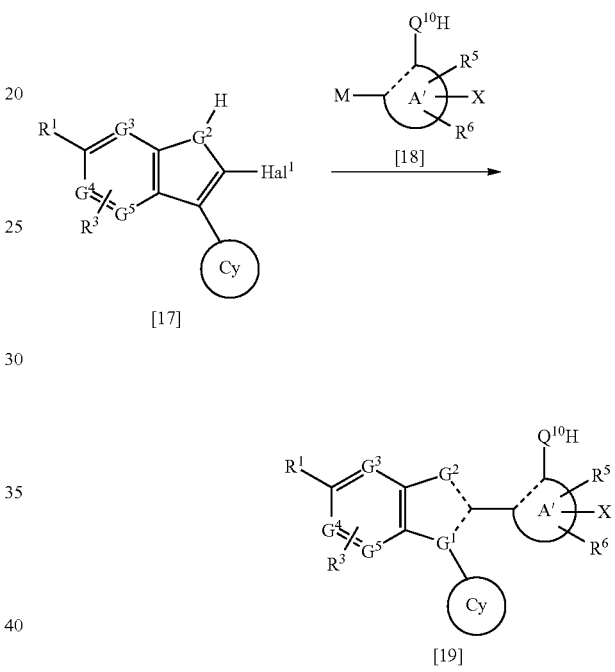

wherein each symbol is as defined above.

Compound [19] can be obtained by reacting compound [17] obtained by a conventional method or in the same manner as in Reference Example 3 with compound [18] obtained by a conventional method or in the same manner as in Reference Example 1 using a Suzuki reaction.

For example, Compound [19] can be obtained by a reaction in a solvent such as DMF, acetonitrile, alcohol solvents (methanol, ethanol etc.), DME, THF, toluene, water, or a mixed solvent thereof and the like in the presence of a palladium catalyst such as tetrakis(triphenylphosphine)palladium, bis(triphenylphosphine)palladium(II) dichloride, palladium acetate-triphenylphosphine and the like, a nickel catalyst such as nickel chloride, 1,3-bis(diphenylphosphino)propane nickel(II) chloride and the like and a base such as sodium carbonate, potassium carbonate, potassium hydrogen carbonate, sodium hydrogen carbonate, potassium phosphate, triethylamine, potassium fluoride, cesium fluoride, sodium hydrogenphosphate, cesium carbonate and the like, at room temperature or under heating.

The reactivity may be increased by adding lithium chloride and the like.

In addition, the following compounds may be used instead of the above-mentioned compounds [17] and [18].

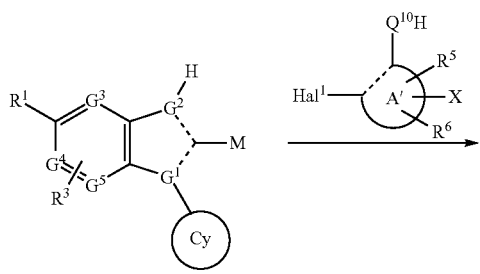

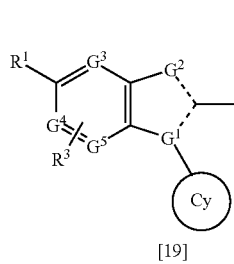

[19]

Protection Method 1-2

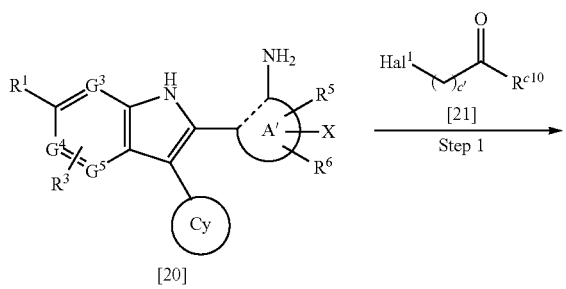

[20]

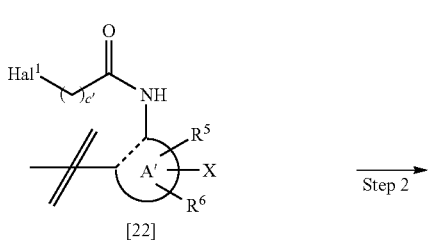

[22]

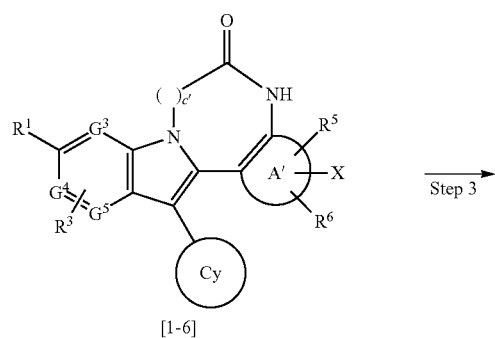

[1-6]

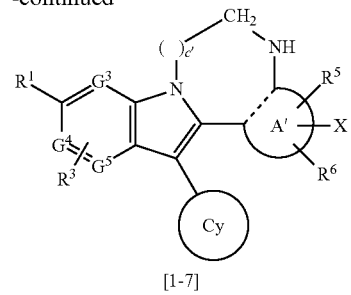

[1-7]

wherein $R^{c10}$ is halogen atom such as chlorine atom, bromine atom and the like or hydroxyl group, and other symbols are as defined above.

Step 1

Compound [22] can be obtained by reacting compound [20] with compound [21].

When $R^{c10}$ is a hydroxyl group, compound [20] is condensed with carboxylic acid compound [21] in a solvent such as DMF, acetonitrile, THF, chloroform, ethyl acetate, methylene chloride, toluene and the like by adding a condensing agent such as dicyclohexylcarbodiimide, 1-ethyl-3-(3-dimethylaminopropyl)carbodiimide hydrochloride, diphenylphosphoryl azide and the like and, where necessary, N-hydroxysuccinimide, 1-hydroxybenzotriazole and the like to give amide compound [22]. Alternatively, amide Compound [22] can be obtained from compound [21] as follows. The carboxylic acid compound [21] is converted to an acid halide with thionyl chloride, oxalyl chloride and the like (a catalyst amount of DMF may be added), or to an active ester of carboxylic acid compound [21] (e.g., converting to a mixed acid anhydride with ethyl chlorocarbonate and the like), which is then reacted with compound [20] in the presence of a base, such as triethylamine, potassium carbonate, pyridine and the like, or in an amine solvent such as pyridine and the like, to give amide compound [22]. For the reaction of active ester with compound [20], dimethylaminopyridine may be added.

When $R^{c10}$ is halogen atom such as chlorine atom, bromine atom and the like, compound [21] is reacted with compound [20] in the presence of a base such as triethylamine, potassium carbonate, pyridine and the like, or in an amine solvent such as pyridine and the like to give amide compound [22].

To increase selectivity of reaction with amino group, acetic acid and sodium acetate may be added at an equivalent ratio.

Step 2

Compound [I-6] can be obtained by condensation cyclization of compound [22] in a solvent such as ethanol, DMF, DMA, DMSO, acetone, acetonitrile, 1,4-dioxane, THF, toluene, water and the like, in the presence or absence of a base such as potassium hydroxide, sodium hydride, potassium carbonate, triethylamine, sodium ethoxide, potassium tert-butoxide and the like, under cooling to under heating.

Step 3

Compound [I-7] can be obtained by reducing compound [I-6] by a conventional method.

For example, reduction is carried out using a borohydride (e.g., sodium borohydride, sodium triacetoxyborohydride and the like), borane-THF complex and the like as a reducing agent. In this case, an acid such as acetic acid, hydrochloric acid and the like may be added.

As a preferable solvent, ether solvents (1,4-dioxane, THF etc.), alcohol solvents (methanol, ethanol etc.), polar solvents (DMF, DMSO, acetonitrile etc.), halogen solvents (dichloromethane, chloroform etc.), hydrocarbon solvents (benzene, toluene etc.), ester solvents (ethyl acetate, butyl acetate etc.), water, or a mixed solvent thereof and the like can be mentioned.

Production Method 2
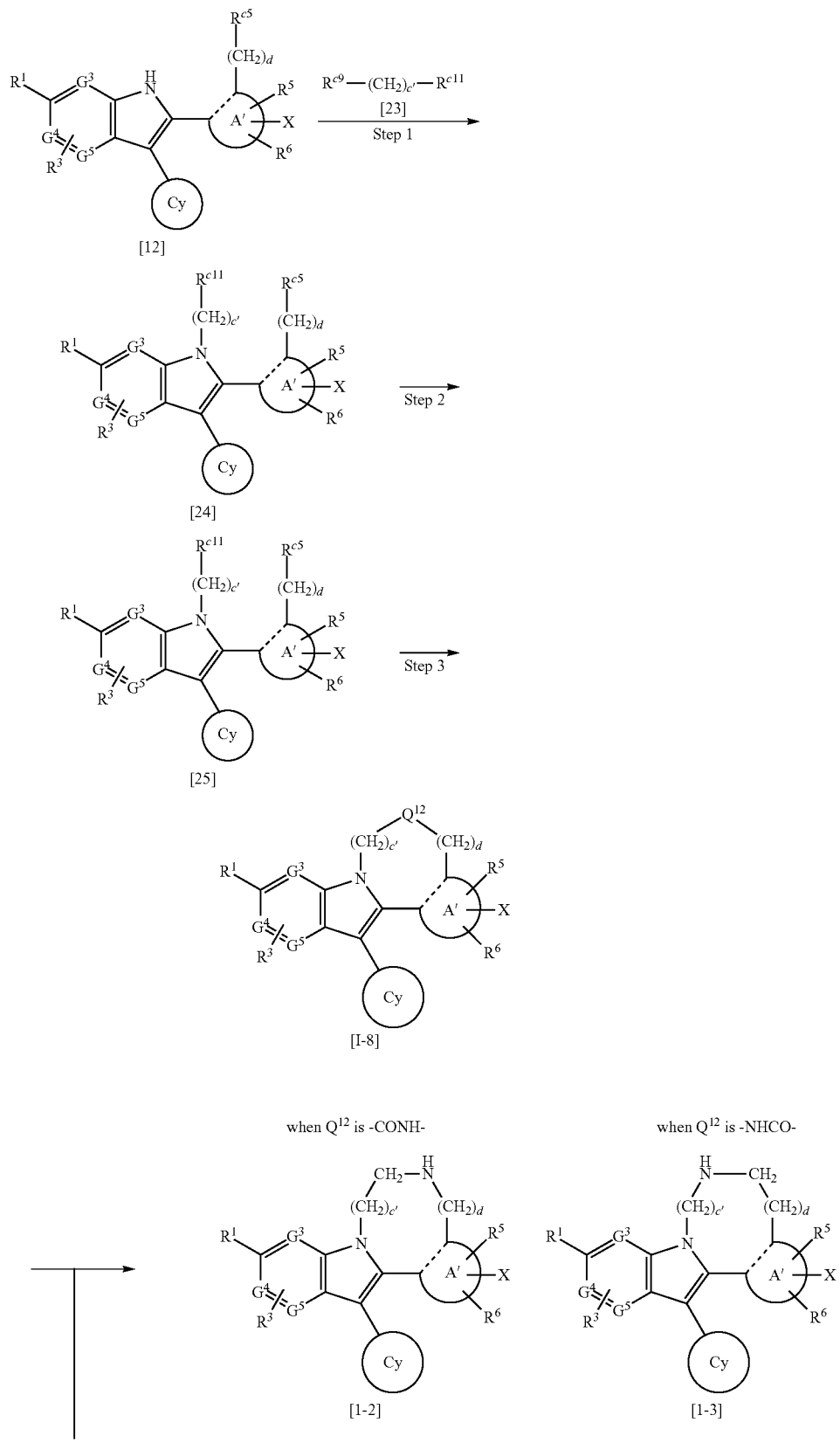

-continued when $Q^{12}$ is -S-

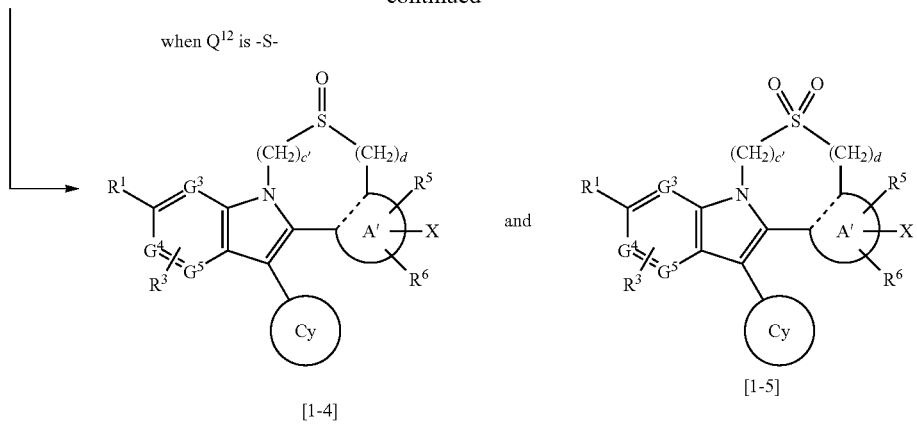

[1-4] and [1-5]

wherein $Q^{12}$ is —O—, —S—, —OCO—, —OCONH—, —NHCO—, —NHSO$_2$—, —NHCOO—, —COO—, —CONH—, —NHCONH—, —NHSO$_2$NH—, —CH=N— or —N=CH—, $R^{c11}$ is —OH, —NH$_2$, —COOH, a protected group thereof, —CHO, -Hal$^2$, —OMs or —OTs, $R^{c12}$ is —OH, —NH$_2$, —COOH, —CHO, -Hal$^2$, —OMs or —OTs, and other symbols are as defined above.

Step 1
Compound [24] can be obtained by reacting compound [12] with commercially available compound [23] or compound [23] obtained by a conventional method.

Step 2
When $R^{c5}$ and/or $R^{c11}$ is a protected group, deprotection is conducted by a conventional method to give compound [25] from compound [24].

Step 3
Compound [I-8] can be obtained by intramolecular cyclization of compound [25].

For example, when desired $Q^{12}$ is —O—, Compound [I-8] can be obtained by etherification of compound [25] wherein $R^{c12}$ is —OH and $R^{c6}$ is HO— using Mitsunobu reaction.

In the following, examples of reaction for each desired $Q^{12}$ are shown in the form of a Table.

TABLE 1-2

| Desired $Q^{12}$ | —$R^{c2}$ | $R^{c6}$— | Reaction |
|---|---|---|---|
| —OCO— | —OH | HOOC— | esterification or amidation by reaction in the |
| —COO— | —COOH | HO— | |
| —CONH— | —COOH | H$_2$N— | |

TABLE 1-2-continued

| Desired $Q^{12}$ | —$R^{c2}$ | $R^{c6}$— | Reaction |
|---|---|---|---|
| —NHCO— | —NH$_2$ | HOOC— | presence of condensing agent, reaction as acid halide, Mitsunobu reaction and the like. |
| —NHCOO— | —NH$_2$ | HO— | amidation with carbodiimidazole, COCl$_2$. |
| —OCONH— | —OH | H$_2$N— | |
| —NHCONH— | —NH$_2$ | H$_2$N— | |
| —NHSO$_2$NH— | —NH$_2$ | H$_2$N— | reaction With SO$_2$Cl$_2$. |
| —NHSO$_2$— | —OH | H$_2$NO$_2$S— | reaction in the presence of condensing agent or by Mitsunobu reaction. |
| —O— | —OH | HO— | |
| —S— | —OH | HS— | |
| —O— | —Hal$^2$, | HO— | alkylation in the presence of a base. |
| —S— | —OMs, —OTs | HS— | |
| —CH=N— | —CHO | H$_2$N— | imine formation with amine and aldehyde. |
| —N=CH— | —NH$_2$ | HOC— | |

Compounds [I-2], [I-3], [I-4] and [I-5] can be obtained from compound [I-8] in the same manner as in Production Method 1, Step 6 or Step 7.

Production Method 2-1

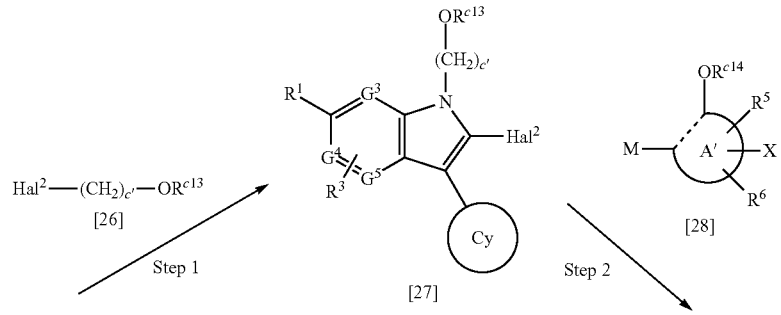

[26] Step 1 [27] Step 2 [28]

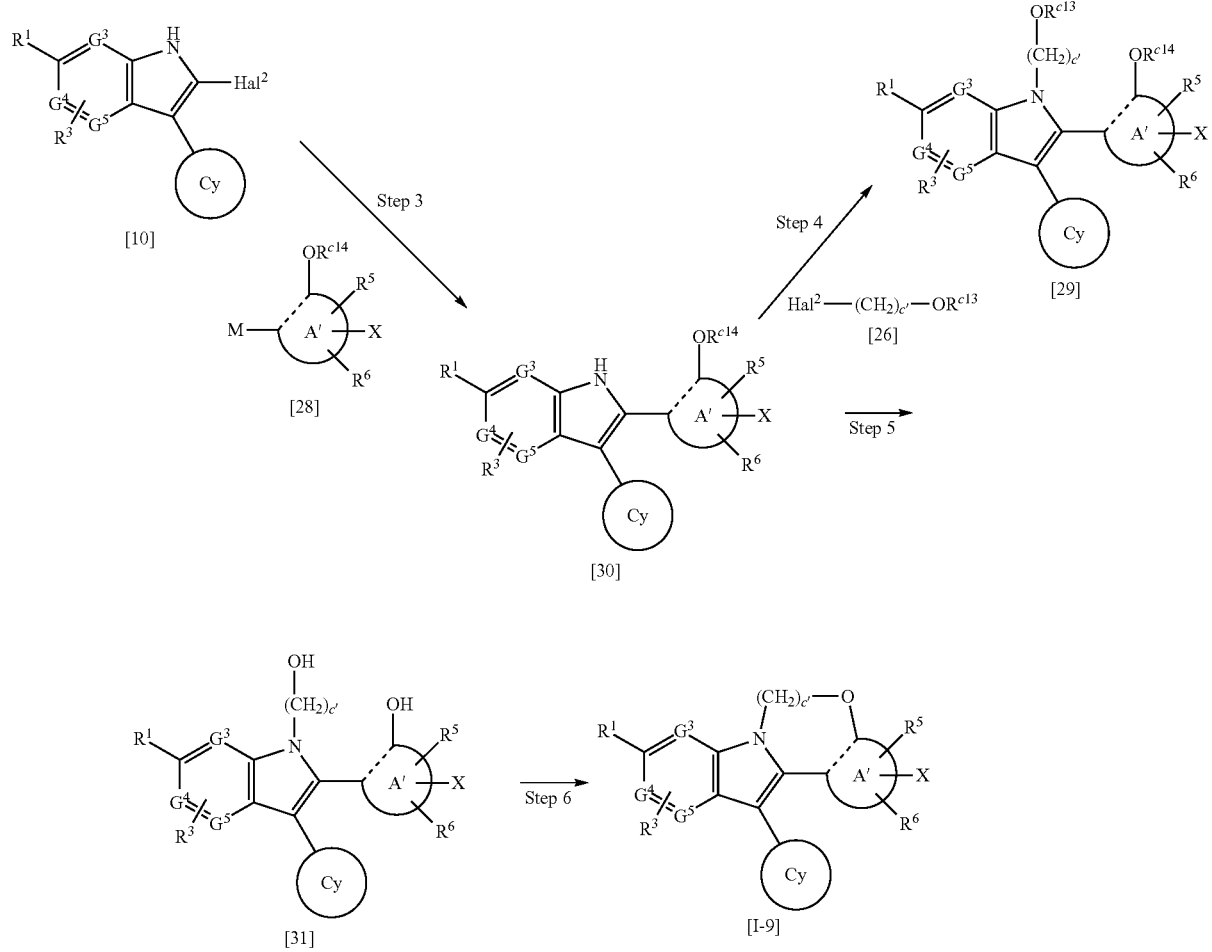

wherein $R^{c13}$ and $R^{c14}$ are the same or different and each is hydroxyl-protecting group, and other symbols are as defined above.

Step 1

Compound [27] can be obtained by reacting compound [10] with commercially available compound [26] or compound [26] obtained by a conventional method, in the same manner as in Production Method 1-2, Step 2.

Step 2

Compound [29] can be obtained by reacting compound [27] with compound [28] obtained by a conventional method or in the same manner as in Reference Example 1, in the same manner as in Production Method 1-1.

Step 3

Compound [30] can be obtained by reacting compound [10] with compound [28], in the same manner as in Production Method 1-1.

Step 4

Compound [29] can be obtained by reacting compound [30] with compound [26], in the same manner as in Production Method 1-2, Step 2.

Step 5

Compound [31] can be obtained by removing hydroxyl-protecting group of compound [29] by a conventional method.

As the hydroxyl-protecting group, tert-butyldimethylsilyl group, acetyl group, benzyl group, methoxymethyl group, methoxyethoxymethyl group, 2-tetrahydropyranyl group and the like can be mentioned.

For example, when $R^{c13}$ and $R^{c14}$ are methoxyethoxymethyl group or 2-tetrahydropyranyl group, deprotection is conducted by a method such as treatment with hydrochloric acid at room temperature in a mixed solvent of tetrahydrofuran and methanol and the like.

In addition, when $R^{c13}$ and $R^{c14}$ are benzyl groups, deprotection is conducted by a method such as treatment with a palladium catalyst at room temperature in a mixed solvent of tetrahydrofuran and methanol under a hydrogen atmosphere, treatment under acidic conditions of hydrobromide/acetic acid and the like, or reaction with an acid such as hydrochloric acid, sulfuric acid, hydrobromic acid and the like in an acetic acid solvent, and the like.

Step 6

Compound [I-9] can be obtained by Mitsunobu reaction using compound [31] in a solvent such as DMF, acetonitrile, THF and, the like, using triphenylphosphine-diethyl azodicarboxylate, triphenylphosphine-diisopropyl azodicarboxylate and the like.

In addition, compound [I-9] can be also obtained by mesylation, tosylation, trifluoromethylsulfonylation of hydroxyl group of compound [31], followed by reaction in the presence of a strong base such as sodium hydride, potassium hydride and the like.

Production Method 3

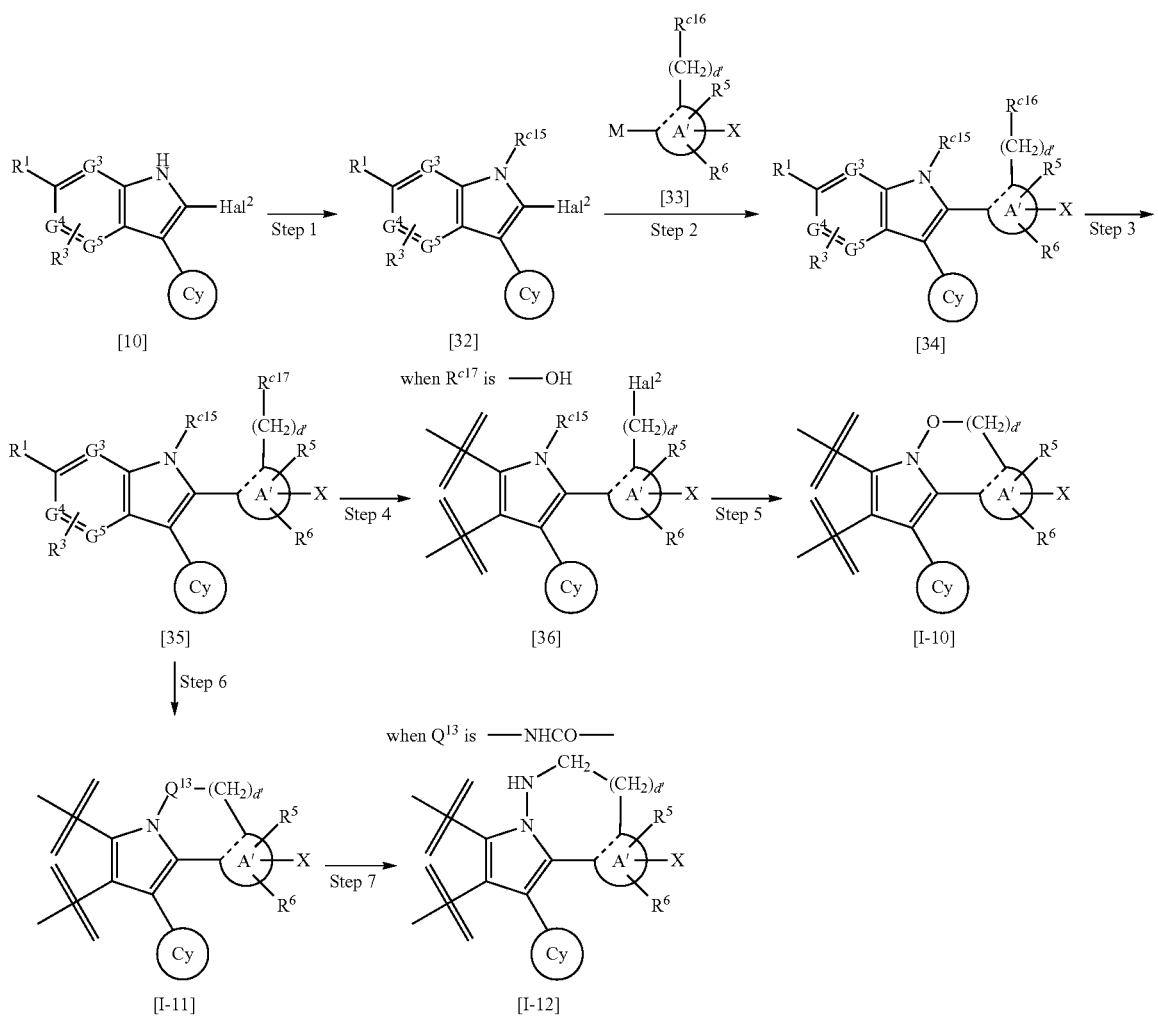

wherein $Q^{13}$ is —OCO—, —OCONH—, —NHCO—, —NHCOO—, —NHCONH— or —NHSO$_2$NH—,
$R^{c15}$ is —NH$_2$ or —OH,
$R^{c16}$ is —OH, —NH$_2$, —COOH or a protected group thereof,
$R^{c17}$ is —OH, —NH$_2$ or —COOH,
d' is an integer of 1 to 4, and other symbols are as defined above.

Step 1

When $R^{c15}$ is —NH$_2$, Compound [32] can be obtained from compound [10] by a method described in Synlett, (2), 222-225, 2001.

When $R^{c15}$ is —OH, Compound [32] can be obtained from compound [10] by a method described in Heterocycles, 46, 91-94, 1997.

Step 2

Compound [34] can be obtained by reacting compound [32] with compound [33] in the same manner as in Production Method 1-1.

Step 3

When $R^{c16}$ is a protected group, Compound [35] can be obtained from compound [34] by deprotection by a conventional method.

Step 4

When $R^{c17}$ is —OH, Compound [36] can be obtained by halogenation by a conventional method.

Step 5

Compound [I-10] can be obtained by intramolecular cyclization of compound [36] in the same manner as in Production Method 1-2, Step 2.

Step 6

Compound [I-11] can be obtained by intramolecular cyclization of compound [35].

For example, when desired $Q^{13}$ is —OCO—, Compound [I-11] can be obtained from compound [35], wherein $R^{c15}$ is —OH and $R^{c17}$ is HOOC—, by esterification by a conventional method.

In the following, examples of reaction for each desired $Q^{13}$ are shown in the form of a Table.

TABLE 1-3

| Desired $Q^{13}$ | —$R^{c15}$ | $R^{c17}$— | Reaction |
|---|---|---|---|
| —OCO— | —OH | HOOC— | esterification or |
| —NHCO— | —NH$_2$ | HOOC— | amidation by reaction in the presence of condensing agent, reaction as acid halide, Mitsunobu reaction and the like. |

TABLE 1-3-continued

| Desired $Q^{13}$ | $-R^{c15}$ | $R^{c17}-$ | Reaction |
|---|---|---|---|
| —NHCOO— | —NH$_2$ | HO— | carbamoylation |
| —OCONH— | —OH | H$_2$N— | with |
| —NHCONH— | —NH$_2$ | H$_2$N— | carbodiimidazole, COCl$_2$. |
| —NHSO$_2$NH— | —NH$_2$ | H$_2$N— | reaction with SO$_2$Cl$_2$. |

Step 7

When $Q^{13}$ is —NHCO—, Compound [I-12] can be obtained by reducing compound [I-11] by a conventional method.

Production Method 4

Here, Hal$^2$ is preferably bromine atom.

As a base, a weak base such as sodium carbonate, potassium carbonate and the like is preferable.

Step 2

Compound [40] can be obtained by reacting compound [37] with compound [39] in a solvent such as ethanol, DMF, DMA, acetone, acetonitrile, THF, toluene, water and the like, in the presence of a base.

Here, Hal$^1$ and Hal$^2$ are each preferably bromine atom and chlorine atom.

As a base, a weak base such as sodium carbonate, potassium carbonate and the like is preferable.

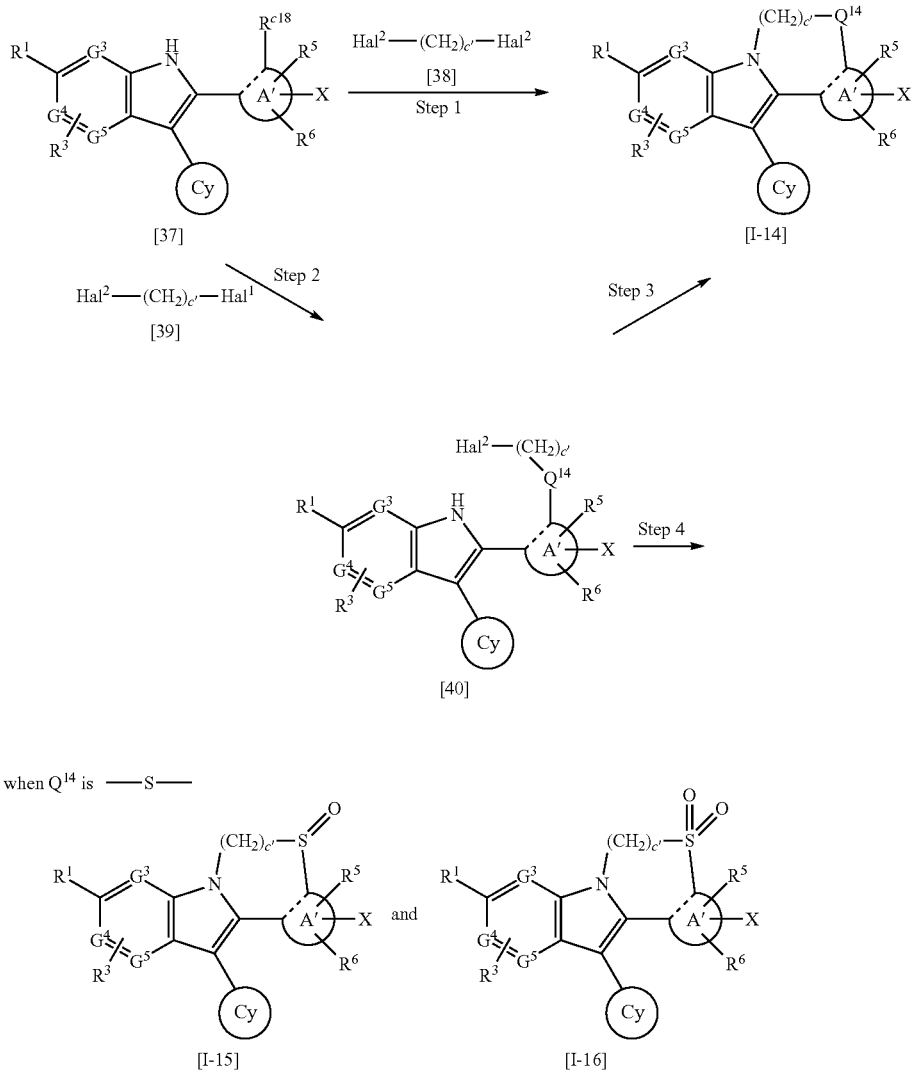

wherein $R^{c18}$ is —OH, —NH$_2$ or —SH, $Q^{14}$ is —O—, —NH— or —S—, and other symbols are as defined above.

Step 1

Compound [I-14] can be obtained by reacting compound [37] obtained in the same manner as in Production Method 1-1 with compound [38] in a solvent such as ethanol, DMF, DMA, acetone, acetonitrile, THF, toluene, water and the like, in the presence of a base.

Step 3

Compound [I-14] can be obtained by cyclization of compound [40] in the same manner as in Production Method 1-2, Step 2.

As a base, a strong base such as sodium hydride, potassium hydroxide, potassium tert-butoxide and the like is preferable.

Step 4

When $Q^{14}$ is —S—, compounds [I-15] and [I-16] can be obtained by oxidation of compound [I-14] by a conventional method.

Production Method 5
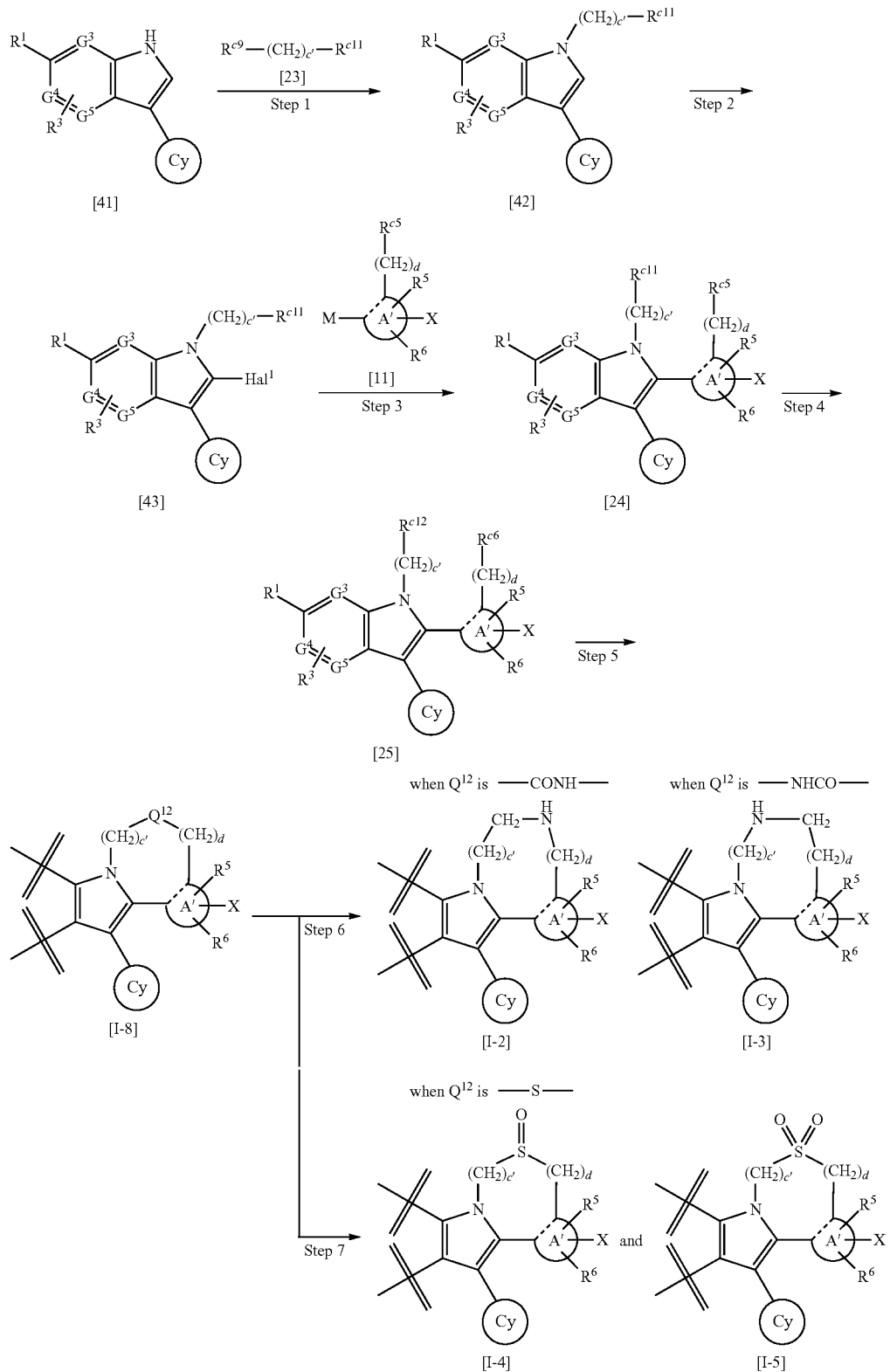
wherein each symbol is as defined above.

Step 1

Compound [42] can be obtained by reacting compound [41] obtained by a conventional method or in the same manner as in Reference Example 2 with compound [23] obtained by a conventional method.

Step 2

Compound [43] can be obtained by halogenation of compound [42] by a conventional method.

Step 3

Compound [24] can be obtained by reacting compound [43] with compound [11].

Step 4-Step 7

Compounds [I-8], [I-2], [I-3], [I-4] and [I-5] can be obtained from compound [24] in the same manner as in Production Method 2.

Production Method 5-1

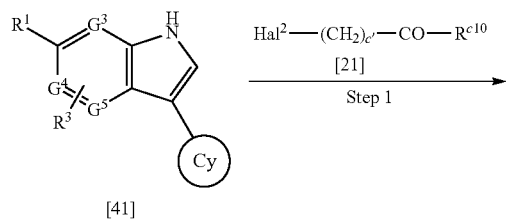

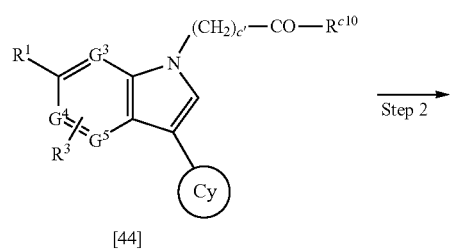

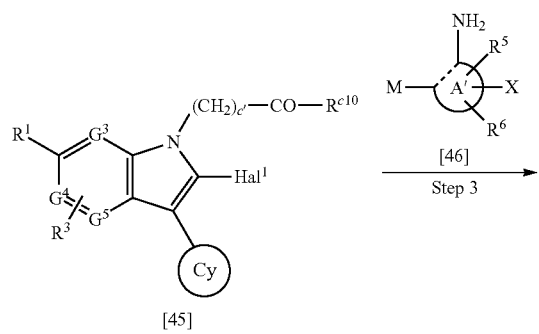

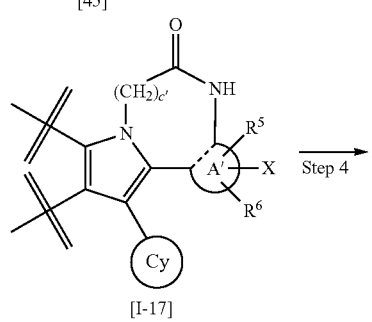

-continued

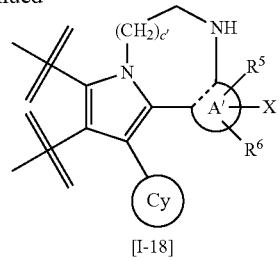

wherein each symbol is as defined above.

Step 1

Compound [44] can be obtained by reacting compound [41] and compound [21] in the same manner as in Production Method 1-2, Step 2.

Step 2

Compound [45] can be obtained by halogenation of compound [44] in the same manner as in Reference Example 3, Step 2.

Step 3

Compound [I-17] can be obtained by reacting compound [45] with compound [46] in the same manner as in Production Method 1-1.

Step 4

Compound [I-18] can be obtained by reducing compound [I-17] in the same manner as in Production Method 1-2, Step 3.

Production Method 5-2

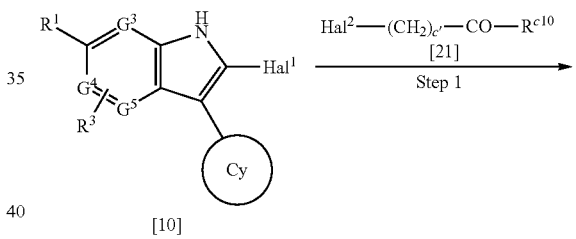

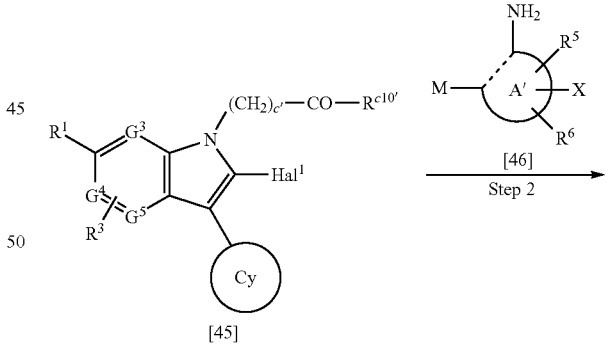

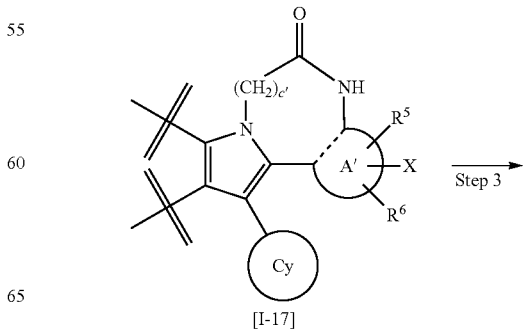

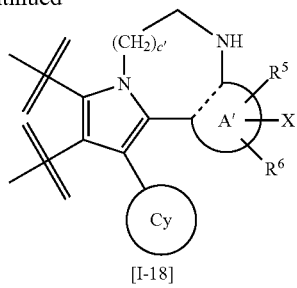

[I-18]

wherein each symbol is as defined above.

Step 1

Compound [45] can be obtained by reacting compound [10] with compound [21] in the same manner as in Production Method 1-2, Step 2.

Step 2

Compound [I-17] can be obtained by reacting compound [45] with compound [46] in the same manner as in Production Method 1-1.

Step 3

Compound [I-18] can be obtained by reducing compound [I-17] in the same manner as in Production Method 1-2, Step 3.

Production Method 6 wherein, when d is 0, $Q^{15}$ is —S—, —SO—, —OCO—, —OCONH—, —NHCO—, —NHSO$_2$—, —NHCOO—, —COO—, —CONH—, —SO$_2$NH—, —NHCONH—, —NHSO$_2$NH—, —CH=CH— or —CO—, when d is an integer of 1 to 4, $Q^{15}$ is, in addition to the above-mentioned, —O— or —NH—, $Q^{16}$ is —CO—, —SO$_2$—, —COO—, —CONH— or —SO$_2$NH—, b' is an integer of 1 to 4, and other symbols are as defined above.

Step 1

Compounds [50], [51] and [52] can be obtained by reacting compound [41] with compounds [47], [48] and [49] obtained by a conventional method, respectively, in the same manner as in Production Method 1-2, Step 2.

Step 2

Compounds [I-19], [I-20] and [I-21] can be obtained by reacting compounds [50], [51] and [52], respectively, in a solvent such as DME, DMF, DMA, 1,4-dioxane and the like, in the presence of a base such as sodium carbonate, potassium acetate, sodium acetate and the like and a palladium catalyst such as tetrakis(triphenylphosphine)palladium, bis(triphenylphosphine)palladium(II) dichloride, palladium acetate-triphenylphosphine and the like, at room temperature or under heating.

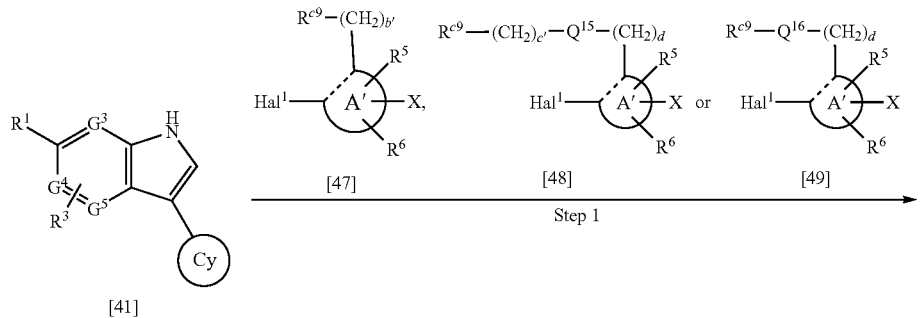

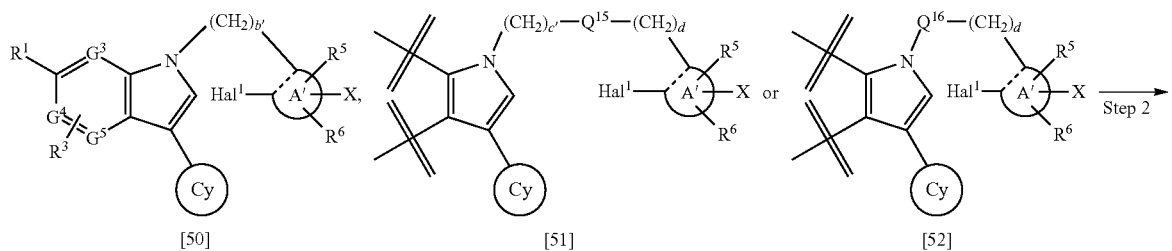

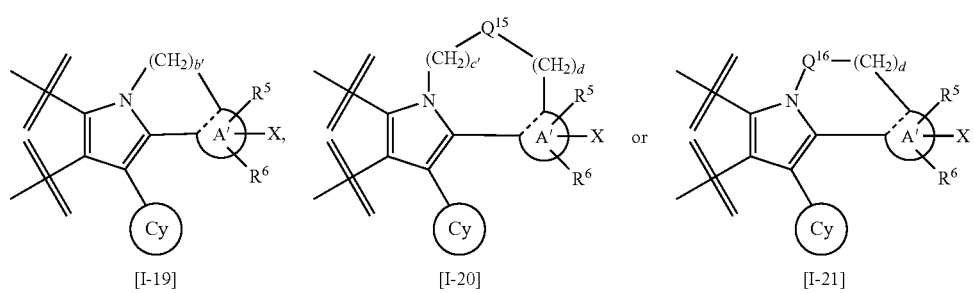

Production Method 7

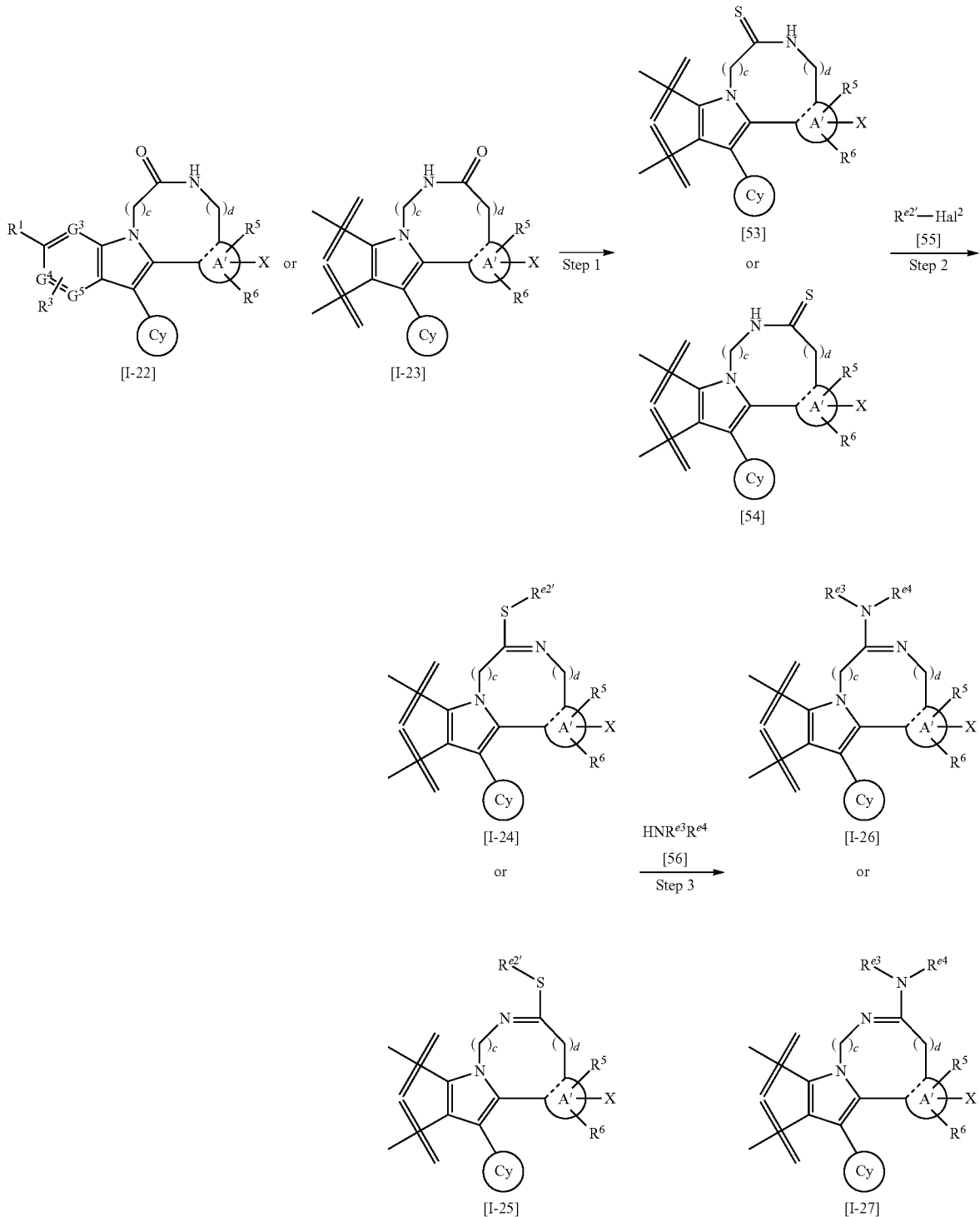

wherein $R^{e2'}$ is a group selected from group F, and other symbols are as defined above.

Step 1

Compounds [53] and [54] can be obtained by treating compounds [I-22] and [I-23] obtained by the above-mentioned Production Method, respectively, with $P_2S_5$ or a Lawesson reagent.

Step 2

Compounds [I-24] and [I-25] can be obtained by reacting compounds [55] with compounds [53] and [54], respectively.

Step 3

Compounds [I-26] and [I-27] can be obtained by reacting compound [56] with compounds [I-24] and [I-25], respectively.

Production Method 8

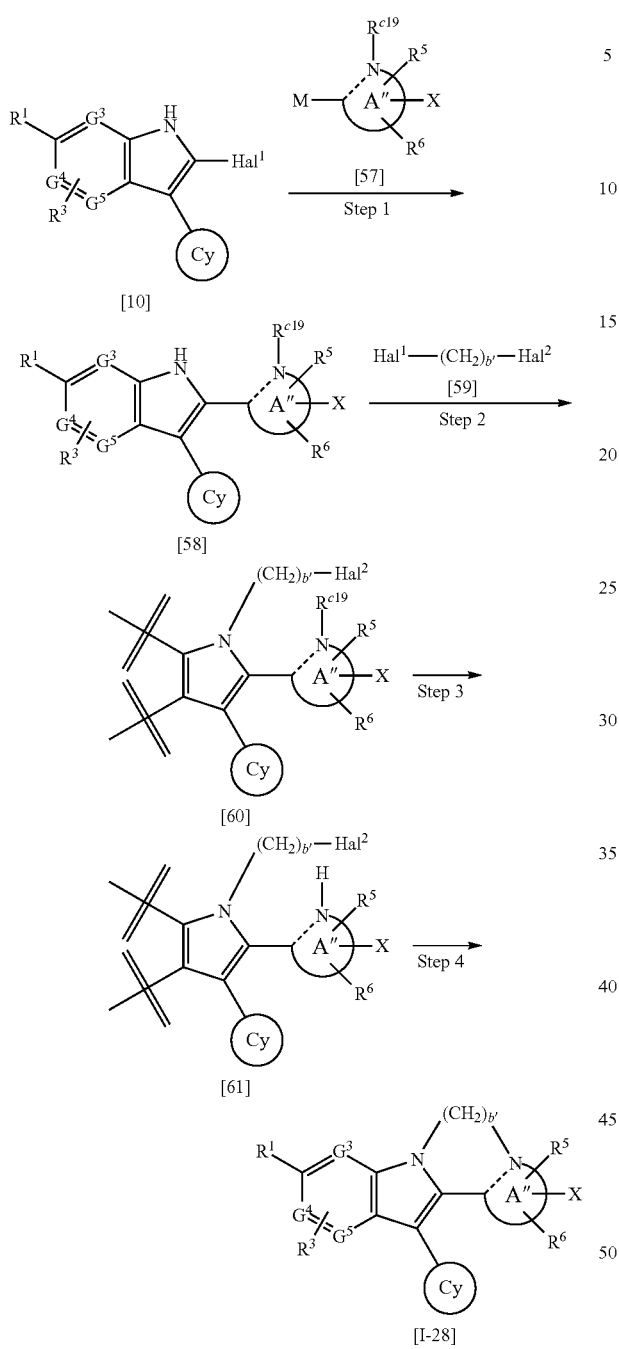

wherein $R^{c19}$ is amino-protecting group, ring A" is ring A wherein $G^6$ is nitrogen atom, and other symbols are as defined above.

Step 1

The Compound [58] can be obtained by reacting compound [10] with compound [57] obtained by a conventional method or in the same manner as in Reference Example 1 in the same manner as in Production Method 1-1.

Step 2

Compound [60] can be obtained by reacting compound [58] with compound [59] obtained by a conventional method in the same manner as in Production Method 4, Step 3.

Here, $Hal^2$ and $Hal^2$ are each preferably bromine atom or chlorine atom.

Step 3

Compound [61] can be obtained by removing amino-protecting group of compound [60] by a conventional method.

As the amino-protecting group, benzoyl group, tert-butyl group, tert-butylcarbonyl group, tert-butoxycarbonyl group and the like can be mentioned.

For example, when $R^{c19}$ is tert-butoxycarbonyl group, deprotection is conducted by a method such as treatment with a solution of hydrochloric acid in ethyl acetate at room temperature in ethyl acetate or methanol solution; treatment with hydrochloric acid at room temperature in tetrahydrofuran; treatment with hydrochloric acid-1,4-dioxane at room temperature in methanol; treatment with trifluoroacetic acid in chloroform solution and the like.

Step 4

Compound [I-28] can be obtained by cyclization of compound [61] in the same manner as in Production Method 4, Step 3.

Reference Example 4

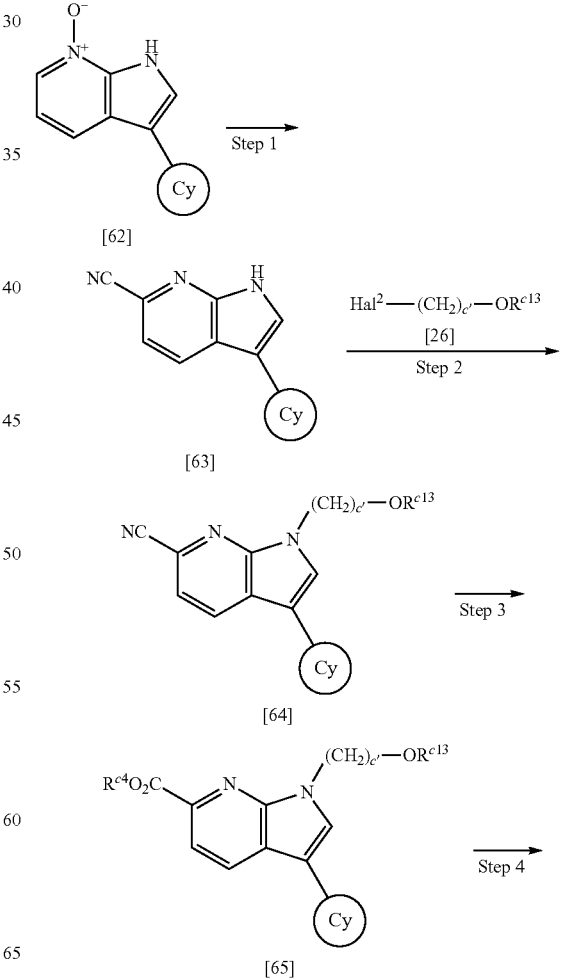

-continued

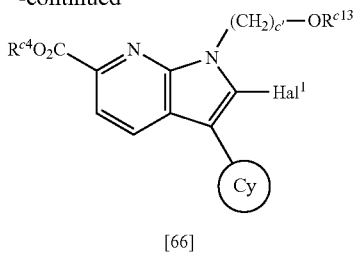
[66]

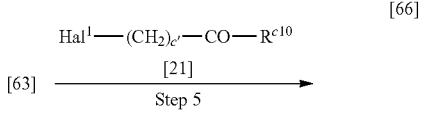

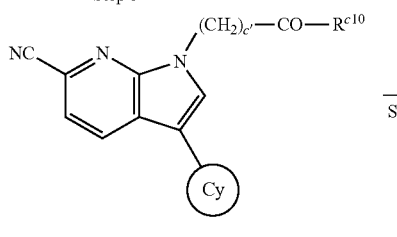
[67]

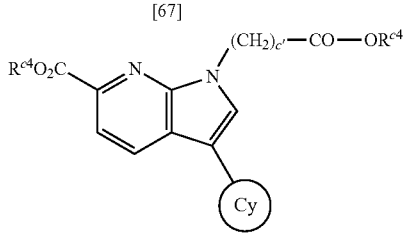
[68]

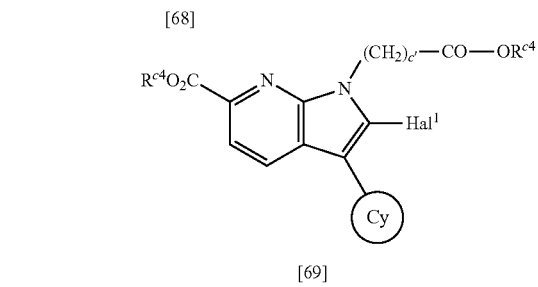
[69]

wherein each symbol is as defined above.

Step 1

Compound [63] can be obtained by introducing cyano group into compound [62] obtained by a conventional method or the method described in WO03/010140, by a conventional method.

For example, Compound [63] can be obtained by reacting compound [62] with trimethylsilyl cyanide under heating in a solvent such as acetonitrile, in the presence of a base such as triethylamine and the like.

Step 2

Compound [64] can be obtained by reacting compound [63] with compound [26] in the same manner as in Production Method 1-2, Step 2.

Step 3

Compound [65] can be obtained by reacting cyano group of compound [64] using acid chloride such as acetyl chloride and the like in an alcohol solvent ($R^{c4}$—OH) that becomes a source of $R^{c4}$, such as ethanol and the like under reflux.

Step 4

Compound [66] can be obtained by halogenation of compound [65] in the same manner as in Reference Example 3, Step 2.

Step 5

Compound [67] can be obtained by reacting compound [63] with compound [21] in the same manner as in Production Method 1-2, Step 2.

Step 6

Compound [68] can be obtained from compound [67] in the same manner as in the above-mentioned Step 3.

Step 7

Compound [69] can be obtained by halogenation of compound [68] in the same manner as in Reference Example 3, Step 2.

Compounds [66] and [69] obtained in this Production Method can be used in the above-mentioned Production Methods to give the final compound.

Production Method 9

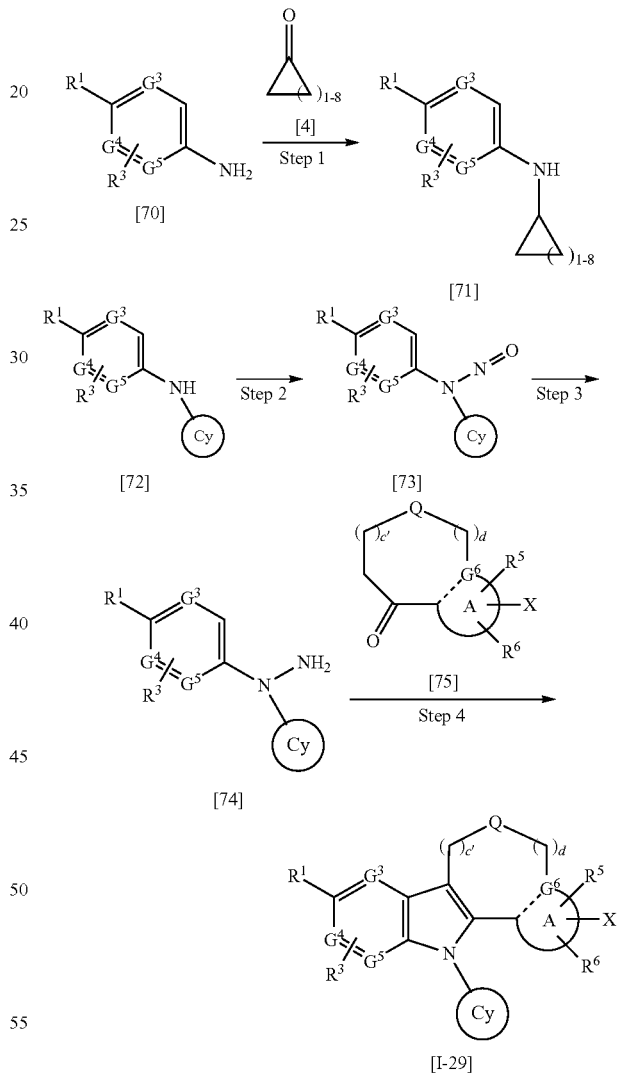

wherein each symbol is as defined above.

Step 1

Compound [71] can be obtained by reacting commercially available compound [70] or compound [70] obtained by a conventional method with compound [4] in a mixed solvent of THF-acetic acid, in the presence of a reducing agent such as a borohydride (e.g., sodium borohydride, sodium cyanoborohydride, sodium triacetoxyborohydride and the like) and the like.

Step 2

Compound [73] can be obtained by treating compound [72] obtained in the same manner as in Step 1, with sodium nitrite in a mixed solvent of acetic acid-water.

Step 3

Compound [74] can be obtained by reducing compound [73] by a conventional method.

Step 4

Compound [I-29] can be obtained by reacting compound [74] with compound [75] obtained by a conventional method, in the same manner as in J. Med. Chem., 42 (15), 2902-2919, 1999.

Production Method 10 nitrile, ethanol, THF and the like or a mixed solvent thereof, in the presence of a base such as sodium hydride, sodium hydroxide, potassium hydroxide, potassium carbonate, sodium ethoxide, potassium tert-butoxide and the like, under ice-cooling to under heating. In addition, potassium iodide or tetrabutylammonium iodide may be used to increase reactivity.

In this Production Method, $R^{2'}$ may be any group as long as it is bonded to nitrogen atom of fused ring via carbon atom, wherein $C_{1-6}$ alkyl group optionally substituted by 1 to 3 substituents selected from group E, as well as, for example, $L^2$ of -$L^2$-ring $D^2$-$L^1$-ring $D^1$ and -$L^2$-$CH_2$-$L^1$-ring $D^1$, and $L^1$ of -$L^1$-$(CH_2)_u$-$L^3$-$(CH_2)_v$-ring $D^1$ and -$L^1$-ring $D^1$ may be

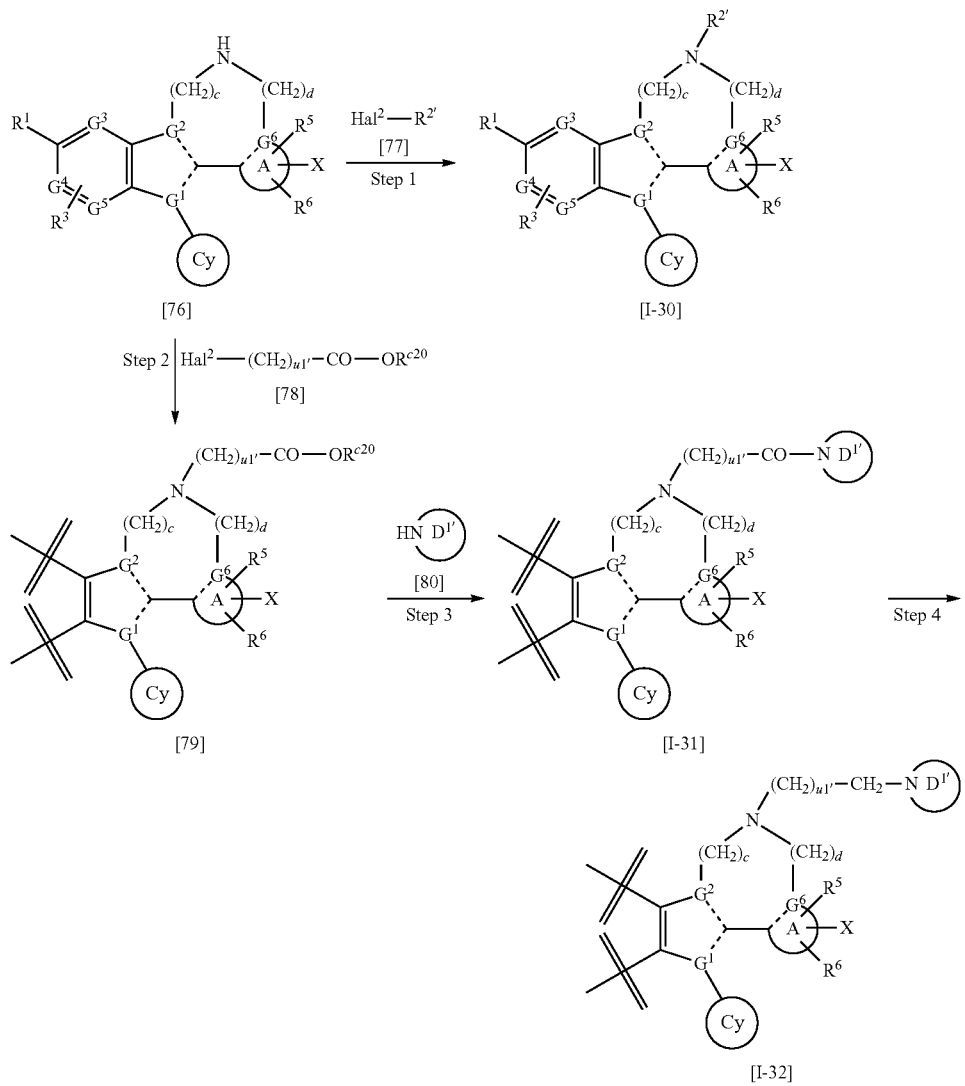

wherein $R^{2'}$ is $C_{1-6}$ alkyl group optionally substituted by 1 to 3 substituents selected from group E and the like, $R^{c20}$ is carboxyl-protecting group, ring $D^{1'}$ is that containing NH as a component constituting a ring such as piperidine, piperazine, pyrrolidine, morpholine, thiomorpholine, azepane and the like, u1' is an integer of 1 to 6, and other symbols are as defined above.

Step 1

Compound [I-30] can be obtained by reacting compound [76] obtained by the above-mentioned Production Method with compound [77] in a solvent such as DMF, DMSO, aceto- $C_{1-6}$ alkylene, $C_{2-6}$ alkenylene, —$(CH_2)_{u1'}$—O—$(CH_2)_{v1}$—, —$(CH_2)_{u1'}$—S—$(CH_2)_{v1}$—, —$(CH_2)_{u1'}$—$NR^{L1}$— $(CH_2)_{v1}$—, —$(CH_2)_{u1'}$—CO—$(CH_2)_{v1}$—, —$(CH_2)_{u1'}$—$CONR^{L2}$—$(CH_2)_{v1}$—, —$(CH_2)_{u1'}$—$NR^{L2}CO_2$—$(CH_2)_{v1}$—, —$(CH_2)_{u1'}$—$NR^{L2}CONR^{L3}$—$(CH_2)_{v1}$—, —$(CH_2)_{u1'}$—$NR^{L2}CO$—$(CH_2)_{v1}$—, —$(CH_2)_{u1'}$—$NR^{L2}SO_2$—$(CH_2)_{v1}$—, —$(CH_2)_{u1'}$—$SO_2$—$(CH_2)_{v1}$—, —$(CH_2)_{u1'}$—$SO_2NR^{L2}$—$(CH_2)_{v1}$— or —$(CH_2)_{u1'}$—$N^+R^{L2}R^{L2'}$—$(CH_2)_{v1}$— wherein each symbol is as defined above.

In addition, $Hal^2$-$R^{2'}$ may be Hal-ring $D^1$ or Hal-ring $D^2$-$L^1$-ring $D^1$.

Step 2

Compound [79] can be obtained by reacting compound [76] with compound [78] in the same manner as in Step 1 above.

Step 3

Compound [I-31] can be obtained by reacting compound [79] with compound [80] in the same manner as in Production Method 1-2, Step 1.

Here, $R^{c20}$, which is a carboxyl-protecting group of compound [79], may be deprotected by a conventional method and then reacted with compound [80].

For example, when $R^{c20}$ is tert-butyl group, deprotection can be conducted by treatment with trifluoroacetic acid in a solvent such as methylene chloride, chloroform and the like.

Step 4

Compound [I-32] can be obtained by reducing compound [I-31] in the same manner as in Production Method 1-2, Step 3.

Production Method 11

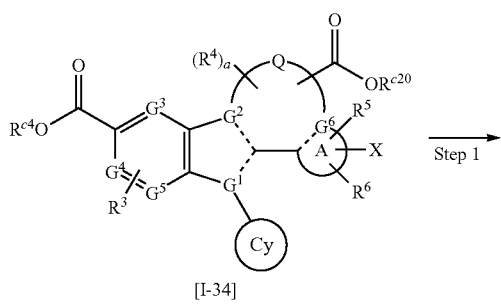

[I-34]

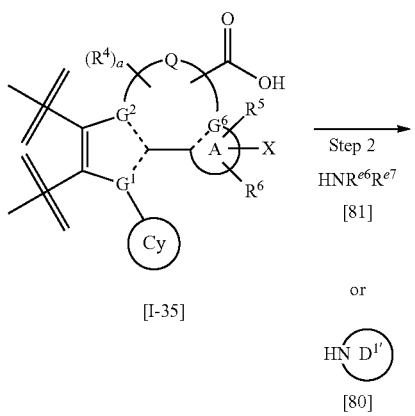

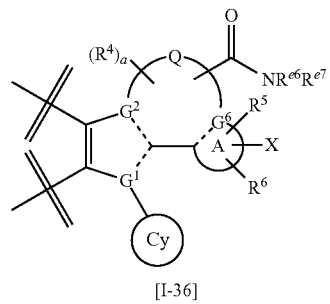

[I-36]

or

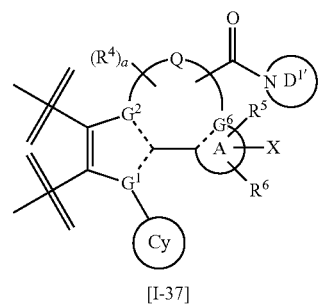

[I-37]

wherein each symbol is as defined above.

Step 1

Compound [I-35] can be obtained by deprotection of carboxyl-protecting group $R^{c20}$ of compound [I-34] obtained by the above-mentioned Production Method, by a conventional method.

Here, a reaction under conditions free from deprotection of $R^{c4}$ is preferable. For example, when $R^{c4}$ is methyl group or ethyl group and $R^{c20}$ is tert-butyl group, deprotection can be conducted by treatment with trifluoroacetic acid in a solvent such as methylene chloride, chloroform and the like.

Step 2

Compounds [I-36] and [I-37] can be obtained by reacting compound [I-35] with compounds [81] and [80], respectively, in the same manner as in Production Method 1-2, Step 1.

Production Method 12

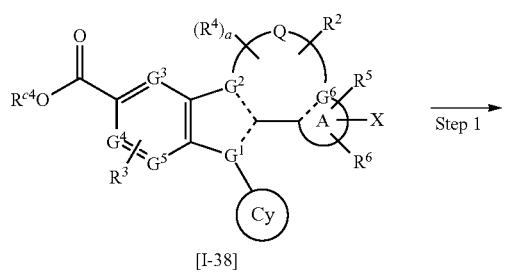

[I-38]

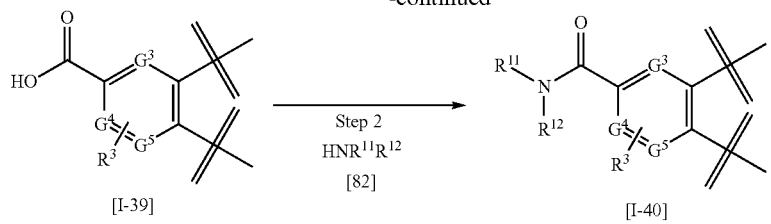

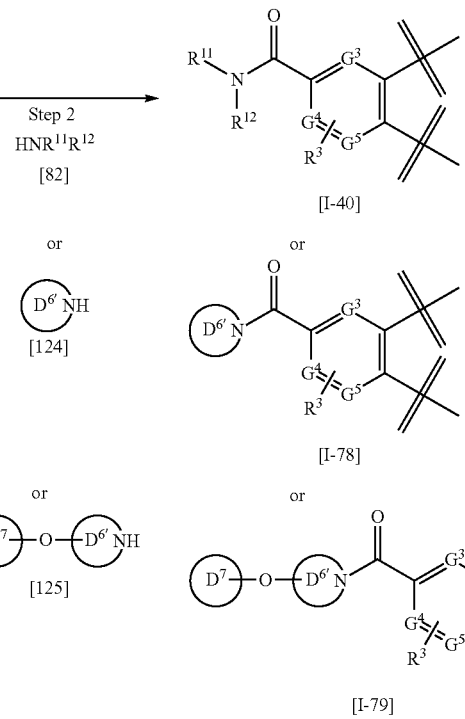

wherein ring $D^{6'}$ is that containing NH as a component constituting a ring such as piperidine, piperazine, pyrrolidine and the like, and each symbol is as defined above.

Step 1

Compound [I-39] can be obtained by hydrolysis of compound [I-38] obtained in the same manner as in the above-mentioned Production Methods, in a solvent such as methanol, ethanol, THF, dioxane, water and the like, or a mixed solvent thereof under basic conditions of sodium hydroxide, potassium hydroxide, potassium carbonate, lithium hydroxide and the like or acidic conditions of hydrochloric acid, sulfuric acid and the like.

Step 2

Compounds [I-40], [I-78] and [I-79] can be obtained by reacting compound [I-39] with compounds [82], [124] and [125], respectively, in the same manner as in Production Method 1-2, Step 1.

For compounds [82], [124] and [125], commercially available products or compounds obtained by conventional methods or compounds obtained by the methods described in WO02/04425, WO03/007945 and WO03/010141 can be used.

Production Method 13

In this Production Method, conversion of the substituents $R^1$ and $R^3$ on the fused ring is shown. This Production Method is applicable irrespective of the position of substitution.

Production Method 13-1

Conversion of cyano group to substituted amidino group

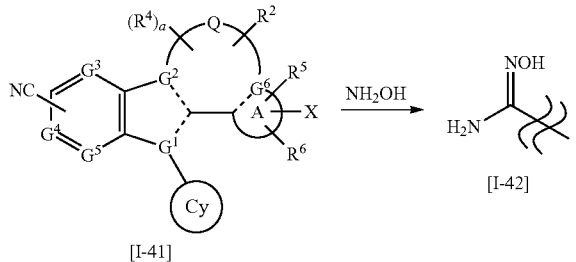

wherein each symbol is as defined above.

The compound [I-41] obtained in the same manner as in the above-mentioned Production Method is reacted with hydroxylamine in a solvent such as water, methanol, ethanol, THF, DMF and the like to give compound [I-42]. When a salt of hydroxylamine such as hydrochloride and the like is used, the reaction is carried out in the presence of a base such as sodium hydrogen carbonate, sodium hydroxide, triethylamine and the like.

Production Method 13-2

Conversion of sulfonic acid ester moiety to sulfonic acid

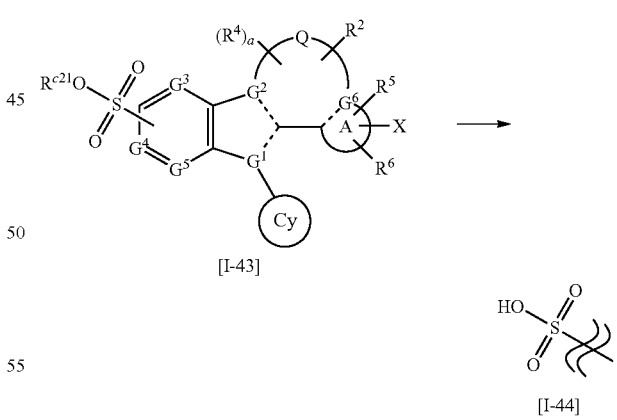

[I-43]
wherein $R^{c21}$ is $C_{1-6}$ alkyl, and other symbols are as defined above.

The compound [I-43] obtained in the same manner as in the above-mentioned Production Method is reacted with iodide salt such as sodium iodide, lithium iodide and the like, bromide salt such as sodium bromide, tetrabutylammonium bromide and the like, amine such as pyridine, trimethylamine, triazole and the like, phosphine such as triphenylphosphine and the like in a solvent such as DMF, DMSO, acetonitrile, methanol, ethanol, water and the like with heating to give compound [I-44].

Production Method 14

This Production Method relates to conversion of the substituent X on the ring A.

Production Method 14-1

Conversion of hydroxyl group to ether

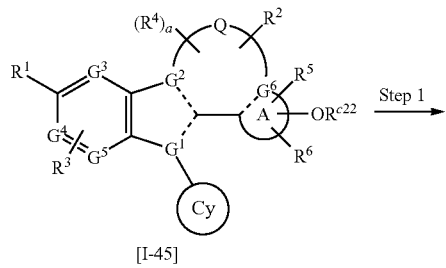

[I-45]

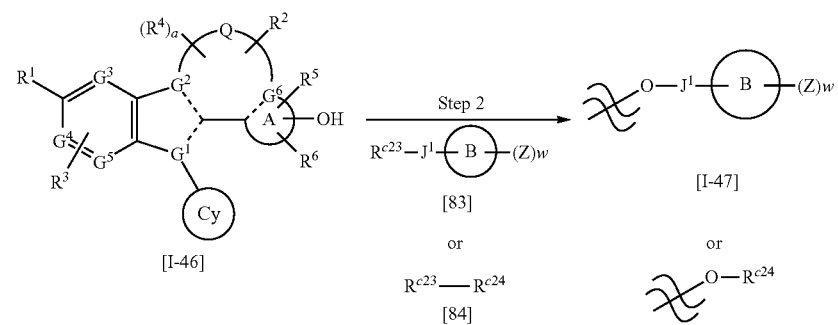

wherein $R^{c22}$ is hydroxyl-protecting group such as acetyl, benzyl and the like, $R^{c23}$ is halogen atom such as chlorine atom, bromine atom and the like, hydroxyl or leaving group such as sulfonate (e.g., mesyloxy, tosyloxy and the like), —B(OR$^{c2}$)(OR$^{c3}$) and the like, $R^{c24}$ is alkyl optionally substituted by 1 to 3 substituents selected from group A corresponding to $R^{a11}$, $J^1$ is a bond, $C_{1-6}$ alkylene, $C_{2-6}$ alkenylene or *—(CH$_2$)$_m$—Y$^2$—(CH$_2$)$_n$—, wherein * shows the side to be bonded to $R^{c23}$, m is an integer of 1 to 6, and other symbols are as defined above.

Step 1

Compound [I-46] can be obtained by deprotection of compound [I-45] obtained in the same manner as in the abovementioned Production Method, by a conventional method.

For example, when $R^{c22}$ is acetyl group, compound [I-45] is hydrolyzed, in a solvent such as methanol, ethanol, THF, 1,4-dioxane and the like, or a mixed solvent thereof, or a mixed solvent of such solvent and water, under basic conditions of sodium hydroxide, potassium hydroxide, potassium carbonate, lithium hydroxide, sodium methoxide, sodium ethoxide and the like or acidic conditions of hydrochloric acid, sulfuric acid and the like to give compound [I-46].

When $R^{c22}$ is benzyl group, compound [I-45] is subjected to catalytic reduction in a solvent such as methanol, ethanol, THF, ethyl acetate, acetic acid, water and the like in the presence of palladium carbon, or by reacting with an acid such as hydrobromic acid and the like in a solvent such as acetic acid to give compound [I-46].

Step 2

When $R^{c23}$ of compound [83] is halogen atom, —OMs or —OTs, compound [I-46] is reacted with compound [83] in a solvent such as DMF, DMSO, acetonitrile, ethanol, THF and the like in the presence of a base such as sodium hydride, sodium hydroxide, potassium hydroxide, potassium carbonate, sodium ethoxide, potassium t-butoxide and the like at room temperature or with heating to give compound [I-47]. The reaction may be accelerated by adding sodium iodide or potassium iodide.

When $R^{c23}$ of compound [83] is hydroxyl group, the hydroxyl group of compound [83] is converted to halogen atom with thionyl chloride, phosphorus trichloride, phosphorus tribromide, carbon tetrabromide triphenylphosphine, N-bromosuccinimide and the like and reacted with compound [I-46] by the aforementioned method to give compound [I-47]. In this case, compound [I-46] may be subjected to Mitsunobu reaction with compound [83] in a solvent such as DMF, acetonitrile, THF and the like using triphenylphosphine-diethyl azodicarboxylate and the like to give compound [I-47].

For example, when $J^1$ is a bond and $R^{23}$ is —B(OR$^{c2}$)(OR$^{c3}$), compound [I-46] is reacted with compound [83] in a solvent such as chloroform, methylene chloride, THF, toluene, 1,4-dioxane and the like in the presence of a base such as copper acetate, pyridine, triethylamine and the like to give compound [I-47].

The Compound [I-48] can be obtained in the same manner as above from compound [I-46] and compound [84].

Production Method 14-2
Conversion of nitro to substituted amino group

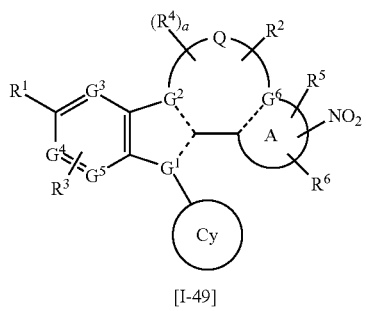

[I-49]

Step 1

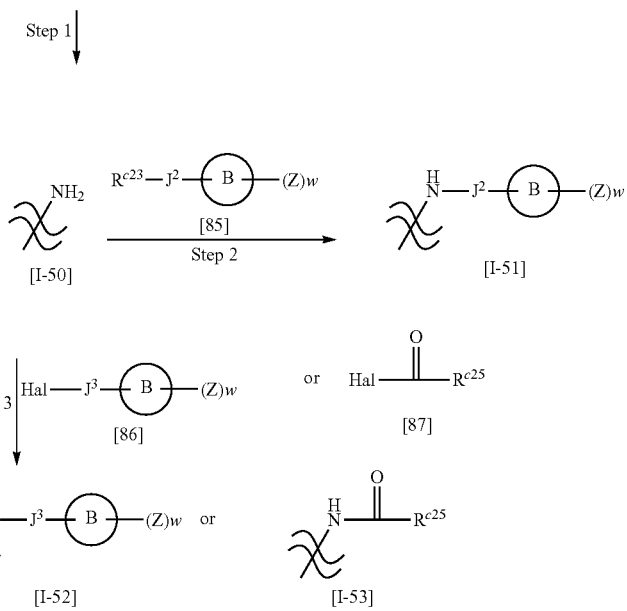

wherein $R^{c25}$ is $C_{1-6}$ alkyl, $J^2$ is —$(CH_2)_n$— or *—$(CH_2)_m$—$Y^2$—$(CH_2)_n$— and m is an integer of 1 to 6, wherein * shows the side to be bonded to $R^{c23}$, $J^3$ is *—CO—$(CH_2)_m$—$Y^2$—$(CH_2)_n$—, *—$CO_2$—$(CH_2)_m$—$Y^2$—$(CH_2)_n$—, *—$CONR^{y3}$—$(CH_2)_m$—$Y^2$—$(CH_2)_n$—, *—$SO_2$—$(CH_2)_m$—$Y^2$—$(CH_2)_n$—, *—CO—$(CH_2)_n$—, *—$CO_2$—$(CH_2)_n$—, *—$CONR^{y3}$—$(CH_2)_n$— or *—$SO_2$—$(CH_2)_n$—, wherein * shows the side to be bonded to Hal, and other symbols are as defined above.

Step 1

The compound [I-49] obtained in the same manner as in the above-mentioned Production Method, is hydrogenated in a solvent such as methanol, ethanol, THF, ethyl acetate, acetic acid, water and the like in the presence of a catalyst such as palladium carbon, palladium hydroxide, platinum oxide, Raney nickel and the like at room temperature or with heating to give compound [I-50]. In addition, compound [I-49] is reduced with a reducing agent such as zinc, iron, tin(II) chloride, sodium sulfite and the like, or reacted with hydrazine in the presence of iron(III) chloride to give compound [I-50]. The compound [I-50] can be also obtained by reacting compound [I-49] with sodium hydrosulfite under alkaline conditions.

Step 2

The compound [I-50] is alkylated with compound [85] in the same manner as in Step 2 of Production Method 14-1 to give compound [I-51].

Step 3

When $J^3$ of compound [86] is *—CO—$(CH_2)_m$—$Y^2$—$(CH_2)_n$—, *—$CO_2$—$(CH_2)_m$—$Y^2$—$(CH_2)_n$—, *—$CONR^{y3}$—$(CH_2)_m$—$Y^2$—$(CH_2)_n$—, *—CO—$(CH_2)_n$—, *—$CO_2$—$(CH_2)_n$— or *—$CONR^{y3}$—$(CH_2)_n$—, compound [I-50] is reacted with compound [86] in a solvent such as DMF, acetonitrile, THF, chloroform, ethyl acetate, methylene chloride, toluene and the like in the presence of, a base such as triethylamine, potassium carbonate, pyridine and the like, or in an amine solvent such as pyridine in the presence of acetic acid and sodium acetate in an equivalent ratio to give compound [I-52].

When $J^3$ of compound [86] is *—$SO_2$—$(CH_2)_m$—$Y^2$—$(CH_2)_n$— or *—$SO_2$—$(CH_2)_n$—, compound [I-50] is sulfonylated with compound [86] in the same manner as above to give compound [I-52].

The compound [I-50] is acylated with compound [87] in the same manner as above to give compound [I-53].

This Production Method is applied in the same manner as above to give disubstituted compounds (tertiary amine) of compound [I-51], compound [I-52] and compound [I-53].

Production Method 14-3

Conversion of Carboxylic Acid Ester Moiety to Amide

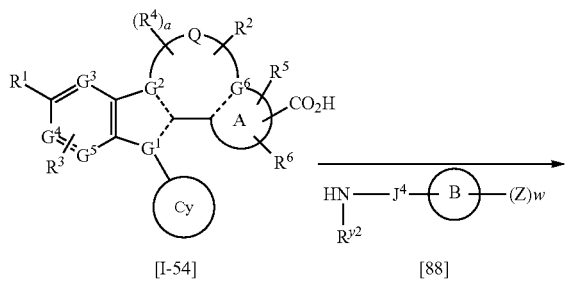

[I-54]   [88]

or

H$_2$N—(CH$_2$)$_i$—R$^{a10}$

[89]

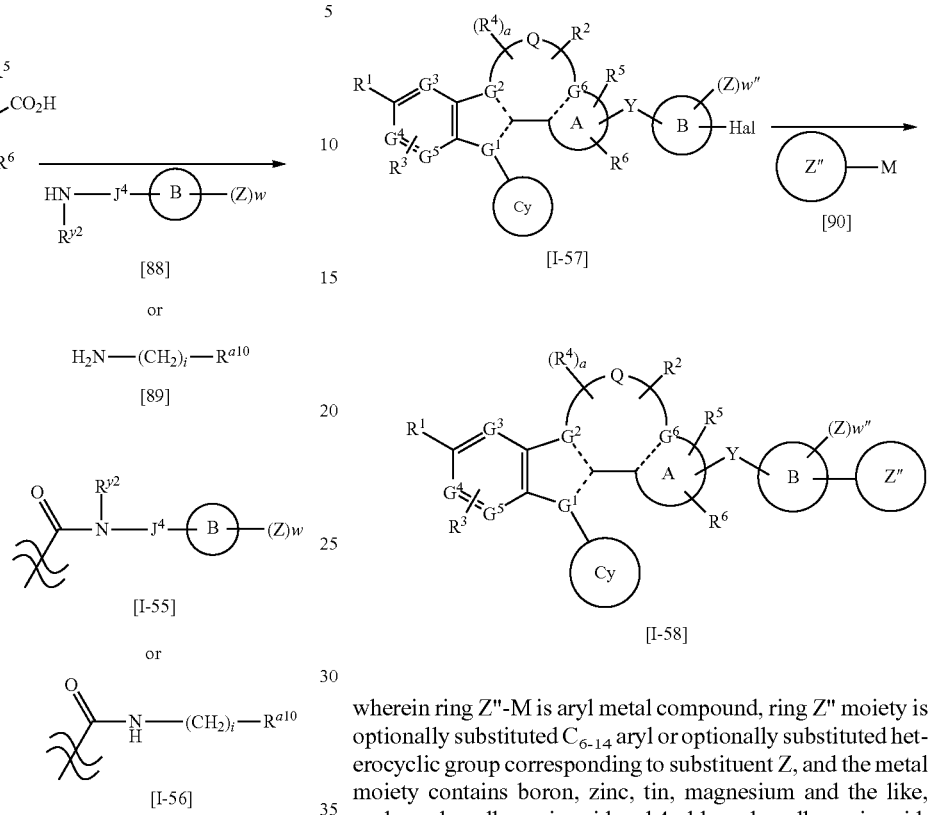

[I-55]

or

[I-56]

wherein J$^4$ is —(CH$_2$)$_n$— or #—(CH$_2$)$_m$—Y$^2$—(CH$_2$)$_n$— wherein # shows the side to be bonded to amine, and other symbols are as defined above.

The carboxylic acid compound [I-54] obtained in the same manner as in the above-mentioned Production Method is condensed with amine compound [88] in a solvent such as DMF, acetonitrile, THF, chloroform, ethyl acetate, methylene chloride, toluene and the like using a condensing agent such as dicyclohexylcarbodiimide, 1-ethyl-3-(3-dimethylaminopropyl)carbodiimide hydrochloride, diphenylphosphoryl azide and the like and, where necessary, adding N-hydroxysuccinimide, 1-hydroxybenzotriazole and the like to give amide compound [I-55]. Alternatively, amide compound [I-55] can be obtained from compound [I-54] as follows. The carboxylic acid compound [I-54] is converted to an acid halide with thionyl chloride, oxalyl chloride and the like, or to an active ester of carboxylic acid compound [I-54] (e.g., converting to a mixed acid anhydride with ethyl chlorocarbonate and the like), which is then reacted with amine compound [88] in the presence of a base such as triethylamine, potassium carbonate, pyridine, 4-(dimethylamino)pyridine and the like, to give amide compound [I-55].

Compound [I-56] can be obtained by reacting carboxylic acid compound [I-54] with amine compound [89] in the same manner as above.

Production Method 15

In this Production Method, additional substituent(s) is(are) introduced into ring B.

Production Method 15-1

Direct bonding of ring Z" to ring B

[I-57]

[90]

[I-58]

wherein ring Z"-M is aryl metal compound, ring Z" moiety is optionally substituted C$_{6-14}$ aryl or optionally substituted heterocyclic group corresponding to substituent Z, and the metal moiety contains boron, zinc, tin, magnesium and the like, such as phenylboronic acid and 4-chlorophenylboronic acid, w" is 0, 1 or 2, and other symbols are as defined above.

The compound [I-57] obtained in the same manner as in the above-mentioned Production Method is reacted with aryl metal compound [90] in a solvent such as DMF, acetonitrile, 1,2-dimethoxyethane, THF, toluene, water and the like in the presence of a palladium catalyst such as tetrakis(triphenylphosphine)-palladium, bis(triphenylphosphine)palladium(II) dichloride, palladium acetate-triphenylphosphine and the like, a nickel catalyst such as nickel chloride, 1,3-bis (diphenylphosphino)-propane nickel(II) chloride and the like, and a base such as potassium carbonate, potassium hydrogen carbonate, sodium hydrogen carbonate, potassium phosphate, triethylamine, potassium fluoride, sodium hydrogen phosphate, cesium carbonate and the like at room temperature or with heating, to give compound [I-58].

Production Method 15-2

Conversion of hydroxyl group to ether

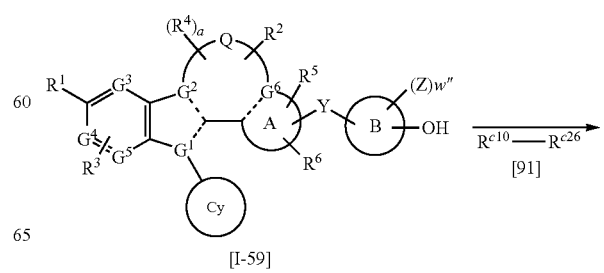

[I-59]   [91]

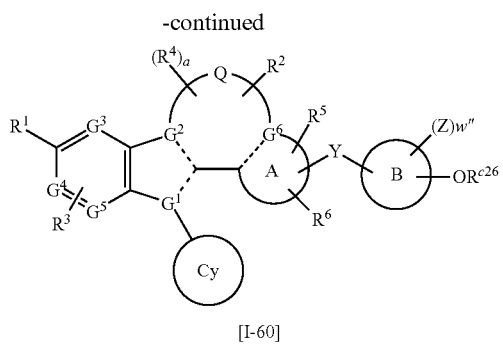

[I-60]

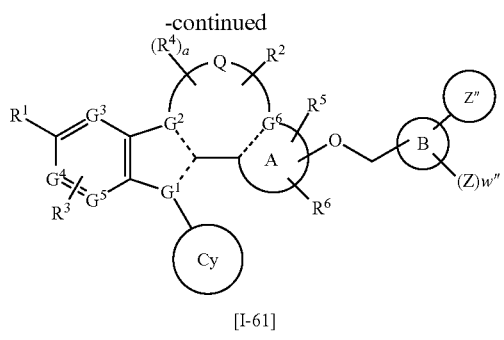

[I-61]

wherein $R^{c26}$ is $R^{d1}$ or —$(CH_2)_p$—$COR^{d25}$ corresponding to substituent Z, and other symbols are as defined above.

The compound [I-59] obtained in the same manner as in the above-mentioned Production Method is reacted with compound [91] in the same manner as in Step 2 of Production Method 14-1 to give compound [I-60].

Production Method 15-3

Synthesis in advance of ring B part such as compound [83] in Production Method 14-1

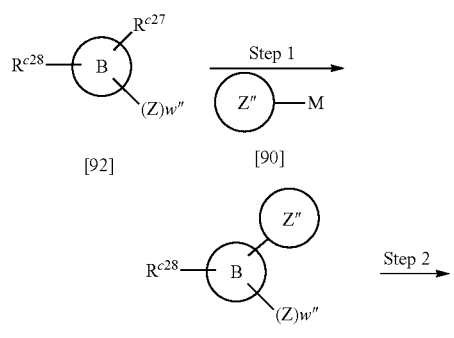

[92]   [90]

[93]

[94]

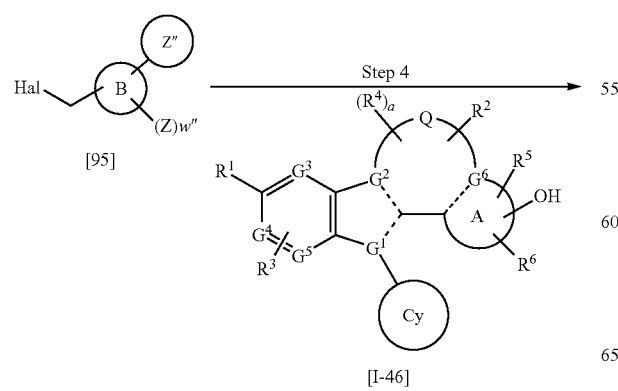

[95]

[I-46]

wherein $R^{c27}$ is leaving group such as chlorine atom, bromine atom, iodine atom, trifluoromethanesulfonyloxy, p-toluenesulfonyloxy, methanesulfonyloxy and the like, $R^{c28}$ is formyl, carboxyl or carboxylic acid ester such as methoxycarbonyl, ethoxycarbonyl, tert-butoxycarbonyl and the like, and other symbols are as defined above.

Step 1

Commercially available compound [92] or compound [92] obtained by a conventional method is reacted with aryl metal compound [90] in the same manner as in Production Method 15-1 to give compound [93].

Step 2

The compound [93] obtained in the same manner as in the above-mentioned Production Method is reduced according to a conventional method to give compound [94].

For example, compound [93] is reacted in a solvent such as methanol, ethanol, THF and the like in the presence of a reducing agent such as lithium aluminum hydride, sodium borohydride and the like under cooling to heating to give compound [94].

Step 3

The compound [94] obtained in the same manner as in the above-mentioned Production Method is reacted in a solvent such as 1,4-dioxane, diethyl ether, THF, methylene chloride, chloroform, toluene and the like with a halogenating agent, such as phosphorus halides (e.g., phosphorus pentachloride, phosphorus tribromide and the like), thionyl chloride and the like, to give compound [95]. For an accelerated reaction, the reaction may be carried out in the presence of a tertiary amine such as triethylamine, DMF, pyridine and the like, or under heating.

Step 4

The compound [94] or [95] obtained in the same manner as in the above-mentioned Production Method is reacted with compound [I-46] in the same manner as in Step 2 of Production Method 14-1 to give compound [I-61].

Production Method 15-4

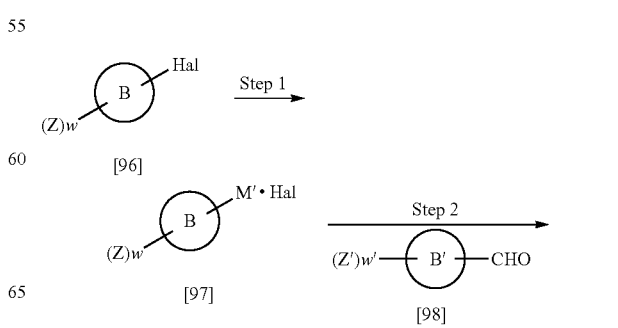

[96]

[97]   [98]

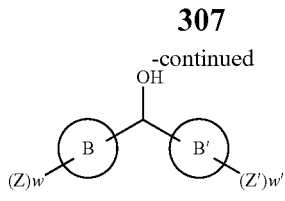

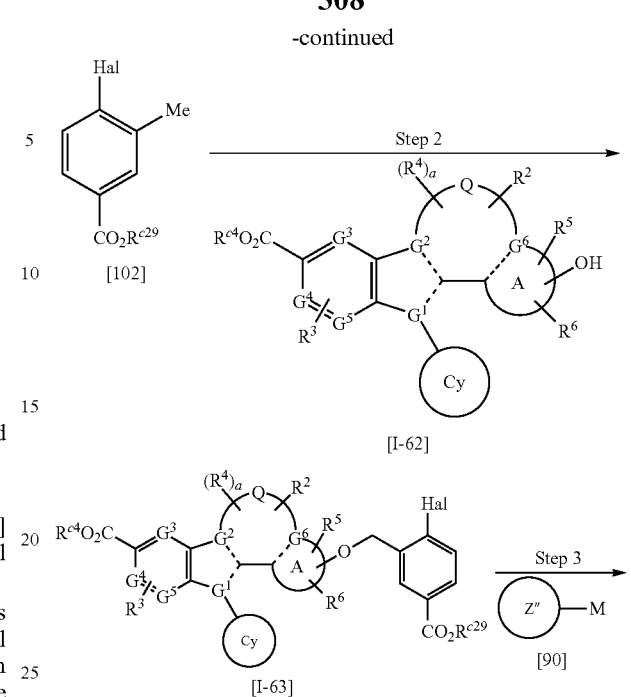

wherein M' is a metal such as magnesium, lithium, zinc and the like, and other symbols are as defined above.

Step 1

Commercially available compound [96] or compound [96] obtained by a conventional method is converted to aryl metal reagent by a conventional method to give compound [97].

For example, when M' is magnesium, magnesium is reacted with compound [96] in a solvent such as THF, diethyl ether, benzene, toluene and the like, preferably THF, from cooling to heating, preferably at −100° C. to 100° C. to give compound [97].

Step 2

The compound [97] obtained in the same manner as in the above-mentioned Production Method is reacted with compound [98] to give compound [99].

The compound [97] is reacted with compound [98] in a solvent such as diethyl ether, benzene, toluene, THF and the like, preferably THF, from cooling to room temperature, preferably at −100° C. to 30° C. to give compound [99].

Step 3

The compound [99] obtained in the same manner as in the above-mentioned Production Method is halogenated in the same manner as in Step 3 of Production Method 15-3 to give compound [100].

The compound [99] is reacted with thionyl chloride and pyridine preferably in toluene solvent to give compound [100].

When compound [100] is symmetric, namely, when the ring B—(Z)w moiety and the ring B''—(Z')w' moiety are the same, compound [97] is reacted with formate such as methyl formate, ethyl formate and the like, preferably ethyl formate, in a solvent such as diethyl ether, benzene, toluene, THF and the like, preferably THF, from cooling to room temperature, preferably at −100° C. to 30° C., to give compound [100].

Production Method 15-5

Method including steps to introduce a protecting group into a functional group

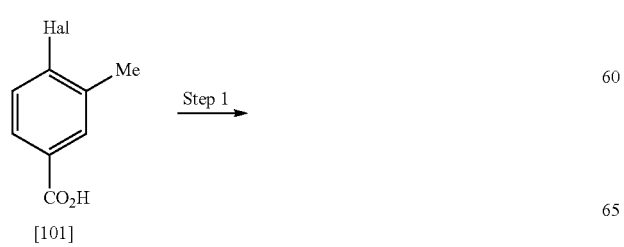

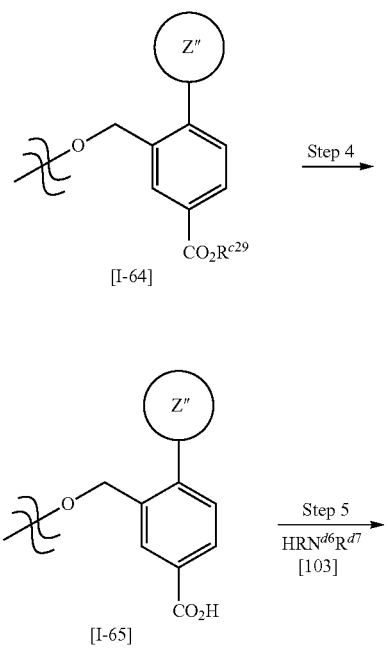

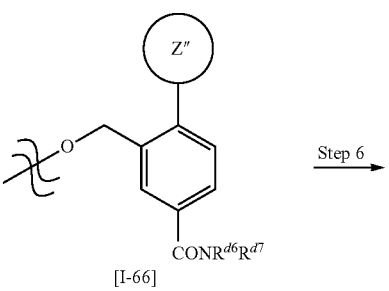

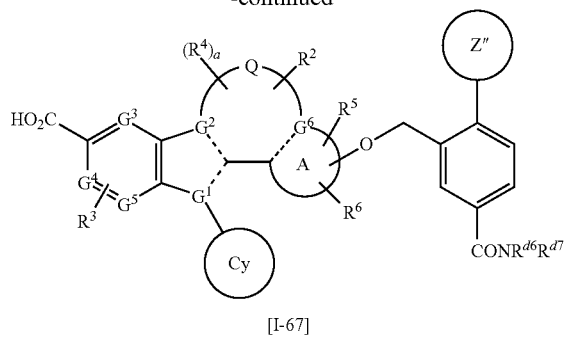

[I-67]

wherein $R^{c29}$ is carboxyl-protecting group such as tert-butyl and the like, and other symbols are as defined above.

Step 1

Commercially available compound [101] or compound [101] obtained by a known method is protected by a conventional method to give compound [102].

For example, when $R^{c29}$ is tert-butyl, compound [101] is converted to acid halide with thionyl chloride, oxalyl chloride and the like in a solvent such as THF, chloroform, methylene chloride, toluene and the like, and reacted with potassium tert-butoxide or di-tert-butyl dicarbonate to give compound [102].

Step 2

The methyl group of compound [102] obtained in the same manner as in the above-mentioned Production Method is converted to bromomethyl with N-bromosuccinimide and N,N'-azobisisobutyronitrile and reacted with compound [I-62] in the same manner as in Step 2 of Production Method 14-1 to give compound [I-63].

Step 3

The compound [I-63] obtained in the same manner as in the above-mentioned Production Method is reacted with aryl metal compound [90] in the same manner as in Production Method 15-1 to give compound [I-64].

Step 4

The $R^{c29}$ of the compound [I-64] obtained in the same manner as in the above-mentioned Production Method is removed by a conventional method to give compound [I-65].

The carboxyl-protecting group can be removed by a conventional deprotection method according to the protecting group. In this Step, the conditions free from reaction of $R^{c4}$ are preferable. For example, when $R^{c29}$ is tert-butyl, compound [I-64] is treated with trifluoroacetic acid in a solvent such as methylene chloride, chloroform and the like to give compound [I-65]. In addition, compound [I-64] may be treated with hydrogen chloride or hydrochloric acid in a solvent such as ethyl acetate, dioxane, alcohol and the like to give compound [I-65].

Step 5

The compound [I-65] obtained in the same manner as in the above-mentioned Production Method is subjected to amide condensation with compound [103] in the same manner as in Production Method 14-3 to give compound [I-66].

Step 6

The compound [I-66] obtained in the same manner as in the above-mentioned Production Method is deprotected in the same manner as in Step 1 of Production Method 12 to give compound [I-67].

As used herein, $R^{c4}$ is preferably a protecting group that does not react during the Step 1 through Step 5 but removed in this Step.

For example, when $R^{c4}$ is methyl, compound [I-66] is reacted in an alcohol solvent such as methanol, ethanol, n-propanol, isopropanol and the like or a mixed solvent of alcohol solvent and water in the presence of a base such as potassium carbonate, sodium carbonate, lithium hydroxide, sodium hydroxide, potassium hydroxide and the like from cooling to heating for deprotection, followed by acidifying the reaction solution to give compound [I-67].

Production Method 15-6

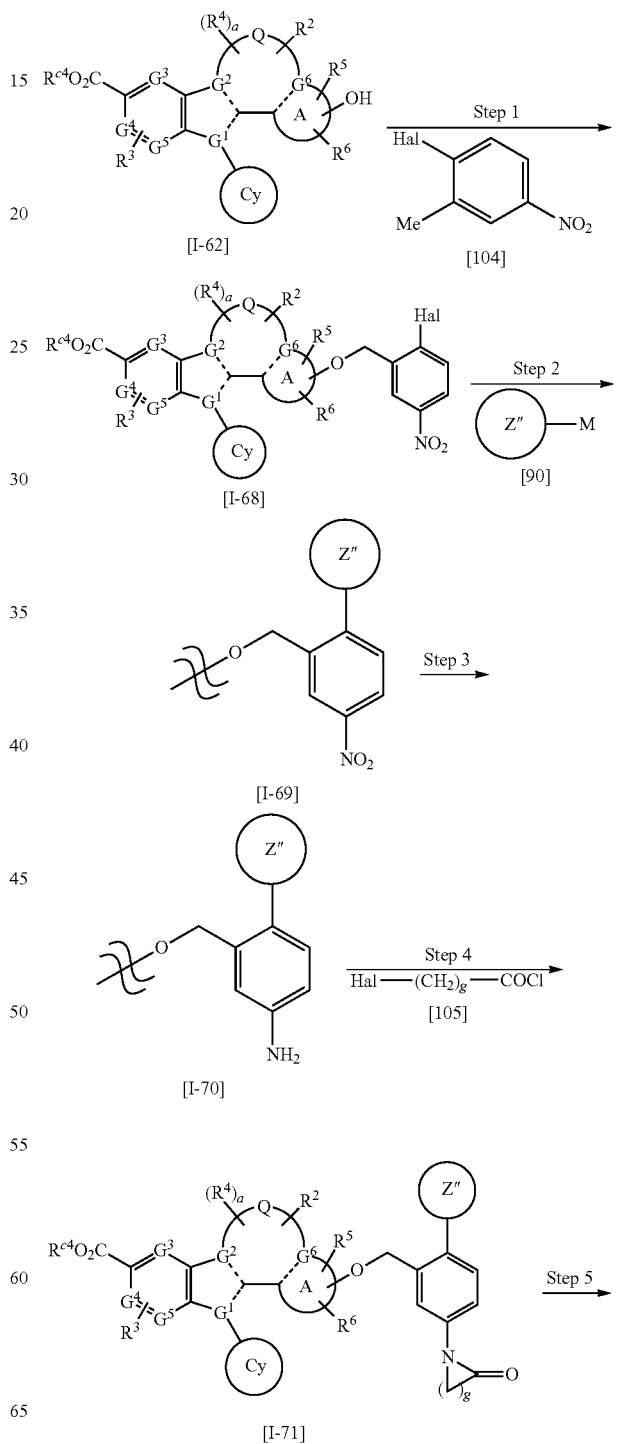

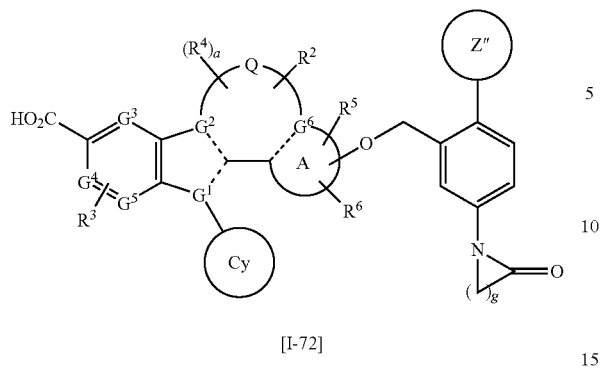

[I-72]

wherein g is an integer of 1 to 5, and other symbols are as defined above.

Step 1

The compound [I-62] obtained by the above-mentioned Production Method is reacted with toluene derivative [104] in the same manner as in Step 2 of Production Method 15-5 to give compound [I-68].

Step 2

The compound [I-68] obtained by the above-mentioned Production Method is reacted with aryl metal compound [90] in the same manner as in Production Method 15-1 to give compound [I-69].

Step 3

The compound [I-69] obtained by the above-mentioned Production Method is reduced in the same manner as in Step 1 of Production Method 14-2 to give compound [I-70].

Step 4

The compound [I-70] obtained by the above-mentioned Production Method is amide condensed with compound [105] in the same manner as in Production Method 14-3, which is then subjected to cyclization in a solvent such as DMF, acetonitrile, THF, toluene and the like in the presence or absence of a base such as potassium carbonate, triethylamine, potassium tert-butoxide and the like at room temperature or with heating, to give compound [I-71].

Step 5

The compound [I-71] obtained by the above-mentioned Production Method is deprotected in the same manner as in Step 1 of Production Method 12 to give compound [I-72].

Production Method 15-7

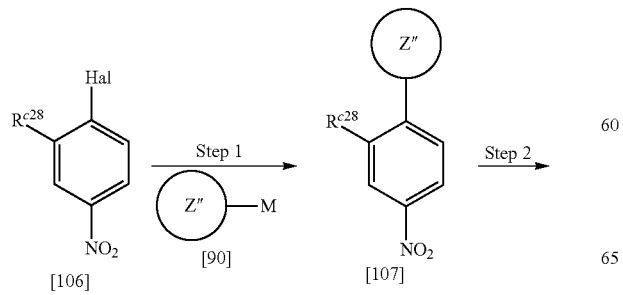

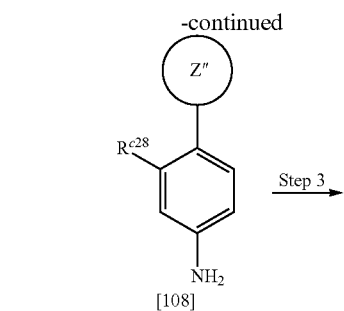

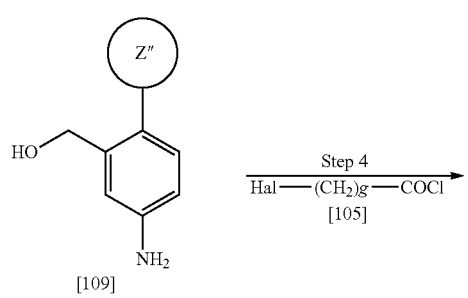

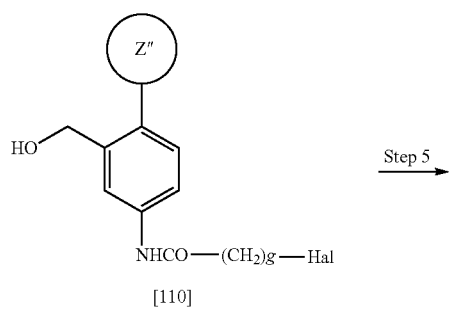

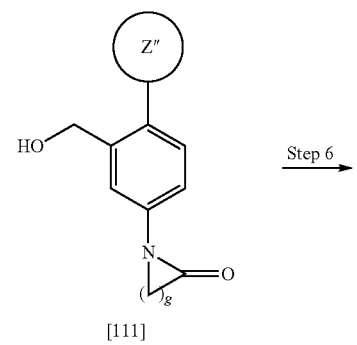

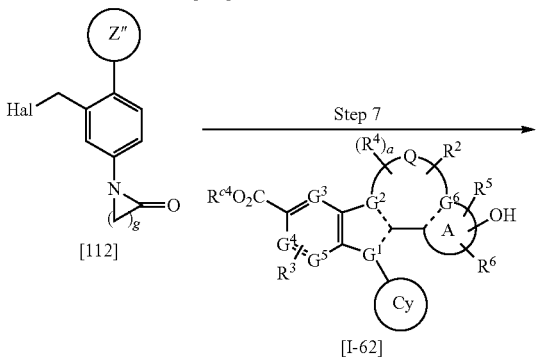

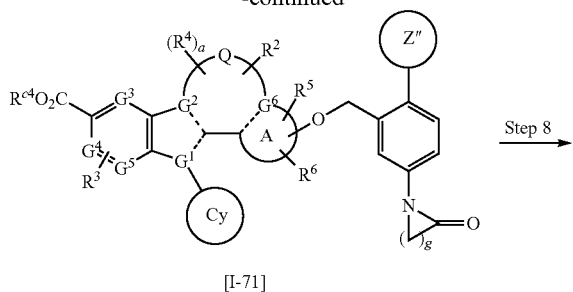

[I-71]

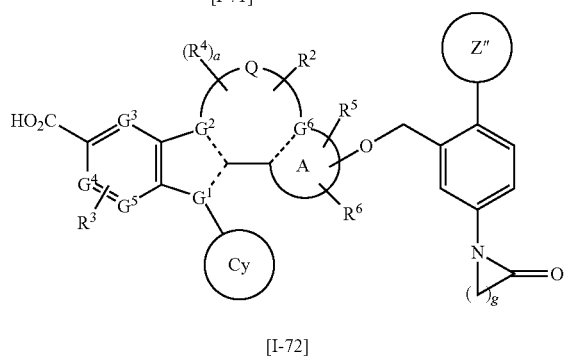

[I-72]

wherein each symbol is as defined above.

Step 1

Commercially available compound [106] or compound [106] obtained by a conventional method is reacted with compound [90] in the same manner as in Production Method 15-1 to give compound [107].

Step 2

The compound [107] obtained in the same manner as in the above-mentioned Production Method is reduced in the same manner as in Step 1 of Production Method 14-2 to give compound [108].

Step 3

The compound [108] obtained in the same manner as in the above-mentioned Production Method is reduced in the same manner as in Step 2 of Production Method 15-3 to give compound [109].

Step 4

The compound [109] obtained in the same manner as in the above-mentioned Production Method is reacted with compound [105] in a solvent such as DMF, acetonitrile, THF, chloroform, ethyl acetate, methylene chloride, toluene and the like to give compound [110]. To enhance the reaction selectivity for amino group, acetic acid and sodium acetate may be added in an equivalent ratio.

Step 5

The compound [110] obtained in the same manner as in the above-mentioned Production Method is subjected to cyclization in a solvent such as ethanol, DMF, acetonitrile, THF, toluene, water and the like in the presence or absence of a base such as potassium hydroxide, potassium carbonate, triethylamine, potassium tert-butoxide and the like at room temperature or with heating, to give compound [111].

Step 6

The compound [111] obtained in the same manner as in the above-mentioned Production Method is halogenated in the same manner as in Step 3 of Production Method 15-3 to give compound [112].

Step 7

The compound [112] obtained in the same manner as in the above-mentioned Production Method is reacted in the same manner as in Step 2 of Production Method 14-1 with compound [I-62] obtained in the same manner as in the above-mentioned Production Method to give compound [I-71].

Step 8

The compound [I-71] obtained in the same manner as in the above-mentioned Production Method is deprotected in the same manner as in Step 1 of Production Method 12 to give compound [I-72].

Production Method 15-8

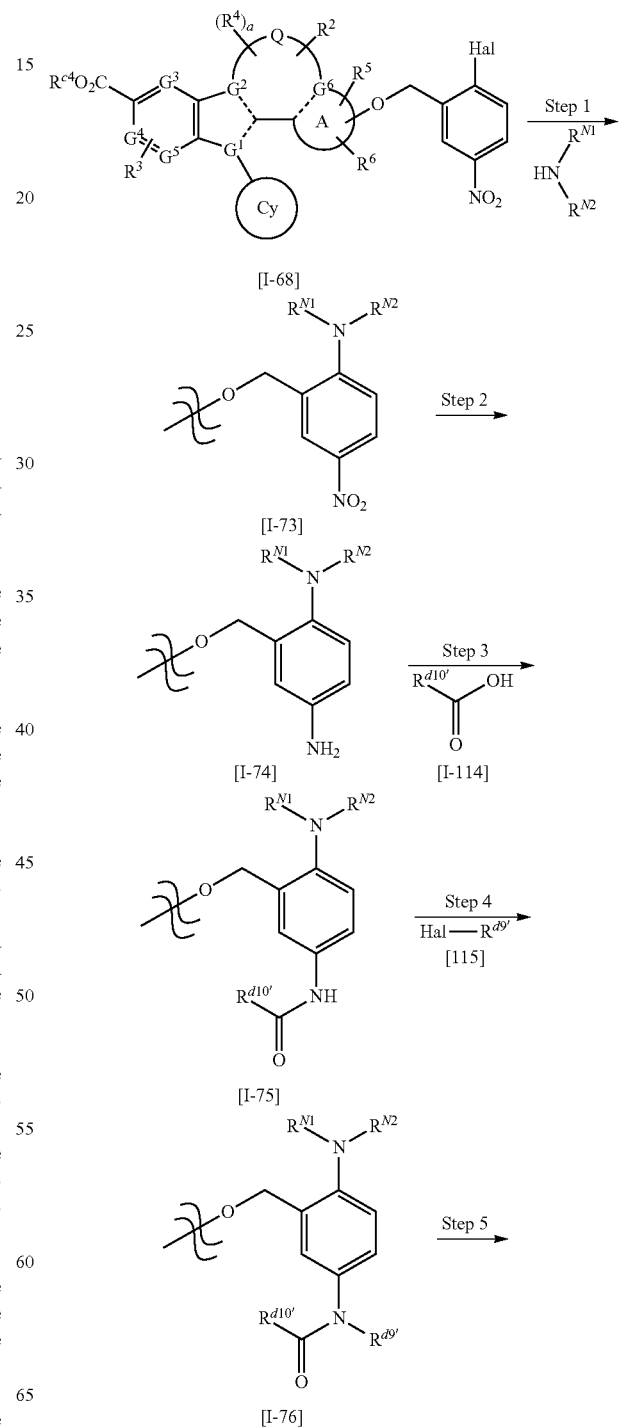

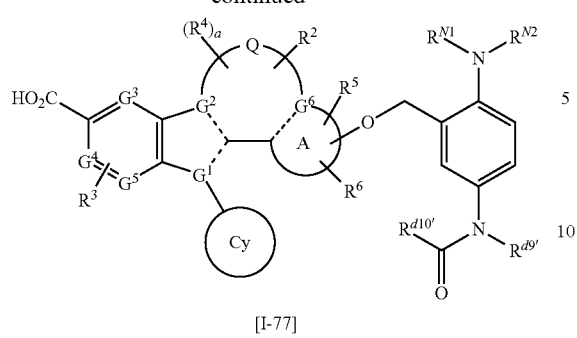

[I-77]

wherein $R^{N1}$ and $R^{N2}$ are the same or different and each is hydrogen atom or a group selected from group F, or $R^{N1}$ and $R^{N2}$ are linked to form a heterocycle containing NH such as piperidine group, 1-piperazinyl group, morpholino group and the like, $R^{d10'}$ is a group selected from group F, $R^{d9'}$ is a $C_{1-6}$ alkyl group optionally substituted by 1 to 3 substituents selected from group A, and other symbols are as defined above.

Step 1

The compound [I-68] obtained in the same manner as in the above-mentioned Production Method is reacted with amine compound [113] in a solvent such as DMSO, DMF, acetonitrile, THF, toluene and the like in the presence or absence of a base such as potassium carbonate, triethylamine, potassium tert-butoxide and the like at room temperature or with heating, to give compound [I-73].

Step 2

The compound [I-73] is reduced in the same manner as in Step 1 of Production Method 14-2 to give compound [I-74].

Step 3

The compound [I-74] is reacted with carboxylic acid compound [114] in the same manner as in Production Method 14-3 to give compound [I-75].

Step 4

The compound [I-75] is alkylated with compound [115] in the same manner as in Step 2 of Production Method 14-1 to give compound [I-76].

Step 5

The compound [I-76] is deprotected in the same manner as in Step 1 of Production Method 12 to give compound [I-77].

Production Method 15-9

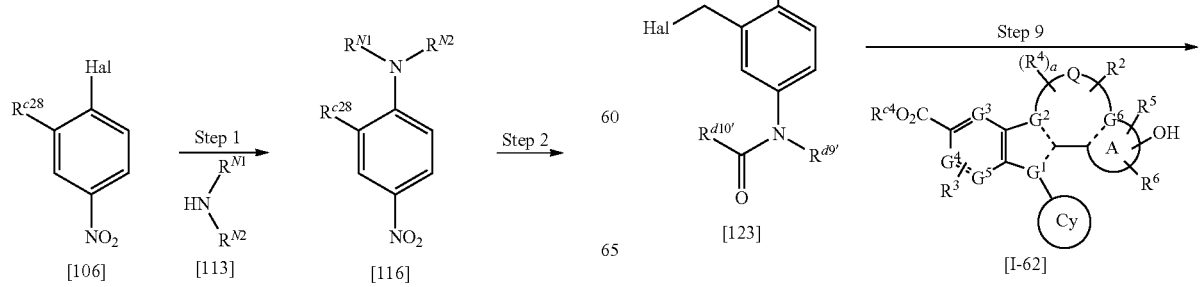

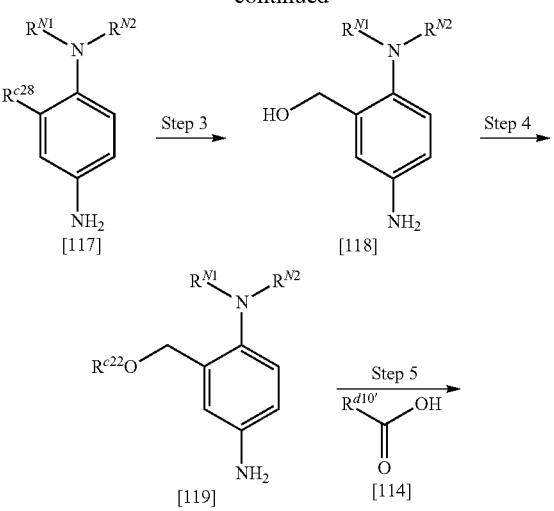

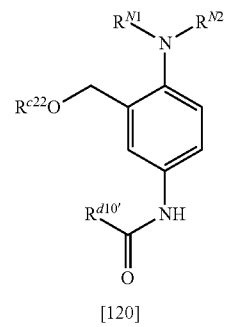

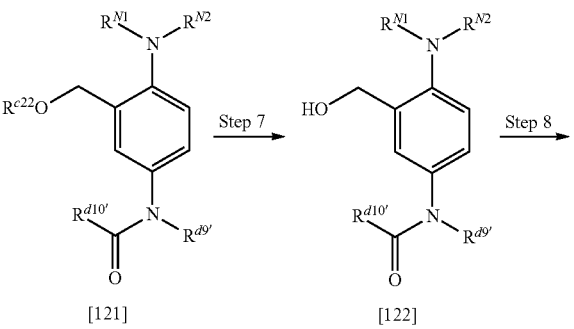

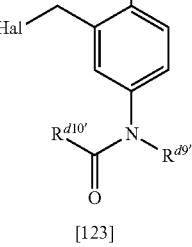

[123]

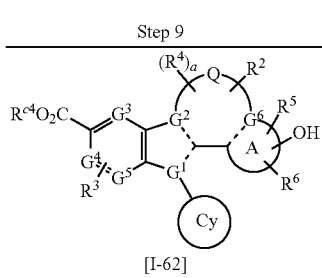

[I-62]

[I-76]

[I-77]

wherein each symbol is as defined above.

Step 1

Commercially available compound [106] or compound [106] obtained by a conventional method is reacted with amine compound [113] in the same manner as in Step 1 of Production Method 15-8 to give compound [116].

Step 2

The compound [116] is reduced in the same manner as in Step 1 of Production Method 14-2 to give compound [117].

Step 3

The compound [117] is reduced in the same manner as in Step 2 of Production Method 15-3 to give compound [118].

Step 4

The hydroxyl group of the compound [118] is protected by a conventional method to give compound [119].

For protection, for example, when $R^{c22}$ is acetyl group, the compound [118] is reacted with acetic anhydride in the presence of pyridine or tertiary amine at room temperature to heating, when $R^{c22}$ is benzyl group, the compound [118] is heated under reflux with benzyl chloride or benzyl bromide in benzene, toluene, acetone, THF, chloroform and the like in the presence of a base such as potassium hydroxide, potassium carbonate and the like, when $R^{c22}$ is tert-butyldiphenylsilyl group, the compound [118] is treated with tert-butyldiphenylsilyl chloride and imidazole at room temperature in DMF, and the like.

In addition, desired $R^{d10'}$—CO group may be introduced as a hydroxyl-protecting group in the next Step 5 without going through this step.

Step 5

The compound [119] is reacted with carboxylic acid compound [114] in the same manner as in Production Method 14-3 to give compound [120].

Step 6

The compound [120] is alkylated with compound [115] in the same manner as in Step 2 of Production Method 14-1 to give compound [121].

Step 7

The compound [121] is deprotected in the same manner as in Step 1 of Production Method 14-1 to give compound [122].

Step 8

The compound [122] is halogenated in the same manner as in Step 3 of Production Method 15-3 to give compound [123].

Step 9

The compound [123] is reacted in the same manner as in Step 2 of Production Method 14-1 with compound [I-62] obtained in the same manner as in the above-mentioned Production Method to give compound [I-76].

Step 10

The compound [I-76] is deprotected in the same manner as in Step 1 of Production Method 12 to give compound [I-77].

Production Method 16

A compound wherein Q is —$(CH_2)_c$-$Q^1$-$(CH_2)_d$—, $Q^1$ is —CO—, and c=d=0 can be obtained by a method similar to the method described in Tetrahedron Lett., 32, 3317-3320, 1991.

A compound wherein Q is —$(CH_2)_c$-$Q^1$-$(CH_2)_d$—, $Q^1$ is —CONH—, c=d=0, and $G^2 \frown G^1$ is C=C—N can be obtained by a method similar to the method described in EP226508.

A compound wherein Q is —$(CH_2)_c$-$Q^1$-$(CH_2)_d$—, $Q^1$ is —CH=CH—, c=d=0, and $G^2 \frown G^1$ is C=C—N can be obtained by a method similar to the method described in Tetrahedron Lett., 39, 8725-8728, 1998.

A compound wherein Q is —$(CH_2)_c$-$Q^1$-$(CH_2)_d$—, $Q^1$ is —CH=N—, c=d=0, and $G^2 \frown G^1$ is C=C—N can be obtained by a method similar to the method described in EP226508 and Organic Lett., 4, 1355-1358, 2002.

A compound wherein Q is —$(CH_2)_c$-$Q^1$-$(CH_2)_d$—, $Q^1$ is —N=CH—, c=d=0, and $G^2 \frown G^1$ is C=C—N can be obtained by a method similar to the method described in J. Heterocycl. Chem., 30(3), 603-609, 1993.

Reference Example 5

[201]

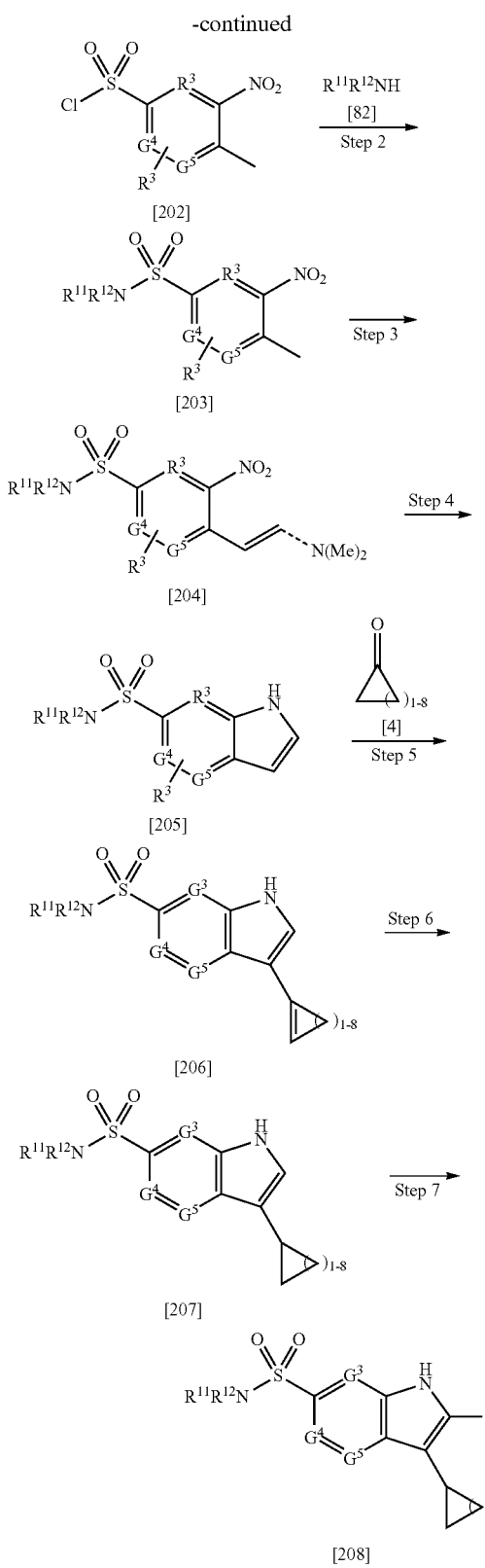

[202]
[203]
[204]
[205]
[206]
[207]
[208]

wherein each symbol is as defined above.

Step 1

Compound [202] can be obtained by introducing a nitro group into compound [201] by a conventional method.

Step 2

Compound [203] can be obtained by reacting compound [202] with compound [82] in a solvent.

For example, compound [82] is added to a solvent such as acetonitrile, THF, chloroform, ethyl acetate, methylene chloride, toluene, pyridine, triethylamine and the like, under cooling and allowed to react at room temperature to under heating.

Step 3

Compound [204] can be obtained by reacting compound [203] with N,N-dimethylformamide dimethyl acetal under heating.

Step 4

Compound [205] can be obtained by reducing and cyclizing compound [204] by a conventional method.

Step 5

Compound [206] can be obtained by reacting compound [205] with compound [4] in the same manner as in Reference Example 2, Step 1.

Step 6

Compound [207] can be obtained by hydrogenating compound [206] in the same manner as in Reference Example 2, Step 2.

Step 7

Compound [208] can be obtained by halogenating compound [207] in the same manner as in Reference Example 3, Step 2.

Production Method 17

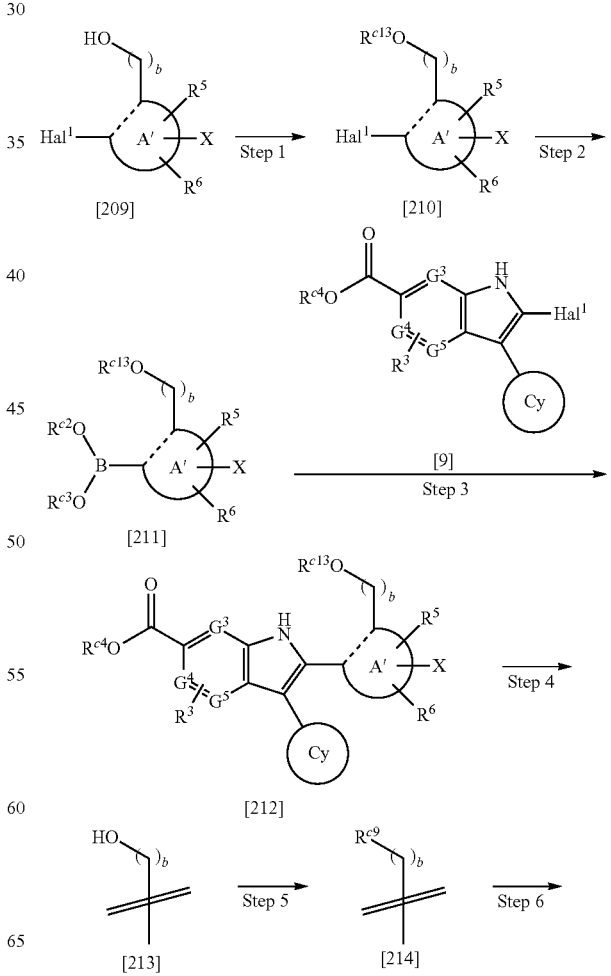

[209]
[210]
[211]
[212]
[213]
[214]

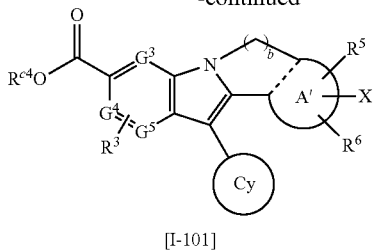

[I-101]

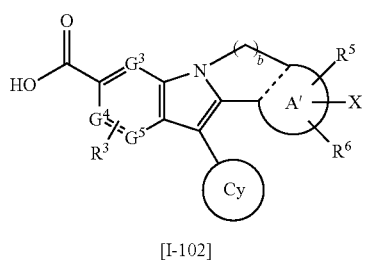

[I-102]

wherein each symbol is as defined above.

Step 1

Compound [210] can be obtained by introducing a protecting group into a hydroxyl group of compound [209] by a conventional method.

For example, when $R^{c13}$ is a tetrahydropyran-2-yl group, 3,4-dihydro-2H-pyran is reacted with compound [209] in a non-alcoholic solvent such as chloroform, dichloromethane, diethyl ether and the like, in the presence of an acid such as p-toluenesulfonic acid, hydrochloric acid, phosphorus oxychloride and the like.

Step 2

Compound [211] can be obtained by reacting compound [210] with boric acid ester in the same manner as in Reference Example 1.

Step 3

Compound [212] can be obtained by reacting compound [211] with compound [9] in the same manner as in Production Method 1-1.

Step 4

Compound [213] can be obtained by eliminating a hydroxyl-protecting group of compound [212] by a conventional method.

Step 5

Compound [214] can be obtained by converting a hydroxyl group a of compound [213] to a leaving group by halogen substitution, mesylation or tosylation by a conventional method.

Step 6

Compound [I-101] can be obtained by subjecting compound [214] to condensation cyclization in the same manner as in Production Method 1-2, Step 2.

Step 7

Compound [I-102] can be obtained by hydrolysis of compound [I-101] in the same manner as in Production Method 12, Step 1.

Production Method 18

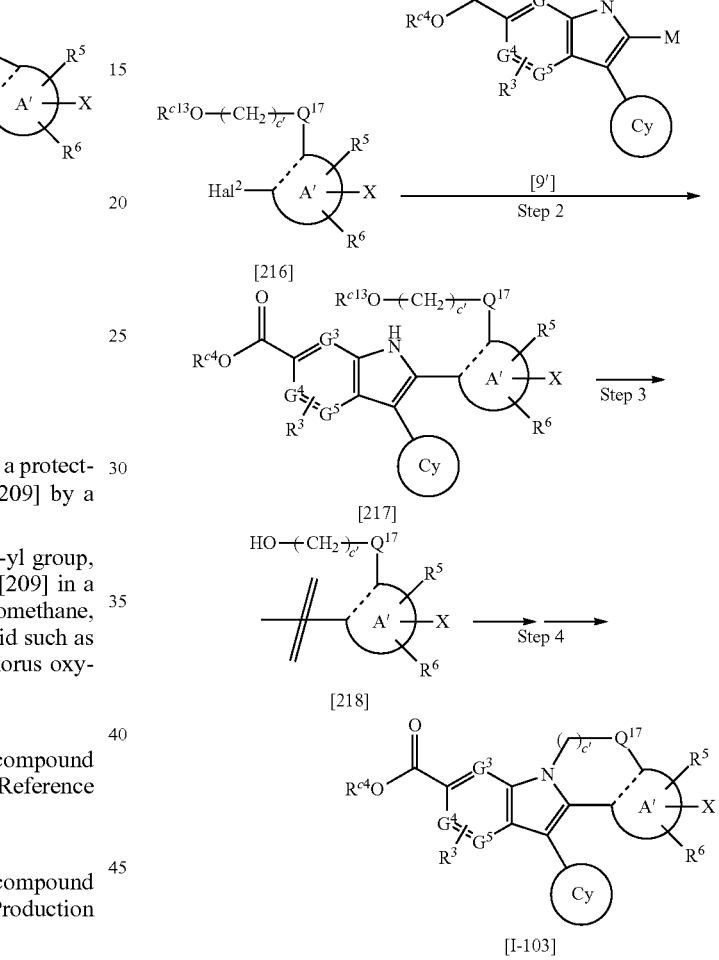

wherein $Q^{17}$ is —O— or —S—, and other symbols are as defined above.

Step 1

Compound [216] can be obtained by reacting compound [215] with compound [26] in the same manner as in Production Method 14-1, Step 2.

Step 2

Compound [217] can be obtained by reacting compound [216] with compound [9'] in the same manner as in Production Method 1-1.

Step 3

Compound [218] can be obtained by eliminating a hydroxyl-protecting group of compound [217] by a conventional method.

Step 4

Compound [I-103] can be obtained converting a hydroxyl group of compound [218] to a leaving group by halogen substitution, mesylation or tosylation by a conventional method, and subjecting the compound to condensation cyclization in the same manner as in Production Method 1-2, Step 2.

Furthermore, a carboxylic acid form can be also obtained, by eliminating a carboxyl-protecting group of compound [I-103] by a conventional method.

Production Method 18-1

Production Method 18-1

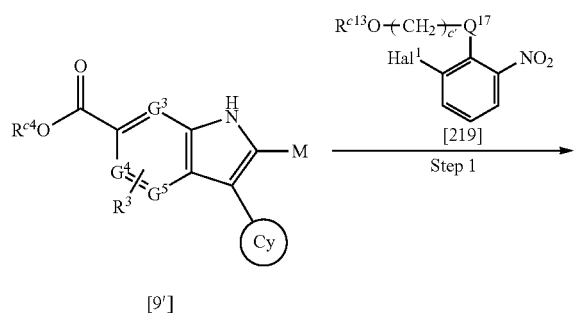

[9']

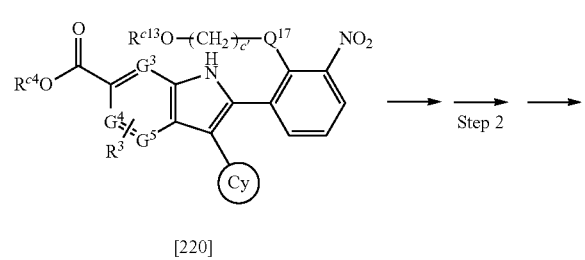

[220]

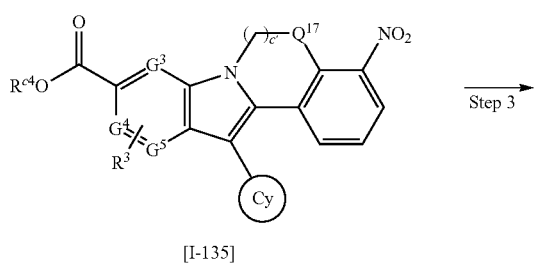

[I-135]

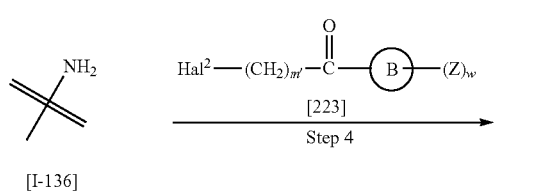

[I-136]

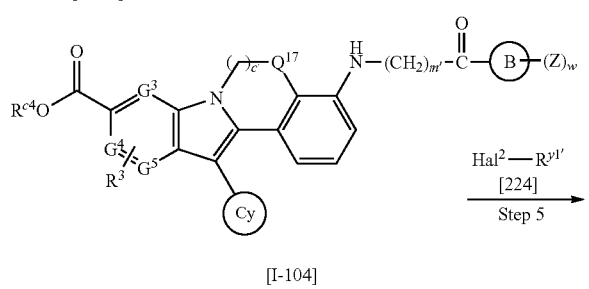

[I-104]

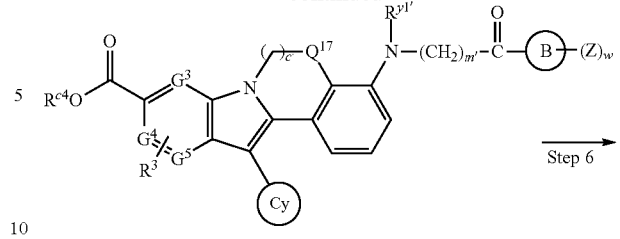

[I-105]

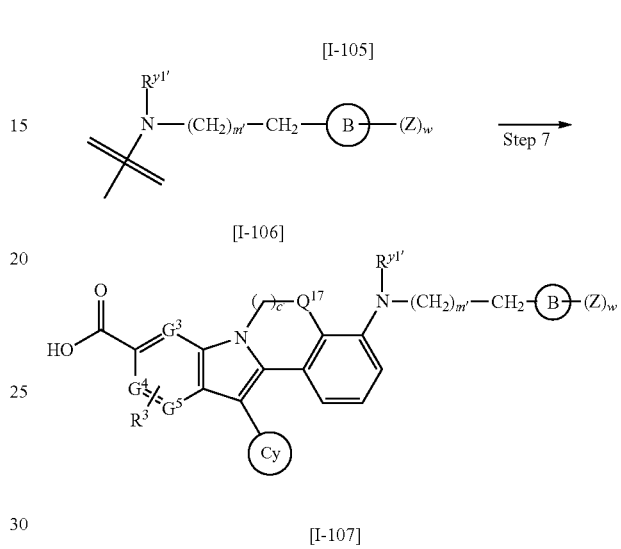

[I-106]

[I-107]

wherein $R^{y1'}$ is a group selected from group C, m' is 0 or an integer of 1 to 5, and other symbols are as defined above.

Step 1

Compound [220] can be obtained by reacting compound [219] with compound [9'] in the same manner as in Production Method 1-1.

Step 2

Compound [I-135] can be obtained by eliminating the hydroxyl-protecting group of compound [220], then converting the hydroxyl group to a leaving group by halogen substitution, mesylation or tosylation by a conventional method, and then subjecting the compound to condensation cyclization in the same manner as in Production Method 1-2, Step 2.

Step 3

Compound [I-136] can be obtained by reducing the nitro group of compound [I-135] by a conventional method.

Step 4

Compound [I-104] can be obtained by reacting compound [I-103] with compound [223] in the same manner as in Production Method 14-1, Step 2.

In this case, a compound wherein amino group is disubstituted by compound [223] may be also obtained. In this event, compound [I-104] isolated then can be used in the next step.

Step 5

Compound [I-105] can be obtained by reacting compound [I-104] with compound [224] in the same manner as in Production Method 14-1, Step 2.

Here, the corresponding substituent can be also introduced by reacting compound [I-104] with an aldehyde compound or a ketone compound instead of compound [224] in the presence of a reducing agent.

As the reducing agent, borohydrides such as sodium borohydride, sodium cyanoborohydride, sodium triacetoxyborohydride and the like can be mentioned.

As a solvent, THF, 1,4-dioxane, dichloromethane, chloroform, methanol, ethanol, toluene, acetic acid and the like can be mentioned. Acetic acid may be added.

Step 6

Compound [I-106] can be obtained by reducing carbonyl of compound [I-105] by a conventional method.

Step 7

Compound [I-107] can be obtained by hydrolyzing compound [I-106] in the same manner as in Production Method 12, Step 1.

Production Method 19

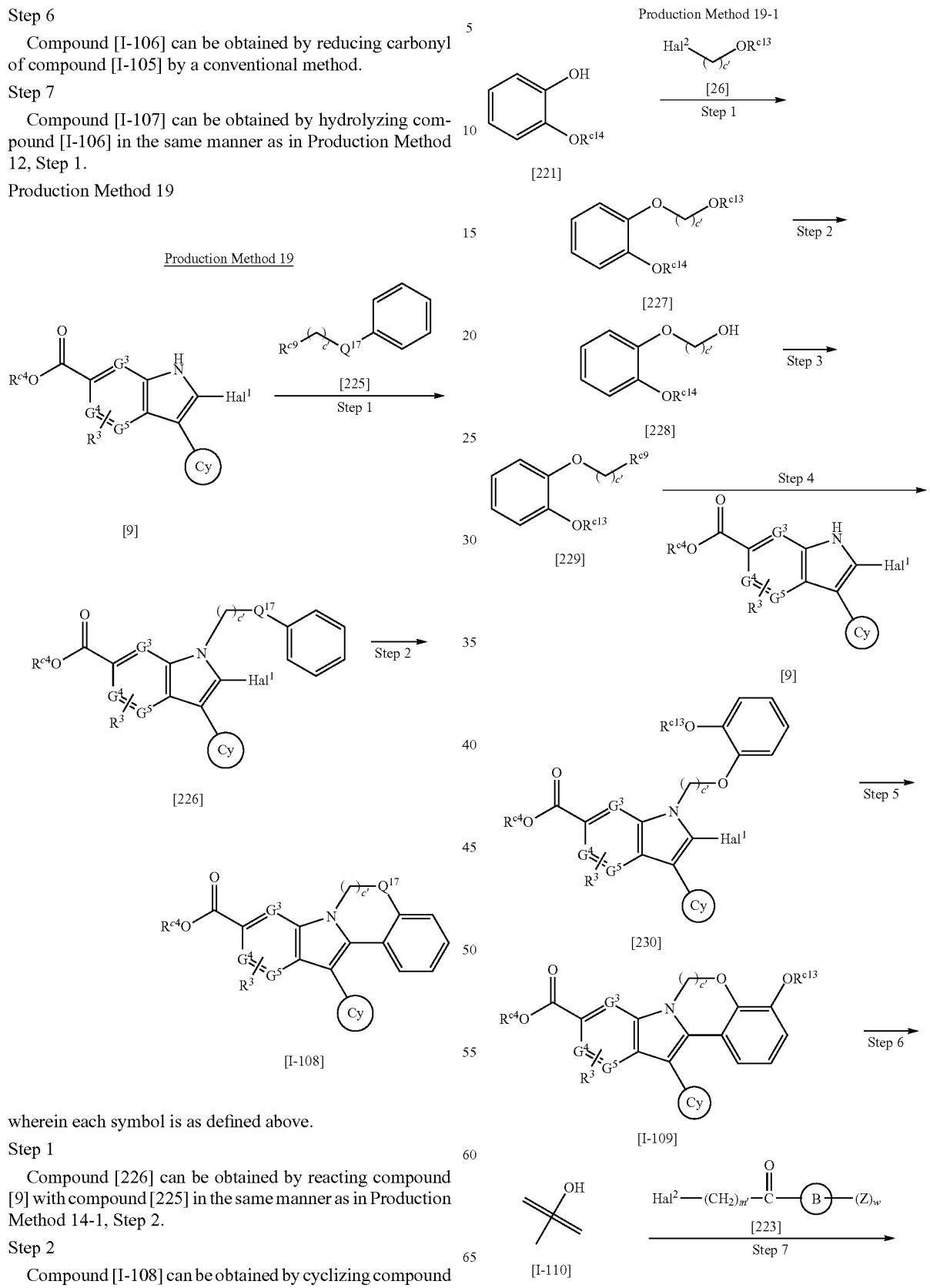

wherein each symbol is as defined above.

Step 1

Compound [226] can be obtained by reacting compound [9] with compound [225] in the same manner as in Production Method 14-1, Step 2.

Step 2

Compound [I-108] can be obtained by cyclizing compound [226] in the same manner as in Production Method 6, Step 2.

Production Method 19-1

-continued

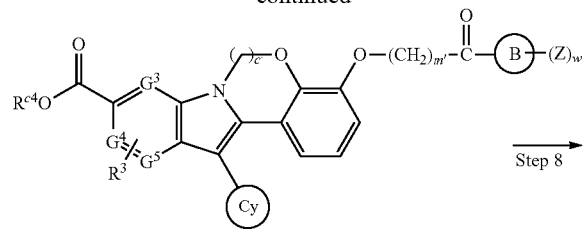

[I-112]

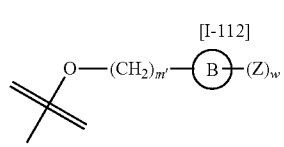

[I-113]

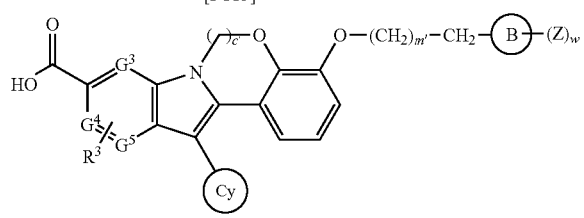

[I-114]

wherein each symbol is as defined above.

Step 1
Compound [227] can be obtained by reacting compound [221] with compound [26] in the same manner as in Production Method 14-1, Step 2.

Step 2
Compound [228] can be obtained by deprotecting the hydroxyl group of compound [227] by a conventional method.
Here, conditions for deprotecting $R^{c13}$ without affecting $R^{c14}$ are preferable, as $R^{c13}$, preferred are tetrahydropyran-2-yl group, tert-butyl group, acetyl group and the like, and as $R^{c14}$, preferred are benzyl group, methyl group and the like.

Step 3
Compound [229] can be obtained by converting the hydroxyl group of compound [228] to a leaving group by halogen substitution, mesylation or tosylation by a conventional method.

Step 4
Compound [230] can be obtained by reacting compound [229] with compound [9] in the same manner as in Production Method 14-1, Step 2.

Step 5
Compound [I-109] can be obtained cyclizing compound [230] in the same manner as in Production Method 6, Step 2.

Step 6
Compound [I-110] can be obtained by eliminating the hydroxyl-protecting group of compound [I-109] by a conventional method.

Step 7
Compound [I-112] can be obtained by reacting compound [I-110] with compound [223] in the same manner as in Production Method 14-1, Step 2.

Step 8
Compound [I-113] can be obtained by reducing carbonyl of compound [I-112] by a conventional method.

Step 9
Compound [I-114] can be obtained by hydrolyzing compound [I-113] in the same manner as in Production Method 12, Step 1.

Production Method 20

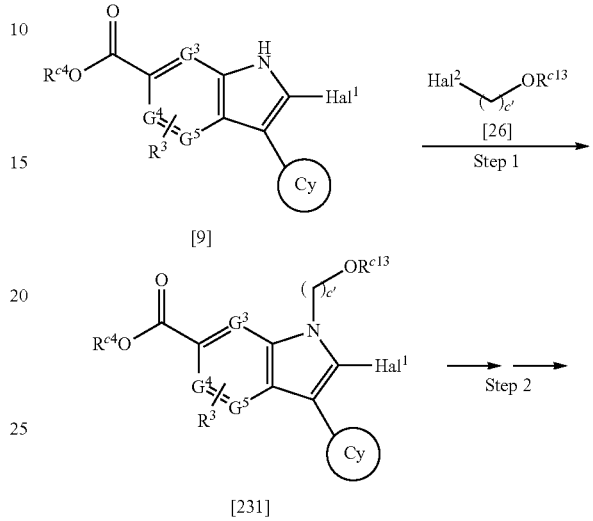

[9]

[231]

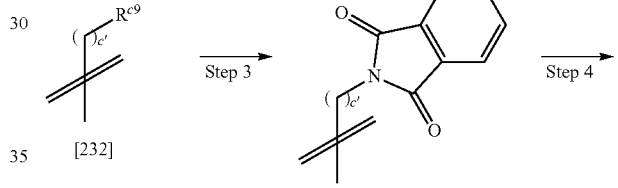

[232]    [233]

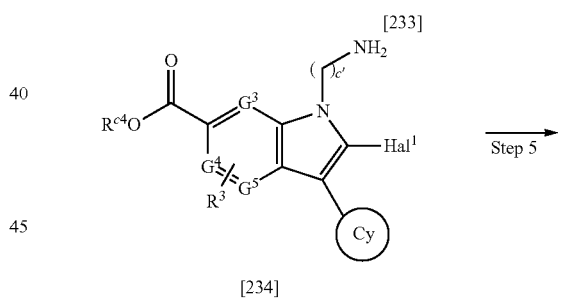

[234]

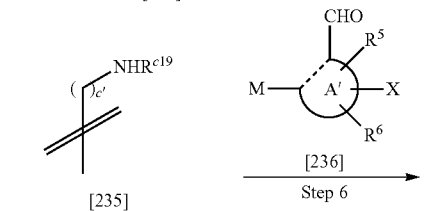

[235]    [236]

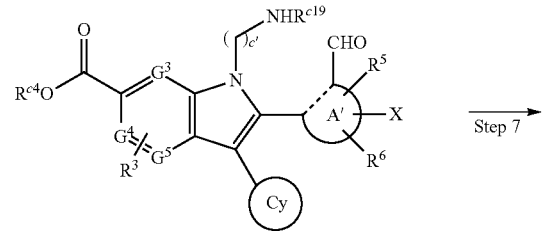

[237]

-continued

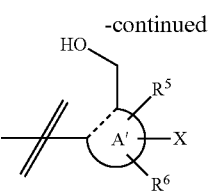

[238]

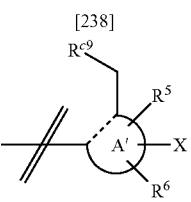

[239]

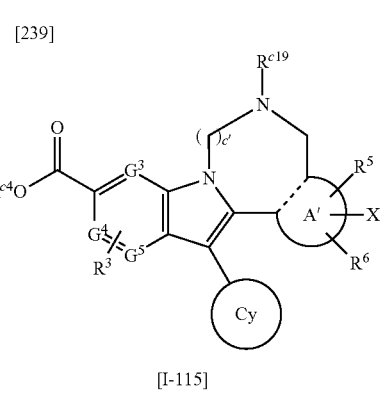

[I-115]

wherein each symbol is as defined above.

Step 1

Compound [231] can be obtained by reacting compound [9] with compound [26] in the same manner as in Production Method 14-1, Step 2.

Step 2

Compound [232], can be obtained by eliminating the hydroxyl-protecting group of compound [231] and then converting the hydroxyl group to a leaving group by halogen substitution, mesylation or tosylation by a conventional method.

Step 3

Compound [233] can be obtained by reacting compound [232] with potassium phthalimide in DMF solvent in the presence of a base such as potassium carbonate and the like at room temperature or under heating.

Step 4

Compound [234] can be obtained by reacting compound [233] in the presence of hydrazine in a solvent such as methanol, ethanol, THF and the like at room temperature or under heating.

Step 5

Compound [235] can be obtained by introducing a protecting group into the amino group of compound [234] by a conventional method.

Step 6

Compound [237] can be obtained by reacting compound [235] with compound [236] in the same manner as in Production Method 1-1.

Step 7

Compound [238] can be obtained by hydrogenating the formyl group of compound [237] to give hydroxymethyl group by a conventional method.

Step 8

Compound [239] can be obtained by converting the hydroxyl group of compound [238] to a leaving group by halogen substitution, mesylation or tosylation by a conventional method.

Step 9

Compound [I-115] can be obtained by subjecting compound [239] to condensation cyclization in the same manner as in Production Method 1-2, Step 2.

Production Method 20-1

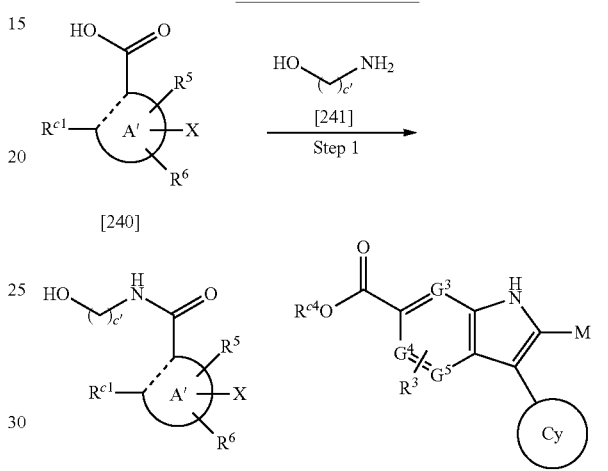

[242]

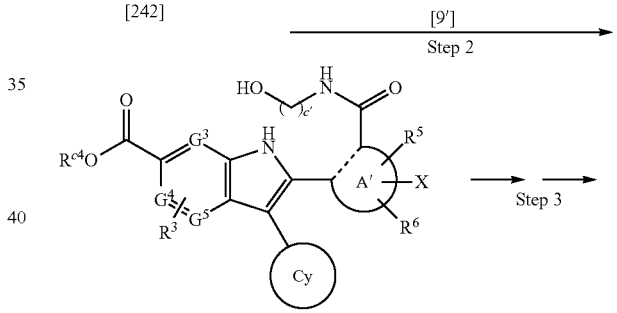

[243]

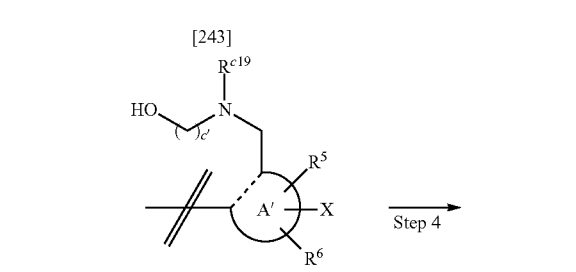

[244]

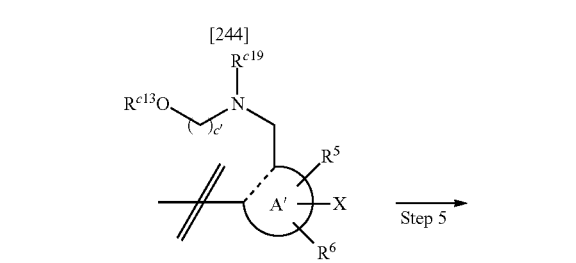

[245]

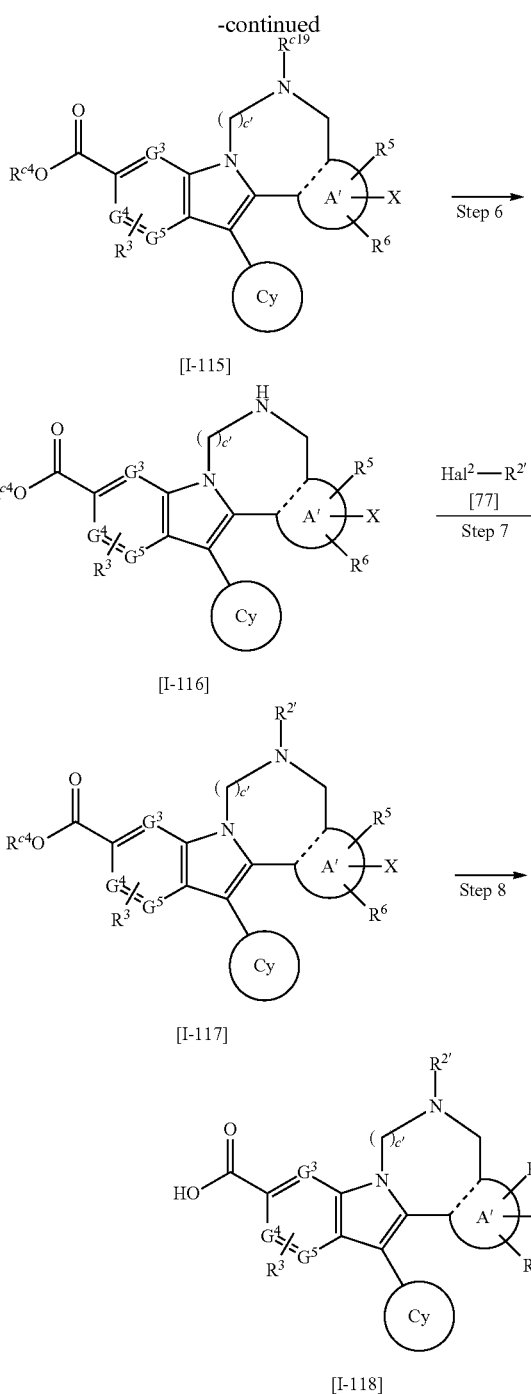

[I-115]

[I-116]

[I-117]

[I-118]

wherein each symbol is as defined above.

Step 1

Compound [242] can be obtained by amide condensation of compound [240] with compound [241] in the same manner as in Production Method 1-2, Step 1.

Step 2

Compound [243] can be obtained by reacting compound [242] with compound [9'] in the same manner as in Production Method 1.

Step 3

Compound [244] can be obtained by reducing the carbonyl of compound [243] and then introducing a protecting group into the nitrogen atom of reduced compound [243] by a conventional method.

Step 4

Compound [245] can be obtained by converting the hydroxyl group of compound [244] to a leaving group by halogen substitution, mesylation or tosylation by a conventional method.

Step 5

Compound [I-115] can be obtained by subjecting compound [245] to condensation cyclization in the same manner as in Production Method 1-2, Step 2.

Step 6

Compound [I-116] can be obtained by eliminating, by a conventional method, the amino-protecting group of compound [I-115] obtained in the previous step or in the same manner as in Production Method 20.

Step 7

Compound [I-117] can be obtained by reacting compound [I-116] with compound [77] in the same manner as in Production Method 10, Step 1.

The substituent can be introduced into the nitrogen atom in the same manner using compound [78] described in Production Method 10, compound [246] described in Production Method 21 and the like instead of compound [77].

The substituent may be also introduced in the same manner as in Production Method 18-1, Step 5, using an aldehyde compound or a ketone compound.

Step 8

Compound [I-118] can be obtained by hydrolyzing compound [I-117] in the same manner as in Production Method 12, Step 1.

Production Method 21

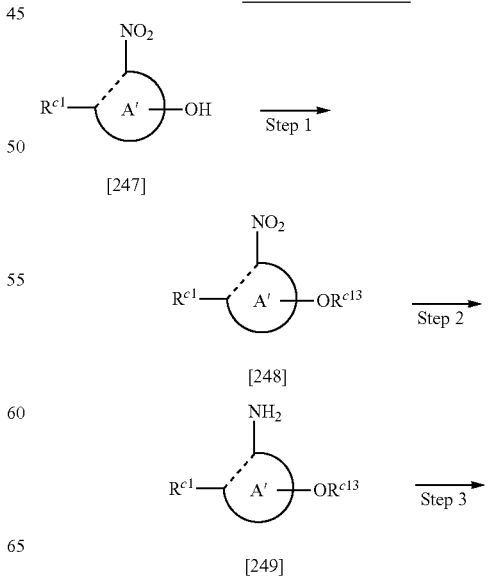

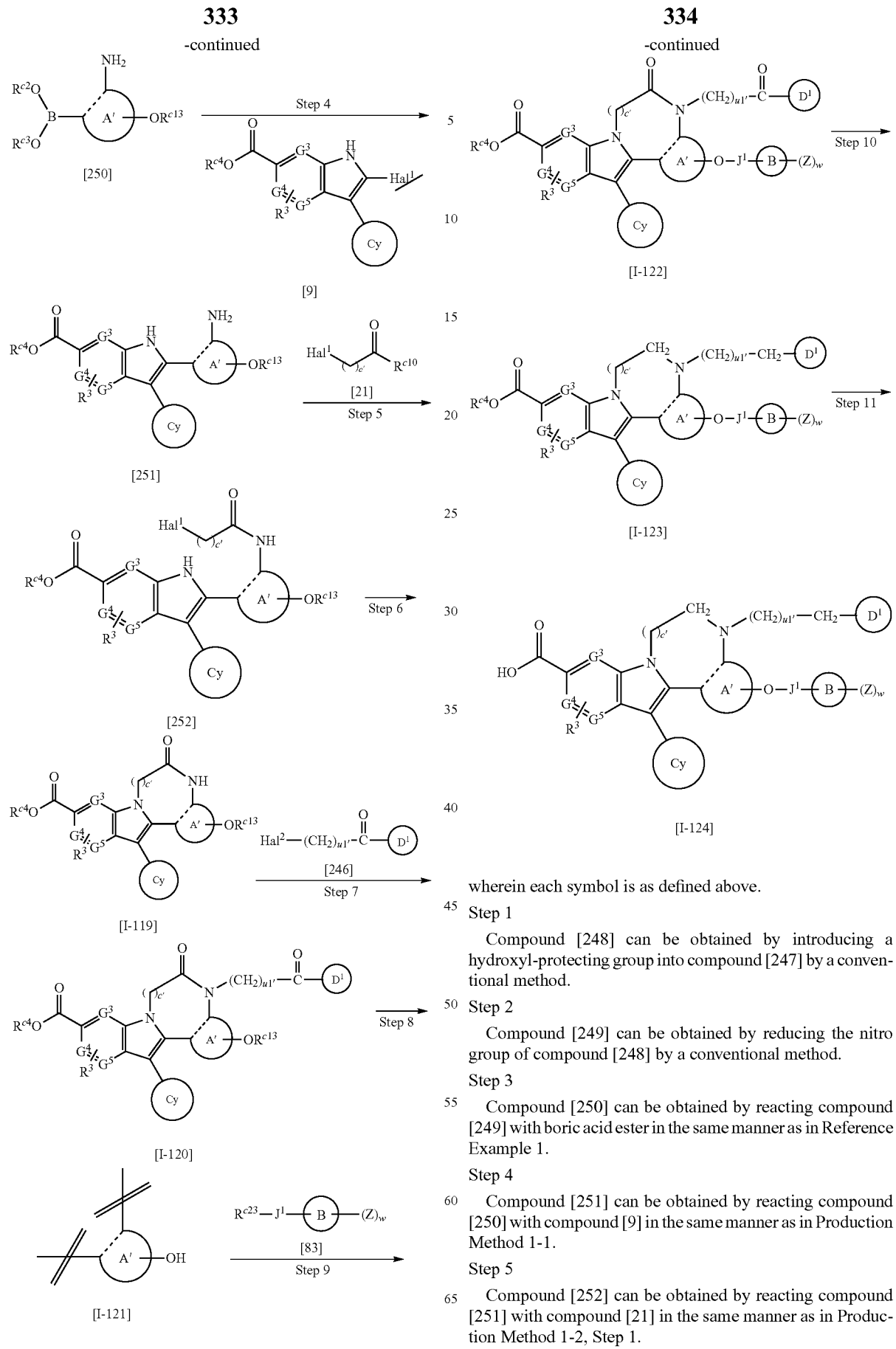

wherein each symbol is as defined above.

Step 1

Compound [248] can be obtained by introducing a hydroxyl-protecting group into compound [247] by a conventional method.

Step 2

Compound [249] can be obtained by reducing the nitro group of compound [248] by a conventional method.

Step 3

Compound [250] can be obtained by reacting compound [249] with boric acid ester in the same manner as in Reference Example 1.

Step 4

Compound [251] can be obtained by reacting compound [250] with compound [9] in the same manner as in Production Method 1-1.

Step 5

Compound [252] can be obtained by reacting compound [251] with compound [21] in the same manner as in Production Method 1-2, Step 1.

Step 6
Compound [I-119] can be obtained by subjecting compound [252] to condensation cyclization in the same manner as in Production Method 1-2, Step 2.

Step 7
Compound [I-120] can be obtained by reacting compound [I-119] with compound [246] in the same manner as in Production Method 10, Step 1.

Step 8
Compound [I-121] can be obtained by eliminating the hydroxyl-protecting group of compound [I-120] by a conventional method.

Step 9
Compound [I-122] can be obtained by reacting compound [I-121] with compound [83] in the same manner as in Production Method 14-1, Step 2.

Step 10
Compound [I-123] can be obtained by reducing carbonyl of compound [I-122] by a conventional method.

Step 11
Compound [I-124] can be obtained by hydrolyzing compound [I-123] in the same manner as in Production Method 12, Step 1.

Production Method 22-1

In general, compound [254], wherein a protecting group has been introduced into an amino group, is used, and after reaction of Step 1, compound [255] obtained by eliminating the amino-protecting group can be used in the next step.

Step 2
Compound [I-126] can be obtained by reacting compound [I-38] with compound [255] in the same manner as in Production Method 1-2, Step 1.

Compound [I-38] can be used for this Step after hydrolyzing the carboxyl-protecting group in the same manner as in Production Method 12, Step 1.

Step 3
Compound [I-125] can be obtained by reacting compound [I-38] with compound [254] in the same manner as in Production Method 1-2, Step 1.

Compound [I-38] can be used for this Step after hydrolyzing the carboxyl-protecting group in the same manner as in Production Method 12, Step 1.

In general, compound [254], wherein a protecting group has been introduced into carboxylic acid, is used, and after

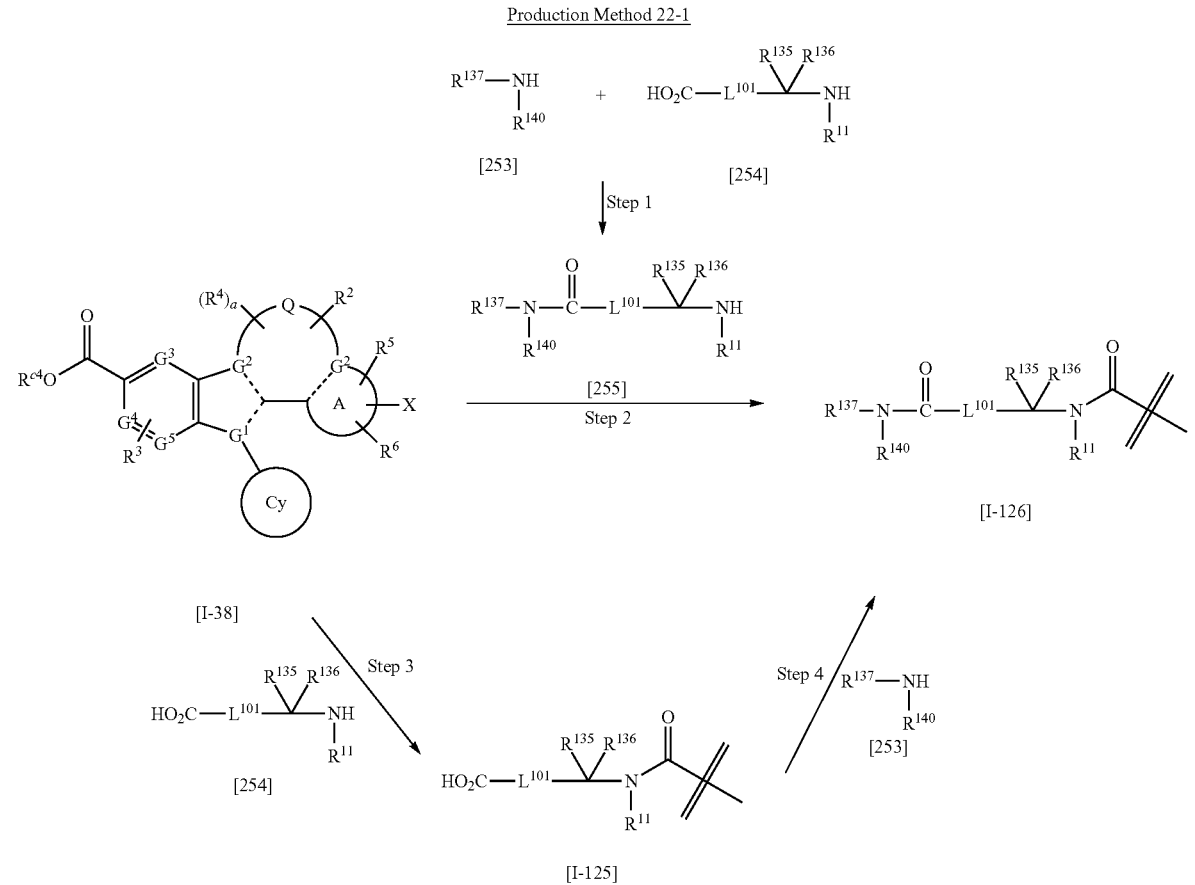

wherein each symbol is as defined above.

Step 1
Compound [255] can be obtained by reacting compound [253] with compound [254] in the same manner as in Production Method 1-2, Step 1.

reaction of Step 3, compound [I-125] obtained by eliminating the carboxyl-protecting group can be used in the next step.

Step 4
Compound [I-126] can be obtained by reacting compound [I-125] with compound [253] in the same manner as in Production Method 1-2, Step 1.

Production Method 22-2

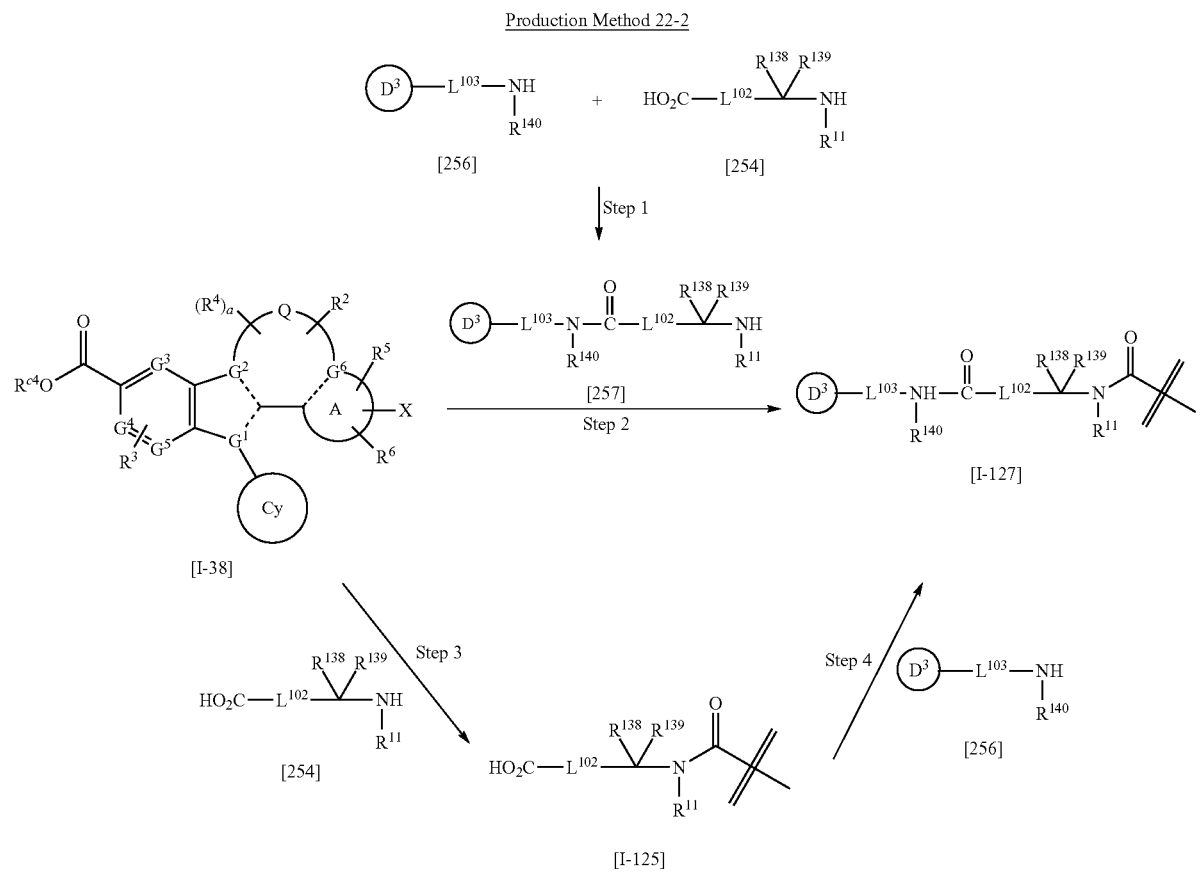

wherein each symbol is as defined above.

Compounds [257] and [I-127] can be obtained in the same manner as in Production Method 22-1, using compound [256] instead of compound [253].

Production Method 22-3

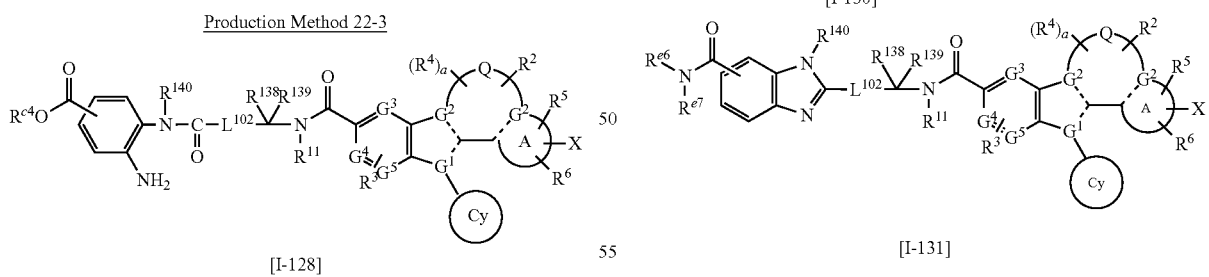

wherein each symbol is as defined above.

Step 1

Compound [I-129] can be obtained by subjecting compound [I-128], obtained in the same manner as in Production Method 22-1 or Production Method 22-2, to condensation cyclization the in a solvent such as an alcohol solvent, acetic acid and the like at room temperature or under heating.

Step 2

Compound [I-130] can be obtained by hydrolyzing compound [I-129] in the same manner as in Production Method 12, Step 1.

Step 3

Compound [I-131] can be obtained by reacting compound [I-130] with compound [258] in the same manner as in Production Method 1-2, Step 1.

Production Method 23

Production Method 23

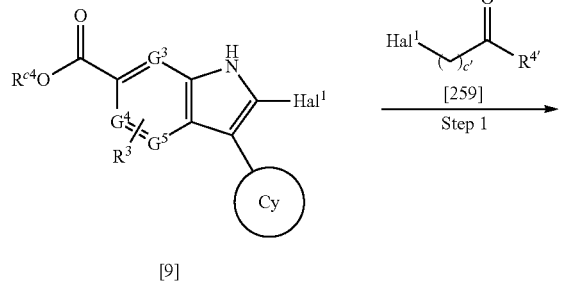

[9]

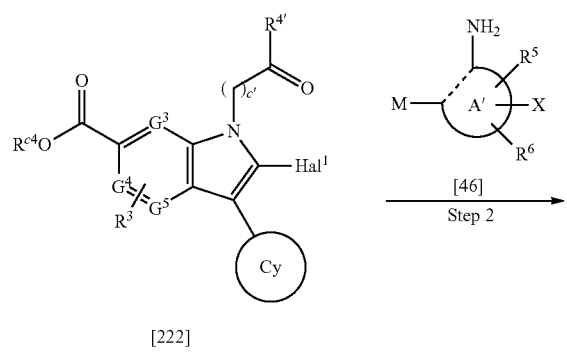

[222]

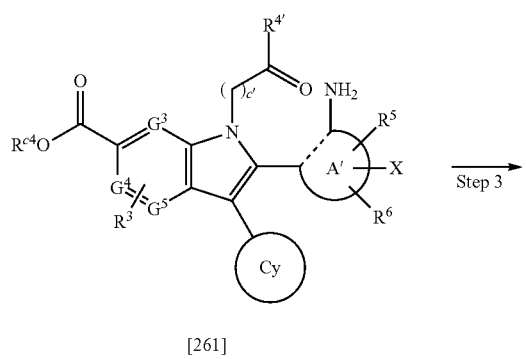

[261]

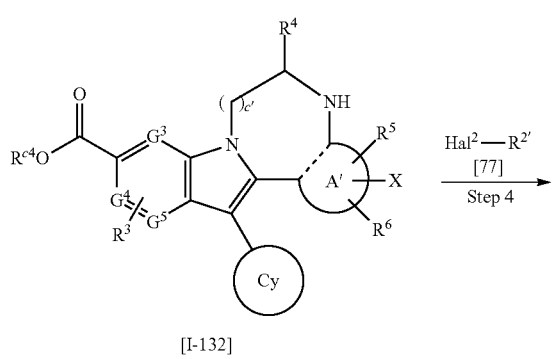

[I-132]

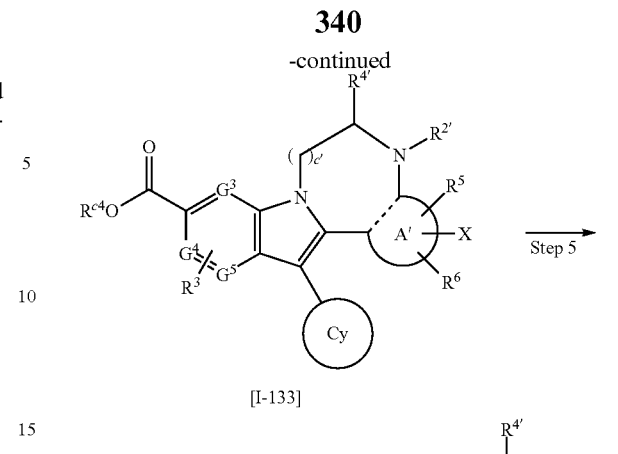

[I-133]

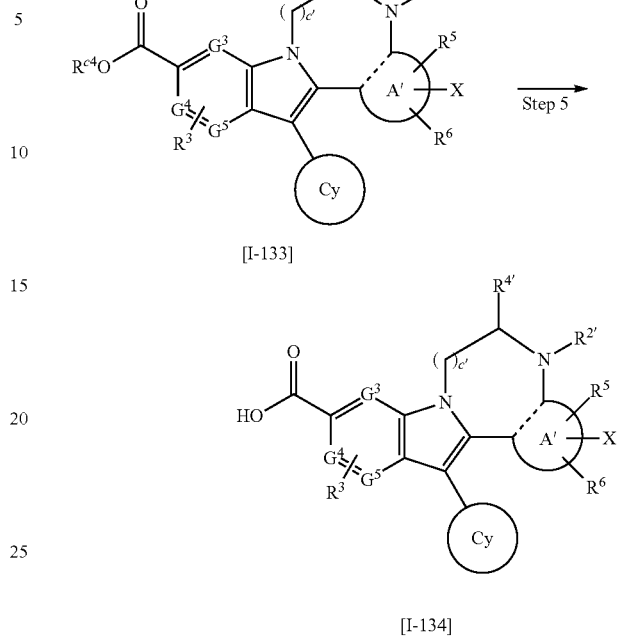

[I-134]

wherein $R^{4'}$ is a $C_{1-6}$ alkyl group optionally substituted by 1 to 3 substituents selected from group A, a $C_{6-14}$ aryl group optionally substituted by 1 to 5 substituents selected from group B or a heterocyclic group optionally substituted by 1 to 5 substituents selected from group B, and each symbol is as defined above.

Step 1

Compound [222] can be obtained by reacting compound [9] with compound [259] in the same manner as in Production Method 14-1, Step 2.

Step 2

Compound [261] can be obtained by reacting compound [222] with compound [46] in the same manner as in Production Method 1-1.

Step 3

Compound [I-132] can be obtained by subjecting compound to condensation cyclization in a solvent in the presence of a reducing agent.

As the reducing agent, borohydrides such as sodium borohydride, sodium cyanoborohydride, sodium triacetoxyborohydride and the like can be mentioned.

As the solvent, THF, 1,4-dioxane, dichloromethane, chloroform, methanol, ethanol, toluene, acetic acid and the like can be mentioned. Acetic acid may be added.

Step 4

Compound [I-133] can be obtained by reacting compound [I-132] with compound [77] in the same manner as in Production Method 20-1, Step 7.

Step 5

Compound [I-134] can be obtained by hydrolyzing compound [I-133] in the same manner as in Production Method 12, Step 1.

In the above-mentioned Production Method, substituents $R^4$ and/or $R^2$ may be present on -Q-, as long as the reaction is not adversely affected.

In the compounds of the formula [I], a desired heterocyclic group (including carboxylic acid equivalent) can be formed according to a method similar to the methods disclosed in known publications. Examples of such heterocyclic group and reference publications are recited in the following.

5-oxo-$\Delta^2$-1,2,4-oxadiazolin-3-yl (or 2,5-dihydro-5-oxo-4H-1,2,4-oxadiazol-3-yl), 5-oxo-$\Delta^2$-1,2,4-thiadiazolin-3-yl (or 2,5-dihydro-5-oxo-4H-1,2,4-thiadiazol-3-yl), 2-oxo-$\Delta^3$-1,2,3,5-oxathiadiazolin-4-yl (or 2-oxo-$\Delta^3$-1,2,3,5-oxathiadiazol-4-yl): Journal of Medicinal Chemistry, 39(26), 5228-35, 1996, based on compound [I-42], for example, 5-oxo-$\Delta^2$-1,2,4-oxadiazolin-3-yl, 5-thioxo-$\Delta^2$-1,2,4-oxadiazolin-3-yl can be formed.

5-oxo-$\Delta^2$-1,2,4-triazolin-3-yl: J Org Chem, 61(24), 8397-8401, 1996, 1-oxo-$\Delta^3$-1,2,3,5-thiatriazoline-4-yl: Liebigs Ann Chem, 1376, 1980, 3-oxo-$\Delta^4$-1,2,4-oxadiazolin-5-yl: EP145095, 5-oxo-$\Delta^2$-1,3,4-oxadiazolin-2-yl: J Org Chem, 20, 412, 1955, 5-oxo-$\Delta^3$-1,2,4-dioxazolin-3-yl: J Prakt Chem, 314, 145, 1972, 3-oxo-$\Delta^4$-1,2,4-thiadiazolin-5-yl: JP-A-61-275271, 5-oxo-$\Delta^3$-1,2,4-dithiazolin-3-yl: J Org Chem, 61(19), 6639-6645, 1996, 2-oxo-$\Delta^4$-1,3,4-dioxazolin-5-yl: J Org Chem, 39, 2472, 1974, 2-oxo-$\Delta^4$-1,3,4-oxathiazolin-5-yl: J Med Chem, 35(20), 3691-98, 1992, 5-oxo-$\Delta^2$-1,3,4-thiadiazolin-2-yl: J Prakt Chem, 332(1), 55, 1990, 5-oxo-$\Delta^2$-1,4,2-oxathiazolin-3-yl: J Org Chem, 31, 2417, 1966, 2-oxo-$\Delta^4$-1,3,4-dithiazolin-5-yl: Tetrahedron Lett, 23, 5453, 1982, 2-oxo-$\Delta^4$-1,3,2,4-dioxathiazolin-5-yl: Tetrahedron Lett, 319, 1968, 3,5-dioxoisoxazolidin-4-yl: Helv Chim Acta, 1973, 48, 1965, 2,5-dioxoimidazolidin-4-yl: Heterocycles, 43(1), 49-52, 1996, 5-oxo-2-thioxoimidazolidin-4-yl: Heterocycles, 5, 391, 1983, 2,4-dioxooxazolidin-5-yl: J Am Chem Soc, 73, 4752, 1951, 4-oxo-2-thioxooxazolidin-5-yl: Chem Ser, 91, 300, 1958, 2,4-dioxothiazolidin-5-yl: JP-A-57-123175, 4-oxo-2-thioxothiazolidin-5-yl: Chem Pharm Bull, 30, 3563, 1982.

Examples

The tetracyclic fused heterocyclic compounds of the formula [I] and production methods thereof of the present invention are explained in detail in the following by way of Examples. It is needless to say that the present invention is not limited by these Examples. In the Examples, Me means methyl group, Et means ethyl group, tBu means tert-butyl group, Ac means acetyl group, Bn means benzyl group, Boc means tert-butoxycarbonyl group, THP means 2-tetrahydropyranyl group, and Tf means trifluoromethanesulfonyl group.

Example 1-1

Production of methyl 13-cyclohexyl-6-oxo-6,7-dihydro-5H-benzo[5,6][1,4]diazepino[7,1-a]indole-10-carboxylate Step 1: Production of 2-(4,4,5,5-tetramethyl-1,3,2-dioxaborolan-2-yl)phenylamine

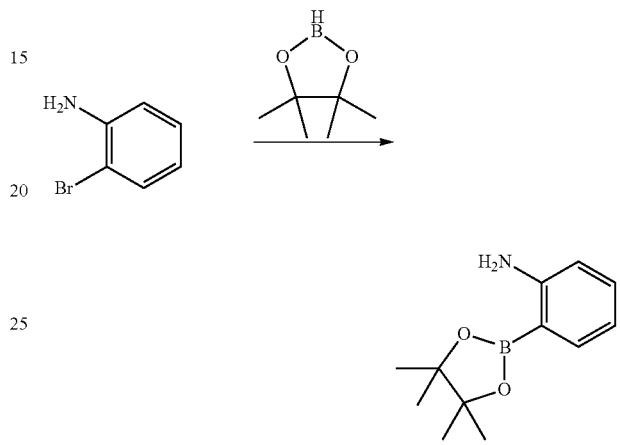

To a solution of 2-bromoaniline (1.0 g, 5.81 mmol) in 1,4-dioxane (15 ml) were added triethylamine (3.24 ml, 23.2 mmol) and [1,1-bis(diphenylphosphino)ferrocene]dichloropalladium(II) dichloromethane complex (PdCl$_2$(dppf)CH$_2$Cl$_2$) (243 mg, 0.30 mmol) at room temperature. To the reaction mixture was added dropwise pinacolborane (2.53 ml, 17.4 mmol), and the reaction mixture was heated to 100° C. and stirred for 3 hr. The reaction mixture was cooled to room temperature and saturated aqueous ammonium chloride solution was added. The mixture was extracted with diethyl ether. The organic layer was washed with saturated brine and dried over anhydrous sodium sulfate. After filtration, the solvent was evaporated under reduced pressure, and the residue was purified by silica gel column chromatography (hexane:ethyl acetate=5:1) to give 2-(4,4,5,5-tetramethyl-1,3,2-dioxaborolan-2-yl)phenylamine (810 mg, yield 63.6%).

$^1$H-NMR (400 MHz, CDCl$_3$): δ(ppm) 7.59 (1H, dd, J=7.2, 1.6 Hz), 7.20 (1H, ddd, J=15.2, 7.2, 2.0 Hz), 6.66 (1H, dd, J=7.4 Hz), 6.58 (1H, d, J=8.0 Hz), 4.72 (2H, brs), 1.33 (12H, s).

Step 2: Production of methyl 2-(2-aminophenyl)-3-cyclohexyl-1H-indole-6-carboxylate

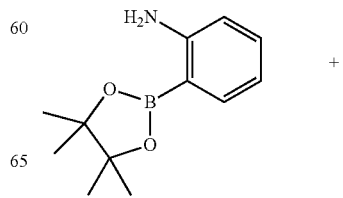

-continued

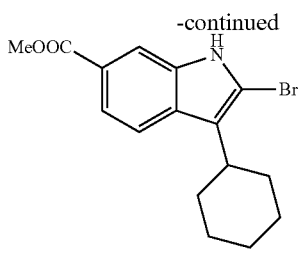

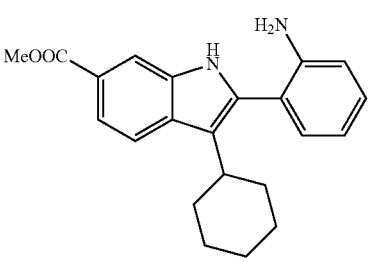

To a suspension of methyl 2-bromo-3-cyclohexyl-1H-indole-6-carboxylate (6.50 g, 19.3 mmol) obtained in the same manner as in the method described in WO03/010140 and 2-(4,4,5,5-tetramethyl-1,3,2-dioxaborolan-2-yl)phenylamine (5.08 g, 23.2 mmol) in 1,2-dimethoxyethane (90 ml) and water (45 ml) were added sodium hydrogen carbonate (4.81 g, 57.9 mmol) and tetrakis(triphenylphosphine)palladium (1.12 mg, 0.965 mmol), and the mixture was heated under reflux for 9 hr. The mixture was allowed to cool to room temperature, and water was added to the reaction mixture. The mixture was extracted with ethyl acetate and the organic layer was washed successively with saturated aqueous sodium hydrogen carbonate solution and saturated brine and dried over anhydrous magnesium sulfate. After filtration, the solvent was evaporated under reduced pressure. The residue was purified by silica gel chromatography (hexane:ethyl acetate=4:1-3:1) to give methyl 2-(2-aminophenyl)-3-cyclohexyl-1H-indole-6-carboxylate (6.48 g, yield 96%).

$^1$H-NMR (400 MHz, DMSO-d$_6$): δ(ppm) 11.30 (1H, s), 7.95 (1H, d, J=1.2 Hz), 7.78 (1H, d, J=8.4 Hz), 7.58 (1H, dd, J=8.4, 1.2 Hz), 7.14 (1H, td, J=8.0, 0.8 Hz), 7.04 (1H, dd, J=7.6, 1.6 Hz), 6.79 (1H, dd, J=8.0, 0.8 Hz), 6.65 (1H, td, J=7.2, 0.4 Hz), 4.81 (2H, brs), 3.84 (3H, s), 2.53-2.63 (1H, m), 1.63-1.94 (7H, m), 1.16-1.37 (3H, m).

Step 3: Production of methyl 2-[2-(2-chloroacetylamino)phenyl]-3-cyclohexyl-1H-indole-6-carboxylate

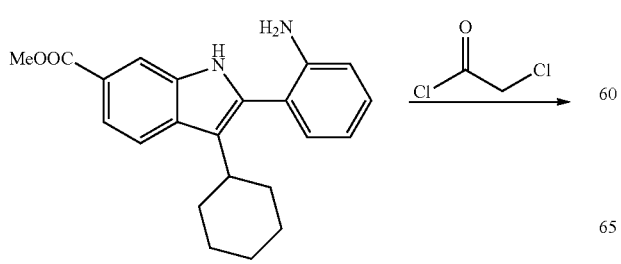

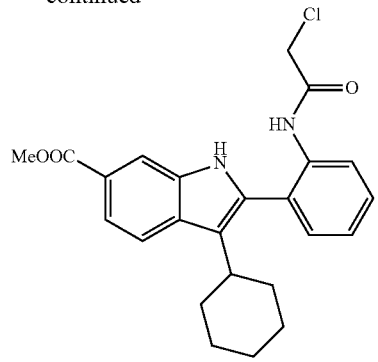

To a suspension of methyl 2-(2-aminophenyl)-3-cyclohexyl-1H-indole-6-carboxylate (6.48 g, 18.6 mmol), sodium acetate (1.68 g, 20.5 mmol) and acetic acid (1.17 ml, 20.5 mmol) in tetrahydrofuran (60 ml) was added dropwise chloroacetyl chloride (1.63 ml, 20.5 mmol), and the mixture was stirred at room temperature for 2 hr. Saturated aqueous sodium hydrogen carbonate solution was added to the reaction mixture and the mixture was extracted with ethyl acetate. The organic layer was m washed successively with saturated aqueous sodium hydrogen carbonate solution and saturated brine and dried over anhydrous magnesium sulfate. After filtration, the solvent was evaporated under reduced pressure to give methyl 2-[2-(2-chloroacetylamino)phenyl]-3-cyclohexyl-1H-indole-6-carboxylate (7.90 g, yield 100%).

$^1$H-NMR (400 MHz, DMSO-d$_6$): δ(ppm) 11.44 (1H, s), 9.38 (1H, s), 7.98 (1H, d, J=1.2 Hz), 7.90 (1H, d, J=8.0 Hz), 7.82 (1H, d, J=8.4 Hz), 7.60 (1H, dd, J=8.0, 1.2 Hz), 7.47 (1H, td, J=8.4, 0.8 Hz), 7.36 (1H, dd, J=7.6, 1.6 Hz), 7.30 (1H, td, J=7.6, 0.6 Hz), 4.19 (2H, s), 3.85 (3H, s), 2.42-2.50 (1H, m), 1.61-1.91 (7H, m), 1.11-1.34 (3H, m).

Step 4: Production of methyl 13-cyclohexyl-6-oxo-6,7-dihydro-5H-benzo[5,6][1,4]diazepino[7,1-a]indole-10-carboxylate

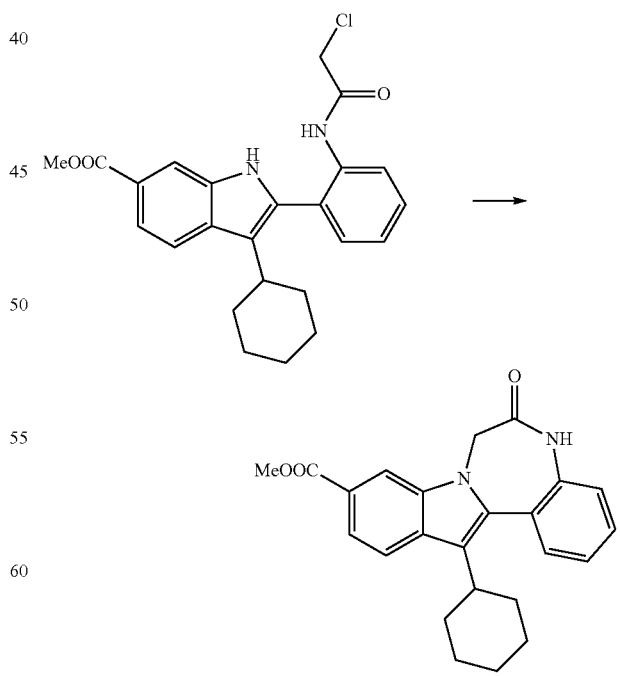

To a solution of methyl 2-[2-(2-chloroacetylamino)phenyl]-3-cyclohexyl-1H-indole-6-carboxylate (7.90 g, 18.6 mmol) in N,N-dimethylformamide (170 ml) was added sodium hydride (1.64 g, 40.9 mmol) under ice-cooling and the mixture was stirred for 2 hr. 1N Hydrochloric, acid (45 ml) and water (200 ml) were added to the reaction mixture and the precipitated solid was collected by filtration. After washing successively with water and hexane, the solid was dried in vacuo to give methyl 13-cyclohexyl-6-oxo-6,7-dihydro-5H-benzo[5,6][1,4]diazepino[7,1-a]indole-10-carboxylate (6.72 g, yield 93%).

$^1$H-NMR (400 MHz, DMSO-$d_6$): δ(ppm) 10.34 (1H, s), 8.27 (1H, d, J=1.2 Hz), 7.96 (1H, d, J=8.4 Hz), 7.68 (1H, dd, J=8.4, 1.6 Hz), 7.49-7.53 (2H, m), 7.38 (1H, t, J=7.6 Hz), 7.28 (1H, d, J=8.0 Hz), 5.07 (1H, d, J=15.6 Hz), 4.52 (1H, d, J=14.8 Hz), 3.89 (3H, s), 2.81-2.91 (1H, m), 1.98-2.11 (3H, m), 1.84-1.94 (1H, m), 1.66-1.78 (2H, m), 1.34-1.56 (3H, m), 1.10-1.27 (1H, m).

Example 1-2

Production of methyl 13-cyclohexyl-6,7-dihydro-5H-benzo[5,6][1,4]diazepino[7,1-a]indole-10-carboxylate

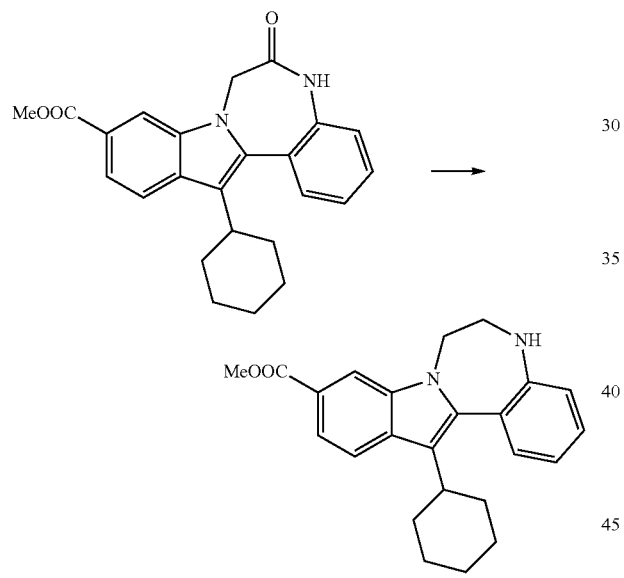

To a suspension of methyl 13-cyclohexyl-6-oxo-6,7-dihydro-5H-benzo[5,6][1,4]diazepino[7,1-a]indole-10-carboxylate (6.72 g, 17.3 mmol) in tetrahydrofuran (13 ml) was added 1M BH$_3$ THF complex tetrahydrofuran solution (67 ml) under ice-cooling, and the mixture was stirred at room temperature for 4 hr. 2N Hydrochloric acid (40 ml) was added to the reaction mixture at room temperature and the mixture was stirred at 70° C. for 1 hr. The mixture was allowed to cool to room temperature and 2N aqueous sodium hydroxide solution (40 ml) was added to the reaction mixture. The mixture was extracted with ethyl acetate. The organic layer was washed successively with saturated aqueous sodium hydrogen carbonate solution and saturated brine and dried over anhydrous magnesium sulfate. After filtration, the solvent was evaporated under reduced pressure to give methyl 13-cyclohexyl-6,7-dihydro-5H-benzo[5,6][1,4]diazepino[7,1-a]indole-10-carboxylate (6.08 g, yield 94%).

$^1$H-NMR (400 MHz, DMSO-$d_6$): δ(ppm) 8.13 (1H, d, J=1.6 Hz), 7.86 (1H, d, J=8.8 Hz), 7.61 (1H, dd, J=8.8, 1.6 Hz), 7.17-7.21 (2H, m), 6.91 (1H, dd, J=8.4, 1.2 Hz), 6.83 (1H, t, J=7.4 Hz), 5.80 (1H, t, J=4.0 Hz), 4.41 (2H, brs), 3.86 (3H, s), 3.45-3.52 (2H, m), 2.80-2.89 (1H, m), 1.97-2.10 (2H, m), 1.68-1.85 (5H, m), 1.21-1.46 (3H, m).

Example 1-3

Production of 13-cyclohexyl-6,7-dihydro-5H-benzo[5,6][1,4]diazepino[7,1-a]indole-10-carboxylic acid monohydrochloride

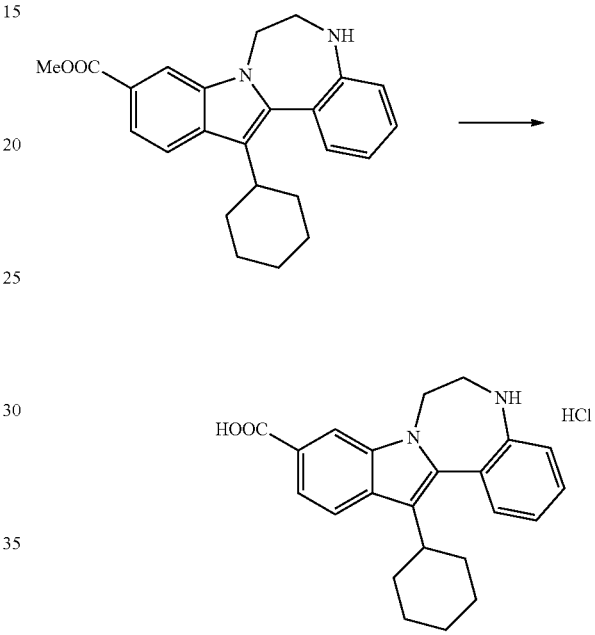

To a solution of methyl 13-cyclohexyl-6,7-dihydro-5H-benzo[5,6][1,4]diazepino[7,1-a]indole-10-carboxylate (60 mg, 0.16 mmol) in tetrahydrofuran (2 ml) and methanol (1 ml) was added 4N aqueous sodium hydroxide solution (1 ml), and the mixture was stirred for 36 hr. 1N Hydrochloric acid (4 ml) was added to adjust to pH 7, and the mixture was extracted with ethyl acetate. The organic layer was washed with saturated brine and dried over anhydrous sodium sulfate. After filtration, the solvent was evaporated under reduced pressure. To a solution of the residue in tetrahydrofuran (2 ml) was added 4N HCl-ethyl acetate solution (1 ml), and the solvent was evaporated under reduced pressure. Diethyl ether was added to the residue and the precipitated solid was collected by filtration, washed with diethyl ether and dried in vacuo to give 13-cyclohexyl-6,7-dihydro-5H-benzo[5,6][1,4]diazepino[7,1-a]indole-10-carboxylic acid monohydrochloride (48 mg, yield 76.4%).

$^1$H-NMR (300 MHz, DMSO-$d_6$): δ(ppm) 8.18 (1H, s), 7.89 (1H, d, J=8.4 Hz), 7.65 (1H, d, J=9.9 Hz), 7.18-7.44 (4H, brm), 3.46-4.47 (4H, brm), 2.81-2.91 (1H, m), 1.96-2.11 (2H, m), 1.68-1.86 (5H, m), 1.22-1.45 (3H, m).

MS 361 (M+1).

Example 1-4

Production of methyl 5-tert-butoxycarbonylmethyl-13-cyclohexyl-6,7-dihydro-5H-benzo[5,6][1,4]diazepino[7,1-a]indole-10-carboxylate

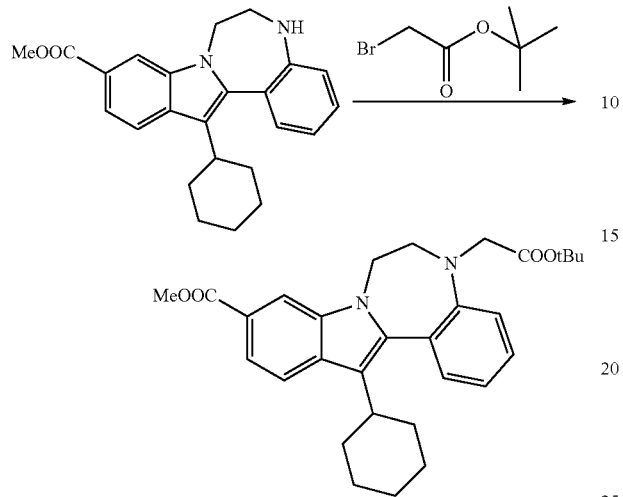

To a solution of methyl 13-cyclohexyl-6,7-dihydro-5H-benzo[5,6][1,4]diazepino[7,1-a]indole-10-carboxylate (2.00 g, 5.34 mmol) obtained in Example 1-2 in N,N-dimethylformamide (16 ml) were added potassium carbonate (1.85 g, 13.4 mmol), sodium iodide (800 mg, 5.34 mmol) and tert-butyl bromoacetate (1.18 ml, 8.01 mmol), and the mixture was stirred at 90° C. for 12 hr. The mixture was allowed to cool to room temperature, and water (40 ml) was added. The precipitated solid was collected by filtration, washed successively with water and hexane and dried in vacuo to give methyl 5-tert-butoxycarbonylmethyl-13-cyclohexyl-6,7-dihydro-5H-benzo[5,6][1,4]diazepino[7,1-a]indole-10-carboxylate (2.47 g, yield 95%).

$^1$H-NMR (400 MHz, DMSO-$d_6$): δ(ppm) 8.18 (1H, d, J=1.2 Hz), 7.88 (1H, d, J=8.8 Hz), 7.62 (1H, dd, J=8.0, 1.2 Hz), 7.38 (1H, t, J=7.8 Hz), 7.28 (1H, d, J=7.6 Hz), 7.14 (1H, t, J=7.4 Hz), 7.02 (1H, d, J=8.0 Hz), 3.87 (5H, s), 3.51 (2H, brs), 2.75-2.85 (1H, m), 1.95-2.09 (2H, m), 1.66-1.86 (5H, m), 1.17-1.45 (3H, m), 1.29 (9H, s).
MS 489 (M+1).

Example 1-5

Production of (13-cyclohexyl-10-methoxycarbonyl-6,7-dihydro-5H-benzo[5,6][1,4]diazepino[7,1-a]indol-5-yl)acetic acid

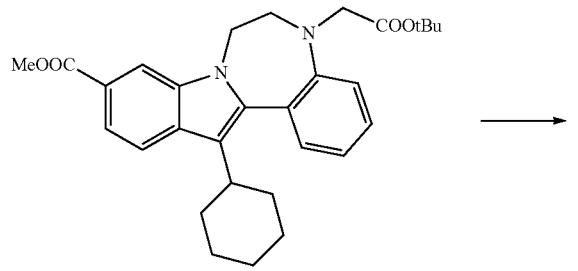

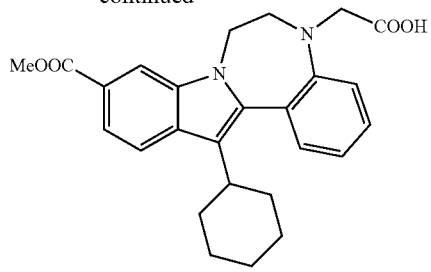

To a solution of methyl 5-tert-butoxycarbonylmethyl-13-cyclohexyl-6,7-dihydro-5H-benzo[5,6][1,4]diazepino[7,1-a]indole-10-carboxylate (2.47 g, 5.05 mmol) in chloroform (17 ml) was added trifluoroacetic acid (17 ml) and the mixture was stirred at room temperature for 5 hr. The reaction mixture was evaporated under reduced pressure and the residue was purified by silica gel chromatography (chloroform:methanol=30:1-15:1) to give (13-cyclohexyl-10-methoxycarbonyl-6,7-dihydro-5H-benzo[5,6][1,4]diazepino[7,1-a]indol-5-yl)acetic acid (1.34 g, yield 61%).

$^1$H-NMR (400 MHz, DMSO-$d_6$): δ(ppm) 12.60 (1H, brs), 8.18 (1H, d, J=1.2 Hz), 7.87 (1H, d, J=8.4 Hz), 7.62 (1H, dd, J=8.8, 1.6 Hz), 7.37 (1H, td, J=8.0, 0.8 Hz), 7.27 (1H, dd, J=7.6, 1.6 Hz), 7.11 (1H, t, J=7.4 Hz), 7.05 (1H, d, J=8.0 Hz), 4.40 (2H, brs), 3.88 (2H, brs), 3.87 (3H, s), 3.58 (2H, t, J=5.4 Hz), 2.76-2.86 (1H, m), 1.94-2.07 (2H, m), 1.66-1.86 (5H, m), 1.20-1.45 (3H, m)
MS 433 (M+1).

Example 1-6

Production of methyl 13-cyclohexyl-5-[2-oxo-2-(thiomorpholin-4-yl)ethyl]-6,7-dihydro-5H-benzo[5,6][1,4]diazepino[7,1-a]indole-10-carboxylate

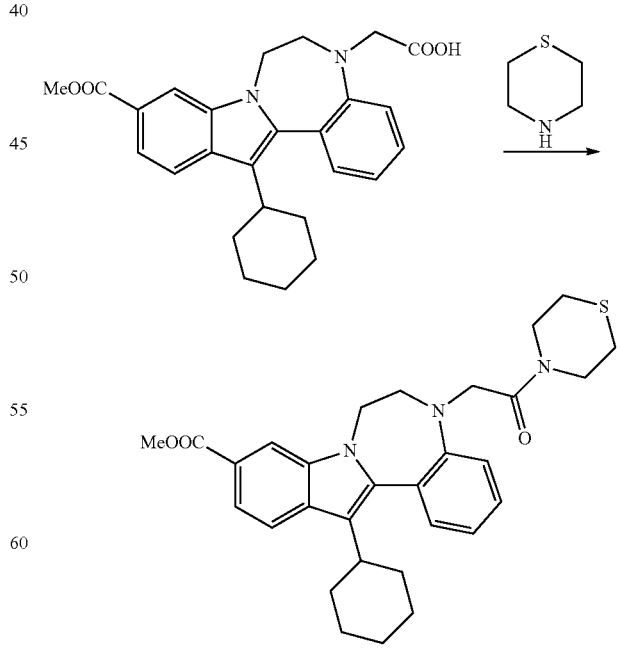

To a solution of (13-cyclohexyl-10-methoxycarbonyl-6,7-dihydro-5H-benzo[5,6][1,4]diazepino[7,1-a]indol-5-yl)acetic acid (400 mg, 0.46 mmol) in N,N-dimethylformamide (2 ml) were added 1-ethyl-3-(3'-dimethylaminopropyl)carbodiimide monohydrochloride (105 mg, 0.54 mmol), 1-hydroxybenzotriazole monohydrate (75 mg, 0.55 mmol) and thiomorpholine (0.05 ml, 0.49 mmol) and the mixture was stirred overnight at room temperature. Water was added to the reaction mixture and the mixture was extracted with ethyl acetate. The organic layer was washed successively with water, saturated aqueous sodium hydrogen carbonate solution and saturated brine and dried over anhydrous sodium sulfate. After filtration, the solvent was evaporated under reduced pressure and the residue was purified by silica gel column chromatography (hexane:ethyl acetate=1:1-2:3) to give methyl 13-cyclohexyl-5-[2-oxo-2-(thiomorpholin-4-yl)ethyl]-6,7-dihydro-5H-benzo[5,6][1,4]diazepino[7,1-a]indole-10-carboxylate (149 mg, yield 62.6%).

MS 518 (M+1).

Example 1-7

Production of 13-cyclohexyl-5-[2-oxo-2-(thiomorpholin-4-yl)ethyl]-6,7-dihydro-5H-benzo[5,6][1,4]diazepino[7,1-a]indole-10-carboxylic acid monohydrochloride

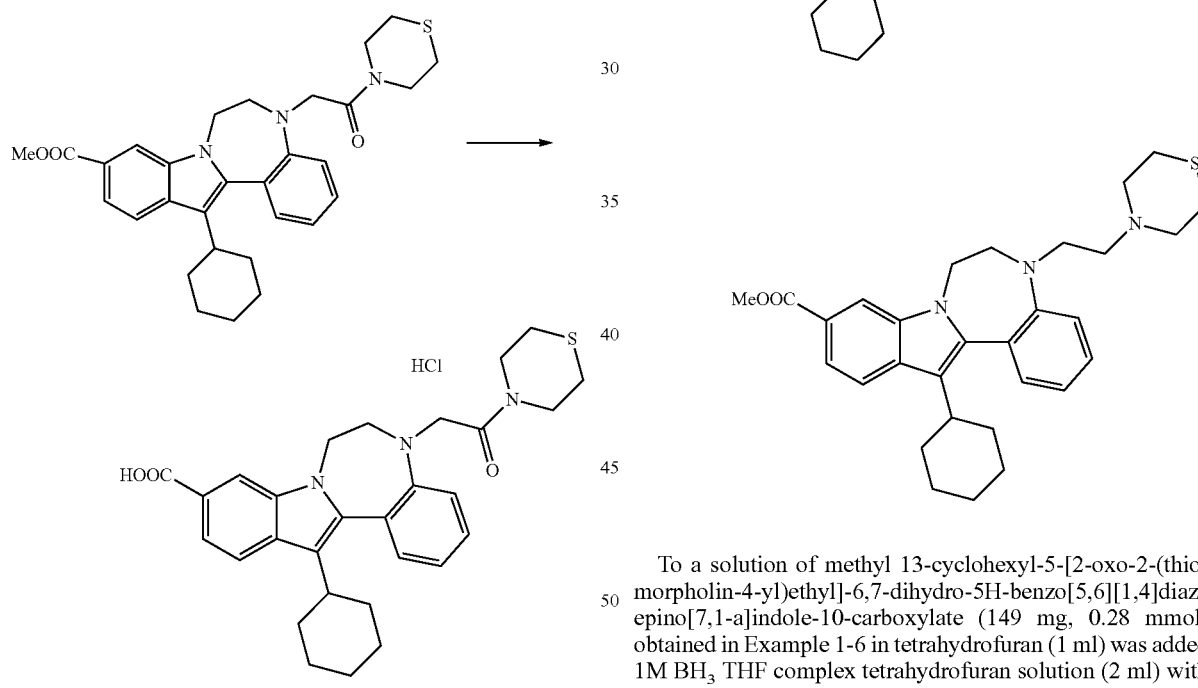

To a solution of methyl 13-cyclohexyl-5-[2-oxo-2-(thiomorpholin-4-yl)ethyl]-6,7-dihydro-5H-benzo[5,6][1,4]diazepino[7,1-a]indole-10-carboxylate (114 mg, 0.22 mmol) in tetrahydrofuran (1 ml) and methanol (1 ml) was added 4N aqueous sodium hydroxide solution (1 ml) and the mixture was stirred at 70° C. for 2 hr. The mixture was allowed to cool to room temperature and 1N hydrochloric acid (4 ml) was added to adjust to pH 7. The mixture was extracted with ethyl acetate. The organic layer was washed with saturated brine and dried over anhydrous sodium sulfate. After filtration, the solvent was evaporated under reduced pressure. To a solution of the residue in ethyl acetate (1 ml) was added 4N HCl-ethyl acetate solution (1 ml) and the solvent was evaporated under reduced pressure. Hexane was added to the residue and the precipitated solid was collected by filtration, washed with hexane, and dried in vacuo to give 13-cyclohexyl-5-[2-oxo-2-(thiomorpholin-4-yl)ethyl]-6,7-dihydro-5H-benzo[5,6][1,4]diazepino[7,1-a]indole-10-carboxylic acid monohydrochloride (68 mg, yield 57.6%).

MS 504 (M+1).

Example 1-8

Production of methyl 13-cyclohexyl-5-[2-(thiomorpholin-4-yl)ethyl]-6,7-dihydro-5H-benzo[5,6][1,4]diazepino[7,1-a]indole-10-carboxylate

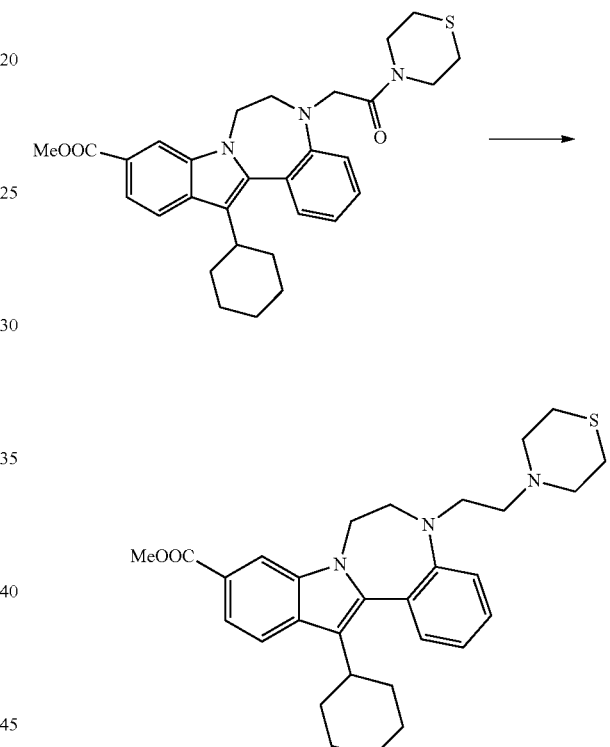

To a solution of methyl 13-cyclohexyl-5-[2-oxo-2-(thiomorpholin-4-yl)ethyl]-6,7-dihydro-5H-benzo[5,6][1,4]diazepino[7,1-a]indole-10-carboxylate (149 mg, 0.28 mmol) obtained in Example 1-6 in tetrahydrofuran (1 ml) was added 1M BH₃ THF complex tetrahydrofuran solution (2 ml) with stirring under ice-cooling, and the mixture was stirred at room temperature for 4 hr. 2N Hydrochloric acid was added to the reaction mixture at room temperature and the mixture was stirred at 70° C. for 2 hr. To the reaction mixture was added 4N aqueous sodium hydroxide solution to adjust to pH 8 and the mixture was extracted with ethyl acetate. The organic layer was washed with saturated brine and dried over anhydrous sodium sulfate. After filtration, the solvent was evaporated under reduced pressure and the residue was purified by silica gel column chromatography (chloroform:methanol=30:1-20:1) to give methyl 13-cyclohexyl-5-[2-(thiomorpholin-4-yl)ethyl]-6,7-dihydro-5H-benzo[5,6][1,4]diazepino[7,1-a]indole-10-carboxylate (88 mg, yield 61.1%).

MS 504 (M+1).

Example 1-9

Production of 13-cyclohexyl-5-[2-(thiomorpholin-4-yl)ethyl]-6,7-dihydro-5H-benzo[5,6][1,4]diazepino[7,1-a]indole-10-carboxylic acid dihydrochloride

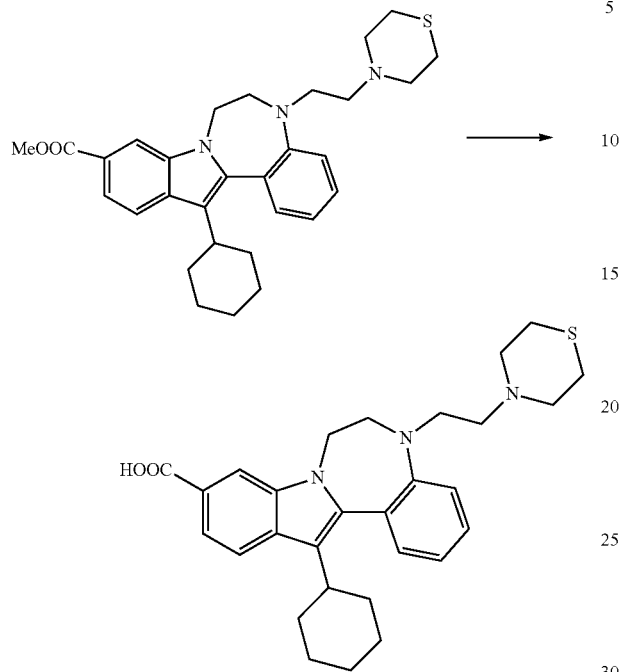

To a solution of methyl 13-cyclohexyl-5-[2-(thiomorpholin-4-yl)ethyl]-6,7-dihydro-5H-benzo[5,6][1,4]diazepino[7,1-a]indole-10-carboxylate (88 mg, 0.17 mmol) in tetrahydrofuran (1 ml) and methanol (1 ml) was added 4N aqueous sodium hydroxide solution (1 ml) and the mixture was stirred at room temperature for 20 hr. To the reaction mixture was added 1N hydrochloric acid to adjust to pH 7. The mixture was extracted with ethyl acetate and the organic layer was washed with saturated brine and dried over anhydrous sodium sulfate. After filtration, the solvent was evaporated under reduced pressure. To a solution of the residue in ethyl acetate (1 ml) was added 4N HCl-ethyl acetate solution (1 ml) and the solvent was evaporated under reduced pressure. Ethyl acetate was added to the residue and the precipitated solid was collected by filtration, washed with hexane and dried in vacuo to give 13-cyclohexyl-5-[2-(thiomorpholin-4-yl)ethyl]-6,7-dihydro-5H-benzo[5,6][1,4]diazepino[7,1-a]indole-10-carboxylic acid dihydrochloride (44 mg, yield 44.9%).
MS 490 (M+1).

Example 1-10

Production of methyl 3-chloro-13-cyclohexyl-6-oxo-6,7-dihydro-5H-benzo[5,6][1,4]diazepino[7,1-a]indole-10-carboxylate Step 1: Production of 5-chloro-2-(4,4,5,5-tetramethyl-1,3,2-dioxaborolan-2-yl)phenylamine

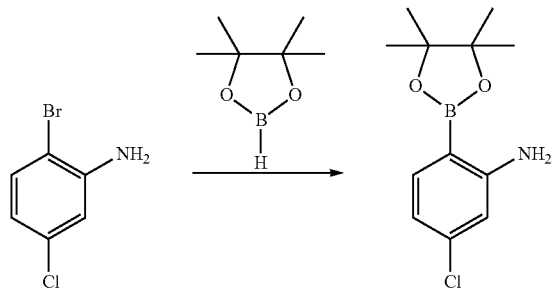

To a solution of 2-bromo-5-chloroaniline (20.0 g, 96.9 mmol) in 1,4-dioxane (200 ml) were added triethylamine (54.0 ml, 487 mmol) and [1,1-bis(diphenylphosphino)ferrocene]dichloropalladium(II) dichloromethane complex (3.96 g, 4.84 mmol), and under a nitrogen stream, 4,4,5,5-tetramethyl-1,3,2-dioxaborolane (42.3 ml, 290 mmol) was added dropwise. The mixture was stirred at 100° C. for 10.5 hr. The mixture was allowed to cool to room temperature and filtered through celite. To the filtrate was added dropwise methanol (25 ml) at 0° C. The solvent was evaporated under reduced pressure, and the obtained residue was purified by silica gel chromatography (hexane:ethyl acetate=20:1) to give 5-chloro-2-(4,4,5,5-tetramethyl-1,3,2-dioxaborolan-2-yl)phenylamine (16.5 g, yield. 65%).
$^1$H-NMR (400 MHz, DMSO-$d_6$): δ(ppm) 7.28 (1H, d, J=6.0 Hz), 6.59 (1H, d, J=1.2 Hz), 6.43 (1H, dd, J=6.3, 1.5 Hz), 5.70 (2H, s), 1.24 (12H, s).

Step 2: Production of methyl 2-(2-amino-4-chlorophenyl)-3-cyclohexyl-1H-indole-6-carboxylate

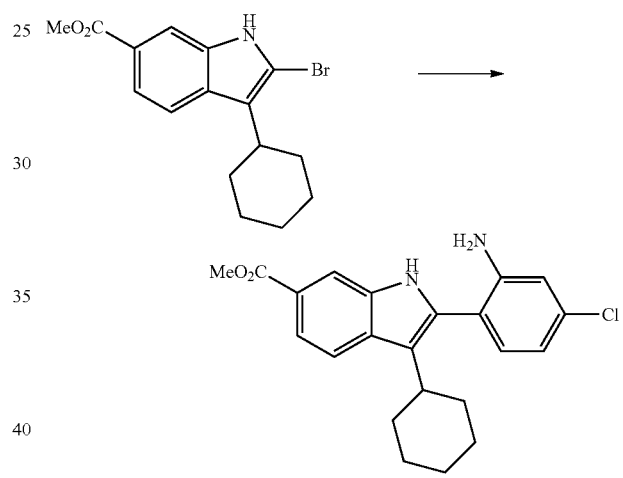

To a suspension of methyl 2-bromo-3-cyclohexyl-1H-indole-6-carboxylate (5.20 g, 15.4 mmol) obtained in the same manner as in the method described in WO03/010140 and 5-chloro-2-(4,4,5,5-tetramethyl-1,3,2-dioxaborolan-2-yl)phenylamine (4.11 g, 16.2 mmol) in 1,2-dimethoxyethane (20 ml) and water (10 ml) were added sodium hydrogen carbonate (4.10 g, 48.6 μmmol) and tetrakis(triphenylphosphine)palladium (1.87 g, 1.62 mmol) and the mixture was heated under reflux for 12 hr. The mixture was allowed to cool to room temperature, and water was added to the reaction mixture. The mixture was extracted with ethyl acetate and the organic layer was washed successively with saturated aqueous sodium hydrogen carbonate solution and saturated brine and dried over anhydrous magnesium sulfate. After filtration, the solvent was evaporated under reduced pressure and the residue was purified by silica gel chromatography (hexane: ethyl acetate=5:1) to give methyl 2-(2-amino-4-chlorophenyl)-3-cyclohexyl-1H-indole-6-carboxylate (6.17 g, yield 100%).
$^1$H-NMR (400 MHz, DMSO-$d_6$): δ(ppm) 11.33 (1H, br), 7.95 (1H, d, J=1.2 Hz), 7.79 (1H, d, J=8.4 Hz), 7.58 (1H, dd, J=8.0, 1.6 Hz), 7.02 (1H, d, J=8.0 Hz), 6.83 (1H, d, J=2.0 Hz), 6.65 (1H, dd, J=8.0, 2.4 Hz), 5.17 (2H, br), 3.84 (3H, s), 2.55-2.55 (1H, m), 1.64-1.91 (6H, m), 1.20-1.37 (4H, m).

Step 3: Production of methyl 2-[4-chloro-2-(2-chloroacetylamino)phenyl]-3-cyclohexyl-1H-indole-6-carboxylate

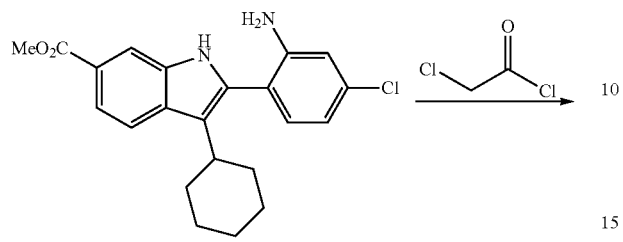

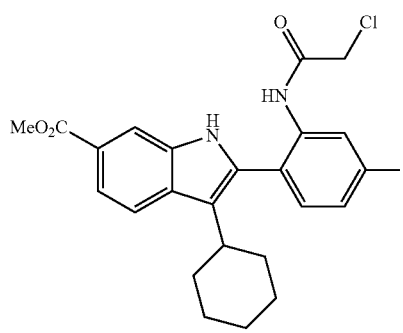

To a suspension of methyl 2-(2-amino-4-chlorophenyl)-3-cyclohexyl-1H-indole-6-carboxylate (6.17 g, 16.1 mmol), sodium acetate (1.39 g, 17.0 mmol) and acetic acid (0.98 ml, 17.0 mmol) in tetrahydrofuran (50 ml) was added dropwise chloroacetyl chloride (1.35 ml, 17.0 mmol), and the mixture was stirred at room temperature for 2 hr. The reaction mixture was concentrated under reduced pressure, and water was added. The precipitate was collected by filtration, washed with water and dried in vacuo to give methyl 2-[(4-chloro-2-(2-chloroacetylamino)phenyl]-3-cyclohexyl-1H-indole-6-carboxylate (6.71 g, yield 95%).

Step 4: Production of methyl 3-chloro-13-cyclohexyl-6-oxo-6,7-dihydro-5H-benzo[5,6][1,4]diazepino[7,1-a]indole-10-carboxylate

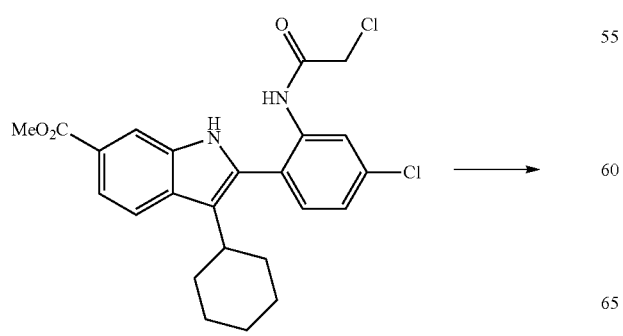

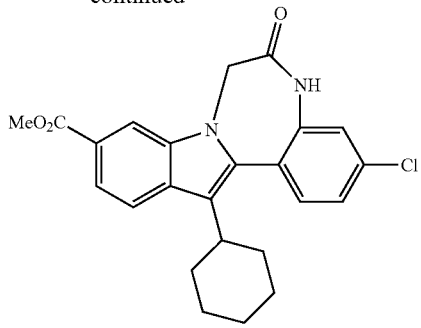

To a solution of methyl 2-[4-chloro-2-(2-chloroacetylamino)phenyl]-3-cyclohexyl-1H-indole-6-carboxylate (6.71 g, 14.6 mmol) in N,N-dimethylformamide (40 ml) and tetrahydrofuran (10 ml) was added sodium hydride (1.29 g, 3.21 mmol) under ice-cooling, and the mixture was stirred for 2 hr. The reaction mixture was concentrated under reduced pressure and water was added. The precipitate was collected by filtration, washed successively with water and hexane and dried in vacuo to give methyl 3-chloro-13-cyclohexyl-6-oxo-6,7-dihydro-5H-benzo[5,6][1,4]diazepino[7,1-a]indole-10-carboxylate (6.97 g, yield 100%).

$^1$H-NMR (400 MHz, DMSO-$d_6$): δ(ppm) 8.28 (1H, d, J=1.2 Hz), 7.96 (1H, d, J=8.4 Hz), 7.68 (1H, dd, J=8.4, 1.6 Hz), 7.52 (1H, d, J=8.4 Hz), 7.44 (1H, dd, J=8.4, 2.0 Hz), 7.31 (1H, d, J=2.0 Hz), 5.10 (1H, d, J=14.4 Hz), 4.58 (1H, d, J=14.8 Hz), 3.89 (3H, s), 2.81-2.81 (1H, m), 1.67-2.10 (5H, m), 1.37-1.56 (2H, m), 1.13-1.29 (3H, m).

Example 1-11

Production of methyl 3-chloro-13-cyclohexyl-6-oxo-5-[2-oxo-2-(piperidin-1-yl)ethyl]-6,7-dihydro-5H-benzo[5,6][1,4]diazepino[7,1-a]indole-10-carboxylate

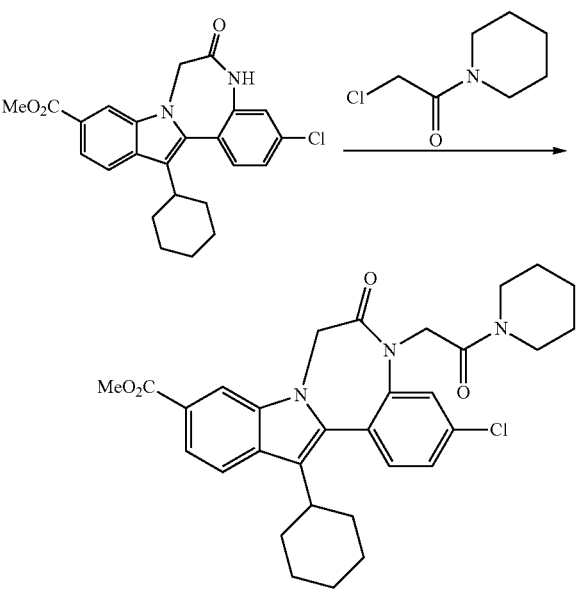

A suspension of methyl 3-chloro-13-cyclohexyl-6-oxo-6,7-dihydro-5H-benzo[5,6][1,4]diazepino[7,1-a]indole-10-carboxylate (2.00 g, 4.73 mmol), 1-(2-chloroacetyl)piperidine (1.15 g, 7.09 mmol) and potassium carbonate (1.31 g, 9.46 mmol) in N,N-dimethylformamide (20 ml) was stirred at 90° C. for 24 hr. The reaction mixture was concentrated under reduced pressure and water was added. The precipitate was collected by filtration, washed with water and dried in vacuo. A crude product was washed with a mixed solvent of hexane (45 ml) and diethyl ether (15 ml) and dried in vacuo to give methyl 3-chloro-13-cyclohexyl-6-oxo-5-[2-oxo-2-(piperidin-1-yl)ethyl]-6,7-dihydro-5H-benzo[5,6][1,4]diazepino[7,1-a]indole-10-carboxylate (2.16 g, yield 83%).

$^1$H-NMR (400 MHz, DMSO-d$_6$): δ(ppm) 8.29 (1H, d, J=1.6 Hz), 7.95 (1H, d, J=8.8 Hz), 7.68 (1H, dd, J=8.8, 1.6 Hz), 7.51-7.57 (3H, m), 5.22 (1H, d, J=14.8 Hz), 4.71 (1H, d, J=16.8 Hz), 4.56 (1H, d, J=14.8 Hz), 4.50 (1H, d, J=16.8 Hz), 3.89 (3H, s), 3.29-3.43 (4H, m), 2.83-2.83 (1H, m), 1.33-2.08 (16H, m).

Example 1-12

Production of methyl 3-chloro-13-cyclohexyl-5-[2-(piperidin-1-s yl)ethyl]-6,7-dihydro-5H-benzo[5,6][1,4]diazepino[7,1-a]indole-10-carboxylate

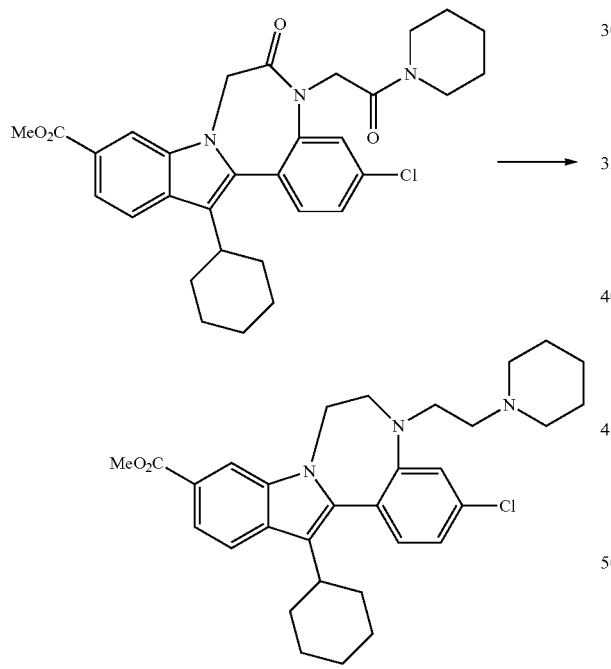

To a solution of methyl 3-chloro-13-cyclohexyl-6-oxo-5-[2-oxo-2-(piperidin-1-yl)ethyl]-6,7-dihydro-5H-benzo[5,6][1,4]diazepino[7,1-a]indole-10-carboxylate (3.80 g, 6.94 mmol) in tetrahydrofuran (10 ml) was added 1M BH$_3$ THF complex tetrahydrofuran solution (50 ml) under ice-cooling, and the mixture was stirred at room temperature for 4 hr. 2N Hydrochloric acid (40 ml) was added to the reaction mixture under ice-cooling, and the mixture was stirred at 70° C. for 12 hr. The reaction mixture was allowed to cool to room temperature, neutralized with saturated aqueous sodium hydrogen carbonate solution and extracted with ethyl acetate. The organic layer was washed with saturated brine and dried over anhydrous magnesium sulfate. After filtration, the solvent was evaporated under reduced pressure, and the residue was purified by silica gel chromatography (ethyl acetate:methanol=50:1) to give methyl 3-chloro-13-cyclohexyl-5-[2-(piperidin-1-yl)ethyl]-6,7-dihydro-5H-benzo[5,6][1,4]diazepino[7,1-a]indole-10-carboxylate (2.30 g, yield 64%).

$^1$H-NMR (400 MHz, DMSO-d$_6$): δ(ppm) 8.15 (1H, d, J=1.6 Hz), 7.84 (1H, d, J=8.8 Hz), 7.59 (1H, dd, J=8.4, 1.2 Hz), 7.30 (1H, d, J=2.0 Hz), 7.24 (1H, d, J=8.0 Hz), 7.15 (1H, dd, J=8.4, 2.4 Hz), 3.86-4.75 (4H, m), 3.84 (3H, s), 3.12-3.51 (4H, m), 2.74-2.74 (1H, m), 1.60-2.33 (12H, m), 1.09-1.40 (8H, m).

Example 1-13

Production of 3-chloro-13-cyclohexyl-5-[2-(piperidin-1-yl)ethyl]-6,7-dihydro-5H-benzo[5,6][1,4]diazepino[7,1-a]indole-10-carboxylic acid

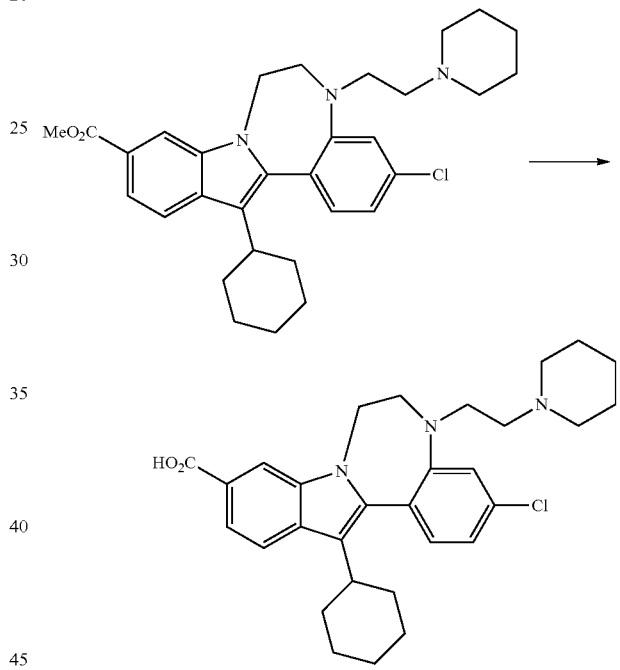

To a suspension of methyl 3-chloro-13-cyclohexyl-5-[2-(piperidin-1-yl)ethyl]-6,7-dihydro-5H-benzo[5,6][1,4]diazepino[7,1-a]indole-10-carboxylate (1.21 g, 2.32 mmol) in tetrahydrofuran (10 ml) and methanol (10 ml) was added 4N aqueous sodium hydroxide solution (3 ml), and the mixture was stirred at 90° C. for 8 hr. 1N Hydrochloric acid (12 ml) was added to adjust to pH 7, and the mixture was extracted with a mixed solvent of ethyl acetate and tetrahydrofuran. The organic layer was washed with saturated brine and dried over anhydrous sodium sulfate. After filtration, the solvent was evaporated under reduced pressure and crude crystals were washed with methanol, collected by filtration and dried in vacuo to give 3-chloro-13-cyclohexyl-5-[2-(piperidin-1-yl)ethyl]-6,7-dihydro-5H-benzo[5,6][1,4]diazepino[7,1-a]indole-10-carboxylic acid (884 mg, yield 72%).

$^1$H-NMR (400 MHz, DMSO-d$_6$): δ(ppm) 11.64 (1H, br), 8.14 (1H, d, J=1.2 Hz), 7.83 (1H, d, J=8.4 Hz), 7.60 (1H, dd, J=8.4, 1.2 Hz), 7.32 (1H, d, J=2.0 Hz), 7.26 (1H, d, J=8.0 Hz), 7.17 (1H, dd, J=8.4, 2.0 Hz), 3.03-4.93 (8H, m), 2.76-2.76 (1H, m), 1.59-2.34 (12H, m), 1.19-1.47 (8H, m).

MS 506 (M+1:Cl$^{35}$), 508 (M+1:Cl$^{37}$).

Example 1-14

Production of 3-chloro-13-cyclohexyl-5-[2-(piperidin-1-yl)ethyl]-6,7-dihydro-5H-benzo[5,6][1,4]diazepino[7,1-a]indole-10-carboxylic acid dihydrochloride

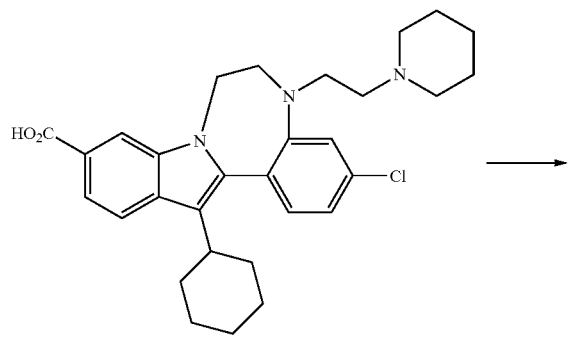

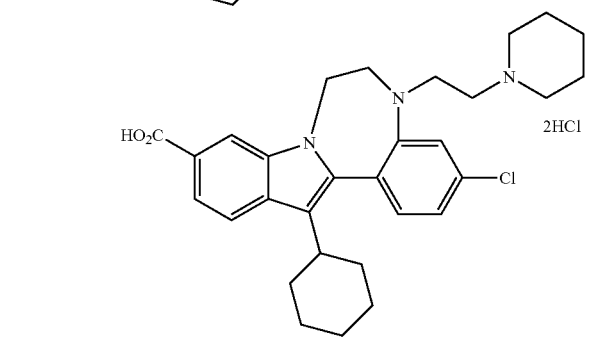

To a solution of 3-chloro-13-cyclohexyl-5-[2-(piperidin-1-yl)ethyl]-6,7-dihydro-5H-benzo[5,6][1,4]diazepino[7,1-a]indole-10-carboxylic acid (1.86 g, 3.67 mmol) in ethyl acetate (20 ml) was added 4N HCl-ethyl acetate solution (7 ml) at room temperature, and the mixture was stirred for 30 min. The reaction mixture was concentrated under reduced pressure. Diethyl ether was added to the crude crystals and the crystals were collected by filtration and washed with diethyl ether. The crystals were dried in vacuo to give 3-chloro-13-cyclohexyl-5-[2-(piperidin-1-yl)ethyl]-6,7-dihydro-5H-benzo[5,6][1,4]diazepino[7,1-a]indole-10-carboxylic acid dihydrochloride (2.13 g, yield 92%).

$^1$H-NMR (400 MHz, DMSO-$d_6$): δ(ppm) 10.23 (1H, br), 8.18 (1H, d, J=1.2 Hz), 7.85 (1H, d, J=8.4 Hz), 7.60 (1H, dd, J=8.4, 1.2 Hz), 7.35-7.38 (2H, m), 7.32 (1H, dd, J=8.0, 1.6 Hz), 2.88-4.98 (6H, m), 2.79-2.79 (1H, m), 2.52-2.61 (2H, m), 0.98-2.07 (20H, m).
MS 506 (M+1).

Example 1-15

Production of methyl 13-cyclohexyl-2-fluoro-6-oxo-6,7-dihydro-5H-benzo[5,6][1,4]diazepino[7,1-a]indole-10-carboxylate

Step 1: Production of 4-fluoro-2-(4,4,5,5-tetramethyl-1,3,2-dioxaborolan-2-yl)phenylamine

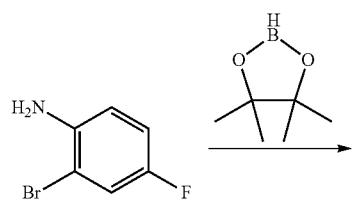

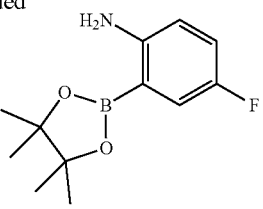

To a solution of 2-bromo-4-fluoroaniline (5.0 g, 26.3 mmol) in 1,4-dioxane (50 ml) were added triethylamine (18.5 ml, 132.7 mmol) and [1,1-bis(diphenylphosphino)ferrocene]dichloropalladium(II) dichloromethane complex (PdCl$_2$(dppf)CH$_2$Cl$_2$) (1.07 g, 1.3 mmol) at room temperature. To the mixture was added dropwise pinacolborane (11.5 ml, 79.2 mmol) at room temperature and the mixture was stirred at 100° C. for 27 hr. Saturated aqueous ammonium chloride solution was added to the reaction mixture and the mixture was extracted with ethyl acetate. The organic layer was washed with saturated brine and dried over anhydrous sodium sulfate. After filtration, the solvent was evaporated under reduced pressure and the residue was purified by silica gel chromatography (toluene) to give 4-fluoro-2-(4,4,5,5-tetramethyl-1,3,2-dioxaborolan-2-yl)phenylamine (2.0 g, yield 32.0%).

$^1$H-NMR (400 MHz, CDCl$_3$): δ(ppm) 7.28 (1H, d, J=3.2 Hz), 6.91 (1H, ddd, J=8.8, 8.8, 3.2 Hz), 6.53 (1H, dd, 3.6 Hz), 4.45 (2H, brs), 1.34 (12H, s).
MS 238 (M+1).

Step 2: Production of methyl 2-(2-amino-5-fluorophenyl)-3-cyclohexyl-1H-indole-6-carboxylate

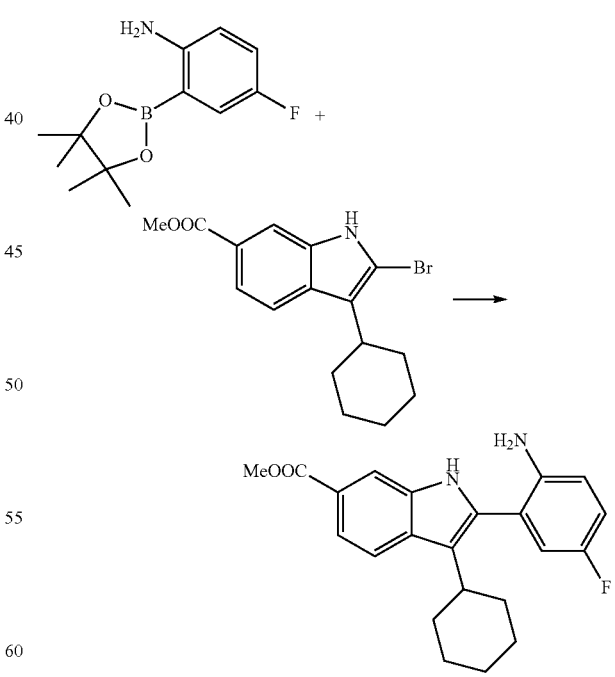

To a suspension of methyl 2-bromo-3-cyclohexyl-1H-indole-6-carboxylate (2.35 g, 6.98 mmol) obtained in the same manner as in the method described in WO03/010140 and 4-fluoro-2-(4,4,5,5-tetramethyl-1,3,2-dioxaborolan-2-yl)phenylamine (1.99 g, 8.38 mmol) in 1,2-dimethoxyethane (24 ml) and water (12 ml) were added sodium hydrogen carbonate (2.00 g, 24.0 mmol) and tetrakis(triphenylphosphine)palladium (400 mg, 0.34 mmol), and the mixture was heated under reflux for 14 hr. The mixture was allowed to cool to room temperature, and water was added to the reaction mixture. The mixture was extracted with ethyl acetate and the organic layer was washed with saturated brine and dried over anhydrous sodium sulfate. After filtration, the solvent was evaporated under reduced pressure and the residue was purified by silica gel chromatography (hexane:ethyl acetate=4:1-3:1) to give methyl 2-(2-amino-5-fluorophenyl)-3-cyclohexyl-1H-indole-6-carboxylate (2.44 g, yield 95.7%).

$^1$H-NMR (300 MHz, CDCl$_3$): δ(ppm) 8.22 (1H, brs), 8.09 (1H, brs), 7.82 (1H, d, J=6.0 Hz), 7.37-7.49 (1H, m), 7.17 (1H, brd, J=6.6 Hz), 6.89-7.03 (1H, m), 6.74 (1H, dd, J=8.1, 4.8 Hz), 3.94 (3H, s), 3.66 (2H, brs), 2.63-2.78 (1H, m), 1.70-2.01 (7H, m), 1.23-1.50 (3H, m).

Step 3: Production of methyl 2-[2-(2-chloroacetylamino)-5-fluorophenyl]-3-cyclohexyl-1H-indole-6-carboxylate

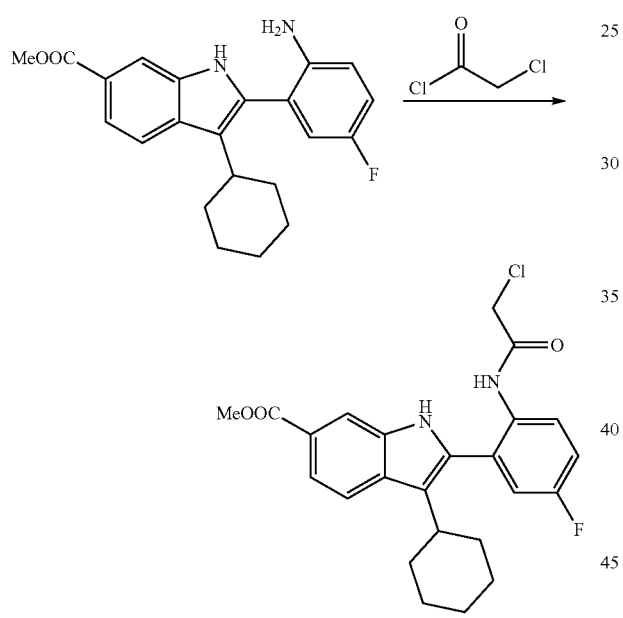

To a suspension of methyl 2-(2-amino-5-fluorophenyl)-3-cyclohexyl-1H-indole-6-carboxylate (2.44 g, 6.68 mmol), sodium acetate (602 mg, 7.3 mmol) and acetic acid (0.45 ml, 7.86 mmol) in tetrahydrofuran (20 ml) was added dropwise chloroacetyl chloride (0.60 ml, 7.53 mmol), and the mixture was stirred at room temperature for 2 hr. Saturated aqueous sodium hydrogen carbonate solution was added to the reaction mixture and the mixture was extracted with ethyl acetate. The organic layer was washed successively with saturated aqueous sodium carbonate solution and saturated brine and dried over anhydrous sodium sulfate. After filtration, the solvent was evaporated under reduced pressure and a mixed solvent of hexane:ethyl acetate (4:1) was added to the residue. The precipitated solid was collected by filtration to give methyl 2-[2-(2-chloroacetylamino)-5-fluorophenyl]-3-cyclohexyl-1H-indole-6-carboxylate (2.5 g, yield 84.7%).

$^1$H-NMR (400 MHz, DMSO-d$_6$): δ(ppm) 11.50 (1H, s), 9.49 (1H, s), 7.99 (1H, d, J=1.6 Hz), 7.85 (1H, dd, J=4.8, 4.8 Hz), 7.83 (1H, d, J=8.8 Hz), 7.60 (1H, dd, J=8.8, 1.6 Hz), 7.34 (1H, ddd, J=8.4, 8.4, 2.8 Hz), 7.21 (1H, dd, J=9.2, 3.2 Hz), 4.18 (2H, s), 3.85 (3H, s), 2.41-2.48 (1H, m), 1.78-1.92 (2H, m), 1.61-1.77 (5H, m), 1.21-1.34 (3H, m).

Step 4: Production of methyl 13-cyclohexyl-2-fluoro-6-oxo-6,7-dihydro-5H-benzo[5,6][1,4]diazepino[7,1-a]indole-10-carboxylate

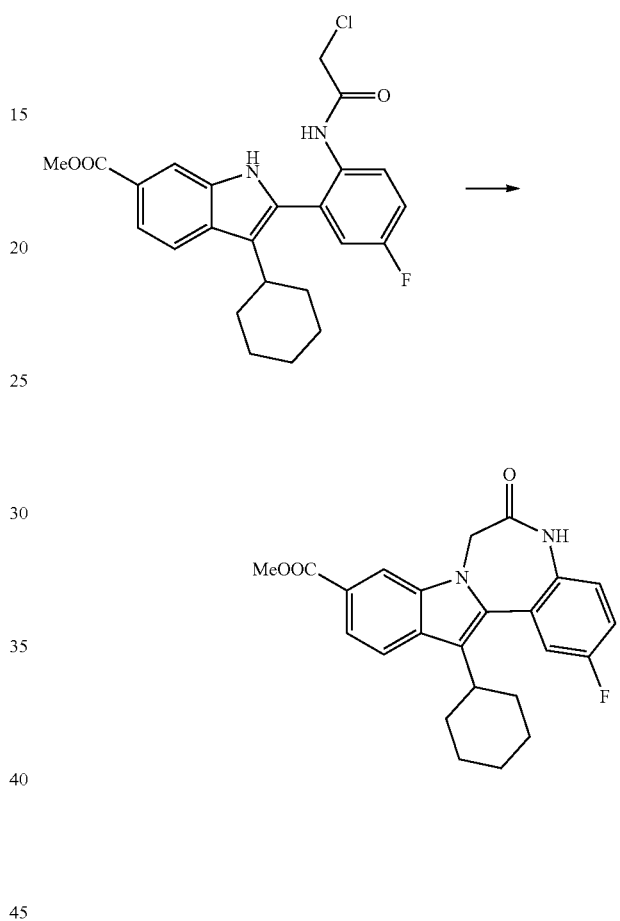

To a solution of methyl 2-[2-(2-chloroacetylamino)-5-fluorophenyl]-3-cyclohexyl-1H-indole-6-carboxylate (2.5 g, 5.6 mmol) in N,N-dimethylformamide was added sodium hydride (250 mg, 6.25 mmol) under ice-cooling, and the mixture was stirred for 2 hr. To the reaction mixture was added 1N hydrochloric acid and the mixture was extracted with ethyl acetate. The organic layer was washed with saturated brine and dried over anhydrous sodium sulfate. After filtration, the solvent was evaporated under reduced pressure and the residue was purified by silica gel chromatography (hexane:ethyl acetate=3:2-2:3) to give methyl 13-cyclohexyl-2-fluoro-6-oxo-6,7-dihydro-5H-benzo[5,6][1,4]diazepino[7,1-a]indole-10-carboxylate (1.81 g, yield 79.7%).

$^1$H-NMR (400 MHz, DMSO-d$_6$): δ(ppm) 10.33 (1H, s), 8.29 (1H, d, J=1.2 Hz), 7.98 (1H, d, J=8.4 Hz), 7.68 (1H, dd, J=8.4, 1.6 Hz), 7.41 (1H, ddd, J=8.4, 8.4, 2.8 Hz), 7.30 (1H, dd, J=8.8, 5.6 Hz), 7.26 (1H, dd, J=9.2, 3.2 Hz), 5.10 (1H, d, J=14.8 Hz), 4.57 (1H, d, J=14.8 Hz), 3.89 (3H, s), 2.79-2.90 (1H, m), 1.98-2.12 (3H, m), 1.86-1.94 (1H, m), 1.67-1.78 (2H, m), 1.48-1.57 (1H, m), 1.34-1.45 (2H, m), 1.16-1.28 (1H, m).

Example 1-16

Production of methyl 13-cyclohexyl-2-fluoro-6-oxo-5-[2-oxo-2-(piperidin-1-yl) ethyl]-6,7-dihydro-5H-benzo[5,6][1,4]diazepino[7,1-a]indole-10-carboxylate

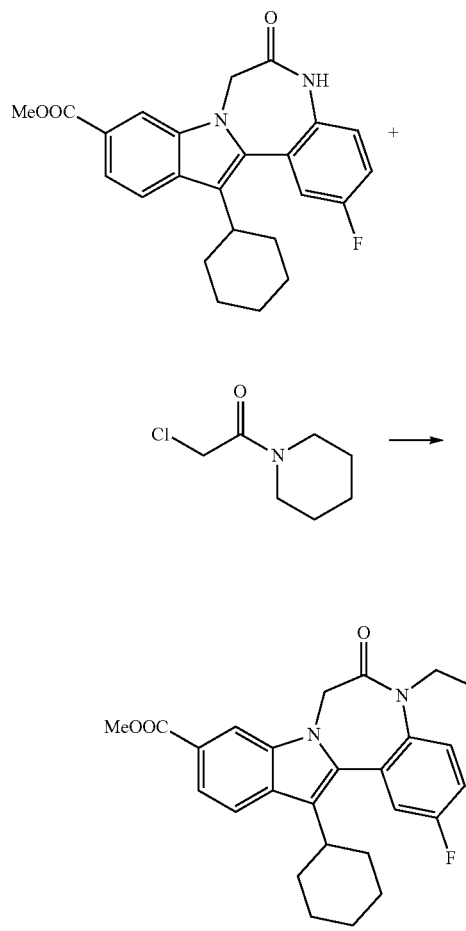

To a solution of methyl 13-cyclohexyl-2-fluoro-6-oxo-6,7-dihydro-5H-benzo[5,6][1,4]diazepino[7,1-a]indole-10-carboxylate (150 mg, 0.37 mmol) and 1-(2-chloroacetyl)piperidine (90 mg, 0.55 mmol) in N,N-dimethylformamide (2 ml) were added potassium carbonate (102 mg, 0.73 mmol) and potassium iodide (5 mg, 0.03 mmol) and the mixture was stirred at 90° C. for 3 hr. Water was added to the reaction mixture and the mixture was extracted with ethyl acetate. The organic layer was washed with saturated brine and dried over anhydrous sodium sulfate. After filtration, the solvent was evaporated under reduced pressure and the residue was purified by silica gel chromatography (hexane:ethyl acetate=1:1-1:2) to give methyl 13-cyclohexyl-2-fluoro-6-oxo-5-[2-oxo-2-(piperidin-1-yl)ethyl]-6,7-dihydro-5H-benzo[5,6][1,4]diazepino[7,1-a]indole-10-carboxylate (137 mg, yield 69.9%).

$^1$H-NMR (400 MHz, CDCl$_3$): δ(ppm) 8.22 (1H, brs), 7.89 (1H, d, J=8.4 Hz), 7.79 (1H, dd, J=8.4, 1.2 Hz), 7.61 (1H, dd, J=9.6, 5.2 Hz), 7.13-7.20 (2H, m), 5.00 (1H, d, J=14.4 Hz), 4.80 (1H, d, J=16.4 Hz), 4.55 (1H, d, J=14.4 Hz), 3.95 (1H, d, J=16.0 Hz), 3.95 (3H, s), 3.66-3.74 (1H, m), 3.49-3.58 (1H, m), 3.33-3.42 (1H, m), 3.22-3.31 (1H, m), 2.88-2.99 (1H, m), 1.92-2.17 (4H, m), 1.76-1.87 (2H, m), 1.23-1.72 (10H, m).

Example 1-17

Production of methyl 13-cyclohexyl-2-fluoro-5-[2-(piperidin-1-yl)ethyl]-6,7-dihydro-5H-benzo[5,6][1,4]diazepino[7,1-a]indole-10-carboxylate

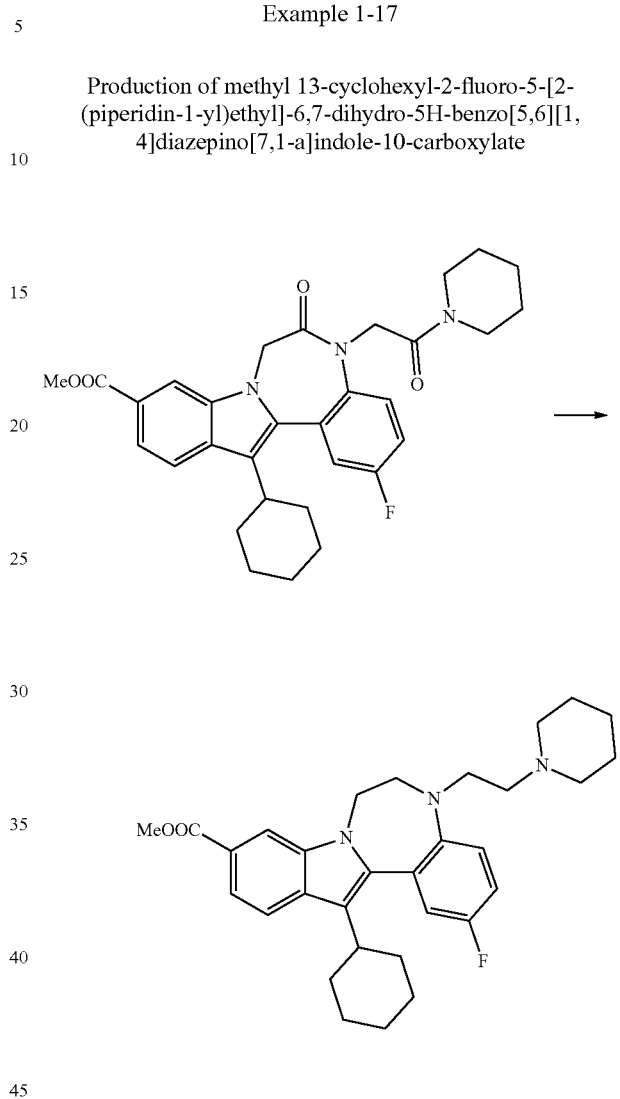

To a solution of methyl 13-cyclohexyl-2-fluoro-6-oxo-5-[2-oxo-2-(piperidin-1-yl)ethyl]-6,7-aihydro-5H-benzo[5,6][1,4]diazepino[7,1-a]indole-10-carboxylate (137 mg, 0.25 mmol) in tetrahydrofuran (1.0 ml) was added 1M BH$_3$ THF complex tetrahydrofuran solution (2.0 ml) under ice-cooling stirred, and the mixture was stirred at room temperature for 3 hr. 2N Hydrochloric acid was added to the reaction mixture, and the mixture was stirred at 70° C. for 3 hr. 4N Aqueous sodium hydroxide solution was added to adjust to pH 8 and the mixture was extracted with ethyl acetate. The organic layer was washed with saturated brine and dried over anhydrous sodium sulfate. After filtration, the solvent was evaporated under reduced pressure and the residue was purified by silica gel chromatography (chloroform:methanol=30:1-10:1) to give methyl 13-cyclohexyl-2-fluoro-5-[2-(piperidin-1-yl)ethyl]-6,7-dihydro-5H-benzo[5,6][1,4]diazepino[7,1-a]indole-10-carboxylate (91 mg, yield 70.5%).

MS 504 (M+1).

Example 1-18

Production of 13-cyclohexyl-2-fluoro-5-[2-(piperidin-1-yl)ethyl]-6,7-dihydro-5H-benzo[5,6][1,4]diazepino[7,1-a]indole-10-carboxylic acid dihydrochloride

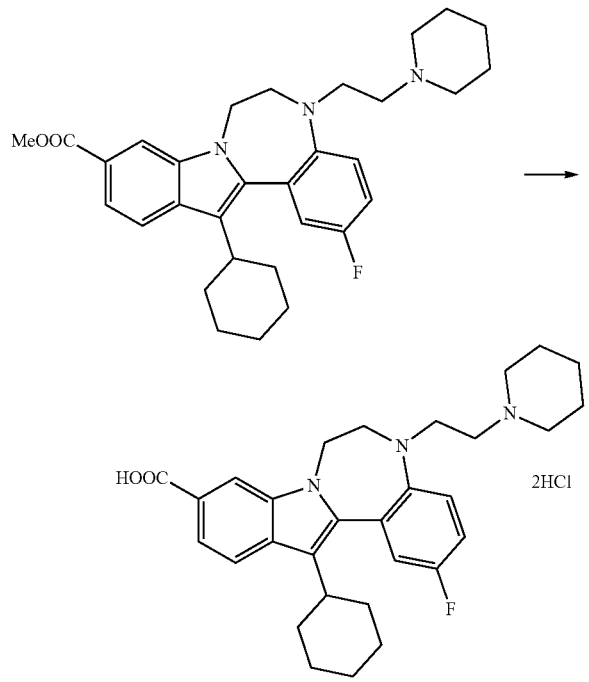

To a solution of methyl 13-cyclohexyl-2-fluoro-5-[2-(piperidin-1-yl)ethyl]-6,7-dihydro-5H-benzo[5,6][1,4]diazepino[7,1-a]indole-10-carboxylate (91 mg, 0.18 mmol) in tetrahydrofuran (1.0 ml) and methanol (1.0 ml) was added 4N aqueous sodium hydroxide solution (1.0 ml), and the mixture was stirred at 60° C. for 3 hr. 1N Hydrochloric acid was added to the reaction mixture to adjust to pH 7 and the mixture was extracted with ethyl acetate. The organic layer was washed with saturated brine and dried over anhydrous sodium sulfate. After filtration, the solvent was evaporated under reduced pressure. To a solution of the residue in tetrahydrofuran (1.0 ml) was added 4N HCl-ethyl acetate solution (1 ml) and the solvent was evaporated under reduced pressure. Hexane was added and the precipitated solid was collected by filtration. The solid was washed with hexane and dried in vacuo to give 13-cyclohexyl-2-fluoro-5-[2-(piperidin-1-yl)ethyl]-6,7-dihydro-5H-benzo[5,6][1,4]diazepino[7,1-a]indole-10-carboxylic acid dihydrochloride (64 mg, yield 63.4%).

MS 490.2 (M+1).

The compounds of Examples 1-19 to 1-95 were produced by the same method as in Examples 1-1 to 1-18 or a method similar thereto, and where necessary, employing other conventional methods. Chemical structural formulas are shown in Tables 2-20.

5-acetyl-13-cyclohexyl-6,7-dihydro-5H-benzo[5,6][1,4]diazepino[7,1-a]indole-10-carboxylic acid (Example 1-19),
13-cyclohexyl-5-methyl-6,7-dihydro-5H-benzo[5,6][1,4]diazepino[7,1-a]indole-10-carboxylic acid (Example 1-20),
13-cyclohexyl-5-dimethylcarbamoylmethyl-6,7-dihydro-5H-benzo[5,6][1,4]diazepino[7,1-a]indole-10-carboxylic acid (Example 1-21),
5-benzyl-13-cyclohexyl-6,7-dihydro-5H-benzo[5,6][1,4]diazepino[7,1-a]indole-10-carboxylic acid (Example 1-22),
13-cyclohexyl-5-isopropyl-6,7-dihydro-5H-benzo[5,6][1,4]diazepino[7,1-a]indole-10-carboxylic acid monohydrochloride (Example 1-23),
13-cyclohexyl-6-oxo-6,7-dihydro-5H-benzo[5,6][1,4]diazepino[7,1-a]indole-10-carboxylic acid (Example 1-24),
5-(benzylcarbamoylmethyl)-13-cyclohexyl-6,7-dihydro-5H-benzo[5,6][1,4]diazepino[7,1-a]indole-10-carboxylic acid (Example 1-25),
13-cyclohexyl-5-[2-(morpholin-4-yl)-2-oxoethyl]-6,7-dihydro-5H-benzo[5,6][1,4]diazepino[7,1-a]indole-10-carboxylic acid (Example 1-26),
13-cyclohexyl-5-[2-(morpholin-4-yl)ethyl]-6,7-dihydro-5H-benzo[5,6][1,4]diazepino[7,1-a]indole-10-carboxylic acid dihydrochloride (Example 1-27),
13-cyclohexyl-5-dimethylcarbamoylmethyl-3-methoxy-6,7-dihydro-5H-benzo[5,6][1,4]diazepino[7,1-a]indole-10-carboxylic acid (Example 1-28),
13-cyclohexyl-5-[2-oxo-2-(piperidin-1-yl)ethyl]-6,7-dihydro-5H-benzo[5,6][1,4]diazepino[7,1-a]indole-10-carboxylic acid (Example 1-29),
13-cyclohexyl-5-[2-(4-ethylpiperazin-1-yl)-2-oxoethyl]-6,7-dihydro-5H-benzo[5,6][1,4]diazepino[7,1-a]indole-10-carboxylic acid dihydrochloride (Example 1-30),
13-cyclohexyl-5-dimethylcarbamoyl-6,7-dihydro-5H-benzo[5,6][1,4]diazepino[7,1-a]indole-10-carboxylic acid (Example 1-31),
13-cyclohexyl-5-[2-(piperidin-1-yl)ethyl]-6,7-dihydro-5H-benzo[5,6][1,4]diazepino[7,1-a]indole-10-carboxylic acid dihydrochloride (Example 1-32),
13-cyclohexyl-5-{[(pyridin-2-ylmethyl)carbamoyl]methyl}-6,7-dihydro-5H-benzo[5,6][1,4]diazepino[7,1-a]indole-10-carboxylic acid dihydrochloride (Example 1-33),
13-cyclohexyl-5-{2-[(pyridin-2-ylmethyl)amino]ethyl}-6,7-dihydro-5H-benzo[5,6][1,4]diazepino[7,1-a]indole-10-carboxylic acid trihydrochloride (Example 1-34),
13-cyclohexyl-5-[2-(4-hydroxypiperidin-1-yl)-2-oxoethyl]-6,7-dihydro-5H-benzo[5,6][1,4]diazepino[7,1-a]indole-10-carboxylic acid monohydrochloride (Example 1-35),
13-cyclohexyl-5-[2-(4-methoxypiperidin-1-yl)-2-oxoethyl]-6,7-dihydro-5H-benzo[5,6][1,4]diazepino[7,1-a]indole-10-carboxylic acid monohydrochloride (Example 1-36),
13-cyclohexyl-5-{[N-(2-methoxyethyl)-N-methylcarbamoyl]methyl}-6,7-dihydro-5H-benzo[5,6][1,4]diazepino[7,1-a]indole-10-carboxylic acid monohydrochloride (Example 1-37),
13-cyclohexyl-5-[2-(4-ethylpiperazin-1-yl)ethyl]-6,7-dihydro-5H-benzo[5,6][1,4]diazepino[7,1-a]indole-10-carboxylic acid dihydrochloride (Example 1-38),
13-cyclohexyl-5-[2-(4-methoxypiperidin-1-yl)ethyl]-6,7-dihydro-5H-benzo[5,6][1,4]diazepino[7,1-a]indole-10-carboxylic acid dihydrochloride (Example 1-39),
13-cyclohexyl-5-{2-[N-(2-methoxyethyl)-N-methylamino]ethyl}-6,7-dihydro-5H-benzo[5,6][1,4]diazepino[7,1-a]indole-10-carboxylic acid dihydrochloride (Example 1-40),
13-cyclohexyl-5-phenethyl-6,7-dihydro-5H-benzo[5,6][1,4]diazepino[7,1-a]indole-10-carboxylic acid monohydrochloride (Example 1-41),
13-cyclohexyl-5-[2-(4-hydroxypiperidin-1-yl)ethyl]-6,7-dihydro-5H-benzo[5,6][1,4]diazepino[7,1-a]indole-10-carboxylic acid dihydrochloride (Example 1-42),
13-cyclohexyl-5-[2-(4-dimethylaminopiperidin-1-yl)-2-oxoethyl]-6,7-dihydro-5H-benzo[5,6][1,4]diazepino[7,1-a]indole-10-carboxylic acid dihydrochloride (Example 1-43), 13-cyclohexyl-5-[2-(4-dimethylaminopiperidin-1-yl)ethyl]-6,7-dihydro-5H-benzo[5,6][1,4]diazepino[7,1-a]indole-10-carboxylic acid trihydrochloride (Example 1-44), 13-cyclohexyl-5-[2-(1,1-dioxothiomorpholin-4-yl)-2-oxoethyl]-6,7-dihydro-5H-benzo[5,6][1,4]diazepino[7,1-a]indole-10-carboxylic acid monohydrochloride (Example 1-45), 13-cyclohexyl-5-[2-(4-ethoxycarbonylpiperazin-1-yl)-2-oxoethyl]-6,7-dihydro-5H-benzo[5,6][1,4]diazepino[7,1-a]indole-10-carboxylic acid monohydrochloride (Example 1-46), 13-cyclohexyl-5-[2-(4-isopropylpiperazin-1-yl)-2-oxoethyl]-6,7-dihydro-5H-benzo[5,6][1,4]diazepino[7,1-a]indole-10-carboxylic acid dihydrochloride (Example 1-47), 13-cyclohexyl-5-[2-(4-isopropylpiperazin-1-yl)ethyl]-6,7-dihydro-5H-benzo[5,6][1,4]diazepino[7,1-a]indole-10-carboxylic acid trihydrochloride (Example 1-48), 13-cyclohexyl-5-[2-(1,4-oxazepan-4-yl)-2-oxoethyl]-6,7-dihydro-5H-benzo[5,6][1,4]diazepino[7,1-a]indole-10-carboxylic acid monohydrochloride (Example 1-49), 13-cyclohexyl-5-[2-(4-methylpiperazin-1-yl)-2-oxoethyl]6,7-dihydro-5H-benzo[5,6][1,4]diazepino[7,1-a]indole-10-carboxylic acid dihydrochloride (Example 1-50), 5-[2-(4-acetylpiperazin-1-yl)-2-oxoethyl]-13-cyclohexyl-6,7-dihydro-5H-benzo[5,6][1,4]diazepino[7,1-a]indole-10-carboxylic acid monohydrochloride (Example 1-51), 13-cyclohexyl-5-[2-(4-methylpiperazin-1-yl)ethyl]-6,7-dihydro-5H-benzo[5,6][1,4]diazepino[7,1-a]indole-10-carboxylic acid trihydrochloride (Example 1-52), 13-cyclohexyl-5-[2-(4-methyl-1,4-diazepan-1-yl)ethyl]-6,7-dihydro-5H-benzo[5,6][1,4]diazepino[7,1-a]indole-10-carboxylic acid trihydrochloride (Example 1-53), 13-cyclohexyl-5-[2-(4-methyl-1,4-diazepan-1-yl)-2-oxoethyl]-6,7-dihydro-5H-benzo[5,6][1,4]diazepino[7,1-a]indole-10-carboxylic acid dihydrochloride (Example 1-54), 13-cyclohexyl-5-[2-(4-ethylpiperazin-1-yl)-2-oxoethyl]-6,7-dihydro-5H-benzo[5,6][1,4]diazepino[7,1-a]indole-10-carboxamide (Example 1-55), 13-cyclohexyl-5-[2-oxo-2-(pyrrolidin-1-yl)ethyl]-6,7-dihydro-5H-benzo[5,6][1,4]diazepino[7,1-a]indole-10-carboxylic acid monohydrochloride (Example 1-56), 13-cyclohexyl-5-[2-(pyrrolidin-1-yl)ethyl]-6,7-dihydro-5H-benzo[5,6][1,4]diazepino[7,1-a]indole-10-carboxylic acid dihydrochloride (Example 1-57), 13-cyclohexyl-5-[2-(morpholin-4-yl)-2-oxoethyl]-7-phenyl-6,7-dihydro-5H-benzo[5,6][1,4]diazepino[7,1-a]indole-10-carboxylic acid monohydrochloride (Example 1-58), 13-cyclohexyl-7-phenyl-6,7-dihydro-5H-benzo[5,6][1,4]diazepino[7,1-a]indole-10-carboxylic acid monohydrochloride (Example 1-59), 3-chloro-13-cyclohexyl-5-[2-(morpholin-4-yl)-2-oxoethyl]-6,7-dihydro-5H-benzo[5,6][1,4]diazepino[7,1-a]indole-10-carboxylic acid monohydrochloride (Example 1-60), 13-cyclohexyl-5-[4-(morpholin-4-yl)-4-oxobutyl]-6,7-dihydro-5H-benzo[5,6][1,4]diazepino[7,1-a]indole-10-carboxylic acid monohydrochloride (Example 1-61), 13-cyclohexyl-5-[4-(4-ethylpiperazin-1-yl)-4-oxobutyl]-6,7-dihydro-5H-benzo[5,6][1,4]diazepino[7,1-a]indole-10-carboxylic acid dihydrochloride (Example 1-62), 13-cyclohexyl-3-methyl-5-[2-(morpholin-4-yl)-2-oxoethyl]-6,7-dihydro-5H-benzo[5,6][1,4]diazepino[7,1-a]indole-10-carboxylic acid monohydrochloride (Example 1-63), 13-cyclohexyl-3-methoxy-5-[2-(morpholin-4-yl)-2-oxoethyl]-6,7-dihydro-5H-benzo[5,6][1,4]diazepino[7,1-a]indole-10-carboxylic acid monohydrochloride (Example 1-64), 13-cyclohexyl-3-methoxy-5-[2-oxo-2-(piperidin-1-yl)ethyl]-6,7-dihydro-5H-benzo[5,6][1,4]diazepino[7,1-a]indole-10-carboxylic acid monohydrochloride (Example 1-65), 13-cyclohexyl-5-[2-(4-ethylpiperazin-1-yl)-2-oxoethyl]-3-methoxy-6,7-dihydro-5H-benzo[5,6][1,4]diazepino[7,1-a]indole-10-carboxylic acid dihydrochloride (Example 1-66), 13-cyclohexyl-3-methoxy-5-[2-(morpholin-4-yl)ethyl]-6,7-dihydro-5H-benzo[5,6][1,4]diazepino[7,1-a]indole-10-carboxylic acid dihydrochloride (Example 1-67), 13-cyclohexyl-3-methyl-5-[2-(morpholin-4-yl)ethyl]-6,7-dihydro-5H-benzo[5,6][1,4]diazepino[7,1-a]indole-10-carboxylic acid dihydrochloride (Example 1-68), 13-cyclohexyl-5-[2-(1,4-oxazepan-4-yl)ethyl]-6,7-dihydro-5H-benzo[5,6][1,4]diazepino[7,1-a]indole-10-carboxylic acid dihydrochloride (Example 1-69), 13-cyclohexyl-5-[2-(4-methanesulfonylpiperazin-1-yl)-2-oxoethyl]-6,7-dihydro-5H-benzo[5,6][1,4]diazepino[7,1-a]indole-10-carboxylic acid monohydrochloride (Example 1-70), 13-cyclohexyl-5-[2-(4-ethylpiperidin-1-yl)-2-oxoethyl]-6,7-dihydro-5H-benzo[5,6][1,4]diazepino[7,1-a]indole-10-carboxylic acid monohydrochloride (Example 1-71), 13-cyclohexyl-5-[2-(4-methylpiperidin-1-yl)-2-oxoethyl]-6,7-dihydro-5H-benzo[5,6][1,4]diazepino[7,1-a]indole-10-carboxylic acid monohydrochloride (Example 1-72), 13-cyclohexyl-5-[2-(4-ethylpiperidin-1-yl)ethyl]-6,7-dihydro-5H-benzo[5,6][1,4]diazepino[7,1-a]indole-10-carboxylic acid dihydrochloride (Example 1-73), 13-cyclohexyl-3-methoxy-5-[2-(piperidin-1-yl)ethyl]-6,7-dihydro-5H-benzo[5,6][1,4]diazepino[7,1-a]indole-10-carboxylic acid dihydrochloride (Example 1-74), 13-cyclohexyl-5-[2-(4-methylpiperidin-1-yl)ethyl]-6,7-dihydro-5H-benzo[5,6][1,4]diazepino[7,1-a]indole-10-carboxylic acid dihydrochloride (Example 1-75), 3-chloro-13-cyclohexyl-5-[2-(4-ethylpiperazin-1-yl)-2-oxoethyl]-6,7-dihydro-5H-benzo[5,6][1,4]diazepino[7,1-a]indole-10-carboxylic acid dihydrochloride (Example 1-76), 3-chloro-13-cyclohexyl-5-[2-oxo-2-(piperidin-1-yl)ethyl]-6,7-dihydro-5H-benzo[5,6][1,4]diazepino[7,1-a]indole-10-carboxylic acid monohydrochloride (Example 1-77), 5-[2-(azepan-1-yl)-2-oxoethyl]-13-cyclohexyl-6,7-dihydro-5H-benzo[5,6][1,4]diazepino[7,1-a]indole-10-carboxylic acid monohydrochloride (Example 1-78), 3-chloro-13-cyclohexyl-5-[2-(morpholin-4-yl)ethyl]-6,7-dihydro-5H-benzo[5,6][1,4]diazepino[7,1-a]indole-10-carboxylic acid dihydrochloride (Example 1-79), 13-cyclohexyl-5-[4-(morpholin-4-yl)butyl]-6,7-dihydro-5H-benzo[5,6][1,4]diazepino[7,1-a]indole-10-carboxylic acid dihydrochloride (Example 1-80), 13-cyclohexyl-5-[2-oxo-2-(4-phenylpiperazin-1-yl)ethyl]-6,7-dihydro-5H-benzo[5,6][1,4]diazepino[7,1-a]indole-10-carboxylic acid dihydrochloride (Example 1-81), 13-cyclohexyl-5-[2-(4-phenylpiperazin-1-yl)ethyl]-6,7-dihydro-5H-benzo[5,6][1,4]diazepino[7,1-a]indole-10-carboxylic acid trihydrochloride (Example 1-82), 5-[2-(azepan-1-yl)ethyl]-13-cyclohexyl-6,7-dihydro-5H-benzo[5,6][1,4]diazepino[7,1-a]indole-10-carboxylic acid dihydrochloride (Example 1-83), 13-cyclohexyl-5-[2-(4-ethylpiperazin-1-yl)-2-oxoethyl]-N-methyl-6,7-dihydro-5H-benzo[5,6][1,4]diazepino[7,1-a]indole-10-carboxamide (Example 1-84), 13-cyclohexyl-5-[2-(4-ethylpiperazin-1-yl)-2-oxoethyl]-N-(2-hydroxyethyl)-6,7-dihydro-5H-benzo[5,6][1,4]diazepino[7,1-a]indole-10-carboxamide (Example 1-85), 13-cyclohexyl-5-[2-(4-ethylpiperazin-1-yl)-2-oxoethyl]-N-(2-hydroxy-1,1-dimethylethyl)-6,7-dihydro-5H-benzo[5,6][1,4]diazepino[7,1-a]indole-10-carboxamide (Example 1-86), 13-cyclohexyl-5-[2-(4-dimethylcarbamoylpiperazin-1-yl)ethyl]-6,7-dihydro-5H-benzo[5,6][1,4]diazepino[7,1-a]indole-10-carboxylic acid dihydrochloride (Example 1-87), 5-[2-(4-benzoylpiperazin-1-yl)ethyl]-13-cyclohexyl-6,7-dihydro-5H-benzo[5,6][1,4]diazepino[7,1-a]indole-10-carboxylic acid dihydrochloride (Example 1-88), 5-[2-(1-tert-butoxycarbonylpiperidin-4-yl)ethyl]-13-cyclohexyl-6,7-dihydro-5H-benzo[5,6][1,4]diazepino[7,1-a]indole-10-carboxylic acid (Example 1-89), 13-cyclohexyl-5-[2-(2-oxopyrrolidin-1-yl)ethyl]-6,7-dihydro-5H-benzo[5,6][1,4]diazepino[7,1-a]indole-10-carboxylic acid monohydrochloride (Example 1-90), 13-cyclohexyl-5-[2-(4-methanesulfonylpiperazin-1-yl)ethyl]-6,7-dihydro-5H-benzo[5,6][1,4]diazepino[7,1-a]indole-10-carboxylic acid dihydrochloride (Example 1-91), 5-[2-(1-acetylpiperidin-4-yl)ethyl]-13-cyclohexyl-6,7-dihydro-5H-benzo[5,6][1,4]diazepino[7,1-a]indole-10-carboxylic acid monohydrochloride (Example 1-92), 13-cyclohexyl-5-[2-(1-ethylpiperidin-4-yl)ethyl]-6,7-dihydro-5H-benzo[5,6][1,4]diazepino[7,1-a]indole-10-carboxylic acid dihydrochloride (Example 1-93), 13-cyclohexyl-5-[2-(1-methanesulfonylpiperidin-4-yl)ethyl]-6,7-dihydro-5H-benzo[5,6][1,4]diazepino[7,1-a]indole-10-carboxylic acid monohydrochloride (Example 1-94), 5-[2-(4-tert-butoxycarbonylpiperazin-1-yl)ethyl]-13-cyclohexyl-6,7-dihydro-5H-benzo[5,6][1,4]diazepino[7,1-a]indole-10-carboxylic acid dihydrochloride (Example 1-95).

Example 1-168

Production of 13-cyclohexyl-3-methyl-5-[2-(1,4-oxazepan-4-yl)ethyl]-6,7-dihydro-5H-benzo[5,6][1,4]diazepino[7,1-a]indole-10-carboxylic acid Step 1: Production of N-chloroacetyl-1,4-oxazepane

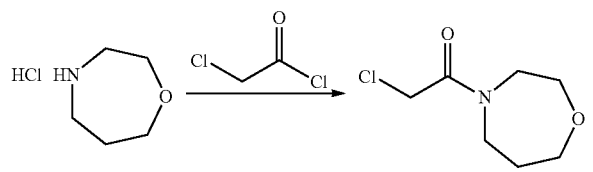

A suspension of 1,4-oxazepane hydrochloride (24.80 g, 180 mmol), sodium acetate (29.60 g, 360 mmol) and acetic acid (20.6 ml, 360 mmol) in tetrahydrofuran (400 ml) was stirred for 1 hr, a solution of chloroacetyl chloride (14.3 ml, 180 mmol) in tetrahydrofuran (100 ml) was added dropwise under ice-cooling, and the mixture was stirred overnight at room temperature. To the reaction mixture was added, sodium hydrogen carbonate (65.7 g, 792 μmmol), and the mixture was stirred for 1 hr. The insoluble material was filtered, and the filtrate was concentrated. The obtained residue was purified by silica gel column chromatography (hexane: ethyl acetate=2:1-1:2) to give N-chloroacetyl-1,4-oxazepane (29.8 g, yield 93%).

$^1$H-NMR (400 MHz, DMSO-d$_6$): δ(ppm) 4.42 (1H, s), 4.39 (1H, s), 3.70-3.72 (1H, m), 3.54-3.65 (7H, m), 1.82-1.88 (1H, m), 1.72-1.78 (1H, m).

Step 2: Production of methyl 13-cyclohexyl-3-methyl-5-[2-(1,4-oxazepan-4-yl)-2-oxoethyl]-6-oxo-6,7-dihydro-5H-benzo[5,6][1,4]diazepino[7,1-a]indole-10-carboxylate

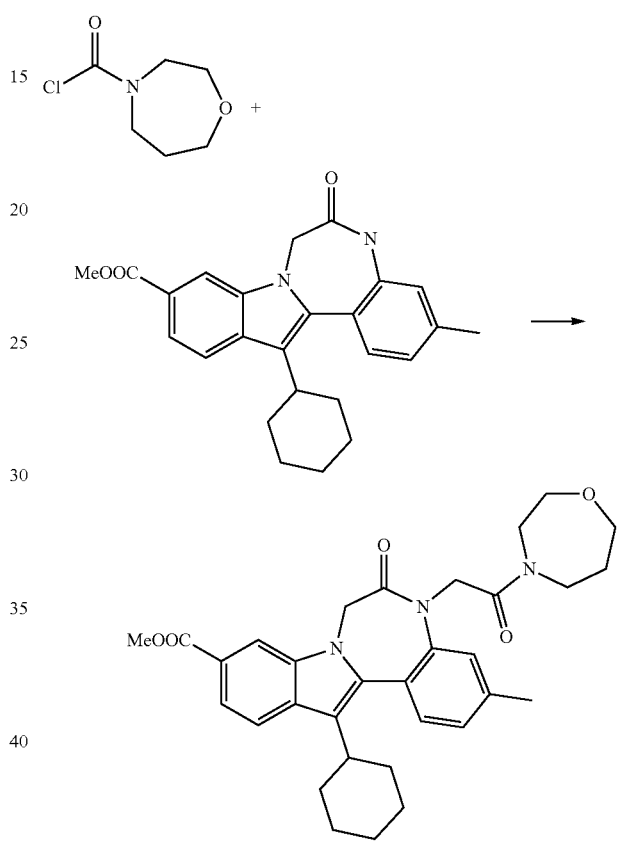

A suspension of methyl 13-cyclohexyl-3-methyl-6-oxo-6,7-dihydro-5H-benzo[5,6][1,4]diazepino[7,1-a]indole-10-carboxylate (2.53 g, 6.30 mmol), N-chloroacetyl-1,4-oxazepane (1.23 g, 6.92 mmol) and potassium carbonate (1.73 g, 12.6 mmol) in N,N-dimethylformamide (13 ml) was stirred at 90° C. for 3 hr. To the reaction mixture was added 2N hydrochloric acid (13 ml), and the precipitated solid was collected by filtration. After washing with water, the solid was dried in vacuo and suspended in methanol. The suspension was stirred for 1 hr, and the obtained crystals were collected by filtration. The crystals were washed with methanol and dried in vacuo to give methyl 13-cyclohexyl-3-methyl-5-[2-(1,4-oxazepan-4-yl)-2-oxoethyl]-6-oxo-6,7-dihydro-5H-benzo[5,6][1,4]diazepino[7,1-a]indole-10-carboxylate (2.85 g, yield 83%).

$^1$H-NMR (400 MHz, DMSO-d$_6$) δ(ppm) 8.28 (1H, s), 7.95 (1H, d, J=8.8 Hz), 7.68 (1H, dd, J=8.0, 1.2 Hz), 7.42 (1H, d, J=7.6 Hz), 7.29-7.33 (2H, m), 5.20 (1H, d, J=14.4 Hz), 4.68 (1H, dd, J=16.8, 9.6 Hz), 4.48 (1H, d, J=14.4 Hz), 4.40 (1H, d, J=18.0 Hz), 3.89 (3H, s), 3.38-3.71 (8H, m), 2.82-2.93 (1H, m), 2.41 (3H, s), 1.67-2.09 (8H, m), 1.53-1.61 (1H, m), 1.34-1.48 (2H, m), 1.12-1.26 (1H, m).

Step 3: Production of methyl 13-cyclohexyl-3-methyl-5-[2-(1,4-oxazepan-4-yl)ethyl]-6,7-dihydro-5H-benzo[5,6][1,4]diazepino[7,1-a]indole-10-carboxylate Step 4: Production of 13-cyclohexyl-3-methyl-5-[2-(1,4-oxazepan-4-yl)ethyl]-6,7-dihydro-5H-benzo[5,6][1,4]diazepino[7,1-a]indole-10-carboxylic acid

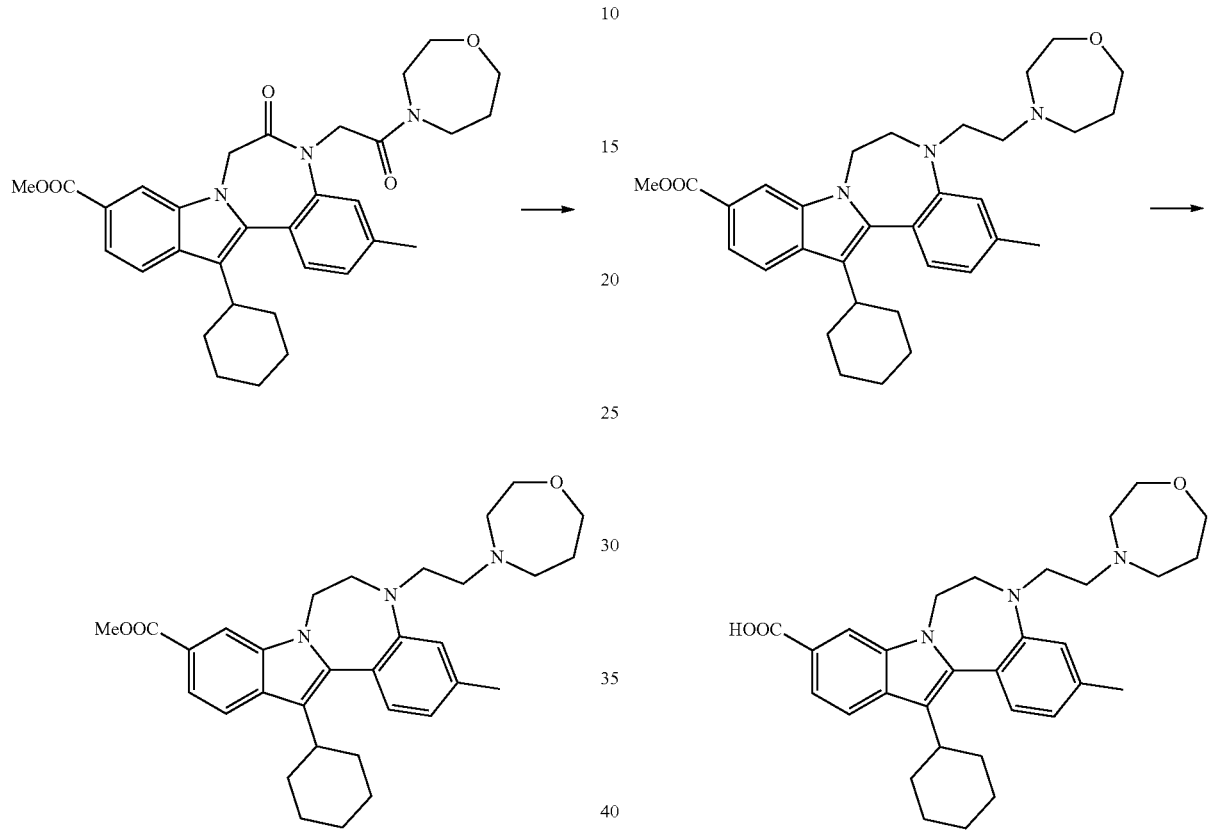

To a solution of methyl 13-cyclohexyl-3-methyl-5-[2-(1,4-oxazepan-4-yl)-2-oxoethyl]-6-oxo-6,7-dihydro-5H-benzo[5,6][1,4]diazepino[7,1-a]indole-10-carboxylate (2.70 g, 4.97 mmol) in tetrahydrofuran (8 ml) was added a solution (20 ml) of 1M BH$_3$ THF complex in tetrahydrofuran, and the mixture was stirred at room temperature for 3 hr. To the reaction mixture was added 4N hydrochloric acid (14 ml), and the mixture was stirred at 70° C. for 4 hr. The reaction mixture was allowed to cool to room temperature, neutralized with 4N aqueous sodium hydroxide solution and saturated aqueous sodium hydrogen carbonate solution, and extracted with ethyl acetate. The organic layer was washed with saturated brine and dried over anhydrous sodium sulfate. After filtration, the solvent was evaporated under reduced pressure. The residue was crystallized from methanol (10 ml) and collected by filtration. After washing with methanol, the crystals were dried in vacuo to give methyl 13-cyclohexyl-3-methyl-5-[2-(1,4-oxazepan-4-yl)ethyl]-6,7-dihydro-5H-benzo[5,6][1,4]diazepino[7,1-a]indole-10-carboxylate (2.27 g, yield 89%).

$^1$H-NMR (400 MHz, DMSO-d$_6$): δ(ppm) 8.17 (1H, d, J=1.2 Hz), 7.85 (1H, d, J=8.8 Hz), 7.61 (1H, dd, J=8.4, 1.2 Hz), 7.19 (1H, d, J=7.6 Hz), 7.07 (1H, s), 6.98 (1H, d, J=7.6 Hz), 3.87 (3H, s), 3.42 (2H, t, J=6.0 Hz), 3.26-3.29 (2H, m), 2.76-2.85 (1H, m), 2.42-2.48 (4H, m), 2.38 (3H, s), 1.91-2.06 (2H, m), 1.63-1.86 (5H, m), 1.49-1.54 (2H, m), 1.19-1.44 (3H, m).

To a solution of methyl 13-cyclohexyl-3-methyl-5-[2-(1,4-oxazepan-4-yl)ethyl]-6,7-dihydro-5H-benzo[5,6][1,4]diazepino[7,1-a]indole-10-carboxylate (2.00 g, 3.88 mmol) in tetrahydrofuran (12 ml) and methanol (12 ml) was added 4N aqueous sodium hydroxide solution (3 ml), and the mixture was stirred at 80° C. for 3 hr. The reaction mixture was adjusted to pH 6.5 with 2N hydrochloric acid, and extracted with chloroform. The organic layer was washed with saturated brine and dried over anhydrous sodium sulfate. After filtration, the solvent was evaporated under reduced pressure. The residue was crystallized from methanol (10 ml) and collected by filtration. After washing with methanol, the crystals were dried in vacuo to give 13-cyclohexyl-3-methyl-5-[2-(1,4-oxazepan-4-yl)ethyl]-6,7-dihydro-5H-benzo[5,6][1,4]diazepino[7,1-a]indole-10-carboxylic acid (1.48 g, yield 76%).

$^1$H-NMR (400 MHz, DMSO-d$_6$): δ (ppm) 12.53 (1H, brs), 8.13 (1H, d, J=1.2 Hz), 7.82 (1H, d, J=8.4 Hz), 7.59 (1H, dd, J=8.4, 1.2 Hz), 7.18 (1H, d, J=7.6 Hz), 7.07 (1H, s), 6.98 (1H, d, J=7.6 Hz), 3.43 (2H, t, J=5.8 Hz), 3.27-3.29 (2H, m), 2.76-2.85 (1H, m), 2.43-2.47 (4H, m), 2.38 (3H, s), 1.92-2.07 (2H, m), 1.59-1.88 (5H, m), 1.49-1.55 (2H, m), 1.19-1.44 (3H, m).

MS 502.3 (M+1).

Example 1-413

Production of 13-cyclohexyl-5-{2-[(S)-3-(2-methoxyethyl)piperidin-1-yl]ethyl}-3-methyl-6,7-dihydro-5H-benzo[5,6][1,4]diazepino[7,1-a]indole-10-carboxylic acid dihydrochloride

Step 1: Production of (3'S)-2-[1-(tert-butoxycarbonyl)piperidin-3-yl]ethanol

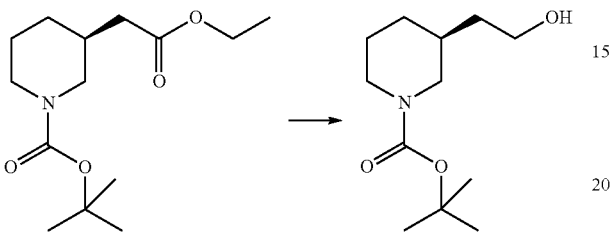

To a suspension of lithium aluminum hydride (11.90 g, 313 mmol) in tetrahydrofuran (250 ml) was added a solution of (3'S)-ethyl-2-[1-(tert-butoxycarbonyl)piperidin-3-yl]acetate (85.0 g, 313 mmol), obtained in the same manner as in the method described in WO97/25041, in tetrahydrofuran (600 ml) over 2 hr under ice-cooling, and the mixture was further stirred for 3 hr. To the reaction mixture were successively added water (12 ml), 4N aqueous sodium hydroxide solution (36 ml), water (12 ml) and anhydrous magnesium sulfate, and the mixture was stirred at room temperature for 1 hr. Insoluble material was filtered off, and the solvent was evaporated under reduced pressure to give (3'S)-2-[1-(tert-butoxycarbonyl)piperidin-3-yl]ethanol (58.10 g, yield 97.6%).

$^1$H-NMR (400 MHz, CDCl$_3$): δ(ppm) 3.84 (1H, m), 3.71 (3H, m), 2.80 (1H, m), 2.53 (1H, br), 1.82 (2H, m), 1.60 (2H, m), 1.46 (3H, m), 1.43 (9H, s), 1.12 (1H, m).

Step 2: Production of tert-butyl (S)-3-(2-methoxyethyl)piperidine-1-carboxylate

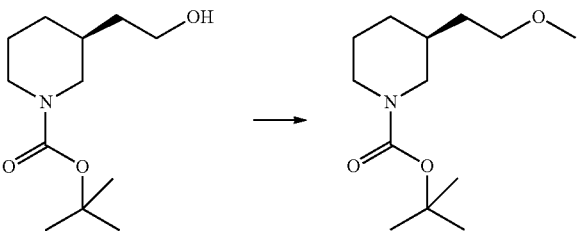

To a suspension of sodium hydride (13.00 g, 325 mmol) in tetrahydrofuran (60 ml) and N,N-dimethylformamide (350 ml) was added a solution of (3'S)-2-[1-(tert-butoxycarbonyl)piperidin-3-yl]ethanol (62.00 g, 270 mmol) in N,N-dimethylformamide (200 ml) at room temperature, and the mixture was stirred for 15 min. To the reaction mixture was added methyl iodide (18.5 ml, 297 mmol) at room temperature, and the mixture was stirred at room temperature for 3 hr. To the reaction mixture was added water, and the mixture was extracted with ethyl acetate. The organic layer was washed with saturated brine and dried over anhydrous magnesium sulfate. After filtration, the solvent was evaporated under reduced pressure to give tert-butyl (S)-3-(2-methoxyethyl)piperidine-1-carboxylate (65.0 g, yield 98%).

$^1$H-NMR (300 MHz, CDCl$_3$): δ(ppm) 3.85-3.88 (1H, m), 3.40 (2H, t, J=6.6 Hz), 3.31 (3H, s), 2.77-2.77 (1H, m), 1.80-1.80 (2H, m), 1.48-1.63 (4H, m), 1.43 (9H, s), 1.10-1.10 (1H, m), 0.84-0.84 (1H, m).

Step 3: Production of (S)-3-(2-methoxyethyl)piperidine hydrochloride

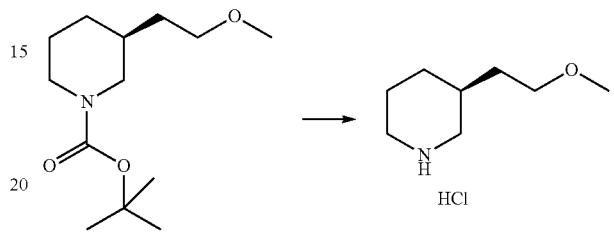

To a solution of tert-butyl (S)-3-(2-methoxyethyl)piperidine-1-carboxylate (64 g, 263 mmol) in ethyl acetate (100 ml) was added 4N HCl-ethyl acetate solution (320 ml), and the mixture was stirred at room temperature for 2 hr. The solvent was evaporated under reduced pressure to give (S)-3-(2-methoxyethyl)piperidine hydrochloride as a crude product (46.7 g, yield 98%). The obtained crude product was used for Step 4 without further purification.

$^1$H-NMR (400 MHz, CDCl$_3$): δ(ppm) 9.59 (1H, br), 9.26 (1H, br), 3.35-3.45 (4H, m), 3.28 (3H, s), 2.67-2.80 (1H, m), 2.48-2.60 (1H, m), 2.03-2.14 (1H, m), 1.80-1.99 (3H, m), 1.45-1.59 (2H, m), 1.09-1.21 (1H, m).

Step 4: Production of (S)-3-(2-methoxyethyl)-N-(chloroacetyl)piperidine

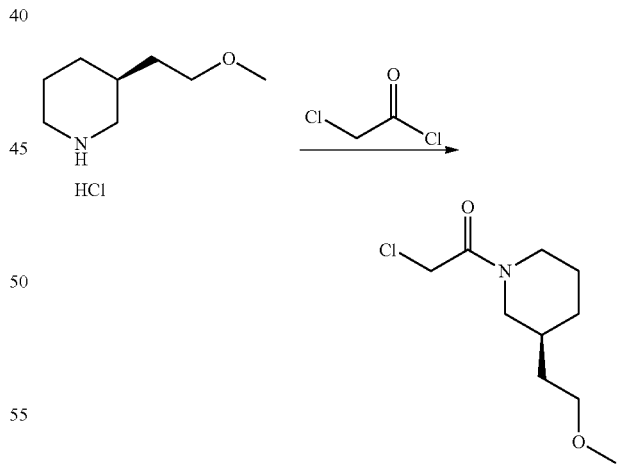

To a suspension of (S)-3-(2-methoxyethyl)piperidine hydrochloride (46.70 g, 260 mmol), sodium acetate (46.90 g, 572 mmol) and acetic acid (33.1 ml, 572 mmol) in tetrahydrofuran (470 ml) was added dropwise chloroacetyl chloride (28.3 ml, 7.53 mmol) under ice-cooling, and the mixture was stirred overnight at temperature. To the reaction mixture was added saturated aqueous sodium hydrogen carbonate solution, and the mixture was extracted with ethyl acetate. The organic layer was washed successively with saturated aqueous sodium hydrogen carbonate solution and saturated brine and dried over anhydrous magnesium sulfate. After filtration, the solvent was evaporated under reduced pressure, and the obtained residue was purified by silica gel column chromatography (hexane:ethyl acetate=1:1) to give (S)-3-(2-methoxyethyl)-N-(chloroacetyl)piperidine (45.0 g, yield 78.8%).

$^1$H-NMR (400 MHz, CDCl$_3$): δ(ppm) 4.28-4.37 (1H, m), 3.69-3.81 (1H, m), 3.37-3.46 (2H, m), 3.32 (1.5H, s), 3.30 (1.5H, s), 3.05-3.12 (0.5H, m), 2.75-2.81 (0.5H, m), 2.63-2.70 (0.5H, m), 2.45-2.51 (0.5H, m), 1.83-1.91 (1H, m), 1.40-1.77 (5H, m), 1.14-1.23 (1H, m).

Step 5: Production of 2-iodo-5-methylphenylamine hydrochloride

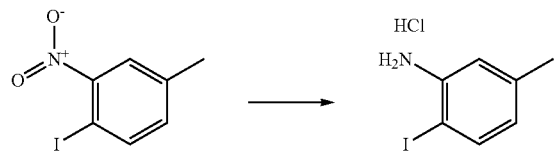

To a solution of 1-iodo-4-methyl-2-nitrobenzene (5.00 g, 19 mmol) in tetrahydrofuran (12.5 ml), methanol (25 ml) and water (6.3 ml) were added reduced iron (5.30 g, 95 mmol) and ammonium chloride (6.10 g, 114 mmol), and the mixture was stirred overnight at 70° C. The reaction mixture was allowed to cool to room temperature, tetrahydrofuran (50 ml) was added to the reaction mixture. After filtration through celite, the filtrate was concentrated under reduced pressure. Water was added to the residue, and the mixture was extracted with ethyl acetate. The organic layer was washed with saturated brine and dried over anhydrous sodium sulfate. After filtration, the solvent was evaporated under reduced pressure. To a solution of the residue in ethyl acetate (20 ml) was added 4N HCl-ethyl acetate solution (10 ml). The precipitated solid was collected by filtration, washed with ethyl acetate, and dried in vacuo to give 2-iodo-5-methylphenylamine hydrochloride (2.56 g, yield 50%).

$^1$H-NMR (300 MHz, DMSO-d$_6$): δ(ppm) 8.34 (2H, brs), 7.56 (1H, d, J=8.1 Hz), 6.93 (1H, s), 6.51 (1H, d, J=7.8 Hz), 2.20 (3H, s).

Step 6: Production of 5-methyl-2-(4,4,5,5-tetramethyl-1,3,2-dioxaborolan-2-yl)phenylamine

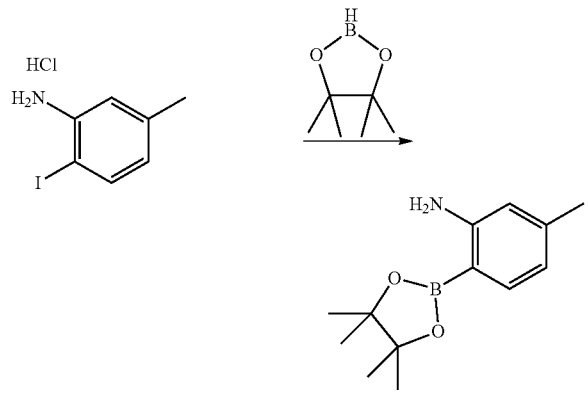

To a solution of 2-iodo-5-methylphenylamine hydrochloride (1.00 g, 3.7 mmol) in 1,4-dioxane (15 ml) were added triethylamine (2.6 ml, 18.6 mmol) and PdCl$_2$(dppf) CH$_2$Cl$_2$ (151 mg, 0.19 mmol) at room temperature. To the mixture was added dropwise pinacolborane (1.62 ml, 11.1 mmol) at room temperature, and the mixture was stirred at 100° C. for 4 hr. To the reaction mixture was added saturated aqueous ammonium chloride solution, and the mixture was extracted with diethyl ether. The organic layer was washed with saturated brine and dried over anhydrous sodium sulfate. After filtration, the solvent was evaporated under reduced pressure, and the obtained residue was purified by silica gel chromatography (hexane:ethyl acetate=5:1) to give 5-methyl-2-(4,4,5,5-tetramethyl-1,3,2-dioxaborolan-2-yl)phenylamine (570 mg, yield 66%).

$^1$H-NMR (400 MHz, CDCl$_3$): δ(ppm) 7.48 (1H, d, J=6.0 Hz), 6.49 (1H, d, J=6.0 Hz), 6.41 (1H, s), 4.66 (2H, brs), 2.24 (3H, s), 1.32 (12H, s).

Step 7: Production of methyl 2-(2-amino-4-methylphenyl)-3-cyclohexyl-1H-indole-6-carboxylate hydrochloride

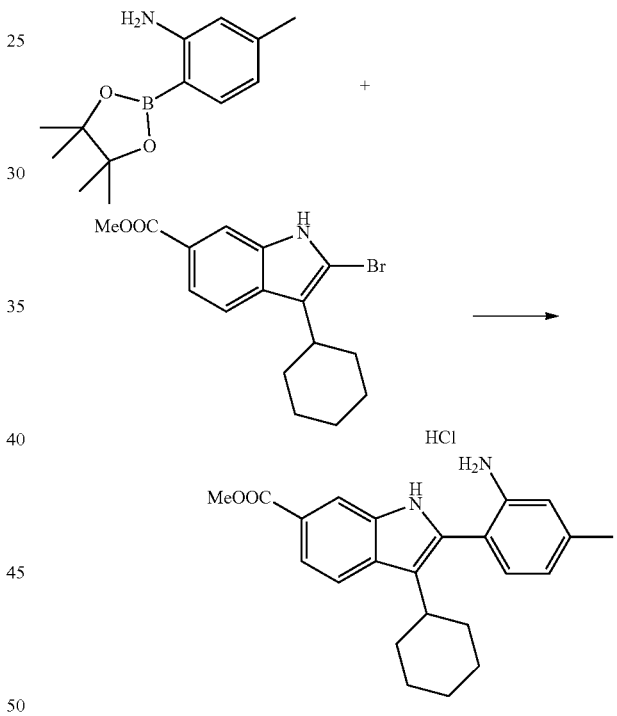

To a suspension of methyl 2-bromo-3-cyclohexyl-1H-indole-6-carboxylate (656 mg, 2.0 mmol), obtained in the same manner as in the method described in WO03/010140, and 5-methyl-2-(4,4,5,5-tetramethyl-1,3,2-dioxaborolan-2-yl) phenylamine (570 mg, 2.4 mmol) in 1,2-dimethoxyethane (13 ml) and water (6.5 ml) were added sodium hydrogen carbonate (508 mg, 7.1 mmol) and tetrakis(triphenylphosphine)palladium (118 mg, 0.10 mmol), and the mixture was stirred at 80° C. for 3 hr. The reaction mixture was allowed to cool to room temperature. Water was added to the reaction mixture, and the mixture was extracted with ethyl acetate. The organic layer was washed with saturated brine and dried over anhydrous sodium sulfate. After filtration, the solvent was evaporated under reduced pressure. To a solution of the residue in ethyl acetate (2 ml) was added 4N HCl-ethyl acetate solution (2 ml). The precipitated solid was collected by filtration, washed with diethyl ether, and dried in vacuo.

The obtained crude product (638 mg) was used for Step 8 without further purification.

Step 8: Production of methyl 2-[2-(2-chloroacetylamino)-4-methylphenyl]-3-cyclohexyl-1H-indole-6-carboxylate

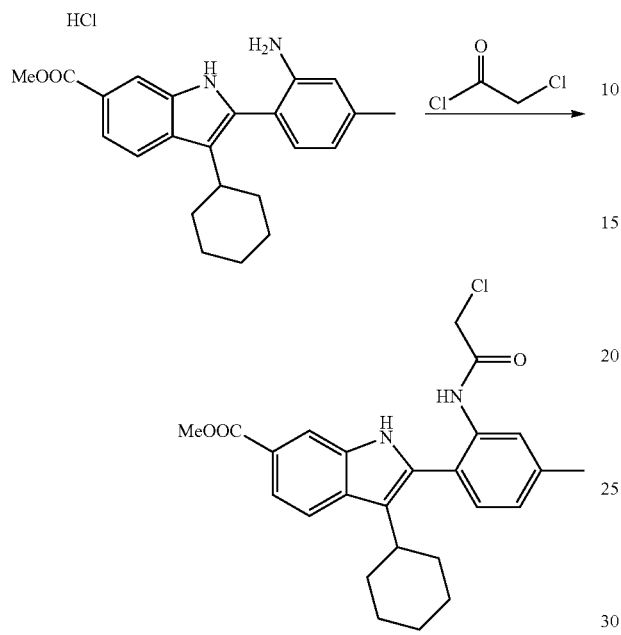

To a suspension of methyl 2-(2-amino-4-methylphenyl)-3-cyclohexyl-1H-indole-6-carboxylate (638 mg, 1.6 mmol), sodium acetate (289 mg, 3.5 mmol) and acetic acid (0.10 ml, 1.8 mmol) in tetrahydrofuran (7 ml) was added dropwise chloroacetyl chloride (0.14 ml, 1.8 mmol), and the mixture was stirred at room temperature for 12 hr. Water was added to the reaction mixture, and the mixture was extracted with ethyl acetate. The organic layer was washed with saturated brine and dried over anhydrous sodium sulfate. After filtration, the solvent was evaporated under reduced pressure. The obtained crude product (640 mg) was used for Step 9 without further purification.

Step 9: Production of methyl 13-cyclohexyl-3-methyl-6-oxo-6,7-dihydro-5H-benzo[5,6][1,4]diazepino[7,1-a]indole-10-carboxylate

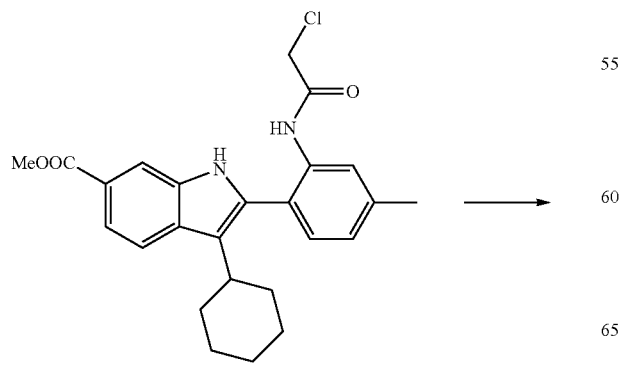

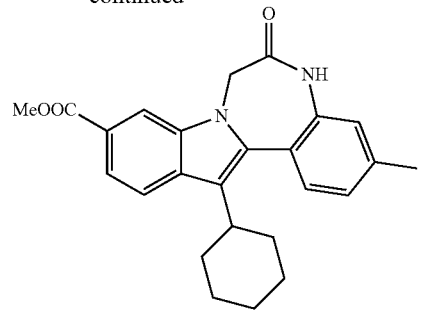

To a solution of methyl 2-[2-(2-chloroacetylamino)-4-methylphenyl]-3-cyclohexyl-1H-indole-6-carboxylate (640 mg, 1.5 mmol) in N,N-dimethylformamide (10 ml) was added sodium hydride (141 mg, 3.5 mmol) under ice-cooling, and the mixture was stirred for 5 hr. 1N Hydrochloric acid (5 ml) was added to the reaction mixture, and the mixture was diluted with water. The precipitated solid was collected by filtration, washed with water and hexane, and dried in vacuo to give methyl 13-cyclohexyl-3-methyl-6-oxo-6,7-dihydro-5H-benzo[5,6][1,4]diazepino[7,1-a]indole-10-carboxylate (614 mg, yield 95%).

$^1$H-NMR (300 MHz, DMSO-$d_6$): δ(ppm) 10.28 (1H, s), 8.26 (1H, s), 7.95 (1H, d, J=8.4 Hz), 7.68 (1H, dd, J=9.0, 1.5 Hz), 7.43 (1H, d, J=8.1 Hz), 7.22 (1H, d, J=7.8 Hz), 7.09 (1H, s), 5.06 (1H, d, J=15.0 Hz), 4.50 (1H, d, J=14.4 Hz), 3.89 (3H, s), 2.80-2.89 (1H, m); 2.40 (3H, s), 1.98-2.08 (3H, m), 1.86-1.93 (1H, m), 1.68-1.79 (2H, m), 1.36-1.55 (3H, m), 1.13-1.25 (1H, m).

Step 10: Production of methyl 13-cyclohexyl-5-{2-[(S)-3-(2-methoxyethyl)piperidin-1-yl]-2-oxoethyl}-3-methyl-6-oxo-6,7-dihydro-5H-benzo[5,6][1,4]diazepino[7,1-a]indole-10-carboxylate

377

-continued

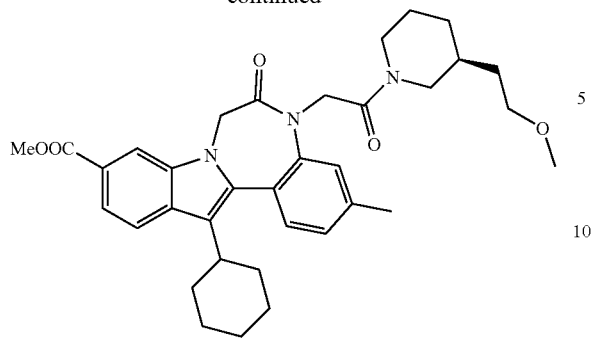

A suspension of methyl 13-cyclohexyl-3-methyl-6-oxo-6,7-dihydro-5H-benzo[5,6][1,4]diazepino[7,1-a]indole-10-carboxylate (1.00 g, 2.48 mmol), (S)-3-(2-methoxyethyl)-N-(chloroacetyl)piperidine (819 mg, 3.72 mmol) and potassium carbonate (696 mg, 4.96 mmol) in N,N-dimethylformamide (20 ml) was stirred at 80° C. for 3 hr. The reaction mixture was allowed to cool to room temperature. Water was added and the mixture was extracted with ethyl acetate. The organic layer was washed successively with saturated aqueous sodium hydrogen carbonate solution and saturated brine, and dried over anhydrous magnesium sulfate. After filtration, the solvent was evaporated under reduced pressure, and the obtained residue was purified by silica gel chromatography (hexane:ethyl acetate=1:1) to give methyl 13-cyclohexyl-5-{2-[(S)-3-(2-methoxyethyl)piperidin-1-yl]-2-oxoethyl}-3-methyl-6-oxo-6,7-dihydro-5H-benzo[5,6][1,4]diazepino[7,1-a]indole-10-carboxylate (967 mg, yield 67%).

$^1$H-NMR (400 MHz, DMSO-d$_6$): δ(ppm) 8.24 (1H, s), 7.91 (1H, d, J=6.0 Hz), 7.65 (1H, dd, J=6.3, 1.2 Hz), 7.38 (1H, d, J=6.0 Hz), 7.24-7.28 (2H, m), 5.15 (1H, d, J=10.8 Hz), 4.56-4.66 (1H, m), 4.34-4.47 (2H, m), 3.93-4.06 (1H, m), 3.86 (3H, s), 3.51-3.67 (1H, m), 3.21-3.31 (1H, m), 3.09-3.18 (3H, m), 2.80-3.02 (2H, m), 2.55-2.68 (1H, m), 2.38 (3H, s), 1.93-2.03 (3H, m), 1.84-1.88 (1H, m), 1.66-1.75 (3H, m), 1.52-1.59 (2H, m), 1.05-1.45 (9H, m).

Step 11: Production of methyl 13-cyclohexyl-5-{2-[(S)-3-(2-methoxyethyl)piperidin-1-yl]ethyl}-3-methyl-6,7-dihydro-5H-benzo[5,6][1,4]diazepino[7,1-a]indole-10-carboxylate

378

-continued

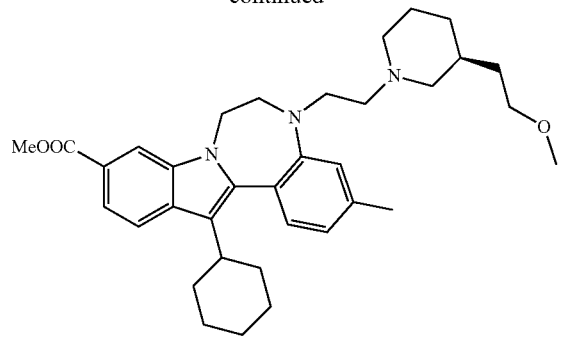

To a solution of methyl 13-cyclohexyl-5-{2-[(S)-3-(2-methoxyethyl)piperidin-1-yl]-2-oxoethyl}-3-methyl-6-oxo-6,7-dihydro-5H-benzo[5,6][1,4]diazepino[7,1-a]indole-10-carboxylate (967 mg, 1.6 mmol) in tetrahydrofuran (3 ml) was added a solution (15 ml) of 1.0M BH$_3$ THF complex in tetrahydrofuran, and the mixture was stirred at room temperature for 1 hr. 5N Hydrochloric acid (18 ml) was added to the reaction mixture, and the mixture was stirred at 60° C. for 5 hr. The reaction mixture was allowed to cool to room temperature, and the reaction mixture was neutralized with 1N aqueous sodium hydroxide solution and saturated aqueous sodium hydrogen carbonate solution, and extracted with ethyl acetate. The organic layer was washed with saturated brine and dried over anhydrous magnesium sulfate. After filtration, the solvent was evaporated under reduced pressure, and the obtained residue was purified by silica gel chromatography (ethyl acetate:methanol=10:1) to give methyl 13-cyclohexyl-5-{2-[(S)-3-(2-methoxyethyl)piperidin-1-yl]ethyl}-3-methyl-6,7-dihydro-5H-benzo[5,6][1,4]diazepino[7,1-a]indole-10-carboxylate (820 mg, yield 89%).

$^1$H-NMR (400 MHz, DMSO-d$_6$): δ(ppm) 8.13 (1H, d, J=0.9 Hz), 7.81 (1H, d, J=6.3 Hz), 7.57 (1H, dd, J=6.6, 1.5 Hz), 7.15 (1H, d, J=5.7 Hz), 7.04 (1H, s), 6.94 (1H, d, J=6.0 Hz), 3.83 (3H, s), 3.05-3.40 (8H, m) 2.75-2.82 (1H, m), 2.48-2.62 (5H, m), 2.22-2.39 (5H, m), 1.88-2.01 (3H, m), 1.62-1.81 (5H, m), 1.41-1.54 (2H, m), 1.06-1.38 (8H, m), 0.60-0.71 (1H, m).

Step 12: Production of 13-cyclohexyl-5-{2-[(S)-3-(2-methoxyethyl)piperidin-1-yl]ethyl}-3-methyl-6,7-dihydro-5H-benzo[5,6][1,4]diazepino[7,1-a]indole-10-carboxylic acid dihydrochloride

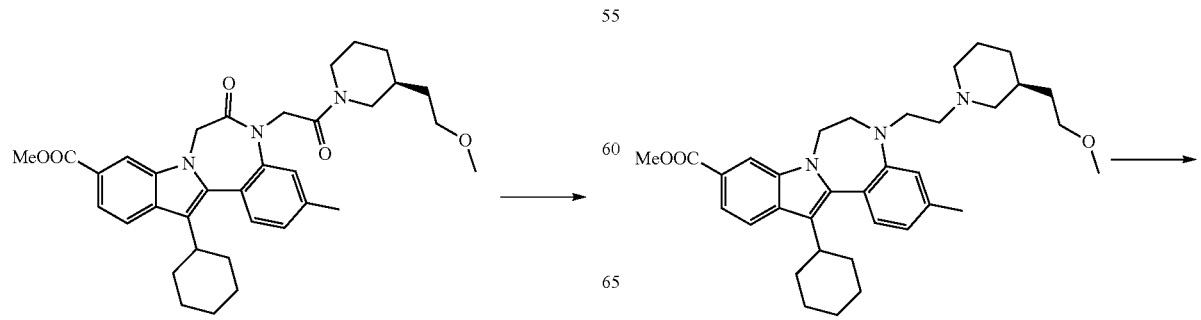

-continued

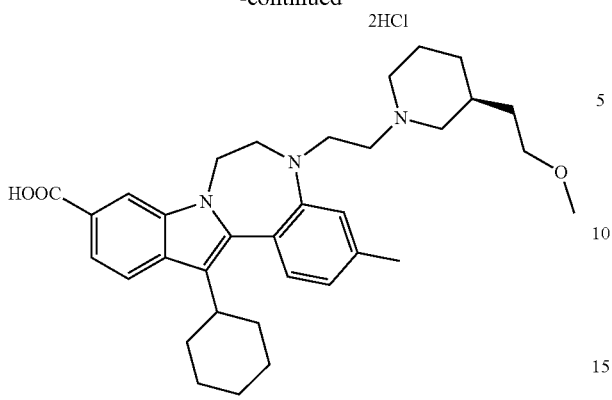

To a solution of methyl 13-cyclohexyl-5-{2-[(S)-3-(2-methoxyethyl)piperidin-1-yl]ethyl}-3-methyl-6,7-dihydro-5H-benzo[5,6][1,4]diazepino[7,1-a]indole-10-carboxylate (820 mg, 1.47 mmol) in tetrahydrofuran (16 ml) and methanol (8 ml) was added 4N aqueous sodium hydroxide solution (8 ml), and the mixture was stirred at 60° C. for 5 hr. The reaction mixture was adjusted to pH 7 with 1N hydrochloric acid, and extracted with ethyl acetate. The organic layer was washed with saturated brine and dried over anhydrous sodium sulfate. After filtration, the solvent was evaporated under reduced pressure. To a solution of the residue in ethyl acetate (10 ml) was added 4N HCl-ethyl acetate solution (5 ml). The solvent was evaporated under reduced pressure and diethyl ether was added. The precipitated solid was collected by filtration, washed with diethyl ether, and dried in vacuo to give 13-cyclohexyl-5-{2-[(S)-3-(2-methoxyethyl)piperidin-1-yl]ethyl}-3-methyl-6,7-dihydro-5H-benzo[5,6][1,4]diazepino[7,1-a]indole-10-carboxylic acid dihydrochloride (535 mg, yield 59%).

$^1$H-NMR (400 MHz, DMSO-d$_6$): δ(ppm) 10.26 (1H, brs), 8.12 (1H, s), 7.78 (1H, d, J=6.3 Hz), 7.56 (1H, dd, J=6.3, 0.9 Hz), 7.21 (1H, d, J=5.7 Hz), 7.13 (1H, s), 7.04 (1H, d, J=5.4 Hz), 2.76-2.84 (1H, m), 2.37 (3H, s), 1.89-2.00 (2H, m), 1.64-1.84 (3H, m), 1.42-1.57 (1H, m), 1.18-1.37 (2H, m), 0.86-0.95 (1H, m).

MS 544.3 (M+1).

Example 1-416

Production of 13-cyclohexyl-5-[2-((R)-3-methoxymethylpiperidin-1-yl)ethyl]-3-methyl-6,7-dihydro-5H-benzo[5,6][1,4]diazepino[7,1-a]indole-10-carboxylic acid dihydrochloride Step 1: Production of 1-tert-butyl 3-ethyl (R)-piperidine-1,3-dicarboxylate

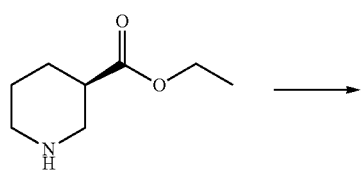 →

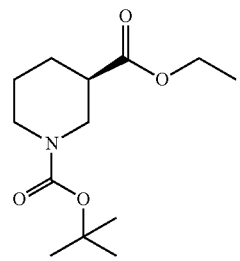

To a solution of ethyl (R)-piperidine-3-carboxylate (10.00 g, 63.6 mmol) in diethyl ether (100 ml) was added dropwise di-tert-butyl dicarbonate (16.00 g, 73.2 mmol) under ice-cooling, and the mixture was stirred for 40 min. The solvent was evaporated under reduced pressure to give 1-tert-butyl 3-ethyl (R)-piperidine-1,3-dicarboxylate (16.80 g). The obtained compound was used for Step 2 without purification.

$^1$H-NMR (300 MHz, CDCl$_3$): δ(ppm) 4.00-4.30 (1H, m), 4.14 (2H, q, J=7.2 Hz), 3.84-3.98 (1H, m), 2.88-3.17 (1H, m), 2.75-2.87 (1H, m), 2.35-2.51 (1H, m), 1.98-2.10 (1H, m), 1.57-1.78 (2H, m), 1.37-1.51 (1H, m), 1.46 (9H, s), 1.27 (3H, t, J=7.2 Hz).

Step 2: Production of tert-butyl (R)-3-hydroxymethylpiperidine-1-carboxylate

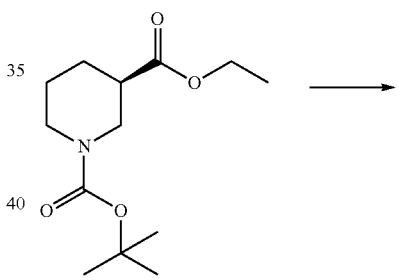 →

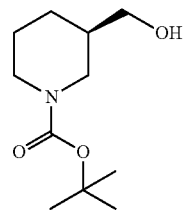

To a suspension of lithium aluminum hydride (2.9.0 g, 76.3 mmol) in tetrahydrofuran (100 ml) was added a solution of 1-tert-butyl 3-ethyl (R)-piperidine-1,3-dicarboxylate (16.30 g, 63.6 mmol) in tetrahydrofuran (60 ml) over 20 min under ice-cooling, and the mixture was further stirred for 20 min. To the reaction mixture were successively added water (2.9 ml), 4N aqueous sodium hydroxide solution (2.9 ml), water (8.7 ml) and anhydrous sodium sulfate, and the mixture was stirred at room temperature for 1 hr. The reaction mixture was filtered, and the solvent was evaporated under reduced pressure to give tert-butyl (R)-3-hydroxymethylpiperidine-1-carboxylate (13.00 g, yield 95.0%).

$^1$H-NMR (300 MHz, CDCl$_3$): δ(ppm) 3.39-3.95 (2H, m), 3.51 (2H, d, J=6.8 Hz), 2.72-3.30 (2H, m), 1.52-1.94 (4H, m), 1.35-1.50 (1H, m), 1.46 (9H, s), 1.15-1.34 (1H, m).

Step 3: Production of tert-butyl (R)-3-methoxymethylpiperidine-1-carboxylate

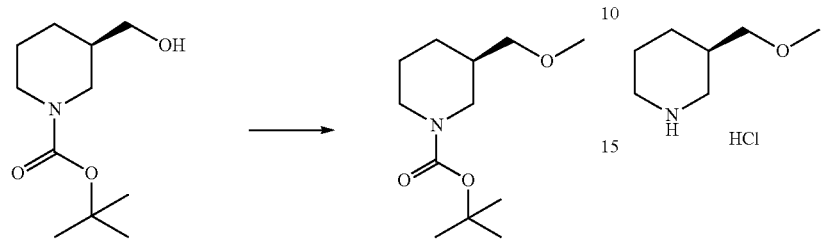

To a solution of tert-butyl (R)-3-hydroxymethylpiperidine-1-carboxylate (11.50 g, 53.7 mmol) in N,N-dimethylformamide (110 ml) was added sodium hydride (3.22 g, 80.6 mmol) under ice-cooling, and the mixture was stirred at room temperature for 20 min. To the reaction mixture was added methyl iodide (4.35 ml, 69.9 mmol) under ice-cooling, and the mixture was stirred at room temperature for 1 hr. Water was added to the reaction mixture, and the mixture was extracted with ethyl acetate. The organic layer was washed with saturated brine and dried over anhydrous sodium sulfate. After filtration, the solvent was evaporated under reduced pressure, and the obtained residue was purified by silica gel column chromatography (hexane:ethyl acetate=1:1) to give tert-butyl (R)-3-methoxymethylpiperidine-1-carboxylate (13.00 g, yield 100%).

$^1$H-NMR (300 MHz, CDCl$_3$): δ(ppm) 3.84-4.05 (2H, m), 3.32 (3H, s), 3.24 (2H, d, J=6.0 Hz), 2.75-2.89 (1H, m), 2.52-2.71 (1H, m), 1.70-1.86 (2H, m), 1.57-1.69 (1H, m), 1.36-1.52 (1H, m), 1.46 (9H, s), 1.15-1.28 (1H, m).

Step 4: Production of (R)-3-methoxymethylpiperidine hydrochloride

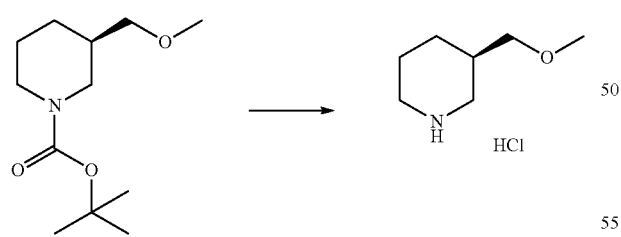

To a solution of tert-butyl (R)-3-methoxymethylpiperidine-1-carboxylate (13.00 g, 56.6 mmol) in ethyl acetate (26 ml) was added 4N HCl-ethyl acetate solution (26 ml), and the mixture was stirred at room temperature for 3 hr. The solvent was evaporated under reduced pressure to give (R)-3-methoxymethylpiperidine hydrochloride as a crude product. A mixed solvent (100 ml) of hexane:ethyl acetate=1:4 was added to the obtained solid, and the mixture was stirred. The solid was collected by filtration to give (R)-3-methoxymethylpiperidine hydrochloride (7.82 g, yield 84%).

$^1$H-NMR (300 MHz, CDCl$_3$): δ(ppm) 9.11 (2H, br), 3.37-3.53 (2H, m), 3.22-3.37 (2H, m), 3.31 (3H, s), 2.62-2.88 (2H, m), 2.19-2.38 (1H, m), 1.72-2.11 (3H, m), 1.21-1.44 (1H, m).

Step 5: Production of (R)-3-methoxymethyl-N-(chloroacetyl)piperidine

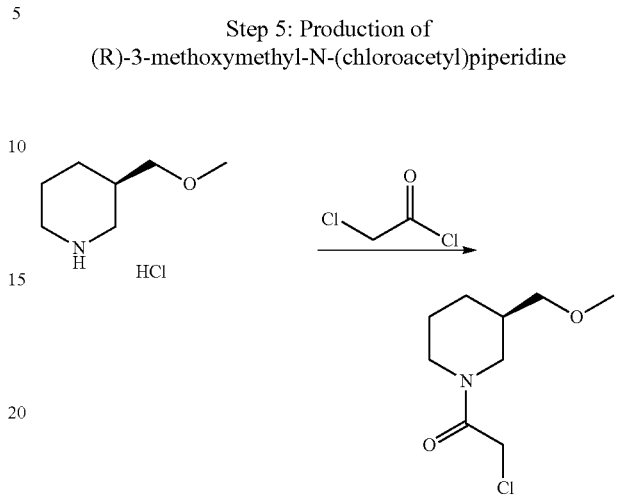

To a suspension of (R)-3-methoxymethylpiperidine hydrochloride (6.00 g, 36.3 mmol), sodium acetate (6.55 g, 79.9 mmol) and acetic acid (4.57 ml, 79.9 mmol) in tetrahydrofuran (120 ml) was added dropwise chloroacetyl chloride (3.18 ml, 39.9 mmol) under ice-cooling, and the mixture was stirred overnight at room temperature. To the reaction mixture was added saturated aqueous sodium hydrogen carbonate solution, and the mixture was extracted with ethyl acetate. The organic layer was washed with saturated brine and dried over anhydrous sodium sulfate. After filtration, the solvent was evaporated under reduced pressure, and the obtained residue was purified by silica gel column chromatography (hexane:ethyl acetate=1:4) to give (R)-3-methoxymethyl-N-(chloroacetyl)piperidine (6.00 g, yield 80.0%).

$^1$H-NMR (400 MHz, CDCl$_3$): δ(ppm) 4.32-4.43 (0.4H, m), 4.02-4.23 (2.6H, m), 3.67-3.85 (1H, m), 3.20-3.39 (5H, m), 3.07-3.18 (0.4H, m), 3.03 (0.6H, dd, J=7.0, 10.1 Hz), 2.87-2.99 (0.6H, m), 2.62 (0.4H, dd, J=7.7, 9.7 Hz), 1.20-2.02 (5H, m).

Step 6: Production of methyl 13-cyclohexyl-5-[2-((R)-3-methoxymethylpiperidin-1-yl)-2-oxoethyl]-3-methyl-6-oxo-6,7-dihydro-5H-benzo[5,6][1,4]diazepino[7,1-a]indole-10-carboxylate

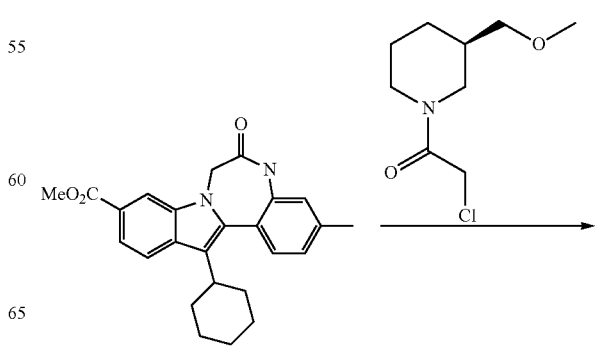

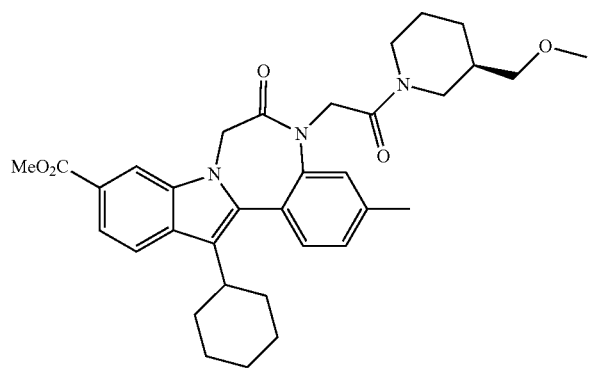

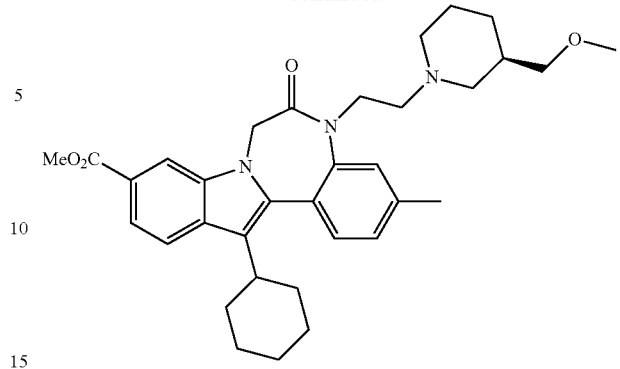

A suspension of methyl 13-cyclohexyl-3-methyl-6-oxo-6,7-dihydro-5H-benzo[5,6][1,4]diazepino[7,1-a]indole-10-carboxylate (1.00 g, 2.48 mmol), (R)-3-methoxymethyl-N-(chloroacetyl)piperidine (613 mg, 2.98 mmol) and potassium carbonate (687 mg, 4.97 mmol) in N,N-dimethylformamide (15 ml) was stirred at 80° C. for 2 hr. The reaction mixture was allowed to cool to room temperature and water was added to the reaction mixture. The precipitate was collected by filtration, washed with water, and dried in vacuo to give methyl 13-cyclohexyl-5-[(2-((R)-3-methoxymethylpiperidin-1-yl)-2-oxoethyl]-3-methyl-6-oxo-6,7-dihydro-5H-benzo[5,6][1,4]diazepino[7,1-a]indole-10-carboxylate (1.45 g) as a crude product. The obtained crude product was used for Step 7 without further purification.

$^1$H-NMR (300 MHz, DMSO-d$_6$) δ(ppm) 8.27 (1H, s), 7.94 (1H, d, J=8.3 Hz), 7.68 (1H, d, J=8.7 Hz), 7.42 (1H, d, J=7.9 Hz), 7.25-7.36 (2H, m), 5.18 (1H, d, J=14.3 Hz), 4.58-4.73 (1H, m), 4.33-4.55 (2H, m), 4.05-4.19 (0.5H, m), 3.78-3.94 (0.5H, m), 3.89 (3H, s), 3.49-3.69 (1H, m), 3.20 (3H, s), 3.17 (2H, d, J=10.2 Hz), 2.79-3.01 (2H, m), 2.41 (3H, s), 1.06-2.15 (16H, m).

Step 7: Production of methyl 13-cyclohexyl-5-[2-((R)-3-methoxymethylpiperidin-1-yl)ethyl]-3-methyl-6,7-dihydro-5H-benzo[5,6][1,4]diazepino[7,1-a]indole-10-carboxylate To a solution of methyl 13-cyclohexyl-5-[2-((R)-3-methoxymethylpiperidin-1-yl)-2-oxoethyl]-3-methyl-6-oxo-6,7-dihydro-5H-benzo[5,6][1,4]diazepino[7,1-a]indole-10-carboxylate (1.40 g, 2.45 mmol) in tetrahydrofuran (5.6 ml) was added a solution (14 ml) of 1.07M BH$_3$ THF complex in tetrahydrofuran under ice-cooling, and the mixture was stirred at room temperature for 16 hr. 5N Hydrochloric acid (5 ml) was added to the reaction mixture under ice-cooling, and the mixture was stirred at 70° C. for 4 hr. The reaction mixture was allowed to cool to room temperature, and the reaction mixture was neutralized with saturated aqueous sodium hydrogen carbonate solution and extracted with ethyl acetate. The organic layer was washed with saturated brine and dried over anhydrous sodium sulfate. After filtration, the solvent was evaporated under reduced pressure, and the obtained residue was purified by silica gel chromatography (chloroform:methanol=9:1) to give methyl 13-cyclohexyl-5-[2-((R)-3-methoxymethylpiperidin-1-yl)ethyl]-3-methyl-6,7-dihydro-5H-benzo[5,6][1,4]diazepino[7,1-a]indole-10-carboxylate (1.19 g, yield 83%).

$^1$H-NMR (300 MHz, DMSO-d$_6$): δ(ppm) 8.15 (1H, d, J=1.6 Hz), 7.84 (1H, d, J=8.8 Hz), 7.59 (1H, dd, J=8.4, 1.2 Hz), 7.30 (1H, d, J=2.0 Hz), 7.24 (1H, d, J=8.0 Hz), 7.15 (1H, dd, J-8.4, 2.4 Hz), 3.86-4.75 (4H, m), 3.84 (3H, s), 3.12-3.51 (4H, m), 2.74-2.74 (1H, m), 1.60-2.33 (12H, m), 1.09-1.40 (8H, m).

Step 8: Production of 13-cyclohexyl-5-[2-((R)-3-methoxymethylpiperidin-1-yl)ethyl]-3-methyl-6,7-dihydro-5H-benzo[5,6][1,4]diazepino[7,1-a]indole-10-carboxylic acid dihydrochloride

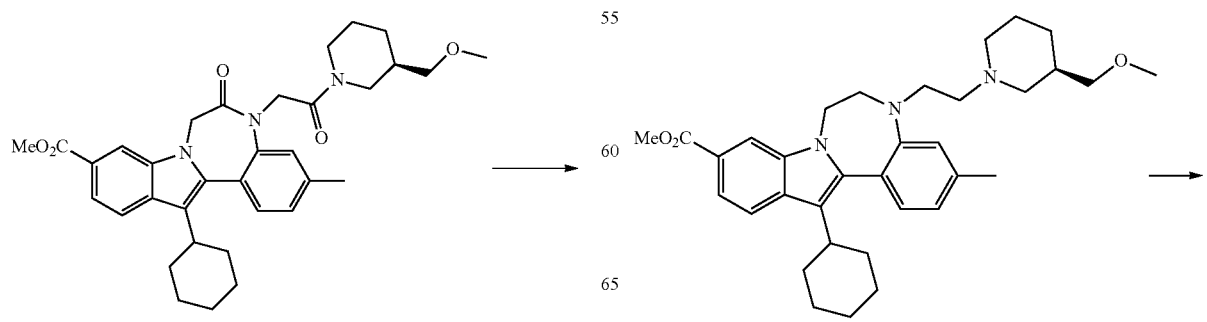

385
-continued

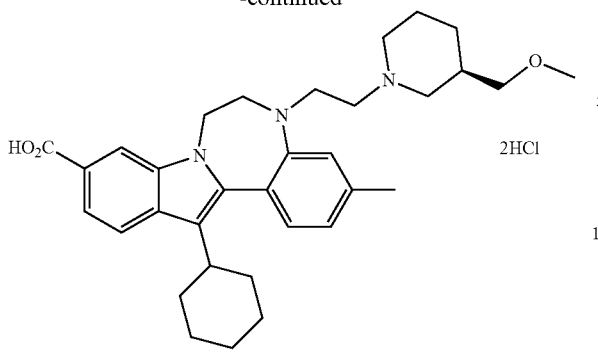

2HCl

To a solution of methyl 13-cyclohexyl-5-[2-((R)-3-methoxymethylpiperidin-1-yl)ethyl]-3-methyl-6,7-dihydro-5H-benzo[5,6][1,4]diazepino[7,1-a]indole-10-carboxylate (1.19 g, 2.18 mmol) in tetrahydrofuran (20 ml) and methanol (15 ml) was added 4N aqueous sodium hydroxide solution (10 ml), and the mixture was stirred at 55° C. for 3 hr. The reaction mixture was adjusted to pH 6.5 with 2N hydrochloric acid (20 ml), and extracted with a mixed solvent of ethyl acetate and tetrahydrofuran. The organic layer was washed with saturated brine and dried over anhydrous sodium sulfate. After filtration, the solvent was evaporated under reduced pressure to give 13-cyclohexyl-5-[2-((R)-3-methoxymethylpiperidin-1-yl)ethyl]-3-methyl-6,7-dihydro-5H-benzo[5,6][1,4]diazepino[7,1-a]indole-10-carboxylic acid as a crude product. To a solution of the obtained crude product in ethyl acetate (5 ml) wad added 4N HCl-ethyl acetate solution (10 ml) at room temperature, and the mixture was stirred for 30 min. The reaction mixture was concentrated under reduced pressure, diethyl ether was added to the obtained solid, and the solid was collected by filtration and dried in vacuo to give 13-cyclohexyl-5-[2-((R)-3-methoxymethylpiperidin-1-yl)ethyl]-3-methyl-6,7-dihydro-5H-benzo[5,6][1,4]diazepino[7,1-a]indole-10-carboxylic acid dihydrochloride (705 mg, yield 61.3%).

$^1$H-NMR (300 MHz, DMSO-$d_6$): δ(ppm) 10.64-11.09 (1H, m), 8.16 (1H, s), 7.84 (1H, d, J=8.7 Hz), 7.61 (1H, d, J=7.9 Hz), 7.25 (1H, d, J=7.9 Hz), 7.19 (1H, s), 7.08 (1H, d, J=7.5 Hz), 4.08-5.02 (2H, m), 3.30-3.96 (2H, m), 3.10-3.25 (2H, m), 2.93-3.09 (2H, m), 3.04 (3H, s), 2.57-2.92 (4H, m), 2.22-2.48 (2H, m), 2.41 (3H, s), 1.90-2.12 (4H, m), 1.45-1.89 (7H, m), 1.21-1.43 (5H, m).

MS 530.3 (M+1)

The compounds of Examples 1-96 to 1-445 were produced by the same methods as in Examples 1-1 to 1-18, 1-168, 1-413 and 1-416 or methods similar thereto, and where necessary, employing other conventional methods. The chemical structural formulas are shown in Tables 20-100.

386

Example 2-1

Production of methyl 12-cyclohexyl-3-hydroxy-6,7-dihydro-5-oxa-7a-azadibenzo[a,e]azulene-9-carboxylate Step 1: Production of 1-bromo-2,4-bismethoxymethoxybenzene

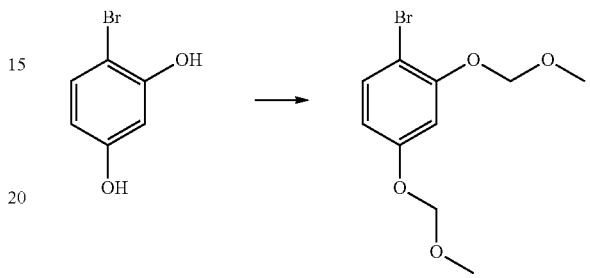

To a solution of 4-bromoresorcinol (30 g, 159 mmol) in acetone (300 ml) were added potassium carbonate (66 g, 471 mmol) and chloromethyl methyl ether (30 ml, 397 mmol) under ice-cooling and the mixture was stirred at room temperature for 22 hr. The reaction mixture was concentrated and water was added. The mixture was extracted with ethyl acetate and the organic layer was washed with saturated brine and dried over anhydrous magnesium sulfate. After filtration, the solvent was evaporated under reduced pressure to give 1-bromo-2,4-bismethoxymethoxybenzene as a crude product. The obtained compound was used in Step 2 without further purification.

$^1$H-NMR (400 MHz, CDCl$_3$): δ(ppm) 7.39 (1H, d, J=8.4 Hz), 6.85 (1H, d, J=2.8 Hz), 6.61 (1H, dd, J=8.8, 2.8 Hz), 5.22 (2H, s), 5.13 (2H, s), 3.51 (3H, s), 3.46 (3H, s).

Step 2: Production of 2,4-bismethoxymethoxyphenylboronic acid

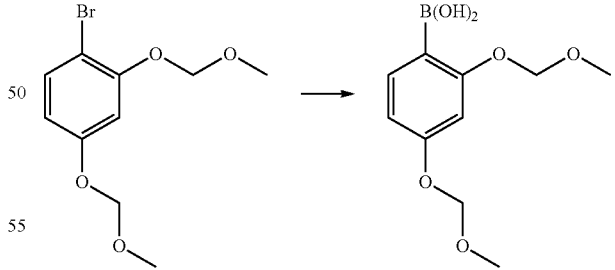

To a solution of 1-bromo-2,4-bismethoxymethoxybenzene in hexane (250 ml) and tetrahydrofuran (110 ml) was added triisopropyl borate (45 g, 238 mmol), and the mixture was cooled to −78° C. A solution (151 ml, 238 mmol) of 1.58M n-butyllithium in hexane was added dropwise and the mixture was stirred for 5 hr. 1N Hydrochloric acid (240 ml) was added under ice-cooling, and the mixture was stirred for 15 min. The reaction mixture was extracted with ethyl acetate, and the organic layer was washed with saturated brine and dried over anhydrous magnesium sulfate. After filtration, the solvent was evaporated under reduced pressure, and the obtained residue was purified by silica gel column chromatography (hexane:ethyl acetate=4:1) to give 2,4-bismethoxymethoxyphenylboronic acid (13.6 g, yield 35%).

$^1$H-NMR (400 MHz, CDCl$_3$): δ(ppm) 7.75 (1H, d, J=8.4 Hz), 6.79 (1H, d, J=2.4 Hz), 6.75 (1H, dd, J=8.0, 2.0 Hz), 5.58 (2H, s), 5.27 (2H, s), 5.19 (2H, s), 3.50 (3H, s), 3.48 (3H, s).

Step 3: Production of methyl 2-(2,4-bis-methoxymethoxyphenyl)-3-cyclohexyl-1H-indole-6-carboxylate

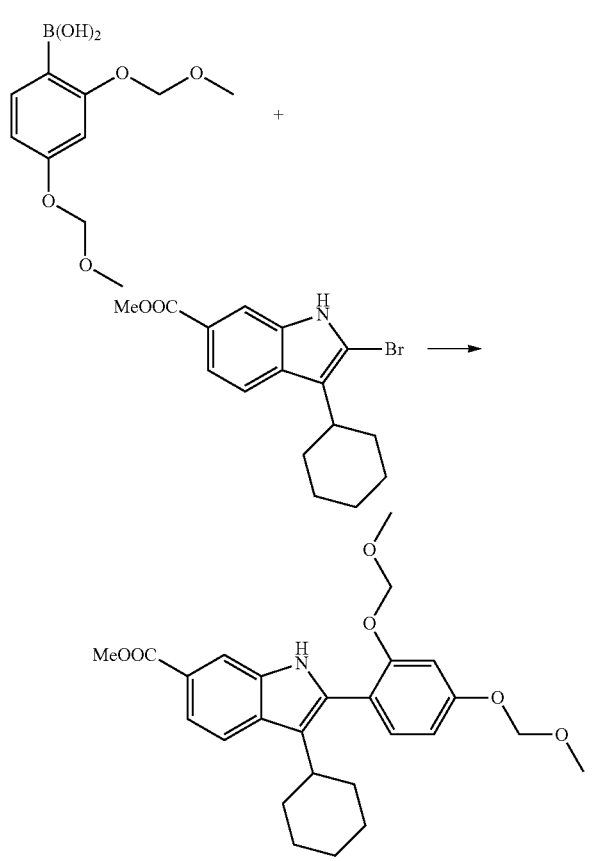

To a suspension of methyl 2-bromo-3-cyclohexyl-1H-indole-6-carboxylate (14.5 g, 43.2 mmol), obtained in the same manner as in the method described in WO03/010140, and 2,4-bismethoxymethoxyphenylboronic acid (13.6 g, 56.2 mmol) in 1,2-dimethoxyethane (140 ml) and water (70 ml) were added lithium chloride (5.5 g, 129 mmol), sodium carbonate (13.7 g, 129 mmol) and tetrakis(triphenylphosphine)palladium (5.0 g, 4.3 mmol), and the mixture was stirred at 90° C. for 22 hr. The mixture was allowed to cool to room temperature, and filtered through celite. The filtrate was extracted with ethyl acetate and the organic layer was washed successively with saturated aqueous ammonium chloride solution and saturated brine, and dried over anhydrous magnesium sulfate. After filtration, the solvent was evaporated under reduced pressure, and the obtained residue was purified by silica gel chromatography (hexane:ethyl acetate=3:1) to give methyl 2-(2,4-bismethoxymethoxyphenyl)-3-cyclohexyl-1H-indole-6-carboxylate (16.9 g, yield 86%).

$^1$H-NMR (400 MHz, CDCl$_3$): δ(ppm) 8.38 (1H, s), 7.82 (1H, d, J=8.4 Hz), 7.74 (1H, dd, J=8.4, 1.2 Hz), 6.96 (1H, d, J=2.4 Hz), 6.83 (1H, dd, J=8.4, 8.4 Hz), 5.22 (2H, s), 5.12 (2H, s), 3.92 (3H, s), 3.53 (3H, s), 3.35 (3H, s), 2.73-2.86 (1H, m), 1.92-2.07 (2H, m), 1.71-1.88 (5H, m), 1.26-1.41 (3H, m).

MS 454 (M+1).

Step 4: Production of methyl 2-(2,4-bis-methoxymethoxyphenyl)-3-cyclohexyl-1-[2-(tetrahydropyran-2-yloxy)ethyl]-1H-indole-6-carboxylate

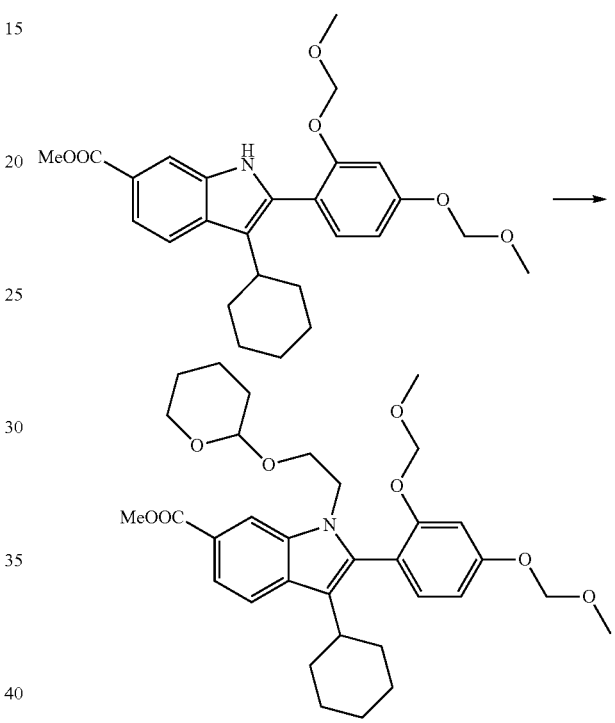

To a solution of methyl 2-(2,4-bismethoxymethoxyphenyl)-3-cyclohexyl-1H-indole-6-carboxylate (16.9 g, 37.3 mmol) in N,N-dimethylformamide (120 ml) was added sodium hydride (2.1 g, 52.2 mmol) under ice-cooling, and the mixture was stirred for 20 min. To the reaction mixture was added 2-(2-bromoethoxy)tetrahydro-2H-pyran (8.5 ml, 55.9 mmol), and the mixture was stirred at room temperature for 4 hr. To the reaction mixture was added saturated aqueous sodium hydrogen carbonate solution and the mixture was extracted with ethyl acetate. The organic layer was washed with saturated brine, and dried over anhydrous magnesium sulfate. After filtration, the solvent was evaporated under reduced pressure to give methyl 2-(2,4-bismethoxymethoxyphenyl)-3-cyclohexyl-1-[2-(tetrahydropyran-2-yloxy)ethyl]-1H-indole-6-carboxylate as a crude product. The obtained compound was used in Step 5 without further purification.

$^1$H-NMR (400 MHz, CDCl$_3$): δ(ppm) 8.21 (1H, d, J=5.2 Hz), 7.70-7.78 (2H, m), 7.11 (1H, dd, J=8.4, 1.6 Hz), 6.95 (1H, t, J=2.2 Hz), 6.78 (1H, dd, J=8.4, 2.4 Hz), 5.23 (2H, s), 5.03 (2H, ddd, J=15.6, 5.4, 1.5 Hz), 4.33-4.40 (1H, m), 3.97-4.24 (3H, m), 3.92 (3H, s), 3.69-3.83 (2H, m), 3.54 (3H, s), 3.42-3.53 (2H, m), 2.44-2.54 (1H, m), 1.22-1.90 (16H, m).

MS 582 (M+1).

Step 5: Production of methyl 3-cyclohexyl-2-(2,4-dihydroxyphenyl)-1-(2-hydroxyethyl)-1H-indole-6-carboxylate

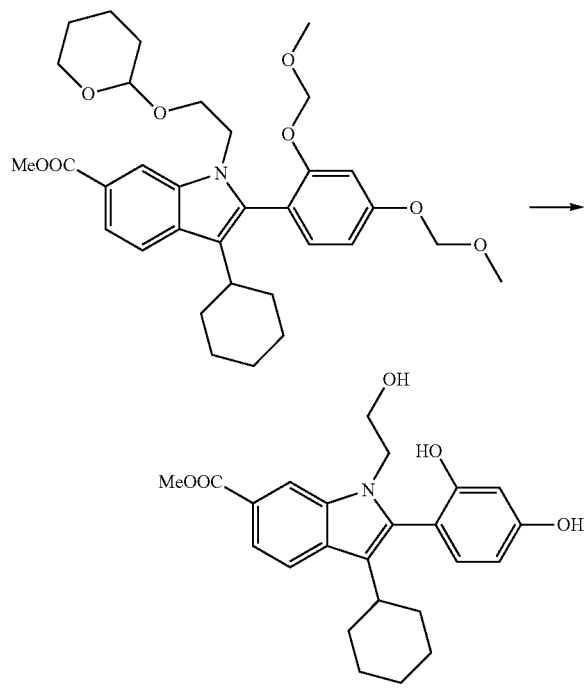

To a solution of methyl 2-(2,4-bismethoxymethoxyphenyl)-3-cyclohexyl-1-[2-(tetrahydropyran-2-yloxy)ethyl]-1H-indole-6-carboxylate in methanol (525 ml) and tetrahydrofuran (30 ml) was added 6N hydrochloric acid (105 ml) and the mixture was stirred for 10 hr. The reaction mixture was concentrated and water was added. The mixture was extracted with ethyl acetate. The organic layer was washed with saturated brine, and dried over anhydrous magnesium sulfate. After filtration, the solvent was evaporated under reduced pressure, and the obtained residue was purified by silica gel chromatography (hexane:ethyl acetate=1:1) to give methyl 3-cyclohexyl-2-(2,4-dihydroxyphenyl)-1-(2-hydroxyethyl)-1H-indole-6-carboxylate (10.3 g, yield 68%).

$^1$H-NMR (400 MHz, CDCl$_3$): δ(ppm) 8.12 (1H, s), 7.76-7.83 (2H, m), 7.00 (1H, d, J=8.0 Hz), 6.49-6.55 (2H, m), 5.67 (1H, brs), 5.18 (1H, s), 4.06-4.15 (2H, m), 3.94 (3H, s), 3.87-3.93 (1H, m), 3.73-3.81 (1H, m), 2.45-2.56 (1H, m), 1.63-1.84 (7H, m), 1.20-1.29 (3H, m).

MS 410 (M+1).

Step 6: Production of methyl 12-cyclohexyl-3-hydroxy-6,7-dihydro-5-oxa-7a-azadibenzo[a,e]azulene-9-carboxylate

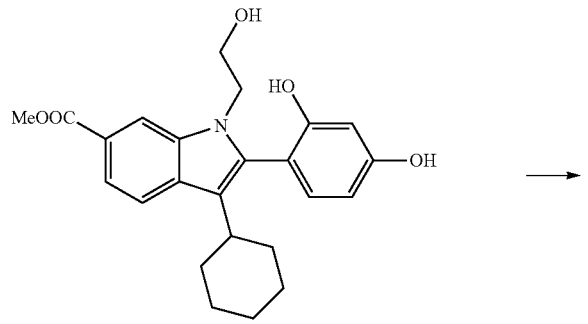

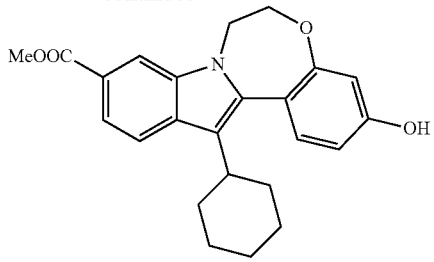

To a solution of methyl 3-cyclohexyl-2-(2,4-dihydroxyphenyl)-1-(2-hydroxyethyl)-1H-indole-6-carboxylate (10.3 g, 28.2 mmol) in tetrahydrofuran (500 ml) were added triphenylphosphine (7.3 g, 27.7 mmol) and diethyl azodicarboxylate (4.4 ml, 27.7 mmol) under ice-cooling, and the mixture was stirred for 4 hr. The reaction mixture was concentrated and the obtained residue was purified by silica gel chromatography (hexane:ethyl acetate=3:2) to give methyl 12-cyclohexyl-3-hydroxy-6,7-dihydro-5-oxa-7a-azadibenzo[a,e]azulene-9-carboxylate (6.5 g, yield 66%).

$^1$H-NMR (400 MHz, CDCl$_3$): δ(ppm) 8.04 (1H, s), 7.85 (1H, d, J=8.4 Hz), 7.74 (1H, dd, J-8.4, 1.2 Hz), 7.27 (1H, d, J=8.4 Hz), 6.76 (1H, dd, J=8.0, 2.4 Hz), 6.72 (1H, d, J=2.4 Hz), 5.18 (1H, s), 4.48 (2H, t, J=5.6 Hz), 4.28 (2H, t, J=5.6 Hz), 3.94 (3H, s), 2.87-2.97 (1H, m), 1.98-2.12 (2H, m), 1.74-1.90 (5H, m), 1.29-1.43 (3H, m).

MS 392 (M+1).

Example 2-2

Production of methyl 3-benzyloxy-12-cyclohexyl-6,7-dihydro-5-oxa-7a-azadibenzo[a,e]azulene-9-carboxylate

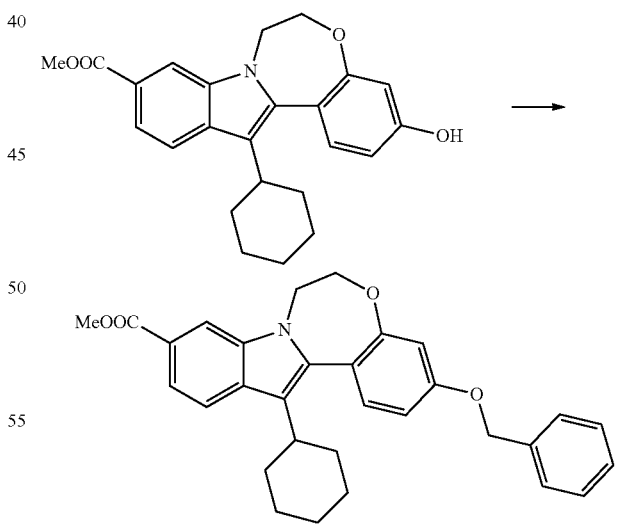

To a solution of methyl 12-cyclohexyl-3-hydroxy-6,7-dihydro-5-oxa-7a-azadibenzo[a,e]azulene-9-carboxylate (150 mg, 0.38 mmol) in N,N-dimethylformamide (2.0 ml) were added potassium carbonate (132 mg, 0.96 mmol) and benzyl bromide (0.07 ml, 0.61 mmol) and the mixture was stirred at 60° C. for 3 hr. To the reaction mixture was added saturated aqueous sodium hydrogen carbonate solution and the mixture was extracted with ethyl acetate. The organic layer was washed with saturated brine, and dried over anhydrous magnesium sulfate. After filtration, the solvent was evaporated under reduced pressure, and the obtained residue was purified by silica gel chromatography (hexane:ethyl acetate=3:1) to give methyl 3-benzyloxy-12-cyclohexyl-6,7-dihydro-5-oxa-7a-azadibenzo[a,e]azulene-9-carboxylate (173 mg, yield 94%).

$^1$H-NMR (400 MHz, CDCl$_3$): δ(ppm) 8.03 (1H, s), 7.85 (1H, d, J=8.4 Hz), 7.73 (1H, dd, J=8.4, 1.2 Hz), 7.25-7.48 (6H, m), 6.90 (1H, dd, J=8.4, 2.8 Hz), 6.85 (1H, d, J=2.4 Hz), 5.11 (2H, s), 4.49 (2H, t, J=5.6 Hz), 4.29 (2H, t, J=5.6 Hz), 3.93 (3H, s), 2.88-2.98 (1H, m), 1.99-2.12 (2H, m), 1.75-1.90 (5H, m), 1.30-1.43 (3H, m).

Example 2-3

Production of 3-benzyloxy-12-cyclohexyl-6,7-dihydro-5-oxa-7a-azadibenzo[a,e]azulene-9-carboxylic acid

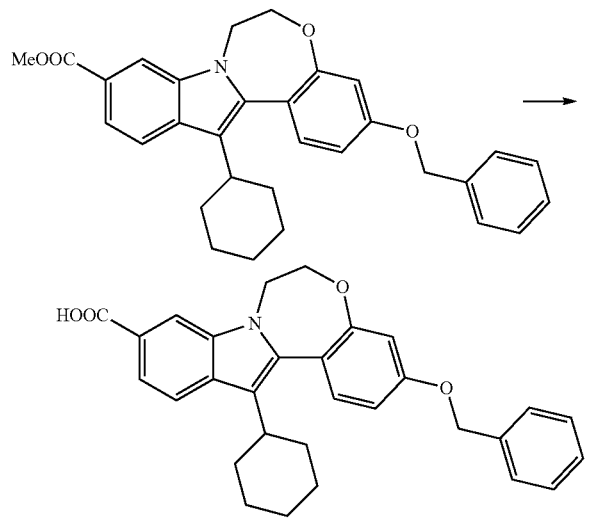

To a solution of methyl 3-benzyloxy-12-cyclohexyl-6,7-dihydro-5-oxa-7a-azadibenzo[a,e]azulene-9-carboxylate (173 mg, 0.36 mmol) in methanol (3.5 ml) and tetrahydrofuran (3.5 ml) was added 4N aqueous sodium hydroxide solution (1.7 ml), and the mixture was stirred for 13 hr. To the reaction mixture were added 2N hydrochloric acid (3.7 ml) and water, and the precipitated solid was collected by filtration and dried in vacuo. The obtained solid was purified by silica gel chromatography (hexane:ethyl acetate=1:1) to give 3-benzyloxy-12-cyclohexyl-6,7-dihydro-5-oxa-7a-azadibenzo[a,e]azulene-9-carboxylic acid (81 mg, yield 48%).

$^1$H-NMR (300 MHz, DMSO-d$_6$): δ(ppm) 12.54 (1H, brs), 8.17 (1H, d, J=1.2 Hz), 7.86 (1H, d, J=8.4 Hz), 7.63 (1H, dd, 1.2 Hz), 7.32-7.53 (6H, m), 7.03 (1H, dd, J=9.0, 2.7 Hz), 6.92 (1H, d, J=2.4 Hz), 5.18 (2H, s), 4.41-4.49 (2H, m), 4.33-4.40 (2H, m), 2.79-2.93 (1H, m), 1.93-2.12 (2H, m), 1.68-1.87 (5H, m), 1.24-1.45 (3H, m).

MS 468 (M+1).

The compounds of Examples 2-4 to 2-53 were produced by the same methods as in Examples 2-1 to 2-3 or methods similar thereto, and where necessary, by employing other conventional methods. The chemical structural formulas are shown in Tables 101-111.

12-cyclohexyl-3-methoxy-6,7-dihydro-5-oxa-7a-azadibenzo[a,e]azulene-9-carboxylic acid (Example 2-4), 12-cyclohexyl-3-[2-(morpholin-4-yl)-5-(2-oxopyrrolidin-1-yl)benzyloxy]-6,7-dihydro-5-oxa-7a-azadibenzo[a,e]azulene-9-carboxylic acid monohydrochloride (Example 2-5), 12-cyclohexyl-2-methoxy-6,7-dihydro-5-oxa-7a-azadibenzo[a,e]azulene-9-carboxylic acid (Example 2-6), 2-benzyloxy-12-cyclohexyl-6,7-dihydro-5-oxa-7a-azadibenzo[a,e]azulene-9-carboxylic acid (Example 2-7), 12-cyclohexyl-2-[2-(morpholin-4-yl)-5-(2-oxopyrrolidin-1-yl)benzyloxy]-6,7-dihydro-5-oxa-7a-azadibenzo[a,e]azulene-9-carboxylic acid monohydrochloride (Example 2-8), 12-cyclohexyl-3-[2-(morpholin-4-yl)-4-(2-oxopyrrolidin-1-yl)benzyloxy]-6,7-dihydro-5-oxa-7a-azadibenzo[a,e]azulene-9-carboxylic acid (Example 2-9), 3-(1-tert-butoxycarbonylpiperidin-4-yloxy)-12-cyclohexyl-6,7-dihydro-5-oxa-7a-azadibenzo[a,e]azulene-9-carboxylic acid (Example 2-10), 3-(1-tert-butoxycarbonylpiperidin-3-yloxy)-12-cyclohexyl-6,7-dihydro-5-oxa-7a-azadibenzo[a,e]azulene-9-carboxylic acid (Example 2-11), 12-cyclohexyl-3-[5-methanesulfonyl-2-(morpholin-4-yl)benzyloxy]-6,7-dihydro-5-oxa-7a-azadibenzo[a,e]azulene-9-carboxylic acid monohydrochloride (Example 2-12), 12-cyclohexyl-3-[2-(4-methanesulfonylpiperazin-1-yl)-5-(2-oxopyrrolidin-1-yl)benzyloxy]-6,7-dihydro-5-oxa-7a-azadibenzo[a,e]azulene-9-carboxylic acid monohydrochloride (Example 2-13), 12-cyclohexyl-3-[2-(morpholin-4-yl)benzyloxy]-6,7-dihydro-5-oxa-7a-azadibenzo[a,e]azulene-9-carboxylic acid monohydrochloride (Example 2-14), 3-[5-acetylamino-2-(morpholin-4-yl)benzyloxy]-12-cyclohexyl-6,7-dihydro-5-oxa-7a-azadibenzo[a,e]azulene-9-carboxylic acid monohydrochloride (Example 2-15), 12-cyclohexyl-3-[5-(2-dimethylaminoacetylamino)-2-(morpholin-4-yl)benzyloxy]-6,7-dihydro-5-oxa-7a-azadibenzo[a,e]azulene-9-carboxylic acid dihydrochloride (Example 2-16), 12-cyclohexyl-3-[5-methanesulfonylamino-2-(morpholin-4-yl)benzyloxy]-6,7-dihydro-5-oxa-7a-azadibenzo[a,e]azulene-9-carboxylic acid monohydrochloride (Example 2-17), 3-[5-(N-acetyl-N-methylamino)-2-(morpholin-4-yl)benzyloxy]-12-cyclohexyl-6,7-dihydro-5-oxa-7a-azadibenzo[a,e]azulene-9-carboxylic acid monohydrochloride (Example 2-18), 12-cyclohexyl-3-[(5-(N-methanesulfonyl-N-methylamino)-2-(morpholin-4-yl)benzyloxy]-6,7-dihydro-5-oxa-7a-azadibenzo[a,e]azulene-9-carboxylic acid monohydrochloride (Example 2-19), 12-cyclohexyl-3-phenoxy-6,7-dihydro-5-oxa-7a-azadibenzo[a,e]azulene-9-carboxylic acid (Example 2-20), 12-cyclohexyl-3-{(2-(morpholin-4-yl)-5-[2-(morpholin-4-yl)acetylamino]benzyloxy}-6,7-dihydro-5-oxa-7a-azadibenzo[a,e]azulene-9-carboxylic acid dihydrochloride (Example 2-21), 12-cyclohexyl-3-[5-{N-methyl-N-[2-(morpholin-4-yl)acetyl]amino}-2-(morpholin-4-yl)benzyloxy]-6,7-dihydro-5-oxa-7a-azadibenzo[a,e]azulene-9-carboxylic acid dihydrochloride (Example 2-22), 12-cyclohexyl-3-{5-[N-(2-dimethylaminoacetyl)-N-methylamino]-2-(morpholin-4-yl)benzyloxy}-6,7-dihydro-5-oxa-7a-azadibenzo[a,e]azulene-9-carboxylic acid dihydrochloride (Example 2-23), 12-cyclohexyl-3-(1-methoxycarbonylpiperidin-3-yloxy) 6,7-dihydro-5-oxa-7a-azadibenzo[a,e]azulene-9-carboxylic acid (Example 2-24), 12-cyclohexyl-3-(4-methoxyphenoxy)-6,7-dihydro-5-oxa-7a-azadibenzo[a,e]azulene-9-carboxylic acid (Example 2-25), 3-(3-chlorophenoxy)-12-cyclohexyl-6,7-dihydro-5-oxa-7a-azadibenzo[a,e]azulene-9-carboxylic acid (Example 2-26), 12-cyclohexyl-3-[2-(4-dimethylcarbamoylmethylpiperazin-1-yl)-5-(2-oxopyrrolidin-1-yl)benzyloxy]-6,7-dihydro-5-oxa-7a-azadibenzo[a,e]azulene-9-carboxylic acid dihydrochloride (Example 2-27), 12-cyclohexyl-3-[(2-(4-ethylpiperazin-1-yl)-5-(2-oxopyrrolidin-1-yl)benzyloxy]-6,7-dihydro-5-oxa-7a-azadibenzo[a,e]azulene-9-carboxylic acid dihydrochloride (Example 2-28), 12-cyclohexyl-3-(pyridin-3-yloxy)-6,7-dihydro-5-oxa-7a-azadibenzo[a,e]azulene-9-carboxylic acid monohydrochloride (Example 2-29), 3-(2-chlorophenoxy)-12-cyclohexyl-6,7-dihydro-5-oxa-7a-azadibenzo[a,e]azulene-9-carboxylic acid (Example 2-30), 3-(4-chlorophenoxy)-12-cyclohexyl-6,7-dihydro-5-oxa-7a-azadibenzo[a,e]azulene-9-carboxylic acid (Example 2-31).

Example 3-1

Production of 6-ethyl 9-methyl 12-cyclohexyl-6,7-dihydro-5-oxa-7a-azadibenzo[a,e]azulene-6,9-dicarboxylate Step 1: Production of methyl 3-cyclohexyl-2-(2-hydroxyphenyl)-1H-indole-6-carboxylate

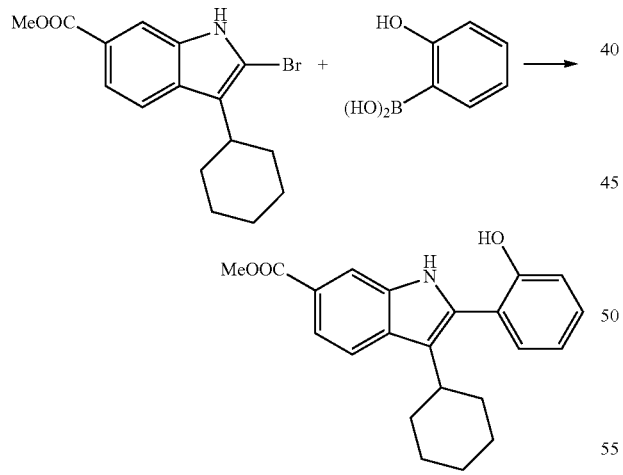

To a suspension of methyl 2-bromo-3-cyclohexyl-1H-indole-6-carboxylate (2 g, 5.95 mmol) obtained in the same manner as in the method described in WO03/010140 and 2-hydroxyphenylboronic acid (1.23 g, 8.91 mmol) in 1,2-dimethoxyethane (20 ml) and water (10 ml) were added lithium chloride (504 mg, 11.9 mmol), sodium carbonate (1.9 g, 17.9 mmol) and tetrakis(triphenylphosphine)palladium (687 mg, 0.59 mmol), and the mixture was heated under reflux for 10 hr. The mixture was allowed to cool to room temperature, and extracted with ethyl acetate. The organic layer was washed with saturated brine and dried over anhydrous sodium sulfate. After filtration, the solvent was evaporated under reduced pressure and the residue was purified by silica gel chromatography (hexane:ethyl acetate=3:1-2:1) to give methyl 3-cyclohexyl-2-(2-hydroxyphenyl)-1H-indole-6-carboxylate (1.81 g, yield 87.7%).

$^1$H-NMR (300 MHz, DMSO-$d_6$): δ(ppm) 11.24 (1H, brs), 9.71 (1H, brs), 7.98 (1H, d, J=1.5 Hz), 7.78 (1H, d, J=8.7 Hz), 7.58 (1H, dd, J=1.5, 8.4 Hz), 7.20-7.31 (2H, m), 7.00 (1H, d, J=7.5 Hz), 6.92 (1H, t, J=7.5 Hz), 3.85 (3H, s), 2.60-2.75 (1H, m), 1.62-1.98 (7H, m), 1.14-1.41 (3H, m).

Step 2: Production of 6-ethyl 9-methyl 12-cyclohexyl-6,7-dihydro-5-oxa-7a-azadibenzo[a,e]azulene-6,9-dicarboxylate

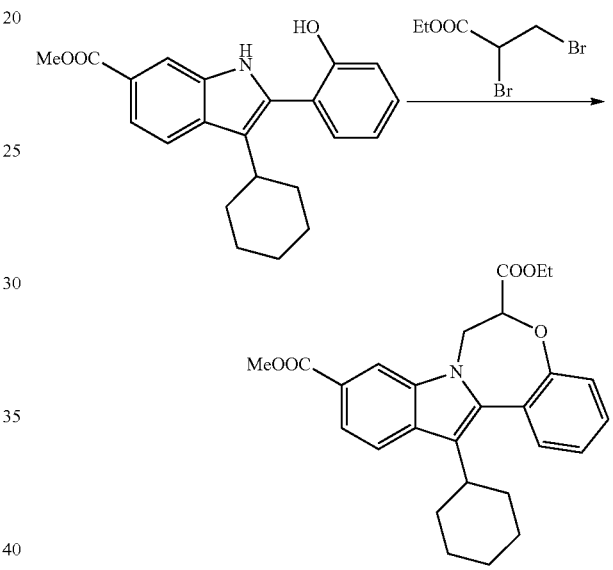

To a solution of methyl 3-cyclohexyl-2-(2-hydroxyphenyl)-1H-indole-6-carboxylate (300 mg, 0.85 mmol) in N,N-dimethylacetamide (15 ml) were added ethyl 2,3-dibromopropionate (0.14 ml, 0.96 mmol) and potassium carbonate (356 mg, 2.57 mmol), and the mixture was stirred at 80° C. for 9 hr. Water was added to the reaction mixture and the mixture was extracted with ethyl acetate. The organic layer was washed successively with water and saturated brine, and dried over anhydrous sodium sulfate.

After filtration, the solvent was evaporated under reduced pressure and the residue was purified by silica gel column chromatography (hexane:ethyl acetate-10:1-6:1) to give 6-ethyl 9-methyl 12-cyclohexyl-6,7-dihydro-5-oxa-7a-azadibenzo[a,e]azulene-6,9-dicarboxylate (186 mg, yield 48.6%).

$^1$H-NMR (400 MHz, DMSO-$d_6$): δ(ppm) 8.18 (1H, brs), 7.92 (1H, d, J=8.4 Hz), 7.65 (1H, dd, J=8.8, 1.6 Hz), 7.42-7.52 (2H, m), 7.39 (1H, td, J=7.6, 0.8 Hz), 7.33 (1H, dd, J=8.0, 1.2 Hz), 5.33 (1H, dd, J=5.6, 5.2 Hz), 4.57-4.85 (2H, m), 4.07-4.21 (2H, m), 3.88 (3H, s), 2.84-2.94 (1H, m), 1.95-2.09 (2H, m), 1.69-1.88 (5H, m), 1.31-1.44 (3H, m), 1.23 (3H, t, J=7.4 Hz).

MS 448 (M+1).

Example 3-2

Production of 12-cyclohexyl-9-methoxycarbonyl-6,7-dihydro-5-oxa-7a-azadibenzo[a,e]azulene-6-carboxylic acid

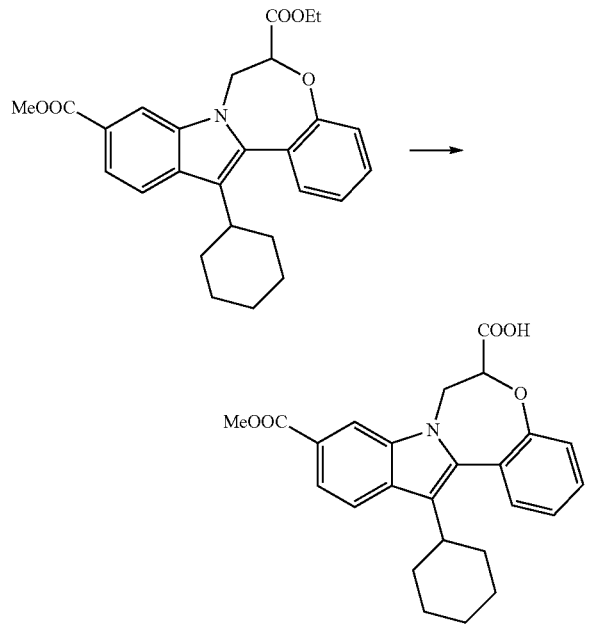

To a solution of 6-ethyl 9-methyl 12-cyclohexyl-6,7-dihydro-5-oxa-7a-azadibenzo[a,e]azulene-6,9-dicarboxylate (270 mg, 0.60 mmol) in tetrahydrofuran (1 ml), methanol (1 ml) and water (1 ml) was added lithium hydroxide monohydrate (30 mg, 0.71 mmol) under ice-cooling, and the mixture was stirred at room temperature for 20 hr. 1N Hydrochloric acid was added to the reaction mixture and the mixture was extracted with ethyl acetate. The organic layer was washed with saturated brine and dried over anhydrous magnesium sulfate. After filtration, the solvent was evaporated under reduced pressure to give 12-cyclohexyl-9-methoxycarbonyl-6,7-dihydro-5-oxa-7a-azadibenzo[a,e]azulene-6-carboxylic acid as a crude product. The obtained crude product was used in Example 3-3 without further purification.

Example 3-3

Production of methyl 12-cyclohexyl-6-dimethylcarbamoyl-6,7-dihydro-5-oxa-7a-azadibenzo[a,e]azulene-9-carboxylate

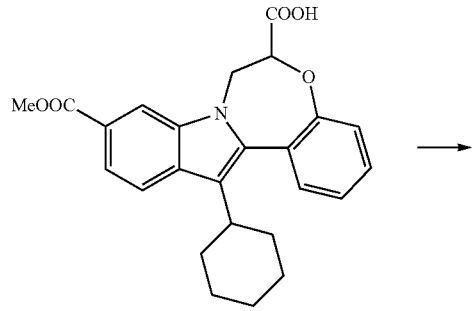

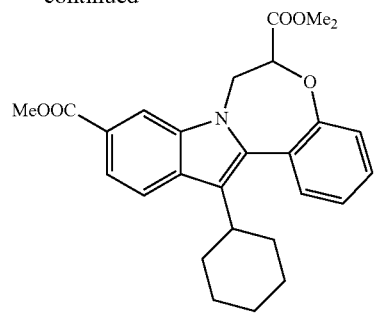

To a solution of 12-cyclohexyl-9-methoxycarbonyl-6,7-dihydro-5-oxa-7a-azadibenzo[a,e]azulene-6-carboxylic acid obtained as a crude product in Example 3-2 in N,N-dimethylformamide (5 ml) were added dimethylamine hydrochloride (246 mg, 3.01 mmol), 1-ethyl-3-(3'-dimethylaminopropyl)carbodiimide monohydrochloride (231 mg, 1.20 mmol), 1-hydroxybenzotriazole monohydrate (163 mg, 1.20 mmol) and triethylamine (0.42 ml, 3.01 mmol), and the mixture was stirred at room temperature for 16 hr. 1N Hydrochloric acid was added to the reaction mixture and the mixture was extracted with ethyl acetate. The organic layer was washed successively with water, saturated aqueous sodium hydrogen carbonate solution and saturated brine, and dried over anhydrous sodium sulfate. After filtration, the solvent was evaporated under reduced pressure and the residue was purified by silica gel chromatography (hexane:ethyl acetate=1:1) to give methyl 12-cyclohexyl-6-dimethylcarbamoyl-6,7-dihydro-5-oxa-7a-azadibenzo[a,e]azulene-9-carboxylate (100 mg, yield 37.2%).

$^1$H-NMR (300 MHz, CDCl$_3$): δ(ppm) 8.11 (1H, d, J=1.2 Hz), 7.90 (1H, d, J=9.0 Hz), 7.77 (1H, dd, J=8.4, 1.5 Hz), 7.44 (1H, td, J=6.6, 1.0 Hz), 7.38 (1H, dd, J=7.5, 1.8 Hz), 7.31 (1H, td, J=7.2, 0.6 Hz), 7.09 (1H, dd, J=7.8, 1.5 Hz), 5.27 (1H, dd, J=8.4, 6.0 Hz), 4.49-4.56 (2H, m), 3.95 (3H, s), 3.25 (3H, s), 3.05 (3H, s), 2.92-3.03 (1H, m), 1.72-2.17 (7H, m), 1.22-1.49 (3H, m).

Example 3-4

Production of 12-cyclohexyl-6-dimethylcarbamoyl-6,7-dihydro-5-oxa-7a-azadibenzo[a,e]azulene-9-carboxylic acid

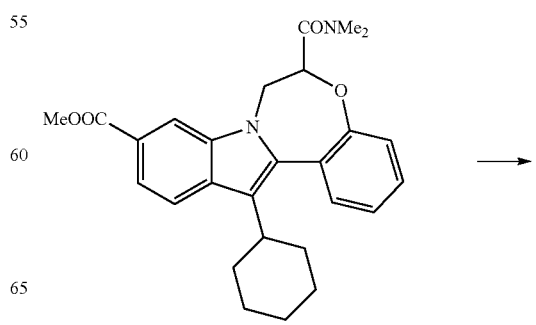

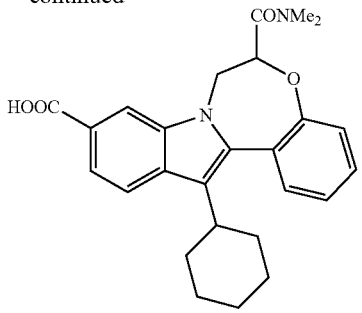

To a solution of methyl 12-cyclohexyl-6-dimethylcarbamoyl-6,7-dihydro-5-oxa-7a-azadibenzo[a,e]azulene-9-carboxylate (100 mg, 0.22 mmol) in tetrahydrofuran (1 ml) and methanol (1 ml) was added 4N aqueous sodium hydroxide solution (1 ml), and the mixture was stirred at room temperature for 18 hr. 1N Hydrochloric acid was added to the reaction mixture and the mixture was extracted with ethyl acetate. The organic layer was washed with saturated brine, and dried over anhydrous magnesium sulfate. After filtration, the solvent was evaporated under reduced pressure and the residue was purified by silica gel chromatography (chloroform:methanol=30:1-20:1) to give 12-cyclohexyl-6-dimethylcarbamoyl-6,7-dihydro-5-oxa-7a-azadibenzo[a,e]azulene-9-carboxylic acid (9 mg, yield 9.4%).

$^1$H-NMR (400 MHz, DMSO-$d_6$): δ(ppm) 12.45 (1H, brs), 8.24 (1H, d, J=1.2 Hz), 7.87 (1H, d, J=8.8 Hz), 7.62 (1H, dd, J=8.4, 1.6 Hz), 7.34-7.48 (3H, m), 7.12 (1H, brd, J=8.0 Hz), 5.52 (1H, dd, J=8.8, 5.2 Hz), 4.52-4.65 (1H, m), 4.23-4.37 (1H, m), 3.21 (3H, s), 2.84-2.94 (1H, m), 2.92 (3H, s), 1.59-2.10 (7H, m), 1.17-1.46 (3H, m).

MS 433 (M+1).

Example 4-1

Production of methyl 11-cyclohexyl-5-oxa-6a-azabenzo[a]fluorene-8-carboxylate

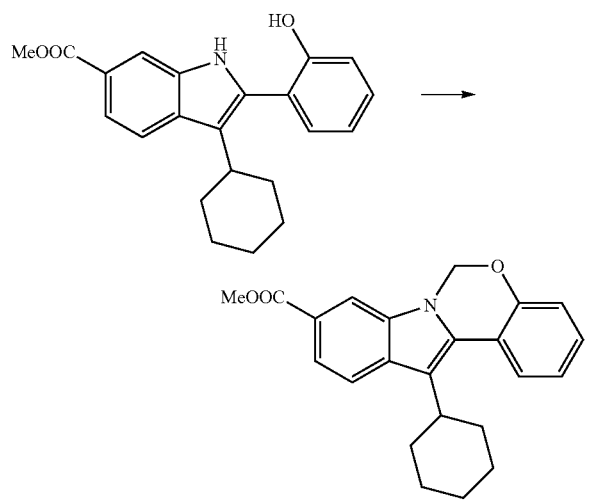

To a solution of methyl 3-cyclohexyl-2-(2-hydroxyphenyl)-1H-indole-6-carboxylate (150 mg, 0.42 mmol) obtained in the same manner as in the method described in Example 3-1, Step 1 in N,N-dimethylformamide (7.5 ml) were added dibromomethane (0.15 ml, 2.13 mmol) and potassium carbonate (1.0 g, 7.23 mmol), and the mixture was stirred at 70° C. for 13 hr. Water was added to the reaction mixture and the mixture was extracted with ethyl acetate. The organic layer was washed successively with water and saturated brine, and dried over anhydrous sodium sulfate. After filtration, the solvent was evaporated under reduced pressure. The residue was purified by silica gel chromatography (hexane:ethyl acetate=10:1-5:1) to give methyl 11-cyclohexyl-5-oxa-6a-azabenzo[a]fluorene-8-carboxylate (30 mg, yield 26.0%).

$^1$H-NMR (400 MHz, CDCl$_3$): δ(ppm) 8.00 (1H, d, J=1.6 Hz), 7.89 (1H, d, J=8.4 Hz), 7.78 (1H, dd, J=8.0, 1.6 Hz), 7.75 (1H, dd, J=8.8, 1.6 Hz), 7.31 (1H, td, J=7.6, 0.8 Hz), 7.19 (1H, td, J=7.6, 0.4 Hz), 7.15 (1H, dd, J=8.0, 1.2 Hz), 5.86 (2H, s), 3.95 (3H, s), 3.24-3.34 (1H, m), 2.02-2.15 (2H, m), 1.81-1.98 (5H, m), 1.36-1.55 (3H, m).

MS 362 (M+1).

Example 4-2

Production of 11-cyclohexyl-5-oxa-6a-azabenzo[a]fluorene-8-carboxylic acid

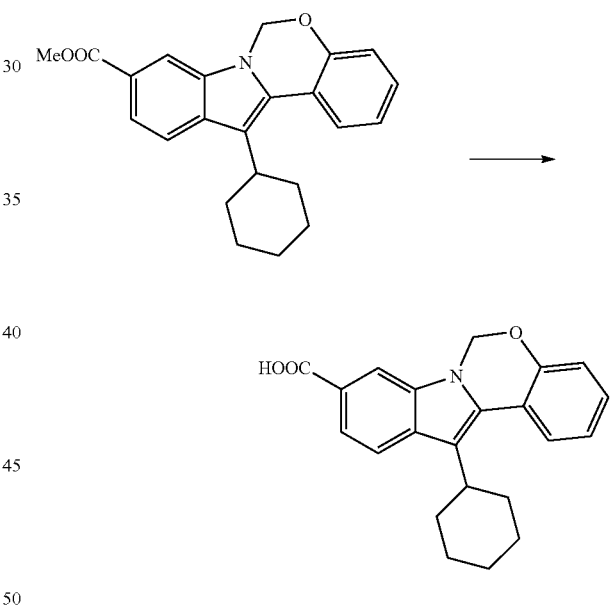

To a solution of methyl 11-cyclohexyl-5-oxa-6a-azabenzo[a]fluorene-8-carboxylate (40 mg, 0.11 mmol) in tetrahydrofuran (1 ml) and methanol (1 ml) was added 4N aqueous sodium hydroxide solution (1 ml), and the mixture was stirred at 60° C. for 3 hr. 1N Hydrochloric acid was added to the reaction mixture, and the precipitated solid was collected by filtration, washed with hexane and dried in vacuo to give 11-cyclohexyl-5-oxa-6a-azabenzo[a]fluorene-8-carboxylic acid (26 mg, yield 68.4%).

$^1$H-NMR (400 MHz, DMSO-$d_6$): δ(ppm) 12.65 (1H, brs), 8.19 (1H, d, J=1.2 Hz), 7.91 (1H, d, J=8.8 Hz), 7.82 (1H, dd, J=8.0, 1.6 Hz), 7.63 (1H, dd, J=8.8, 1.6 Hz), 7.37 (1H, td, J=8.4, 1.0 Hz), 7.27 (1H, td, J=7.6, 0.8 Hz), 7.21 (1H, dd, J=8.0, 1.2 Hz), 6.07 (2H, s), 3.21-3.35 (1H, m), 1.99-2.13 (2H, m), 1.72-1.91 (5H, m), 1.37-1.55 (3H, m).

MS 348 (M+1).

Example 5-1

Production of methyl 13-cyclohexyl-6,7-dihydro-5H-benzo[3,4]azepino[1,2-a]indole-10-carboxylate Step 1: Production of methyl 1-[3-(2-bromophenyl)propyl]-3-cyclohexyl-1H-indole-6-carboxylate

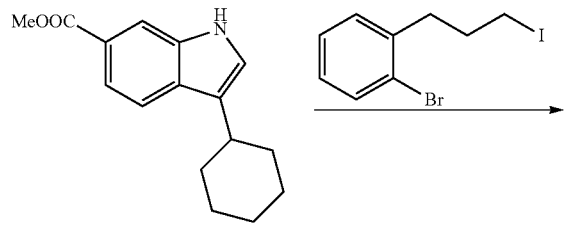

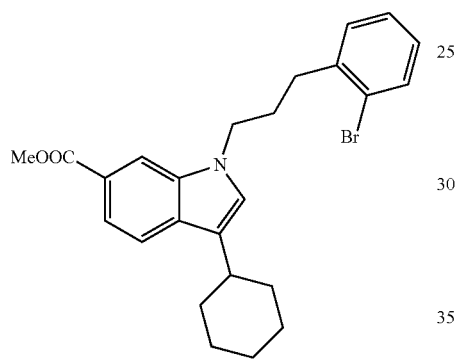

Step 2: Production of methyl 13-cyclohexyl-6,7-dihydro-5H-benzo[3,4]azepino[1,2-a]indole-10-carboxylate

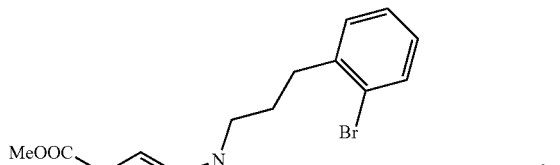

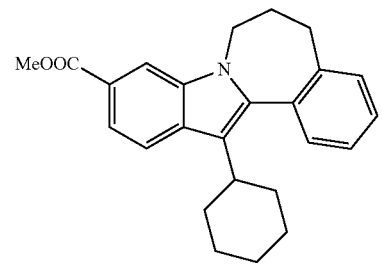

To a solution of methyl 3-cyclohexyl-1H-indole-6-carboxylate (500 mg, 1.94 mmol) obtained in the same manner as in the method described in WO03/010140 in N,N-dimethylformamide (2 ml) was added sodium hydride (93 mg, 2.33 mmol) under ice-cooling, and the mixture was stirred for 30 min. A solution of 1-bromo-2-(3-iodopropyl)benzene (695 mg, 2.14 mmol), obtained in the same manner as in the method described Tetrahedron Letter, Vol. 32, No. 28, pp. 3317-3320, 1991, in N,N-dimethylformamide (1.5 ml) was added and the mixture was stirred for 1 hr. Saturated aqueous ammonium chloride solution was added to the reaction mixture and the mixture was extracted with ethyl acetate. The organic layer was washed successively with water and saturated brine, and dried over anhydrous magnesium sulfate. After filtration, the solvent was evaporated under reduced pressure and the residue was purified by silica gel chromatography (hexane:ethyl acetate=6:1) to give methyl 1-[3-(2-bromophenyl)propyl]-3-cyclohexyl-1H-indole-6-carboxylate (770 mg, yield 79%).

$^1$H-NMR (400 MHz, DMSO-d$_6$): δ(ppm) 8.03 (1H, s), 7.65 (1H, d, J=8.0 Hz), 7.60 (1H, dd, J=8.0, 1.2 Hz), 7.54 (1H, d, J=7.6 Hz), 7.40 (1H, s), 7.27-7.33 (2H, m), 7.11-7.15 (1H, m), 4.27 (2H, t, J=7.0 Hz), 3.85 (3H, s), 2.75-2.83 (1H, m), 2.67 (2H, dd, J=8.4, 5.6 Hz), 1.92-2.10 (4H, m), 1.69-1.84 (3H, m), 1.37-1.50 (4H, m), 1.21-1.32 (1H, m).

To a solution of methyl 1-[3-(2-bromophenyl)propyl]-3-cyclohexyl-1H-indole-6-carboxylate (250 mg, 0.550 mmol) in N,N-dimethylacetamide (7.5 ml) were added potassium acetate (59 mg, 0.605 mmol) and tetrakis(triphenylphosphine)palladium (32 mg, 0.0275 mmol), and the mixture was stirred at 160° C. for 5 hr. The reaction mixture was allowed to cool to room temperature. Water was added to the reaction mixture and the mixture was extracted with ethyl acetate. The organic layer was washed successively with water and saturated brine, and dried over anhydrous magnesium sulfate. After filtration, the solvent was evaporated under reduced pressure and the residue was purified by silica gel chromatography (hexane:ethyl acetate=8:1-4:1) to give methyl 13-cyclohexyl-6,7-dihydro-5H-benzo[3,4]azepino[1,2-a]indole-10-carboxylate (55 mg, yield 27%).

$^1$H-NMR (400 MHz, DMSO-d$_6$): δ(ppm) 8.14 (1H, d, J=1.2 Hz), 7.89 (1H, d, J=8.0 Hz), 7.61 (1H, dd, J=8.4, 1.6 Hz), 7.37-7.46 (4H, m), 4.56-4.65 (1H, m), 3.87 (3H, s), 3.47-3.57 (1H, m), 2.77-2.88 (1H, m), 2.66-2.75 (1H, m), 2.27-2.41 (2H, m), 1.12-2.08 (10H, m).

MS 374 (M+1).

Example 5-2

Production of 13-cyclohexyl-6,7-dihydro-5H-benzo[3,4]azepino[1,2-a]indole-10-carboxylic acid

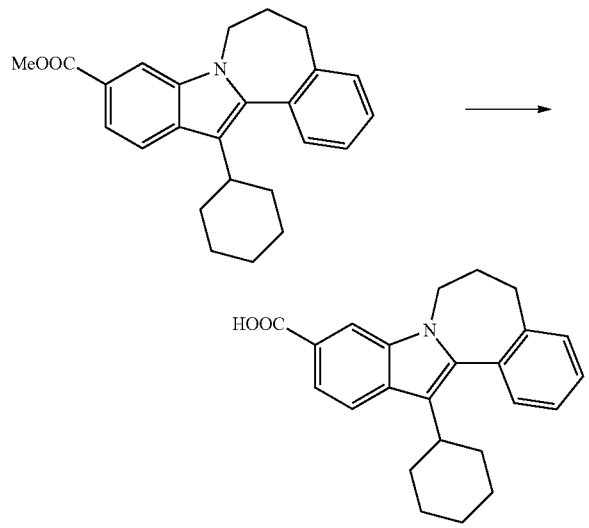

To a solution of methyl 13-cyclohexyl-6,7-dihydro-5H-benzo[3,4]azepino[1,2-a]indole-10-carboxylate (55 mg, 0.147 mmol) in tetrahydrofuran (2 ml) and methanol (2 ml) was added 4N aqueous sodium hydroxide solution (1 ml), and the mixture was stirred at 50° C. for 2 hr. The reaction mixture was allowed to cool to room temperature, and 2N hydrochloric acid (2.5 ml) and water were added to the reaction mixture. The precipitated solid was collected by filtration, washed with water and dried in vacuo to give 13-cyclohexyl-6,7-dihydro-5H-benzo[3,4]azepino[1,2-a]indole-10-carboxylic acid (44 mg, yield 83%).

$^1$H-NMR (400 MHz, DMSO-$d_6$): δ(ppm) 12.54 (1H, brs), 8.10 (1H, s), 7.85 (1H, d, J=8.4 Hz), 7.60 (1H, d, J=8.4 Hz), 7.36-7.45 (4H, m), 4.53-4.62 (1H, m), 3.45-3.58 (1H, m), 2.77-2.88 (1H, m), 2.65-2.75 (1H, m), 2.27-2.42 (2H, m), 1.11-2.10 (10H, m).

MS 360 (M+1).

The compound of Example 5-3 was produced by the same method as in Examples 5-1 to 5-2 or a method similar thereto, and where necessary, by employing other conventional methods. The chemical structural formulas are shown in Table 112. 11-cyclohexyl-6H-isoindolo[2,1-a]indole-3-carboxylic acid (Example 5-3).

Example 6-1

Production of methyl 13-cyclohexyl-6,7-dihydro-5H-pyrrolo[2',1':3,4][1,4]diazepino[1,2-a]indole-10-carboxylate Step 1: Production of methyl 2-(1-tert-butoxycarbonyl-1H-pyrrol-2-yl)-3-cyclohexyl-1H-indole-6-carboxylate

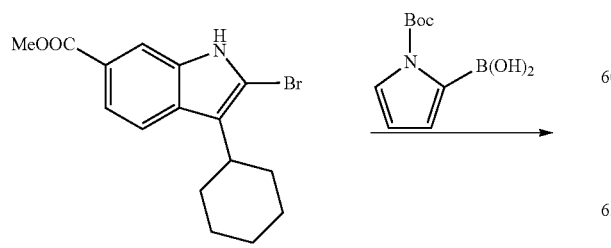

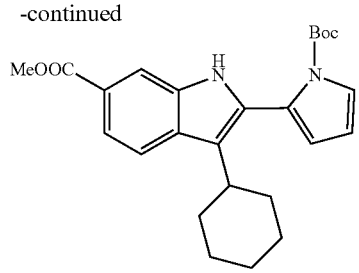

To a suspension of methyl 2-bromo-3-cyclohexyl-1H-indole-6-carboxylate (800 mg, 2.38 mmol) obtained in the same manner as in the method described in WO03/010140 and N-tert-butoxycarbonylpyrrole-2-boronic acid (1.00 g, 4.76 mmol) in dimethoxyethane (10 ml) and water (5 ml) were added sodium carbonate (757 mg, 7.14 mmol), lithium chloride (202 mg, 4.76 mmol) and tetrakis(triphenylphosphine)palladium (275 mg, 0.238 mmol), and the mixture was heated under reflux for 9 hr. The reaction mixture was allowed to cool to room temperature. Water was added to the reaction mixture and the mixture was extracted with ethyl acetate. The organic layer was washed successively with saturated aqueous sodium hydrogen carbonate solution and saturated brine, and dried over anhydrous magnesium sulfate. After filtration, the solvent was evaporated under reduced pressure and the residue was purified by silica gel chromatography (hexane: ethyl acetate=8:1-6:1) to give methyl 2-(1-tert-butoxycarbonyl-1H-pyrrol-2-yl)-3-cyclohexyl-1H-indole-6-carboxylate (642 mg, yield 64%).

$^1$H-NMR (400 MHz, DMSO-$d_6$): δ(ppm) 11.41 (1H, s), 7.90 (1H, d, J=1.2 Hz), 7.75 (1H, d, J=8.4 Hz), 7.56 (1H, dd, J=8.0, 1.2 Hz), 7.48 (1H, t, J=2.6 Hz), 6.38 (2H, d, J=2.8 Hz), 3.84 (3H, s), 1.62-1.84 (7H, m), 1.21-1.32 (3H, m), 1.12 (9H, s).

Step 2: Production of methyl 2-(1-tert-butoxycarbonyl-1H-pyrrol-2-yl)-1-(3-chloropropyl)-3-cyclohexyl-1H-indole-6-carboxylate

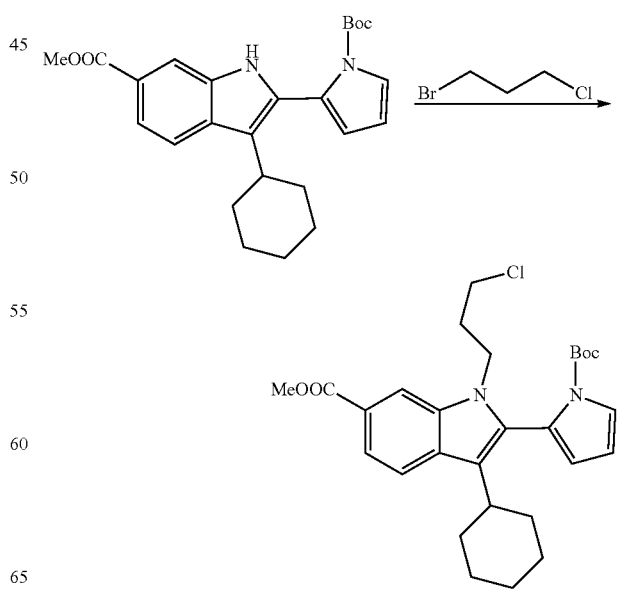

403

To a solution of methyl 2-(1-tert-butoxycarbonyl-1H-pyrrol-2-yl)-3-cyclohexyl-1H-indole-6-carboxylate (140 mg, 0.331 mmol) and 1-bromo-3-chloropropane (156 mg, 0.994 mmol) in N,N-dimethylformamide (4 ml) was added sodium hydride (17 mg, 0.430 mmol) under ice-cooling, and the mixture was stirred for 2 hr. Water was added to the reaction mixture and the mixture was extracted with ethyl acetate. The organic layer was washed successively with water and saturated brine, and dried over anhydrous magnesium sulfate. After filtration, the solvent was evaporated under reduced pressure and the residue was purified by silica gel chromatography (hexane:ethyl acetate=5:1) to give methyl 2-(1-tert-butoxycarbonyl-1H-pyrrol-2-yl)-1-(3-chloropropyl)-3-cyclohexyl-1H-indole-6-carboxylate (167 mg, yield 100%).

$^1$H-NMR (400 MHz, DMSO-d$_6$): δ(ppm) 11.39 (1H, s), 7.88 (1H, d, J=1.2 Hz), 7.73 (1H, d, J=8.4 Hz), 7.54 (1H, dd, J=8.4, 1.6 Hz), 7.46 (1H, t, J=2.6 Hz), 6.36 (2H, d, J=2.8 Hz), 3.82 (3H, s), 2.62-2.72 (1H, m), 1.60-1.82 (7H, m), 1.19-1.30 (3H, m), 1.10 (9H, s).

Step 3: Production of methyl 1-(3-chloropropyl)-3-cyclohexyl-2-(1H-pyrrol-2-yl)-1H-indole-6-carboxylate

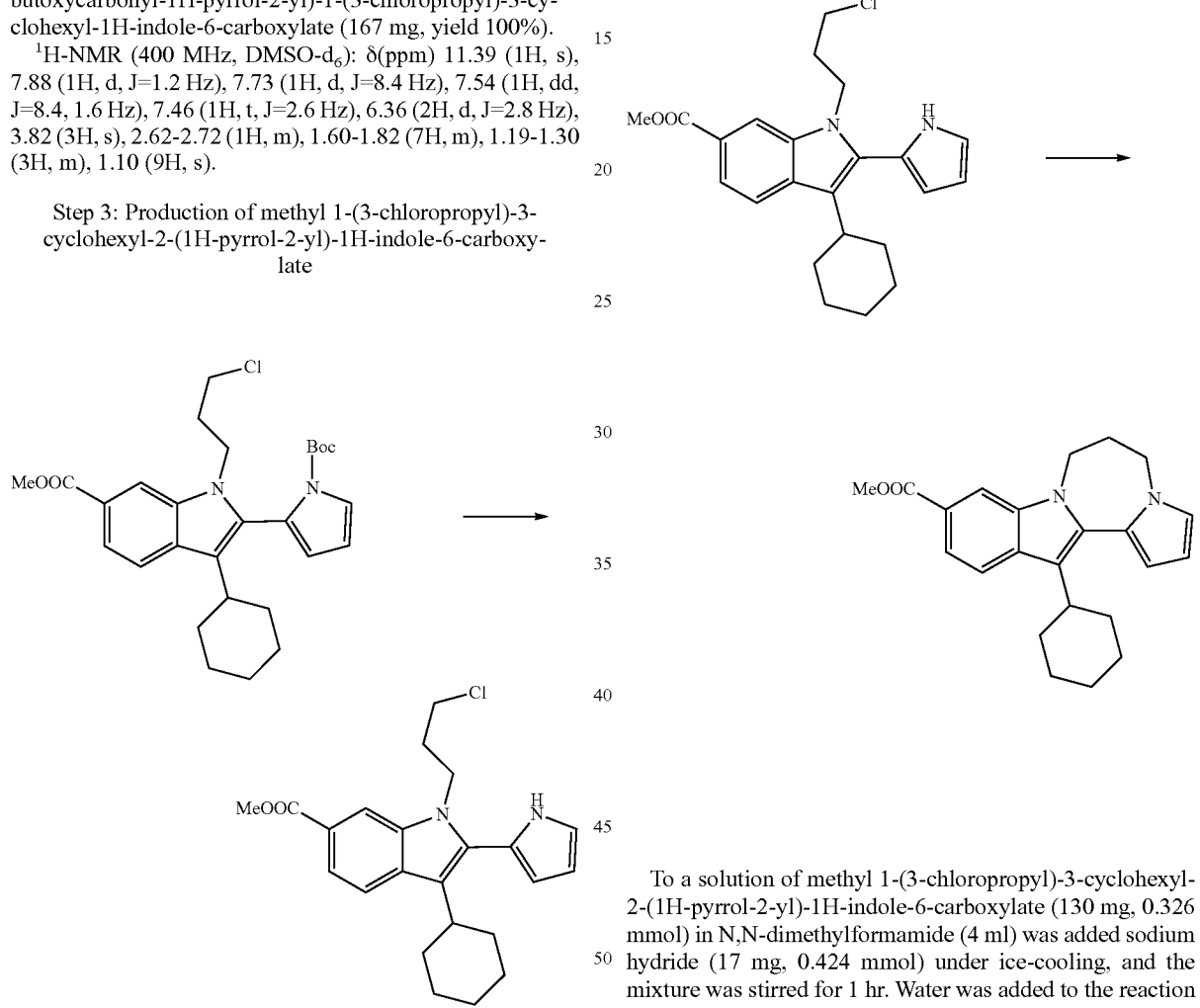

To a solution of methyl 2-(1-tert-butoxycarbonyl-1H-pyrrol-2-yl)-1-(3-chloropropyl)-3-cyclohexyl-1H-indole-6-carboxylate (167 mg, 0.344 mmol) in chloroform (1.5 ml) was added trifluoroacetic acid (1 ml), and the mixture was stirred at room temperature for 8 hr. The reaction mixture was evaporated under reduced pressure. To the residue was added saturated aqueous sodium hydrogen carbonate solution and the mixture was extracted with ethyl acetate. The organic layer was washed successively with saturated aqueous sodium hydrogen carbonate solution and saturated brine, and dried over anhydrous magnesium sulfate. After filtration, the solvent was evaporated under reduced pressure to give methyl 1-(3-chloropropyl)-3-cyclohexyl-2-(1H-pyrrol-2-yl)-1H-indole-6-carboxylate (135 mg, yield 98%).

404

$^1$H-NMR (400 MHz, DMSO-d$_6$): δ(ppm) 11.13 (1H, brs), 8.13 (1H, s), 7.82 (1H, d, J=8.4 Hz), 7.64 (1H, d, J=8.4 Hz), 6.97-7.02 (1H, m), 6.20-6.26 (2H, m), 4.21 (2H, t, J=7.3 Hz), 3.87 (3H, s), 3.48 (2H, t, J=6.3 Hz), 2.63-2.76 (1H, m), 1.63-1.97 (9H, m), 1.18-1.33 (3H, m).

Step 4: Production of methyl 13-cyclohexyl-6,7-dihydro-5H-pyrrolo[2',1':3,4][1,4]diazepino[1,2-a]indole-10-carboxylate To a solution of methyl 1-(3-chloropropyl)-3-cyclohexyl-2-(1H-pyrrol-2-yl)-1H-indole-6-carboxylate (130 mg, 0.326 mmol) in N,N-dimethylformamide (4 ml) was added sodium hydride (17 mg, 0.424 mmol) under ice-cooling, and the mixture was stirred for 1 hr. Water was added to the reaction mixture and the mixture was extracted with ethyl acetate. The organic layer was washed successively with water and saturated brine, and dried over anhydrous magnesium sulfate. After filtration, the solvent was evaporated under reduced pressure and the residue was purified by silica gel chromatography (hexane:ethyl acetate=4:1) to give methyl 13-cyclohexyl-6,7-dihydro-5H-pyrrolo[2',1':3,4][1,4]diazepino[1,2-a]indole-10-carboxylate (91 mg, yield 77%).

$^1$H-NMR (400 MHz, DMSO-d$_6$): δ(ppm) 8.13 (1H, d, J=1.2 Hz), 7.82 (1H, d, J=8.8 Hz), 7.60 (1H, dd, J=8.4, 1.6 Hz), 7.04 (1H, dd, 1.6 Hz), 6.29 (1H, dd, J=3.6, 1.6 Hz), 6.18 (1H, dd, J=4.0, 2.8 Hz), 4.11 (2H, t, J=6.4 Hz), 3.98 (2H, t, J=6.4 Hz), 3.86 (3H, s), 2.91-3.01 (1H, m), 2.25-2.33 (2H, m), 1.91-2.03 (2H, m), 1.69-1.85 (5H, m), 1.26-1.43 (3H, m).

MS 363 (M+1).

Example 6-2

Production of 13-cyclohexyl-6,7-dihydro-5H-pyrrolo[2',1':3,4][1,4]diazepino[1,2-a]indole-10-carboxylic acid

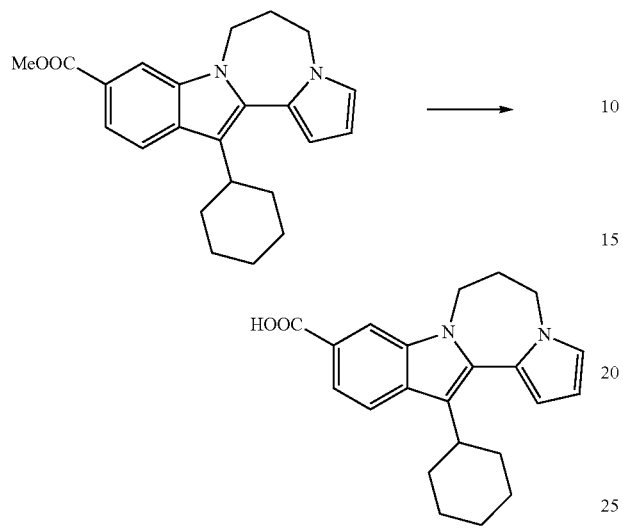

To a solution of methyl 13-cyclohexyl-6,7-dihydro-5H-pyrrolo[2',1':3,4][1,4]diazepino[1,2-a]indole-10-carboxylate (88 mg, 0.17 mmol) in tetrahydrofuran (2 ml) and methanol (2 ml) was added 4N aqueous sodium hydroxide solution (1 ml) and the mixture was stirred at 50° C. for 2 hr. The reaction mixture was allowed to cool to room temperature, and 2N hydrochloric acid (2.5 ml) and water were added to the reaction mixture. The precipitated solid was collected by filtration, washed with water and dried in vacuo to give 13-cyclohexyl-6,7-dihydro-5H-pyrrolo[2',1':3,4][1,4]diazepino[1,2-a]indole-10-carboxylic acid (74 mg, yield 85%).

$^1$H-NMR (400 MHz, DMSO-d$_6$): δ(ppm) 12.54 (1H, brs), 8.09 (1H, d, J=1.6 Hz), 7.78 (1H, d, J=8.4 Hz), 7.58 (1H, dd, J=8.8, 1.6 Hz), 7.04 (1H, dd, J=2.4, 1.6 Hz), 6.28 (1H, dd, J=4.0, 1.6 Hz), 6.17 (1H, dd, J=3.2, 2.4 Hz), 4.09 (2H, t, J=6.0 Hz), 3.97 (2H, t, J=6.4 Hz), 3.32 (3H, s), 2.91-3.01 (1H, m), 2.25-2.32 (2H, m), 1.90-2.04 (2H, m), 1.69-1.85 (5H, m), 1.27-1.42 (3H, m).

MS 349 (M+1).

Example 7-1

Production of ethyl 12-cyclohexyl-3-hydroxy-6,7-dihydro-5-oxo-7a,8-diazadibenzo[a,e]azulene-9-carboxylate Step 1: Production of 3-cyclohexyl-1H-pyrrolo[2,3-b]pyridine-6-carbonitrile

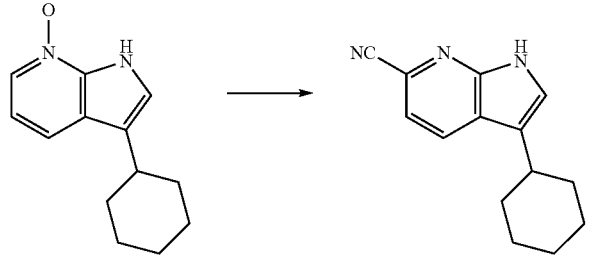

To a solution of 3-cyclohexyl-1H-pyrrolo[2,3-b]pyridine-N-oxide (3.0 g, 13.7 mmol) obtained in the same manner as in the method described in WO03/010140 in acetonitrile (30 ml) were added triethylamine (5.8 ml, 41.2 mmol) and trimethylsilyl cyanide (8.3 ml, 61.8 mmol), and the mixture was heated under reflux at 110° C. for 10 hr. The mixture was allowed to cool to room temperature, and saturated aqueous sodium hydrogen carbonate solution was added. The precipitated solid was collected by filtration and the obtained solid was purified by silica gel chromatography (hexane:ethyl acetate=2:1) to give 3-cyclohexyl-1H-pyrrolo[2,3-b]pyridine-6-carbonitrile (1.60 g, yield 52%).

$^1$H-NMR (400 MHz, CDCl$_3$): δ(ppm) 9.48 (1H, brs), 8.03 (1H, d, J=8.0 Hz), 7.44 (1H, d, J=8.0 Hz), 7.32 (1H, d, J=2.4 Hz), 2.74-2.88 (1H, m), 2.00-2.11 (2H, m), 1.74-1.92 (3H, m), 1.39-1.53 (4H, m), 1.24-1.36 (1H, m).

MS 226 (M+1).

Step 2: Production of 1-(2-benzyloxyethyl)-3-cyclohexyl-1H-pyrrolo[2,3-b]pyridine-6-carbonitrile

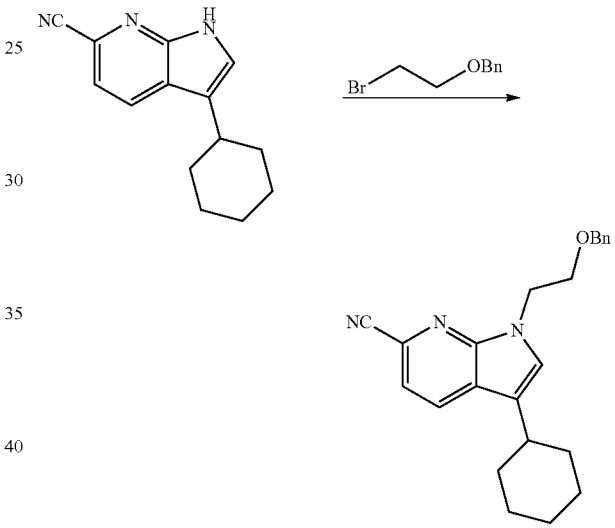

To a solution of 3-cyclohexyl-1H-pyrrolo[2,3-b]pyridine-6-carbonitrile (1.0 g, 13.7 mmol) in N,N-dimethylformamide (10 ml) was added sodium hydride (213 mg, 5.33 mmol) under ice-cooling, and the mixture was stirred for 15 min. After stirring, benzyl 2-bromoethyl ether (0.77 ml, 4.88 mmol) was added and the mixture was stirred at 50° C. for 1 hr. The mixture was allowed to cool to room temperature and water was added. The mixture was extracted with ethyl acetate. The organic layer was washed successively with water and saturated brine, and dried over anhydrous magnesium sulfate. After filtration, the solvent was evaporated under reduced pressure and the residue was purified by silica gel chromatography (hexane:ethyl acetate=4:1) to give 1-(2-benzyloxyethyl)-3-cyclohexyl-1H-pyrrolo[2,3-b]pyridine-6-carbonitrile (1.44 g, yield 90%).

$^1$H-NMR (400 MHz, CDCl$_3$): δ(ppm) 7.95 (1H, d, J=8.0 Hz), 7.37 (1H, d, J=8.0 Hz), 7.33 (1H, s), 7.16-7.29 (5H, m), 4.48 (2H, s), 4.46 (2H, t, J=5.2 Hz), 3.81 (2H, t, J=5.0 Hz), 2.73-2.83 (1H, m), 2.00-2.07 (2H, m), 1.74-2.00 (3H, m), 1.37-1.52 (4H, m), 1.26-1.35 (1H, m).

MS 360 (M+1).

Step 3: Production of ethyl 1-(2-benzyloxyethyl)-3-cyclohexyl-1H-pyrrolo[2,3-b]pyridine-6-carboxylate

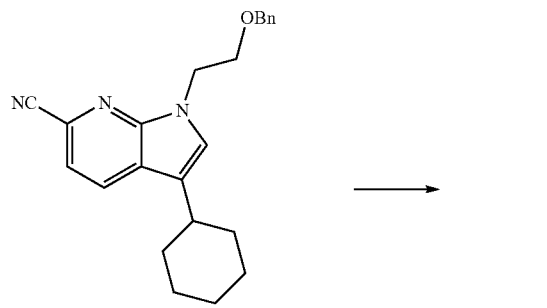

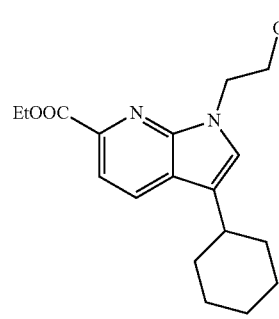

To a solution of 1-(2-benzyloxyethyl)-3-cyclohexyl-1H-pyrrolo[2,3-b]pyridine-6-carbonitrile (1.44 g, 4.00 mmol) in ethanol (30 ml) was added acetyl chloride (8.5 ml, 120 mmol) under ice-cooling, and the mixture was heated under reflux for 3 hr. The mixture was allowed to cool to room temperature, and the solvent was evaporated under reduced pressure. The residue was dissolved in ethyl acetate and water was added. The mixture was extracted with ethyl acetate, and the organic layer was washed successively with water and saturated brine, and dried over anhydrous magnesium sulfate. After filtration, the solvent was evaporated under reduced pressure and the residue was purified by silica gel chromatography (hexane:ethyl acetate=4:1) to give ethyl 1-(2-benzyloxyethyl)-3-cyclohexyl-1H-pyrrolo[2,3-b]pyridine-6-carboxylate (1.14 g, yield 70%).

$^1$H-NMR (400 MHz, CDCl$_3$): δ(ppm) 7.96 (1H, d, J=8.0 Hz), 7.86 (1H, d, J=8.0 Hz), 7.32 (1H, s), 7.19-7.30 (5H, m), 4.55 (2H, t, J=5.2 Hz), 4.49 (2H, s), 4.44 (2H, q, J=7.2 Hz), 3.84 (2H, t, J=5.0 Hz), 2.75-2.85 (1H, m), 2.01-2.12 (2H, m), 1.73-1.90 (3H, m), 1.38-1.53 (7H, m), 1.26-1.34 (1H, m).

MS 407 (M+1).

Step 4: Production of ethyl 1-(2-benzyloxyethyl)-2-bromo-3-cyclohexyl-1H-pyrrolo[2,3-b]pyridine-6-carboxylate

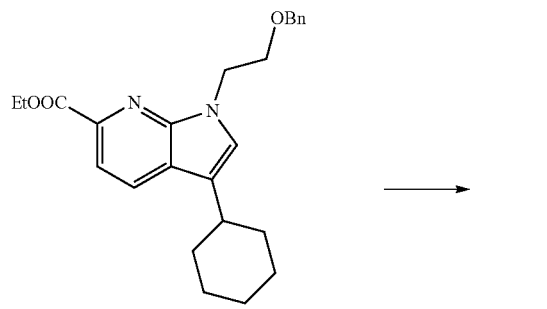

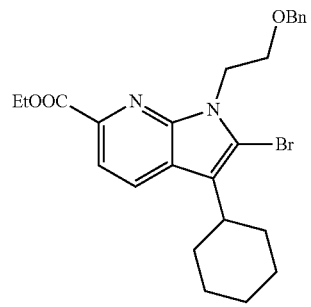

To a solution of ethyl 1-(2-benzyloxyethyl)-3-cyclohexyl-1H-pyrrolo[2,3-b]pyridine-6-carboxylate (888 mg, 2.18 mmol) in carbon tetrachloride (20 ml) was added N-bromosuccinimide (505 mg, 2.84 mmol), and the mixture was heated under reflux for 12 hr. The mixture was allowed to cool to room temperature, and the solvent was evaporated under reduced pressure. The residue was purified by silica gel chromatography (hexane:ethyl acetate=6:1) to give ethyl 1-(2-benzyloxyethyl)-2-bromo-3-cyclohexyl-1H-pyrrolo[2,3-b]pyridine-6-carboxylate (592 mg, yield 56%).

$^1$H-NMR (400 MHz, CDCl$_3$): δ(ppm) 8.03 (1H, d, J=8.0 Hz), 7.84 (1H, d, J=8.0 Hz), 7.15-7.25 (5H, m), 4.66 (2H, t, J=6.2 Hz), 4.55 (2H, s), 4.43 (2H, q, J=7.1 Hz), 3.88 (2H, t, J=6.0 Hz), 2.80-2.93 (1H, m), 1.76-1.92 (6H, m), 1.23-1.49 (7H, m).

MS 485 (M+1).

Step 5: Production of ethyl 1-(2-benzyloxyethyl)-2-(2,4-bismethoxymethoxyphenyl)-3-cyclohexyl-1H-pyrrolo[2,3-b]pyridine-6-carboxylate

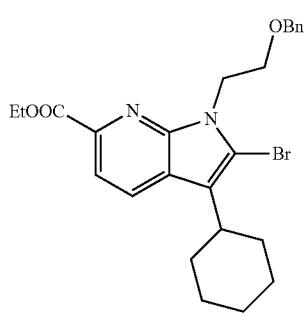

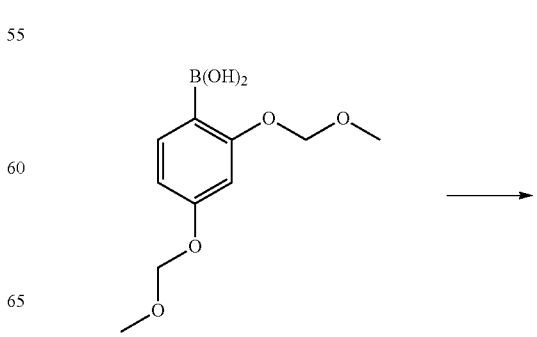

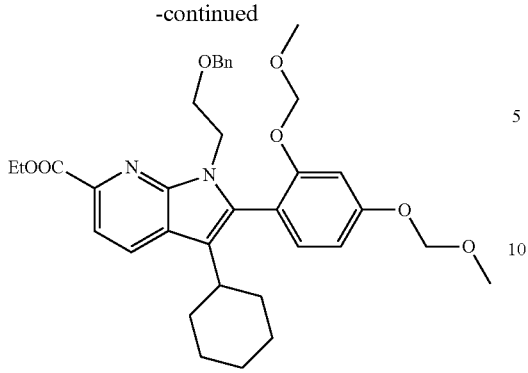

To a suspension of ethyl 1-(2-benzyloxyethyl)-2-bromo-3-cyclohexyl-1H-pyrrolo[2,3-b]pyridine-6-carboxylate (592 mg, 1.22 mmol) and 2,4-bismethoxymethoxyphenylboronic acid (384 mg, 1.59 mmol) obtained in the same manner as in Example 2-1, Step 2 in 1,2-dimethoxyethane (12 ml) and water (6 ml) were added lithium chloride (155 mg, 3.66 mmol), sodium carbonate (388 mg, 3.66 mmol) and tetrakis(triphenylphosphine)palladium (141 mg, 0.12 mmol), and the mixture was stirred with heating at 110° C. for 2.5 hr. The reaction mixture was allowed to cool to room temperature. Water was added to the reaction mixture and the mixture was extracted with ethyl acetate. The organic layer was washed with saturated brine and dried over anhydrous magnesium sulfate. After filtration, the solvent was evaporated under reduced pressure and the obtained residue was purified by silica gel chromatography (hexane:ethyl acetate=3:1) to give ethyl 1-(2-benzyloxyethyl)-2-(2,4-bismethoxymethoxyphenyl)-3-cyclohexyl-1H-pyrrolo[2,3-b]pyridine-6-carboxylate (727 mg, yield 99%).

$^1$H-NMR (400 MHz, CDCl$_3$): δ(ppm) 8.07 (1H, d, J=8.0 Hz), 7.87 (1H, d, J=8.0 Hz), 7.18-7.21 (3H, m), 7.06-7.09 (3H, m), 6.92 (1H, d, J=2.4 Hz), 6.74 (1H, dd, J=8.4, 2.4 Hz), 5.23 (2H, s), 4.97 (2H, dd, J=21.6, 6.8 Hz), 4.55-4.64 (1H, m), 4.33-4.49 (4H, m), 4.07-4.18 (1H, m), 3.66-3.75 (1H, m), 3.56-3.64 (1H, m), 3.54 (3H, s), 3.27 (3H, s), 2.43-2.54 (1H, m), 1.65-1.84 (7H, m), 1.43 (3H, t, J=7.0 Hz), 1.17-1.31 (3H, m).

MS 603 (M+1).

Step 6: Production of ethyl 2-(2,4-bismethoxymethoxyphenyl)-3-cyclohexyl-1-(2-hydroxyethyl)-1H-pyrrolo[2,3-b]pyridine-6-carboxylate

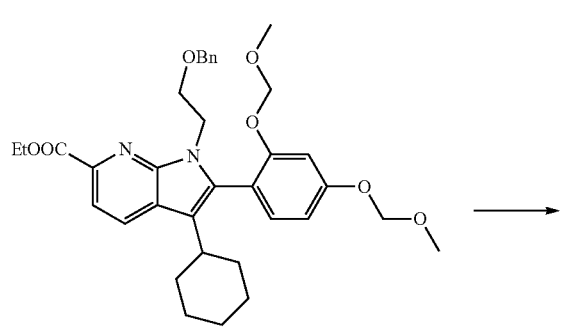

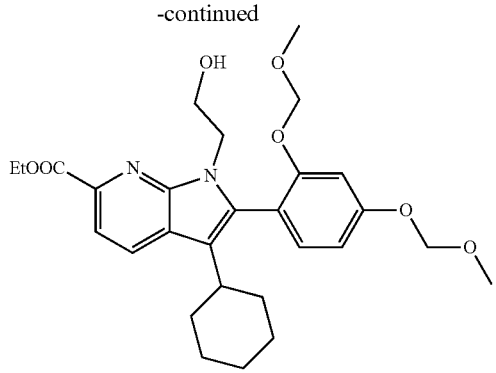

To a solution of ethyl 1-(2-benzyloxyethyl)-2-(2,4-bismethoxymethoxyphenyl)-3-cyclohexyl-1H-pyrrolo[2,3-b]pyridine-6-carboxylate (727 mg, 1.20 mmol) in tetrahydrofuran (10 ml) and methanol (10 ml) was added 7.5% palladium carbon (225 mg), and the mixture was stirred at atmospheric pressure and in a hydrogen atmosphere at room temperature for 12 hr. The reaction mixture was filtered and the filtrate was concentrated under reduced pressure to give ethyl 2-(2,4-bismethoxymethoxyphenyl)-3-cyclohexyl-1-(2-hydroxyethyl)-1H-pyrrolo[2,3-b]pyridine-6-carboxylate as a crude product. The obtained compound was used in Step 7 without further purification.

$^1$H-NMR (400 MHz, CDCl$_3$): δ(ppm) 8.15 (1H, d, J=8.4 Hz), 7.91 (1H, d, J=8.4 Hz), 7.10 (1H, d, J=8.4 Hz), 6.97 (1H, d, J=2.0 Hz), 6.82 (1H, dd, J=8.4, 2.4 Hz), 5.24 (2H, s), 5.05 (2H, dd, J=22.0, 7.2 Hz), 4.45 (2H, q, J=7.2 Hz), 3.87-4.15 (4H, m), 3.55 (3H, s), 3.30 (3H, s), 2.44-2.56 (1H, m), 1.66-1.84 (7H, m), 1.45 (3H, t, J=7.0 Hz), 1.19-1.34 (3H, m).

MS 513 (M+1).

Step 7: Production of ethyl 3-cyclohexyl-2-(2,4-dihydroxyphenyl)-1-(2-hydroxyethyl)-1H-pyrrolo[2,3-b]pyridine-6-carboxylate

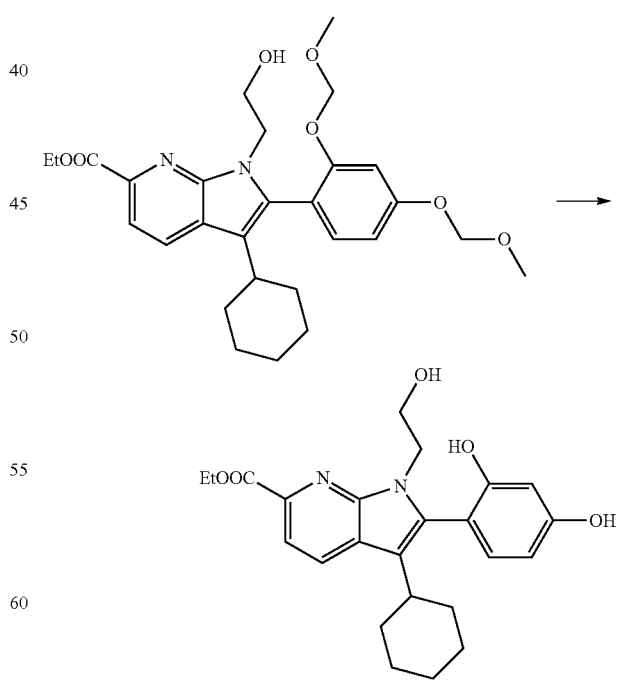

To a solution of ethyl 2-(2,4-bismethoxymethoxyphenyl)-3-cyclohexyl-1-(2-hydroxyethyl)-1H-pyrrolo[2,3-b]pyridine-6-carboxylate obtained as a crude product in the previous step in tetrahydrofuran (10 ml) and methanol (10 ml) was added 6N hydrochloric acid (10 ml), and the mixture was stirred at room temperature for 1 hr. The reaction mixture was ice-cooled. 4N Aqueous sodium hydroxide solution (15 ml) was added and the mixture was extracted with ethyl acetate. The organic layer was washed with saturated brine and dried over anhydrous magnesium sulfate. After filtration, the solvent was evaporated under reduced pressure to give ethyl 3-cyclohexyl-2-(2,4-dihydroxyphenyl)-1-(2-hydroxyethyl)-1H-pyrrolo[2,3-b]pyridine-6-carboxylate as a crude product. The obtained compound was used in Step 8 without further purification.

$^1$H-NMR (400 MHz, CDCl$_3$): δ(ppm) 8.15 (1H, d, J=8.4 Hz), 7.89 (1H, d, J=8.0 Hz), 6.98 (1H, d, J=8.4 Hz), 6.89 (1H, d, J=2.4 Hz), 6.52 (1H, dd, J=8.0, 2.0 Hz), 4.40-4.48 (2H, m), 4.08-4.15 (2H, m), 4.00-4.08 (1H, m), 3.92-3.99 (1H, m), 2.53-2.66 (1H, m), 1.64-1.89 (7H, m), 1.43 (3H, t, J=7.0 Hz), 1.33-1.33 (3H, m).

MS 425 (M+1).

Step 8: Production of ethyl 12-cyclohexyl-3-hydroxy-6,7-dihydro-5-oxo-7a,8-diazadibenzo[a,e]azulene-9-carboxylate

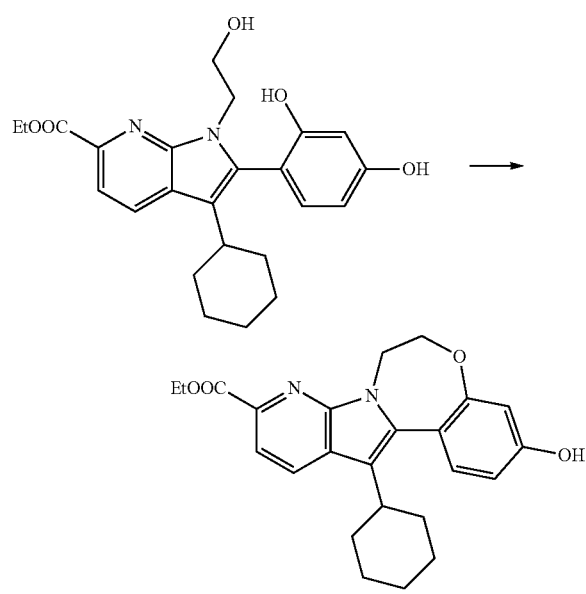

To a solution of ethyl 3-cyclohexyl-2-(2,4-dihydroxyphenyl)-1-(2-hydroxyethyl)-1H-pyrrolo[2,3-b]pyridine-6-carboxylate in tetrahydrofuran (25 ml) obtained as a crude product in the previous step were added triphenylphosphine (463 mg, 1.77 mmol) and diisopropyl azodicarboxylate (0.35 ml, 1.77 mmol) under ice-cooling, and the mixture was stirred at room temperature for 2 hr. The reaction mixture was concentrated and the obtained residue was purified by silica gel chromatography (hexane:ethyl acetate=3:2) to give ethyl 12-cyclohexyl-3-hydroxy-6,7-dihydro-5-oxo-7a,8-diazadibenzo[a,e]azulene-9-carboxylate (344 mg, yield 72%).

$^1$H-NMR (400 MHz, CDCl$_3$): δ(ppm) 8.15 (1H, d, J=8.0 Hz), 7.88 (1H, d, J=8.4 Hz), 7.27 (1H, d, J=8.0 Hz), 6.77 (1H, dd, J=8.4, 2.8 Hz), 6.72 (1H, d, J=2.8 Hz), 5.85 (1H, brs), 4.52-4.58 (2H, m), 4.43-4.51 (4H, m), 2.88-2.98 (1H, m), 1.74-2.01 (7H, m), 1.45 (3H, t, J=7.2 Hz), 1.32-1.40 (3H, m).

MS 407 (M+1).

Example 7-2

Production of ethyl 3-benzyloxy-12-cyclohexyl-6,7-dihydro-5-oxo-7a,8-diazadibenzo[a,e]azulene-9-carboxylate

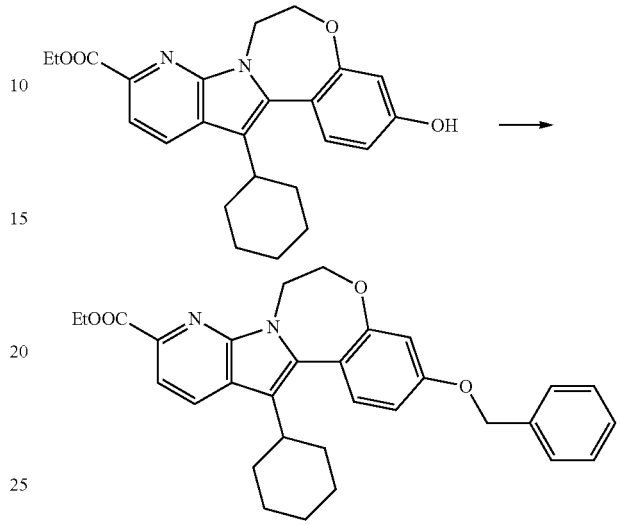

To a solution of ethyl 12-cyclohexyl-3-hydroxy-6,7-dihydro-5-oxo-7a,8-diazadibenzo[a,e]azulene-9-carboxylate (50 mg, 0.12 mmol) in N,N-dimethylformamide (1 ml) were added potassium carbonate (20 mg, 0.15 mmol) and benzyl bromide (0.02 ml, 0.14 mmol), and the mixture was stirred at 80° C. for 3 hr. The reaction mixture was allowed to cool to room temperature. To the reaction mixture was added saturated aqueous sodium hydrogen carbonate solution and the mixture was extracted with ethyl acetate. The organic layer was washed with saturated brine and dried over anhydrous magnesium sulfate. After filtration, the solvent was evaporated under reduced pressure and the obtained residue was purified by silica gel chromatography (hexane:ethyl acetate=3:1) to give ethyl 3-benzyloxy-12-cyclohexyl-6,7-dihydro-5-oxo-7a,8-diazadibenzo[a,e]azulene-9-carboxylate (50 mg, yield 82%).

$^1$H-NMR (400 MHz, CDCl$_3$): δ(ppm) 8.15 (1H, d, J=8.4 Hz), 7.88 (1H, d, J=8.4 Hz), 7.31-7.48 (6H, m), 6.90 (1H, dd, J=8.4, 2.4 Hz), 6.86 (1H, d, J=2.8 Hz), 5.11 (2H, s), 4.51-4.61 (4H, m), 4.47 (2H, q, J=7.1 Hz), 2.90-3.00 (1H, m), 1.72-2.00 (7H, m), 1.45 (3H, t, J=7.0 Hz), 1.32-1.41 (3H, m).

MS 497 (M+1).

Example 7-3

Production of 3-benzyloxy-12-cyclohexyl-6,7-dihydro-5-oxo-7a,8-diazadibenzo[a,e]azulene-9-carboxylic acid

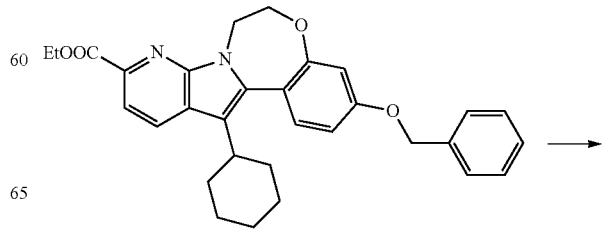

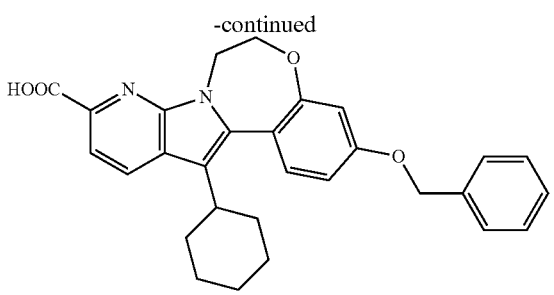

To a solution of ethyl 3-benzyloxy-12-cyclohexyl-6,7-dihydro-5-oxo-7a,8-diazadibenzo[a,e]azulene-9-carboxylate (50 mg, 0.10 mmol) in tetrahydrofuran (2 ml) and methanol (2 ml) was added 4N aqueous sodium hydroxide solution (1 ml), and the mixture was stirred with heating at 60° C. for 1 hr. The reaction mixture was allowed to cool to room temperature. 2N Hydrochloric acid (2 ml) was added to the reaction mixture and the mixture was extracted with ethyl acetate. The organic layer was washed with saturated brine and dried over anhydrous magnesium sulfate. After filtration, the solvent was evaporated under reduced pressure. Hexane was added to the residue, and the precipitated solid was collected by filtration and dried in vacuo to give 3-benzyloxy-12-cyclohexyl-6,7-dihydro-5-oxo-7a,8-diazadibenzo[a,e]azulene-9-carboxylic acid (21 mg, yield 41%).

$^1$H-NMR (400 MHz, DMSO-d$_6$): δ(ppm) 12.75 (1H, brs), 8.30 (1H, d, J=8.4 Hz), 7.78 (1H, d, J=8.0 Hz), 7.45-7.49 (2H, m), 7.31-7.44 (4H, m), 7.02 (1H, dd, J=8.8, 2.8 Hz), 6.93 (1H, d, J=2.8 Hz), 5.17 (2H, s), 4.45 (4H, brs), 2.82-2.92 (1H, m), 1.88-2.01 (2H, m), 1.65-1.85 (4H, m), 1.19-1.46 (3H, m).

MS 469 (M+1).

The compounds of Examples 7-4 to 7-8 were produced by the same methods as in Examples 7-1 to 7-3 or methods similar thereto, and where necessary, by employing other conventional methods. The chemical structural formulas are shown in Tables 113 and 114.

12-cyclohexyl-3-[2-(morpholin-4-yl)-5-(2-oxopyrrolidin-1-yl)benzyloxy]-6,7-dihydro-5-oxa-7a,8-diazadibenzo[a,e]azulene-9-carboxylic acid dihydrochloride (Example 7-4), 12-cyclohexyl-3-[5-methanesulfonyl-2-(morpholin-4-yl)benzyloxy]-6,7-dihydro-5-oxa-7a,8-diazadibenzo[a,e]azulene-9-carboxylic acid monohydrochloride (Example 7-5), 3-[5-(N-acetyl-N-methylamino)-2-(morpholin-4-yl)benzyloxy]-12-cyclohexyl-6,7-dihydro-5-oxa-7a,8-diazadibenzo[a,e]azulene-9-carboxylic acid dihydrochloride (Example 7-6), 12-cyclohexyl-3-[2-(4-methanesulfonylpiperazin-1-yl)-5-(2-oxopyrrolidin-1-yl)benzyloxy]-6,7-dihydro-5-oxa-7a,8-diazadibenzo[a,e]azulene-9-carboxylic acid dihydrochloride (Example 7-7).

3-benzyloxy-12-cyclohexyl-6,7-dihydro-5-oxa-7a,8-diazadibenzo[a,e]azulene-9-carboxylic acid (Example 7-8)

Example 8-1

Production of ethyl 12-cyclohexyl-6-oxo-6,7-dihydro-5H-5,7a,8-triazadibenzo[a,e]azulene-9-carboxylate

Step 1: Production of methyl (6-cyano-3-cyclohexylpyrrolo[2,3-b]pyridin-1-yl)acetate

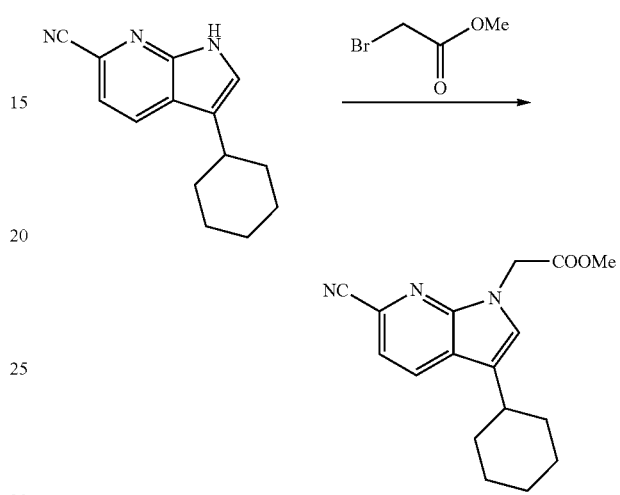

To a solution of 3-cyclohexyl-1H-pyrrolo[2,3-b]pyridine-6-carbonitrile (541 mg, 2.40 mmol) obtained in the same manner as in the method described in Example 7-1, Step 1 in N,N-dimethylformamide (5 ml) was added sodium hydride (115 mg, 2.88 mmol) under ice-cooling, and the mixture was stirred for 20 min. Methyl bromoacetate (0.27 ml, 2.88 mmol) was added and the mixture was stirred at room temperature for 1.5 hr. Water was added to the reaction mixture, and the precipitated solid was collected by filtration, washed with water and dried in vacuo to give methyl (6-cyano-3-cyclohexylpyrrolo[2,3-b]pyridin-1-yl)acetate (647 mg, yield 91%).

$^1$H-NMR (400 MHz, CDCl$_3$): δ(ppm) 7.98 (1H, d, J=8.0 Hz), 7.41 (1H, d, J=8.0 Hz), 7.17 (1H, s), 5.03 (2H, s), 3.78 (3H, s), 2.72-2.85 (1H, m), 1.99-2.11 (2H, m), 1.73-1.92 (3H, m), 1.37-1.51 (4H, m), 1.20-1.34 (1H, m).

MS 297 (M+1).

Step 2: Production of ethyl 3-cyclohexyl-1-ethoxycarbonylmethyl-1H-pyrrolo[2,3-b]pyridine-6-carboxylate

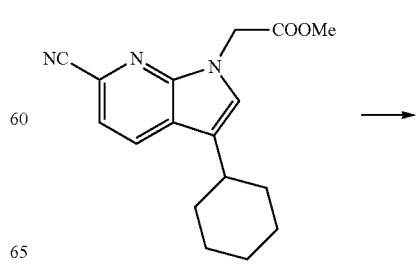

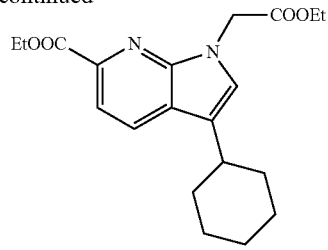

To a solution of methyl (6-cyano-3-cyclohexylpyrrolo[2,3-b]pyridin-1-yl)acetate (647 mg, 2.18 mmol) in ethanol (13 ml) was added acetyl chloride (4.7 ml, 65.4 mmol) under ice-cooling, and the mixture was heated under reflux for 3 hr. The mixture was allowed to cool to room temperature and the solvent was evaporated under reduced pressure. Water was added to the residue and the mixture was extracted with ethyl acetate. The organic layer was washed successively with water and saturated brine, and dried over anhydrous magnesium sulfate. After filtration, the solvent was evaporated under reduced pressure and the residue was purified by silica gel chromatography (hexane:ethyl acetate=4:1) to give ethyl 3-cyclohexyl-1-ethoxycarbonylmethyl-1H-pyrrolo[2,3-b]pyridine-6-carboxylate (563 mg, yield 75%).

$^1$H-NMR (400 MHz, CDCl$_3$): δ(ppm) 7.98 (1H, d, J=8.0 Hz), 7.89 (1H, d, J=8.4 Hz), 7.15 (1H, s), 5.11 (2H, s), 4.45 (2H, q, J=7.1 Hz), 4.22 (2H, q, J=7.1 Hz), 2.75-2.85 (1H, m), 2.02-2.14 (2H, m), 1.71-1.91 (3H, m), 1.37-1.53 (7H, m), 1.23-1.33 (4H, m).

MS 359 (M+1).

Step 3: Production of ethyl 2-bromo-3-cyclohexyl-1-ethoxycarbonylmethyl-1H-pyrrolo[2,3-b]pyridine-6-carboxylate

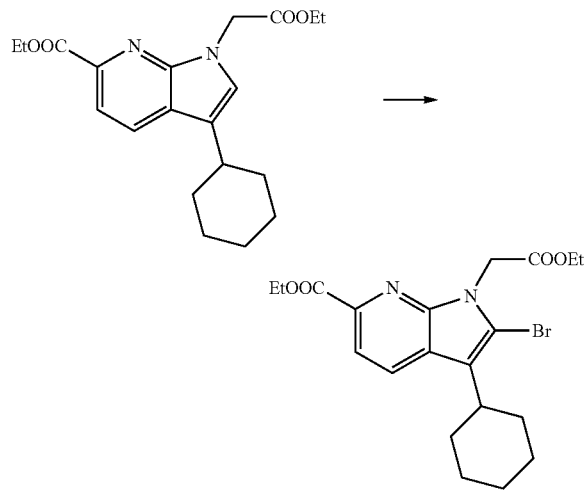

To a solution of ethyl 3-cyclohexyl-1-ethoxycarbonylmethyl-1H-pyrrolo[2,3-b]pyridine-6-carboxylate (463 mg, 1.34 mmol) in carbon tetrachloride (10 ml) was added N-bromosuccinimide (287 mg, 1.61 mmol), and the mixture was heated under reflux for 4 hr. The mixture was allowed to cool to room temperature and the solvent was evaporated under reduced pressure. The residue was purified by silica gel chromatography (hexane:ethyl acetate=5:1) to give ethyl 2-bromo-3-cyclohexyl-1-ethoxycarbonylmethyl-1H-pyrrolo[2,3-b]pyridine-6-carboxylate (457 mg, yield 64%).

$^1$H-NMR (400 MHz, CDCl$_3$): δ(ppm) 8.06 (1H, d, J=8.0 Hz), 7.88 (1H, d, J=8.4 Hz), 5.18 (2H, s), 4.44 (2H, q, J=7.1 Hz), 4.21 (2H, q, J=7.1 Hz), 2.82-2.93 (1H, m), 1.76-1.93 (7H, m), 1.36-1.48 (6H, m), 1.27 (3H, t, J=7.2 Hz).

MS 438 (M+1).

Step 4: Production of ethyl 12-cyclohexyl-6-oxo-6,7-dihydro-5H-5,7a,8-triazadibenzo[a,e]azulene-9-carboxylate

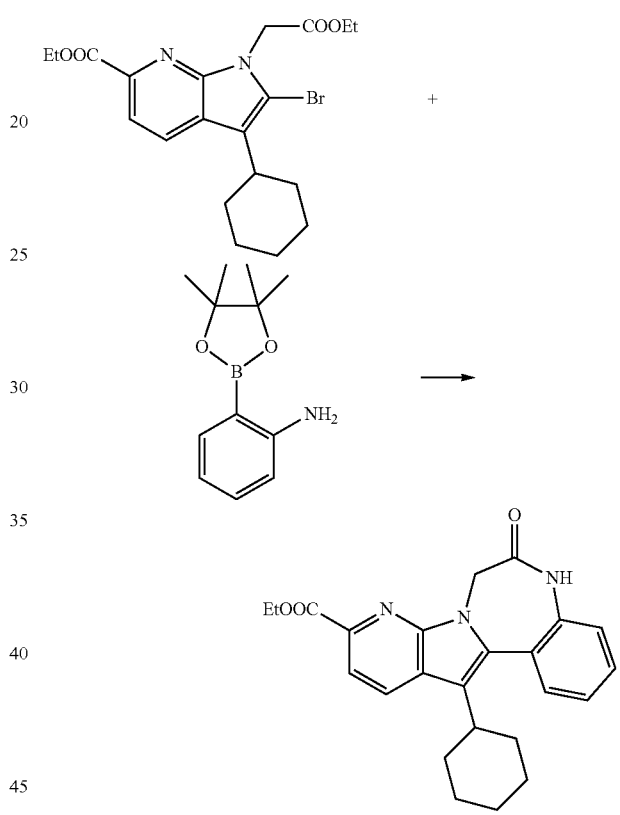

To a suspension of ethyl 2-bromo-3-cyclohexyl-1-ethoxycarbonylmethyl-1H-pyrrolo[2,3-b]pyridine-6-carboxylate (457 mg, 1.05 mmol) and 2-(4,4,5,5-tetramethyl-1,3,2-dioxaborolan-2-yl)phenylamine (275 mg, 1.25 mmol) obtained in the same manner as in the method described in Example 1-1, Step 1 in 1,2-dimethoxyethane (7.5 ml) and water (3.5 ml) were added sodium hydrogen carbonate (260 mg, 3.14 mmol) and tetrakis(triphenylphosphine)palladium (60 mg, 0.05 mmol) and the mixture was stirred with heating at 110° C. for 3.5 hr. The mixture was allowed to cool to room temperature and the reaction mixture was extracted with ethyl acetate. The organic layer was washed with saturated brine and dried over anhydrous magnesium sulfate. After filtration, the solvent was evaporated under reduced pressure and the obtained residue was purified by silica gel chromatography (hexane:ethyl acetate=1:1) to give ethyl 12-cyclohexyl-6-oxo-6,7-dihydro-5H-5,7a,8-triazadibenzo[a,e]azulene-9-carboxylate (111 mg, yield 26%).

MS 404 (M+1).

Example 8-2

Production of ethyl 12-cyclohexyl-6,7-dihydro-5H-5,7a,8-triazadibenzo[a,e]azulene-9-carboxylate

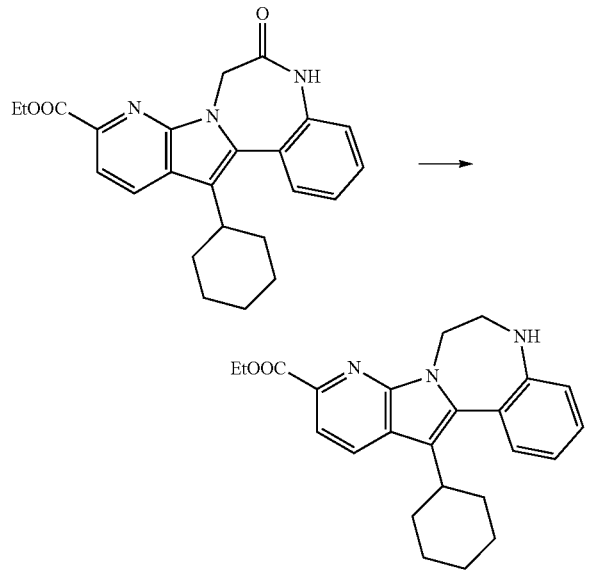

To a solution of ethyl 12-cyclohexyl-6-oxo-6,7-dihydro-5H-5,7a,8-triazadibenzo[a,e]azulene-9-carboxylate (111 mg, 0.28 mmol) in tetrahydrofuran (1 ml) was added 1M BH₃ THF complex tetrahydrofuran solution (1.6 ml) with stirring under ice-cooling, and the mixture was stirred at room temperature for 5 hr. To the reaction mixture was added saturated aqueous sodium hydrogen carbonate solution, and the mixture was extracted with ethyl acetate. The organic layer was washed with saturated brine and dried over anhydrous magnesium sulfate. After filtration, the solvent was evaporated under reduced pressure and the obtained residue was purified by silica gel chromatography (hexane:ethyl acetate=3:2) to give ethyl 12-cyclohexyl-6,7-dihydro-5H-5,7a,8-triazadibenzo[a,e]azulene-9-carboxylate (74 mg, yield 69%).

$^1$H-NMR (400 MHz, CDCl$_3$): δ(ppm) 8.15 (1H, d, J=8.4 Hz), 7.87 (1H, d, J=8.0 Hz), 7.34 (1H, d, J=8.0 Hz), 7.24-7.29 (1H, m), 6.99 (1H, t, J=7.8Hz), 6.85 (1H, d, J=8.0 Hz), 4.67 (2H, brs), 4.47 (2H, q, J=7.2 Hz), 3.69 (2H, t, J=5.2 Hz), 2.90-3.02 (1H, m), 1.71-2.03 (7H, m), 1.45 (3H, t, J=7.0 Hz), 1.30-1.41 (3H, m).

MS 404 (M+1).

Example 8-3

Production of ethyl 12-cyclohexyl-5-[2-oxo-2-(morpholin-4-yl)ethyl]-6,7-dihydro-5H-5,7a,8-triazadibenzo[a,e]azulene-9-carboxylate

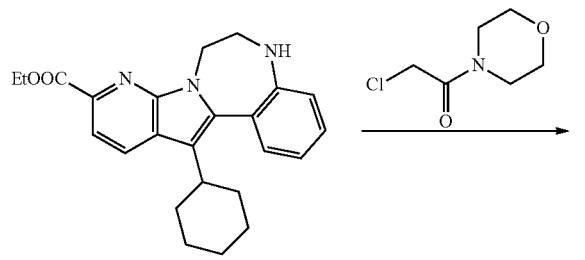

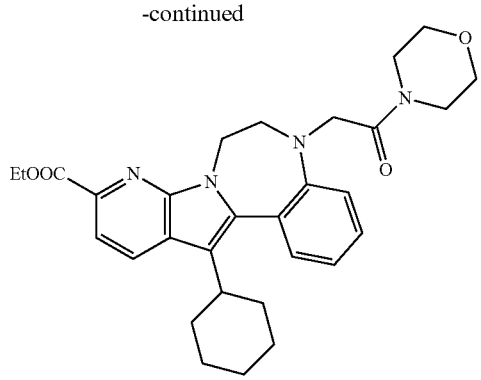

To a solution of ethyl 12-cyclohexyl-6,7-dihydro-5H-5,7a,8-triazadibenzo[a,e]azulene-9-carboxylate (74 mg, 0.19 mmol) in N,N-dimethylformamide (2 ml) and acetonitrile (2 ml) were added 4-(2-chloroacetyl)morpholine (94 mg, 0.57 mmol), potassium iodide (64 mg, 0.38 mmol) and potassium carbonate (66 mg, 0.48 mmol), and the mixture was stirred with heating at 90° C. for 12 hr. The reaction mixture was allowed to cool to room temperature, and water was added to the reaction mixture. The mixture was extracted with ethyl acetate, and the organic layer was washed with saturated brine and dried over anhydrous magnesium sulfate. After filtration, the solvent was evaporated under reduced pressure and the obtained residue was purified by silica gel chromatography (ethyl acetate) to give ethyl 12-cyclohexyl-5-[2-oxo-2-(morpholin-4-yl)ethyl]-6,7-dihydro-5H-5,7a,8-triazadibenzo[a,e]azulene-9-carboxylate (62 mg, yield 63%).

MS 517 (M+1).

Example 8-4

Production of 12-cyclohexyl-5-[2-oxo-2-(morpholin-4-yl)ethyl]-6,7-dihydro-5H-5,7a,8-triazadibenzo[a,e]azulene-9-carboxylic acid dihydrochloride

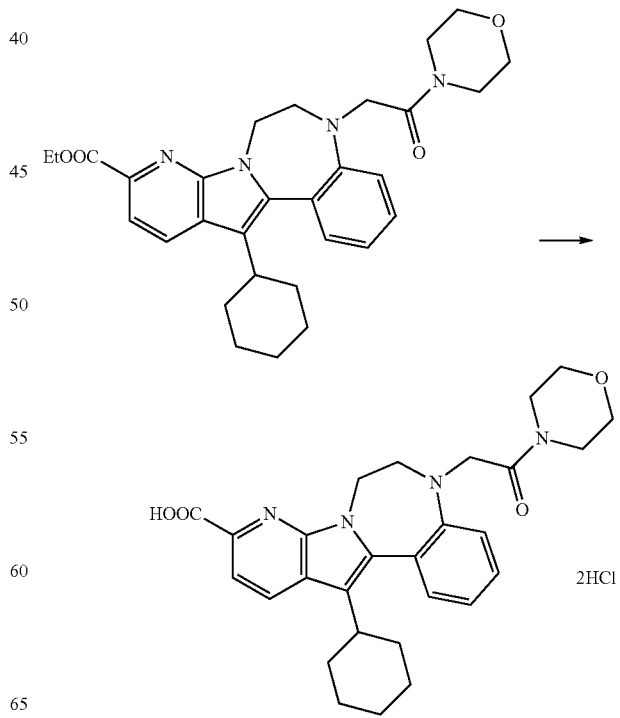

To a solution of ethyl 12-cyclohexyl-5-[2-oxo-2-(morpholin-4-yl)ethyl]-6,7-dihydro-5H-5,7a,8-triazadibenzo[a,e]azulene-9-carboxylate (62 mg, 0.12 mmol) in tetrahydrofuran (3 ml) and methanol (3 ml) was added 4N aqueous sodium hydroxide solution (1.5 ml) under ice-cooling, and the mixture was stirred at room temperature for 2 hr. 2N Hydrochloric acid (3 ml) was added to the reaction mixture to adjust to pH 7, and the mixture was extracted with ethyl acetate. The organic layer was washed with saturated brine and dried over anhydrous sodium sulfate. After filtration, the solvent was evaporated under reduced pressure and the obtained residue was purified by silica gel chromatography (chloroform:methanol=8:1) and the solvent was evaporated under reduced pressure. To a solution of the residue in ethyl acetate (1 ml) was added 4N HCl-ethyl acetate solution (1 ml) and the solvent was evaporated under reduced pressure. Hexane was added to the residue, and the precipitated solid was collected by filtration, washed with hexane and dried in vacuo to give 12-cyclohexyl-5-[2-oxo-2-(morpholin-4-yl)ethyl]-6,7-dihydro-5H-5,7a,8-triazadibenzo[a,e]azulene-9-carboxylic acid dihydrochloride (20 mg, yield 30%).

MS 562 (M+1).

Example 8-7

Production of 3-chloro-14-cyclohexyl-5-[2-(piperidin-1-yl)ethyl]-5,6,7,8-tetrahydrobenzo[6,7][1,5]diazocino[8,1-a]indole-11-carboxylic acid dihydrochloride Step 1: Production of methyl 2-bromo-3-cyclohexyl-1-(2-ethoxycarbonylethyl)-1H-indole-6-carboxylate

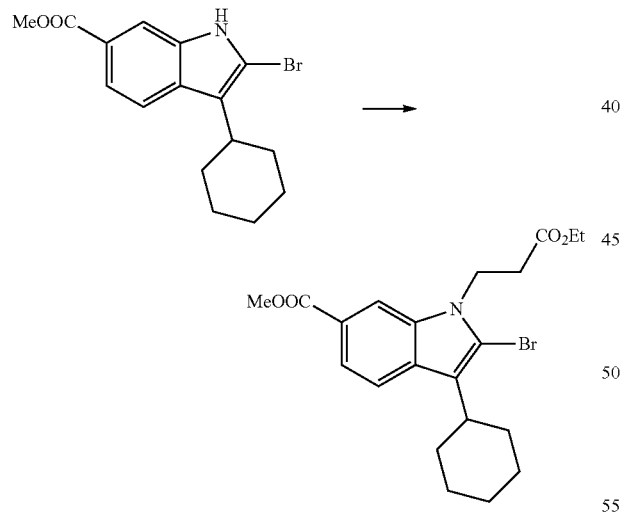

To a solution of methyl 2-bromo-3-cyclohexyl-1H-indole-6-carboxylate (5.00 g, 14.9 mmol) obtained in the same manner as in the method described in WO03/010140 in N,N-dimethylformamide (30 ml) were added ethyl 3-bromopropionate (3.84 ml, 30.1 mmol) and potassium carbonate (6.20 g, 44.6 mmol), and the mixture was stirred at 90° C. for 3.5 hr. The reaction mixture was allowed to cool to room temperature, water was added to the reaction mixture and the mixture was extracted with ethyl acetate. The organic layer was successively washed with water and saturated brine and dried over anhydrous magnesium sulfate. After filtration, the solvent was evaporated under reduced pressure. The residue was purified by silica gel chromatography (hexane:ethyl acetate=4:1) to give methyl 2-bromo-3-cyclohexyl-1-(2-ethoxycarbonylethyl)-1H-indole-6-carboxylate (6.40 g, yield 98%).

$^1$H-NMR (400 MHz, CDCl$_3$): δ(ppm) 8.04 (1H, s), 7.70-7.76 (2H, m), 4.53 (2H, t, J=5.8 Hz), 4.13 (2H, q, J=5.4 Hz), 3.93 (3H, s), 2.81-2.90 (1H, m), 2.75 (2H, t, J=5.7 Hz), 1.73-1.95 (7H, m), 1.29-1.48 (3H, m), 1.22 (3H, t, J=5.4 Hz).

Step 2: Production of methyl 2-(2-amino-4-chlorophenyl)-3-cyclohexyl-1-(2-ethoxycarbonylethyl)-1H-indole-6-carboxylate

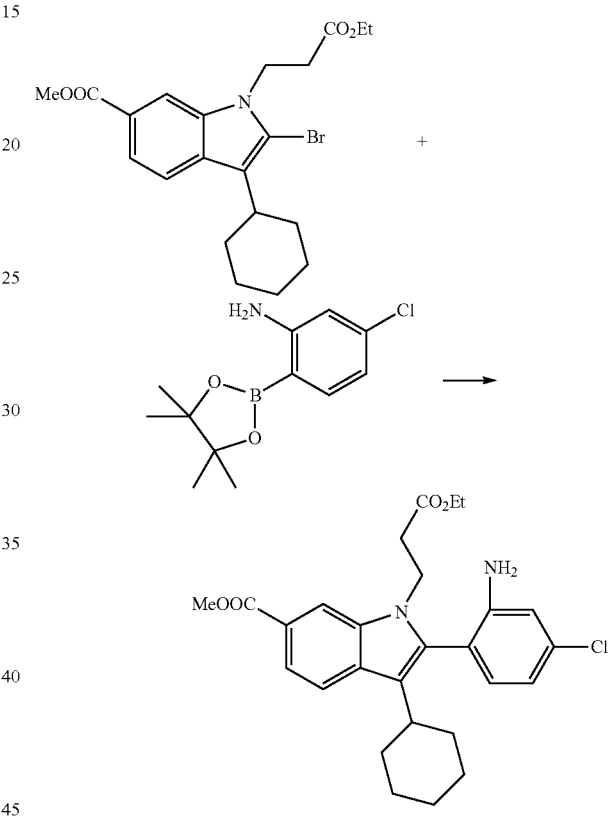

To a suspension of methyl 2-bromo-3-cyclohexyl-1-(2-ethoxycarbonylethyl)-1H-indole-6-carboxylate (1.00 g, 2.29 mmol) and 2-dioxaborolan-2-yl)phenylamine (697 mg, 2.75 mmol) in 1,2-dimethoxyethane (12 ml) and water (6 ml) were added lithium chloride (291 mg, 6.87 mmol), sodium carbonate (729 mg, 6.87 mmol) and tetrakis(triphenyl)phosphine)palladium (265 mg, 0.229 mmol), and the mixture was stirred at 90° C. for 3.5 hr. The mixture was allowed to cool to room temperature and saturated aqueous ammonium chloride solution and ethyl acetate were added. The mixture was filtered through celite, and the filtrate was washed with saturated brine and dried over anhydrous sodium sulfate. After filtration, the solvent was evaporated under reduced pressure and the residue was purified by silica gel chromatography (hexane:acetone=3:1) to give methyl 2-(2-amino-4-chlorophenyl)-3-cyclohexyl-1-(2-ethoxycarbonylethyl)-1H-indole-6-carboxylate (1.10 g, yield 100%).

$^1$H-NMR (400 MHz, CDCl$_3$): δ(ppm) 8.10 (1H, s), 7.78 (2H, s), 6.99 (1H, dd, J=6.0, 0,6 Hz), 6.79-6.83 (2H, m), 4.12-4.31 (2H, m), 4.01 (2H, q, J=5.4 Hz), 3.94 (3H, s), 3.76 (2H, brs), 2.45-2.64 (3H, m), 1.66-1.85 (7H, m), 1.21-1.31 (3H, m), 1.15 (3H, t, J=5.4 Hz).

Step 3: Production of methyl 2-(2-amino-4-chlorophenyl)-1-(2-carboxyethyl)-3-cyclohexyl-1H-indole-6-carboxylate

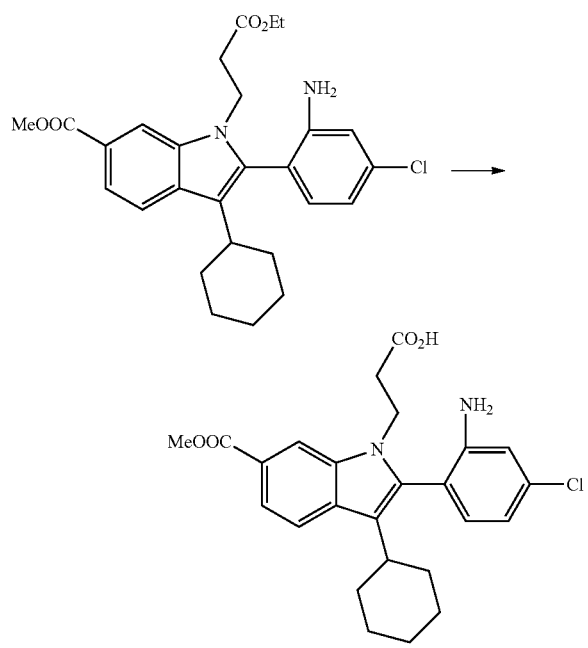

To a suspension of methyl 2-(2-amino-4-chlorophenyl)-3-cyclohexyl-1-(2-ethoxycarbonylethyl)-1H-indole-6-carboxylate (1.05 g, 2.17 mmol) in tetrahydrofuran (11 ml) and methanol (11 ml) was added 4N aqueous sodium hydroxide solution (1.08 ml, 4.34 mmol), and the mixture was stirred for 2 hr. 2N Hydrochloric acid (2.2 ml) and water were added to the reaction mixture and the mixture was extracted with ethyl acetate. The organic layer was washed with saturated brine and dried over anhydrous magnesium sulfate. After filtration, the solvent was evaporated under reduced pressure to give methyl 2-(2-amino-4-chlorophenyl)-1-(2-carboxyethyl)-3-cyclohexyl-1H-indole-6-carboxylate (949 mg) as a crude product. The obtained crude product was used for Step 4 without further purification.

$^1$H-NMR (400 MHz, CDCl$_3$): δ(ppm) 8.12 (1H, s), 7.78 (2H, s), 6.98 (1H, d, J=5.7 Hz), 6.77-6.83 (2H, m), 4.14-4.31 (2H, m), 3.94 (3H, s), 2.45-2.73 (3H, m), 1.66-1.85 (7H, m), 1.20-1.30 (3H, m).

Step 4: Production of methyl 3-chloro-14-cyclohexyl-6-oxo-5,6,7,8-tetrahydrobenzo[6,7][1,5]diazocino[8,1-a]indole-11-carboxylate

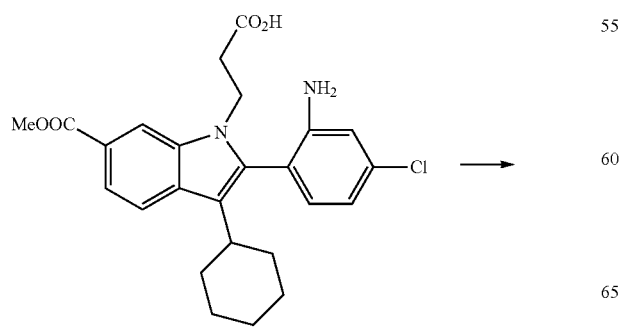

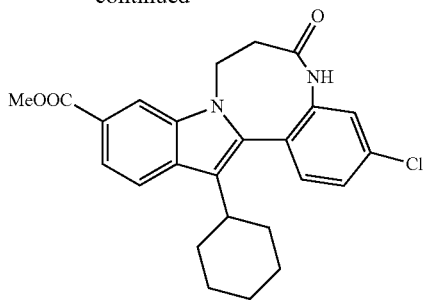

To a solution of methyl 2-(2-amino-4-chlorophenyl)-1-(2-carboxyethyl)-3-cyclohexyl-1H-indole-6-carboxylate (949 mg) in N,N-dimethylformamide (33 ml) were added triethylamine (0.61 ml, 4.35 mmol) and benzotriazol-1-yloxytris(pyrrolidino)phosphonium hexafluorophosphate (1.36 g, 2.61 mmol) under ice-cooling, and the mixture was stirred for 22.5 hr. Water was added to the reaction mixture and the mixture was extracted with ethyl acetate. The organic layer was successively washed with water and saturated brine and dried over anhydrous magnesium sulfate. After filtration, the solvent was evaporated under reduced pressure. The residue was purified by silica gel chromatography (hexane:ethyl acetate=2:3), and hexane:diisopropy ether (3:2) mixture was added to the obtained residue. The precipitated solid was collected by filtration and washed with hexane:diisopropy ether (3:2) mixture. The obtained solid was dried in vacuo to give methyl 3-chloro-14-cyclohexyl-6-oxo-5,6,7,8-tetrahydrobenzo[6,7][1,5]diazocino[8,1-a]indole-11-carboxylate (657 mg, yield 72%).

$^1$H-NMR (400 MHz, CDCl$_3$): δ(ppm) 8.08 (1H, s), 7.80 (1H, d, J=6.3 Hz), 7.77 (1H, dd, J=6.3, 0.6 Hz), 7.41-7.45 (2H, m), 7.36 (1H, d, J=6.0 Hz), 7.29 (1H, d, J=1.5 Hz), 4.59-4.66 (1H, m), 3.93 (3H, s), 3.87-3.92 (1H, m), 2.83-2.99 (2H, m), 2.40-2.49 (1H, m), 1.51-1.94 (7H, m), 1.13-1.32 (3H, m).

Step 5: Production of methyl 3-chloro-14-cyclohexyl-6-oxo-5-[2-oxo-2-(piperidin-1-yl)ethyl]-5,6,7,8-tetrahydrobenzo[6,7][1,5]diazocino[8,1-a]indole-1'-carboxylate

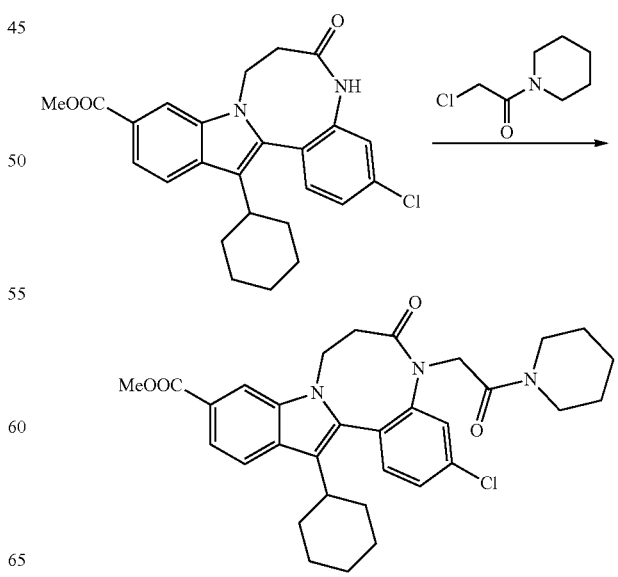

A suspension of methyl 3-chloro-14-cyclohexyl-6-oxo-5,6,7,8-tetrahydrobenzo[6,7][1,5]diazocino[8,1-a]indole-11-carboxylate (200 mg, 0.457 mmol), 1-(chloroacetyl)piperidine (85 mg, 0.526 mmol) and potassium carbonate (126 mg, 0.914 mmol) in N,N-dimethylformamide (4 ml) was stirred at 80° C. for 4.5 hr. The mixture was allowed to cool to room temperature and water was added. The precipitate was collected by filtration, washed with water, and dried in vacuo to give methyl 3-chloro-14-cyclohexyl-6-oxo-5-[2-oxo-2-(piperidin-1-yl)ethyl]-5,6,7,8-tetrahydrobenzo[6,7][1,5]diazocino[8,1-a]indole-11-carboxylate (245 mg, yield 95%) as a crude product. The obtained crude product was used for Step 6 without further purification.

$^1$H-NMR (400 MHz, CDCl$_3$): δ(ppm) 8.09 (1H, s), 7.96 (1H, d, J=1.8 Hz), 7.77 (2H, s), 7.44 (1H, dd, J=6.3, 1.5 Hz), 7.36 (1H, d, J=6.0 Hz), 4.69-4.79 (2H, m), 3.92 (3H, s), 3.81-3.89 (1H, m), 3.62-3.69 (1H, m), 3.41-3.48 (1H, m), 3.36 (1H, d, J=12.0 Hz), 3.23-3.30 (1H, m), 3.12-3.20 (1H, m), 2.99-3.08 (1H, m), 2.77-2.85 (1H, m), 2.38-2.48 (1H, m), 1.68-1.92 (7H, m), 1.41-1.64 (6H, m), 1.15-1.32 (3H, m).

Step 6: Production of methyl 3-chloro-14-cyclohexyl-5-[2-(piperidin-1-yl)ethyl]-5,6,7,8-tetrahydrobenzo[6,7][1,5]diazocino[8,1-a]indole-11-carboxylate

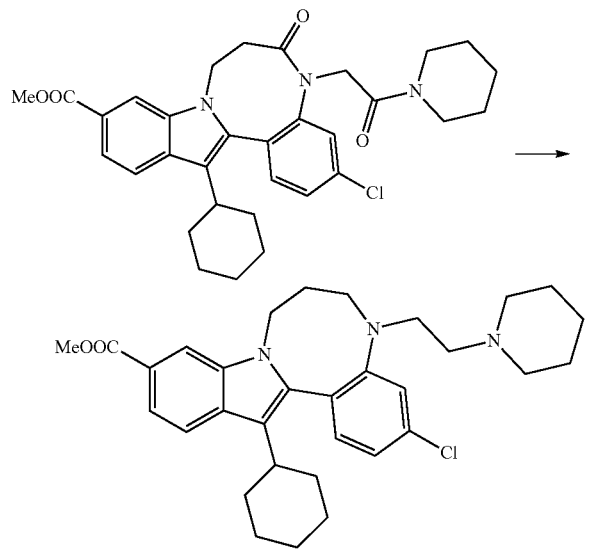

To a solution of methyl 3-chloro-14-cyclohexyl-6-oxo-5-[2-oxo-2-(piperidin-1-yl)ethyl]-5,6,7,8-tetrahydrobenzo[6,7][1,5]diazocino[8,1-a]indole-11-carboxylate (245 mg, 0.436 mmol) in tetrahydrofuran (2 ml) was added a solution (3 ml) of 1.0M BH$_3$ THF complex in tetrahydrofuran, and the mixture was stirred at room temperature for 17.5 hr. 4N Hydrochloric acid (3 ml) was added to the reaction mixture, and the mixture was stirred at 70° C. for 7.5 hr. The reaction mixture was allowed to cool to room temperature, neutralized with 2N aqueous sodium hydroxide solution and saturated aqueous sodium hydrogen carbonate solution, and extracted with ethyl acetate. The organic layer was washed with saturated brine and dried over anhydrous magnesium sulfate. After filtration, the solvent was evaporated under reduced pressure, and the residue was purified by silica gel chromatography (chloroform:methanol=50:1-20:1) to give methyl 3-chloro-14-cyclohexyl-5-[2-(piperidin-1-yl)ethyl]-5,6,7,8-tetrahydrobenzo[6,7][1,5]diazocino[8,1-a]indole-11-carboxylate (50 mg, yield 21%).

$^1$H-NMR (400 MHz, CDCl$_3$): δ(ppm) 8.05 (1H, s), 7.81 (1H, d, J=6.3 Hz), 7.75 (1H, dd, J=6.6, 1.2 Hz), 6.99 (1H, d, J=6.3 Hz), 6.84 (1H, s), 6.66-6.71 (1H, m), 4.39-4.47 (1H, m), 3.93 (3H, s), 3.76-3.86 (1H, m), 3.28-3.72 (6H, m), 2.82-2.90 (2H, m), 2.64-2.75 (1H, m), 2.40-2.64 (4H, m), 1.20-2.09 (16H, m).

Step 7: Production of 3-chloro-14-cyclohexyl-5-[2-(piperidin-1-yl)ethyl]-5,6,7,8-tetrahydrobenzo[6,7][1,5]diazocino[8,1-a]indole-11-carboxylic acid dihydrochloride

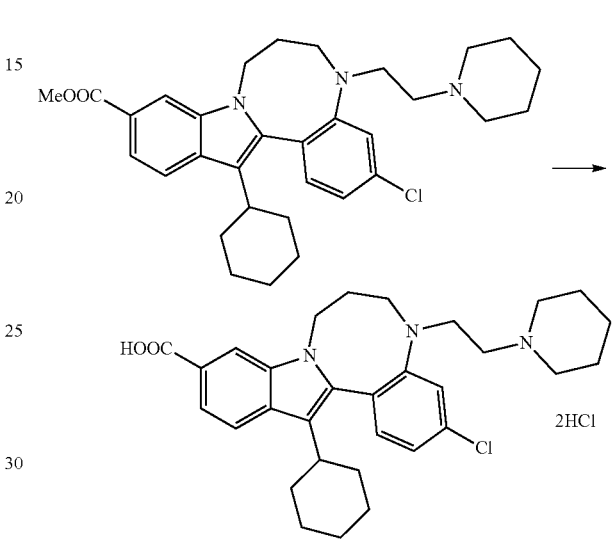

To a solution of methyl 3-chloro-14-cyclohexyl-5-[2-(piperidin-1-yl)ethyl]-5,6,7,8-tetrahydrobenzo[6,7][1,5]diazocino[8,1-a]indole-11-carboxylate (50 mg, 0.094 mmol) in tetrahydrofuran (1 ml) and methanol (1 ml) was added 4N aqueous sodium hydroxide solution (0.5 ml), and the mixture was stirred at 60° C. for 2 hr. 2N Hydrochloric acid (1.1 ml) was added to the reaction mixture, and the mixture was extracted with ethyl acetate:tetrahydrofuran (2:1). The organic layer was washed saturated brine and dried over anhydrous magnesium sulfate. After filtration, the solvent was evaporated under reduced pressure. To a solution of the obtained residue in tetrahydrofuran (1 ml) was added 4N HCl-ethyl acetate solution (1 ml), and the solvent was evaporated under reduced pressure. Hexane:ethyl acetate (4:1) was added and the precipitated solid was collected by filtration, washed with hexane:ethyl acetate (4:1) and dried in vacuo to give 3-chloro-14-cyclohexyl-5-[2-(piperidin-1-yl)ethyl]-5,6,7,8-tetrahydrobenzo[6,7][1,5]diazocino[8,1-a]indole-11-carboxylic acid dihydrochloride (26 mg, yield 47%).

$^1$H-NMR (300 MHz, DMSO-d$_6$): δ(ppm) 12.57 (1H, s), 9.96 (1H, s), 8.12 (1H, s), 7.84 (1H, d, J=8.4 Hz), 7.65 (1H, d, J=8.4 Hz), 7.05-7.10 (2H, m), 6.88 (1H, d, J=8.1 Hz), 4.58-4.68 (1H, m), 3.56-3.78 (4H, m), 3.41-3.50 (2H, m), 3.11-3.29 (1H, m), 2.54-3.04 (7H, m), 1.21-2.04 (16H, m).

MS 520.2 (M+1).

The compounds of Examples 8-5 and 8-6 were produced by the same methods as in Examples 8-1 to 8-4 and 8-7 or methods similar thereto, and where necessary, by employing other conventional methods. The chemical structural formulas are shown in Table 115.

3-chloro-12-cyclohexyl-5-(2-piperidin-1-ylethyl)-6,7-dihydro-5H-5,7a,8-triazadibenzo[a,e]azulene-9-carboxylic acid trihydrochloride (Example 8-5)

3-chloro-12-cyclohexyl-5-[2-(4-ethylpiperazin-1-yl)ethyl]-6,7-dihydro-5H-5,7a,8-triazadibenzo[a,e]azulene-9-carboxylic acid trihydrochloride (Example 8-6)

Example 9-1

Production of methyl 12-cyclohexyl-6,7-dihydro-5-oxa-7a-azadibenzo[a,e]azulene-9-carboxylate Step 1: Production of methyl 2-[2-(2-chloroethoxy)phenyl]-3-cyclohexyl-1H-indole-6-carboxylate

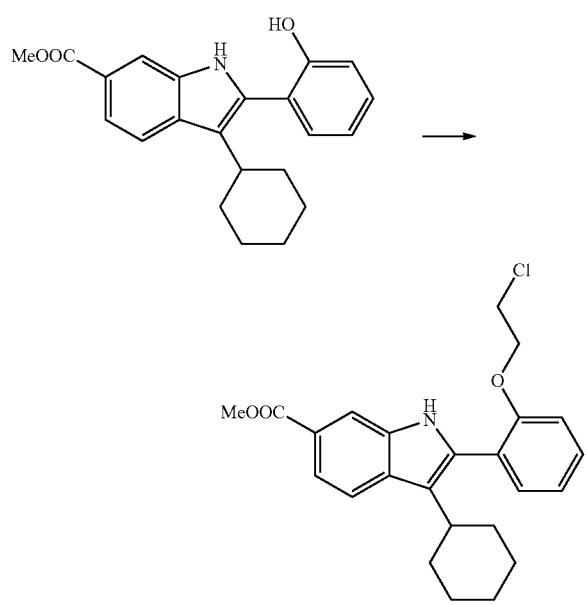

To a solution of methyl 3-cyclohexyl-2-(2-hydroxyphenyl)-1H-indole-6-carboxylate (500 mg, 1.43 mmol), obtained in the same manner as in the method described in Example 3-1, Step 1, in acetone (20 ml) were added 1-bromo-2-chloroethane (0.14 ml, 1.72 mmol) and potassium carbonate (237 mg, 1.72 mmol), and the mixture was stirred at 50° C. for 2 hr. 1-Bromo-2-chloroethane (0.28 ml, 3.44 mmol) and potassium carbonate (474 mg, 3.44 mmol) were further added and the mixture was stirred at 50° C. for 24 hr. The reaction mixture was allowed to cool to room temperature. Water was added to the reaction mixture and the mixture was extracted with ethyl acetate. The organic layer was washed with saturated brine and dried over anhydrous sodium sulfate. After filtration, the solvent was evaporated under reduced pressure and the residue was purified by silica gel column chromatography (hexane:ethyl acetate=3:1) to give methyl 2-[2-(2-chloroethoxy)phenyl]-3-cyclohexyl-1H-indole-6-carboxylate (370 mg, yield 62.8%).

$^1$H-NMR (400 MHz, CDCl$_3$): δ(ppm) 9.00 (1H, s), 8.06-8.07 (1H, m), 7.85 (1H, d, J=8.4 Hz), 7.74 (1H, ddd, J=10.0, 8.0, 1.2 Hz), 7.41 (1H, dd, J=7.6, 1.6 Hz), 7.37 (1H, td, J=7.8, 1.8 Hz), 7.12 (1H, t, J=7.6 Hz), 6.99 (1H, d, J=8.0 Hz), 4.28 (2H, t, J=5.2 Hz), 3.93 (3H, s), 3.81 (2H, t, J=5.2 Hz), 2.88-2.95 (1H, m), 1.99-2.10 (2H, m), 1.76-1.87 (5H, m), 1.32-1.41 (3H, m).

Step 2: Production of methyl 12-cyclohexyl-6,7-dihydro-5-oxa-7a-azadibenzo[a,e]azulene-9-carboxylate

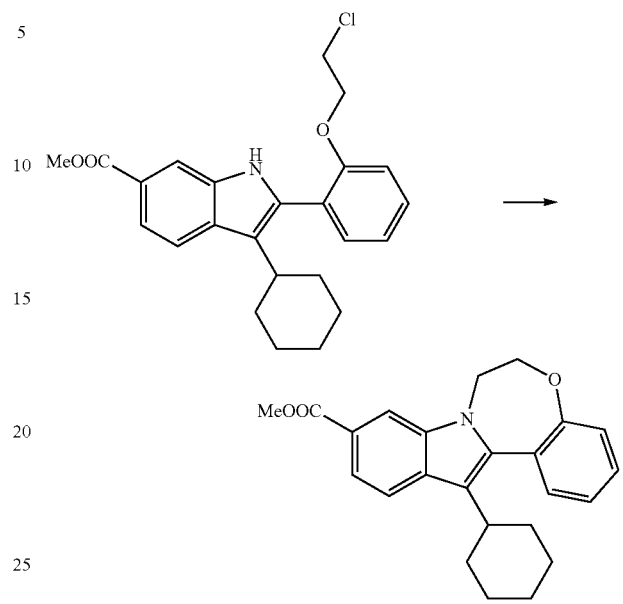

To a solution of methyl 2-[2-(2-chloroethoxy)phenyl]-3-cyclohexyl-1H-indole-6-carboxylate (180 mg, 0.44 mmol) in N,N-dimethylformamide (6 ml) was added sodium hydride (20 mg, 0.49 mmol) under ice-cooling, and the mixture was stirred at room temperature for 24 hr. Water was added to the reaction mixture and the mixture was extracted with ethyl acetate. The organic layer was washed with saturated brine and dried over anhydrous sodium sulfate. After filtration, the solvent was evaporated under reduced pressure, and diisopropyl ether was added to the residue. The precipitated solid was collected by filtration, washed with diisopropyl ether and dried in vacuo to give methyl 12-cyclohexyl-6,7-dihydro-5-oxa-7a-azadibenzo[a,e]azulene-9-carboxylate (70 mg, yield 42.3%).

$^1$H-NMR (400 MHz, DMSO-d$_6$): δ(ppm) 8.20 (1H, d, J=1.6 Hz), 7.89 (1H, d, J=8.4 Hz), 7.62 (1H, dd, J=8.4, 1.2 Hz), 7.40-7.47 (2H, m), 7.33 (1H, td, J=7.4, 1.2 Hz), 7.23 (1H, dd, J=8.0, 1.2 Hz), 4.33-4.45 (4H, m), 3.85 (3H, s), 2.83-2.90 (1H, m), 1.95-2.06 (2H, m), 1.67-1.83 (5H, m), 1.24-1.44 (3H, m).

MS 376 (M+1).

Example 9-2

Production of 12-cyclohexyl-6,7-dihydro-5-oxa-7a-azadibenzo[a,e]azulene-9-carboxylic acid

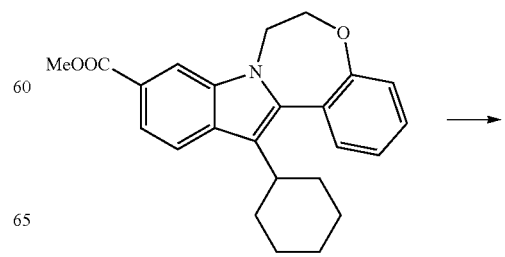

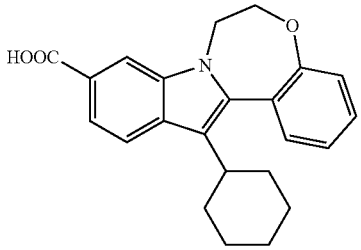

To a solution of methyl 12-cyclohexyl-6,7-dihydro-5-oxa-7a-azadibenzo[a,e]azulene-9-carboxylate (70 mg, 0.19 mmol) in tetrahydrofuran (2 ml) and methanol (1 ml) was added 4N aqueous sodium hydroxide solution (1 ml) and the mixture was stirred at room temperature for 24 hr. 1N Hydrochloric acid was added to the reaction mixture, and the precipitated solid was collected by filtration, washed with water and dried in vacuo to give 12-cyclohexyl-6,7-dihydro-5-oxa-7a-azadibenzo[a,e]azulene-9-carboxylic acid (59 mg, yield 85.2%).

$^1$H-NMR (400 MHz, DMSO-$d_6$): δ (ppm) 12.54 (1H, brs), 8.17 (1H, s), 7.86 (1H, d, J=8.4 Hz), 7.60 (1H, dd, J=8.8, 1.6 Hz), 7.40-7.47 (2H, m), 7.33 (1H, td, J=7.4, 0.8 Hz), 7.22 (1H, d, J=8.0 Hz), 4.33-4.44 (4H, m), 2.83-2.91 (1H, m), 1.95-2.05 (2H, m), 1.68-1.81 (5H, m), 1.25-1.37 (3H, m).

MS 362 (M+1).

The compounds of Examples 9-3 and 9-4 were produced by the same methods as in Examples 9-1 and 9-2 or methods similar thereto, and where necessary, by employing other conventional methods. The chemical structural formulas are shown in Tables 116.

13-cyclohexyl-7,8-dihydro-6H-indolo[2,1-d]benzo[b][1,5]oxazocine-10-carboxylic acid (Example 9-3), 3-chloro-12-cyclohexyl-6,7-dihydro-5-oxa-7a-azadibenzo[a,e]azulene-9-carboxylic acid (Example 9-4).

Example 10-2

Production of ethyl 3-chloro-12-cyclohexyl-5-[2-(piperidin-1-yl)ethyl]-5,6,7,12-tetrahydrobenzo[2,3]azepino[4,5-b]indole-9-carboxylate Step 1: Production of methyl 4-chloro-2-(3-ethoxycarbonylpropionylamino)benzoate

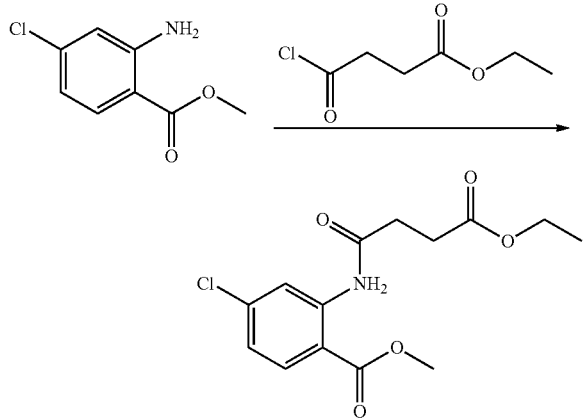

To a solution of methyl 2-amino-4-chlorobenzoate (18.60 g, 100 mmol) and pyridine (11.5 ml, 142 mmol) in toluene (138 ml), was added dropwise a solution of ethyl succinyl chloride (18.9 ml, 133 mmol) in toluene (19 ml) at a temperature between 0° C. and 10° C. The mixture was stirred at 10° C. for 1 hr, water was added and the mixture was extracted with ethyl acetate. The organic layer was successively washed with 0.1N hydrochloric acid and 10% aqueous sodium hydrogen carbonate solution and dried over anhydrous magnesium sulfate. After filtration, the solvent was evaporated under reduced pressure to give methyl 4-chloro-2-(3-ethoxycarbonylpropionylamino)benzoate (27.90 g, yield 89%).

$^1$H-NMR (300 MHz, DMSO-$d_6$): δ(ppm) 10.73 (1H, s), 8.40 (1H, d, J=2.3 Hz), 7.93 (1H, d, J=8.3 Hz), 7.26 (1H, d, J=12.8 Hz), 4.06 (2H, q, J=7.0 Hz), 3.87 (3H, s), 2.70-2.68 (2H, m), 2.63-2.61 (2H, m), 1.18 (3H, t, J=7.2 Hz).

Step 2: Production of a mixture of ethyl 8-chloro-5-hydroxy-2-oxo-2,3-dihydro-1H-benzo[b]azepine-4-carboxylate and methyl 8-chloro-5-hydroxy-2-oxo-2,3-dihydro-1H-benzo[b]azepine-4-carboxylate

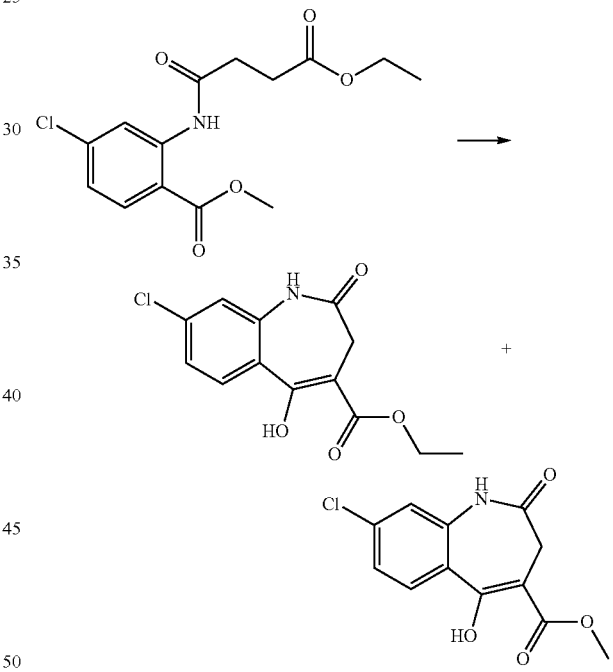

To a suspension of sodium hydride (60% in oil) (25.90 g, 648 mmol) in N,N-dimethylformamide (250 ml) was added dropwise a solution of methyl 4-chloro-2-(3-ethoxycarbonylpropionylamino)benzoate (27.90 g, 88.9 mmol) in N,N-dimethylformamide (300 ml). The reaction mixture was stirred at room temperature for 1 hr, and poured into diluted hydrochloric acid under ice-cooling. The mixture was stirred under ice-cooling for 1 hr, and the precipitated solid was collected by filtration to give a crude product of a mixture of ethyl 8-chloro-5-hydroxy-2-oxo-2,3-dihydro-1H-benzo[b]azepine-4-carboxylate and methyl 8-chloro-5-hydroxy-2-oxo-2,3-dihydro-1H-benzo[b]azepine-4-carboxylate (wet weight 21.30 g). The obtained crude product was used for Step 3 without purification. ethyl 8-chloro-5-hydroxy-2-oxo-2,3-dihydro-1H-benzo[b]azepine-4-carboxylate ¹H-NMR (300 MHz, DMSO-d₆): δ(ppm) 12.51 (1H, brs), 10.48 (1H, s), 7.81 (1H, d, J=8.7 Hz), 7.33 (1H, dd, J=8.7, 2.3 Hz), 7.26 (1H, d, J=1.9 Hz), 4.30 (2H, q, J=7.2 Hz), 2.97 (2H, s), 1.30 (3H, t, J=7.0 Hz).

methyl 8-chloro-5-hydroxy-2-oxo-2,3-dihydro-1H-benzo[b]azepine-4-carboxylate

¹H-NMR (300 MHz, DMSO-d₆): δ(ppm) 12.44 (1H, brs), 10.48 (1H, s), 7.81 (1H, d, J=8.7 Hz), 7.33 (1H, dd, J=8.7, 2.3 Hz), 7.26 (1H, d, J=1.9 Hz), 3.84 (3H, s), 2.97 (2H, s).

Step 3: Production of 8-chloro-3,4-dihydro-1H-benzo[b]azepine-2,5-dione

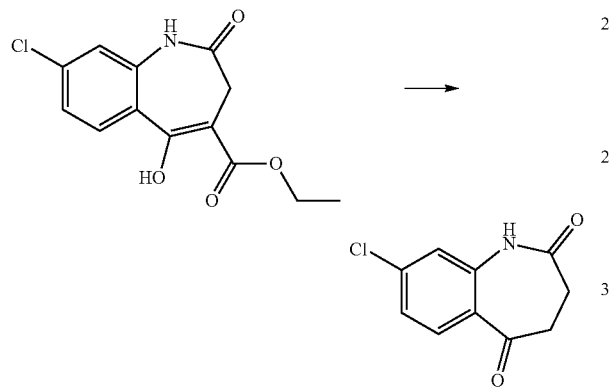

A solution of ethyl 8-chloro-5-hydroxy-2-oxo-2,3-dihydro-1H-benzo[b]azepine-4-carboxylate (wet weight 21.3 g) obtained as a crude product in Step 2 in dimethyl sulfoxide (200 ml) and water (10 ml) was heated at 150° C. Under stirring, water was added 3 times in total by 10 ml every one hour. The mixture was allowed to cool to room temperature, water (400 ml) was added, and the precipitated solid was collected by filtration. The crude product was washed with water and dried in vacuo. A mixed solvent (200 ml) of hexane:ethyl acetate (10:1) was added to the obtained crude product to give a suspension. After filtration, the obtained solid was washed with a mixed solvent (50 ml) of hexane:ethyl acetate (10:1) and dried in vacuo to give 8-chloro-3,4-dihydro-1H-benzo[b]azepine-2,5-dione (12.60 g, yield 80%).

¹H-NMR (300 MHz, DMSO-d₆): δ(ppm) 10.18 (1H, s), 7.86-7.80 (1H, m), 7.25-7.18 (2H, m), 2.93-2.87 (2H, m), 2.71-2.64 (2H, m).

Step 4: Production of ethyl 4-cyclohexylaminobenzoate

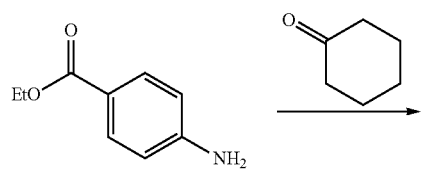

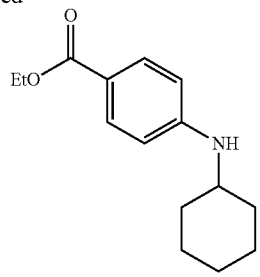

To a solution of ethyl 4-aminobenzoate (20.00 g, 0.120 mol) and cyclohexanone (17.80 g, 0.180 mol) in tetrahydrofuran (100 ml) and acetic acid (10 ml) was added sodium triacetoxyborohydride (38.50 g, 0.180 mol) at room temperature, and the mixture was stirred for 2 hr. Water was added to the reaction mixture and the mixture was extracted with toluene. The organic layer was successively washed with water, saturated aqueous sodium hydrogen carbonate and saturated brine and dried over anhydrous magnesium sulfate. After filtration, the solvent was evaporated under reduced pressure, and hexane was added to the obtained residue. The precipitated solid was collected by filtration and washed with hexane. The obtained solid was dried in vacuo to give ethyl 4-cyclohexylaminobenzoate (25.20 g, yield 84%).

¹H-NMR (400 MHz, CDCl₃): δ(ppm) 7.85 (2H, d, J=8.8 Hz), 6.53 (2H, d, J=8.8 Hz), 4.32 (2H, q, J=7.1 Hz), 4.03 (1H, brs), 3.34 (1H, brs), 2.08-2.05 (2H, m), 1.80-1.78 (2H, m), 1.68-1.65 (2H, m), 1.44-1.43 (2H, m), 1.37 (3H, t, J=7.2 Hz), 1.26-1.19 (2H, m).

Step 5: Production of ethyl 4-(N-cyclohexylnitroso)benzoate

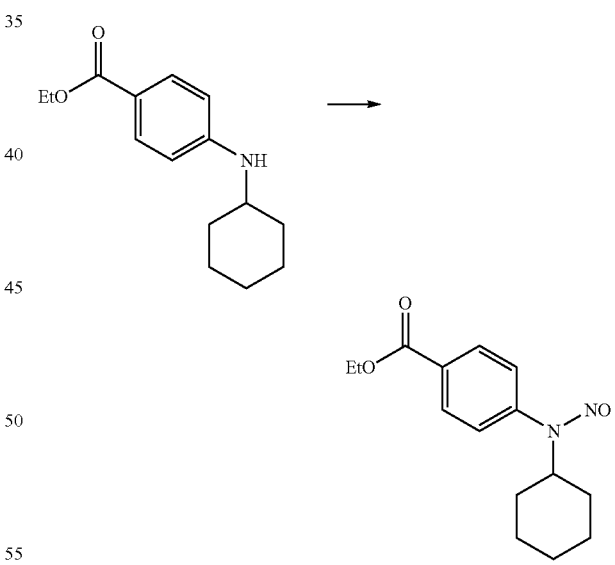

To a solution of ethyl 4-cyclohexylaminobenzoate (24.00 g, 97.0 mmol) in acetic acid (120 ml) was added dropwise an aqueous solution (120 ml) of sodium nitrite (13.40 g, 194 mmol) over 15 min at room temperature, and the mixture was further stirred for 2 hr. Water was added to the reaction mixture and the mixture was extracted with ethyl acetate. The organic layer was successively washed with water and saturated brine and dried over anhydrous magnesium sulfate. After filtration, the solvent was evaporated under reduced pressure to give ethyl 4-(N-cyclohexylnitroso)benzoate (26.90 g). The obtained compound was used for Step 6 without purification.

$^1$H-NMR (400 MHz, CDCl$_3$): δ(ppm) 8.17 (2H, d, J=8.8 Hz), 8.13 (2H, d, J=8.8 Hz), 4.92-4.88 (1H, m), 4.43 (2H, q, J=7.1 Hz), 2.21-2.18 (1H, m), 1.94-1.58 (6H, m), 1.51-1.49 (2H, m), 1.44 (3H, t, J=7.0 Hz), 1.17-1.13 (1H, m).

Step 6: Production of ethyl 4-(N-cyclohexylhydrazino)benzoate

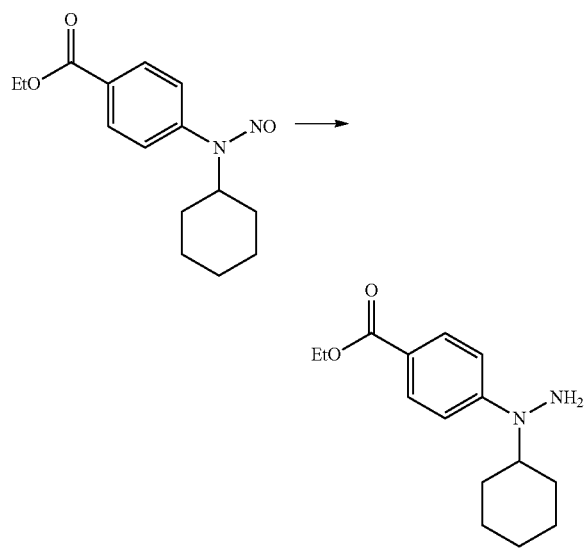

To a suspension of zinc powder (18.50 g, 282 mmol) in water (130 ml) was added dropwise a solution of ethyl 4-(N-cyclohexylnitroso)benzoate (26.00 g, 94.1 mmol) in acetic acid (250 ml) over 15 min under ice-cooling, and the mixture was stirred at room temperature for 2 hr. The reaction mixture was filtered through celite, and the filtrate was extracted with ethyl acetate. The organic layer was successively washed with water and saturated brine and dried over anhydrous magnesium sulfate. After filtration, the solvent was evaporated under reduced pressure. The obtained residue was purified by silica gel chromatography (hexane:ethyl acetate=10:1) to give ethyl 4-(N-cyclohexylhydrazino)benzoate (7.60 g, yield 31%).

$^1$H-NMR (400 MHz, CDCl$_3$): δ(ppm) 7.91 (2H, d, J=8.3 Hz), 6.97 (2H, d, J=8.3 Hz), 4.34 (2H, q, J=7.1 Hz), 3.71 (1H, tt, J=11.4, 3.6 Hz), 1.92-1.88 (2H, m), 1.77-1.73 (3H, m), 1.64-1.58 (2H, m), 1.47-1.42 (2H, m), 1.38 (3H, t, J=7.2 Hz), 1.20 (1H, tt, J=13.0, 3.7 Hz).

Step 7: Production of ethyl 3-chloro-12-cyclohexyl-6-oxo-5,6,7,12-tetrahydrobenzo[2,3]azepino[4,5-b]indole-9-carboxylate (Example 10-5)

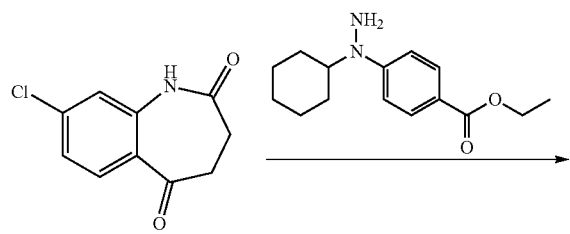

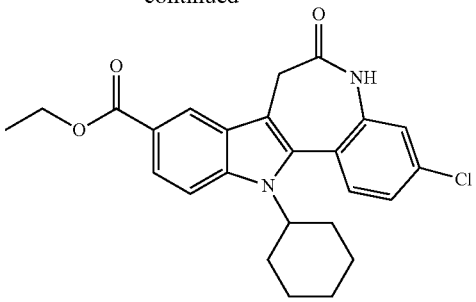

A mixture of 8-chloro-3,4-dihydro-1H-benzo[b]azepine-2,5-dione (1.18 g, 5.65 mmol) and ethyl 4-(N-cyclohexylhydrazino)benzoate (1.14 g, 4.35 mmol) in acetic acid (11 ml) was stirred at 85° C. for 1 hr. The reaction mixture was allowed to cool to room temperature, and conc. sulfuric acid (0.55 ml) was added to the reaction mixture. The mixture was stirred at 85° C. for 3 hr. The mixture was allowed to cool, and the reaction mixture was poured into water (230 ml) and extracted with a mixed solvent of ethyl acetate (200 ml) and ethanol (30 ml). The organic layer was washed twice with saturated brine and dried over anhydrous magnesium sulfate. After filtration, the solvent was evaporated under reduced pressure. Water (10 ml) and ethanol (10 ml) were added to the obtained crude product and the precipitated solid was collected by filtration. The obtained solid was washed with a mixed solvent (10 ml) of water:ethanol (1:1) and dried in vacuo to give ethyl 3-chloro-12-cyclohexyl-6-oxo-5,6,7,12-tetrahydrobenzo[2,3]azepino[4,5-b]indole-9-carboxylate (0.97 g, yield 39%).

$^1$H-NMR (300 MHz, DMSO-d$_6$): δ(ppm) 10.18 (1H, s), 8.37 (1H, s), 7.93 (1H, d, J=9.0 Hz), 7.82 (1H, dd, J=9.0, 1.5 Hz), 7.51 (1H, d, J=8.3 Hz), 7.45-7.39 (2H, m), 4.40-4.23 (1H, m), 4.35 (2H, q, J=7.0 Hz), 3.84 (1H, d, J=14.3 Hz), 3.09 (1H, d, J=14.3 Hz), 2.48-2.17 (3H, m), 2.05-1.93 (1H, m), 1.79-1.60 (2H, m), 1.54-1.11 (4H, m), 1.37 (3H, t, J=7.0 Hz).

Step 8: Production of ethyl 3-chloro-12-cyclohexyl-6-oxo-5-[2-oxo-2-(piperidin-1-yl)ethyl]-5,6,7,12-tetrahydrobenzo[2,3]azepino[4,5-b]indole-9-carboxylate (Example 10-6)

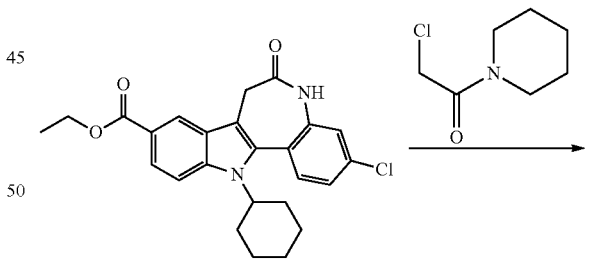

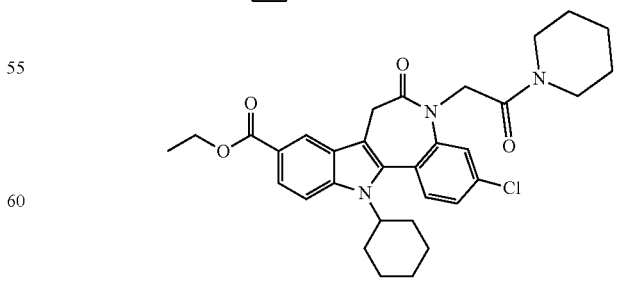

To a suspension of ethyl 3-chloro-12-cyclohexyl-6-oxo-5,6,7,12-tetrahydrobenzo[2,3]azepino[4,5-b]indole-9-carboxylate (772 mg, 1.77 mmol) in N,N-dimethylformamide (7.7 ml) were added a solution of 1-(2-chloroacetyl)piperidine (343 mg, 2.12 mmol) in N,N-dimethylformamide (2 ml) and potassium carbonate (488 mg, 3.53 mmol), and the mixture was stirred at 90° C. for 1 hr. Furthermore, a solution of 1-(2-chloroacetyl)piperidine (171 mg, 1.06 mmol) in N,N-dimethylformamide (1 ml) and potassium carbonate (244 mg, 1.77 mmol) were added, and the mixture was stirred at 90° C. for 1.5 hr. The mixture was allowed to cool to room temperature, water (10 ml) was added, and the precipitated solid was collected by filtration. The obtained solid was washed with water (10 ml) and dried in vacuo to give ethyl 3-chloro-12-cyclohexyl-6-oxo-5-[2-oxo-2-(piperidin-1-yl)ethyl]-5,6,7,12-tetrahydrobenzo[2,3]azepino[4,5-b]indole-9-carboxylate (911 mg, yield 92%).

$^1$H-NMR (300 MHz, DMSO-d$_6$): δ(ppm) 8.37 (1H, s), 7.97-7.87 (1H, m), 7.82 (1H, d, J=8.7 Hz), 7.71 (1H, s), 7.52 (1H, d, J=8.3 Hz), 7.51 (1H, s), 4.74-4.55 (2H, m), 4.40-4.26 (1H, m), 4.35 (2H, q, J=7.0 Hz), 3.94 (1H, d, J=13.9 Hz), 3.44-3.18 (4H, m), 3.02 (1H, d, J=13.6 Hz), 2.47-2.12 (3H, m), 2.05-1.94 (1H, m), 1.83-1.10 (12H, m), 1.37 (3H, t, J=7.2 Hz).

Step 9: Production of ethyl 3-chloro-12-cyclohexyl-5-[2-(piperidin-1-yl)ethyl]-5,6,7,12-tetrahydrobenzo[2,3]azepino[4,5-b]indole-9-carboxylate (Example 10-2)

for 2 hr. The reaction mixture was neutralized with 1N aqueous sodium hydroxide solution under ice-cooling, saturated sodium hydrogen carbonate solution was added and the mixture was extracted with ethyl acetate. The organic layer was successively washed with water and saturated brine and dried over anhydrous magnesium sulfate. After filtration, the solvent was evaporated under reduced pressure and the residue was purified by silica gel column chromatography (ethyl acetate) to give ethyl 3-chloro-12-cyclohexyl-5-[2-(piperidin-1-yl)ethyl]-5,6,7,12-tetrahydrobenzo[2,3]azepino[4,5-b]indole-9-carboxylate (512 mg, yield 61%).

$^1$H-NMR (300 MHz, DMSO-d$_6$): δ(ppm) 8.22 (1H, s), 7.82 (1H, d, J=8.7 Hz), 7.73 (1H, dd, J=9.0, 1.9 Hz), 7.36 (1H, s), 7.23-7.16 (2H, m), 4.32 (2H, q, J=7.2 Hz), 4.27-4.14 (1H, m), 3.53-3.42 (2H, m), 3.29-3.20 (2H, m), 2.89-2.71 (2H, m), 2.40-2.15 (9H, m), 1.90-1.59 (5H, m), 1.40-1.19 (8H, m), 1.34 (3H, t, J=7.5 Hz).

Example 10-1

Production of 3-chloro-12-cyclohexyl-5-[2-(piperidin-1-yl)ethyl]-5,6,7,12-tetrahydrobenzo[2,3]azepino[4,5-b]indole-9-carboxylic acid

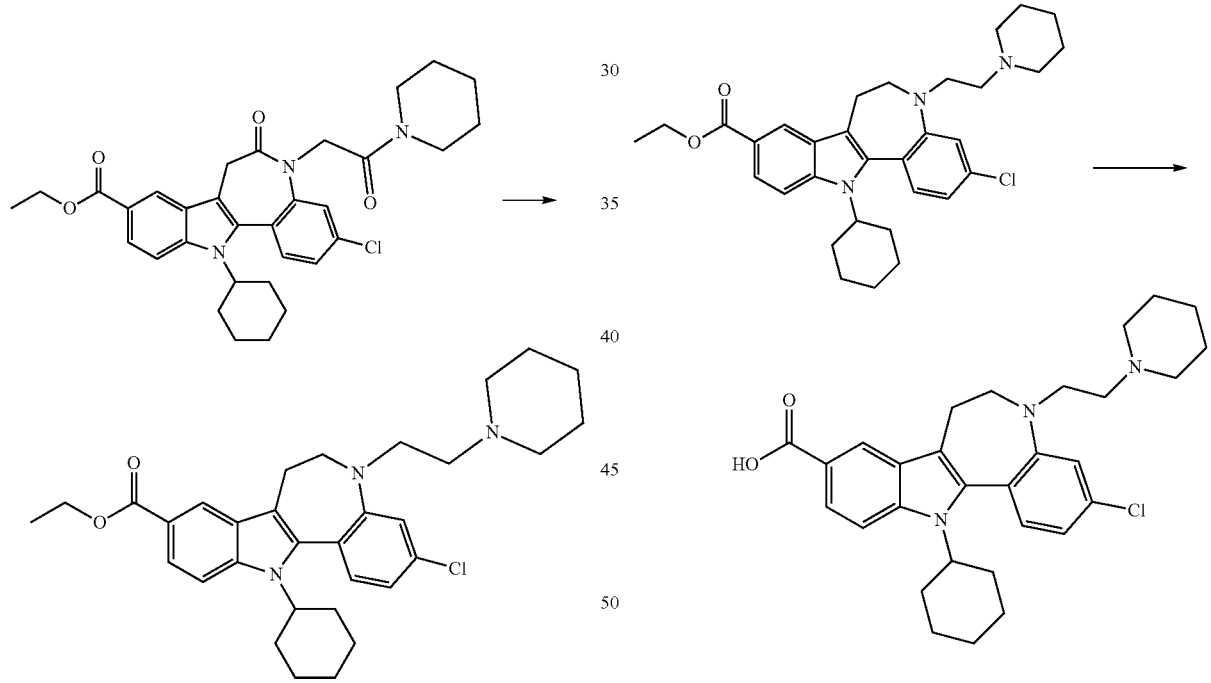

To a solution of ethyl 3-chloro-12-cyclohexyl-6-oxo-5-[2-oxo-2-(piperidin-1-yl)ethyl]-5,6,7,12-tetrahydrobenzo[2,3]azepino[4,5-b]indole-9-carboxylate (886 mg, 1.57 mmol) in tetrahydrofuran (15 ml) was added dropwise a solution (8.2 ml) of 1M BH$_3$ THF complex in tetrahydrofuran under ice-cooling, and the mixture was stirred under ice-cooling for 30 min., at room temperature for 3 hr, at 30° C. for 2 hr, and further at 60-70° C. for 1 hr. The reaction mixture was allowed to cool, a solution (4.1 ml) of 1M BH$_3$ THF complex in tetrahydrofuran was added, and the mixture was allowed to stand overnight at room temperature. The reaction mixture was stirred at 70° C. for 2 hr, 5M hydrochloric acid (8 ml) was added under ice-cooling, and the mixture was stirred at 70° C.

To a solution of ethyl 3-chloro-12-cyclohexyl-5-[2-(piperidin-1-yl)ethyl]-5,6,7,12-tetrahydrobenzo[2,3]azepino[4,5-b]indole-9-carboxylate (309 mg, 0.579 mmol) in tetrahydrofuran (4 ml) and methanol (4 ml) was added 1N aqueous sodium hydroxide solution (2 ml), and the mixture was stirred at 70° C. for 2 hr. The mixture was allowed to cool to room temperature, 4N aqueous lithium hydroxide solution (2 ml) was added, and the mixture was stirred at 70° C. for 2 hr. The mixture was allowed to cool to room temperature, water (100 ml) was added, and the mixture was extracted with ethyl acetate (20 ml) and ether (10 ml). The aqueous layer was adjusted to pH 7 with 1N hydrochloric acid, and the precipitated solid was collected by filtration. The obtained solid was washed with water and dried in vacuo to give 3-chloro-12- cyclohexyl-5-[2-(piperidin-1-yl)ethyl]-5,6,7,12-tetrahydrobenzo[2,3]azepino[4,5-b]indole-9-carboxylic acid (212 mg, yield 72%).

$^1$H-NMR (300 MHz, DMSO-d$_6$): δ(ppm) 8.22 (1H, s), 7.80 (1H, d, J=8.7 Hz), 7.74 (1H, d, J=8.7 Hz), 7.37 (1H, s), 7.21 (2H, brs), 4.26-4.15 (1H, m), 3.55-3.45 (2H, m), 3.32-3.20 (2H, m), 2.89-2.75 (2H, m), 2.45-2.20 (8H, m), 1.90-1.60 (5H, m), 1.49-1.20 (9H, m).

Example 10-3

Production of 3-chloro-12-cyclohexyl-5-[2-(piperidin-1-yl)ethyl]-5,6,7,12-tetrahydrobenzo[2,3]azepino[4,5-b]indole-9-carboxamide

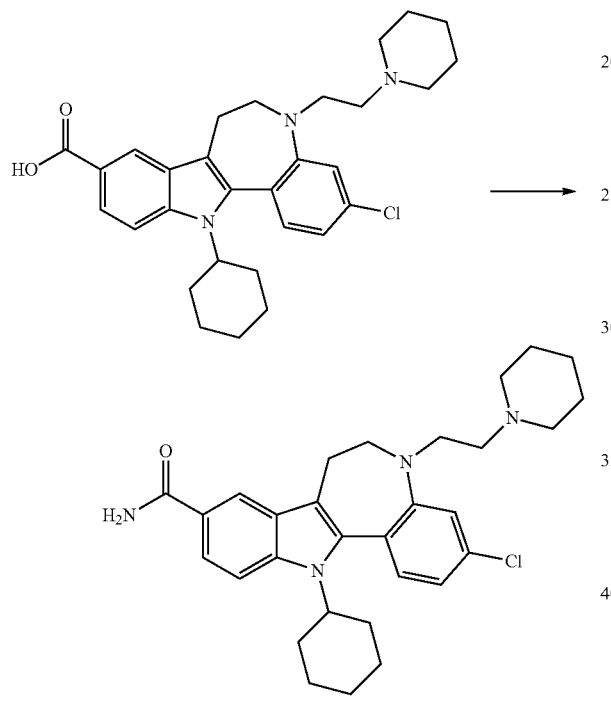

To a solution of 3-chloro-12-cyclohexyl-5-[2-(piperidin-1-yl)ethyl]-5,6,7,12-tetrahydrobenzo[2,3]azepino[4,5-b]indole-9-carboxylic acid (100 mg, 0.198 mmol) in N,N-dimethylformamide (3 ml) were added triethylamine (0.041 ml, 0.297 mmol), (benzotriazol-1-yloxy)tripyrrolidinophosphonium hexafluorophosphate (155 mg, 0.297 mmol) and 28% aqueous ammonia (0.1 ml), and the mixture was stirred overnight at room temperature. Water (15 ml) was added to the reaction mixture, and the mixture was extracted with ethyl acetate (20 ml). The organic layer was washed with saturated brine (15 ml) and dried over anhydrous magnesium sulfate. After filtration, the solvent was evaporated under reduced pressure. The residue was purified by silica gel column chromatography to give an oil (36 mg). Tetrahydrofuran (2 ml), methanol (2 ml) and water (2 ml) were added to the oil, and the precipitated solid was collected by filtration. The obtained solid was dried in vacuo to give 3-chloro-12-cyclohexyl-5-[2-(piperidin-1-yl)ethyl]-5,6,7,12-tetrahydrobenzo[2,3]azepino[4,5-b]indole-9-carboxamide (32 mg, yield 32%).

$^1$H-NMR (300 MHz, DMSO-d$_6$): δ(ppm) 8.18 (1H, s), 7.84 (1H, brs), 7.74 (1H, d, J=8.7 Hz), 7.69 (1H, dd, J=8.7, 1.9 Hz), 7.36 (1H, d, J=1.9 Hz), 7.25-7.15 (2H, m), 7.10 (1H, brs), 4.26-4.10 (1H, m), 3.51-3.47 (2H, m), 3.40-3.29 (2H, m), 2.81 (2H, brs), 2.40-2.20 (8H, m), 1.90-1.55 (5H, m), 1.40-1.15 (9H, m).

The compound of Example 10-4 was produced by the same method as in Examples 10-1 and 10-2 or methods similar thereto, and where necessary, by employing other conventional methods. The chemical structural formula is shown in Table 118.

12-cyclohexyl-5-[2-(piperidin-1-yl)ethyl]-5,6,7,12-tetrahydrobenzo[2,3]azepino[4,5-b]indole-9-carboxylic acid (Example 10-4)

Example 1-157

Production of 13-cyclohexyl-5-[2-(1-cyclopentylpiperidin-4-yl)ethyl]-6,7-dihydro-5H-benzo[5,6][1,4]diazepino[7,1-a]indole-10-carboxylic acid dihydrochloride Step 1: Production of methyl 5-[2-(1-tert-butoxycarbonylpiperidin-4-yl)ethyl]-13-cyclohexyl-6,7-dihydro-5H-benzo[5,6][1,4]diazepino[7,1-a]indole-10-carboxylate (Example 1-601)

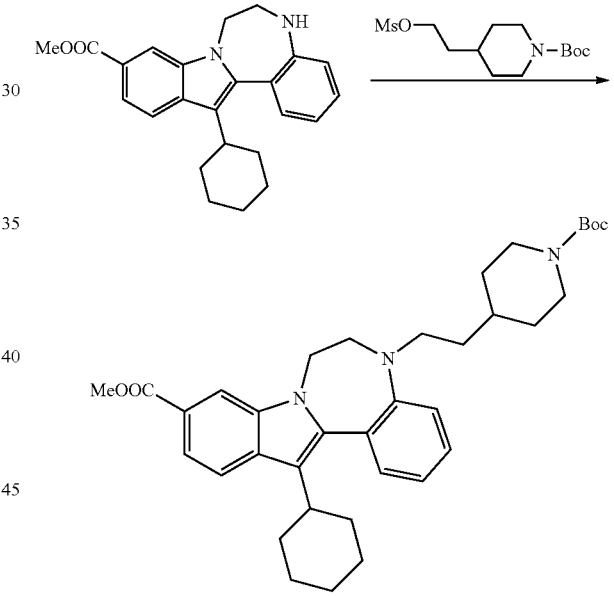

To a solution of methyl 13-cyclohexyl-6,7-dihydro-5H-benzo[5,6][1,4]diazepino[7,1-a]indole-10-carboxylate (1.00 g, 2.67 mmol) obtained in Example 1-2 and 1-(tert-butoxycarbonyl)-4-(2-methanesulfonyloxyethyl)piperidine (2.46 g, 8.02 mmol) in N,N-dimethylformamide (10 ml) were added potassium carbonate (1.85 g, 13.4 mmol) and potassium iodide (2.00 g, 8.02 mmol), and the mixture was stirred at 90° C. for 36 hr. The reaction mixture was cooled to room temperature, water was added, and the mixture was extracted with ethyl acetate. The organic layer was washed successively with water and saturated brine and dried over anhydrous magnesium sulfate. After filtration, the solvent was evaporated under reduced pressure. The residue was purified by silica gel column chromatography (hexane:ethyl acetate-4:1-2:1) to give methyl 5-[2-(1-tert-butoxycarbonylpiperidin-4-yl)ethyl]-13-cyclohexyl-6,7-dihydro-5H-benzo[5,6][1,4]diazepino[7,1-a]indole-10-carboxylate (1.16 g, yield 74%).

¹H-NMR (400 MHz, DMSO-d₆): δ(ppm) 8.18 (1H, d, J=1.4 Hz), 7.87 (1H, d, J=8.3 Hz), 7.61 (1H, dd, J=8.3, 1.4 Hz), 7.44 (1H, td, J=7.6, 1.4 Hz), 7.31 (1H, dd, J=7.6, 1.4 Hz), 7.22 (1H, d, J=7.6 Hz), 7.18 (1H, t, J=7.6 Hz), 3.87 (3H, s), 3.65 (2H, brs), 3.10 (2H, brs), 2.83 (1H, brt, J=12.8 Hz), 2.33 (2H, brs), 2.07-1.92 (2H, m), 1.87-1.49 (4H, m), 1.41-1.10 (11H, m), 1.33 (9H, s), 0.85-0.67 (2H, m).

MS 586.2 (M+1).

Step 2: Production of methyl 13-cyclohexyl-5-[2-(piperidin-4-yl)ethyl]-6,7-dihydro-5H-benzo[5,6][1,4]diazepino[7,1-a]indole-10-carboxylate (Example 1-602)

Step 3: Production of methyl 13-cyclohexyl-5-[2-(1-cyclopentylpiperidin-4-yl)ethyl]-6,7-dihydro-5H-benzo[5,6][1,4]diazepino[7,1-a]indole-10-carboxylate (Example 1-603)

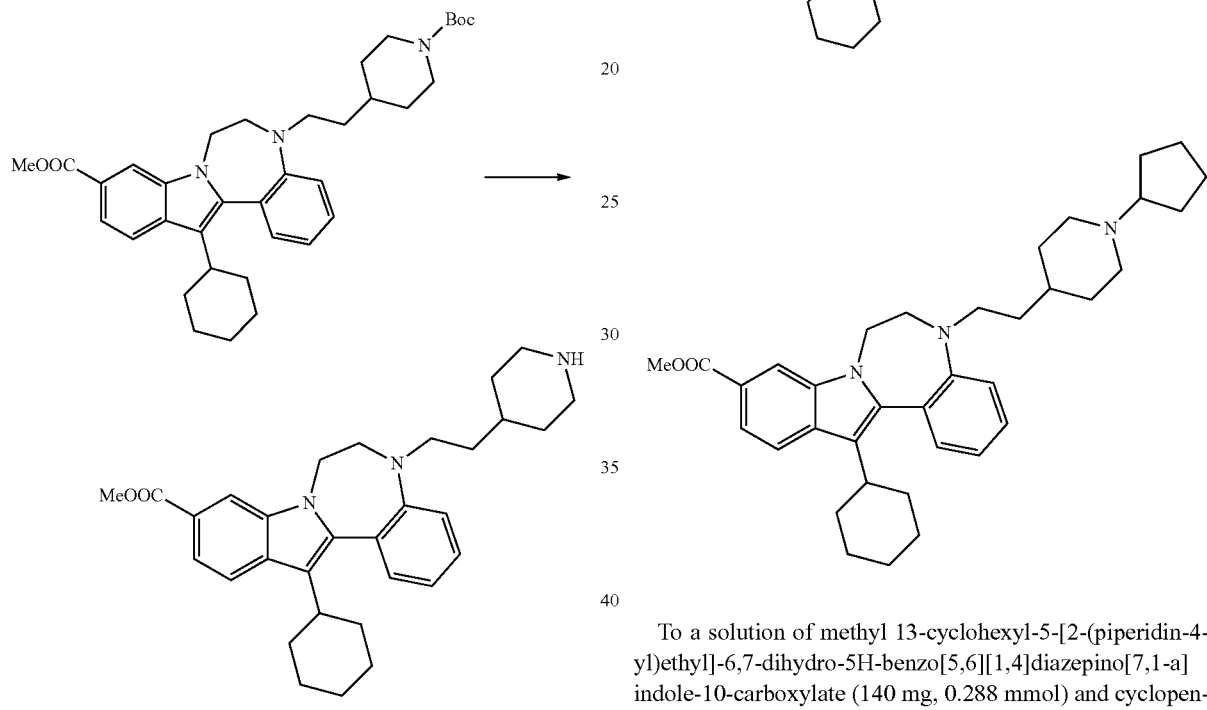

To a solution of methyl 5-[2-(1-tert-butoxycarbonylpiperidin-4-yl)ethyl]-13-cyclohexyl-6,7-dihydro-5H-benzo[5,6][1,4]diazepino[7,1-a]indole-10-carboxylate (1.06 g, 1.81 mmol) in chloroform (10 ml) was added trifluoroacetic acid (2 ml), and the mixture was stirred at room temperature for 2 hr. Saturated aqueous sodium hydrogen carbonate solution was added to the reaction mixture and the mixture was extracted with ethyl acetate. The organic layer was successively washed with saturated aqueous sodium hydrogen carbonate solution and saturated brine and dried over anhydrous sodium sulfate. After filtration, the solvent was evaporated under reduced pressure to give methyl 13-cyclohexyl-5-[2-(piperidin-4-yl)ethyl]-6,7-dihydro-5H-benzo[5,6][1,4]diazepino[7,1-a]indole-10-carboxylate (859 mg, yield 98%).

¹H-NMR (400 MHz, DMSO-d₆): δ(ppm) 8.17 (1H, d, J=1.4 Hz), 7.87 (1H, d, J=8.5 Hz), 7.61 (1H, dd, J=8.5, 1.4 Hz), 7.43 (1H, td, J=7.7, 1.4 Hz), 7.30 (1H, dd, J=7.7, 1.6 Hz), 7.26-7.11 (3H, m), 6.16 (1H, brs), 4.68 (1H, brs), 3.87 (3H, s), 3.71-2.92 (4H, m), 2.88-2.72 (3H, m), 2.37-2.21 (2H, m), 2.09-1.53 (6H, m), 1.48-1.09 (8H, m), 1.03-0.86 (2H, m).

MS 468.3 (M+1)

To a solution of methyl 13-cyclohexyl-5-[2-(piperidin-4-yl)ethyl]-6,7-dihydro-5H-benzo[5,6][1,4]diazepino[7,1-a]indole-10-carboxylate (140 mg, 0.288 mmol) and cyclopentanone (127 μl, 1.44 mmol) in tetrahydrofuran (60 ml) and acetic acid (0.3 ml), was added sodium triacetoxyborohydride (183 mg, 0.865 mmol) under ice-cooling, and the mixture was stirred for 2 days. Saturated aqueous sodium hydrogen carbonate solution was added to the reaction mixture and the mixture was extracted with ethyl acetate. The organic layer was successively washed with saturated aqueous sodium hydrogen carbonate solution and saturated brine and dried over anhydrous magnesium sulfate. After filtration, the solvent was evaporated under reduced pressure. The residue was purified by silica gel column chromatography (chloroform:methanol=30:1-15:1) to give methyl 13-cyclohexyl-5-[2-(1-cyclopentylpiperidin-4-yl)ethyl]-6,7-dihydro-5H-benzo[5,6][1,4]diazepino[7,1-a]indole-10-carboxylate (124 mg, yield 78%).

¹H-NMR (400 MHz, DMSO-d₆): δ(ppm) 8.17 (1H, s), 7.86 (1H, d, J=8.3 Hz), 7.60 (1H, d, J=8.3 Hz), 7.43 (1H, t, J=7.4 Hz), 7.30 (1H, d, J=7.4 Hz), 7.21 (1H, d, J=7.4 Hz), 7.16 (1H, t, J=7.4 Hz), 4.69 (2H, brs), 3.86 (3H, s), 3.11 (4H, brs), 2.87-2.75 (1H, m), 2.69-2.54 (1H, m), 2.31-2.13 (1H, m), 2.07-0.78 (28H, m).

439

Step 4: Production of 13-cyclohexyl-5-[2-(1-cyclopentylpiperidin-4-yl)ethyl]-6,7-dihydro-5H-benzo[5,6][1,4]diazepino[7,1-a]indole-10-carboxylic acid dihydrochloride (Example 1-157)

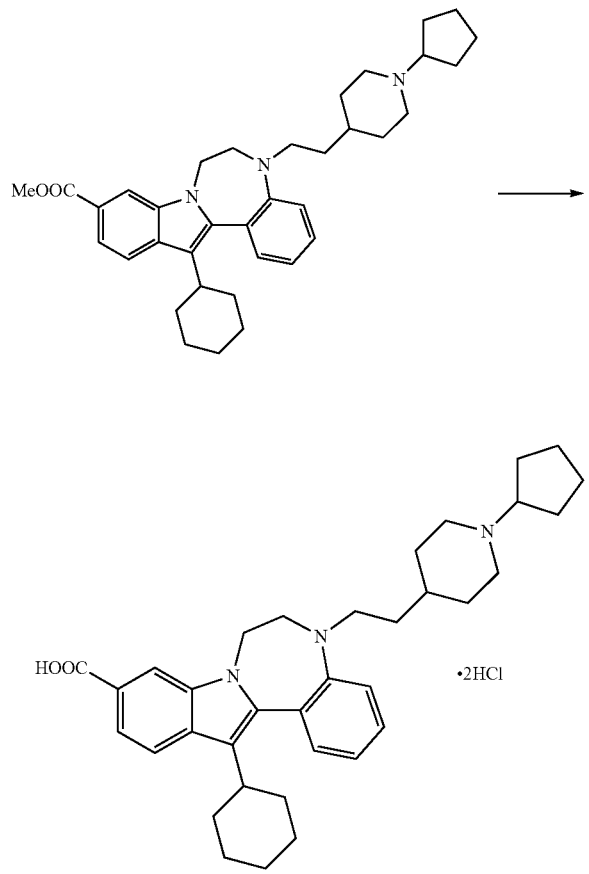

To a solution of methyl 13-cyclohexyl-5-[2-(1-cyclopentylpiperidin-4-yl)ethyl]-6,7-dihydro-5H-benzo[5,6][1,4]diazepino[7,1-a]indole-10-carboxylate (124 mg, 0.224 mmol) in tetrahydrofuran (2 ml) and methanol (2 ml) was added 4N aqueous sodium hydroxide solution (1 ml), and the mixture was stirred at 70° C. for 2 hr. The reaction mixture was adjusted to pH 6.5 by adding 2N hydrochloric acid, and the mixture was extracted with chloroform. The organic layer was washed with saturated brine and dried over anhydrous sodium sulfate. After filtration, the solvent was evaporated under reduced pressure. To a solution of the obtained residue in chloroform was added 4N HCl-ethyl acetate solution (10 ml), and the solvent was evaporated under reduced pressure. A mixed solvent (hexane:ethyl acetate=4:1) was added to the residue. The precipitated solid was collected by filtration to give 13-cyclohexyl-5-[2-(1-cyclopentylpiperidin-4-yl)ethyl]-6,7-dihydro-5H-benzo[5,6][1,4]diazepino[7,1-a]indole-10-carboxylic acid dihydrochloride (125 mg, yield 91%).

$^1$H-NMR (400 MHz, DMSO-$d_6$): δ(ppm) 9.55-9.35 (1H, m), 8.15 (1H, d, J=1.2 Hz), 7.85 (1H, d, J=8.4 Hz), 7.60 (1H, dd, J=8.4, 1.2 Hz), 7.44 (1H, t, J=7.4 Hz), 7.32 (1H, d, J=7.4 Hz), 7.26-7.15 (2H, m), 4.53 (3H, brs), 3.17 (4H, brs), 2.88-2.76 (1H, m), 2.10-1.11 (29H, m).

MS 540.4 (M+1).

440

Example 2-44

Production of 12-cyclohexyl-3-(1-methanesulfonylpiperidin-3-yloxy)-6,7-dihydro-5-oxa-7a-azadibenzo[a,e]azulene-9-carboxylic acid Step 1: Production of tert-butyl 3-(toluene-4-sulfonyloxy)piperidine-1-carboxylate

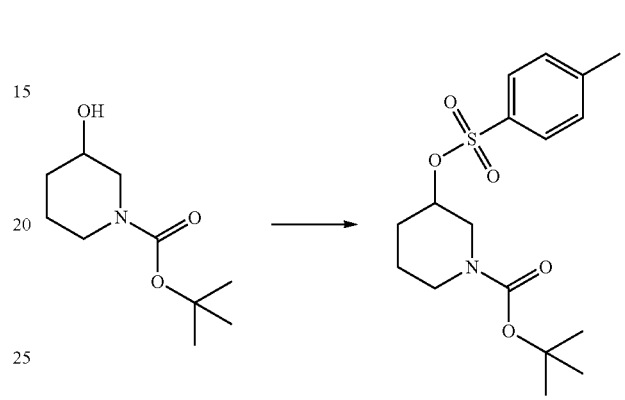

To a solution of tert-butyl 3-hydroxypiperidine-1-carboxylate (2.00 g, 9.94 mmol) in chloroform (20 ml) were successively added p-toluenesulfonyl chloride (2.27 g, 11.9 mmol) and triethylamine (1.66 ml, 11.9 mmol) at 0° C., and the mixture was stirred at 70° C. for 9 hr. The reaction mixture was allowed to cool to room temperature, water was added to the reaction mixture and the mixture was extracted with chloroform. The organic layer was successively washed with water and saturated brine and dried over anhydrous magnesium sulfate. After filtration, the solvent was concentrated under reduced pressure, and the residue was purified by silica gel chromatography (ethyl acetate:hexane=1:1) to give tert-butyl 3-(toluene-4-sulfonyloxy)piperidine-1-carboxylate (1.00 g, yield 28%).

$^1$H-NMR (300 MHz, DMSO-$d_6$): δ(ppm) 7.81 (2H, d, J=9.0 Hz), 7.49 (2H, d, J=9.0 Hz), 4.54-4.36 (1H, m), 3.67-2.89 (4H, m), 2.42 (3H, s), 1.81-1.52 (3H, m), 1.47-1.21 (1H, m), 1.35 (9H, s).

Step 2: Production of methyl 3-(1-tert-butoxycarbonylpiperidin-3-yloxy)-12-cyclohexyl-6,7-dihydro-5-oxa-7a-azadibenzo[a,e]azulene-9-carboxylate (Example 2-501)

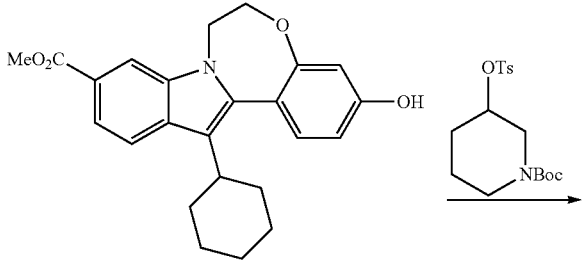

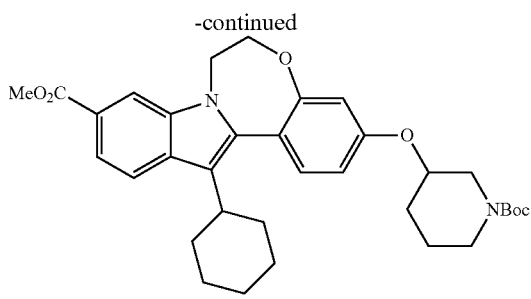

To a solution of methyl 12-cyclohexyl-3-hydroxy-6,7-dihydro-5-oxa-7a-azadibenzo[a,e]azulene-9-carboxylate (0.80 g, 2.04 mmol) in N,N-dimethylformamide (8 ml) were successively added tert-butyl 3-(toluene-4-sulfonyloxy)piperidine-1-carboxylate (1.09 g, 3.07 mmol) and potassium carbonate (0.57 g, 4.08 mmol) at room temperature, and the mixture was stirred overnight at 60° C. The reaction mixture was allowed to cool to room temperature, water was added to the reaction mixture and the mixture was extracted with ethyl acetate. The organic layer was successively washed with water and saturated brine and dried over anhydrous magnesium sulfate. After filtration, the solvent was concentrated under reduced pressure to give methyl 3-(1-tert-butoxycarbonylpiperidin-3-yloxy)-12-cyclohexyl-6,7-dihydro-5-oxa-7a-azadibenzo[a,e]azulene-9-carboxylate (0.68 g). The obtained compound was used for Step 3 without purification.

Step 3: Production of methyl 12-cyclohexyl-3-(piperidin-3-yloxy)-6,7-dihydro-5-oxa-7a-azadibenzo[a,e]azulene-9-carboxylate (Example 2-502)

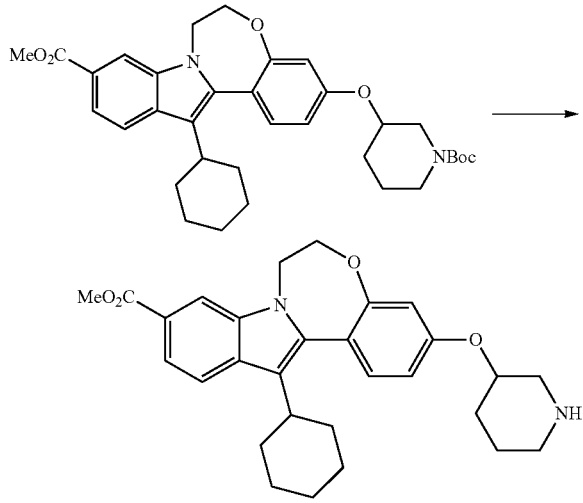

Methyl 3-(1-tert-butoxycarbonylpiperidin-3-yloxy)-12-cyclohexyl-6,7-dihydro-5-oxa-7a-azadibenzo[a,e]azulene-9-carboxylate (0.68 g) was dissolved in trifluoroacetic acid (20 ml), and the mixture was stirred at room temperature for 3 hr. Toluene was added to the reaction mixture and the solvent was evaporated under reduced pressure. 4N HCl-ethyl acetate solution (2.0 ml) was added to the obtained residue and the mixture was stirred, and the solvent was evaporated under reduced pressure. The residue was neutralized with saturated aqueous sodium hydrogen carbonate solution and extracted with ethyl acetate. The organic layer was successively washed with water and saturated brine and dried over anhydrous magnesium sulfate. After filtration, the solvent was concentrated under reduced pressure, and the residue was purified by silica gel chromatography (chloroform:methanol=9:1) to give methyl 12-cyclohexyl-3-(piperidin-3-yloxy)-6,7-dihydro-5-oxa-7a-azadibenzo[a,e]azulene-9-carboxylate (0.16 g, yield 17%).

$^1$H-NMR (300 MHz, CDCl$_3$): δ(ppm) 8.05 (1H, s), 7.87 (1H, d, J=8.3 Hz), 7.75 (1H, d, J=8.7 Hz), 7.31 (1H, d, J=8.3 Hz), 6.85 (1H, dd, J=2.3, 8.3 Hz), 6.79 (1H, d, J=2.3 Hz), 4.50 (1H, t, J=5.5 Hz), 4.39-4.24 (3H, m), 3.94 (3H, s), 3.28-3.17 (1H, m), 3.02-2.73 (4H, m), 2.17-1.96 (4H, m), 1.95-1.74 (7H, m), 1.64-1.48 (1H, m), 1.47-1.30 (3H, m).

Step 4: Production of methyl 12-cyclohexyl-3-(1-methanesulfonylpiperidin-3-yloxy)-6,7-dihydro-5-oxa-7a-azadibenzo[a,e]azulene-9-carboxylate (Example 2-503)

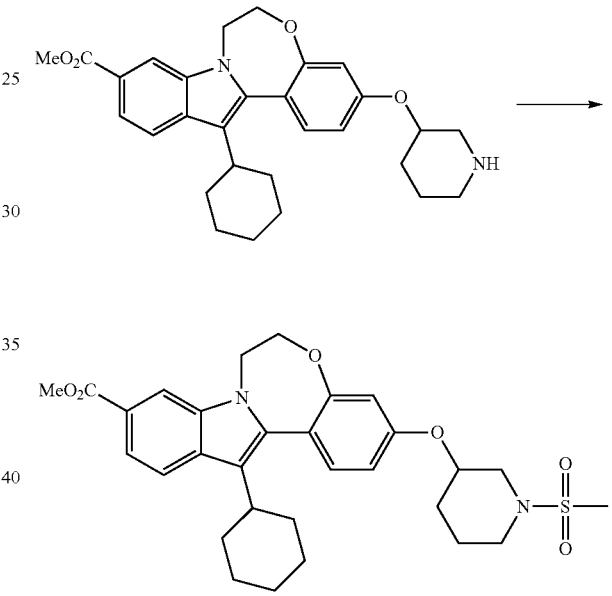

To a solution of methyl 12-cyclohexyl-3-(piperidin-3-yloxy)-6,7-dihydro-5-oxa-7a-azadibenzo[a,e]azulene-9-carboxylate (43 mg, 0.091 mmol) in pyridine (0.5 ml) was added dropwise methanesulfonyl chloride (8.5 μl, 0.11 mmol), and the mixture was stirred at 0° C. for 2 hr. Toluene was added to the reaction mixture and the solvent was evaporated under reduced pressure. Hexane and ethyl acetate were added to the obtained residue, and the precipitate was collected by filtration, washed with hexane, and dried in vacuo to give methyl 12-cyclohexyl-3-(1-methanesulfonylpiperidin-3-yloxy)-6,7-dihydro-5-oxa-7a-azadibenzo[a,e]azulene-9-carboxylate (47 mg, yield 94%).

$^1$H-NMR (300 MHz, DMSO-d$_6$): δ(ppm) 8.20 (1H, s), 7.89 (1H, d, J=8.6 Hz), 7.63 (1H, dd, J=1.1, 8.3 Hz), 7.35 (1H, d, J=8.3 Hz), 6.99 (1H, dd, J=2.3, 8.3 Hz), 6.89 (1H, d, J=2.6 Hz), 4.67-4.56 (1H, m), 4.51-4.31 (4H, m), 3.87 (3H, s), 3.59-3.51 (1H, m), 3.32-3.05 (3H, m), 2.94 (3H, s), 2.92-2.79 (1H, m), 2.11-1.92 (4H, m), 1.92-1.59 (7H, m), 1.46-1.22 (3H, m).

Step 5: Production of 12-cyclohexyl-3-(1-methanesulfonylpiperidin-3-yloxy)-6,7-dihydro-5-oxa-7a-azadibenzo[a,e]azulene-9-carboxylic acid (Example 2-44)

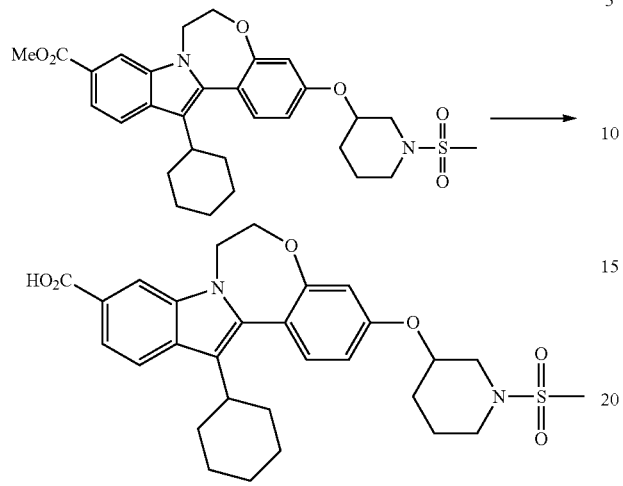

To a solution of methyl 12-cyclohexyl-3-(1-methanesulfonylpiperidin-3-yloxy)-6,7-dihydro-5-oxa-7a-azadibenzo[a, e]azulene-9-carboxylate (47 mg, 0.085 mmol) in tetrahydrofuran (1 ml) and methanol (1 ml) was added 4N aqueous sodium hydroxide solution (0.5 ml), and the mixture was stirred at 55° C. for 2 hr. The mixture was adjusted to pH 6.5 by adding 1N hydrochloric acid (2 ml), and extracted with a mixed solvent of ethyl acetate and tetrahydrofuran. The organic layer was washed with saturated brine and dried over anhydrous sodium sulfate. After filtration, the solvent was concentrated under reduced pressure. Hexane and ethyl acetate were added to the obtained residue, and the precipitate was collected by filtration, washed with hexane and dried in vacuo to give 12-cyclohexyl-3-(1-methanesulfonylpiperidin-3-yloxy)-6,7-dihydro-5-oxa-7a-azadibenzo[a,e]azulene-9-carboxylic acid (25 mg, yield 56%).

$^1$H-NMR (300 MHz, DMSO-d$_6$): δ(ppm) 12.55 (1H, brs), 8.17 (1H, s), 7.86 (1H, d, J=8.7 Hz), 7.62 (1H, d, J=7.9 Hz), 7.34 (1H, d, J=7.9 Hz), 6.98 (1H, d, J=7.9 Hz), 6.88 (1H, s), 4.71-4.55 (1H, m), 4.53-4.25 (4H, m), 3.67-3.49 (2H, m), 3.29-3.02 (3H, m), 3.00-2.78 (1H, m), 2.94 (3H, s), 2.14-1.53 (11H, m), 1.47-1.29 (2H, m).

MS 539.2 (M+1).

Example 2-53

Production of 12-cyclohexyl-4-[2-(piperidin-1-yl)ethoxy]-6,7-dihydro-5-oxa-7a-azadibenzo[a,e]azulene-9-carboxylic acid hydrochloride Step 1: Production of 2-[2-(2-benzyloxyphenoxy)ethoxy]tetrahydropyran

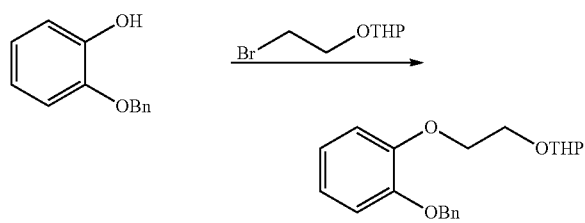

To a solution of 2-benzyloxyphenol (3.00 g, 15.0 mmol) in N,N-dimethylformamide (15 ml) was added sodium hydride (60% in oil) (719 mg, 18.0 mmol) under ice-cooling, and the mixture was stirred at 30 min. 2-(2-Bromoethoxy)tetrahydropyran (2.72 ml, 18.0 mmol) was added to the reaction mixture and the mixture was stirred at 18 hr. Water was added to the reaction mixture and the mixture was extracted with ethyl acetate. The organic layer was washed with saturated brine and dried over anhydrous magnesium sulfate. After filtration, the solvent was evaporated under reduced pressure to give 2-[2-(2-benzyloxyphenoxy)ethoxy]tetrahydropyran (4.90 g). The obtained compound was used for Step 2 without purification.

$^1$H-NMR (400 MHz, CDCl$_3$): δ(ppm) 7.47-7.28 (5H, m), 6.99-6.85 (4H, m), 5.13 (2H, s), 4.73 (1H, t, J=3.5 Hz), 4.23 (2H, t, J=5.1 Hz), 3.92-3.83 (2H, m), 3.55-3.45 (2H, m), 1.87-1.77 (1H, m), 1.74-1.67 (1H, m), 1.64-1.46 (4H, m).

Step 2: Production of 2-(2-benzyloxyphenoxy)ethanol

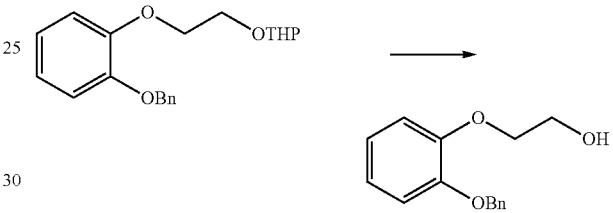

To a solution of 2-[2-(2-benzyloxyphenoxy)ethoxy]tetrahydropyran (4.90 g) in tetrahydrofuran (25 ml) and methanol (25 ml) was added 6N hydrochloric acid (15 ml), and the mixture was stirred at room temperature for 1 hr. Water was added to the reaction mixture and the mixture was extracted with ethyl acetate. The organic layer was washed successively with saturated aqueous sodium hydrogen carbonate solution and saturated brine and dried over anhydrous magnesium sulfate. After filtration, the solvent was evaporated under reduced pressure. The obtained residue was purified by silica gel chromatography (hexane:ethyl acetate=1:1) to give 2-(2-benzyloxyphenoxy)ethanol (3.07 g, yield 84%).

$^1$H-NMR (400 MHz, CDCl$_3$): δ(ppm) 7.47-7.31 (5H, m), 7.01-6.93 (4H, m), 5.13 (2H, s), 4.15 (2H, t, J=4.4 Hz), 3.89 (2H, t, J=4.4 Hz), 2.48 (1H, brs).

Step 3: Production of 2-(2-benzyloxyphenoxy)ethyl methanesulfonate

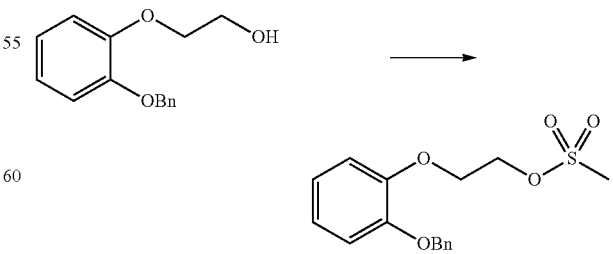

To a solution of 2-(2-benzyloxyphenoxy)ethanol (3.07 g, 12.6 mmol) and triethylamine (2.63 ml, 18.8 mmol) in chloroform (30 ml) was added methanesulfonyl chloride (1.12 ml, 14.4 mmol) under ice-cooling, and the mixture was stirred for 2 hr. Saturated aqueous ammonium chloride solution was added to the reaction mixture, and the mixture was extracted with ethyl acetate. The organic layer was washed with saturated brine and dried over anhydrous magnesium sulfate. After filtration, the solvent was evaporated under reduced pressure. Hexane was added to the obtained residue and the precipitated solid was collected by filtration and washed with hexane. The obtained solid was dried in vacuo to give 2-(2-benzyloxyphenoxy)ethyl methanesulfonate (3.77 g, yield 93%).

$^1$H-NMR (400 MHz, CDCl$_3$): δ(ppm) 7.46-7.35 (5H, m), 7.00-6.91 (4H, m), 5.06 (2H, s), 4.59 (2H, t, J=4.4 Hz), 4.26 (2H, t, J=4.4 Hz), 2.88 (3H, s).

Step 4: Production of methyl 1-[2-(2-benzyloxyphenoxy)ethyl]-2-bromo-3-cyclohexyl-1H-indole-6-carboxylate

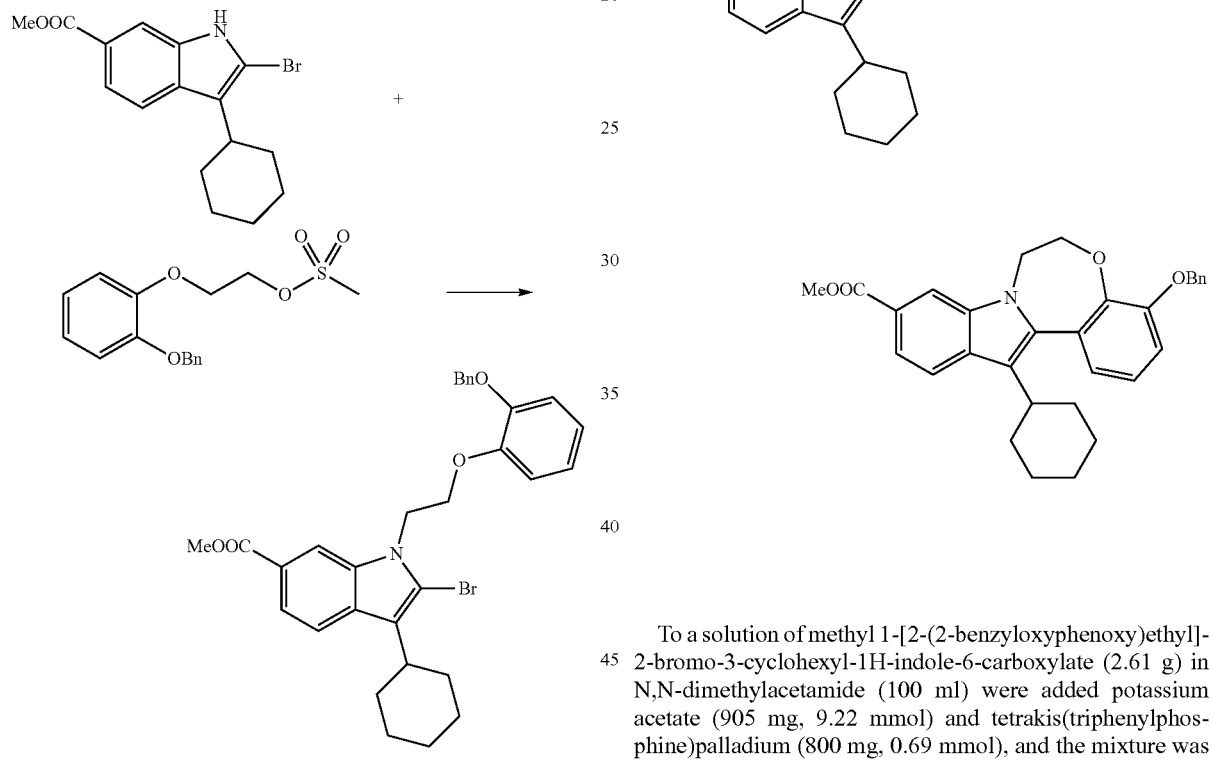

To a solution of methyl 2-bromo-3-cyclohexyl-1H-indole-6-carboxylate (1.50 g, 4.46 mmol) obtained in the same manner as in the method described in WO03/010140 and 2-(2-benzyloxyphenoxy)ethyl methanesulfonate (1.73 g, 5.35 mmol) in N,N-dimethylformamide (15 ml) were added potassium iodide (740 mg, 4.46 mmol) and potassium carbonate (1.85 g, 13.4 mmol), and the mixture was stirred at 90° C. for 7 hr. The reaction mixture was allowed to cool to room temperature, water was added to the reaction mixture and the mixture was extracted with ethyl acetate. The organic layer was washed with saturated brine and dried over anhydrous magnesium sulfate. After filtration, the solvent was evaporated under reduced pressure and the obtained residue was purified by silica gel chromatography (hexane:ethyl acetate=6:1) to give methyl 1-[2-(2-benzyloxyphenoxy)ethyl]-2-bromo-3-cyclohexyl-1H-indole-6-carboxylate (2.61 g). The obtained compound was used as it was for Step 5.

$^1$H-NMR (400 MHz, CDCl$_3$): δ(ppm) 8.15 (1H, s), 7.76-7.75 (2H, m), 7.35-7.29 (5H, m), 6.89-6.81 (4H, m), 5.06 (2H, s), 4.68 (2H, t, J=6.3 Hz), 4.34 (2H, t, J=6.3 Hz), 3.88 (3H, s), 2.93-2.85 (1H, m), 1.98-1.78 (7H, m), 1.49-1.35 (3H, m).

Step 5: Production of methyl 4-benzyloxy-12-cyclohexyl-6,7-dihydro-5-oxa-7a-azadibenzo[a,e]azulene-9-carboxylate (Example 2-504)

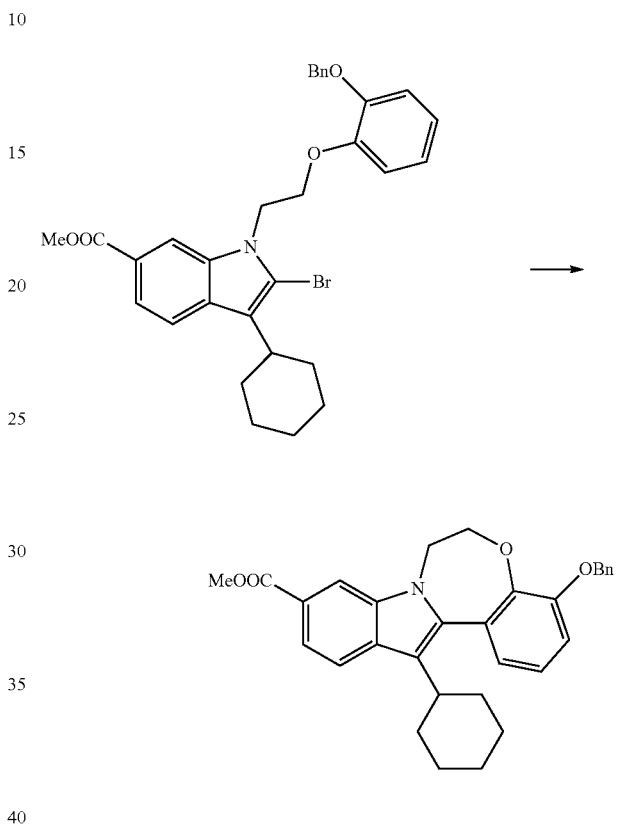

To a solution of methyl 1-[2-(2-benzyloxyphenoxy)ethyl]-2-bromo-3-cyclohexyl-1H-indole-6-carboxylate (2.61 g) in N,N-dimethylacetamide (100 ml) were added potassium acetate (905 mg, 9.22 mmol) and tetrakis(triphenylphosphine)palladium (800 mg, 0.69 mmol), and the mixture was stirred at 130° C. for 41 hr. The mixture was allowed to cool to room temperature, and filtered through celite. Saturated aqueous ammonium chloride solution was added to the filtrate, and the mixture was extracted with ethyl acetate. The organic layer was washed successively with saturated aqueous ammonium chloride solution and saturated brine and dried over anhydrous magnesium sulfate. After filtration, the solvent was evaporated under reduced pressure and the obtained residue was purified by silica gel chromatography (hexane:ethyl acetate=6:1) to give methyl 4-benzyloxy-12-cyclohexyl-6,7-dihydro-5-oxa-7a-azadibenzo[a,e]azulene-9-carboxylate (745 mg, yield 34%).

$^1$H-NMR (400 MHz, CDCl$_3$): δ(ppm) 8.09 (1H, s), 7.90 (1H, d, J=8.8 Hz), 7.77 (1H, dd, J=8.3, 1.4 Hz), 7.48 (2H, d, J=7.0 Hz), 7.43-7.39 (2H, m), 7.36-7.33 (1H, m), 7.18 (1H, t, J=7.9 Hz), 7.08-7.03 (2H, m), 5.22 (2H, s), 4.53 (2H, t, J=5.8 Hz), 4.32-4.26 (2H, m), 3.96 (3H, s), 3.04-2.96 (1H, m), 2.12-2.02 (2H, m 1.92-1.77 (5H, m), 1.43-1.34 (3H, m).

Step 6: Production of methyl 12-cyclohexyl-4-hydroxy-6,7-dihydro-5-oxa-7a-azadibenzo[a,e]azulene-9-carboxylate (Example 2-505)

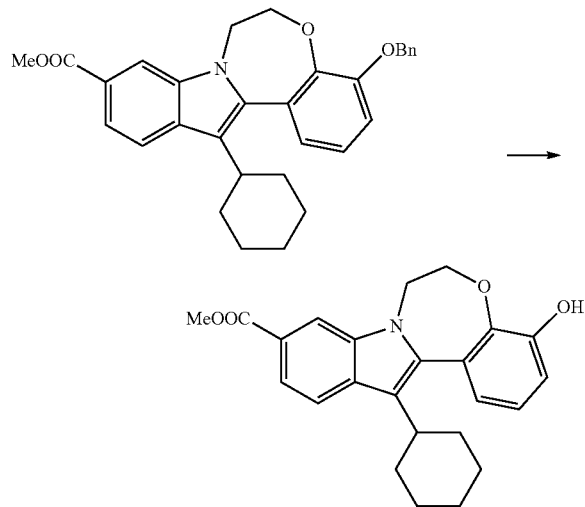

To methyl 4-benzyloxy-12-cyclohexyl-6,7-dihydro-5-oxa-7a-azadibenzo[a,e]azulene-9-carboxylate (745 mg, 1.55 mmol) was added 25% hydrogen bromide-acetic acid solution (5 ml), and the mixture was stirred at room temperature for 30 min. Water was added to the reaction mixture and the mixture was extracted with ethyl acetate. The organic layer was washed successively with saturated aqueous sodium hydrogen carbonate solution and saturated brine and dried over anhydrous magnesium sulfate. After filtration, the solvent was evaporated under reduced pressure. Hexane:diisopropy ether (3:1) solution was added to the obtained residue and the precipitated solid was collected by filtration. The solid was washed with hexane:diisopropy ether (3:1) solution. The obtained solid was dried in vacuo to give methyl 12-cyclohexyl-4-hydroxy-6,7-dihydro-5-oxa-7a-azadibenzo[a,e]azulene-9-carboxylate (470 mg, yield 78%).

$^1$H-NMR (400 MHz, CDCl$_3$): δ(ppm) 8.09 (1H, s), 7.91 (1H, d, J=8.3 Hz), 7.78 (1H, dd, J=8.3, 1.4 Hz), 7.17 (1H, t, J=7.9 Hz), 7.08 (1H, dd, J=8.1, 1.6 Hz), 6.97 (1H, dd, J=7.7, 1.6 Hz), 5.88 (1H, s), 4.60 (2H, t, J=5.6 Hz), 4.37 (2H, t, J=5.6 Hz), 3.96 (3H, s), 3.04-2.96 (1H, m), 2.12-2.02 (2H, m), 1.91-1.78 (5H, m), 1.43-1.34 (3H, m).

Step 7: Production of methyl 12-cyclohexyl-4-[2-oxo-2-(piperidin-1-yl)ethoxy]-6,7-dihydro-5-oxa-7a-azadibenzo[a,e]azulene-9-carboxylate (Example 2-506)

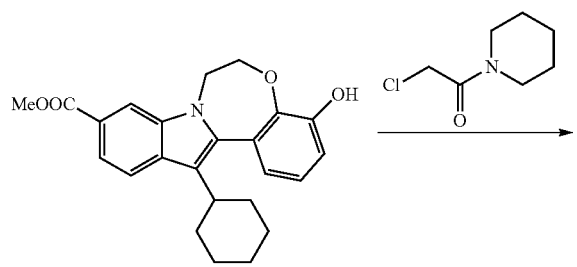

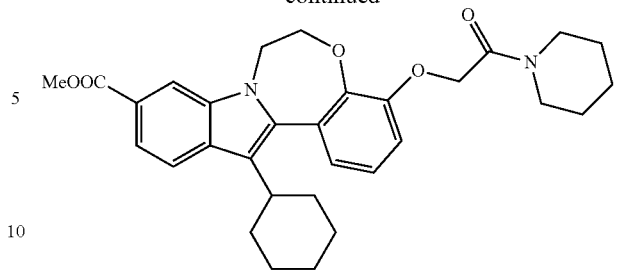

To a solution of methyl 12-cyclohexyl-4-hydroxy-6,7-dihydro-5-oxa-7a-azadibenzo[a,e]azulene-9-carboxylate (200 mg, 0.51 mmol) and 1-chloroacetylpiperidine (99 mg, 0.61 mmol) in N,N-dimethylformamide (4 ml) was added potassium carbonate (106 mg, 0.77 mmol), and the mixture was stirred at room temperature for 13 hr. The mixture was heated to 80° C., and the mixture was stirred for 3 hr. The mixture was allowed to cool to room temperature and water was added. The precipitated solid was collected by filtration and washed with water, and the obtained solid was dried in vacuo to give methyl 12-cyclohexyl-4-[2-oxo-2-(piperidin-1-yl)ethoxy]-6,7-dihydro-5-oxa-7a-azadibenzo[a,e]azulene-9-carboxylate (254 mg, yield 96%).

$^1$H-NMR (400 MHz, CDCl$_3$): δ(ppm) 8.08 (1H, s), 7.90 (1H, d, J=8.3 Hz), 7.77 (1H, dd, J=8.3, 1.4 Hz), 7.21 (1H, t, J=7.9 Hz), 7.11-7.06 (2H, m), 4.82 (2H, s), 4.55 (2H, t, J=5.8 Hz), 4.33-4.27 (2H, m), 3.96 (3H, s), 3.60 (2H, t, J=5.3 Hz), 3.53 (2H, t, J=5.1 Hz), 3.03-2.95 (1H, m), 2.12-2.01 (2H, m), 1.91-1.77 (5H, m), 1.69-1.53 (6H, m), 1.43-1.34 (3H, m).

Step 8: Production of methyl 12-cyclohexyl-4-[2-(piperidin-1-yl)ethoxy]-6,7-dihydro-5-oxa-7a-azadibenzo[a,e]azulene-9-carboxylate (Example 2-507)

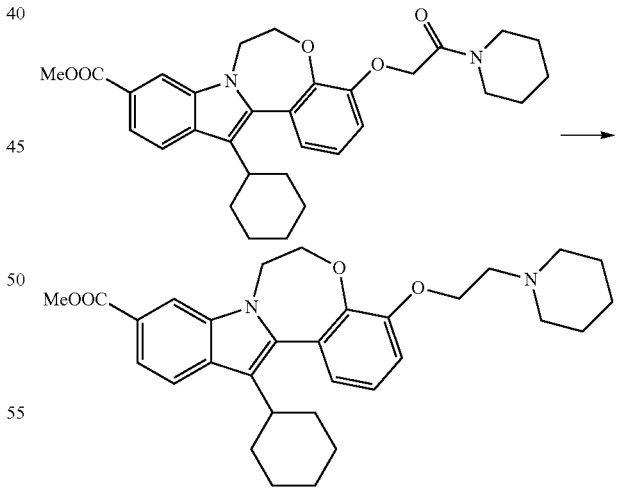

To a solution of methyl 12-cyclohexyl-4-[2-oxo-2-(piperidin-1-yl)ethoxy]-6,7-dihydro-5-oxa-7a-azadibenzo[a,e]azulene-9-carboxylate (254 mg, 0.49 mmol) in tetrahydrofuran (1 ml) was added a solution (1 ml) of 1M BH$_3$ THF complex in tetrahydrofuran, and the mixture was stirred at room temperature for 3 hr. 2N Hydrochloric acid (2 ml) was added to the reaction mixture, and the mixture was stirred at 70° C. for 4 hr. The reaction mixture was allowed to cool to room tem-

449 perature, and the reaction mixture was neutralized by adding 2N aqueous sodium hydroxide solution and saturated aqueous sodium hydrogen carbonate solution. Water was added, and the precipitated solid was collected by filtration and washed with water. The obtained solid was dried in vacuo to give methyl 12-cyclohexyl-4-[2-(piperidin-1-yl)ethoxy]-6,7-dihydro-5-oxa-7a-azadibenzo[a,e]azulene-9-carboxylate (240 mg, yield 97%).

$^1$H-NMR (400 MHz, CDCl$_3$): δ(ppm) 8.09 (1H, s), 7.91 (1H, d, J=8.3 Hz), 7.77 (1H, d, J=8.8 Hz), 7.26-7.22 (1H, m), 7.09 (2H, t, J=7.4 Hz), 4.68 (2H, t, J=4.4 Hz), 4.52 (2H, t, J=5.6 Hz), 4.34-4.29 (2H, m), 3.96 (3H, s), 3.79-3.69 (2H, m), 3.44 (2H, t, J=4.2 Hz), 3.02-2.84 (3H, m), 2.38-2.23 (2H, m), 2.12-2.00 (2H, m), 1.95-1.77 (5H, m), 1.69-1.33 (7H, m).

Step 9: Production of 12-cyclohexyl-4-[2-(piperidin-1-yl)ethoxy]-6,7-dihydro-5-oxa-7a-azadibenzo[a,e]azulene-9-carboxylic acid hydrochloride (Example 2-53)

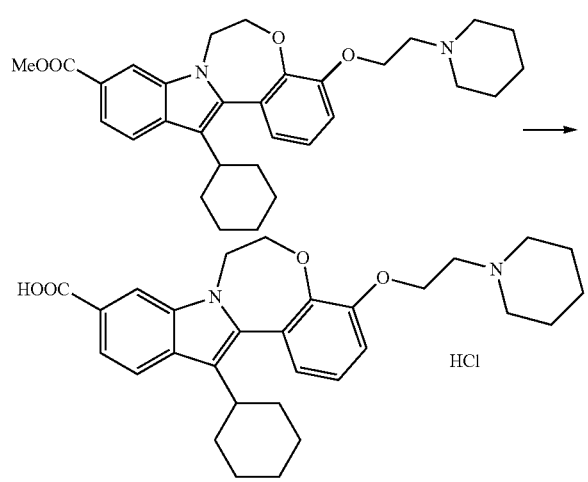

To a solution of methyl 12-cyclohexyl-4-[2-(piperidin-1-yl)ethoxy]-6,7-dihydro-5-oxa-7a-azadibenzo[a,e]azulene-9-carboxylate (240 mg, 0.48 mmol) in tetrahydrofuran (4 ml) and methanol (4 ml) was added 4N aqueous sodium hydroxide (2.5 ml), and the mixture was stirred at 60° C. for 2 hr. 2N Hydrochloric acid (5.1 ml) was added to the reaction mixture, and the mixture was extracted with ethyl acetate:tetrahydrofuran (2:1). The organic layer was washed with saturated brine and dried over anhydrous magnesium sulfate. After filtration, the solvent was evaporated under reduced pressure. To a solution of the obtained residue in tetrahydrofuran (1 ml) was added 4N HCl-ethyl acetate solution (2 ml). The solvent was evaporated under reduced pressure, and hexane:ethyl acetate (4:1) solution was added to the obtained residue. The precipitated solid was collected by filtration and washed with hexane:ethyl acetate (4:1) solution. The obtained solid was dried in vacuo to give 12-cyclohexyl-4-[2-(piperidin-1-yl)ethoxy]-6,7-dihydro-5-oxa-7a-azadibenzo[a,e]azulene-9-carboxylic acid hydrochloride (160 mg, yield 64%).

$^1$H-NMR (400 MHz, DMSO-d$_6$): δ(ppm) 12.59 (1H, brs), 10.26 (1H, brs), 8.20 (1H, s), 7.88 (1H, d, J=8.3 Hz), 7.63 (1H, dd, J=8.3, 1.4 Hz), 7.32 (1H, t, J=7.9 Hz), 7.25 (1H, d, J=8.3 Hz), 7.07 (1H, dd, J=7.4, 1.4 Hz), 4.54-4.25 (6H, m), 3.63-3.46 (4H, m), 3.13-2.99 (2H, m), 2.93-2.85 (1H, m), 2.07-1.96 (2H, m), 1.86-1.65 (9H, m), 1.46-1.21 (5H, m).

MS 489.2 (M+1).

450

Example 2-57

Production of (E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylic acid

Step 1: Production of ethyl (E)-3-{4-[(1-tert-butoxycarbonylaminocyclobutanecarbonyl)amino]phenyl}acrylate

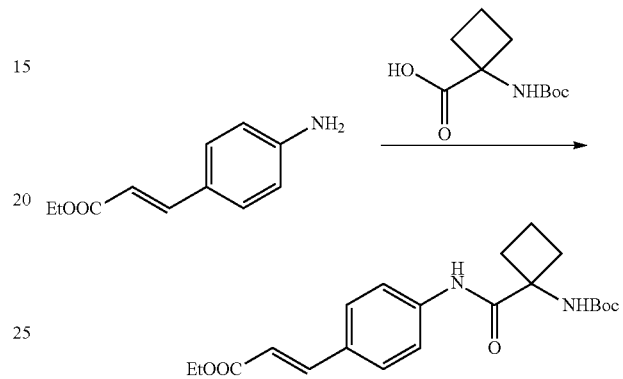

To a solution of ethyl 4-aminocinnamate (1.00 g, 5.23 mmol) and 1-tert-butoxycarbonylaminocyclobutanecarboxylic acid (1.24 g, 5.75 mmol) in N,N-dimethylformamide (10 ml) were added 1-hydroxybenzotriazole monohydrate (1.44 g, 9.41 mmol) and 1-ethyl-3-(3'-dimethylaminopropyl)carbodiimide hydrochloride (1.80 g, 9.41 mmol) under ice-cooling, and the mixture was stirred at room temperature for 21 hr. Water was added to the reaction mixture and the mixture was extracted with ethyl acetate. The organic layer was successively washed with saturated aqueous sodium hydrogen carbonate solution and saturated brine and dried over anhydrous magnesium sulfate. After filtration, the solvent was evaporated under reduced pressure and hexane:diethyl ether (2:3) solution was added to the obtained residue. The precipitated solid was collected by filtration and washed with hexane:diethyl ether (2:3) solution. The obtained solid was dried in vacuo to give ethyl (E)-3-{4-[(1-tert-butoxycarbonylaminocyclobutanecarbonyl)amino]phenyl}acrylate (943 mg, yield 46%).

$^1$H-NMR (400 MHz, CDCl$_3$): δ(pp) 9.43 (1H, s), 7.64 (1H, d, J=16.2 Hz), 7.58 (2H, d, J=8.8 Hz), 7.49 (2H, d, J=8.3 Hz), 6.36 (1H, d, J=15.8 Hz), 5.08 (1H, s), 4.26 (2H, q, J=7.3 Hz), 2.83-2.77 (2H, m), 2.21-1.93 (4H, m), 1.46 (9H, s), 1.33 (3H, t, J=7.7 Hz).

Step 2: Production of ethyl (E)-3-{4-[(1-aminocyclobutanecarbonyl)amino]phenyl)acrylate hydrochloride

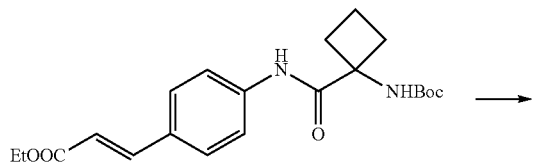

-continued

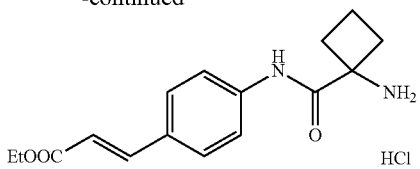

To a solution of ethyl (E)-3-{4-[(1-tert-butoxycarbonylaminocyclobutanecarbonyl)amino]phenyl}acrylate (943 mg, 2.43 mmol) in chloroform (10 ml) was added 4N HCl-ethyl acetate solution (10 ml) under ice-cooling, and the mixture was stirred for 4 hr. The solvent was evaporated under reduced pressure and hexane:diethyl ether (1:1) solution was added to the obtained residue. The precipitated solid was collected by filtration and washed with hexane:diethyl ether (1:1) solution. The obtained solid was dried in vacuo to give ethyl (E)-3-{4-[(1-aminocyclobutanecarbonyl)amino]phenyl}acrylate hydrochloride (720 mg, yield 91%).

$^1$H-NMR (400 MHz, DMSO-$d_6$): δ(ppm) 10.73 (1H, s), 8.94 (3H, s), 7.80 (2H, d, J=8.3 Hz), 7.72 (2H, d, J=8.8 Hz), 7.59 (1H, d, J=15.8 Hz), 6.55 (1H, d, J=15.8 Hz), 4.17 (2H, q, J=7.1 Hz), 2.80-2.73 (2H, m), 2.35-2.20 (3H, m), 2.01-1.91 (1H, m), 1.24 (3H, t, J=7.2 Hz).

Step 3: Production of ethyl (E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylate (Example 2-508)

To a solution of 12-cyclohexyl-3-methoxy-6,7-dihydro-5-oxa-7a-azadibenzo[a,e]azulene-9-carboxylic acid (100 mg, 0.26 mmol) and ethyl (E)-3-{(4-[(1-aminocyclobutanecarbonyl)amino]phenyl}acrylate hydrochloride (74 mg, 0.26 mmol) in N,N-dimethylformamide (2 ml) were added 1-hydroxybenzotriazole monohydrate (59 mg, 0.38 mmol), 1-ethyl-3-(3'-dimethylaminopropyl)carbodiimide hydrochloride (73 mg, 0.38 mmol) and triethylamine (78 μl, 0.56 mmol) under ice-cooling, and the mixture was stirred at room temperature for 18 hr. Water was added to the reaction mixture and the mixture was extracted with ethyl acetate. The organic layer was successively washed with saturated aqueous sodium hydrogen carbonate solution and saturated brine and dried over anhydrous magnesium sulfate. After filtration, the solvent was evaporated under reduced pressure, and the obtained residue was purified by silica gel chromatography (hexane:ethyl acetate-2:1-1:2). Hexane:diethyl ether (1:1) solution was added to the obtained residue, and the precipitated solid was collected by filtration, and washed with hexane:diethyl ether (1:1) solution. The obtained solid was dried in vacuo to give ethyl (E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylate (102 mg, yield 60%).

$^1$H-NMR (400 MHz, CDCl$_3$): δ(ppm) 10.20 (1H, s), 7.94 (1H, s), 7.89 (1H, d, J=8.3 Hz), 7.65-7.61 (3H, m), 7.48 (2H, d, J=8.3 Hz), 7.35 (2H, t, J=9.0 Hz), 6.86 (1H, d, J=8.3 Hz), 6.80 (1H, s), 6.73 (1H, s), 6.35 (1H, d, J=15.8 Hz), 4.51 (2H, t, J=5.3 Hz), 4.34-4.28 (2H, m), 4.25 (2H, q, J=7.1 Hz), 3.88 (3H, s), 3.03-2.90 (3H, m), 2.45-2.36 (2H, m), 2.12-1.98 (4H, m), 1.91-1.76 (5H, m), 1.43-1.28 (6H, m).

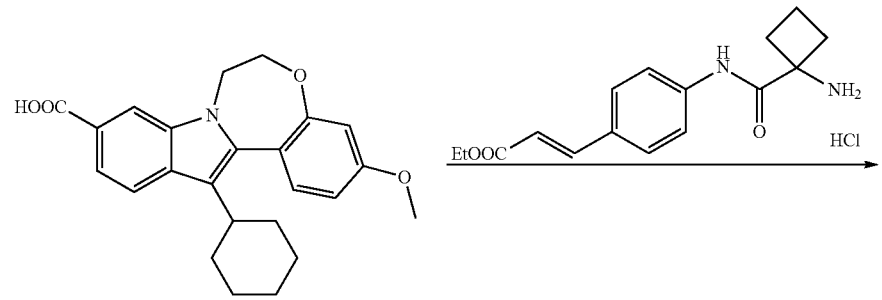

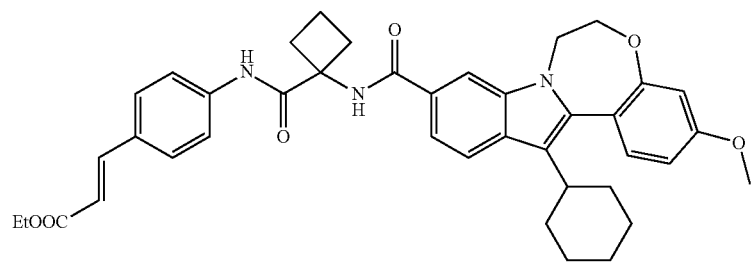

Step 4: Production of (E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylic acid
(Example 2-57)

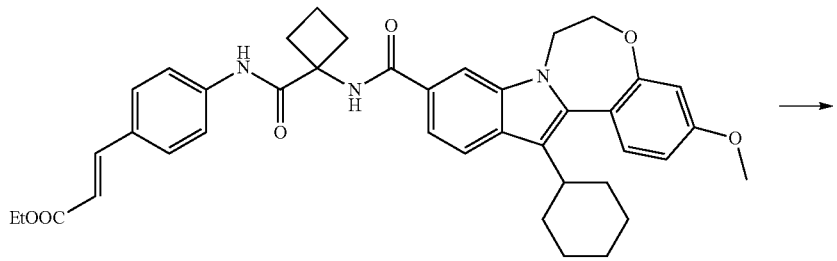

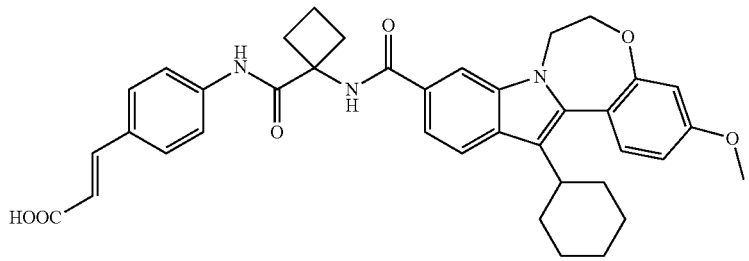

To a solution of ethyl (E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylate (102 mg, 0.154 mmol) in tetrahydrofuran (3 ml) and methanol (2 ml), was added 2N aqueous sodium hydroxide solution (1.2 ml), and the mixture was stirred at room temperature for 17 hr. 2N Hydrochloric acid (1.3 ml) was added and the mixture was extracted with ethyl acetat. The organic layer was washed with saturated brine and dried over anhydrous magnesium sulfate. After filtration, the solvent was evaporated under reduced pressure. Hexane:diethyl ether (1:1) solution was added to the obtained residue, and the precipitated solid was collected by filtration and washed with hexane:diethyl ether (1:1) solution. The obtained solid was dried in vacuo to give (E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylic acid (84 mg, yield 86%).

$^1$H-NMR (300 MHz, DMSO-d$_6$): δ(ppm) 12.22 (1H, s), 9.67 (1H, s), 8.74 (1H, s), 8.21 (1H, s), 7.83 (1H, d, J=8.4 Hz), 7.68-7.58 (5H, m), 7.50 (1H, d, J=16.1 Hz), 7.35 (1H, d, J=8.4 Hz), 6.95 (1H, dd, J=8.6, 2.8 Hz), 6.83 (1H, d, J=2.6 Hz), 6.39 (1H, d, J=16.1 Hz), 4.50-4.43 (2H, m), 4.40-4.32 (2H, m), 3.83 (3H, s), 2.91-2.81 (1H, m), 2.80-2.69 (2H, m), 2.41-2.30 (2H, m), 2.08-1.69 (9H, m), 1.44-1.23 (3H, m).
MS 634.3 (M+1).

Example 1-520

Production of N-acetyl-13-cyclohexyl-3-methyl-5-[2-(piperidin-1-yl)ethyl]-6,7-dihydro-5H-benzo[5,6][1,4]diazepino[7,1-a]indole-10-sulfonamide dihydrochloride Step 1: Production of 4-methyl-3-nitrobenzenesulfonyl chloride

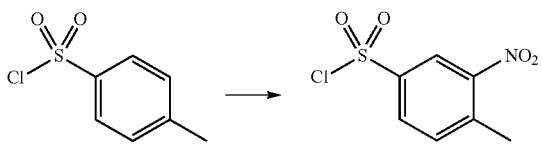

To a mixed solution of fuming nitric acid (3.5 ml) and conc. sulfuric acid (5.4 ml) was added p-toluenesulfonyl chloride (5.00 g, 26.2 mmol) in several portions under ice-cooling, and the mixture was stirred under ice-cooling for 2 hr. To the reaction mixture was added ice, and the mixture was extracted with diethyl ether. The organic layer was successively washed with water, saturated aqueous sodium hydrogen carbonate solution and saturated brine and dried over anhydrous sodium sulfate. After filtration, the solvent was evaporated under reduced pressure to give 4-methyl-3-nitrobenzenesulfonyl chloride (5.43 g, yield 88.0%).

¹H-NMR (400 MHz, CDCl₃): δ(ppm) 8.64 (1H, d, J=1.9 Hz), 8.16 (1H, dd, J=8.2, 2.1 Hz), 7.67 (1H, d, J=8.3 Hz), 2.77 (3H, s).

Step 2: Production of
N-tert-butyl-4-methyl-3-nitrobenzenesulfonamide

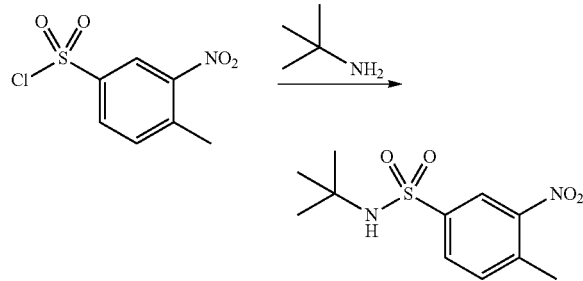

To a solution of 4-methyl-3-nitrobenzenesulfonyl chloride (5.40 g, 22.9 mmol) in chloroform (50 ml) was added tert-butylamine (6.00 ml, 57.1 mmol) under ice-cooling, and the mixture was stirred at room temperature for 2.5 hr. To the reaction mixture was added 1N hydrochloric acid, and the mixture was extracted with chloroform. The organic layer was successively washed with water, saturated aqueous sodium hydrogen carbonate solution and saturated brine, and dried over anhydrous sodium sulfate. After filtration, the solvent was evaporated under reduced pressure, and hexane was added to the residue. The precipitated solid was collected by filtration and dried in vacuo to give N-tert-butyl-4-methyl-3-nitrobenzenesulfonamide (5.89 g, yield 94.6%).

¹H-NMR (400 MHz, CDCl₃): δ(ppm) (1H, d, J=2.3 Hz), 8.01 (1H, dd, J=8.1, 2.1 Hz), 7.50 (1H, d, J=7.9 Hz), 4.64 (1H, s), 2.69 (3H, s), 1.28 (9H, s).

Step 3: Production of N-tert-butyl-4-((E)-2-dimethylaminovinyl)-3-nitrobenzenesulfonamide

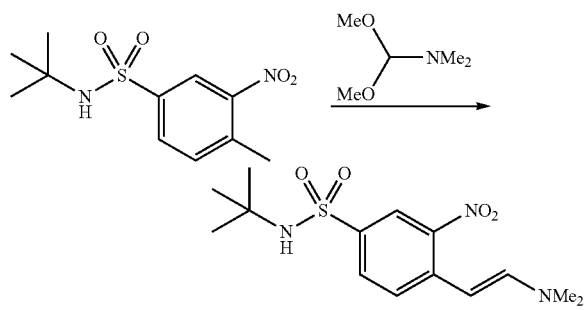

A solution of N-tert-butyl-4-methyl-3-nitrobenzenesulfonamide (5.89 g, 21.6 mmol) in N,N-dimethylformamide dimethyl acetal (10 ml) was stirred with heating at 110° C. for 10 hr. The reaction solvent was evaporated under reduced pressure and diethyl ether was added. The precipitated solid was collected by filtration, washed with diethyl ether and dried in vacuo to give N-tert-butyl-4-((E)-2-dimethylaminovinyl)-3-nitrobenzenesulfonamide (5.41 g, yield 76.6%).

¹H-NMR (400 MHz, CDCl₃): δ(ppm) (1H, d, J=1.9 Hz), 7.74-7.71 (1H, m), 7.51 (1H, d, J=8.1 Hz), 7.16 (1H, d, J=10.7 Hz), 5.95 (1H, d, J=6.7 Hz), 4.56 (1H, s), 3.00 (6H, s), 1.26 (9H, s).

Step 4: Production of
N-tert-butyl-1H-indole-6-sulfonamide

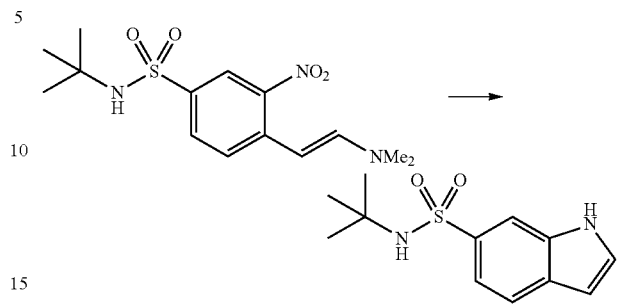

A suspension of N-tert-butyl-4-((E)-2-dimethylaminovinyl)-3-nitrobenzenesulfonamide (5.41 g, 16.5 mmol) and 7.5% palladium/carbon (500 mg) in tetrahydrofuran (50 ml) and ethanol (50 ml) was stirred at room temperature for 3.5 hr under a hydrogen atmosphere of 3.5 atm. The reaction mixture was filtered through celite and the filtrate was concentrated under reduced pressure. Ethyl acetate was added to the residue, and the mixture was successively washed with 1N hydrochloric acid and saturated brine and dried over anhydrous sodium sulfate. After filtration, the solvent was evaporated under reduced pressure to give N-tert-butyl-1H-indole-6-sulfonamide (3.62 g, yield 87.1%).

MS 253.1 (M+1).

Step 5: Production of N-tert-butyl-3-(cyclohex-1-enyl)-1H-indole-6-sulfonamide

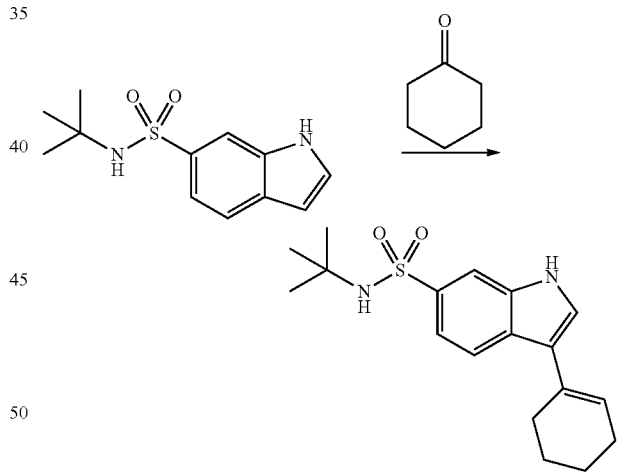

To a solution of N-tert-butyl-1H-indole-6-sulfonamide (3.60 g, 14.2 mmol) and cyclohexanone (4.50 ml, 43.4 mmol) in methanol (72 ml) was added 28% sodium methoxide in methanol solution (17 ml), and the mixture was stirred for 12 hr with heating under reflux. The reaction mixture was cooled to room temperature and concentrated under reduced pressure. 2N Hydrochloric acid was added to the residue, and the mixture was extracted with ethyl acetate. The organic layer was washed with saturated brine and dried over anhydrous sodium sulfate. After filtration, the solvent was evaporated under reduced pressure. The residue was purified by silica gel chromatography (hexane:ethyl acetate=3:1-2:1) to give N-tert-butyl-3-(cyclohex-1-enyl)-1H-indole-6-sulfonamide (2.82 g, yield 59.7%).

457

¹H-NMR (300 MHz, CDCl₃): δ(ppm) 8.62 (1H, brs), 7.98 (1H, d, J=1.1 Hz), 7.95 (1H, d, J=8.4 Hz), 7.59 (1H, dd, J=8.4, 1.8 Hz), 7.32 (1H, d, J=2.6 Hz), 6.28-6.23 (1H, m), 4.56 (1H, s), 2.50-2.40 (2H, m), 2.31-2.22 (2H, m), 1.86-1.78 (2H, m), 1.73-1.69 (2H, m), 1.20 (9H, s).

Step 6: Production of
N-tert-butyl-3-cyclohexyl-1H-indole-6-sulfonamide

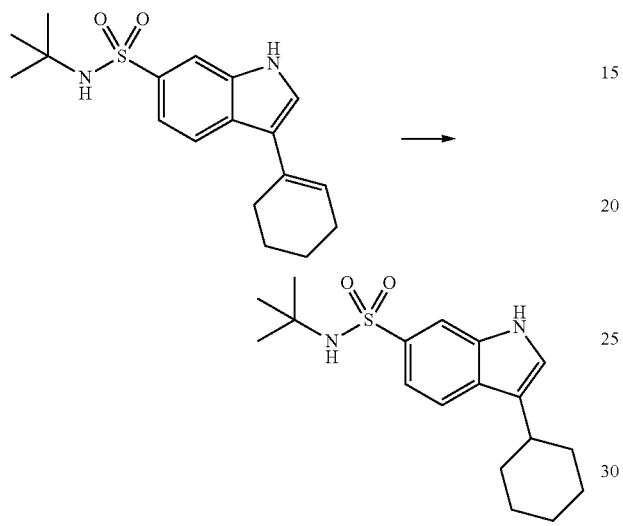

A suspension of N-tert-butyl-3-(2-cyclohexen-1-yl)-1H-indole-6-sulfonamide (2.82 g, 8.48 mmol) and 20% palladium hydroxide/carbon (300 mg) in methanol (30 ml) was stirred at room temperature for 4 hr under a hydrogen atmosphere of 1 atm. The reaction mixture was filtered through celite and the filtrate was concentrated under reduced pressure. Hexane was added to the residue. The precipitated solid was collected by filtration and dried in vacuo to give N-tert-butyl-3-cyclohexyl-1H-indole-6-sulfonamide (2.29 g, yield 82.0%).

¹H-NMR (300 MHz, CDCl₃): δ(ppm) 8.41 (1H, brs), 7.98 (1H, d, J=1.5 Hz), 7.71 (1H, d, J=8.4 Hz), 7.56 (1H, dd, J=8.4, 1.5 Hz), 7.13 (1H, d, J=2.6 Hz), 4.55 (1H, brs), 2.90-2.75 (1H, m), 2.15-2.04 (2H, m), 1.92-1.72 (3H, m), 1.52-1.40 (3H, m), 1.35-1.20 (2H, m), 1.20 (9H, s).

Step 7: Production of N-tert-butyl-2-bromo-3-cyclohexyl-1H-indole-6-sulfonamide

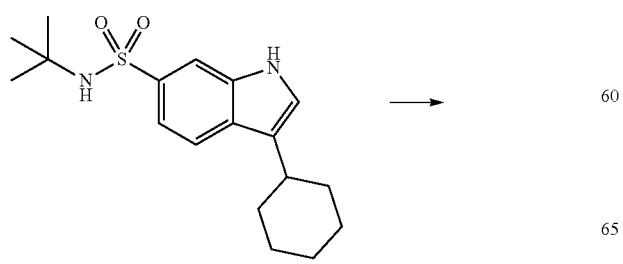

458

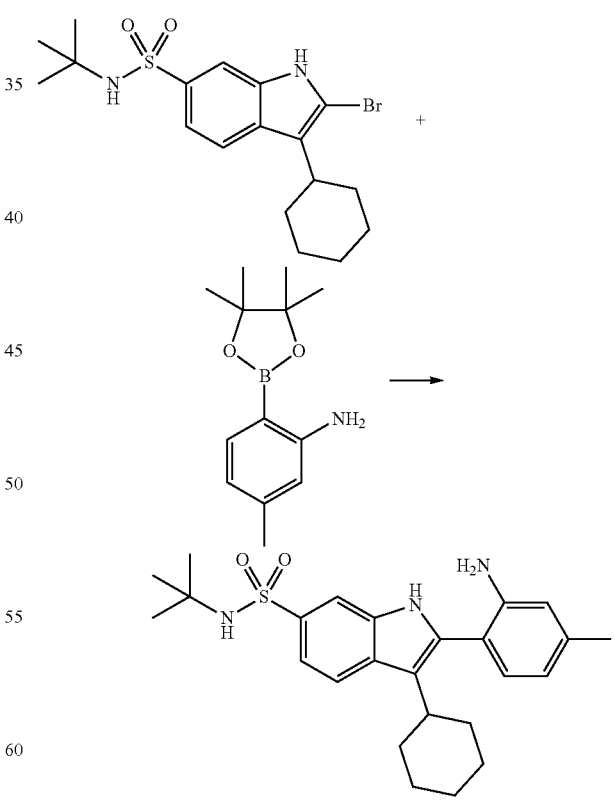

To a solution of N-tert-butyl-3-cyclohexyl-1H-indole-6-sulfonamide (2.29 g, 6.86 mmol) in chloroform (30 ml) was added pyridinium hydrobromide perbromide (2.40 g, 7.50 mmol) under ice-cooling, and the mixture was stirred under ice-cooling for 30 min. 1M aqueous sodium hydrogen sulfite solution was added to the reaction mixture and the mixture was extracted with chloroform. The organic layer was washed with saturated brine and dried over anhydrous sodium sulfate. After filtration, the solvent was evaporated under reduced pressure. A mixed solvent of hexane:ethyl acetate (5:1) was added to the residue. The precipitated solid was collected by filtration and dried in vacuo to give N-tert-butyl-2-bromo-3-cyclohexyl-1H-indole-6-sulfonamide (2.19 g, yield 78.3%).

¹H-NMR (300 MHz, CDCl₃): δ(ppm) 8.48 (1H, brs), 7.90 (1H, d, J=1.1 Hz), 7.76 (1H, d, J=8.4 Hz), 7.55 (1H, dd, J=8.6, 1.7 Hz), 4.58 (1H, brs), 2.90-2.77 (1H, m), 1.95-1.79 (7H, m), 1.45-1.26 (3H, m), 1.23 (9H, s).

Step 8: Production of N-tert-butyl-2-(2-amino-4-methylphenyl)-3-cyclohexyl-1H-indole-6-sulfonamide To a suspension of N-tert-butyl-2-bromo-3-cyclohexyl-1H-indole-6-sulfonamide (2.10 g, 5.08 mmol) and 2-(4,4,5,5-tetramethyl-1,3,2-dioxaborolan-2-yl)-5-methylphenylamine (1.86 g, 8.00 mmol) in 1,2-dimethoxyethane (20 ml)

and water (10 ml) were added sodium hydrogen carbonate (1.60 g, 19.2 mmol) and tetrakis(triphenylphosphine)palladium (176 mg, 0.15 mmol), and the mixture was heated under reflux for 14 hr. The reaction mixture was allowed to cool to room temperature, water was added to the reaction mixture and the mixture was extracted with toluene. The organic layer was successively washed with water and saturated brine and dried over anhydrous sodium sulfate. After filtration, the solvent was evaporated under reduced pressure and diisopropy ether was added to the residue. The precipitated solid was collected by filtration and dried in vacuo to give N-tert-butyl-2-(2-amino-4-methylphenyl)-3-cyclohexyl-1H-indole-6-sulfonamide (2.14 g, yield 96.3%).

$^1$H-NMR (300 MHz, CDCl$_3$): δ(ppm) 8.23 (1H, s), 7.90 (1H, d, J=1.8 Hz), 7.86 (1H, d, J=8.4 Hz), 7.55 (1H, dd, J=8.4, 1.8 Hz), 7.07 (1H, d, J=7.7 Hz), 6.67 (1H, d, J=8.1 Hz), 6.64 (1H, 4.43 (1H, s), 3.72 (2H, s), 2.76-2.68 (1H, m), 2.34 (3H, s), 1.89-1.84 (7H, m), 1.30-1.23 (3H, m), 1.25 (9H, s).

Step 9: Production of N-tert-butyl-2-[2-(chloroacetylamino)-4-methylphenyl]-3-cyclohexyl-1H-indole-6-sulfonamide

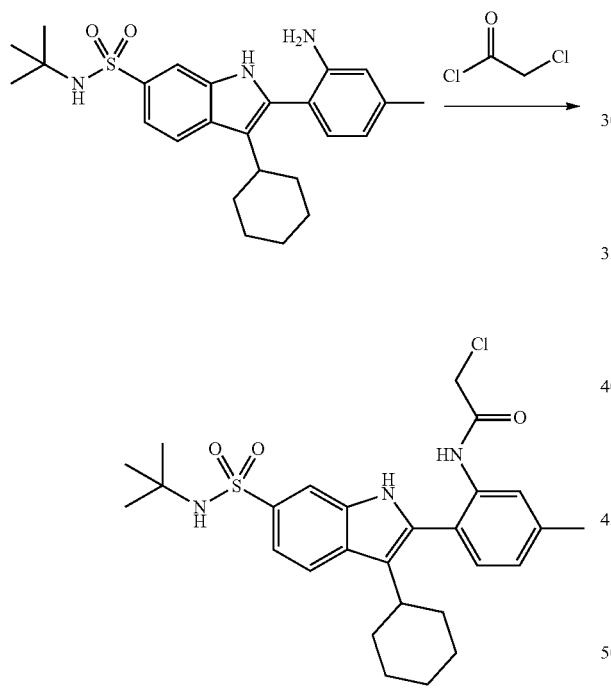

To a suspension of N-tert-butyl-2-(2-amino-4-methylphenyl)-3-cyclohexyl-1H-indole-6-sulfonamide (2.14 g, 4.86 mmol), sodium acetate (472 mg, 5.75 mmol) and acetic acid (0.33 ml, 5.76 mmol) in tetrahydrofuran (20 ml) was added dropwise chloroacetyl chloride (0.45 ml, 5.64 mmol) under ice-cooling, and the mixture was stirred at room temperature for 2 hr. the reaction mixture was concentrated under reduced pressure, and water was added to the residue. The precipitated solid was collected by filtration and dried in vacuo. A suspension of the obtained solid in diethyl ether was stirred at room temperature for 1 hr. The solid was collected by filtration and dried in vacuo to give N-tert-butyl-2-[2-(chloroacetylamino)-4-methylphenyl]-3-cyclohexyl-1H-indole-6-sulfonamide (2.22 g, yield 89.9%). The obtained crude product was used for Step 10 without further purification.

Step 10: Production of N-tert-butyl-13-cyclohexyl-3-methyl-6-oxo-6,7-dihydro-5H-benzo[5,6][1,4]diazepino[7,1-a]indole-10-sulfonamide (Example 1-604)

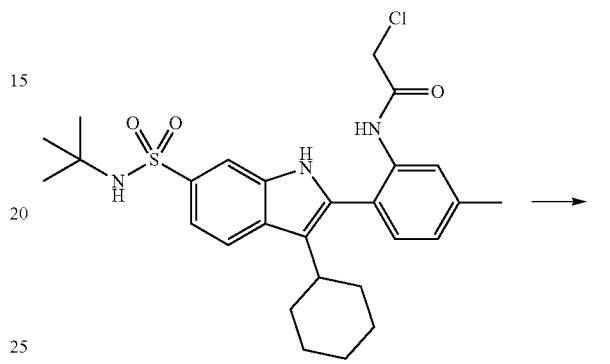

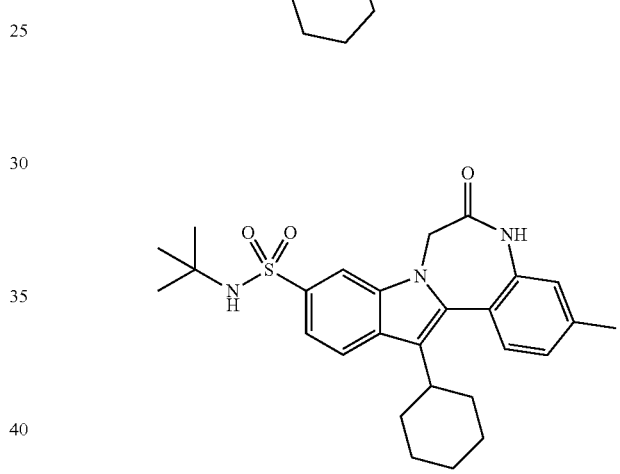

A suspension of N-tert-butyl-2-[2-(chloroacetylamino)-4-methylphenyl]-3-cyclohexyl-1H-indole-6-sulfonamide (2.22 g, 4.30 mmol) and potassium carbonate (714 mg, 5.16 mmol) in N,N-dimethylformamide (22 ml) was stirred at 80° C. for 1 hr. The reaction mixture was allowed to cool to room temperature, and 1N hydrochloric acid and water were added to the reaction mixture. The precipitated solid was collected by filtration and dried in vacuo. A mixed solvent of hexane: ethyl acetate (1:1) was added to the obtained solid, and the mixture was stirred at room temperature for 1 hr. The solid was collected by filtration and dried in vacuo to give N-tert-butyl-13-cyclohexyl-3-methyl-6-oxo-6,7-dihydro-5H-benzo[5,6][1,4]diazepino[7,1-a]indole-10-sulfonamide (1.77 g, yield 86.2%).

$^1$H-NMR (300 MHz, CDCl$_3$): δ(ppm) 10.29 (1H, s), 8.10 (1H, d, J=1.5 Hz), 8.01 (1H, d, J=8.8 Hz), 7.52 (1H, dd, J=8.4, 1.5 Hz), 7.42 (1H, d, J=7.7 Hz), 7.40 (1H, s), 7.21 (1H, d, J=8.1 Hz), 7.09 (1H, s), 4.96 (1H, d, J=15.0 Hz), 4.54 (1H, d, J=15.4 Hz), 2.89-2.84 (1H, m), 2.39 (3H, s), 2.10-2.02 (3H, m), 1.89-1.73 (4H, m), 1.52-1.41 (3H, m), 1.08 (9H, s).

Step 11: Production of N-tert-butyl-13-cyclohexyl-3-methyl-6-oxo-5-[2-oxo-2-(piperidin-1-yl)ethyl]-6,7-dihydro-5H-benzo[5,6][1,4]diazepino[7,1-a]indole-10-sulfonamide (Example 1-605)

Step 12: Production of N-tert-butyl-13-cyclohexyl-3-methyl-5-[2-(piperidin-1-yl)ethyl]-6,7-dihydro-5H-benzo[5,6][1,4]diazepino[7,1-a]indole-10-sulfonamide (Example 1-606)

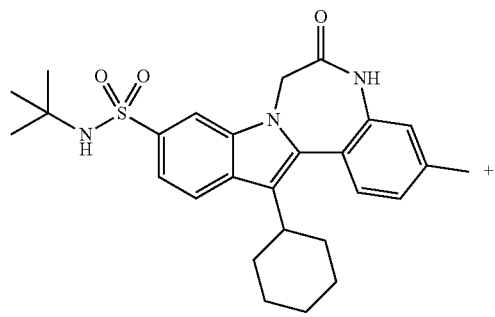

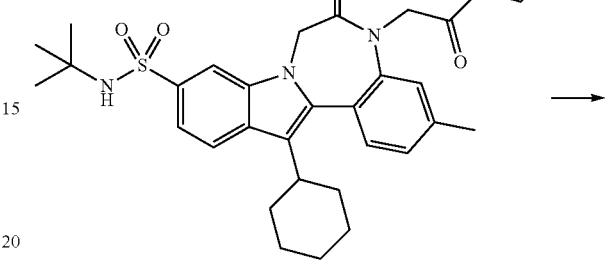

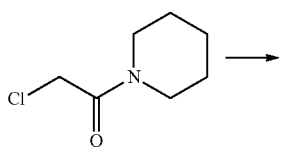

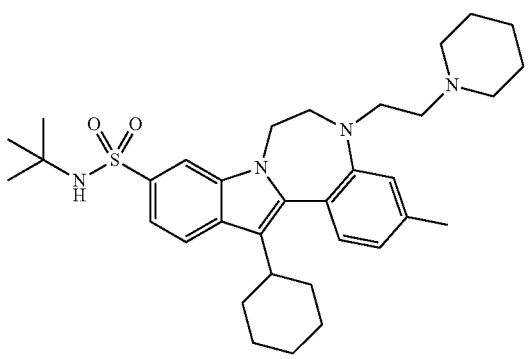

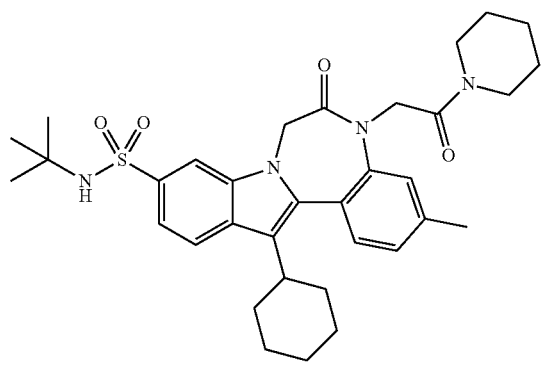

A suspension of N-tert-butyl-13-cyclohexyl-3-methyl-6-oxo-6,7-dihydro-5H-benzo[5,6][1,4]diazepino[7,1-a]indole-10-sulfonamide (150 mg, 0.31 mmol), 1-(2-chloroacetyl)piperidine (55 mg, 0.34 mmol) and potassium carbonate (107 mg, 0.77 mmol) in N,N-dimethylformamide (2 ml) was stirred at 80° C. for 2 hr. The reaction mixture was allowed to cool to room temperature, and 2N hydrochloric acid and water were added to the reaction mixture. The precipitated solid was collected by filtration and dried in vacuo to give N-tert-butyl-13-cyclohexyl-3-methyl-6-oxo-5-[2-oxo-2-(piperidin-1-yl)ethyl]-6,7-dihydro-5H-benzo[5,6][1,4]diazepino[7,1-a]indole-10-sulfonamide (202 mg, yield 100%). The obtained crude product was used for Step 12 without further purification.

To a suspension of N-tert-butyl-13-cyclohexyl-3-methyl-6-oxo-5-[2-oxo-2-(piperidin-1-yl)ethyl]-6,7-dihydro-5H-benzo[5,6][1,4]diazepino[7,1-a]indole-10-sulfonamide (184 mg, 0.30 mmol) in tetrahydrofuran (1 ml) was added 1M $BH_3$ THF complex tetrahydrofuran solution (2.0 ml) under ice-cooling, and the mixture was stirred at room temperature for 12 hr. 2N Hydrochloric acid (3 ml) was added to the reaction-mixture, and the mixture was stirred at 70° C. for 4 hr. The reaction mixture was allowed to cool to room temperature, neutralized with 4N aqueous sodium hydroxide solution and saturated aqueous sodium hydrogen carbonate solution, and extracted with ethyl acetate. The organic layer was washed with saturated brine and dried over anhydrous sodium sulfate. After filtration, the solvent was evaporated under reduced pressure. The residue was purified by silica gel chromatography (chloroform:methanol=20:1-10:1) to give N-tert-butyl-13-cyclohexyl-3-methyl-5-[2-(piperidin-1-yl)ethyl]-6,7-dihydro-5H-benzo[5,6][1,4]diazepino[7,1-a]indole-10-sulfonamide (169 mg, yield 94.9%).

MS 577.1 (M+1).

Step 13: Production of 13-cyclohexyl-3-methyl-5-[2-(piperidin-1-yl)ethyl]-6,7-dihydro-5H-benzo[5,6][1,4]diazepino[7,1-a]indole-10-sulfonamide (Example 1-607)

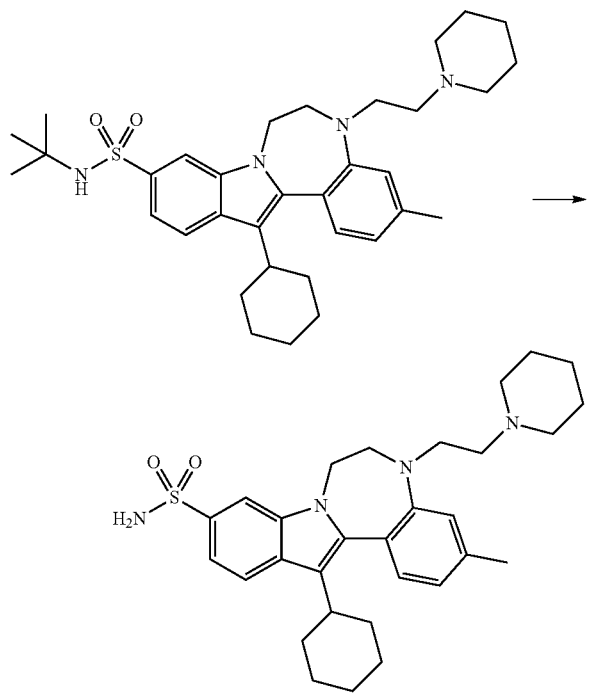

A solution of N-tert-butyl-13-cyclohexyl-3-methyl-5-[2-(piperidin-1-yl)ethyl]-6,7-dihydro-5H-benzo[5,6][1,4]diazepino[7,1-a]indole-10-sulfonamide (169 mg, 0.29 mmol) in trifluoroacetic acid (2 ml) was stirred at 60° C. for 1 hr. The mixture was allowed to cool to room temperature and concentrated under reduced pressure. Saturated aqueous sodium carbonate solution was added to the residue, and the mixture was extracted with ethyl acetate. The organic layer was washed with saturated brine and dried over anhydrous sodium sulfate. After filtration, the solvent was evaporated under reduced pressure to give 13-cyclohexyl-3-methyl-5-[2-(piperidin-1-yl)ethyl]-6,7-dihydro-5H-benzo[5,6][1,4]diazepino[7,1-a]indole-10-sulfonamide (152 mg, yield 100%).

MS 521.2 (M+1).

Step 14: Production of N-acetyl-13-cyclohexyl-3-methyl-5-[2-(piperidin-1-yl)ethyl]-6,7-dihydro-5H-benzo[5,6][1,4]diazepino[7,1-a]indole-10-sulfonamide dihydrochloride (Example 1-520)

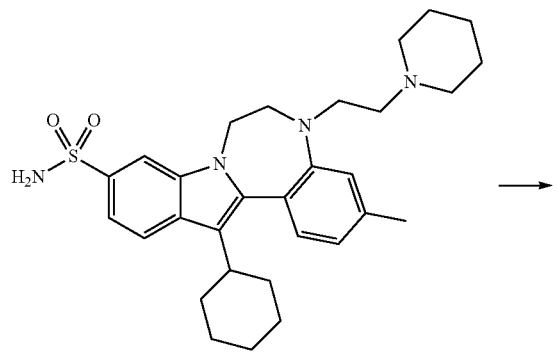

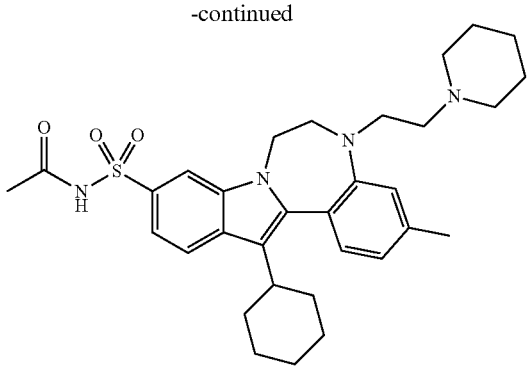

To a suspension of 13-cyclohexyl-3-methyl-5-[2-(piperidin-1-yl)ethyl]-6,7-dihydro-5H-benzo[5,6][1,4]diazepino[7,1-a]indole-10-sulfonamide (152 mg, 0.29 mmol) and potassium carbonate (88 mg, 0.63 mmol) in acetone (2 ml) was added acetyl chloride (0.02 ml, 0.30 mmol), and the mixture was stirred at room temperature for 12 hr. 2N Hydrochloric acid was added to the reaction mixture, and the mixture was extracted with ethyl acetate. The organic layer was washed with saturated brine and dried over anhydrous sodium sulfate. After filtration, the solvent was evaporated under reduced pressure. The residue was purified by silica gel chromatography (chloroform:methanol=20:1-10:1) to give N-acetyl-13-cyclohexyl-3-methyl-5-[2-(piperidin-1-yl)ethyl]-6,7-dihydro-5H-benzo[5,6][1,4]diazepino[7,1-a]indole-10-sulfonamide. To a solution of the obtained N-acetyl-13-cyclohexyl-3-methyl-5-[2-(piperidin-1-yl)ethyl]-6,7-dihydro-5H-benzo[5,6][1,4]diazepino[7,1-a]indole-10-sulfonamide in ethyl acetate was added 4N HCl-ethyl acetate solution (2 ml), and the mixture was concentrated under reduced pressure. Hexane was added to the residue. The precipitated solid was collected by filtration and dried in vacuo to give N-acetyl-13-cyclohexyl-3-methyl-5-[2-(piperidin-1-yl)ethyl]-6,7-dihydro-5H-benzo[5,6][1,4]diazepino[7,1-a]indole-10-sulfonamide dihydrochloride (74 mg, yield 40%).

$^1$H-NMR (300 MHz, DMSO-$d_6$): δ(ppm) 11.91 (1H, s), 9.96 (1H, s), 8.12 (1H, d, J=2.4 Hz), 7.98 (1H, d, J=8.4 Hz), 7.48 (1H, dd, J=8.6, 1.7 Hz), 7.26 (1H, d, J=7.3 Hz), 7.19 (1H, s), 7.10 (1H, d, J=7.7 Hz), 3.62-3.58 (4H, m), 3.10-3.07 (4H, m), 2.85-2.82 (1H, m), 2.62-2.57 (2H, m), 2.42 (3H, s), 1.99-1.95 (2H, m), 1.91 (3H, s), 1.88-1.75 (4H, m), 1.79-1.70 (2H, m), 1.34-1.12 (6H, m).

MS 563.3 (M+1).

Example 1-567

Production of 13-cyclohexyl-3,5,6-trimethyl-6,7-dihydro-5H-benzo[5,6][1,4]diazepino[7,1-a]indole-10-carboxylic acid Step 1: Production of methyl 2-bromo-3-cyclohexyl-1-(2-oxopropyl)-1H-indole-6-carboxylate

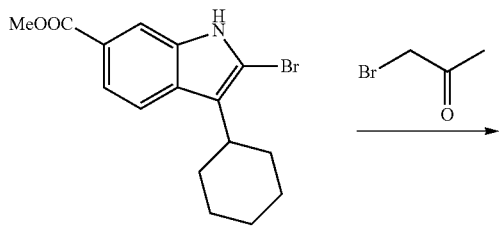

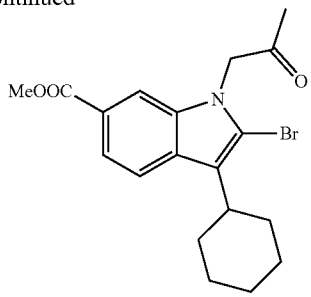

To a solution of methyl 2-bromo-3-cyclohexyl-1H-indole-6-carboxylate (2.00 g, 5.95 mmol) obtained in the same manner as in the method described in WO03/010140 and bromoacetone (0.55 ml, 6.55 mmol) in N,N-dimethylformamide (10 ml) was added sodium hydride (60% in oil) (262 mg, 6.55 mmol) under ice-cooling, and the mixture was stirred for 2 hr. Water was added to the reaction mixture and the mixture was extracted with ethyl acetate. The organic layer was successively washed with water and saturated brine and dried over anhydrous magnesium sulfate. After filtration, the solvent was evaporated under reduced pressure. The residue was purified by silica gel chromatography (hexane:ethyl acetate=4:1) to give methyl 2-bromo-3-cyclohexyl-1-(2-oxopropyl)-1H-indole-6-carboxylate (1.72 g, yield 74%).

$^1$H-NMR (400 MHz, CDCl$_3$): δ(ppm) 7.83 (1H, s), 7.79-7.71 (2H, m), 4.92 (2H, s), 3.91 (3H, s), 2.93-2.83 (1H, m), 2.08 (3H, s), 1.98-1.74 (7H, m), 1.49-1.31 (3H, m).

Step 2: Production of methyl 2-(2-amino-4-methylphenyl)-3-cyclohexyl-1-(2-oxopropyl)-1H-indole-6-carboxylate

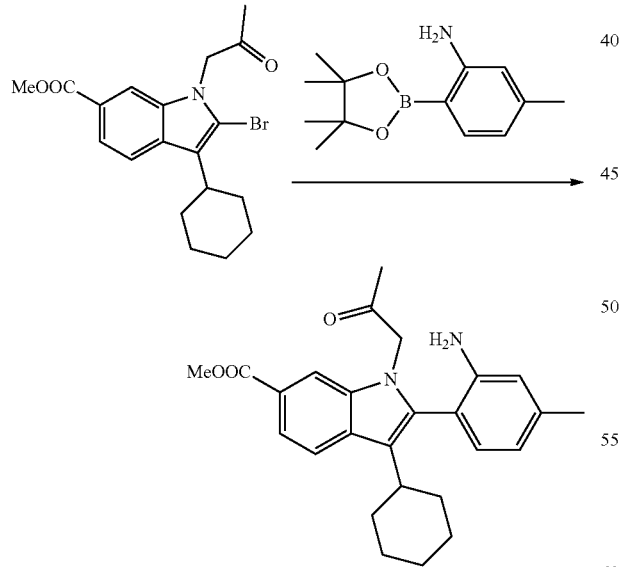

To a suspension of methyl 2-bromo-3-cyclohexyl-1-(2-oxopropyl)-1H-indole-6-carboxylate (700 mg, 1.78 mmol) and 5-methyl-2-(4,4,5,5-tetramethyl-1,3,2-dioxaborolan-2-yl)phenylamine (456 mg, 1.96 mmol) in 1,2-dimethoxyethane (6 ml) and water (2 ml) were added sodium hydrogen carbonate (177 mg, 2.14 mmol) and tetrakis(triphenylphosphine)palladium (103 mg, 0.09 mmol), and the mixture was heated under reflux for 4 hr. The reaction mixture was allowed to cool to room temperature, water was added to the reaction mixture and the mixture was extracted with ethyl acetate. The organic layer was successively washed with saturated aqueous sodium hydrogen carbonate solution and saturated brine and dried over anhydrous magnesium sulfate. After filtration, the solvent was evaporated under reduced pressure, and the residue was purified by silica gel chromatography (hexane:ethyl acetate=3:1) to give methyl 2-(2-amino-4-methylphenyl)-3-cyclohexyl-1-(2-oxopropyl)-1H-indole-6-carboxylate (727 mg, yield 97%).

$^1$H-NMR (400 MHz, CDCl$_3$): δ(ppm) 8.14 (1H, s), 7.88 (1H, d, J=8.8 Hz), 7.76 (1H, d, J=8.8 Hz), 7.40 (1H, d, J=8.0 Hz), 7.17 (1H, s), 7.12 (1H, d, J=8.0 Hz), 4.88 (1H, d, J=13.6 Hz), 4.15 (1H, d, J=13.6 Hz), 3.95 (3H, s), 3.00-2.91 (1H, m), 2.44 (3H, s), 2.32 (3H, s), 2.10-1.98 (3H, m), 1.81-1.72 (2H, m), 1.68-1.59 (1H, m), 1.50-1.29 (4H, m).

Step 3: Production of methyl 13-cyclohexyl-3,6-dimethyl-6,7-dihydro-5H-benzo[5,6][1,4]diazepino[7,1-a]indole-10-carboxylate (Example 1-608)

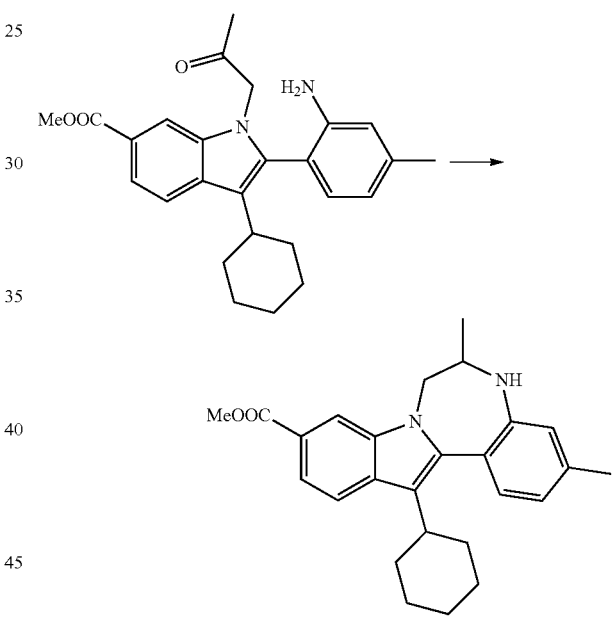

To a solution of methyl 2-(2-amino-4-methylphenyl)-3-cyclohexyl-1-(2-oxopropyl)-1H-indole-6-carboxylate (727 mg, 1.74 mmol) in tetrahydrofuran (10 ml) and acetic acid (3 ml) was added sodium triacetoxyborohydride (736 mg, 3.47 mmol) at room temperature, and the mixture was stirred for 1 hr. Water was added to the reaction mixture and the mixture was extracted with ethyl acetate. The organic layer was successively washed with saturated aqueous sodium hydrogen carbonate and saturated brine and dried over anhydrous magnesium sulfate. After filtration, the solvent was evaporated under reduced pressure, and the residue was purified by silica gel chromatography (hexane:ethyl acetate-2:1) to give methyl 13-cyclohexyl-3,6-dimethyl-6,7-dihydro-5H-benzo[5,6][1,4]diazepino[7,1-a]indole-10-carboxylate (578 mg, yield 83%).

$^1$H-NMR (400 MHz, CDCl$_3$): δ(ppm) 8.04 (1H, s), 7.85 (1H, d, J=8.4 Hz), 7.72 (1H, dd, J=8.4, 1.6 Hz), 7.24 (1H, d, J=7.6 Hz), 6.88 (1H, d, J=7.6 Hz), 6.71 (1H, s), 4.29-4.26 (1H, m), 3.93 (3H, s), 3.97-3.88 (2H, m), 2.97-2.88 (1H, m), 2.35 (3H, s), 2.12-1.99 (2H, m), 1.92-1.72 (5H, m), 1.66-1.53 (1H, m), 1.41-1.30 (3H, m), 1.21 (3H, d, J=6.4 Hz).

Step 4: Production of methyl 13-cyclohexyl-3,5,6-trimethyl-6,7-dihydro-5H-benzo[5,6][1,4]diazepino[7,1-a]indole-10-carboxylate (Example 1-609)

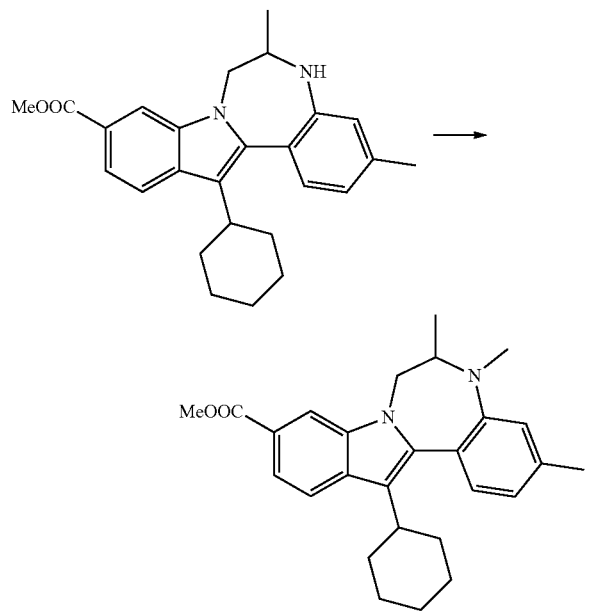

To a solution of methyl 13-cyclohexyl-3,6-dimethyl-6,7-dihydro-5H-benzo[5,6][1,4]diazepino[7,1-a]indole-10-carboxylate (150 mg, 0.373 mmol) in 37% aqueous formalin solution (1.5 ml), chloroform (3 mL) and acetic acid (0.3 ml) was added sodium triacetoxyborohydride (395 mg, 1.86 mmol) at room temperature, and the mixture was stirred overnight. Water was added to the reaction mixture and the mixture was extracted with ethyl acetate. The organic layer was successively washed with saturated aqueous sodium hydrogen carbonate and saturated brine and dried over anhydrous magnesium sulfate. After filtration, the solvent was evaporated under reduced pressure to give methyl 13-cyclohexyl-3,5,6-trimethyl-6,7-dihydro-5H-benzo[5,6][1,4]diazepino[7,1-a]indole-10-carboxylate (155 mg, yield 98%).

$^1$H-NMR (400 MHz, CDCl$_3$): δ(ppm) 8.05 (1H, s), 7.84 (1H, d, J=8.4 Hz), 7.71 (1H, dd, J=8.4, 1.2 Hz), 7.23-7.19 (1H, m), 6.98-6.90 (2H, m), 4.41-4.30 (1H, m), 3.93 (3H, s), 3.87-3.78 (1H, m), 3.56-3.44 (1H, m), 2.95-2.85 (1H, m), 2.76 (3H, s), 2.41 (3H, s), 2.12-1.64 (7H, m), 1.45-1.30 (3H, m), 1.09 (3H, d, J=6.0 Hz).

Step 5: Production of 13-cyclohexyl-3,5,6-trimethyl-6,7-dihydro-5H-benzo[5,6][1,4]diazepino[7,1-a]indole-10-carboxylic acid (Example 1-567)

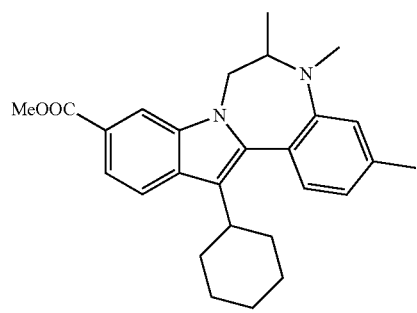

To a solution of methyl 13-cyclohexyl-3,5,6-trimethyl-6,7-dihydro-5H-benzo[5,6][1,4]diazepino[7,1-a]indole-10-carboxylate (155 mg, 0.373 mmol) in tetrahydrofuran (3 ml) and methanol (1 ml) was added 4N aqueous sodium hydroxide solution (2 ml), and the mixture was stirred at 60° C. for 1 hr. The mixture was adjusted to pH 7 by adding 2N hydrochloric acid (4 ml), and extracted with chloroform. The organic layer was washed with saturated brine and dried over anhydrous sodium sulfate. After filtration, the solvent was evaporated under reduced pressure, and the residue was purified by silica gel chromatography (chloroformmethanol=15:1) to give 13-cyclohexyl-3,5,6-trimethyl-6,7-dihydro-5H-benzo[5,6][1,4]diazepino[7,1-a]indole-10-carboxylic acid (100 mg, yield 67%).

$^1$H-NMR (400 MHz, DMSO-d$_6$): δ(ppm) 12.46 (1H, brs), 8.15 (1H, s), 7.79 (1H, d, J=8.4 Hz), 7.56 (1H, dd, J=8.4, 1.2 Hz), 7.21-7.09 (1H, m), 7.01-7.6.90 (2H, m), 4.69 (1H, brm), 3.75 (1H, brm), 2.82-2.72 (1H, m), 2.67 (3H, s), 2.34 (3H, s), 2.04-1.60 (7H, m), 1.52-1.28 (3H, m), 0.98 (1H, d, J=5.6 Hz).
MS 403.2 (M+1).

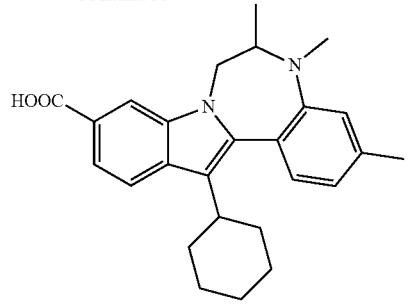

Example 1-595

Production of 13-cyclohexyl-5-[2-(piperidin-1-yl)ethyl]-3-(pyridin-2-ylmethoxy)-6,7-dihydro-5H-benzo[5,6][1,4]diazepino[7,1-a]indole-10-carboxylic acid trihydrochloride

Step 1: Production of 4-benzyloxy-1-iodo-2-nitrobenzene

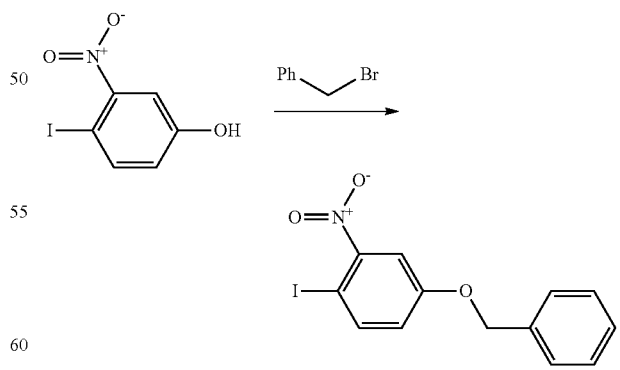

To a solution of 4-iodo-3-nitrophenol (5.00 g, 18.9 mmol) in acetone (50 ml) were added potassium carbonate (3.39 g, 24.6 mmol) and benzyl bromide (2.92 ml, 24.6 mmol), and the mixture was stirred at 50° C. for 6 hr. Water was added to the reaction mixture and the mixture was extracted with ethyl acetate. The organic layer was washed with saturated brine and dried over anhydrous sodium sulfate. After filtration, the solvent was evaporated under reduced pressure to give 4-benzyloxy-1-iodo-2-nitrobenzene. The obtained crude product (6.20 g) was used for Step 2 without further purification.

Step 2: Production of 5-benzyloxy-2-iodophenylamine hydrochloride

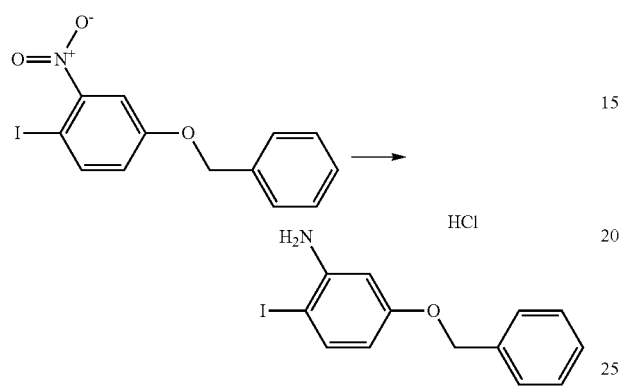

To a solution of 4-benzyloxy-1-iodo-2-nitrobenzene (6.20 g, 17.5 mmol) in methanol (31 ml) were added iron trichloride hexahydrate (142 mg, 0.53 mmol) and activated carbon (1.24 g), m and the mixture was stirred at 60° C. for 5 min. The mixture was heated to 70° C., a solution of hydrazine monohydrate (2.55 ml) in methanol (4.3 ml) was added dropwise, and the mixture was stirred for 3 hr. After filtration through celite, the filtrate was concentrated under reduced pressure. Water was added to the residue and the mixture was extracted with ethyl acetate. The organic layer was washed with saturated brine and dried over anhydrous sodium sulfate. After filtration, the solvent was evaporated under reduced pressure. To a solution of the residue in ethyl acetate (30 ml) was added 4N HCl-ethyl acetate solution (20 ml). The precipitated solid was collected by filtration, washed with ethyl acetate and dried in vacuo to give 5-benzyloxy-2-iodophenylamine hydrochloride. The obtained crude product (5.70 g) was used for Step 3 without further purification.

Step 3: Production of 5-benzyloxy-2-(4,4,5,5-tetramethyl-1,3,2-dioxaborolan-2-yl)phenylamine

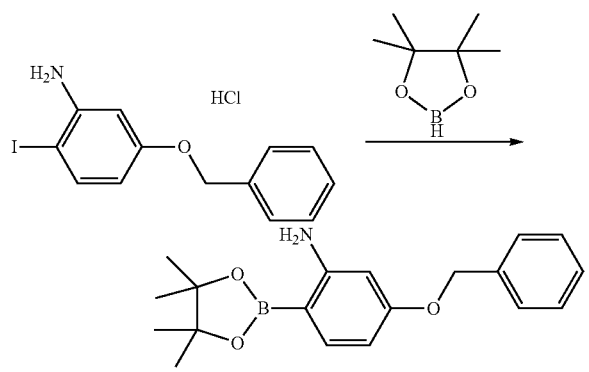

To a solution of 5-benzyloxy-2-iodophenylamine hydrochloride (5.70 g, 15.8 mmol) in 1,4-dioxane (86 ml) were added triethylamine (11.0 ml, 79.0 mmol) and PdCl$_2$(dppf)·CH$_2$Cl$_2$ (645 mg, 0.79 mmol) at room temperature. To the mixture was added dropwise pinacolborane (6.86 ml, 47.4 mmol) at room temperature, and the mixture was stirred at 100° C. for 12 hr. A saturated aqueous ammonium chloride solution was added to the reaction mixture, and the mixture was extracted with diethyl ether. The organic layer was washed with saturated brine and dried over anhydrous sodium sulfate. After filtration, the solvent was evaporated under reduced pressure, and the residue was purified by silica gel chromatography (hexane:ethyl acetate=5:1) to give 5-benzyloxy-2-(4,4,5,5-tetramethyl-1,3,2-dioxaborolan-2-yl)phenylamine (3.93 g, yield 76%).

$^1$H-NMR (400 MHz, DMSO-d$_6$): δ(ppm) 7.42-7.25 (6H, m), 6.20-6.15 (2H, m), 5.50 (2H, s), 5.02 (2H, s), 1.26 (12H, s).

Step 4: Production of methyl 2-(2-amino-4-benzyloxyphenyl)-3-cyclohexyl-1H-indole-6-carboxylate

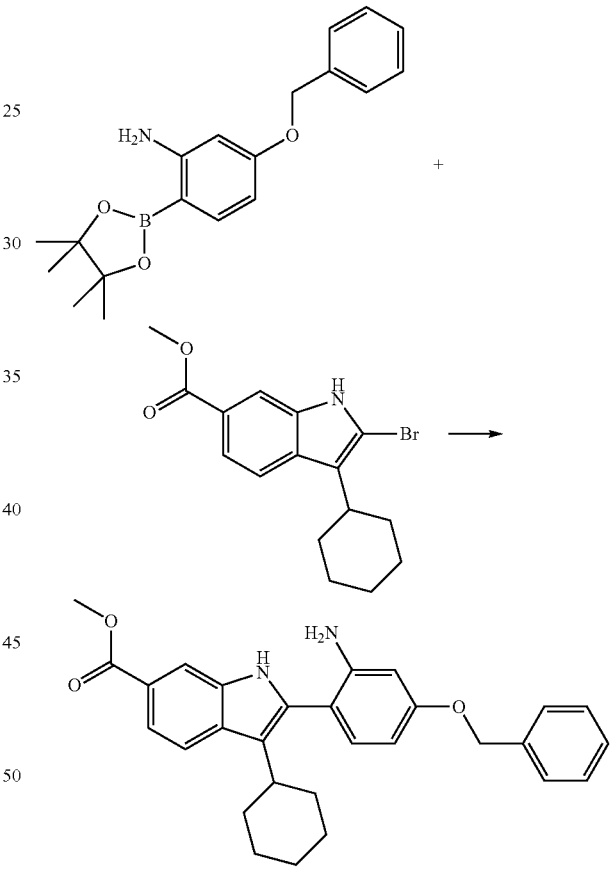

To a suspension of methyl 2-bromo-3-cyclohexyl-1H-indole-6-carboxylate (3.38 g, 10.0 mmol) obtained in the same manner as in the method described in WO03/010140 and 5-benzyloxy-2-(4,4,5,5-tetramethyl-1,3,2-dioxaborolan-2-yl)phenylamine (3.93 g, 12.1 mmol) in 1,2-dimethoxyethane (70 ml) and water (35 ml) were added sodium hydrogen carbonate (2.49 g, 30.0 mmol) and tetrakis(triphenylphosphine)palladium (582 mg, 0.50 mmol), and the mixture was stirred at 90° C. for 3 hr. The reaction mixture was allowed to cool to room temperature, saturated aqueous ammonium chloride solution was added to the reaction mixture, and the mixture was extracted with diethyl ether. The organic layer was washed with saturated brine and dried over anhydrous sodium sulfate. The obtained crude product (6.20 g) was used for Step 5 without further purification.

Step 5: Production of methyl 2-[4-benzyloxy-2-(2-chloroacetylamino)phenyl]-3-cyclohexyl-1H-indole-6-carboxylate

Step 6: Production of methyl 3-benzyloxy-13-cyclohexyl-6-oxo-6,7-dihydro-5H-benzo[5,6][1,4]diazepino[7,1-a]indole-10-carboxylate (Example 1-610)

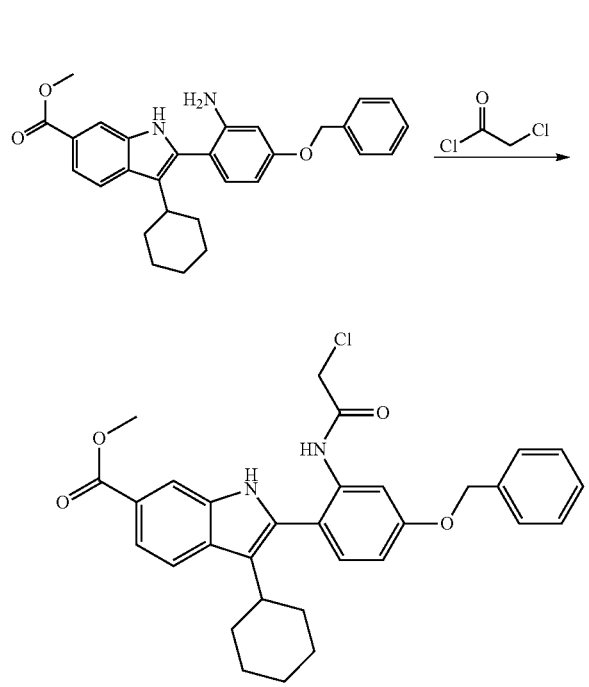

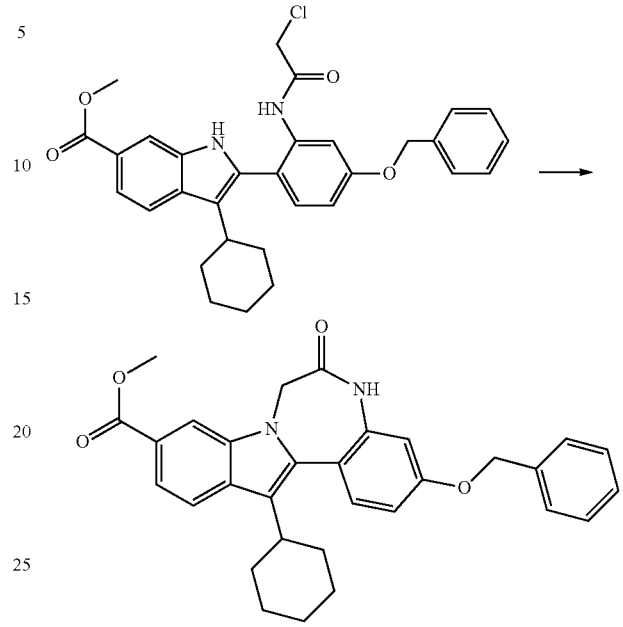

To a suspension of methyl 2-(2-amino-4-benzyloxyphenyl)-3-cyclohexyl-1H-indole-6-carboxylate (6.17 g, 13.5 mmol), sodium acetate (1.22 g, 14.9 mmol) and acetic acid (0.86 ml, 14.9 mmol) in tetrahydrofuran (62 ml) was added dropwise chloroacetyl chloride (1.19 ml, 14.9 mmol), and the mixture was stirred at room temperature for 2 hr. Water was added to the reaction mixture and the mixture was extracted with ethyl acetate. The organic layer was washed with saturated brine and dried over anhydrous sodium sulfate. After filtration, the solvent was evaporated under reduced pressure and methanol was added. The precipitated solid was collected by filtration, washed with methanol and dried in vacuo to give methyl 2-[4-benzyloxy-2-(2-chloroacetylamino)phenyl]-3-cyclohexyl-1H-indole-6-carboxylate (3.90 g, yield 54%).

$^1$H-NMR (400 MHz, DMSO-d$_6$): δ(ppm) 11.38 (1H, s), 9.32 (1H, s), 7.96 (1H, d, J=0.9 Hz), 7.80 (1H, d, J=8.8 Hz), 7.66 (1H, d, J=2.3 Hz), 7.59 (1H, dd, J=8.3, 1.4 Hz), 7.50 (2H, d, J=7.9 Hz), 7.45-7.40 (2H, m), 7.35 (1H, t, J=8.6 Hz), 7.27 (1H, d, J=8.8 Hz), 6.97 (1H, dd, J=8.6, 2.6 Hz), 5.17 (2H, s), 4.20 (2H, s), 3.84 (3H, s), 2.50-2.43 (1H, m), 1.85-1.71 (7H, m), 1.34-1.13 (3H, m).

To a solution of methyl 2-[4-benzyloxy-2-(2-chloroacetylamino)phenyl]-3-cyclohexyl-1H-indole-6-carboxylate (3.90 g, 7.34 mmol) in N,N-dimethylformamide (98 ml) was added 60% sodium hydride (1.08 g, 16.1 mmol) under ice-cooling, and the mixture was stirred for 5 hr. Water was added to the reaction mixture, and the precipitated solid was collected by filtration and washed with water and hexane. The obtained solid was dried in vacuo to give methyl 3-benzyloxy-13-cyclohexyl-6-oxo-6,7-dihydro-5H-benzo[5,6][1,4]diazepino[7,1-a]indole-10-carboxylate (3.60 g, yield 99%).

$^1$H-NMR (400 MHz, DMSO-d$_6$): δ(ppm) 10.31 (1H, s), 8.25 (1H, s), 7.93 (1H, d, J=8.8 Hz), 7.67 (1H, dd, J=8.4, 1.1 Hz), 7.52-7.37 (6H, m), 7.10 (1H, dd, J=8.4, 2.6 Hz), 6.91 (1H, d, J=2.6 Hz), 5.18 (2H, d, J=8.1 Hz), 5.06 (1H, d, J=15.4 Hz), 4.52 (1H, d, J=14.7 Hz), 3.89 (3H, s), 2.75-2.71 (1H, m), 2.04-2.00 (3H, m), 1.92-1.89 (1H, m), 1.73-1.70 (2H, m), 1.43-1.40 (3H, m), 1.25-1.22 (1H, m).

Step 7: Production of methyl 3-benzyloxy-13-cyclohexyl-6-oxo-5-[2-oxo-2-(piperidin-1-yl)ethyl]-6,7-dihydro-5H-benzo[5,6][1,4]diazepino[7,1-a]indole-10-carboxylate (Example 1-611)

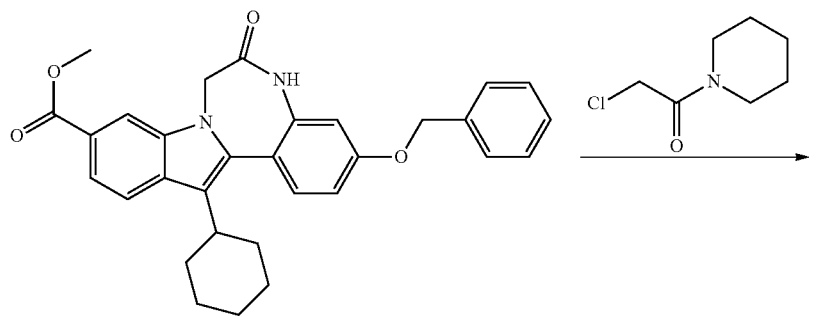

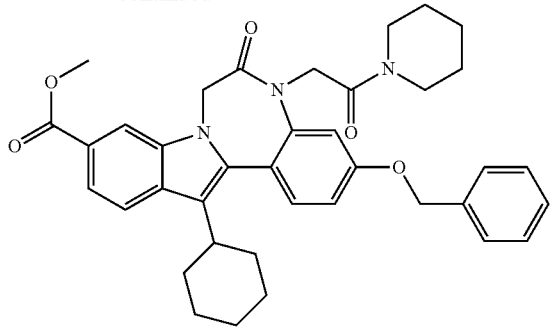

A suspension of methyl 3-benzyloxy-13-cyclohexyl-6-oxo-6,7-dihydro-5H-benzo[5,6][1,4]diazepino[7,1-a]indole-10-carboxylate (1.00 g, 2.02 mmol), 1-chloroacetylpiperidine (425 mg, 2.63 mmol) and potassium carbonate (558 mg, 4.02 mmol) in N,N-dimethylformamide (20 ml) was stirred at 90° C. for 4 hr. The reaction mixture was allowed to cool to room temperature, water was added to the reaction mixture and the mixture was extracted with ethyl acetate. The organic layer was washed with saturated brine and dried over anhydrous sodium sulfate. After filtration, the solvent was evaporated under reduced pressure. The obtained crude product was suspended in a mixed solvent (hexane:ethyl acetate=5:1) and filtered. The solid was collected by filtration and dried in vacuo to give methyl 3-benzyloxy-13-cyclohexyl-6-oxo-5-[2-oxo-2-(piperidin-1-yl)ethyl]-6,7-dihydro-5H-benzo[5,6][1,4]diazepino[7,1-a]indole-10-carboxylate (800 mg, yield 64%).

$^1$H-NMR (400 MHz, DMSO-$d_6$): δ(ppm) 8.26 (1H, d, J=1.4 Hz), 7.93 (1H, d, J=8.8 Hz), 7.67 (1H, dd, J=8.3, 1.4 Hz), 7.52-7.35 (6H, m), 7.18 (1H, dd, J=8.8, 2.3 Hz), 7.12 (1H, d, J=2.3 Hz), 5.19 (2H, s), 5.17 (1H, d, J=14.8 Hz), 4.68 (1H, d, J=16.2 Hz), 4.49 (1H, d, J=14.8 Hz), 4.40 (1H, d, J=16.2 Hz), 3.89 (3H, s), 3.44-3.26 (4H, m), 2.91-2.81 (1H, m), 2.10-1.83 (4H, m), 1.79-1.66 (2H, m), 1.63-1.32 (9H, m), 1.27-1.12 (1H, m).

Step 8: Production of methyl 3-cyclohexyl-3-hydroxy-6-oxo-5-[2-oxo-2-(piperidin-1-yl)ethyl]-6,7-dihydro-5H-benzo[5,6][1,4]diazepino[7,1-a]indole-10-carboxylate (Example 1-612)

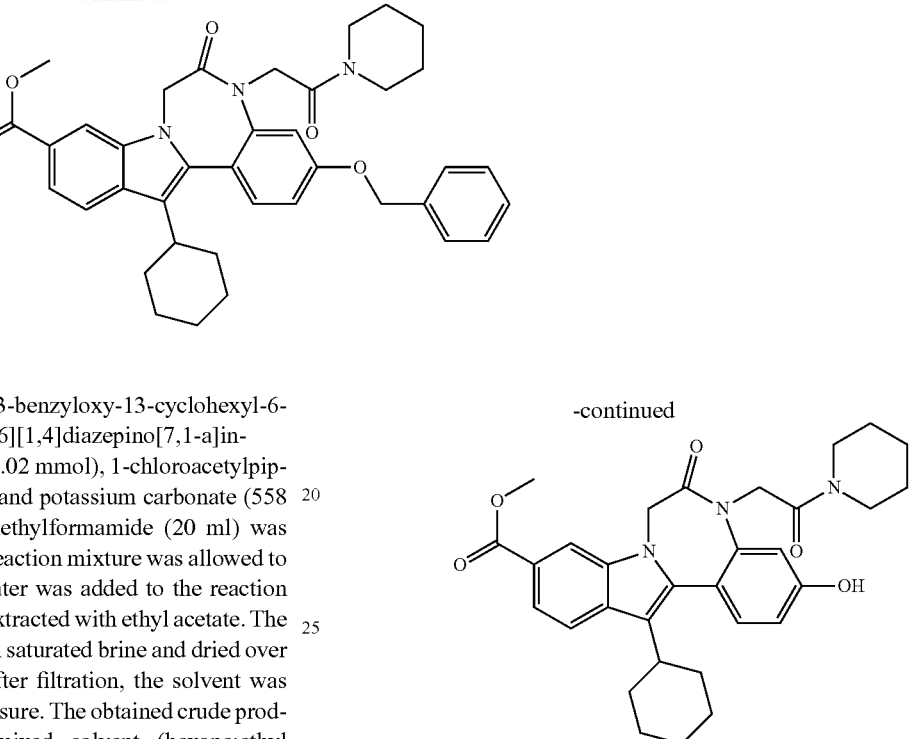

To a solution of methyl 3-benzyloxy-13-cyclohexyl-6-oxo-5-[2-oxo-2-(piperidin-1-yl)ethyl]-6,7-dihydro-5H-benzo[5,6][1,4]diazepino[7,1-a]indole-10-carboxylate (7.40 g, 11.9 mmol) in acetic acid (15 ml) was added 25% hydrogen bromide -acetic acid solution (15 ml), and the mixture was stirred at room temperature for 2 hr. The reaction mixture was concentrated under reduced pressure. Toluene was added to the residue and the mixture was concentrated to dryness under reduced pressure. The obtained crystals were suspended in a mixed solvent (hexane:ethyl acetate=3:1) and filtered. The solid was collected by filtration and dried in vacuo to give methyl 13-cyclohexyl-3-hydroxy-6-oxo-5-[2-oxo-2-(piperidin-1-yl)ethyl]-6,7-dihydro-5H-benzo[5,6][1,4]diazepino[7,1-a]indole-10-carboxylate (6.30 g, yield 100%).

$^1$H-NMR (400 MHz, DMSO-$d_6$): δ(ppm) 8.24 (1H, d, J=0.9 Hz), 7.91 (1H, d, J=8.8 Hz), 7.66 (1H, dd, J=8.3, 1.4 Hz), 7.33 (1H, d, J=7.9 Hz), 6.90-6.85 (2H, m), 5.15 (1H, d, J=14.4 Hz), 4.64 (1H, d, J=16.7 Hz), 4.47 (1H, d, J=14.4 Hz), 4.31 (1H, d, J=16.7 Hz), 3.88 (3H, s), 3.51-3.26 (5H, m), 2.91-2.79 (1H, m), 2.10-1.81 (4H, m), 1.80-1.66 (2H, m), 1.64-1.33 (9H, m), 1.29-1.12 (1H, m).

Step 9: Production of methyl 13-cyclohexyl-6-oxo-5-[2-oxo-2-(piperidin-1-yl)ethyl]-3-(pyridin-2-ylmethoxy)-6,7-dihydro-5H-benzo[5,6][1,4]diazepino[7,1-a]indole-10-carboxylate (Example 1-613)

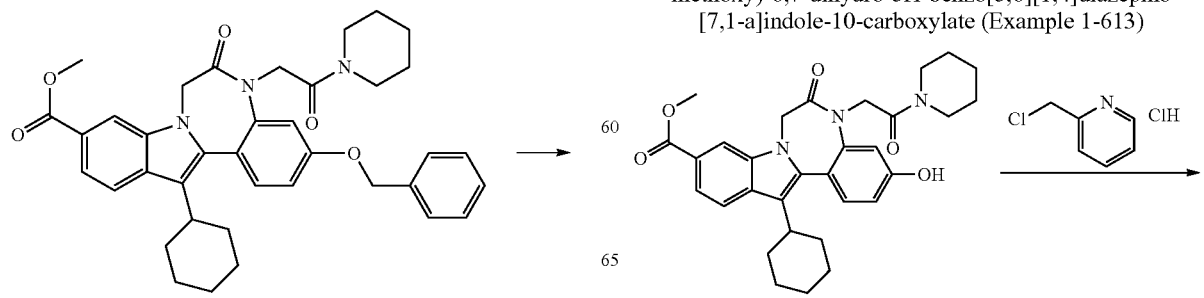

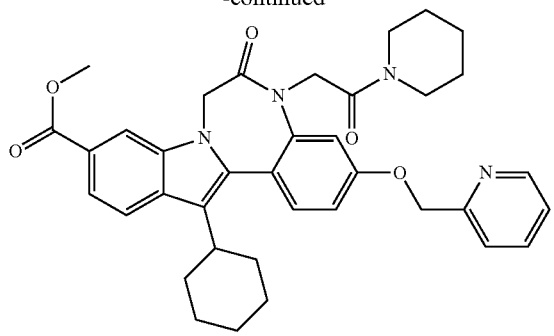

A suspension of methyl 13-cyclohexyl-3-hydroxy-6-oxo-5-[2-oxo-2-(piperidin-1-yl)ethyl]-6,7-dihydro-5H-benzo[5,6][1,4]diazepino[7,1-a]indole-10-carboxylate (400 mg, 0.76 mmol), 2-chloromethylpyridine hydrochloride (186 mg, 1.14 mmol), potassium carbonate (315 mg, 2.28 mmol) and potassium iodide (63.0 mg, 0.38 mmol) in N,N-dimethylformamide (8 ml) was stirred at 80° C. for 3 hr. The reaction mixture was allowed to cool to room temperature and 1N aqueous hydrochloric acid solution was added to the reaction mixture. The precipitated solid was collected by filtration, washed with water and dried in vacuo. The obtained crude product (393 mg) was used for Step 10 without further purification.

Step 10: Production of methyl 13-cyclohexyl-5-[2-(piperidin-1-yl)ethyl]-3-(piperidin-2-ylmethoxy)-6,7-dihydro-5H-benzo[5,6][1,4]diazepino[7,1-a]indole-10-carboxylate (Example 1-614)

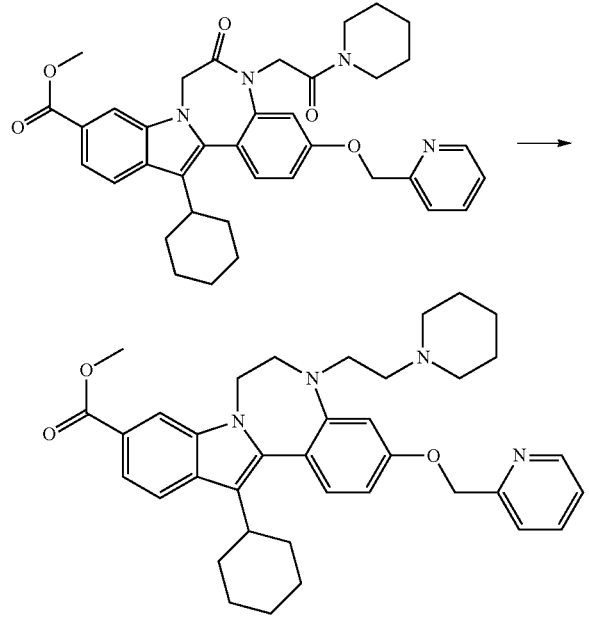

To a solution of methyl 13-cyclohexyl-6-oxo-5-[2-oxo-2-(piperidin-1-yl)ethyl]-3-(pyridin-2-ylmethoxy)-6,7-dihydro-5H-benzo[5,6][1,4]diazepino[7,1-a]indole-10-carboxylate (393 mg, 0.63 mmol) in tetrahydrofuran (1.2 ml) was added a solution (3.2 ml) of 1M BH$_3$ THF complex in tetrahydrofuran under ice-cooling, and the mixture was stirred at room temperature for 3 hr. 4N Aqueous hydrochloric acid solution (4.4 ml) was added to the reaction mixture, and the mixture was stirred at 60° C. for 12 hr. The reaction mixture was allowed to cool to room temperature. The reaction mixture was adjusted to pH 7 with 1N aqueous sodium hydroxide solution, and extracted with ethyl acetate. The organic layer was washed with saturated brine and dried over anhydrous sodium sulfate. After filtration, the solvent was evaporated under reduced pressure. The obtained crude product (298 mg) was used for Step 11 without further purification. Step 11: Production of 13-cyclohexyl-5-[2-(piperidin-1-yl)ethyl]-3-(pyridin-2-ylmethoxy)-6,7-dihydro-5H-benzo[5,6][1,4]diazepino[7,1-a]indole-10-carboxylic acid trihydrochloride (Example 1-595)

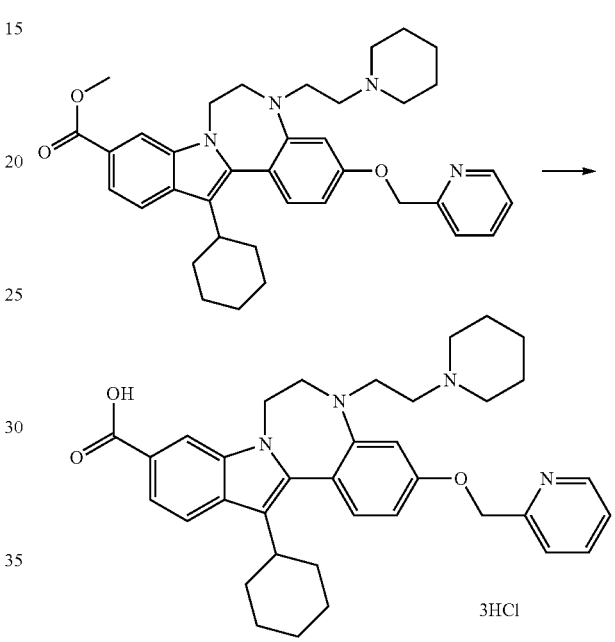

To a solution of methyl 13-cyclohexyl-5-[2-(piperidin-1-yl)ethyl]-3-(pyridin-2-ylmethoxy)-6,7-dihydro-5H-benzo[5,6][1,4]diazepino[7,1-a]indole-10-carboxylate (298 mg, 0.50 mmol) in tetrahydrofuran (6 ml) and methanol (3 ml) was added 4N aqueous sodium hydroxide solution (3 ml), and the mixture was stirred at room temperature for 24 hr. The reaction solution was adjusted to pH 7 with 1N aqueous hydrochloric acid solution, and extracted with ethyl acetate. The organic layer was washed with saturated brine and dried over anhydrous sodium sulfate. After filtration, the solvent was concentrated under reduced pressure. Ethyl acetate (6 ml) and 4N HCl-ethyl acetate solution (3 ml) were added to the crude product at room temperature, and the mixture was concentrated under reduced pressure. The obtained solid was suspended in diethyl ether, collected by filtration and washed with diethyl ether. The solid was dried in vacuo to give 13-cyclohexyl-5-(2-piperidin-1-ylethyl)-3-(pyridin-2-ylmethoxy)-6,7-dihydro-5H-benzo[5,6][1,4]diazepino[7,1-a]indole-10-carboxylic acid trihydrochloride (242 mg, yield 70%).

$^1$H-NMR (400 MHz, DMSO-d$_6$): δ(ppm) 10.08 (1H, br s), 8.71 (1H, d, J=4.6 Hz), 8.15 (1H, d, J=1.4 Hz), 8.09 (1H, t, J=7.2 Hz), 7.82 (1H, d, J=8.8 Hz), 7.78 (1H, d, J=7.4 Hz), 7.59 (1H, dd, J=8.6, 1.2 Hz), 7.56 (1H, d, J=5.6 Hz), 7.30 (1H, d, J=8.3 Hz), 7.01 (1H, d, J=2.3 Hz), 6.97 (1H, dd, J=8.3, 2.3 Hz), 5.38 (2H, s), 4.98-4.42 (1H, m), 3.94-3.36 (2H, m), 3.20-3.01 (4H, m), 2.81 (1H, t, J=12.1 Hz), 2.59-2.50 (2H, m), 2.05-1.96 (3H, m), 1.89-1.73 (6H, m), 1.48-1.28 (9H, m), 1.10-1.00 (1H, m).

MS 579.3 (M+1).

Example 2-175

Production of methyl (S)-2-[(12-cyclohexyl-6,7-dihydro-5-oxa-7a-azadibenzo[a,e]azulene-9-carbonyl)amino]-3-(4-hydroxyphenyl)propionate Step 1: Production of 12-cyclohexyl-6,7-dihydro-5-oxa-7a-azadibenzo[a,e]azulene-9-carbonyl chloride

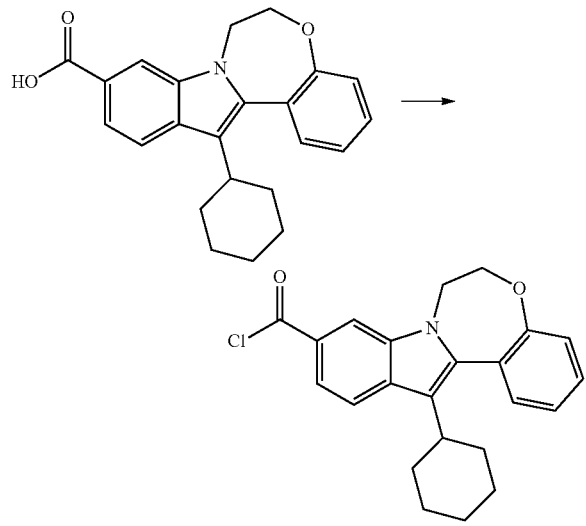

To a solution of 12-cyclohexyl-6,7-dihydro-5-oxa-7a-azadibenzo[a,e]azulene-9-carboxylic acid (500 mg, 1.38 mmol) in chloroform (10 ml) were added oxalyl chloride (0.15 ml, 1.66 mmol) and several drops of N,N-dimethylformamide. The mixture was stirred at room temperature for 2 hr and concentrated. Hexane was added to the obtained residue, and the precipitated solid was collected by filtration. The solid was washed with hexane to give 12-cyclohexyl-6,7-dihydro-5-oxa-7a-azadibenzo[a,e]azulene-9-carbonyl chloride (476 mg, yield 91%).

$^1$H-NMR (400 MHz, CDCl$_3$): δ(ppm) 8.16 (1H, d, J=1.4 Hz), 7.94 (1H, d, J=8.3 Hz), 7.83 (1H, dd, J=8.6, 1.6 Hz), 7.49-7.42 (2H, m), 7.33 (1H, td, J=7.5, 1.4 Hz), 7.30-7.25 (1H, m), 4.57-4.52 (2H, m), 4.33 (2H, t, J=5.8 Hz), 3.01-2.97 (1H, m), 2.14-2.06 (2H, m), 1.75-1.95 (5H, m), 1.40-1.35 (3H, m).

Step 2: Production of methyl (S)-2-[(12-cyclohexyl-6,7-dihydro-5-oxa-7a-azadibenzo[a,e]azulene-9-carbonyl)amino]-3-(4-hydroxyphenyl)propionate (Example 2-175)

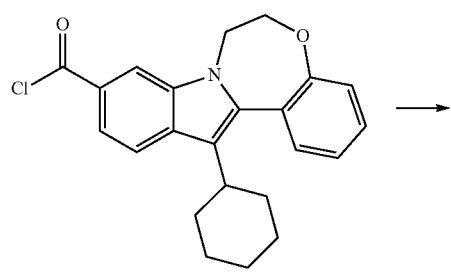

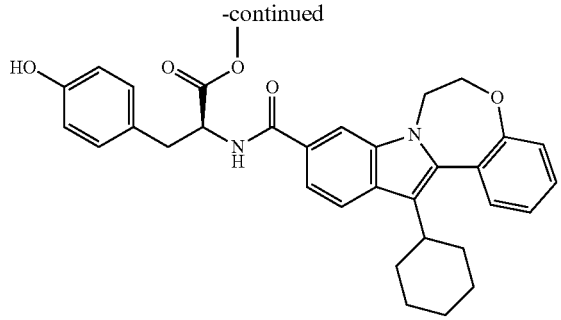

To a solution of 12-cyclohexyl-6,7-dihydro-5-oxa-7a-azadibenzo[a,e]azulene-9-carbonyl chloride (100 mg, 0.26 mmol) in chloroform (2 ml) was added methyl (S)-2-amino-3-(4-hydroxyphenyl)propionate (154 mg, 0.78 mmol). The mixture was stirred at room temperature for 12 hr, 1N hydrochloric acid was added to the reaction solution, and the mixture was extracted with ethyl acetate. The organic layer was successively washed with water and saturated brine and dried over anhydrous sodium sulfate. After filtration and concentration, diethyl ether was added to the obtained residue, and the precipitated solid was collected by filtration. The solid was washed with diethyl ether to give methyl (S)-2-[(12-cyclohexyl-6,7-dihydro-5-oxa-7a-azadibenzo[a,e]azulene-9-carbonyl)amino]-3-(4-hydroxyphenyl)propionate (102 mg, yield 82%).

$^1$H-NMR (400 MHz, DMSO-d$_6$): δ(ppm) 9.18 (1H, s), 8.58 (1H, d, J=7.4 Hz), 8.08 (1H, d, J=0.9 Hz), 7.85 (1H, d, J=8.3 Hz), 7.53-7.42 (3H, m), 7.35 (1H, td, J=7.4, 0.9 Hz), 7.25 (1H, dd, J=8.1, 1.2 Hz), 7.09 (2H, d, J=8.3 Hz), 6.65 (2H, d, J=5.8 Hz), 4.64-4.59 (1H, m), 4.46 (2H, t, J=5.6 Hz), 4.32 (2H, s), 3.64 (3H, s), 3.08-2.98 (2H, m), 2.88 (1H, t, J=12.3 Hz), 2.05-1.94 (1H, m), 1.89-1.70 (6H, m), 1.43-1.23 (3H, m).
MS 539.3 (M+1).

Example 2-180

Production of (S)-2-[(12-cyclohexyl-6,7-dihydro-5-oxa-7a-azadibenzo[a,e]azulene-9-carbonyl)amino]-3-(4-hydroxyphenyl)propionic acid

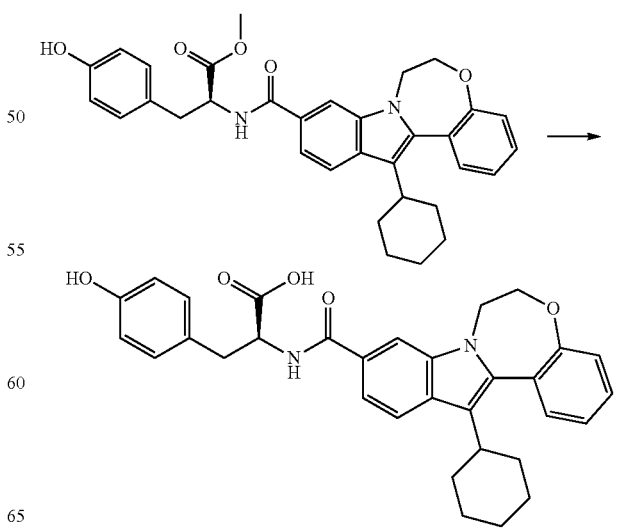

To a solution of methyl (S)-2-[(12-cyclohexyl-6,7-dihydro-5-oxa-7a-azadibenzo[a,e]azulene-9-carbonyl)amino]-3-(4-hydroxyphenyl)propionate (87 mg, 0.16 mmol) in tetrahydrofuran (2 ml) and methanol (1 ml) was added 4N aqueous sodium hydroxide solution (1 ml), and the mixture was stirred at room temperature for 12 hr. The mixture was adjusted to pH 6.5 with 1N hydrochloric acid (4 ml) and extracted with ethyl acetate. The organic layer was washed with saturated brine and dried over anhydrous sodium sulfate. After filtration and concentration, diethyl ether was added to the obtained residue, and the precipitated solid was collected by filtration. The solid was washed with diethyl ether to give (S)-2-[(12-cyclohexyl-6,7-dihydro-5-oxa-7a-azadibenzo[a,e]azulene-9-carbonyl)amino]-3-(4-hydroxyphenyl)propionic acid (61 mg, yield 74%).

$^1$H-NMR (400 MHz, DMSO-$d_6$): δ(ppm) 8.15-8.03 (2H, m), 7.83 (1H, d, J=8.3 Hz), 7.43-7.36 (3H, m), 7.34 (1H, ddd, J=15.3, 7.9, 6.5 Hz), 7.24 (1H, dd, J=7.9, 1.4 Hz), 7.02 (2H, d, J=8.3 Hz), 6.58 (2H, d, J=8.8 Hz), 4.45 (2H, t, J=5.3 Hz), 4.25-4.40 (3H, m), 3.10 (1H, dd, J=4.6, 13.4 Hz), 2.97 (1H, dd, J=7.9, 13.4 Hz), 2.88 (1H, dd, J=13.2, 10.9 Hz), 2.04-2.01 (2H, m), 1.82-1.76 (5H, m), 1.36-1.29 (3H, m).

MS 525.3 (M+1).

Example 2-298

Production of 12-cyclohexyl-4-(pyridin-3-yl)-6,7-dihydro-5-oxa-7a-azadibenzo[a,e]azulene-9-carboxylic acid hydrochloride Step 1: Production of methyl 12-cyclohexyl-4-trifluoromethanesulfonyloxy-6,7-dihydro-5-oxa-7a-azadibenzo[a,e]azulene-9-carboxylate (Example 2-509)

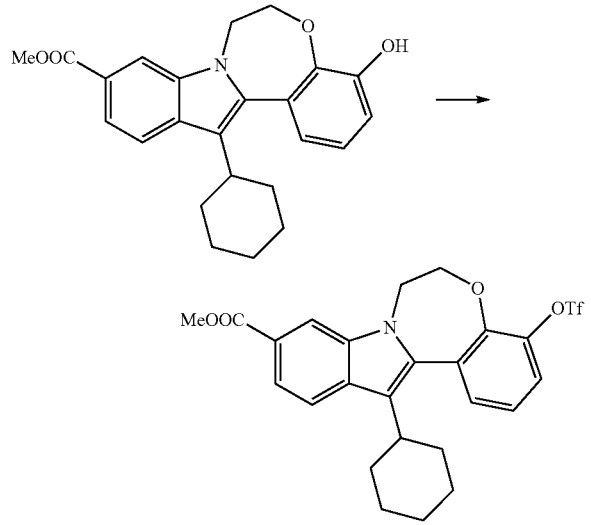

To a solution of methyl 12-cyclohexyl-4-hydroxy-6,7-dihydro-5-oxa-7a-azadibenzo[a,e]azulene-9-carboxylate (1.00 g, 2.55 mmol) obtained in the same manner as in Step 6 of Example 2-53 and triethylamine (427 μl, 3.06 mmol) in chloroform (10 ml) was added dropwise trifluoromethanesulfonic anhydride (476 μl, 2.81 mmol) under ice-cooling, and the mixture was stirred for 3 hr. Saturated aqueous ammonium chloride solution was added to the reaction mixture, and the mixture was extracted with ethyl acetate. The organic layer was successively washed with saturated aqueous ammonium chloride solution, saturated aqueous sodium hydrogen carbonate solution and saturated brine, and dried over anhydrous magnesium sulfate. After filtration, the solvent was evaporated under reduced pressure to give methyl 12-cyclohexyl-4-trifluoromethanesulfonyloxy-6,7-dihydro-5-oxa-7a-azadibenzo[a,e]azulene-9-carboxylate (1.30 g, yield 97%).

$^1$H-NMR (400 MHz, CDCl$_3$): δ(ppm) 8.27 (1H, d, J=1.4 Hz), 7.97 (1H, d, J=8.4 Hz), 7.68 (1H, dd, J=8.4, 1.4 Hz), 7.63 (1H, dd, J=7.9, 1.9 Hz), 7.54 (1H, dd, J=7.9, 1.9 Hz), 7.49 (1H, t, J=7.9 Hz), 4.62 (2H, brt, J=5.1 Hz), 4.52 (1H, brs), 3.88 (3H, s), 2.87 (1H, brt, J=12.3 Hz), 2.10-1.96 (2H, m), 1.86-1.68 (5H, m), 1.48-1.26 (3H, m).

Step 2: Production of methyl 12-cyclohexyl-4-(pyridin-3-yl)-6,7-dihydro-5-oxa-7a-azadibenzo[a,e]azulene-9-carboxylate (Example 2-510)

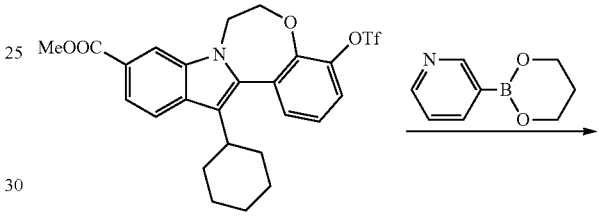

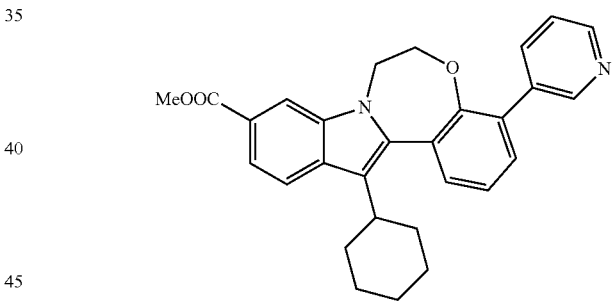

To a suspension of methyl 12-cyclohexyl-4-trifluoromethanesulfonyloxy-6,7-dihydro-5-oxa-7a-azadibenzo[a,e]azulene-9-carboxylate (130 mg, 0.248 mmol), 3-(1,3,2-dioxaborinan-2-yl)pyridine (53 mg, 0.323 mmol) and sodium hydrogen carbonate (62 mg, 0.744 mmol) in 1,2-dimethoxyethane (2 ml) and water (0.75 ml) was added tetrakis(triphenylphosphine)palladium (16 mg, 0.014 mmol), and the mixture was heated at 90° C. for 3 hr. The reaction mixture was cooled to room temperature, saturated aqueous sodium hydrogen carbonate solution was added, and the mixture was extracted with ethyl acetate. The organic layer was successively washed with saturated sodium hydrogen carbonate solution and saturated brine, and dried over anhydrous magnesium sulfate. After filtration, the solvent was evaporated under reduced pressure and the residue was purified by silica gel column chromatography (hexane:ethyl acetate=1:2) to give methyl 12-cyclohexyl-4-(pyridin-3-yl)-6,7-dihydro-5-oxa-7a-azadibenzo[a,e]azulene-9-carboxylate (92 mg, yield 82%).

¹H-NMR (400 MHz, DMSO-d₆): δ(ppm) 8.77 (1H, d, J=2.2 Hz), 8.60 (1H, dd, J=6.3, 2.2 Hz), 8.25 (1H, d, J=1.5 Hz), 8.00 (1H, dt, J=8.0, 2.2 Hz), 7.94 (1H, d, J=8.5 Hz), 7.66 (1H, dd, J=8.5, 1.5 Hz), 7.57 (1H, dd, J=6.3, 2.2 Hz), 7.53-7.44 (3H, m), 4.46 (2H, brs), 4.34 (2H, brs), 3.87 (3H, s), 2.92 (1H, brt, J=11.6 Hz), 2.12-1.97 (2H, m), 1.89-1.70 (5H, m), 1.48-1.27 (3H, m), Step 3: Production of 12-cyclohexyl-4-(pyridin-3-yl)-6,7-dihydro-5-oxa-7a-azadibenzo[a,e]azulene-9-carboxylic acid hydrochloride (Example 2-298)

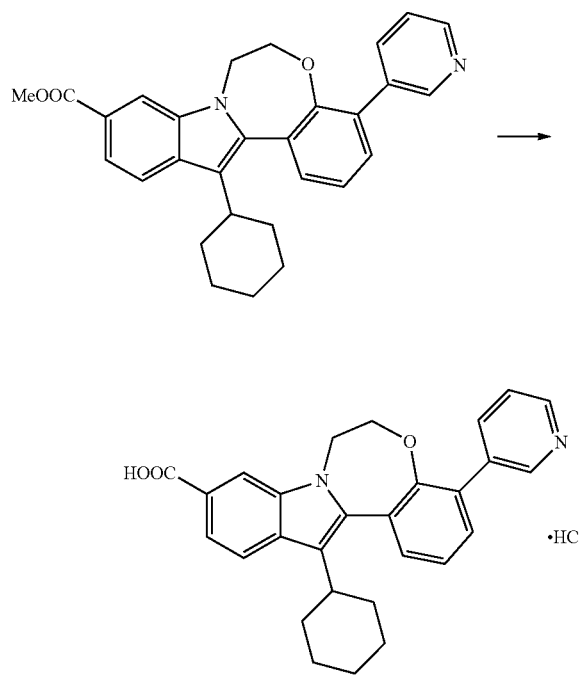

To a solution of methyl 12-cyclohexyl-4-(pyridin-3-yl)-6,7-dihydro-5-oxa-7a-azadibenzo[a,e]azulene-9-carboxylate (130 mg, 0.203 mmol) in tetrahydrofuran (2 ml) and methanol (2 ml) was added 4N aqueous sodium hydroxide solution (1 ml), and the mixture was stirred at room temperature for 12 hr. The reaction mixture was adjusted to pH 6.5 with 2N hydrochloric acid, and extracted with chloroform. The organic layer was washed with saturated brine and dried over anhydrous sodium sulfate. After filtration, the solvent was evaporated under reduced pressure. To a solution of the residue in chloroform was added 4N HCl-ethyl acetate solution (0.5 ml), and the solvent was evaporated under reduced pressure. A mixed solvent (hexane:ethyl acetate=4:1) was added to the residue. The precipitated solid was collected by filtration to give 12-cyclohexyl-4-(pyridin-3-yl)-6,7-dihydro-5-oxa-7a-azadibenzo[a,e]azulene-9-carboxylic acid hydrochloride (88 mg, yield 91%).

¹H-NMR (400 MHz, DMSO-d₆): δ(ppm) 9.01 (1H, s), 8.82 (1H, d, J=5.1 Hz), 8.50 (1H, d, J=7.9 Hz), 8.23 (1H, d, J=0.9 Hz), 7.92 (2H, d, J=8.3 Hz), 7.68-7.63 (2H, m), 7.58-7.50 (2H, m), 4.48 (2H, brs), 4.37 (2H, brs), 2.91 (1H, brt, J=11.8 Hz), 2.12-1.98 (2H, m), 1.90-1.69 (5H, m), 1.49-1.22 (3H, m).

MS 439.2 (M+1).

Example 2-332

Production of 2-{1-[(12-cyclohexyl-3-methoxy-6,7-dihydro-5-oxa-7a-azadibenzo[a,e]azulene-9-carbonyl)amino]-1-methylethyl}-3H-benzimidazole-5-carboxylic acid Step 1: Production of methyl 2-[(12-cyclohexyl-3-methoxy-6,7-dihydro-5-oxa-7a-azadibenzo[a,e]azulene-9-carbonyl)amino]-2-methylpropionate (Example 2-511)

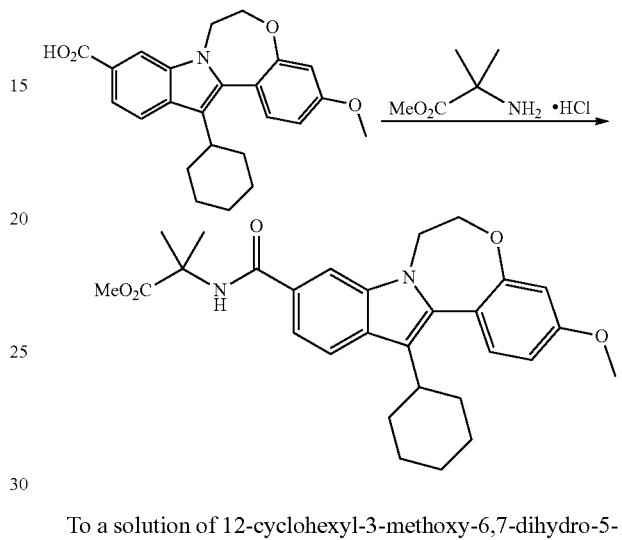

To a solution of 12-cyclohexyl-3-methoxy-6,7-dihydro-5-oxa-7a-azadibenzo[a,e]azulene-9-carboxylic acid (2.40 g, 6.13 mmol) in N,N-dimethylformamide (20.0 mL) were successively added methyl 2-amino-2-methylpropionate hydrochloride (1.13 g, 7.36 mmol), 1-ethyl-3-(3'-dimethylaminopropyl)carbodiimide monohydrochloride (1.41 g, 7.36 mmol), 1-hydroxybenzotriazole (0.99 g, 7.36 mmol) and triethylamine (1.00 ml, 7.36 mmol) at room temperature, and the mixture was stirred overnight. To the reaction mixture were added saturated aqueous sodium hydrogen carbonate solution, methanol and water. The precipitate was collected by filtration, washed with water, and dried in vacuo to give methyl 2-[(12-cyclohexyl-3-methoxy-6,7-dihydro-5-oxa-7a-azadibenzo[a,e]azulene-9-carbonyl)amino]-2-methylpropionate (3.10 g). The obtained compound was used for Step 2 without purification.

¹H-NMR (300 MHz, DMSO-d₆): δ(ppm) 8.40 (1H, s), 8.12 (1H, s), 7.81 (1H, d, J=8.7 Hz), 7.56 (1H, d, J=8.3 Hz), 7.34 (1H, d, J=8.3 Hz), 6.94 (1H, dd, J=2.6, 8.7 Hz), 6.84 (1H, d, J=2.6 Hz), 4.51-4.28 (4H, m), 3.83 (3H, s), 3.59 (3H, s), 2.93-2.79 (1H, m), 2.12-1.91 (2H, m), 1.88-1.61 (5H, m), 1.50 (6H, s), 1.45-1.22 (3H, m).

Step 2: Production of 2-[(12-cyclohexyl-3-methoxy-6,7-dihydro-5-oxa-7a-azadibenzo[a,e]azulene-9-carbonyl)amino]-2-methylpropionic acid (Example 2-512)

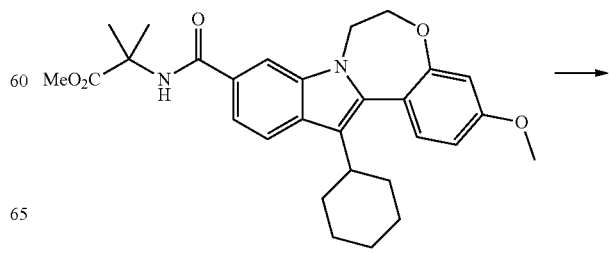

-continued

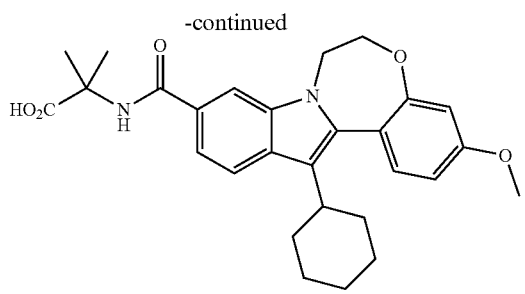

To a solution of methyl 2-[(12-cyclohexyl-3-methoxy-6,7-dihydro-5-oxa-7a-azadibenzo[a,e]azulene-9-carbonyl)amino]-2-methylpropionate (3.00 g, 6.11 mmol) in tetrahydrofuran (20.0 ml) and methanol (20.0 ml) was added 2N aqueous sodium hydroxide solution (10.00 ml, 20.00 mmol) at room temperature, and the mixture was stirred overnight. To the reaction mixture were successively added 2N hydrochloric acid (11.00 ml, 22.00 mmol), water and methanol, and the mixture was stirred at room temperature for 30 min. The precipitate was collected by filtration, washed with water, and dried in vacuo to give 2-[(12-cyclohexyl-3-methoxy-6,7-dihydro-5-oxa-7a-azadibenzo[a,e]azulene-9-carbonyl)amino]-2-methylpropionic acid (2.60 g, yield 89%).

$^1$H-NMR (300 MHz, DMSO-$d_6$): δ(ppm) 8.27 (1H, s), 8.10 (1H, s), 7.81 (1H, d, J=8.3 Hz), 7.54 (1H, d, J=9.0 Hz), 7.34 (1H, d, J=8.3 Hz), 6.94 (1H, d, J=8.7 Hz), 6.83 (1H, d, J=2.3 Hz), 4.52-4.28 (4H, m), 3.83 (3H, s), 2.93-2.78 (1H, m), 2.12-1.91 (2H, m), 1.88-1.64 (5H, m), 1.50 (6H, s), 1.44-1.21 (3H, m).

Step 3: Production of methyl 4-amino-3-{2-[(12-cyclohexyl-3-methoxy-6,7-dihydro-5-oxa-7a-azadibenzo[a,e]azulene-9-carbonyl)amino]-2-methylpropionylamino}benzoate (Example 2-513)

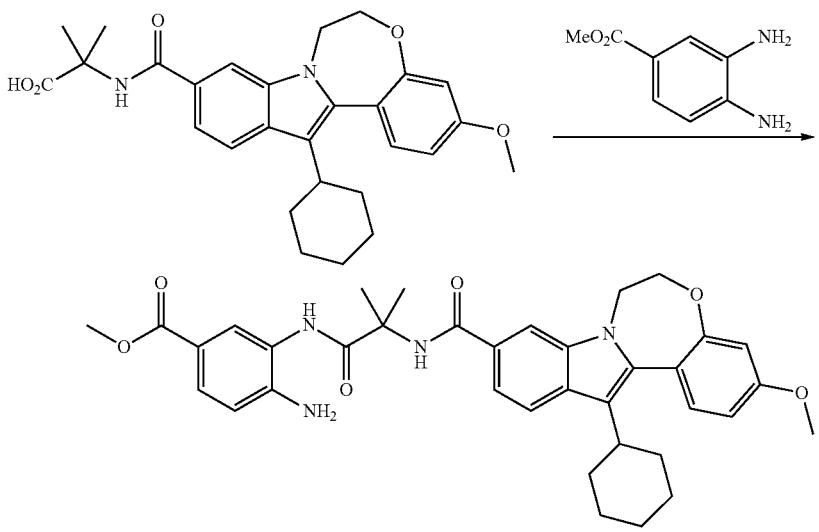

To a solution of 2-[(12-cyclohexyl-3-methoxy-6,7-dihydro-5-oxa-7a-azadibenzo[a,e]azulene-9-carbonyl)amino]-2-methylpropionic acid (0.60 g, 1.26 mmol) in chloroform (18.0 ml) was added a catalytic amount of N,N-dimethylformamide, and thionyl chloride (0.28 ml, 3.78 mmol) was added dropwise under ice-cooling. The mixture was stirred for 2 hr. Then, the reaction mixture was evaporated under reduced pressure to give a yellow solid. Further, the obtained solid was dissolved in chloroform (2.5 ml) and added dropwise to a solution of methyl 3,4-diaminobenzoate (0.29 g, 1.76 mmol) in pyridine (1.5 ml) under ice-cooling. After dropwise addition, the mixture was warmed to room temperature, and the mixture was stirred at overnight. To the reaction mixture were added saturated aqueous sodium hydrogen carbonate solution, methanol and water. The precipitate was collected by filtration, washed with water, and dried in vacuo to give methyl 4-amino-3-{2-[(12-cyclohexyl-3-methoxy-6,7-dihydro-5-oxa-7a-azadibenzo[a,e]azulene-9-carbonyl)amino]-2-methylpropionylamino}benzoate (0.73 g, yield 93%).

$^1$H-NMR (400 MHz, DMSO-$d_6$): δ(ppm) 9.14 (1H, s), 8.45 (1H, s), 8.17 (1H, s), 7.83 (1H, d, J=6.3 Hz), 7.60 (1H, d, J=6.4 Hz), 7.56 (1H, dd, J=6.2, 1.2 Hz), 7.49 (1H, d, J=1.1 Hz), 7.35 (1H, d, J=6.2 Hz), 6.94 (1H, dd, J=1.6, 6.2 Hz), 6.84 (1H, d, J=1.7 Hz), 6.67 (1H, d, J=6.2 Hz), 5.87 (2H, br), 4.51-4.30 (4H, m), 3.83 (3H, s), 3.74 (3H, s), 2.91-2.79 (1H, m), 2.10-1.94 (2H, m), 1.86-1.66 (5H, m), 1.57 (6H, s), 1.43-1.21 (3H, m).

Step 4: Production of methyl 2-{1-[(12-cyclohexyl-3-methoxy-6,7-dihydro-5-oxa-7a-azadibenzo[a,e]azulene-9-carbonyl)amino]-1-methylethyl}-3H-benzimidazole-5-carboxylate (Example 2-514)

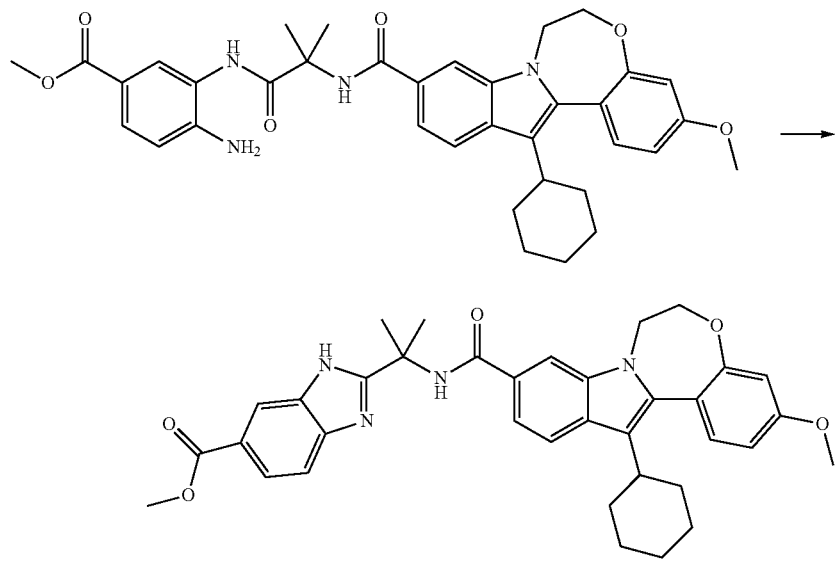

Methyl 4-amino-3-{2-[(12-cyclohexyl-3-methoxy-6,7-dihydro-5-oxa-7a-azadibenzo[a,e]azulene-9-carbonyl)amino]-2-methylpropionylamino}benzoate (0.73 g, 1.16 mmol) was dissolved in acetic acid (14.0 ml), and the mixture was stirred at 100° C. for 2 hr. The mixture was allowed to cool to room temperature, toluene was added, and the solvent was evaporated under reduced pressure. To the obtained residue were added methanol and water. The precipitate was collected by filtration, washed with water, and dried in vacuo to give methyl 2-{1-[(12-cyclohexyl-3-methoxy-6,7-dihydro-5-oxa-7a-azadibenzo[a,e]azulene-9-carbonyl)amino]-1-methylethyl}-3H-benzimidazole-5-carboxylate (0.67 g, yield 95%).

$^1$H-NMR (400 MHz, DMSO-$d_6$): δ(ppm) 12.49-12.40 (1H, m), 8.49-8.43 (1H, m), 8.18-8.14 (1.5H, m), 8.04-8.01 (0.5H, m), 7.85-7.75 (2H, m), 7.65-7.60 (0.5H, m), 7.60-7.55 (1H, m), 7.50-7.47 (0.5H, m), 7.37-7.33 (1H, m), 7.27-7.22 (0.5H, m), 7.20-7.14 (0.5H, m), 6.97-6.92 (1H, m), 6.84 (1H, d, J=1.7 Hz), 4.50-4.31 (4H, m), 3.86 (3H, s), 2.91-2.80 (1H, m), 2.09-1.95 (2H, m), 1.82 (6H, s), 1.87-1.68 (5H, m), 1.43-1.25 (3H, m).

Step 5: Production of 2-{1-[(12-cyclohexyl-3-methoxy-6,7-dihydro-5-oxa-7a-azadibenzo[a,e]azulene-9-carbonyl)amino]-1-methylethyl}-3H-benzimidazole-5-carboxylic acid (Example 2-332)

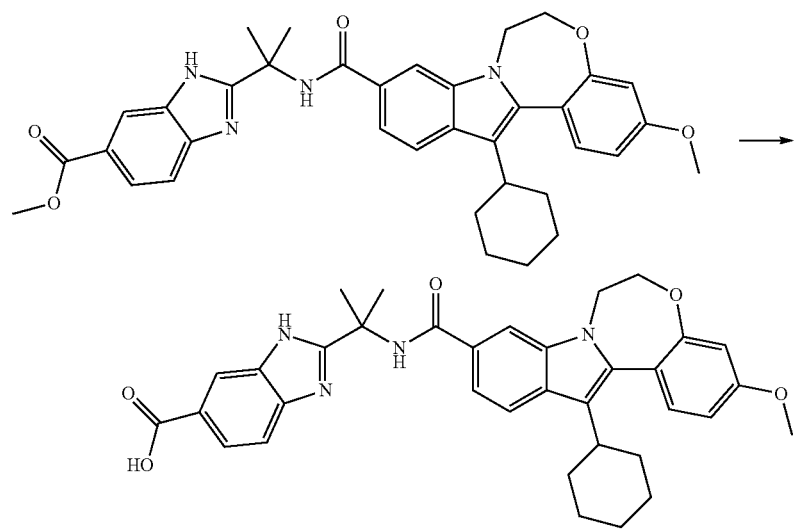

To a mixed solution of methyl 2-{(1-[(12-cyclohexyl-3-methoxy-6,7-dihydro-5-oxa-7a-azadibenzo[a,e]azulene-9-carbonyl)amino]-1-methylethyl}-3H-benzimidazole-5-carboxylate (0.66 g, 1.09 mmol) in tetrahydrofuran (10.0 ml) and methanol (10.0 ml) was added 4N aqueous lithium hydroxide solution (5.00 ml, 20.00 mmol) at room temperature, and the mixture was stirred at 70° C. for 7 hr. The mixture was allowed to cool to room temperature, and 2N hydrochloric acid (11.00 ml, 22.00 mmol) and water were successively added. The mixture was stirred at room temperature for 30 min. Then, the precipitate was collected by filtration, washed with water, and dried in vacuo to give 2-{1-[(12-cyclohexyl-3-methoxy-6,7-dihydro-5-oxa-7a-azadibenzo[a,e]azulene-9-carbonyl)amino]-1-methylethyl}-3H-benzimidazole-5-carboxylic acid (0.65 g, yield 100%).

$^1$H-NMR (300 MHz, DMSO-$d_6$): δ(ppm) 12.49 (1H, brs), 9.00 (1H, s), 8.26 (1H, d, J=12.4 Hz), 8.03 (1H, d, J=8.3 Hz), 7.88-7.74 (2H, m), 7.59 (1H, d, J=8.7 Hz), 7.35 (1H, d, J=8.3 Hz), 6.95 (1H, dd, J=2.6, 8.7 Hz), 6.84 (1H, d, J=2.6Hz), 4.54-4.30 (4H, m), 3.83 (3H, s), 2.94-2.78 (1H, m), 2.12-1.95 (2H, m), 1.92 (6H, s), 1.87-1.65 (5H, m), 1.45-1.20 (3H, m).
MS 593.3 (M+1).

Example 2-346

Production of N-[1-(6-dimethylcarbamoyl-1H-benzimidazol-2-yl)-1-methylethyl]-12-cyclohexyl-3-methoxy-6,7-dihydro-5-oxa-7a-azadibenzo[a,e]azulene-9-carboxamide

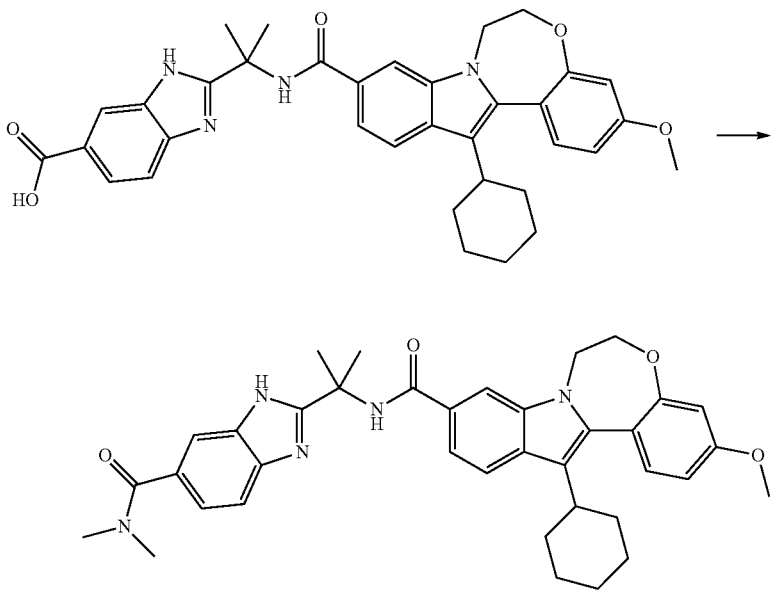

To a solution of 2-{1-[(12-cyclohexyl-3-methoxy-6,7-dihydro-5-oxa-7a-azadibenzo[a,e]azulene-9-carbonyl)amino]-1-methylethyl}-3H-benzimidazole-5-carboxylic acid (0.07 g, 0.12 mmol) in N,N-dimethylformamide (1.0 ml) were successively added 2M dimethylamine-tetrahydrofuran solution (0.30 ml, 0.59 mmol), N-ethyl-N'-3-dimethylaminopropylcarbodiimide hydrochloride (0.03 g, 0.15 mmol) and 1-hydroxybenzotriazole monohydrate (0.02 g, 0.15 mmol) at room temperature, and the mixture was stirred overnight. Saturated aqueous sodium hydrogen carbonate solution, methanol and water were added to the reaction mixture. The precipitate was collected by filtration, washed with water, and dried in vacuo to give N-[1-(6-dimethylcarbamoyl-1H-benzimidazol-2-yl)-1-methylethyl]-12-cyclohexyl-3-methoxy-6,7-dihydro-5-oxa-7a-azadibenzo[a,e]azulene-9-carboxamide (0.05 g, yield 63%).

$^1$H-NMR (300 MHz, DMSO-$d_6$): δ(ppm) 12.67-11.54 (1H, m), 8.56 (1H, brs), 8.15 (1H, s), 7.83 (1H, d, J=8.7 Hz), 7.56 (1H, d, J=8.3 Hz), 7.49 (1H, s), 7.46 (1H, d, J=8.3 Hz), 7.35 (1H, d, J=8.6 Hz), 7.13 (1H, d, J=9.4 Hz), 6.95 (1H, dd, J=2.6, 8.7 Hz), 6.84 (1H, d, J=2.6 Hz), 4.51-4.28 (4H, m), 3.83 (3H, s), 2.98 (6H, s), 2.93-2.79 (1H, m), 2.13-1.93 (2H, m), 1.82 (6H, s), 1.89-1.66 (5H, m), 1.45-1.21 (3H, m)
MS 620.3 (M+1).

Example 2-349

Production of methyl 4-(2-[(12-cyclohexyl-3-methoxy-6,7-dihydro-5-oxa-7a-azadibenzo[a,e]azulene-9-carbonyl)amino]-2-methylpropionylamino)benzoate

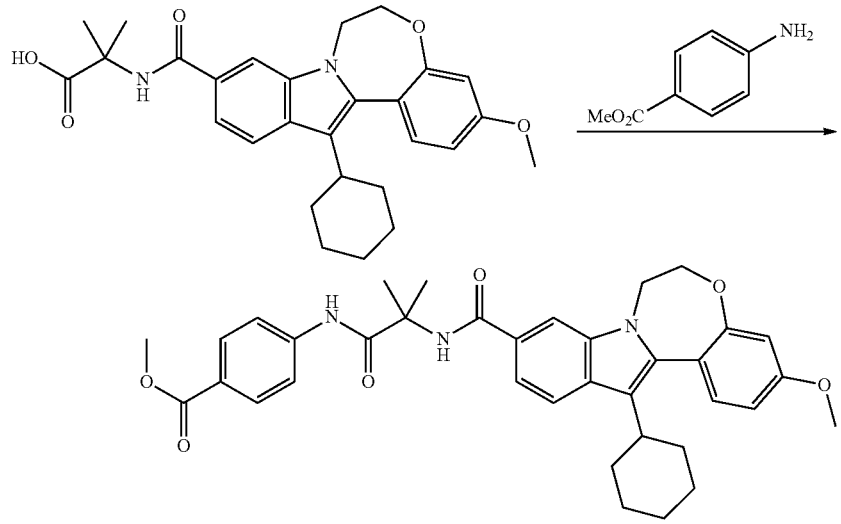

To a solution of 2-[(12-cyclohexyl-3-methoxy-6,7-dihydro-5-oxa-7a-azadibenzo[a,e]azulene-9-carbonyl)amino]-2-methylpropionic acid (200 mg, 0.42 mmol) in chloroform (4.0 ml) was added a catalytic amount of N,N-dimethylformamide solution, thionyl chloride (0.07 ml, 1.26 mmol) was added dropwise under ice-cooling, and the mixture was stirred at room temperature for 3 hr. Then, and the solvent was evaporated under reduced pressure to give a yellow solid. The obtained solid was dissolved in chloroform (1.5 ml), and added dropwise to a solution of methyl 4-aminobenzoate (95.2 mg, 0.63 mmol) in a mixture of chloroform (1.0 ml) and pyridine (1.0 ml) under ice-cooling. Then, methyl 4-aminobenzoate (32 mg, 0.21 mmol) and pyridine (2.0 ml) were added, and the mixture was stirred at room temperature for 24 hr. To the reaction mixture was added aqueous sodium hydrogen carbonate solution and the mixture was extracted with chloroform. The organic layer was washed with saturated brine and dried over anhydrous sodium sulfate. After filtration, the solvent was evaporated under reduced pressure. Methanol and chloroform were added to the residue, and the mixture was stirred. The precipitate was collected by filtration to give methyl 4-{2-[(12-cyclohexyl-3-methoxy-6,7-dihydro-5-oxa-7a-azadibenzo[a,e]azulene-9-carbonyl)amino]-2-methylpropionylamino}benzoate (105 mg, yield 41%).

$^1$H-NMR (300 MHz, CDCl$_3$): δ(ppm) 9.75 (1H, s), 8.21 (2H, d, J=15.0 Hz), 7.89-7.75 (5H, m), 7.61 (1H, d, J=9.0 Hz), 7.34 (1H, d, J=12.0 Hz), 6.96-6.91 (1H, m), 6.84 (1H, d, J=3.0 Hz), 4.49-4.43 (2H, m), 4.39-4.33 (2H, m), 3.83 (3H, s), 3.81 (3H, s), 2.91-2.80 (1H, m), 2.10-1.95 (2H, m), 1.87-1.69 (5H, m), 1.58 (6H, s), 1.44-1.25 (3H, m), 610.3 (M+1).

Example 2-350

Production of 4-{2-[(12-cyclohexyl-3-methoxy-6,7-dihydro-5-oxa-7a-azadibenzo[a,e]azulene-9-carbonyl)amino]-2-methylpropionylamino}benzoic acid

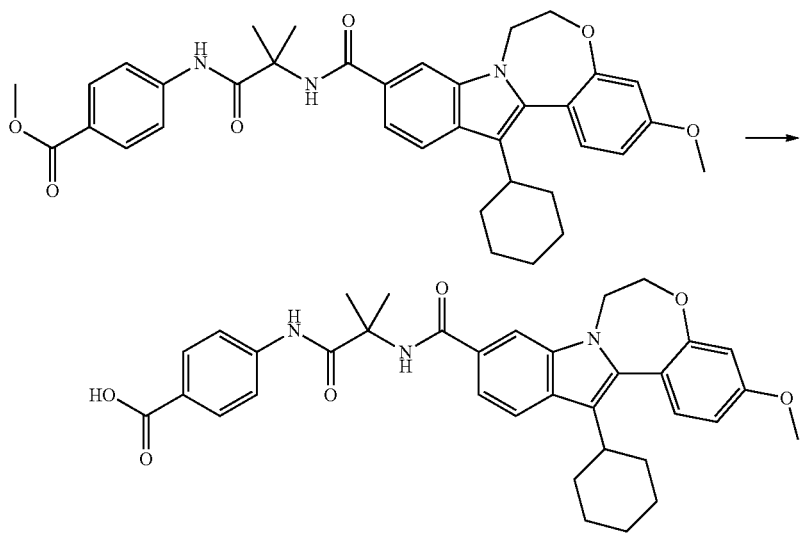

To a solution of methyl 4-{2-[(12-cyclohexyl-3-methoxy-6,7-dihydro-5-oxa-7a-azadibenzo[a,e]azulene-9-carbonyl)amino]-2-methylpropionylamino}benzoate (81 mg, 0.13 mmol) in tetrahydrofuran (8.0 ml) and methanol (2.0 ml) was added 2N aqueous sodium hydroxide solution (1.0 ml, 2.0 mmol), and the mixture was stirred at room temperature for 64 hr. The solvent was evaporated under reduced pressure, 1N aqueous HCl solution (3.0 ml, 3.0 mmol) and methanol (1.0 ml) were added, and the mixture was stirred. The precipitate was collected by filtration to give 4-{2-[(12-cyclohexyl-3-methoxy-6,7-dihydro-5-oxa-7a-azadibenzo[a,e]azulene-9-carbonyl)amino]-2-methylpropionylamino}benzoic acid (73 mg, yield 92%).

$^1$H-NMR (300 MHz, CDCl$_3$): δ(ppm) 12.63 (1H, s), 9.72 (1H, s), 8.21 (2H, d, J=12.0 Hz), 7.86-7.72 (5H, m), 7.61 (1H, d, J=9.0 Hz), 7.35 (1H, d, J=4.0 Hz), 6.96-6.93 (1H, m), 6.84 (1H, d, J=3.0 Hz), 4.51-4.45 (2H, m), 4.39-4.34 (2H, m), 3.83 (3H, s), 2.92-2.79 (1H, m), 2.13-1.93 (2H, m), 1.87-1.69 (5H, m), 1.58 (6H, s), 1.46-1.27 (3H, m), 596.2 (M+1).

Example 2-369

Production of N—(S)-[2-(4-benzyloxyphenyl)-1-(thiazol-2-yl)ethyl]-12-cyclohexyl-3-methoxy-6,7-dihydro-5-oxa-7a-azadibenzo[a,e]azulene-9-carboxamide Step 1: Production of tert-butyl (S)-[2-(4-benzyloxyphenyl)-1-carbamoylethyl]carbamate

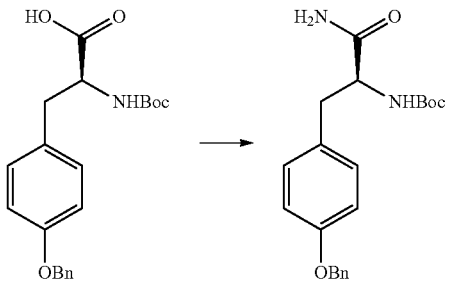

To a solution of (S)-3-(4-benzyloxyphenyl)-2-tert-butoxycarbonylaminopropionic acid (5.00 g, 13.5 mmol) and 1-hydroxybenzotriazole monohydrate (2.50 g, 16.1 mmol) in N,N-dimethylformamide (50 ml) were added 1-ethyl-3-(3'-dimethylaminopropyl)carbodiimide hydrochloride (3.10 g, 16.1 mmol) and 28% aqueous ammonia solution (5 ml) under ice-cooling, and the mixture was stirred at room temperature for 24 hr. Water was added to the reaction mixture and the mixture was extracted with ethyl acetate. The organic layer was successively washed with saturated aqueous sodium hydrogen carbonate solution and saturated brine and dried over anhydrous magnesium sulfate. After filtration, the solvent was evaporated under reduced pressure, and the residue was purified by silica gel chromatography (chloroform:ethyl acetate=2:1-1:1) to give tert-butyl (S)-[2-(4-benzyloxyphenyl)-1-carbamoylethyl]carbamate (1.53 g, yield 31%).

$^1$H-NMR (400 MHz, CDCl$_3$): δ(ppm) 7.44-7.32 (5H, m), 7.15 (2H, d, J=8.8 Hz), 6.93 (2H, d, J=8.3 Hz), 5.79 (1H, brs), 5.48 (1H, brs), 5.07-5.00 (3H, m), 4.37-4.26 (1H, m), 3.09-2.95 (2H, m), 1.42 (9H, s).

Step 2: Production of tert-butyl (S)-[2-(4-benzyloxyphenyl)-1-thiocarbamoylethyl]carbamate

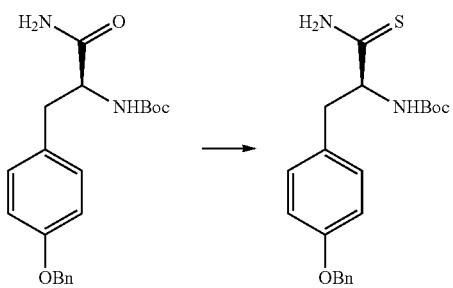

To a solution of tert-butyl (S)-[2-(4-benzyloxyphenyl)-1-carbamoylethyl]carbamate (1.53 g, 4.12 mmol) in tetrahydrofuran (15 ml) was added Lawesson reagent (1.70 g, 4.12 mmol), and the mixture was stirred at room temperature for 5 hr. Saturated aqueous sodium hydrogen carbonate solution was added to the reaction mixture, and the mixture was extracted with ethyl acetate. The organic layer was washed with saturated brine and dried over anhydrous magnesium sulfate. After filtration, the solvent was evaporated under reduced pressure, and the residue was purified by silica gel chromatography (chloroform:ethyl acetate=8:1-5:1). Diisopropy ether was added to the obtained residue. The precipitated solid was collected by filtration and washed with diisopropy ether. The obtained solid was dried in vacuo to give tert-butyl (S)-[2-(4-benzyloxyphenyl)-1-thiocarbamoylethyl]carbamate (540 mg, yield 34%).

$^1$H-NMR (400 MHz, CDCl$_3$): δ(ppm) 7.44-7.31 (6H, m), 7.21 (1H, brs), 7.17 (2H, d, J=8.3 Hz), 6.92 (2H, d, J=8.8 Hz), 5.29 (1H, brs), 5.04 (2H, s), 4.56 (1H, dd, J=7.3, 3.6 Hz), 3.18-3.03 (2H, m), 1.42 (9H, s).

Step 3: Production of tert-butyl (S)-[2-(4-benzyloxyphenyl)-1-(thiazol-2-yl)ethyl]carbamate

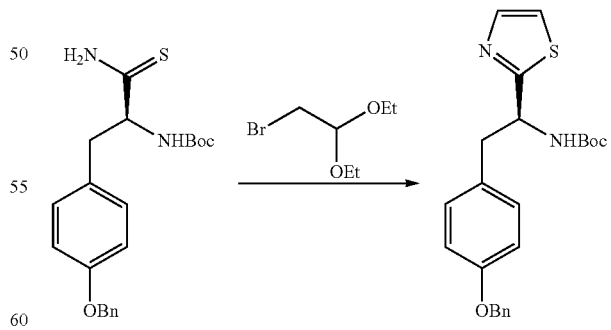

To a solution of tert-butyl (S)-[2-(4-benzyloxyphenyl)-1-thiocarbamoylethyl]carbamate (250 mg, 0.647 mmol) in acetone (5 ml) was added bromoacetaldehyde diethyl acetal (149 μl, 0.970 mmol), and the mixture was stirred at 65° C. for 14 hr. The mixture was further heated to 75° C. and stirred for 5 hr. The solvent was evaporated under reduced pressure, and the obtained residue was purified by silica gel chromatography (hexane:ethyl acetate=4:1) to give text-butyl (S)-[2-(4-benzyloxyphenyl)-1-(thiazol-2-yl)ethyl]carbamate (112 mg, yield 42%).

$^1$H-NMR (400 MHz, CDCl$_3$): δ(ppm) 7.76 (1H, d, J=3.2 Hz), 7.44-7.30 (5H, m), 7.22 (1H, d, J=3.2 Hz), 6.99 (2H, d, J=8.3 Hz), 6.87 (2H, d, J=8.3 Hz), 5.25 (2H, brs), 5.03 (2H, s), 3.27-3.19 (2H, m), 1.42 (9H, s).

Step 4: Production of (S)-2-(4-benzyloxyphenyl)-1-(thiazol-2-yl)ethylamine hydrochloride

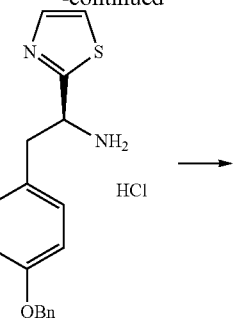

To a solution of tert-butyl (S)-[2-(4-benzyloxyphenyl)-1-(thiazol-2-yl)ethyl]carbamate (112 mg, 0.273 mmol) in ethyl acetate (1 ml) was added 4N HCl-ethyl acetate solution (1 ml), and the mixture was stirred at room temperature for 30 min. The solvent was evaporated under reduced pressure, and hexane:diethyl ether (3:1) solution was added to the obtained residue. The precipitated solid was collected by filtration and washed with hexane:diethyl ether (3:1) solution. The obtained solid was dried in vacuo to give (S)-2-(4-benzyloxyphenyl)-1-(thiazol-2-yl)ethylamine hydrochloride (66 mg, yield 70%).

$^1$H-NMR (400 MHz, DMSO-d$_6$): δ(ppm) 8.81 (3H, brs), 7.87 (1H, d, J=3.2 Hz), 7.74 (1H, d, J=3.2 Hz), 7.43-7.29 (5H, m), 7.05 (2H, d, J=8.8 Hz), 6.90 (2H, d, J=8.3 Hz), 5.04 (2H, s), 5.03-4.94 (1H, m), 3.34 (1H, dd, J=13.7, 5.3 Hz), 3.10 (1H, dd. J=13.4, 9.7 Hz).

Step 5: Production of N—(S)-[2-(4-benzyloxyphenyl)-1-(thiazol-2-yl)ethyl]-12-cyclohexyl-3-methoxy-6,7-dihydro-5-oxa-7a-azadibenzo[a,e]azulene-9-carboxamide (Example 2-369)

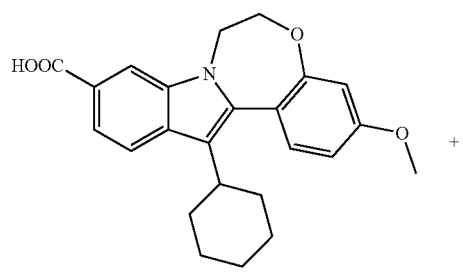

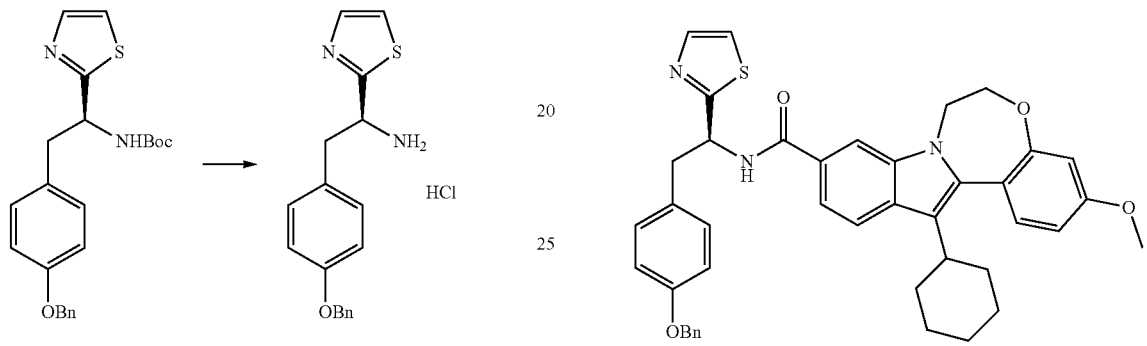

To a solution of 12-cyclohexyl-3-methoxy-6,7-dihydro-5-oxa-7a-azadibenzo[a,e]azulene-9-carboxylic acid (50 mg, 0.13 mmol) and (S)-2-(4-benzyloxyphenyl)-1-(thiazol-2-yl)ethylamine hydrochloride (49 mg, 0.14 mmol) in N,N-dimethylformamide (1 ml) were added 1-hydroxybenzotriazole monohydrate (24 mg, 0.15 mmol), 1-ethyl-3-(3'-dimethylaminopropyl)carbodiimide hydrochloride (29 mg, 0.15 mmol) and triethylamine (43 μl, 0.31 mmol) under ice-cooling, and the mixture was stirred at room temperature for 18 hr. Water was added to the reaction mixture and the mixture was extracted with ethyl acetate. The organic layer was successively washed with saturated aqueous sodium hydrogen carbonate solution and saturated brine and dried over anhydrous magnesium sulfate. After filtration, the solvent was evaporated under reduced pressure. Hexane:diethyl ether (2:1) solution was added to the obtained residue. The precipitated solid was collected by filtration and washed with hexane:diethyl ether (2:1) solution. The obtained solid was dried in vacuo to give N—(S)-[2-(4-benzyloxyphenyl)-1-(thiazol-2-yl)ethyl]-12-cyclohexyl-3-methoxy-6,7-dihydro-5-oxa-7a-azadibenzo[a,e]azulene-9-carboxamide (68 mg, yield 77%).

$^1$H-NMR (300 MHz, DMSO-d$_6$): δ(ppm) 8.95 (1H, d, J=8.8 Hz), 8.06 (1H, s), 7.82 (1H, d, J=8.8 Hz), 7.78 (1H, d, J=3.3 Hz), 7.63 (1H, d, J=3.3 Hz), 7.54 (1H, d, J=8.8 Hz), 7.34 (8H, m), 6.94 (1H, dd, J=8.4, 2.6 Hz), 6.89 (2H, d, J=8.8 Hz), 6.83 (1H, d, J=2.6 Hz), 5.62-5.53 (1H, m), 5.01 (2H, s), 4.49-4.42 (2H, m), 4.36-4.28 (2H, m), 3.83 (3H, s), 3.45 (1H, dd, J=13.9, 4.0 Hz), 3.27-3.20 (1H, m), 2.91-2.80 (1H, m), 2.08-1.94 (2H, m), 1.86-1.68 (5H, m), 1.41-1.25 (3H, m).
MS 684.2 (M+1).

Example 2-381

Production of N—(S)-[2-(4-hydroxyphenyl)-1-(thiazol-2-yl)ethyl]-12-cyclohexyl-3-methoxy-6,7-dihydro-5-oxa-7a-azadibenzo[a,e]azulene-9-carboxamide

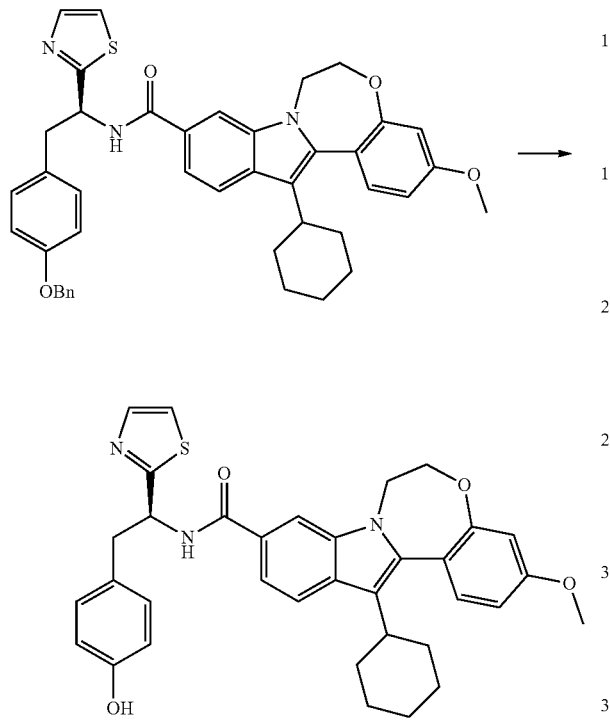

To N—(S)-[2-(4-benzyloxyphenyl)-1-(thiazol-2-yl)ethyl]-12-cyclohexyl-3-methoxy-6,7-dihydro-5-oxa-7a-azadibenzo[a,e]azulene-9-carboxamide (58 mg, 0.10 mmol) was added 25% hydrogen bromide-acetic acid solution (1 ml), and the mixture was stirred at room temperature for 30 min. Saturated aqueous sodium hydrogen carbonate solution was added to the reaction mixture, and the mixture was extracted with ethyl acetate. The organic layer was washed with saturated brine and dried over anhydrous magnesium sulfate. After filtration, the solvent was evaporated under reduced pressure. To the obtained residue was added hexane:diethyl ether (2:1) solution, and the precipitated solid was collected by filtration and washed with hexane:diethyl ether (2:1) solution. The obtained solid was dried in vacuo to give N-(S)-[2-(4-hydroxyphenyl)-1-(thiazol-2-yl)ethyl]-12-cyclohexyl-3-methoxy-6,7-dihydro-5-oxa-7a-azadibenzo[a,e]azulene-9-carboxamide (50 mg, yield 85%).

$^1$H-NMR (300 MHz, DMSO-$d_6$): δ(ppm) 9.12 (1H, s), 8.91 (1H, d, J=8.8 Hz), 8.05 (1H, s), 7.82 (1H, d, J=8.4 Hz), 7.78 (1H, d, J=2.9 Hz), 7.62 (1H, d, J=3.3 Hz), 7.53 (1H, d, J=7.3 Hz), 7.33 (1H, d, J=8.4 Hz), 7.14 (2H, d, J=8.4 Hz), 6.94 (1H, dd, J=8.4, 2.6 Hz), 6.83 (1H, d, J=2.6 Hz), 6.63 (2H, d, J=8.4 Hz), 5.57-5.49 (1H, m), 4.49-4.42 (2H, m), 4.36-4.28 (2H, m), 3.83 (3H, s), 3.43-3.35 (1H, m), 3.22-3.14 (1H, m), 2.90-2.80 (1H, m), 2.08-1.94 (2H, m), 1.85-1.69 (5H, m), 1.41-1.23 (3H, m).

MS 594.2 (M+1).

Example 2-427

Production of N—[(S)-2-(4-hydroxyphenyl)-1-(N-methoxy-N-methylcarbamoyl)ethyl]-12-cyclohexyl-3-methoxy-6,7-dihydro-5-oxa-7a-azadibenzo[a,e]azulene-9-carboxamide

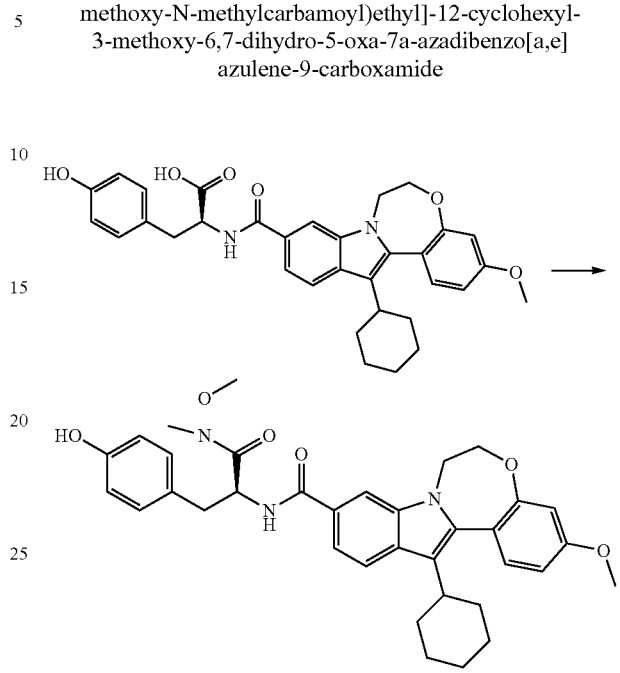

To a solution of (S)-2-[(12-cyclohexyl-3-methoxy-6,7-dihydro-5-oxa-7a-azadibenzo[a,e]azulene-9-carbonyl)amino]-3-(4-hydroxyphenyl)propionic acid (50.0 mg, 0.090 mmol) synthesized in the same manner as in Examples 2-175 and 2-180, N,O-dimethylhydroxylamine hydrochloride (10.5 mg, 0.180 mmol), 1-hydroxybenzotriazole monohydrate (15.2 mg, 0.38 mmol) and 1-ethyl-3-(3'-dimethylaminopropyl)carbodiimide hydrochloride (20.7 mg, 0.108 mmol) in N,N-dimethylformamide (1 ml) was added triethylamine (25.1 μl, 0.180 mmol), and the mixture was stirred overnight at room temperature. Saturated aqueous sodium hydrogen carbonate solution was added to the reaction mixture. The precipitated solid was collected by filtration, further washed with water and dried in vacuo. The obtained residue was purified by silica gel chromatography (hexane:ethyl acetate=1:4). To the obtained residue was added a mixed solvent of hexane:ethyl acetate (5:1), and the precipitated solid was collected by filtration and washed with a mixed solvent of hexane:ethyl acetate (5:1). The obtained solid was dried in vacuo to give N-[(S)-2-(4-hydroxyphenyl)-1-(N-methoxy-N-methylcarbamoyl)ethyl]-12-cyclohexyl-3-methoxy-6,7-dihydro-5-oxa-7a-azadibenzo[a,e]azulene-9-carboxamide (30.0 mg, yield 54.1%).

$^1$H-NMR (400 MHz, DMSO-$d_6$): δ(ppm) 9.18 (1H, s), 8.46 (1H, d, J=8.6 Hz), 8.12 (1H, brs), 7.81 (1H, d, J=8.6 Hz), 7.53 (1H, dd, J=8.6, 1.4 Hz), 7.34 (1H, d, J=8.6 Hz), 7.13 (2H, d, J=8.6 Hz), 6.95 (1H, dd, J=8.6, 2.6 Hz), 6.84 (1H, d, J=2.6 Hz), 6.66 (2H, d, J=8.6 Hz), 5.18-5.04 (1H, m), 4.47 (2H, brt, J=5.6 Hz), 4.37-4.30 (2H, brm), 3.83 (1H, s), 3.80 (3H, brs), 3.14 (3H, s), 2.95-2.79 (3H, m), 2.08-1.95 (2H, m), 1.85-1.67 (5H, m), 1.48-1.21 (3H, m).

MS 598.2 (M+1).

Example 2-481

Production of 12-cyclohexyl-4-{N-[2-(piperidin-1-yl)ethyl]-N-propylamino}-6,7-dihydro-5-oxa-7a-azadibenzo[a,e]azulene-9-carboxylic acid dihydrochloride

Step 1: Production of methyl 3-cyclohexyl-2-(4,4,5,5-tetramethyl-1,3,2-dioxaborolan-2-yl)-1H-indole-6-carboxylate

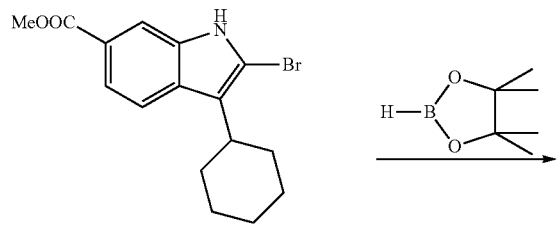

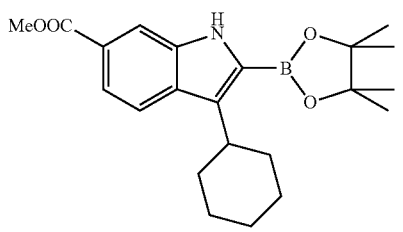

To a solution of methyl 2-bromo-3-cyclohexyl-1H-indole-6-carboxylate (40.00 g, 119.0 mmol) obtained in the same manner as in the method described in WO03/010140 in 1,4-dioxane (400 ml) was added pinacolborane (51.8 ml, 357.0 mmol). Triethylamine (66.3 ml, 476.0 mmol) was added dropwise at room temperature and the mixture was stirred for 3 hr. (2-Biphenyl)dicyclohexylphosphine (5.01 g, 14.3 mmol) and palladium(II) acetate (802 mg, 3.57 mmol) were added and the reaction mixture was heated to 85° C. and stirred for 1.5 hr. The reaction mixture was cooled to room temperature, saturated aqueous ammonium chloride solution was added, and the mixture was extracted with ethyl acetate. The organic layer was successively washed with saturated aqueous ammonium chloride solution and saturated brine and dried over anhydrous magnesium sulfate. After filtration, the solvent was evaporated under reduced pressure. The residue was subjected to azeotropic evaporation with toluene and the precipitated solid was washed with a mixed solvent of (hexane:ethyl acetate=20:1). The solid was collected by filtration to give methyl 3-cyclohexyl-2-(4,4,5,5-tetramethyl-1,3,2-dioxaborolan-2-yl)-1H-indole-6-carboxylate (39.20 g, yield 86%).

$^1$H-NMR (400 MHz, DMSO-d$_6$): δ(ppm) 11.28 (1H, s), 8.04 (1H, d, J=1.4 Hz), 7.82 (1H, d, J=8.6 Hz), 7.53 (1H, dd, J=8.6, 1.4 Hz), 3.85 (3H, s), 2.53-2.48 (1H, m), 2.00-1.64 (7H, m), 1.45-1.27 (3H, m), 1.35 (12H, s).

Step 2: Production of methyl 3-cyclohexyl-2-[(3-nitro-2-[2-(tetrahydropyran-2-yloxy)ethoxy]phenyl]-1H-indole-6-carboxylate

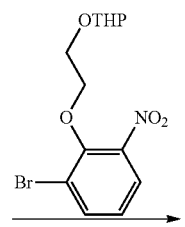

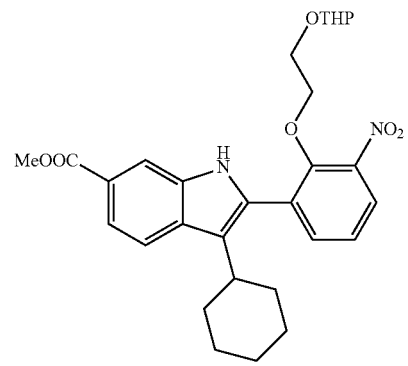

To a solution of 2-[2-(2-bromo-6-nitrophenoxy)ethoxy]tetrahydropyran (12.30 g, 35.6 mmol) in 1,2-dimethoxyethane (150 ml) and water (75 ml) was added sodium hydrogen carbonate (9.74 g, 117.0 mmol) and tetrakis(triphenylphosphine)palladium (4.52 g, 3.91 mmol) and the mixture was heated at 85° C. for 15 min. Methyl 3-cyclohexyl-2-(4,4,5,5-tetramethyl-1,3,2-dioxaborolan-2-yl)-1H-indole-6-carboxylate (16.40 g, 35.6 mmol) was added in 6 divided portions to the reaction mixture at 30 min intervals, and the mixture was stirred at the same temperature for 1 hr. The reaction mixture was allowed to cool to room temperature, water was added to the reaction mixture and the mixture was extracted with ethyl acetate. The organic layer was successively washed with saturated aqueous sodium hydrogen carbonate solution and saturated brine and dried over anhydrous magnesium sulfate. After filtration, the solvent was evaporated under reduced pressure, and the residue was purified by silica gel chromatography (hexane:ethyl acetate=3.5:1) to give methyl 3-cyclohexyl-2-{3-nitro-2-[2-(tetrahydropyran-2-yloxy)ethoxy]phenyl}-1H-indole-6-carboxylate (14.40 g, yield 77%).

$^1$H-NMR (400 MHz, DMSO-d$_6$): δ(ppm) 11.65 (1H, s), 8.02 (1H, d, J=1.4 Hz), 7.98 (1H, dd, J=8.8, 1.4 Hz), 7.87 (1H, d, J=8.8 Hz), 7.66 (1H, dd, J=8.1, 1.6 Hz), 7.62 (1H, dd, J=8.1, 1.6 Hz), 7.45 (1H, t, J=8.1 Hz), 4.27-4.24 (1H, m), 3.86 (3H, s), 3.73-3.63 (2H, m), 3.53-3.13 (4H, m), 2.64 (1H, brt, J=12.3 Hz), 2.01-1.62 (7H, m), 1.55-1.15 (9H, m).

499

Step 3: Production of methyl 3-cyclohexyl-2-[2-(2-hydroxyethoxy)-3-nitrophenyl]-1H-indole-6-carboxylate

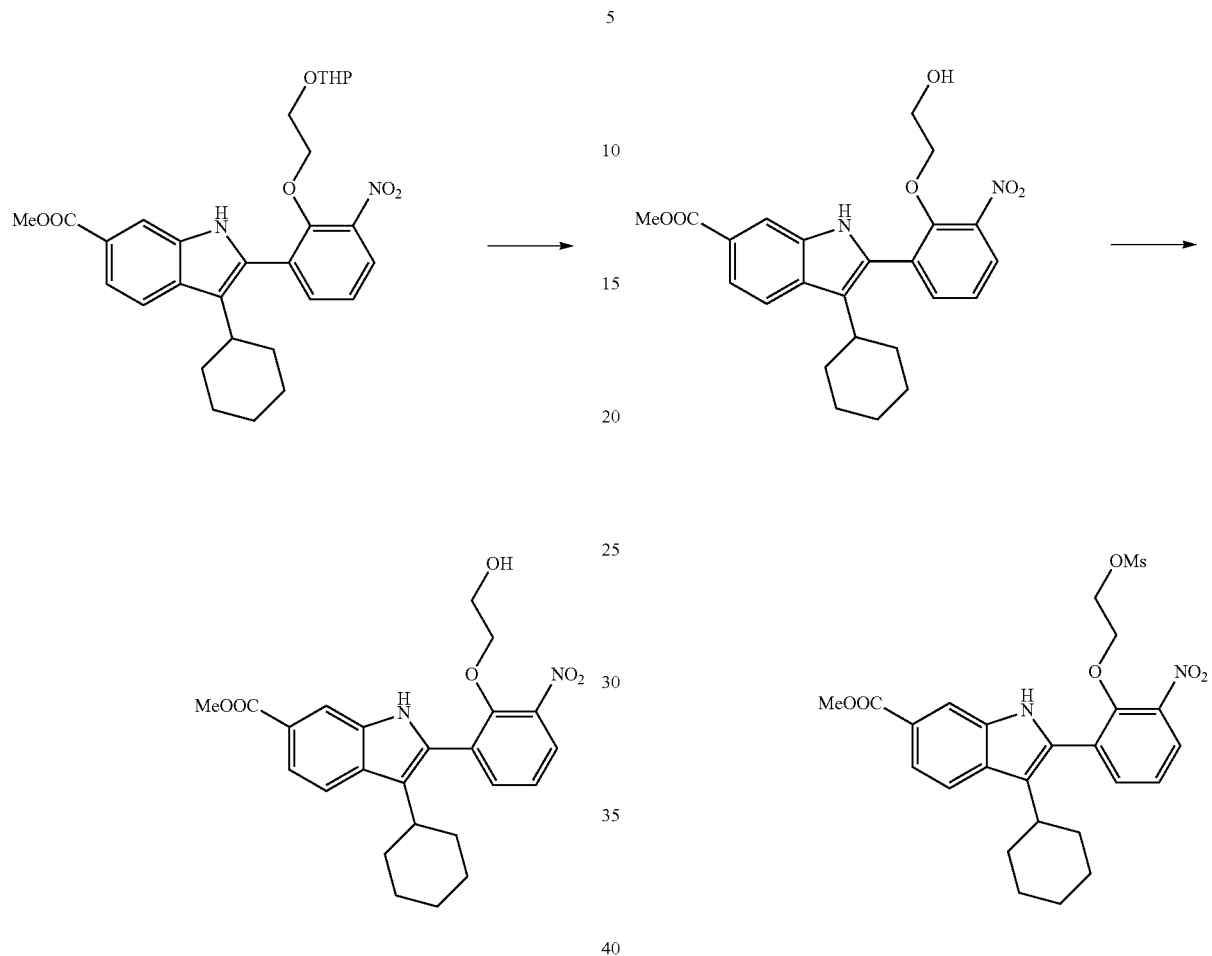

500

Step 4: Production of methyl 3-cyclohexyl-2-[2-(2-methanesulfonyloxyethoxy)-3-nitrophenyl]-1H-indole-6-carboxylate

To a solution of methyl 3-cyclohexyl-2-{3-nitro-2-[2-(tetrahydropyran-2-yloxy)ethoxy]phenyl}-1H-indole-6-carboxylate (6.48 g, 18.6 mmol) in tetrahydrofuran (30 ml) and methanol (90 ml) was added 6N hydrochloric acid (15 ml), and the mixture was stirred at room temperature for 1 hr. The reaction mixture was neutralized with 4N aqueous sodium hydroxide solution (22.5 ml), saturated aqueous sodium hydrogen carbonate solution was added, and the mixture was extracted with ethyl acetate. The organic layer was washed with saturated brine and dried over anhydrous magnesium sulfate. After filtration, the solvent was evaporated under reduced pressure, and the residue was purified by silica gel chromatography (hexane:ethyl acetate=3:1-2:1) to give methyl 3-cyclohexyl-2-[2-(2-hydroxyethoxy)-3-nitrophenyl]-1H-indole-6-carboxylate (11.00 g, yield 91%).

$^1$H-NMR (400 MHz, DMSO-$d_6$): δ(ppm) 11.63 (1H, s), 8.02 (1H, d, J=1.6 Hz), 7.97 (1H, dd, J=8.1, 1.6 Hz), 7.88 (1H, d, J=8.1 Hz), 7.65 (1H, dd, J=7.9, 1.4 Hz), 7.62 (1H, dd, J=7.9, 1.4 Hz), 7.44 (1H, t, J=7.9 Hz), 4.61 (1H, t, J=5.1 Hz), 3.87 (3H, s), 3.56 (2H, t, J=5.6 Hz), 3.33 (2H, t, J=5.6 Hz), 2.64 (1H, brt, J=12.1 Hz), 2.01-1.63 (7H, m), 1.43-1.17 (3H, m).

To a solution of methyl 3-cyclohexyl-2-[2-(2-hydroxyethoxy)-3-nitrophenyl]-1H-indole-6-carboxylate (11.00 g, 25.1 mmol) and triethylamine (5.25 ml, 37.7 mmol) in chloroform (77 ml) was added dropwise methanesulfonyl chloride (2.33 ml, 30.1 mmol) under ice-cooling, and the mixture was stirred for 30 min. Saturated aqueous sodium hydrogen carbonate solution was added to the reaction mixture, and the mixture was extracted with ethyl acetate. The organic layer was successively washed with saturated aqueous ammonium chloride solution, saturated aqueous sodium hydrogen carbonate solution and saturated brine and dried over anhydrous magnesium sulfate. After filtration, the solvent was evaporated under reduced pressure to give methyl 3-cyclohexyl-2-[2-(2-methanesulfonyloxyethoxy)-3-nitrophenyl]1H-indole-6-carboxylate (12.60 g, yield 97%).

$^1$H-NMR (400 MHz, DMSO-$d_6$): δ (ppm) 11.66 (1H, s), 8.02 (1H, d, J=1.4 Hz), 8.02 (1H, dd, J=8.3, 1.4 Hz), 7.88 (1H, d, J=8.3 Hz), 7.68 (1H, dd, J=8.3, 1.4 Hz), 7.63 (1H, dd, J=8.3, 1.4 Hz), 7.49 (1H, t, J=8.3 Hz), 4.14-4.10 (2H, m), 3.86 (3H, s), 3.80-3.75 (2H, m), 2.94 (3H, s), 2.64 (1H, brt, J=12.1 Hz), 1.99-1.96 (7H, m), 1.42-1.40 (3H, m).

Step 5: Production of methyl 12-cyclohexyl-4-nitro-6,7-dihydro-5-oxa-7a-azadibenzo[a,e]azulene-9-carboxylate (Example 2-515)

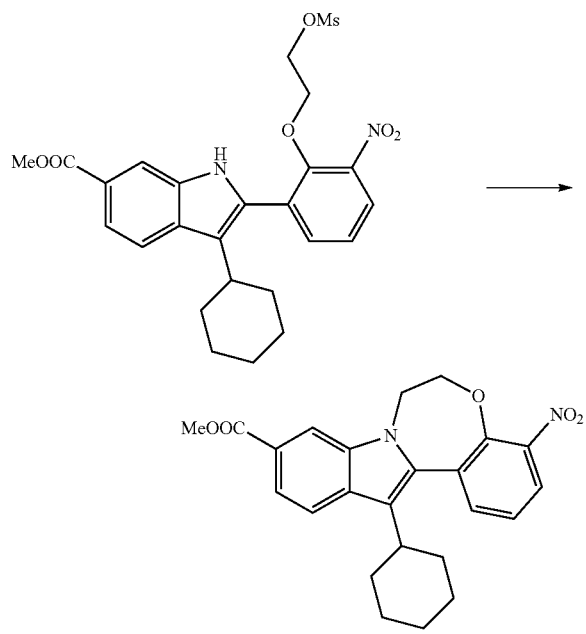

To a solution of methyl 3-cyclohexyl-2-[2-(2-methane-sulfonyloxyethoxy)-3-nitrophenyl]-1H-indole-6-carboxylate (12.60 g, 24.4 mmol) in N,N-dimethylformamide (190 ml) was added potassium carbonate (5.06 g, 36.6 mmol), and the mixture was stirred at 90° C. for 1.5 hr. The reaction mixture was allowed to iv cool to room temperature, water was added to the reaction mixture, and the mixture was extracted with ethyl acetate. The organic layer was successively washed with water and saturated brine and dried over anhydrous magnesium sulfate. After filtration, the solvent was concentrated under reduced pressure to give methyl 12-cyclohexyl-4-nitro-6,7-dihydro-5-oxa-7a-azadibenzo[a,e]azulene-9-carboxylate (9.96 g, yield 97%).

¹H-NMR (400 MHz, DMSO-d₆): δ(ppm) 8.29 (1H, d, J=1.4 Hz), 8.05 (1H, dd, J=8.5, 1.4 Hz), 7.97 (1H, d, J=8.5 Hz), 7.75 (1H, dd, J=8.0, 1.4 Hz), 7.67 (1H, dd, J=8.0, 1.4 Hz), 7.58 (1H, t, J=8.0 Hz), 4.68-4.61 (2H, m), 4.55 (2H, brs), 3.89 (3H, s), 2.84 (1H, brt, J=12.1 Hz), 2.10-1.95 (2H, m), 1.88-1.68 (5H, m), 1.48-1.26 (3H, m).

Step 6: Production of methyl 4-amino-12-cyclohexyl-6,7-dihydro-5-oxa-7a-azadibenzo[a,e]azulene-9-carboxylate (Example 2-516)

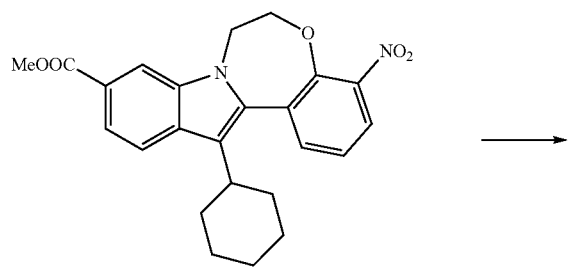

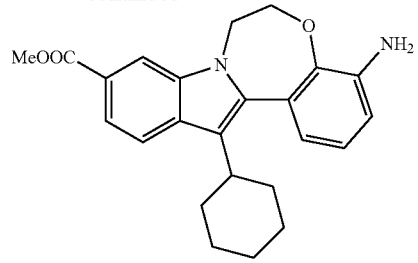

To a solution of methyl 12-cyclohexyl-4-nitro-6,7-dihydro-5-oxa-7a-azadibenzo[a,e]azulene-9-carboxylate (9.94 g, 23.6 mmol) in tetrahydrofuran (85 ml), ethanol (170 ml) and water (42.5 ml) were added ammonium chloride (6.31 g, 118 mmol) and reduced iron (6.60 g, 118 mmol), and the mixture was stirred at 100° C. for 2 hr. After filtration of the reaction solution, saturated aqueous sodium hydrogen carbonate solution was added to the filtrate, and the mixture was extracted with ethyl acetate. The organic layer was washed with saturated brine and dried over anhydrous magnesium sulfate. After filtration, the solvent was concentrated under reduced pressure to give a solid. The obtained solid was washed with a mixed solvent (hexane:ethyl acetate-20:1). The solid was collected by filtration to give methyl 4-amino-12-cyclohexyl-6,7-dihydro-5-oxa-7a-azadibenzo[a,e]azulene-9-carboxylate (8.62 g, yield 93%).

¹H-NMR (300 MHz, DMSO-d₆): δ(ppm) 8.20 (1H, d, J=1.4 Hz), 7.88 (1H, d, J=8.3 Hz), 7.63 (1H, dd, J=8.3, 1.4 Hz), 7.01 (1H, t, J=7.9 Hz), 6.82 (1H, dd, J=7.9, 1.4 Hz), 6.58 (1H, dd, J 7.9, 1.4 Hz), 5.15 (2H, s), 4.44-4.38 (2H, m), 4.33 (2H, brs), 2.95 (1H, brt, J=12.1 Hz), 2.07-1.93 (2H, m), 1.86-1.65 (5H, m), 1.46-1.21 (3H, m).

Step 7: Production of methyl 4-{bis[2-oxo-2-(piperidin-1-yl)ethyl]amino}-12-cyclohexyl-6,7-dihydro-5-oxa-7a-azadibenzo[a,e]azulene-9-carboxylate (Example 2-517) and methyl 12-cyclohexyl-4-[2-oxo-2-(piperidin-1-yl)ethylamino]-6,7-dihydro-5-oxa-7a-azadibenzo[a,e]azulene-9-carboxylate (Example 2-518)

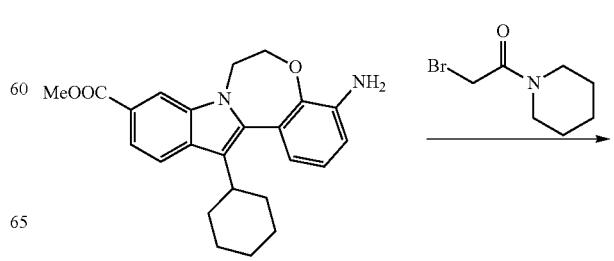

-continued

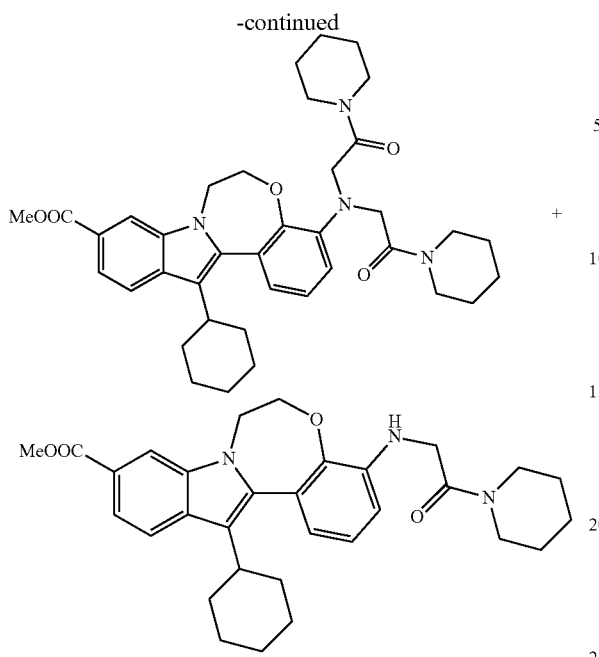

To a solution of methyl 4-amino-12-cyclohexyl-6,7-dihydro-5-oxa-7a-azadibenzo[a,e]azulene-9-carboxylate (3.50 g, 8.96 mmol) in N,N-dimethylformamide (35.0 ml) were added potassium carbonate (6.20 g, 44.8 mmol), sodium iodide (1.48 g, 8.91 mmol) and 1-(2-bromoacetyl)piperidine (3.60 g, 17.4 mmol), and the mixture was stirred at 90° C. for 3 hr. The mixture was allowed to cool to room temperature and water was added, and the mixture was extracted with ethyl acetate. The organic layer was successively washed with water and hexane and dried in vacuo. The residue was purified by silica gel chromatography (hexane:ethyl acetate=2:1-1:5) to give methyl 4-{bis[2-oxo-2-(piperidin-1-yl)ethyl]amino}-12-cyclohexyl-6,7-dihydro-5-oxa-7a-azadibenzo[a,e]azulene-9-carboxylate (3.31 g, yield 58%) and methyl 12-cyclohexyl-4-[2-oxo-2-(piperidin-1-yl)ethyl]amino)-6,7-dihydro-5-oxa-7a-azadibenzo[a,e]azulene-9-carboxylate (2.15 g, yield 47%).

methyl 4-{bis[2-oxo-2-(piperidin-1-yl)ethyl]amino}-12-cyclohexyl-6,7-dihydro-5-oxa-7a-azadibenzo[a,e]azulene-9-carboxylate (Example 2-517)

$^1$H-NMR (300 MHz, CDCl$_3$): δ(ppm) 8.05 (1H, d, J=1.5 Hz), 7.87 (1H, d, J=8.4 Hz), 7.74 (1H, dd, J=8.4, 1.5 Hz), 7.10 (1H, t, J=7.9 Hz), 6.87 (1H, dd, J=7.7, 1.5 Hz), 6.82 (1H, d, J=8.1 Hz), 4.39 (2H, t, J=5.7 Hz), 4.30 (4H, brs), 4.25-4.12 (2H, m), 3.94 (3H, s), 3.58 (4H, t, J=5.1 Hz), 3.37 (4H, t, J=5.1 Hz), 2.95 (1H, brt, J=10.5 Hz), 2.12-1.95 (3H, m), 1.91-1.74 (3H, m), 1.69-1.47 (14H, m), 1.42-1.30 (2H, m).

methyl 12-cyclohexyl-4-[2-oxo-2-(piperidin-1-yl)ethylamino]-6,7-dihydro-5-oxa-7a-azadibenzo[a,e]azulene-9-carboxylate (Example 2-518)

$^1$H-NMR (300 MHz, CDCl$_3$): δ(ppm) 8.07 (1H, s), 7.88 (1H, d, J=8.4 Hz), 7.75 (1H, dd, J=8.4, 1.5 Hz), 7.13 (1H, t, J=7.9 Hz), 6.76 (1H, dd, J=7.7, 1.5 Hz), 6.64 (1H, dd, J=7.7, 1.5 Hz), 5.62 (1H, brs), 4.57 (2H, t, J=5.7 Hz), 4.30 (2H, t, J=5.1 Hz), 3.96-3.92 (2H, m), 3.94 (3H, s), 3.65-3.61 (2H, m), 3.43-3.40 (2H, m), 3.02 (1H, t, J=11.9 Hz), 2.07-2.00 (2H, m), 1.90-1.50 (12H, m), 1.36 (2H, s).

Step 8: Production of methyl 4-{bis[2-(piperidin-1-yl)ethyl]amino}-12-cyclohexyl-6,7-dihydro-5-oxa-7a-azadibenzo[a,e]azulene-9-carboxylate (Example 2-519)

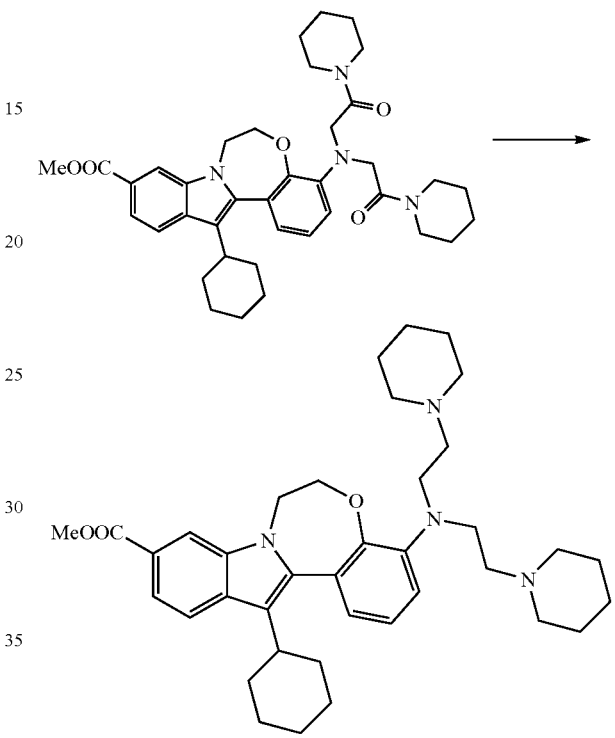

To a solution of methyl 4-{bis[2-oxo-2-(piperidin-1-yl)ethyl]amino}-12-cyclohexyl-6,7-dihydro-5-oxa-7a-azadibenzo[a,e]azulene-9-carboxylate (500 mg, 0.78 mmol) in tetrahydrofuran (2.0 ml) was added a solution (5.0 ml) of 1M BH$_3$ THF complex in tetrahydrofuran, and the mixture was stirred at room temperature for 14 hr. 2N Hydrochloric acid was added to the reaction mixture, and the mixture was stirred at 70° C. for 4 hr. The reaction mixture was allowed to cool to room temperature, neutralized with 4N aqueous sodium hydroxide solution and saturated aqueous sodium hydrogen carbonate solution, and extracted with ethyl acetate. The organic layer was washed with saturated brine and dried over anhydrous sodium sulfate. After filtration, the solvent was evaporated under reduced pressure, and the residue was purified by silica gel chromatography (chloroform:methanol-10:1-5:1) to give methyl 4-{bis[2-(piperidin-1-yl)ethyl]amino}-12-cyclohexyl-6,7-dihydro-5-oxa-7a-azadibenzo[a,e]azulene-9-carboxylate (401 mg, yield 84%).

$^1$H-NMR (300 MHz, CDCl$_3$): δ(ppm) 8.06 (1H, s), 7.88 (1H, d, J=8.4 Hz), 7.75 (1H, d, J=8.4 Hz), 7.20-7.05 (2H, m), 6.97 (1H, d, J=6.6 Hz), 4.46 (2H, t, J=5.7 Hz), 4.23 (2H, brs), 3.95 (3H, s), 3.50-3.33 (4H, m), 3.02-2.95 (1H, m), 2.60-2.47 (4H, m), 2.46-2.36 (6H, m), 2.17-1.98 (2H, m), 1.95-1.75 (6H, m), 1.70-1.49 (9H, m), 1.47-1.33 (7H, m).

Step 9: Production of 4-{bis[2-(piperidin-1-yl)ethyl]amino}-12-cyclohexyl-6,7-dihydro-5-oxa-7a-azadibenzo[a,e]azulene-9-carboxylic acid trihydrochloride (Example 2-520)

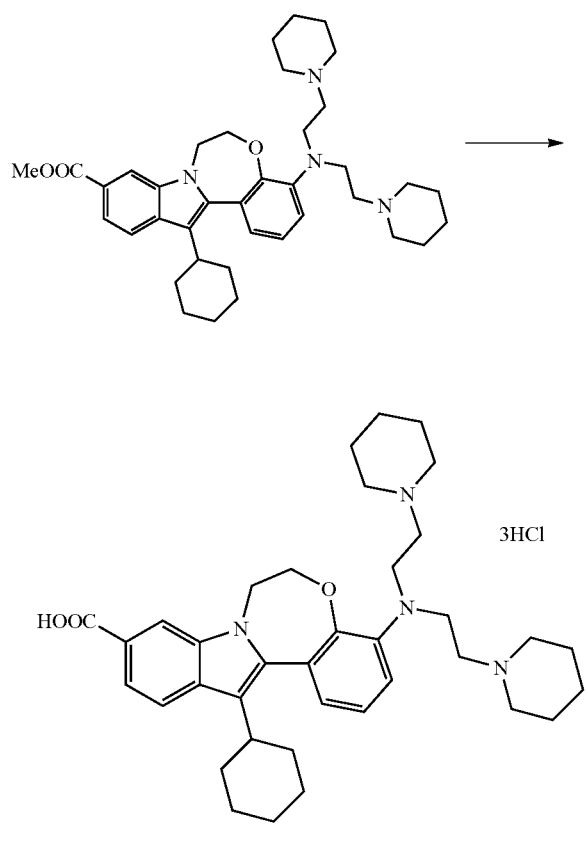

To a solution of methyl 4-{bis[2-(piperidin-1-yl)ethyl]amino}-12-cyclohexyl-6,7-dihydro-5-oxa-7a-azadibenzo[a,e]azulene-9-carboxylate (401 mg, 0.65 mmol) in tetrahydrofuran (4.0 ml) and methanol (4.0 ml) was added 4N aqueous sodium hydroxide solution (4.0 ml), and the mixture was stirred at room temperature for 12 hr. The reaction mixture was adjusted to pH 6 with 2N hydrochloric acid, and extracted with chloroform. The organic layer was washed with saturated brine and dried over anhydrous sodium sulfate. After filtration, the mixture was concentrated under reduced pressure, and ethyl acetate was added to the residue. The precipitated solid was collected by filtration to give 4-{bis[2-(piperidin-1-yl)ethyl]amino}-12-cyclohexyl-6,7-dihydro-5-oxa-7a-azadibenzo[a,e]azulene-9-carboxylic acid. To a solution of the obtained 4-{bis[2-(piperidin-1-yl)ethyl]amino}-12-cyclohexyl-6,7-dihydro-5-oxa-7a-azadibenzo[a,e]azulene-9-carboxylic acid in chloroform was added 4N HCl-ethyl acetate solution (4.0 ml). The reaction mixture was concentrated under reduced pressure and ethyl acetate was added. The precipitated solid was collected by filtration and dried in vacuo to give 4-{bis[2-(piperidin-1-yl)ethyl]amino}-12-cyclohexyl-6,7-dihydro-5-oxa-7a-azadibenzo[a,e]azulene-9-carboxylic acid trihydrochloride (338 mg, yield 73%).

$^1$H-NMR (400 MHz, DMSO-d$_6$): δ(ppm) 10.61 (2H, brs), 8.22 (1H, d, J=0.9 Hz), 7.89 (1H, d, J=8.3 Hz), 7.63 (1H, dd, J=8.3, 1.4 Hz), 7.41 (1H, t, J=4.6 Hz), 7.29 (1H, t, J=7.9 Hz), 7.09 (1H, dd, J=16.5, 7.2 Hz), 5.20 (1H, brs), 4.50 (2H, t, J=5.1 Hz), 4.45-4.21 (2H, m), 3.59 (4H, t, J=7.0 Hz), 3.45 (4H, d, J=11.6 Hz), 3.24 (4H, dd, J=11.6, 7.0 Hz), 2.97-2.77 (5H, m), 2.10-1.95 (2H, m), 1.90-1.67 (15H, m), 1.45-1.20 (5H, m).

MS 599.4 (M+1).

Step 10: Production of methyl 12-cyclohexyl-4-{N-[2-oxo-2-(piperidin-1-yl)ethyl]-N-propylamino}-6,7-dihydro-5-oxa-7a-azadibenzo[a,e]azulene-9-carboxylate (Example 2-521)

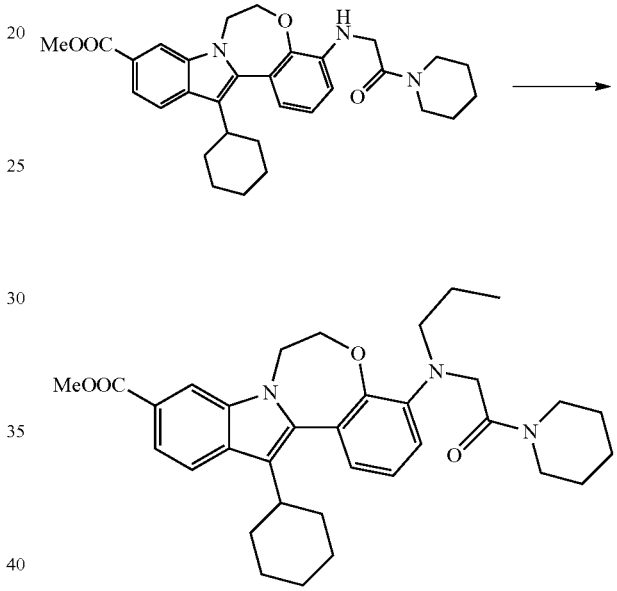

To a solution of methyl 12-cyclohexyl-4-[2-oxo-2-(piperidin-1-yl)ethylamino]-6,7-dihydro-5-oxa-7a-azadibenzo[a,e]azulene-9-carboxylate (3.40 g, 6.59 mmol) obtained in Step 7 and propionaldehyde (4.76 ml, 65.9 mmol) in chloroform (20 ml), water (20 ml) and acetic acid (1 ml) was added sodium triacetoxyborohydride (6.98 g, 33.0 mmol) under ice-cooling, and the mixture was stirred for 8 hr. Saturated aqueous sodium hydrogen carbonate solution was added to the reaction mixture, and the mixture was extracted with ethyl acetate. The organic layer was successively washed with saturated aqueous sodium hydrogen carbonate solution, water and saturated brine and dried over anhydrous magnesium sulfate.

After filtration, the solvent was evaporated under reduced pressure, and the residue was purified by silica gel column chromatography (hexane:ethyl acetate=2:1-1.5:1) to give methyl 12-cyclohexyl-4-{N-[2-oxo-2-(piperidin-1-yl)ethyl]-N-propylamino}-6,7-dihydro-5-oxa-7a-azadibenzo[a,e]azulene-9-carboxylate (3.63 g, yield 99%).

$^1$H-NMR (400 MHz, CDCl$_3$): δ(ppm) 8.20 (1H, d, J=1.4 Hz), 7.89 (1H, d, J=8.5 Hz), 7.63 (1H, dd, J=8.5, 1.4 Hz), 7.18 (1H, t, J=7.9 Hz), 7.07 (1H, dd, J=7.9, 1.4 Hz), 6.87 (1H, dd, J=7.9, 1.4 Hz), 4.37 (2H, brs), 4.12 (2H, brs), 3.87 (3H, s), 3.37 (4H, brs), 3.21 (2H, brs), 2.88 (1H, brt, J=12.1 Hz), 2.08-1.93 (2H, m), 1.86-1.66 (5H, m), 1.60-1.47 (4H, m), 1.46-1.22 (7H, m), 0.86 (3H, t, J=7.2 Hz).

Step 11: Production of methyl 12-cyclohexyl-4-[(N-[2-(piperidin-1-yl)ethyl]-N-propylamino]-6,7-dihydro-5-oxa-7a-azadibenzo[a,e]azulene-9-carboxylate (Example 2-522)

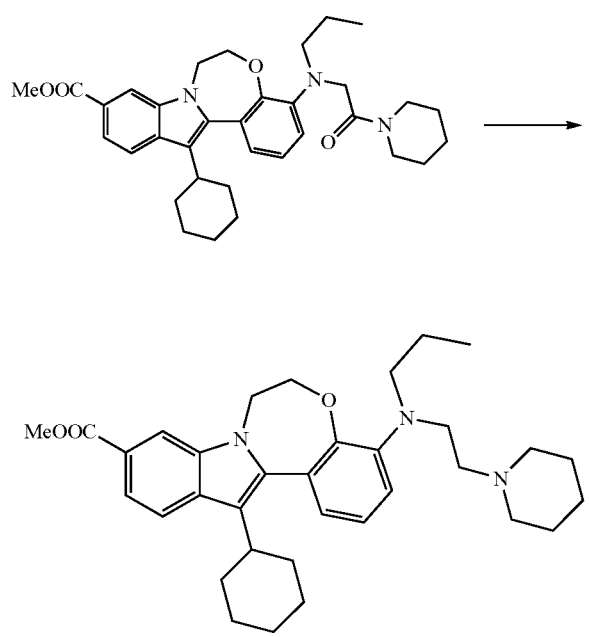

To a solution of methyl 12-cyclohexyl-4-{N-[2-oxo-2-(piperidin-1-yl)ethyl]-N-propylamino}-6,7-dihydro-5-oxa-7a-azadibenzo[a,e]azulene-9-carboxylate (3.63 g, 6.51 mmol) in tetrahydrofuran (7 ml) was added a solution (50 ml) of 1M BH$_3$ THF complex in tetrahydrofuran under ice-cooling, and the mixture was stirred at room temperature for 11 hr. 4N Hydrochloric acid was added to the reaction mixture under ice-cooling, and the mixture was stirred at 65° C. for 3 hr. The reaction mixture was adjusted to pH 8 with 4N aqueous sodium hydroxide solution, and extracted with ethyl acetate. The organic layer was washed with saturated brine and dried over anhydrous sodium sulfate. After filtration, the solvent was evaporated under reduced pressure, and the residue was purified by silica gel column chromatography (chloroform:methanol=35:1-15:1) to give methyl 12-cyclohexyl-4-{N-[2-(piperidin-1-yl)ethyl]-N-propylamino}-6,7-dihydro-5-oxa-7a-azadibenzo[a,e]azulene-9-carboxylate (3.25 g, yield 92%).

$^1$H-NMR (400 MHz, DMSO-d$_6$): δ(ppm) 8.21 (1H, d, J=1.4 Hz), 7.90 (1H, d, J=8.3 Hz), 7.64 (1H, dd, J=8.3, 1.4 Hz), 7.20 (1H, t, J=7.3 Hz), 7.12 (1H, d, J=7.3 Hz), 6.92 (1H, d, J=7.3 Hz), 4.40 (4H, brs), 3.87 (3H, s), 3.28 (2H, brs), 3.13 (2H, brs), 2.90 (1H, brt, J=12.1 Hz), 2.41 (2H, brs), 2.29 (2H, brs), 2.09-1.92 (2H, m), 1.87-1.65 (5H, m), 1.57-1.21 (14H, m), 0.86 (3H, t, J=7.4 Hz).

Step 12: Production of 12-cyclohexyl-4-{N-[2-(piperidin-1-yl)ethyl]-N-propylamino}-6,7-dihydro-5-oxa-7a-azadibenzo[a,e]azulene-9-carboxylic acid dihydrochloride (Example 2-481)

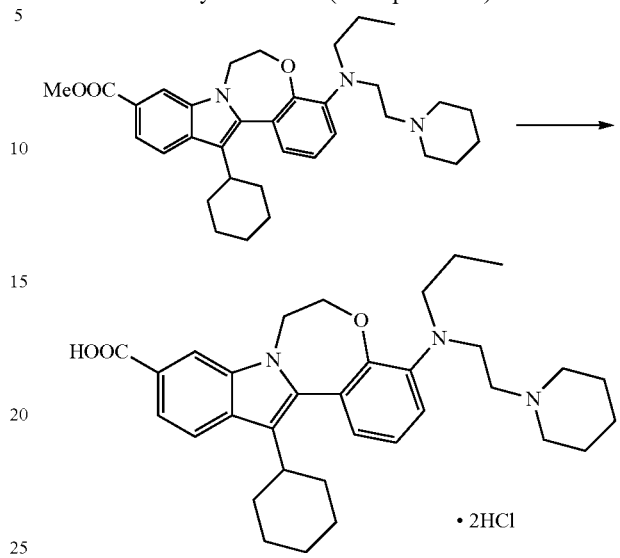

To a solution of methyl 12-cyclohexyl-4-{N-[2-(piperidin-1-yl)ethyl]-N-propylamino}-6,7-dihydro-5-oxa-7a-azadibenzo[a,e]azulene-9-carboxylate (3.25 g, 5.98 mmol) in tetrahydrofuran (16 ml) and methanol (8 ml) was added 4N aqueous sodium hydroxide solution (4.5 ml), and the mixture was stirred at 65° C. for 2 hr. The reaction mixture was adjusted to pH 6.5 with 2N hydrochloric acid and extracted with chloroform. The organic layer was washed with saturated brine and dried over anhydrous sodium sulfate. After filtration, the solvent was evaporated under reduced pressure. 4N HCl-ethyl acetate solution (10 ml) was added to a solution of the residue in chloroform, and the solvent was evaporated under reduced pressure. A mixed solvent (hexane:ethyl acetate=4:1) was added to the residue and the precipitated solid was collected by filtration to give 12-cyclohexyl-4-{N-[2-(piperidin-1-yl)ethyl]-N-propylamino}-6,7-dihydro-5-oxa-7a-azadibenzo[a,e]azulene-9-carboxylic acid dihydrochloride (3.41 g, yield 95%).

$^1$H-NMR (400 MHz, DMSO-d$_6$): δ(ppm) 10.53 (1H, brs), 8.21 (1H, d, J=1.4 Hz), 7.89 (1H, d, J=8.6 Hz), 7.64 (1H, dd, J=8.6, 1.4 Hz), 7.29 (2H, brs), 7.09 (1H, brs), 4.48 (4H, brs), 3.62 (2H, brs), 3.45 (2H, brs), 3.17 (4H, brs), 2.99-2.80 (2H, m), 2.11-1.95 (2H, m), 1.87-1.61 (10H, m), 1.57-1.22 (6H, m), 0.87 (3H, t, J=7.2 Hz).

MS 530.3 (M+1).

Example 5-4

Production of 12-cyclohexyl-5,6-dihydroindolo[2,1-a]isoquinoline-9-carboxylic acid Step 1: Production of 2-[2-(2-bromophenyl)ethoxy]tetrahydropyran

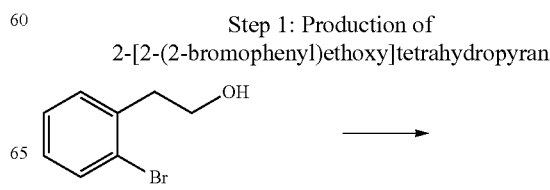

-continued

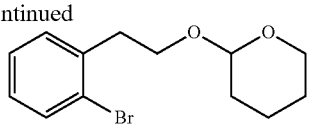

A solution of 2-(2-bromophenyl)ethanol (3.10 g, 15.4 mmol), 3,4-dihydro-2H-pyran (1.70 ml, 18.6 mmol) and p-toluenesulfonic acid monohydrate (10.0 mg, 5.35 mmol) in chloroform (30 ml) was stirred at room temperature for 1 hr. Saturated aqueous sodium hydrogen carbonate solution was added to the reaction mixture, and the mixture was extracted with chloroform. The organic layer was washed with saturated brine and dried over anhydrous sodium carbonate. After filtration, the solvent was evaporated under reduced pressure, and the residue was purified by silica gel chromatography (hexane:ethyl acetate=30:1-10:1) to give 2-[2-(2-bromophenyl)ethoxy]tetrahydropyran (3.58 g, yield 81.7%).

$^1$H-NMR (400 MHz, CDCl$_3$): δ(ppm) 7.53 (1H, dd, J=8.1, 1.2 Hz), 7.30 (1H, dd, J=7.4, 1.9 Hz), 7.23 (1H, td, J=7.4, 1.4 Hz), 7.07 (1H, td, J=7.7, 1.7 Hz), 4.61 (1H, t, J=3.7 Hz), 3.95 (1H, dt, J=12.8, 4.9 Hz), 3.79-3.73 (1H, m), 3.65 (1H, dt, J=12.8, 4.9 Hz), 3.47-3.45 (1H, m), 3.07 (2H, t, J=7.2 Hz), 1.82-1.80 (1H, m), 1.72-1.67 (1H, m), 1.57-1.53 (4H, m).

Step 2: Production of 2-[2-(tetrahydropyran-2-yloxy)ethyl]phenylboronic acid

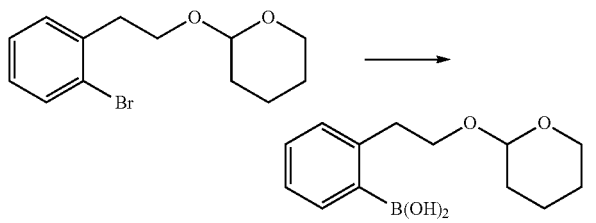

To a solution of 2-[2-(2-bromophenyl)ethoxy]tetrahydropyran (3.58 g, 12.5 mmol) and triisopropyl borate (3.70 ml, 16.1 mmol) in tetrahydrofuran (10.0 ml) was added a solution (10.0 ml) of 1.6M n-butyllithium in hexane at −78° C., and the mixture was stirred for 2 hr while gradually raising the temperature to 0° C. 1N hydrochloric acid was added to the reaction mixture, and the mixture was extracted with ethyl acetate. The organic layer was washed with saturated brine and dried over anhydrous sodium sulfate. After filtration, the solvent was evaporated under reduced pressure, and the residue was purified by silica gel chromatography (hexane:ethyl acetate=3:1-2:1) to give 2-[2-(tetrahydropyran-2-yloxy)ethyl]phenylboronic acid (1.77 g, yield 56.6%).

$^1$H-NMR (400 MHz, CDCl$_3$): δ(ppm) 7.67 (1H, d, J=7.4 Hz), 7.38 (1H, t, J=7.7 Hz), 7.24-7.23 (2H, m), 6.42 (2H, brs), 4.60-4.58 (1H, m), 4.34-4.31 (1H, m), 3.71-3.66 (1H, m), 3.36-3.33 (2H, m), 3.05-3.01 (2H, m), 1.66-1.26 (4H, m), 0.95-0.90 (2H, m).

Step 3: Production of methyl 3-cyclohexyl-2-{2-[2-(tetrahydropyran-2-yloxy)ethyl]phenyl}-1H-indole-6-carboxylate

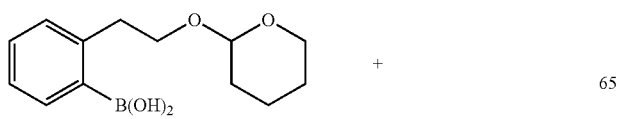

+

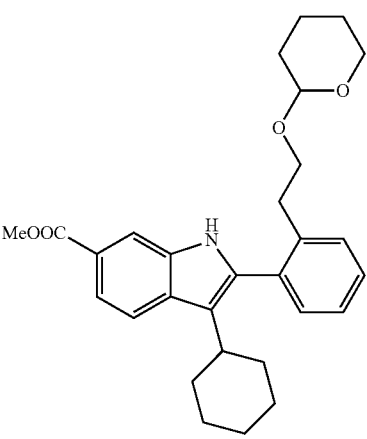

To a suspension of methyl 2-bromo-3-cyclohexyl-1H-indole-6-carboxylate (2.10 g, 6.24 mmol) obtained in the same manner as in the method described in WO03/010140 and 2-[2-(tetrahydropyran-2-yloxy)ethyl]phenylboronic acid (1.77 g, 7.10 mmol) in 1,2-dimethoxyethane (20 ml) and water (10 ml) were added sodium hydrogen carbonate (2.00 g, 24.0 mmol) and tetrakis(triphenylphosphine)palladium (360 mg, 0.31 mmol), and the mixture was heated under reflux for 7 hr. The reaction mixture was allowed to cool to room temperature, water was added to the reaction mixture and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=6:1-5:1) to give methyl 3-cyclohexyl-2-{2-[(2-(tetrahydropyran-2-yloxy)ethyl]phenyl}-1H-indole-6-carboxylate (2.21 g, yield 77.2%).

MS 462.0 (M+1).

Step 4: Production of methyl 3-cyclohexyl-2-[2-(2-hydroxyethyl)phenyl]-1H-indole-6-carboxylate -continued

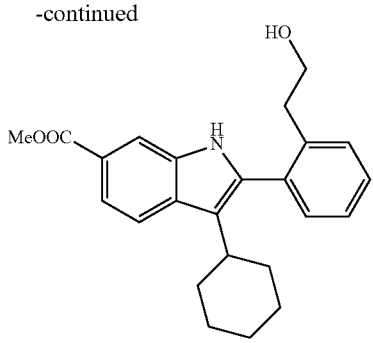

A solution of methyl 3-cyclohexyl-2-{2-[2-(tetrahydropyran-2-yloxy)ethyl]phenyl}-1H-indole-6-carboxylate (2.21 g, 4.80 mmol) in tetrahydrofuran (10 ml), methanol (10 ml) and 6N hydrochloric acid (20 ml) was stirred at room temperature for 2 hr. Water was added to the reaction mixture and the mixture was extracted with ethyl acetate. The organic layer was successively washed with water, saturated aqueous sodium hydrogen carbonate solution and saturated brine and dried over anhydrous sodium sulfate. After filtration, the solvent was evaporated under reduced pressure, and the residue was purified by silica gel chromatography (hexane:ethyl acetate=5:1-2:1) to give methyl 3-cyclohexyl-2-[2-(2-hydroxyethyl)phenyl]-1H-indole-6-carboxylate (1.20 g, yield 66.7%).

$^1$H-NMR (400 MHz, CDCl$_3$): δ(ppm) 9.85 (1H, s), 8.10 (1H, s), 7.84 (1H, d, J=8.3 Hz), 7.76 (1H, dd, J=8.3, 1.4 Hz), 7.46-7.31 (4H, m), 4.01-3.97 (2H, m), 3.94 (3H, s), 2.72-2.69 (3H, m), 1.98-1.80 (7H, m), 1.30-1.26 (3H, m).

Step 5: Production of methyl 2-[2-(2-bromomethyl)phenyl]-3-cyclohexyl-1H-indole-6-carboxylate

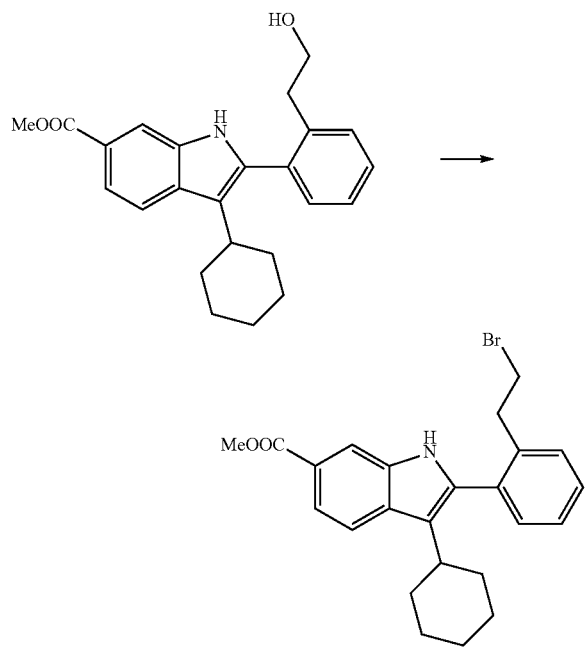

To a solution of methyl 3-cyclohexyl-2-[2-(2-hydroxyethyl)phenyl]-1H-indole-6-carboxylate (600 mg, 1.58 mmol) in chloroform (6 ml) were added carbon tetrabromide (790 mg, 2.38 mmol) and triphenylphosphine (497 mg, 1.89 mmol), and the mixture was stirred at room temperature for 5 min. Saturated aqueous sodium hydrogen carbonate solution was added to the reaction mixture, and the mixture was extracted with chloroform. The organic layer was washed with saturated brine and dried over anhydrous sodium sulfate. After filtration, the solvent was evaporated under reduced pressure, and the residue was purified by silica gel chromatography (hexane:ethyl acetate=7:1-6:1) to give methyl 2-[2-(2-bromomethyl)phenyl]-3-cyclohexyl-1H-indole-6-carboxylate (500 mg, yield 71.9%).

Step 6: Production of methyl 12-cyclohexyl-5,6-dihydroindolo[2,1-a]isoquinoline-9-carboxylate (Example 5-5)

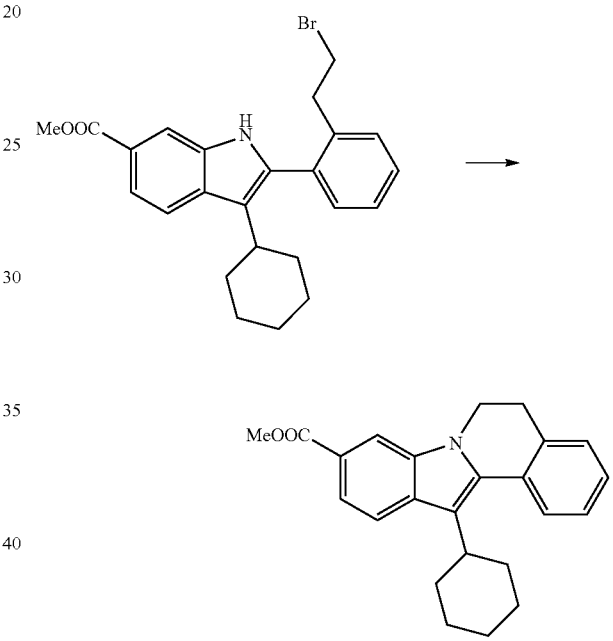

To a solution of methyl 2-[2-(2-bromomethyl)phenyl]-3-cyclohexyl-1H-indole-6-carboxylate (500 mg, 1.13 mmol) in N,N-dimethylformamide (10 ml) was added sodium hydride (60% in oil, 48 mg, 1.20 mmol) under ice-cooling, and the mixture was stirred for 30 min. 2N Hydrochloric acid was added to the reaction mixture and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=10:1-8:1) to give methyl 12-cyclohexyl-5,6-dihydroindolo[2,1-a]isoquinoline-9-carboxylate (337 mg, yield 83.0%).

$^1$H-NMR (400 MHz, CDCl$_3$): δ(ppm) 8.06 (1H, d, J=1.4 Hz), 7.88 (1H, d, J=8.3 Hz), 7.71 (1H, d, J=8.3 Hz), 7.40-7.25 (4H, m), 4.24 (2H, t, J=6.3 Hz), 3.94 (3H, s), 3.34 (1H, brt, J=12.3 Hz), 3.11 (2H, t, J=6.3 Hz), 2.14-2.11 (2H, m), 1.92-1.87 (5H, m), 1.50-1.45 (3H, m).

MS 360.1 (M+1).

Step 7: Production of 12-cyclohexyl-5,6-dihydroindolo[2,1-a]isoquinoline-9-carboxylic acid (Example 5-4)

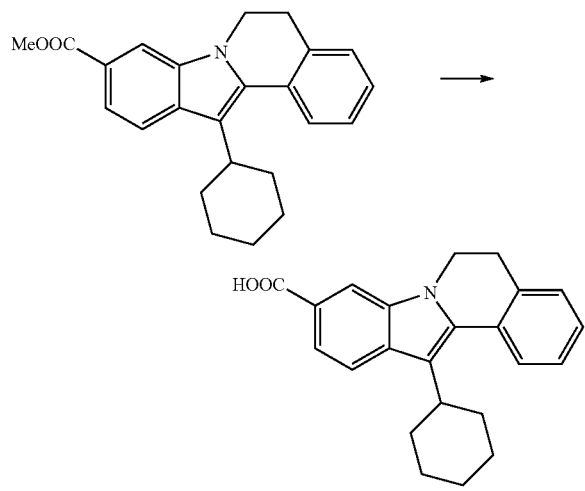

To a solution of methyl 12-cyclohexyl-5,6-dihydroindolo[2,1-a]isoquinoline-9-carboxylate (337 mg, 0.93 mmol) in tetrahydrofuran (3 ml) and methanol (3 ml) was added 4N aqueous sodium hydroxide solution (3.0 ml), and the mixture was stirred at room temperature for 15 hr. The reaction mixture was acidified with 2N hydrochloric acid. The precipitated solid was collected by filtration and dried in vacuo to give 12-cyclohexyl-5,6-dihydroindolo[2,1-a]isoquinoline-9-carboxylic acid (298 mg, yield 92.3%).

$^1$H-NMR (300 MHz, DMSO-$d_6$): δ(ppm) 12.5 (1H, br s), 8.06 (1H, s), 7.88 (1H, d, J=8.4 Hz), 7.68 (1H, d, J=8.1 Hz), 7.59 (1H, d, J=8.4 Hz), 7.44-7.42 (1H, m), 7.33 (1H, t, J=7.5 Hz), 4.27 (2H, br s), 3.08 (2H, brs), 2.57-2.45 (1H, m), 2.08-2.04 (2H, m), 1.85-1.76 (5H, m), 1.46-1.42 (3H, m).

MS 346.2 (M+1).

Example 11-1

Production of 14-cyclohexyl-6-methyl-5,6,7,8-tetrahydrobenzo[6,7][1,4]diazocino[8,1-a]indole-11-carboxylic acid monohydrochloride

Step 1: Production of N-(2-hydroxyethyl)-2-iodobenzamide

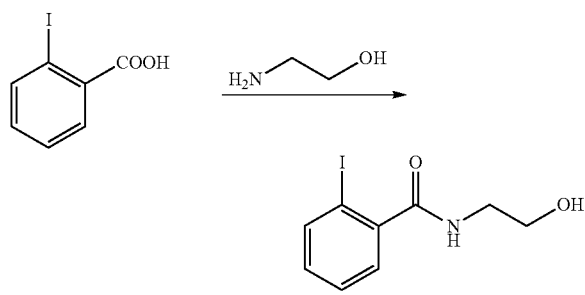

To a solution of 2-iodobenzoic acid (5.00 g, 20.1 mmol) in chloroform (50 ml) were added oxalyl chloride (1.9 ml, 21.7 mmol) and N,N-dimethylformamide (5 drops with Pasteur pipette) under ice-cooling, and the mixture was stirred at room temperature for 2 hr. The reaction mixture was concentrated under reduced pressure and ethyl acetate (5 ml) was added to the residue to give a solution of 2-iodobenzoyl chloride in ethyl acetate.

To a solution of sodium hydrogen carbonate (3.30 g, 39.7 mmol) and 2-aminoethanol (1.80 ml, 29.8 mmol) in ethyl acetate (25 ml) and water (15 ml) was added dropwise the solution of 2-iodobenzoyl chloride in ethyl acetate prepared above under ice-cooling, and the mixture was stirred at room temperature for 12 hr. Water was added to the reaction mixture and the mixture was extracted with ethyl acetate. The organic layer was washed with saturated brine and dried over anhydrous sodium sulfate. After filtration, the solvent was evaporated under reduced pressure to give N-(2-hydroxyethyl)-2-iodobenzamide (5.12 g, yield 87.6%).

$^1$H-NMR (400 MHz, CDCl$_3$): δ(ppm) 7.86 (1H, d, J=7.9 Hz), 7.40-7.38 (2H, m), 7.11 (1H, ddd, J=8.6, 6.3, 1.6 Hz), 6.29 (1H, brs), 3.86 (2H, dd, J=5.6, 4.6 Hz), 3.62 (2H, dt, J=5.3, 4.9 Hz), 2.22 (1H, brs).

Step 2: Production of methyl 3-cyclohexyl-2-[2-(2-hydroxyethylcarbamoyl)phenyl]-1H-indole-6-carboxylate

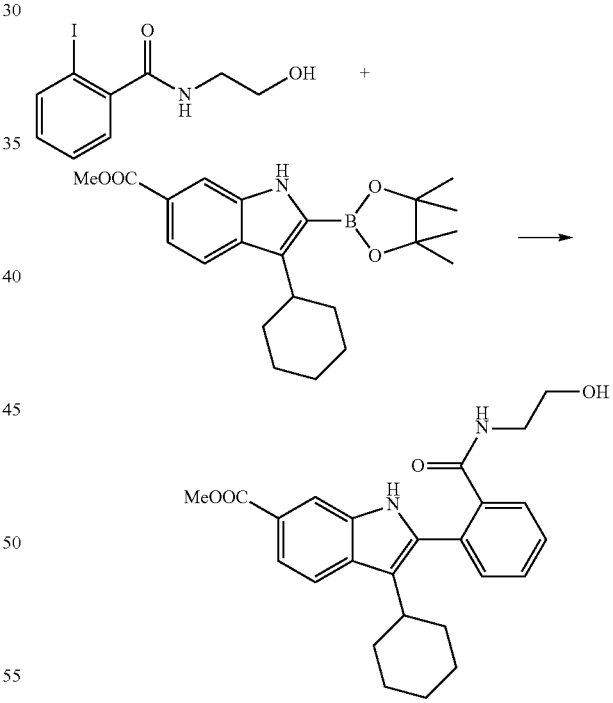

To a suspension of N-(2-hydroxyethyl)-2-iodobenzamide (5.12 g, 17.5 mmol), sodium hydrogen carbonate (5.80 g, 69.8 mmol) and tetrakis(triphenylphosphine)palladium (2.00 g, 1.73 mmol) in 1,2-dimethoxyethane (70 ml) and water (35 ml) was added methyl 3-cyclohexyl-2-(4,4,5,5-tetramethyl-1,3,2-dioxaborolan-2-yl)-1H-indole-6-carboxylate (7.50 g, 19.5 mmol) in five divided portions at 90° C., and the mixture was stirred for 1 hr. Water was added to the reaction mixture and the mixture was extracted with ethyl acetate. The organic layer was successively washed with water and saturated brine and dried over anhydrous sodium is sulfate. After filtration, the solvent was evaporated under reduced pressure, and the residue was purified by silica gel column chromatography (chloroform:methanol=30:1-20:1) to give methyl 3-cyclohexyl-2-[2-(2-hydroxyethylcarbamoyl)phenyl]-1H-indole-6-carboxylate (7.40 g, yield 100%).

$^1$H-NMR (400 MHz, CDCl$_3$): δ(ppm) 9.94 (1H, brs), 8.17 (1H, s), 7.85 (1H, d, J=8.3 Hz), 7.80 (1H, dd, J=8.3, 1.4 Hz), 7.73 (1H, dd, J=8.5, 1.4 Hz), 7.49 (1H, dd, J=7.2, 1.4 Hz), 7.42-7.38 (2H, m), 5.98 (1H, t, J=5.6 Hz), 3.94 (3H, s), 3.22 (2H, dt, J 5.6, 4.6 Hz), 3.15 (2H, t, J=4.6 Hz), 2.75 (1H, br t, J=12.1 Hz), 1.96-1.77 (8H, m), 1.32-1.26 (3H, m).

Step 3: Production of methyl 2-(2-{[N-tert-butoxycarbonyl-N-(2-hydroxyethyl)amino]methyl}phenyl)-3-cyclohexyl-1H-indole-6-carboxylate

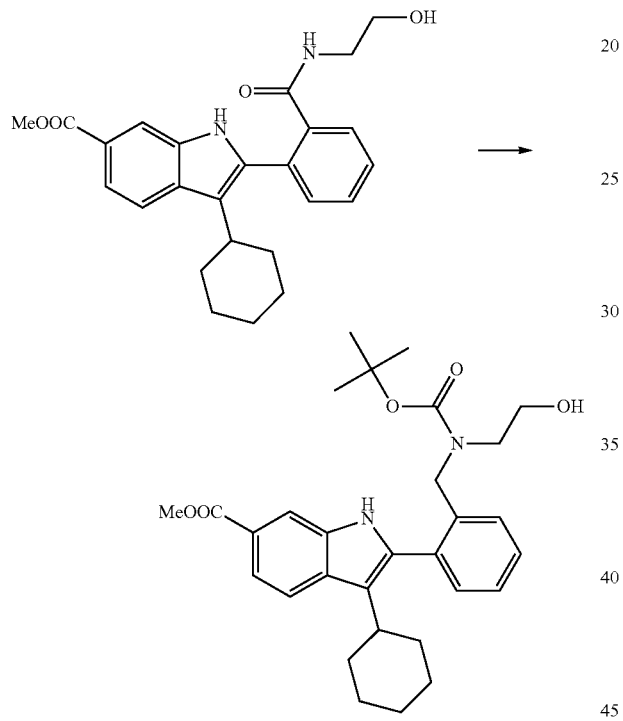

To a solution of methyl 3-cyclohexyl-2-[2-(2-hydroxyethylcarbamoyl)phenyl]-1H-indole-6-carboxylate (2.00 g, 4.75 mmol) in tetrahydrofuran (5.0 ml) was added a solution (20.0 ml, 20.0 mmol) of 1M BH$_3$ THF complex in tetrahydrofuran under ice-cooling, and the mixture was stirred at room temperature for 17 hr. 2N Hydrochloric acid (20 ml) was added to the reaction mixture, and the mixture was stirred at 70° C. for 1.5 hr. The reaction mixture was allowed to cool to room temperature, the reaction mixture was neutralized with 4N aqueous sodium hydroxide solution and aqueous sodium hydrogen carbonate solution. To this mixture was added di-tert-butyl dicarbonate (1.60 g, 7.33 mmol), and the mixture was stirred at room temperature for 6 hr. The reaction mixture was extracted with ethyl acetate, and the organic layer was washed with saturated brine and dried over anhydrous sodium sulfate. After filtration, the solvent was evaporated under reduced pressure, and the residue was purified by silica gel chromatography (chloroform:methanol=30:1-10:1) to give methyl 2-(2-{[N-tert-butoxycarbonyl-N-(2-hydroxyethyl)amino]methyl}phenyl)-3-cyclohexyl-1H-indole-6-carboxylate (524 mg, yield 22.1%).

$^1$H-NMR (400 MHz, CDCl$_3$): δ(ppm) 8.08 (1H, s), 7.82 (1H, d, J=8.3 Hz), 7.78 (1H, dd, J=8.3, 1.4 Hz), 7.46-7.39 (3H, m), 7.32 (1H, d, J=7.0 Hz), 4.37-4.35 (2H, m), 3.94 (3H, s), 3.41-3.39 (4H, m), 2.55 (1H, brs), 1.96-1.71 (7H, m), 1.40-1.09 (3H, m), 1.25 (9H, s).
MS 407.0 (M+1).

Step 4: Production of methyl 2-(2-{[N-tert-butoxycarbonyl-N-(2-methanesulfonyloxyethyl)amino]methyl}phenyl)-3-cyclohexyl-1H-indole-6-carboxylate

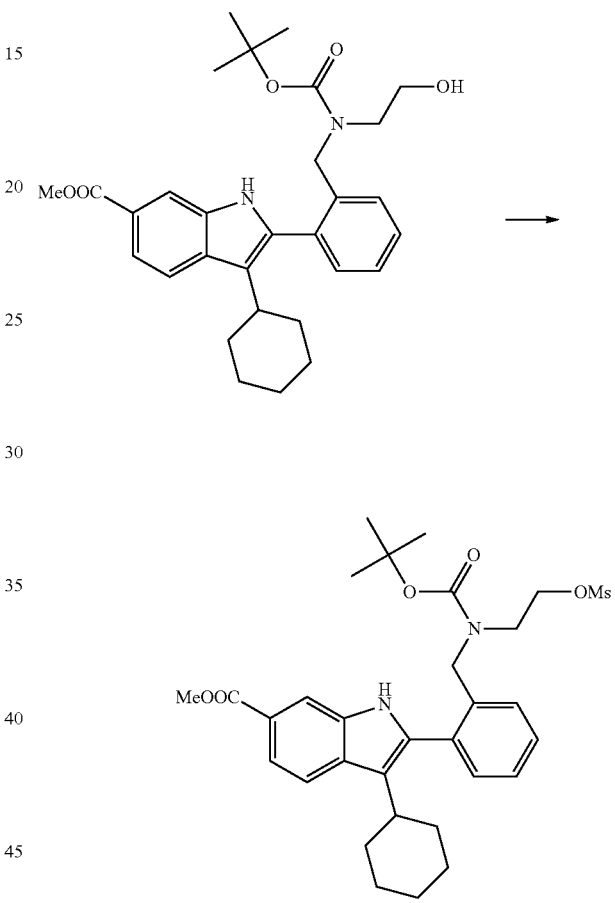

To a solution of methyl 2-(2-{[N-tert-butoxycarbonyl-N-(2-hydroxyethyl)amino]methyl}phenyl)-3-cyclohexyl-1H-indole-6-carboxylate (424 mg, 0.830 mmol) and triethylamine (0.14 ml, 1.0 mmol) in chloroform (5.0 ml) was added dropwise methanesulfonyl chloride (0.07 ml, 0.90 mmol) under ice-cooling, and the mixture was stirred at room temperature for 1 hr. 1N Hydrochloric acid was added to the reaction mixture, and the mixture was extracted with chloroform. The organic layer was washed with saturated brine and dried over anhydrous sodium sulfate. After filtration, the solvent was evaporated under reduced pressure to give methyl 2-(2-{[N-tert-butoxycarbonyl-N-(2-methanesulfonyloxyethyl)amino]methyl}phenyl)-3-cyclohexyl-1H-indole-6-carboxylate as a crude product. The obtained crude product was used for Step 5 without purification.

Step 5: Production of methyl 6-tert-butoxycarbonyl-14-cyclohexyl-5,6,7,8-tetrahydrobenzo[6,7][1,4]diazocino[8,1-a]indole-11-carboxylate (Example 11-2)

Step 6: Production of methyl 14-cyclohexyl-6-methyl-5,6,7,8-tetrahydrobenzo[6,7][1,4]diazocino[8,1-a]indole-11-carboxylate (Example 11-3)

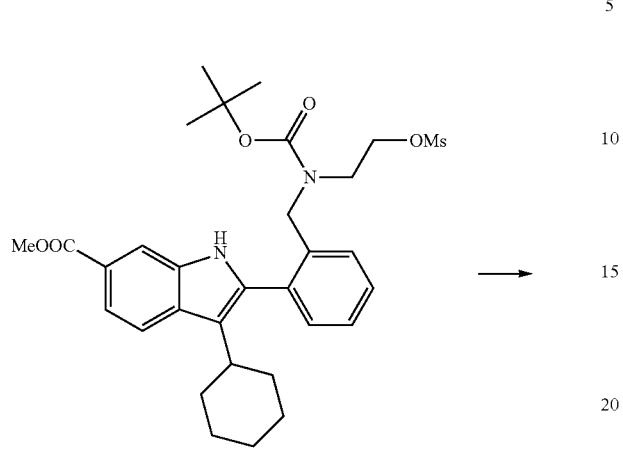

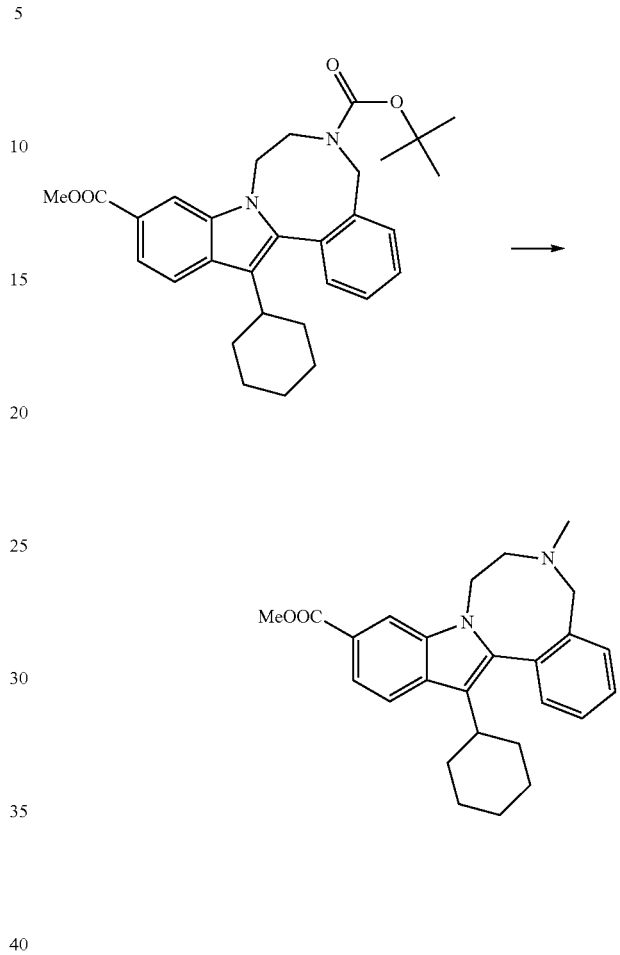

To a solution of methyl 2-(2-{[N-tert-butoxycarbonyl-N-(2-methanesulfonyloxyethyl)amino]methyl}phenyl)-3-cyclohexyl-1H-indole-6-carboxylate (crude product obtained in Step 4) in N,N-dimethylformamide (10 ml) was added sodium hydride (60% in oil, 36 mg, 0.90 mmol) under ice-cooling, and the mixture was stirred at room temperature for 4 hr. Water was added to the reaction mixture and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=2:1-3:2) to give methyl 6-tert-butoxycarbonyl-14-cyclohexyl-5,6,7,8-tetrahydrobenzo[6,7][1,4]diazocino[8,1-a]indole-11-carboxylate (89 mg, yield 21.9%).

$^1$H-NMR (400 MHz, CDCl$_3$): δ(ppm) 8.08 (0.5H, s), 8.07 (0.5H, s), 7.90-7.78 (3.0H, m), 7.53-7.34 (3.0H, m), 4.98 (0.5H, d, J=14.8 Hz), 4.90 (0.5H, d, J=14.4 Hz), 4.66 (0.5H, dd, J=14.6, 4.9 Hz), 4.50 (1.0H, dd, J=19.5, 8.3 Hz), 4.31 (0.5H, d, J=14.4 Hz), 3.97 (3.0H, s), 3.75-3.67 (1.0H, m), 3.43 (0.5H, d, J=14.8 Hz), 3.29 (0.5H, d, J=14.8 Hz), 3.26 (0.5H, d, J=9.3 Hz), 3.03-2.97 (0.5H, m), 2.75-2.57 (1.0H, m), 2.03-1.72 (4.0H, m), 1.77-1.74 (2.0H, m), 1.60 (4.5H, s), 1.41 (4.5H, s), 1.35-1.18 (4.0H, m).

A solution of methyl 6-tert-butoxycarbonyl-14-cyclohexyl-5,6,7,8-tetrahydrobenzo[6,7][1,4]diazocino[8,1-a]indole-11-carboxylate (89 mg, 0.18 mmol) in 4N HCl-ethyl acetate was stirred at room temperature for 3 hr. The reaction mixture was concentrated under reduced pressure and chloroform (2.0 ml) was added to the residue. To this solution were successively added sodium acetate (30 mg, 0.36 mmol), acetic acid (0.01 ml, 0.20 mmol), 37% aqueous formaldehyde solution (2.0 ml) and sodium triacetoxyborohydride (46 mg, 0.21 mmol), and the mixture was stirred for 13 hr. Saturated aqueous sodium hydrogen carbonate solution was added to the reaction mixture, and the mixture was extracted with chloroform. The organic layer was washed with saturated brine and dried over anhydrous sodium sulfate. After filtration, the solvent was evaporated under reduced pressure, and the residue was purified by silica gel chromatography (chloroform:methanol=50:1-40:1) to give methyl 14-cyclohexyl-6-methyl-5,6,7,8-tetrahydrobenzo[6,7][1,4]diazocino[8,1-a]indole-11-carboxylate (73 mg, yield 100%).

$^1$H-NMR (300 MHz, CDCl$_3$): δ(ppm) 8.06 (1H, s), 7.88 (1H, d, J=8.4 Hz), 7.81 (1H, t, J=4.2 Hz), 7.52-7.30 (4H, m), 4.31 (1H, dd, J=15.4, 5.5 Hz), 4.03-3.92 (1H, m), 3.95 (3H, s), 3.72 (1H, dd, J=15.6, 10.1 Hz), 3.61 (1H, d, J=13.2 Hz), 3.22 (1H, dd, J=13.2, 5.9 Hz), 3.04 (1H, d, J=13.6 Hz), 2.72-2.62 (1H, m), 2.51 (3H, s), 2.10-1.81 (3H, m), 1.80-1.55 (5H, m), 1.40-1.10 (2H, m).

Step 7: Production of 14-cyclohexyl-6-methyl-5,6,7,8-tetrahydrobenzo[6,7][1,4]diazocino[8,1-a]indole-11-carboxylic acid monohydrochloride (Example 11-1)

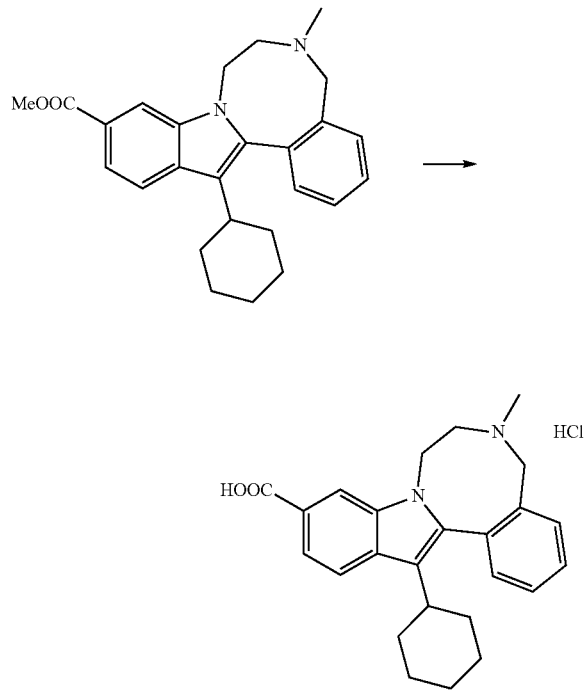

To a solution of methyl 14-cyclohexyl-6-methyl-5,6,7,8-tetrahydrobenzo[6,7][1,4]diazocino[8,1-a]indole-11-carboxylate (73 mg, 0.18 mmol) in tetrahydrofuran (1 ml) and methanol (1 ml) solution was added 4N aqueous sodium hydroxide solution (1 ml), and the mixture was stirred at room temperature for 3 hr. 2N Hydrochloric acid was added to the reaction mixture, and the mixture was extracted with ethyl acetate and dried over anhydrous sodium carbonate. After filtration, the solvent was evaporated under reduced pressure, and the residue was purified by silica gel chromatography (chloroform:methanol=30:1-10:1) to give 14-cyclohexyl-6-methyl-5,6,7,8-tetrahydrobenzo[6,7][1,4]diazocino[8,1-a]indole-1'-carboxylic acid. To a solution of the obtained 14-cyclohexyl-6-methyl-5,6,7,8-tetrahydrobenzo[6,7][1,4]diazocino[8,1-a]indole-11-carboxylic acid in ethyl acetate was added 4N HCl-ethyl acetate solution (2 ml), and the mixture was concentrated under reduced pressure. A mixed solvent of ethyl acetate:hexane (1:1) was added to the residue. The precipitated solid was collected by filtration and dried in vacuo to give 14-cyclohexyl-6-methyl-5,6,7,8-tetrahydrobenzo[6,7][1,4]diazocino[8,1-a]indole-11-carboxylic acid hydrochloride (25 mg, yield 32.9%).

$^1$H-NMR (400 MHz, DMSO-$d_6$): δ(ppm) 12.69 (1H, brs), 10.68 (1H, brs), 8.21 (1H, s), 7.96-7.90 (2H, m), 7.93 (2H, d, J=8.8 Hz), 7.73 (1H, dd, J=8.6, 1.2 Hz), 7.67-7.60 (2H, m), 7.49-7.42 (1H, m), 4.79 (1H, d, J=13.0 Hz), 4.40 (1H, d, J=13.0 Hz), 3.73-3.62 (3H, m), 3.47-3.30 (1H, m), 2.98 (3H, s), 2.68-2.55 (1H, m), 2.01-1.75 (4H, m), 1.72-1.52 (3H, m), 1.40-1.05 (3H, m).

MS 389.2 (M+1).

Example 12-1

Production of 12-cyclohexyl-6,7-dihydro-5-thia-7a-azadibenzo[a,e]azulene-9-carboxylic acid Step 1: Production of 2-[2-(2-bromophenylsulfanyl)ethoxy]tetrahydropyran

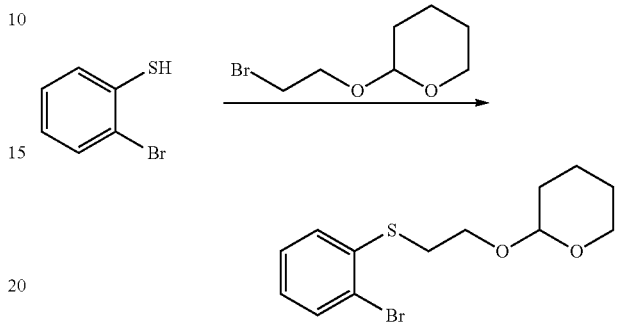

To a solution of 2-bromobenzenethiol (3.0 ml, 24.9 mmol) in N,N-dimethylformamide (50 ml) was added sodium hydride (60% in oil, 1.10 g, 27.5 mmol) under ice-cooling, and the mixture was stirred for 1 hr. To this reaction mixture was added 2-(2-bromoethoxy)tetrahydropyran (4.5 ml, 29.7 mmol) under ice-cooling, and the mixture was stirred at room temperature for 3 hr. Aqueous sodium carbonate solution was added to the reaction mixture and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=10:1) to give 2-[2-(2-bromophenylsulfanyl)ethoxy]tetrahydropyran (7.91 g, yield 100%).

$^1$H-NMR (400 MHz, CDCl$_3$): δ(ppm) 7.55 (1H, dd, J=8.1, 1.2 Hz), 7.36 (1H, dd, J=8.1, 1.6 Hz), 7.29-7.25 (1H, m), 7.03 (1H, dt, J=1.4, 7.7 Hz), 4.65 (1H, t, J=3.5 Hz), 4.00-3.94 (1H, m), 3.91-3.85 (1H, m), 3.70 (1H, dt, J=12.8, 5.3 Hz), 3.54-3.49 (1H, m), 3.20 (2H, dt, J=2.0, 6.8 Hz), 1.83-1.69 (2H, m), 1.63-1.50 (4H, m).

Step 2: Production of methyl 3-cyclohexyl-2-{2-[2-(tetrahydropyran-2-yloxy)ethylsulfanyl]phenyl}-1H-indole-6-carboxylate

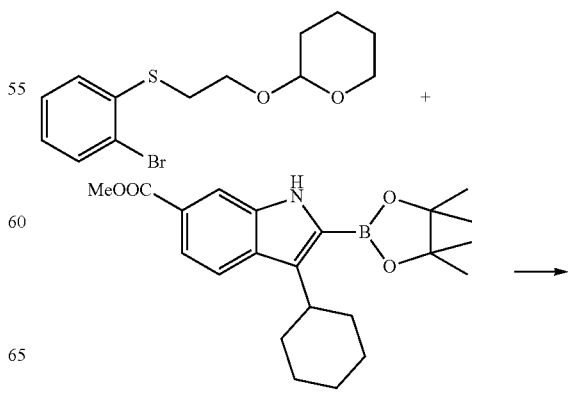

-continued

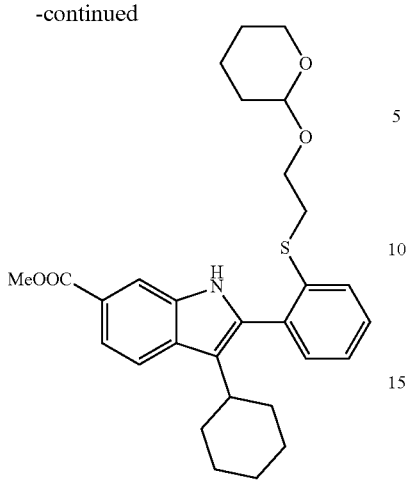

To a suspension of 2-[2-(2-bromophenylsulfanyl)ethoxy]tetrahydropyran (1.00 g, 3.2 mmol), sodium hydrogen carbonate (1.10 g, 13.2 mmol) and tetrakis(triphenylphosphine)palladium (363 mg, 0.310 mmol) in 1,2-dimethoxyethane (10 ml) and water (5 ml) was added methyl 3-cyclohexyl-2-(4,4,5,5-tetramethyl-1,3,2-dioxaborolan-2-yl)-1H-indole-6-carboxylate (1.45 g, 3.78 mmol) with heating under reflux and the mixture was heated under reflux for 2.5 hr. The reaction mixture was allowed to cool to room temperature, water was added to the reaction mixture and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=5:1-3:1) to give methyl 3-cyclohexyl-2-{2-[2-(tetrahydropyran-2-yloxy)ethylsulfanyl]phenyl}-1H-indole-6-carboxylate (1.38 g, yield 74.5%).

$^1$H-NMR (300 MHz, CDCl$_3$): δ(ppm) 8.86 (1H, s), 8.11 (1H, d, J=0.7 Hz), 7.82 (1H, d, J=8.4 Hz), 7.76 (1H, dd, J=8.4, 0.7 Hz), 7.54 (1H, d, J=7.7 Hz), 7.41-7.25 (3H, m), 4.50 (1H, t, J=3.9 Hz), 4.12 (1H, q, J=7.1 Hz), 3.93 (3H, s), 3.84 (1H, tt, J=11.6, 4.7 Hz), 3.61 (1H, dt, J=11.6, 5.3 Hz), 3.44 (1H, q, J=5.5 Hz), 3.05 (1H, dt, J=5.9, 5.8 Hz), 2.96 (1H, dt, J=6.1, 6.2 Hz), 2.69-2.59 (1H, m), 1.98-1.69 (7H, m), 1.68-1.40 (7H, m), 1.38-1.22 (2H, m).

Step 3: Production of methyl 3-cyclohexyl-2-[2-(2-hydroxyethylsulfanyl)phenyl]-1H-indole-6-carboxylate

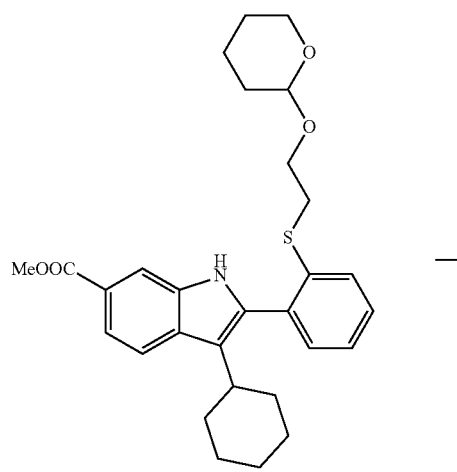

To a solution of methyl 3-cyclohexyl-2-{2-[2-(tetrahydropyran-2-yloxy)ethylsulfanyl]phenyl}-1H-indole-6-carboxylate (1.38 g, 2.81 mmol) in tetrahydrofuran (4 ml) and methanol (4 ml) was added 6N hydrochloric acid (4 ml), and the mixture was stirred at room temperature for 30 min. Water was added to the reaction mixture and the mixture was extracted with ethyl acetate. The organic layer was successively washed with water, saturated aqueous sodium hydrogen carbonate solution and saturated brine and dried over anhydrous sodium sulfate. After filtration, the solvent was evaporated under reduced pressure, and the residue was purified by silica gel chromatography (hexane:ethyl acetate=2:1-1:1) to give methyl 3-cyclohexyl-2-[2-(2-hydroxyethylsulfanyl)phenyl]-1H-indole-6-carboxylate (1.00 g, yield 87.5%).

Step 4: Production of methyl 3-cyclohexyl-2-[2-(2-methanesulfonyloxyethylsulfanyl)phenyl]-1H-indole-6-carboxylate

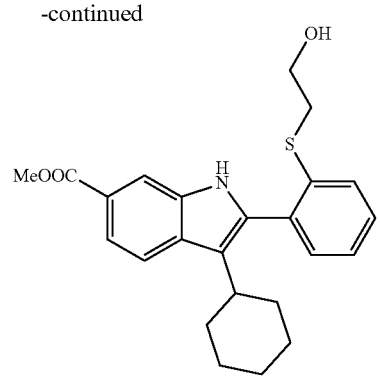

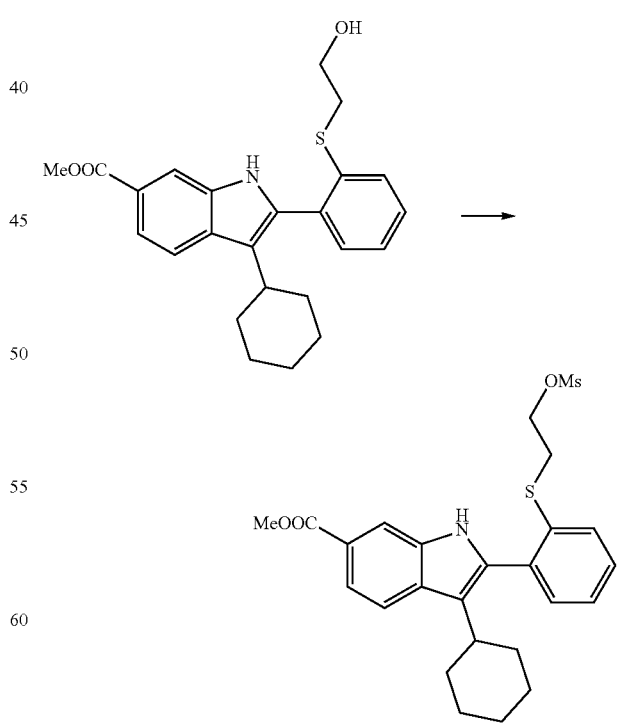

To a solution of methyl 3-cyclohexyl-2-[2-(2-hydroxyethylsulfanyl)phenyl]-1H-indole-6-carboxylate (500 mg, 1.22 mmol) and triethylamine (0.19 ml, 1.4 mmol) in chloroform (5 ml) was added dropwise methanesulfonyl chloride (0.10 ml, 1.3 mmol) under ice-cooling, and the mixture was stirred for 30 min.

Water was added to the reaction mixture and the mixture was extracted with chloroform. The organic layer was successively washed with water and saturated brine and dried over anhydrous sodium sulfate. After filtration, the solvent was evaporated under reduced pressure to give methyl 3-cyclohexyl-2-[2-(2-methanesulfonyloxyethylsulfanyl)phenyl]-1H-indole-6-carboxylate as a crude product. The obtained crude product was used for Step 5 without purification.

Step 5: Production of methyl 12-cyclohexyl-6,7-dihydro-5-thia-7a-azadibenzo[a,e]azulene-9-carboxylate (Example 12-3)

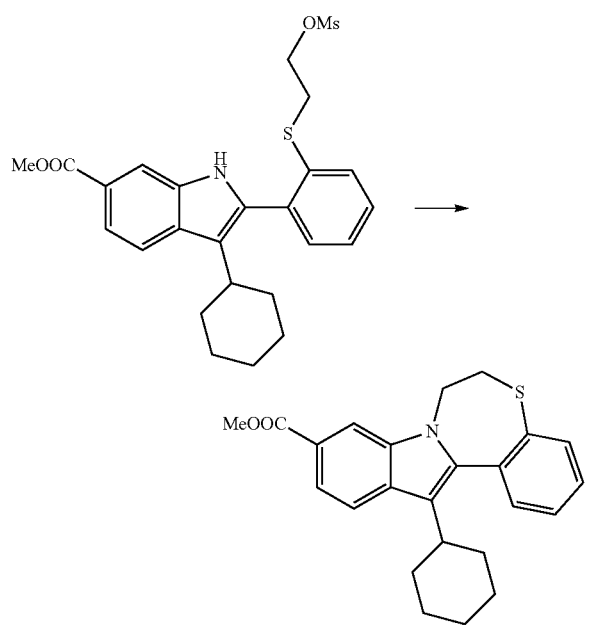

To a solution of methyl 3-cyclohexyl-2-[2-(2-methanesulfonyloxyethylsulfanyl)phenyl]-1H-indole-6-carboxylate obtained as a crude product in Step 4 in N,N-dimethylformamide (10 ml) was added sodium hydride (60% in oil, 53 mg, 1.3 mmol) under ice-cooling, and the mixture was stirred for 30 min. 2N Hydrochloric acid was added to the reaction mixture, and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=30:1-10:1) to give methyl 12-cyclohexyl-6,7-dihydro-5-thia-7a-azadibenzo[a,e]azulene-9-carboxylate (186 mg, yield 39.0%).

$^1$H-NMR (300 MHz, CDCl$_3$): δ(ppm) 8.08 (1H, d, J=1.1 Hz), 7.90 (1H, d, J=8.4 Hz), 7.77 (1H, dd, J=8.4, 1.5 Hz), 7.72 (1H, dd, J=7.3, 1.1 Hz), 7.52-7.37 (3H, m), 4.70 (1H, dd, J=15.0, 4.8 Hz), 3.95 (3H, s), 3.92-3.88 (1H, m), 3.47 (1H, dd, J=11.7, 3.3 Hz), 3.28 (1H, dt, J=5.5, 12.5 Hz), 2.89-2.80 (1H, m), 2.06-1.95 (4H, m), 1.75-1.71 (3H, m), 1.35-1.28 (3H, m).

MS 392.1 (M+1).

Step 6: Production of 12-cyclohexyl-6,7-dihydro-5-thia-7a-azadibenzo[a,e]azulene-9-carboxylate (Example 12-1)

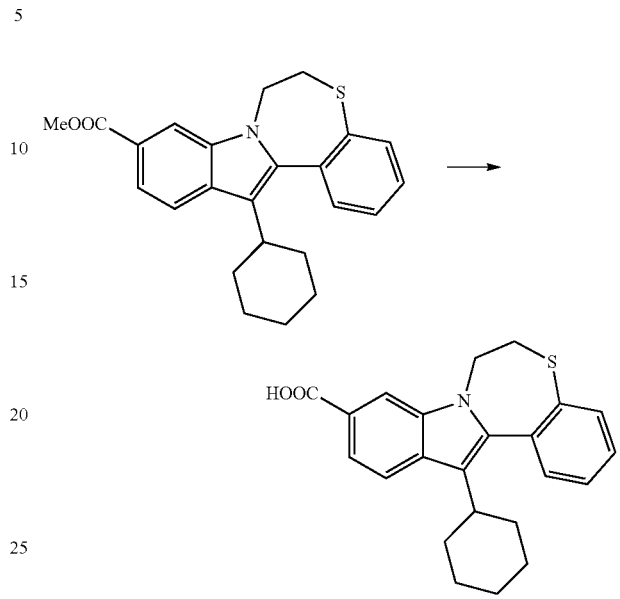

To a solution of methyl 12-cyclohexyl-6,7-dihydro-5-thia-7a-azadibenzo[a,e]azulene-9-carboxylate (186 mg, 0.470 mmol) in tetrahydrofuran (2 ml) and methanol (2 ml) was added 4N aqueous sodium hydroxide solution (2 ml), and the mixture was stirred at room temperature for 13 hr. 2N hydrochloric acid and water were added to the reaction mixture. The precipitated solid was collected by filtration and dried in vacuo to give 12-cyclohexyl-6,7-dihydro-5-thia-7a-azadibenzo[a,e]azulene-9-carboxylic acid (157 mg, yield 87.7%).

$^1$H-NMR (300 MHz, DMSO-d$_6$): δ(ppm) 12.57 (1H, brs), 8.18 (1H, d, J=1.1 Hz), 7.89 (1H, d, J=8.4 Hz), 7.73-7.70 (1H, m), 7.65 (1H, dd, J=8.4, 1.5 Hz), 7.59 (1H, d, J=4.4 Hz), 7.49-7.47 (2H, m), 4.93 (1H, dd, J=15.0, 4.8 Hz), 3.80-3.70 (1H, m), 3.44 (1H, dd, J=12.1, 3.7 Hz), 3.36-3.28 (1H, m), 2.76-2.73 (1H, m), 1.99-1.89 (4H, m), 1.78-1.71 (2H, m), 1.49-1.24 (4H, m).

MS 378.1 (M+1).

Example 12-2

Production of 11-cyclohexyl-5-thia-6a-azabenzo[a]fluorene-8-carboxylic acid

Step 1: Production of methyl 2-bromo-3-cyclohexyl-1-phenylsulfanylmethyl-1H-indole-6-carboxylate

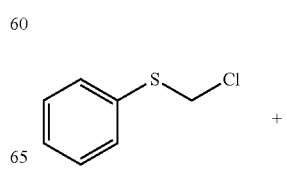 +

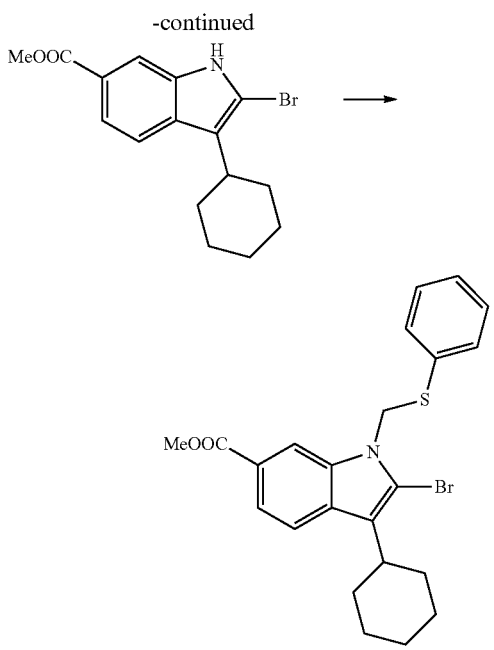

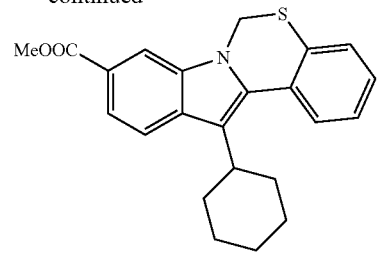

To a solution of methyl 2-bromo-3-cyclohexyl-1H-indole-6-carboxylate (1.00 g, 2.97 mmol) in N,N-dimethylformamide (10 ml) was added sodium hydride (60% in oil, 139 mg, 3.47 mmol) under ice-cooling, and the mixture was stirred for 1 hr. To this reaction mixture was added chloromethylsulfanylbenzene (0.38 ml, 2.94 mmol) under ice-cooling, and the mixture was stirred at room temperature for 1.5 hr. Water was added to the reaction mixture and the mixture was extracted with ethyl acetate. The organic layer was washed with saturated brine and dried over anhydrous sodium sulfate. After filtration, the solvent was evaporated under reduced pressure, and the residue was purified by silica gel chromatography (hexane:ethyl acetate=20:1-7:1) to give methyl 2-bromo-3-cyclohexyl-1-phenylsulfanylmethyl-1H-indole-6-carboxylate (1.10 g, yield 84.0%).

$^1$H-NMR (300 MHz, CDCl$_3$): δ(ppm) 7.79 (1H, brs), 7.74 (1H, dd, J=8.4, 1.6 Hz), 7.69 (1H, brd, J=8.4 Hz), 7.23-7.29 (1H, m), 7.21 (2H, brd, J=6.8 Hz), 7.16 (2H, dd, J=8.4, 7.6 Hz), 5.52 (2H, s), 3.92 (3H, s), 2.75-2.85 (1H, m), 1.95-1.83 (4H, m), 1.82-1.71 (3H, m), 1.48-1.30 (3H, m).

Step 2: Production of methyl 11-cyclohexyl-5-thia-6a-azabenzo[a]fluorene-8-carboxylate (Example 12-4)

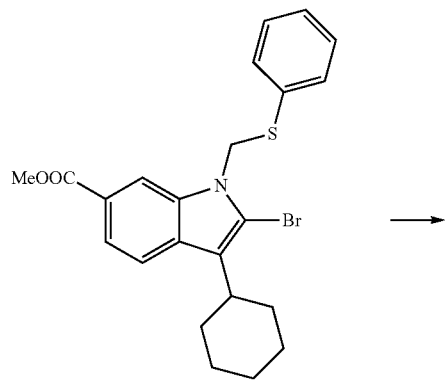

A suspension of methyl 2-bromo-3-cyclohexyl-1-phenylsulfanylmethyl-1H-indole-6-carboxylate (1.10 g, 2.41 mmol), potassium acetate (260 mg, 2.64 mmol) and tetrakis(triphenylphosphine)palladium (279 mg, 0.24 mmol) in N,N-dimethylacetamide (30 ml) was stirred at 100° C. for 3 hr. The reaction mixture was allowed to cool to room temperature, 2N hydrochloric acid was added to the reaction mixture, and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=20:1-7:1) to give methyl 11-cyclohexyl-5-thia-6a-azabenzo[a]fluorene-8-carboxylate (100 mg, yield 11.0%).

$^1$H-NMR (300 MHz, CDCl$_3$): δ(ppm) 8.08 (1H, d, J=0.7 Hz), 7.91 (1H, d, J=8.4 Hz), 7.75 (1H, dd, J=8.8, 1.5 Hz), 7.65 (1H, dd, J=7.7, 1.5 Hz), 7.52 (1H, dd, J=7.5, 1.3 Hz), 7.37 (1H, dt, J=1.6, 7.6 Hz), 7.29 (1H, dt, J=1.6, 7.5 Hz), 5.22 (2H, s), 3.95 (3H, s), 3.19 (1H, t, J=12.3 Hz), 2.12-2.05 (2H, m), 1.90-1.85 (5H, m), 1.44-1.41 (3H, m).

Step 3: Production of 11-cyclohexyl-5-thia-6a-azabenzo[a]fluorene-8-carboxylic acid (Example 12-2)

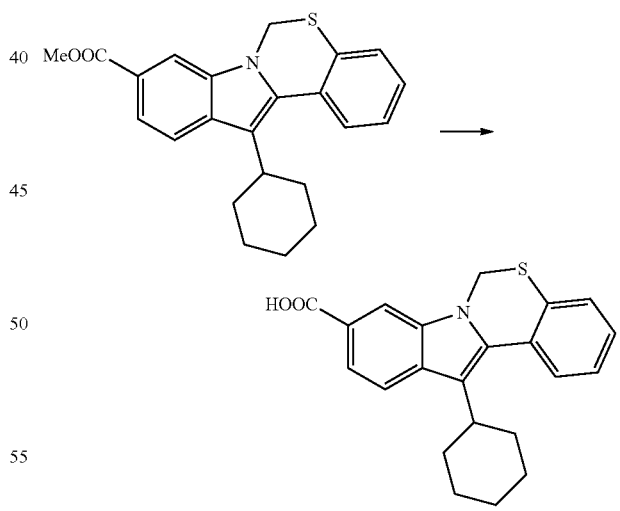

To a solution of methyl 11-cyclohexyl-5-thia-6a-azabenzo[a]fluorene-8-carboxylate (100 mg, 0.26 mmol) in tetrahydrofuran (2 ml) and methanol (2 ml) was added 4N aqueous sodium hydroxide solution (2 ml), and the mixture was stirred at room temperature for 15 hr. 2N Hydrochloric acid was added to the reaction mixture, and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=2:1-1:1) to give 11-cyclohexyl-5-thia-6a-azabenzo[a]fluorene-8-carboxylic acid (32 mg, yield 33.3%).

$^1$H-NMR (300 MHz, DMSO-d$_6$): δ(ppm) 12.62 (1H, brs), 8.23 (1H, d, J=1.1 Hz), 7.94 (1H, d, J=8.4 Hz), 7.64-7.61 (3H, m), 7.47 (1H, td, J=7.6, 1.2 Hz), 7.40-7.35 (1H, m), 5.53 (2H, s), 3.13 (1H, t, J=11.7 Hz), 2.12-2.08 (2H, m), 1.82-1.76 (5H, m), 1.42-1.38 (3H, m).

MS 364.0 (M+1).

Example 11-2 (2)

Production of methyl 6-tert-butoxycarbonyl-14-cyclohexyl-5,6,7,8-tetrahydrobenzo[6,7][1,4]diazocino[8,1-a]indole-11-carboxylate Step 1: Production of methyl 2-bromo-3-cyclohexyl-1-[2-(tetrahydropyran-2-yloxy)ethyl]-1H-indole-6-carboxylate

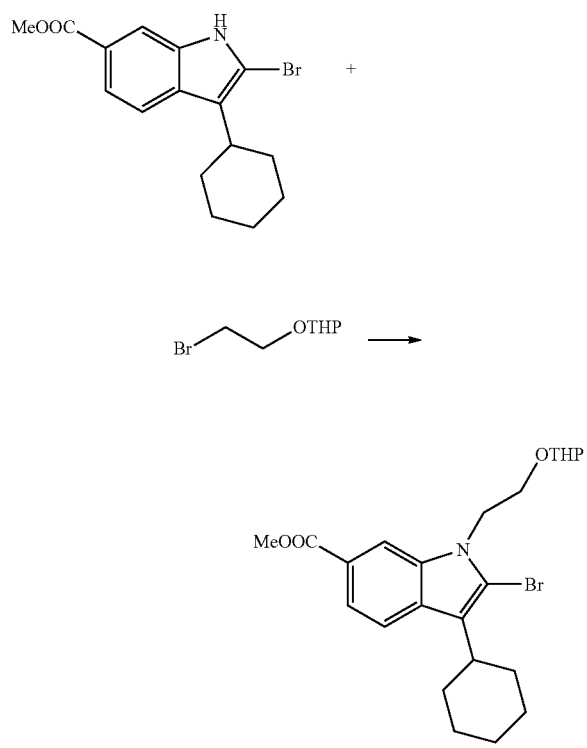

To a solution of methyl 2-bromo-3-cyclohexyl-1H-indole-6-carboxylate (5.00 g, 14.8 mmol) in N,N-dimethylformamide (50 ml) was added sodium hydride (60% in oil, 713 mg, 17.8 mmol) under ice-cooling, and the mixture was stirred under ice-cooling for 1 hr. 2-(2-Bromoethoxy)tetrahydropyran (2.90 ml, 19.2 mmol) was added to the reaction mixture under ice-cooling, and the mixture m was stirred at room temperature for 4 hr. Water was added to the reaction mixture and the mixture was extracted with ethyl acetate. The organic layer was successively washed with water and saturated brine and dried over anhydrous sodium sulfate. After filtration, the solvent was evaporated under reduced pressure to give methyl 2-bromo-3-cyclohexyl-1-[2-(tetrahydropyran-2-yloxy)ethyl]-1H-indole-6-carboxylate as a crude product. The obtained crude product was used for Step 2 without purification.

Step 2: Production of methyl 2-bromo-3-cyclohexyl-1-(2-hydroxyethyl)-1H-indole-6-carboxylate

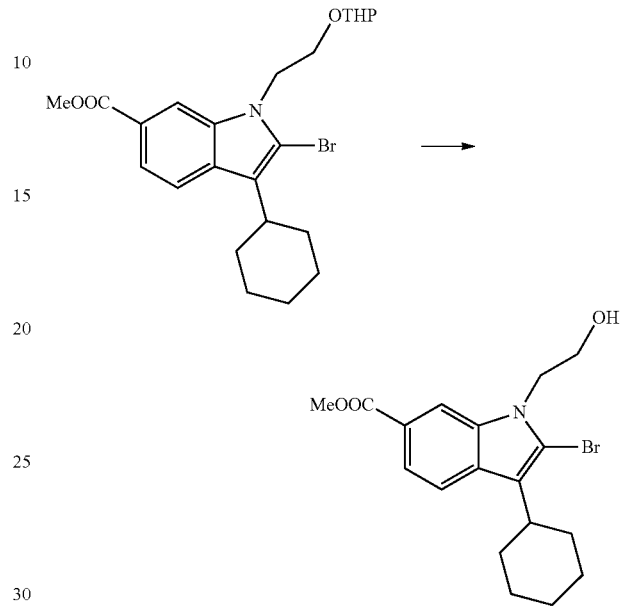

To a solution of methyl 2-bromo-3-cyclohexyl-1-[2-(tetrahydropyran-2-yloxy)ethyl]-1H-indole-6-carboxylate obtained as a crude product in Step 1 in tetrahydropyran (30 ml) and methanol (30 ml) was added 6N hydrochloric acid (30 ml), and the mixture was stirred at room temperature for 3 hr. Water was added to the reaction mixture and the mixture was extracted with ethyl acetate. The organic layer was washed with saturated brine and dried over anhydrous sodium sulfate. After filtration, the solvent was evaporated under reduced pressure, and the residue was purified by silica gel chromatography (hexane:ethyl acetate=4:1-1:1) to give methyl 2-bromo-3-cyclohexyl-1-(2-hydroxyethyl)-1H-indole-6-carboxylate (3.43 g, yield 61%).

$^1$H-NMR (400 MHz, CDCl$_3$): δ(ppm) 8.12 (1H, s), 7.79-7.71 (2H, m), 4.43 (2H, t, J=5.8 Hz), 3.99 (2H, t, J=5.6 Hz), 3.94 (3H, s), 2.95-2.84 (1H, m), 1.99-1.76 (7H, m), 1.51-1.33 (3H, m).

Step 3: Production of methyl 2-bromo-3-cyclohexyl-1-(2-methanesulfonyloxyethyl)-1H-indole-6-carboxylate

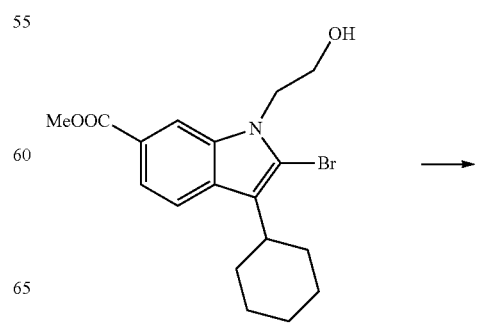

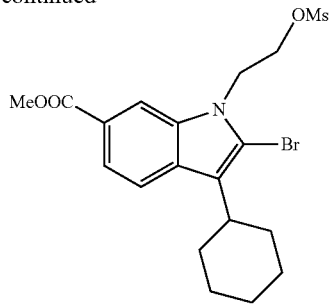

To a solution of methyl 2-bromo-3-cyclohexyl-1-(2-hydroxyethyl)-1H-indole-6-carboxylate (3.43 g, 9.01 mmol) in chloroform (30 ml) were added triethylamine (1.40 ml, 10.0 mmol) and methanesulfonyl chloride (0.77 ml, 9.90 mmol) under ice-cooling, and the mixture was stirred under ice-cooling for 30 min. Water was added to the reaction mixture and the mixture was extracted with chloroform. The organic layer was successively washed with 1N hydrochloric acid, saturated aqueous sodium hydrogen carbonate solution and saturated brine and dried over anhydrous sodium sulfate. After filtration, the solvent was evaporated under reduced pressure to give methyl 2-bromo-3-cyclohexyl-1-(2-methanesulfonyloxyethyl)-1H-indole-6-carboxylate as a crude product. The obtained crude product was used for Step 4 without purification.

Step 4: Production of methyl 2-bromo-3-cyclohexyl-1-[2-(1,3-dioxo-1,3-dihydroisoindol-2-yl)ethyl]-1H-indole-6-carboxylate

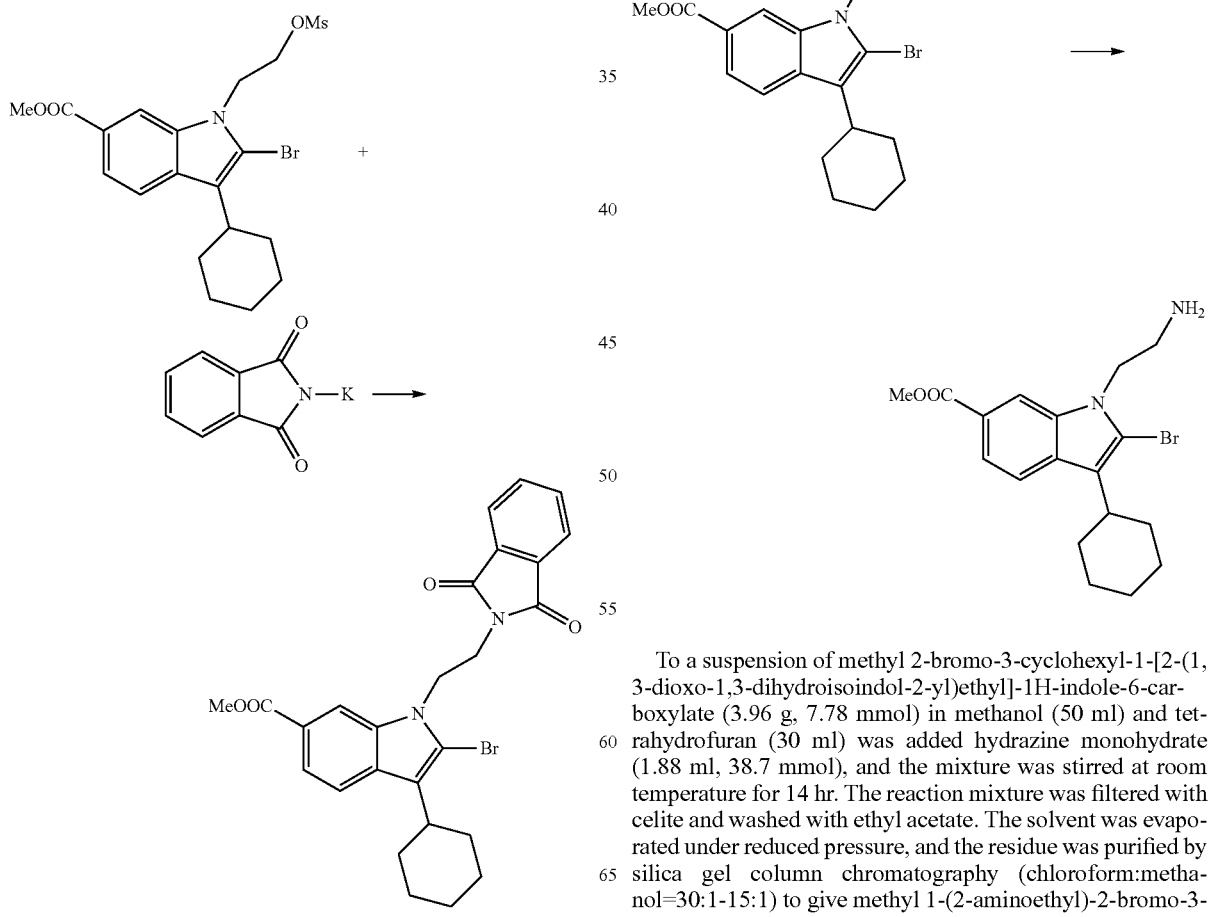

To a solution of methyl 2-bromo-3-cyclohexyl-1-(2-methanesulfonyloxyethyl)-1H-indole-6-carboxylate obtained as a crude product in Step 3 in N,N-dimethylformamide (40 ml) were added potassium phthalimide (2.50 g, 13.4 mmol) and potassium carbonate (2.50 g, 18.0 mmol), and the mixture was stirred at 80° C. for 7 hr. Water was added to the reaction mixture, and the mixture was stirred at room temperature for 1 hr. The precipitated solid was collected by filtration and dried in vacuo to give methyl 2-bromo-3-cyclohexyl-1-[2-(1,3-dioxo-1,3-dihydroisoindol-2-yl)ethyl]-1H-indole-6-carboxylate (3.96 g, yield 86%).

$^1$H-NMR (400 MHz, CDCl$_3$): δ(ppm) 8.02 (1H, s), 7.75 (1H, d, J=2.8 Hz), 7.74 (1H, d, J=2.8 Hz), 7.68-7.65 (4H, m), 4.54 (2H, t, J=6.0 Hz), 4.04 (2H, t, J=6.0 Hz), 3.91 (3H, s), 2.82 (1H, brt, J=12.1 Hz), 1.95-1.72 (7H, m), 1.46-1.30 (3H, m).

Step 5: Production of methyl 1-(2-aminoethyl)-2-bromo-3-cyclohexyl-1H-indole-6-carboxylate

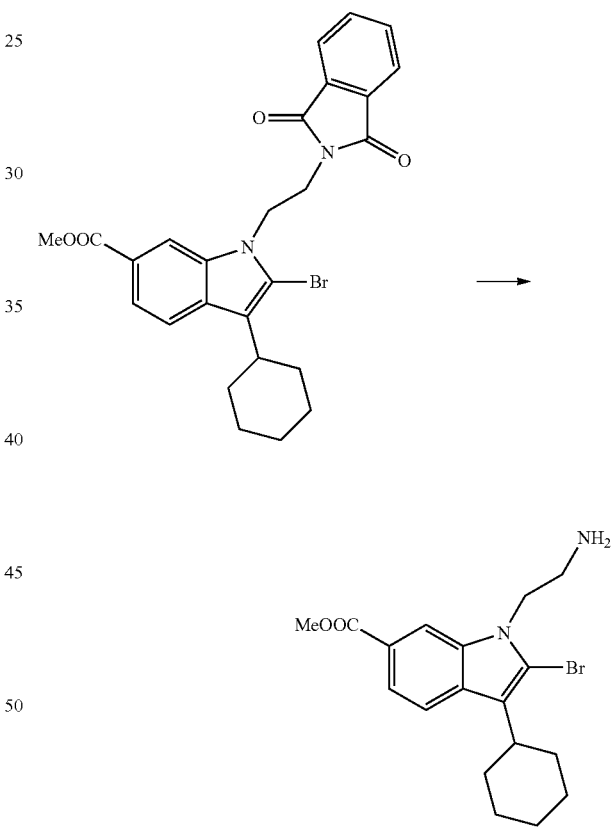

To a suspension of methyl 2-bromo-3-cyclohexyl-1-[2-(1,3-dioxo-1,3-dihydroisoindol-2-yl)ethyl]-1H-indole-6-carboxylate (3.96 g, 7.78 mmol) in methanol (50 ml) and tetrahydrofuran (30 ml) was added hydrazine monohydrate (1.88 ml, 38.7 mmol), and the mixture was stirred at room temperature for 14 hr. The reaction mixture was filtered with celite and washed with ethyl acetate. The solvent was evaporated under reduced pressure, and the residue was purified by silica gel column chromatography (chloroform:methanol=30:1-15:1) to give methyl 1-(2-aminoethyl)-2-bromo-3-cyclohexyl-1H-indole-6-carboxylate (2.95 g, yield 100%).

¹H-NMR (400 MHz, CDCl₃): δ(ppm) 8.07 (1H, brs), 7.77-7.73 (2H, m), 4.30 (2H, t, J=6.5 Hz), 3.94 (3H, s), 3.10 (2H, t, J=6.7 Hz), 2.89 (1H, brt, J=12.3 Hz), 2.00-1.75 (7H, m), 1.50-1.30 (4H, m).

Step 6: Production of methyl 2-bromo-1-(2-tert-butoxycarbonylaminoethyl)-3-cyclohexyl-1H-indole-6-carboxylate

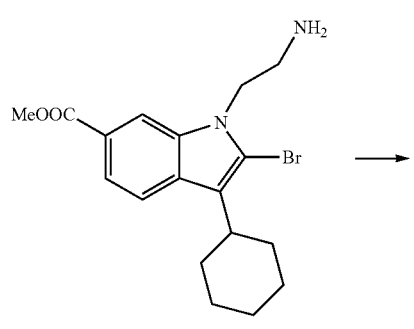

To a solution of methyl 1-(2-aminoethyl)-2-bromo-3-cyclohexyl-1H-indole-6-carboxylate (2.95 g, 7.78 mmol) in ethyl acetate (30 ml) and saturated aqueous sodium hydrogen carbonate solution (10 ml) was added di-tert-butyl dicarbonate (2.10 g, 9.62 mmol), and the mixture was stirred at room temperature for 3 hr. Water was added to the reaction mixture and the mixture was extracted with ethyl acetate. The organic layer was washed with saturated brine and dried over anhydrous sodium sulfate. After filtration, the solvent was evaporated under reduced pressure, and the residue was purified by silica gel column chromatography (hexane:ethyl acetate=8:1-3:1) to give methyl 2-bromo-1-(2-tert-butoxycarbonylaminoethyl)-3-cyclohexyl-1H-indole-6-carboxylate (2.78 g, yield 74%).

¹H-NMR (400 MHz, CDCl₃): δ(ppm) 8.04 (1H, s), 7.76 (2H, brs), 4.58 (1H, brs), 4.39 (2H, t, J=6.0 Hz), 3.93 (3H, s), 3.51 (2H, q, J=6.0 Hz), 2.92-2.86 (1H, m), 2.00-1.76 (7H, m), 1.50-1.32 (3H, m), 1.42 (9H, s).

Step 7: Production of methyl 1-(2-tert-butoxycarbonylaminoethyl)-3-cyclohexyl-2-(2-formylphenyl)-1H-indole-6-carboxylate

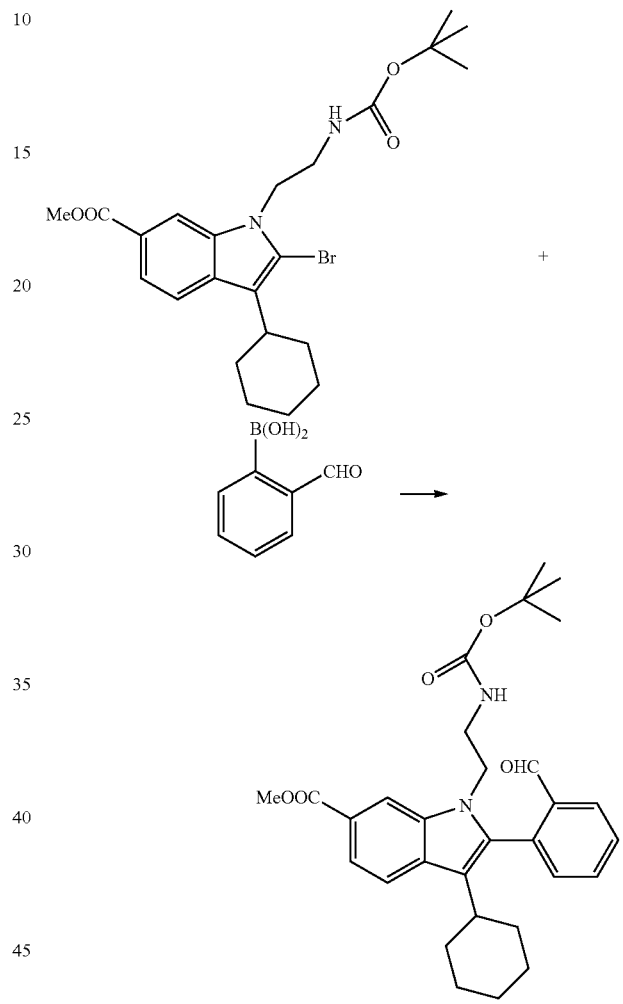

To a suspension of methyl 2-bromo-1-(2-tert-butoxycarbonylaminoethyl)-3-cyclohexyl-1H-indole-6-carboxylate (500 mg, 1.04 mmol), 2-formylphenylbononic acid (187 mg, 1.24 mmol) and sodium hydrogen carbonate (345 mg, 4.15 mmol) in 1,2-dimethoxyethane (5 ml) and water (2.5 ml) was added tetrakis(triphenylphosphine)palladium (60.0 mg, 0.05 mmol), and the mixture was stirred at 90° C. for 2 hr. Water was added to the reaction mixture and the mixture was extracted with ethyl acetate. The organic layer was successively washed with water and saturated brine and dried over anhydrous sodium sulfate. After filtration, the solvent was evaporated under reduced pressure, and the residue was purified by silica gel chromatography (hexane:ethyl acetate=5:1-3:1) to give methyl 1-(2-tert-butoxycarbonylaminoethyl)-3-cyclohexyl-2-(2-formylphenyl)-1H-indole-6-carboxylate (450 mg, yield 85%).

¹H-NMR (400 MHz, CDCl₃): δ(ppm) 9.79 (1H, brs), 8.15 (1H, brs), 8.11 (1H, dd, J=7.7, 1.2 Hz), 7.84 (2H, brs), 7.75 (1H, t, J=7.2 Hz), 7.67 (1H, t, J=7.4 Hz), 7.46 (1H, d, J=7.4

Hz), 4.38 (1H, brs), 4.16-4.10 (2H, m), 3.96 (3H, s), 3.27 (2H, t, J=5.8 Hz), 2.49-2.36 (1H, m), 1.85-1.60 (7H, m), 1.31 (9H, s), 1.26-1.10 (3H, m).

Step 8: Production of methyl 1-(2-tert-butoxycarbonylaminoethyl)-3-cyclohexyl-2-(2-hydroxymethylphenyl)-1H-indole-6-carboxylate (1H, t, J=7.7 Hz), 7.23 (1H, d, J=7.9 Hz), 4.63 (1H, brs), 4.53 (2H, s), 4.03 (2H, t, J=6.0 Hz), 3.96 (3H, s), 3.30 (1H, q, J=6.0 Hz), 2.41-2.30 (1H, m), 1.88-1.55 (7H, m), 1.29-1.10 (3H, m), 1.29 (9H, s).

Step 9: Production of methyl 1-(2-tert-butoxycarbonylaminoethyl)-3-cyclohexyl-2-(2-methanesulfonyloxymethylphenyl)-1H-indole-6-carboxylate

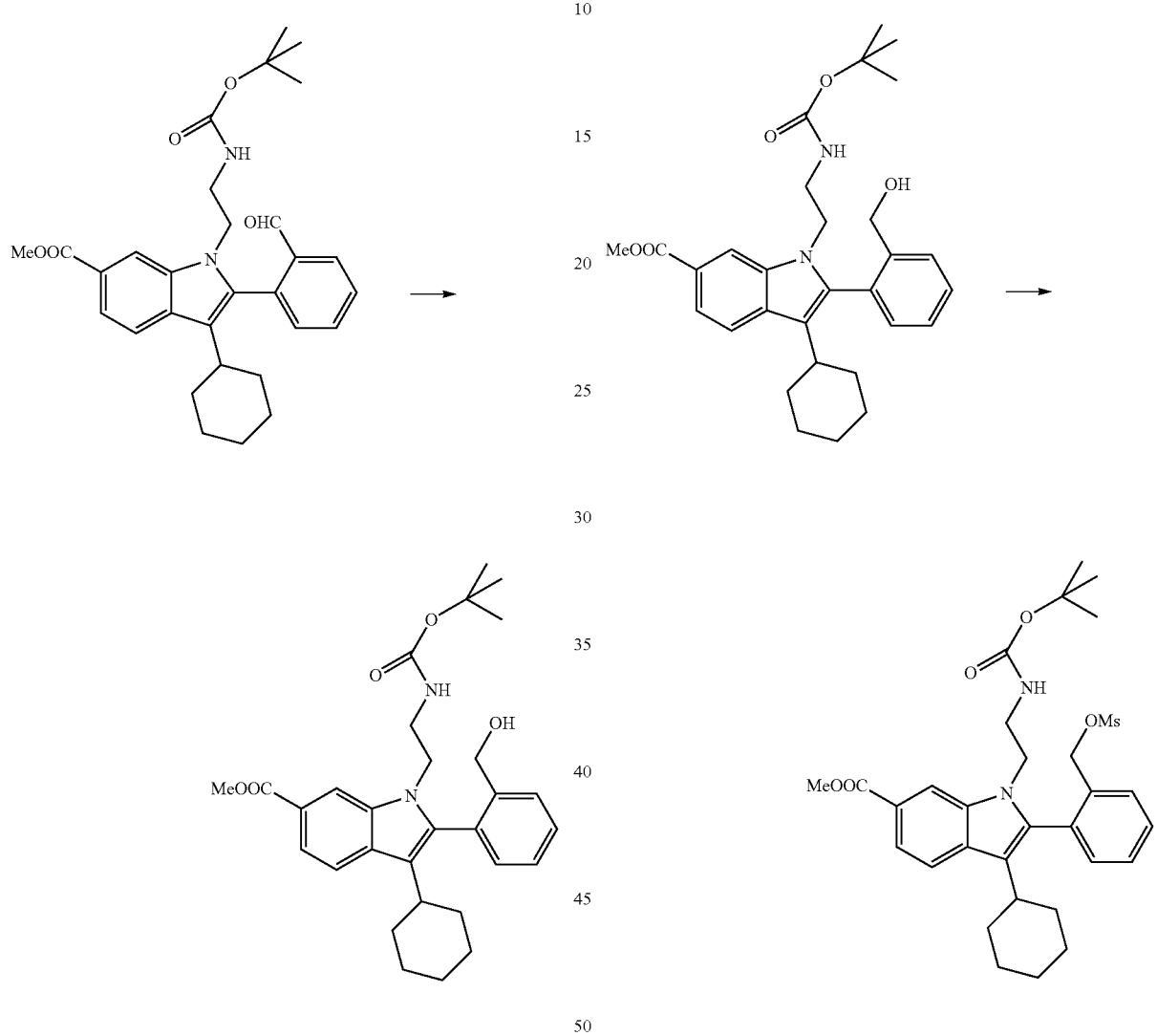

To a solution of methyl 1-(2-tert-butoxycarbonylaminoethyl)-3-cyclohexyl-2-(2-formylphenyl)-1H-indole-6-carboxylate (450 mg, 0.89 mmol) in methanol (4 ml) was added borosodium hydride (50.0 mg, 1.32 mmol) under ice-cooling, and the mixture was stirred under ice-cooling for 1 hr. 1N Hydrochloric acid was added to the reaction mixture, and the mixture was extracted with ethyl acetate. The organic layer was washed with saturated brine and dried over anhydrous sodium sulfate. After filtration, the solvent was evaporated under reduced pressure to give methyl 1-(2-tert-butoxycarbonylaminoethyl)-3-cyclohexyl-2-(2-hydroxymethylphenyl)-1H-indole-6-carboxylate (440 mg, yield 97%).

$^1$H-NMR (400 MHz, CDCl$_3$): δ(ppm) 8.11 (1H, brs), 7.81 (2H, brs), 7.72 (1H, d, J=7.9 Hz), 7.53 (1H, t, J=7.7 Hz), 7.40

To a solution of methyl 1-(2-tert-butoxycarbonylaminoethyl)-3-cyclohexyl-2-(2-hydroxymethylphenyl)-1H-indole-6-carboxylate (100 mg, 0.19 mmol) in chloroform (2 ml) was added triethylamine (0.04 ml, 0.28 mmol) and methanesulfonyl chloride (0.02 ml, 0.25 mmol) under ice-cooling, and the mixture was stirred under ice-cooling for 10 min. Water was added to the reaction mixture and the mixture was extracted with chloroform. The organic layer was so successively washed with 1N hydrochloric acid, saturated aqueous sodium hydrogen carbonate solution and saturated brine and dried over anhydrous sodium sulfate. After filtration, the solvent was evaporated under reduced pressure to give methyl 1-(2-tert-butoxycarbonylaminoethyl)-3-cyclohexyl-2-(2-methanesulfonyloxymethylphenyl)-1H-indole-6-carboxylate as a crude product. The obtained crude product was used for Step 10 without purification.

Step 10: Production of methyl 6-tert-butoxycarbonyl-14-cyclohexyl-5,6,7,8-tetrahydrobenzo[6,7][1,4]diazocino[8,1-a]indole-11-carboxylate (Example 11-2)

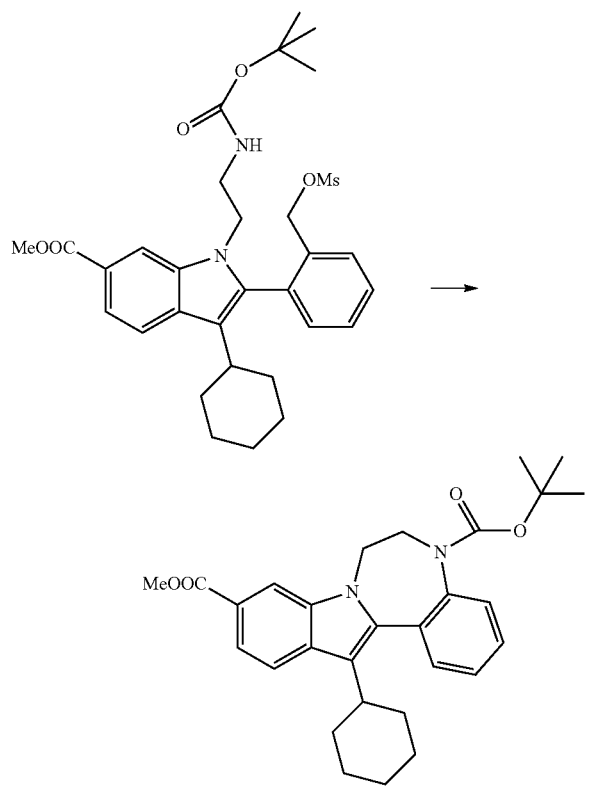

To a solution of methyl 1-(2-tert-butoxycarbonylaminoethyl)-3-cyclohexyl-2-(2-methanesulfonyloxymethylphenyl)-1H-indole-6-carboxylate obtained as a crude product in Step 9 in N,N-dimethylformamide (5 ml) was added sodium hydride (60% in oil, 12 mg, 0.30 mmol) under ice-cooling, and the mixture was stirred at room temperature for 1.5 hr. 1N Hydrochloric acid was added to the reaction mixture, and the mixture was stirred at room temperature for 1 hr. The precipitated solid was collected by filtration and dried in vacuo to give methyl 6-tert-butoxycarbonyl-14-cyclohexyl-5,6,7,8-tetrahydrobenzo[6,7][1,4]diazocino[8,1-a]indole-11-carboxylate (92 mg, yield 100%).

$^1$H-NMR (400 MHz, CDCl$_3$): δ(ppm) 8.08 (0.5H, s) 8.07 (0.5H, s), 7.90-7.78 (3H, m), 7.53-7.34 (3H, m), 4.98 (0.5H, d, J=14.8 Hz), 4.90 (0.5H, d, J=14.4 Hz), 4.66 (0.5H, dd, J=14.6, 4.9 Hz), 4.50 (1H, dd, J=19.5, 8.3 Hz), 4.31 (0.5H, d, J=14.4 Hz), 3.97 (3H, s), 3.75-3.67 (1H, m), 3.43 (0.5H, d, J=14.8 Hz), 3.29 (0.5H, d, J=14.8 Hz), 3.26 (0.5H, d, J=9.3 Hz), 3.03-2.97 (0.5H, m), 2.75-2.57 (1H, m), 2.03-1.72 (4H, m), 1.77-1.74 (2H, m), 1.60 (4.5H, s), 1.41 (4.5H, s), 1.35-1.18 (4H, m). MS 489.0 (M+1).

The compounds of Examples 1-446 to 1-472 and Examples 2-54 to 2-150 were produced by the same methods as in the above-mentioned Examples, particularly, Examples 2-57, 2-175, 2-180, 2-332, 2-346, 2-349, 2-350, 2-369 and 2-381 or methods similar thereto, and where necessary, by employing other conventional methods. The chemical structural formulas are shown in Tables 119-144.

The compounds of Examples 1-473 to 1-623, Examples 2-151 to 2-556, Examples 5-6 and 5-7, Examples 7-9 and 7-10, Examples 8-8 and 8-9 and Examples 11-4 to 11-8 were produced by the same methods as in the above-mentioned Examples or methods similar thereto, and where necessary, by employing other conventional methods. The chemical structural formulas are shown in Tables 145-268.

2-[13-cyclohexyl-10-(2H-tetrazol-5-yl)-6,7-dihydrobenzo[5,6][1,4]diazepino[7,1-a]indol-5-yl]-1-(4-ethylpiperazin-1-yl)ethanone (Example 1-96)

13-cyclohexyl-5-[2-(4-ethoxycarbonylpiperazin-1-yl)ethyl]-6,7-dihydro-5H-benzo[5,6][1,4]diazepino[7,1-a]indole-10-carboxylic acid dihydrochloride (Example 1-97)

5-[2-(4-acetylpiperazin-1-yl)ethyl]-13-cyclohexyl-6,7-dihydro-5H-benzo[5,6][1,4]diazepino[7,1-a]indole-10-carboxylic acid dihydrochloride (Example 1-98)

13-cyclohexyl-5-(2-dimethylaminoethyl)-6,7-dihydro-5H-benzo[5,6][1,4]diazepino[7,1-a]indole-10-carboxylic acid dihydrochloride (Example 1-99)

13-cyclohexyl-3-[2-(morpholin-4-yl)-5-(2-oxopyrrolidin-1-yl)benzyloxy]-6,7-dihydro-5H-benzo[5,6][1,4]diazepino[7,1-a]indole-10-carboxylic acid dihydrochloride (Example 1-100)

13-cyclohexyl-3-[5-methanesulfonyl-2-(morpholin-4-yl)benzyloxy]-6,7-dihydro-5H-benzo[5,6][1,4]diazepino[7,1-a]indole-10-carboxylic acid dihydrochloride (Example 1-101)

N-acetyl-13-cyclohexyl-5-[2-(4-ethylpiperazin-1-yl)-2-oxoethyl]-6,7-dihydro-5H-benzo[5,6][1,4]diazepino[7,1-a]indole-10-carboxamide (Example 1-102)

13-cyclohexyl-3-[5-methanesulfonyl-2-(morpholin-4-yl)benzyloxy]-5-methyl-6,7-dihydro-5H-benzo[5,6][1,4]diazepino[7,1-a]indole-10-carboxylic acid dihydrochloride (Example 1-103)

13-cyclohexyl-5-[2-(4-methoxycarbonylpiperazin-1-yl)ethyl]-6,7-dihydro-5H-benzo[5,6][1,4]diazepino[7,1-a]indole-10-carboxylic acid dihydrochloride (Example 1-104)

13-cyclohexyl-5-[3-(tetrahydropyran-2-yloxy)propyl]-6,7-dihydro-5H-benzo[5,6][1,4]diazepino[7,1-a]indole-10-carboxylic acid (Example 1-105)

13-cyclohexyl-5-[2-(3-hydroxypiperidin-1-yl)-2-oxoethyl]-6,7-dihydro-5H-benzo[5,6][1,4]diazepino[7,1-a]indole-10-carboxylic acid monohydrochloride (Example 1-106)

13-cyclohexyl-3-fluoro-5-[2-(morpholin-4-yl)ethyl]-6,7-dihydro-5H-benzo[5,6][1,4]diazepino[7,1-a]indole-10-carboxylic acid dihydrochloride (Example 1-107)

13-cyclohexyl-3-methyl-5-[2-(piperidin-1-yl)ethyl]-6,7-dihydro-5H-benzo[5,6][1,4]diazepino[7,1-a]indole-10-carboxylic acid dihydrochloride (Example 1-108)

13-cyclohexyl-3-fluoro-5-[2-(morpholin-4-yl)-2-oxoethyl]-6,7-dihydro-5H-benzo[5,6][1,4]diazepino[7,1-a]indole-10-carboxylic acid monohydrochloride (Example 1-109)

13-cyclohexyl-5-[2-(4-ethylpiperazin-1-yl)ethyl]-3-methyl-6,7-dihydro-5H-benzo[5,6][1,4]diazepino[7,1-a]indole-10-carboxylic acid trihydrochloride (Example 1-110)

13-cyclohexyl-5-[3-(piperidin-1-yl)propyl]-6,7-dihydro-5H-benzo[5,6][1,4]diazepino[7,1-a]indole-10-carboxylic acid dihydrochloride (Example 1-111)

13-cyclohexyl-5-(3-hydroxypropyl)-6,7-dihydro-5H-benzo[5,6][1,4]diazepino[7,1-a]indole-10-carboxylic acid monohydrochloride (Example 1-112)

13-cyclohexyl-5-[2-(3-hydroxypiperidin-1-yl)ethyl]-6,7-dihydro-5H-benzo[5,6][1,4]diazepino[7,1-a]indole-10-carboxylic acid dihydrochloride (Example 1-113)
13-cyclohexyl-3-fluoro-5-[2-oxo-2-(piperidin-1-yl)ethyl]-6,7-dihydro-5H-benzo[5,6][1,4]diazepino[7,1-a]indole-10-carboxylic acid monohydrochloride (Example 1-114)
13-cyclohexyl-3-methyl-5-[2-oxo-2-(piperidin-1-yl)ethyl]-6,7-dihydro-5H-benzo[5,6][1,4]diazepino[7,1-a]indole-10-carboxylic acid monohydrochloride (Example 1-115)
13-cyclohexyl-3-fluoro-5-[2-(piperidin-1-yl)ethyl]-6,7-dihydro-5H-benzo[5,6][1,4]diazepino[7,1-a]indole-10-carboxylic acid dihydrochloride (Example 1-116)
13-cyclohexyl-5-[2-(4-ethylpiperazin-1-yl)-2-oxoethyl]-3-methyl-6,7-dihydro-5H-benzo[5,6][1,4]diazepino[7,1-a]indole-10-carboxylic acid dihydrochloride (Example 1-117)
5-(1-acetylpiperidin-4-ylmethyl)-13-cyclohexyl-6,7-dihydro-5H-benzo[5,6][1,4]diazepino[7,1-a]indole-10-carboxylic acid monohydrochloride (Example 1-118)
13-cyclohexyl-5-[2-(1-isopropylpiperidin-4-yl)ethyl]-6,7-dihydro-5H-benzo[5,6][1,4]diazepino[7,1-a]indole-10-carboxylic acid dihydrochloride (Example 1-119)
13-cyclohexyl-5-(tetrahydropyran-4-ylmethyl)-6,7-dihydro-5H-benzo[5,6][1,4]diazepino[7,1-a]indole-10-carboxylic acid monohydrochloride (Example 1-120)
13-cyclohexyl-2-fluoro-5-[2-(piperidin-1-yl)ethyl]-6,7-dihydro-5H-benzo[5,6][1,4]diazepino[7,1-a]indole-10-carboxylic acid dihydrochloride (Example 1-121)
13-cyclohexyl-5-[2-(3-methylpiperidin-1-yl)-2-oxoethyl]-6,7-dihydro-5H-benzo[5,6][1,4]diazepino[7,1-a]indole-10-carboxylic acid monohydrochloride (Example 1-122)
13-cyclohexyl-5-[2-(1-ethylpiperidin-4-ylidene)ethyl]-6,7-dihydro-5H-benzo[5,6][1,4]diazepino[7,1-a]indole-10-carboxylic acid dihydrochloride (Example 1-123)
13-cyclohexyl-5-[2-(4-isopropylpiperidin-1-yl)-2-oxoethyl]-6,7-dihydro-5H-benzo[5,6][1,4]diazepino[7,1-a]indole-10-carboxylic acid monohydrochloride (Example 1-124)
13-cyclohexyl-5-[2-(3-methoxypiperidin-1-yl)-2-oxoethyl]-6,7-dihydro-5H-benzo[5,6][1,4]diazepino[7,1-a]indole-10-carboxylic acid monohydrochloride (Example 1-125)
13-cyclohexyl-5-(pyridin-2-ylmethyl)-6,7-dihydro-5H-benzo[5,6][1,4]diazepino[7,1-a]indole-10-carboxylic acid dihydrochloride (Example 1-126)
3-chloro-13-cyclohexyl-5-[2-(piperidin-1-yl)ethyl]-6,7-dihydro-5H-benzo[5,6][1,4]diazepino[7,1-a]indole-10-carboxylic acid (Example 1-127)
methyl 3-chloro-13-cyclohexyl-5-[2-(piperidin-1-yl)ethyl]-6,7-dihydro-5H-benzo[5,6][1,4]diazepino[7,1-a]indole-10-carboxylate (Example 1-128)
N-{13-cyclohexyl-5-[2-(4-ethylpiperazin-1-yl)-2-oxoethyl]-6,7-dihydro-5H-benzo[5,6][1,4]diazepino[7,1-a]indole-10-carbonyl}propane-1-sulfonamide dihydrochloride (Example 1-129)
13-cyclohexyl-5-(1-ethylpiperidin-4-ylmethyl)-6,7-dihydro-5H-benzo[5,6][1,4]diazepino[7,1-a]indole-10-carboxylic acid (Example 1-130)
5-[2-(azocan-1-yl)-2-oxoethyl]-13-cyclohexyl-6,7-dihydro-5H-benzo[5,6][1,4]diazepino[7,1-a]indole-10-carboxylic acid (Example 1-131)
5-[2-(azonan-1-yl)-2-oxoethyl]-13-cyclohexyl-6,7-dihydro-5H-benzo[5,6][1,4]diazepino[7,1-a]indole-10-carboxylic acid (Example 1-132)
13-cyclohexyl-5-(1-ethylpiperidin-4-ylmethyl)-6,7-dihydro-5H-benzo[5,6][1,4]diazepino[7,1-a]indole-10-carboxylic acid dihydrochloride (Example 1-133)
13-cyclohexyl-5-(pyridin-4-ylmethyl)-6,7-dihydro-5H-benzo[5,6][1,4]diazepino[7,1-a]indole-10-carboxylic acid dihydrochloride (Example 1-134)
13-cyclohexyl-5-(pyridin-3-ylmethyl)-6,7-dihydro-5H-benzo[5,6][1,4]diazepino[7,1-a]indole-10-carboxylic acid dihydrochloride (Example 1-135)
13-cyclohexyl-5-[2-(3,6-dihydro-2H-pyridin-1-yl)-2-oxoethyl]-6,7-dihydro-5H-benzo[5,6][1,4]diazepino[7,1-a]indole-10-carboxylic acid (Example 1-136)
13-cyclohexyl-5-[2-(2-methylpiperidin-1-yl)-2-oxoethyl]-6,7-dihydro-5H-benzo[5,6][1,4]diazepino[7,1-a]indole-10-carboxylic acid (Example 1-137)
13-cyclohexyl-5-[2-(3,4-dihydro-1H-isoquinolin-2-yl)-2-oxoethyl]-6,7-dihydro-5H-benzo[5,6][1,4]diazepino[7,1-a]indole-10-carboxylic acid monohydrochloride (Example 1-138)
13-cyclohexyl-5-[2-(octahydroquinolin-1-yl)-2-oxoethyl]-6,7-dihydro-5H-benzo[5,6][1,4]diazepino[7,1-a]indole-10-carboxylic acid monohydrochloride (Example 1-139)
13-cyclohexyl-5-[2-(1,3-dihydroisoindol-2-yl)-2-oxoethyl]-6,7-dihydro-5H-benzo[5,6][1,4]diazepino[7,1-a]indole-10-carboxylic acid monohydrochloride (Example 1-140)
13-cyclohexyl-5-[2-(octahydroisoquinolin-2-yl)-2-oxoethyl]-6,7-dihydro-5H-benzo[5,6][1,4]diazepino[7,1-a]indole-10-carboxylic acid monohydrochloride (Example 1-141)
13-cyclohexyl-5-[2-(3,4-dihydro-1H-isoquinolin-2-yl)ethyl]-6,7-dihydro-5H-benzo[5,6][1,4]diazepino[7,1-a]indole-10-carboxylic acid dihydrochloride (Example 1-142)
13-cyclohexyl-5-[2-(3-methylpiperidin-1-yl)ethyl]-6,7-dihydro-5H-benzo[5,6][1,4]diazepino[7,1-a]indole-10-carboxylic acid dihydrochloride (Example 1-143)
13-cyclohexyl-5-[2-(octahydroquinolin-1-yl)ethyl]-6,7-dihydro-5H-benzo[5,6][1,4]diazepino[7,1-a]indole-10-carboxylic acid dihydrochloride (Example 1-144)
13-cyclohexyl-5-[2-(1,3-dihydroisoindol-2-yl)ethyl]-6,7-dihydro-5H-benzo[5,6][1,4]diazepino[7,1-a]indole-10-carboxylic acid dihydrochloride (Example 1-145)
13-cyclohexyl-5-[2-(octahydroisoquinolin-2-yl)ethyl]-6,7-dihydro-5H-benzo[5,6][1,4]diazepino[7,1-a]indole-10-carboxylic acid dihydrochloride (Example 1-146)
3-chloro-13-cyclohexyl-5-[2-(piperidin-1-yl)ethyl]-6,7-dihydro-5H-benzo[5,6][1,4]diazepino[7,1-a]indole-10-carboxylic acid monohydrochloride (Example 1-147)
13-cyclohexyl-5-(3-dimethylaminopropyl)-6,7-dihydro-5H-benzo[5,6][1,4]diazepino[7,1-a]indole-10-carboxylic acid dihydrochloride (Example 1-148)
13-cyclohexyl-4-fluoro-5-[2-(piperidin-1-yl)ethyl]-6,7-dihydro-5H-benzo[5,6][1,4]diazepino[7,1-a]indole-10-carboxylic acid dihydrochloride (Example 1-149)
13-cyclohexyl-5-[2-(4-isopropylpiperidin-1-yl)ethyl]-6,7-dihydro-5H-benzo[5,6][1,4]diazepino[7,1-a]indole-10-carboxylic acid dihydrochloride (Example 1-150)
13-cyclohexyl-5-[2-(3-methoxypiperidin-1-yl)ethyl]-6,7-dihydro-5H-benzo[5,6][1,4]diazepino[7,1-a]indole-10-carboxylic acid dihydrochloride (Example 1-151)
5-(1-tert-butoxycarbonylpiperidin-3-ylmethyl)-13-cyclohexyl-6,7-dihydro-5H-benzo[5,6][1,4]diazepino[7,1-a]indole-10-carboxylic acid (Example 1-152)
13-cyclohexyl-5-(1-ethylpiperidin-3-ylmethyl)-6,7-dihydro-5H-benzo[5,6][1,4]diazepino[7,1-a]indole-10-carboxylic acid dihydrochloride (Example 1-153)
5-[2-(azocan-1-yl)ethyl]-13-cyclohexyl-6,7-dihydro-5H-benzo[5,6][1,4]diazepino[7,1-a]indole-10-carboxylic acid (Example 1-154)

5-[2-(azonan-1-yl)ethyl]-13-cyclohexyl-6,7-dihydro-5H-benzo[5,6][1,4]diazepino[7,1-a]indole-10-carboxylic acid (Example 1-155)

13-cyclohexyl-5-[2-(2-methylpiperidin-1-yl)ethyl]-6,7-dihydro-5H-benzo[5,6][1,4]diazepino[7,1-a]indole-10-carboxylic acid (Example 1-156)

13-cyclohexyl-5-[2-(1-cyclopentylpiperidin-4-yl)ethyl]-6,7-dihydro-5H-benzo[5,6][1,4]diazepino[7,1-a]indole-10-carboxylic acid dihydrochloride (Example 1-157)

13-cyclohexyl-5-[2-oxo-2-(4-trifluoromethylpiperidin-1-yl)ethyl]-6,7-dihydro-5H-benzo[5,6][1,4]diazepino[7,1-a]indole-10-carboxylic acid monohydrochloride (Example 1-158)

13-cyclohexyl-5-[2-(piperidin-1-yl)ethyl]-3-trifluoromethyl-6,7-dihydro-5H-benzo[5,6][1,4]diazepino[7,1-a]indole-10-carboxylic acid dihydrochloride (Example 1-159)

13-cyclohexyl-5-[2-(4-ethylpiperazin-1-yl)ethyl]-3-fluoro-6,7-dihydro-5H-benzo[5,6][1,4]diazepino[7,1-a]indole-10-carboxylic acid trihydrochloride (Example 1-160)

5-[2-(1-tert-butoxycarbonylpiperidin-2-yl)ethyl]-13-cyclohexyl-6,7-dihydro-5H-benzo[5,6][1,4]diazepino[7,1-a]indole-10-carboxylic acid monohydrochloride (Example 1-161)

13-cyclohexyl-5-[2-(4-ethylpiperazin-1-yl)-2-oxoethyl]-3-fluoro-6,7-dihydro-5H-benzo[5,6][1,4]diazepino[7,1-a]indole-10-carboxylic acid dihydrochloride (Example 1-162)

13-cyclohexyl-5-[2-(pyridin-2-yl)ethyl]-6,7-dihydro-5H-benzo[5,6][1,4]diazepino[7,1-a]indole-10-carboxylic acid dihydrochloride (Example 1-163)

13-cyclohexyl-5-(2-methoxyethyl)-6,7-dihydro-5H-benzo[5,6][1,4]diazepino[7,1-a]indole-10-carboxylic acid monohydrochloride (Example 1-164)

13-cyclohexyl-5-[2-(piperidin-3-yl)ethyl]-6,7-dihydro-5H-benzo[5,6][1,4]diazepino[7,1-a]indole-10-carboxylic acid dihydrochloride (Example 1-165)

13-cyclohexyl-5-[2-(1-ethylpiperidin-3-yl)ethyl]-6,7-dihydro-5H-benzo[5,6][1,4]diazepino[7,1-a]indole-10-carboxylic acid dihydrochloride (Example 1-166)

5-[2-(1-tert-butoxycarbonylpiperidin-3-yl)ethyl]-13-cyclohexyl-6,7-dihydro-5H-benzo[5,6][1,4]diazepino[7,1-a]indole-10-carboxylic acid (Example 1-167)

13-cyclohexyl-3-methyl-5-[2-(1,4-oxazepan-4-yl)ethyl]-6,7-dihydro-5H-benzo[5,6][1,4]diazepino[7,1-a]indole-10-carboxylic is acid dihydrochloride (Example 1-168)

3-chloro-13-cyclohexyl-5-[2-(1,4-oxazepan-4-yl)ethyl]-6,7-dihydro-5H-benzo[5,6][1,4]diazepino[7,1-a]indole-10-carboxylic acid monohydrochloride (Example 1-169)

13-cyclohexyl-3-fluoro-5-[2-(1,4-oxazepan-4-yl)ethyl]-6,7-dihydro-5H-benzo[5,6][1,4]diazepino[7,1-a]indole-10-carboxylic acid dihydrochloride (Example 1-170)

13-cyclohexyl-5-[2-(4,4-difluoropiperidin-1-yl)-2-oxoethyl]-6,7-dihydro-5H-benzo[5,6][1,4]diazepino[7,1-a]indole-10-carboxylic acid monohydrochloride (Example 1-171)

13-cyclohexyl-5-[2-(4-trifluoromethylpiperidin-1-yl)ethyl]-6,7-dihydro-5H-benzo[5,6][1,4]diazepino[7,1-a]indole-10-carboxylic acid dihydrochloride (Example 1-172)

13-cyclohexyl-5-[2-(1-propylpiperidin-4-yl)ethyl]-6,7-dihydro-5H-benzo[5,6][1,4]diazepino[7,1-a]indole-10-carboxylic acid dihydrochloride (Example 1-173)

13-cyclohexyl-5-[2-(4,4-difluoropiperidin-1-yl)ethyl]-6,7-dihydro-5H-benzo[5,6][1,4]diazepino[7,1-a]indole-10-carboxylic acid dihydrochloride (Example 1-174)

13-cyclohexyl-5-[2-(1-ethylpiperidin-4-ylidene)-2-fluoroethyl]-6,7-dihydro-5H-benzo[5,6][1,4]diazepino[7,1-a]indole-10-carboxylic acid dihydrochloride (Example 1-175)

2-chloro-13-cyclohexyl-5-[2-(piperidin-1-yl)ethyl]-6,7-dihydro-5H-benzo[5,6][1,4]diazepino[7,1-a]indole-10-carboxylic acid dihydrochloride (Example 1-176)

13-cyclohexyl-5-[2-(piperidin-2-yl)ethyl]-6,7-dihydro-5H-benzo[5,6][1,4]diazepino[7,1-a]indole-10-carboxylic acid dihydrochloride (Example 1-177)

13-cyclohexyl-5-[2-(1-ethylpiperidin-2-yl)ethyl]-6,7-dihydro-5H-benzo[5,6][1,4]diazepino[7,1-a]indole-10-carboxylic acid dihydrochloride (Example 1-178)

13-cyclohexyl-3-methylsulfanyl-5-[2-(piperidin-1-yl)ethyl]-6,7-dihydro-5H-benzo[5,6][1,4]diazepino[7,1-a]indole-10-carboxylic acid dihydrochloride (Example 1-179)

3-chloro-13-cyclohexyl-5-[2-(piperidin-1-yl)ethyl]-6,7-dihydro-5H-benzo[5,6][1,4]diazepino[7,1-a]indole-10-carboxamide dihydrochloride (Example 1-180)

13-cyclohexyl-5-[2-(pyridin-3-yl)ethyl]-6,7-dihydro-5H-benzo[5,6][1,4]diazepino[7,1-a]indole-10-carboxylic acid dihydrochloride (Example 1-181)

13-cyclohexyl-5-[2-(pyridin-4-yl)ethyl]-6,7-dihydro-5H-benzo[5,6][1,4]diazepino[7,1-a]indole-10-carboxylic acid dihydrochloride (Example 1-182)

13-cyclohexyl-5-[3aS ,7aR)-2-(octahydroisoindol-2-yl)ethyl]-6,7-dihydro-5H-benzo[5,6][1,4]diazepino[7,1-a]indole-10-carboxylic acid dihydrochloride (Example 1-183)

5-[2-(8-azaspiro[4.5]decan-8-yl)ethyl]-13-cyclohexyl-6,7-dihydro-5H-benzo[5,6][1,4]diazepino[7,1-a]indole-10-carboxylic acid dihydrochloride (Example 1-184)

13-cyclohexyl-5-(2-diethylaminoethyl)-6,7-dihydro-5H-benzo[5,6][1,4]diazepino[7,1-a]indole-10-carboxylic acid dihydrochloride (Example 1-185)

13-cyclohexyl-5-(2-diisopropylaminoethyl)-6,7-dihydro-5H-benzo[5,6][1,4]diazepino[7,1-a]indole-10-carboxylic acid dihydrochloride (Example 1-186)

13-cyclohexyl-5-[2-(3,5-dimethylpiperidin-1-yl)-2-oxoethyl]-6,7-dihydro-5H-benzo[5,6][1,4]diazepino[7,1-a]indole-10-carboxylic acid monohydrochloride (Example 1-187)

13-cyclohexyl-5-[2-(3-ethylpiperidin-1-yl)-2-oxoethyl]-6,7-dihydro-5H-benzo[5,6][1,4]diazepino[7,1-a]indole-10-carboxylic acid monohydrochloride (Example 1-188)

13-cyclohexyl-5-[2-(3,5-dimethylpiperidin-1-yl)ethyl]-6,7-dihydro-5H-benzo[5,6][1,4]diazepino[7,1-a]indole-10-carboxylic acid dihydrochloride (Example 1-189)

13-cyclohexyl-5-[2-(3-ethylpiperidin-1-yl)ethyl]-6,7-dihydro-5H-benzo[5,6][1,4]diazepino[7,1-a]indole-10-carboxylic acid dihydrochloride (Example 1-190)

13-cyclohexyl-2-methyl-5-[2-(piperidin-1-yl)ethyl]-6,7-dihydro-5H-benzo[5,6][1,4]diazepino[7,1-a]indole-10-carboxylic acid dihydrochloride (Example 1-191)

13-cyclohexyl-5-[2-(4-propylpiperidin-1-yl)ethyl]-6,7-dihydro-5H-benzo[5,6][1,4]diazepino[7,1-a]indole-10-carboxylic acid dihydrochloride (Example 1-192)

13-cyclohexyl-5-[2-((2S,6R)-2,6-dimethylpiperidin-1-yl)ethyl]-6,7-dihydro-5H-benzo[5,6][1,4]diazepino[7,1-a]indole-10-carboxylic acid dihydrochloride (Example 1-193)

5-[3-(azepan-1-yl)propyl]-13-cyclohexyl-6,7-dihydro-5H-benzo[5,6][1,4]diazepino[7,1-a]indole-10-carboxylic acid dihydrochloride (Example 1-194)

5-(adamantan-1-ylcarbamoylmethyl)-13-cyclohexyl-6,7-dihydro-5H-benzo[5,6][1,4]diazepino[7,1-a]indole-10-carboxylic acid monohydrochloride (Example 1-195)

5-[2-(adamantan-1-ylamino)ethyl]-13-cyclohexyl-6,7-dihydro-5H-benzo[5,6][1,4]diazepino[7,1-a]indole-10-carboxylic acid dihydrochloride (Example 1-196)

13-cyclohexyl-5-[2-(4-methoxymethylpiperidin-1-yl)ethyl]-6,7-dihydro-5H-benzo[5,6][1,4]diazepino[7,1-a]indole-10-carboxylic acid dihydrochloride (Example 1-197)

13-cyclohexyl-5-[2-(N-methyl-N-propylamino)ethyl]-6,7-dihydro-5H-benzo[5,6][1,4]diazepino[7,1-a]indole-10-carboxylic acid dihydrochloride (Example 1-198)

13-cyclohexyl-5-[2-(4,4-dimethylpiperidin-1-yl)ethyl]-6,7-dihydro-5H-benzo[5,6][1,4]diazepino[7,1-a]indole-10-carboxylic acid dihydrochloride (Example 1-199)

13-cyclohexyl-5-[2-(3-methoxymethylpiperidin-1-yl)ethyl]-6,7-dihydro-5H-benzo[5,6][1,4]diazepino[7,1-a]indole-10-carboxylic acid dihydrochloride (Example 1-200)

13-cyclohexyl-5-[2-(1-methylpiperidin-3-yl)ethyl]-6,7-dihydro-5H-benzo[5,6][1,4]diazepino[7,1-a]indole-10-carboxylic acid dihydrochloride (Example 1-201)

13-cyclohexyl-5-[2-(1-isopropylpiperidin-3-yl)ethyl]-6,7-dihydro-5H-benzo[5,6][1,4]diazepino[7,1-a]indole-10-carboxylic acid dihydrochloride (Example 1-202)

13-cyclohexyl-6-oxo-5-[2-oxo-2-(piperidin-1-yl)ethyl]-6,7-dihydro-5H-benzo[5,6][1,4]diazepino[7,1-a]indole-10-carboxylic acid (Example 1-203)

13-cyclohexyl-5-[2-(4-ethylpiperazin-1-yl)-2-oxoethyl]-6-oxo-6,7-dihydro-5H-benzo[5,6][1,4]diazepino[7,1-a]indole-10-carboxylic acid monohydrochloride (Example 1-204)

13-cyclohexyl-5-[2-(3,6-dihydro-2H-pyridin-1-yl)ethyl]-6,7-dihydro-5H-benzo[5,6][1,4]diazepino[7,1-a]indole-10-carboxylic acid (Example 1-205)

13-cyclohexyl-4-methyl-5-[2-(piperidin-1-yl)ethyl]-6,7-dihydro-5H-benzo[5,6][1,4]diazepino[7,1-a]indole-10-carboxylic acid dihydrochloride (Example 1-206)

13-cyclohexyl-5-[2-((S)-2-methoxymethylpyrrolidin-1-yl)ethyl]-6,7-dihydro-5H-benzo[5,6][1,4]diazepino[7,1-a]indole-10-carboxylic acid dihydrochloride (Example 1-207)

13-cyclohexyl-5-[2-(2-methylpyrrolidin-1-yl)ethyl]-6,7-dihydro-5H-benzo[5,6][1,4]diazepino[7,1-a]indole-10-carboxylic acid dihydrochloride (Example 1-208)

13-cyclohexyl-5-[2-(N-isobutyl-N-methylamino)ethyl]-6,7-dihydro-5H-benzo[5,6][1,4]diazepino[7,1-a]indole-10-carboxylic acid dihydrochloride (Example 1-209)

13-cyclohexyl-5-[2-(morpholin-4-yl)-2-oxoethyl]-6-oxo-6,7-dihydro-5H-benzo[5,6][1,4]diazepino[7,1-a]indole-10-carboxylic acid (Example 1-210)

3-benzyloxy-13-cyclohexyl-5-[2-(piperidin-1-yl)ethyl]-6,7-dihydro-5H-benzo[5,6][1,4]diazepino[7,1-a]indole-10-carboxylic acid dihydrochloride (Example 1-211)

13-cyclohexyl-5-[2-(N-isopropyl-N-methylamino)ethyl]-6,7-dihydro-5H-benzo[5,6][1,4]diazepino[7,1-a]indole-10-carboxylic acid dihydrochloride (Example 1-212)

3-chloro-13-cyclohexyl-5-[2-(2-methylpiperidin-1-yl)ethyl]-6,7-dihydro-5H-benzo[5,6][1,4]diazepino[7,1-a]indole-10-carboxylic acid dihydrochloride (Example 1-213)

3-chloro-13-cyclohexyl-5-[2-(3-methylpiperidin-1-yl)ethyl]-6,7-dihydro-5H-benzo[5,6][1,4]diazepino[7,1-a]indole-10-carboxylic acid dihydrochloride (Example 1-214)

3-chloro-13-cyclohexyl-5-[2-(4-methylpiperidin-1-yl)ethyl]-6,7-dihydro-5H-benzo[5,6][1,4]diazepino[7,1-a]indole-10-carboxylic acid dihydrochloride (Example 1-215)

3-chloro-13-cyclohexyl-5-[2-(pyrrolidin-1-yl)ethyl]-6,7-dihydro-5H-benzo[5,6][1,4]diazepino[7,1-a]indole-10-carboxylic acid dihydrochloride (Example 1-216)

5-[2-(azepan-1-yl)ethyl]-3-chloro-13-cyclohexyl-6,7-dihydro-5H-benzo[5,6][1,4]diazepino[7,1-a]indole-10-carboxylic acid dihydrochloride (Example 1-217)

5-[2-(azepan-1-yl)ethyl]-13-cyclohexyl-3-methyl-6,7-dihydro-5H-benzo[5,6][1,4]diazepino[7,1-a]indole-10-carboxylic acid dihydrochloride (Example 1-218)

3-chloro-13-cyclohexyl-5-[2-(piperidin-3-yl)ethyl]-6,7-dihydro-5H-benzo[5,6][1,4]diazepino[7,1-a]indole-10-carboxylic acid dihydrochloride (Example 1-219)

13-cyclohexyl-5-[2-(3-methylmorpholin-4-yl)ethyl]-6,7-dihydro-5H-benzo[5,6][1,4]diazepino[7,1-a]indole-10-carboxylic acid dihydrochloride (Example 1-220)

3-chloro-13-cyclohexyl-5-[2-(1-methylpiperidin-3-yl)ethyl]-6,7-dihydro-5H-benzo[5,6][1,4]diazepino[7,1-a]indole-10-carboxylic acid dihydrochloride (Example 1-221)

13-cyclohexyl-5-{[N-(2-dimethylaminoethyl)-N-methylcarbamoyl]methyl}-6,7-dihydro-5H-benzo[5,6][1,4]diazepino[7,1-a]indole-10-carboxylic acid dihydrochloride (Example 1-222)

13-cyclohexyl-5-{2-[N-(2-dimethylaminoethyl)-N-methylamino]ethyl}-6,7-dihydro-5H-benzo[5,6][1,4]diazepino[7,1-a]indole-10-carboxylic acid trihydrochloride (Example 1-223)

13-cyclohexyl-5-[2-(4-ethanesulfonylpiperazin-1-yl)ethyl]-6,7-dihydro-5H-benzo[5,6][1,4]diazepino[7,1-a]indole-10-carboxylic acid dihydrochloride (Example 1-224)

13-cyclohexyl-5-[2-(4-propionylpiperazin-1-yl)ethyl]-6,7-dihydro-5H-benzo[5,6][1,4]diazepino[7,1-a]indole-10-carboxylic acid dihydrochloride (Example 1-225)

13-cyclohexyl-5-[2-(4-isopropoxycarbonylpiperazin-1-yl)ethyl]-6,7-dihydro-5H-benzo[5,6][1,4]diazepino[7,1-a]indole-10-carboxylic acid dihydrochloride (Example 1-226)

13-cyclohexyl-3-isopropoxy-5-[2-(piperidin-1-yl)ethyl]-6,7-dihydro-5H-benzo[5,6][1,4]diazepino[7,1-a]indole-10-carboxylic acid dihydrochloride (Example 1-227)

3-benzyloxy-13-cyclohexyl-5-(2-dimethylaminoethyl)-6,7-dihydro-5H-benzo[5,6][1,4]diazepino[7,1-a]indole-10-carboxylic acid dihydrochloride (Example 1-228)

3-chloro-13-cyclohexyl-5-[2-(1-isopropylpiperidin-3-yl)ethyl]-6,7-dihydro-5H-benzo[5,6][1,4]diazepino[7,1-a]indole-10-carboxylic acid dihydrochloride (Example 1-229)

3-chloro-13-cyclohexyl-5-[2-(1-propylpiperidin-3-yl)ethyl]-6,7-dihydro-5H-benzo[5,6][1,4]diazepino[7,1-a]indole-10-carboxylic acid dihydrochloride (Example 1-230)

13-cyclohexyl-5-[2-(N-cyclohexyl-N-methylamino)ethyl]-6,7-dihydro-5H-benzo[5,6][1,4]diazepino[7,1-a]indole-10-carboxylic acid (Example 1-231)

13-cyclohexyl-5-[2-(4-methanesulfonyl-1,4-diazepan-1-yl)ethyl]-6,7-dihydro-5H-benzo[5,6][1,4]diazepino[7,1-a]indole-10-carboxylic acid dihydrochloride (Example 1-232)

13-cyclohexyl-5-[2-(4-methoxycarbonyl-1,4-diazepan-1-yl)ethyl]-6,7-dihydro-5H-benzo[5,6][1,4]diazepino[7,1-a]indole-10-carboxylic acid dihydrochloride (Example 1-233)

5-[2-(azepan-1-yl)ethyl]-13-cyclohexyl-3-fluoro-6,7-dihydro-5H-benzo[5,6][1,4]diazepino[7,1-a]indole-10-carboxylic acid dihydrochloride (Example 1-234)

13-cyclohexyl-6-oxo-5-[2-(piperidin-1-yl)ethyl]-6,7-dihydro-5H-benzo[5,6][1,4]diazepino[7,1-a]indole-10-carboxylic acid monohydrochloride (Example 1-235)

13-cyclohexyl-5-[2-(N-[2-(N-methoxycarbonyl-N-methylamino)ethyl]-N-methylamino)ethyl]-6,7-dihydro-5H-benzo[5,6][1,4]diazepino[7,1-a]indole-10-carboxylic acid dihydrochloride (Example 1-236)

13-cyclohexyl-5-[2-(3-methylpyrrolidin-1-yl)ethyl]-6,7-dihydro-5H-benzo[5,6][1,4]diazepino[7,1-a]indole-10-carboxylic acid dihydrochloride (Example 1-237)

13-cyclohexyl-5-[2-(3-methoxypyrrolidin-1-yl)ethyl]-6,7-dihydro-5H-benzo[5,6][1,4]diazepino[7,1-a]indole-10-carboxylic acid dihydrochloride (Example 1-238)

13-cyclohexyl-5-[2-(4-ethyl-1,4-diazepan-1-yl)-2-oxoethyl]-6,7-dihydro-5H-benzo[5,6][1,4]diazepino[7,1-a]indole-10-carboxylic acid dihydrochloride (Example 1-239)

3-chloro-13-cyclohexyl-5-[2-(1-isopropylpiperidin-4-yl)ethyl]-6,7-dihydro-5H-benzo[5,6][1,4]diazepino[7,1-a]indole-10-carboxylic acid dihydrochloride (Example 1-240)

13-cyclohexyl-1-methyl-5-[2-(piperidin-1-yl) ethyl]-6,7-dihydro-5H-benzo[5,6][1,4]diazepino[7,1-a]indole-10-carboxylic acid dihydrochloride (Example 1-241)

3-chloro-13-cyclohexyl-5-[3-(piperidin-1-yl)propyl]-6,7-dihydro-5H-benzo[5,6][1,4]diazepino[7,1-a]indole-10-carboxylic acid dihydrochloride (Example 1-242)

3-chloro-13-cyclohexyl-5-[2-(1-ethylpiperidin-4-yl)ethyl]-6,7-dihydro-5H-benzo[5,6][1,4]diazepino[7,1-a]indole-10-carboxylic acid dihydrochloride (Example 1-243)

3-chloro-13-cyclohexyl-5-[2-(piperidin-4-yl)ethyl]-6,7-dihydro-5H-benzo[5,6][1,4]diazepino[7,1-a]indole-10-carboxylic acid dihydrochloride (Example 1-244)

5-[3-(azepan-1-yl)propyl]-3-chloro-13-cyclohexyl-6,7-dihydro-5H-benzo[5,6][1,4]diazepino[7,1-a]indole-10-carboxylic acid dihydrochloride (Example 1-245)

3-chloro-13-cyclohexyl-5-[2-(1-methylpiperidin-4-yl)ethyl]-6,7-dihydro-5H-benzo[5,6][1,4]diazepino[7,1-a]indole-10-carboxylic acid dihydrochloride (Example 1-246)

3-chloro-13-cyclohexyl-5-(3-dimethylaminopropyl)-6,7-dihydro-5H -benzo[5,6][1,4]diazepino[7,1-a]indole-10-carboxylic acid dihydrochloride (Example 1-247)

13-cyclohexyl-2,3-difluoro-5-[2-(piperidin-1-yl)ethyl]-6,7-dihydro-5H-benzo[5,6][1,4]diazepino[7,1-a]indole-10-carboxylic acid dihydrochloride (Example 1-248)

3-chloro-13-cyclohexyl-5-[2-(3-ethylpiperidin-1-yl)ethyl]-6,7-dihydro-5H-benzo[5,6][1,4]diazepino[7,1-a]indole-10-carboxylic acid dihydrochloride (Example 1-249)

13-cyclohexyl-5-{2-[N-(1-methoxycarbonylpyrrolidin-3-yl)-N-methylamino]ethyl}-6,7-dihydro-5H-benzo[5,6][1,4]diazepino[7,1a]indole-10-carboxylic acid monohydrochloride (Example 1-250)

5-{2-[N-(1-acetylpyrrolidin-3-yl)-N-methylamino]ethyl}-13-cyclohexyl-6,7-dihydro-5H-benzo[5,6][1,4]diazepino[7,1-a]indole-10-carboxylic acid monohydrochloride (Example 1-251)

13-cyclohexyl-5-{2-[N-(1-methanesulfonylpyrrolidin-3-yl)-N-methylamino]ethyl}-6,7-dihydro-5H-benzo[5,6][1,4]diazepino[7,1-a]indole-10-carboxylic acid (Example 1-252)

13-cyclohexyl-3-methyl-5-[2-(3-methylpiperidin-1-yl)ethyl]-6,7-dihydro-5H-benzo[5,6][1,4]diazepino[7,1-a]indole-10-carboxylic acid dihydrochloride (Example 1-253)

13-cyclohexyl-3-fluoro-5-[2-(3-methylpiperidin-1-yl)ethyl]-6,7-dihydro-5H-benzo[5,6][1,4]diazepino[7,1-a]indole-10-carboxylic acid dihydrochloride (Example 1-254)

13-cyclohexyl-5-[2-(2-methylmorpholin-4-yl)ethyl]-6,7-dihydro-5H-benzo[5,6][1,4]diazepino[7,1-a]indole-10-carboxylic acid dihydrochloride (Example 1-255)

13-cyclohexyl-5-[2-(2-ethylmorpholin-4-yl)ethyl]-6,7-dihydro-5H-benzo[5,6][1,4]diazepino[7,1-a]indole-10-carboxylic acid dihydrochloride (Example 1-256)

13-cyclohexyl-5-[2-(3-ethylmorpholin-4-yl)ethyl]-6,7-dihydro-5H-benzo[5,6][1,4]diazepino[7,1-a]indole-10-carboxylic acid dihydrochloride (Example 1-257)

13-cyclohexyl-3-methyl-5-[2-(2-methylpiperidin-1-yl)ethyl]-6,7-dihydro-5H-benzo[5,6][1,4]diazepino[7,1-a]indole-10-carboxylic acid dihydrochloride (Example 1-258)

13-cyclohexyl-3-methyl-5-[2-(4-methylpiperidin-1-yl)ethyl]-6,7-dihydro-5H-benzo[5,6][1,4]diazepino[7,1-a]indole-10-carboxylic acid dihydrochloride (Example 1-259)

13-cyclohexyl-3-methyl-5-[2-(pyrrolidin-1-yl)ethyl]-6,7-dihydro-5H-benzo[5,6][1,4]diazepino[7,1-a]indole-10-carboxylic acid dihydrochloride (Example 1-260)

3-chloro-13-cyclohexyl-5-[2-(1-ethylpiperidin-3-yl)ethyl]-6,7-dihydro-5H-benzo[5,6][1,4]diazepino[7,1-a]indole-10-carboxylic acid dihydrochloride (Example 1-261)

3-chloro-13-cyclohexyl-5-[2-(1-methylpiperidin-4-yloxy)ethyl]-6,7-dihydro-5H-benzo[5,6][1,4]diazepino[7,1-a]indole-10-carboxylic acid dihydrochloride (Example 1-262)

3-chloro-13-cyclohexyl-5-[2-(1-isobutylpiperidin-3-yl)ethyl]-6,7-dihydro-5H-benzo[5,6][1,4]diazepino[7,1-a]indole-10-carboxylic acid dihydrochloride (Example 1-263)

3-chloro-13-cyclohexyl-5-[2-(1-cyclopentylpiperidin-3-yl)ethyl]-6,7-dihydro-5H-benzo[5,6][1,4]diazepino[7,1-a]indole-10-carboxylic acid dihydrochloride (Example 1-264)

3-chloro-13-cyclohexyl-5-[2-(3-methoxypiperidin-1-yl)ethyl]-6,7-dihydro-5H-benzo[5,6][1,4]diazepino[7,1-a]indole-10-carboxylic acid dihydrochloride (Example 1-265)

13-cyclohexyl-5-[2-(3-methoxypiperidin-1-yl)ethyl]-3-methyl-6,7-dihydro-5H-benzo[5,6][1,4]diazepino[7,1-a]indole-10-carboxylic acid dihydrochloride (Example 1-266)

3-chloro-13-cyclohexyl-5-[2-(3-propylpiperidin-1-yl)ethyl]-6,7-dihydro-5H-benzo[5,6][1,4]diazepino[7,1-a]indole-10-carboxylic acid dihydrochloride (Example 1-267)

13-cyclohexyl-3-methyl-5-[2-(3-propylpiperidin-1-yl)ethyl]-6,7-dihydro-5H-benzo[5,6][1,4]diazepino[7,1-a]indole-10-carboxylic acid dihydrochloride (Example 1-268)

3-chloro-13-cyclohexyl-5-[3-(pyrrolidin-1-yl)propyl]-6,7-dihydro-5H-benzo[5,6][1,4]diazepino[7,1-a]indole-10-carboxylic acid dihydrochloride (Example 1-269)

3-chloro-13-cyclohexyl-5-[3-(1,4-oxazepan-4-yl)propyl]-6,7-dihydro-5H-benzo[5,6][1,4]diazepino[7,1-a]indole-10-carboxylic acid dihydrochloride (Example 1-270)

13-cyclohexyl-5-[2-(2-methoxymethylpiperidin-1-yl)ethyl]-6,7-dihydro-5H-benzo[5,6][1,4]diazepino[7,1-a]indole-10-carboxylic acid dihydrochloride (Example 1-271)

13-cyclohexyl-5-[2-(3-ethylpiperidin-1-yl)ethyl]-3-methyl-6,7-dihydro-5H-benzo[5,6][1,4]diazepino[7,1-a]indole-10-carboxylic acid dihydrochloride (Example 1-272)

13-cyclohexyl-5-[2-(1-ethylpiperidin-3-yl)ethyl]-3-methyl-6,7-dihydro-5H-benzo[5,6][1,4]diazepino[7,1-a]indole-10-carboxylic acid dihydrochloride (Example 1-273)

13-cyclohexyl-3-methyl-5-[2-(1-methylpiperidin-3-yl)ethyl]-6,7-dihydro-5H-benzo[5,6][1,4]diazepino[7,1-a]indole-10-carboxylic acid dihydrochloride (Example 1-274)

13-cyclohexyl-5-[2-(1-isopropylpiperidin-3-yl)ethyl]-3-methyl-6,7-dihydro-5H-benzo[5,6][1,4]diazepino[7,1-a]indole-10-carboxylic acid dihydrochloride (Example 1-275)

13-cyclohexyl-3-ethoxy-5-[2-(piperidin-1-yl)ethyl]-6,7-dihydro-5H-benzo[5,6][1,4]diazepino[7,1-a]indole-10-carboxylic acid dihydrochloride (Example 1-276)

5-[2-(azocan-1-yl)ethyl]-3-chloro-13-cyclohexyl-6,7-dihydro-5H-benzo[5,6][1,4]diazepino[7,1-a]indole-10-carboxylic acid dihydrochloride (Example 1-277)

5-[2-(azocan-1-yl)ethyl]-13-cyclohexyl-3-methyl-6,7-dihydro-5H-benzo[5,6][1,4]diazepino[7,1-a]indole-10-carboxylic acid dihydrochloride (Example 1-278)

5-{2-[N-(1-acetylpiperidin-4-yl)-N-methylamino]ethyl}-13-cyclohexyl-6,7-dihydro-5H-benzo[5,6][1,4]diazepino[7,1-a]indole-10-carboxylic acid monohydrochloride (Example 1-279)

13-cyclohexyl-5-(2-[N-(1-methanesulfonylpiperidin-4-yl)-N-methylamino]ethyl)-6,7-dihydro-5H-benzo[5,6][1,4]diazepino[7,1-a]indole-10-carboxylic acid (Example 1-280)

13-cyclohexyl-5-[2-[N-(1-methoxycarbonylpiperidin-4-yl)-N-methylamino]ethyl]-6,7-dihydro-5H-benzo[5,6][1,4]diazepino[7,1-a]indole-10-carboxylic acid monohydrochloride (Example 1-281)

13-cyclohexyl-5-{2-[N-methyl-N-(1-methylpiperidin-4-yl)amino]ethyl}-6,7-dihydro-5H-benzo[5,6][1,4]diazepino[7,1-a]indole-10-carboxylic acid dihydrochloride (Example 1-282)

13-cyclohexyl-5-{2-[N-methyl-N-(tetrahydropyran-4-yl)amino]ethyl}-6,7-dihydro-5H-benzo[5,6][1,4]diazepino[7,1-a]indole-10-carboxylic acid (Example 1-283)

13-cyclohexyl-5-{2-[N-methyl-N-(1-methylpyrrolidin-3-yl)amino]ethyl}-6,7-dihydro-5H-benzo[5,6][1,4]diazepino[7,1-a]indole-10-carboxylic acid dihydrochloride (Example 1-284)

13-cyclohexyl-5-[2-{N-methyl-N-(pyrrolidin-3-yl)amino]ethyl}-6,7-dihydro-5H-benzo[5,6][1,4]diazepino[7,1-a]indole-10-carboxylic acid dihydrochloride (Example 1-285)

13-cyclohexyl-5-[2-(4-ethyl-1,4-diazepan-1-yl)ethyl]-6,7-dihydro-5H-benzo[5,6][1,4]diazepino[7,1-a]indole-10-carboxylic acid trihydrochloride (Example 1-286)

13-cyclohexyl-3-methyl-5-[2-(1-methylpiperidin-2-yl)ethyl]-6,7-dihydro-5H-benzo[5,6][1,4]diazepino[7,1-a]indole-10-carboxylic acid dihydrochloride (Example 1-287)

13-cyclohexyl-5-[2-(1-ethylpiperidin-2-yl)ethyl]-3-methyl-6,7-dihydro-5H-benzo[5,6][1,4]diazepino[7,1-a]indole-10-carboxylic acid dihydrochloride (Example 1-288)

5-[2-(azepan-1-yl)ethyl]-13-cyclohexyl-3-methylsulfanyl-6,7-dihydro-5H-benzo[5,6][1,4]diazepino[7,1-a]indole-10-carboxylic acid dihydrochloride (Example 1-289)

3-chloro-13-cyclohexyl-5-[2-(2-ethylmorpholin-4-yl)ethyl]-6,7-dihydro-5H-benzo[5,6][1,4]diazepino[7,1-a]indole-10-carboxylic acid dihydrochloride (Example 1-290)

13-cyclohexyl-5-[2-(2-ethylmorpholin-4-yl)ethyl]-3-methyl-6,7-dihydro-5H-benzo[5,6][1,4]diazepino[7,1-a]indole-10-carboxylic acid dihydrochloride (Example 1-291)

13-cyclohexyl-5-[2-(3-ethylmorpholin-4-yl)ethyl]-3-methyl-6,7-dihydro-5H-benzo[5,6][1,4]diazepino[7,1-a]indole-10-carboxylic acid dihydrochloride (Example 1-292)

3-chloro-13-cyclohexyl-5-[2-(3-methoxymethylpiperidin-1-yl)ethyl]-6,7-dihydro-5H-benzo[5,6][1,4]diazepino[7,1-a]indole-10-carboxylic acid dihydrochloride (Example 1-293)

13-cyclohexyl-5-[2-(3-methoxymethylpiperidin-1-yl)ethyl]-3-methyl-6,7-dihydro-5H-benzo[5,6][1,4]diazepino[7,1-a]indole-10-carboxylic acid dihydrochloride (Example 1-294)

13-cyclohexyl-3-ethyl-5-[2-(piperidin-1-yl)ethyl]-6,7-dihydro-5H-benzo[5,6][1,4]diazepino[7,1-a]indole-10-carboxylic acid dihydrochloride (Example 1-295)

13-cyclohexyl-3-isopropyl-5-[2-(piperidin-1-yl)ethyl]-6,7-dihydro-5H-benzo[5,6][1,4]diazepino[7,1-a]indole-10-carboxylic acid dihydrochloride (Example 1-296)

13-cyclohexyl-3-methylsulfanyl-5-[3-(piperidin-1-yl)propyl]-6,7-dihydro-5H-benzo[5,6][1,4]diazepino[7,1-a]indole-10-carboxylic acid dihydrochloride (Example 1-297)

13-cyclohexyl-3-methyl-5-[3-(piperidin-1-yl)propyl]-6,7-dihydro-5H-benzo[5,6][1,4]diazepino[7,1-a]indole-10-carboxylic acid dihydrochloride (Example 1-298)

13-cyclohexyl-3-methyl-5-[3-(pyrrolidin-1-yl)propyl]-6,7-dihydro-5H-benzo[5,6][1,4]diazepino[7,1-a]indole-10-carboxylic acid dihydrochloride (Example 1-299)

5-[3-(azepan-1-yl)propyl]-13-cyclohexyl-3-methyl-6,7-dihydro-5H-benzo[5,6][1,4]diazepino[7,1-a]indole-10-carboxylic acid dihydrochloride (Example 1-300)

13-cyclohexyl-5-(3-dimethylaminopropyl)-3-methyl-6,7-dihydro-5H-benzo[5,6][1,4]diazepino[7,1-a]indole-10-carboxylic acid dihydrochloride (Example 1-301)

3-chloro-13-cyclohexyl-5-(3-diethylaminopropyl)-6,7-dihydro-5H-benzo[5,6][1,4]diazepino[7,1-a]indole-10-carboxylic acid dihydrochloride (Example 1-302)

13-cyclohexyl-3-methylsulfanyl-5-[2-(pyrrolidin-1-yl)ethyl]-6,7-dihydro-5H-benzo[5,6][1,4]diazepino[7,1-a]indole-10-carboxylic acid dihydrochloride (Example 1-303)

3-chloro-13-cyclohexyl-5-[2-(2-methoxymethylpiperidin-1-yl)ethyl]-6,7-dihydro-5H-benzo[5,6][1,4]diazepino[7,1-a]indole-10-carboxylic acid dihydrochloride (Example 1-304)

13-cyclohexyl-5-[2-(2-methoxymethylpiperidin-1-yl)ethyl]-3-methyl-6,7-dihydro-5H-benzo[5,6][1,4]diazepino[7,1-a]indole-10-carboxylic acid dihydrochloride (Example 1-305)

13-cyclohexyl-5-{2-[3-(2-methoxyethyl)piperidin-1-yl]ethyl}-6,7-dihydro-5H-benzo[5,6][1,4]diazepino[7,1-a]indole-10-carboxylic acid dihydrochloride (Example 1-306)

3-chloro-13-cyclohexyl-5-{2-[3-(2-methoxyethyl)piperidin-1-yl]ethyl}-6,7-dihydro-5H-benzo[5,6][1,4]diazepino[7,1-a]indole-10-carboxylic acid dihydrochloride (Example 1-307)

13-cyclohexyl-5-{2-[3-(2-methoxyethyl)piperidin-1-yl]ethyl}-3-methyl-6,7-dihydro-5H-benzo[5,6][1,4]diazepino[7,1-a]indole-10-carboxylic acid dihydrochloride (Example 1-308)

13-cyclohexyl-5-(2-dimethylaminoethyl)-3-[5-methanesulfonyl-2-(morpholin-4-yl)benzyloxy]-6,7-dihydro-5H-benzo[5,6][1,4]diazepino[7,1-a]indole-10-carboxylic acid trihydrochloride (Example 1-309)

13-cyclohexyl-5-(2-dimethylaminoethyl)-3-methoxycarbonyloxy-6,7-dihydro-5H-benzo[5,6][1,4]diazepino[7,1-a]indole-10-carboxylic acid dihydrochloride (Example 1-310)

13-cyclohexyl-5-(2-dimethylaminoethyl)-3-phenoxy-6,7-dihydro-5H-benzo[5,6][1,4]diazepino[7,1-a]indole-10-carboxylic acid dihydrochloride (Example 1-311)

3-chloro-13-cyclohexyl-5-[2-(1-methylpiperidin-2-yl)ethyl]-6,7-dihydro-5H-benzo[5,6][1,4]diazepino[7,1-a]indole-10-carboxylic acid dihydrochloride (Example 1-312)

3-chloro-13-cyclohexyl-5-[2-(piperidin-1-yl)ethyl]-6,7-dihydro-5H-benzo[5,6][1,4]diazepino[7,1-a]indole-10-carboxylic acid dihydrochloride (Example 1-313)

3-chloro-13-cyclohexyl-5-[2-(4-methoxymethylpiperidin-1-yl)ethyl]-6,7-dihydro-5H-benzo[5,6][1,4]diazepino[7,1-a]indole-10-carboxylic acid dihydrochloride (Example 1-314)

13-cyclohexyl-5-[2-(4-methoxymethylpiperidin-1-yl)ethyl]-3-methyl-6,7-dihydro-5H-benzo[5,6][1,4]diazepino[7,1-a]indole-10-carboxylic acid dihydrochloride (Example 1-315)

13-cyclohexyl-5-[2-((R)-2-methoxymethylpyrrolidin-1-yl)ethyl]-6,7-dihydro-5H-benzo[5,6][1,4]diazepino[7,1-a]indole-10-carboxylic acid dihydrochloride (Example 1-316)

3-chloro-13-cyclohexyl-5-[2-(1-ethylpiperidin-4-yloxy)ethyl]-6,7-dihydro-5H-benzo[5,6][1,4]diazepino[7,1-a]indole-10-carboxylic acid dihydrochloride (Example 1-317)

3-chloro-13-cyclohexyl-5-[2-(1-isopropylpiperidin-4-yloxy)ethyl]-6,7-dihydro-5H-benzo[5,6][1,4]diazepino[7,1-a]indole-10-carboxylic acid dihydrochloride (Example 1-318)

13-cyclohexyl-5-[2-(N-cyclopentyl-N-methylamino)ethyl]-6,7-dihydro-5H-benzo[5,6][1,4]diazepino[7,1-a]indole-10-carboxylic acid (Example 1-319)

3-chloro-13-cyclohexyl-5-[3-(3-methylpiperidin-1-yl)propyl]-6,7-dihydro-5H-benzo[5,6][1,4]diazepino[7,1-a]indole-10-carboxylic acid (Example 1-320)

13-cyclohexyl-5-{[N-methyl-N-(tetrahydrofuran-3-yl)amino]ethyl}-6,7-dihydro-5H-benzo[5,6][1,4]diazepino[7,1-a]indole-10-carboxylic acid (Example 1-321)

3-chloro-13-cyclohexyl-5-[3-(2-methylpiperidin-1-yl)propyl]-6,7-dihydro-5H-benzo[5,6][1,4]diazepino[7,1-a]indole-10-carboxylic acid (Example 1-322)

3-chloro-13-cyclohexyl-5-[2-(1-ethylpiperidin-2-yl)ethyl]-6,7-dihydro-5H-benzo[5,6][1,4]diazepino[7,1-a]indole-10-carboxylic acid dihydrochloride (Example 1-323)

13-cyclohexyl-5-[2-(3-ethoxypiperidin-1-yl)ethyl]-6,7-dihydro-5H-benzo[5,6][1,4]diazepino[7,1-a]indole-10-carboxylic acid monohydrochloride (Example 1-324)

13-cyclohexyl-5-[2-(3-ethoxypiperidin-1-yl)ethyl]-3-methyl-6,7-dihydro-5H-benzo[5,6][1,4]diazepino[7,1-a]indole-10-carboxylic acid monohydrochloride (Example 1-325)

3-chloro-13-cyclohexyl-5-[2-(3-ethoxypiperidin-1-yl)ethyl]-6,7-dihydro-5H-benzo[5,6][1,4]diazepino[7,1-a]indole-10-carboxylic acid monohydrochloride (Example 1-326)

3-chloro-13-cyclohexyl-5-[2-(3-ethylmorpholin-4-yl)ethyl]-6,7-dihydro-5H-benzo[5,6][1,4]diazepino[7,1-a]indole-10-carboxylic acid dihydrochloride (Example 1-327)

3-chloro-13-cyclohexyl-5-[2-(2-methylmorpholin-4-yl)ethyl]-6,7-dihydro-5H-benzo[5,6][1,4]diazepino[7,1-a]indole-10-carboxylic acid dihydrochloride (Example 1-328)

13-cyclohexyl-3-methyl-5-[2-(2-methylmorpholin-4-yl)ethyl]-6,7-dihydro-5H-benzo[5,6][1,4]diazepino[7,1-a]indole-10-carboxylic acid dihydrochloride (Example 1-329)

13-cyclohexyl-5-[2-(4-methylcarbamoylpiperazin-1-yl)ethyl]-6,7-dihydro-5H-benzo[5,6][1,4]diazepino[7,1-a]indole-10-carboxylic acid dihydrochloride (Example 1-330)

13-cyclohexyl-5-[2-(3-propylpiperidin-1-yl)ethyl]-6,7-dihydro-5H-benzo[5,6)(1,4]diazepino[7,1-a]indole-10-carboxylic acid dihydrochloride (Example 1-331)

13-cyclohexyl-5-[2-(2-ethylpiperidin-1-yl)ethyl]-6,7-dihydro-5H-benzo[5,6][1,4]diazepino[7,1-a]indole-10-carboxylic acid dihydrochloride (Example 1-332)

13-cyclohexyl-5-[2-(2-ethylpiperidin-1-yl)ethyl]-3-methyl-6,7-dihydro-5H-benzo[5,6][1,4]diazepino[7,1-a]indole-10-carboxylic acid dihydrochloride (Example 1-333)

3-chloro-13-cyclohexyl-5-[2-(2-ethylpiperidin-1-yl)ethyl]-6,7-dihydro-5H-benzo[5,6][1,4]diazepino[7,1-a]indole-10-carboxylic acid dihydrochloride (Example 1-334)

3-chloro-13-cyclohexyl-5-[2-((S)-3-ethylpiperidin-1-yl)ethyl]-6,7-dihydro-5H-benzo[5,6][1,4]diazepino[7,1-a]indole-10-carboxylic acid dihydrochloride (Example 1-335)

3-chloro-13-cyclohexyl-5-[2-((R)-3-ethylpiperidin-1-yl)ethyl]-6,7-dihydro-5H-benzo[5,6][1,4]diazepino[7,1-a]indole-10-carboxylic acid dihydrochloride (Example 1-336)

5-[2-(azepan-1-yl)ethyl]-13-cyclohexyl-3-isopropyl-6,7-dihydro-5H-benzo[5,6][1,4]diazepino[7,1-a]indole-10-carboxylic acid dihydrochloride (Example 1-337)

5-[2-(azepan-1-yl)ethyl]-13-cyclohexyl-3-ethyl-6,7-dihydro-5H-benzo[5,6][1,4]diazepino[7,1-a]indole-10-carboxylic acid dihydrochloride (Example 1-338)

13-cyclohexyl-3-ethyl-5-[2-(3-methylpiperidin-1-yl)ethyl]-6,7-dihydro-5H-benzo[5,6][1,4]diazepino[7,1-a]indole-10-carboxylic acid dihydrochloride (Example 1-339)

13-cyclohexyl-3-isopropyl-5-[2-(3-methylpiperidin-1-yl)ethyl]-6,7-dihydro-5H-benzo[5,6][1,4]diazepino[7,1-a]indole-10-carboxylic acid dihydrochloride (Example 1-340)

13-cyclohexyl-5-[2-(3-ethylpiperidin-1-yl)ethyl]-3-isopropyl-6,7-dihydro-5H-benzo[5,6][1,4]diazepino[7,1-a]indole-10-carboxylic acid dihydrochloride (Example 1-341)

3-chloro-13-cyclohexyl-5-[2-(1-cyclopropylpiperidin-3-yl)ethyl]-6,7-dihydro-5H-benzo[5,6][1,4]diazepino[7,1-a]indole-10-carboxylic acid dihydrochloride (Example 1-342)

13-cyclohexyl-5-[2-(piperidin-1-yl)ethyl]-3-propyl-6,7-dihydro-5H-benzo[5,6][1,4]diazepino[7,1-a]indole-10-carboxylic acid dihydrochloride (Example 1-343)

N-{2-[10-carboxy-13-cyclohexyl-3-(5-methylisoxazol-3-ylmethoxy)-6,7-dihydro-benzo[5,6][1,4]diazepino[7,1-a]indol-5-yl]ethyl}-N,N-dimethyl-N-(5-methylisoxazol-3-ylmethyl)ammonium chloride monohydrochloride (Example 1-344)

13-cyclohexyl-3-ethoxy-5-[2-(3-methylpiperidin-1-yl)ethyl]-6,7-dihydro-5H-benzo[5,6][1,4]diazepino[7,1-a]indole-10-carboxylic acid dihydrochloride (Example 1-345)

13-cyclohexyl-5-[2-(3-methoxymethylpiperidin-1-yl)ethyl]-3-propyl-6,7-dihydro-5H-benzo[5,6][1,4]diazepino[7,1-a]indole-10-carboxylic acid dihydrochloride (Example 1-346)

13-cyclohexyl-3-ethoxy-5-[2-(3-ethylpiperidin-1-yl)ethyl]-6,7-dihydro-5H-benzo[5,6][1,4]diazepino[7,1-a]indole-10-carboxylic acid dihydrochloride (Example 1-347)

3-benzyloxy-13-cyclohexyl-5-[2-(3-ethylpiperidin-1-yl)ethyl]-6,7-dihydro-5H-benzo[5,6][1,4]diazepino[7,1-a]indole-10-carboxylic acid dihydrochloride (Example 1-348)

13-cyclohexyl-3-ethoxy-5-[2-(1-isopropylpiperidin-3-yl)ethyl]-6,7-dihydro-5H-benzo[5,6][1,4]diazepino[7,1-a]indole-10-carboxylic acid dihydrochloride (Example 1-349)

13-cyclohexyl-3-ethyl-5-[2-(3-ethylpiperidin-1-yl)ethyl]-6,7-dihydro-5H-benzo[5,6][1,4]diazepino[7,1-a]indole-10-carboxylic acid dihydrochloride (Example 1-350)

3-chloro-13-cyclohexyl-5-[2-(3-isopropylpiperidin-1-yl)ethyl]-6,7-dihydro-5H-benzo[5,6][1,4]diazepino[7,1-a]indole-10-carboxylic acid dihydrochloride (Example 1-351)

3-chloro-13-cyclohexyl-5-[3-(3-methoxymethylpiperidin-1-yl)propyl]-6,7-dihydro-5H-benzo[5,6][1,4]diazepino[7,1-a]indole-10-carboxylic acid monohydrochloride (Example 1-352)

3-chloro-13-cyclohexyl-5-[3-(2-ethylpiperidin-1-yl)propyl]-6,7-dihydro-5H-benzo[5,6][1,4]diazepino[7,1-a]indole-10-carboxylic acid dihydrochloride (Example 1-353)

13-cyclohexyl-5-[2-(1-isopropylpiperidin-3-yl)ethyl]-3-propyl-6,7-dihydro-5H-benzo[5,6][1,4]diazepino[7,1-a]indole-10-carboxylic acid dihydrochloride (Example 1-354)

3-chloro-13-cyclohexyl-5-[3-(2-methoxymethylpiperidin-1-yl)propyl]-6,7-dihydro-5H-benzo[5,6][1,4]diazepino[7,1-a]indole-10-carboxylic acid dihydrochloride (Example 1-355)

13-cyclohexyl-5-[2-(3-methylpiperidin-1-yl)ethyl]-3-propyl-6,7-dihydro-5H-benzo[5,6][1,4]diazepino[7,1-a]indole-10-carboxylic acid dihydrochloride (Example 1-356)

13-cyclohexyl-5-[2-(3-ethylpiperidin-1-yl)ethyl]-3-propyl-6,7-dihydro-5H-benzo[5,6][1,4]diazepino[7,1-a]indole-10-carboxylic acid dihydrochloride (Example 1-357)

3-benzyloxy-13-cyclohexyl-5-[2-(3-methoxymethylpiperidin-1-yl)ethyl]-6,7-dihydro-5H-benzo[5,6][1,4]diazepino[7,1-a]indole-10-carboxylic acid dihydrochloride (Example 1-358)

13-cyclohexyl-3-isopropyl-5-[2-(pyrrolidin-1-yl)ethyl]-6,7-dihydro-5H-benzo[5,6][1,4]diazepino[7,1-a]indole-10-carboxylic acid monohydrochloride (Example 1-359)

13-cyclohexyl-3-ethyl-5-[2-(pyrrolidin-1-yl)ethyl]-6,7-dihydro-5H-benzo[5,6][1,4]diazepino[7,1-a]indole-10-carboxylic acid monohydrochloride (Example 1-360).

3-benzyloxy-13-cyclohexyl-5-[2-(3-methylpiperidin-1-yl)ethyl]-6,7-dihydro-5H-benzo[5,6][1,4]diazepino[7,1-a]indole-10-carboxylic acid dihydrochloride (Example 1-361)

3-benzyloxy-13-cyclohexyl-5-[2-(1-isopropylpiperidin-3-yl)ethyl]-6,7-dihydro-5H-benzo[5,6][1,4]diazepino[7,1-a]indole-10-carboxylic acid dihydrochloride (Example 1-362)

13-cyclohexyl-3-(5-methylisoxazol-3-ylmethoxy)-5-[2-(piperidin-1-yl)ethyl]-6,7-dihydro-5H-benzo[5,6][1,4]diazepino[7,1-a]indole-10-carboxylic acid dihydrochloride (Example 1-363)

13-cyclohexyl-5-[2-(3-isopropylpiperidin-1-yl)ethyl]-6,7-dihydro-5H-benzo[5,6][1,4]diazepino[7,1-a]indole-10-carboxylic acid dihydrochloride (Example 1-364)

13-cyclohexyl-5-[2-(3-isopropylpiperidin-1-yl)ethyl]-3-methyl-6,7-dihydro-5H-benzo[5,6][1,4]diazepino[7,1-a]indole-10-carboxylic acid dihydrochloride (Example 1-365)

13-cyclohexyl-3-ethyl-5-[2-(3-methoxymethylpiperidin-1-yl)ethyl]-6,7-dihydro-5H-benzo[5,6][1,4]diazepino[7,1-a]indole-10-carboxylic acid dihydrochloride (Example 1-366)

13-cyclohexyl-3-isopropyl-5-[2-(3-methoxymethylpiperidin-1-yl)ethyl]-6,7-dihydro-5H-benzo[5,6][1,4]diazepino[7,1-a]indole-10-carboxylic acid dihydrochloride (Example 1-367)

3-chloro-13-cyclohexyl-5-[3-(2-methylpyrrolidin-1-yl)propyl]-6,7-dihydro-5H-benzo[5,6][1,4]diazepino[7,1-a]indole-10-carboxylic acid (Example 1-368)

13-cyclohexyl-3-ethyl-5-[2-(1-isopropylpiperidin-3-yl)ethyl]-6,7-dihydro-5H-benzo[5,6][1,4]diazepino[7,1-a]indole-10-carboxylic acid (Example 1-369)

13-cyclohexyl-3-ethoxy-5-[2-(3-methoxymethylpiperidin-1-yl)ethyl]-6,7-dihydro-5H-benzo[5,6][1,4]diazepino[7,1-a]indole-10-carboxylic acid (Example 1-370)

3-chloro-13-cyclohexyl-5-[2-(1-isopropylpiperidin-3-yloxy)ethyl]-6,7-dihydro-5H-benzo[5,6][1,4]diazepino[7,1-a]indole-10-carboxylic acid (Example 1-371)

3-chloro-13-cyclohexyl-5-[3-(3-ethylpiperidin-1-yl)propyl]-6,7-dihydro-5H-benzo[5,6][1,4]diazepino[7,1-a]indole-10-carboxylic acid dihydrochloride (Example 1-372)

13-cyclohexyl-3-isobutoxy-5-[2-(piperidin-1-yl)ethyl]-6,7-dihydro-5H-benzo[5,6][1,4]diazepino[7,1-a]indole-10-carboxylic acid dihydrochloride (Example 1-373)

13-cyclohexyl-5-(2-dimethylaminoethyl)-3-(5-methylisoxazol-3-ylmethoxy)-6,7-dihydro-5H-benzo[5,6][1,4]diazepino[7,1-a]indole-10-carboxylic acid dihydrochloride (Example 1-374)

13-cyclohexyl-3-isobutoxy-5-[2-(3-methylpiperidin-1-yl)ethyl]-6,7-dihydro-5H-benzo[5,6][1,4]diazepino[7,1-a]indole-10-carboxylic acid dihydrochloride (Example 1-375)

13-cyclohexyl-5-[2-(3-ethylpiperidin-1-yl)ethyl]-3-isobutoxy-6,7-dihydro-5H-benzo[5,6][1,4]diazepino[7,1-a]indole-10-carboxylic acid dihydrochloride (Example 1-376)

13-cyclohexyl-3-isobutoxy-5-[2-(3-methoxymethylpiperidin-1-yl)ethyl]-6,7-dihydro-5H-benzo[5,6][1,4]diazepino[7,1-a]indole-10-carboxylic acid dihydrochloride (Example 1-377)

13-cyclohexyl-5-(3-diethylaminopropyl)-3-methyl-6,7-dihydro-5H-benzo[5,6][1,4]diazepino[7,1-a]indole-10-carboxylic acid dihydrochloride (Example 1-378)

3-chloro-13-cyclohexyl-5-[2-(1-cyclohexylpiperidin-3-yl)ethyl]-6,7-dihydro-5H-benzo[5,6][1,4]diazepino[7,1-a]indole-10-carboxylic acid dihydrochloride (Example 1-379)

13-cyclohexyl-5-[2-(1-cyclopentylpiperidin-3-yl)ethyl]-3-methyl-6,7-dihydro-5H-benzo[5,6][1,4]diazepino[7,1-a]indole-10-carboxylic acid dihydrochloride (Example 1-380)

13-cyclohexyl-3-isopropyl-5-[2-(1-isopropylpiperidin-3-yl)ethyl]-6,7-dihydro-5H-benzo[5,6][1,4]diazepino[7,1-a]indole-10-carboxylic acid dihydrochloride (Example 1-381)

13-cyclohexyl-5-[2-(3-ethylpyrrolidin-1-yl)ethyl]-6,7-dihydro-5H-benzo[5,6][1,4]diazepino[7,1-a]indole-10-carboxylic acid dihydrochloride (Example 1-382)

3-chloro-13-cyclohexyl-5-[2-(3-ethylpyrrolidin-1-yl)ethyl]-6,7-dihydro-5H-benzo[5,6][1,4]diazepino[7,1-a]indole-10-carboxylic acid dihydrochloride (Example 1-383)

13-cyclohexyl-5-[2-(3-ethylpyrrolidin-1-yl)ethyl]-3-methyl-6,7-dihydro-5H-benzo[5,6][1,4]diazepino[7,1-a]indole-10-carboxylic acid dihydrochloride (Example 1-384)

13-cyclohexyl-3-isobutoxy-5-[2-(1-isopropylpiperidin-3-yl)ethyl]-6,7-dihydro-5H-benzo[5,6][1,4]diazepino[7,1-a]indole-10-carboxylic acid dihydrochloride (Example 1-385)

3-chloro-13-cyclohexyl-5-[2-(1-(1-ethylpropyl)piperidin-3-yl)ethyl]-6,7-dihydro-5H-benzo[5,6][1,4]diazepino[7,1-a]indole-10-carboxylic acid dihydrochloride (Example 1-386)

13-cyclohexyl-5-[2-(3-ethoxymethylpiperidin-1-yl)ethyl]-6,7-dihydro-5H-benzo[5,6][1,4]diazepino[7,1-a]indole-10-carboxylic acid dihydrochloride (Example 1-387)

3-chloro-13-cyclohexyl-5-[2-(piperidin-1-yl)ethyl]-6,7-dihydro-5H-benzo[5,6][1,4]diazepino[7,1-a]indole-10-carboxylic acid (Example 1-388)

3-chloro-13-cyclopentyl-5-[2-(3-ethylpiperidin-1-yl)ethyl] 6,7-dihydro-5H-benzo[5,6][1,4]diazepino[7,1-a]indole-10-carboxylic acid (Example 1-389)

3-chloro-13-cyclopentyl-5-[2-(3-methoxymethylpiperidin-1-yl)ethyl]-6,7-dihydro-5H-benzo[5,6][1,4]diazepino[7,1-a]indole-10-carboxylic acid (Example 1-390)

3-chloro-13-cyclohexyl-5-[2-(3-ethoxymethylpiperidin-1-yl)ethyl]-6,7-dihydro-5H-benzo[5,6][1,4]diazepino[7,1-a]indole-10-carboxylic acid dihydrochloride (Example 1-391)

13-cyclohexyl-5-[2-(3-ethoxymethylpiperidin-1-yl)ethyl]-3-methyl-6,7-dihydro-5H-benzo[5,6][1,4]diazepino[7,1-a]indole-10-carboxylic acid dihydrochloride (Example 1-392)

3-chloro-13-cyclohexyl-5-[2-(3-isopropoxypiperidin-1-yl)ethyl]-6,7-dihydro-5H-benzo[5,6][1,4]diazepino[7,1-a]indole-10-carboxylic acid monohydrochloride (Example 1-393)

13-cyclohexyl-5-[2-(3-isopropoxypiperidin-1-yl)ethyl]-3-methyl-6,7-dihydro-5H-benzo[5,6][1,4]diazepino[7,1-a]indole-10-carboxylic acid monohydrochloride (Example 1-394)

13-cyclohexyl-5-[2-(3-isopropoxypiperidin-1-yl)ethyl]-6,7-dihydro-5H-benzo[5,6][1,4]diazepino[7,1-a]indole-10-carboxylic acid monohydrochloride (Example 1-395)

3-chloro-13-cyclohexyl-5-[3-(1-isopropylpiperidin-3-yl)propyl]-6,7-dihydro-5H-benzo[5,6][1,4]diazepino[7,1-a]indole-10-carboxylic acid dihydrochloride (Example 1-396)

3-chloro-13-cyclohexyl-5-{2-[(S)-3-(2-methoxyethyl)piperidin-1-yl]ethyl}-6,7-dihydro-5H-benzo[5,6][1,4]diazepino[7,1-a]indole-10-carboxylic acid dihydrochloride (Example 1-397)

3-chloro-13-cyclohexyl-5-(2-[(R)-3-(2-methoxyethyl)piperidin-1-yl)ethyl]-6,7-dihydro-5H-benzo[5,6][1,4]diazepino[7,1-a]indole-10-carboxylic acid dihydrochloride (Example 1-398)

13-cyclopentyl-5-[2-(piperidin-1-yl)ethyl]-6,7-dihydro-5H-benzo[5,6][1,4]diazepino[7,1-a]indole-10-carboxylic acid monohydrochloride (Example 1-399)

3-chloro-13-cyclohexyl-5-[2-(1-ethylpiperidin-3-yloxy)ethyl]-6,7-dihydro-5H-benzo[5,6][1,4]diazepino[7,1-a]indole-10-carboxylic acid dihydrochloride (Example 1-400)

13-cyclohexyl-3-(2-methylthiazol-4-ylmethoxy)-5-[2-(piperidin-1-yl)ethyl]-6,7-dihydro-5H-benzo[5,6][1,4]diazepino[7,1-a]indole-10-carboxylic acid dihydrochloride (Example 1-401)

13-cyclohexyl-3-(2,4-dimethylthiazol-5-ylmethoxy)-5-[2-(piperidin-1-yl)ethyl]-6,7-dihydro-5H-benzo[5,6][1,4]diazepino[7,1-a]indole-10-carboxylic acid dihydrochloride (Example 1-402)

3-chloro-13-cyclohexyl-5-[3-(N-ethyl-N-isopropylamino)propyl]6,7-dihydro-5H-benzo[5,6][1,4]diazepino[7,1-a]indole-10-carboxylic acid dihydrochloride (Example 1-403)

3-chloro-13-cyclohexyl-5-[2-((S)-1-cyclopentylpiperidin-3-yl)ethyl]-6,7-dihydro-5H-benzo[5,6][1,4]diazepino[7,1-a]indole-10-carboxylic acid dihydrochloride (Example 1-404)

13-cyclohexyl-5-[2-(3-isopropoxymethylpiperidin-1-yl)ethyl]-6,7-dihydro-5H-benzo[5,6][1,4]diazepino[7,1-a]indole-10-carboxylic acid dihydrochloride (Example 1-405)

3-chloro-13-cyclohexyl-5-[2-(3-isopropoxymethylpiperidin-1-yl)ethyl]-6,7-dihydro-5H-benzo[5,6][1,4]diazepino[7,1-a]indole-10-carboxylic acid dihydrochloride (Example 1-406)

13-cyclohexyl-5-[2-(3-isopropoxymethylpiperidin-1-yl)ethyl]-3-methyl-6,7-dihydro-5H-benzo[5,6][1,4]diazepino[7,1-a]indole-10-carboxylic acid dihydrochloride (Example 1-407)

3-chloro-13-cyclohexyl-5-[2-((R)-1-cyclopentylpiperidin-3-yl)ethyl]-6,7-dihydro-5H-benzo[5,6][1,4]diazepino[7,1-a]indole-10-carboxylic acid dihydrochloride (Example 1-408)

13-cyclohexyl-5-{2-[(R)-3-(2-methoxyethyl)piperidin-1-yl]ethyl}-3-methyl-6,7-dihydro-5H-benzo[5,6][1,4]diazepino[7,1-a]indole-10-carboxylic acid dihydrochloride (Example 1-409)

13-cyclohexyl-3-methyl-5-[2-(1-propylpiperidin-3-yl)ethyl]-6,7-dihydro-5H-benzo[5,6][1,4]diazepino[7,1-a]indole-10-carboxylic acid dihydrochloride (Example 1-410)

3-chloro-13-cyclohexyl-5-[3-(1-ethylpiperidin-3-yl)propyl]-6,7-dihydro-5H-benzo[5,6][1,4]diazepino[7,1-a]indole-10-carboxylic acid dihydrochloride (Example 1-411)

3-chloro-13-cyclohexyl-5-[3-(1-cyclopentylpiperidin-3-yl)propyl]-6,7-dihydro-5H-benzo[5,6][1,4]diazepino[7,1-a]indole-10-carboxylic acid dihydrochloride (Example 1-412)

13-cyclohexyl-5-{2-[(S)-3-(2-methoxyethyl)piperidin-1-yl]ethyl}-3-methyl-6,7-dihydro-5H-benzo[5,6][1,4]diazepino[7,1-a]indole-10-carboxylic acid dihydrochloride (Example 1-413)

3-chloro-13-cyclopentyl-5-[2-(1-isopropylpiperidin-3-yl)ethyl]-6,7-dihydro-5H-benzo[5,6][1,4]diazepino[7,1-a]indole-10-carboxylic acid monohydrochloride (Example 1-414)

3-chloro-13-cyclohexyl-5-[4-(piperidin-1-yl)butyl]-6,7-dihydro-5H-benzo[5,6][1,4]diazepino[7,1-a]indole-10-carboxylic acid (Example 1-415)

13-cyclohexyl-5-[2-((R)-3-methoxymethylpiperidin-1-yl)ethyl]-3-methyl-6,7-dihydro-5H-benzo[5,6][1,4]diazepino[7,1-a]indole-10-carboxylic acid dihydrochloride (Example 1-416)

13-cyclohexyl-5-[2-((S)-3-methoxymethylpiperidin-1-yl)ethyl]-3-methyl-6,7-dihydro-5H-benzo[5,6][1,4]diazepino[7,1-a]indole-10-carboxylic acid dihydrochloride (Example 1-417)

13-cyclohexyl-3-(3-methanesulfonylbenzyloxy)-5-[2-(piperidin-1-yl)ethyl]-6,7-dihydro-5H-1-benzo[5,6][1,4]diazepino[7,1-a]indole-10-carboxylic acid dihydrochloride (Example 1-418)

3-chloro-13-cyclohexyl-5-[2-((R)-3-ethylpiperidin-1-yl)ethyl]-6,7-dihydro-5H-benzo[5,6][1,4]diazepino[7,1-a]indole-10-carboxylic acid (Example 1-419)

13-cyclohexyl-5-[2-((R)-3-ethylpiperidin-1-yl)ethyl]-3-methyl-6,7-dihydro-5H-benzo[5,6][1,4]diazepino[7,1-a]indole-10-carboxylic acid dihydrochloride (Example 1-420)

3-chloro-13-cyclohexyl-5-[2-((S)-3-ethylpiperidin-1-yl)ethyl]-6,7-dihydro-5H-benzo[5,6][1,4]diazepino[7,1-a]indole-10-carboxylic acid (Example 1-421)

13-cyclohexyl-5-[2-((S)-3-ethylpiperidin-1-yl)ethyl]-3-methyl-6,7-dihydro-5H-benzo[5,6][1,4]diazepino[7,1-a]indole-10-carboxylic acid dihydrochloride (Example 1-422)

5-[2-(azocan-1-yl)ethyl]-13-cyclohexyl-6,7-dihydro-5H-benzo[5,6][1,4]diazepino[7,1-a]indole-10-carboxylic acid dihydrochloride (Example 1-423)

3-chloro-13-cyclohexyl-5-(4-diethylaminobutyl)-6,7-dihydro-5H-benzo[5,6][1,4]diazepino[7,1-a]indole-10-carboxylic acid (Example 1-424)

13-cyclohexyl-3-methyl-5-[4-(piperidin-1-yl)butyl]-6,7-dihydro-5H-benzo[5,6][1,4]diazepino[7,1-a]indole-10-carboxylic acid dihydrochloride (Example 1-425)

3-chloro-13-cyclohexyl-5-[2-(1-methylpyrrolidin-2-yl)ethyl]-6,7-dihydro-5H-benzo[5,6][1,4]diazepino[7,1-a]indole-10-carboxylic acid dihydrochloride (Example 1-426)

13-cyclohexyl-3-ethoxy-5-{2-[(S)-3-(2-methoxyethyl)piperidin-1-yl]ethyl}-6,7-dihydro-5H-benzo[5,6][1,4]diazepino[7,1-a]indole-10-carboxylic acid dihydrochloride (Example 1-427)

3-chloro-13-cyclohexyl-5-[3-(N-ethyl-N-propylamino)propyl]-6,7-dihydro-5H-benzo[5,6][1,4]diazepino[7,1-a]indole-10-carboxylic acid dihydrochloride (Example 1-428)

3-chloro-13-cyclohexyl-5-(3-diisopropylaminopropyl)-6,7-dihydro-5H-benzo[5,6][1,4]diazepino[7,1-a]indole-10-carboxylic acid dihydrochloride (Example 1-429)

13-cyclohexyl-3-ethyl-5-{2-[(S)-3-(2-methoxyethyl)piperidin-1-yl]ethyl}-6,7-dihydro-5H-benzo[5,6][1,4]diazepino[7,1-a]indole-10-carboxylic acid dihydrochloride (Example 1-430)

3-chloro-13-cyclohexyl-5-{3-[N-ethyl-N-(2-methoxyethyl)amino]propyl}-6,7-dihydro-5H-benzo[5,6][1,4]diazepino[7,1-a]indole-10-carboxylic acid dihydrochloride (Example 1-431)

3-chloro-13-cyclohexyl-5-{3-[N-ethyl-N-(3-methoxypropyl)amino]propyl}-6,7-dihydro-5H-benzo[5,6][1,4]diazepino[7,1-a]indole-10-carboxylic acid dihydrochloride (Example 1-432)

3-chloro-13-cyclohexyl-5-{3-[N-(3-ethoxypropyl)-N-ethylamino]propyl}-6,7-dihydro-5H-benzo[5,6][1,4]diazepino[7,1-a]indole-10-carboxylic acid dihydrochloride (Example 1-433)

13-cyclohexyl-3-fluoro-5-{2-[(S)-3-(2-methoxyethyl)piperidin-1-yl]ethyl}-6,7-dihydro-5H-benzo[5,6][1,4]diazepino[7,1-a]indole-10-carboxylic acid dihydrochloride (Example 1-434)

13-cyclohexyl-5-[2-(3-hydroxymethylpiperidin-1-yl)ethyl]-3-methyl-6,7-dihydro-5H-benzo[5,6][1,4]diazepino[7,1-a]indole-10-carboxylic acid dihydrochloride (Example 1-435)

3-chloro-13-cyclohexyl-5-(3-diethylamino-2,2-dimethylpropyl)-6,7-dihydro-5H-benzo[5,6][1,4]diazepino[7,1-a]indole-10-carboxylic acid dihydrochloride (Example 1-436)

13-cyclohexyl-5-methyl-3-[2-(piperidin-1-yl)ethoxy]-6,7-dihydro-5H-benzo[5,6][1,4]diazepino[7,1-a]indole-10-carboxylic acid dihydrochloride (Example 1-437)

13-cyclohexyl-5-methyl-3-[2-(piperidin-4-yl)ethoxy]-6,7-dihydro-5H-benzo[5,6][1,4]diazepino[7,1-a]indole-10-carboxylic acid dihydrochloride (Example 1-438)

13-cyclohexyl-5-methyl-3-[2-(1-methylpiperidin-4-yl)ethoxy]-6,7-dihydro-5H-benzo[5,6][1,4]diazepino[7,1-a]indole-10-carboxylic acid dihydrochloride (Example 1-439)

13-cyclohexyl-5-[2-(3,3-dimethylpiperidin-1-yl)ethyl]-3-methyl-6,7-dihydro-5H-benzo[5,6][1,4]diazepino[7,1-a]indole-10-carboxylic acid dihydrochloride (Example 1-440)

3-chloro-13-cyclohexyl-5-(3-diethylamino-2-methoxypropyl)-6,7-dihydro-5H-benzo[5,6][1,4]diazepino[7,1-a]indole-10-carboxylic acid dihydrochloride (Example 1-441)

3-chloro-13-cyclohexyl-5-[3-[N-ethyl-N-(2-hydroxyethyl)amino]propyl]-6,7-dihydro-5H-benzo[5,6][1,4]diazepino[7,1-a]indole-10-carboxylic acid dihydrochloride (Example 1-442)

13-cyclohexyl-5-[2-(4-hydroxymethylpiperidin-1-yl)ethyl]-3-methyl-6,7-dihydro-5H-benzo[5,6][1,4]diazepino[7,1-a]indole-10-carboxylic acid dihydrochloride (Example 1-443)

13-cyclohexyl-5-(2-[(3)-3-(2-phenoxyethyl)piperidin-1-yl]ethyl)-6,7-dihydro-5H-benzo[5,6][1,4]diazepino[7,1-a]indole-10-carboxylic acid dihydrochloride (Example 1-444)

13-cyclohexyl-3-methoxy-5-{2-[(S)-3-(2-methoxyethyl)piperidin-1-yl]ethyl}-6,7-dihydro-5H-benzo[5,6][1,4]diazepino[7,1-a]indole-10-carboxylic acid dihydrochloride (Example 1-445)

12-cyclohexyl-3-(5-methylisoxazol-3-ylmethoxy)-6,7-dihydro-5-oxa-7a-azadibenzo[a,e]azulene-9-carboxylic acid (Example 2-32)

3-[2-(tert-butoxycarbonylamino)ethoxy]-12-cyclohexyl-6,7-dihydro-5-oxa-7a-azadibenzo[a,e]azulene-9-carboxylic acid (Example 2-33)

12-cyclohexyl-3-(2-methylthiazol-4-ylmethoxy)-6,7-dihydro-5-oxa-7a-azadibenzo[a,e]azulene-9-carboxylic acid (Example 2-34)

3-[(S)-1-(tert-butoxycarbonyl)pyrrolidin-2-ylmethoxy]-12-cyclohexyl-6,7-dihydro-5-oxa-7a-azadibenzo[a,e]azulene-9-carboxylic acid (Example 2-35)

12-cyclohexyl-3-[2-(methoxycarbonylamino)ethoxy]-6,7-dihydro-5-oxa-7a-azadibenzo[a,e]azulene-9-carboxylic acid (Example 2-36)

12-cyclohexyl-3-((S)-1-methoxycarbonylpyrrolidin-2-ylmethoxy)-6,7-dihydro-5-oxa-7a-azadibenzo[a,e]azulene-9-carboxylic acid (Example 2-37)

12-cyclohexyl-3-[2-(2-oxooxazolidin-3-yl)ethoxy]-6,7-dihydro-5-oxa-7a-azadibenzo[a,e]azulene-9-carboxylic acid (Example 2-38)

4-benzyloxy-12-cyclohexyl-6,7-dihydro-5-oxa-7a-azadibenzo[a,e]azulene-9-carboxylic acid (Example 2-39)

3-[(S)-1-(tert-butoxycarbonyl)pyrrolidin-3-yloxy]-12-cyclohexyl-6,7-dihydro-5-oxa-7a-azadibenzo[a,e]azulene-9-carboxylic acid (Example 2-40)

3-((S)-2-tert-butoxycarbonylamino-3-phenylpropoxy)-12-cyclohexyl-6,7-dihydro-5-oxa-7a-azadibenzo[a,e]azulene-9-carboxylic acid (Example 2-41)

12-cyclohexyl-3-((S)-pyrrolidin-3-yloxy)-6,7-dihydro-5-oxa-7a-azadibenzo[a,e]azulene-9-carboxylic acid monohydrochloride (Example 2-42)

3-((S)-2-tert-butoxycarbonylamino-3-methylbutoxy)-12-cyclohexyl-6,7-dihydro-5-oxa-7a-azadibenzo[a,e]azulene-9-carboxylic acid (Example 2-43)

12-cyclohexyl-3-(1-methanesulfonylpiperidin-3-yloxy)-6,7-dihydro-5-oxa-7a-azadibenzo[a,e]azulene-9-carboxylic acid (Example 2-44)

12-cyclohexyl-3-(1-methylpiperidin-2-ylmethoxy)-6,7-dihydro-5-oxa-7a-azadibenzo[a,e]azulene-9-carboxylic acid (Example 2-45)

12-cyclohexyl-3-(piperidin-3-yloxy)-6,7-dihydro-5-oxa-7a-azadibenzo[a,e]azulene-9-carboxylic acid monohydrochloride (Example 2-46)

12-cyclohexyl-3-[2-(morpholin-4-yl)-5-(2-oxopyrrolidin-1-yl)benzyloxy]-6,7-dihydro-5-oxa-7a-azadibenzo[a,e]azulene-9-carboxamide monohydrochloride (Example 2-47)

12-cyclohexyl-3-[5-methanesulfonyl-2-(morpholin-4-yl)benzyloxy]-6,7-dihydro-5-oxa-7a-azadibenzo[a,e]azulene-9-carboxamide monohydrochloride (Example 2-48)

12-cyclohexyl-3-((S)-2-methoxycarbonylamino-3-phenylpropoxy)-6,7-dihydro-5-oxa-7a-azadibenzo[a,e]azulene-9-carboxylic acid (Example 2-49)

12-cyclohexyl-3-((S)-1-methoxycarbonylpyrrolidin-3-yloxy)-6,7-dihydro-5-oxa-7a-azadibenzo[a,e]azulene-9-carboxylic acid (Example 2-50)

12-cyclohexyl-3-((S)-2-methanesulfonylamino-3-methylbutoxy)-6,7-dihydro-5-oxa-7a-azadibenzo[a,e]azulene-9-carboxylic acid (Example 2-51)

12-cyclohexyl-3-[2-(methoxycarbonylamino)phenoxy]-6,7-dihydro-5-oxa-7a-azadibenzo[a,e]azulene-9-carboxylic acid (Example 2-52)

12-cyclohexyl-4-[2-(piperidin-1-yl)ethoxy]-6,7-dihydro-5-oxa-7a-azadibenzo[a,e]azulene-9-carboxylic acid monohydrochloride (Example 2-53)

3-benzyloxy-12-cyclohexyl-6,7-dihydro-5-oxa-7a,8-diazadibenzo[a,e]azulene-9-carboxylic acid (Example 7-8)

3-chloro-12-cyclohexyl-5-[2-(piperidin-1-yl)ethyl]-6,7-dihydro-5H-5,7a,8-triazadibenzo[a,e]azulene-9-carboxylic acid trihydrochloride (Example 8-5)

3-chloro-12-cyclohexyl-5-[2-(4-ethylpiperazin-1-yl)ethyl]-6,7-dihydro-5H-5,7a,8-triazadibenzo[a,e]azulene-9-carboxylic acid trihydrochloride (Example 8-6)

3-chloro-12-cyclohexyl-5-[2-(piperidin-1-yl)ethyl]-5,6,7,12-tetrahydrobenzo[2,3]azepino[4,5-b]indole-9-carboxylic acid (Example 10-1)

ethyl 3-chloro-12-cyclohexyl-5-[2-(piperidin-1-yl)ethyl]-5,6,7,12-tetrahydrobenzo[2,3]azepino[4,5-b]indole-9-carboxylate (Example 10-2)

3-chloro-12-cyclohexyl-5-[2-(piperidin-1-yl)ethyl]-5,6,7,12-tetrahydrobenzo[2,3]azepino[4,5-b]indole-9-carboxamide (Example 10-3)

12-cyclohexyl-5-[2-(piperidin-1-yl)ethyl]-5,6,7,12-tetrahydrobenzo[2,3]azepino[4,5-b]indole-9-carboxylic acid (Example 10-4)

13-cyclohexyl-5-[2-(4-ethylpiperazin-1-yl)-2-oxoethyl]-6,7-dihydro-5H-benzo[5,6][1,4]diazepino[7,1-a]indole-10-carboxamide (Example 1-446)

N-methyl-13-cyclohexyl-5-[2-(4-ethylpiperazin-1-yl)-2-oxoethyl]-6,7-dihydro-5H-benzo[5,6][1,4]diazepino[7,1-a]indole-10-carboxamide (Example 1-447)

N-(2-hydroxyethyl)-13-cyclohexyl-5-[2-(4-ethylpiperazin-1-yl)-2-oxoethyl]-6,7-dihydro-5H-benzo[5,6][1,4]diazepino[7,1-a]indole-10-carboxamide (Example 1-448)

N-(2-hydroxy-1,1-dimethylethyl)-13-cyclohexyl-5-[2-(4-ethylpiperazin-1-yl)-2-oxoethyl]-6,7-dihydro-5H-benzo[5,6][1,4]diazepino[7,1-a]indole-10-carboxamide (Example 1-449)

(E)-3-[4-({1-[(13-cyclohexyl-5-methyl-3-methylsulfanyl-6,7-dihydro-5H-benzo[5,6][1,4]diazepino[7,1-a]indole-10-carbonyl)amino]cyclobutanecarbonyl}amino)phenyl]acrylic acid (Example 1-450)

9-chloro-13-cyclohexyl-3-methyl-5-[2-(piperidin-1-yl)ethyl]-6,7-dihydro-5H-benzo[5,6][1,4]diazepino[7,1-a]indole-10-carboxylic acid dihydrochloride (Example 1-451)

9-chloro-13-cyclohexyl-3,5-dimethyl-6,7-dihydro-5H-benzo[5,6][1,4]diazepino[7,1-a]indole-10-carboxylic acid (Example 1-452)

(S)-6-amino-2-({13-cyclohexyl-3-methyl-5-[2-(piperidin-1-yl)ethyl]-6,7-dihydro-5H-benzo[5,6][1,4]diazepino[7,1-a]indole-10-carbonyl}amino)hexanoic acid dihydrochloride (Example 1-453) benzyl 4-(13-cyclohexyl-3-methyl-10-methylcarbamoyl-6,7-dihydrobenzo[5,6][1,4]diazepino[7,1-a]indol-5-yl)piperidine-1-carboxylate (Example 1-454)

(E)-3-[4-({1-[(13-cyclohexyl-3,5-dimethyl-6,7-dihydro-5H-benzo[5,6][1,4]diazepino[7,1-a]indole-10-carbonyl)amino]cyclobutanecarbonyl}amino)phenyl]acrylic acid (Example 1-455)

N-methyl-5-(1-acetylpiperidin-4-yl)-13-cyclohexyl-3-methyl-6,7-dihydro-5H-benzo[5,6][1,4]diazepino[7,1-a]indole-10-carboxamide (Example 1-456)

N-methyl-13-cyclohexyl-5-{2-[(S)-3-(2-methoxyethyl)piperidin-1-yl]-2-oxoethyl}-3-methyl-6,7-dihydro-5H-benzo[5,6][1,4]diazepino[7,1-a]indole-10-carboxamide (Example 1-457)

N-methyl-13-cyclohexyl-5-[2-(4-methoxypiperidin-1-yl)-2-oxoethyl]-3-methyl-6,7-dihydro-5H-benzo[5,6][1,4]diazepino[7,1-a]indole-10-carboxamide (Example 1-458)

[(13-cyclohexyl-3,5-dimethyl-6,7-dihydro-5H-benzo[5,6][1,4]diazepino[7,1-a]indole-10-carbonyl)amino]acetic acid (Example 1-459)

methyl 4-[2-(3-chloro-13-cyclohexyl-10-methylcarbamoyl-6,7-dihydrobenzo[5,6][1,4]diazepino[7,1-a]indol-5-yl)ethyl]piperidine-1-carboxylate (Example 1-460)

N-methyl-13-cyclohexyl-5-[2-(4-fluorophenyl)ethyl]-3-methyl-6,7-dihydro-5H-benzo[5,6][1,4]diazepino[7,1-a]indole-10-carboxamide (Example 1-461)

(E)-3-[4-({1-[(13-cyclohexyl-3-isopropoxy-5-methyl-6,7-dihydro-5H-benzo[5,6][1,4]diazepino[7,1-a]indole-10-carbonyl)amino]cyclobutanecarbonyl}amino)phenyl]acrylic acid (Example 1-462)

(E)-3-[4-({1-[(13-cyclohexyl-3-fluoro-5-methyl-6,7-dihydro-5H-benzo[5,6][1,4]diazepino[7,1-a]indole-10-carbonyl)amino]cyclobutanecarbonyl}amino)phenyl]acrylic acid (Example 1-463)

(E)-1-[4-({1-[(13-cyclohexyl-3-methoxy-5-methyl-6,7-dihydro-5H-benzo[5,6][1,4]diazepino[7,1-a]indole-10-carbonyl)amino]cyclobutanecarbonyl}amino)phenyl]acrylic acid (Example 1-464)

(E)-3-[4-({1-[(3-chloro-13-cyclohexyl-5-methyl-6,7-dihydro-5H-benzo[5,6][1,4]diazepino[7,1-a]indole-10-carbonyl)amino]cyclobutanecarbonyl}amino)phenyl]acrylic acid (Example 1-465)

(E)-3-[4-({1-[(13-cyclohexyl-2,3-difluoro-5-methyl-6,7-dihydro-5H-benzo[5,6][1,4]diazepino[7,1-a]indole-10-carbonyl)amino]cyclobutanecarbonyl}amino)phenyl]acrylic acid (Example 1-466)

(E)-3-(4-{[1-({13-cyclohexyl-3-methyl-5-[2-(1,4-oxazepan-4-yl)ethyl]-6,7-dihydro-5H-benzo[5,6][1,4]diazepino[7,1-a]indole-10-carbonyl}amino)cyclobutanecarbonyl]amino}phenyl)acrylic acid (Example 1-467)

(E)-3-[4-({1-[(3-benzyloxy-13-cyclohexyl-5-methyl-6,7-dihydro-5H-benzo[5,6][1,4]diazepino[7,1-a]indole-10-carbonyl)amino]cyclobutanecarbonyl}amino)phenyl]acrylic acid (Example 1-468)

(E)-3-[4-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)phenyl]acrylic acid (Example 1-469)

(E)-3-[4-({1-[(13-cyclohexyl-4-fluoro-5-methyl-6,7-dihydro-5H-benzo[5,6][1,4]diazepino[7,1-a]indole-10-carbonyl)amino]cyclobutanecarbonyl}amino)phenyl]acrylic acid (Example 1-470)

(E)-3-[4-({1-[(13-cyclohexyl-3-ethyl-5-methyl-6,7-dihydro-5H-benzo[5,6][1,4]diazepino[7,1-a]indole-10-carbonyl)amino]cyclobutanecarbonyl}amino)phenyl]acrylic acid (Example 1-471)

(E)-3-[4-({1-[(5-acetyl-13-cyclohexyl-3-methyl-6,7-dihydro-5H-benzo[5,6][1,4]diazepino[7,1-a]indole-10-carbonyl)amino]cyclobutanecarbonyl}amino)phenyl]acrylic acid (Example 1-472)

6-({1-[(12-cyclohexyl-6,7-dihydro-5-oxa-7a-azadibenzo[a, e]azulene-9-carbonyl)amino]cyclobutanecarbonyl}amino)nicotinic acid (Example 2-54)
({1-[(12-cyclohexyl-6,7-dihydro-5-oxa-7a-azadibenzo[a,e]azulene-9-carbonyl)amino]cyclobutanecarbonyl}amino)acetic acid (Example 2-55)
N-methyl-12-cyclohexyl-4-[2-(piperidin-1-yl)ethoxy]-6,7-dihydro-5-oxa-7a-azadibenzo[a,e]azulene-9-carboxamide monohydrochloride (Example 2-56)
(E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylic acid (Example 2-57)
1-[2-(12-cyclohexyl-9-methylcarbamoyl-6,7-dihydro-5-oxa-7a-azadibenzo[a,e]azulen-4-yloxy)ethyl]piperidine-4-carboxylic acid monohydrochloride (Example 2-58)
N-benzyloxy-12-cyclohexyl-6,7-dihydro-5-oxa-7a-azadibenzo[a,e]azulene-9-carboxamide (Example 2-59) ethyl 4-[(12-cyclohexyl-6,7-dihydro-5-oxa-7a-azadibenzo[a,e]azulene-9-carbonyl)amino]piperidine-1-carboxylate (Example 2-60)
(12-cyclohexyl-6,7-dihydro-5-oxa-7a-azadibenzo[a,e]azulen-9-yl)-(4-hydroxypiperidin-1-yl)-methanone (Example 2-61)
4-(12-cyclohexyl-6,7-dihydro-5-oxa-7a-azadibenzo[a,e]azulene-9-carbonyl)piperazine-2,6-dione (Example 2-62)
1-(12-cyclohexyl-6,7-dihydro-5-oxa-7a-azadibenzo[a,e]azulene-9-carbonyl)piperidine-4-carboxylic acid (Example 2-63)
(12-cyclohexyl-6,7-dihydro-5-oxa-7a-azadibenzo[a,e]azulen-9-yl)-(piperazin-1-yl)-methanone monohydrochloride (Example 2-64)
[(12-cyclohexyl-6,7-dihydro-5-oxa-7a-azadibenzo[a,e]azulene-9-carbonyl)amino]acetic acid (Example 2-65)
[N-(12-cyclohexyl-6,7-dihydro-5-oxa-7a-azadibenzo[a,e]azulene-9-carbonyl)-N-methylamino]acetic acid (Example 2-66)
2-[(12-cyclohexyl-6,7-dihydro-5-oxa-7a-azadibenzo[a,e]azulene-9-carbonyl)amino]-4-methylpentanoic acid (Example 2-67)
2-[(12-cyclohexyl-6,7-dihydro-5-oxa-7a-azadibenzo[a,e]azulene-9-carbonyl)amino]-3-methoxypropionic acid (Example 2-68)
2-[(12-cyclohexyl-6,7-dihydro-5-oxa-7a-azadibenzo[a,e]azulene-9-carbonyl)amino]-3-methylsulfanylpropionic acid (Example 2-69)
2-[(12-cyclohexyl-6,7-dihydro-5-oxa-7a-azadibenzo[a,e]azulene-9-carbonyl)amino]-3-dimethylaminopropionic acid (Example 2-70)
(E)-3-(4-{2-[(12-cyclohexyl-6,7-dihydro-5-oxa-7a-azadibenzo[a,e]azulene-9-carbonyl)amino]acetylamino}phenyl)acrylic acid (Example 2-71)
1-[(12-cyclohexyl-6,7-dihydro-5-oxa-7a-azadibenzo[a,e]azulene-9-carbonyl)amino]cyclopentanecarboxylic acid (Example 2-72)
2-[(12-cyclohexyl-6,7-dihydro-5-oxa-7a-azadibenzo[a,e]azulene-9-carbonyl)amino]-2-methylpropionic acid (Example 2-73)
2-[(12-cyclohexyl-6,7-dihydro-5-oxa-7a-azadibenzo[a,e]azulene-9-carbonyl)amino]-2-phenylacetic acid (Example 2-74)
2-[(12-cyclohexyl-6,7-dihydro-5-oxa-7a-azadibenzo[a,e]azulene-9-carbonyl)amino]-3-phenylpropionic acid (Example 2-75)
2-{[(12-cyclohexyl-6,7-dihydro-5-oxa-7a-azadibenzo[a,e]azulene-9-carbonyl)amino]methyl}benzoic acid (Example 2-76)
4-{[(12-cyclohexyl-6,7-dihydro-5-oxa-7a-azadibenzo[a,e]azulene-9-carbonyl)amino]methyl}benzoic acid (Example 2-77)
ethyl (E)-3-[4-({1-[(12-cyclohexyl-6,7-dihydro-5-oxa-7a-azadibenzo[a,e]azulene-9-carbonyl)amino]cyclobutanecarbonyl}amino)phenyl]acrylate (Example 2-78)
(E)-3-[4-({1-[(12-cyclohexyl-6,7-dihydro-5-oxa-7a-azadibenzo[a,e]azulene-9-carbonyl)amino]cyclobutanecarbonyl}amino)phenyl]acrylic acid (Example 2-79)
[4-(12-cyclohexyl-6,7-dihydro-5-oxa-7a-azadibenzo[a,e]azulene-9-carbonyl)piperazin-1-yl]acetic acid (Example 2-80)
3-[4-({1-[(12-cyclohexyl-6,7-dihydro-5-oxa-7a-azadibenzo[a,e]azulene-9-carbonyl)amino]cyclobutanecarbonyl}amino)phenyl]propionic acid (Example 2-81)
cis-4-[(12-cyclohexyl-6,7-dihydro-5-oxa-7a-azadibenzo[a,e]azulene-9-carbonyl)amino]cyclohexanecarboxylic acid (Example 2-82)
6-[(12-cyclohexyl-6,7-dihydro-5-oxa-7a-azadibenzo[a,e]azulene-9-carbonyl)amino]hexanoic acid (Example 2-83)
1-{6-[(12-cyclohexyl-6,7-dihydro-5-oxa-7a-azadibenzo[a,e]azulene-9-carbonyl)amino]hexanoyl}piperidine-4-carboxylic acid (Example 2-84)
trans-4-[(12-cyclohexyl-6,7-dihydro-5-oxa-7a-azadibenzo[a,e]azulene-9-carbonyl)amino]cyclohexanecarboxylic acid (Example 2-85)
N-tert-butoxy-12-cyclohexyl-6,7-dihydro-5-oxa-7a-azadibenzo[a,e]azulene-9-carboxamide (Example 2-86)
(4-{6-[(12-cyclohexyl-6,7-dihydro-5-oxa-7a-azadibenzo[a,e]azulene-9-carbonyl)amino]hexanoylamino}phenyl)acetic acid (Example 2-87)
{4-[(12-cyclohexyl-6,7-dihydro-5-oxa-7a-azadibenzo[a,e]azulene-9-carbonyl)amino]phenyl}acetic acid (Example 2-88)
(E)-3-(4-{2-[(12-cyclohexyl-6,7-dihydro-5-oxa-7a-azadibenzo[a,e]azulene-9-carbonyl)amino]-2-methylpropionylamino}phenyl)acrylic acid (Example 2-89)
(E)-3-(4-{2-[(12-cyclohexyl-6,7-dihydro-5-oxa-7a-azadibenzo[a,e]azulene-9-carbonyl)amino]-3-phenylpropionylamino}phenyl)acrylic acid (Example 2-90)
4-{2-[(12-cyclohexyl-6,7-dihydro-5-oxa-7a-azadibenzo[a,e]azulene-9-carbonyl)amino]-2-methylpropionylamino}benzoic acid (Example 2-91)
3-{[(12-cyclohexyl-6,7-dihydro-5-oxa-7a-azadibenzo[a,e]azulene-9-carbonyl)amino]methyl}benzoic acid (Example 2-92)
1-(2-{4-[(12-cyclohexyl-6,7-dihydro-5-oxa-7a-azadibenzo[a,e]azulene-9-carbonyl)amino]phenyl}acetylamino)cyclopentanecarboxylic acid (Example 2-93)
(E)-3-[4-({1-[(12-cyclohexyl-3-fluoro-6,7-dihydro oxa-7a-azadibenzo[a,e]azulene-9-carbonyl)amino]cyclobutanecarbonyl}amino)phenyl]acrylic acid (Example 2-94)
(E)-3-[4-({1-[(12-cyclohexyl-6,7-dihydro-5-oxa-7a-azadibenzo[a,e]azulene-9-carbonyl)amino]cyclopentanecarbonyl}amino)phenyl]acrylic acid (Example 2-95)

1-[(12-cyclohexyl-6,7-dihydro-5-oxa-7a-azadibenzo[a,e]azulene-9-carbonyl)amino]cyclopropanecarboxylic acid (Example 2-96)

1-[(12-cyclohexyl-6,7-dihydro-5-oxa-7a-azadibenzo[a,e]azulene-9-carbonyl)amino]cyclohexanecarboxylic acid (Example 2-97)

1-[(12-cyclohexyl-6,7-dihydro-5-oxa-7a-azadibenzo[a,e]azulene-9-carbonyl)amino]-4,4-dimethylcyclohexanecarboxylic acid (Example 2-98)

2-[(12-cyclohexyl-6,7-dihydro-5-oxa-7a-azadibenzo[a,e]azulene-9-carbonyl)amino]-2-ethylbutyric acid (Example 2-99)

4-({1-[(12-cyclohexyl-6,7-dihydro-5-oxa-7a-azadibenzo[a,e]azulene-9-carbonyl)amino]cyclobutanecarbonyl}amino)benzoic acid (Example 2-100)

(E)-3-[4-({1-[N-(12-cyclohexyl-6,7-dihydro-5-oxa-7a-azadibenzo[a,e]azulene-9-carbonyl)-N-methylamino]cyclobutanecarbonyl}amino)phenyl]acrylic acid (Example 2-101)

[4-({1-[(12-cyclohexyl-6,7-dihydro-5-oxa-7a-azadibenzo[a,e]azulene-9-carbonyl)amino]cyclobutanecarbonyl}amino)phenyl]acetic acid (Example 2-102)

N-(1-phenylcarbamoylcyclobutyl)-12-cyclohexyl-6,7-dihydro-5-oxa-7a-azadibenzo[a,e]azulene-9-carboxamide (Example 2-103)

4-[({1-[(12-cyclohexyl-6,7-dihydro-5-oxa-7a-azadibenzo[a,e]azulene-9-carbonyl)amino]cyclobutanecarbonyl}amino)methyl]benzoic acid (Example 2-104)

(E)-3-[4-({cis-4-[(12-cyclohexyl-6,7-dihydro-5-oxa-7a-azadibenzo[a,e]azulene-9-carbonyl)amino]cyclohexanecarbonyl}amino)phenyl]acrylic acid (Example 2-105)

6-({1-[(12-cyclohexyl-6,7-dihydro-5-oxa-7a-azadibenzo[a,e]azulene-9-carbonyl)amino]cyclobutanecarbonyl}amino)hexanoic acid (Example 2-106)

4-[(12-cyclohexyl-6,7-dihydro-5-oxa-7a-azadibenzo[a,e]azulene-9-carbonyl)amino]benzoic acid (Example 2-107)

[N-(12-cyclohexyl-6,7-dihydro-5-oxa-7a-azadibenzo[a,e]azulene-9-carbonyl)-N-(2-methoxyethyl)amino]acetic acid (Example 2-108)

(E)-3-(4-{2-[N-(12-cyclohexyl-6,7-dihydro-5-oxa-7a-azadibenzo[a,e]azulene-9-carbonyl)-N-(2-methoxyethyl)amino]acetylamino}phenyl)acrylic acid (Example 2-109)

3-[(12-cyclohexyl-6,7-dihydro-5-oxa-7a-azadibenzo[a,e]azulene-9-carbonyl)amino]-3-methylbutyric acid (Example 2-110)

(E)-3-(4-{2-[(12-cyclohexyl-6,7-dihydro-5-oxa-7a-azadibenzo[a,e]azulene-9-carbonyl)amino]-4-methylpentanoylamino}phenyl)acrylic acid (Example 2-111)

1-[(12-cyclohexyl-6,7-dihydro-5-oxa-7a-azadibenzo[a,e]azulene-9-carbonyl)amino]cyclobutanecarboxylic acid (Example 2-112)

1-[N-(12-cyclohexyl-6,7-dihydro-5-oxa-7a-azadibenzo[a,e]azulene-9-carbonyl)-N-methylamino]cyclobutanecarboxylic acid (Example 2-113)

4-({1-[(12-cyclohexyl-6,7-dihydro-5-oxa-7a-azadibenzo[a,e]azulene-9-carbonyl)amino]cyclobutanecarbonyl}amino)cyclohexanecarboxylic acid (Example 2-114)

1-{(1-[(12-cyclohexyl-6,7-dihydro-5-oxa-7a-azadibenzo[a,e]azulene-9-carbonyl)amino]cyclobutanecarbonyl}piperidine-4-carboxylic acid (Example 2-115)

(E)-3-[4-({1-[(12-cyclohexyl-6,7-dihydro-5-oxa-7a-azadibenzo[a,e]azulene-9-carbonyl)amino]cyclopropanecarbonyl}amino)phenyl]acrylic acid (Example 2-116)

(E)-3-[4-({1-[(12-cyclohexyl-6,7-dihydro-5-oxa-7a-azadibenzo[a,e]azulene-9-carbonyl)amino]-4,4-dimethylcyclohexanecarbonyl}amino)phenyl]acrylic acid (Example 2-117)

(E)-3-[4-({1-[(12-cyclohexyl-6,7-dihydro-5-oxa-7a-azadibenzo[a,e]azulene-9-carbonyl)amino]cyclohexanecarbonyl}amino)phenyl]acrylic acid (Example 2-118)

(E)-3-[4-({4-[(12-cyclohexyl-6,7-dihydro-5-oxa-7a-azadibenzo[a,e]azulene-9-carbonyl)amino]piperidine-1-carbonyl}amino)phenyl]acrylic acid (Example 2-119)

N-{1-[4-(3-hydroxypropyl)phenylcarbamoyl]cyclobutyl}-12-cyclohexyl-6,7-dihydro-5-oxa-7a-azadibenzo[a,e]azulene-9-carboxamide (Example 2-120)

[4-({1-[(12-cyclohexyl-6,7-dihydro-5-oxa-7a-azadibenzo[a,e]azulene-9-carbonyl)amino]cyclobutanecarbonyl}amino)phenoxy]acetic acid (Example 2-121)

(E)-3-[4-({1-[(12-cyclohexyl-4-methoxy-6,7-dihydro-5-oxa-7a-azadibenzo[a,e]azulene-9-carbonyl)amino]cyclobutanecarbonyl}amino)phenyl]acrylic acid (Example 2-122)

(E)-3-(4-{2-[(12-cyclohexyl-6,7-dihydro-5-oxa-7a-azadibenzo[a,e]azulene-9-carbonyl)amino]-2-ethylbutyrylamino}phenyl)acrylic acid (Example 2-123)

(E)-3-[4-({1-[(12-cyclohexyl-3-methyl-6,7-dihydro-5-oxa-7a-azadibenzo[a,e]azulene-9-carbonyl)amino]cyclobutanecarbonyl}amino)phenyl]acrylic acid (Example 2-124)

3-{4-[(12-cyclohexyl-6,7-dihydro-5-oxa-7a-azadibenzo[a,e]azulene-9-carbonyl)sulfamoyl]phenyl}propionic acid (Example 2-125)

(E)-3-(4-{3-[(12-cyclohexyl-6,7-dihydro-5-oxa-7a-azadibenzo[a,e]azulene-9-carbonyl)amino]-3-methylbutyrylamino}phenyl)acrylic acid (Example 2-126)

N-[1-(4-acetylphenylcarbamoyl)cyclobutyl]-12-cyclohexyl-6,7-dihydro-5-oxa-7a-azadibenzo[a,e]azulene-9-carboxamide (Example 2-127)

2-({1-[(12-cyclohexyl-6,7-dihydro-5-oxa-7a-azadibenzo[a,e]azulene-9-carbonyl)amino]cyclobutanecarbonyl}amino)benzoic acid (Example 2-128)

4-(N-{1-[(12-cyclohexyl-6,7-dihydro-5-oxa-7a-azadibenzo[a,e]azulene-9-carbonyl)amino]cyclobutanecarbonyl}-N-methylamino)benzoic acid (Example 2-129)

3-({1-[(12-cyclohexyl-6,7-dihydro-5-oxa-7a-azadibenzo[a,e]azulene-9-carbonyl)amino]cyclobutanecarbonyl}amino)benzoic acid (Example 2-130)

2-[(12-cyclohexyl-6,7-dihydro-5-oxa-7a-azadibenzo[a,e]azulene-9-carbonyl)amino]-2,4-dimethylpentanoic acid (Example 2-131)

(E)-3-[4-({1-[(3-chloro-12-cyclohexyl-6,7-dihydro-5-oxa-7a-azadibenzo[a,e]azulene-9-carbonyl)amino]cyclobutanecarbonyl}amino)phenyl]acrylic acid (Example 2-132)

4-[1-[(12-cyclohexyl-6,7-dihydro-5-oxa-7a-azadibenzo[a,e]azulene-9-carbonyl)amino]-1-methylethyl]benzoic acid (Example 2-133)

(E)-3-[4-({1-[(12-cyclohexyl-4-dimethylamino-6,7-dihydro-5-oxa-7a-azadibenzo[a,e]azulene-9-carbonyl)amino]cyclobutanecarbonyl}amino)phenyl]acrylic acid (Example 2-134)

(E)-3-(4-{2-[(12-cyclohexyl-6,7-dihydro-5-oxa-7a-azadibenzo[a,e]azulene-9-carbonyl)amino]-2,4-dimethylpentanoylamino}phenyl)acrylic acid (Example 2-135)

3-[(12-cyclohexyl-6,7-dihydro-5-oxa-7a-azadibenzo[a,e]azulene-9-carbonyl)amino]cyclohexanecarboxylic acid (Example 2-136)

(E)-3-[(4-({1-[(12-cyclohexyl-1-fluoro-6,7-dihydro-5-oxa-7a-azadibenzo[a,e]azulene-9-carbonyl)amino]cyclobutanecarbonyl}amino)phenyl]acrylic acid (Example 2-137)

(1R,2R)-2-[(12-cyclohexyl-6,7-dihydro-5-oxa-7a-azadibenzo[a,e]azulene-9-carbonyl)amino]cyclohexanecarboxylic acid (Example 2-138)

(E)-3-[4-({3-[(12-cyclohexyl-6,7-dihydro-5-oxa-7a-azadibenzo[a,e]azulene-9-carbonyl)amino]cyclohexanecarbonyl}amino)phenyl]acrylic acid (Example 2-139)

2-[(12-cyclohexyl-6,7-dihydro-5-oxa-7a-azadibenzo[a,e]azulene-9-carbonyl)amino]-3-methyl-3-methylsulfanylbutyric acid (Example 2-140)

(E)-3-[4-({1-[(12-cyclohexyl-2,3-difluoro-6,7-dihydro-5-oxa-7a-azadibenzo[a,e]azulene-9-carbonyl)amino]cyclobutanecarbonyl}amino)phenyl]acrylic acid (Example 2-141)

(E)-3-[(4-({(1R,2R)-2-[(12-cyclohexyl-6,7-dihydro-5-oxa-7a-azadibenzo[a,e]azulene-9-carbonyl)amino]cyclohexanecarbonyl}amino)phenyl]acrylic acid (Example 2-142)

2-[(12-cyclohexyl-6,7-dihydro-5-oxa-7a-azadibenzo[a,e]azulene-9-carbonyl)amino]-3,3-dimethylbutyric acid (Example 2-143)

(E)-3-(4-{2-[(12-cyclohexyl-6,7-dihydro-5-oxa-7a-azadibenzo[a,e]azulene-9-carbonyl)amino]-3,3-dimethylbutyrylamino}phenyl)acrylic acid (Example 2-144)

4-[1-({1-[(12-cyclohexyl-6,7-dihydro-5-oxa-7a-azadibenzo[a,e]azulene-9-carbonyl)amino]cyclobutanecarbonyl}amino)-1-methylethyl]benzoic acid (Example 2-145)

N-[1-(2-hydroxyethylcarbamoyl)cyclobutyl]-12-cyclohexyl-6,7-dihydro-5-oxa-7a-azadibenzo[a,e]azulene-9-carboxamide (Example 2-146)

N-[1-(2-methoxyethylcarbamoyl)cyclobutyl]-12-cyclohexyl-6,7-dihydro-5-oxa-7a-azadibenzo[a,e]azulene-9-carboxamide (Example 2-147)

12-cyclohexyl-6,7-dihydro-5-oxa-7a-azadibenzo[a,e]azulene-9-carboxamide (Example 2-148)

N-[(1R,2R)-2-(4-cyanophenylamino)cyclohexyl]-12-cyclohexyl-6,7-dihydro-5-oxa-7a-azadibenzo[a,e]azulene-9-carboxamide (Example 2-149).

(E)-3-[3-({1-[(12-cyclohexyl-6,7-dihydro-5-oxa-7a-azadibenzo[a,e]azulene-9-carbonyl)amino]cyclobutanecarbonyl}amino)phenyl]acrylic acid (Example 2-150)

methyl (S)-2-[(13-cyclohexyl-3,5-dimethyl-6,7-dihydro-5H-benzo[5,6][1,4]diazepino[7,1-a]indole-10-carbonyl)amino]-3-(4-hydroxyphenyl)propionate (Example 1-473)

13-cyclohexyl-5-ethyl-3-methoxy-6,7-dihydro-5H-benzo[5,6][1,4]diazepino[7,1-a]indole-10-carboxylic acid (Example 1-474)

13-cyclohexyl-5-isopropyl-3-methoxy-6,7-dihydro-5H-benzo[5,6][1,4]diazepino[7,1-a]indole-10-carboxylic acid monohydrochloride (Example 1-475)

sodium salt of 13-cyclohexyl-3-methyl-5-[2-(1,4-oxazepan-4-yl)-2-oxoethyl]-6,7-dihydro-5H-benzo[5,6][1,4]diazepino[7,1-a]indole-10-carboxylic acid (Example 1-476)

(E)-3-[4-({1-[(13-cyclohexyl-5-ethyl-3-methoxy-6,7-dihydro-5H-benzo[5,6][1,4]diazepino[7,1-a]indole-10-carbonyl)amino]cyclobutanecarbonyl}amino)phenyl]acrylic acid (Example 1-477)

(E)-3-[4-({1-[(13-cyclohexyl-5-isopropyl-3-methoxy-6,7-dihydro-5H-benzo[5,6][1,4]diazepino[7,1-a]indole-10-carbonyl)amino]cyclobutanecarbonyl}amino)phenyl]acrylic acid (Example 1-478)

13-cyclohexyl-3-methoxy-5-(2-methoxyethyl)-6,7-dihydro-5H-benzo[5,6][1,4]diazepino[7,1-a]indole-10-carboxylic acid (Example 1-479)

13-cyclohexyl-5-(2-isopropoxyethyl)-3-methoxy-6,7-dihydro-5H-benzo[5,6][1,4]diazepino[7,1-a]indole-10-carboxylic acid (Example 1-480)

(E)-3-{4-[(1-{[13-cyclohexyl-3-methoxy-5-(2-methoxyethyl)-6,7-dihydro-5H-benzo[5,6][1,4]diazepino[7,1-a]indole-10-carbonyl]amino}cyclobutanecarbonyl)amino]phenyl}acrylic acid (Example 1-481)

(E)-3-{(4-[(1-{[13-cyclohexyl-5-(2-isopropoxyethyl)-3-methoxy-6,7-dihydro-5H-benzo[5,6][1,4]diazepino[7,1-a]indole-10-carbonyl]amino}cyclobutanecarbonyl)amino]phenyl}acrylic acid (Example 1-482)

13-cyclohexyl-5-isobutyl-3-methoxy-6,7-dihydro-5H-benzo[5,6][1,4]diazepino[7,1-a]indole-10-carboxylic acid (Example 1-483)

(E)-3-[4-({1-[(13-cyclohexyl-5-isobutyl-3-methoxy-6,7-dihydro-5H-benzo[5,6][1,4]diazepino[7,1-a]indole-10-carbonyl)amino]cyclobutanecarbonyl}amino)phenyl]acrylic acid (Example 1-484)

1-({1-[(12-cyclohexyl-6,7-dihydro-5-oxa-7a-azadibenzo[a,e]azulene-9-carbonyl)amino]cyclobutanecarbonyl}amino)cyclobutanecarboxylic acid (Example 2-151)

methyl 2-{1-[(12-cyclohexyl-6,7-dihydro-5-oxa-7a-azadibenzo[a,e]azulene-9-carbonyl)amino]cyclobutyl}-3H-benzimidazole-5-carboxylate (Example 2-152)

4-{(1R,2R)-2-[(12-cyclohexyl-6,7-dihydro-5-oxa-7a-azadibenzo[a,e]azulene-9-carbonyl)amino]cyclohexylamino}benzoic acid (Example 2-153)

2-[(12-cyclohexyl-6,7-dihydro-5-oxa-7a-azadibenzo[a,e]azulene-9-carbonyl)amino]-3-methoxy-2-methylpropionic acid (Example 2-154)

tert-butyl 4-[4-((E)-2-carboxyvinyl)phenylcarbamoyl]-4-[(12-cyclohexyl-6,7-dihydro-5-oxa-7a-azadibenzo[a,e]azulene-9-carbonyl)amino]piperidine-1-carboxylate (Example 2-155)

4-{2-[(12-cyclohexyl-6,7-dihydro-5-oxa-7a-azadibenzo[a,e]azulene-9-carbonyl)amino]-2-methylpropoxy}benzoic acid (Example 2-156)

N-[2-(4-cyanophenoxy)-1,1-dimethylethyl]-12-cyclohexyl-6,7-dihydro-5-oxa-7a-azadibenzo[a,e]azulene-9-carboxamide (Example 2-157)

N-[2-(4-cyanophenylamino)-1,1-dimethylethyl]-12-cyclohexyl-6,7-dihydro-5-oxa-7a-azadibenzo[a,e]azulene-9-carboxamide (Example 2-158)

N-(2-hydroxy-1,1-dimethylethyl)-12-cyclohexyl-6,7-dihydro-5-oxa-7a-azadibenzo[a,e]azulene-9-carboxamide (Example 2-159)

2-{1-[(12-cyclohexyl-6,7-dihydro-5-oxa-7a-azadibenzo[a,e]azulene-9-carbonyl)amino]cyclobutyl}-3H-benzimidazole-5-carboxylic acid (Example 2-160)

12-cyclohexyl-4-{N-isopropyl-N-[2-(piperidin-1-yl)ethyl]amino}-6,7-dihydro-5-oxa-7a-azadibenzo[a,e]azulene-9-carboxylic acid dihydrochloride (Example 2-161)

12-cyclohexyl-4-[N-(2-dimethylaminoethyl)-N-methylamino]-6,7-dihydro-5-oxa-7a-azadibenzo[a,e]azulene-9-carboxylic acid dihydrochloride (Example 2-162)

(E)-3-(4-{2-[(12-cyclohexyl-6,7-dihydro-5-oxa-7a-azadibenzo[a,e]azulene-9-carbonyl)amino]-3-methoxy-2-methylpropionylamino}phenyl)acrylic acid (Example 2-163)

N-[2-(2-hydroxyethoxy)ethyl]-12-cyclohexyl-6,7-dihydro-5-oxa-7a-azadibenzo[a,e]azulene-9-carboxamide (Example 2-164)

N-tert-butyl-12-cyclohexyl-6,7-dihydro-5-oxa-7a-azadibenzo[a,e]azulene-9-carboxamide (Example 2-165)

N-(trans-4-hydroxycyclohexyl)-12-cyclohexyl-6,7-dihydro-5-oxa-7a-azadibenzo[a,e]azulene-9-carboxamide (Example 2-166)

2-{1-[(12-cyclohexyl-6,7-dihydro-5-oxa-7a-azadibenzo[a,e]azulene-9-carbonyl)amino]-1-methylethyl}thiazole-4-carboxylic acid (Example 2-167)

12-cyclohexyl-4-{N-ethyl-N-[2-(1,4-oxazepan-4-yl)ethyl]amino}-6,7-dihydro-5-oxa-7a-azadibenzo[a,e]azulene-9-carboxylic acid dihydrochloride (Example 2-168)

12-cyclohexyl-4-{N-ethyl-N-[3-(piperidin-1-yl)propyl]amino}-6,7-dihydro-5-oxa-7a-azadibenzo[a,e]azulene-9-carboxylic acid dihydrochloride (Example 2-169)

12-cyclohexyl-4-[N-ethyl-N-[2-(morpholin-4-yl)ethyl]amino]-6,7-dihydro-5-oxa-7a-azadibenzo[a,e]azulene-9-carboxylic acid dihydrochloride (Example 2-170)

N-[1-(4-hydroxymethylphenyl)-1-methylethyl]-12-cyclohexyl-6,7-dihydro-5-oxa-7a-azadibenzo[a,e]azulene-9-carboxamide (Example 2-171)

ethyl 2-{1-[(12-cyclohexyl-6,7-dihydro-5-oxa-7a-azadibenzo[a,e]azulene-9-carbonyl)amino]-1-methylethyl}thiazole-4-carboxylate (Example 2-172)

N-methyl-12-cyclohexyl-6,7-dihydro-5-oxa-7a-azadibenzo[a,e]azulene-9-carboxamide (Example 2-173)

(E)-3-[4-({4-[(12-cyclohexyl-6,7-dihydro-5-oxa-7a-azadibenzo[a,e]azulene-9-carbonyl)amino]piperidine-4-carbonyl}amino)phenyl]acrylic acid (Example 2-174)

methyl (S)-2-[(12-cyclohexyl-6,7-dihydro-5-oxa-7a-azadibenzo[a,e]azulene-9-carbonyl)amino]-3-(4-hydroxyphenyl)propionate (Example 2-175)

12-cyclohexyl-4-(dimethylcarbamoylmethylamino)-6,7-dihydro-5-oxa-7a-azadibenzo[a,e]azulene-9-carboxylic acid (Example 2-176)

N-[1-(trans-4-hydroxycyclohexylcarbamoyl)-1-methylethyl]-12-cyclohexyl-6,7-dihydro-5-oxa-7a-azadibenzo[a,e]azulene-9-carboxamide (Example 2-177)

12-cyclohexyl-4-{N-ethyl-N-[2-(piperidin-1-yl)acetyl]amino}-6,7-dihydro-5-oxa-7a-azadibenzo[a,e]azulene-9-carboxylic acid monohydrochloride (Example 2-178)

N-(4-benzyloxyphenyl)-12-cyclohexyl-6,7-dihydro-5-oxa-7a-azadibenzo[a,e]azulene-9-carboxamide (Example 2-179)

(S)-2-[(12-cyclohexyl-6,7-dihydro-5-oxa-7a-azadibenzo[a,e]azulene-9-carbonyl)amino]-3-(4-hydroxyphenyl)propionic acid (Example 2-180)

1-acetyl-4-[(12-cyclohexyl-6,7-dihydro-5-oxa-7a-azadibenzo[a,e]azulene-9-carbonyl)amino]piperidine-4-carboxylic acid (Example 2-181)

4-[(12-cyclohexyl-6,7-dihydro-5-oxa-7a-azadibenzo[a,e]azulene-9-carbonyl)amino]-1-methylpiperidine-4-carboxylic acid (Example 2-182)

4-{2-[(12-cyclohexyl-6,7-dihydro-5-oxa-7a-azadibenzo[a,e]azulene-9-carbonyl)amino]-2-methylpropylamino}benzoic acid (Example 2-183)

N-[2-(4-carbamoylphenylamino)-1,1-dimethylethyl]-12-cyclohexyl-6,7-dihydro-5-oxa-7a-azadibenzo[a,e]azulene-9-carboxamide (Example 2-184)

tert-butyl {2-[(12-cyclohexyl-6,7-dihydro-5-oxa-7a-azadibenzo[a,e]azulene-9-carbonyl)amino]-2-methylpropyl}carbamate (Example 2-185)

N-(2-amino-1,1-dimethylethyl)-12-cyclohexyl-6,7-dihydro-5-oxa-7a-azadibenzo[a,e]azulene-9-carboxamide monohydrochloride (Example 2-186)

{2-[(12-cyclohexyl-6,7-dihydro-5-oxa-7a-azadibenzo[a,e]azulene-9-carbonyl)amino]-2-methylpropylamino}acetic acid (Example 2-187)

N-[1,1-dimethyl-2-(4-nitrophenoxy)ethyl]-12-cyclohexyl-6,7-dihydro-5-oxa-7a-azadibenzo[a,e]azulene-9-carboxamide (Example 2-188)

2-[(12-cyclohexyl-6,7-dihydro-5-oxa-7a-azadibenzo[a,e]azulene-9-carbonyl)amino]-3-dimethylamino-2-methylpropionic acid (Example 2-189)

N-[2-(4-hydroxypiperidin-1-yl)-1,1-dimethyl-2-oxoethyl]-12-cyclohexyl-6,7-dihydro-5-oxa-7a-azadibenzo[a,e]azulene-9-carboxamide (Example 2-190)

4-{N-benzyl-N-[2-(piperidin-1-yl)ethyl]amino}-12-cyclohexyl-6,7-dihydro-5-oxa-7a-azadibenzo[a,e]azulene-9-carboxylic acid dihydrochloride (Example 2-191)

N-(4-hydroxyphenyl)-12-cyclohexyl-6,7-dihydro-5-oxa-7a-azadibenzo[a,e]azulene-9-carboxamide (Example 2-192)

N-[1-(4-carbamoylphenylcarbamoyl)-1-methylethyl]-12-cyclohexyl-6,7-dihydro-5-oxa-7a-azadibenzo[a,e]azulene-9-carboxamide (Example 2-193)

N-[1-(4-dimethylcarbamoylphenylcarbamoyl)-1-methylethyl]-12-cyclohexyl-6,7-dihydro-5-oxa-7a-azadibenzo[a,e]azulene-9-carboxamide (Example 2-194)

N-[1-(4-hydroxymethylphenylcarbamoyl)-1-methylethyl]-12-cyclohexyl-6,7-dihydro-5-oxa-7a-azadibenzo[a,e]azulene-9-carboxamide (Example 2-195)

methyl 2-[1-[(12-cyclohexyl-6,7-dihydro-5-oxa-7a-azadibenzo[a,e]azulene-9-carbonyl)amino]-1-methylethyl]-3H-benzimidazole-5-carboxylate (Example 2-196)

2-{[(12-cyclohexyl-6,7-dihydro-5-oxa-7a-azadibenzo[a,e]azulene-9-carbonyl)amino]methyl}-3H-benzimidazole-5-carboxylic acid (Example 2-197)

N-[1-(1H-benzimidazol-2-yl)-1-methylethyl]-12-cyclohexyl-6,7-dihydro-5-oxa-7a-azadibenzo[a,e]azulene-9-carboxamide (Example 2-198)

N-[1-(5-chloro-1H-benzimidazol-2-yl)-1-methylethyl]-12-cyclohexyl-6,7-dihydro-5-oxa-7a-azadibenzo[a,e]azulene-9-carboxamide (Example 2-199)

5-{2-[(12-cyclohexyl-6,7-dihydro-5-oxa-7a-azadibenzo[a,e]azulene-9-carbonyl)amino]-2-methylpropionylamino}-2-methylbenzoic acid (Example 2-200)

3-{2-[(12-cyclohexyl-6,7-dihydro-5-oxa-7a-azadibenzo[a,e]azulene-9-carbonyl)amino]-2-methylpropionylamino}benzoic acid (Example 2-201)

N-[1-(4-hydroxyphenylcarbamoyl)-1-methylethyl]-12-cyclohexyl-6,7-dihydro-5-oxa-7a-azadibenzo[a,e]azulene-9-carboxamide (Example 2-202)

N-{1-[2-(4-hydroxyphenyl)ethylcarbamoyl]-1-methylethyl}-12-cyclohexyl-6,7-dihydro-5-oxa-7a-azadibenzo[a,e]azulene-9-carboxamide (Example 2-203)

N-[1-(4-fluorophenylcarbamoyl)-1-methylethyl]-12-cyclohexyl-6,7-dihydro-5-oxa-7a-azadibenzo[a,e]azulene-9-carboxamide (Example 2-204)

N-[2-(4-hydroxyphenyl)ethyl]-12-cyclohexyl-6,7-dihydro-5-oxa-7a-azadibenzo[a,e]azulene-9-carboxamide (Example 2-205)

N-(1-hydroxycyclohexylmethyl)-12-cyclohexyl-6,7-dihydro-5-oxa-7a-azadibenzo[a,e]azulene-9-carboxamide (Example 2-206)

N—[(S)-1-carbamoyl-2-(4-hydroxyphenyl)ethyl]-12-cyclohexyl-6,7-dihydro-5-oxa-7a-azadibenzo[a,e]azulene-9-carboxamide (Example 2-207)

4-{1-[(12-cyclohexyl-6,7-dihydro-5-oxa-7a-azadibenzo[a,e]azulene-9-carbonyl)amino]-1-methylethyl}cyclohexanecarboxylic acid (Example 2-208)

methyl 2-[(1-[(12-cyclohexyl-6,7-dihydro-5-oxa-7a-azadibenzo[a,e]azulene-9-carbonyl)amino]-1-methylethyl]-5-methyl-3H-imidazole-4-carboxylate (Example 2-209)

methyl 2-[(12-cyclohexyl-6,7-dihydro-5-oxa-7a-azadibenzo[a,e]azulene-9-carbonyl)amino]-3-(5-hydroxy-1H-indol-2-yl)propionate (Example 2-210)

N-{2-[(12-cyclohexyl-6,7-dihydro-5-oxa-7a-azadibenzo[a,e]azulene-9-carbonyl)amino]-2-methylpropyl}terephthalamic acid (Example 2-211)

methyl N-{2-[(12-cyclohexyl-6,7-dihydro-5-oxa-7a-azadibenzo[a,e]azulene-9-carbonyl)amino]-2-methylpropyl}-terephthalamate (Example 2-212)

N-[1-(4-dimethylaminomethylphenylcarbamoyl)-1-methylethyl]-12-cyclohexyl-6,7-dihydro-5-oxa-7a-azadibenzo[a,e]azulene-9-carboxamide (Example 2-213)

2-{1-[(12-cyclohexyl-6,7-dihydro-5-oxa-7a-azadibenzo[a,e]azulene-9-carbonyl)amino]-1-methylethyl}-1H-benzimidazole-5-carboxylic acid (Example 2-214)

methyl 4-{2-[(12-cyclohexyl-6,7-dihydro-5-oxa-7a-azadibenzo[a,e]azulene-9-carbonyl)amino]-2-methylpropyl}benzoate (Example 2-215)

4-{2-[(12-cyclohexyl-6,7-dihydro-5-oxa-7a-azadibenzo[a,e]azulene-9-carbonyl)amino]-2-methylpropyl}benzoic acid (Example 2-216)

N—[(S)-1-hydroxymethyl-2-(4-hydroxyphenyl)ethyl]-12-cyclohexyl-6,7-dihydro-5-oxa-7a-azadibenzo[a,e]azulene-9-carboxamide (Example 2-217)

methyl (S)-2-[(12-cyclohexyl-6,7-dihydro-5-oxa-7a-azadibenzo[a,e]azulene-9-carbonyl)amino]-3 (4-methoxyphenyl)propionate (Example 2-218)

N-[2-(4-methoxyphenyl)-1,1-dimethylethyl]-12-cyclohexyl-6,7-dihydro-5-oxa-7a-azadibenzo[a,e]azulene-9-carboxamide (Example 2-219)

N-[2-(4-hydroxyphenyl)-1,1-dimethylethyl]-12-cyclohexyl-6,7-dihydro-5-oxa-7a-azadibenzo[a,e]azulene-9-carboxamide (Example 2-220)

12-cyclohexyl-4-(N-phenethyl-N-[2-(piperidin-1-yl)ethyl]amino)-6,7-dihydro-5-oxa-7a-azadibenzo[a,e]azulene-9-carboxylic acid (Example 2-221)

(E)-3-[(4-({1-acetyl-4-[(12-cyclohexyl-6,7-dihydro-5-oxa-7a-azadibenzo[a,e]azulene-9-carbonyl)amino]piperidine-4-carbonyl}amino)phenyl]acrylic acid (Example 2-222)

(E)-3-[4-({4-[(12-cyclohexyl-6,7-dihydro-5-oxa-7a-azadibenzo[a,e]azulene-9-carbonyl)amino]-1-methylpiperidine-4-carbonyl}amino) phenyl]acrylic acid (Example 2-223)

N-[2-(4-aminophenoxy)-1,1-dimethylethyl]-12-cyclohexyl-6,7-dihydro-5-oxa-7a-azadibenzo[a,e]azulene-9-carboxamide (Example 2-224)

N-[1-(6-carbamoyl-1H-benzimidazol-2-yl)-1-methylethyl]-12-cyclohexyl-6,7-dihydro-5-oxa-7a-azadibenzo[a,e]azulene-9-carboxamide (Example 2-225)

N-{1,1-dimethyl-2-[4-(2-oxopyrrolidin-1-yl)phenoxy]ethyl}-12-cyclohexyl-6,7-dihydro-5-oxa-7a-azadibenzo[a,e]azulene-9-carboxamide (Example 2-226)

2-{1-[(12-cyclohexyl-6,7-dihydro-5-oxa-7a-azadibenzo[a,e]azulene-9-carbonyl)amino]-1-methylethyl}-5-methyl-3H-imidazole-4-carboxylic acid (Example 2-227)

N-[1-(4-benzyloxyphenyl)-1-methylethyl]-12-cyclohexyl-6,7-dihydro-5-oxa-7a-azadibenzo[a,e]azulene-9-carboxamide (Example 2-228)

1-carboxymethyl-4-[(12-cyclohexyl-6,7-dihydro-5-oxa-7a-azadibenzo[a,e]azulene-9-carbonyl)amino]piperidine-4-carboxylic acid monohydrochloride (Example 2-229)

N-[1-(4-hydroxyphenyl)-1-methylethyl]-12-cyclohexyl-6,7-dihydro-5-oxa-7a-azadibenzo[a,e]azulene-9-carboxamide (Example 2-230)

4-{N-[2-(azepan-1-yl)ethyl]-N-ethylamino}-12-cyclohexyl-6,7-dihydro-5-oxa-7a-azadibenzo[a,e]azulene-9-carboxylic acid dihydrochloride (Example 2-231)

4-{N-[2-(1-acetylpiperidin-4-yl)ethyl]-N-ethylamino}-12-cyclohexyl-6,7-dihydro-5-oxa-7a-azadibenzo[a,e]azulene-9-carboxylic acid (Example 2-232)

4-{N-acetyl-N-[2-(1-acetylpiperidin-4-yl)ethyl]amino}-12-cyclohexyl-6,7-dihydro-5-oxa-7a-azadibenzo[a,e]azulene-9-carboxylic acid (Example 2-233)

N-[2-(4-hydroxypiperidin-1-yl)-1,1-dimethylethyl]-12-cyclohexyl-6,7-dihydro-5-oxa-7a-azadibenzo[a,e]azulene-9-carboxamide (Example 2-234)

methyl 2-{1-[(12-cyclohexyl-6,7-dihydro-5-oxa-7a-azadibenzo[a,e]azulene-9-carbonyl)amino]-1-methylethyl}-5-methyloxazole-4-carboxylate (Example 2-235)

2-(1-[(12-cyclohexyl-6,7-dihydro-5-oxa-7a-azadibenzo[a,e]azulene-9-carbonyl)amino]-1-methylethyl)-5-methyloxazole-4-carboxylic acid (Example 2-236)

(S)-2-[(12-cyclohexyl-6,7-dihydro-5-oxa-7a-azadibenzo[a,e]azulene-9-carbonyl)amino]-3-(4-methoxyphenyl)propionic acid (Example 2-237)

methyl (R)-2-[(12-cyclohexyl-6,7-dihydro-5-oxa-7a-azadibenzo[a,e]azulene-9-carbonyl)amino]-3-(4-hydroxyphenyl)propionate (Example 2-238)

N-[2-(trans-4-hydroxycyclohexylamino)-1,1-dimethylethyl]-12-cyclohexyl-6,7-dihydro-5-oxa-7a-azadibenzo[a,e]azulene-9-carboxamide (Example 2-239)

N-[2-(3-hydroxypiperidin-1-yl)-1,1-dimethyl-2-oxoethyl]-12-cyclohexyl-6,7-dihydro-5-oxa-7a-azadibenzo[a,e]azulene-9-carboxamide (Example 2-240)

(4-{1-[(12-cyclohexyl-6,7-dihydro-5-oxa-7a-azadibenzo[a,e]azulene-9-carbonyl)amino]-1-methylethyl}phenoxy)acetic acid (Example 2-241)

N-[2-(4-hydroxymethylpiperidin-1-yl)-1,1-dimethyl-2-oxoethyl]-12-cyclohexyl-6,7-dihydro-5-oxa-7a-azadibenzo[a,e]azulene-9-carboxamide (Example 2-242)

12-cyclohexyl-4-(N-ethyl-N-[2-(1-ethylpiperidin-4-yl)ethyl]amino)-6,7-dihydro-5-oxa-7a-azadibenzo[a,e]azulene-9-carboxylic acid dihydrochloride (Example 2-243)

N-[2-[4-(2-hydroxyethyl)piperazin-1-yl]-1,1-dimethylethyl]-12-cyclohexyl-6,7-dihydro-5-oxa-7a-azadibenzo[a,e]azulene-9-carboxamide (Example 2-244)

[(S)-2-(4-hydroxyphenyl)-1-(methylcarbamoyl)ethyl]-12-cyclohexyl-6,7-dihydro-5-oxa-7a-azadibenzo[a,e]azulene-9-carboxamide (Example 2-245)

(R)-2-[(12-cyclohexyl-6,7-dihydro-5-oxa-7a-azadibenzo[a,e]azulene-9-carbonyl)amino]-3-(4-hydroxyphenyl)propionic acid (Example 2-246)

{4-(1H-benzimidazol-2-yl)-4-[(12-cyclohexyl-6,7-dihydro-5-oxa-7a-azadibenzo[a,e]azulene-9-carbonyl)amino]piperidin-1-yl}acetic acid (Example 2-247)

methyl {4-(1H-benzimidazol-2-yl)-4-[(12-cyclohexyl-6,7-dihydro-5-oxa-7a-azadibenzo[a,e]azulene-9-carbonyl)amino]piperidin-1-yl}acetate monohydrochloride (Example 2-248)

N-(1-methyl-1H-benzimidazol-2-ylmethyl)-12-cyclohexyl-6,7-dihydro-5-oxa-7a-azadibenzo[a,e]azulene-9-carboxamide (Example 2-249)

(2-{[(12-cyclohexyl-6,7-dihydro-5-oxa-7a-azadibenzo[a,e]azulene-9-carbonyl)amino]methyl}benzimidazol-1-yl)acetic acid (Example 2-250)

methyl (2-{[(12-cyclohexyl-6,7-dihydro-5-oxa-7a-azadibenzo[a,e]azulene-9-carbonyl)amino]methyl}benzimidazol-1-yl)acetate (Example 2-251)

N-(1H-benzimidazol-2-ylmethyl)-12-cyclohexyl-6,7-dihydro-5-oxa-7a-azadibenzo[a,e]azulene-9-carboxamide (Example 2-252)

2-[(12-cyclohexyl-6,7-dihydro-5-oxa-7a-azadibenzo[a,e]azulene-9-carbonyl)amino]-3-(5-hydroxy-1H-indol-2-yl)propionic acid (Example 2-253)

(E)-3-{2-[(12-cyclohexyl-6,7-dihydro-5-oxa-7a-azadibenzo[a,e]azulene-9-carbonyl)amino]-2-methylpropylamino}acrylic acid (Example 2-254)

6-{2-[(12-cyclohexyl-6,7-dihydro-5-oxa-7a-azadibenzo[a,e]azulene-9-carbonyl)amino]-2-methylpropylamino}nicotinic acid (Example 2-255)

4-{(N-(2-benzyloxyethyl)-N-[2-(piperidin-1-yl)ethyl]amino}-12-cyclohexyl-6,7-dihydro-5-oxa-7a-azadibenzo[a,e]azulene-9-carboxylic acid dihydrochloride (Example 2-256)

12-cyclohexyl-4-{N-(2-isopropoxyethyl)-N-[2-(piperidin-1-yl)ethyl]amino}-6,7-dihydro-5-oxa-7a-azadibenzo[a,e]azulene-9-carboxylic acid dihydrochloride (Example 2-257)

N-[1-(4,5-dimethyl-1H-imidazol-2-yl)-1-methylethyl]-12-cyclohexyl-6,7-dihydro-5-oxa-7a-azadibenzo[a,e]azulene-9-carboxamide (Example 2-258)

N-[1-methyl-1-(1,4,5-trimethyl-1H-imidazol-2-yl)ethyl]-12-cyclohexyl-6,7-dihydro-5-oxa-7a-azadibenzo[a,e]azulene-9-carboxamide (Example 2-259)

N-[1-(3-hydroxyphenylcarbamoyl)-1-methylethyl]-12-cyclohexyl-6,7-dihydro-5-oxa-7a-azadibenzo[a,e]azulene-9-carboxamide (Example 2-260)

12-cyclohexyl-4-{N-(2-hydroxyethyl)-N-[2-(piperidin-1-yl)ethyl]amino}-6,7-dihydro-5-oxa-7a-azadibenzo[a,e]azulene-9-carboxylic acid dihydrochloride (Example 2-261)

N—[(S)-1-dimethylcarbamoyl-2-(4-hydroxyphenyl)ethyl]-12-cyclohexyl-3-methoxy-6,7-dihydro-5-oxa-7a-azadibenzo[a,e]azulene-9-carboxamide (Example 2-262)

N—[(S)-2-(4-hydroxyphenyl)-1-(methylcarbamoyl)ethyl]-12-cyclohexyl-3-methoxy-6,7-dihydro-5-oxa-7a-azadibenzo[a,e]azulene-9-carboxamide (Example 2-263)

methyl (2-{1-[(12-cyclohexyl-6,7-dihydro-5-oxa-7a-azadibenzo[a,e]azulene-9-carbonyl)amino]-1-methylethyl}-4,5-dimethylimidazol-1-yl)acetate (Example 2-264)

(2-{1-[(12-cyclohexyl-6,7-dihydro-5-oxa-7a-azadibenzo[a,e]azulene-9-carbonyl)amino]-1-methylethyl}-4,5-dimethylimidazol-1-yl)acetic acid (Example 2-265)

methyl 2-[(12-cyclohexyl-6,7-dihydro-5-oxa-7a-azadibenzo[a,e]azulene-9-carbonyl)amino]-3H-benzimidazole-5-carboxylate (Example 2-266)

N-(1H-benzimidazol-2-yl)-12-cyclohexyl-6,7-dihydro-5-oxa-7a-azadibenzo[a,e]azulene-9-carboxamide (Example 2-267)

2-[(12-cyclohexyl-6,7-dihydro-5-oxa-7a-azadibenzo[a,e]azulene-9-carbonyl)amino]-3H-benzimidazole-5-carboxylic acid (Example 2-268)

N-[1-(6-cyano-1H-benzimidazol-2-yl)-1-methylethyl]-12-cyclohexyl-6,7-dihydro-5-oxa-7a-azadibenzo[a,e]azulene-9-carboxamide (Example 2-269)

methyl (S)-2-[(12-cyclohexyl-3-methoxy-6,7-dihydro-5-oxa-7a-azadibenzo[a,e]azulene-9-carbonyl)amino]-2-(4-hydroxyphenyl)acetate (Example 2-270)

methyl (R)-2-[(12-cyclohexyl-3-methoxy-6,7-dihydro-5-oxa-7a-azadibenzo[a,e]azulene-9-carbonyl)amino]-2-(4-hydroxyphenyl)acetate (Example 2-271)

12-cyclohexyl-4-{N-ethyl-N-[2-(4-methoxypiperidin-1-yl)ethyl]amino}-6,7-dihydro-5-oxa-7a-azadibenzo[a,e]azulene-9-carboxylic acid dihydrochloride (Example 2-272)

12-cyclohexyl-4-phenyl-6,7-dihydro-5-oxa-7a-azadibenzo[a,e]azulene-9-carboxylic acid (Example 2-273)

12-cyclohexyl-4-{N-ethyl-N-[2-(3-methoxymethylpiperidine-1-yl)ethyl]amino}-6,7-dihydro-5-oxa-7a-azadibenzo[a,e]azulene-9-carboxylic acid dihydrochloride (Example 2-274)

12-cyclohexyl-4-[(N-ethyl-N-[2-(4-methoxymethylpiperidine-1-yl)ethyl]amino}-6,7-dihydro-5-oxa-7a-azadibenzo[a,e]azulene-9-carboxylic acid dihydrochloride (Example 2-275)

2-[(12-cyclohexyl-4-{N-[2-(piperidin-1-yl)ethyl]-N-propylamino}-6,7-dihydro-5-oxa-7a-azadibenzo[a,e]azulene-9-carbonyl)amino]-2-methylpropionic acid (Example 2-276)

4-{bis[2-oxo-2-(piperidin-1-yl)ethyl]amino}-12-cyclohexyl-6,7-dihydro-5-oxa-7a-azadibenzo[a,e]azulene-9-carboxylic acid (Example 2-277)

4-[(bis[2-(piperidin-1-yl)ethyl]amino]-12-cyclohexyl-6,7-dihydro-5-oxa-7a-azadibenzo[a,e]azulene-9-carboxylic acid dihydrochloride (Example 2-278)

methyl (S)-2-[(12-cyclohexyl-3-methoxy-6,7-dihydro-5-oxa-7a-azadibenzo[a,e]azulene-9-carbonyl)amino]-3-(4-fluorophenyl)propionate (Example 2-279)

methyl (S)-2-[(12-cyclohexyl-3-methoxy-6,7-dihydro-5-oxa-7a-azadibenzo[a,e]azulene-9-carbonyl)amino]-3-(1H-imidazol-4-yl)propionate (Example 2-280)

methyl (S)-2-(12-cyclohexyl-3-methoxy-6,7-dihydro-5-oxa-7a-azadibenzo[a,e]azulene-9-carbonyl)-7-hydroxy-1,2,3,4-tetrahydroisoquinoline-3-carboxylate (Example 2-281)

methyl 2-{1-[(12-cyclohexyl-6,7-dihydro-5-oxa-7a-azadibenzo[a,e]azulene-9-carbonyl)amino]-1-methylethyl}-6-methyl-3H-benzimidazole-5-carboxylate (Example 2-282)

2-{1-[(12-cyclohexyl-6,7-dihydro-5-oxa-7a-azadibenzo[a,e]azulene-9-carbonyl)amino]-1-methylethyl}-6-methyl-3H-benzimidazole-5-carboxylic acid (Example 2-283)

methyl (2-[(1-[(12-cyclohexyl-6,7-dihydro-5-oxa-7a-azadibenzo[a,e]azulene-9-carbonyl)amino]-1-methylethyl]benzimidazol-1-yl)acetate (Example 2-284)

N-[1-methyl-1-(1-methyl-1H-benzimidazol-2-yl)ethyl]-12-cyclohexyl-6,7-dihydro-5-oxa-7a-azadibenzo[a,e]azulene-9-carboxamide (Example 2-285)

N-(1-methyl-1H-benzimidazol-2-yl)-12-cyclohexyl-6,7-dihydro-5-oxa-7a-azadibenzo[a,e]azulene-9-carboxamide (Example 2-286)

{4-[(12-cyclohexyl-6,7-dihydro-5-oxa-7a-azadibenzo[a,e]azulene-9-carbonyl)amino]-4-hydroxymethylpiperidin-1-yl}acetic acid monohydrochloride (Example 2-287)

N-[1-(2-hydroxyethyl)-1H-benzimidazol-2-ylmethyl]-12-cyclohexyl-6,7-dihydro-5-oxa-7a-azadibenzo[a,e]azulene-9-carboxamide (Example 2-288)

N-[1,1-dimethyl-2-(morpholin-4-yl)-2-oxoethyl]-12-cyclohexyl-6,7-dihydro-5-oxa-7a-azadibenzo[a,e]azulene-9-carboxamide (Example 2-289)

N-[1,1-dimethyl-2-(4-methylpiperazin-1-yl)-2-oxoethyl]-12-cyclohexyl-6,7-dihydro-5-oxa-7a-azadibenzo[a,e]azulene-9-carboxamide (Example 2-290)

N-[1,1-dimethyl-2-oxo-2-(4-phenylpiperazin-1-yl)ethyl]-12-cyclohexyl-6,7-dihydro-5-oxa-7a-azadibenzo[a,e]azulene-9-carboxamide (Example 2-291)

N-{1-[1-(2-hydroxyethyl)-4,5-dimethyl-1H-imidazol-2-yl]-1-methylethyl}-12-cyclohexyl-6,7-dihydro-5-oxa-7a-azadibenzo[a,e]azulene-9-carboxamide (Example 2-292)

N-[1-(1-dimethylcarbamoylmethyl-4,5-dimethyl-1H-imidazol-2-yl)-1-methylethyl]-12-cyclohexyl-6,7-dihydro-5-oxa-7a-azadibenzo[a,e]azulene-9-carboxamide (Example 2-293)

N-[2-(4-methoxypiperidin-1-yl)-1,1-dimethyl-2-oxoethyl]-12-cyclohexyl-6,7-dihydro-5-oxa-7a-azadibenzo[a,e]azulene-9-carboxamide (Example 2-294)

N-{(S)-2-(4-hydroxyphenyl)-1-[N-(2-methoxyethyl)-N-methylcarbamoyl]ethyl}-12-cyclohexyl-3-methoxy-6,7-dihydro-5-oxa-7a-azadibenzo[a,e]azulene-9-carboxamide (Example 2-295)

N—[(S)-2-(4-hydroxyphenyl)-1-(2-methoxyethylcarbamoyl)ethyl]-12-cyclohexyl-3-methoxy-6,7-dihydro-5-oxa-7a-azadibenzo[a,e]azulene-9-carboxamide (Example 2-296)

N—[(S)-1-(4-hydroxybenzyl)-2-(4-methoxypiperidin-1-yl)-2-oxoethyl]-12-cyclohexyl-3-methoxy-6,7-dihydro-5-oxa-7a-azadibenzo[a,e]azulene-9-carboxamide (Example 2-297)

12-cyclohexyl-4-(pyridin-3-yl)-6,7-dihydro-5-oxa-7a-azadibenzo[a,e]azulene-9-carboxylic acid monohydrochloride (Example 2-298)

12-cyclohexyl-4-(pyridin-4-yl)-6,7-dihydro-5-oxa-7a-azadibenzo[a,e]azulene-9-carboxylic acid monohydrochloride (Example 2-299)

12-cyclohexyl-4-{N-[2-(piperidin-1-yl)ethyl]-N-propylamino}-6,7-dihydro-5-oxa-7a-azadibenzo[a,e]azulene-9-carboxamide (Example 2-300)

12-cyclohexyl-4-{N-ethyl-N-[2-(4-ethylpiperazin-1-yl)-2-oxoethyl]amino}-6,7-dihydro-5-oxa-7a-azadibenzo[a,e]azulene-9-carboxylic acid dihydrochloride (Example 2-301)

12-cyclohexyl-4-(3-hydroxymethylphenyl)-6,7-dihydro-5-oxa-7a-azadibenzo[a,e]azulene-9-carboxylic acid (Example 2-302)

N-[2-(4-acetylpiperazin-1-yl)-1,1-dimethyl-2-oxoethyl]-12-cyclohexyl-6,7-dihydro-5-oxa-7a-azadibenzo[a,e]azulene-9-carboxamide (Example 2-303)

N-{2-[4-(2-hydroxyethyl)piperazin-1-yl]-1,1-dimethyl-2-oxoethyl}-12-cyclohexyl-6,7-dihydro-5-oxa-7a-azadibenzo[a,e]azulene-9-carboxamide (Example 2-304)

N-{2-[4-(2-methoxyethyl)piperazin-1-yl]-1,1-dimethyl-2-oxoethyl}-12-cyclohexyl-6,7-dihydro-5-oxa-7a-azadibenzo[a,e]azulene-9-carboxamide (Example 2-305)

4-{2-[(12-cyclohexyl-4-methoxy-6,7-dihydro-5-oxa-7a-azadibenzo[a,e]azulene-9-carbonyl)amino]-2-methylpropionylamino}benzoic acid (Example 2-306)

N-{1-[5-(4-methoxyphenyl)-1H-imidazol-2-yl]-1-methylethyl}-12-cyclohexyl-6,7-dihydro-5-oxa-7a-azadibenzo[a,e]azulene-9-carboxamide (Example 2-307)

N—[(S)-2-dimethylamino-1-(4-hydroxybenzyl)ethyl]-12-cyclohexyl-3-methoxy-6,7-dihydro-5-oxa-7a-azadibenzo[a,e]azulene-9-carboxamide (Example 2-308)

methyl (S)-6-tert-butoxycarbonylamino-2-[(12-cyclohexyl-3-methoxy-6,7-dihydro-5-oxa-7a-azadibenzo[a,e]azulene-9-carbonyl)amino]hexanoate (Example 2-309)

(S)-2-[(12-cyclohexyl-3-methoxy-6,7-dihydro-5-oxa-7a-azadibenzo[a,e]azulene-9-carbonyl)amino]-3-(1H-imidazol-4-yl)propionic acid (Example 2-310)

N-{1-methyl-1-[5-(1H-tetrazol-5-yl)-1H-benzimidazol-2-yl]ethyl}-12-cyclohexyl-6,7-dihydro-5-oxa-7a-azadibenzo[a,e]azulene-9-carboxamide (Example 2-311)

(2-{1-[(12-cyclohexyl-6,7-dihydro-5-oxa-7a-azadibenzo[a,e]azulene-9-carbonyl)amino]-1-methylethyl}benzimidazol-1-yl)acetic acid (Example 2-312)

methyl 2-{4-[(12-cyclohexyl-6,7-dihydro-5-oxa-7a-azadibenzo[a,e]azulene-9-carbonyl)amino]-1-methylpiperidin-4-yl}-3H-benzimidazole-5-carboxylate (Example 2-313)

N—[(S)-1-(4-hydroxybenzyl)-2-methoxyethyl]-12-cyclohexyl-3-methoxy-6,7-dihydro-5-oxa-7a-azadibenzo[a,e]azulene-9-carboxamide (Example 2-314)

methyl 2-[(12-cyclohexyl-3-methoxy-6,7-dihydro-5-oxa-7a-azadibenzo[a,e]azulene-9-carbonyl)amino]-3-(3-fluoro-4-hydroxyphenyl)propionate (Example 2-315)

methyl (S)-2-[(12-cyclohexyl-3-methoxy-6,7-dihydro-5-oxa-7a-azadibenzo[a,e]azulene-9-carbonyl)amino]-3-(5-hydroxy-1H-indol-3-yl)propionate (Example 2-316)

methyl (S)-3-(4-benzyloxycarbonylaminophenyl)-2-[(12-cyclohexyl-3-methoxy-6,7-dihydro-5-oxa-7a-azadibenzo[a,e]azulene-9-carbonyl)amino]propionate (Example 2-317)

(S)-3-(4-benzyloxycarbonylaminophenyl)-2-[(12-cyclohexyl-3-methoxy-6,7-dihydro-5-oxa-7a-azadibenzo[a,e]azulene-9-carbonyl)amino]propionic acid (Example 2-318)

methyl (S)-3-(4-aminophenyl)-2-[(12-cyclohexyl-3-methoxy-6,7-dihydro-5-oxa-7a-azadibenzo[a,e]azulene-9-carbonyl)amino]propionate (Example 2-319)

(S)-3-(4-aminophenyl)-2-[(12-cyclohexyl-3-methoxy-6,7-dihydro-5-oxa-7a-azadibenzo[a,e]azulene-9-carbonyl)amino]propionic acid (Example 2-320)

tert-butyl (1-{2-[(12-cyclohexyl-6,7-dihydro-5-oxa-7a-azadibenzo[a,e]azulene-9-carbonyl)amino]-2-methylpropionyl}piperidin-4-yl)carbamate (Example 2-321)

N-[2-(3-hydroxypyrrolidin-1-yl)-1,1-dimethyl-2-oxoethyl]-12-cyclohexyl-6,7-dihydro-5-oxa-7a-azadibenzo[a,e]azulene-9-carboxamide (Example 2-322)

12-cyclohexyl-4-(3-methoxymethylphenyl)-6,7-dihydro-5-oxa-7a-azadibenzo[a,e]azulene-9-carboxylic acid (Example 2-323)

12-cyclohexyl-4-phenylamino-6,7-dihydro-5-oxa-7a-azadibenzo[a,e]azulene-9-carboxylic acid (Example 2-324)

12-cyclohexyl-4-(2-hydroxymethylphenyl)-6,7-dihydro-5-oxa-7a-azadibenzo[a,e]azulene-9-carboxylic acid (Example 2-325)

N-[12-cyclohexyl-9-(1H-tetrazol-5-yl)-6,7-dihydro-5-oxa-7a-azadibenzo[a,e]azulen-4-yl]-N-[2-(piperidin-1-yl)ethyl]propylamine (Example 2-326)

12-cyclohexyl-4-(2-methoxymethylphenyl)-6,7-dihydro-5-oxa-7a-azadibenzo[a,e]azulene-9-carboxylic acid (Example 2-327)

12-cyclohexyl-4-(3-dimethylaminomethylphenyl)-6,7-dihydro-5-oxa-7a-azadibenzo[a,e]azulene-9-carboxylic acid monohydrochloride (Example 2-328)

ethyl 2-{1-[(12-cyclohexyl-6,7-dihydro-5-oxa-7a-azadibenzo[a,e]azulene-9-carbonyl)amino]-1-methylethyl}-1-methyl-1H-benzimidazole-5-carboxylate (Example 2-329)
2-{1-[(12-cyclohexyl-6,7-dihydro-5-oxa-7a-azadibenzo[a,e]azulene-9-carbonyl)amino]-1-methylethyl}-1-methyl-1H-benzimidazole-5-carboxylic acid (Example 2-330)
methyl 2-{1-[(12-cyclohexyl-3-methoxy-6,7-dihydro-5-oxa-7a-azadibenzo[a,e]azulene-9-carbonyl)amino]-1-methylethyl}-6-methoxy-1H-benzimidazole-5-carboxylate (Example 2-331)
2-{1-[(12-cyclohexyl-3-methoxy-6,7-dihydro-5-oxa-7a-azadibenzo[a,e]azulene-9-carbonyl)amino]-1-methylethyl}-1H-benzimidazole-5-carboxylic acid (Example 2-332)
N-{1-[N-ethyl-N-(4-methoxybutyl)carbamoyl]-1-methylethyl}-12-cyclohexyl-6,7-dihydro-5-oxa-7a-azadibenzo[a,e]azulene-9-carboxamide (Example 2-333)
N-[2-(4-acetylaminopiperidin-1-yl)-1,1-dimethyl-2-oxoethyl]-12-cyclohexyl-6,7-dihydro-5-oxa-7a-azadibenzo[a,e]azulene-9-carboxamide (Example 2-334)
N-[2-(4-methanesulfonylaminopiperidin-1-yl)-1,1-dimethyl-2-oxoethyl]-12-cyclohexyl-6,7-dihydro-5-oxa-7a-azadibenzo[a,e]azulene-9-carboxamide (Example 2-335)
methyl 2-{1-[(12-cyclohexyl-6,7-dihydro-5-oxa-7a-azadibenzo[a,e]azulene-9-carbonyl)amino]-1-methylethyl}-3-methyl-3H-benzimidazole-5-carboxylate (Example 2-336)
2-{1-[(12-cyclohexyl-6,7-dihydro-5-oxa-7a-azadibenzo[a,e]azulene-9-carbonyl)amino]-1-methylethyl}-3-methyl-3H-benzimidazole-5-carboxylic acid (Example 2-337)
methyl (S)-3-(4-acetylaminophenyl)-2-[(12-cyclohexyl-3-methoxy-6,7-dihydro-5-oxa-7a-azadibenzo[a,e]azulene-9-carbonyl)amino]propionate (Example 2-338)
methyl (S)-2-[(12-cyclohexyl-3-methoxy-6,7-dihydro-5-oxa-7a-azadibenzo[a,e]azulene-9-carbonyl)amino]-3-(4-methanesulfonylaminophenyl)propionate (Example 2-339)
(S)-3-(4-acetylaminophenyl)-2-[(12-cyclohexyl-3-methoxy-6,7-dihydro-5-oxa-7a-azadibenzo[a,e]azulene-9-carbonyl)amino]propionic acid (Example 2-340)
(S)-2-[(12-cyclohexyl-3-methoxy-6,7-dihydro-5-oxa-7a-azadibenzo[a,e]azulene-9-carbonyl)amino]-3-(4-methanesulfonylaminophenyl)propionic acid (Example 2-341)
12-cyclohexyl-4-{N-(3-methoxypropyl)-N-[2-(piperidin-1-yl)ethyl]amino}-6,7-dihydro-5-oxa-7a-azadibenzo[a,e]azulene-9-carboxylic acid (Example 2-342)
12-cyclohexyl-4-(2-dimethylaminomethylphenyl)-6,7-dihydro-5-oxa-7a-azadibenzo[a,e]azulene-9-carboxylic acid (Example 2-343)
12-cyclohexyl-4-(2-oxopiperidin-1-yl)-6,7-dihydro-5-oxa-7a-azadibenzo[a,e]azulene-9-carboxylic acid (Example 2-344)
12-cyclohexyl-4-(piperidin-1-yl)-6,7-dihydro-5-oxa-7a-azadibenzo[a,e]azulene-9-carboxylic acid (Example 2-345)
N-[1-(5-dimethylcarbamoyl-1H-benzimidazol-2-yl)-1-methylethyl]-12-cyclohexyl-3-methoxy-6,7-dihydro-5-oxa-7a-azadibenzo[a,e]azulene-9-carboxamide (Example 2-346)
2-{1-[(12-cyclohexyl-3-methoxy-6,7-dihydro-5-oxa-7a-azadibenzo[a,e]azulene-9-carbonyl)amino]-1-methylethyl}-6-methoxy-1H-benzimidazole-5-carboxylic acid (Example 2-347)
N-[1-(benzoxazol-2-yl)-1-methylethyl]-12-cyclohexyl-3-methoxy-6,7-dihydro-5-oxa-7a-azadibenzo[a,e]azulene-9-carboxamide (Example 2-348)
methyl 4-{2-[(12-cyclohexyl-3-methoxy-6,7-dihydro-5-oxa-7a-azadibenzo[a,e]azulene-9-carbonyl)amino]-2-methylpropionylamino}benzoate (Example 2-349)
4-{2-[(12-cyclohexyl-3-methoxy-6,7-dihydro-5-oxa-7a-azadibenzo[a,e]azulene-9-carbonyl)amino]-2-methylpropionylamino}benzoic acid (Example 2-350)
N-{1-[1-(2-hydroxyethyl)-1H-benzimidazol-2-yl]-1-methylethyl}-12-cyclohexyl-6,7-dihydro-5-oxa-7a-azadibenzo[a,e]azulene-9-carboxamide (Example 2-351)
methyl (S)-2-[(12-cyclohexyl-3-methoxy-6,7-dihydro-5-oxa-7a-azadibenzo[a,e]azulene-9-carbonyl)amino]-3-(3-trifluoromethylphenyl)propionate (Example 2-352)
methyl 2-[(12-cyclohexyl-3-methoxy-6,7-dihydro-5-oxa-7a-azadibenzo[a,e]azulene-9-carbonyl)amino]-3-(3-hydroxyphenyl) propionate (Example 2-353)
(S)-2-[(12-cyclohexyl-3-methoxy-6,7-dihydro-5-oxa-7a-azadibenzo[a,e]azulene-9-carbonyl)amino]-3-(3-trifluoromethylphenyl)propionic acid (Example 2-354)
2-[(12-cyclohexyl-3-methoxy-6,7-dihydro-5-oxa-7a-azadibenzo[a,e]azulene-9-carbonyl)amino]-3-(3-hydroxyphenyl)propionic acid (Example 2-355)
methyl (S)-2-[(12-cyclohexyl-3-methoxy-6,7-dihydro-5-oxa-7a-azadibenzo[a,e]azulene-9-carbonyl)amino]-3-(pyridin-4-yl)propionate (Example 2-356)
4-{bis[2-(1,4-oxazepan-4-yl)-2-oxoethyl]amino}-12-cyclohexyl-6,7-dihydro-5-oxa-7a-azadibenzo[a,e]azulene-9-carboxylic acid (Example 2-357)
N-{2-[4-(4-fluorophenyl)-4-hydroxypiperidin-1-yl]-1,1-dimethyl-2-oxoethyl}-12-cyclohexyl-6,7-dihydro-5-oxa-7a-azadibenzo[a,e]azulene-9-carboxamide (Example 2-358)
4-{bis[2-(morpholin-4-yl)-2-oxoethyl]amino}-12-cyclohexyl-6,7-dihydro-5-oxa-7a-azadibenzo[a,e]azulene-9-carboxylic acid (Example 2-359)
4-{bis[2-(1,4-oxazepan-4-yl)ethyl]amino}-12-cyclohexyl-6,7-dihydro-5-oxa-7a-azadibenzo[a,e]azulene-9-carboxylic acid trihydrochloride (Example 2-360)
4-{bis[2-(morpholin-4-yl)ethyl]amino}-12-cyclohexyl-6,7-dihydro-5-oxa-7a-azadibenzo[a,e]azulene-9-carboxylic acid trihydrochloride (Example 2-361)
methyl (S)-2-[(12-cyclohexyl-3-methoxy-6,7-dihydro-5-oxa-7a-azadibenzo[a,e]azulene-9-carbonyl)amino]-3-(4-methoxycarbonylaminophenyl)propionate (Example 2-362)
methyl (S)-3-(3-chloro-4-hydroxyphenyl)-2-[(12-cyclohexyl-3-methoxy-6,7-dihydro-5-oxa-7a-azadibenzo[a,e]azulene-9-carbonyl)amino]propionate (Example 2-363)
(S)-2-[(12-cyclohexyl-3-methoxy-6,7-dihydro-5-oxa-7a-azadibenzo[a,e]azulene-9-carbonyl)amino]-3-(4-methoxycarbonylaminophenyl)propionic acid (Example 2-364)
(S)-3-(3-chloro-4-hydroxyphenyl)-2-[(12-cyclohexyl-3-methoxy-6,7-dihydro-5-oxa-7a-azadibenzo[a,e]azulene-9-carbonyl)amino]propionic acid (Example 2-365)
methyl (S)-2-[(12-cyclohexyl-3-methoxy-6,7-dihydro-5-oxa-7a-azadibenzo[a,e]azulene-9-carbonyl)amino]-4-(4-hydroxyphenyl)butyrate (Example 2-366)
N-[1-(5-dimethylamino-1H-benzimidazol-2-yl)-1-methylethyl]-12-cyclohexyl-3-methoxy-6,7-dihydro-5-oxa-7a-azadibenzo[a,e]azulene-9-carboxamide (Example 2-367)
N-[2-(4-hydroxypiperidin-1-yl)-1-methoxymethyl-2-oxoethyl]-12-cyclohexyl-3-methoxy-6,7-dihydro-5-oxa-7a-azadibenzo[a,e]azulene-9-carboxamide (Example 2-368)
N—[(S)-2-(4-benzyloxyphenyl)-1-(thiazol-2-yl)ethyl]-12-cyclohexyl-3-methoxy-6,7-dihydro-5-oxa-7a-azadibenzo[a,e]azulene-9-carboxamide (Example 2-369)

N-{1-methyl-1-[5-(3-methyl-1,2,4-oxadiazol-5-yl)-1H-benzimidazol-2-yl]ethyl}-12-cyclohexyl-3-methoxy-6,7-dihydro-5-oxa-7a-azadibenzo[a,e]azulene-9-carboxamide (Example 2-370)

tert-butyl (S)-4-carbamoyl-2-[(12-cyclohexyl-3-methoxy-6,7-dihydro-5-oxa-7a-azadibenzo[a,e]azulene-9-carbonyl)amino]butyrate (Example 2-371)

(S)-4-carbamoyl-2-[(12-cyclohexyl-3-methoxy-6,7-dihydro-5-oxa-7a-azadibenzo[a,e]azulene-9-carbonyl)amino]butyric acid (Example 2-372)

methyl (S)-2-[(12-cyclohexyl-3-methoxy-6,7-dihydro-5-oxa-7a-azadibenzo[a,e]azulene-9-carbonyl)amino]-3-(4-hydroxyphenyl) propionate (Example 2-373)

methyl 2-[(12-cyclohexyl-3-methoxy-6,7-dihydro-5-oxa-7a-azadibenzo[a,e]azulene-9-carbonyl)amino]-3-(4-trifluoromethylphenyl)propionate (Example 2-374)

(S)-2-[(12-cyclohexyl-3-methoxy-6,7-dihydro-5-oxa-7a-azadibenzo[a,e]azulene-9-carbonyl)amino]-3-(4-hydroxyphenyl)propionic acid (Example 2-375)

(S)-2-[(12-cyclohexyl-3-methoxy-6,7-dihydro-5-oxa-7a-azadibenzo[a,e]azulene-9-carbonyl)amino]-4-(4-hydroxyphenyl)butyric acid (Example 2-376)

methyl (S)-3-(4-tert-butoxycarbonylmethoxyphenyl)-2-[(12-cyclohexyl-3-methoxy-6,7-dihydro-5-oxa-7a-azadibenzo[a,e]azulene-9-carbonyl)amino]propionate (Example 2-377)

methyl (S)-3-(4-carboxymethoxyphenyl)-2-[(12-cyclohexyl-3-methoxy-6,7-dihydro-5-oxa-7a-azadibenzo[a,e]azulene-9-carbonyl)amino]propionate (Example 2-378)

methyl 2-[(12-cyclohexyl-3-methoxy-6,7-dihydro-5-oxa-7a-azadibenzo[a,e]azulene-9-carbonyl)amino]-3-(4-hydroxypiperidin-1-yl)propionate monohydrochloride (Example 2-379)

N-[1-(5-fluoro-1H-benzimidazol-2-yl)-1-methylethyl]-12-cyclohexyl-3-methoxy-6,7-dihydro-5-oxa-7a-azadibenzo[a,e]azulene-9-carboxamide (Example 2-380)

N—[(S)-2-(4-hydroxyphenyl)-1-(thiazol-2-yl)ethyl]-12-cyclohexyl-3-methoxy-6,7-dihydro-5-oxa-7a-azadibenzo[a,e]azulene-9-carboxamide (Example 2-381)

methyl (S)-2-[(12-cyclohexyl-3-methoxy-6,7-dihydro-5-oxa-7a-azadibenzo[a,e]azulene-9-carbonyl)amino]-3-[4-(methylcarbamoylmethoxy)phenyl]propionate (Example 2-382)

methyl (S)-2-[(12-cyclohexyl-3-methoxy-6,7-dihydro-5-oxa-7a-azadibenzo[a,e]azulene-9-carbonyl)amino]-3-[4-(dimethylcarbamoylmethoxy)phenyl]propionate (Example 2-383)

methyl (4-{(S)-2-[(12-cyclohexyl-3-methoxy-6,7-dihydro-5-oxa-7a-azadibenzo[a,e]azulene-9-carbonyl)amino]-2-(methylcarbamoyl)ethyl}phenyl)carbamate (Example 2-384)

[(S)-2-(5-hydroxy-1H-indol-3-yl)-1-(2-methylthiazol-4-yl)ethyl]-12-cyclohexyl-3-methoxy-6,7-dihydro-5-oxa-7a-azadibenzo[a,e]azulene-9-carboxamide (Example 2-385)

N-{1-[5-(4-hydroxypiperidine-1-carbonyl)-1H-benzimidazol-2-yl]-1-methylethyl}-12-cyclohexyl-3-methoxy-6,7-dihydro-5-oxa-7a-azadibenzo[a,e]azulene-9-carboxamide (Example 2-386)

N—[(S)-1-(2-hydroxyethylcarbamoyl)-2-(4-hydroxyphenyl)ethyl]-12-cyclohexyl-3-methoxy-6,7-dihydro-5-oxa-7a-azadibenzo[a,e]azulene-9-carboxamide (Example 2-387)

N—[(S)-2-(4-hydroxyphenyl)-1-(3-methyl-1,2,4-oxadiazol-5-yl)ethyl]-12-cyclohexyl-3-methoxy-6,7-dihydro-5-oxa-7a-azadibenzo[a,e]azulene-9-carboxamide (Example 2-388)

N—[(S)-1-(2-dimethylaminoethylcarbamoyl)-2-(4-hydroxyphenyl)ethyl]-12-cyclohexyl-3-methoxy-6,7-dihydro-5-oxa-7a-azadibenzo[a,e]azulene-9-carboxamide (Example 2-389)

N-{1-[5-(2-hydroxyethylcarbamyl)-1H-benzimidazol-2-yl]-1-methylethyl}-12-cyclohexyl-3-methoxy-6,7-dihydro-5-oxa-7a-azadibenzo[a,e]azulene-9-carboxamide (Example 2-390)

methyl (S)-2-[(12-cyclohexyl-3-methoxy-6,7-dihydro-5-oxa-7a-azadibenzo[a,e]azulene-9-carbonyl)amino]-3-[4-(3,3-dimethylureido) phenyl]propionate (Example 2-391)

methyl (S)-2-[(12-cyclohexyl-3-methoxy-6,7-dihydro-5-oxa-7a-azadibenzo[a,e]azulene-9-carbonyl)amino]-3-[4-(3-hydroxypropoxy)phenyl]propionate (Example 2-392)

methyl 2-[(12-cyclohexyl-3-methoxy-6,7-dihydro-5-oxa-7a-azadibenzo[a,e]azulene-9-carbonyl)amino]-3-(4-hydroxymethylphenyl)propionate (Example 2-393)

N-{1-(3H-imidazo[4,5-b]pyridin-2-yl)-1-methylethyl}-12-cyclohexyl-3-methoxy-6,7-dihydro-5-oxa-7a-azadibenzo[a,e]azulene-9-carboxamide (Example 2-394)

2-{1-[(12-cyclohexyl-3-methoxy-6,7-dihydro-5-oxa-7a-azadibenzo[a,e]azulene-9-carbonyl)amino]-1-methylethyl}-1-[2-(morpholin-4-yl)ethyl]-1H-benzimidazole-5-carboxylic acid (Example 2-395)

N-[1-methyl-1-(5-methylcarbamoyl-1H-benzimidazol-2-yl)ethyl]-12-cyclohexyl-3-methoxy-6,7-dihydro-5-oxa-7a-azadibenzo[a,e]azulene-9-carboxamide (Example 2-396)

4-({4-[(12-cyclohexyl-3-methoxy-6,7-dihydro-5-oxa-7a-azadibenzo[a,e]azulene-9-carbonyl)amino]-1-methylpiperidine-4-carbonyl}amino)benzoic acid (Example 2-397)

ethyl 4-(2-{1-[(12-cyclohexyl-3-methoxy-6,7-dihydro-5-oxa-7a-azadibenzo[a,e]azulene-9-carbonyl)amino]-1-methylethyl}-3H-imidazol-4-yl)benzoate (Example 2-398)

4-(2-{1-[(12-cyclohexyl-3-methoxy-6,7-dihydro-5-oxa-7a-azadibenzo[a,e]azulene-9-carbonyl)amino]-1-methylethyl}-3H-imidazol-4-yl)benzoic acid (Example 2-399)

4-[(12-cyclohexyl-3-methoxy-6,7-dihydro-5-oxa-7a-azadibenzo[a,e]azulene-9-carbonyl)amino]tetrahydropyran-4-carboxylic acid (Example 2-400)

(E)-3-[4-({4-[(12-cyclohexyl-3-methoxy-6,7-dihydro-5-oxa-7a-azadibenzo[a,e]azulene-9-carbonyl)amino]tetrahydropyran-4-carbonyl}amino)phenyl]acrylic acid (Example 2-401)

4-({4-[(12-cyclohexyl-3-methoxy-6,7-dihydro-5-oxa-7a-azadibenzo[a,e]azulene-9-carbonyl)amino]tetrahydropyran-4-carbonyl}amino)benzoic acid (Example 2-402)

2-{1-[(12-cyclohexyl-3-methoxy-6,7-dihydro-5-oxa-7a-azadibenzo[a,e]azulene-9-carbonyl)amino]-1-methylethyl}-4-oxo-3,4-dihydroquinazoline-7-carboxylic acid (Example 2-403)

2-{1-[(12-cyclohexyl-3-methoxy-6,7-dihydro-5-oxa-7a-azadibenzo[a,e]azulene-9-carbonyl)amino]-1-methylethyl}-4-dimethylaminoquinazoline-7-carboxylic acid (Example 2-404)

N-[1-(5-hydroxymethyl-1H-benzimidazol-2-yl)-1-methylethyl]-12-cyclohexyl-3-methoxy-6,7-dihydro-5-oxa-7a-azadibenzo[a,e]azulene-9-carboxamide (Example 2-405)

2-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]-2-methylpropionic acid (Example 2-406)

methyl {4-[(S)-2-[(12-cyclohexyl-3-methoxy-6,7-dihydro-5-oxa-7a-azadibenzo[a,e]azulene-9-carbonyl)amino]-2-(3-methyl-1,2,4-oxadiazol-5-yl)ethyl]phenyl}carbamate (Example 2-407)

N-[1-(1H-benzimidazol-2-yl)-1-methylethyl]-12-cyclohexyl-3-methoxy-6,7-dihydro-5-oxa-7a-azadibenzo[a,e]azulene-9-carboxamide (Example 2-408)

2-{4-[(12-cyclohexyl-3-methoxy-6,7-dihydro-5-oxa-7a-azadibenzo[a,e]azulene-9-carbonyl)amino]tetrahydropyran-4-yl}-3H-benzimidazole-5-carboxylic acid (Example 2-409)

benzyl {4-[(S)-2-[(12-cyclohexyl-3-methoxy-6,7-dihydro-5-oxa-7a-azadibenzo[a,e]azulene-9-carbonyl)amino]-2-(2-methylthiazol-4-yl)ethyl]phenyl}carbamate (Example 2-410)

(E)-3-(2-{1-[(12-cyclohexyl-3-methoxy-6,7-dihydro-5-oxa-7a-azadibenzo[a,e]azulene-9-carbonyl)amino]-1-methylethyl}-1H-benzimidazol-5-yl)acrylic acid (Example 2-411)

3-(2-{1-[(12-cyclohexyl-3-methoxy-6,7-dihydro-5-oxa-7a-azadibenzo[a,e]azulene-9-carbonyl)amino]-1-methylethyl}-1H-benzimidazol-5-yl)propionic acid (Example 2-412)

N-[1-(5-hydroxymethyl-6-methoxy-1H-benzimidazol-2-yl)cyclobutyl]-12-cyclohexyl-3-methoxy-6,7-dihydro-5-oxa-7a-azadibenzo[a,e]azulene-9-carboxamide (Example 2-413)

N—[(S)-2-(4-aminophenyl)-1-(2-methylthiazol-4-yl)ethyl]-12-cyclohexyl-3-methoxy-6,7-dihydro-5-oxa-7a-azadibenzo[a,e]azulene-9-carboxamide (Example 2-414)

methyl {4-[(S)-2-[(12-cyclohexyl-3-methoxy-6,7-dihydro-5-oxa-7a-azadibenzo[a,e]azulene-9-carbonyl)amino]-2-(2-methylthiazol-4-yl)ethyl]phenyl}carbamate (Example 2-415)

2-[(S)-2-[(12-cyclohexyl-3-methoxy-6,7-dihydro-5-oxa-7a-azadibenzo[a,e]azulene-9-carbonyl)amino]-3-(4-hydroxyphenyl)propionylamino]-2-methylpropionic acid (Example 2-416)

methyl {3-[(S)-2-[(12-cyclohexyl-3-methoxy-6,7-dihydro-5-oxa-7a-azadibenzo[a,e]azulene-9-carbonyl)amino]-2-(2-methylthiazol-4-yl)ethyl]-1H-indol-5-yloxy}acetate (Example 2-417)

N-{1-methyl-1-[6-(4-methylpiperazine-1-carbonyl)-1H-benzimidazol-2-yl]ethyl}-12-cyclohexyl-3-methoxy-6,7-dihydro-5-oxa-7a-azadibenzo[a,e]azulene-9-carboxamide (Example 2-418)

N-{1-methyl-1-[6-(morpholine-4-carbonyl)-1H-benzimidazol-2-yl]ethyl}-12-cyclohexyl-3-methoxy-6,7-dihydro-5-oxa-7a-azadibenzo[a,e]azulene-9-carboxamide (Example 2-419)

N-[1-(6-benzyloxy-1H-benzimidazol-2-yl)cyclobutyl]-12-cyclohexyl-3-methoxy-6,7-dihydro-5-oxa-7a-azadibenzo[a,e]azulene-9-carboxamide (Example 2-420)

N—[(S)-2-[5-(2-hydroxyethoxy)-1H-indol-3-yl]-1-(2-methylthiazol-4-yl)ethyl]-12-cyclohexyl-3-methoxy-6,7-dihydro-5-oxa-7a-azadibenzo[a,e]azulene-9-carboxamide (Example 2-421)

(E)-3-(4-{1-[(12-cyclohexyl-3-methoxy-6,7-dihydro-5-oxa-7a-azadibenzo[a,e]azulene-9-carbonyl)amino]-1-methylethyl}phenyl)acrylic acid (Example 2-422)

3-(4-{1-[(12-cyclohexyl-3-methoxy-6,7-dihydro-5-oxa-7a-azadibenzo[a,e]azulene-9-carbonyl)amino]-1-methylethyl}phenyl)propionic acid (Example 2-423)

methyl (S)-2-[(12-cyclohexyl-3-methoxy-6,7-dihydro-5-oxa-7a-azadibenzo[a,e]azulene-9-carbonyl)amino]-3-[4-(3-methoxypropoxy)phenyl]propionate (Example 2-424)

(S)-2-[(12-cyclohexyl-3-methoxy-6,7-dihydro-5-oxa-7a-azadibenzo[a,e]azulene-9-carbonyl)amino]-3-[4-(3,3-dimethylureido)phenyl]propionic acid (Example 2-425)

N—[(S)-2-(4-hydroxyphenyl)-1-(methoxycarbamoyl)ethyl]-12-cyclohexyl-3-methoxy-6,7-dihydro-5-oxa-7a-azadibenzo[a,e]azulene-9-carboxamide (Example 2-426)

N—[(S)-2-(4-hydroxyphenyl)-1-(N-methoxy-N-methylcarbamoyl)ethyl]-12-cyclohexyl-3-methoxy-6,7-dihydro-5-oxa-7a-azadibenzo[a,e]azulene-9-carboxamide (Example 2-427)

N—[(S)-2-(4-benzyloxyphenyl)-1-(5-oxo-4,5-dihydro-1,2,4-oxadiazol-3-yl)ethyl]-12-cyclohexyl-3-methoxy-6,7-dihydro-5-oxa-7a-azadibenzo[a,e]azulene-9-carboxamide (Example 2-428)

N—[(S)-2-(4-hydroxyphenyl)-1-(5-oxo-4,5-dihydro-1,2,4-oxadiazol-3-yl)ethyl]-12-cyclohexyl-3-methoxy-6,7-dihydro-5-oxa-7a-azadibenzo[a,e]azulene-9-carboxamide (Example 2-429)

4-[(S)-2-[(12-cyclohexyl-3-methoxy-6,7-dihydro-5-oxa-7a-azadibenzo[a,e]azulene-9-carbonyl)amino]-2-(5-oxo-4,5-dihydro-1,2,4-oxadiazol-3-yl)ethyl]phenyl acetate (Example 2-430)

4-[(S)-2-[(12-cyclohexyl-3-methoxy-6,7-dihydro-5-oxa-7a-azadibenzo[a,e]azulene-9-carbonyl)amino]-2-(4,4-dimethyl-5-oxo-4,5-dihydrooxazol-2-yl)ethyl]phenyl acetate (Example 2-431)

N-(1-methyl-1-{1-[2-(morpholin-4-yl)ethyl]-1H-benzimidazol-2-yl}ethyl)-12-cyclohexyl-3-methoxy-6,7-dihydro-5-oxa-7a-azadibenzo[a,e]azulene-9-carboxamide (Example 2-432)

N-{1-[1-(2-hydroxyethyl)-1H-benzimidazol-2-yl]-1-methylethyl}-12-cyclohexyl-3-methoxy-6,7-dihydro-5-oxa-7a-azadibenzo[a,e]azulene-9-carboxamide (Example 2-433)

N-{1-[1-(2-methoxyethyl)-1H-benzimidazol-2-yl]-1-methylethyl}-12-cyclohexyl-3-methoxy-6,7-dihydro-5-oxa-7a-azadibenzo[a,e]azulene-9-carboxamide (Example 2-434)

ethyl (S)-2-[(12-cyclohexyl-3-methoxy-6,7-dihydro-5-oxa-7a-azadibenzo[a,e]azulene-9-carbonyl)amino]-3-(4-hydroxyphenyl)propionate (Example 2-435)

N-[1-(4-hydroxybenzyl)-2-methylpropyl]-12-cyclohexyl-3-methoxy-6,7-dihydro-5-oxa-7a-azadibenzo[a,e]azulene-9-carboxamide (Example 2-436)

2-{1-[(12-cyclohexyl-3-methoxy-6,7-dihydro-5-oxa-7a-azadibenzo[a,e]azulene-9-carbonyl)amino]cyclobutyl}-6-(2-methoxyethoxy)-1H-benzimidazole-5-carboxylic acid (Example 2-437)

N-{1-[5-hydroxymethyl-6-(2-methoxyethoxy)-1H-benzimidazol-2-yl]cyclobutyl}-12-cyclohexyl-3-methoxy-6,7-dihydro-5-oxa-7a-azadibenzo[a,e]azulene-9-carboxamide (Example 2-438)

N-[1-(6-hydroxy-1H-benzimidazol-2-yl)cyclobutyl]-12-cyclohexyl-3-methoxy-6,7-dihydro-5-oxa-7a-azadibenzo[a,e]azulene-9-carboxamide (Example 2-439)

{3-[(S)-2-[(12-cyclohexyl-3-methoxy-6,7-dihydro-5-oxa-7a-azadibenzo[a,e]azulene-9-carbonyl)amino]-2-(2-methylthiazol-4-yl)ethyl]-1H-indol-5-yloxy}acetic acid (Example 2-440)

N—[(S)-cyano-(4-hydroxybenzyl)-methyl]-12-cyclohexyl-3-methoxy-6,7-dihydro-5-oxa-7a-azadibenzo[a,e]azulene-9-carboxamide (Example 2-441)

methyl 2-amino-3-(4-{1-[(12-cyclohexyl-3-methoxy-6,7-dihydro-5-oxa-7a-azadibenzo[a,e]azulene-9-carbonyl)amino]-1-methylethyl}phenyl)propionate monohydrochloride (Example 2-442)

2-acetylamino-3-(4-{1-[(12-cyclohexyl-3-methoxy-6,7-dihydro-5-oxa-7a-azadibenzo[a,e]azulene-9-carbonyl)amino]-1-methylethyl}phenyl)propionic acid (Example 2-443)

2-amino-3-(4-{1-[(12-cyclohexyl-3-methoxy-6,7-dihydro-5-oxa-7a-azadibenzo[a,e]azulene-9-carbonyl)amino]-1-methylethyl}phenyl)propionic acid (Example 2-444)

2-(2-({1-[(12-cyclohexyl-3-methoxy-6,7-dihydro-5-oxo-7a-azadibenzo[a,e]azulene-9-carbonyl)amino]cyclobutyl}-3H-benzimidazol-5-yl)-2-methylpropionic acid (Example 2-445)

(E)-3-[4-({1-[(12-cyclohexyl-3-ethoxy-6,7-dihydro-5-oxa-7a-azadibenzo[a,e]azulene-9-carbonyl)amino]cyclobutanecarbonyl}amino)phenyl]acrylic acid (Example 2-446)

N-{1-[5-(1-hydroxy-1-methylethyl)-6-methoxy-1H-benzimidazol-2-yl]cyclobutyl}-12-cyclohexyl-3-methoxy-6,7-dihydro-5-oxa-7a-azadibenzo[a,e]azulene-9-carboxamide (Example 2-447)

N-[1-(3H-benzimidazol-5-ylcarbamoyl)cyclobutyl]-12-cyclohexyl-3-methoxy-6,7-dihydro-5-oxa-7a-azadibenzo[a,e]azulene-9-carboxamide (Example 2-448)

2-{4-[(12-cyclohexyl-3-methoxy-6,7-dihydro-5-oxa-7a-azadibenzo[a,e]azulene-9-carbonyl)amino]-1-methylpiperidin-4-yl}-3H-benzimidazole-5-carboxylic acid (Example 2-449)

N—[(S)-1-(4,5-dihydro-1H-imidazol-2-yl)-2-(4-hydroxyphenyl)ethyl]-12-cyclohexyl-3-methoxy-6,7-dihydro-5-oxa-7a-azadibenzo[a,e]azulene-9-carboxamide (Example 2-450)

(E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)-3-methoxyphenyl]acrylic acid (Example 2-451)

tert-butyl (S)-2-[(12-cyclohexyl-3-methoxy-6,7-dihydro-5-oxa-7a-azadibenzo[a,e]azulene-9-carbonyl)amino]-3-(4-hydroxyphenyl)propionate (Example 2-452)

N—[(S)-2-(4-hydroxyphenyl)-1-(2-methyl-5-oxo-2,5-dihydro-1,2,4-oxadiazol-3-yl)ethyl]-12-cyclohexyl-3-methoxy-6,7-dihydro-5-oxa-7a-azadibenzo[a,e]azulene-9-carboxamide (Example 2-453)

N—[(S)-2-(4-hydroxyphenyl)-1-(1-methyl-1H-tetrazol-5-yl)ethyl]-12-cyclohexyl-3-methoxy-6,7-dihydro-5-oxa-7a-azadibenzo[a,e]azulene-9-carboxamide (Example 2-454)

(2-{1-[(12-cyclohexyl-3-methoxy-6,7-dihydro-5-oxa-7a-azadibenzo[a,e]azulene-9-carbonyl)amino]cyclobutyl}-1H-benzimidazol-5-yloxy)acetic acid (Example 2-455)

13-cyclohexyl-5-[2-((S)-3-phenoxymethylpiperidin-1-yl)ethyl]-6,7-dihydro-5H-benzo[5,6][1,4]diazepino[7,1-a]indole-10-carboxylic acid dihydrochloride (Example 1-485)

3-chloro-13-cycloheptyl-5-[2-(piperidin-1-yl)ethyl]-6,7-dihydro-5H-benzo[5,6][1,4]diazepino[7,1-a]indole-10-carboxylic acid (Example 1-486)

5-[2-(7-benzyl-7-azabicyclo[2.2.1]hept-1-yl)ethyl]-13-cyclohexyl-3-methyl-6,7-dihydro-5H-benzo[5,6][1,4]diazepino[7,1-a]indole-10-carboxylic acid (Example 1-487)

5-[2-(7-azabicyclo[2.2.1]hept-1-yl)ethyl]-13-cyclohexyl-3-methyl-6,7-dihydro-5H-benzo[5,6][1,4]diazepino[7,1-a]indole-10-carboxylic acid monohydrochloride (Example 1-488)

5-[2-(7-carboxymethyl-7-azabicyclo[2.2.1]hept-1-yl)ethyl]-13-cyclohexyl-3-methyl-6,7-dihydro-5H-benzo[5,6][1,4]diazepino[7,1-a]indole-10-carboxylic acid (Example 1-489)

3-cyano-13-cyclohexyl-5-[2-(piperidin-1-yl)ethyl]-6,7-dihydro-5H-benzo[5,6][1,4]diazepino[7,1-a]indole-10-carboxylic acid monohydrochloride (Example 1-490)

3-carbamoyl-13-cyclohexyl-5-[2-(piperidin-1-yl)ethyl]-6,7-dihydro-5H-benzo[5,6][1,4]diazepino[7,1-a]indole-10-carboxylic acid monohydrochloride (Example 1-491)

13-cyclohexyl-5-(2-cyclohexylethyl)-3-methyl-6,7-dihydro-5H-benzo[5,6][1,4]diazepino[7,1-a]indole-10-carboxylic acid (Example 1-492)

13-cyclohexyl-5-(4-diethylaminobutyl)-3-methyl-6,7-dihydro-5H-benzo[5,6][1,4]diazepino[7,1-a]indole-10-carboxylic acid dihydrochloride (Example 1-493)

13-cyclohexyl-5-{2-[(S)-3-(2-hydroxyethyl)piperidin-1-yl]ethyl}-3-methyl-6,7-dihydro-5H-benzo[5,6][1,4]diazepino[7,1-a]indole-10-carboxylic acid dihydrochloride (Example 1-494)

13-cyclohexyl-5-[2-(piperidin-1-yl)ethyl]-6,7-dihydro-5H-benzo[5,6][1,4]diazepino[7,1-a]indole-3,10-dicarboxylic acid monohydrochloride (Example 1-495)

13-cyclohexyl-5-methyl-3-[3-(piperidin-1-yl)propoxy]-6,7-dihydro-5H-benzo[5,6][1,4]diazepino[7,1-a]indole-10-carboxylic acid dihydrochloride (Example 1-496)

13-cyclohexyl-5-[2-((R)-3-phenoxymethylpiperidin-1-yl)ethyl]-6,7-dihydro-5H-benzo[5,6][1,4]diazepino[7,1-a]indole-10-carboxylic acid dihydrochloride (Example 1-497)

5-[2-(azocan-1-yl)ethyl]-13-cyclohexyl-3-ethoxy-6,7-dihydro-5H-benzo[5,6][1,4]diazepino[7,1-a]indole-10-carboxylic acid monohydrochloride 13-cyclohexyl-3-ethoxy-5-[2-((R)-3-methoxymethylpiperidin-1-yl)ethyl]-6,7-dihydro-5H-benzo[5,6][1,4]diazepino[7,1-a]indole-10-carboxylic acid (Example 1-499)

13-cyclohexyl-3-ethoxy-5-[2-(1,4-oxazepan-4-yl)ethyl]-6,7-dihydro-5H-benzo[5,6][1,4]diazepino[7,1-a]indole-10-carboxylic acid dihydrochloride (Example 1-500)

13-cyclohexyl-3-ethoxy-5-{2-[4-(2-methoxyethyl)piperidin-1-yl]ethyl}-6,7-dihydro-5H-benzo[5,6][1,4]diazepino[7,1-a]indole-10-carboxylic acid dihydrochloride (Example 1-501)

13-cyclohexyl-5-{2-[4-(2-methoxyethyl)piperidin-1-yl]ethyl}-3-methyl-6,7-dihydro-5H-benzo[5,6][1,4]diazepino[7,1-a]indole-10-carboxylic acid dihydrochloride (Example 1-502)

3-chloro-13-cyclohexyl-5-(3-diethylamino-2-hydroxypropyl)-6,7-dihydro-5H-benzo[5,6][1,4]diazepino[7,1-a]indole-10-carboxylic acid dihydrochloride (Example 1-503)

5-[2-(4-acetyl-1,4-diazepan-1-yl)ethyl]-13-cyclohexyl-3-methyl-6,7-dihydro-5H-benzo[5,6][1,4]diazepino[7,1-a]indole-10-carboxylic acid (Example 1-504)

N-tert-butyl-13-cyclohexyl-3-methyl-6,7-dihydro-5H-benzo[5,6][1,4]diazepino[7,1-a]indole-10-sulfonamide (Example 1-505)

13-cyclohexyl-3-methyl-6,7-dihydro-5H-benzo[5,6][1,4]diazepino[7,1-a]indole-10-sulfonamide (Example 1-506)

13-cyclohexyl-3-methyl-5-[2-(piperidin-1-yl)ethyl]-6,7-dihydro-5H-benzo[5,6][1,4]diazepino[7,1-a]indole-10-sulfonamide dihydrochloride (Example 1-507)

13-cyclohexyl-3-methoxy-5-[2-((R)-3-methoxymethylpiperidin-1-yl)ethyl]-6,7-dihydro-5H-benzo[5,6][1,4]diazepino[7,1-a]indole-10-carboxylic acid dihydrochloride (Example 1-508)

13-cyclohexyl-3-fluoro-5-[2-((R)-3-methoxymethylpiperidin-1-yl)ethyl]-6,7-dihydro-5H-benzo[5,6][1,4]diazepino[7,1-a]indole-10-carboxylic acid dihydrochloride (Example 1-509)

13-cyclohexyl-3-methoxy-5-[2-(1,4-oxazepan-4-yl)ethyl]-6,7-dihydro-5H-benzo[5,6][1,4]diazepino[7,1-a]indole-10-carboxylic acid dihydrochloride (Example 1-510)

13-cyclohexyl-5-{3-[N-ethyl-N-(2-methoxyethyl)amino]propyl}-3-methyl-6,7-dihydro-5H-benzo[5,6][1,4]diazepino[7,1-a]indole-10-carboxylic acid dihydrochloride (Example 1-511)

13-cyclohexyl-5-{3-[N-ethyl-N-(2-hydroxyethyl)amino]propyl}-3-methyl-6,7-dihydro-5H-benzo[5,6][1,4]diazepino[7,1-a]indole-10-carboxylic acid dihydrochloride (Example 1-512)

13-cyclohexyl-5-{3-[N-ethyl-N-(3-methoxypropyl)amino]propyl}-3-methyl-6,7-dihydro-5H-benzo[5,6][1,4]diazepino[7,1-a]indole-10-carboxylic acid dihydrochloride (Example 1-513)

13-cyclohexyl-5-{2-[(S)-3-(2-ethoxyethyl)piperidin-1-yl]ethyl}-3-methyl-6,7-dihydro-5H-benzo[5,6][1,4]diazepino[7,1-a]indole-10-carboxylic acid dihydrochloride (Example 1-514).

13-cyclohexyl-3-ethoxy-5-{2-[(S)-3-(2-ethoxyethyl)piperidin-1-yl]ethyl}-6,7-dihydro-5H-benzo[5,6][1,4]diazepino[7,1-a]indole-10-carboxylic acid dihydrochloride (Example 1-515)

N-tert-butyl-13-cyclohexyl-3,5-dimethyl-6,7-dihydro-5H-benzo[5,6][1,4]diazepino[7,1-a]indole-10-sulfonamide (Example 1-516)

13-cyclohexyl-3,5-dimethyl-6,7-dihydro-5H-benzo[5,6][1,4]diazepino[7,1-a]indole-10-sulfonamide (Example 1-517)

13-cyclohexyl-5-[2-(4-methoxycarbonyl-1,4-diazepan-1-yl)ethyl]-3-methyl-6,7-dihydro-5H-benzo[5,6][1,4]diazepino[7,1-a]indole-10-carboxylic acid dihydrochloride (Example 1-518)

13-cyclohexyl-5-[2-(5-oxo-1,4-diazepan-1-yl)ethyl]-6,7-dihydro-5H-benzo[5,6][1,4]diazepino[7,1-a]indole-10-carboxylic acid dihydrochloride (Example 1-519)

N-acetyl-13-cyclohexyl-3-methyl-5-[2-(piperidin-1-yl)ethyl]-6,7-dihydro-5H-benzo[5,6][1,4]diazepino[7,1-a]indole-10-sulfonamide dihydrochloride (Example 1-520)

13-cyclohexyl-5-(3-diisopropylaminopropyl)-3-methyl-6,7-dihydro-5H-benzo[5,6][1,4]diazepino[7,1-a]indole-10-carboxylic acid dihydrochloride (Example 1-521)

13-cyclohexyl-5-[2-(piperidin-1-yl)ethyl]-3-trifluoromethoxy-6,7-dihydro-5H-benzo[5,6][1,4]diazepino[7,1-a]indole-10-carboxylic acid dihydrochloride (Example 1-522)

13-cyclohexyl-5-{2-[(S)-3-(2-methoxyethyl)piperidin-1-yl]ethyl}-3-trifluoromethoxy-6,7-dihydro-5H-benzo[5,6][1,4]diazepino[7,1-a]indole-10-carboxylic acid dihydrochloride (Example 1-523)

13-cyclohexyl-5-[3-(N-ethyl-N-isopropylamino)propyl]-3-methyl-6,7-dihydro-5H-benzo[5,6][1,4]diazepino[7,1-a]indole-10-carboxylic acid dihydrochloride (Example 1-524)

13-cyclohexyl-5-[2-(4-methoxyazepan-1-yl)ethyl]-3-methyl-6,7-dihydro-5H-benzo[5,6][1,4]diazepino[7,1-a]indole-10-carboxylic acid dihydrochloride (Example 1-525)

13-cyclohexyl-3-methyl-5-[2-(4-methyl-5-oxo-1,4-diazepan-1-yl)ethyl]-6,7-dihydro-5H-benzo[5,6][1,4]diazepino[7,1-a]indole-10-carboxylic acid dihydrochloride (Example 1-526)

13-cyclohexyl-5-{2-[(S)-3-(dimethylcarbamoylmethyl)piperidin-1-yl]ethyl}-3-methyl-6,7-dihydro-5H-benzo[5,6][1,4]diazepino[7,1-a]indole-10-carboxylic acid dihydrochloride (Example 1-527)

13-cyclohexyl-5-{2-[(R)-3-(2-methoxyethoxymethyl)piperidin-1-yl]ethyl}-3-methyl-6,7-dihydro-5H-benzo[5,6][1,4]diazepino[7,1-a]indole-10-carboxylic acid dihydrochloride (Example 1-528)

13-cyclohexyl-5-{2-[(S)-3-(2-hydroxy-2-methylpropyl)piperidin-1-yl]ethyl}-3-methyl-6,7-dihydro-5H-benzo[5,6][1,4]diazepino[7,1-a]indole-10-carboxylic acid dihydrochloride (Example 1-529)

13-cyclohexyl-2,3-difluoro-5-[2-((R)-3-methoxymethylpiperidin-1-yl)ethyl]-6,7-dihydro-5H-benzo[5,6][1,4]diazepino[7,1-a]indole-10-carboxylic acid dihydrochloride (Example 1-530)

13-cyclohexyl-5-{2-[N-ethyl-N-(3-methoxypropyl)amino]ethyl}-3-methyl-6,7-dihydro-5H-benzo[5,6][1,4]diazepino[7,1-a]indole-10-carboxylic acid dihydrochloride (Example 1-531)

13-cyclohexyl-3-methyl-5-[2-(6-methyl-1,4-oxazepan-4-yl)ethyl]-6,7-dihydro-5H-benzo[5,6][1,4]diazepino[7,1-a]indole-10-carboxylic acid dihydrochloride (Example 1-532)

13-cyclohexyl-5-{2-[(R)-3-(1-hydroxy-1-methylethyl)piperidin-1-yl]ethyl}-3-methyl-6,7-dihydro-5H-benzo[5,6][1,4]diazepino[7,1-a]indole-10-carboxylic acid dihydrochloride (Example 1-533)

3-chloro-13-cyclohexyl-5-{2-[1-(2-methoxyethyl)piperidin-3-yl]ethyl}-6,7-dihydro-5H-benzo[5,6][1,4]diazepino[7,1-a]indole-10-carboxylic acid dihydrochloride (Example 1-534)

13-cyclohexyl-5-(2-dimethylaminoethyl)-3-(3,5-dimethylisoxazol-4-ylmethoxy)-6,7-dihydro-5H-benzo[5,6][1,4]diazepino[7,1-a]indole-10-carboxylic acid dihydrochloride (Example 1-535)

13-cyclohexyl-3-methyl-5-[2-(4-oxoazepan-1-yl)ethyl]-6,7-dihydro-5H-benzo[5,6][1,4]diazepino[7,1-a]indole-10-carboxylic acid dihydrochloride (Example 1-536)

13-cyclohexyl-5-{2-[(S)-3-(2-dimethylcarbamoylethyl)piperidin-1-yl]ethyl}-3-methyl-6,7-dihydro-5H-benzo[5,6][1,4]diazepino[7,1-a]indole-10-carboxylic acid dihydrochloride (Example 1-537)

13-cyclohexyl-5-[2-(4-hydroxyazepan-1-yl)ethyl]-3-methyl-6,7-dihydro-5H-benzo[5,6][1,4]diazepino[7,1-a]indole-10-carboxylic acid dihydrochloride (Example 1-538)

13-cyclohexyl-5-{2-[N-ethyl-N-(4-methoxybutyl)amino]ethyl}-3-methyl-6,7-dihydro-5H-benzo[5,6][1,4]diazepino[7,1-a]indole-10-carboxylic acid dihydrochloride (Example 1-539)

13-cyclohexyl-5-{2-[(S)-3-(3-methoxypropyl)piperidin-1-yl]ethyl}-3-methyl-6,7-dihydro-5H-benzo[5,6][1,4]diazepino[7,1-a]indole-10-carboxylic acid dihydrochloride (Example 1-540)

13-cyclohexyl-5-{2-[(R)-3-(1-methoxy-1-methylethyl)piperidin-1-yl]ethyl}-3-methyl-6,7-dihydro-5H-benzo[5,6][1,4]diazepino[7,1-a]indole-10-carboxylic acid dihydrochloride (Example 1-541)

13-cyclohexyl-5-{2-[2-(2-methoxyethyl)piperidin-1-yl]ethyl}-3-methyl-6,7-dihydro-5H-benzo[5,6][1,4]diazepino[7,1-a]indole-10-carboxylic acid dihydrochloride (Example 1-542)

13-cyclohexyl-5-(2-dimethylaminoethyl)-3-(pyridin-2-ylmethoxy)-6,7-dihydro-5H-benzo[5,6][1,4]diazepino[7,1-a]indole-10-carboxylic acid trihydrochloride (Example 1-543)

13-cyclohexyl-2,3-difluoro-5-{2-[(S)-3-(2-methoxyethyl)piperidin-1-yl]ethyl}-6,7-dihydro-5H-benzo[5,6][1,4]diazepino[7,1-a]indole-10-carboxylic acid dihydrochloride (Example 1-544)

13-cyclohexyl-5-[2-(3-dimethylcarbamoylpiperidin-1-yl)ethyl]-3-methyl-6,7-dihydro-5H-benzo[5,6][1,4]diazepino[7,1-a]indole-10-carboxylic acid dihydrochloride (Example 1-545)

13-cyclohexyl-3-(2-methoxyethoxy)-5-[2-(piperidin-1-yl)ethyl]-6,7-dihydro-5H-benzo[5,6][1,4]diazepino[7,1-a]indole-10-carboxylic acid dihydrochloride (Example 1-546)

13-cyclohexyl-5-{2-[(R)-3-(2-methoxyethoxy)piperidin-1-yl]ethyl}-3-methyl-6,7-dihydro-5H-benzo[5,6][1,4]diazepino[7,1-a]indole-10-carboxylic acid dihydrochloride (Example 1-547)

13-cyclohexyl-5-(2-dimethylaminoethyl)-3-(2-phenoxyethoxy)-6,7-dihydro-5H-benzo[5,6][1,4]diazepino[7,1-a]indole-10-carboxylic acid dihydrochloride (Example 1-548)

12-cyclohexyl-5-[2-(piperidin-1-yl)ethyl]-6,7-dihydro-5H-4,5,7a-triazadibenzo[a,e]azulene-9-carboxylic acid dihydrochloride (Example 1-549)

13-cyclohexyl-2,3-difluoro-5-[2-(1,4-oxazepan-4-yl)ethyl]-6,7-dihydro-5H-benzo[5,6][1,4]diazepino[7,1-a]indole-10-carboxylic acid dihydrochloride (Example 1-550)

13-cyclohexyl-5-[2-(3-methoxymethylazepan-1-yl)ethyl]-3-methyl-6,7-dihydro-5H-benzo[5,6][1,4]diazepino[7,1-a]indole-10-carboxylic acid dihydrochloride (Example 1-551)

13-cyclohexyl-5-methyl-4-[2-(piperidin-1-yl)ethoxy]-6,7-dihydro-5H-benzo[5,6][1,4]diazepino[7,1-a]indole-10-carboxylic acid dihydrochloride (Example 1-552)

5-(2-{(S)-3-[2-(N-acetyl-N-methylamino)ethyl]piperidin-1-yl}ethyl)-13-cyclohexyl-3-methyl-6,7-dihydro-5H-benzo[5,6][1,4]diazepino[7,1-a]indole-10-carboxylic acid dihydrochloride (Example 1-553)

13-cyclohexyl-3,9-dimethyl-5-[2-(piperidin-1-yl)ethyl]-6,7-dihydro-5H-benzo[5,6][1,4]diazepino[7,1-a]indole-10-carboxylic acid dihydrochloride (Example 1-554)

13-cyclohexyl-5-{2-[(S)-3-(2-dimethylaminoethyl)piperidin-1-yl]ethyl}-3-methyl-6,7-dihydro-5H-benzo[5,6][1,4]diazepino[7,1-a]indole-10-carboxylic acid dihydrochloride (Example 1-555)

5-[2-((S)-3-carboxymethylpiperidin-1-yl)ethyl]-13-cyclohexyl-3-methyl-6,7-dihydro-5H-benzo[5,6][1,4]diazepino[7,1-a]indole-10-carboxylic acid dihydrochloride (Example 1-556)

5-(2-{(S)-3-[2-(N-tert-butoxycarbonyl-N-methylamino)ethyl]piperidin-1-yl}ethyl)-13-cyclohexyl-3-methyl-6,7-dihydro-5H-benzo[5,6][1,4]diazepino[7,1-a]indole-10-carboxylic acid monohydrochloride (Example 1-557)

5-(1-benzyloxycarbonylpiperidin-4-yl)-13-cyclohexyl-3-methyl-6,7-dihydro-5H-benzo[5,6][1,4]diazepino[7,1-a]indole-10-carboxylic acid (Example 1-558)

13-cyclohexyl-3-methyl-5-(2-{(S)-3-[2-(trimethylureido)ethyl]piperidin-1-yl}ethyl)-6,7-dihydro-5H-piperidin-1-yl)ethyl)-6,7-dihydro-5H-benzo[5,6][1,4]diazepino[7,1-a]indole-10-carboxylic acid dihydrochloride (Example 1-559)

3-(5-chlorothiophen-2-ylmethoxy)-13-cyclohexyl-5-(2-dimethylaminoethyl)-6,7-dihydro-5H-benzo[5,6][1,4]diazepino[7,1-a]indole-10-carboxylic acid dihydrochloride (Example 1-560)

13-cyclohexyl-3-methyl-5-[2-(thiomorpholin-4-yl)ethyl]-6,7-dihydro-5H-benzo[5,6][1,4]diazepino[7,1-a]indole-10-carboxylic acid dihydrochloride (Example 1-561)

13-cyclohexyl-3-methyl-5-(piperidin-4-yl)-6,7-dihydro-5H-benzo[5,6][1,4]diazepino[7,1-a]indole-10-carboxylic acid dihydrochloride (Example 1-562)

5-(1-acetylpiperidin-4-yl)-13-cyclohexyl-3-methyl-6,7-dihydro-5H-benzo[5,6][1,4]diazepino[7,1-a]indole-10-carboxylic acid (Example 1-563)

13-cyclohexyl-3-methyl-5-(1-methylpiperidin-4-yl)-6,7-dihydro-5,1-benzo[5,6][1,4]diazepino[7,1-a]indole-10-carboxylic acid dihydrochloride (Example 1-564)

13-cyclohexyl-5-(2-dimethylaminoethyl)-3-(pyridin-4-ylmethoxy)-6,7-dihydro-5H-benzo[5,6][1,4]diazepino[7,1-a]indole-10-carboxylic acid trihydrochloride (Example 1-565)

13-cyclohexyl-3-methyl-5-(2-[(S)-3-[2-(2-oxopyrrolidin-1-yl)ethyl]piperidin-1-yl]ethyl)-6,7-dihydro-5H-benzo[5,6][1,4]diazepino[7,1-a]indole-10-carboxylic acid dihydrochloride (Example 1-566)

13-cyclohexyl-3,5,6-trimethyl-6,7-dihydro-5H-benzo[5,6][1,4]diazepino[7,1-a]indole-10-carboxylic acid (Example 1-567)

13-cyclohexyl-3-methoxy-5-[2-(thiomorpholin-4-yl)ethyl]-6,7-dihydro-5H-benzo[5,6][1,4]diazepino[7,1-a]indole-10-carboxylic acid dihydrochloride (Example 1-568)

13-cyclohexyl-3,5,9-trimethyl-6,7-dihydro-5H-benzo[5,6][1,4]diazepino[7,1-a]indole-10-carboxylic acid (Example 1-569)

13-cyclohexyl-5-{2-[(S)-3-(2-methoxyethyl)piperidin-1-yl]-2-oxoethyl}-3-methyl-6,7-dihydro-5H-benzo[5,6][1,4]diazepino[7,1-a]indole-10-carboxylic acid (Example 1-570)

13-cyclohexyl-5-[2-(4-methanesulfonylpiperazin-1-yl)-2-oxoethyl]-3-methyl-6,7-dihydro-5H-benzo[5,6][1,4]diazepino[7,1-a]indole-10-carboxylic acid (Example 1-571)

13-cyclohexyl-5-[2-(4-methoxypiperidin-1-yl)-2-oxoethyl]-3-methyl-6,7-dihydro-5H-benzo[5,6][1,4]diazepino[7,1-a]indole-10-carboxylic acid (Example 1-572)

N-methyl-13-cyclohexyl-5-[2-(4-methanesulfonylpiperazin-1-yl)-2-oxoethyl]-3-methyl-6,7-dihydro-5H-benzo[5,6][1,4]diazepino[7,1-a]indole-10-carboxamide (Example 1-573)

13-cyclohexyl-3,5-dimethyl-6,7-dihydro-5H-benzo[5,6][1,4]diazepino[7,1-a]indole-10-carboxylic acid (Example 1-574)

13-cyclohexyl-5-(2-dimethylaminoethyl)-3-[2-(2-oxooxazolidin-3-yl)ethoxy]-6,7-dihydro-5H-benzo[5,6][1,4]diazepino[7,1-a]indole-10-carboxylic acid dihydrochloride (Example 1-575)

13-cyclohexyl-5-(2-dimethylaminoethyl)-3-[2-(2-hydroxyethylamino)ethoxy]-6,7-dihydro-5H-benzo[5,6][1,4]diazepino[7,1-a]indole-10-carboxylic acid trihydrochloride (Example 1-576)

13-cyclohexyl-5-(2-dimethylaminoethyl)-3-(3-methoxybenzyloxy)-6,7-dihydro-5H-benzo[5,6][1,4]diazepino[7,1-a]indole-10-carboxylic acid dihydrochloride (Example 1-577)

3-(3-aminobenzoyloxy)-13-cyclohexyl-5-(2-dimethylaminoethyl)-6,7-dihydro-5H-benzo[5,6][1,4]diazepino[7,1-a]indole-10-carboxylic acid trihydrochloride (Example 1-578)

13-cyclohexyl-5-(2-dimethylaminoethyl)-3-(3-nitrobenzyloxy)-6,7-dihydro-5H-benzo[5,6][1,4]diazepino[7,1-a]indole-10-carboxylic acid dihydrochloride (Example 1-579)

3-chloro-13-cyclohexyl-5-[2-(1-methoxycarbonylpiperidin-4-yl)ethyl]-6,7-dihydro-5H-benzo[5,6][1,4]diazepino[7,1-a]indole-10-carboxylic acid (Example 1-580)

13-cyclohexyl-5-[2-(4-fluorophenyl)ethyl]-3-methyl-6,7-dihydro-5H-benzo[5,6][1,4]diazepino[7,1-a]indole-10-carboxylic acid (Example 1-581)

3-(3-acetylaminobenzyloxy)-13-cyclohexyl-5-(2-dimethylaminoethyl)-6,7-dihydro-5H-benzo[5,6][1,4]diazepino[7,1-a]indole-10-carboxylic acid dihydrochloride (Example 1-582)

methyl 3-(3-carboxybenzyloxy)-13-cyclohexyl-5-(2-dimethylaminoethyl)-6,7-dihydro-5H-benzo[5,6][1,4]diazepino[7,1-a]indole-10-carboxylate dihydrochloride (Example 1-583)

13-cyclohexyl-5-(2-dimethylaminoethyl)-3-[3-(piperidin-1-yl)propoxy]-6,7-dihydro-5H-benzo[5,6][1,4]diazepino[7,1-a]indole-10-carboxylic acid trihydrochloride (Example 1-584)

13-cyclohexyl-5-(2-dimethylaminoethyl)-3-[3-(2-oxopyrrolidin-1-yl)benzyloxy]-6,7-dihydro-5H-benzo[5,6][1,4]diazepino[7,1-a]indole-10-carboxylic acid trihydrochloride (Example 1-585)

3-(3-carboxybenzyloxy)-13-cyclohexyl-5-(2-dimethylaminoethyl)-6,7-dihydro-5H-benzo[5,6][1,4]diazepino[7,1-a]indole-10-carboxylic acid dihydrochloride (Example 1-586)

13-cyclohexyl-5-(2-dimethylaminoethyl)-3-(3-dimethylcarbamoylbenzyloxy)-6,7-dihydro-5H-benzo[5,6][1,4]diazepino[7,1-a]indole-10-carboxylic acid dihydrochloride (Example 1-587)

13-cyclohexyl-3-methyl-5-[2-(4-methylthiazol-2-yl)ethyl]-6,7-dihydro-5H-benzo[5,6][1,4]diazepino[7,1-a]indole-10-carboxylic acid (Example 1-588)

13-cyclohexyl-5-(2-dimethylaminoethyl)-3-(6-methylpyridin-2-ylmethoxy)-6,7-dihydro-5H-benzo[5,6][1,4]diazepino[7,1-a]indole-10-carboxylic acid trihydrochloride (Example 1-589)

13-cyclohexyl-5-(2-dimethylaminoethyl)-3-(3-methylcarbamoylbenzyloxy)-6,7-dihydro-5H-benzo[5,6][1,4]diazepino[7,1-a]indole-10-carboxylic acid dihydrochloride (Example 1-590)

13-cyclohexyl-3-(3-dimethylaminobenzyloxy)-5-(2-dimethylaminoethyl)-6,7-dihydro-5H-benzo[5,6][1,4]diazepino[7,1-a]indole-10-carboxylic acid trihydrochloride (Example 1-591)

13-cyclohexyl-3-ethoxy-5-methyl-6,7-dihydro-5H-benzo[5,6][1,4]diazepino[7,1-a]indole-10-carboxylic acid (Example 1-592)

3-benzyloxy-13-cyclohexyl-5-methyl-6,7-dihydro-5H-benzo[5,6][1,4]diazepino[7,1-a]indole-10-carboxylic acid (Example 1-593)

13-cyclohexyl-3-methoxy-5-methyl-6,7-dihydro-5H-benzo[5,6][1,4]diazepino[7,1-a]indole-10-carboxylic acid (Example 1-594)

13-cyclohexyl-5-[2-(piperidin-1-yl)ethyl]-3-(pyridin-2-ylmethoxy)-6,7-dihydro-5H-benzo[5,6][1,4]diazepino[7,1-a]indole-10-carboxylic acid trihydrochloride (Example 1-595)

methyl 5-[2-(1-tert-butoxycarbonylpiperidin-4-yl)ethyl]-13-cyclohexyl-6,7-dihydro-5H-benzo[5,6][1,4]diazepino[7,1-a]indole-10-carboxylate (Example 1-601)

methyl 13-cyclohexyl-5-{2-(piperidin-4-yl)ethyl}-6,7-dihydro-5H-benzo[5,6][1,4]diazepino[7,1-a]indole-10-carboxylate (Example 1-602)

methyl 13-cyclohexyl-5-[2-(1-cyclopentylpiperidin-4-yl)ethyl]-6,7-dihydro-5H-benzo[5,6][1,4]diazepino[7,1-a]indole-10-carboxylate (Example 1-603)

N-tert-butyl-13-cyclohexyl-3-methyl-6-oxo-6,7-dihydro-5H-benzo[5,6][1,4]diazepino[7,1-a]indole-10-sulfonamide (Example 1-604)

N-tert-butyl-13-cyclohexyl-3-methyl-6-oxo-5-[2-oxo-2-(piperidin-1-yl)ethyl]-6,7-dihydro-5H-benzo[5,6][1,4]diazepino[7,1-a]indole-10-sulfonamide (Example 1-605)

N-tert-butyl-13-cyclohexyl-3-methyl-5-[2-(piperidin-1-yl)ethyl]-6,7-dihydro-5H-benzo[5,6][1,4]diazepino[7,1-a]indole-10-sulfonamide (Example 1-606)

13-cyclohexyl-3-methyl-5-[2-(piperidin-1-yl)ethyl]-6,7-dihydro-5H-benzo[5,6][1,4]diazepino[7,1-a]indole-10-sulfonamide (Example 1-607)

methyl 13-cyclohexyl-3,6-dimethyl-6,7-dihydro-5H-benzo[5,6][1,4]diazepino[7,1-a]indole-10-carboxylate (Example 1-608)

methyl 13-cyclohexyl-3,5,6-trimethyl-6,7-dihydro-5H-benzo[5,6][1,4]diazepino[7,1-a]indole-10-carboxylate (Example 1-609)

methyl 3-benzyloxy-13-cyclohexyl-6-oxo-6,7-dihydro-5H-benzo[5,6][1,4]diazepino[7,1-a]indole-10-carboxylate (Example 1-610)

methyl 3-benzyloxy-13-cyclohexyl-6-oxo-5-[2-oxo-2-(piperidin-1-yl)ethyl]-6,7-dihydro-5H-benzo[5,6][1,4]diazepino[7,1-a]indole-10-carboxylate (Example 1-611)

methyl 13-cyclohexyl-3-hydroxy-6-oxo-5-[2-oxo-2-(piperidin-1-yl)ethyl]-6,7-dihydro-5H-benzo[5,6][1,4]diazepino[7,1-a]indole-10-carboxylate (Example 1-612)

methyl 13-cyclohexyl-6-oxo-5-[2-oxo-2-(piperidin-1-yl)ethyl]-3-(pyridin-2-ylmethoxy)-6,7-dihydro-5H-benzo[5,6][1,4]diazepino[7,1-a]indole-10-carboxylate (Example 1-613)

methyl 13-cyclohexyl-5-[2-(piperidin-1-yl)ethyl]-3-(pyridin-2-ylmethoxy)-6,7-dihydro-5H-benzo[5,6][1,4]diazepino[7,1-a]indole-10-carboxylate (Example 1-614)

12-cyclohexyl-4-[2-(4-ethylpiperazin-1-yl)ethoxy]-6,7-dihydro-5-oxa-7a-azadibenzo[a,e]azulene-9-carboxylic acid dihydrochloride (Example 2-456)

4-[2-(1-tert-butoxycarbonylpiperidin-4-yl)ethoxy]-12-cyclohexyl-6,7-dihydro-5-oxa-7a-azadibenzo[a,e]azulene-9-carboxylic acid (Example 2-457)

12-cyclohexyl-4-[2-(piperidin-4-yl)ethoxy]-6,7-dihydro-5-oxa-7a-azadibenzo[a,e]azulene-9-carboxylic acid monohydrochloride (Example 2-458)

12-cyclohexyl-4-[2-(1-methylpiperidin-4-yl)ethoxy]-6,7-dihydro-5-oxa-7a-azadibenzo[a,e]azulene-9-carboxylic acid monohydrochloride (Example 2-459)

12-cyclohexyl-4-[3-(piperidin-1-yl)propoxy]-6,7-dihydro-5-oxa-7a-azadibenzo[a,e]azulene-9-carboxylic acid monohydrochloride (Example 2-460)

12-cyclohexyl-4-[2-oxo-2-(piperidin-1-yl)ethyl]-6,7-dihydro-5-oxa-7a-azadibenzo[a,e]azulene-9-carboxylic acid (Example 2-461)

12-cyclohexyl-4-[2-(morpholin-4-yl)ethoxy]-6,7-dihydro-5-oxa-7a-azadibenzo[a,e]azulene-9-carboxylic acid monohydrochloride (Example 2-462)

12-cyclohexyl-4-(2-dimethylaminoethoxy)-6,7-dihydro-5-oxa-7a-azadibenzo[a,e]azulene-9-carboxylic acid monohydrochloride (Example 2-463)

12-cyclohexyl-4-[2-(piperidin-1-yl)ethyl]-6,7-dihydro-5-oxa-7a-azadibenzo[a,e]azulene-9-carboxylic acid monohydrochloride (Example 2-464)

4-[2-(1-tert-butoxycarbonylpiperidin-4-yloxy)ethoxy]-12-cyclohexyl-6,7-dihydro-5-oxa-7a-azadibenzo[a,e]azulene-9-carboxylic acid (Example 2-465)

12-cyclohexyl-4-[2-(piperidin-4-yloxy)ethoxy]-6,7-dihydro-5-oxa-7a-azadibenzo[a,e]azulene-9-carboxylic acid monohydrochloride (Example 2-466)

12-cyclohexyl-4-[2-(1-methylpiperidin-4-yloxy)ethoxy]-6,7-dihydro-5-oxa-7a-azadibenzo[a,e]azulene-9-carboxylic acid monohydrochloride (Example 2-467)

12-cyclohexyl-4-[2-(1-cyclopentylpiperidin-4-yl)ethoxy]-6,7-dihydro-5-oxa-7a-azadibenzo[a,e]azulene-9-carboxylic acid monohydrochloride (Example 2-468)

12-cyclohexyl-4-(1-methylpiperidin-3-yloxy)-6,7-dihydro-5-oxa-7a-azadibenzo[a,e]azulene-9-carboxylic acid monohydrochloride (Example 2-469)

12-cyclohexyl-4-[1-(2-methoxyethyl)piperidin-3-yloxy]-6,7-dihydro-5-oxa-7a-azadibenzo[a,e]azulene-9-carboxylic acid monohydrochloride (Example 2-470)

12-cyclohexyl-4-[2-(morpholin-4-yl)-5-(2-oxopyrrolidin-1-yl)benzyloxy]-6,7-dihydro-5-oxa-7a-azadibenzo[a,e]azulene-9-carboxylic acid monohydrochloride (Example 2-471)

12-cyclohexyl-4-{2-[N-methyl-N-(1-methylpiperidin-4-yl)amino]ethoxy}-6,7-dihydro-5-oxa-7a-azadibenzo[a,e]azulene-9-carboxylic acid trihydrochloride (Example 2-472)

methyl 4-carboxymethoxy-12-cyclohexyl-6,7-dihydro-5-oxa-7a-azadibenzo[a,e]azulene-9-carboxylate (Example 2-473)

12-cyclohexyl-4-{N-methyl-N-[2-(piperidin-1-yl)ethyl]amino}-6,7-dihydro-5-oxa-7a-azadibenzo[a,e]azulene-9-carboxylic acid dihydrochloride (Example 2-474)

12-cyclohexyl-4-methoxy-6,7-dihydro-5-oxa-7a-azadibenzo[a,e]azulene-9-carboxylic acid (Example 2-475)

4-amino-12-cyclohexyl-6,7-dihydro-5-oxa-7a-azadibenzo[a,e]azulene-9-carboxylic acid (Example 2-476)

12-cyclohexyl-4-nitro-6,7-dihydro-5-oxa-7a-azadibenzo[a,e]azulene-9-carboxylic acid (Example 2-477)

12-cyclohexyl-4-[2-(piperidin-1-yl)ethylamino]-6,7-dihydro-5-oxa-7a-azadibenzo[a,e]azulene-9-carboxylic acid dihydrochloride (Example 2-478)

12-cyclohexyl-3-methyl-6,7-dihydro-5-oxa-7a-azadibenzo[a,e]azulene-9-carboxylic acid (Example 2-479)

12-cyclohexyl-4-(N-ethyl-N-[2-(piperidin-1-yl)ethyl]amino)-6,7-dihydro-5-oxa-7a-azadibenzo[a,e]azulene-9-carboxylic acid dihydrochloride (Example 2-480)

12-cyclohexyl-4-{N-[2-(piperidin-1-yl)ethyl]-N-propylamino}-6,7-dihydro-5-oxa-7a-azadibenzo[a,e]azulene-9-carboxylic acid dihydrochloride (Example 2-481)

12-cyclohexyl-4-{N-(2-methoxyethyl)-N-[2-(piperidin-1-yl)ethyl]amino}-6,7-dihydro-5-oxa-7a-azadibenzo[a,e]azulene-9-carboxylic acid dihydrochloride (Example 2-482)

12-cyclohexyl-4-dimethylamino-6,7-dihydro-5-oxa-7a-azadibenzo[a,e]azulene-9-carboxylic acid (Example 2-483)

12-cyclohexyl-1-fluoro-6,7-dihydro-5-oxa-7a-azadibenzo[a,e]azulene-9-carboxylic acid (Example 2-484)

4-{N-acetyl-N-[2-(piperidin-1-yl)ethyl]amino}-12-cyclohexyl-6,7-dihydro-5-oxa-7a-azadibenzo[a,e]azulene-9-carboxylic acid (Example 2-485)

12-cyclohexyl-4-{N-methyl-N-[2-oxo-2-(piperidin-1-yl)ethyl]amino}-6,7-dihydro-5-oxa-7a-azadibenzo[a,e]azulene-9-carboxylic acid (Example 2-486)

methyl 3-(1-tert-butoxycarbonylpiperidin-3-yloxy)-12-cyclohexyl-6,7-dihydro-5-oxa-7a-azadibenzo[a,e]azulene-9-carboxylate (Example 2-501)

methyl 12-cyclohexyl-3-(piperidin-3-yloxy)-6,7-dihydro-5-oxa-7a-azadibenzo[a,e]azulene-9-carboxylate (Example 2-502)

methyl 12-cyclohexyl-3-(1-methanesulfonylpiperidin-3-yloxy)-6,7-dihydro-5-oxa-7a-azadibenzo[a,e]azulene-9-carboxylate (Example 2-503).

methyl 4-benzyloxy-12-cyclohexyl-6,7-dihydro-5-oxa-7a-azadibenzo[a,e]azulene-9-carboxylate (Example 2-504)

methyl 12-cyclohexyl-4-hydroxy-6,7-dihydro-5-oxa-7a-azadibenzo[a,e]azulene-9-carboxylate (Example 2-505)

methyl 12-cyclohexyl-4-[2-oxo-2-(piperidin-1-yl)ethoxy]-6,7-dihydro-5-oxa-7a-azadibenzo[a,e]azulene-9-carboxylate (Example 2-506)

methyl 12-cyclohexyl-4-[2-(piperidin-1-yl)ethoxy]-6,7-dihydro-5-oxa-7a-azadibenzo[a,e]azulene-9-carboxylate (Example 2-507)

ethyl (E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylate (Example 2-508)

methyl 12-cyclohexyl-4-trifluoromethanesulfonyloxy-6,7-dihydro-5-oxa-7a-azadibenzo[a,e]azulene-9-carboxylate (Example 2-509)

methyl 12-cyclohexyl-4-(pyridin-3-yl)-6,7-dihydro-5-oxa-7a-azadibenzo[a,e]azulene-9-carboxylate (Example 2-510)

methyl 2-[(12-cyclohexyl-3-methoxy-6,7-dihydro-5-oxa-7a-azadibenzo[a,e]azulene-9-carbonyl)amino]-2-methylpropionate (Example 2-511)

2-[(12-cyclohexyl-3-methoxy-6,7-dihydro-5-oxa-7a-azadibenzo[a,e]azulene-9-carbonyl)amino]-2-methylpropionic acid (Example 2-512)

methyl 4-amino-3-{2-[(12-cyclohexyl-3-methoxy-6,7-dihydro-5-oxa-7a-azadibenzo[a,e]azulene-9-carbonyl)amino]-2-methylpropionylamino}benzoate (Example 2-513)

methyl 2-{1-[(12-cyclohexyl-3-methoxy-6,7-dihydro-5-oxa-7a-azadibenzo[a,e]azulene-9-carbonyl)amino]-1-methylethyl}-3H-benzimidazole-5-carboxylate (Example 2-514)

methyl 12-cyclohexyl-4-nitro-6,7-dihydro-5-oxa-7a-azadibenzo[a,e]azulene-9-carboxylate (Example 2-515)

methyl 4-amino-12-cyclohexyl-6,7-dihydro-5-oxa-7a-azadibenzo[a,e]azulene-9-carboxylate (Example 2-516)

methyl 4-{bis[2-oxo-2-(piperidin-1-yl)ethyl]amino}-12-cyclohexyl-6,7-dihydro-5-oxa-7a-azadibenzo[a,e]azulene-9-carboxylate (Example 2-517)

methyl 12-cyclohexyl-4-[2-oxo-2-(piperidin-1-yl)ethylamino]-6,7-dihydro-5-oxa-7a-azadibenzo[a,e]azulene-9-carboxylate (Example 2-518)

methyl 4-{bis[2-(piperidin-1-yl)ethyl]amino}-12-cyclohexyl-6,7-dihydro-5-oxa-7a-azadibenzo[a,e]azulene-9-carboxylate (Example 2-519)

4-{bis[2-(piperidin-1-yl)ethyl]amino}-12-cyclohexyl-6,7-dihydro-5-oxa-7a-azadibenzo[a,e]azulene-9-carboxylic acid trihydrochloride (Example 2-520)

methyl 12-cyclohexyl-4-{N-[2-oxo-2-(piperidin-1-yl)ethyl]-N-propylamino}-6,7-dihydro-5-oxa-7a-azadibenzo[a,e]azulene-9-carboxylate (Example 2-521)

methyl 12-cyclohexyl-4-{N-[2-(piperidin-1-yl)ethyl]-N-propylamino-}-6,7-dihydro-5-oxa-7a-azadibenzo[a,e]azulene-9-carboxylate (Example 2-522)

12-cyclohexyl-5,6-dihydroindolo[2,1-a]isoquinoline-9-carboxylic acid (Example 5-4)

methyl 12-cyclohexyl-5,6-dihydroindolo[2,1-a]isoquinoline-9-carboxylate (Example 5-5)

11-cyclohexyl-6-hydroxy-6H-isoindolo[2,1-a]indole-3-carboxylic acid (Example 5-6)

11-cyclohexyl-6-methoxy-6H-isoindolo[2,1-a]indole-3-carboxylic acid (Example 5-7)

12-cyclohexyl-3-methoxy-6,7-dihydro-5-oxa-7a,8-diazadibenzo[a,e]azulene-9-carboxylic acid (Example 7-9)

(E)-3-[4-({1-[(12-cyclohexyl-3-methoxy-6,7-dihydro-5-oxa-7a,8-diazadibenzo[a,e]azulene-9-carbonyl)amino]cyclobutanecarbonyl}amino)phenyl]acrylic acid (Example 7-10)

12-cyclohexyl-3,5-dimethyl-6,7-dihydro-5H-5,7a,8-triazadibenzo[a,e]azulene-9-carboxylic acid (Example 8-8)

(E)-3-[4-({1-[(12-cyclohexyl-3,5-dimethyl-6,7-dihydro-5H-5,7a,8-triazadibenzo[a,e]azulene-9-carbonyl)amino]cyclobutanecarbonyl}amino)phenyl]acrylic acid (Example 8-9)

14-cyclohexyl-6-methyl-5,6,7,8-tetrahydrobenzo[6,7][1,4]diazocino[8,1-a]indole-11-carboxylic acid monohydrochloride (Example 11-1)

methyl 6-tert-butoxycarbonyl-14-cyclohexyl-5,6,7,8-tetrahydrobenzo[6,7][1,4]diazocino[8,1-a]indole-11-carboxylate (Example 11-2)

methyl 14-cyclohexyl-6-methyl-5,6,7,8-tetrahydrobenzo[6,7][1,4]diazocino[8,1-a]indole-11-carboxylate (Example 11-3)

6-tert-butoxycarbonyl-14-cyclohexyl-3-methoxy-5,6,7,8-tetrahydrobenzo[6,7][1,4]diazocino[8,1-a]indole-11-carboxylic acid (Example 11-4)

14-cyclohexyl-3-methoxy-5,6,7,8-tetrahydrobenzo[6,7][1,4]diazocino[8,1-a]indole-11-carboxylic acid monohydrochloride (Example 11-5)

14-cyclohexyl-3-methoxy-6-methyl-5,6,7,8-tetrahydrobenzo[6,7][1,4]diazocino[8,1-a]indole-11-carboxylic acid monohydrochloride (Example 11-6)

14-cyclohexyl-3-methoxy-6-(2-methoxyacetyl)-5,6,7,8-tetrahydrobenzo[6,7][1,4]diazocino[8,1-a]indole-11-carboxylic acid (Example 11-7)

(E)-3-[4-({1-[(14-cyclohexyl-6-methyl-5,6,7,8-tetrahydrobenzo[6,7][1,4]diazocino[8,1-a]indole-11-carbonyl)amino]cyclobutanecarbonyl}amino)phenyl]acrylic acid monohydrochloride (Example 11-8)

12-cyclohexyl-6,7-dihydro-5-thia-7a-azadibenzo[a,e]azulene-9-carboxylic acid (Example 12-1)

11-cyclohexyl-5-thia-6a-azabenzo[a]fluorene-8-carboxylic acid (Example 12-2)

methyl 12-cyclohexyl-6,7-dihydro-5-thia-7a-azadibenzo[a,e]azulene-9-carboxylate (Example 12-3)

methyl 11-cyclohexyl-5-thia-6a-azabenzo[a]fluorene-8-carboxylate (Example 12-4)

(E)-3-(4-{2-[(13-cyclohexyl-3-ethoxy-5-methyl-6,7-dihydro-5H-benzo[5,6][1,4]diazepino[7,1-a]indole-10-carbonyl)amino]-2-methylpropionylamino}phenyl)acrylic acid (Example 1-615)

(E)-3-[3-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)phenyl]acrylic acid (Example 1-616)

(E)-3-[4-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)-3-methoxyphenyl]acrylic acid (Example 1-617)

(E)-3-[2-chloro-5-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)phenyl]acrylic acid (Example 1-618)

(E)-3-[5-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)-2-methoxyphenyl]acrylic acid (Example 1-619)

(E)-3-[5-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)-2-methylphenyl]acrylic acid (Example 1-620)

(E)-3-[4-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)-2-methylphenyl]acrylic acid (Example 1-621)

(E)-3-[4-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)-2-methoxyphenyl]acrylic acid (Example 1-622)

(E)-3-[2-chloro-4-({1-[(13-cyclohexyl-3-ethoxy-5-methyl-6,7-dihydro-5H-benzo[5,6][1,4]diazepino[7,1-a]indole-10-carbonyl)amino]cyclobutanecarbonyl}amino)phenyl]acrylic acid (Example 1-623)

4-({1-[(12-cyclohexyl-3-methoxy-6,7-dihydro-5-oxa-7a-azadibenzo[a,e]azulene-9-carbonyl)amino]cyclobutanecarbonyl}amino)benzenesulfonic acid (Example 2-523)

N—[(S)-1-(4,4-dimethyl-5-oxo-4,5-dihydrooxazol-2-yl)-2-(4-hydroxyphenyl)ethyl]-12-cyclohexyl-3-methoxy-6,7-dihydro-5-oxa-7a-azadibenzo[a,e]azulene-9-carboxamide (Example 2-524)

N—[(S)-2-(4-benzyloxyphenyl)-1-(5-methyl-1H-1,2,4-triazol-3-yl)ethyl]-12-cyclohexyl-3-methoxy-6,7-dihydro-5-oxa-7a-azadibenzo[a,e]azulene-9-carboxamide (Example 2-525)

N—[(S)-2-(4-hydroxyphenyl)-1-(5-methyl-1H-1,2,4-triazol-3-yl)ethyl]-12-cyclohexyl-3-methoxy-6,7-dihydro-5-oxa-7a-azadibenzo[a,e]azulene-9-carboxamide (Example 2-526)

N-[1-(5-methylcarbamoylmethoxy-1H-benzimidazol-2-yl)cyclobutyl]-12-cyclohexyl-3-methoxy-6,7-dihydro-5-oxa-7a-azadibenzo[a,e]azulene-9-carboxamide (Example 2-527)

(E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]-2-methylacrylic acid (Example 2-528)

(E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)phenyl]but-2-enoic acid (Example 2-529)

(E)-3-[3-(2-benzyloxyethoxy)-4-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylic acid (Example 2-530)

(E)-3-[4-({1-[(12-cyclohexyl-3-methoxy-6,7-dihydro-5-oxa-7a-azadibenzo[a,e]azulene-9-carbonyl)amino]cyclobutanecarbonyl}amino)-2-methoxyphenyl]acrylic acid (Example 2-531)

(S)-2-[(12-cyclohexyl-3-methoxy-6,7-dihydro-5-oxa-7a-azadibenzo[a,e]azulene-9-carbonyl)amino]-3-methoxy-2-methylpropionic acid (Example 2-532)

N—[(S)-1-(4-ethyl-5-oxo-4,5-dihydro-1H-1,2,4-triazol-3-yl)-2-(4-hydroxyphenyl)ethyl]-12-cyclohexyl-3-methoxy-6,7-dihydro-5-oxa-7a-azadibenzo[a,e]azulene-9-carboxamide (Example 2-533)

12-cyclohexyl-4-{2-[(E)-3-oxo-3-(piperidin-1-yl)propenyl]phenyl}-6,7-dihydro-5-oxa-7a-azadibenzo[a,e]azulene-9-carboxylic acid (Example 2-534)

12-cyclohexyl-4-{2-[3-oxo-3-(piperidin-1-yl)propyl]phenyl}-6,7-dihydro-5-oxa-7a-azadibenzo[a,e]azulene-9-carboxylic acid (Example 2-535)

12-cyclohexyl-4-{2-[3-(piperidin-1-yl)propyl]phenyl}-6,7-dihydro-5-oxa-7a-azadibenzo[a,e]azulene-9-carboxylic acid monohydrochloride (Example 2-536)

(E)-3-(4-{(S)-2-[(12-cyclohexyl-3-methoxy-6,7-dihydro-5-oxa-7a-azadibenzo[a,e]azulene-9-carbonyl)amino]-3-methoxy-2-methylpropionylamino}phenyl)acrylic acid (Example 2-537)

N—[(S)-2-(4-benzyloxyphenyl)-1-(1,3-dioxolan-2-yl)ethyl]-12-cyclohexyl-3-methoxy-6,7-dihydro-5-oxa-7a-azadibenzo[a,e]azulene-9-carboxamide (Example 2-538)

N-(4-{2-[(12-cyclohexyl-3-methoxy-6,7-dihydro-5-oxa-7a-azadibenzo[a,e]azulene-9-carbonyl)amino]-2-(methoxycarbonyl)ethyl}benzyl)-N,N,N-triethylammonium chloride (Example 2-539)

4-(2-{1-[(12-cyclohexyl-3-methoxy-6,7-dihydro-5-oxa-7a-azadibenzo[a,e]azulene-9-carbonyl)amino]-1-methylethyl}-3H-imidazol-4-yl)benzoic acid monohydrochloride (Example 2-540)

N-[1-(2-oxo-2H-chromen-6-ylcarbamoyl)cyclobutyl]-12-cyclohexyl-3-methoxy-6,7-dihydro-5-oxa-7a-azadibenzo[a,e]azulene-9-carboxamide (Example 2-541)

N—[(S)-2-(4-benzyloxyphenyl)-1-(5-methyl-1,2,4-oxadiazol-3-yl)ethyl]-12-cyclohexyl-3-methoxy-6,7-dihydro-5-oxa-7a-azadibenzo[a,e]azulene-9-carboxamide (Example 2-542)

N-{1-[4-((E)-2-carbamoylvinyl)phenylcarbamoyl]cyclobutyl}-12-cyclohexyl-3-methoxy-6,7-dihydro-5-oxa-7a-azadibenzo[a,e]azulene-9-carboxamide (Example 2-543)

N-{1-[4-((E)-2-methylcarbamoylvinyl)phenylcarbamoyl]cyclobutyl}-12-cyclohexyl-3-methoxy-6,7-dihydro-5-oxa-7a-azadibenzo[a,e]azulene-9-carboxamide (Example 2-544)

N-{1-[5-(4-hydroxymethylphenyl)-1H-imidazol-2-yl]-1-methylethyl}-12-cyclohexyl-3-methoxy-6,7-dihydro-5-oxa-7a-azadibenzo[a,e]azulene-9-carboxamide (Example 2-545)

N-{1-[5-(4-carbamoylphenyl)-1H-imidazol-2-yl]-1-methylethyl}-12-cyclohexyl-3-methoxy-6,7-dihydro-5-oxa-7a-azadibenzo[a,e]azulene-9-carboxamide (Example 2-546)

N-{1-methyl-1-[5-(4-methylcarbamoylphenyl)-1H-imidazol-2-yl]ethyl}-12-cyclohexyl-3-methoxy-6,7-dihydro-5-oxa-7a-azadibenzo[a,e]azulene-9-carboxamide (Example 2-547)

(E)-3-[4-(2-{1-[(12-cyclohexyl-3-methoxy-6,7-dihydro-5-oxa-7a-azadibenzo[a,e]azulene-9-carbonyl)amino]-1-methylethyl}-3H-imidazol-4-yl)phenyl]acrylic acid (Example 2-548)

12-cyclohexyl-4-[(2-[2-(piperidin-1-yl)acetylamino]phenyl]-6,7-dihydro-5-oxa-7a-azadibenzo[a,e]azulene-9-carboxylic acid (Example 2-549)

(E)-3-[3-({1-[(12-cyclohexyl-3-methoxy-6,7-dihydro-5-oxa-7a-azadibenzo[a,e]azulene-9-carbonyl)amino]cyclobutanecarbonyl}amino)phenyl]acrylic acid (Example 2-550)

(E)-3-[3-({1-[(12-cyclohexyl-3-ethoxy-6,7-dihydro-5-oxa-7a-azadibenzo[a,e]azulene-9-carbonyl)amino]cyclobutanecarbonyl}amino)phenyl]acrylic acid (Example 2-551)

(E)-3-[4-({1-[(12-cyclohexyl-3-ethoxy-6,7-dihydro-5-oxa-7a-azadibenzo[a,e]azulene-9-carbonyl)amino]cyclobutanecarbonyl}amino)-3-methoxyphenyl]acrylic acid (Example 2-552)

12-cyclohexyl-4-{2-[2-(piperidin-1-yl)ethyl]phenyl}-6,7-dihydro-5-oxa-7a-azadibenzo[a,e]azulene-9-carboxylic acid monohydrochloride (Example 2-553)

12-cyclohexyl-4-{2-[2-(piperidin-1-yl)ethylamino]phenyl}-6,7-dihydro-5-oxa-7a-azadibenzo[a,e]azulene-9-carboxylic acid dihydrochloride (Example 2-554)

12-cyclohexyl-3-isopropoxy-6,7-dihydro-5-oxa-7a-azadibenzo[a,e]azulene-9-carboxylic acid (Example 2-555)

(E)-3-[4-({1-[(12-cyclohexyl-3-isopropoxy-6,7-dihydro-5-oxa-7a-azadibenzo[a,e]azulene-9-carbonyl)amino]cyclobutanecarbonyl}amino)phenyl]acrylic acid (Example 2-556)

TABLE 2

| Ex. | formula | positive MS (M + 1) (free form) |
|---|---|---|
| 1-19 | | 403.2 |
| 1-20 | | 375.2 |
| 1-21 | | 446.2 |
| 1-22 | | 451.2 |
| 1-23 | | 403.2 |

TABLE 3

| Ex. | formula | positive MS (M + 1)(free form) |
|---|---|---|
| 1-24 | | 375.1 |
| 1-25 | | 508.3 |
| 1-26 | | 488.2 |
| 1-27 | | 474.2 2HCl |

TABLE 4

| Ex. | formula | positive MS (M + 1)(free form) |
|---|---|---|
| 1-28 | | 476.2 |
| 1-29 | | 486.3 |
| 1-30 | | 515.3 2HCl |
| 1-31 | | 432.2 |

TABLE 5
| Ex. | formula | positive MS (M + 1)(free form) |
|---|---|---|
| 1-32 | 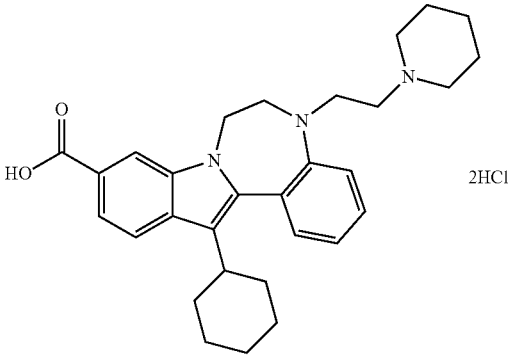 2HCl | 472.3 |
| 1-33 | 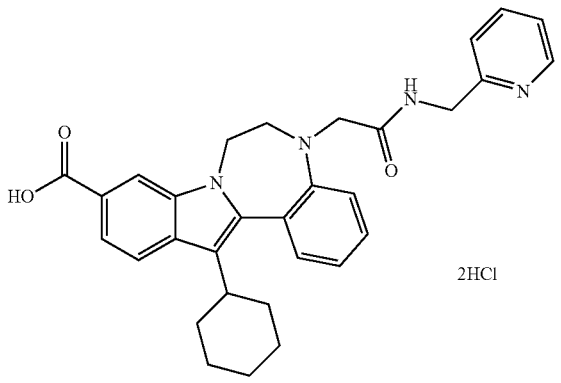 2HCl | 509.2 |
| 1-34 | 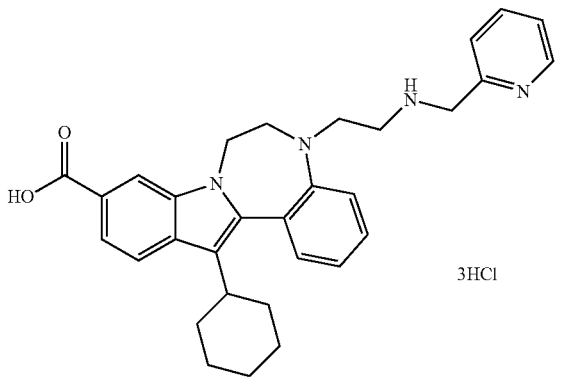 3HCl | 495.3 |
| 1-35 | 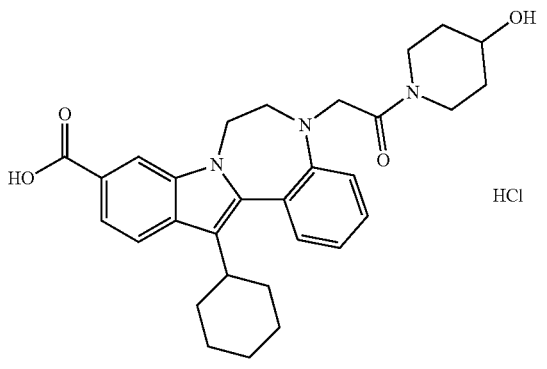 HCl | 502.3 |

TABLE 6
| Ex. | formula | positive MS (M + 1)(free form) |
|---|---|---|
| 1-36 | 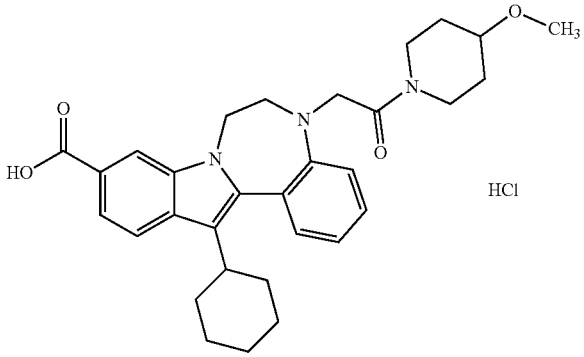 HCl | 516.2 |
| 1-37 | 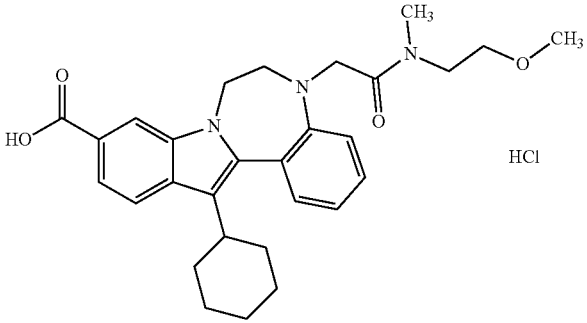 HCl | 490.2 |
| 1-38 | 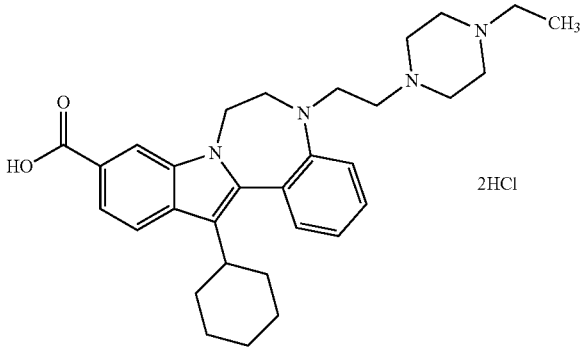 2HCl | 501.3 |
| 1-39 | 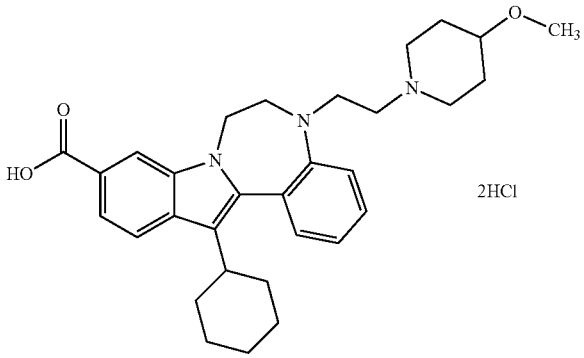 2HCl | 502.3 |

TABLE 7
| Ex. | formula | positive MS (M + 1)(free form) |
|---|---|---|
| 1-40 | 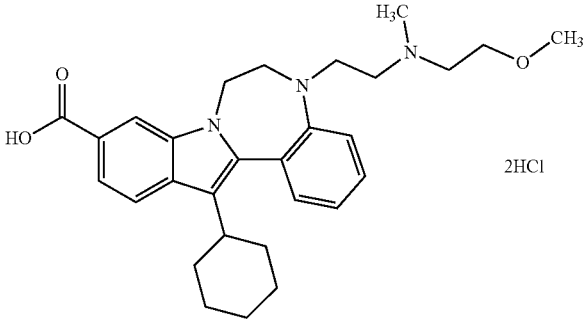 2HCl | 476.3 |
| 1-41 | 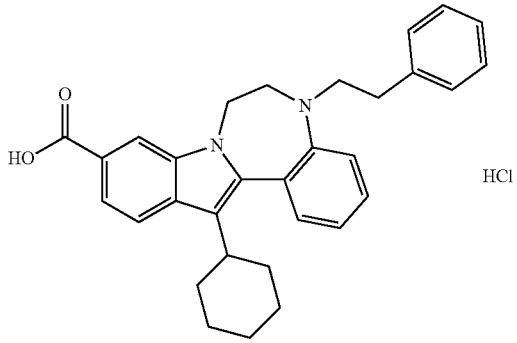 HCl | 465.2 |
| 1-42 | 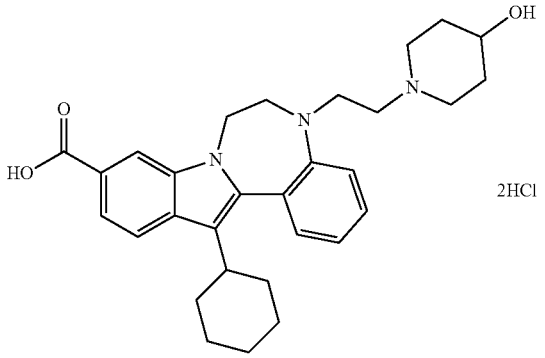 2HCl | 488.3 |
| 1-43 | 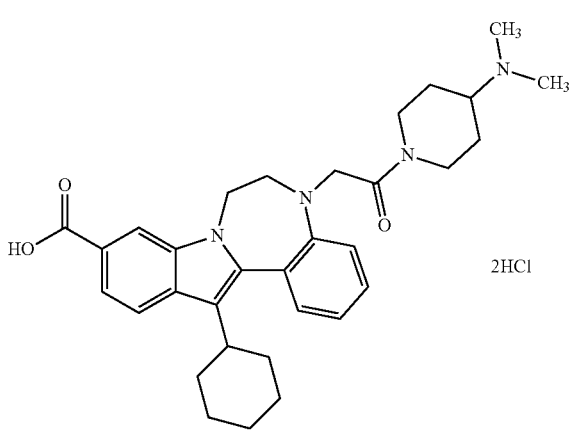 2HCl | 529.3 |

TABLE 8
| Ex. | formula | positive MS (M + 1)(free form) |
|---|---|---|
| 1-44 | 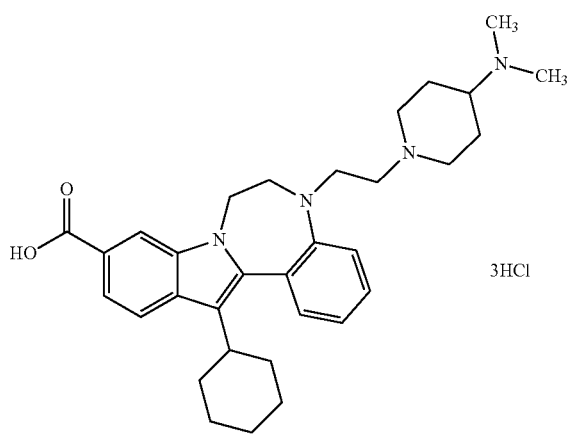 3HCl | 515.3 |
| 1-45 | 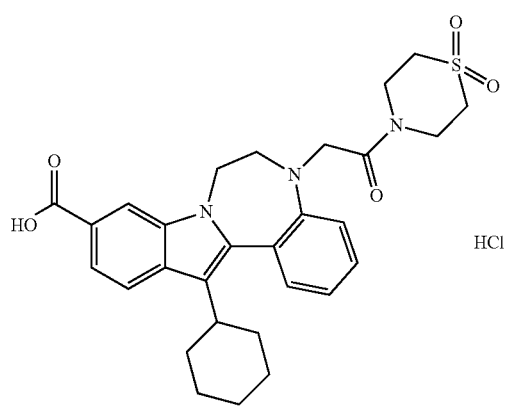 HCl | 536.2 |
| 1-46 | 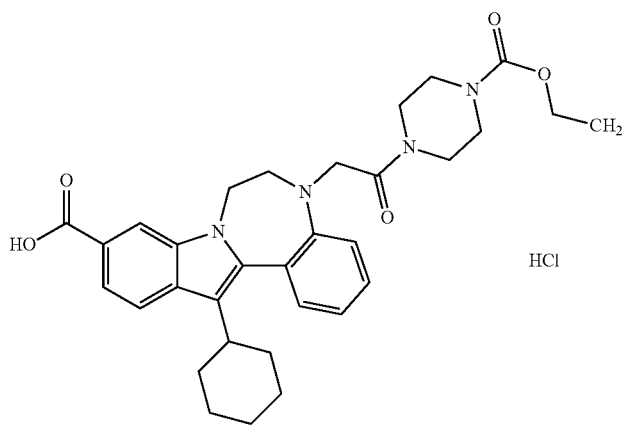 HCl | 559.3 |

TABLE 8-continued
| Ex. | formula | positive MS (M + 1)(free form) |
|---|---|---|
| 1-47 | 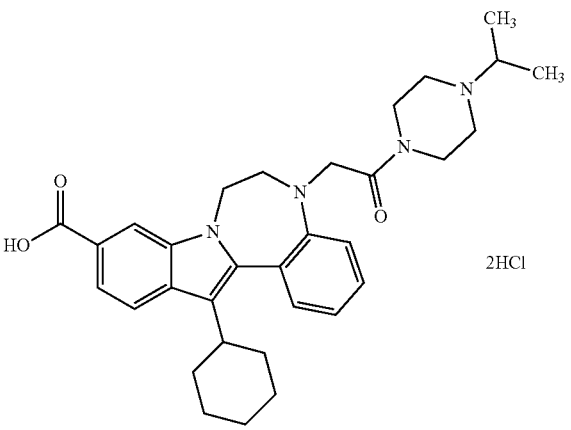 2HCl | 529.3 |
TABLE 9
| Ex. | formula | positive MS (M + 1)(free form) |
|---|---|---|
| 1-48 | 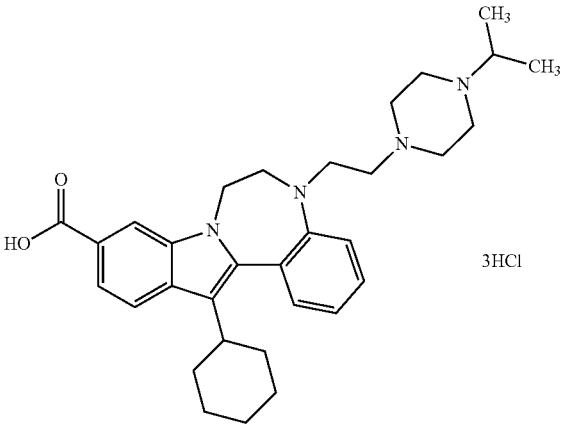 3HCl | 515.3 |
| 1-49 | 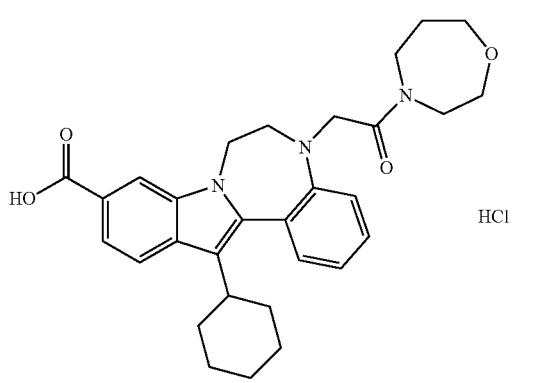 HCl | 502.2 |

TABLE 9-continued
| Ex. | formula | positive MS (M + 1)(free form) |
|---|---|---|
| 1-50 | 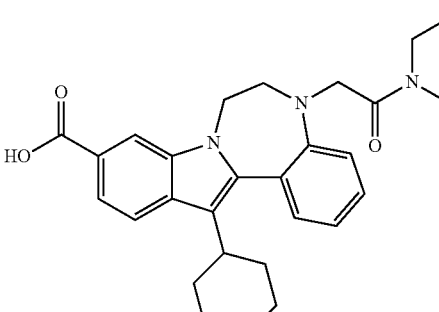 2HCl | 501.2 |
| 1-51 | 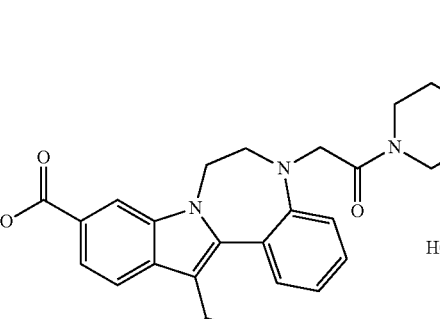 HCl | 529.2 |
TABLE 10
| Ex. | formula | positive MS (M + 1)(free form) |
|---|---|---|
| 1-52 | 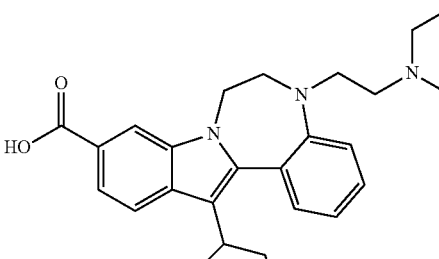 3HCl | 487.3 |
| 1-53 |  3HCl | 501.3 |

TABLE 10-continued
| Ex. | formula | positive MS (M + 1)(free form) |
|---|---|---|
| 1-54 | 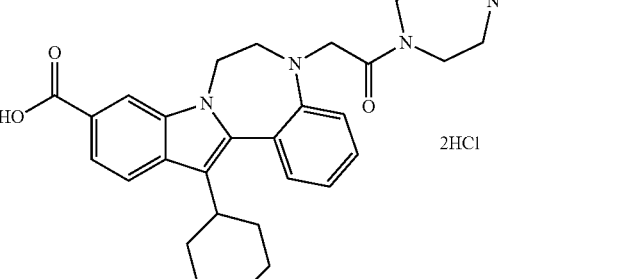 2HCl | 515.3 |
| 1-55 | | 514.3 |
| 1-56 | 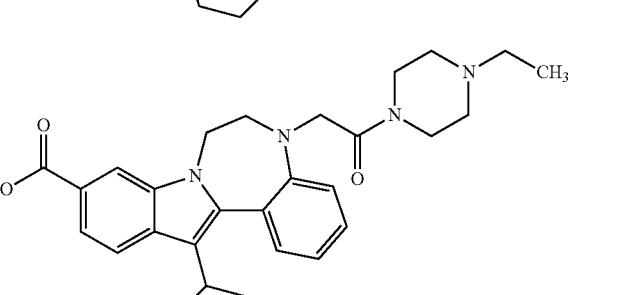 HCl | 472.2 |
TABLE 11
| Ex. | formula | positive MS (M + 1)(free form) |
|---|---|---|
| 1-57 | 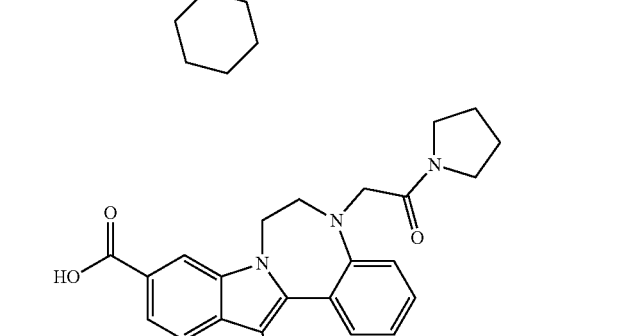 2HCl | 458.3 |

TABLE 11-continued
| Ex. | formula | positive MS (M + 1)(free form) |
|---|---|---|
| 1-58 | 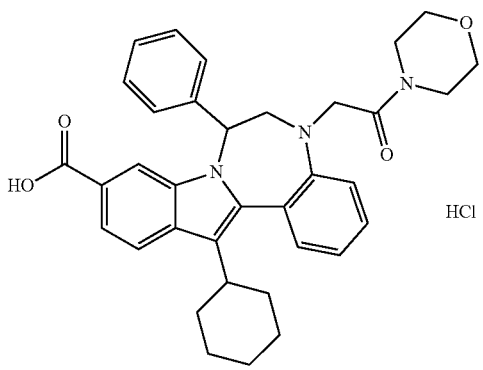 HCl | 564.2 |
| 1-59 | 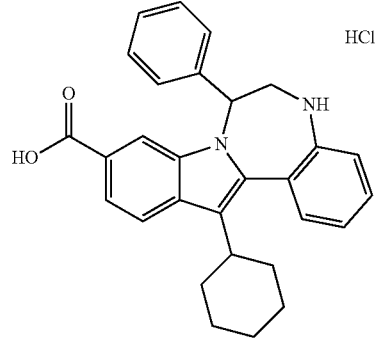 HCl | 437.2 |
| 1-60 | 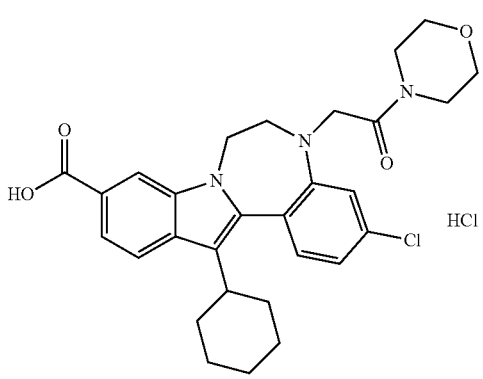 HCl | 522.2 |

TABLE 12
| Ex. | formula | positive MS (M + 1)(free form) |
|---|---|---|
| 1-61 | 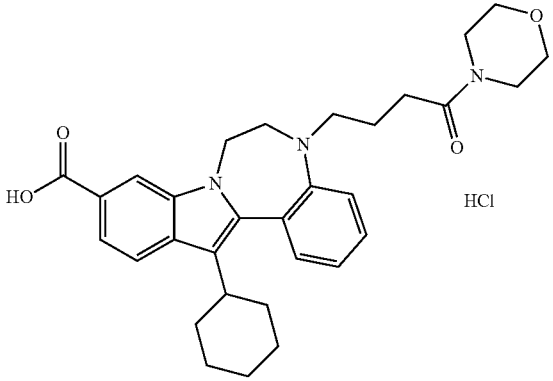 HCl | 516.3 |
| 1-62 | 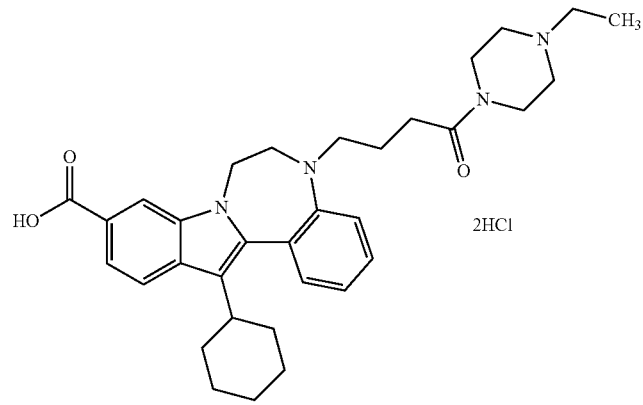 2HCl | 543.3 |
| 1-63 | 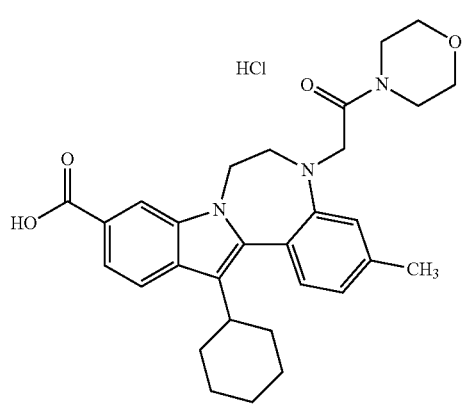 HCl | 502.2 |

TABLE 12-continued
| Ex. | formula | positive MS (M + 1)(free form) |
|---|---|---|
| 1-64 | 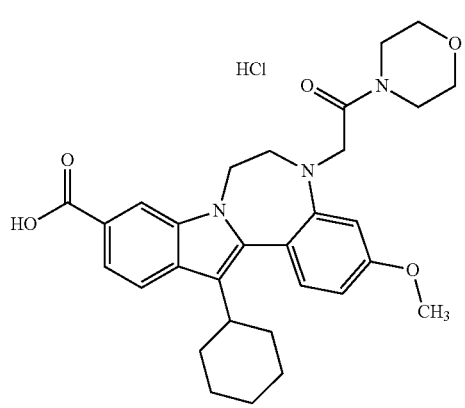 | 518.2 |
TABLE 13
| Ex. | formula | positive MS (M + 1)(free form) |
|---|---|---|
| 1-65 | 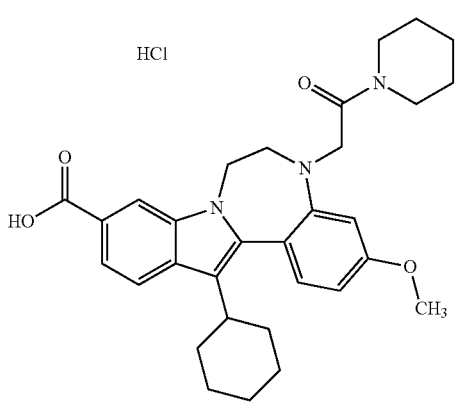 | 516.3 |
| 1-66 | 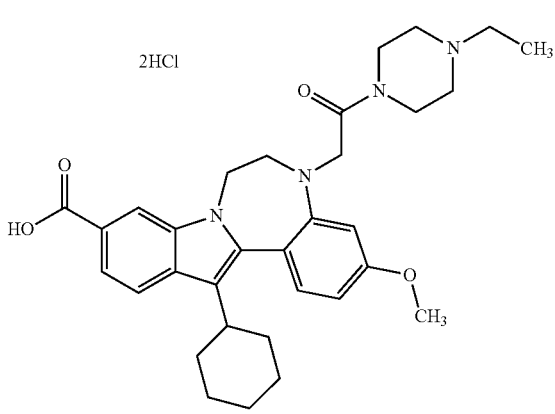 | 545.3 |

TABLE 13-continued
| Ex. | formula | positive MS (M + 1)(free form) |
|---|---|---|
| 1-67 | 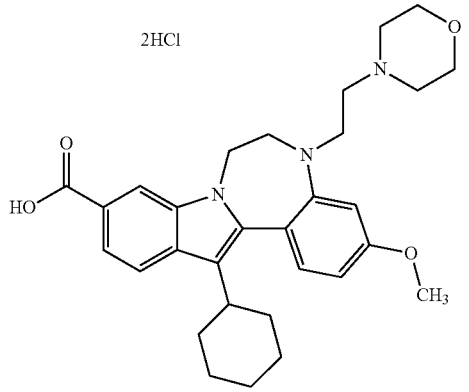 2HCl | 504.3 |
| 1-68 | 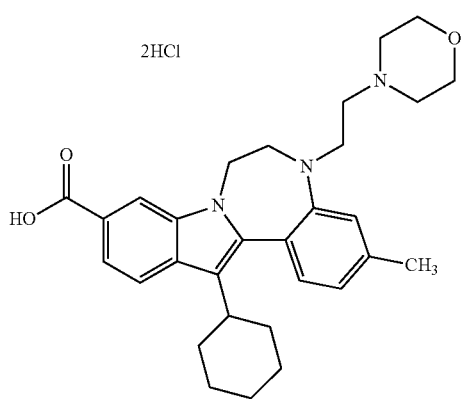 2HCl | 488.3 |
TABLE 14
| Ex. | formula | positive MS (M + 1)(free form) |
|---|---|---|
| 1-69 | 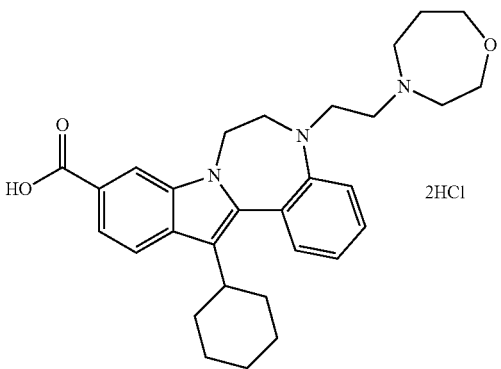 2HCl | 488.3 |

TABLE 14-continued

| Ex. | formula | positive MS (M + 1)(free form) |
|---|---|---|
| 1-70 | | 565.2 |
| 1-71 | | 514.3 |
| 1-72 | | 500.3 |

TABLE 15
| Ex. | formula | positive MS (M + 1)(free form) |
|---|---|---|
| 1-73 | 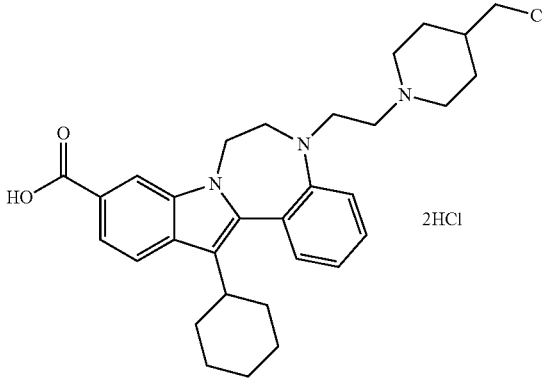 2HCl | 500.3 |
| 1-74 | 2HCl 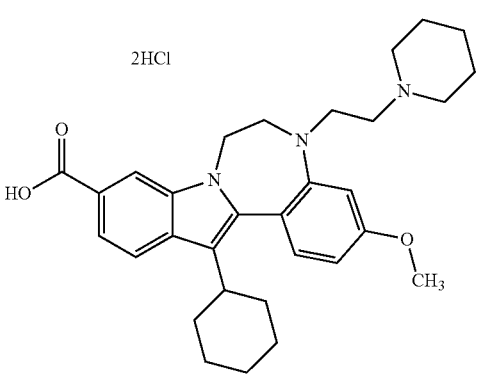 | 502.3 |
| 1-75 | 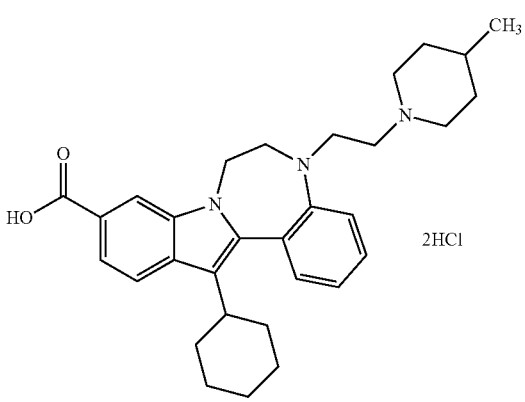 2HCl | 486.3 |
| 1-76 | 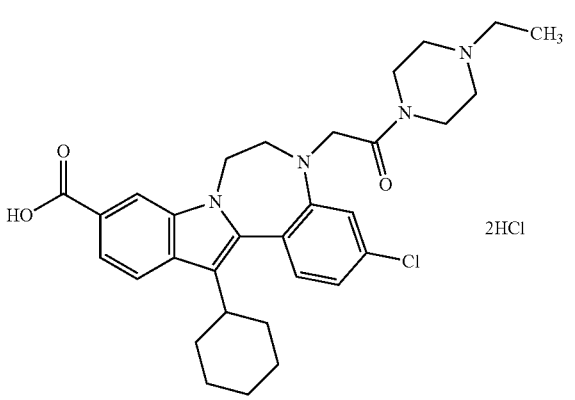 2HCl | 549.2 |

TABLE 16
| Ex. | formula | positive MS (M + 1)(free form) |
|---|---|---|
| 1-77 | 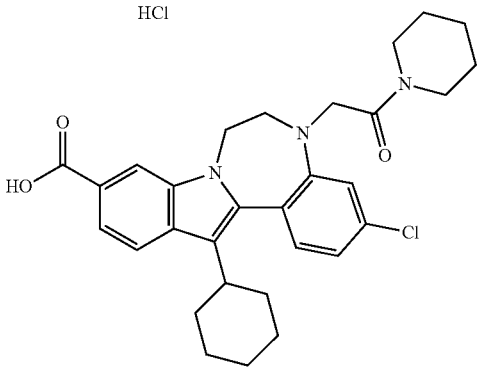 HCl | 520.2 |
| 1-78 | 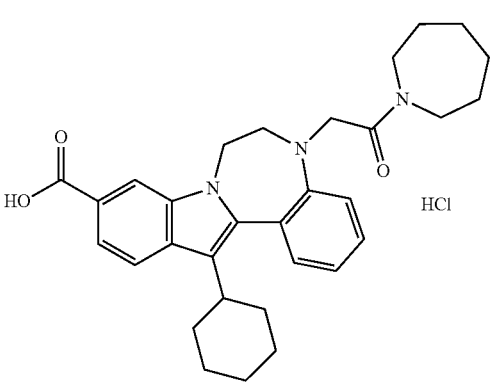 HCl | 500.3 |
| 1-79 | 2HCl 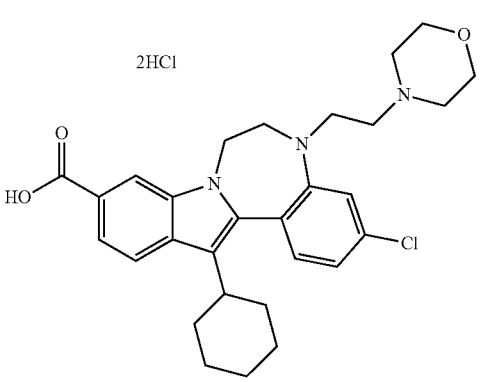 | 508.2 |
| 1-80 | 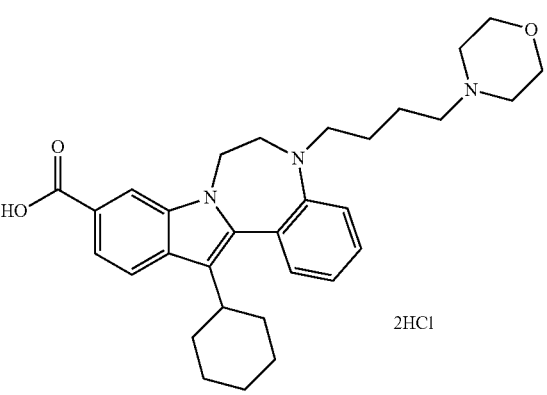 2HCl | 502.3 |

TABLE 17
| Ex. | formula | positive MS (M + 1)(free form) |
|---|---|---|
| 1-81 | 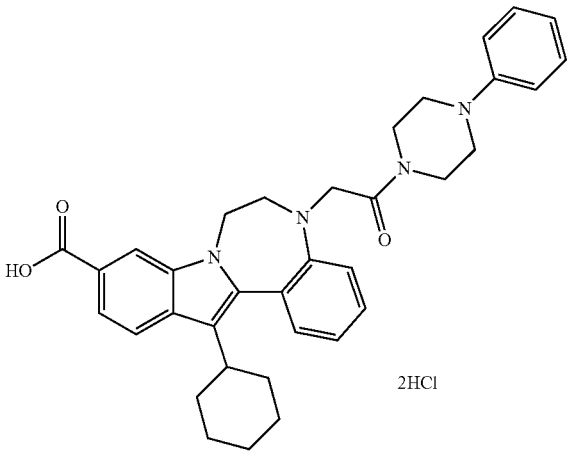 2HCl | 563.3 |
| 1-82 | 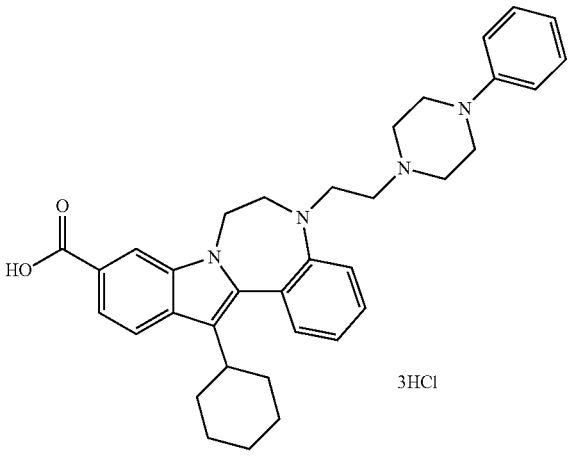 3HCl | 549.3 |
| 1-83 | 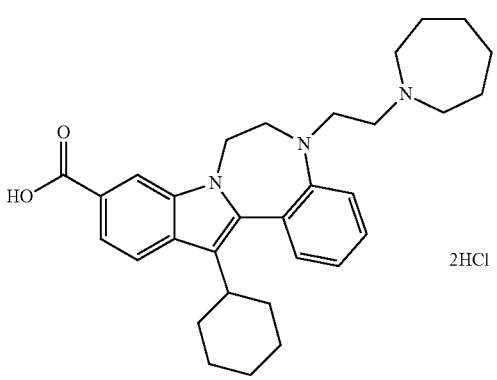 2HCl | 486.3 |

TABLE 17-continued

| Ex. | formula | positive MS (M + 1)(free form) |
|---|---|---|
| 1-84 | | 528.3 |

TABLE 18

| Ex. | formula | positive MS (M + 1)(free form) |
|---|---|---|
| 1-85 | | 558.3 |
| 1-86 | | 586.4 |

TABLE 18-continued
| Ex. | formula | positive MS (M + 1)(free form) |
|---|---|---|
| 1-87 | 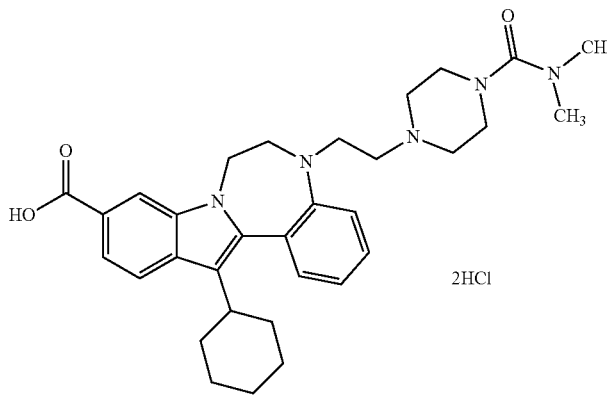 2HCl | 544.3 |
| 1-88 | 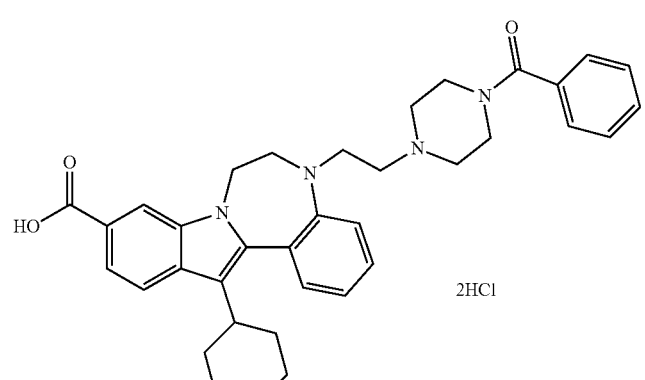 2HCl | 577.3 |
TABLE 19
| Ex. | formula | positive MS (M + 1)(free form) |
|---|---|---|
| 1-89 | 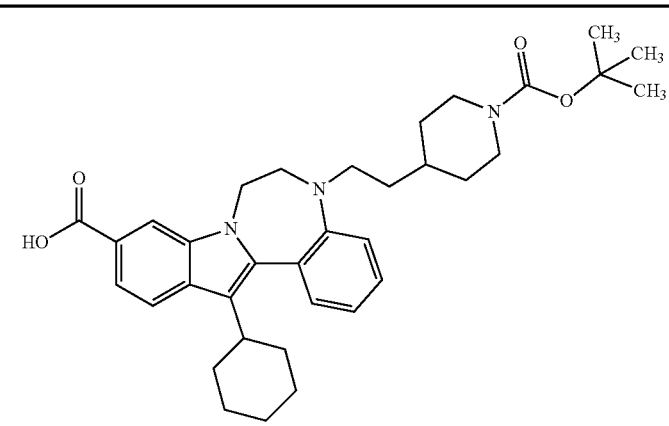 | 572.3 |

TABLE 19-continued
| Ex. | formula | positive MS (M + 1)(free form) |
|---|---|---|
| 1-90 | 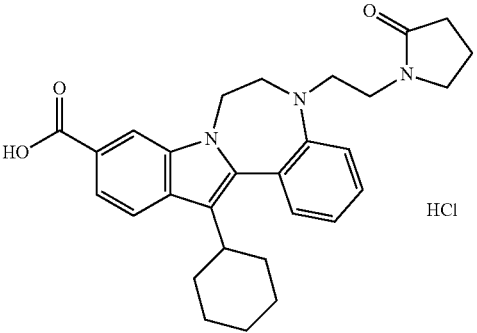 HCl | 472.3 |
| 1-91 | 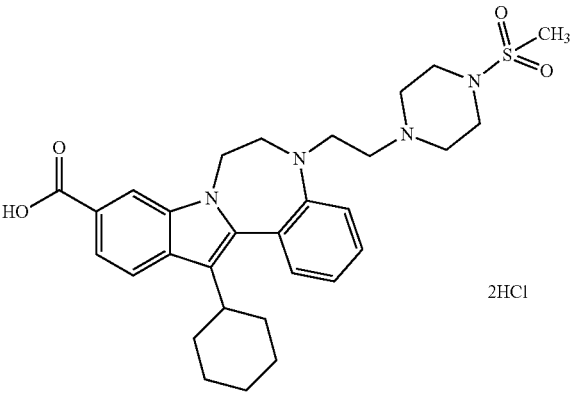 2HCl | 551.3 |
| 1-92 | 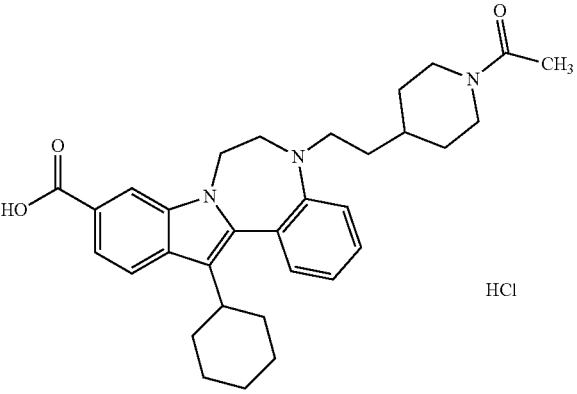 HCl | 514.3 |

TABLE 20
| Ex. | formula | positive MS (M + 1)(free form) |
|---|---|---|
| 1-93 | 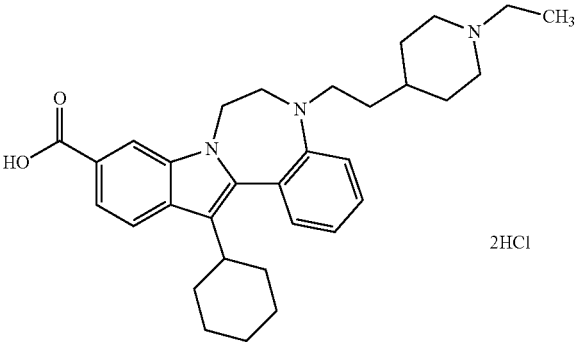 2HCl | 500.3 |
| 1-94 | 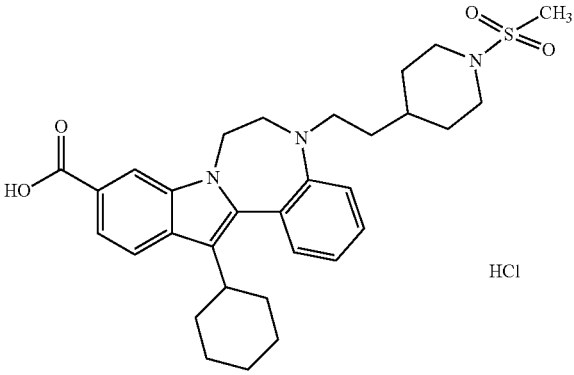 HCl | 550.2 |
| 1-95 | 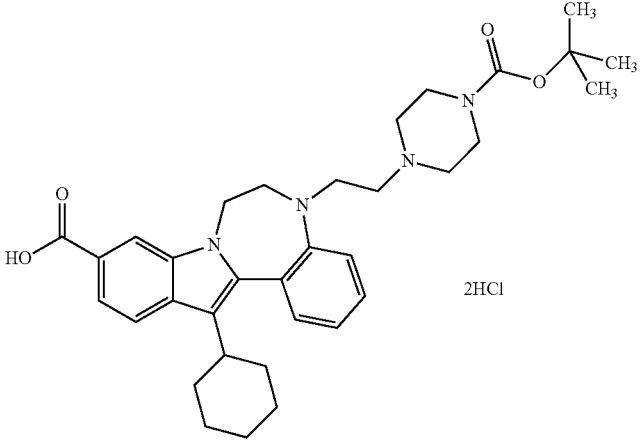 2HCl | 577.3 |
| 1-96 | 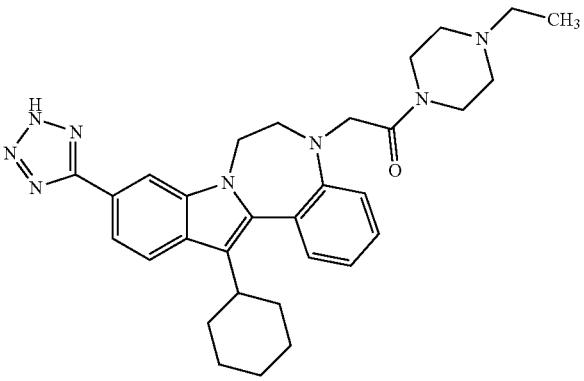 | 539.3 |

TABLE 21
| Ex. | formula | positive MS (M + 1)(free form) |
|---|---|---|
| 1-97 | 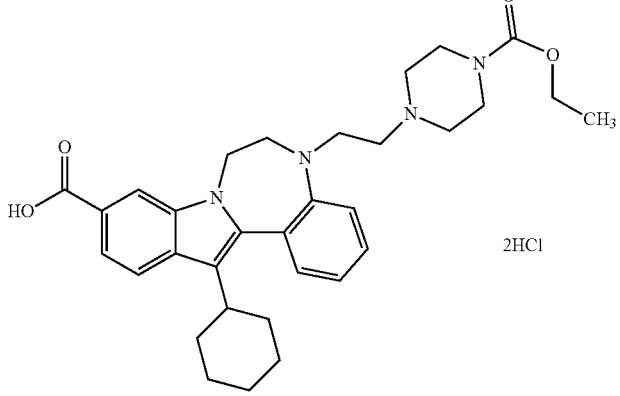 2HCl | 545.3 |
| 1-98 | 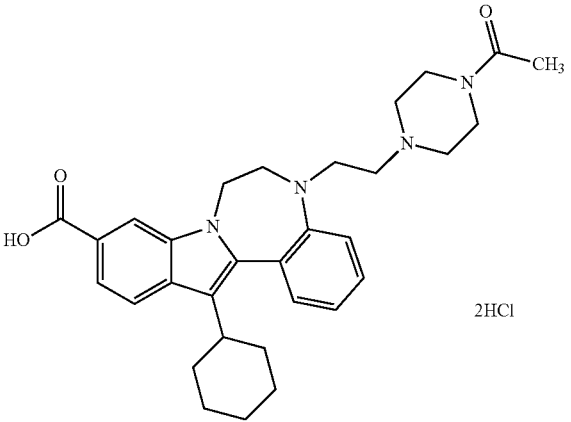 2HCl | 515.2 |
| 1-99 | 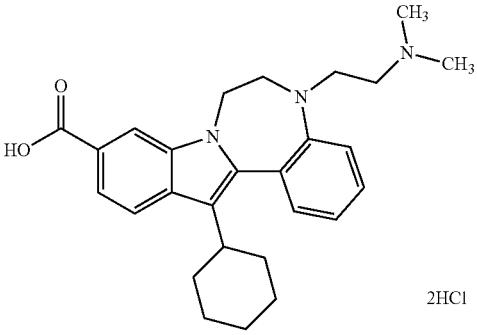 2HCl | 432.2 |
| 1-100 | 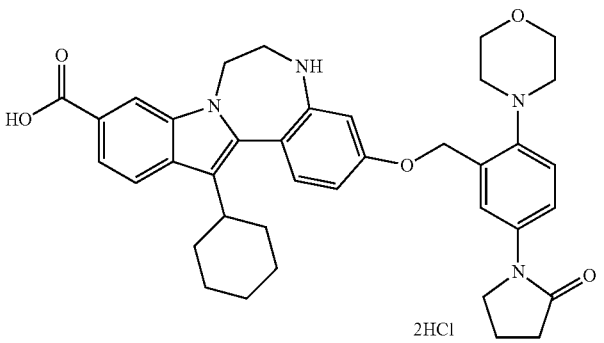 2HCl | 635.2 |

TABLE 22
| Ex. | formula | positive MS (M + 1)(free form) |
|---|---|---|
| 1-101 | 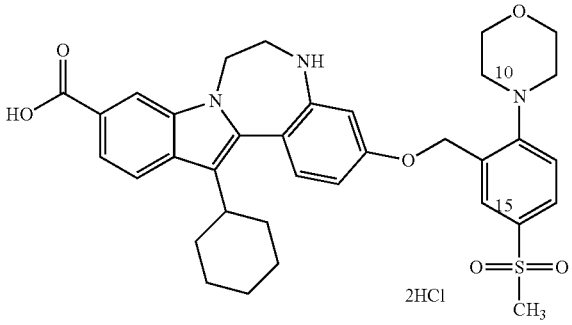 2HCl | 630.1 |
| 1-102 | 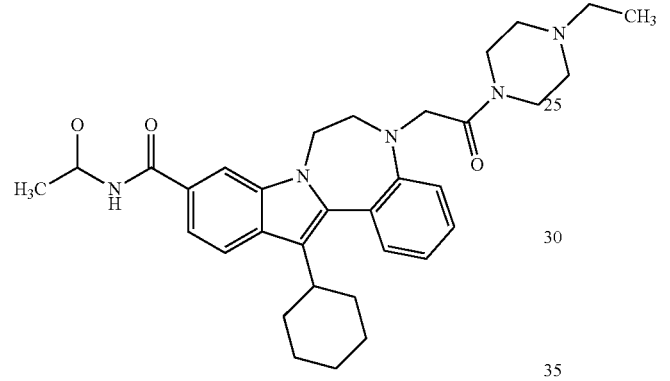 | 556.3 |
| 1-103 |  2HCl | 644.2 |
| 1-104 |  2HCl | 531.2 |

TABLE 23
| Ex. | formula | positive MS (M + 1)(free form) |
|---|---|---|
| 1-105 | 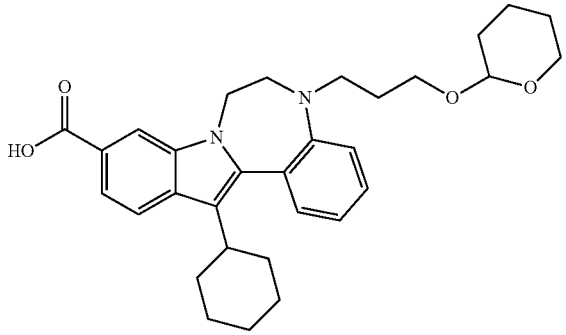 | 503.2 |
| 1-106 | 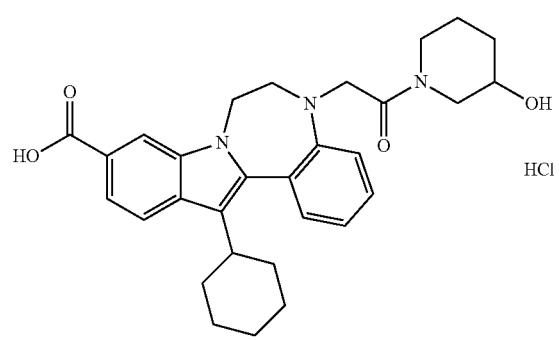 HCl | 502.2 |
| 1-107 | 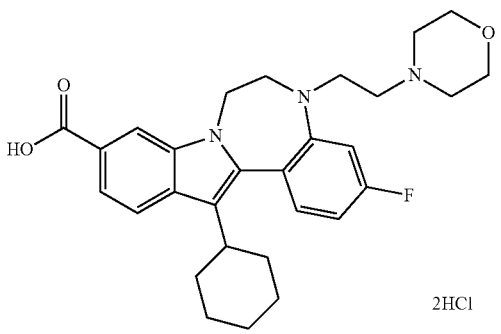 2HCl | 492.3 |
| 1-108 | 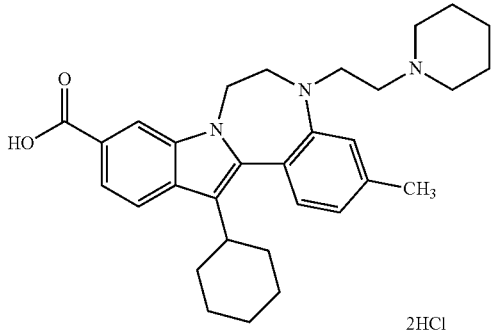 2HCl | 486.3 |

TABLE 24
| Ex. | formula | positive MS (M + 1)(free form) |
|---|---|---|
| 1-109 | 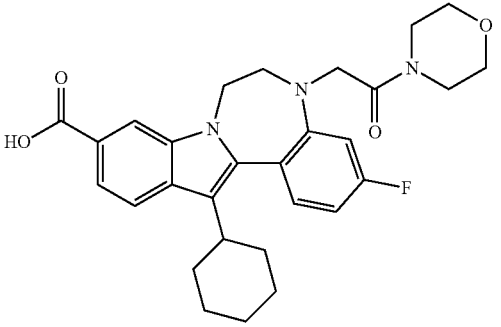 | 506.2 |
| 1-110 | 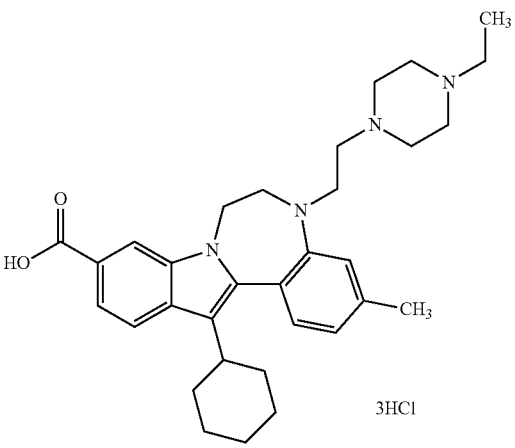 3HCl | 515.3 |
| 1-111 | 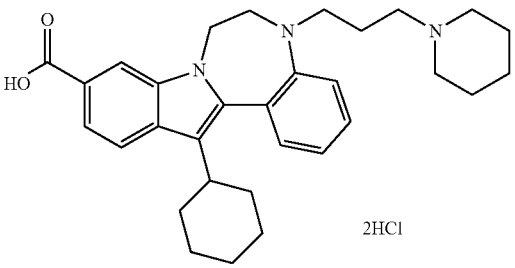 2HCl | 486.3 |
| 1-112 | HCl 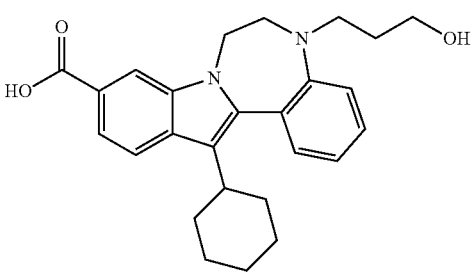 | 419.2 |

TABLE 25
| Ex. | formula | positive MS (M + 1)(free form) |
|---|---|---|
| 1-113 | 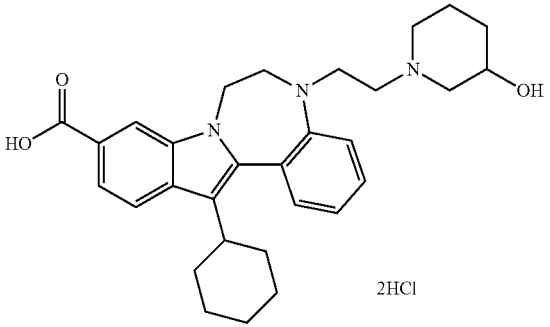 2HCl | 488.2 |
| 1-114 | 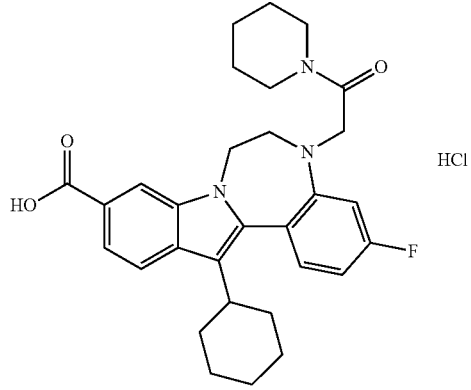 HCl | 504.2 |
| 1-115 | 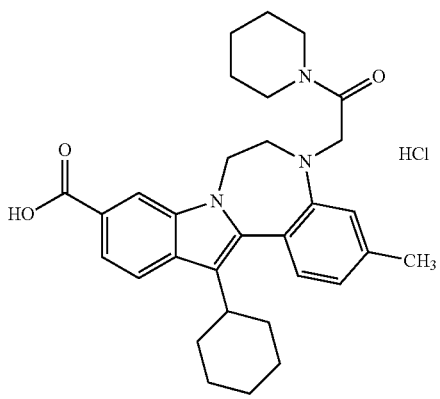 HCl | 500.3 |
| 1-116 | 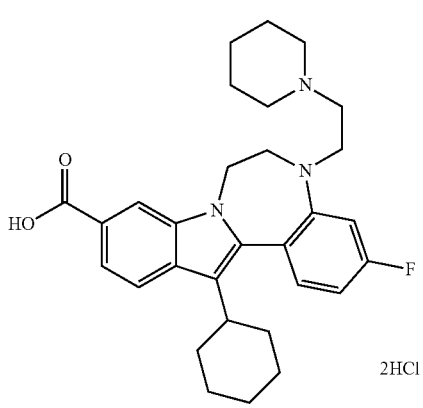 2HCl | 490.3 |

TABLE 26
| Ex. | formula | positive MS (M + 1)(free form) |
|---|---|---|
| 1-117 | 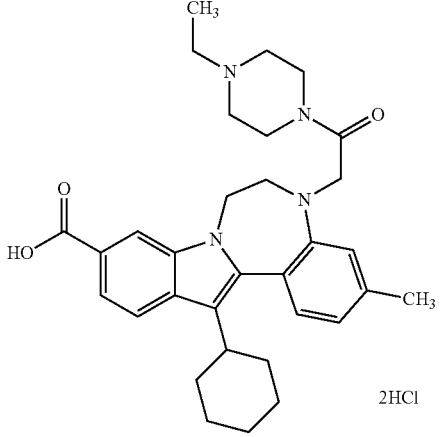 2HCl | 529.3 |
| 1-118 | 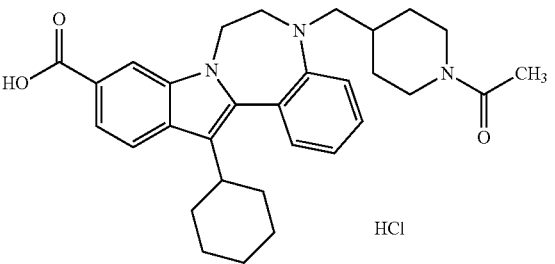 HCl | 500.3 |
| 1-119 | 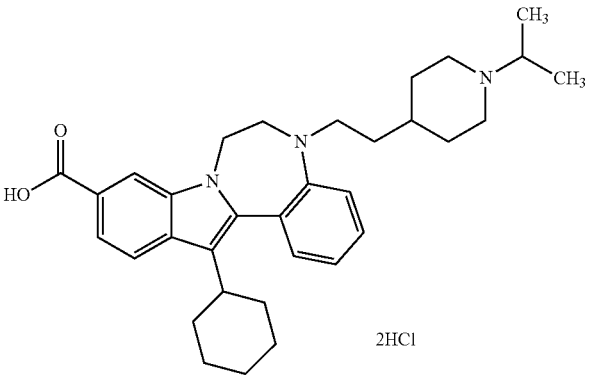 2HCl | 514.3 |
| 1-120 | HCl 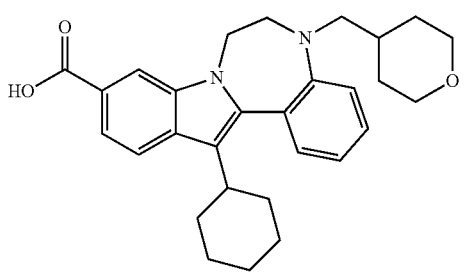 | 459.2 |

TABLE 27
| Ex. | formula | positive MS (M + 1)(free form) |
|---|---|---|
| 1-121 | 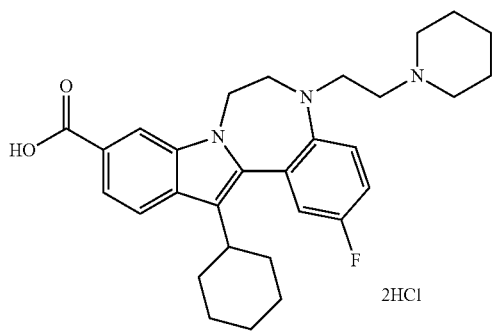 2HCl | 490.2 |
| 1-122 | HCl 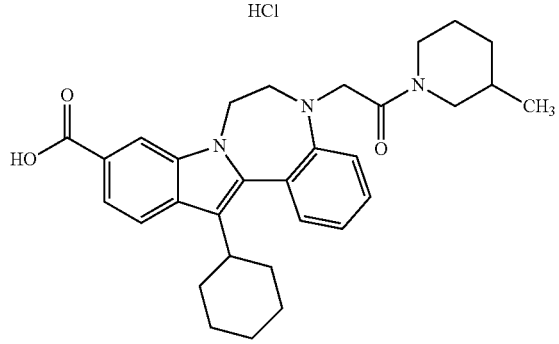 | 500.3 |
| 1-123 | 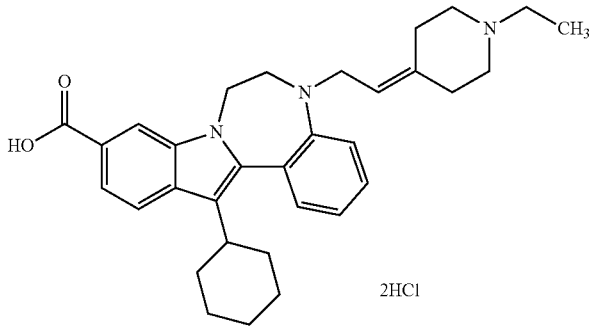 2HCl | 498.3 |
| 1-124 | 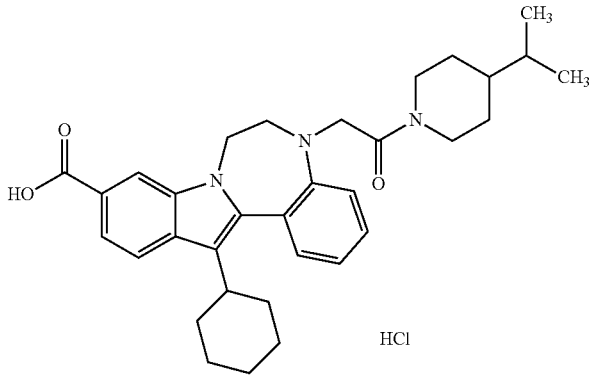 HCl | 528.3 |

TABLE 28
| Ex. | formula | positive MS (M + 1)(free form) |
|---|---|---|
| 1-125 | 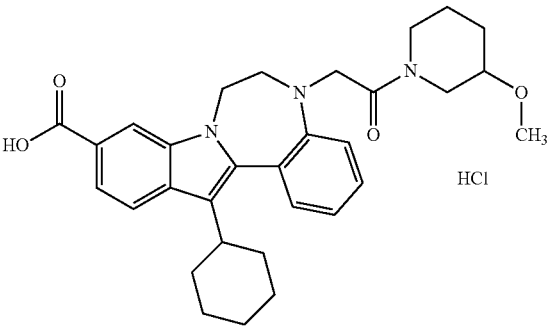 HCl | 516.2 |
| 1-126 | 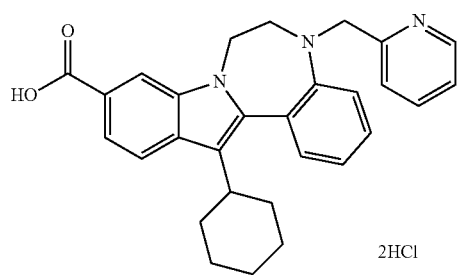 2HCl | 452.2 |
| 1-127 | 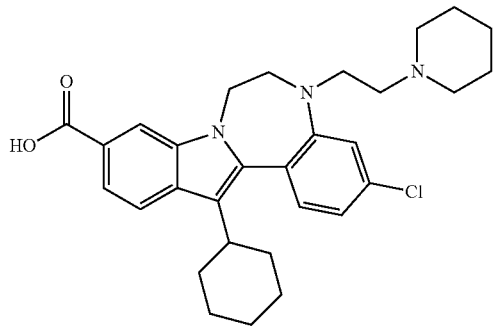 | 506.3 |
| 1-128 | 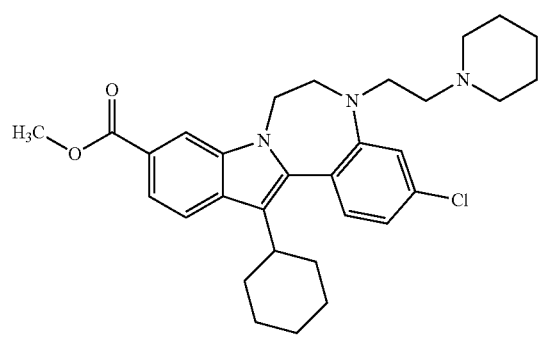 | 520.3 |

TABLE 28-continued
| Ex. | formula | positive MS (M + 1)(free form) |
|---|---|---|
| 1-129 | 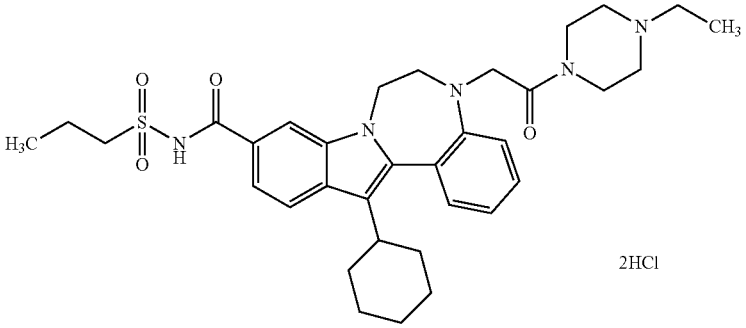 2HCl | 620.3 |
TABLE 29
| Ex. | formula | positive MS (M + 1)(free form) |
|---|---|---|
| 1-130 | | 486.3 |
| 1-131 | | 514.3 |
| 1-132 | | 528.3 |

TABLE 29-continued

| Ex. | formula | positive MS (M + 1)(free form) |
|---|---|---|
| 1-133 | | 486.3 |
| 1-134 | | 452.2 |

TABLE 30

| Ex. | formula | positive MS (M + 1)(free form) |
|---|---|---|
| 1-135 | | 452.2 |
| 1-136 | | 484.3 |

TABLE 30-continued

| Ex. | formula | positive MS (M + 1)(free form) |
|---|---|---|
| 1-137 | | 500.3 |
| 1-138 | | 534.3 |
| 1-139 | | 540.3 |

TABLE 31

| Ex. | formula | positive MS (M + 1)(free form) |
|---|---|---|
| 1-140 | | 520.3 |

TABLE 31-continued

| Ex. | formula | positive MS (M + 1)(free form) |
|---|---|---|
| 1-141 | (structure) HCl | 540.3 |
| 1-142 | (structure) 2HCl | 520.3 |
| 1-143 | (structure) 2HCl | 486.3 |

TABLE 32

| Ex. | formula | positive MS (M + 1)(free form) |
|---|---|---|
| 1-144 | (structure) 2HCl | 526.3 |

TABLE 32-continued
| Ex. | formula | positive MS (M + 1)(free form) |
|---|---|---|
| 1-145 | 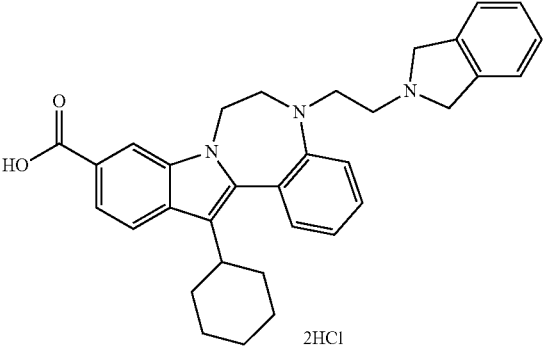 2HCl | 506.3 |
| 1-146 | 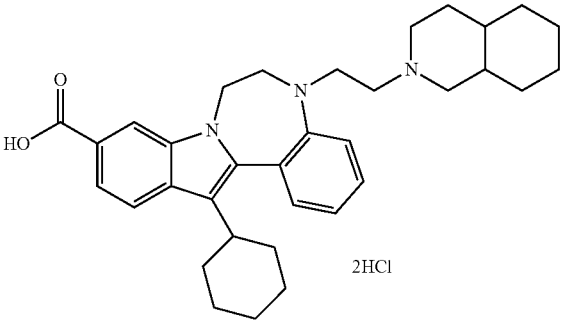 2HCl | 526.3 |
| 1-147 | 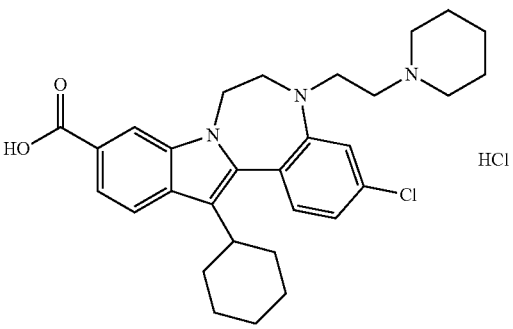 HCl | 506.1 |
| 1-148 | 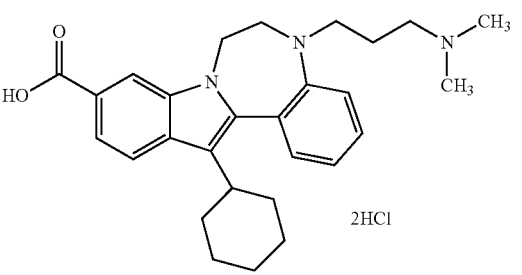 2HCl | 446.3 |

TABLE 33
| Ex. | formula | positive MS (M + 1)(free form) |
|---|---|---|
| 1-149 | 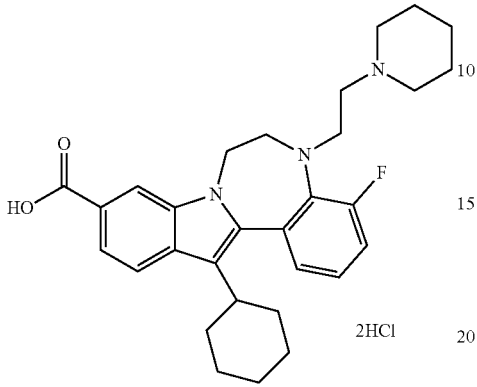 2HCl | 506.3 |
| 1-150 | 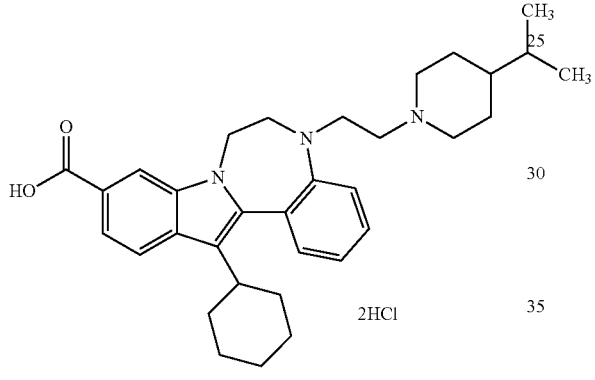 2HCl | 514.4 |
| 1-151 | 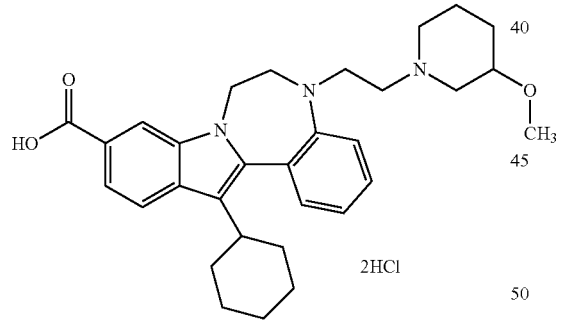 2HCl | 502.3 |
| 1-152 | 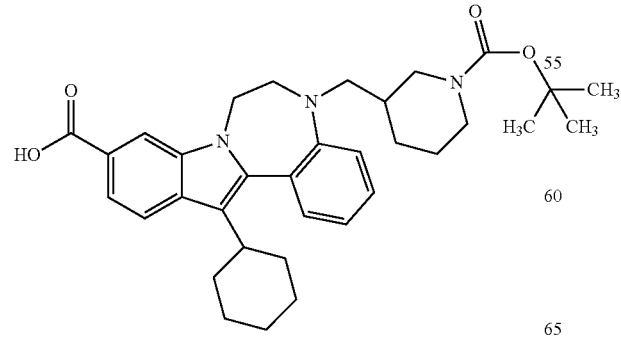 | 558.3 |

TABLE 34
| Ex. | formula | positive MS (M + 1)(free form) |
|---|---|---|
| 1-153 | 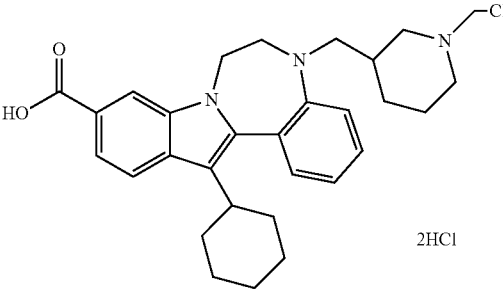 2HCl | 486.3 |
| 1-154 | 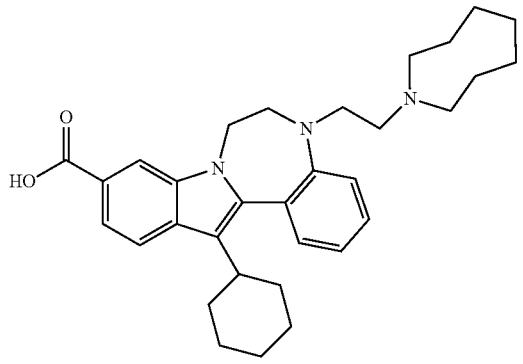 | 500.3 |
| 1-155 | 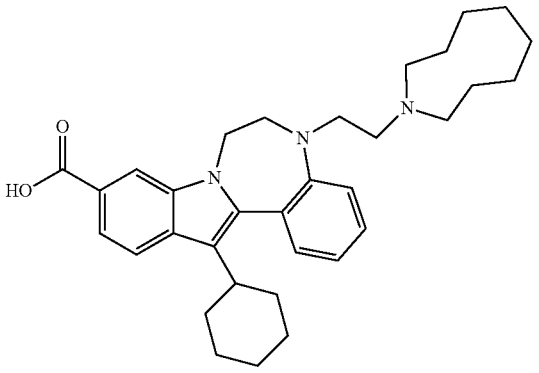 | 514.3 |
| 1-156 | 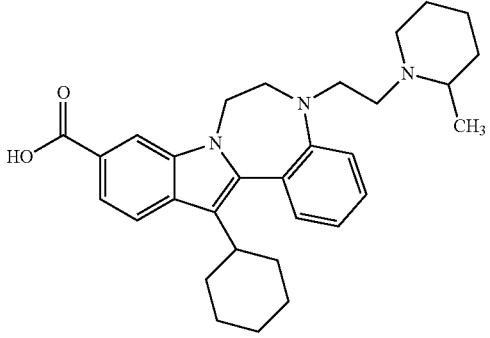 | 486.3 |

TABLE 35
| Ex. | formula | positive MS (M + 1)(free form) |
|---|---|---|
| 1-157 | 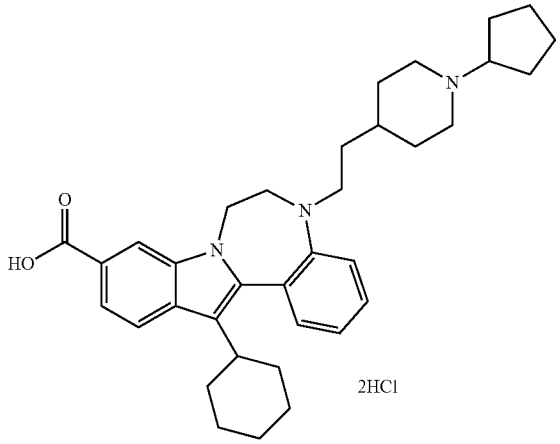 2HCl | 540.4 |
| 1-158 | 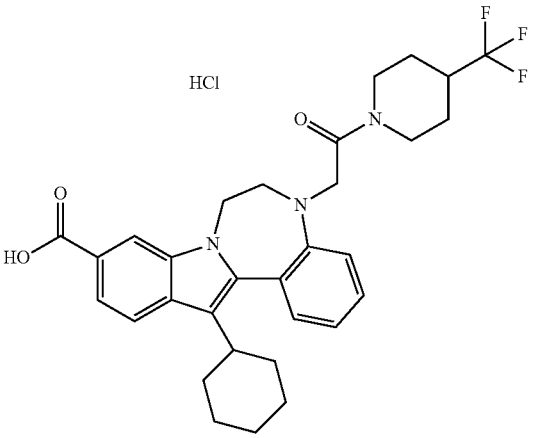 HCl | 554.3 |
| 1-159 | 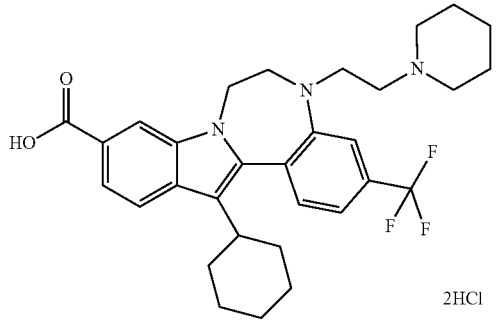 2HCl | 540.3 |
| 1-160 | 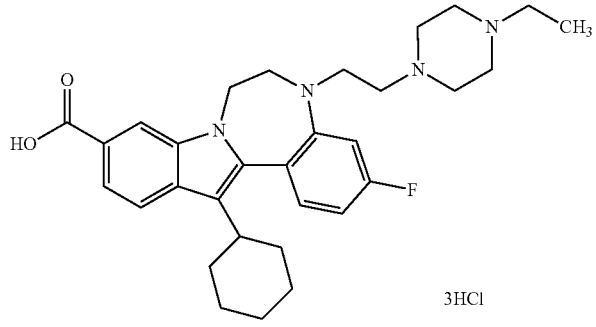 3HCl | 519.3 |

TABLE 36
| Ex. | formula | positive MS (M + 1)(free form) |
|---|---|---|
| 1-161 | 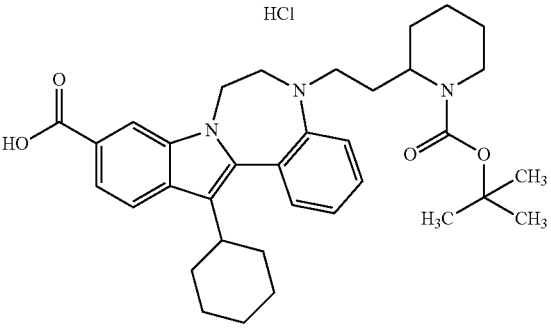 HCl | 572.3 |
| 1-162 | 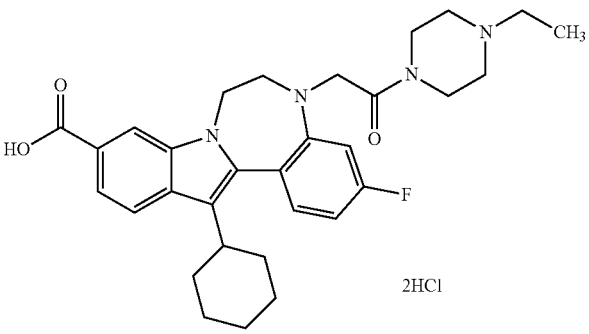 2HCl | 533.3 |
| 1-163 | 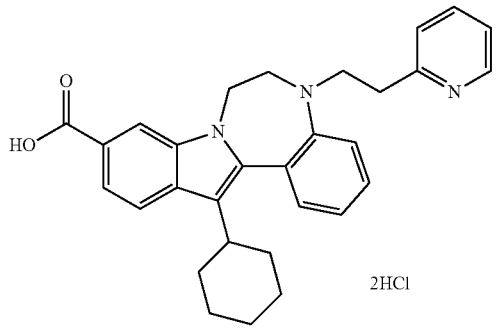 2HCl | 466.3 |
| 1-164 | 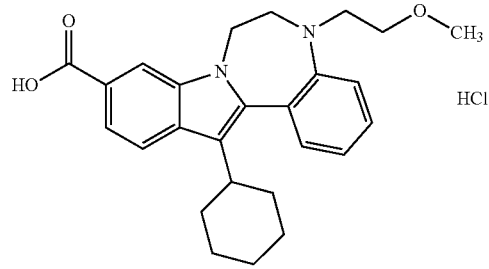 HCl | 419.2 |

TABLE 36-continued
| Ex. | formula | positive MS (M + 1)(free form) |
|---|---|---|
| 1-165 | 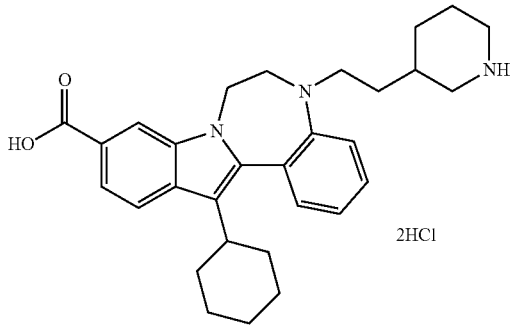 2HCl | 472.3 |
TABLE 38
| Ex. | formula | positive MS (M + 1)(free form) |
|---|---|---|
| 1-171 | 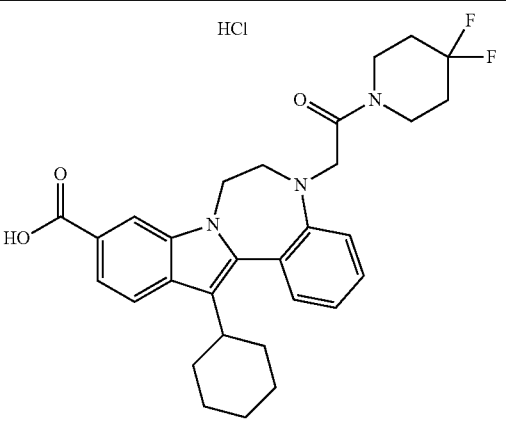 HCl | 522.3 |
| 1-172 | 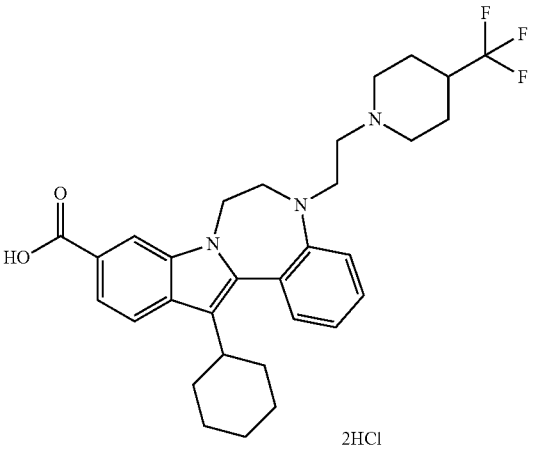 2HCl | 540.3 |

TABLE 38-continued
| Ex. | formula | positive MS (M + 1)(free form) |
|---|---|---|
| 1-173 | 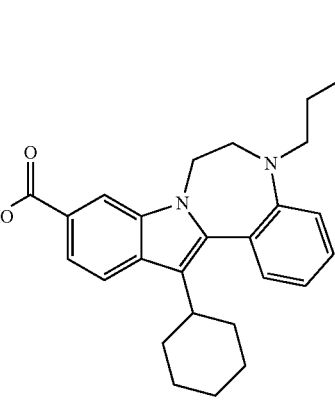 2HCl | 514.4 |
| 1-174 | 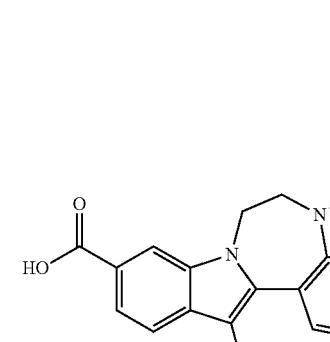 2HCl | 508.3 |
Table 39
| Ex. | formula | positive MS (M + 1)(free form) |
|---|---|---|
| 1-175 | 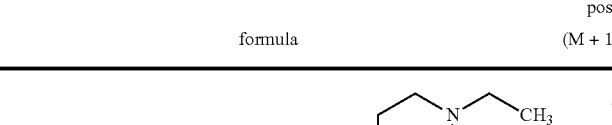 2HCl | 516.3 |

Table 39-continued
| Ex. | formula | positive MS (M + 1)(free form) |
|---|---|---|
| 1-176 | 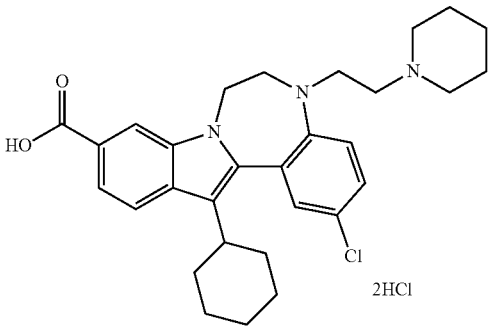 2HCl | 506.3 |
| 1-177 | 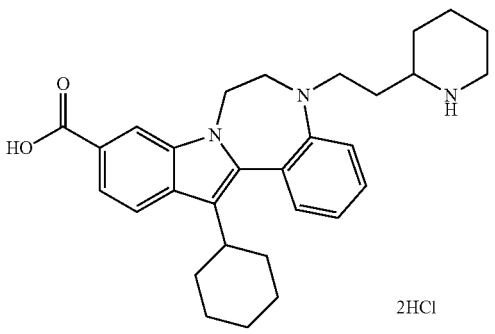 2HCl | 472.3 |
| 1-178 | 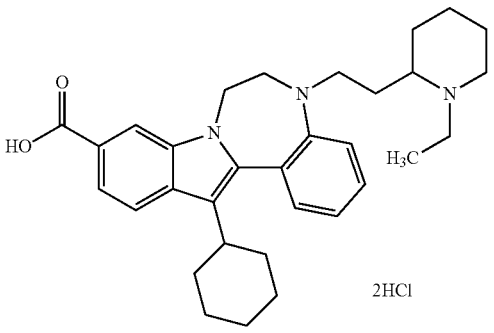 2HCl | 500.4 |
| 1-179 | 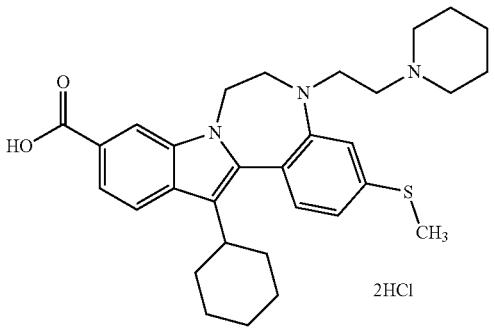 2HCl | 518.3 |

TABLE 40
| Ex. | formula | positive MS (M + 1)(free form) |
|---|---|---|
| 1-180 | 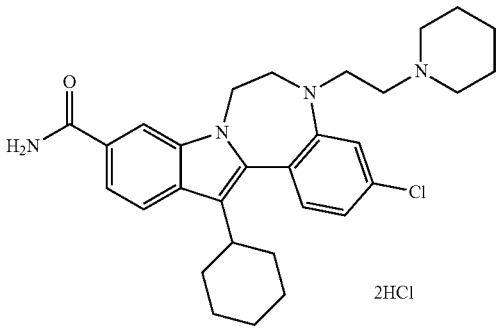 2HCl | 505.3 |
| 1-181 | 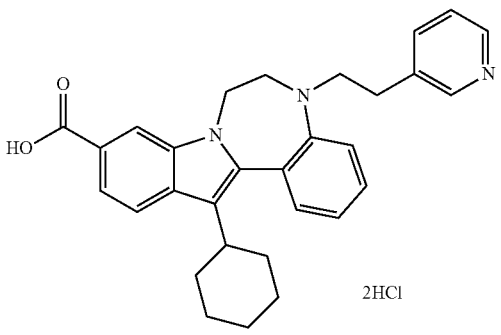 2HCl | 466.3 |
| 1-182 | 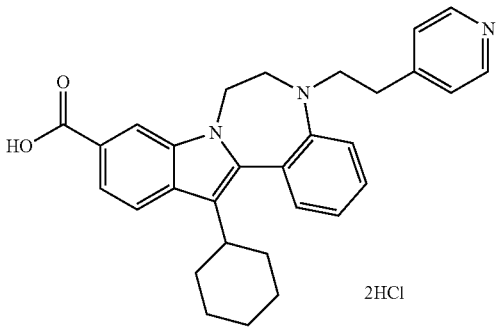 2HCl | 466.3 |
| 1-183 | 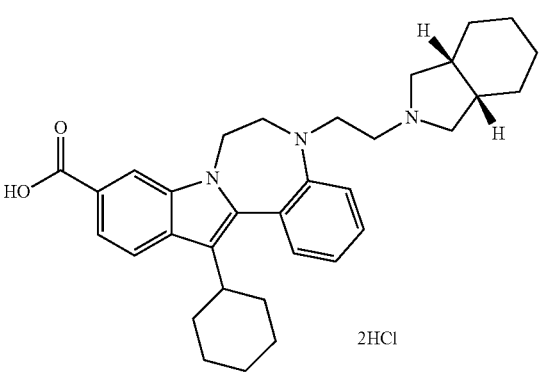 2HCl | 512.3 |

TABLE 41

| Ex. | formula | positive MS (M + 1)(free form) |
|---|---|---|
| 1-184 | 2HCl | 526.4 |
| 1-185 | 2HCl | 460.3 |
| 1-186 | 2HCl | 488.3 |
| 1-187 | HCl | 514.3 |

TABLE 42
| Ex. | formula | positive MS (M + 1)(free form) |
|---|---|---|
| 1-188 | 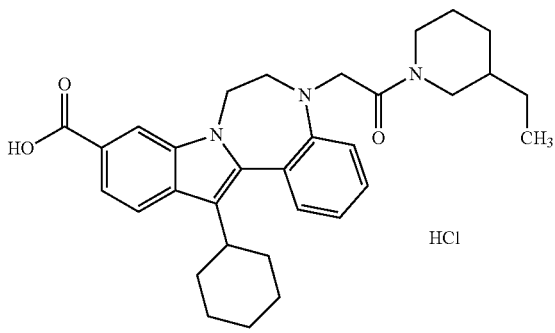 HCl | 514.3 |
| 1-189 | 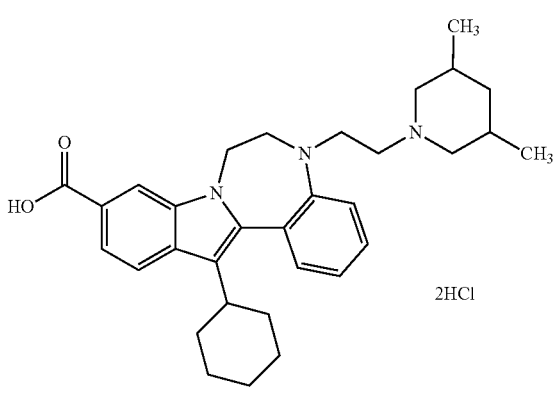 2HCl | 500.3 |
| 1-190 | 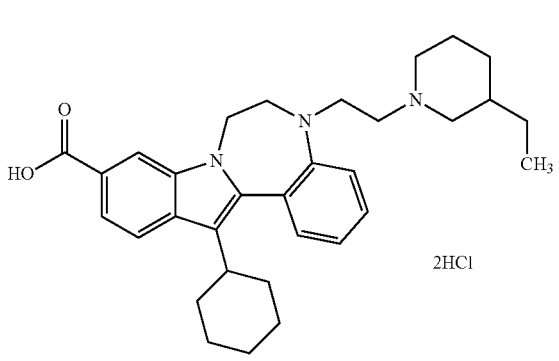 2HCl | 500.3 |
| 1-191 | 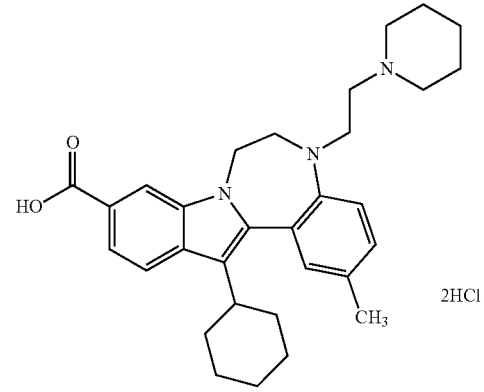 2HCl | 486.3 |

TABLE 43
| Ex. | formula | positive MS (M + 1)(free form) |
|---|---|---|
| 1-192 | 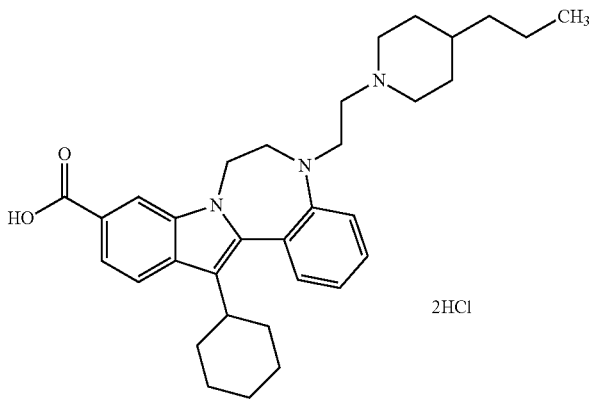 2HCl | 514.4 |
| 1-193 | 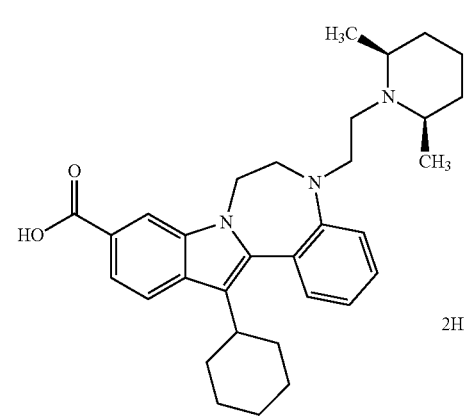 2HCl | 500.3 |
| 1-194 | 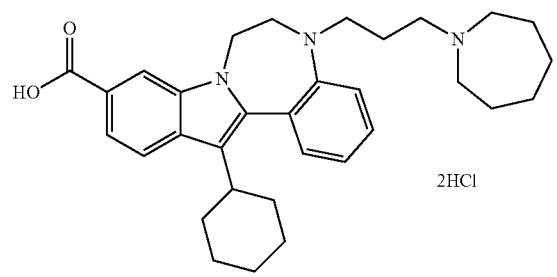 2HCl | 500.4 |
| 1-195 | 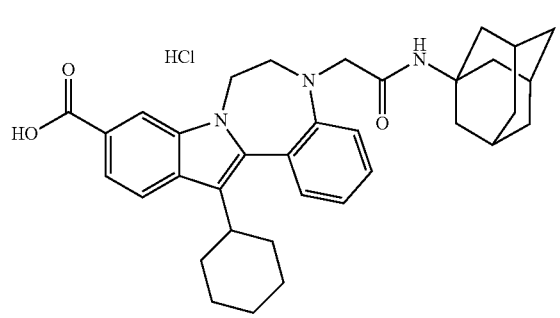 HCl | 552.3 |

TABLE 44
| Ex. | formula | positive MS (M + 1) (free form) |
|---|---|---|
| 1-196 | 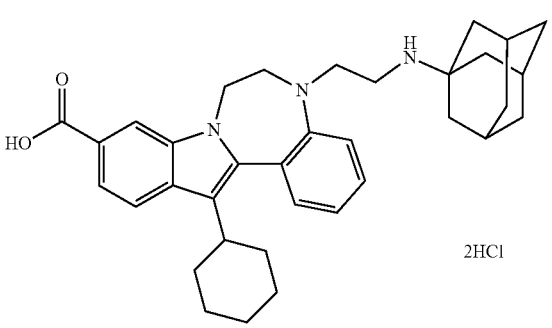 2HCl | 538.3 |
| 1-197 | 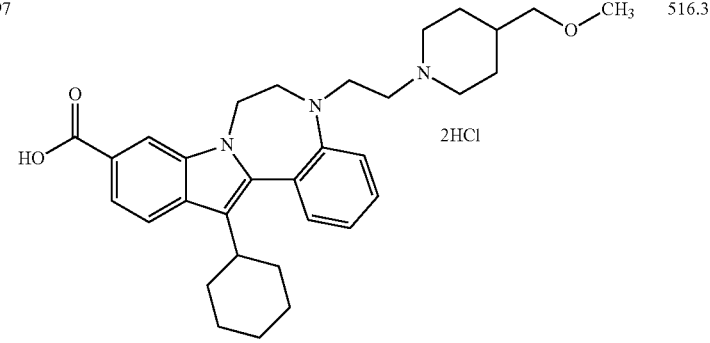 2HCl | 516.3 |
| 1-198 | 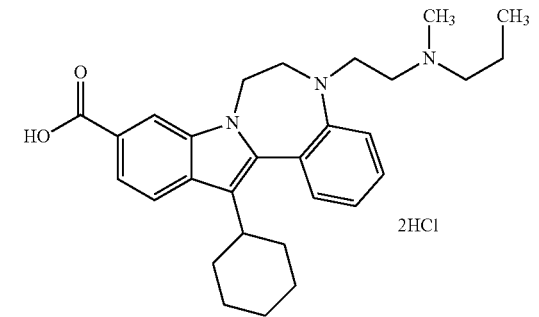 2HCl | 460.3 |
| 1-199 | 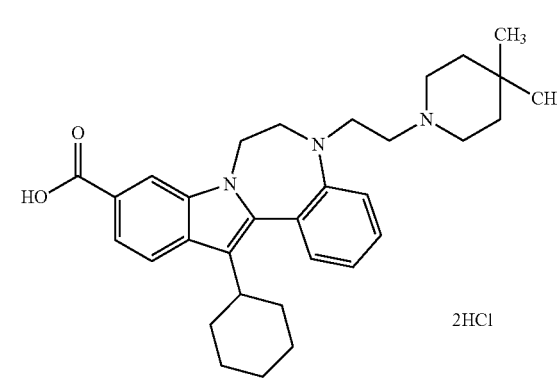 2HCl | 500.3 |

TABLE 45
| Ex. | formula | positive MS (M + 1) (free from) |
|---|---|---|
| 1-200 | 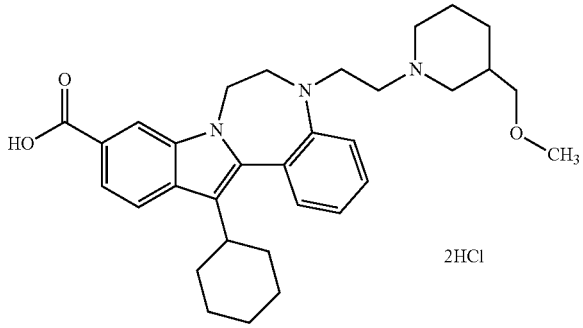 2HCl | 516.3 |
| 1-201 | 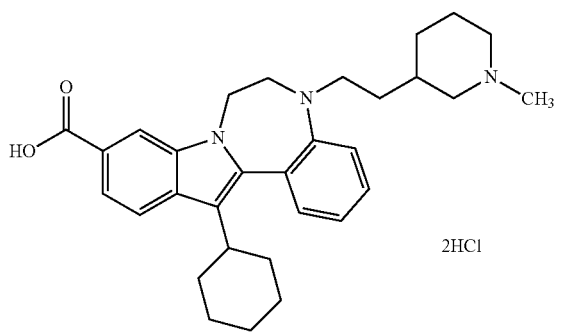 2HCl | 486.3 |
| 1-202 | 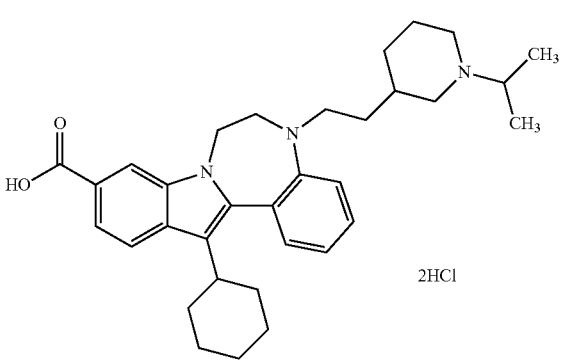 2HCl | 514.3 |
| 1-203 | 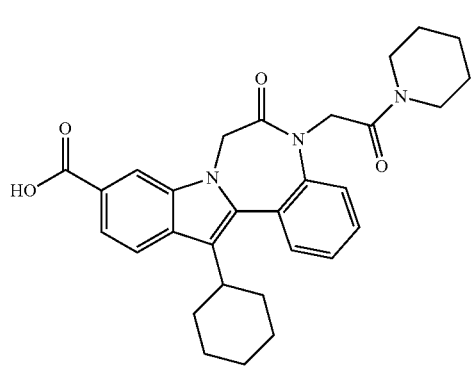 | 500.3 |

TABLE 45-continued
| Ex. | formula | positive MS (M + 1) (free from) |
|---|---|---|
| 1-204 | 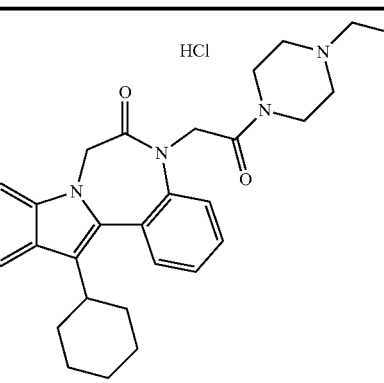 | 529.3 |
TABLE 46
| Ex. | formula | positive MS (M + 1) (free form) |
|---|---|---|
| 1-205 | 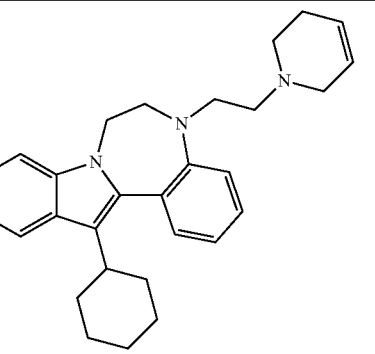 | 470.3 |
| 1-206 | 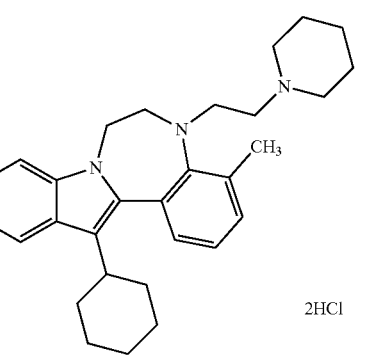 2HCl | 486.3 |
| 1-207 | 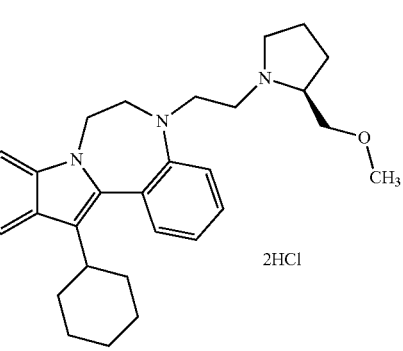 2HCl | 502.2 |

TABLE 46-continued
| Ex. | formula | positive MS (M + 1) (free form) |
|---|---|---|
| 1-208 | 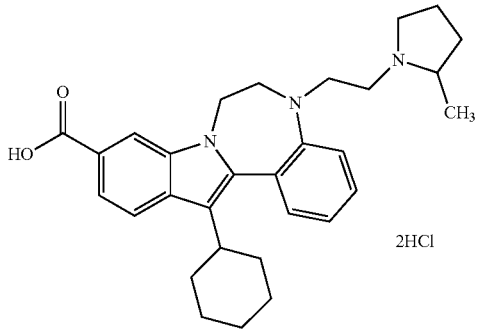 2HCl | 472.3 |
| 1-209 | 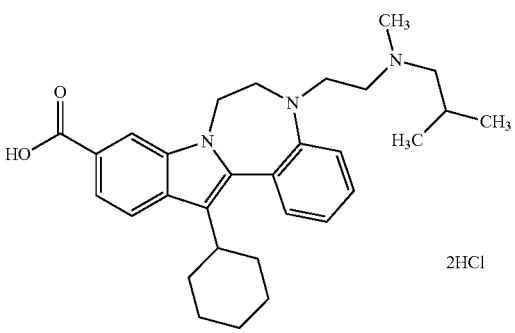 2HCl | 474.3 |
TABLE 47
| Ex. | formula | positive MS (M + 1) (free form) |
|---|---|---|
| 1-210 | 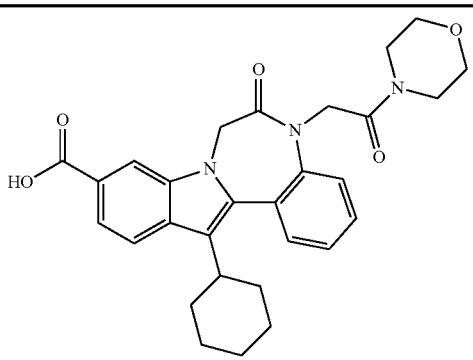 | 502.3 |
| 1-211 | 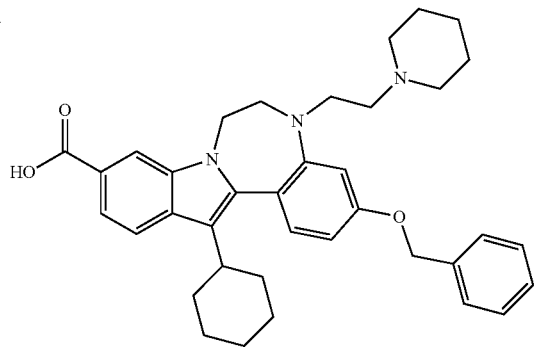 | 578.3 |

TABLE 47-continued
| Ex. | formula | positive MS (M + 1) (free form) |
|---|---|---|
| 1-212 | 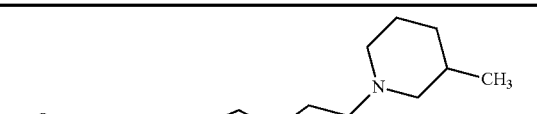 2HCl | 460.3 |
| 1-213 | 2HCl | 520.3 |
TABLE 48
| Ex. | formula | positive MS (M + 1) (free form) |
|---|---|---|
| 1-214 | 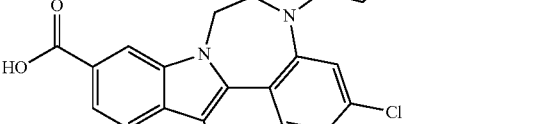 2HCl | 520.3 |
| 1-215 | 2HCl | 520.3 |

TABLE 48-continued
| Ex. | formula | positive MS (M + 1) (free form) |
|---|---|---|
| 1-216 | 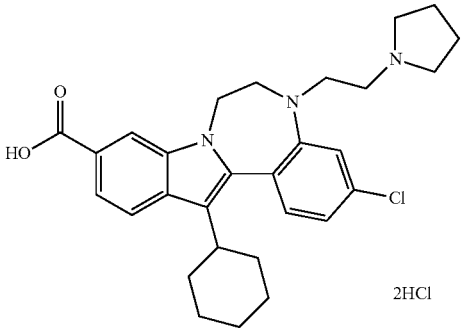 2HCl | 492.3 |
| 1-217 | 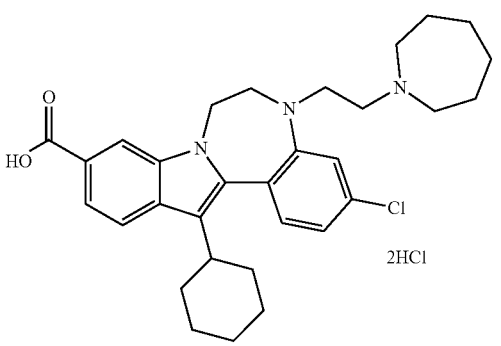 2HCl | 520.3 |
| 1-218 | 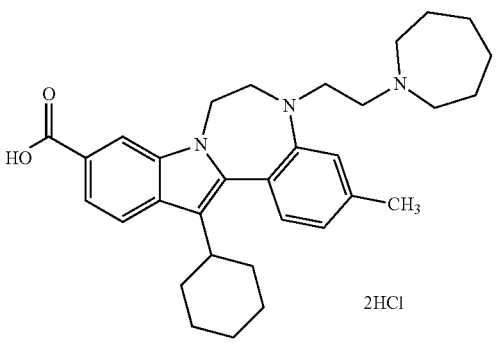 2HCl | 500.3 |
TABLE 49
| Ex. | formula | positive MS (M + 1) (free form) |
|---|---|---|
| 1-219 | 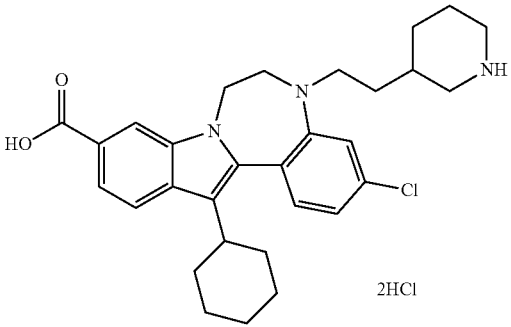 2HCl | 506.3 |

TABLE 49-continued
| Ex. | formula | positive MS (M + 1) (free form) |
|---|---|---|
| 1-220 | 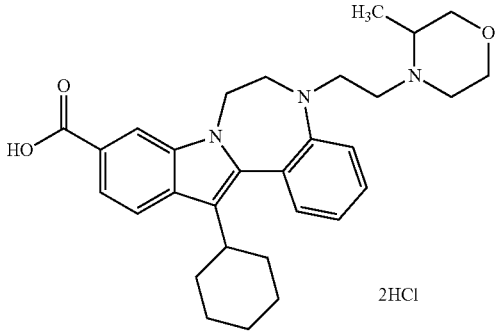 2HCl | 488.3 |
| 1-221 | 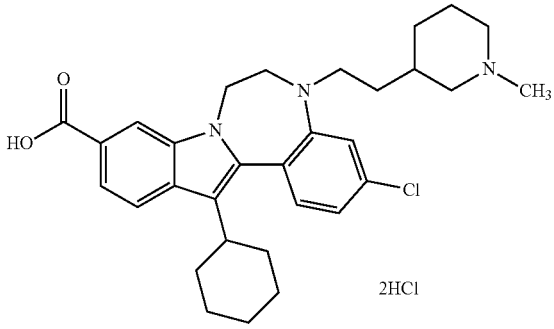 2HCl | 520.3 |
| 1-222 | 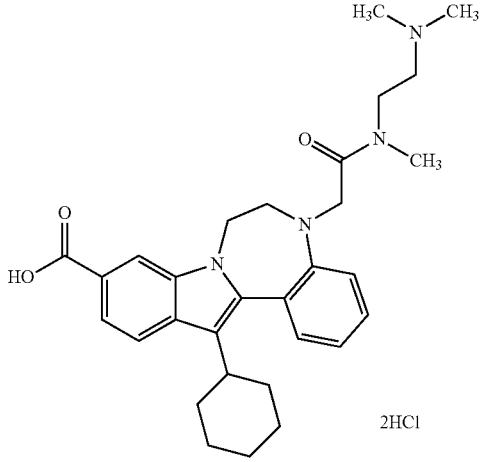 2HCl | 503.3 |

TABLE 50
| Ex. | formula | positive MS (M + 1) (free form) |
|---|---|---|
| 1-223 | 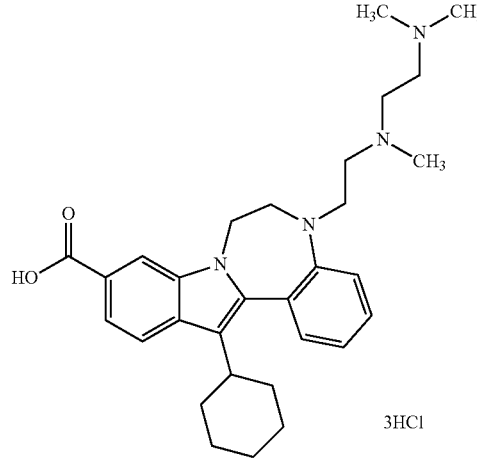 3HCl | 489.3 |
| 1-224 | 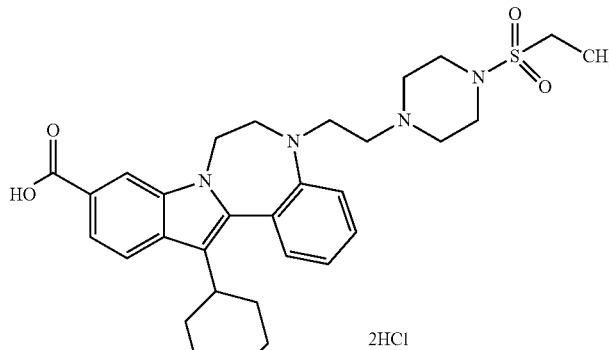 2HCl | 565.3 |
| 1-225 | 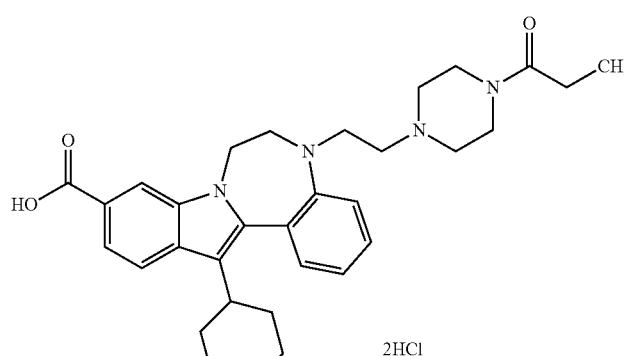 2HCl | 529.3 |

TABLE 50-continued
| Ex. | formula | positive MS (M + 1) (free form) |
|---|---|---|
| 1-226 | 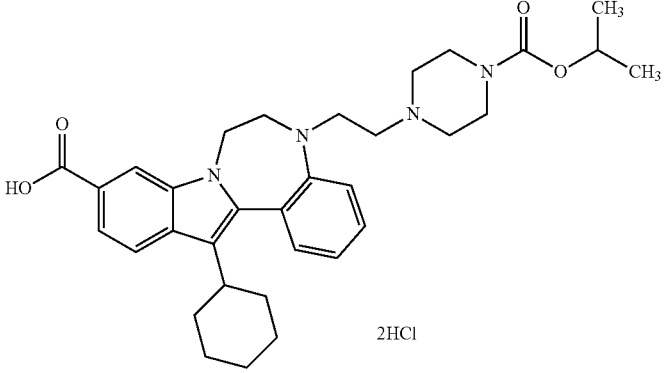 2HCl | 559.4 |
TABLE 51
| Ex. | formula | positive MS (M + 1) (free form) |
|---|---|---|
| 1-227 | 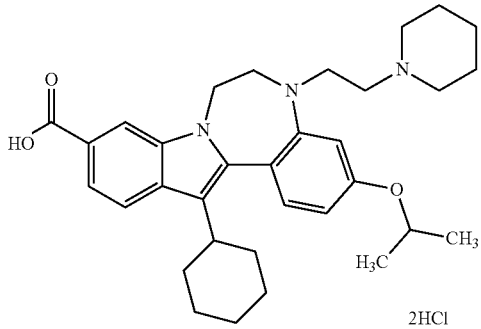 2HCl | 530.3 |
| 1-228 | 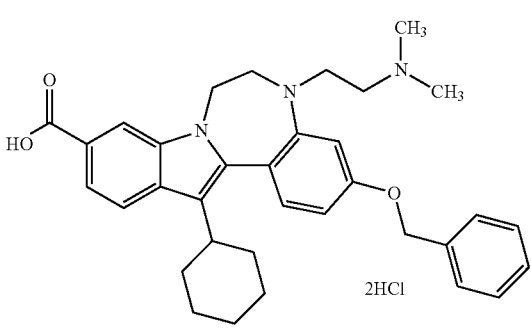 2HCl | 538.3 |
| 1-229 | 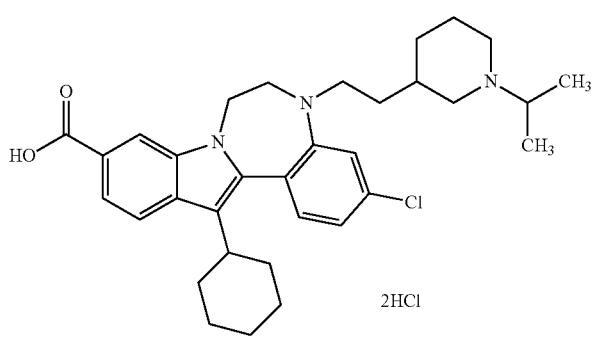 2HCl | 548.3 |

TABLE 51-continued
| Ex. | formula | positive MS (M + 1) (free form) |
|---|---|---|
| 1-230 | 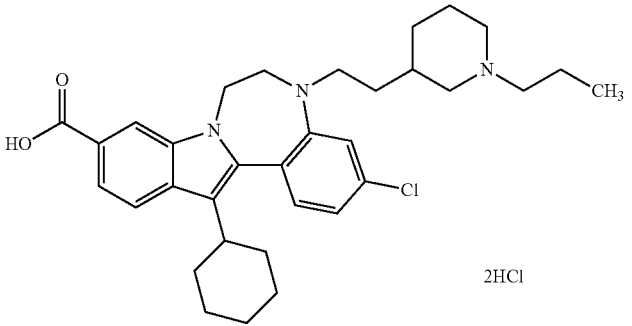 2HCl | 548.3 |
| 1-231 | 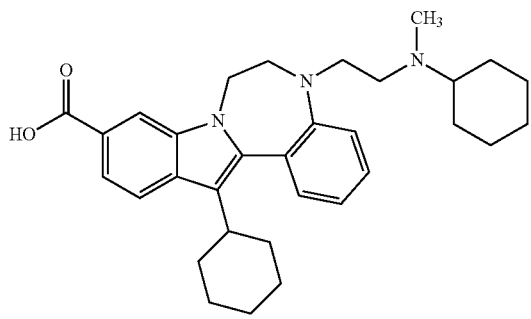 | 500.3 |
TABLE 52
| Ex. | formula | positive MS (M + 1) (free form) |
|---|---|---|
| 1-232 | 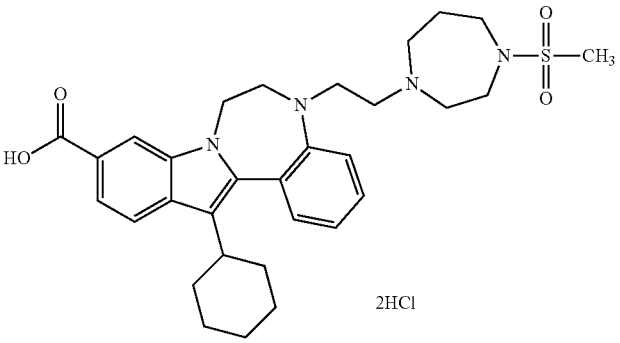 2HCl | 565.3 |
| 1-233 | 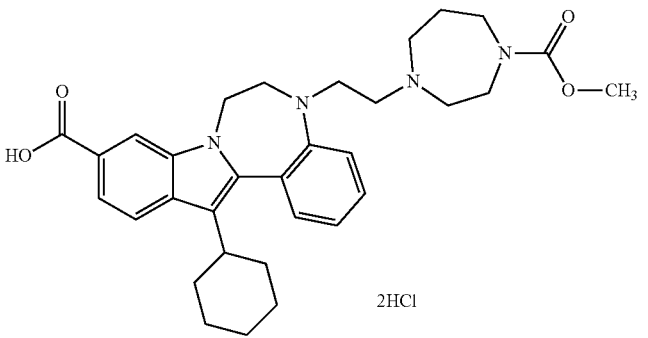 2HCl | 545.3 |

TABLE 52-continued
| Ex. | formula | positive MS (M + 1) (free form) |
|---|---|---|
| 1-234 | 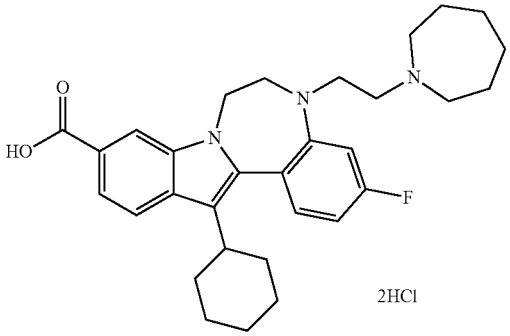 2HCl | 504.3 |
| 1-235 | 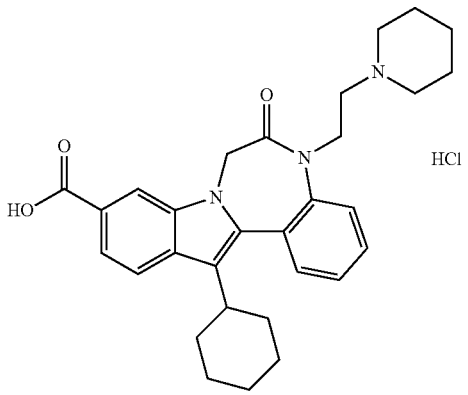 HCl | 486.3 |
TABLE 53
| Ex. | formula | positive MS (M + 1) (free form) |
|---|---|---|
| 1-236 | 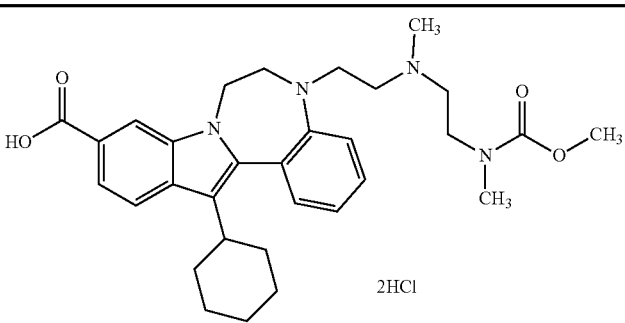 2HCl | 533.3 |
| 1-237 | 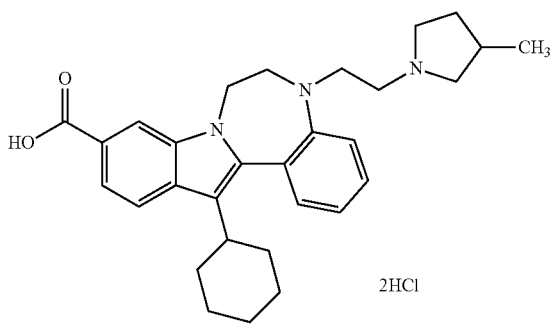 2HCl | 472.3 |

TABLE 53-continued
| Ex. | formula | positive MS (M + 1) (free form) |
|---|---|---|
| 1-238 | 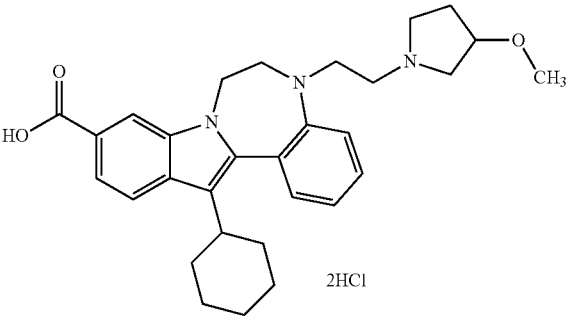 2HCl | 488.3 |
| 1-239 | 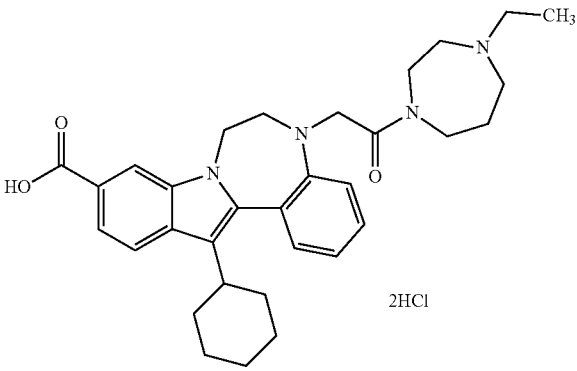 2HCl | 529.3 |
TABLE 54
| Ex. | formula | positive MS (M + 1) (free form) |
|---|---|---|
| 1-240 | 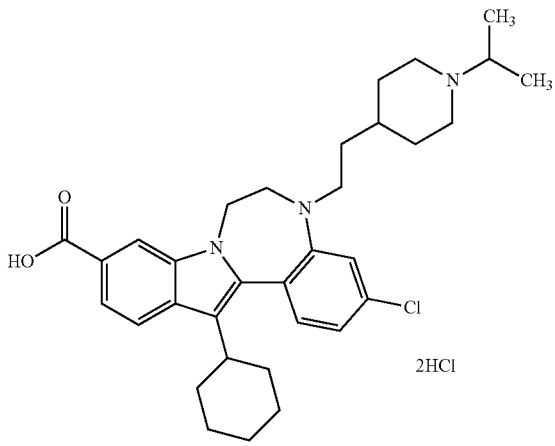 2HCl | 548.3 |

TABLE 54-continued

| Ex. | formula | positive MS (M + 1) (free form) |
|---|---|---|
| 1-241 | | 486.3 |
| 1-242 | (2HCl) | 520.3 |
| 1-243 | (2HCl) | 534.3 |

TABLE 55
| Ex. | formula | positive MS (M + 1) (free form) |
|---|---|---|
| 1-244 | 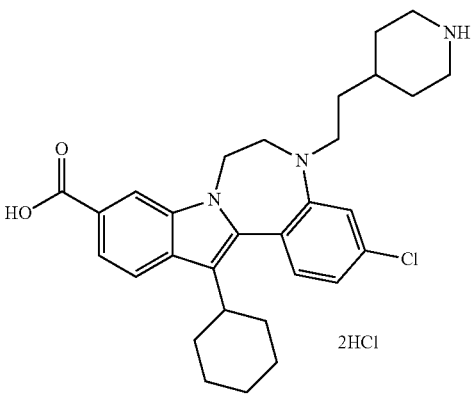 2HCl | 506.3 |
| 1-245 | 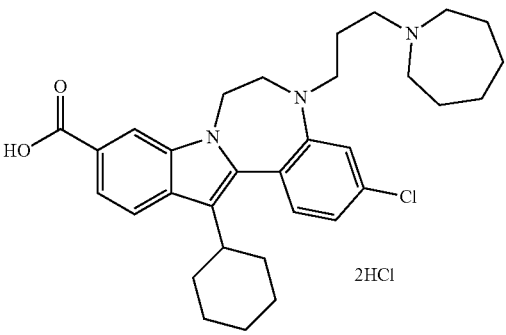 2HCl | 534.3 |
| 1-246 | 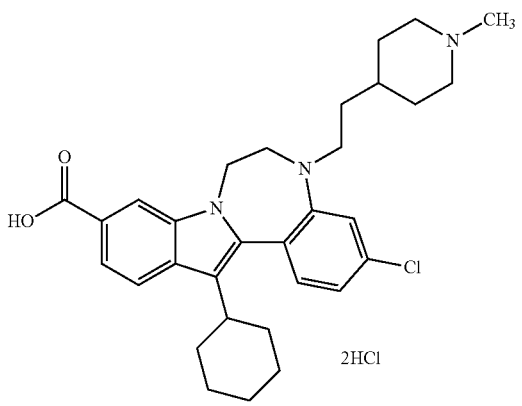 2HCl | 520.3 |
| 1-247 | 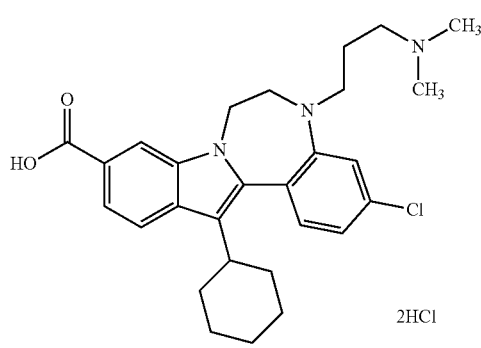 2HCl | 480.2 |

TABLE 56
| Ex. | formula | positive MS (M + 1) (free form) |
|---|---|---|
| 1-248 | 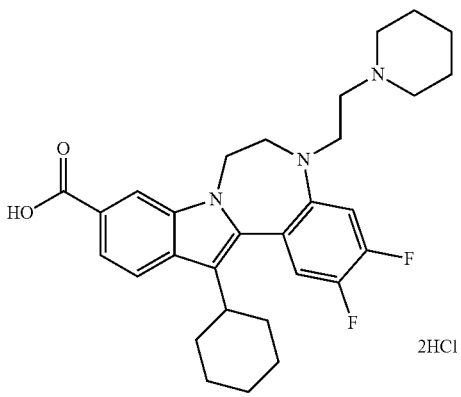 2HCl | 508.3 |
| 1-249 | 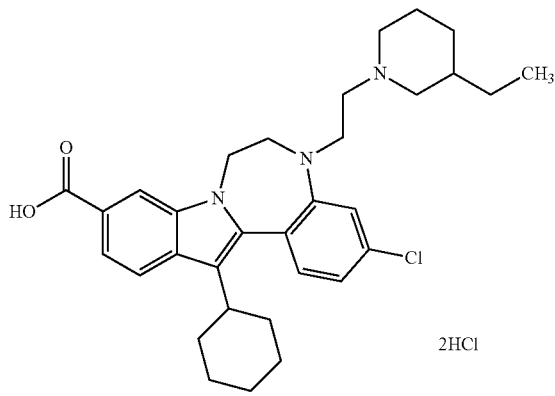 2HCl | 534.3 |
| 1-250 | 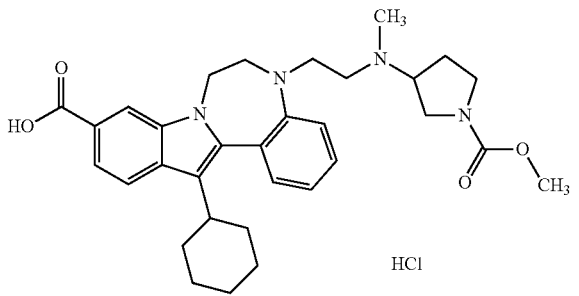 HCl | 545.3 |
| 1-251 | 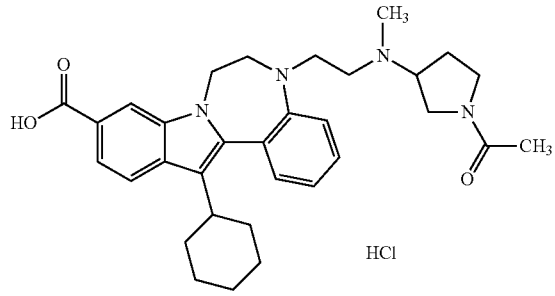 HCl | 529.3 |

TABLE 57
| Ex. | formula | positive MS (M + 1) (free form) |
| --- | --- | --- |
| 1-252 | 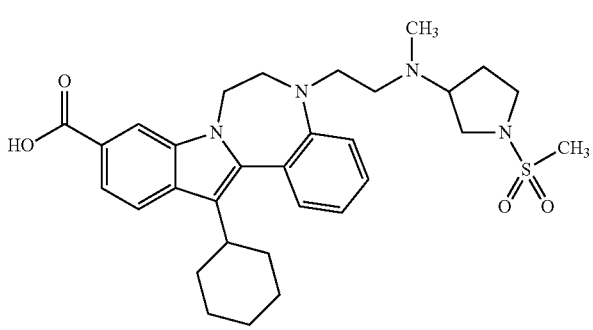 | 565.3 |
| 1-253 | 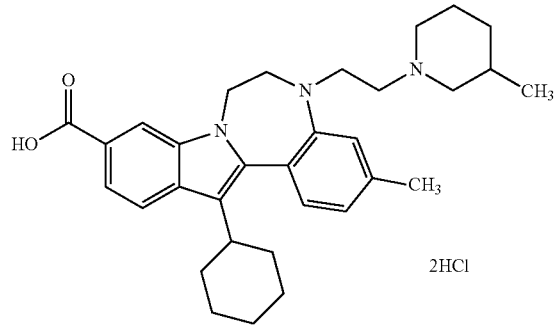 | 500.3 |
| 1-254 | 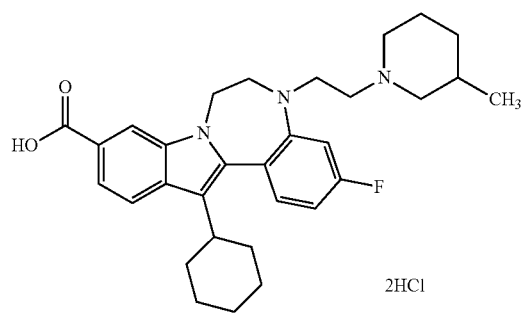 | 504.3 |
| 1-255 | 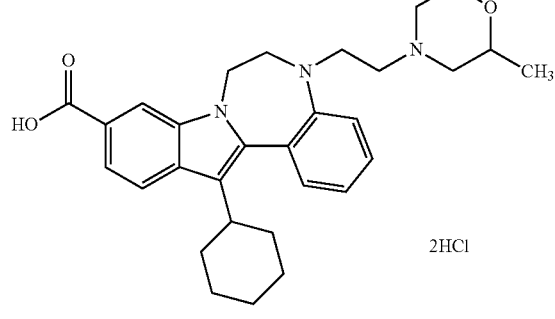 | 488.3 |

TABLE 57-continued

| Ex. | formula | positive MS (M + 1) (free form) |
|---|---|---|
| 1-256 | [structure: carboxylic acid-substituted indole fused diazepine with cyclohexyl, phenyl, and 2-ethylmorpholinyl-ethyl substituents; 2HCl] | 502.3 |

TABLE 58

| Ex. | formula | positive MS (M + 1) (free form) |
|---|---|---|
| 1-257 | [structure: carboxylic acid-substituted indole fused diazepine with cyclohexyl, phenyl, and 3-ethylmorpholinyl-ethyl substituents; 2HCl] | 502.3 |
| 1-258 | [structure: carboxylic acid-substituted indole fused diazepine with cyclohexyl, methyl-phenyl, and 2-methylpiperidinyl-ethyl substituents; 2HCl] | 500.3 |
| 1-259 | [structure: carboxylic acid-substituted indole fused diazepine with cyclohexyl, methyl-phenyl, and 4-methylpiperidinyl-ethyl substituents; 2HCl] | 500.3 |

TABLE 58-continued
| Ex. | formula | positive MS (M + 1) (free form) |
|---|---|---|
| 1-260 | 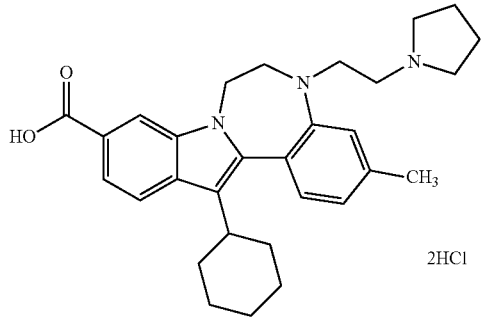 2HCl | 472.3 |
| 1-261 | 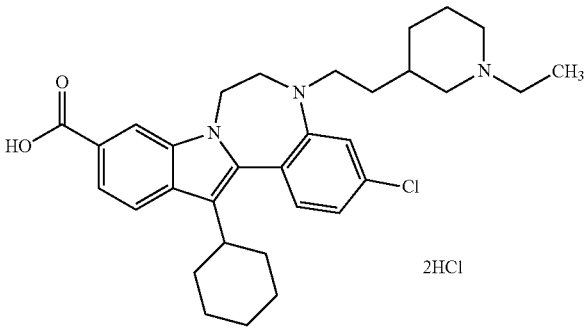 2HCl | 534.3 |
TABLE 59
| Ex. | formula | positive MS (M + 1) (free form) |
|---|---|---|
| 1-262 | 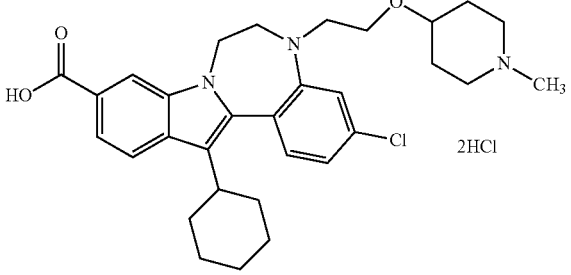 2HCl | 536.3 |
| 1-263 | 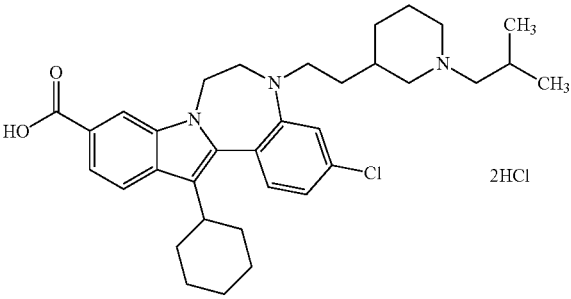 2HCl | 562.3 |

TABLE 59-continued
| Ex. | formula | positive MS (M + 1) (free form) |
|---|---|---|
| 1-264 | 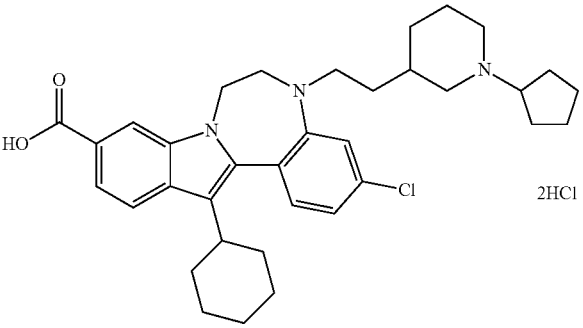 2HCl | 574.3 |
| 1-265 | 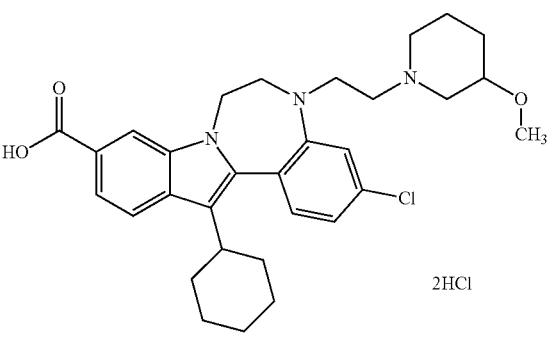 2HCl | 536.3 |
| 1-266 | 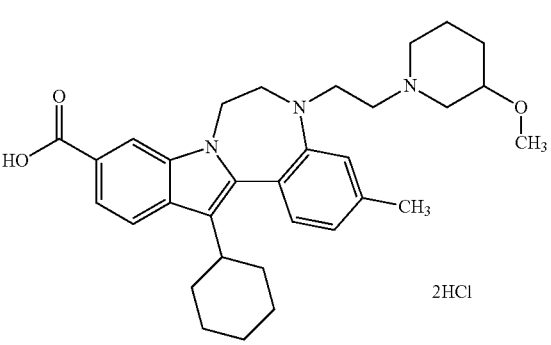 2HCl | 516.3 |
TABLE 60
| Ex. | formula | positive MS (M + 1)(free form) |
|---|---|---|
| 1-267 | 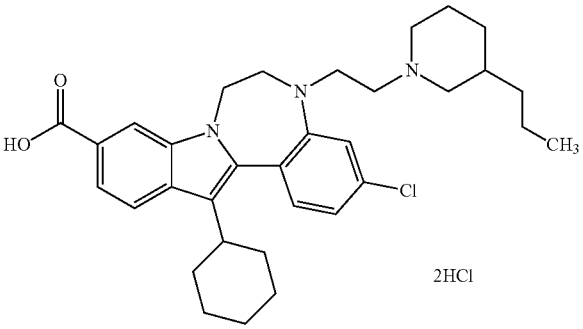 2HCl | 548.3 |

TABLE 60-continued
| Ex. | formula | positive MS (M + 1)(free form) |
|---|---|---|
| 1-268 | 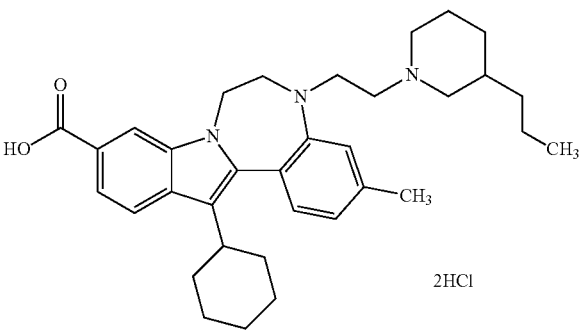 2HCl | 528.4 |
| 1-269 | 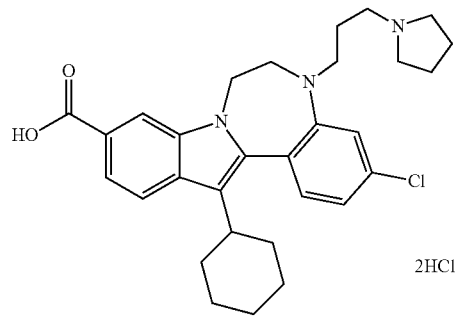 2HCl | 506.3 |
| 1-270 | 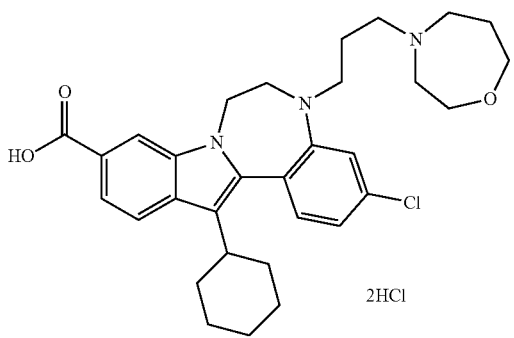 2HCl | 536.3 |
TABLE 61
| Ex. | formula | positive MS (M + 1)(free form) |
|---|---|---|
| 1-271 | 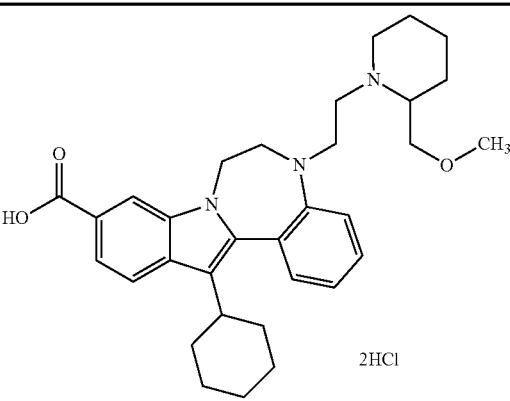 2HCl | 516.3 |

TABLE 61-continued
| Ex. | formula | positive MS (M + 1)(free form) |
|---|---|---|
| 1-272 | 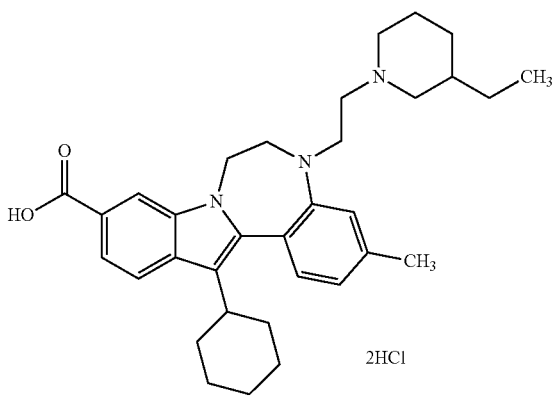 2HCl | 514.3 |
| 1-273 | 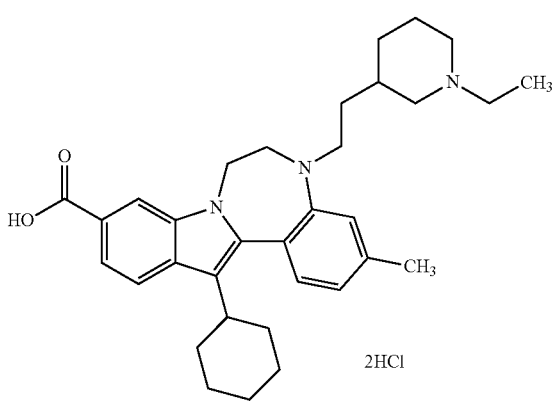 2HCl | 514.4 |
| 1-274 | 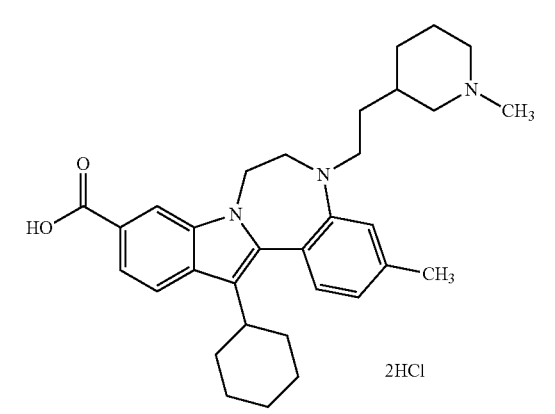 2HCl | 500.3 |

TABLE 62
| Ex. | formula | positive MS (M + 1)(free form) |
|---|---|---|
| 1-275 | 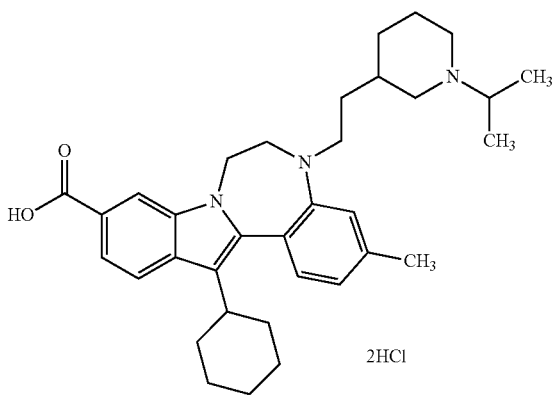 2HCl | 528.4 |
| 1-276 | 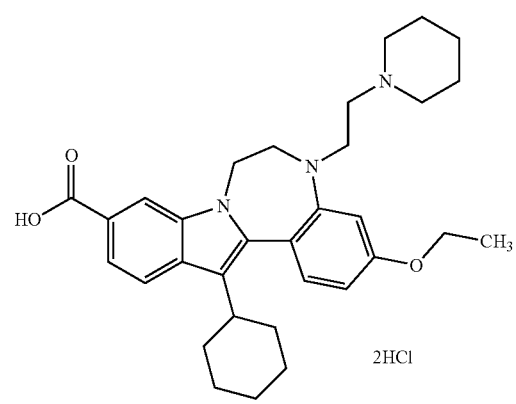 2HCl | 516.3 |
| 1-277 | 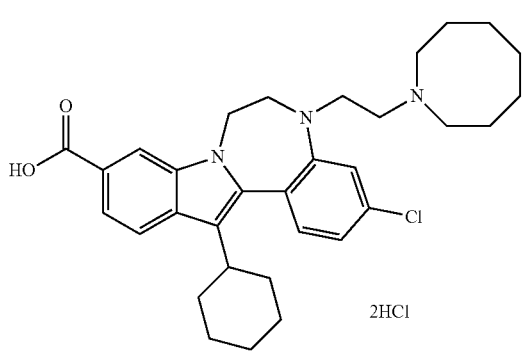 2HCl | 534.3 |
| 1-278 | 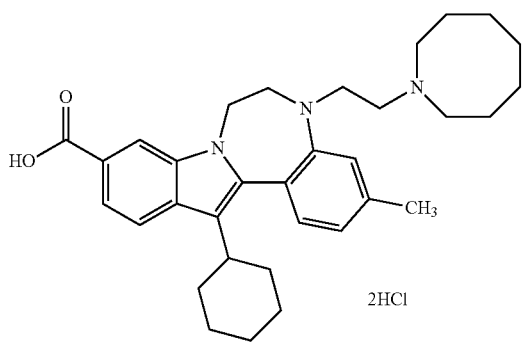 2HCl | 514.4 |

TABLE 63
| Ex. | formula | positive MS (M + 1)(free form) |
|---|---|---|
| 1-279 | 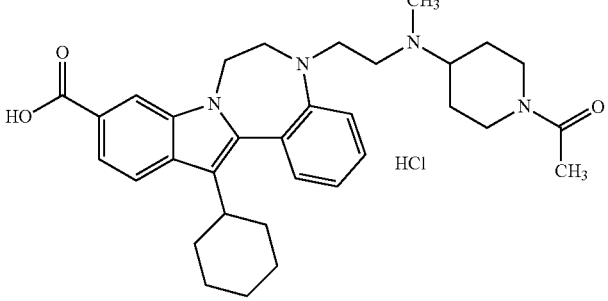 HCl | 543.4 |
| 1-280 | 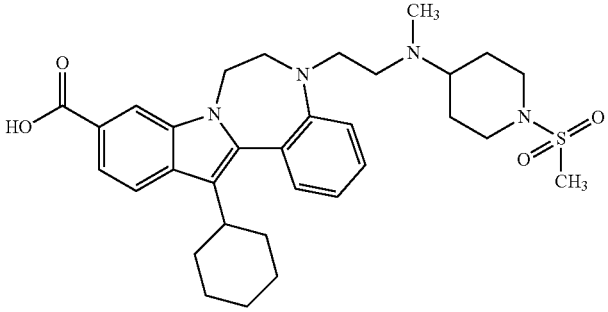 | 579.3 |
| 1-281 | 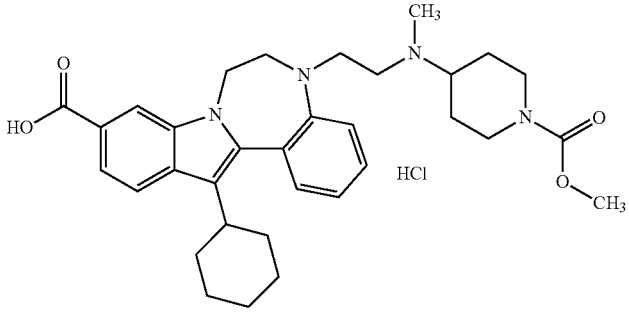 HCl | 559.3 |
| 1-282 | 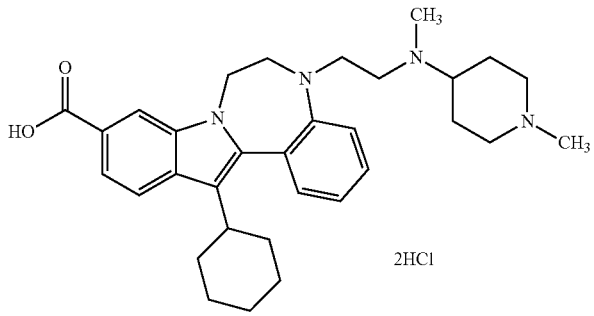 2HCl | 515.3 |

TABLE 63-continued

| Ex. | formula | positive MS (M + 1)(free form) |
|---|---|---|
| 1-283 | | 502.3 |

TABLE 64

| Ex. | formula | positive MS (M + 1)(free form) |
|---|---|---|
| 1-284 | 2HCl | 501.4 |
| 1-285 | 2HCl | 487.3 |
| 1-286 | 3HCl | 515.4 |

TABLE 64-continued
| Ex. | formula | positive MS (M + 1)(free form) |
|---|---|---|
| 1-287 | 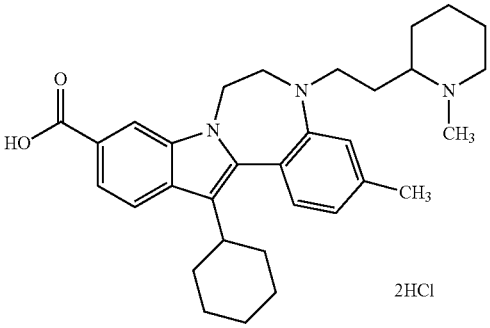 2HCl | 500.4 |
TABLE 65
| Ex. | formula | positive MS (M+ 1)(free form) |
|---|---|---|
| 1-288 | 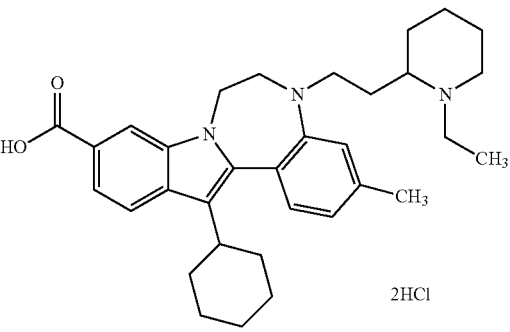 2HCl | 514.4 |
| 1-289 | 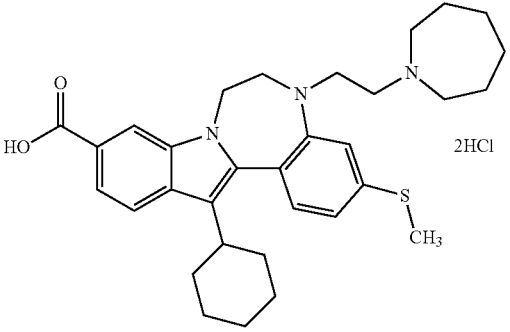 2HCl | 523.3 |
| 1-290 | 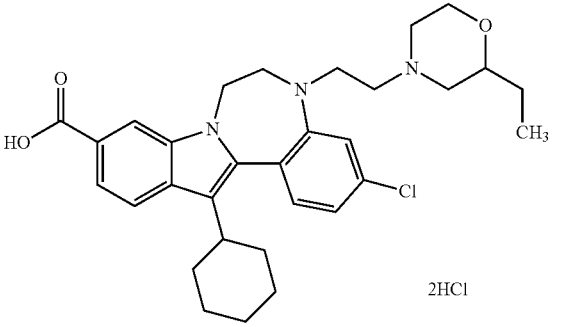 2HCl | 536.3 |

TABLE 65-continued
| Ex. | formula | positive MS (M+ 1)(free form) |
|---|---|---|
| 1-291 | 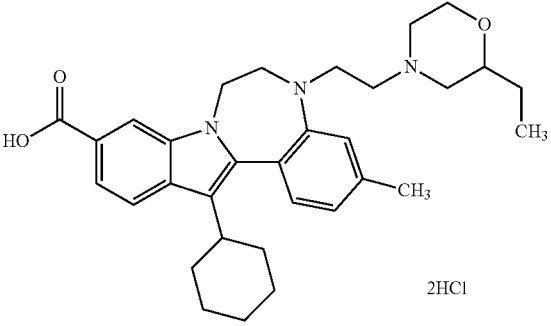 2HCl | 516.3 |
| 1-292 | 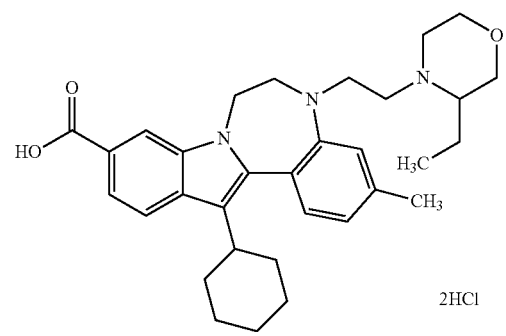 2HCl | 516.4 |
TABLE 66
| Ex. | formula | positive MS (M + 1)(free form) |
|---|---|---|
| 1-293 | 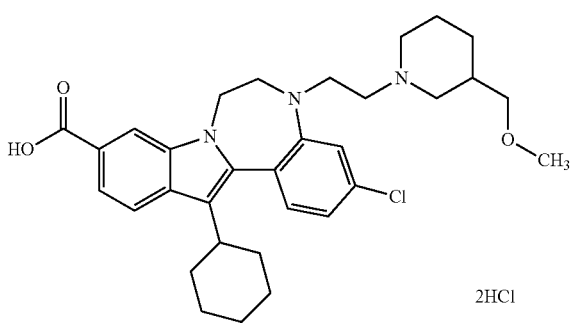 2HCl | 550.3 |
| 1-294 | 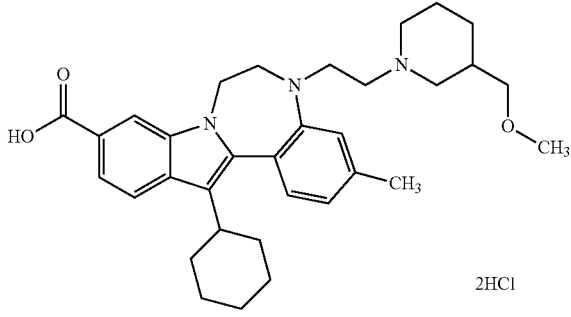 2HCl | 530.4 |

TABLE 66-continued
| Ex. | formula | positive MS (M + 1)(free form) |
|---|---|---|
| 1-295 | 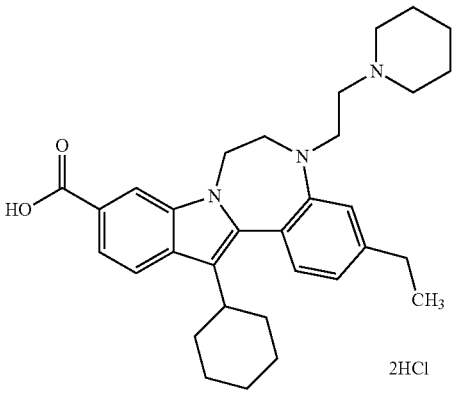 2HCl | 500.3 |
| 1-296 | 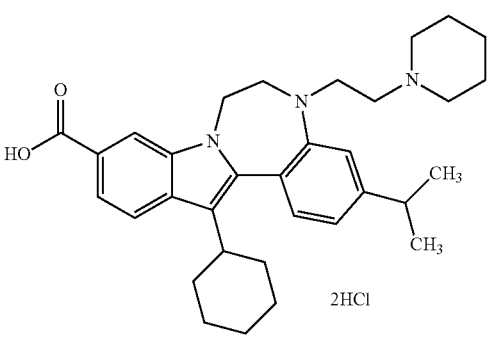 2HCl | 514.4 |
| 1-297 | 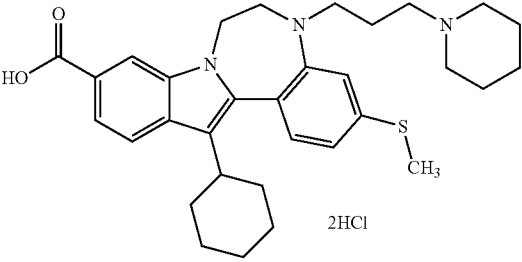 2HCl | 532.3 |
Table 67
| Ex. | formula | positive MS (M + 1)(free form) |
|---|---|---|
| 1-298 | 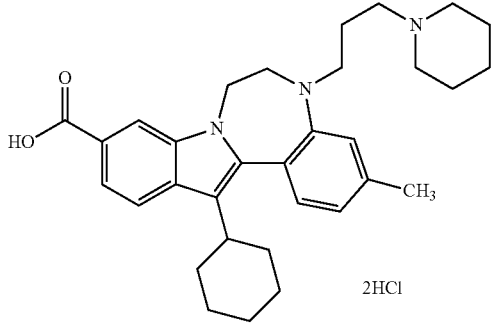 2HCl | 500.4 |

Table 67-continued
| Ex. | formula | positive MS (M + 1)(free form) |
|---|---|---|
| 1-299 | 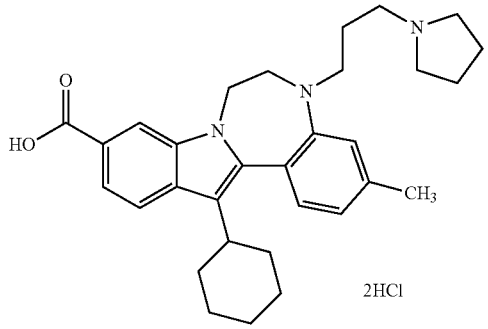 2HCl | 486.3 |
| 1-300 | 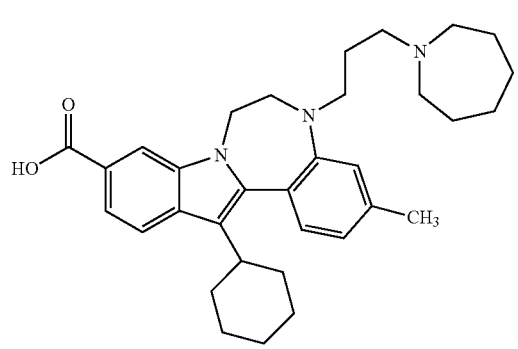 2HCl | 514.4 |
| 1-301 | 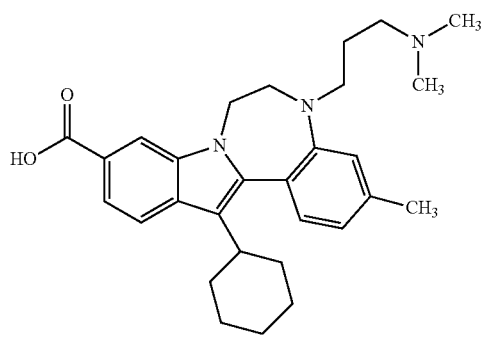 2HCl | 460.3 |
| 1-302 | 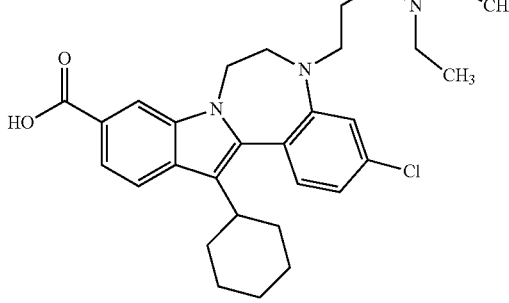 2HCl | 508.3 |

TABLE 68
| Ex. | formula | positive MS (M+1)(free form) |
|---|---|---|
| 1-303 | 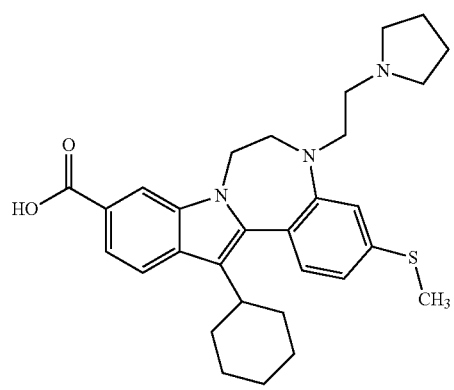<br>2 HCl | 504.3 |
| 1-304 | 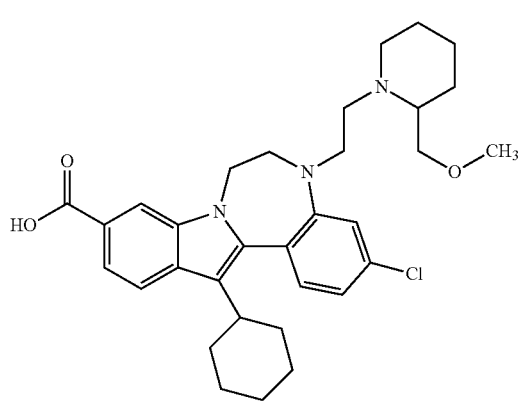<br>2HCl | 550.3 |
| 1-305 | 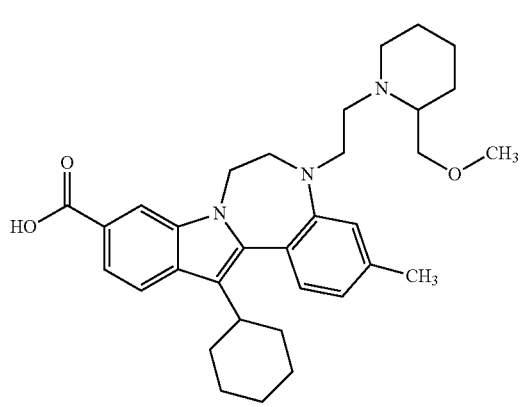<br>2HCl | 530.4 |

TABLE 68-continued
| Ex. | formula | positive MS (M+ 1)(free form) |
|---|---|---|
| 1-306 | 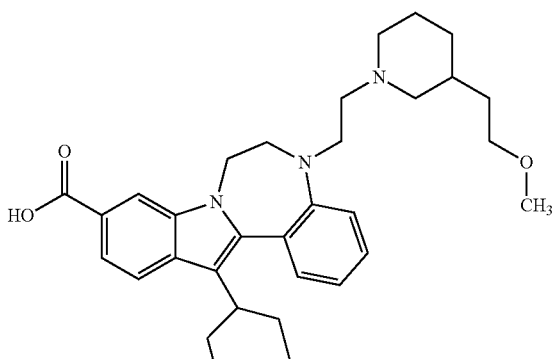 2HCl | 530.3 |
TABLE 69
| Ex. | formula | positive MS (M + 1)(free form) |
|---|---|---|
| 1-307 | 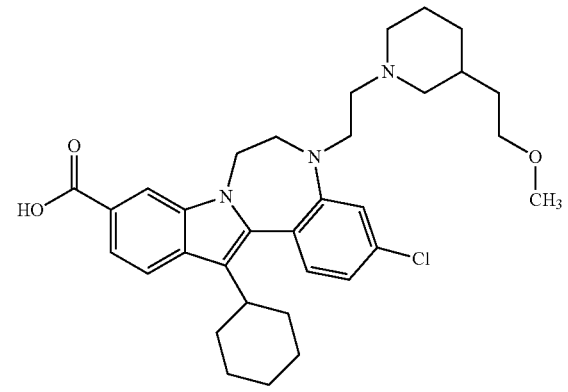 2 HCl | 564.3 |
| 1-308 | 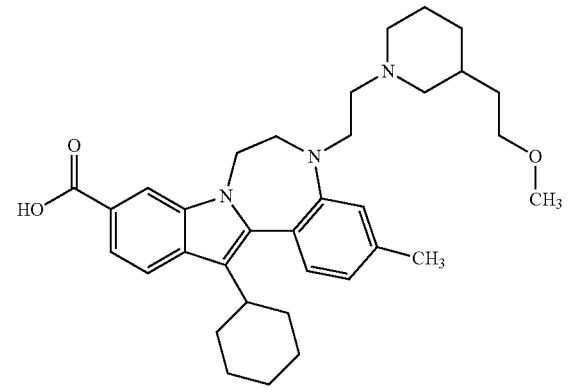 2HCl | 544.4 |

TABLE 69-continued

| Ex. | formula | positive MS (M + 1)(free form) |
|---|---|---|
| 1-309 | (structure) 3HCl | 701.3 |
| 1-310 | (structure) 2HCl | 506.2 |

TABLE 70

| Ex. | formula | positive MS (M + 1)(free form) |
|---|---|---|
| 1-311 | (structure) 2HCl | 524.3 |

TABLE 70-continued
| Ex. | formula | positive MS (M + 1)(free form) |
|---|---|---|
| 1-312 | 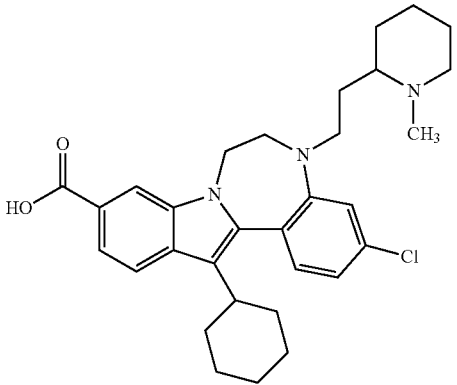 2 HCl | 520.3 |
| 1-313 | 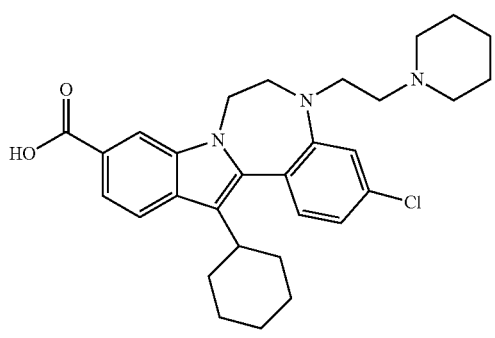 2HCl | 506.3 |
| 1-314 | 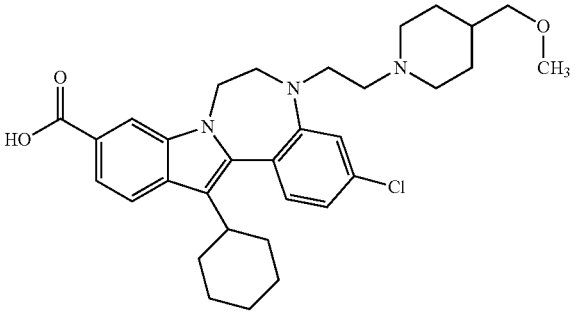 2HCl | 550.3 |

TABLE 71
| Ex. | formula | positive MS (M + 1)(free form) |
|---|---|---|
| 1-315 | 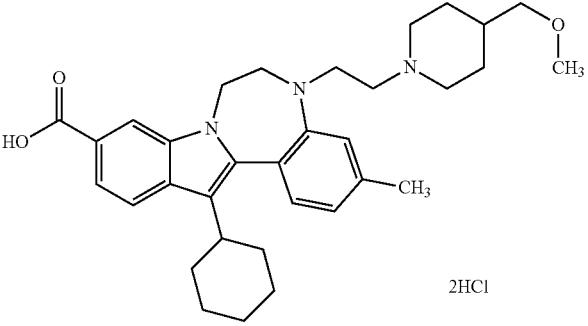 2HCl | 530.4 |
| 1-316 | 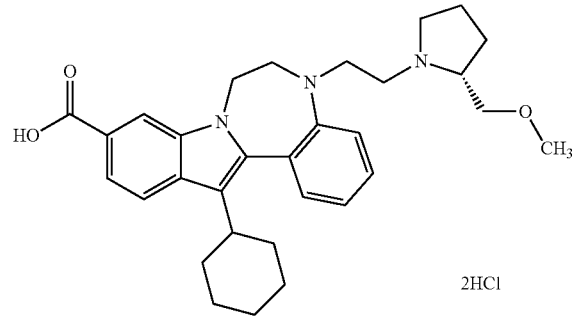 2HCl | 502.3 |
| 1-317 | 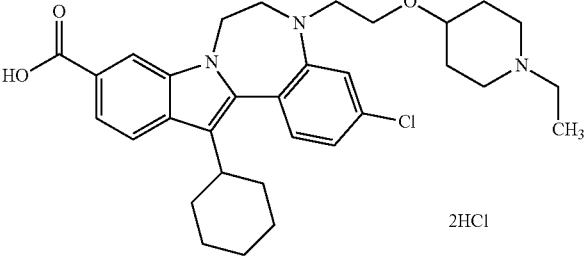 2HCl | 550.3 |
| 1-318 | 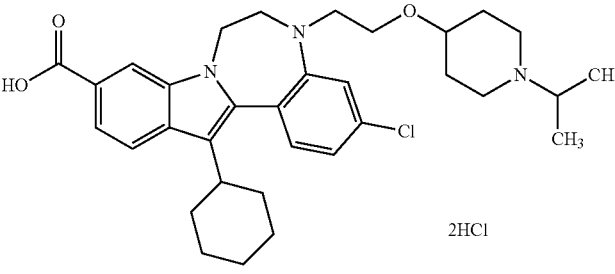 2HCl | 564.3 |
| 1-319 | 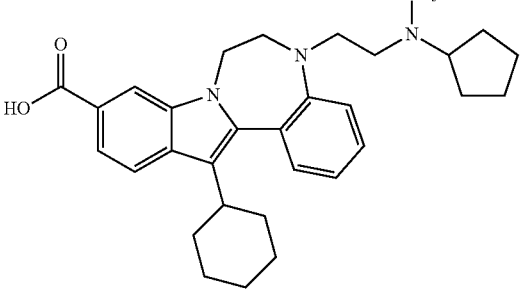 | 486.3 |

TABLE 72
| Ex. | formula | positive MS (M + 1) (free form) |
|---|---|---|
| 1-320 | 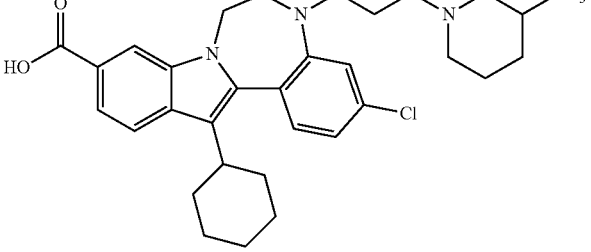 | 534.3 |
| 1-321 | 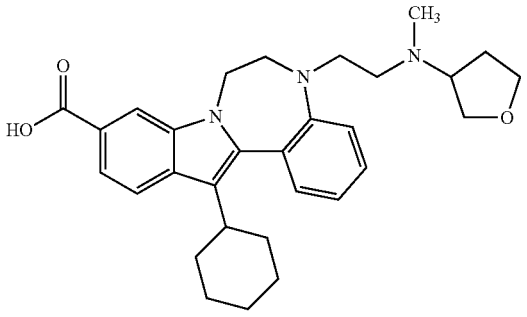 | 488.3 |
| 1-322 | 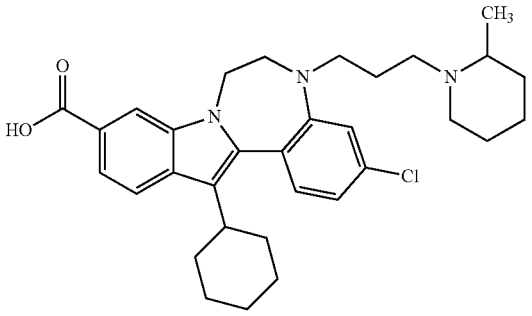 | 534.3 |
| 1-323 | 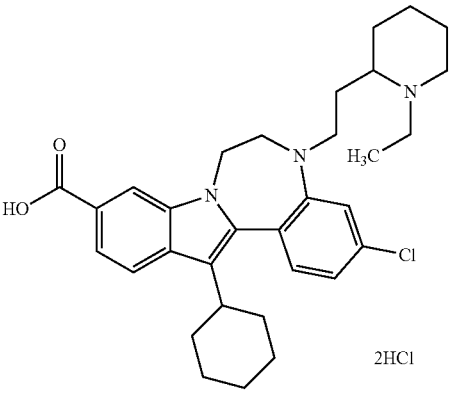 | 534.3 |

TABLE 72-continued
| Ex. | formula | positive MS (M + 1) (free form) |
|---|---|---|
| 1-324 | 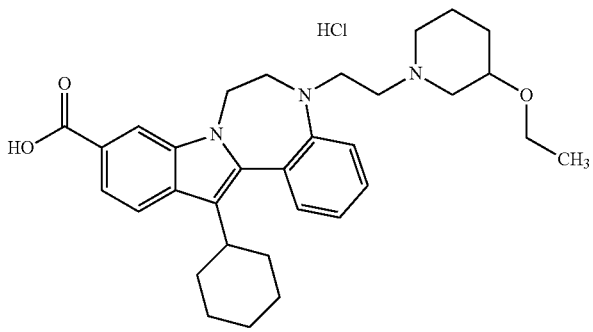 | 516.3 |
TABLE 73
| Ex. | formula | positive MS (M+ 1)(free form) |
|---|---|---|
| 1-325 | 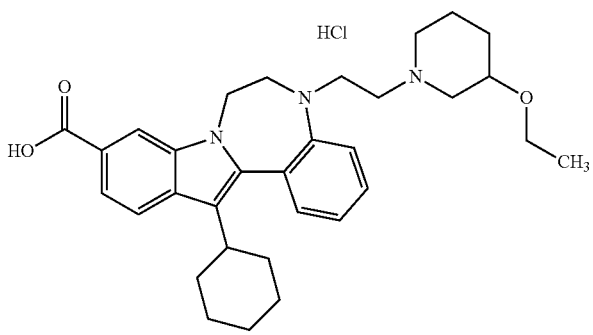 | 530.4 |
| 1-326 | 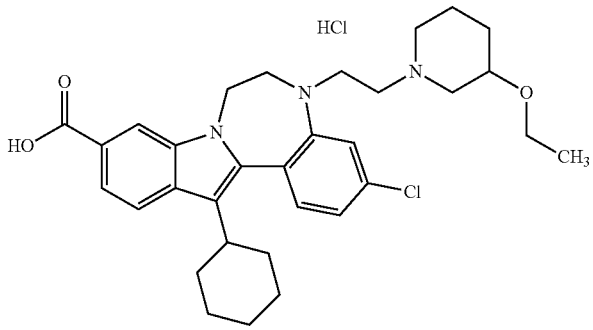 | 550.3 |
| 1-327 | 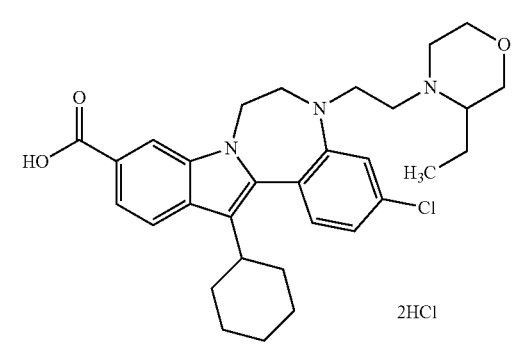 | 536.3 |

TABLE 73-continued
| Ex. | formula | positive MS (M+1)(free form) |
|---|---|---|
| 1-328 | 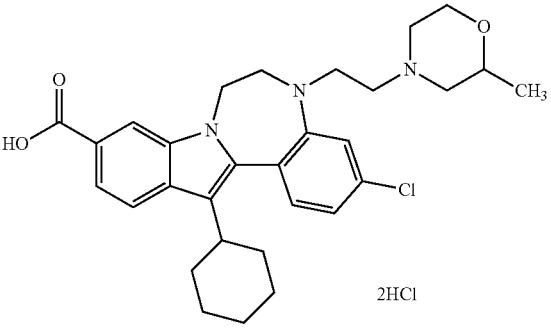 2HCl | 522.3 |
| 1-329 | 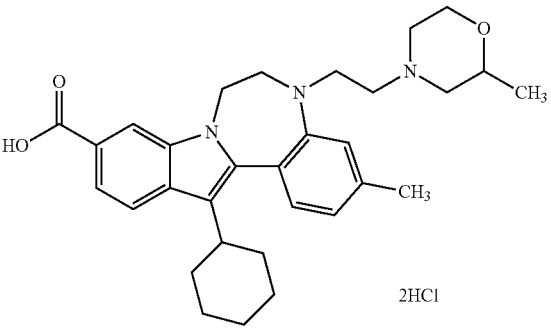 2HCl | 502.3 |
TABLE 74
| Ex. | formula | positive MS (M + 1)(free form) |
|---|---|---|
| 1-330 | 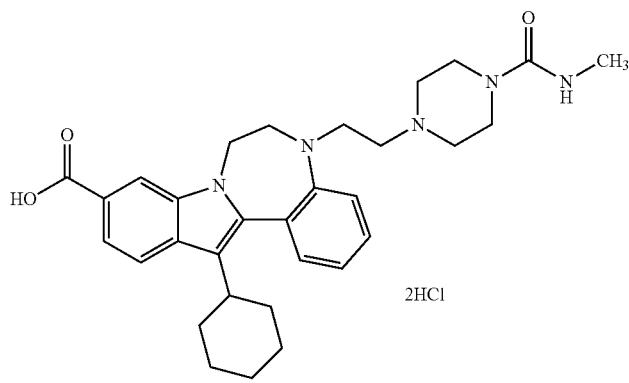 2HCl | 530.3 |
| 1-331 | 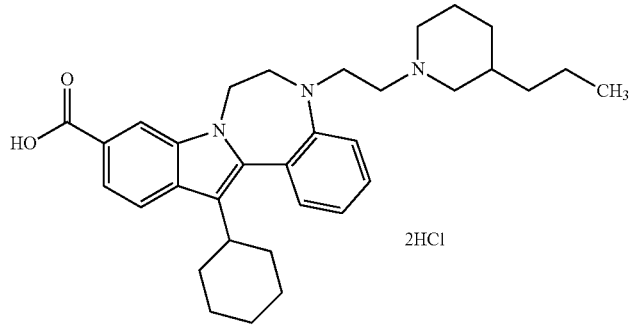 2HCl | 514.3 |

TABLE 74-continued
| Ex. | formula | positive MS (M + 1)(free form) |
|---|---|---|
| 1-332 | 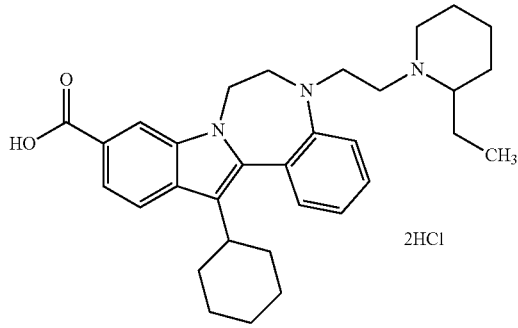 2HCl | 500.4 |
| 1-333 | 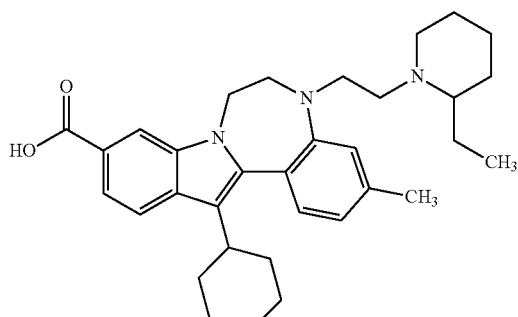 2HCl | 514.3 |
TABLE 75
| Ex. | formula | positive MS (M + 1)(free form) |
|---|---|---|
| 1-334 | 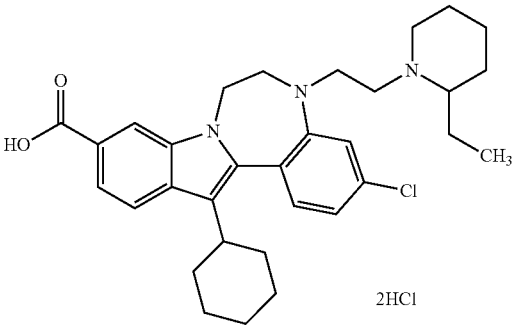 2HCl | 534.3 |
| 1-335 | 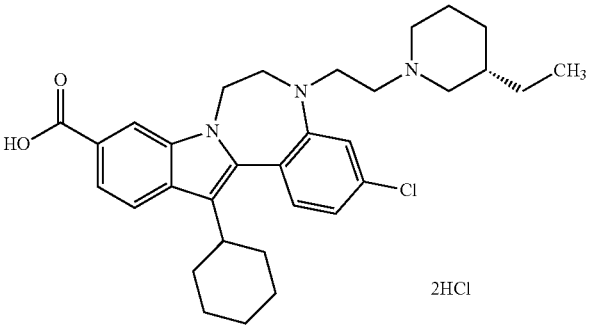 2HCl | 534.3 |

TABLE 75-continued
| Ex. | formula | positive MS (M + 1)(free form) |
|---|---|---|
| 1-336 | 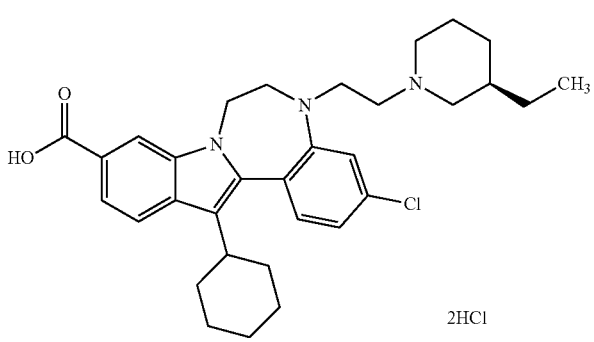 2HCl | 534.3 |
| 1-337 | 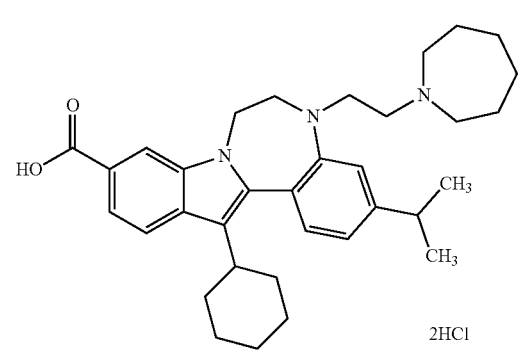 2HCl | 528.4 |
| 1-338 | 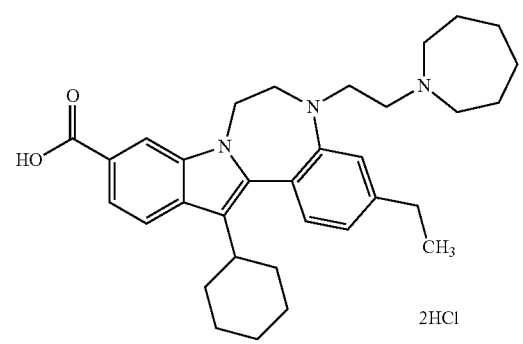 2HCl | 514.4 |
TABLE 76
| Ex. | formula | positive MS (M + 1)(free form) |
|---|---|---|
| 1-339 | 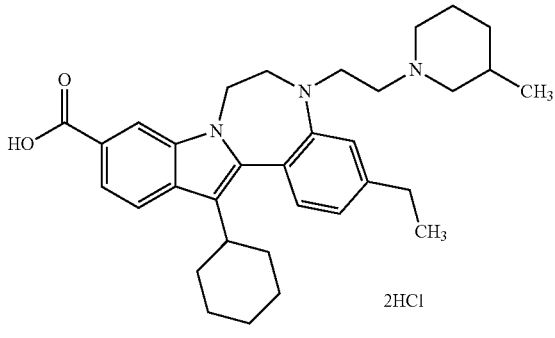 2HCl | 514.4 |

TABLE 76-continued
| Ex. | formula | positive MS (M + 1)(free form) |
|---|---|---|
| 1-340 | 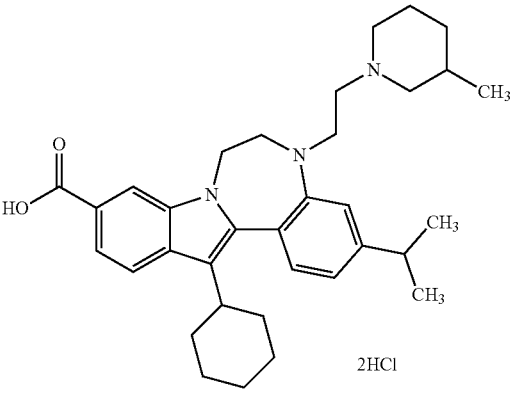 2HCl | 528.4 |
| 1-341 | 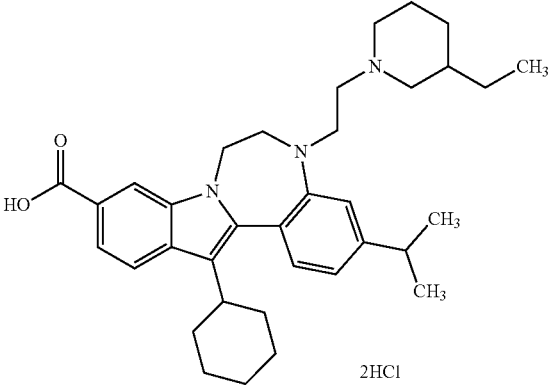 2HCl | 542.4 |
| 1-342 | 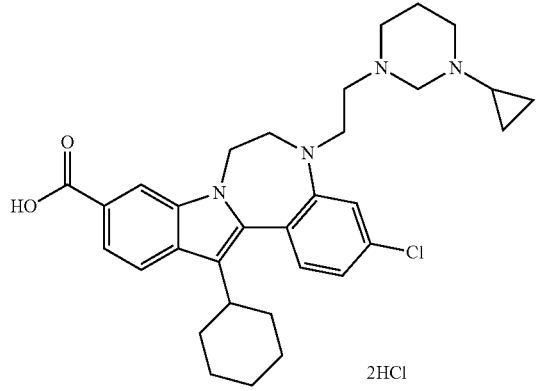 2HCl | 546.3 |

TABLE 77
| Ex. | formula | positive MS (M + 1)(free form) |
|---|---|---|
| 1-343 | 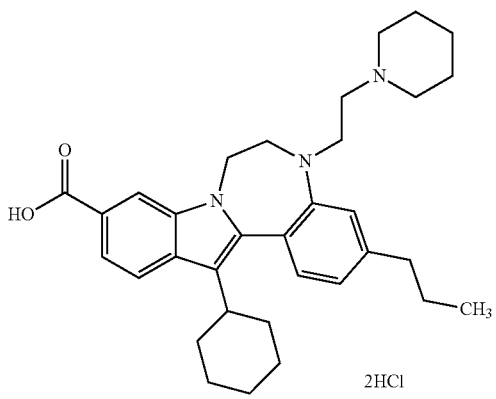 2HCl | 514.4 |
| 1-344 | 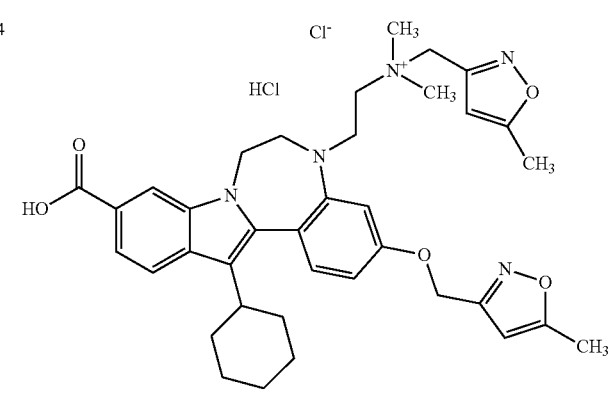 | 638.4 |
| 1-345 | 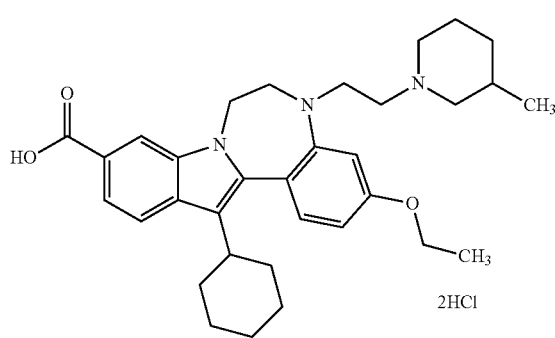 2HCl | 530.4 |
| 1-346 | 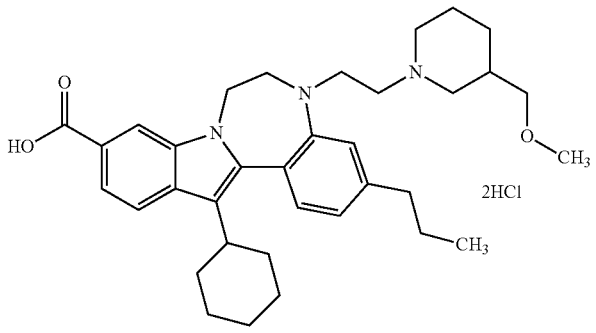 2HCl | 558.4 |

TABLE 78
| Ex. | formula | positive MS (M + 1)(free form) |
|---|---|---|
| 1-347 | 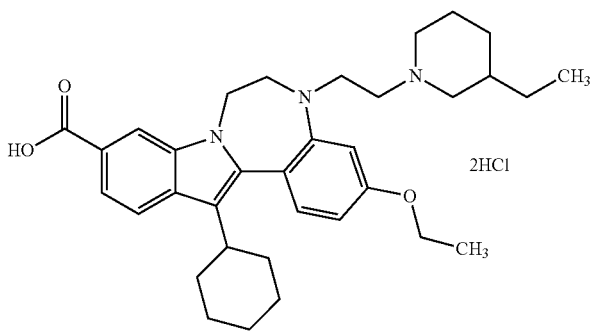 2HCl | 544.4 |
| 1-348 | 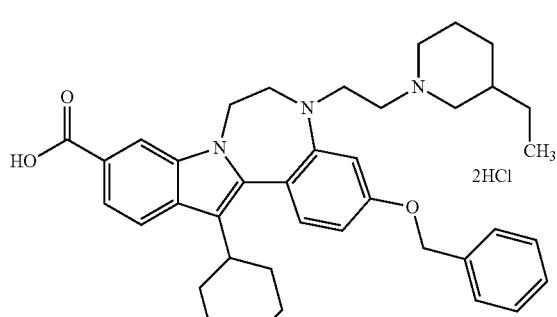 2HCl | 606.4 |
| 1-349 | 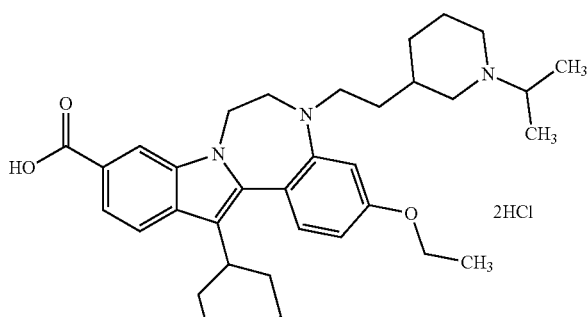 2HCl | 558.4 |
| 1-350 | 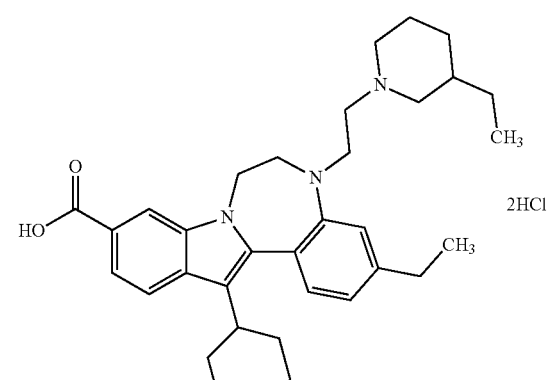 2HCl | 528.4 |

TABLE 79
| Ex. | formula | positive MS (M + 1)(free form) |
|---|---|---|
| 1-351 | 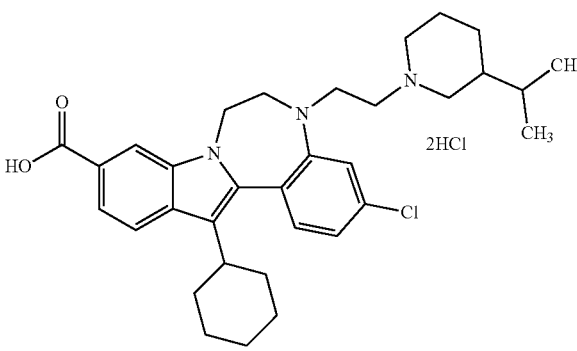 2HCl | 548.3 |
| 1-352 | 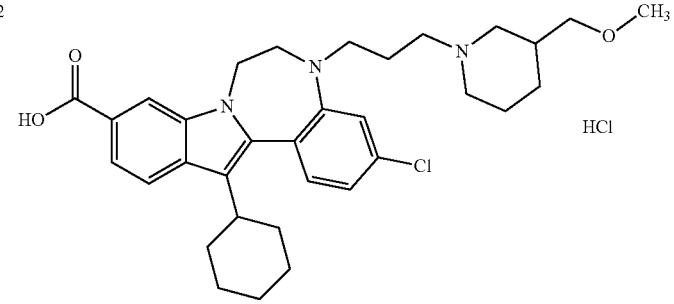 HCl | 564.3 |
| 1-353 | 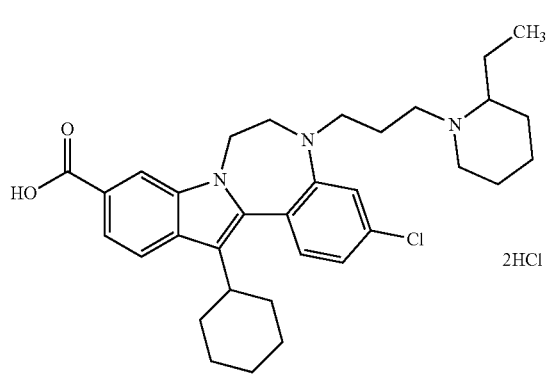 2HCl | 548.3 |
| 1-354 | 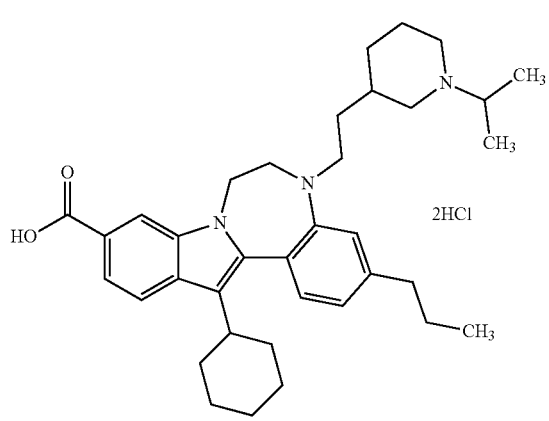 2HCl | 556.4 |

TABLE 80
| Ex. | formula | positive MS (M + 1)(free form) |
|---|---|---|
| 1-355 | 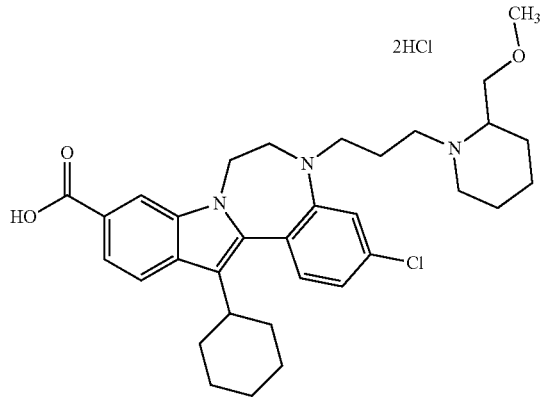 | 564.3 |
| 1-356 | 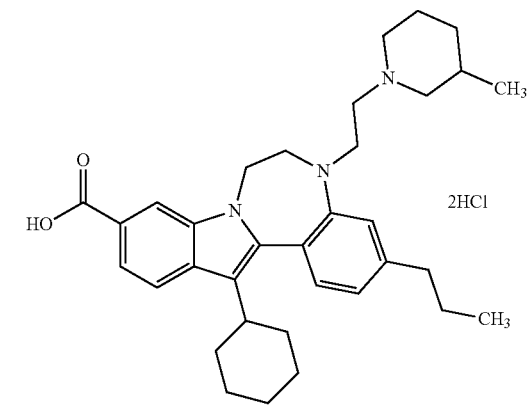 | 528.3 |
| 1-357 | 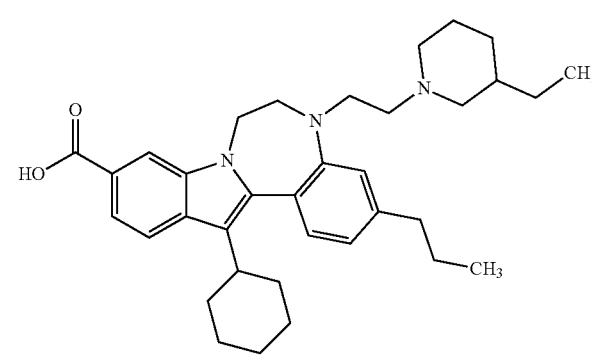 | 542.4 |
| 1-358 | 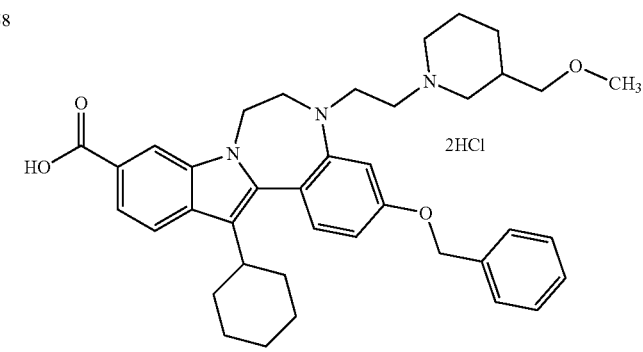 | 622.4 |

TABLE 81
| Ex. | formula | positive MS (M + 1)(free form) |
|---|---|---|
| 1-359 | 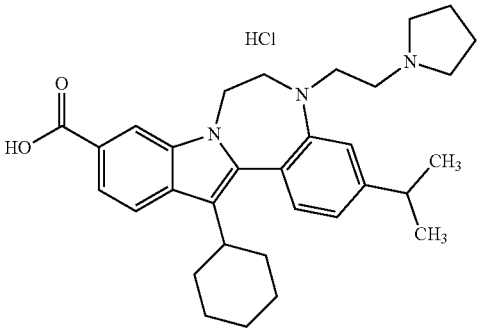 | 500.4 |
| 1-360 | 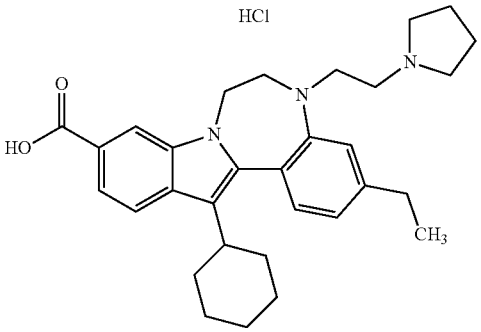 | 486.4 |
| 1-361 | 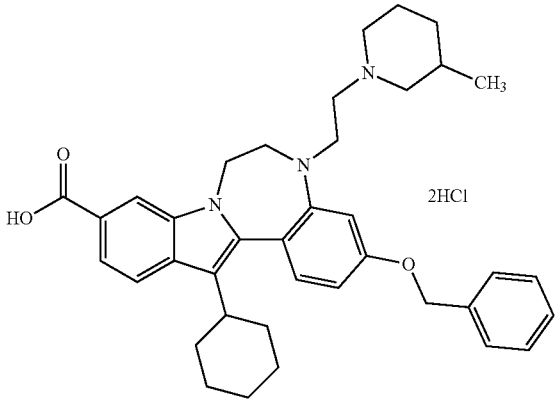 | 592.3 |
| 1-362 | 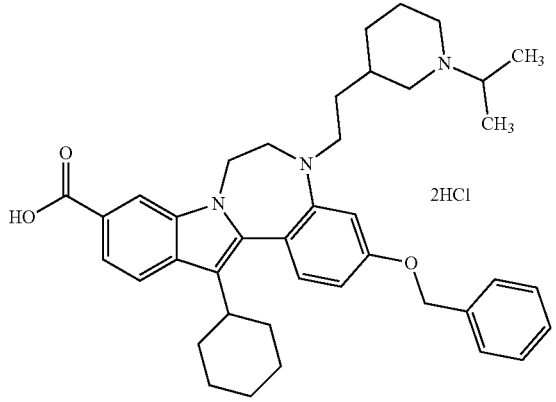 | 620.4 |

TABLE 82
| Ex. | formula | positive MS (M + 1)(free form) |
|---|---|---|
| 1-363 | 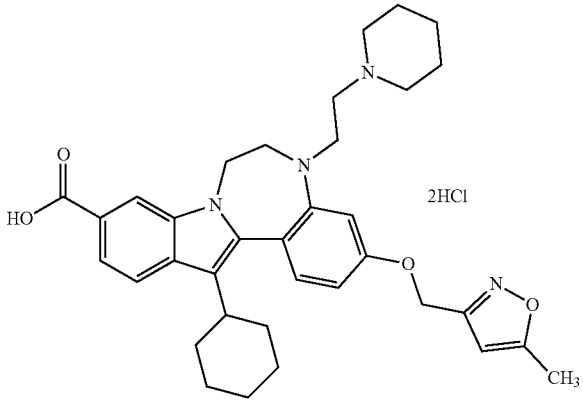 2HCl | 583.3 |
| 1-364 | 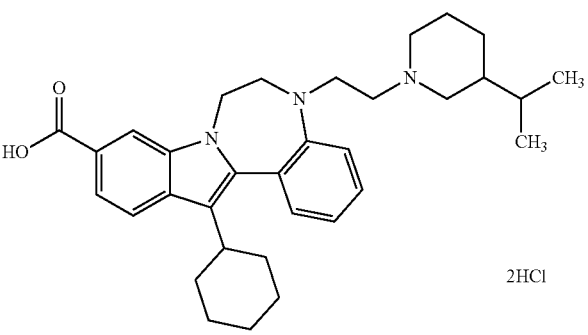 2HCl | 514.3 |
| 1-365 | 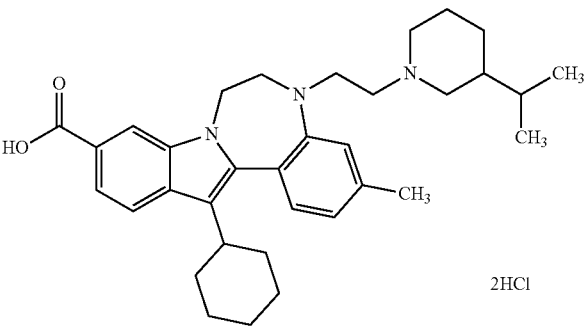 2HCl | 528.3 |
| 1-366 | 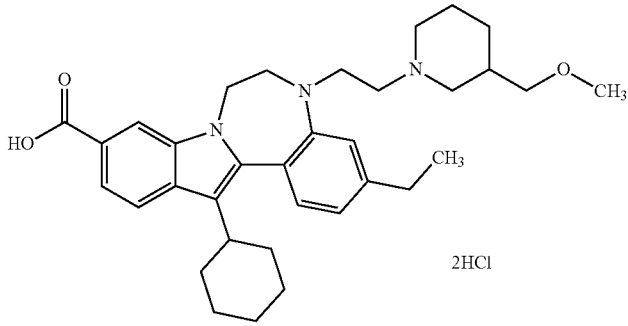 2HCl | 544.3 |

TABLE 83
| Ex. | formula | positive MS (M + 1)(free form) |
|---|---|---|
| 1-367 | 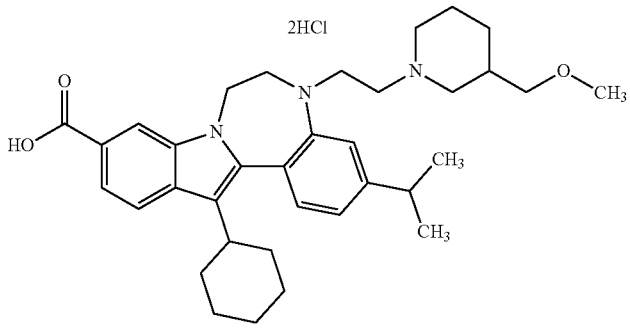 | 558.3 |
| 1-368 | 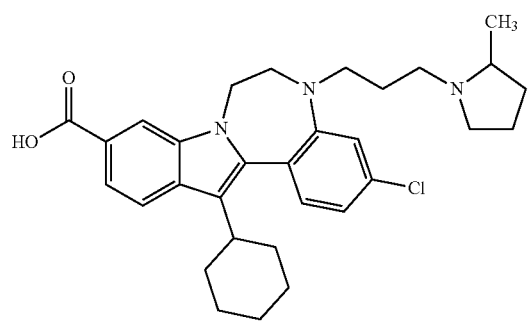 | 520.2 |
| 1-369 | 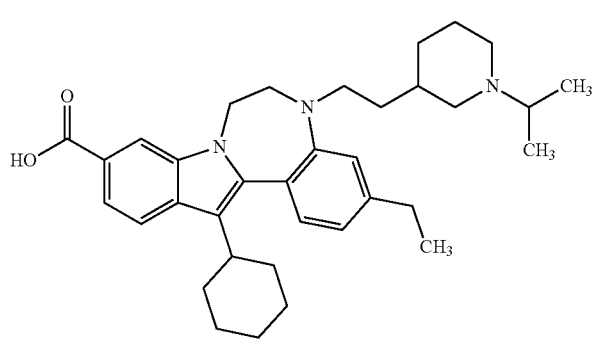 | 542.3 |
| 1-370 | 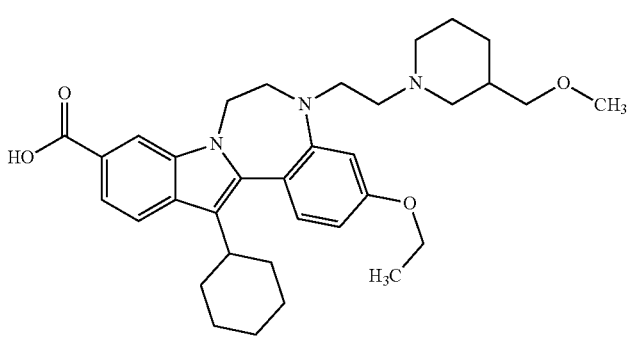 | 560.3 |

TABLE 83-continued

| Ex. | formula | positive MS (M + 1)(free form) |
|---|---|---|
| 1-371 | | 564.3 |

TABLE 84

| Ex. | formula | positive MS (M + 1)(free form) |
|---|---|---|
| 1-372 | | 548.3 |
| 1-373 | | 544.3 |
| 1-374 | | 543.3 |

TABLE 84-continued
| Ex. | formula | positive MS (M + 1)(free form) |
|---|---|---|
| 1-375 | 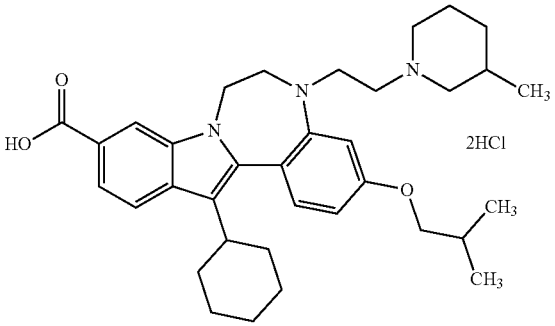 | 558.3 |
| 1-376 | 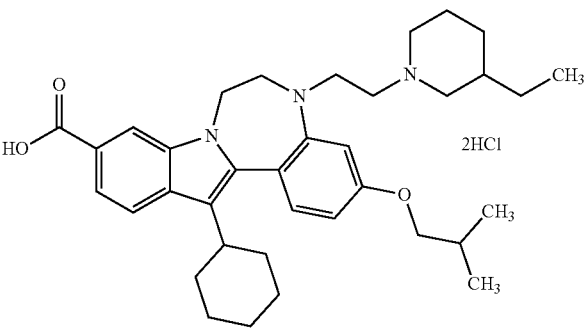 | 572.3 |
TABLE 85
| Ex. | formula | positive MS (M + 1)(free form) |
|---|---|---|
| 1-377 | 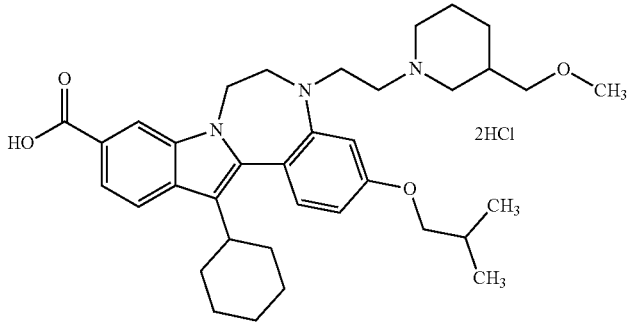 | 588.3 |
| 1-378 | 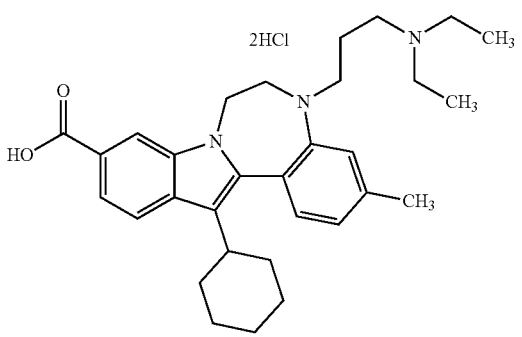 | 488.3 |

TABLE 85-continued
| Ex. | formula | positive MS (M + 1)(free form) |
|---|---|---|
| 1-379 | 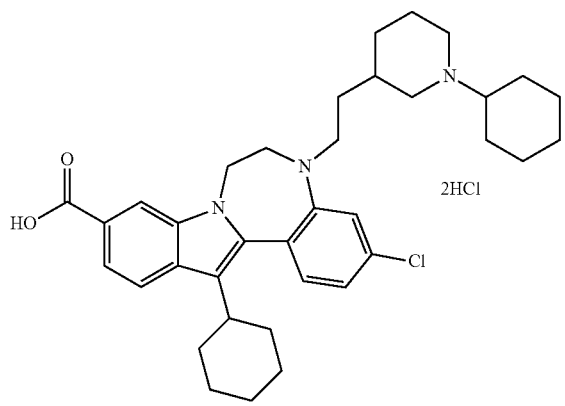 2HCl | 588.3 |
| 1-380 | 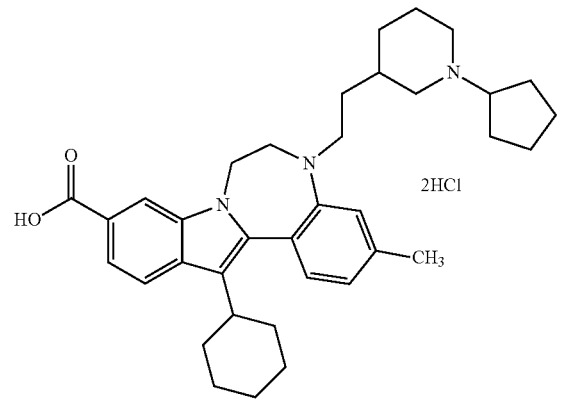 2HCl | 554.3 |
TABLE 37
| Ex. | formula | positive MS (M + 1)(free form) |
|---|---|---|
| 1-166 | 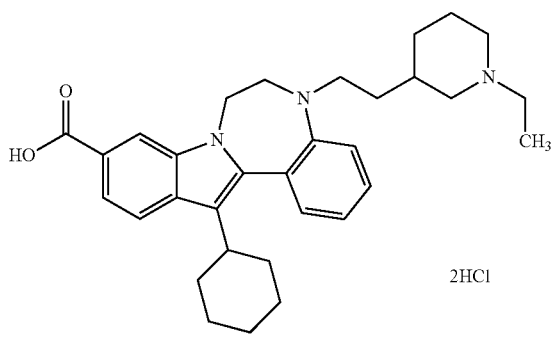 2HCl | 500.3 |

TABLE 37-continued
| Ex. | formula | positive MS (M + 1)(free form) |
|---|---|---|
| 1-167 | 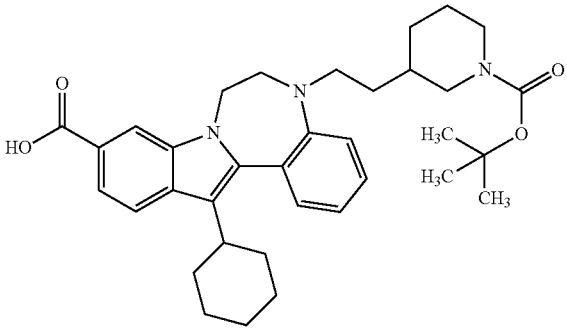 | 572.4 |
| 1-168 | 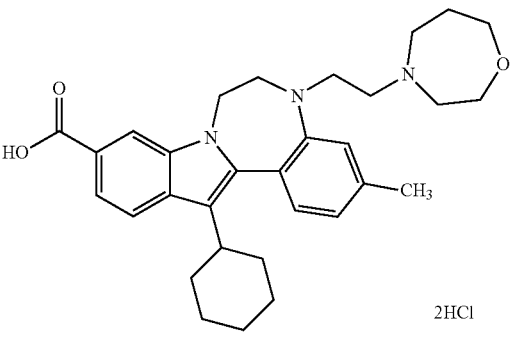 2HCl | 502.3 |
| 1-169 | 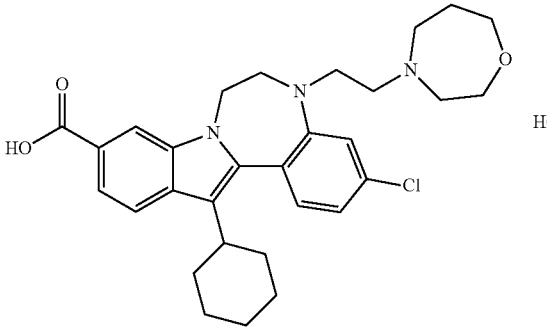 HCl | 522.3 |
| 1-170 | 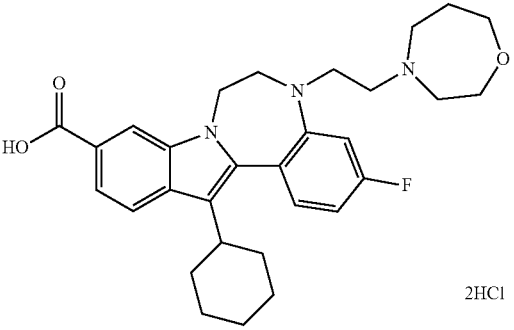 2HCl | 506.3 |

TABLE 86
| Ex. | formula | positive MS (M + 1)(free form) |
|---|---|---|
| 1-381 | 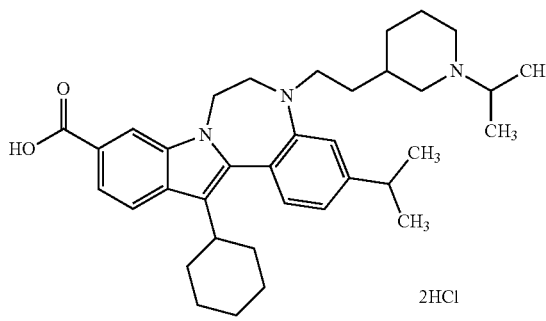 2HCl | 556.3 |
| 1-382 | 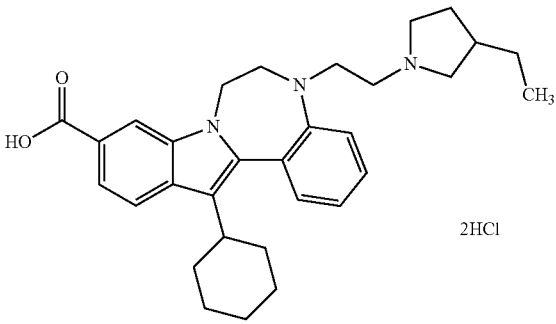 2HCl | 486.2 |
| 1-383 | 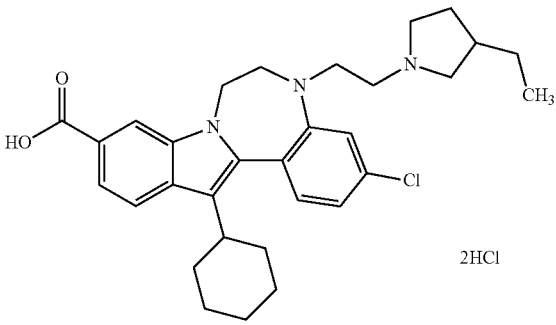 2HCl | 520.2 |
| 1-384 | 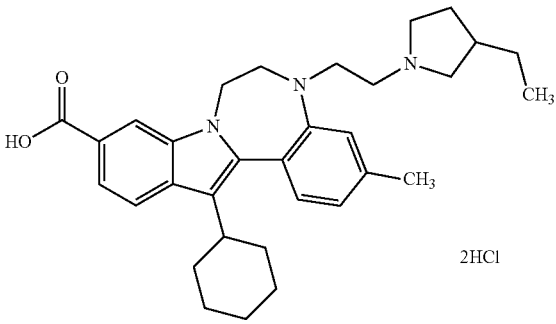 2HCl | 500.3 |

TABLE 87
| Ex. | formula | positive MS (M + 1)(free form) |
|---|---|---|
| 1-385 | 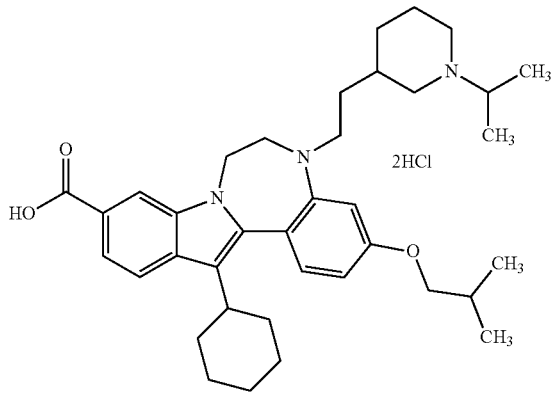 | 586.4 |
| 1-386 | 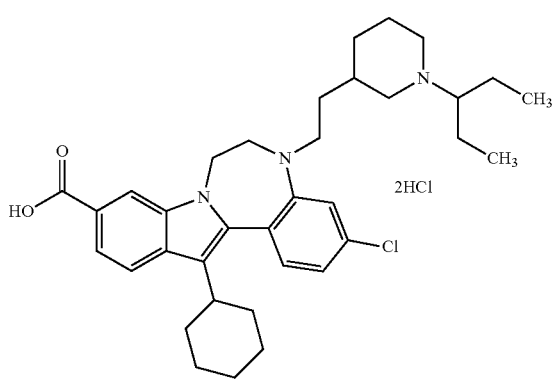 | 576.4 |
| 1-387 | 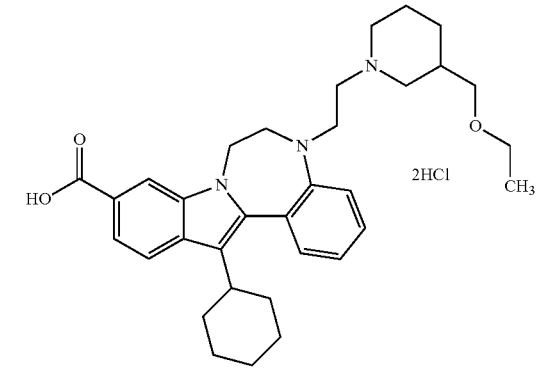 | 530.3 |
| 1-388 | 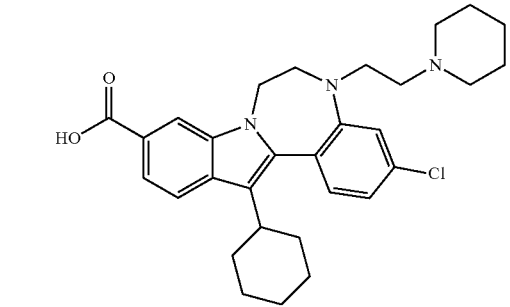 | 492.2 |

TABLE 88
| Ex. | formula | positive MS (M + 1)(free form) |
|---|---|---|
| 1-389 | 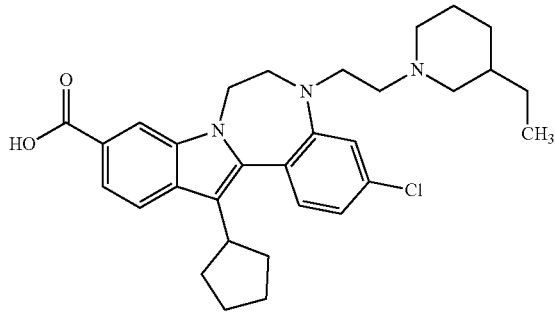 | 520.2 |
| 1-390 | 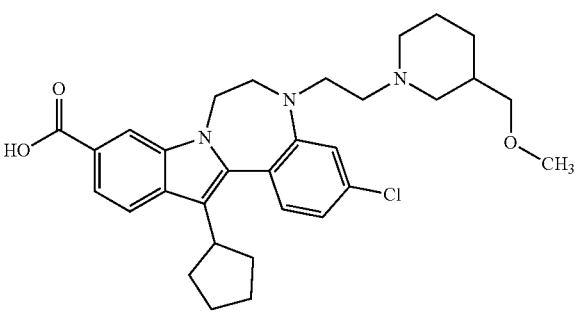 | 536.2 |
| 1-391 | 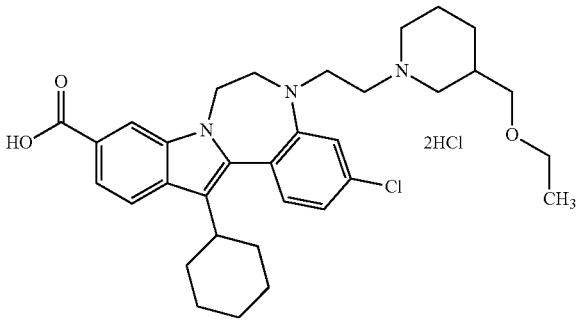 | 564.2 |
| 1-392 | 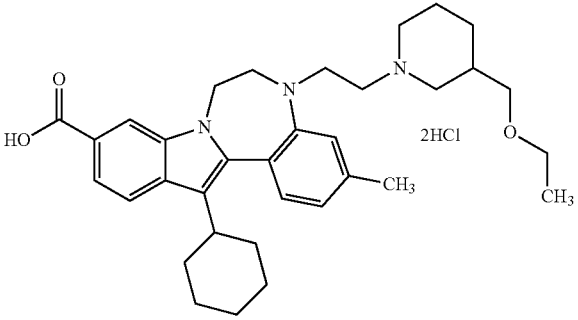 | 544.3 |

TABLE 88-continued
| Ex. | formula | positive MS (M + 1)(free form) |
|---|---|---|
| 1-393 | HCl 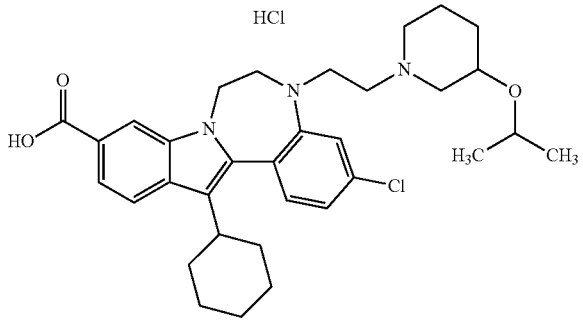 | 564.3 |
TABLE 89
| Ex. | formula | positive MS (M + 1)(free form) |
|---|---|---|
| 1-394 | HCl | 544.3 |
| 1-395 | HCl | 530.3 |
| 1-396 | 2HCl | 562.2 |

TABLE 89-continued
| Ex. | formula | positive MS (M + 1)(free form) |
|---|---|---|
| 1-397 | 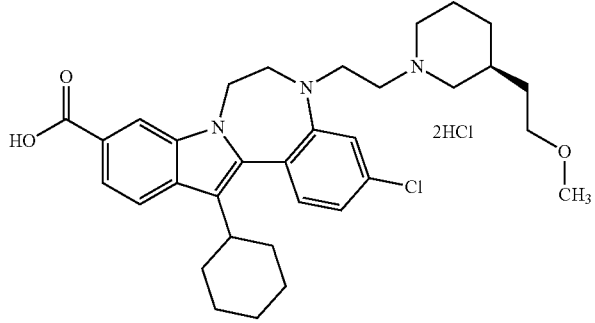 2HCl | 564.2 |
| 1-398 | 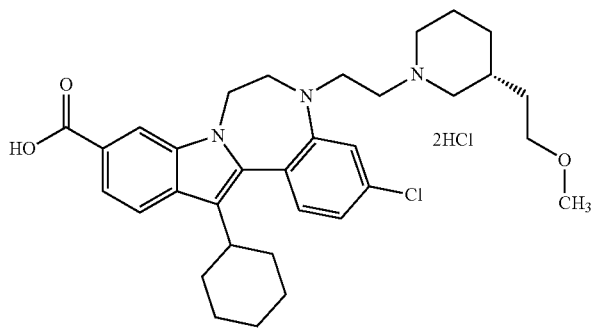 2HCl | 564.2 |
TABLE 90
| Ex. | formula | positive MS (M + 1)(free form) |
|---|---|---|
| 1-399 | 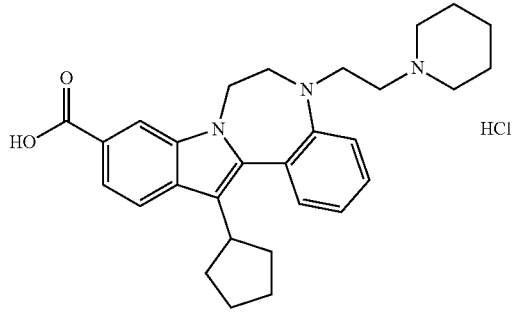 HCl | 458.2 |
| 1-400 | 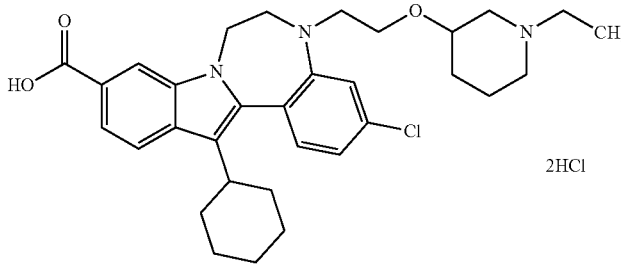 2HCl | 550.2 |

TABLE 90-continued
| Ex. | formula | positive MS (M + 1)(free form) |
|---|---|---|
| 1-401 | 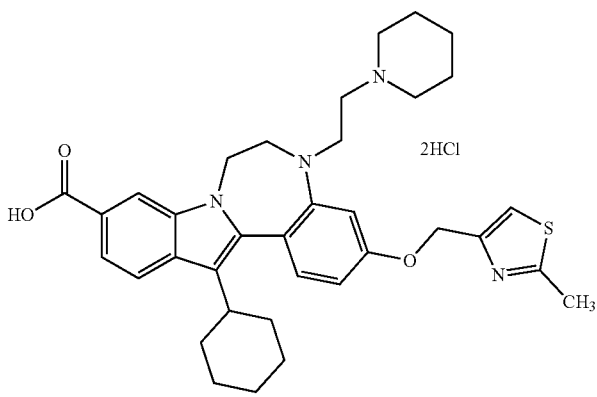 | 599.3 |
| 1-402 | 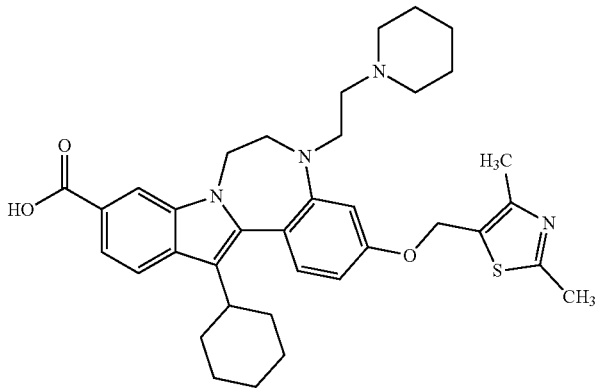 | 613.2 |
TABLE 91
| Ex. | formula | positive MS (M + 1)(free form) |
|---|---|---|
| 1-403 | 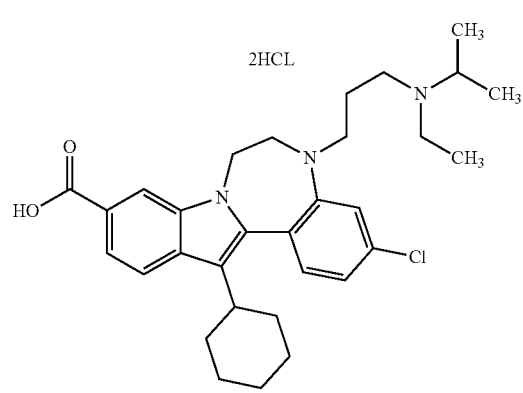 | 522.2 |

TABLE 91-continued
| Ex. | formula | positive MS (M + 1)(free form) |
|---|---|---|
| 1-404 | 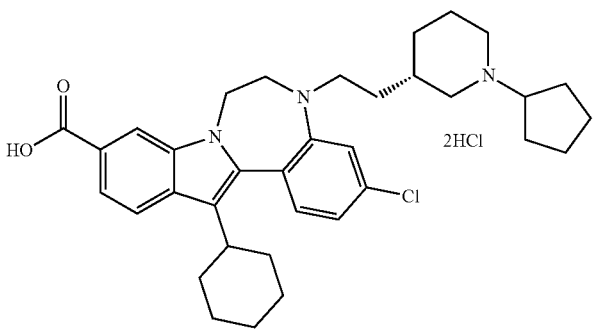 2HCl | 574.2 |
| 1-405 | 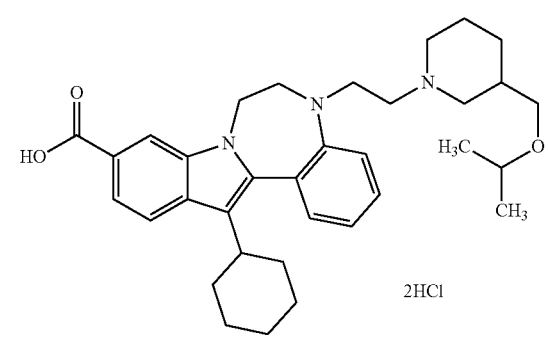 2HCl | 544.3 |
| 1-406 | 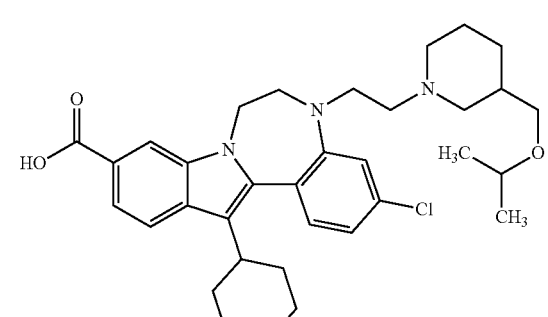 2HCl | 578.3 |
TABLE 92
| Ex. | formula | positive MS (M + 1)(free form) |
|---|---|---|
| 1-407 | 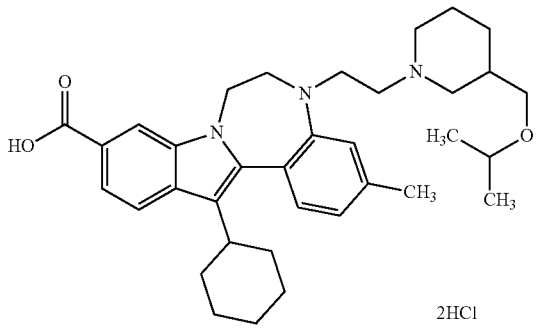 2HCl | 558.3 |

TABLE 92-continued
| Ex. | formula | positive MS (M + 1)(free form) |
|---|---|---|
| 1-408 | 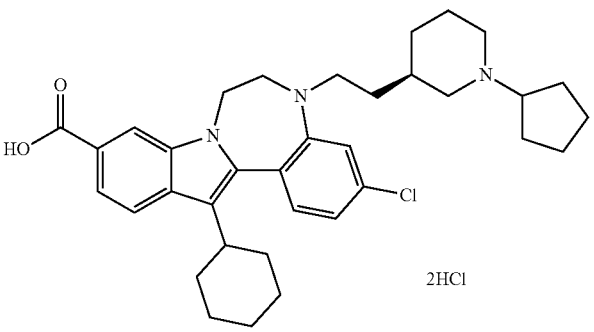 2HCl | 574.3 |
| 1-409 | 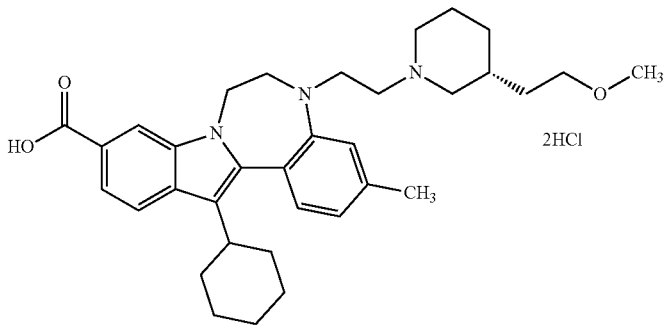 2HCl | 544.3 |
| 1-410 | 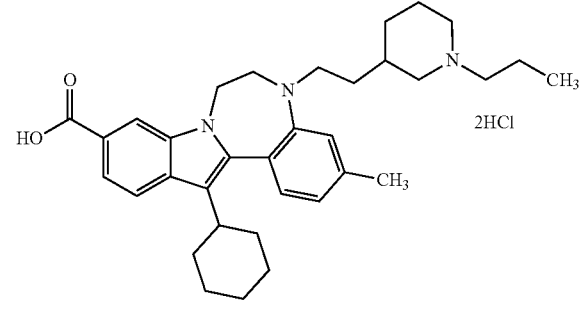 2HCl | 528.3 |
| 1-411 | 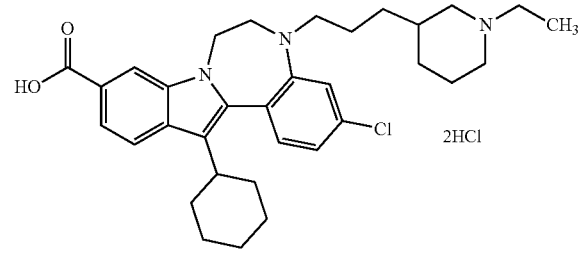 2HCl | 548.3 |

TABLE 93
| Ex. | formula | positive MS (M + 1)(free form) |
|---|---|---|
| 1-412 | 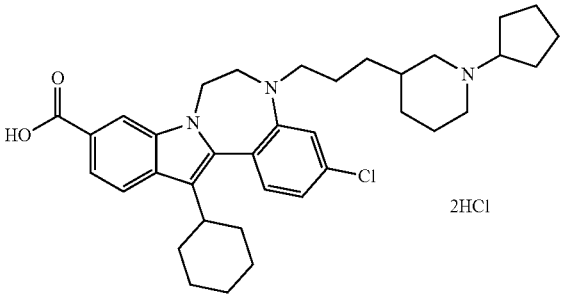 2HCl | 588.3 |
| 1-413 | 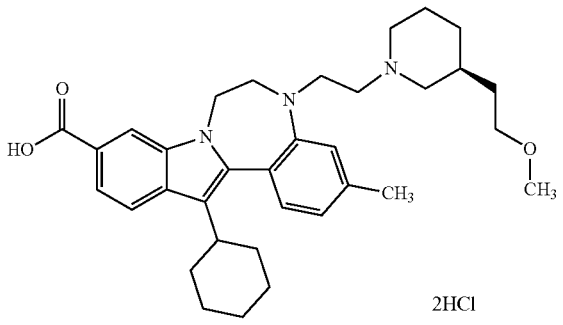 2HCl | 544.3 |
| 1-414 | 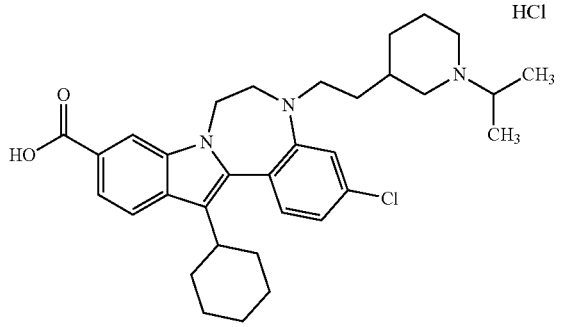 HCl | 534.2 |
| 1-415 | 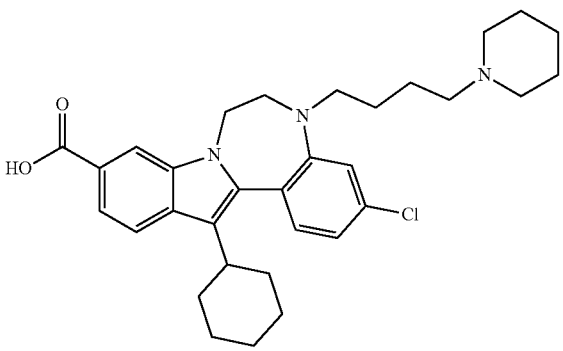 | 534.2 |

TABLE 93-continued
| Ex. | formula | positive MS (M + 1)(free form) |
|---|---|---|
| 1-416 | 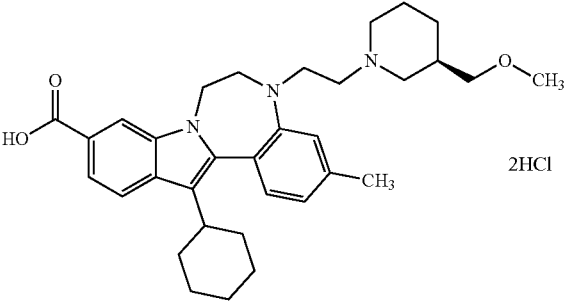 2HCl | 530.3 |
TABLE 94
| Ex. | formula | positive MS (M + 1)(free form) |
|---|---|---|
| 1-417 | 2HCl | 530.3 |
| 1-418 | 2HCl | 656.2 |
| 1-419 | | 534.2 |

TABLE 94-continued
| Ex. | formula | positive MS (M + 1)(free form) |
|---|---|---|
| 1-420 | 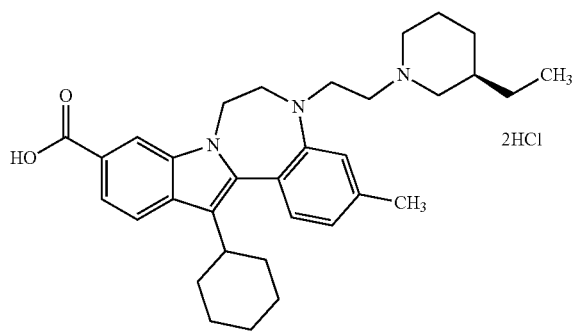 2HCl | 514.2 |
TABLE 95
| Ex. | formula | positive MS (M + 1)(free form) |
|---|---|---|
| 1-421 | | 534.2 |
| 1-422 | 2HCl | 514.2 |
| 1-423 | 2HCl | 500.3 |

TABLE 95-continued

| Ex. | formula | positive MS (M + 1)(free form) |
|---|---|---|
| 1-424 | | 522.2 |
| 1-425 | | 514.3 (2HCl) |

TABLE 96

| Ex. | formula | positive MS (M + 1)(free form) |
|---|---|---|
| 1-426 | (2HCl) | 506.2 |
| 1-427 | (2HCl) | 574.3 |

TABLE 96-continued
| Ex. | formula | positive MS (M + 1)(free form) |
|---|---|---|
| 1-428 | 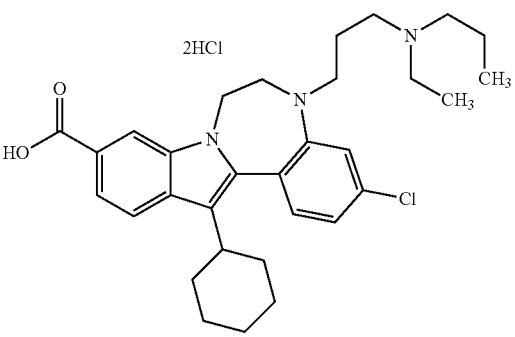 | 522.2 |
| 1-429 | 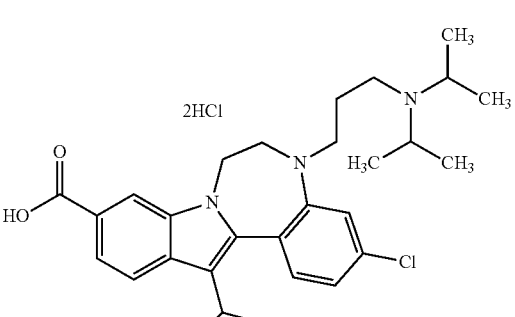 | 536.2 |
TABLE 97
| Ex. | formula | positive MS (M + 1)(free form) |
|---|---|---|
| 1-430 | 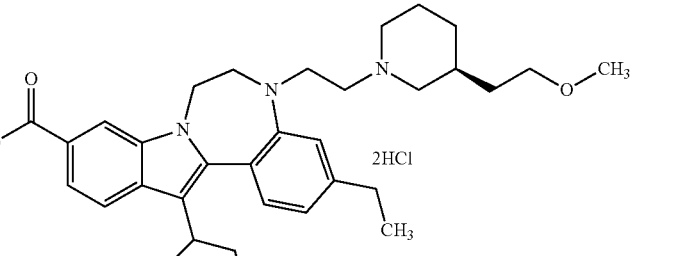 | 558.3 |
| 1-431 |  | 538.2 |

TABLE 97-continued
| Ex. | formula | positive MS (M + 1)(free form) |
|---|---|---|
| 1-432 | 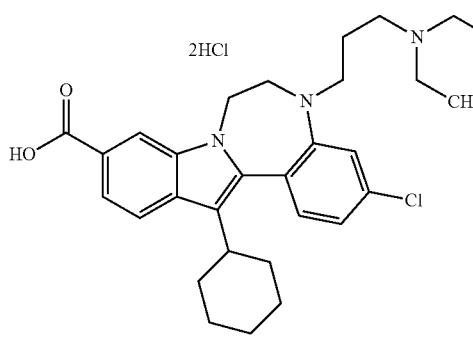 | 552.2 |
| 1-433 | 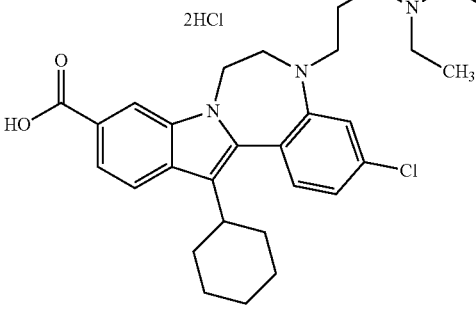 | 566.3 |
| 1-434 | 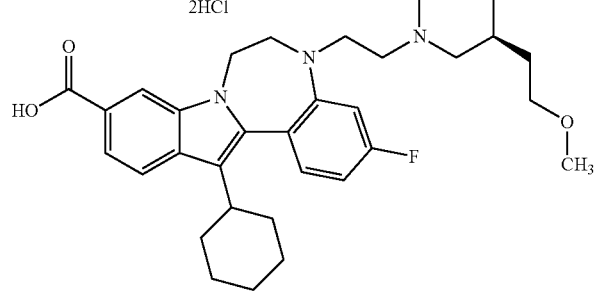 | 548.3 |
TABLE 98
| Ex. | formula | positive MS (M + 1)(free form) |
|---|---|---|
| 1-435 | 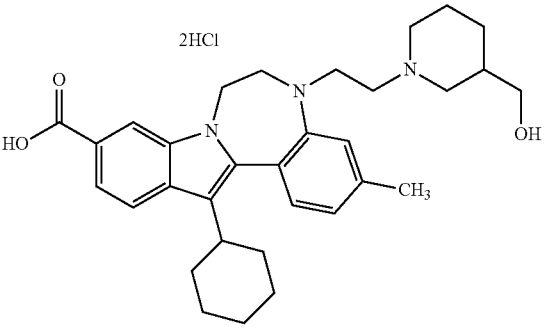 | 516.3 |

TABLE 98-continued

| Ex. | formula | positive MS (M + 1)(free form) |
|---|---|---|
| 1-436 | | 536.2 |
| 1-437 | | 502.3 |
| 1-438 | | 502.3 |

TABLE 99

| Ex. | formula | positive MS (M + 1)(free form) |
|---|---|---|
| 1-439 | | 516.3 |

TABLE 99-continued

| Ex. | formula | positive MS (M + 1)(free form) |
|---|---|---|
| 1-440 | | 514.3 |
| 1-441 | 2HCl | 538.3 |
| 1-442 | 2HCl | 524.2 |

TABLE 100

| Ex. | formula | positive MS (M + 1)(free form) |
|---|---|---|
| 1-443 | 2HCl | 516.3 |

TABLE 100-continued

| Ex. | formula | positive MS (M + 1)(free form) |
|---|---|---|
| 1-444 | [structure: 2HCl salt] | 592.3 |
| 1-445 | [structure: 2HCl salt] | 560.3 |

TABLE 101

| Ex. | formula | positive MS (M + 1)(free form) |
|---|---|---|
| 2-4 | [structure] | 392.1 |
| 2-5 | [structure: HCl salt] | 636.3 |

TABLE 101-continued
| Ex. | formula | positive MS (M + 1)(free form) |
|---|---|---|
| 2-6 | 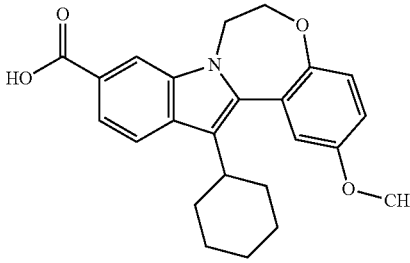 | 392.2 |
| 2-7 | 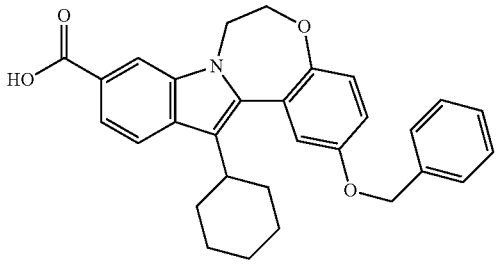 | 468.2 |
| 2-8 | 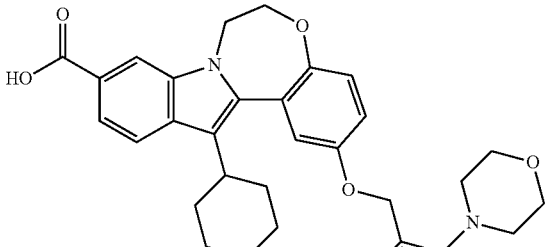 | 636.3 |
TABLE 102
| Ex. | formula | positive MS (M + 1)(free form) |
|---|---|---|
| 2-9 |  | 636.2 |

TABLE 102-continued
| Ex. | formula | positive MS (M + 1)(free form) |
|---|---|---|
| 2-10 | 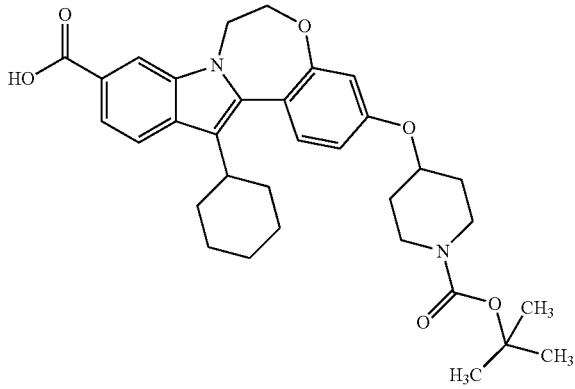 | 561.3 |
| 2-11 | 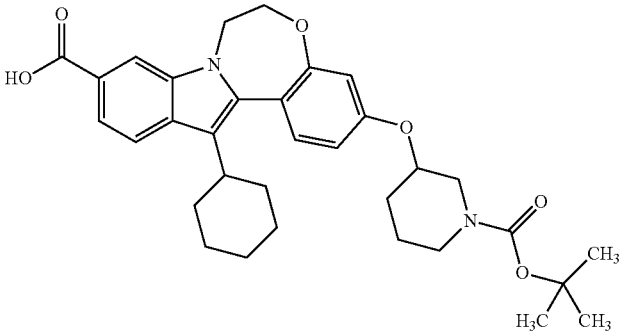 | 561.3 |
| 2-12 | 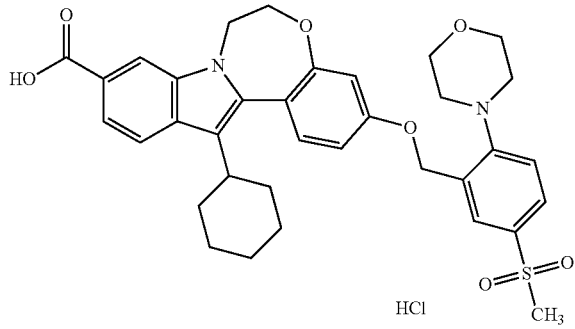 | 631.2 |

TABLE 103

| Ex. | formula | positive MS (M + 1)(free form) |
|---|---|---|
| 2-13 | HCl | 713.2 |
| 2-14 | HCl | 553.2 |
| 2-15 | HCl | 610.2 |
| 2-16 | 2HCl | 653.3 |

TABLE 103-continued
| Ex. | formula | positive MS (M + 1)(free form) |
|---|---|---|
| 2-17 | 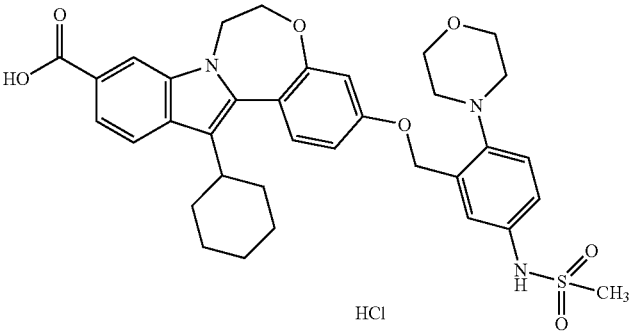 HCl | 646.2 |
TABLE 104
| Ex. | formula | positive MS (M + 1)(free form) |
|---|---|---|
| 2-18 | 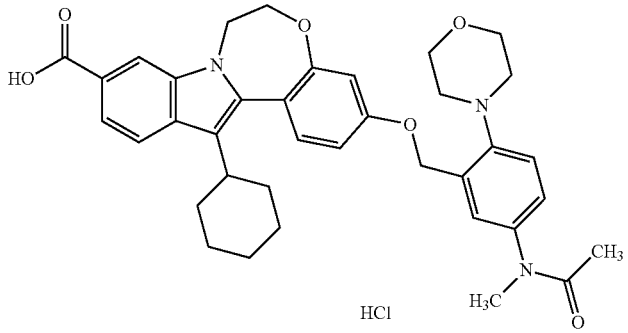 HCl | 624.2 |
| 2-19 | 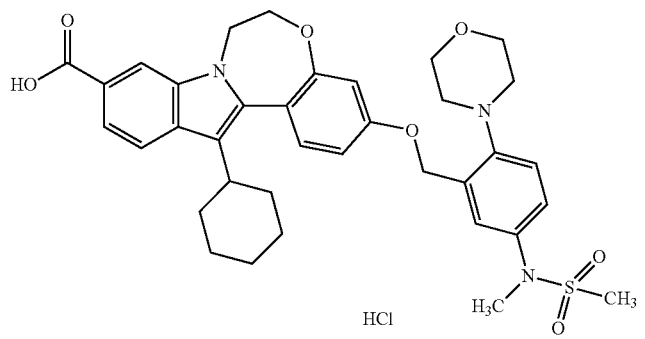 HCl | 660.2 |
| 2-20 | 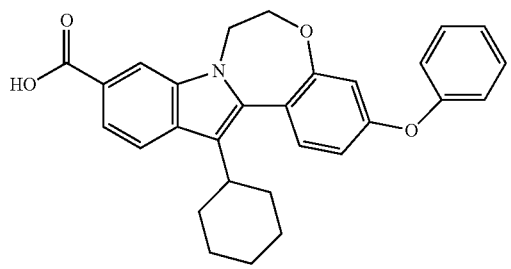 | 454.1 |

823 824
TABLE 104-continued
| Ex. | formula | positive MS (M + 1)(free form) |
|---|---|---|
| 2-21 | 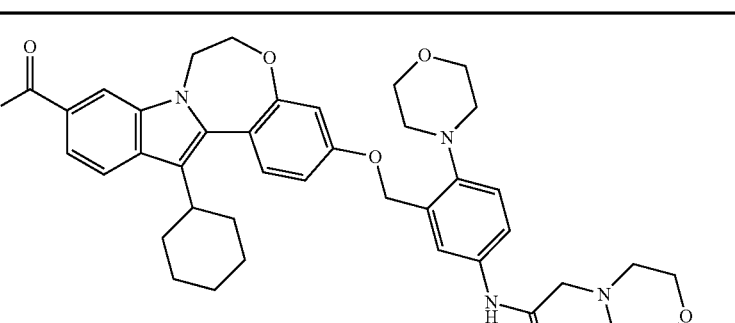 2HCl | 695.3 |
| 2-22 | 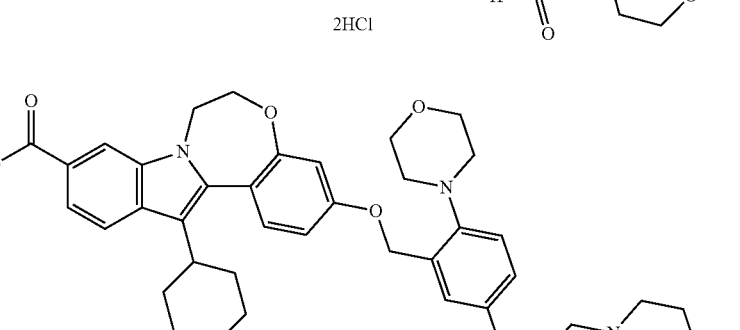 2HCl | 709.3 |
TABLE 105
| Ex. | formula | positive MS (M + 1)(free form) |
|---|---|---|
| 2-23 | 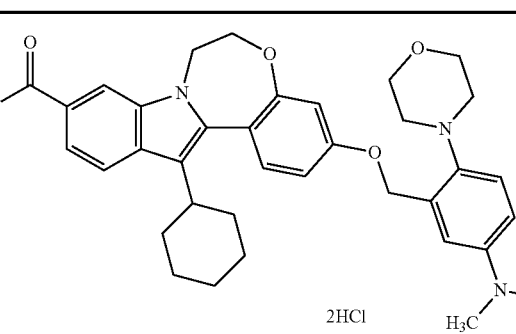 2HCl | 667.3 |
| 2-24 | 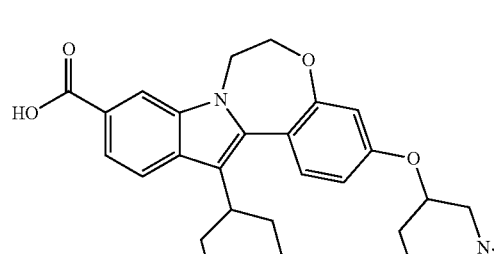 | 519.2 |

TABLE 105-continued
| Ex. | formula | positive MS (M + 1)(free form) |
|---|---|---|
| 2-25 | | 484.2 |
| 2-26 | | 488.1 |
| 2-27 | | 720.3 |
TABLE 106
| Ex. | formula | positive MS (M + 1)(free form) |
|---|---|---|
| 2-28 | 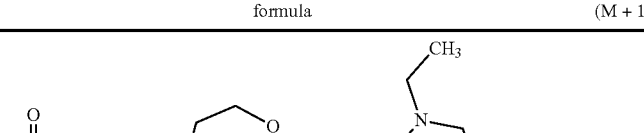 | 663.3 |

TABLE 106-continued
| Ex. | formula | positive MS (M + 1)(free form) |
|---|---|---|
| 2-29 | 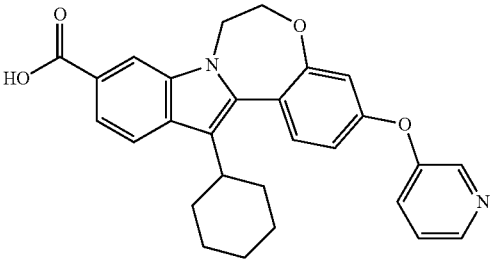 HCl | 455.2 |
| 2-30 | 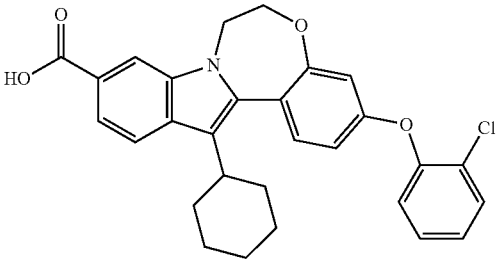 | 488.1 |
| 2-31 | 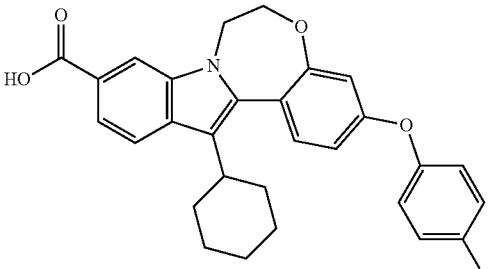 | 488.1 |
| 2-32 | 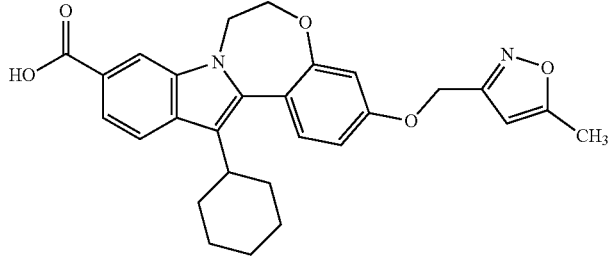 | 473.1 |

TABLE 107
| Ex. | formula | positive MS (M + 1)(free form) |
|---|---|---|
| 2-33 | 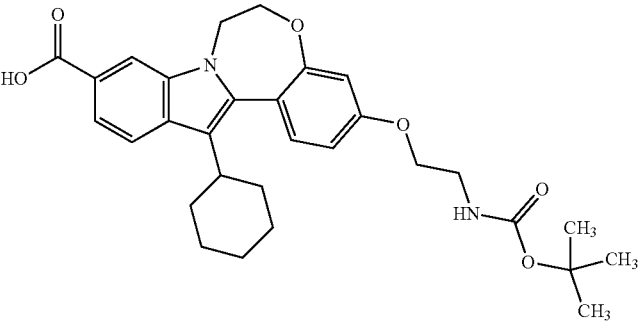 | 521.2 |
| 2-34 | 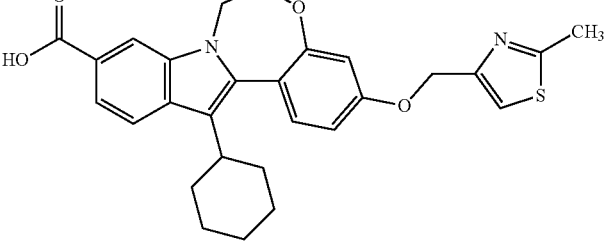 | 561.2 |
| 2-35 | 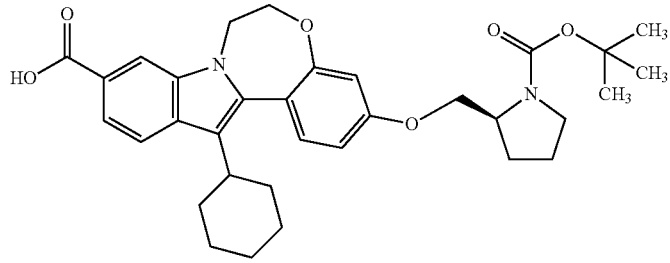 | 489.2 |
| 2-36 | 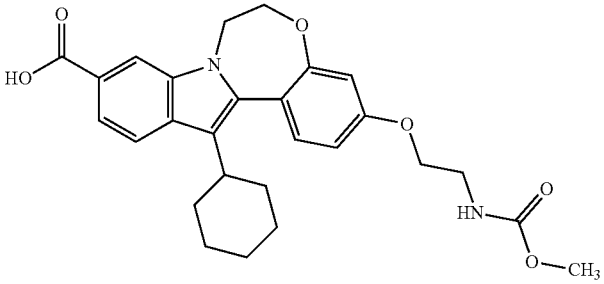 | 479.2 |
| 2-37 | 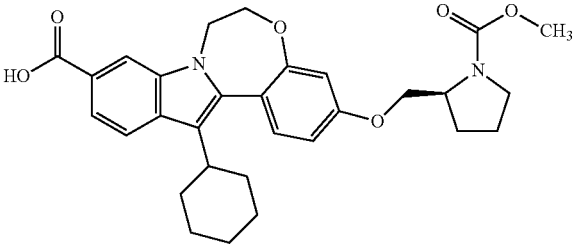 | 519.2 |

TABLE 108

| Ex. | formula | positive MS (M + 1)(free form) |
|---|---|---|
| 2-38 | | 491.2 |
| 2-39 | | 468.2 |
| 2-40 | | 547.3 |
| 2-41 | | 611.3 |
| 2-42 | | 447.2 |

TABLE 109
| Ex. | formula | positive MS (M + 1)(free form) |
|---|---|---|
| 2-43 | 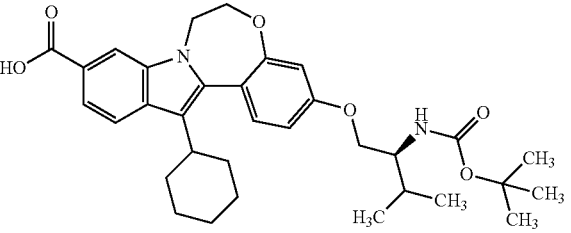 | 563.3 |
| 2-44 | 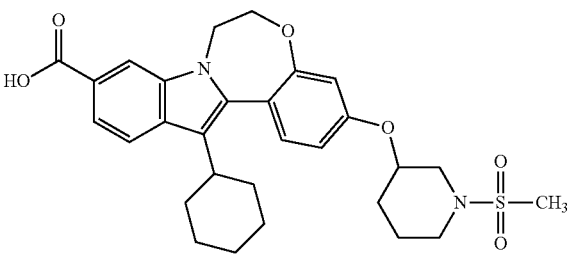 | 539.2 |
| 2-45 | 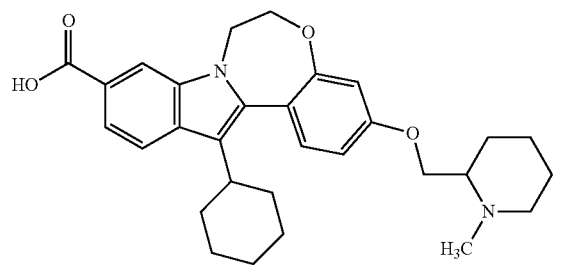 | 489.3 |
| 2-46 | 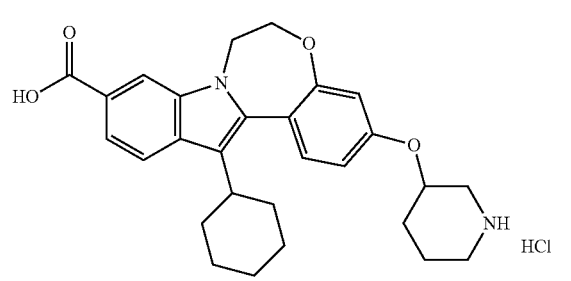 | 461.2 |
| 2-47 | 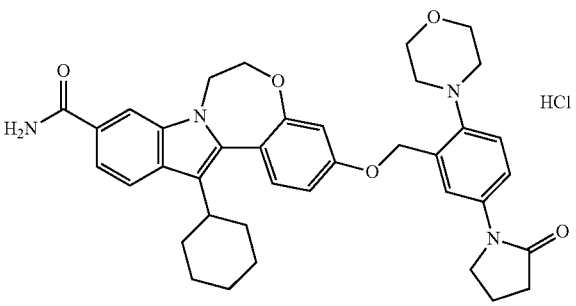 | 635.3 |

TABLE 110
| Ex. | formula | positive MS (M + 1)(free form) |
|---|---|---|
| 2-48 | 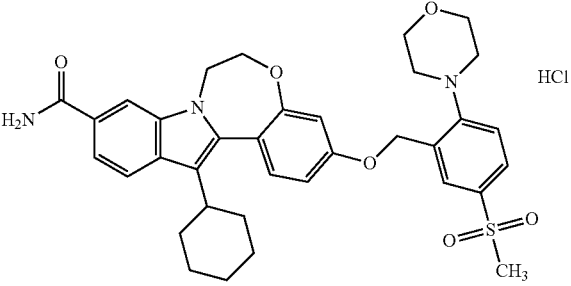 HCl | 630.2 |
| 2-49 | 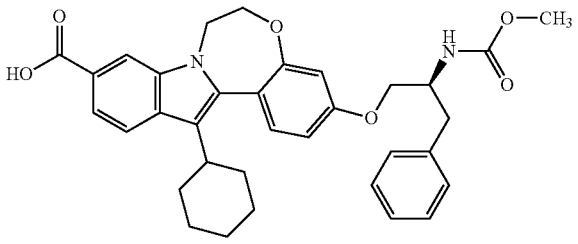 | 569.3 |
| 2-50 | 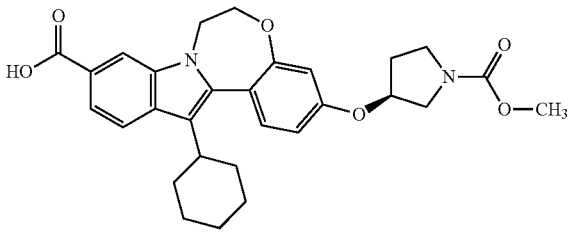 | 505.2 |
| 2-51 | 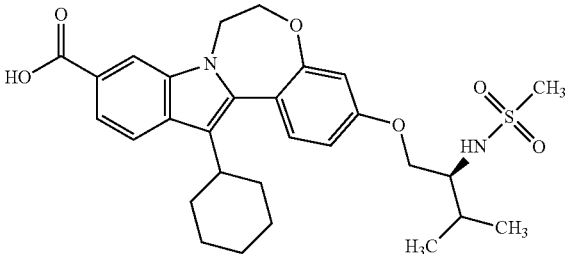 | 541.3 |
| 2-52 | 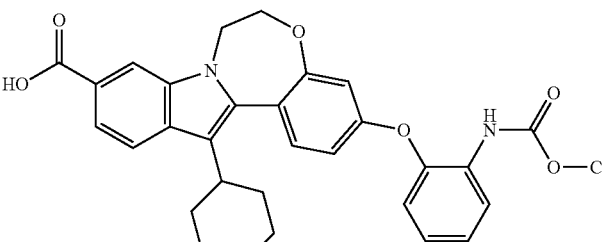 | 527.2 |

TABLE 111
| Ex. | formula | positive MS (M + 1)(free form) |
|---|---|---|
| 2-53 | 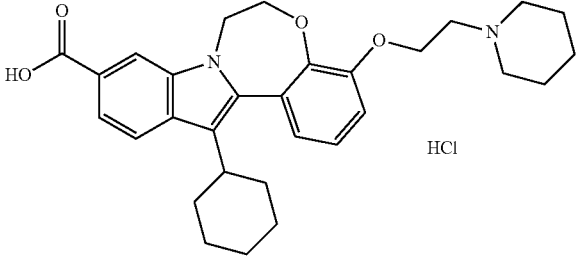 HCl | 489.2 |
TABLE 112
| Ex. | formula | positive MS (M + 1)(free form) |
|---|---|---|
| 5-3 | 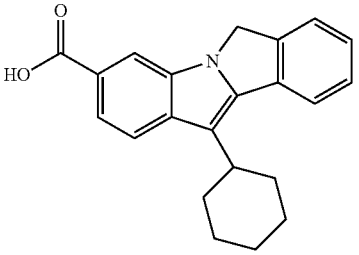 | 332.1 |
TABLE 113
| Ex. | formula | positive MS (M + 1)(free form) |
|---|---|---|
| 7-4 | 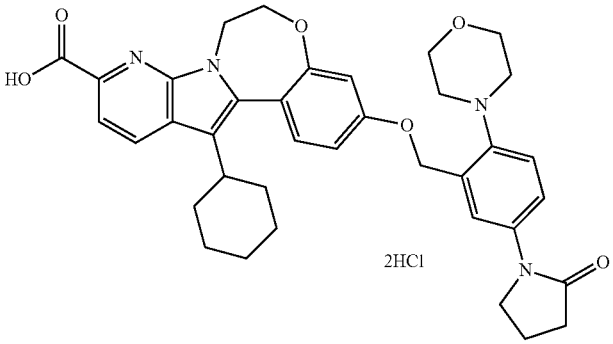 2HCl | 637.2 |
| 7-5 | 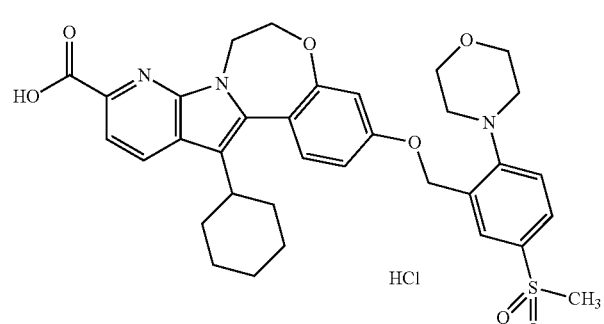 HCl | 632.2 |

TABLE 113-continued
| Ex. | formula | positive MS (M + 1)(free form) |
|---|---|---|
| 7-6 | 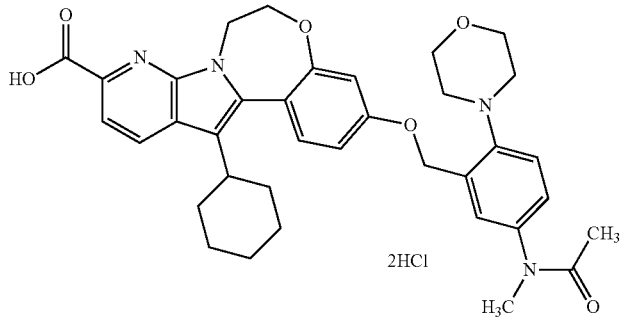 2HCl | 625.3 |
| 7-7 | 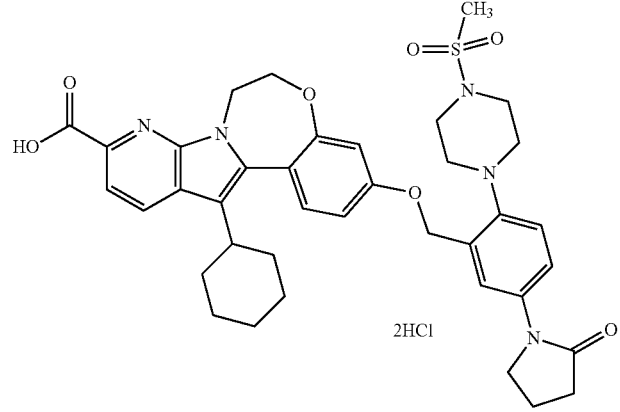 2HCl | 714.2 |
TABLE 114
| Ex. | formula | positive MS (M + 1) (free form) |
|---|---|---|
| 7-8 | 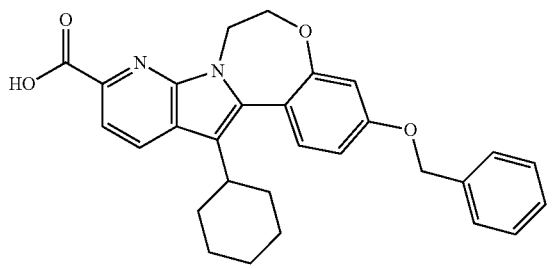 | 469.1 |

TABLE 115

| Ex. | formula | positive MS (M + 1)(free form) |
|---|---|---|
| 8-5 | | 507.1 |
| 8-6 | | 536.2 |
| 8-7 | | 520.2 |

TABLE 116

| Ex. | formula | positive MS (M + 1) (free form) |
|---|---|---|
| 9-3 | | 376.2 |
| 9-4 | | 396.1 |

TABLE 117
| Ex. | formula | positive MS (M + 1)(free form) |
|---|---|---|
| 10-1 | 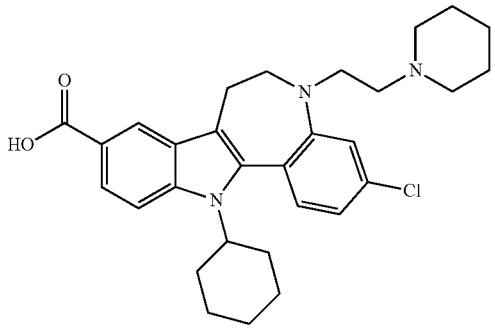 | 506.3 |
| 10-2 | 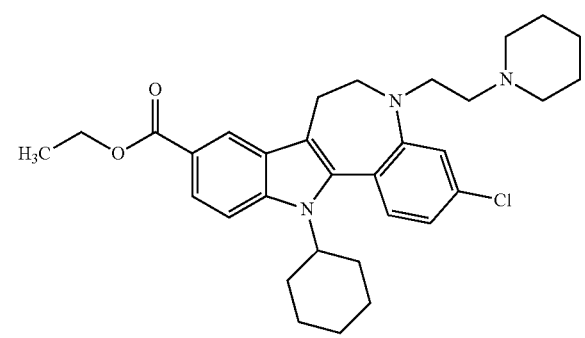 | 534.3 |
TABLE 118
| Ex. | formula | positive MS (M + 1) (free form) |
|---|---|---|
| 10-3 | 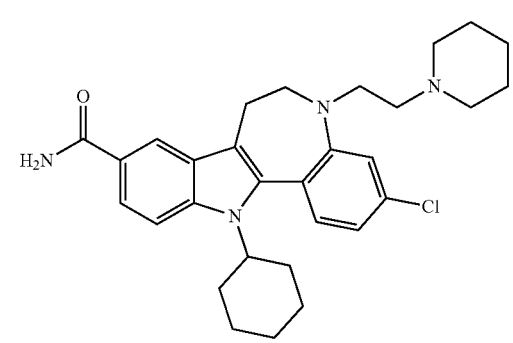 | 505.3 |
| 10-4 | 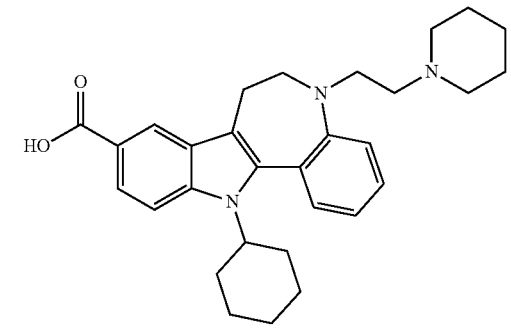 | 472.3 |

TABLE 118-continued
| Ex. | formula | positive MS (M + 1) (free form) |
|---|---|---|
| 10-5 | 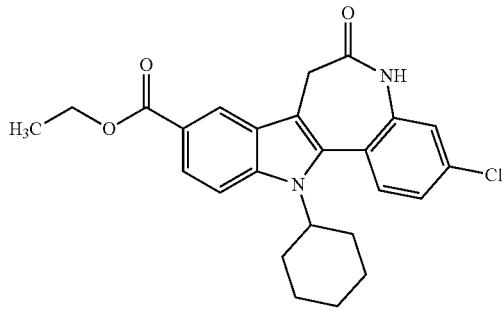 | |
| 10-6 | 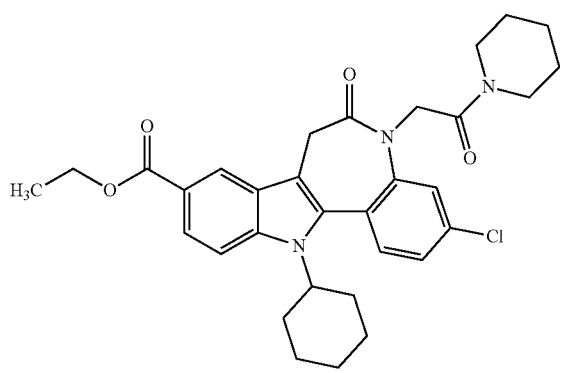 | |
TABLE 119
| Ex. | formula | positive MS (M + 1) (free form) |
|---|---|---|
| 1-446 | 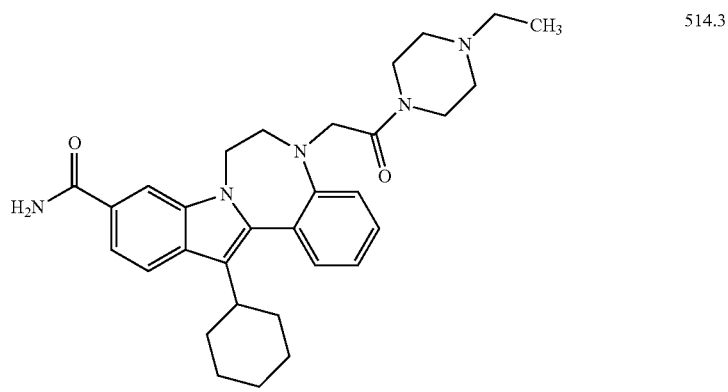 | 514.3 |

TABLE 119-continued
| Ex. | formula | positive MS (M + 1) (free form) |
|---|---|---|
| 1-447 | 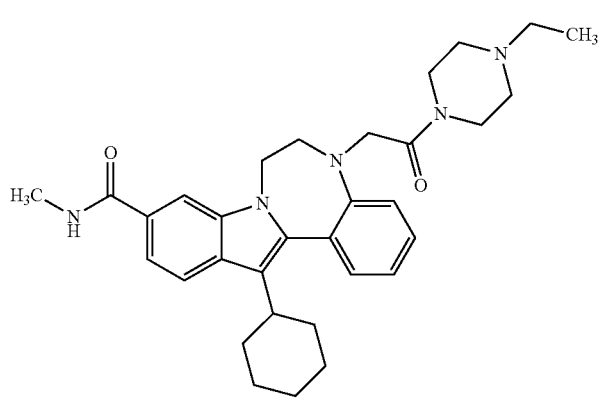 | 528.3 |
| 1-448 | 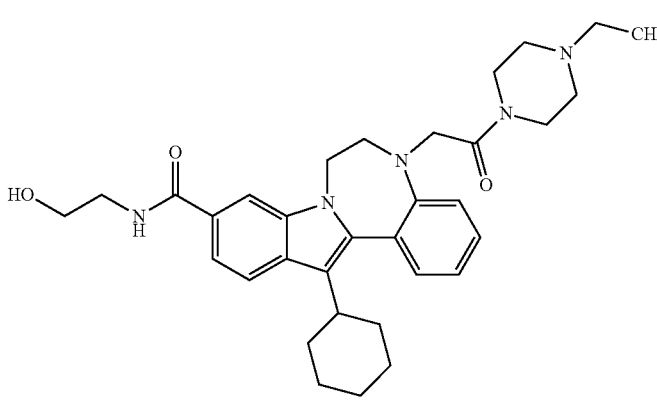 | 558.3 |
| 1-449 | 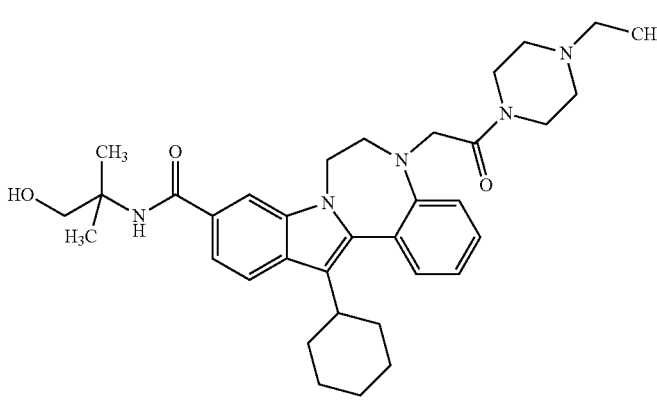 | 586.4 |

TABLE 120

| Ex. | formula | positive MS (M + 1) (free form) |
|---|---|---|
| 1-450 | | 663.2 |
| 1-451 | | 520.3 |
| 1-452 | | 423.1 |
| 1-453 | | 592.3(M-21) |

TABLE 121

| Ex. | formula | positive MS (M + 1) (free form) |
|---|---|---|
| 1-454 | | 605.4 |
| 1-455 | | 631.3 |
| 1-456 | | 513.3 |
| 1-457 | | 472.3 |

TABLE 122
| Ex. | formula | positive MS (M + 1) (free form) |
|---|---|---|
| 1-458 | 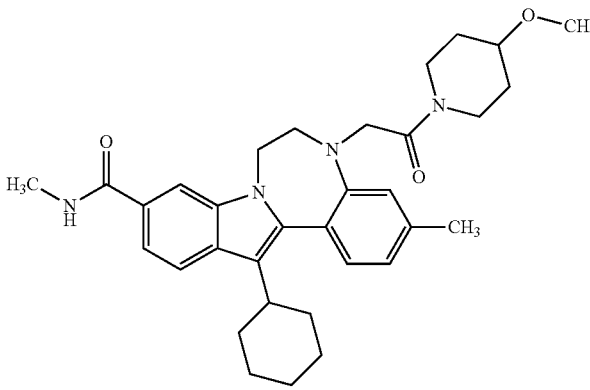 | 543.3 |
| 1-459 | 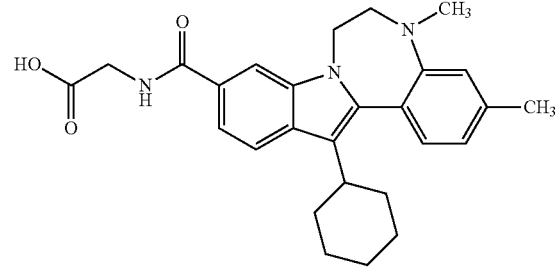 | 446.2 |
| 1-460 | 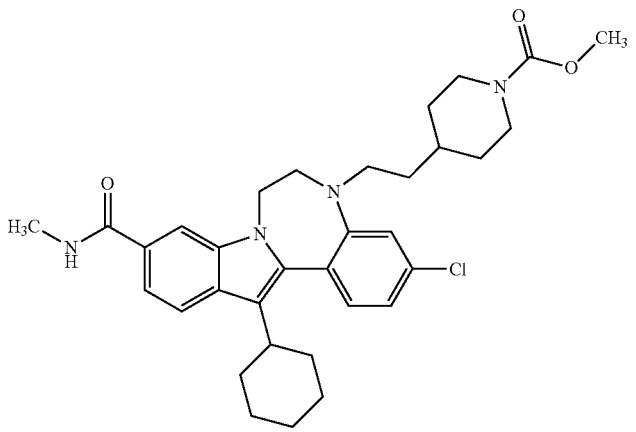 | 577.3 |
| 1-461 | 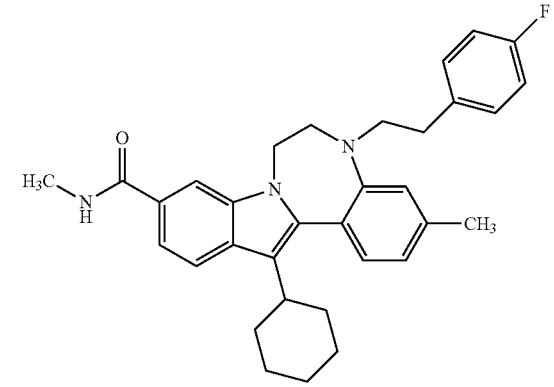 | 510.3 |

TABLE 123

| Ex. | formula | positive MS (M + 1) (free form) |
|---|---|---|
| 1-462 | | 675.4 |
| 1-463 | | 635.3 |
| 1-464 | | 647.3 |
| 1-465 | | 651.2 |
| 1-466 | | 653.3 |

TABLE 124

| Ex. | formula | positive MS (M + 1) (free form) |
|---|---|---|
| 1-467 | | 744.4 |
| 1-468 | | 723.3 |
| 1-469 | | 661.4 |
| 1-470 | | 635.3 |
| 1-471 | | 645.3 |

TABLE 125
| Ex. | formula | positive MS (M + 1) (free form) |
|---|---|---|
| 1-472 | 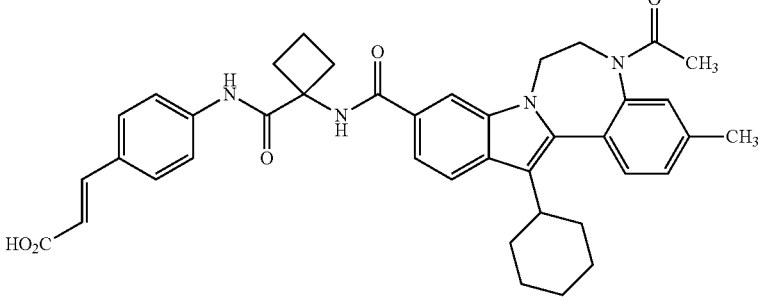 | 659.3 |
| 2-54 | 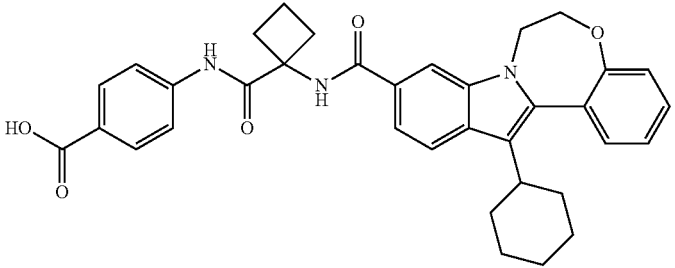 | 579.2 |
| 2-55 | 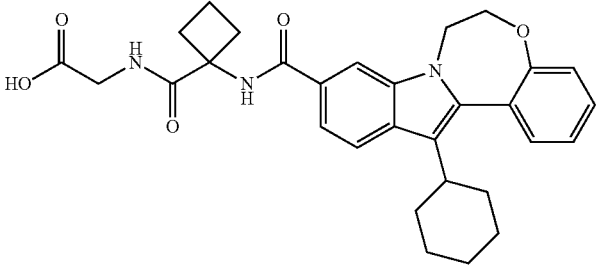 | 516.2 |
| 2-56 | 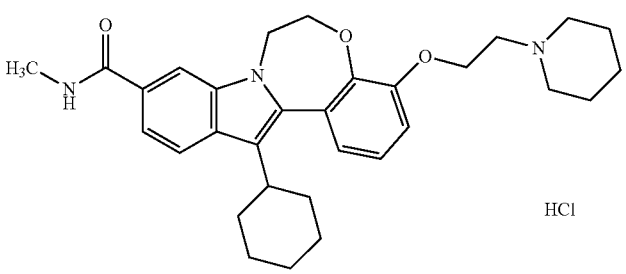 HCl | 502.3 |
| 2-57 | 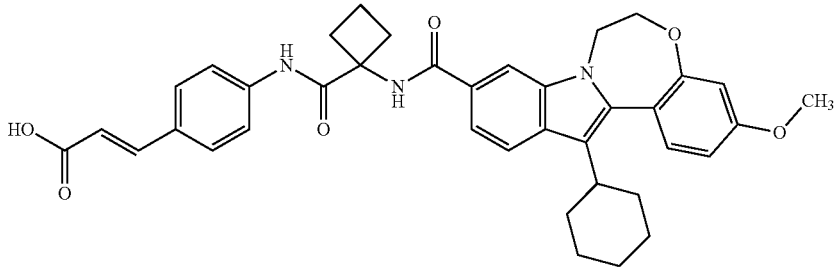 | 634.3 |

TABLE 126
| Ex. | formula | positive MS (M + 1) (free form) |
|---|---|---|
| 2-58 | 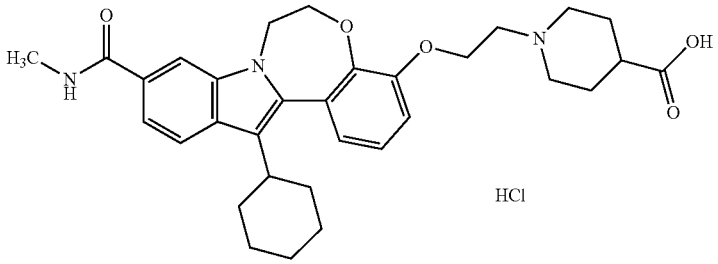 HCl | 546.3 |
| 2-59 | 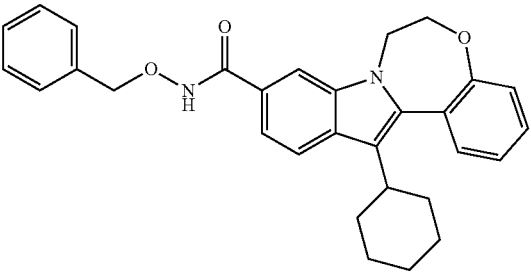 | 467.3 |
| 2-60 | 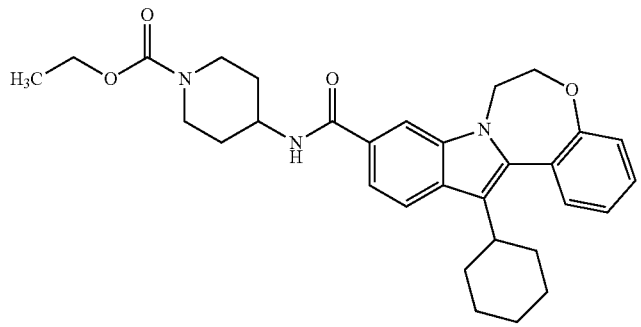 | 516.3 |
| 2-61 | 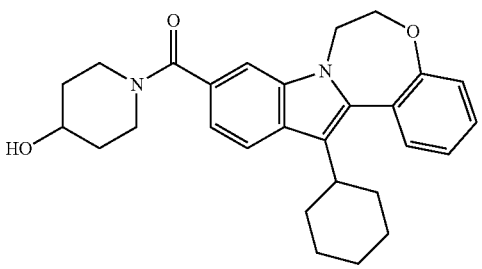 | 445.2 |
| 2-62 | 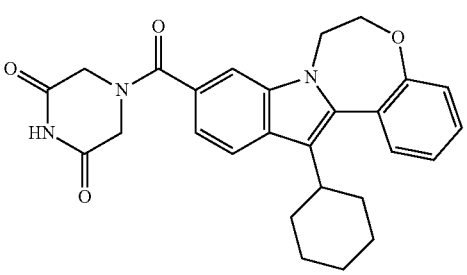 | 458.2 |

TABLE 127

| Ex. | formula | positive MS (M + 1) (free form) |
|---|---|---|
| 2-63 | | 473.2 |
| 2-64 | | 430.2 |
| 2-65 | | 419.2 |
| 2-66 | | 433.2 |
| 2-67 | | 475.2 |

TABLE 128

| Ex. | formula | positive MS (M + 1) (free form) |
|---|---|---|
| 2-68 | | 463.2 |
| 2-69 | | 479.2 |
| 2-70 | | 476.3 |
| 2-71 | | 564.3 |
| 2-72 | | 473.3 |

TABLE 129

| Ex. | formula | positive MS (M + 1) (free form) |
|---|---|---|
| 2-73 | | 447.2 |
| 2-74 | | 495.2 |
| 2-75 | | 509.2 |
| 2-76 | | 495.2 |
| 2-77 | | 495.2 |

TABLE 130

| Ex. | formula | positive MS (M + 1) (free form) |
|---|---|---|
| 2-78 | | 632.3 |
| 2-79 | | 604.2 |
| 2-80 | | 488.2 |
| 2-81 | | 606.3 |
| 2-82 | | 487.2 |

TABLE 131

| Ex. | formula | positive MS (M + 1) (free form) |
|---|---|---|
| 2-83 | | 475.3 |
| 2-84 | | 586.3 |
| 2-85 | | 487.3 |
| 2-86 | | 433.2 |
| 2-87 | | 608.3 |

TABLE 132
| Ex. | formula | positive MS (M + 1) (free form) |
|---|---|---|
| 2-88 | 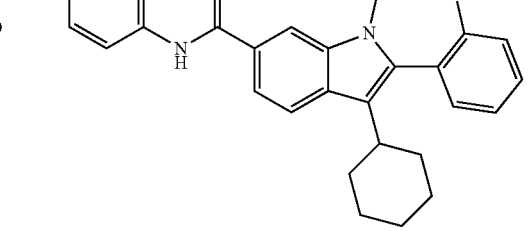 | 495.2 |
| 2-89 | 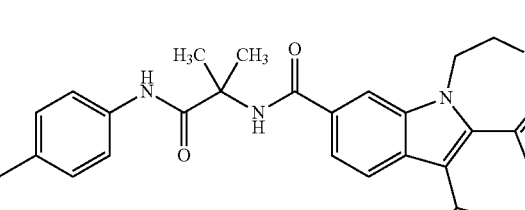 | 592.3 |
| 2-90 | 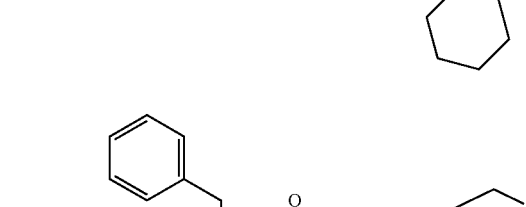 | 654.3 |
| 2-91 | 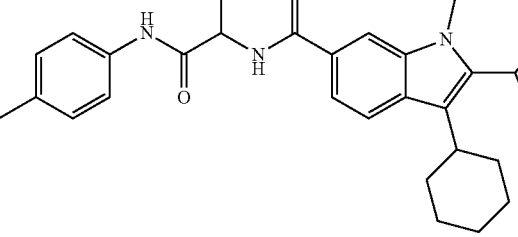 | 566.3 |
| 2-92 | 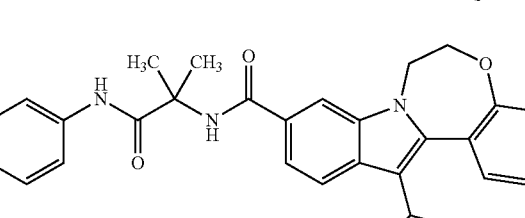 | 495.2 |

TABLE 133

| Ex. | formula | positive MS (M + 1)(free form) |
|---|---|---|
| 2-93 | | 606.3 |
| 2-94 | | 622.2 |
| 2-95 | | 618.3 |
| 2-96 | | 445.2 |
| 2-97 | | 487.3 |

TABLE 134
| Ex. | formula | positive MS (M + 1)(free form) |
|---|---|---|
| 2-98 | 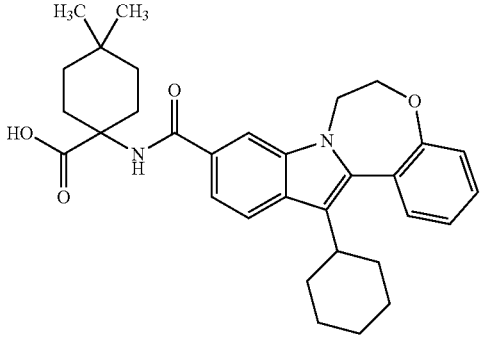 | 515.3 |
| 2-99 | 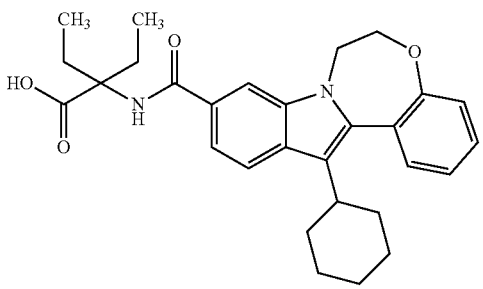 | 475.2 |
| 2-100 | 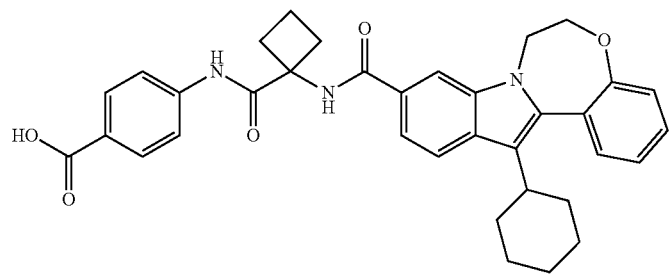 | 578.3 |
| 2-101 | 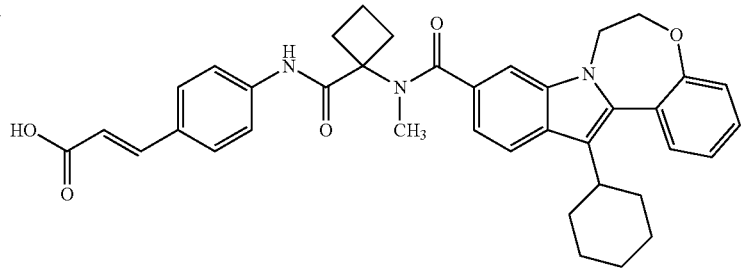 | 618.3 |
| 2-102 | 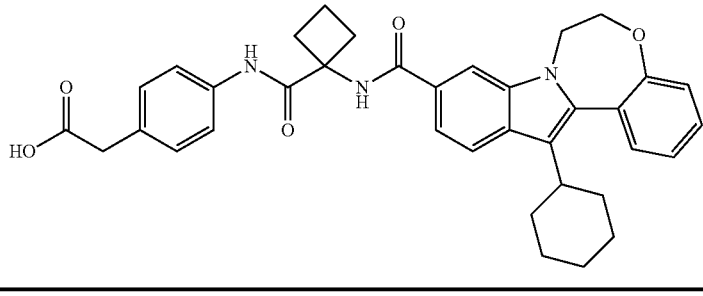 | 592.3 |

TABLE 135
| Ex. | formula | positive MS (M + 1)(free form) |
|---|---|---|
| 2-103 | 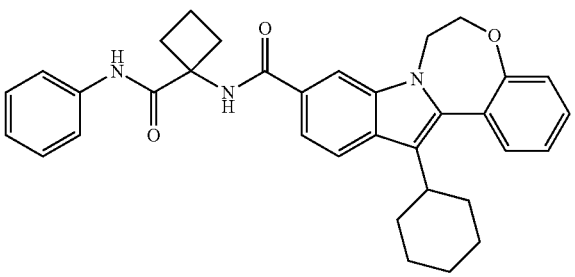 | 534.3 |
| 2-104 | 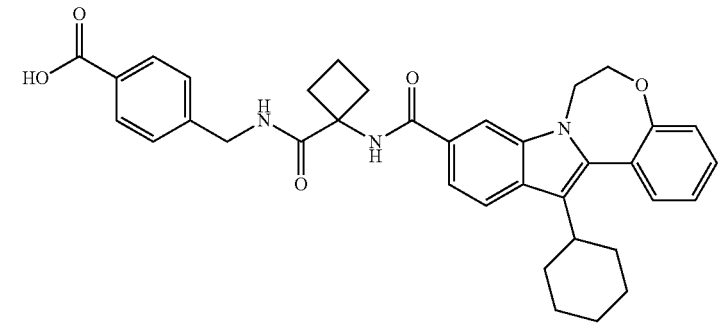 | 592.3 |
| 2-105 | 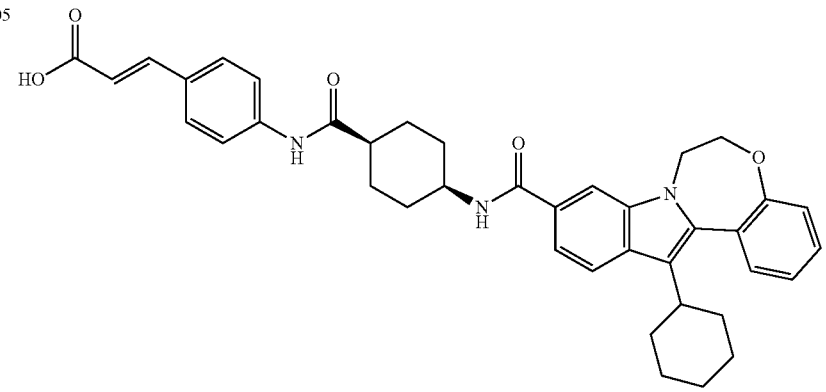 | 632.3 |
| 2-106 | 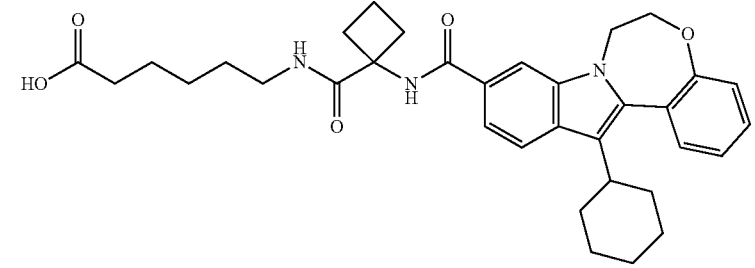 | 572.3 |

TABLE 135-continued
| Ex. | formula | positive MS (M + 1)(free form) |
|---|---|---|
| 2-107 | 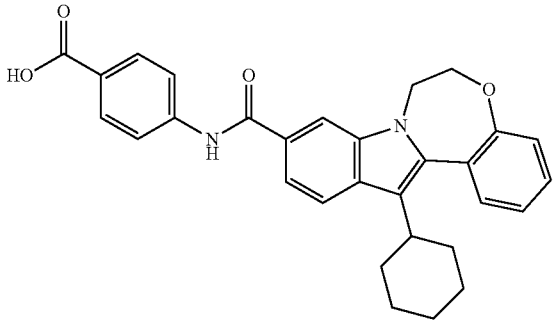 | 481.2 |
TABLE 136
| Ex. | formula | positive MS (M + 1)(free form) |
|---|---|---|
| 2-108 | 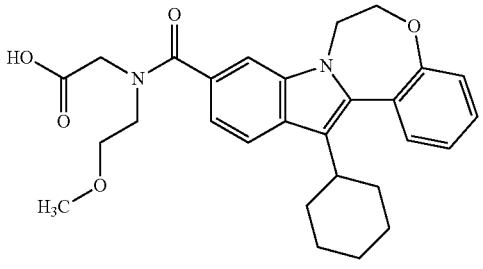 | 477.2 |
| 2-109 | 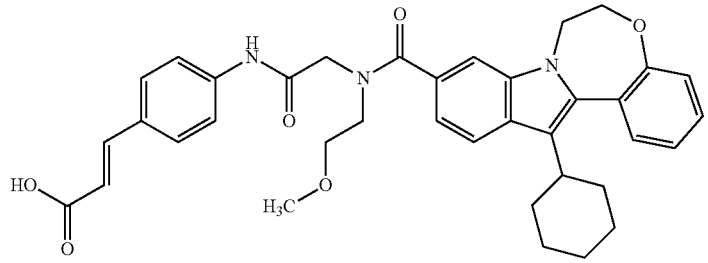 | 622.3 |
| 2-110 | 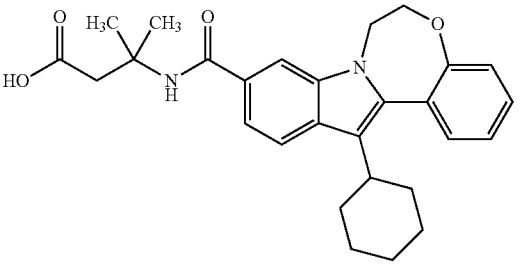 | 461.2 |

TABLE 136-continued

| Ex. | formula | positive MS (M + 1)(free form) |
|---|---|---|
| 2-111 | | 620.3 |
| 2-112 | | 459.2 |

TABLE 137

| Ex. | formula | positive MS (M + 1)(free form) |
|---|---|---|
| 2-113 | | 473.2 |
| 2-114 | | 584.3 |

TABLE 137-continued

| Ex. | formula | positive MS (M + 1)(free form) |
|---|---|---|
| 2-115 | | 570.3 |
| 2-116 | | 590.2 |
| 2-117 | | 660.3 |

TABLE 138

| Ex. | formula | positive MS (M + 1)(free form) |
|---|---|---|
| 2-118 | | 632.3 |

TABLE 138-continued
| Ex. | formula | positive MS (M + 1)(free form) |
|---|---|---|
| 2-119 | 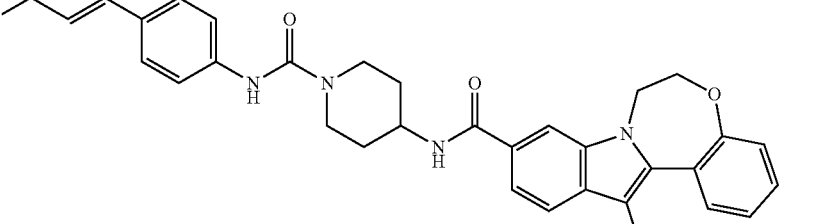 | 633.3 |
| 2-120 |  | 592.3 |
| 2-121 |  | 608.3 |
| 2-122 |  | 634.2 |

TABLE 139
| Ex. | formula | positive MS (M + 1)(free form) |
|---|---|---|
| 2-123 | 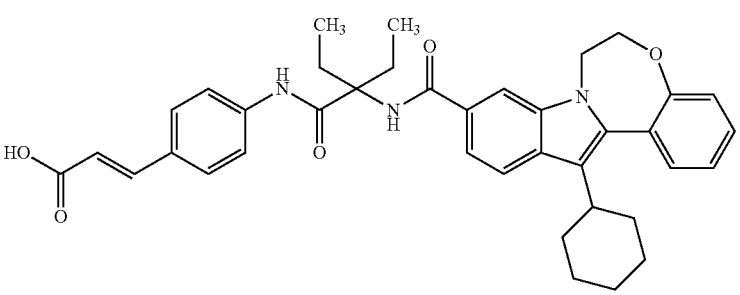 | 620.3 |
| 2-124 | 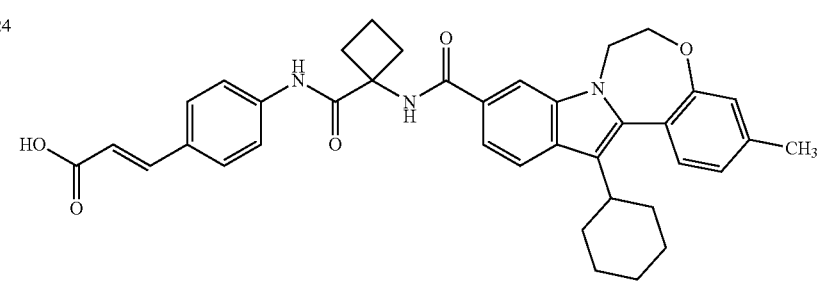 | 618.3 |
| 2-125 | 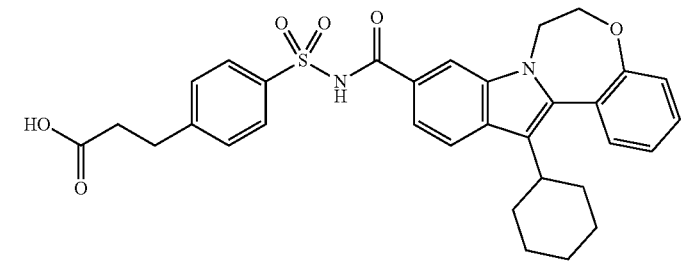 | 573.2 |
| 2-126 | 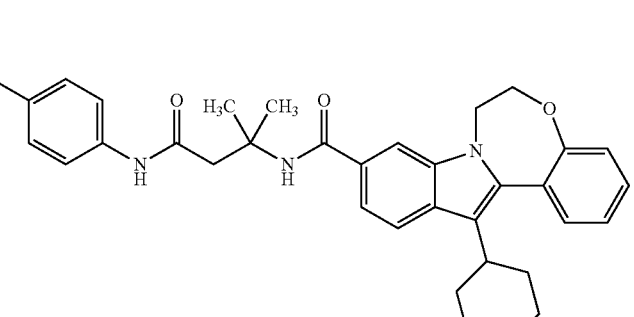 | 606.2 |
| 2-127 | 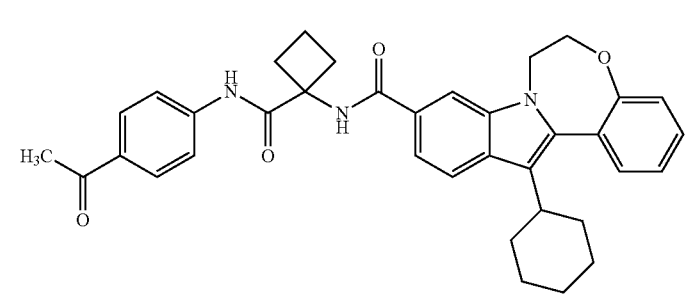 | 576.2 |

TABLE 140
| Ex. | formula | positive MS (M + 1)(free form) |
|---|---|---|
| 2-128 | 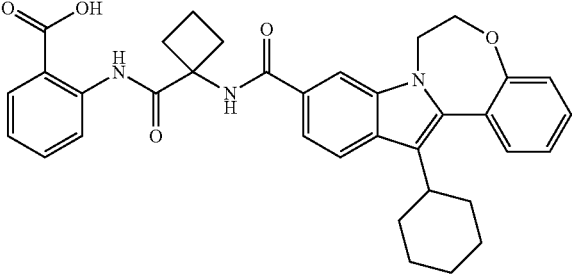 | 578.3 |
| 2-129 | 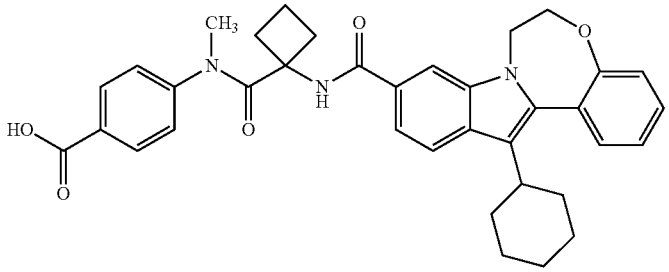 | 592.3 |
| 2-130 | 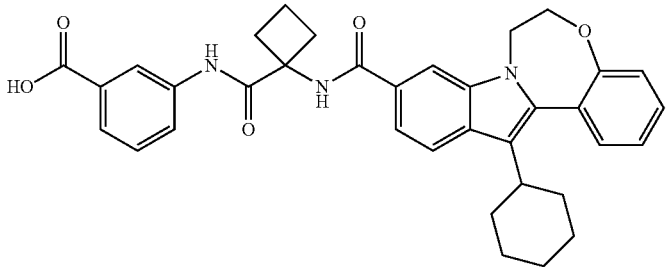 | 578.3 |
| 2-131 | 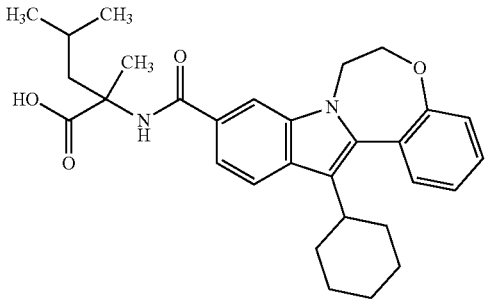 | 489.2 |
| 2-132 | 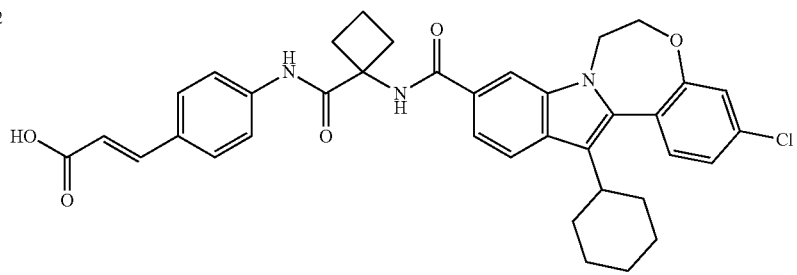 | 638.3 |

TABLE 141
| Ex. | formula | positive MS (M + 1)(free form) |
|---|---|---|
| 2-133 | 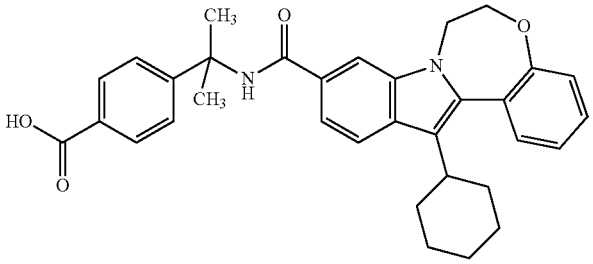 | 523.2 |
| 2-134 | 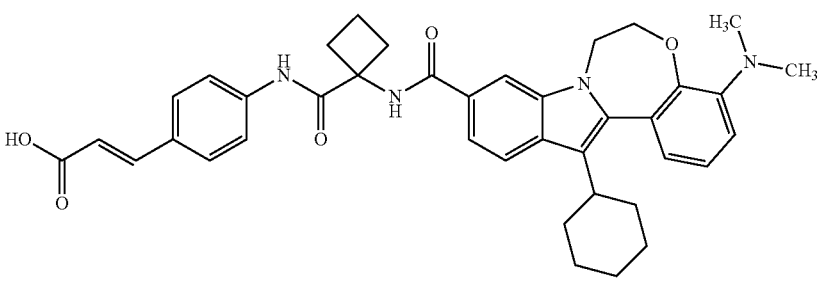 | 647.3 |
| 2-135 | 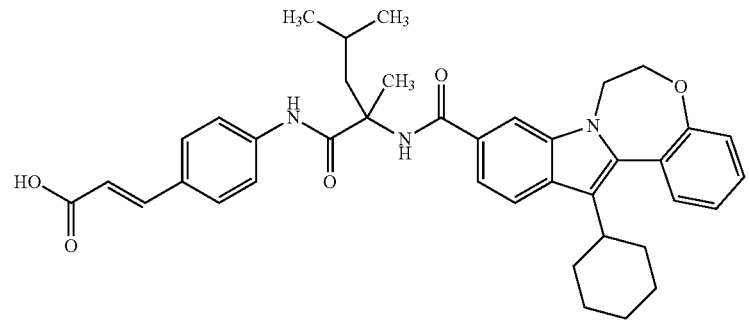 | 634.3 |
| 2-136 | 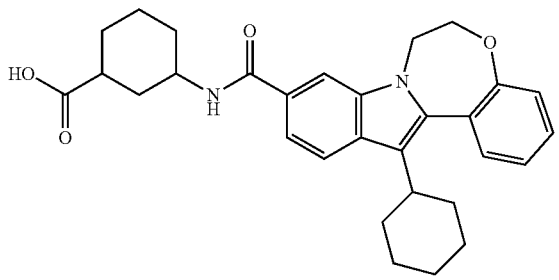 | 487.3 |
| 2-137 | 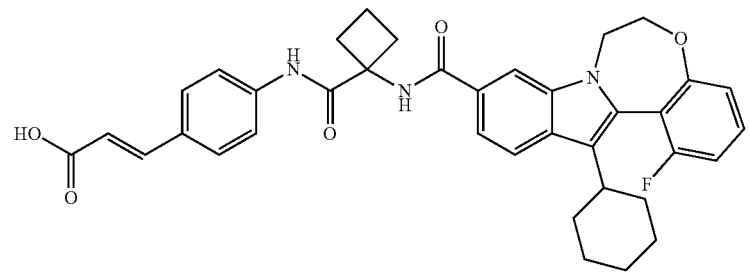 | 622.2 |

TABLE 142

| Ex. | formula | positive MS (M + 1)(free form) |
|---|---|---|
| 2-138 | | 487.3 |
| 2-139 | | 632.4 |
| 2-140 | | 507.3 |
| 2-141 | | 640.3 |
| 2-142 | | 632.2 |

TABLE 143
| Ex. | formula | positive MS (M + 1)(free form) |
|---|---|---|
| 2-143 | 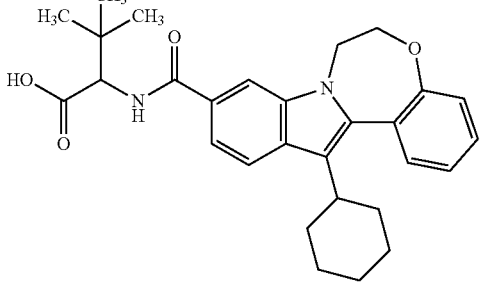 | 475.2 |
| 2-144 | 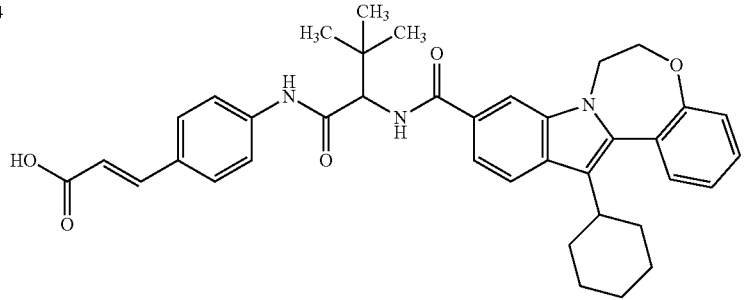 | 620.3 |
| 2-145 | 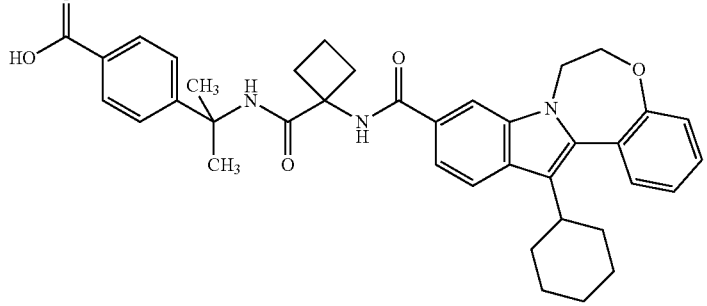 | 620.3 |
| 2-146 | 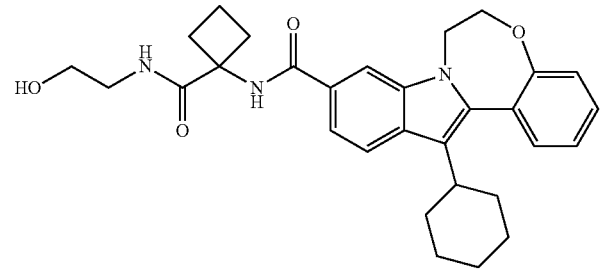 | 502.3 |
| 2-147 | 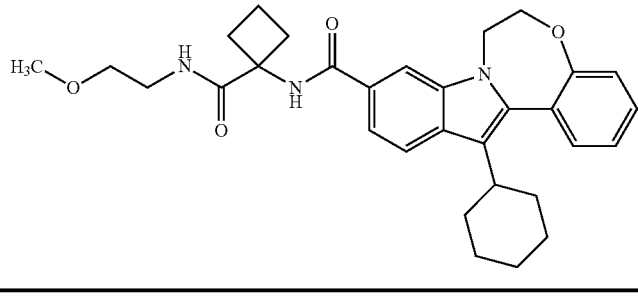 | 516.3 |

TABLE 144

| Ex. | formula | positive MS (M + 1)(free form) |
|---|---|---|
| 2-148 | | 361.2 |
| 2-149 | | 559.2 |
| 2-150 | | 604.2 |

TABLE 145

| Ex. | formula | positive MS (M + 1)(free form) |
|---|---|---|
| 1-473 | | 566.3 |
| 1-474 | | 419.3 |

TABLE 145-continued
| Ex. | formula | positive MS (M + 1)(free form) |
|---|---|---|
| 1-475 | 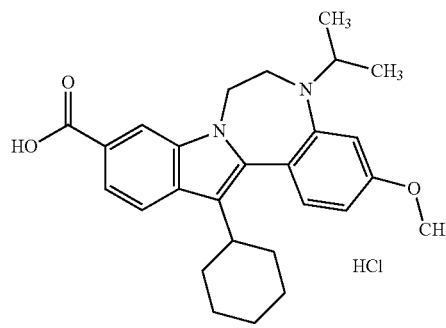 HCl | 433.3 |
| 1-476 | 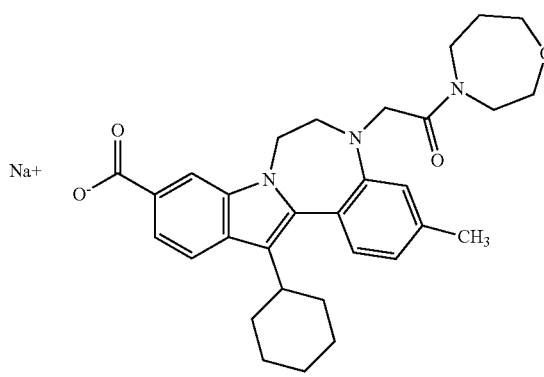 | 516.3 |
| 1-477 | 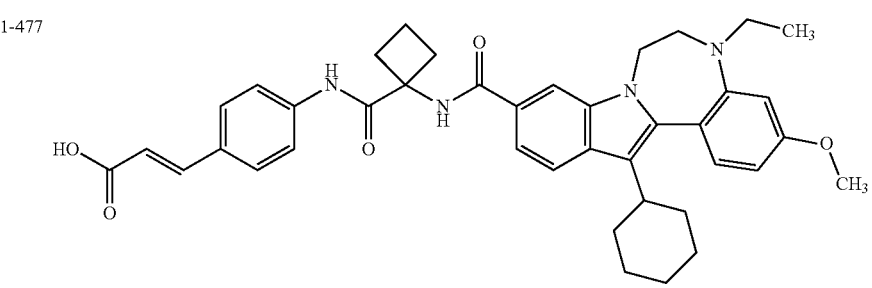 | 661.3 |
TABLE 146
| Ex. | formula | positive MS (M + 1)(free form) |
|---|---|---|
| 1-478 | 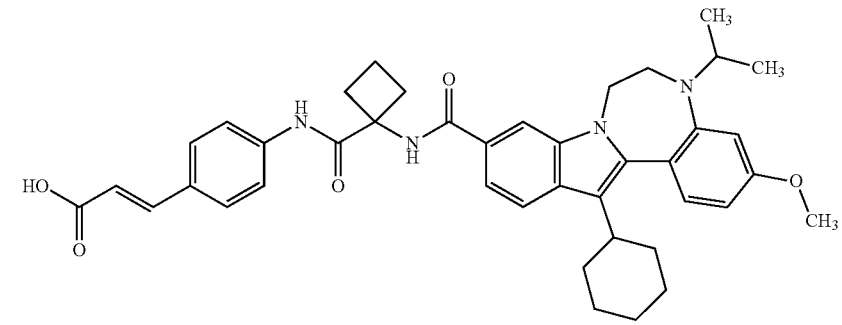 | 675.3 |

TABLE 146-continued
| Ex. | formula | positive MS (M + 1)(free form) |
|---|---|---|
| 1-479 | 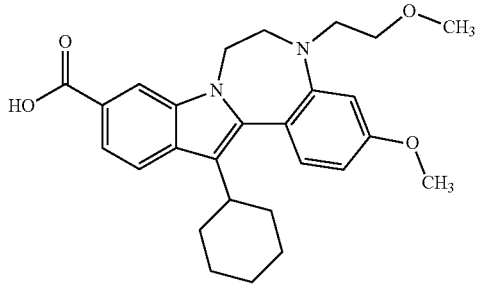 | 449.2 |
| 1-480 | 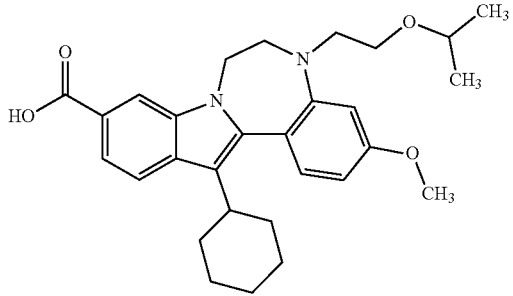 | 477.3 |
| 1-481 | 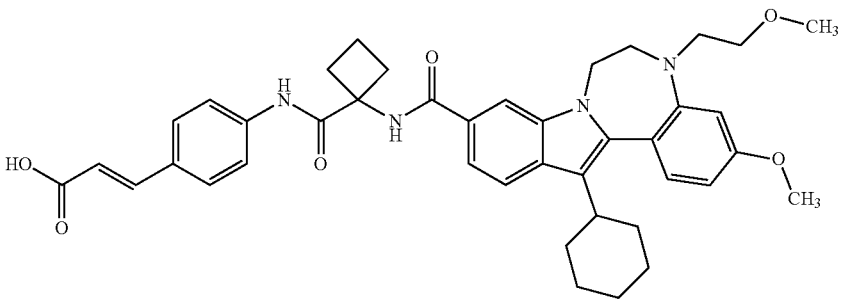 | 691.3 |
| 1-482 | 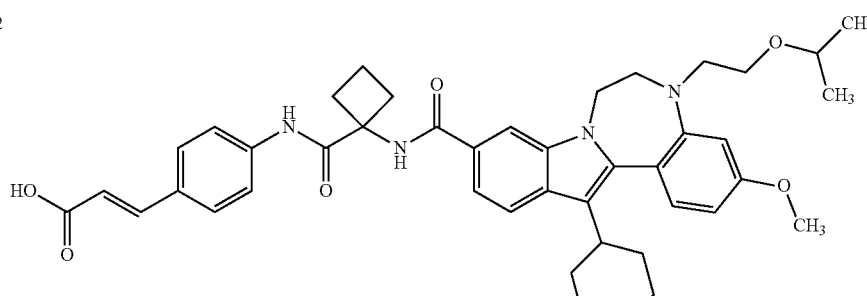 | 719.3 |

TABLE 147
| Ex. | formula | positive MS (M + 1)(free form) |
|---|---|---|
| 1-483 | 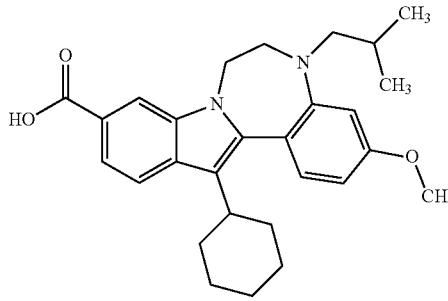 | 447.3 |
| 1-484 | 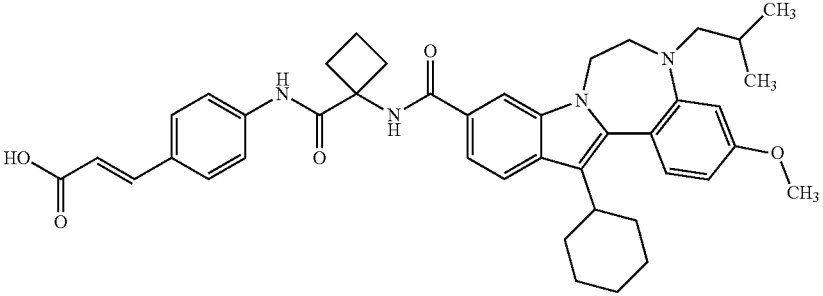 | 689.3 |
TABLE 148
| Ex. | formula | positive MS (M + 1) (free form) |
|---|---|---|
| 2-151 | 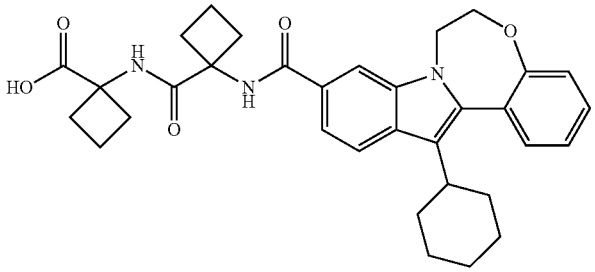 | 556.2 |
| 2-152 | 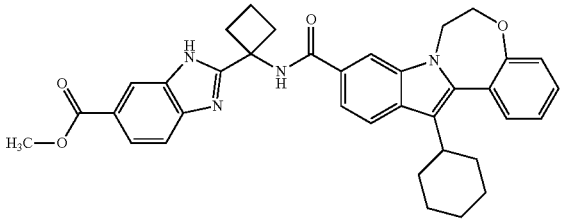 | 589.3 |
| 2-153 | 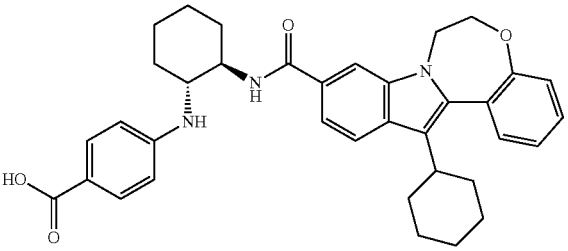 | 578.3 |

TABLE 148-continued

| Ex. | formula | positive MS (M + 1) (free form) |
|---|---|---|
| 2-154 | | 477.2 |
| 2-155 | | 733.3 |

TABLE 149

| Ex. | formula | positive MS (M + 1) (free form) |
|---|---|---|
| 2-156 | | 553.2 |
| 2-157 | | 543.2 |
| 2-158 | | 533.3 |

TABLE 149-continued

| Ex. | formula | positive MS (M + 1) (free form) |
|---|---|---|
| 2-159 | | 433.2 |
| 2-160 | | 575.2 |

TABLE 150

| Ex. | formula | positive MS (M + 1) (free form) |
|---|---|---|
| 2-161 | | 530.3 |
| 2-162 | | 462.3 |
| 2-163 | | 622.2 |

TABLE 150-continued

| Ex. | formula | positive MS (M + 1) (free form) |
|---|---|---|
| 2-164 | | 449.2 |

TABLE 151

| Ex. | formula | positive MS (M + 1) (free form) |
|---|---|---|
| 2-165 | | 417.2 |
| 2-166 | | 459.3 |
| 2-167 | | 428.2 |

TABLE 151-continued
| Ex. | formula | positive MS (M + 1) (free form) |
|---|---|---|
| 2-168 | 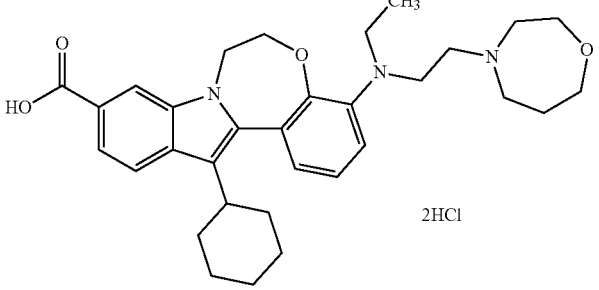 2HCl | 532.3 |
| 2-169 | 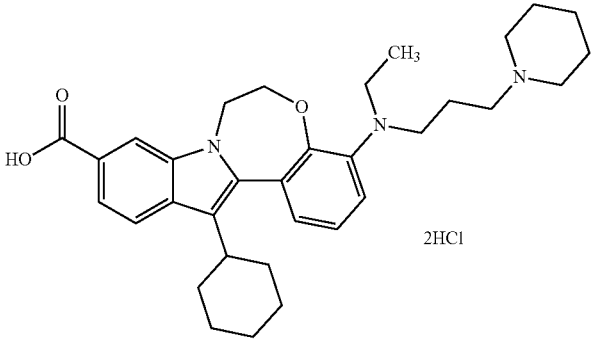 2HCl | 530.3 |
TABLE 152
| Ex. | formula | positive MS (M + 1) (free form) |
|---|---|---|
| 2-170 | 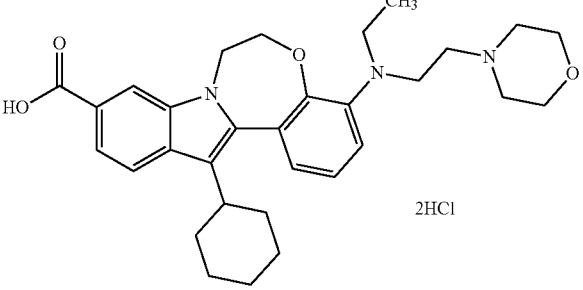 2HCl | 518.3 |
| 2-171 | 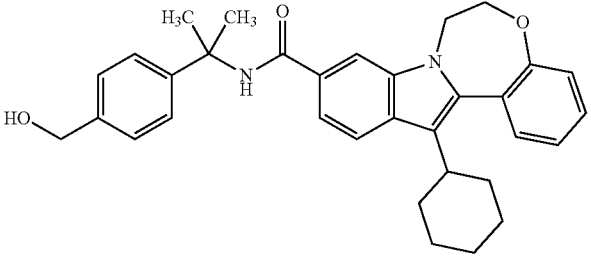 | 509.2 |

TABLE 152-continued

| Ex. | formula | positive MS (M + 1) (free form) |
|---|---|---|
| 2-172 | | 558.2 |
| 2-173 | | 375.2 |
| 2-174 | | 633.3 |

TABLE 153

| Ex. | formula | positive MS (M + 1) (free form) |
|---|---|---|
| 2-175 | | 539.3 |

TABLE 153-continued
| Ex. | formula | positive MS (M + 1) (free form) |
|---|---|---|
| 2-176 | 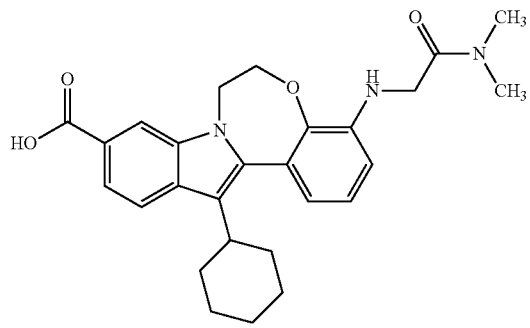 | 462.1 |
| 2-177 | 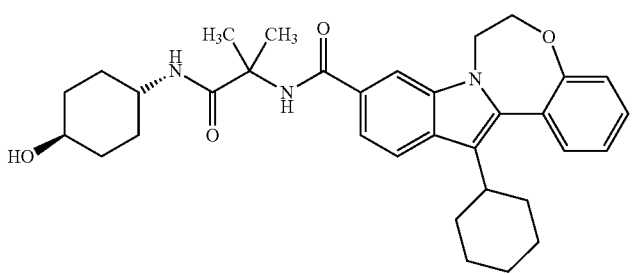 | 544.3 |
| 2-178 | 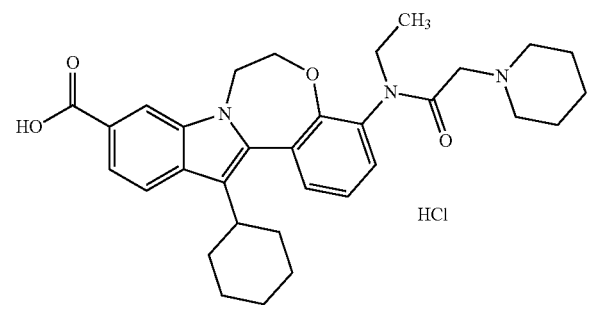 | 530.3 |
| 2-179 | 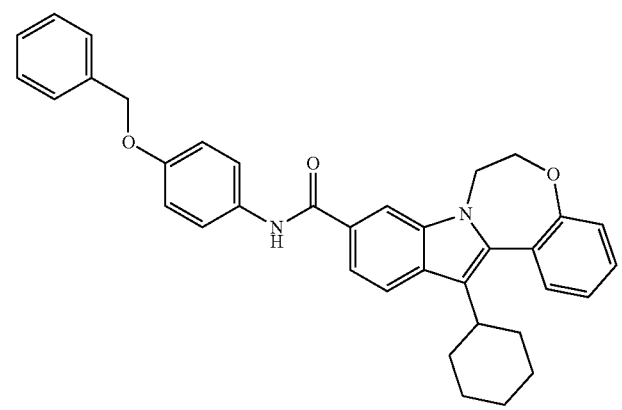 | 543.2 |

TABLE 154

| Ex. | formula | positive MS (M + 1) (free form) |
|---|---|---|
| 2-180 | | 525.3 |
| 2-181 | | 530.2 |
| 2-182 | | 502.3 |
| 2-183 | | 552.2 |
| 2-184 | | 551.2 |

TABLE 155
| Ex. | formula | positive MS (M + 1) (free form) |
|---|---|---|
| 2-185 | 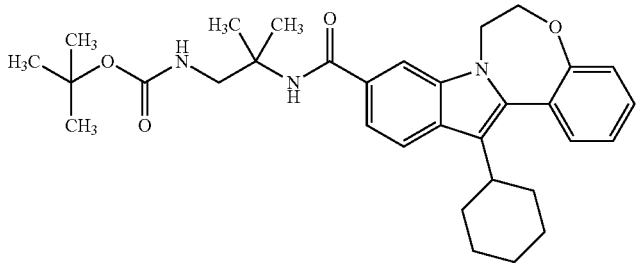 | 532.3 |
| 2-186 | 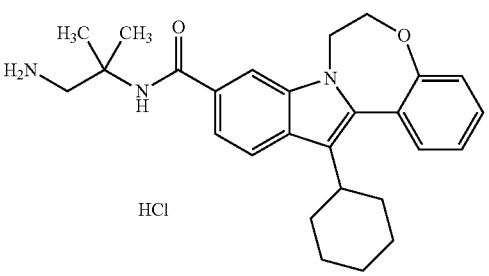 HCl | 432.2 |
| 2-187 | 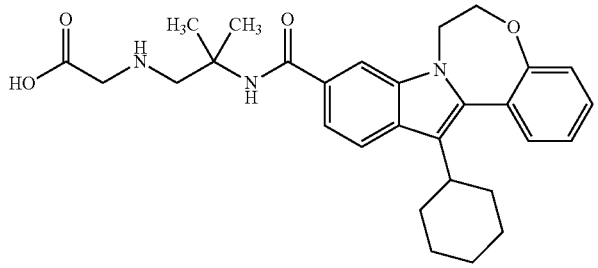 | 490.2 |
| 2-188 | 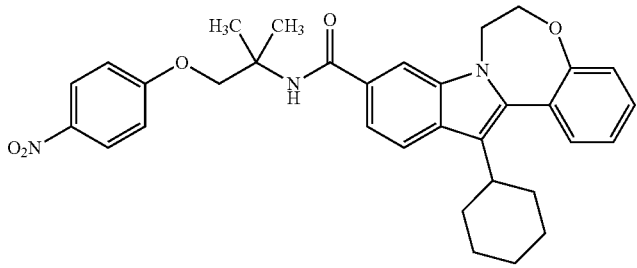 | 554.3 |
| 2-189 | 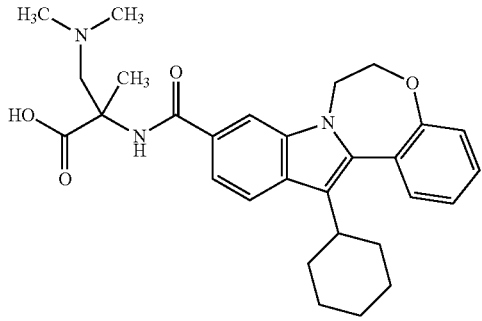 | 490.2 |

923

924

TABLE 156

| Ex. | formula | positive MS (M + 1) (free form) |
|---|---|---|
| 2-190 | | 429.1 (M - 100) negative MS 528.4 (M - 1) |
| 2-191 | | 578.3 |
| 2-192 | | 453.2 |
| 2-193 | | 565.3 |
| 2-194 | | 593.3 |

TABLE 157
| Ex, | formula | positive MS (M + 1) (free form) |
|---|---|---|
| 2-195 | 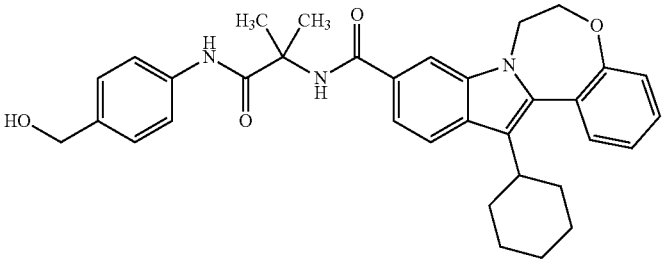 | 552.3 |
| 2-196 | 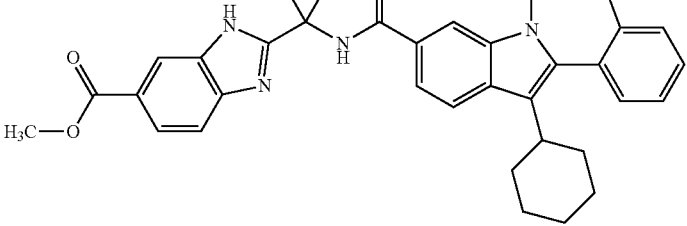 | 577.2 |
| 2-197 | 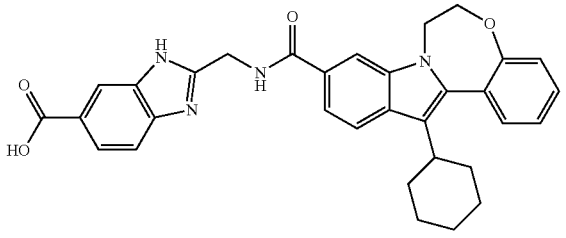 | 535.2 |
| 2-198 | 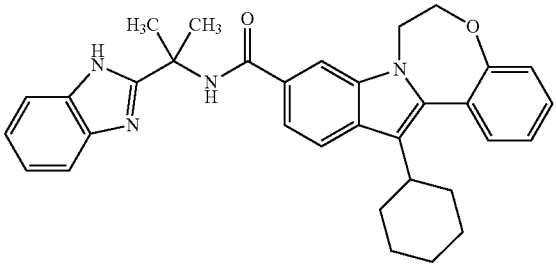 | 519.3 |
| 2-199 | 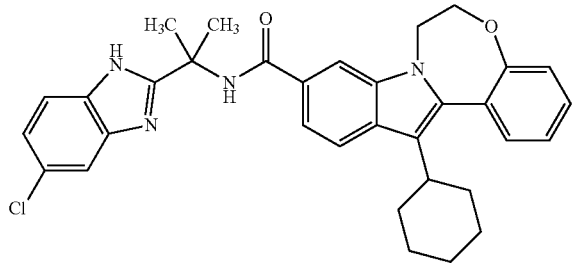 | 553.2 |

TABLE 157-continued

| Ex. | formula | positive MS (M + 1) (free form) |
|---|---|---|
| 2-200 | | 580.3 |

TABLE 158

| Ex. | formula | positive MS (M + 1) (free form) |
|---|---|---|
| 2-201 | | 566.2 |
| 2-202 | | 538.3 |
| 2-203 | | 566.3 |
| 2-204 | | 540.3 |

TABLE 158-continued

| Ex. | formula | positive MS (M + 1) (free form) |
|---|---|---|
| 2-205 | | 481.2 |
| 2-206 | | 473.3 |

TABLE 159

| Ex. | formula | positive MS (M + 1) (free form) |
|---|---|---|
| 2-207 | | 524.2 |
| 2-208 | | 529.3 |
| 2-209 | | 541.3 |

TABLE 159-continued

| Ex. | formula | positive MS (M + 1) (free form) |
|---|---|---|
| 2-210 | | 578.3 |
| 2-211 | | 580.2 |

TABLE 160

| Ex. | formula | positive MS (M + 1)(free form) |
|---|---|---|
| 2-212 | | 594.2 |
| 2-213 | | 579.2 |

TABLE 160-continued
| Ex. | formula | positive MS (M + 1)(free form) |
|---|---|---|
| 2-214 | 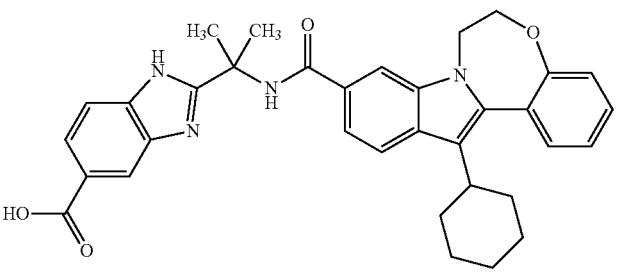 | 563.3 |
| 2-215 | 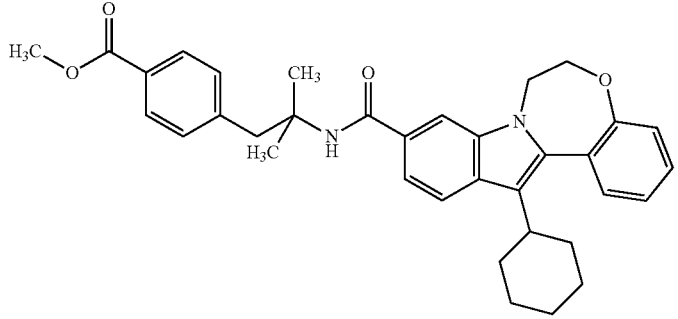 | 551.3 |
| 2-216 | 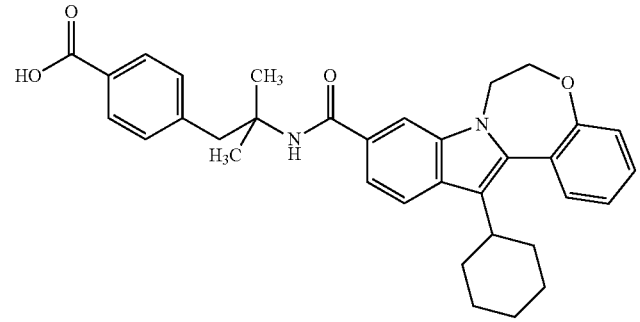 | 537.3 |
TABLE 161
| Ex. | formula | positive MS (M + 1) (free form) |
|---|---|---|
| 2-217 | 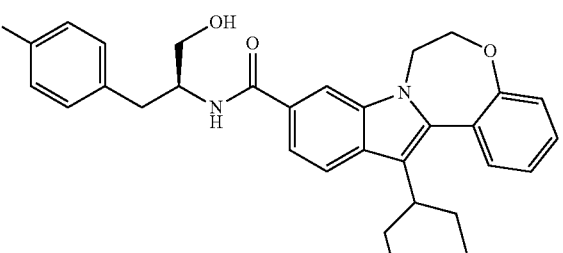 | 511.2 |

TABLE 161-continued
| Ex. | formula | positive MS (M + 1) (free form) |
|---|---|---|
| 2-218 | 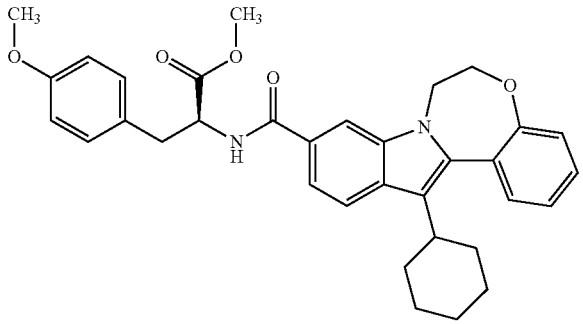 | 553.3 |
| 2-219 | 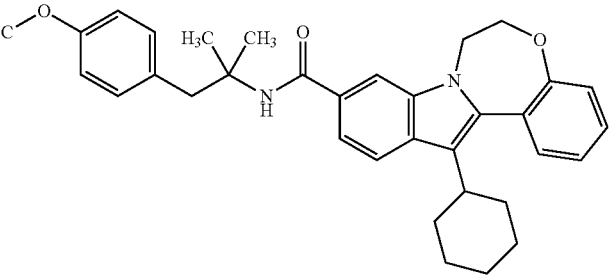 | 523.3 |
| 2-220 | 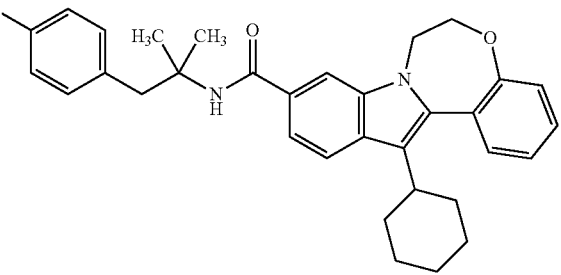 | 509.3 |
| 2-221 | 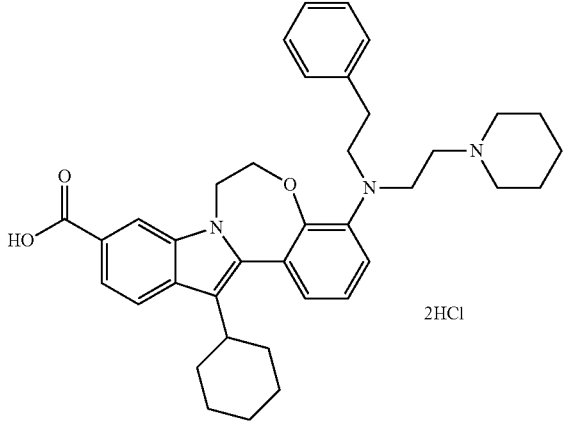 | 592.3 |

TABLE 162

| Ex. | formula | positive MS (M + 1) (free form) |
|---|---|---|
| 2-222 | | 675.2 |
| 2-223 | | 647.2 |
| 2-224 | | 524.3 |
| 2-225 | | 562.3 |
| 2-226 | | 592.3 |

TABLE 163

| Ex. | formula | positive MS (M + 1)(free form) |
|---|---|---|
| 2-227 | | 527.3 |
| 2-228 | | 585.3 |
| 2-229 | HCl | 546.3 |
| 2-230 | | 495.2 |
| 2-231 | 2HCl | 530.3 |

TABLE 164

| Ex. | formula | positive MS (M + 1)(free form) |
|---|---|---|
| 2-232 | | 558.3 |
| 2-233 | | 572.3 |
| 2-234 | | 516.3 |
| 2-235 | | 542.3 |
| 2-236 | | 528.2 |

TABLE 165
| Ex. | formula | positive MS (M + 1)(free form) |
|---|---|---|
| 2-237 | 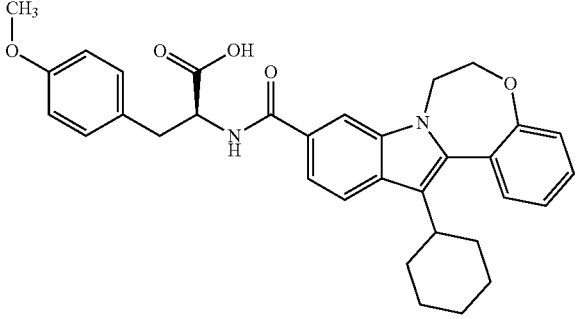 | 539.3 |
| 2-238 | 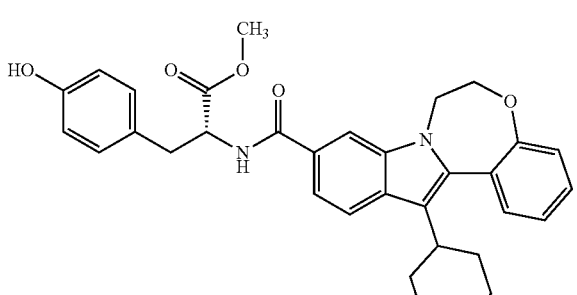 | 539.2 |
| 2-239 | 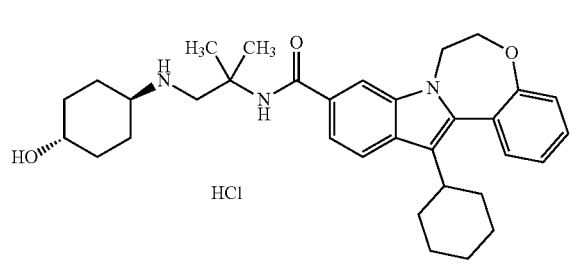 HCl | 530.3 |
| 2-240 | 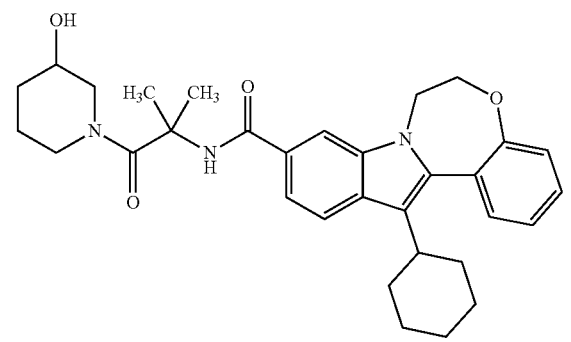 | 429.1(M − 100) negative MS 528.3(M − 1) |
| 2-241 | 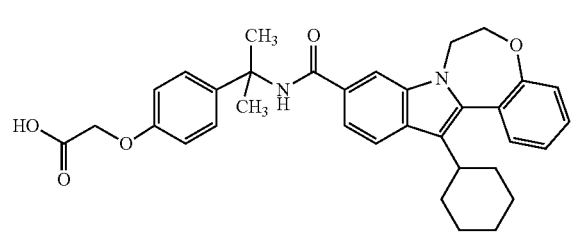 | 553.3 |

TABLE 166

| Ex. | formula | positive MS (M + 1)(free form) |
|---|---|---|
| 2-242 | | 429.2(M − 114) negative MS 542.3(M − 1) |
| 2-243 | | 544.3 |
| 2-244 | | 545.3 |
| 2-245 | | 538.3 |
| 2-246 | | 525.2 |

TABLE 167
| Ex. | formula | positive MS (M + 1)(free form) |
|---|---|---|
| 2-247 | 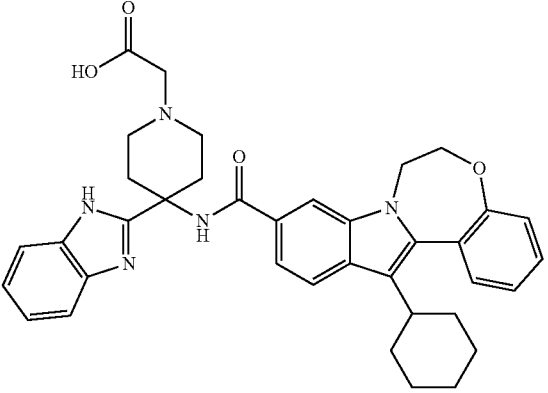 | 618.3 |
| 2-248 | 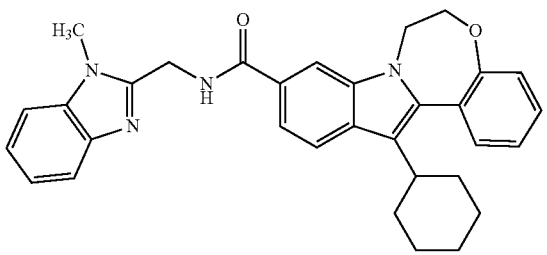 HCl | 632.3 |
| 2-249 | 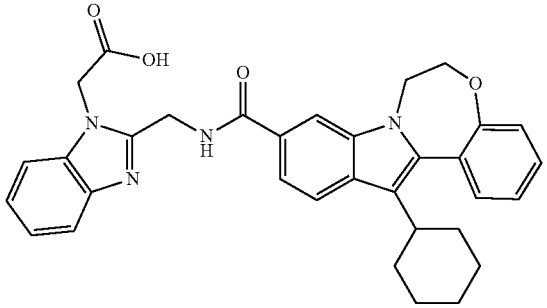 | 505.2 |
| 2-250 | | 549.3 |

TABLE 168
| Ex. | formula | positive MS (M + 1)(free form) |
|---|---|---|
| 2-251 | 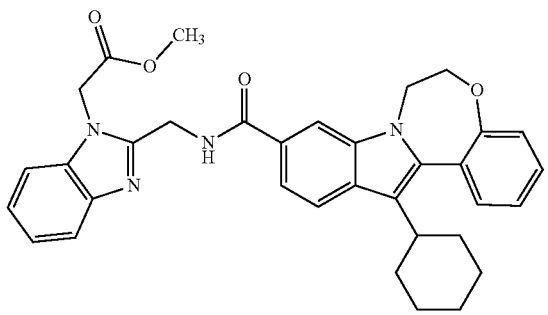 | 563.2 |
| 2-252 | 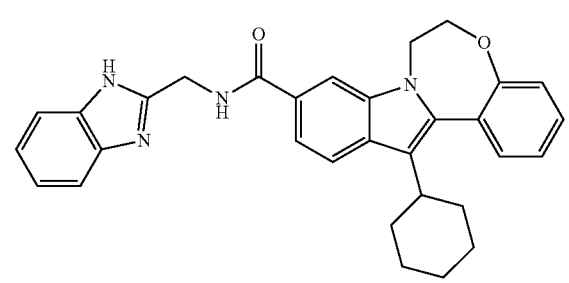 | 491.2 |
| 2-253 | 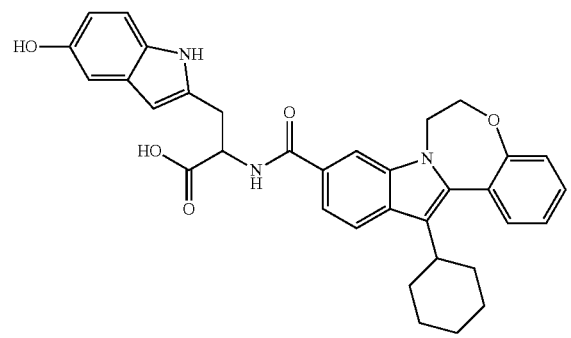 | 564.2 |
| 2-254 | 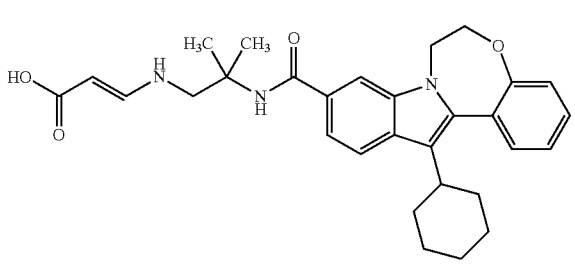 | 530.3 |
| 2-255 | 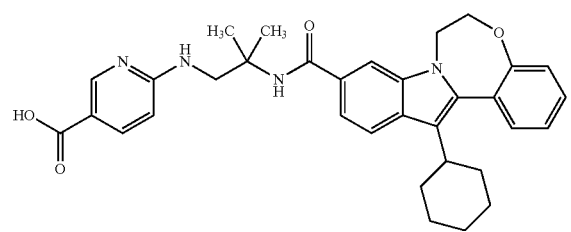 | 553.3 |

TABLE 169
| Ex. | formula | positive MS (M + 1)(free form) |
|---|---|---|
| 2-256 | 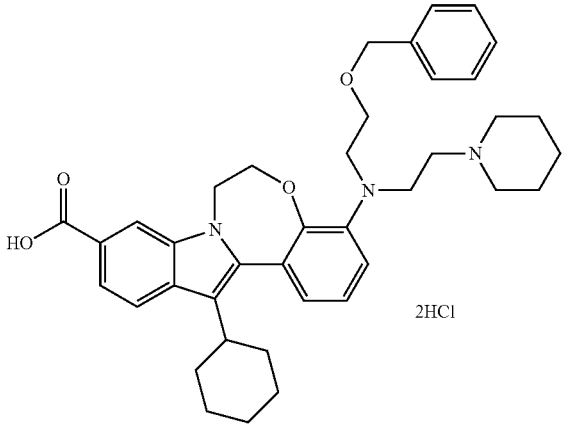 | 622.3 |
| 2-257 | 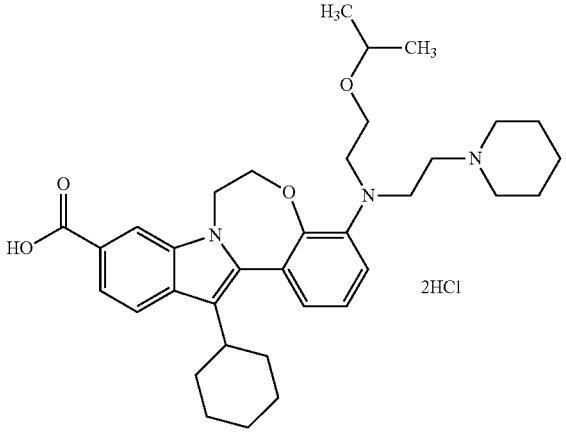 | 574.3 |
| 2-258 | 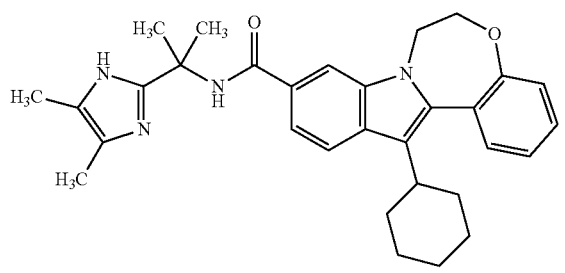 | 498.2 |
| 2-259 | 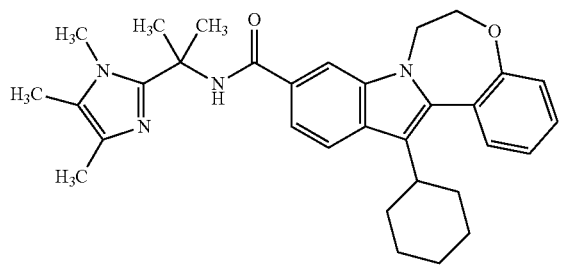 | 511.2 |

TABLE 170

| Ex. | formula | positive MS (M + 1)(free form) |
|---|---|---|
| 2-260 | | 538.0 |
| 2-261 | | 532.3 |
| 2-262 | | 581.9 |
| 2-263 | | 568.3 |

TABLE 170-continued

| Ex. | formula | positive MS (M + 1)(free form) |
|---|---|---|
| 2-264 | | 569.3 |

TABLE 171

| Ex. | formula | positive MS (M + 1)(free form) |
|---|---|---|
| 2-265 | | 555.3 |
| 2-266 | | 535.2 |
| 2-267 | | 477.2 |

TABLE 171-continued
| Ex. | formula | positive MS (M + 1)(free form) |
|---|---|---|
| 2-268 | 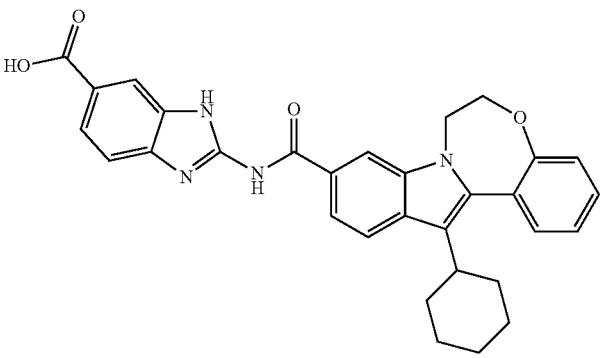 | 521.2 |
TABLE 172
| Ex. | formula | positive MS (M + 1)(free form) |
|---|---|---|
| 2-269 | | 544.3 |
| 2-270 | | 555.2 |
| 2-271 | | 555.2 |

TABLE 172-continued
| Ex. | formula | positive MS (M + 1)(free form) |
|---|---|---|
| 2-272 | 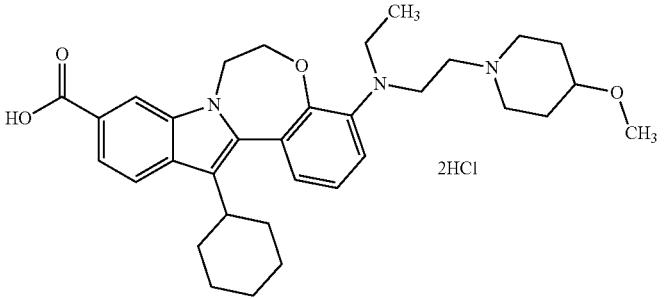 2HCl | 546.3 |
| 2-273 | 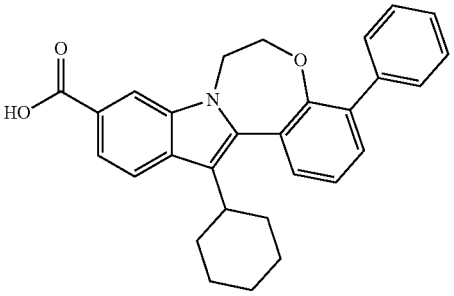 | 438.2 |
TABLE 173
| Ex. | formula | positive MS (M + 1)(free form) |
|---|---|---|
| 2-274 | 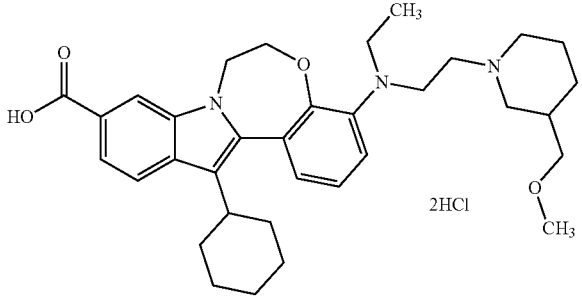 2HCl | 560.3 |
| 2-275 | 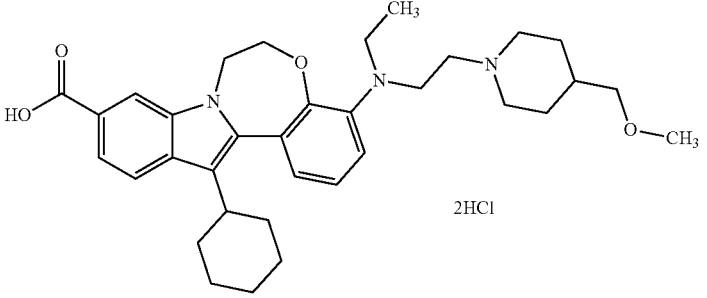 2HCl | 560.3 |

TABLE 173-continued

| Ex. | formula | positive MS (M + 1)(free form) |
|---|---|---|
| 2-276 | | 615.4 |
| 2-277 | | 627.3 |

TABLE 174

| Ex. | formula | positive MS (M + 1)(free form) |
|---|---|---|
| 2-278 | | 599.4 |

TABLE 174-continued
| Ex. | formula | positive MS (M + 1)(free form) |
|---|---|---|
| 2-279 | 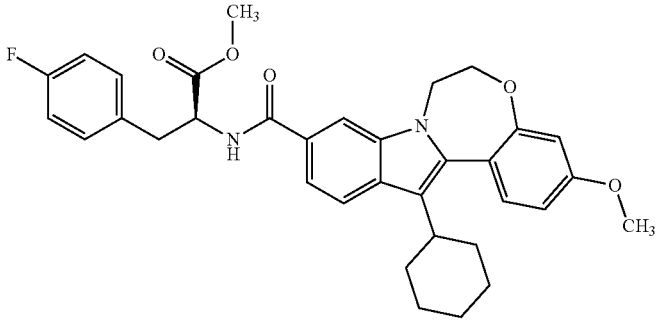 | 571.3 |
| 2-280 | 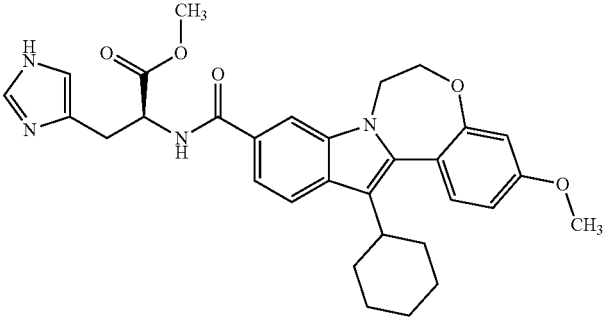 | 543.2 |
| 2-281 | 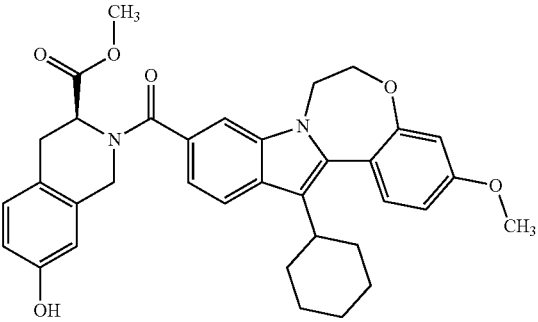 | 581.2 |
TABLE 175
| Ex. | formula | positive MS (M + 1)(free form) |
|---|---|---|
| 2-282 | 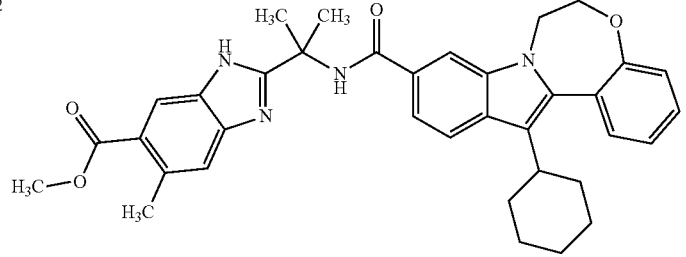 | 591.3 |

TABLE 175-continued
| Ex. | formula | positive MS (M + 1)(free form) |
|---|---|---|
| 2-283 | 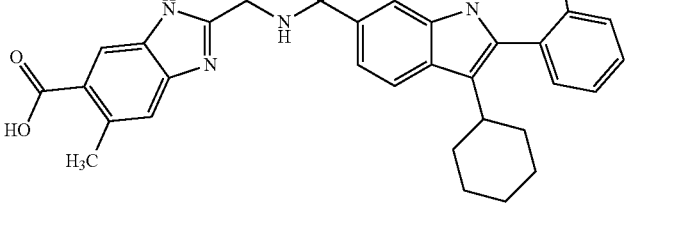 | 577.3 |
| 2-284 | 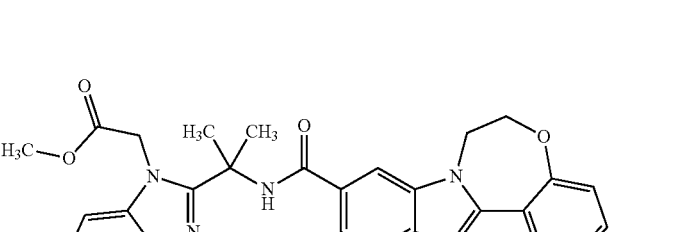 | 591.3 |
| 2-285 | 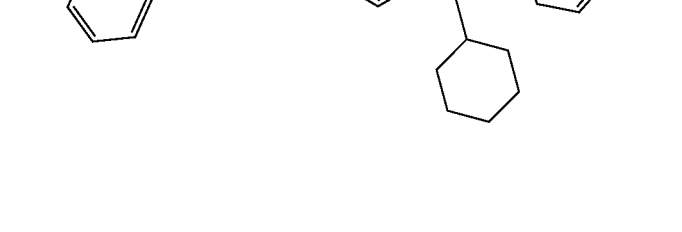 | 533.3 |
| 2-286 | 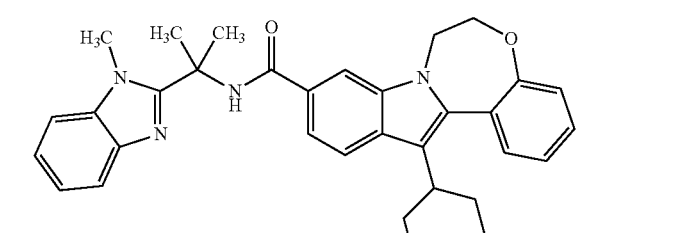 | 491.2 |

TABLE 176

| Ex. | formula | positive MS (M + 1)(free form) |
|---|---|---|
| 2-287 | | 532.3 |
| 2-288 | | 535.3 |
| 2-289 | | 429.2(M − 86) negative MS 514.2(M − 1) |
| 2-290 | | 529.3 |

TABLE 176-continued

| Ex. | formula | positive MS (M + 1)(free form) |
|---|---|---|
| 2-291 | | 591.3 |

TABLE 177

| Ex. | formula | positive MS (M + 1)(free form) |
|---|---|---|
| 2-292 | | 541.3 |
| 2-293 | | 582.3 |
| 2-294 | | 429.2(M − 114) negative MS 542.3(M − 1) |

TABLE 177-continued

| Ex. | formula | positive MS (M + 1)(free form) |
|---|---|---|
| 2-295 | (structure) | 626.3 |
| 2-296 | (structure) | 612.3 |

TABLE 178

| Ex. | formula | positive MS (M + 1)(free form) |
|---|---|---|
| 2-297 | (structure) | 652.3 |
| 2-298 | (structure) HCl | 439.2 |

TABLE 178-continued
| Ex. | formula | positive MS (M + 1)(free form) |
|---|---|---|
| 2-299 | 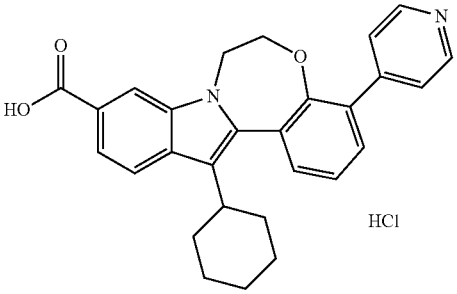 HCl | 439.2 |
| 2-300 | 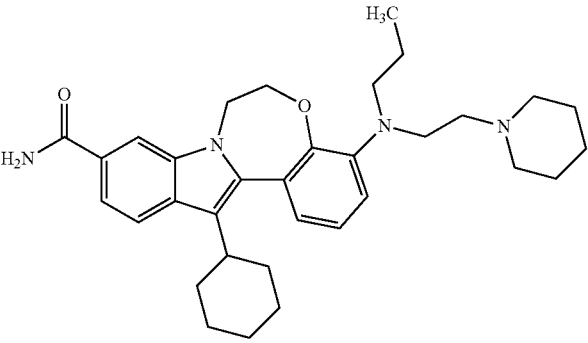 | 529.3 |
TABLE 179
| Ex. | formula | positive MS (M + 1)(free form) |
|---|---|---|
| 2-301 | 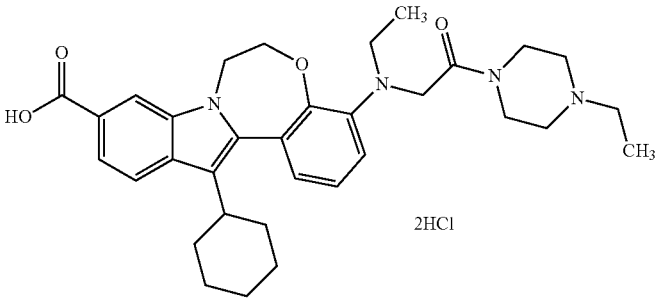 2HCl | 559.3 |
| 2-302 | 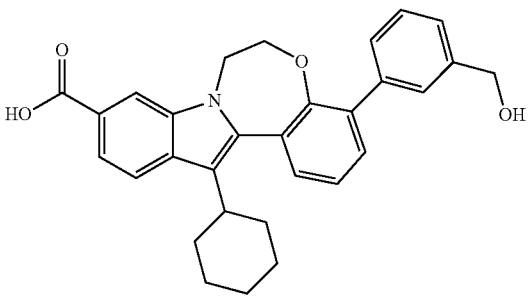 | 468.2 |

TABLE 179-continued
| Ex. | formula | positive MS (M + 1)(free form) |
|---|---|---|
| 2-303 | | 429.2(M-128) negative MS 555.3(M-1) |
| 2-304 | | 559.3 |
| 2-305 | | 573.3 |
TABLE 180
| Ex. | formula | positive MS (M + 1)(free form) |
|---|---|---|
| 2-306 | 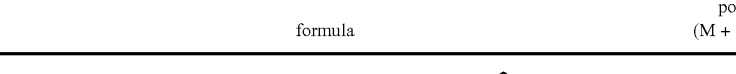 | 596.2 |

TABLE 180-continued

| Ex. | formula | positive MS (M + 1)(free form) |
|---|---|---|
| 2-307 | | 575.3 |
| 2-308 | | 568.3 |
| 2-309 | | 634.3 |
| 2-310 | | 529.2 |

TABLE 181
| Ex. | formula | positive MS (M + 1)(free form) |
|---|---|---|
| 2-311 | 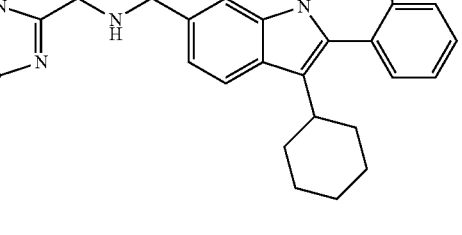 | 587.3 |
| 2-312 | 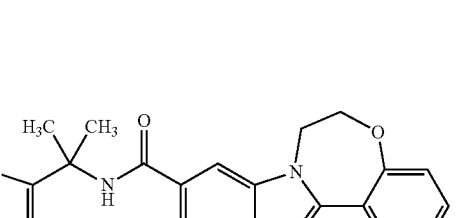 | 577.2 |
| 2-313 | 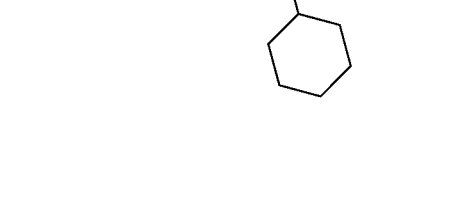 | 632.3 |
| 2-314 | 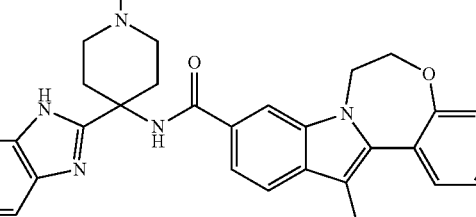 | 555.2 |

TABLE 181-continued
| Ex. | formula | positive MS (M + 1)(free form) |
|---|---|---|
| 2-315 | 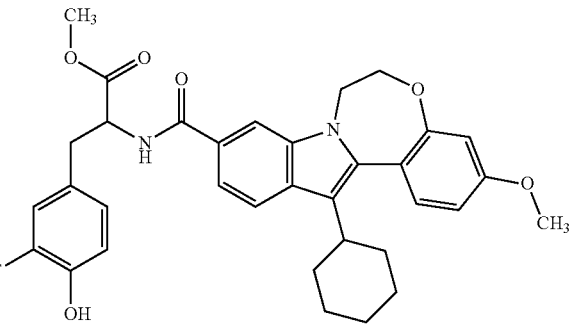 | 587.2 |
TABLE 182
| Ex. | formula | positive MS (M + 1)(free form) |
|---|---|---|
| 2-316 | | 608.3 |
| 2-317 | | 702.2 |
| 2-318 | | 688.3 |

TABLE 182-continued
| Ex. | formula | positive MS (M + 1)(free form) |
|---|---|---|
| 2-319 | 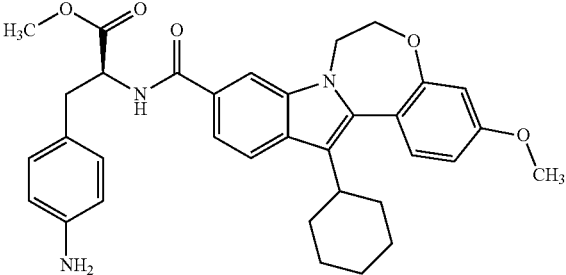 | 568.3 |
| 2-320 | 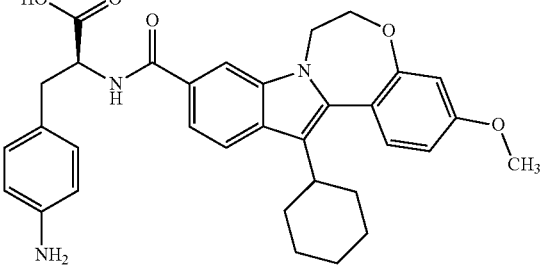 | 554.2 |
TABLE 183
| Ex. | formula | positive MS (M + 1)(free form) |
|---|---|---|
| 2-321 | 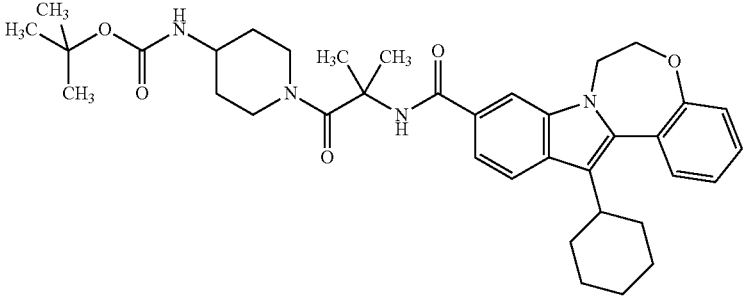 | 429.2(M-199) negative MS 627.3(M-1) |
| 2-322 | 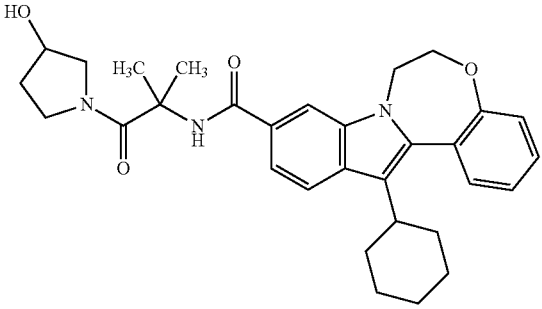 | 516.3 |

TABLE 183-continued
| Ex. | formula | positive MS (M + 1)(free form) |
|---|---|---|
| 2-323 | 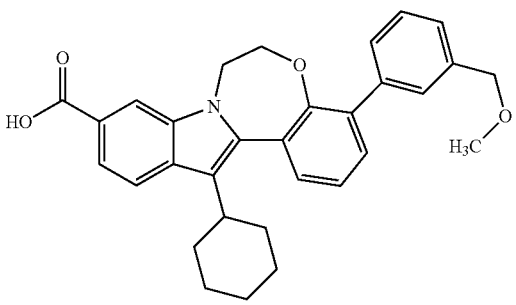 | 482.2 |
| 2-324 | 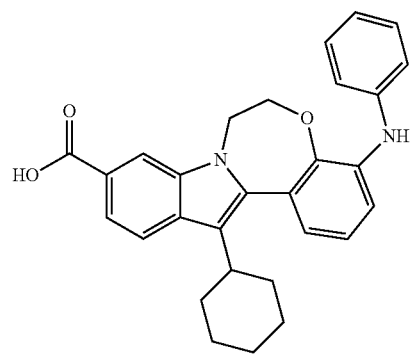 | 453.2 |
| 2-325 | 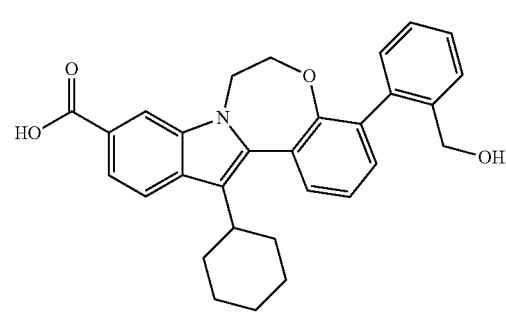 | 468.2 |
TABLE 184
| Ex. | formula | positive MS (M + 1)(free form) |
|---|---|---|
| 2-326 | 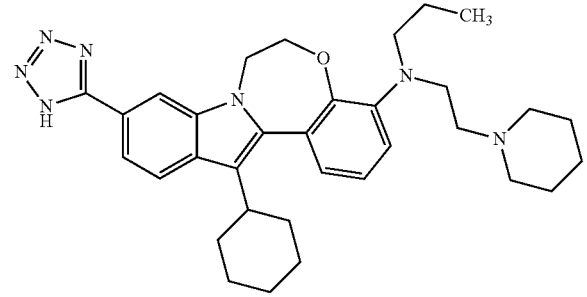 | 554.3 |

TABLE 184-continued
| Ex. | formula | positive MS (M + 1)(free form) |
|---|---|---|
| 2-327 | 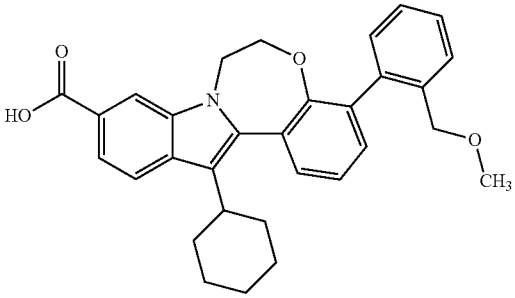 | 482.2 |
| 2-328 | 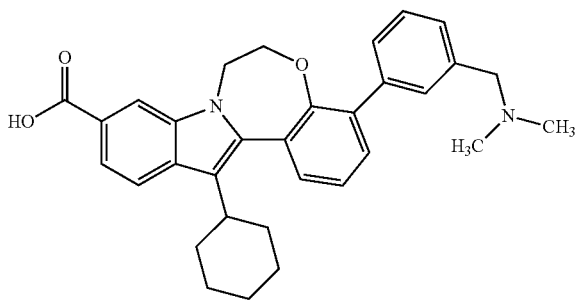 | 495.2 |
| 2-329 | 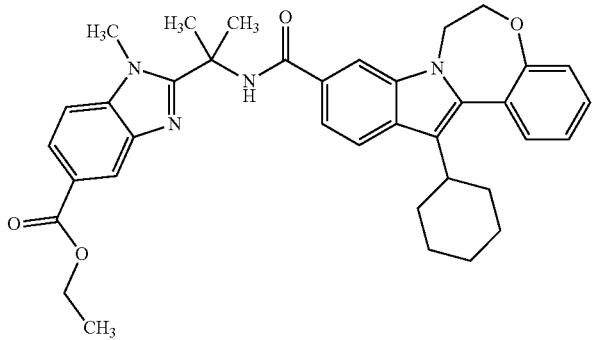 | 605.3 |
| 2-330 | 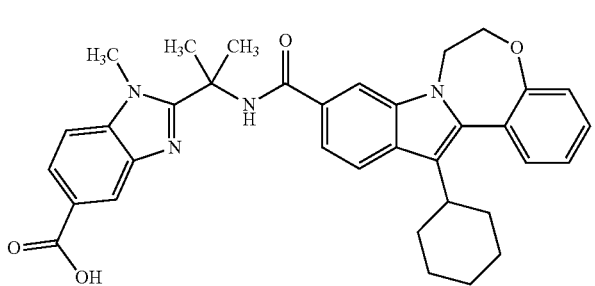 | 577.2 |

Table 185

| Ex. | formula | positive MS (M + 1)(free form) |
|---|---|---|
| 2-331 | | 637.3 |
| 2-332 | | 593.3 |
| 2-333 | | 429.2(M-130) negative MS 558.3(M-1) |
| 2-334 | | 429.2(M-141) negative MS 569.3(M-1) |
| 2-335 | | 429.2(M-177) negative MS 605.3(M-1) |

TABLE 186

| Ex. | formula | positive MS (M + 1)(free form) |
|---|---|---|
| 2-336 | | 591.3 |
| 2-337 | | 577.3 |
| 2-338 | | 610.3 |
| 2-339 | | 646.2 |

TABLE 186-continued
| Ex. | formula | positive MS (M + 1)(free form) |
|---|---|---|
| 2-340 | 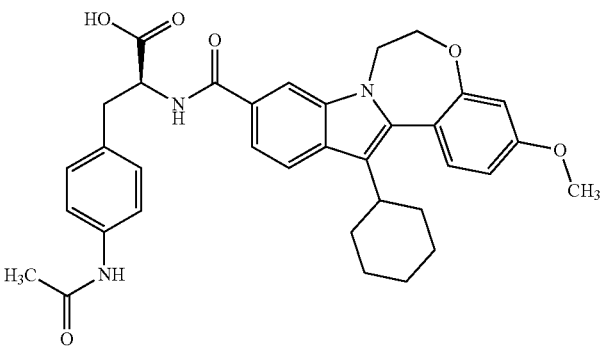 | 596.2 |
TABLE 187
| Ex. | formula | positive MS (M + 1)(free form) |
|---|---|---|
| 2-341 | 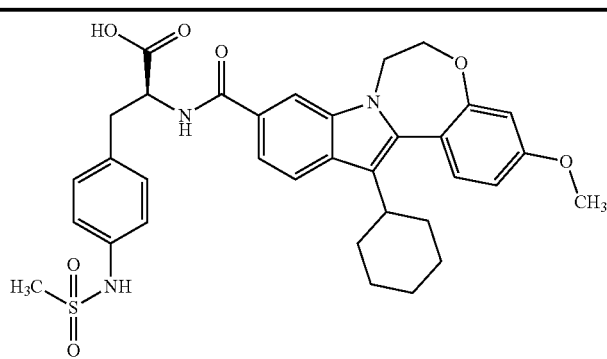 | 632.2 |
| 2-342 | 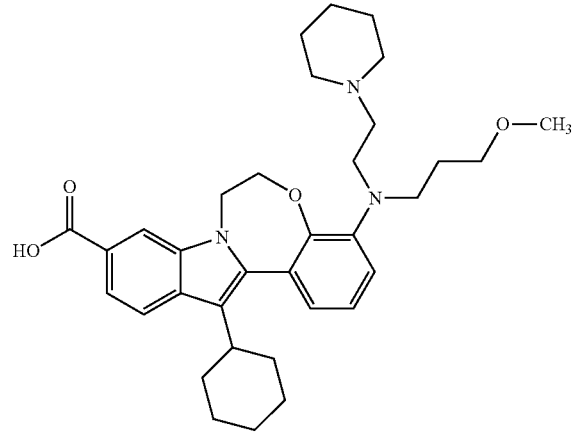 | 560.3 |
| 2-343 | 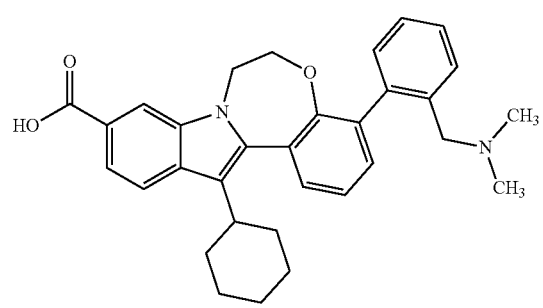 | 495.3 |

TABLE 187-continued

| Ex. | formula | positive MS (M + 1)(free form) |
|---|---|---|
| 2-344 | | 459.2 |

Table 188

| Ex. | formula | positive MS (M + 1)(free form) |
|---|---|---|
| 2-345 | | 445.2 |
| 2-346 | | 620.3 |
| 2-347 | | 623.2 |

Table 188-continued
| Ex. | formula | positive MS (M + 1)(free form) |
|---|---|---|
| 2-348 | 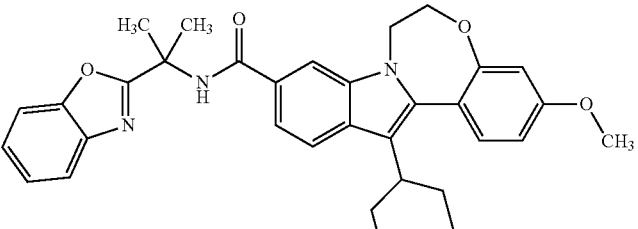 | 550.2 |
| 2-349 | 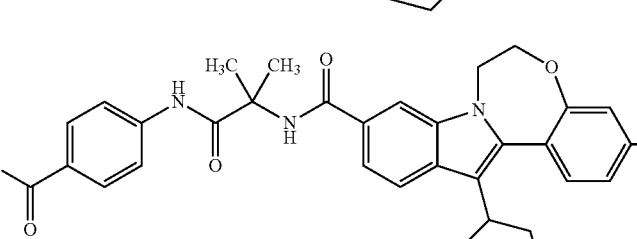 | 610.3 |
TABLE 189
| Ex. | formula | positive MS (M + 1)(free form) |
|---|---|---|
| 2-350 | 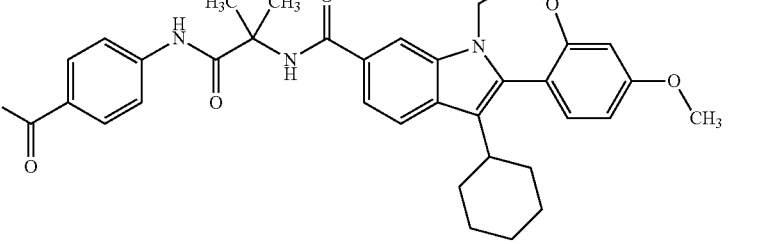 | 596.3 |
| 2-351 | 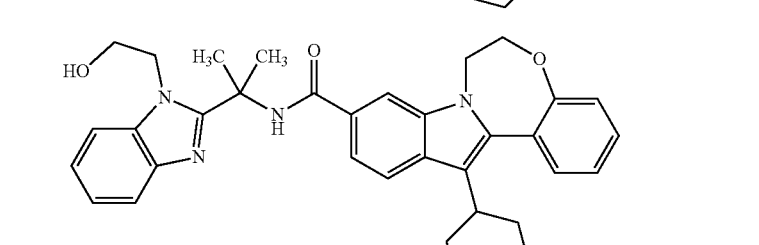 | 563.3 |
| 2-352 | 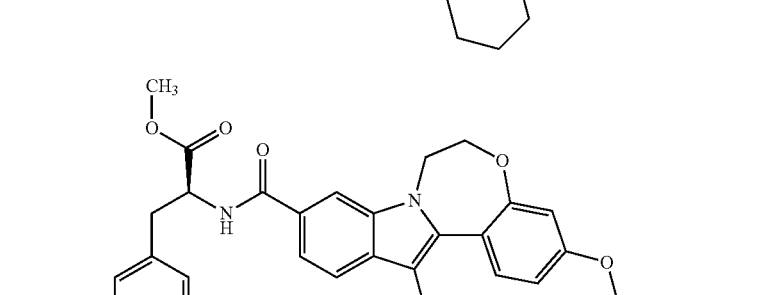 | 621.2 |

TABLE 189-continued

| Ex. | formula | positive MS (M + 1)(free form) |
|---|---|---|
| 2-353 | | 569.3 |
| 2-354 | | 607.2 |

TABLE 190

| Ex. | formula | positive MS (M + 1)(free form) |
|---|---|---|
| 2-355 | | 555.2 |
| 2-356 | | 554.2 |

TABLE 190-continued

| Ex. | formula | positive MS (M + 1)(free form) |
|---|---|---|
| 2-357 | | 659.3 |
| 2-358 | | 429.2(M-194) negative MS 622.3(M-1) |

Table 191

| Ex. | formula | positive MS (M + 1)(free form) |
|---|---|---|
| 2-359 | | 631.3 |

Table 191-continued
| Ex. | formula | positive MS (M + 1)(free form) |
|---|---|---|
| 2-360 | 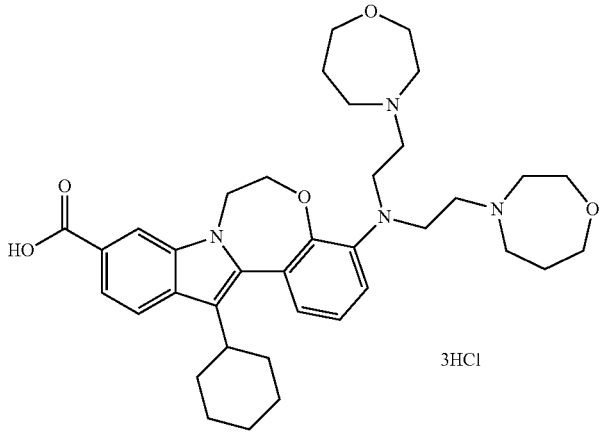 3HCl | 631.3 |
| 2-361 | 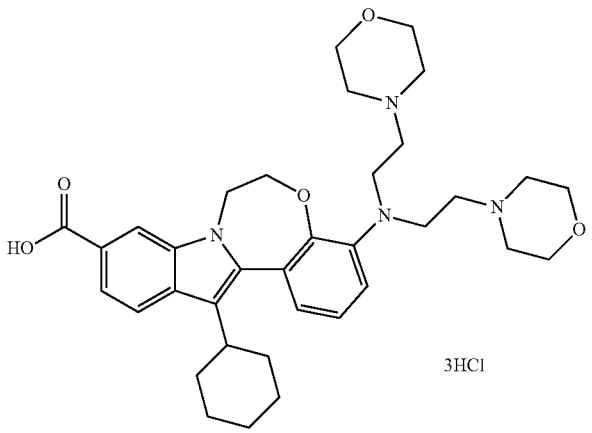 3HCl | 603.3 |
TABLE 192
| Ex. | formula | positive MS (M + 1)(free form) |
|---|---|---|
| 2-362 | 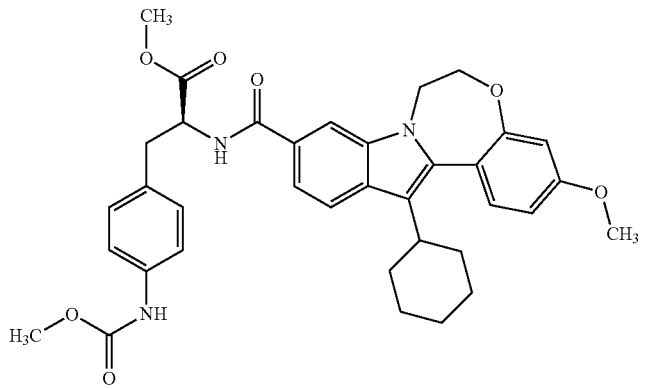 | 626.3 |

TABLE 192-continued

| Ex. | formula | positive MS (M + 1)(free form) |
|---|---|---|
| 2-363 | | 603.2 |
| 2-364 | | 612.3 |
| 2-365 | | 589.2 |
| 2-366 | | 583.3 |

TABLE 193
| Ex. | formula | positive MS (M + 1)(free form) |
|---|---|---|
| 2-367 | 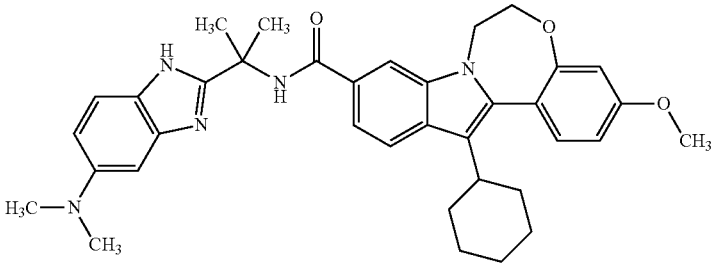 | 592.3 |
| 2-368 | 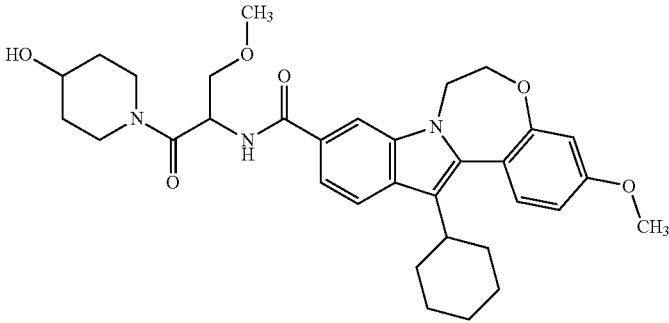 | 576.3 |
| 2-369 | 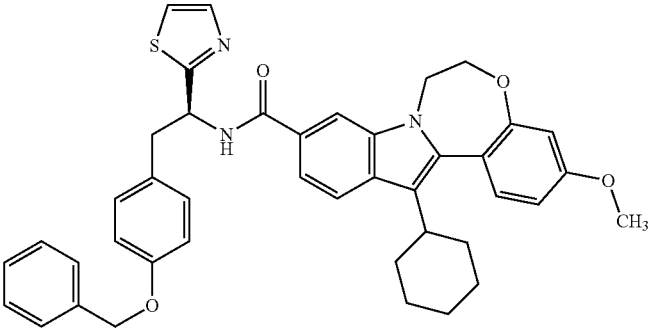 | 684.2 |
| 2-370 | 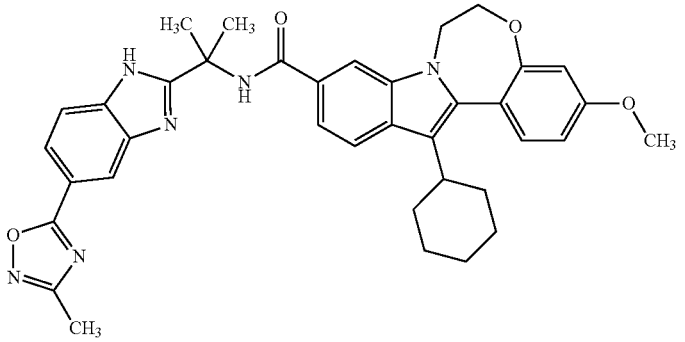 | 631.3 |

TABLE 193-continued
| Ex. | formula | positive MS (M + 1)(free form) |
|---|---|---|
| 2-371 | 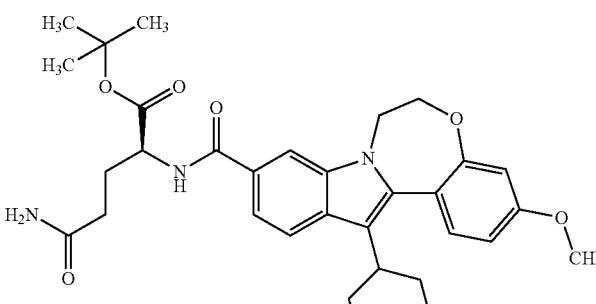 | 576.3 |
TABLE 194
| Ex. | formula | positive MS (M + 1)(free form) |
|---|---|---|
| 2-372 | | 520.2 |
| 2-373 | | 569.2 |
| 2-374 | | 621.2 |

TABLE 194-continued
| Ex. | formula | positive MS (M + 1)(free form) |
|---|---|---|
| 2-375 | 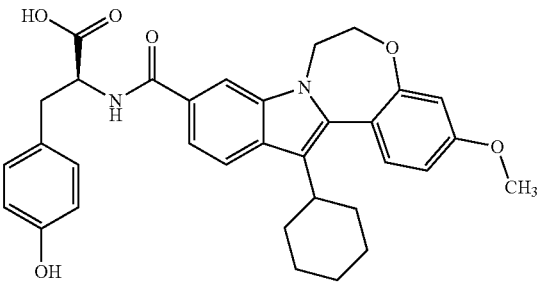 | 555.2 |
| 2-376 | 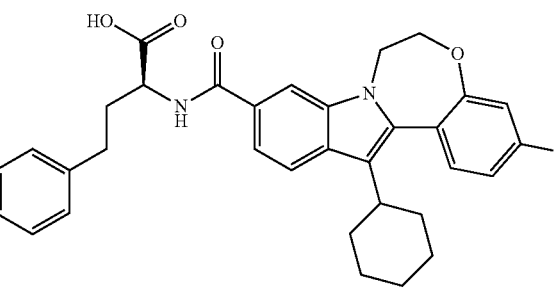 | 569.2 |
TABLE 195
| Ex. | formula | positive MS (M + 1)(free form) |
|---|---|---|
| 2-377 | 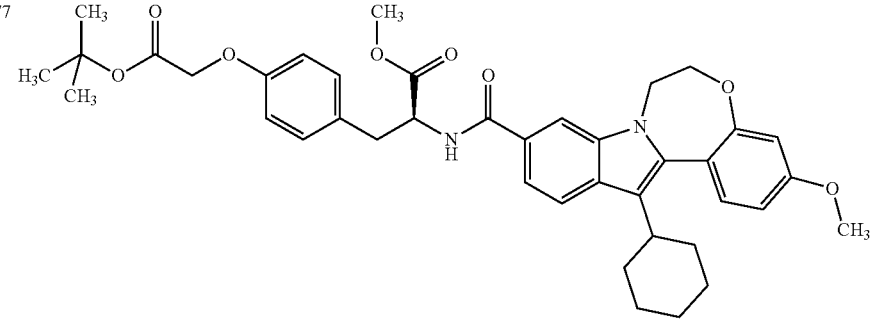 | 683.3 |
| 2-378 | 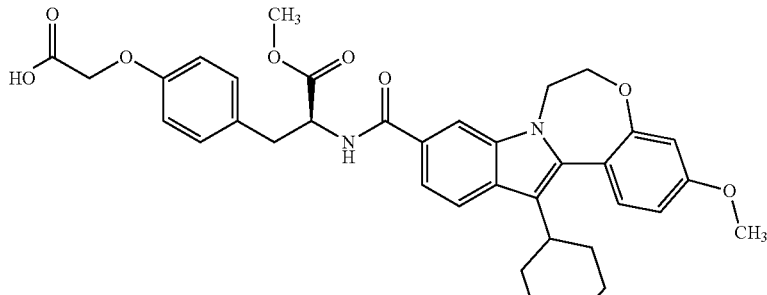 | 627.2 |

TABLE 195-continued
| Ex. | formula | positive MS (M + 1)(free form) |
|---|---|---|
| 2-379 | 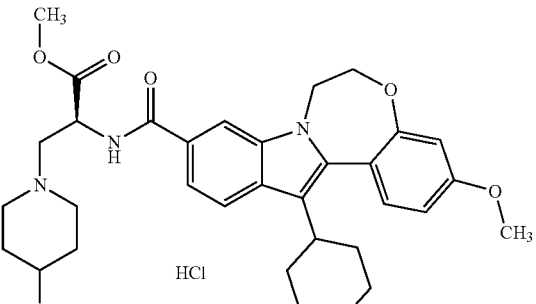 | 576.3 |
| 2-380 | | 567.3 |
| 2-381 | | 594.2 |
TABLE 196
| Ex. | formula | positive MS (M + 1)(free form) |
|---|---|---|
| 2-382 | 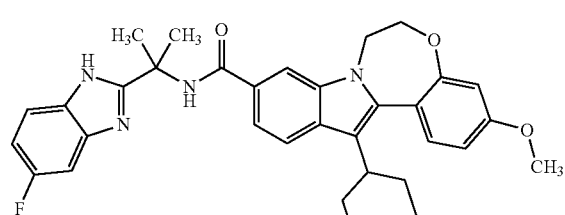 | 640.3 |

TABLE 196-continued
| Ex. | formula | positive MS (M + 1)(free form) |
|---|---|---|
| 2-383 | 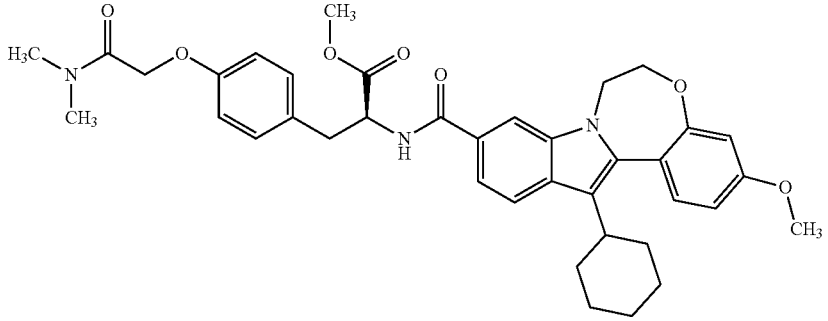 | 654.3 |
| 2-384 | 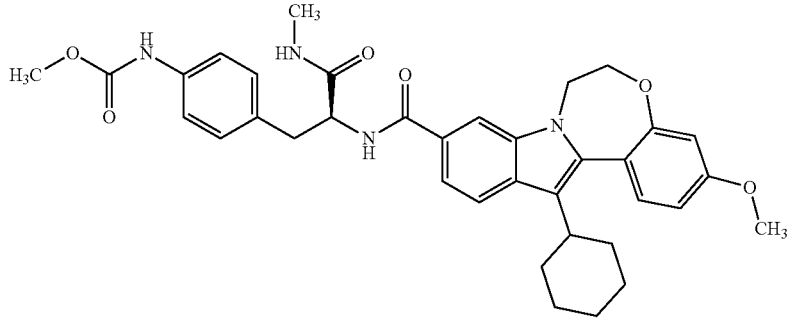 | 625.3 |
| 2-385 | 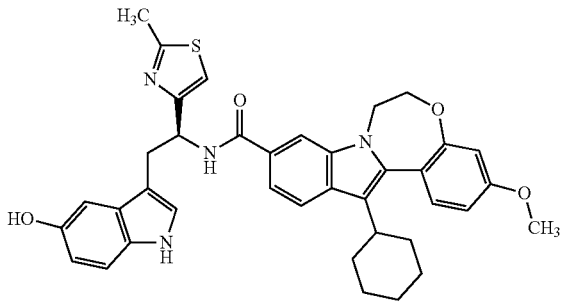 | 647.2 |
| 2-386 | 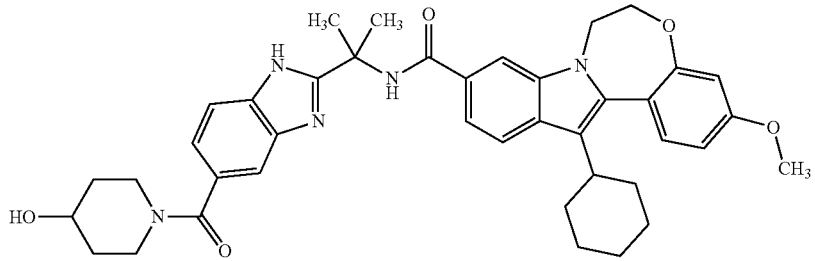 | 676.3 |

TABLE 197
| Ex. | formula | positive MS (M + 1)(free form) |
|---|---|---|
| 2-387 | 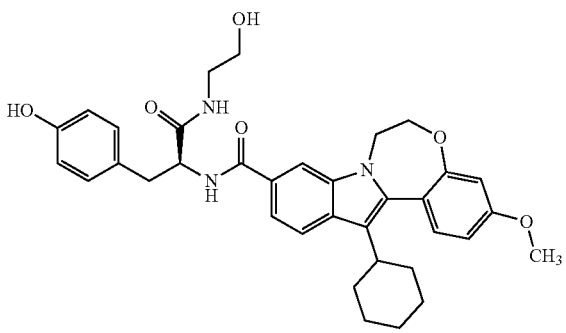 | 598.3 |
| 2-388 | 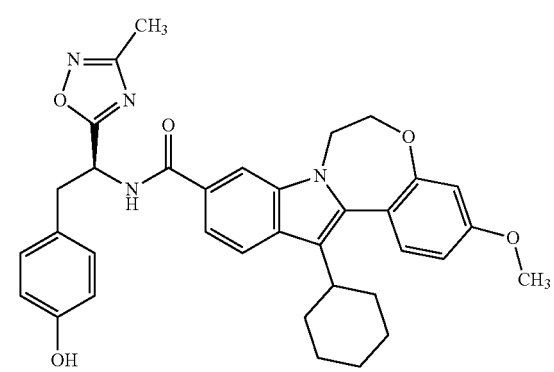 | 593.3 |
| 2-389 | 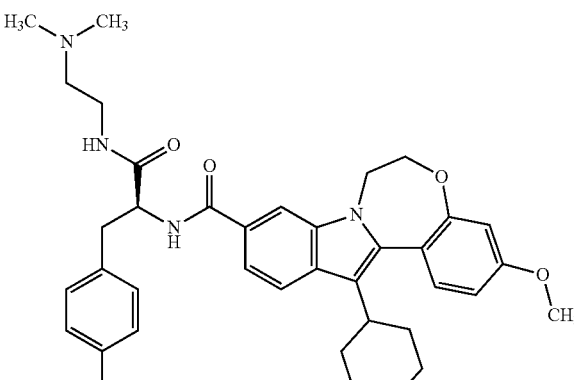 | 625.3 |
| 2-390 | 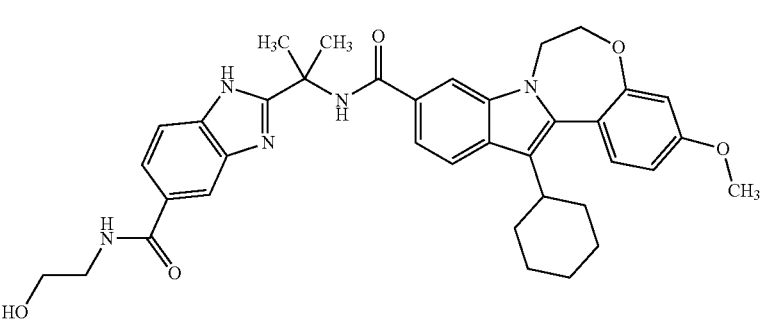 | 636.3 |

TABLE 198
| Ex. | formula | positive MS (M + 1)(free form) |
|---|---|---|
| 2-391 | 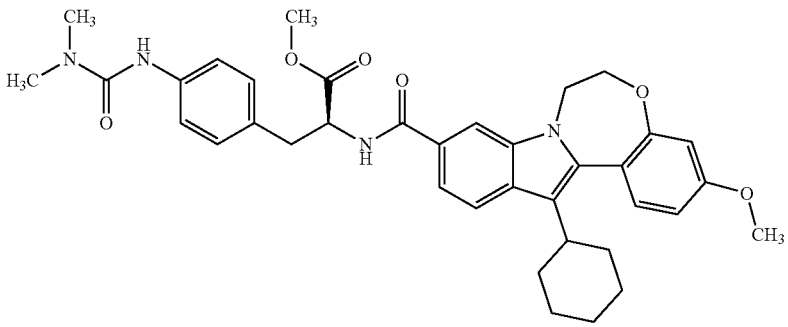 | 639.3 |
| 2-392 | 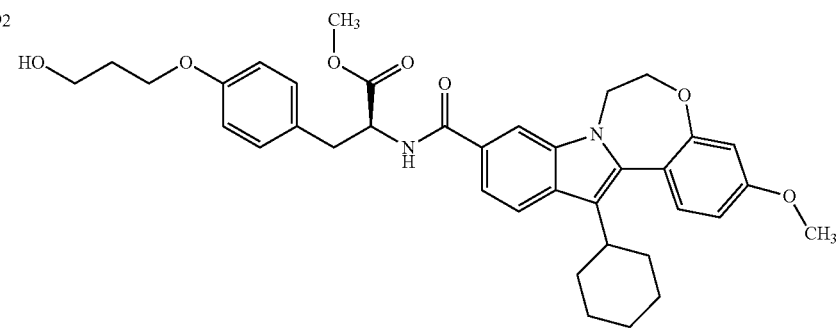 | 627.3 |
| 2-393 | 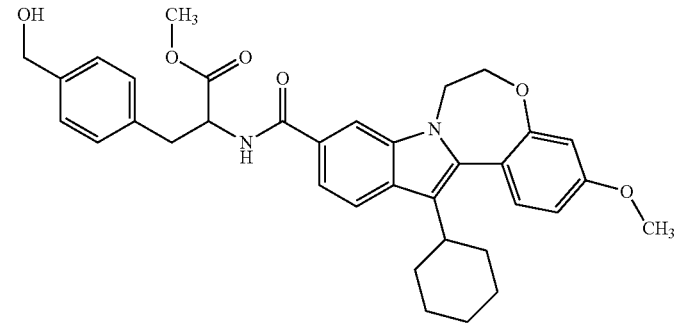 | 583.3 |
| 2-394 | 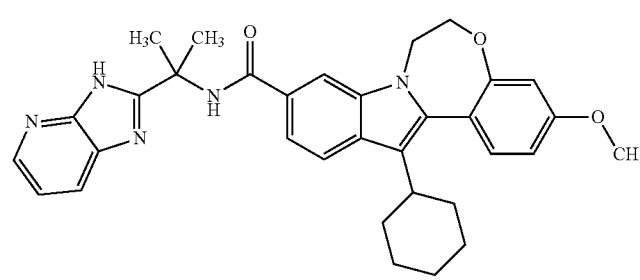 | 550.3 |

TABLE 198-continued
| Ex. | formula | positive MS (M + 1)(free form) |
|---|---|---|
| 2-395 | 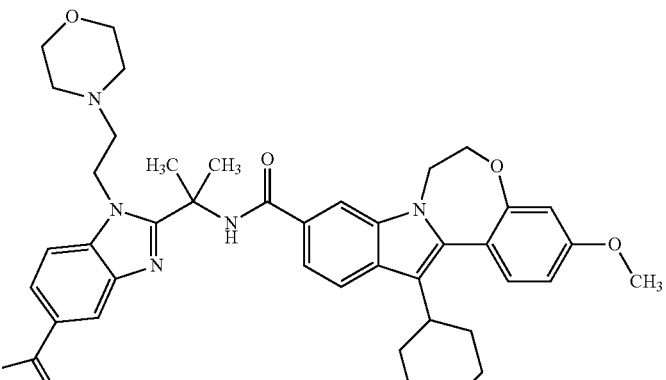 | 706.3 |
TABLE 199
| Ex. | formula | positive MS (M + 1)(free form) |
|---|---|---|
| 2-396 | 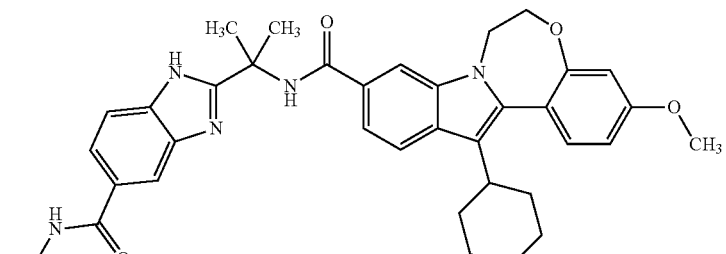 | 606.3 |
| 2-397 | 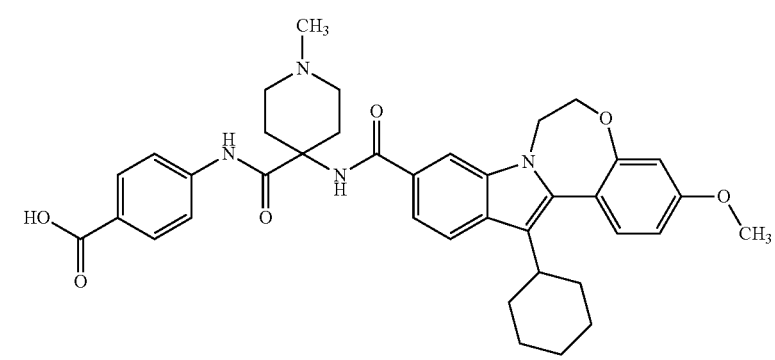 | 651.3 |
| 2-398 | 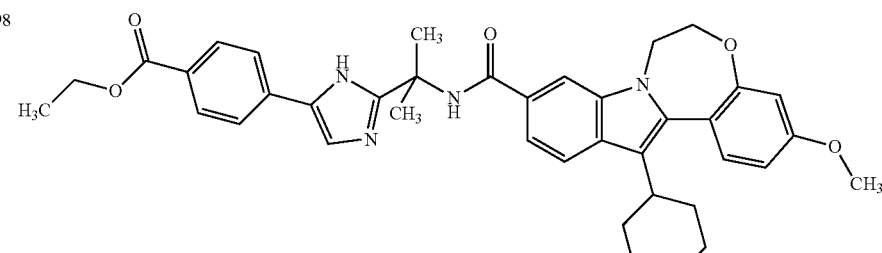 | 647.3 |

TABLE 199-continued
| Ex. | formula | positive MS (M + 1)(free form) |
|---|---|---|
| 2-399 | 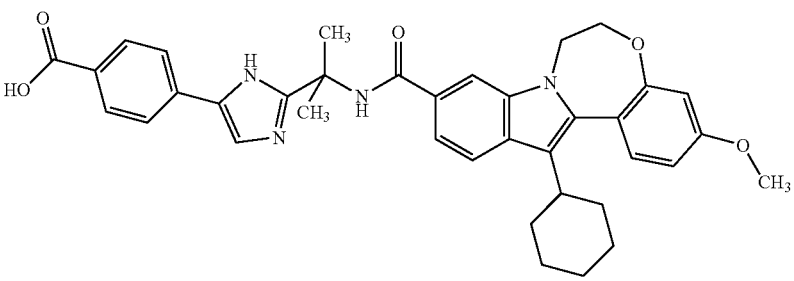 | 619.2 |
| 2-400 | 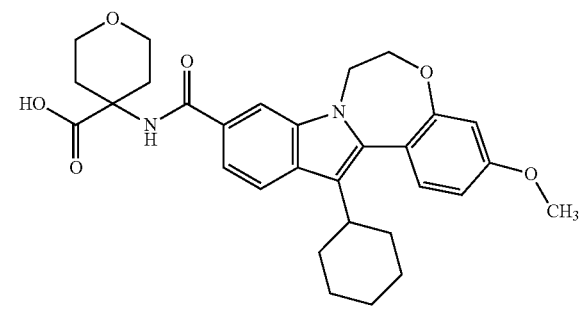 | 519.2 |
TABLE 200
| Ex. | formula | positive MS (M + 1)(free form) |
|---|---|---|
| 2-401 | 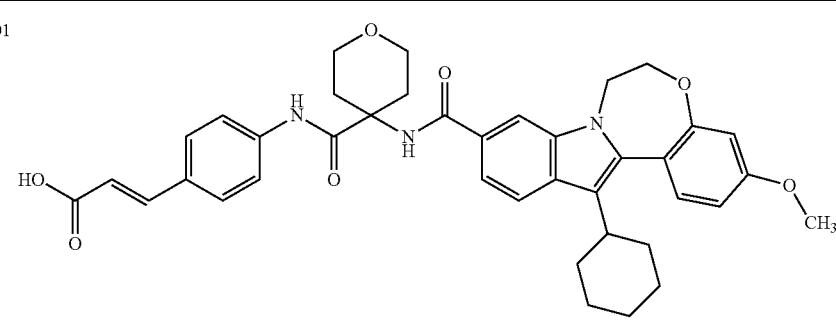 | 664.2 |
| 2-402 | 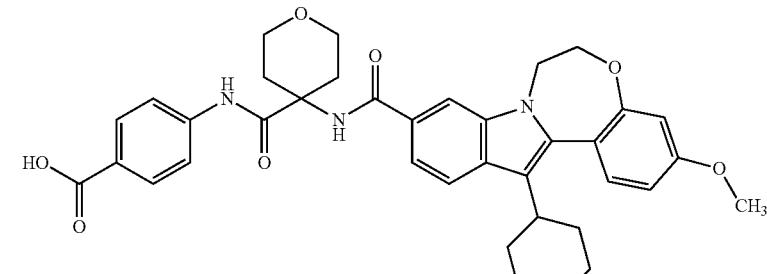 | 638.3 |

TABLE 200-continued

| Ex. | formula | positive MS (M + 1)(free form) |
|---|---|---|
| 2-403 | | 621.2 |
| 2-404 | | 648.3 |
| 2-405 | | 579.2 |

TABLE 201

| Ex. | formula | positive MS (M + 1)(free form) |
|---|---|---|
| 2-406 | | 650.3 |

TABLE 201-continued

| Ex. | formula | positive MS (M + 1)(free form) |
|---|---|---|
| 2-407 | | 650.3 |
| 2-408 | | 549.3 |
| 2-409 | | 635.3 |

TABLE 202
| Ex. | formula | positive MS (M + 1)(free form) |
|---|---|---|
| 2-410 | 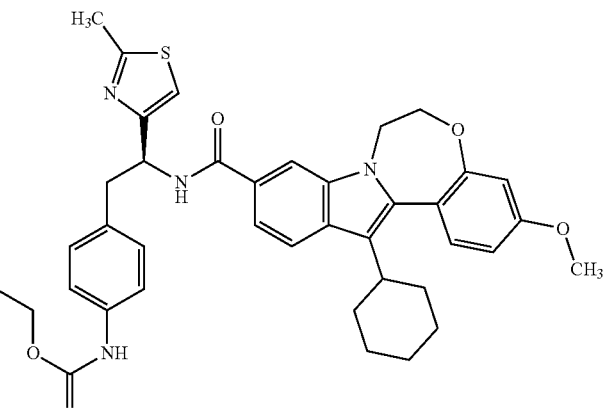 | 741.2 |
| 2-411 | 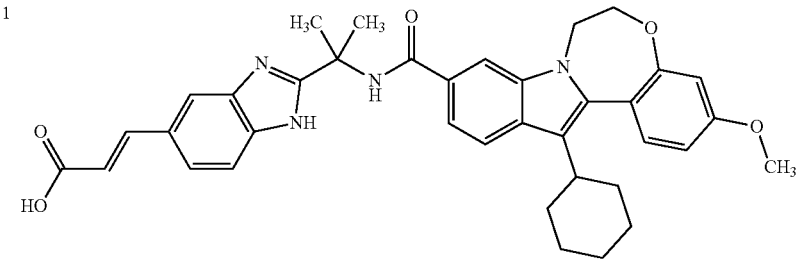 | 619.3 |
| 2-412 | 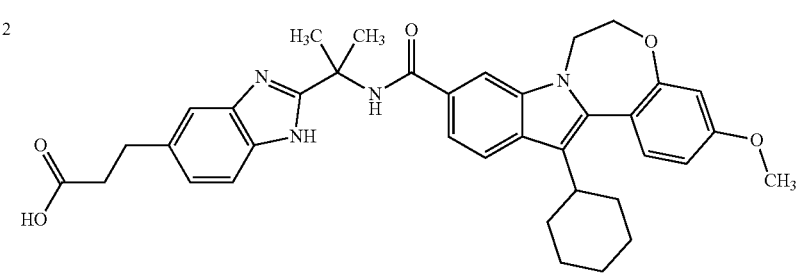 | 621.3 |
| 2-413 | 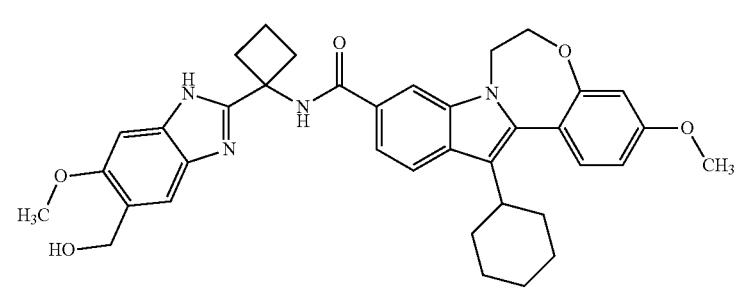 | 621.3 |

TABLE 202-continued

| Ex. | formula | positive MS (M + 1)(free form) |
|---|---|---|
| 2-414 | | 607.2 |

TABLE 203

| Ex. | formula | positive MS (M + 1)(free form) |
|---|---|---|
| 2-415 | | 665.3 |
| 2-416 | | 640.3 |

TABLE 203-continued

| Ex. | formula | positive MS (M + 1)(free form) |
|---|---|---|
| 2-417 | | 719.2 |
| 2-418 | | 675.3 |

TABLE 204

| Ex. | formula | positive MS (M + 1)(free form) |
|---|---|---|
| 2-419 | | 662.3 |
| 2-420 | | 667.3 |

TABLE 204-continued
| Ex. | formula | positive MS (M + 1)(free form) |
|---|---|---|
| 2-421 | 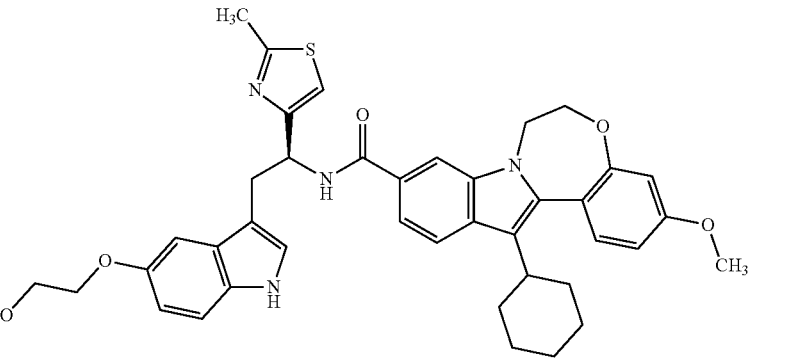 | 691.2 |
| 2-422 | | 579.3 |
| 2-423 | | 581.3 |
TABLE 205
| Ex. | formula | positive MS (M + 1)(free form) |
|---|---|---|
| 2-424 | 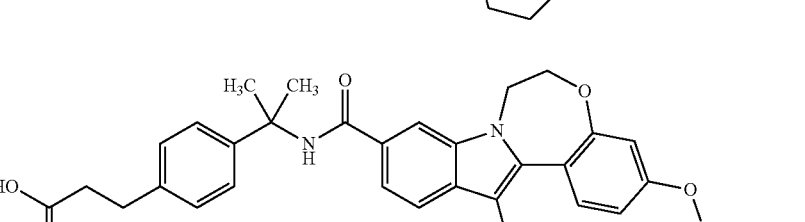 | 641.3 |

TABLE 205-continued

| Ex. | formula | positive MS (M + 1)(free form) |
|---|---|---|
| 2-425 | | 625.3 |
| 2-426 | | 584.2 |
| 2-427 | | 598.2 |

TABLE 206

| Ex. | formula | positive MS (M + 1)(free form) |
|---|---|---|
| 2-428 | | 685.2 |

TABLE 206-continued
| Ex. | formula | positive MS (M + 1)(free form) |
|---|---|---|
| 2-429 | 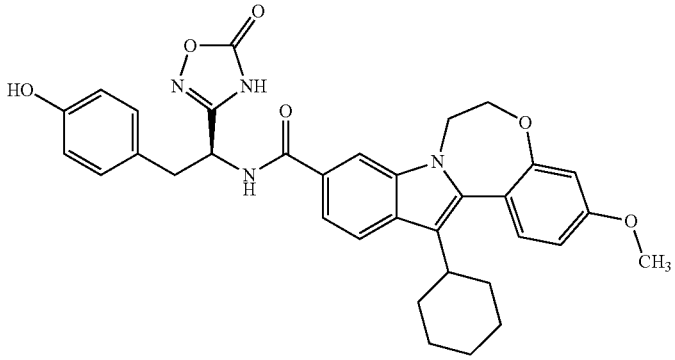 | 595.2 |
| 2-430 | 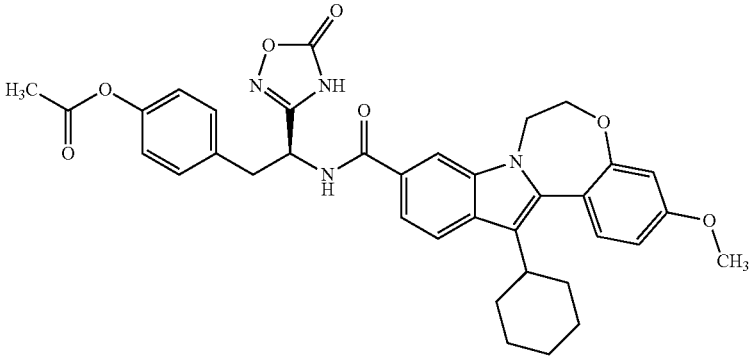 | 637.3 |
| 2-431 | 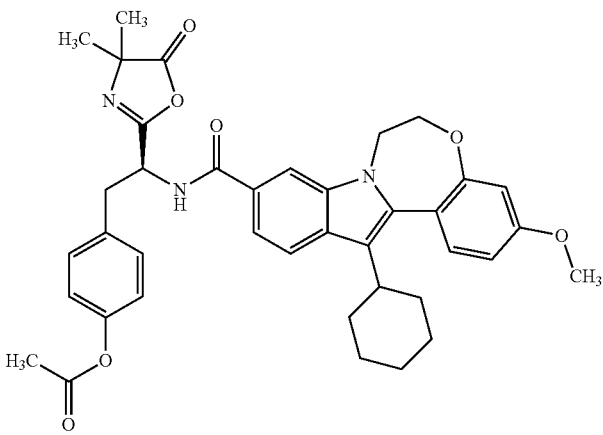 | 664.3 |

TABLE 207

| Ex. | formula | positive MS (M + 1)(free form) |
|---|---|---|
| 2-432 | | 662.3 |
| 2-433 | | 593.3 |
| 2-434 | | 607.3 |
| 2-435 | | 583.3 |
| 2-436 | | 553.3 |

TABLE 208
| Ex. | formula | positive MS (M + 1)(free form) |
|---|---|---|
| 2-437 | 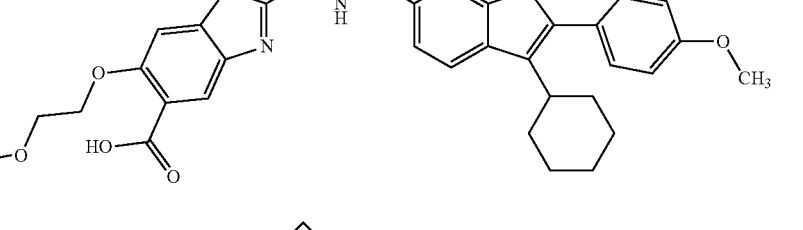 | 679.2 |
| 2-438 | 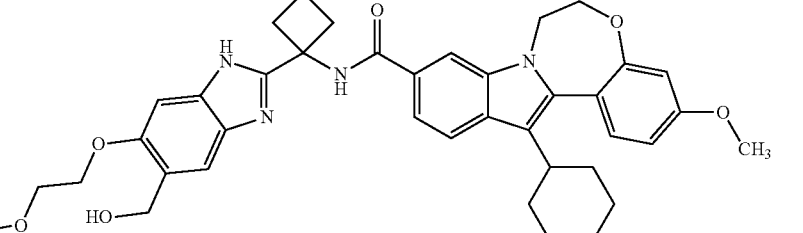 | 665.3 |
| 2-439 | 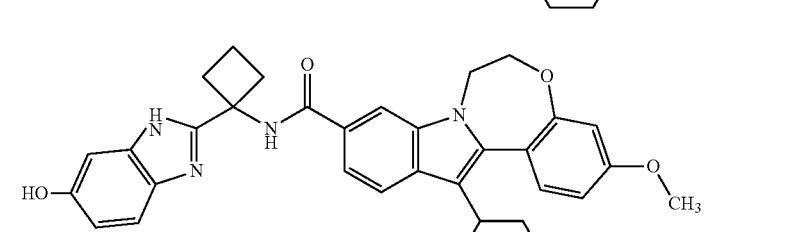 | 577.3 |
| 2-440 | 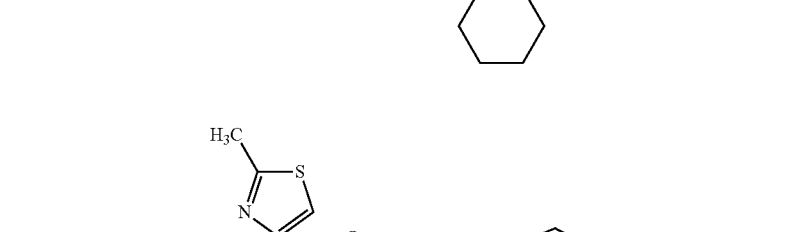 | 705.2 |
| 2-441 | 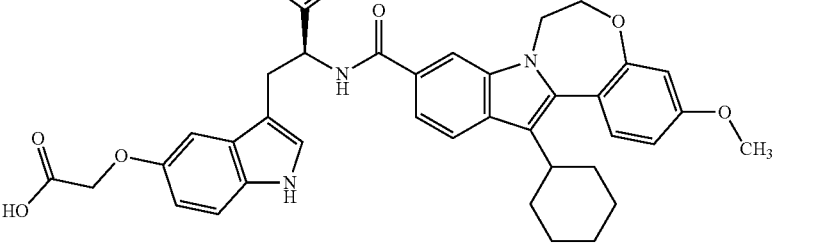 | 536.2 |

TABLE 209
| Ex. | formula | positive MS (M + 1)(free form) |
|---|---|---|
| 2-442 | 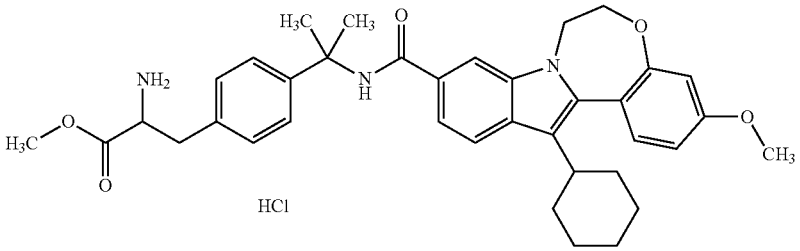 | 610.3 |
| 2-443 | 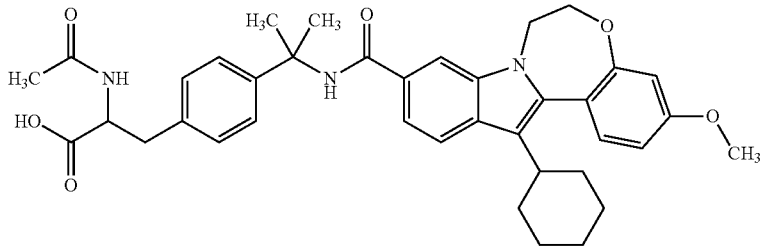 | 638.3 |
| 2-444 | 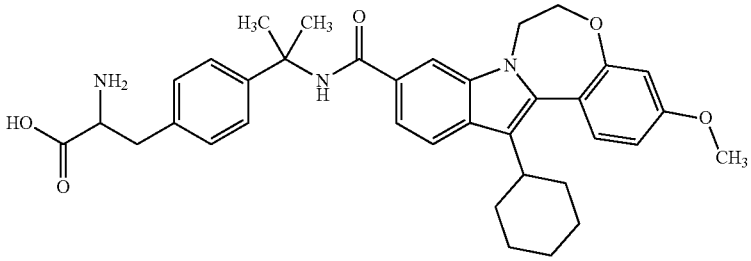 | 596.3 |
| 2-445 | 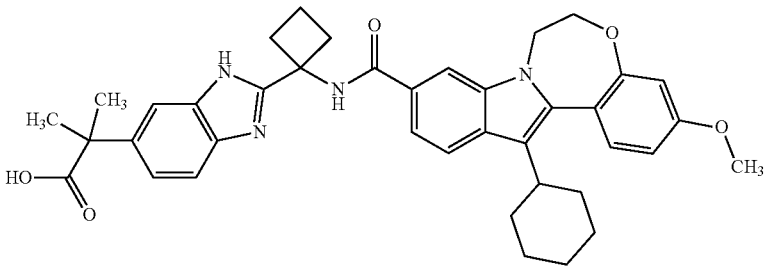 | 647.3 |
| 2-446 | 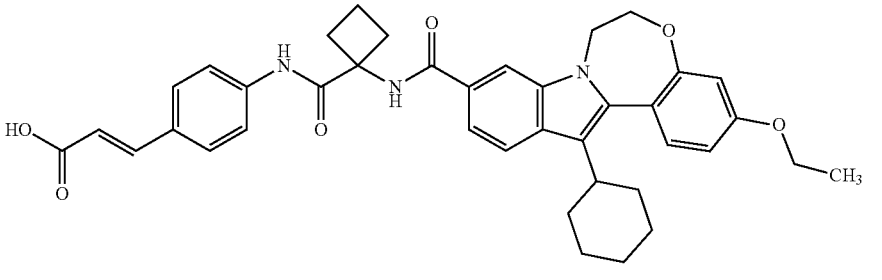 | 648.3 |

TABLE 210

| Ex. | formula | positive MS (M + 1)(free form) |
|---|---|---|
| 2-447 | | 649.3 |
| 2-448 | | 604.3 |
| 2-449 | | 648.4 |
| 2-450 | | 579.3 |
| 2-451 | | 664.2 |

TABLE 211
| Ex. | formula | positive MS (M + 1)(free form) |
|---|---|---|
| 2-452 | 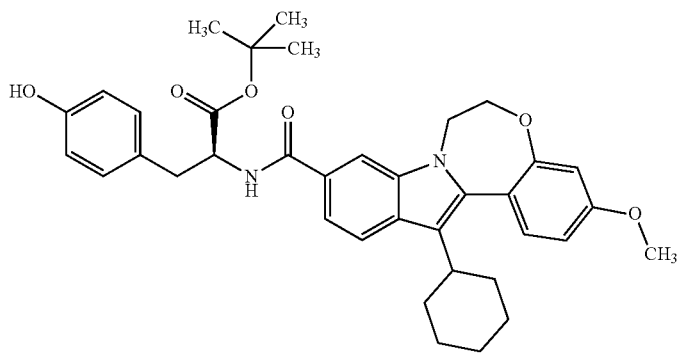 | 611.3 |
| 2-453 | 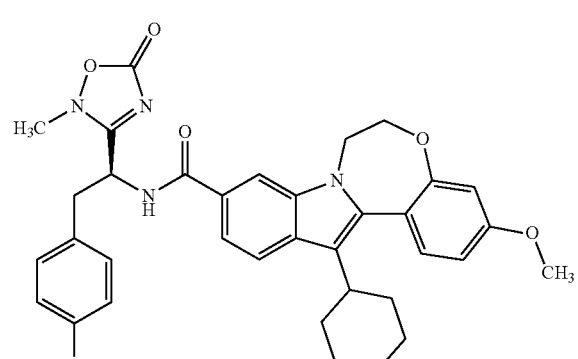 | 609.3 |
| 2-454 | 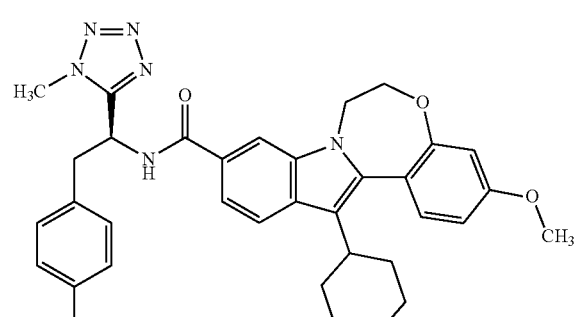 | 593.3 |
| 2-455 | 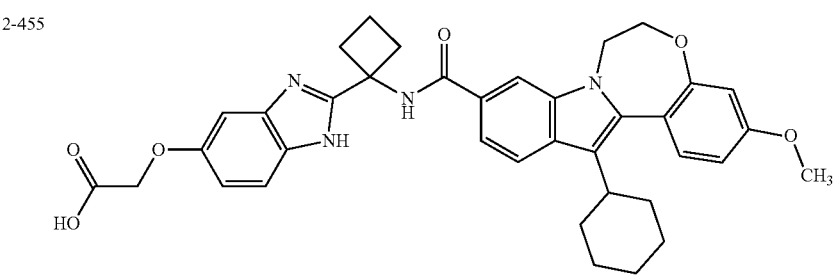 | 635.3 |

TABLE 212
| Ex. | formula | positive MS (M + 1)(free form) |
|---|---|---|
| 1-485 | 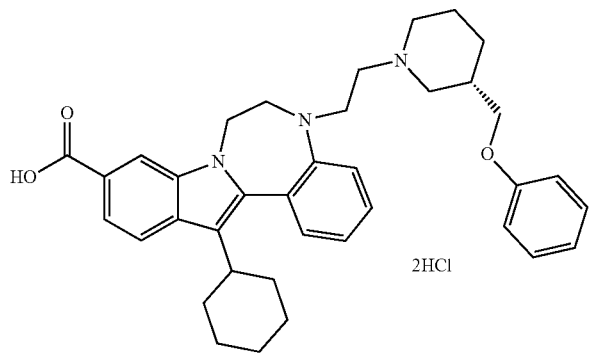 2HCl | 578.3 |
| 1-486 | 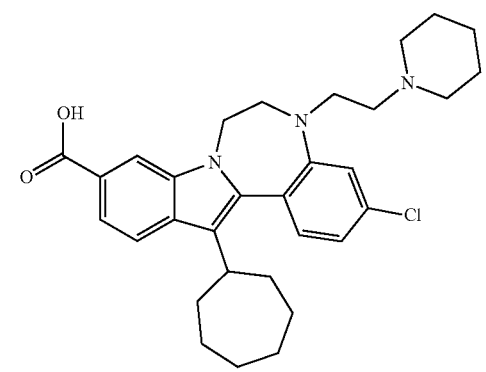 | 520.2 |
| 1-487 | 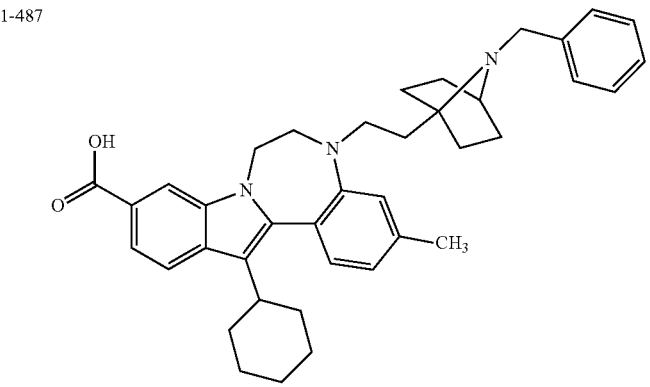 | 588.3 |
| 1-488 | 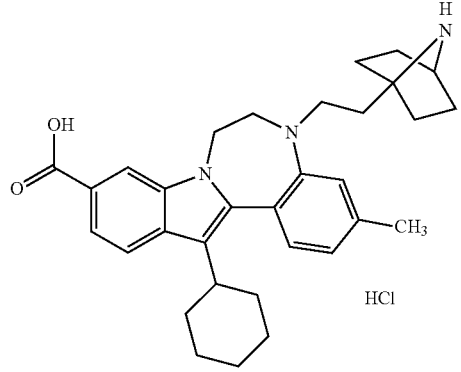 HCl | 498.2 |

TABLE 213
| Ex. | formula | positive MS (M + 1)(free form) |
|---|---|---|
| 1-489 | 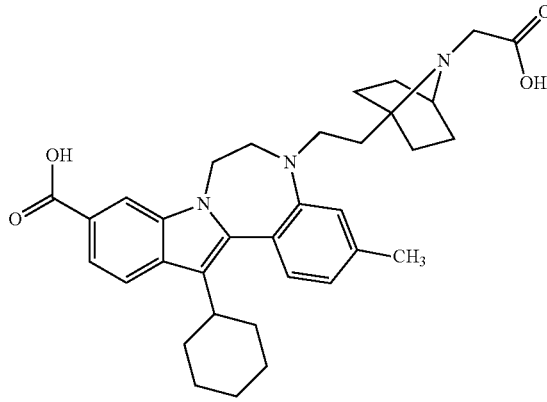 | 556.3 |
| 1-490 | 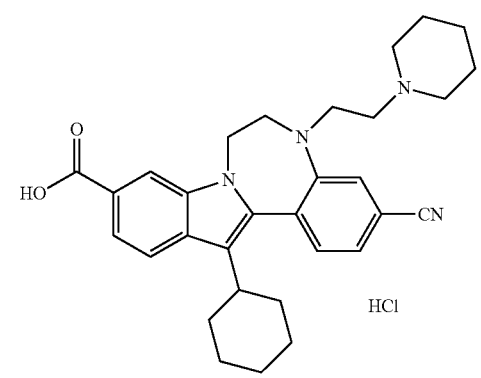 | 497.2 |
| 1-491 | 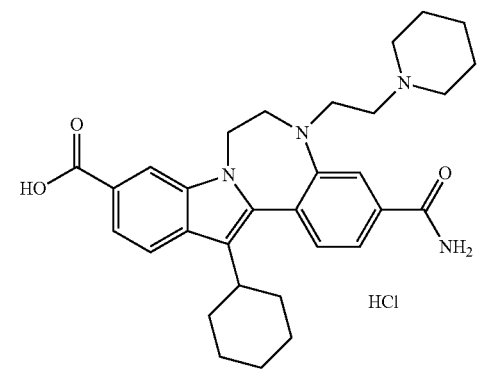 | 515.2 |
| 1-492 | 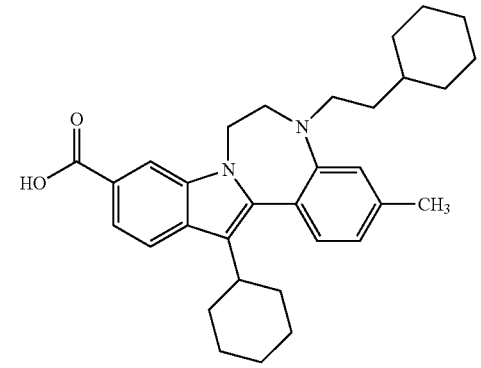 | 485.2 |

TABLE 214
| Ex. | formula | positive MS (M + 1)(free form) |
|---|---|---|
| 1-493 | 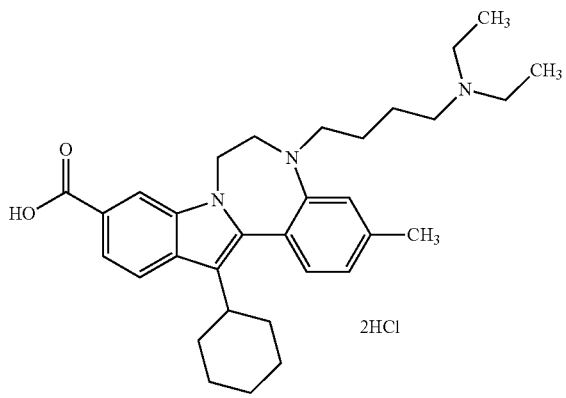 | 502.3 |
| 1-494 | 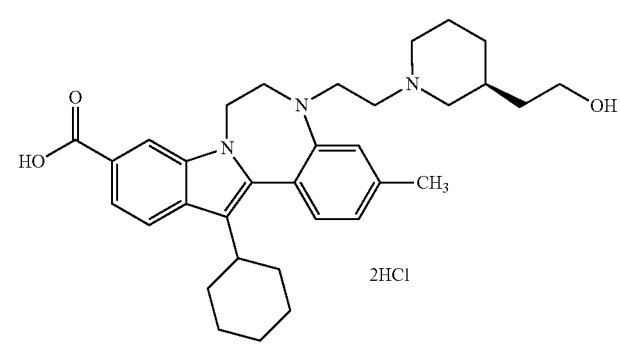 | 530.3 |
| 1-495 | 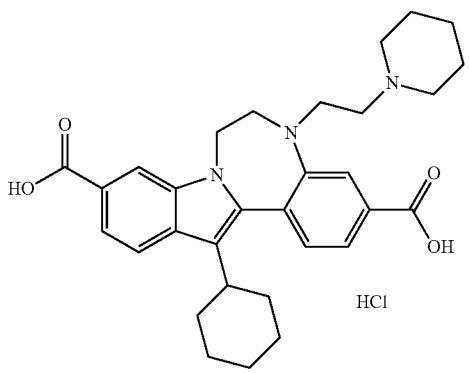 | 516.1 |
| 1-496 | 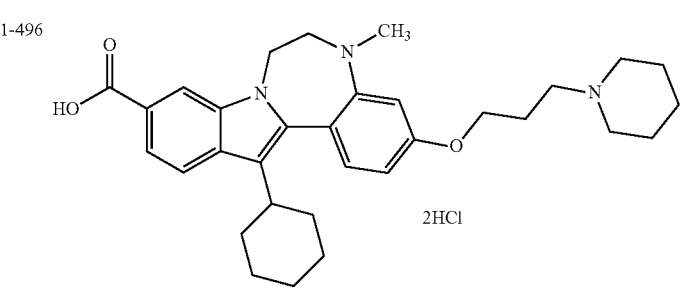 | 516.3 |

TABLE 215
| Ex. | formula | positive MS (M + 1)(free form) |
|---|---|---|
| 1-497 | 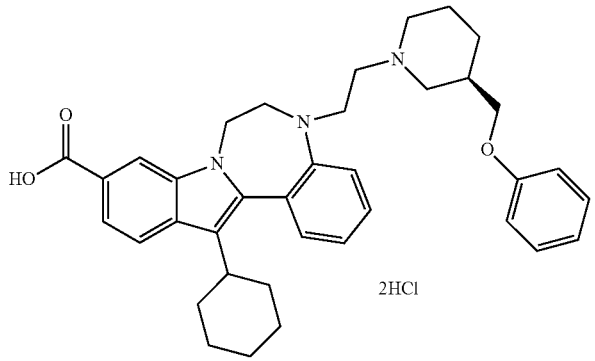 2HCl | 578.3 |
| 1-498 | 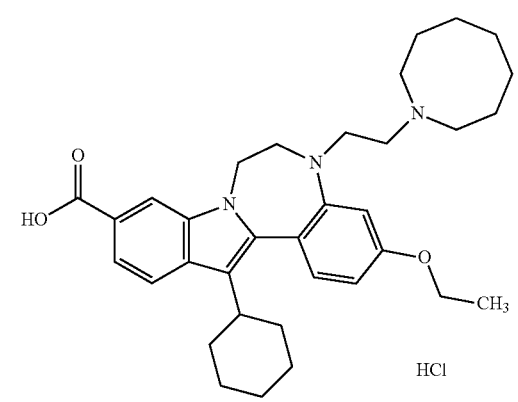 HCl | 544.3 |
| 1-499 | 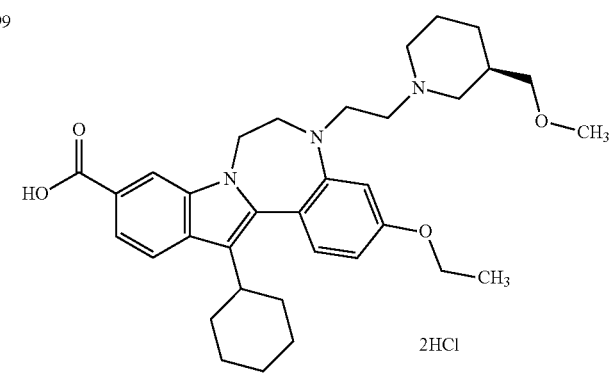 2HCl | 560.3 |
| 1-500 | 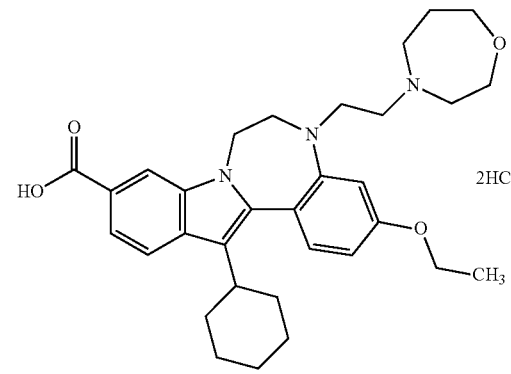 2HCl | 522.3 |

TABLE 216
| Ex. | formula | positive MS (M + 1)(free form) |
|---|---|---|
| 1-501 | 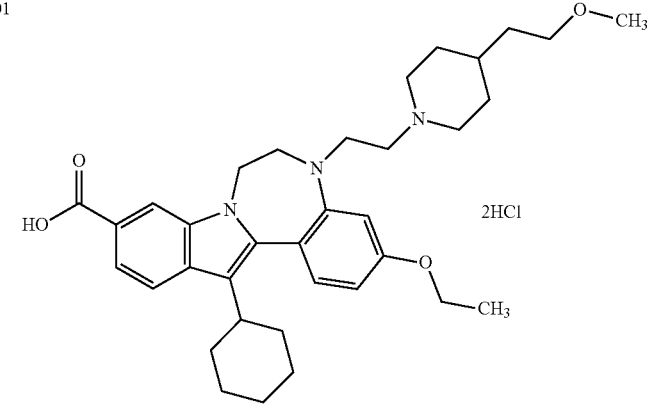 2HCl | 574.3 |
| 1-502 | 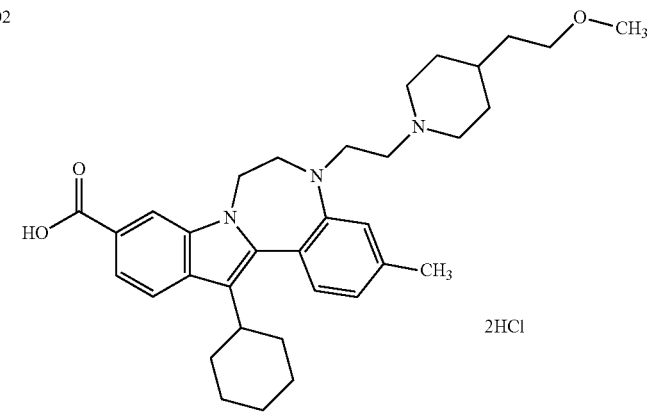 2HCl | 544.3 |
| 1-503 | 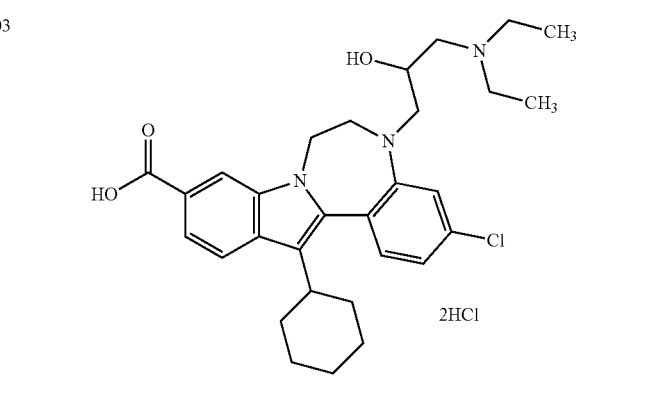 2HCl | 524.2 |
| 1-504 | 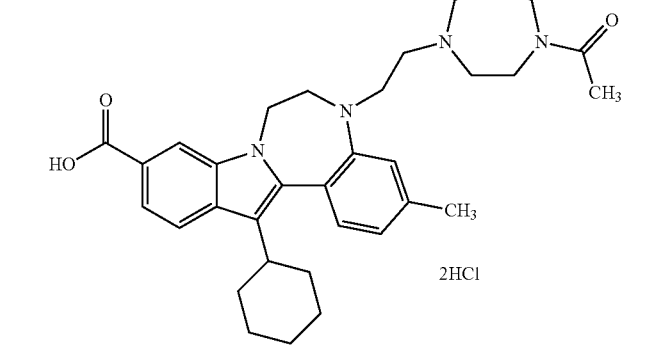 2HCl | 543.3 |

TABLE 217

| Ex. | formula | positive MS (M + 1)(free form) |
|---|---|---|
| 1-505 | | 466.2 |
| 1-506 | | 410.2 |
| 1-507 | | 521.2 |
| 1-508 | | 546.3 |

TABLE 217-continued
| Ex. | formula | positive MS (M + 1)(free form) |
|---|---|---|
| 1-509 | 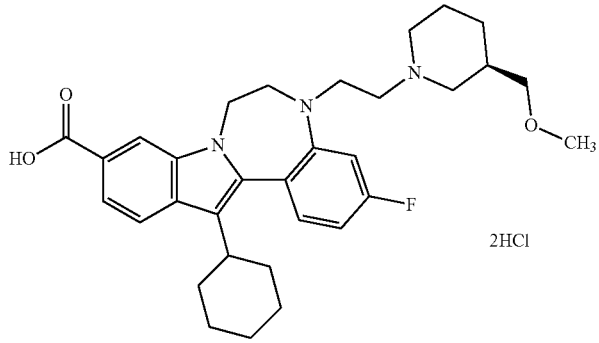 2HCl | 532.2 |
TABLE 218
| Ex. | formula | positive MS (M + 1)(free form) |
|---|---|---|
| 1-510 | 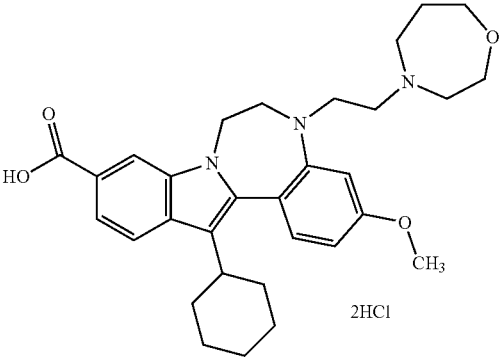 2HCl | 518.2 |
| 1-511 | 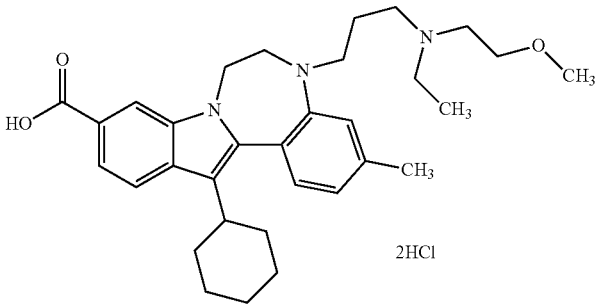 2HCl | 518.3 |
| 1-512 | 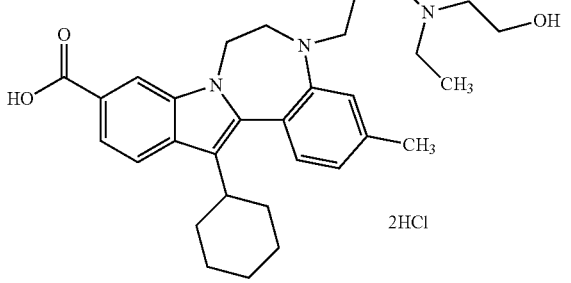 2HCl | 504.3 |

TABLE 218-continued
| Ex. | formula | positive MS (M + 1)(free form) |
|---|---|---|
| 1-513 | 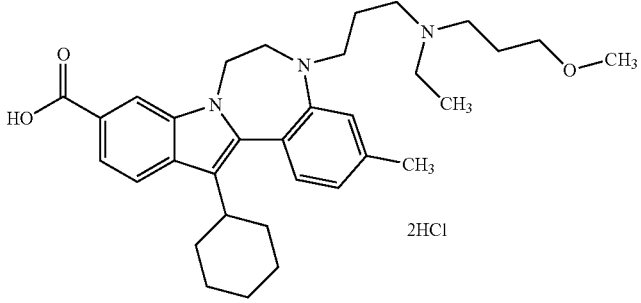 2HCl | 532.3 |
| 1-514 | 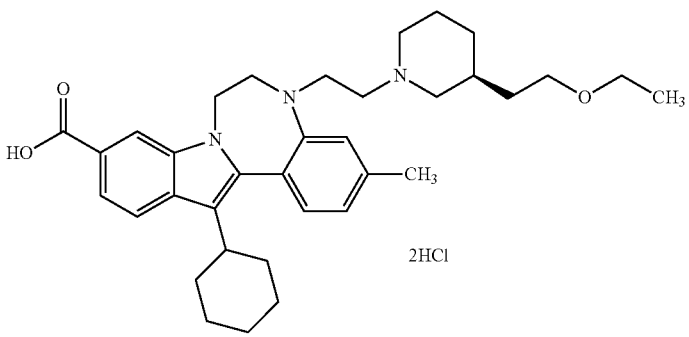 2HCl | 558.3 |
TABLE 219
| Ex. | formula | positive MS (M + 1)(free form) |
|---|---|---|
| 1-515 | 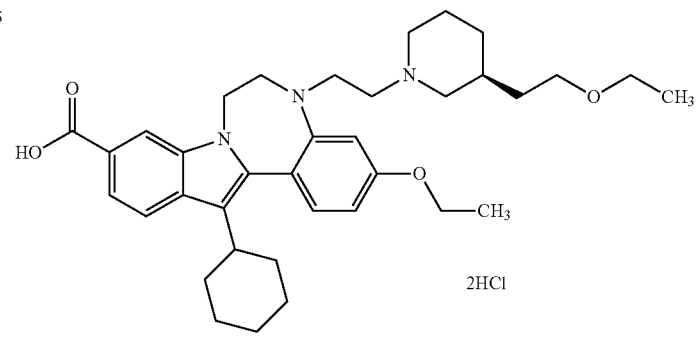 2HCl | 588.3 |
| 1-516 | 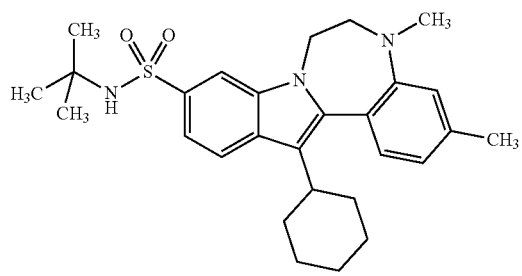 | 480.2 |

TABLE 219-continued

| Ex. | formula | positive MS (M + 1)(free form) |
|---|---|---|
| 1-517 | | 424.2 |
| 1-518 | | 559.3 |
| 1-519 | | 501.2 |

TABLE 220

| Ex. | formula | positive MS (M + 1)(free form) |
|---|---|---|
| 1-520 | | 563.3 |

TABLE 220-continued
| Ex. | formula | positive MS (M + 1)(free form) |
|---|---|---|
| 1-521 | 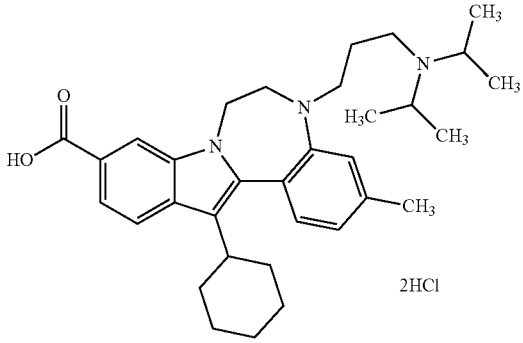 2HCl | 516.4 |
| 1-522 | 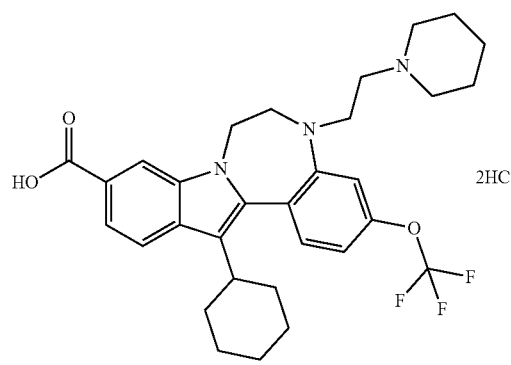 2HCl | 556.3 |
| 1-523 | 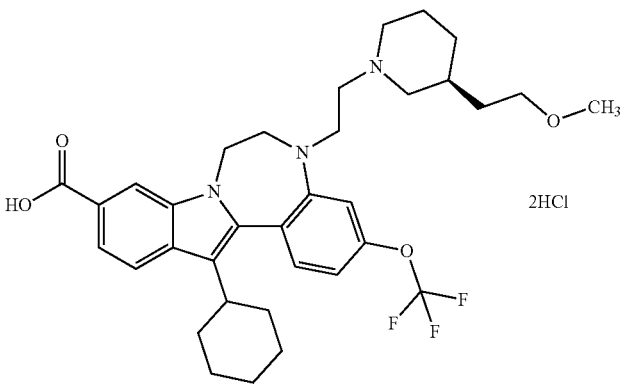 2HCl | 614.3 |
| 1-524 | 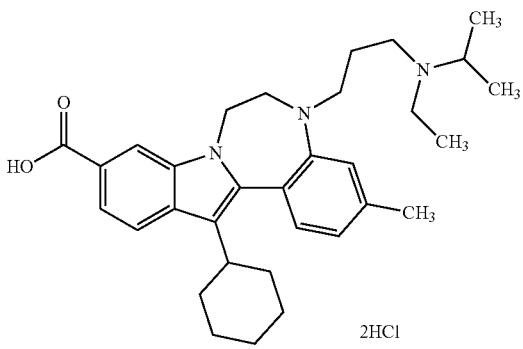 2HCl | 502.3 |

TABLE 221
| Ex. | formula | positive MS (M + 1)(free form) |
|---|---|---|
| 1-525 | 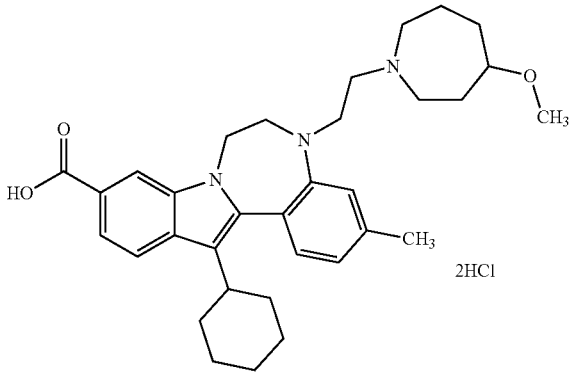 2HCl | 530.3 |
| 1-526 | 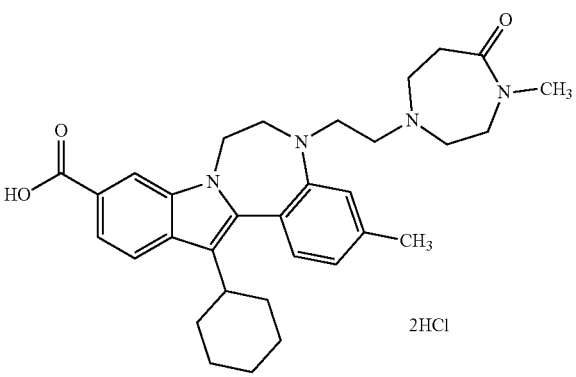 2HCl | 529.3 |
| 1-527 | 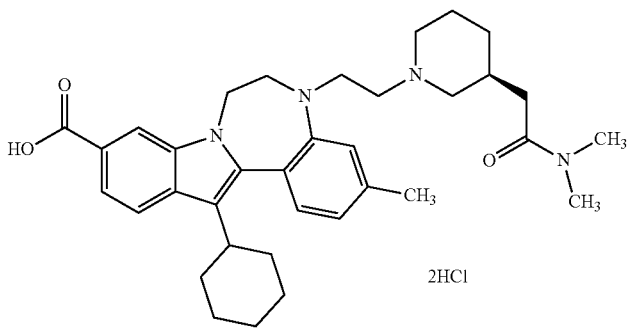 2HCl | 571.4 |
| 1-528 | 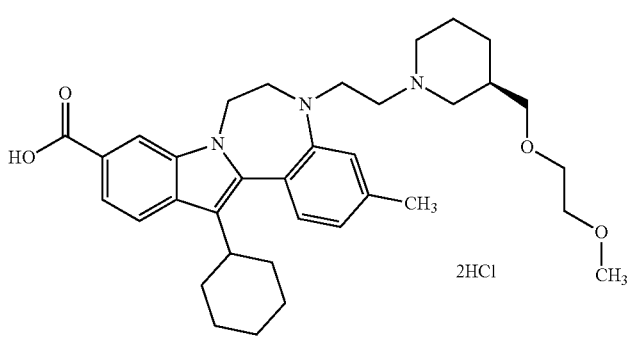 2HCl | 574.4 |

TABLE 222
| Ex. | formula | positive MS (M + 1)(free form) |
|---|---|---|
| 1-529 | 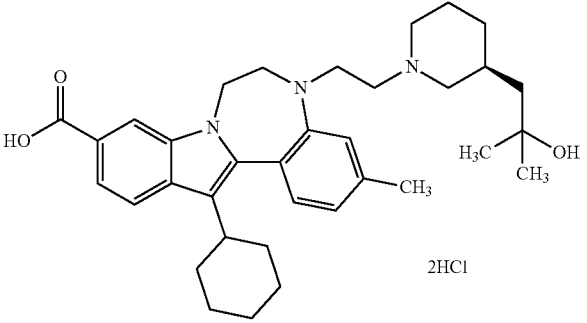 2HCl | 558.4 |
| 1-530 | 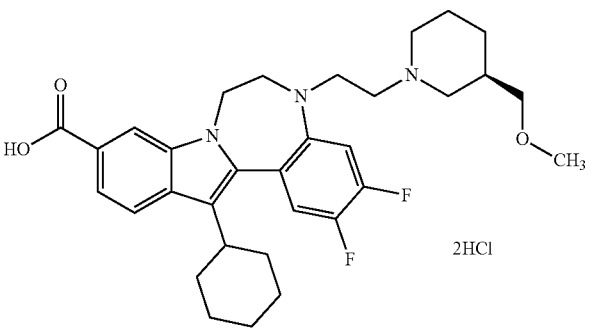 2HCl | 552.3 |
| 1-531 | 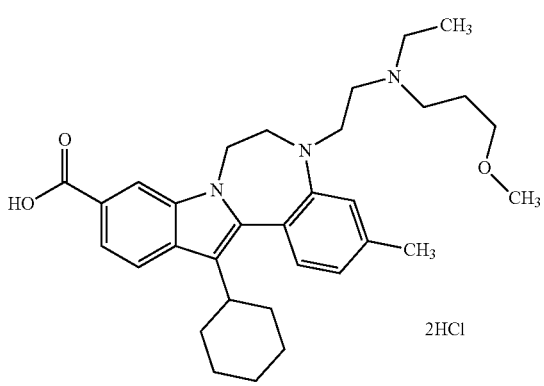 2HCl | 518.3 |
| 1-532 | 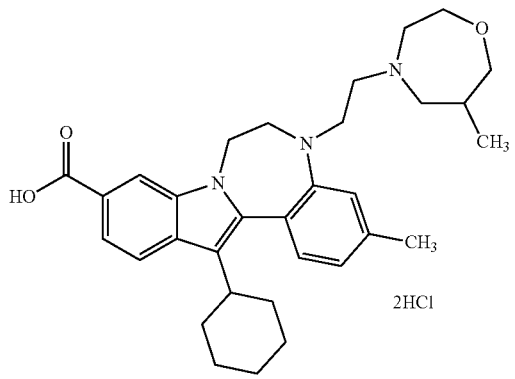 2HCl | 516.3 |

TABLE 223
| Ex. | formula | positive MS (M + 1)(free form) |
|---|---|---|
| 1-533 | 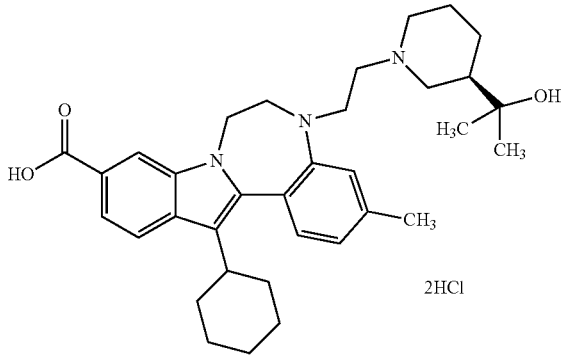 2HCl | 544.4 |
| 1-534 | 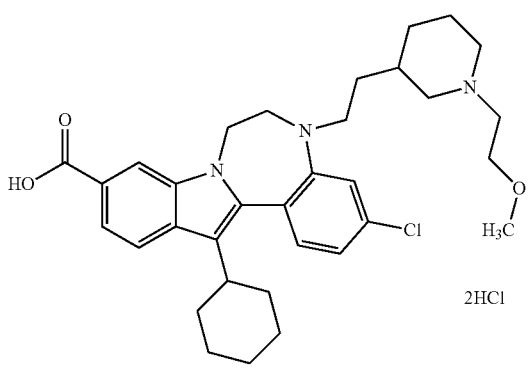 2HCl | 564.3 |
| 1-535 | 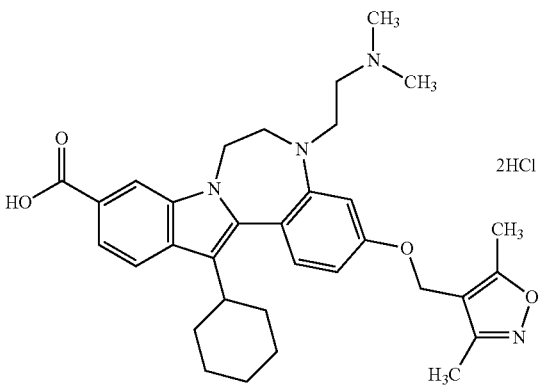 2HCl | 557.4 |
| 1-536 | 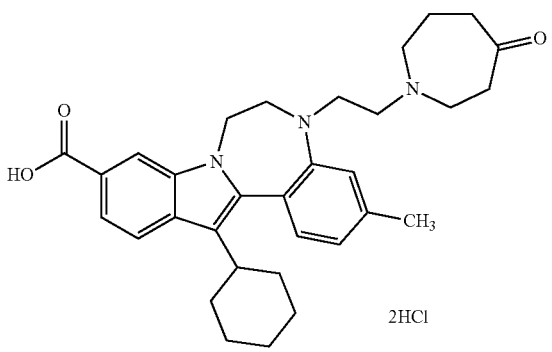 2HCl | 514.4 |

TABLE 224
| Ex. | formula | positive MS (M + 1)(free form) |
|---|---|---|
| 1-537 | 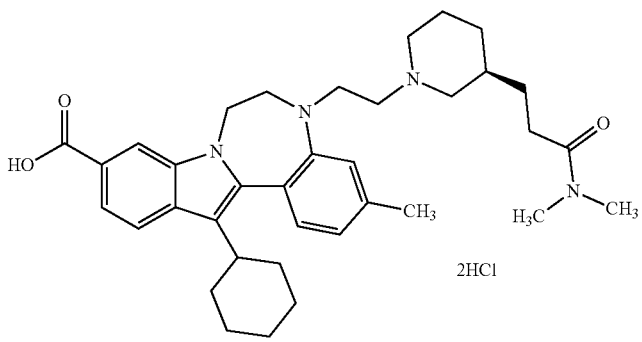 2HCl | 585.4 |
| 1-538 | 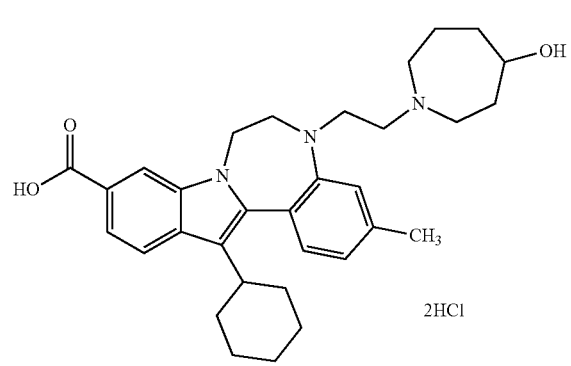 2HCl | 516.4 |
| 1-539 | 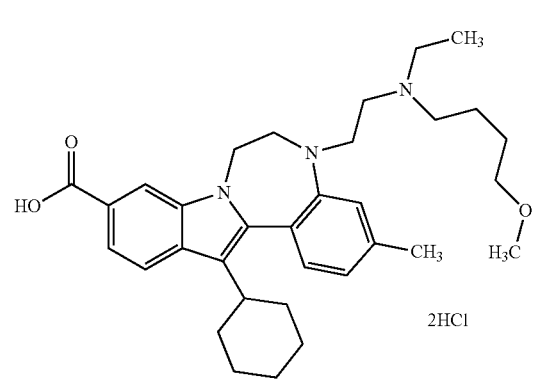 2HCl | 532.4 |
| 1-540 | 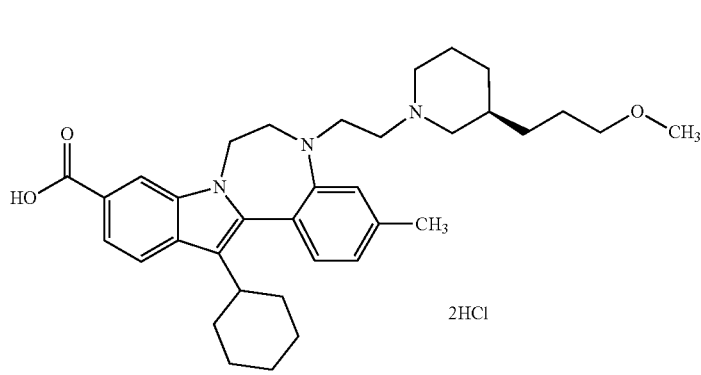 2HCl | 558.4 |

TABLE 224-continued
| Ex. | formula | positive MS (M + 1)(free form) |
|---|---|---|
| 1-541 | 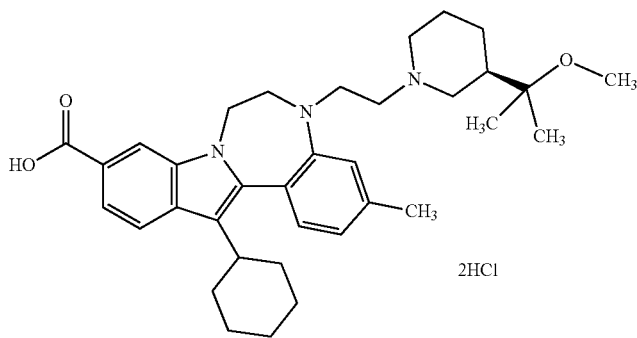 2HCl | 558.4 |
TABLE 225
| Ex. | formula | positive MS (M + 1)(free form) |
|---|---|---|
| 1-542 | 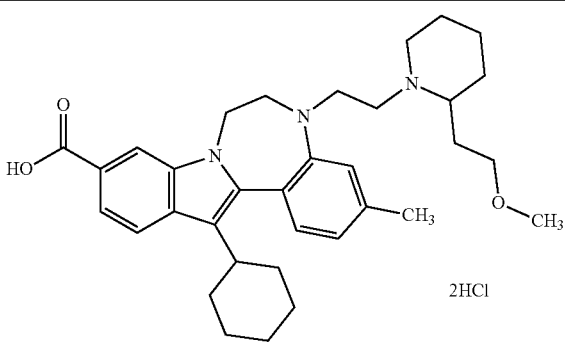 2HCl | 544.4 |
| 1-543 | 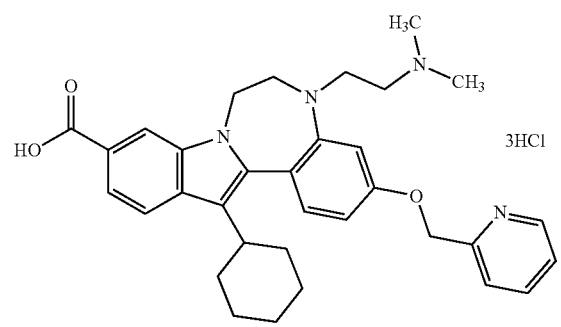 3HCl | 539.3 |
| 1-544 | 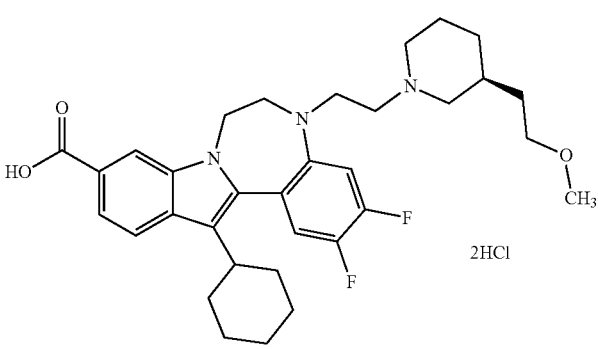 2HCl | 566.3 |

TABLE 225-continued
| Ex. | formula | positive MS (M + 1)(free form) |
|---|---|---|
| 1-545 | 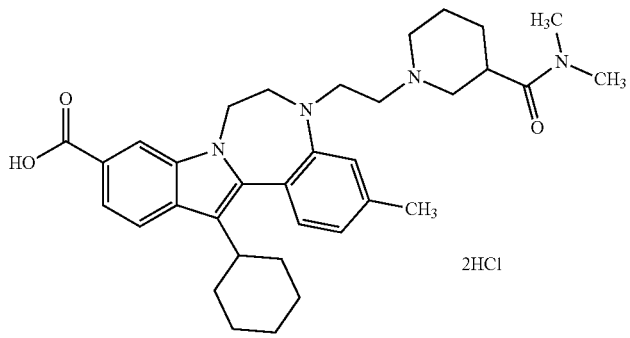 2HCl | 557.4 |
| 1-546 | 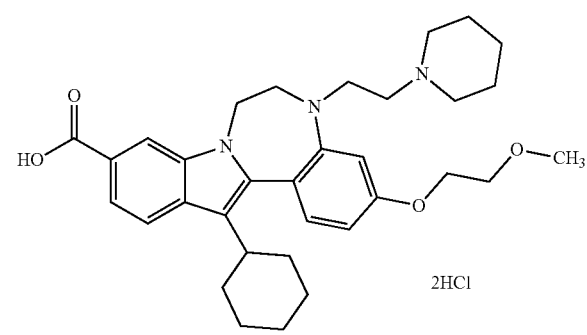 2HCl | 546.4 |
TABLE 226
| Ex. | formula | positive MS (M + 1)(free form) |
|---|---|---|
| 1-547 | 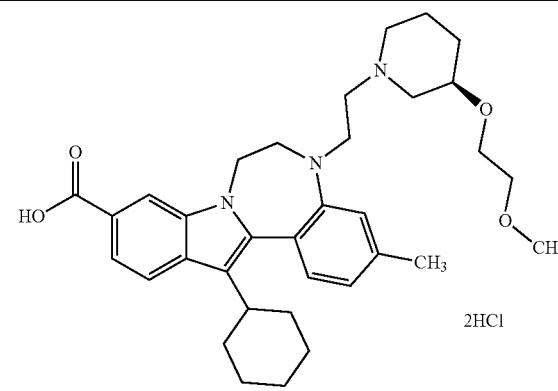 2HCl | 560.4 |
| 1-548 | 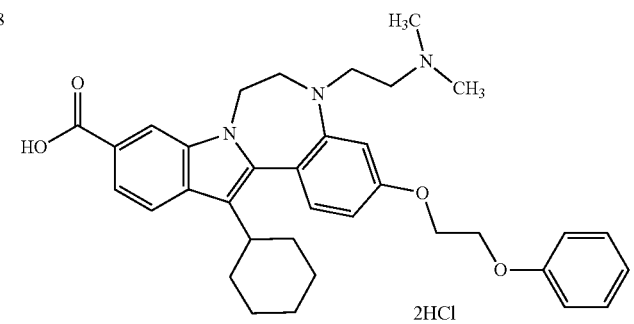 2HCl | 568.3 |

TABLE 226-continued
| Ex. | formula | positive MS (M + 1)(free form) |
|---|---|---|
| 1-549 | 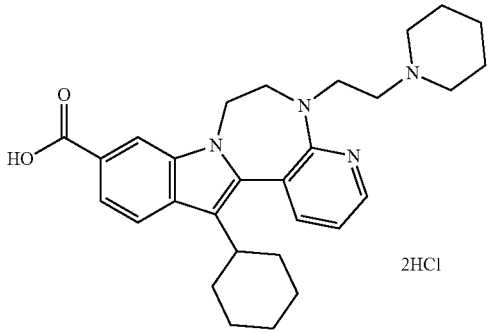 2HCl | 473.3 |
| 1-550 | 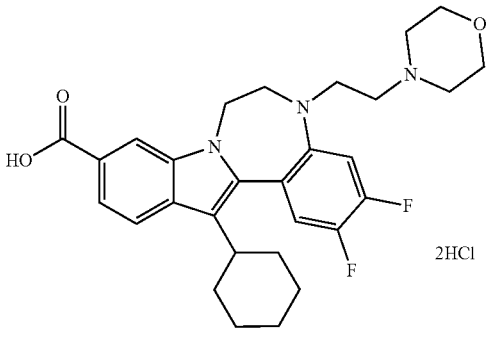 2HCl | 524.3 |
| 1-551 | 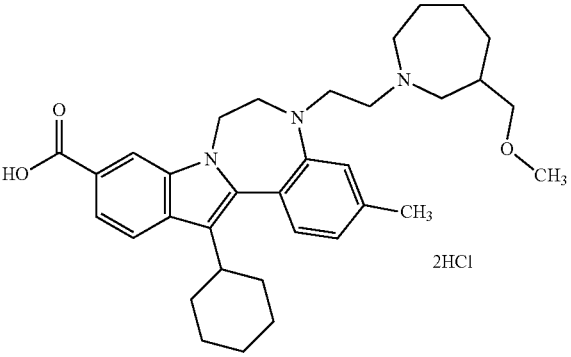 2HCl | 544.4 |
TABLE 227
| Ex. | formula | positive MS (M + 1)(free form) |
|---|---|---|
| 1-552 | 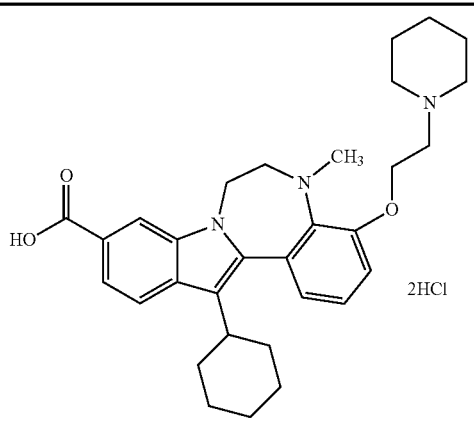 2HCl | 502.3 |

TABLE 227-continued
| Ex. | formula | positive MS (M + 1)(free form) |
|---|---|---|
| 1-553 | 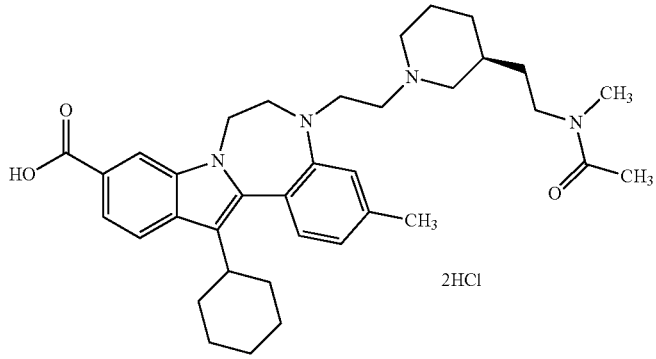 2HCl | 585.4 |
| 1-554 | 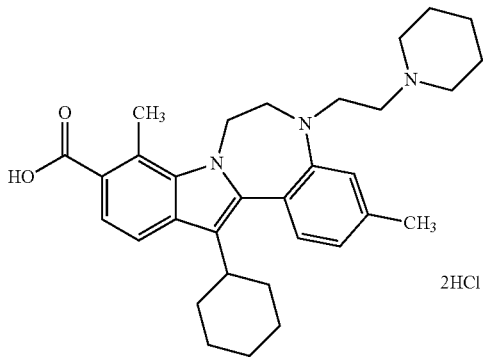 2HCl | 500.4 |
| 1-555 | 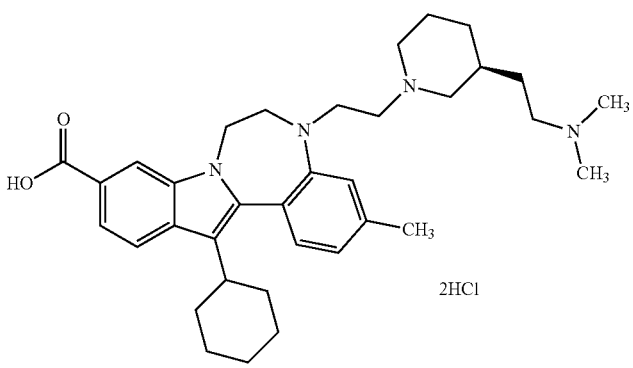 2HCl | 557.4 |

TABLE 228
| Ex. | formula | positive MS (M + 1)(free form) |
|---|---|---|
| 1-556 | 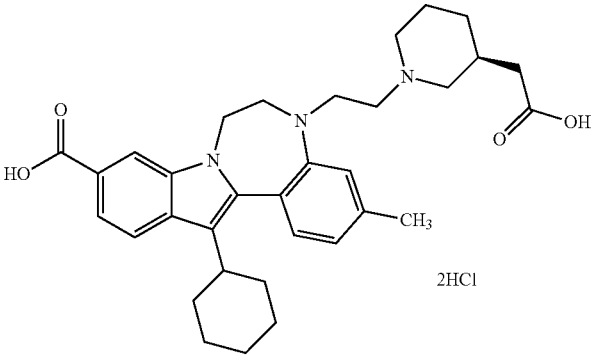 2HCl | 544.4 |
| 1-557 | 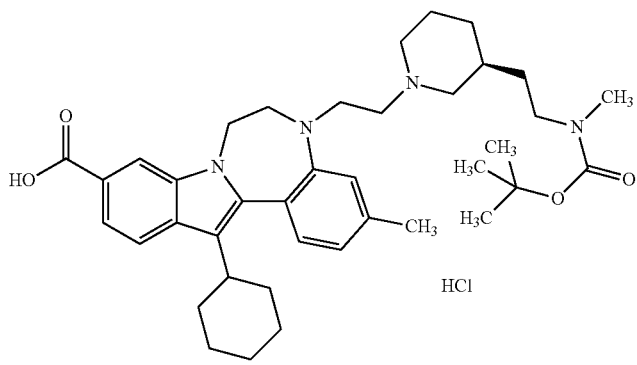 HCl | 643.4 |
| 1-558 | 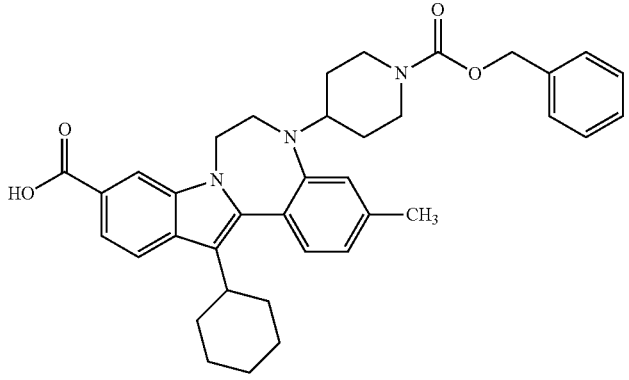 | 592.3 |
| 1-559 | 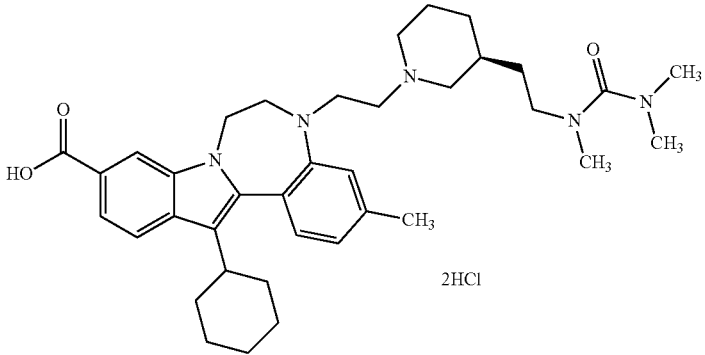 2HCl | 614.5 |

TABLE 229
| Ex. | formula | positive MS (M + 1)(free form) |
|---|---|---|
| 1-560 | 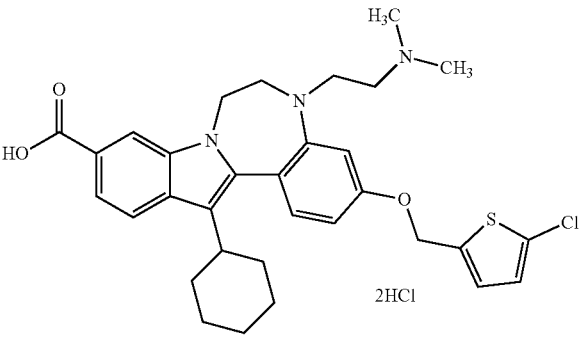 2HCl | 578.3 |
| 1-561 | 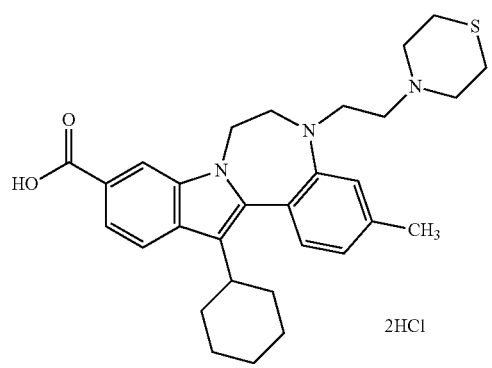 2HCl | 504.3 |
| 1-562 | 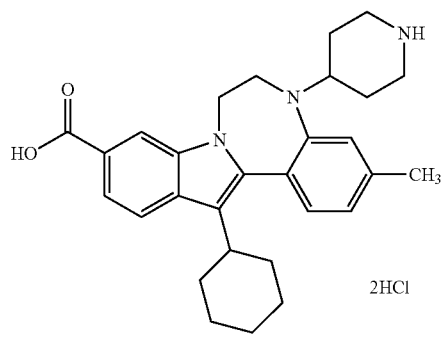 2HCl | 458.3 |
| 1-563 | 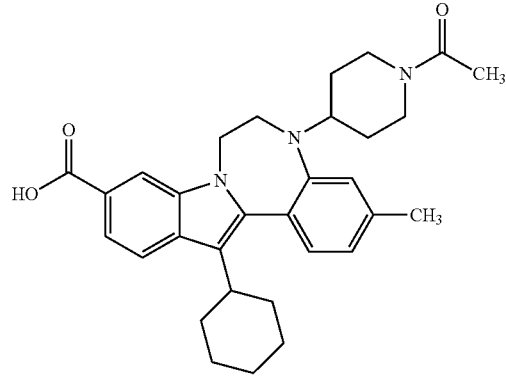 | 500.3 |

TABLE 230
| Ex. | formula | positive MS (M + 1)(free form) |
|---|---|---|
| 1-564 | 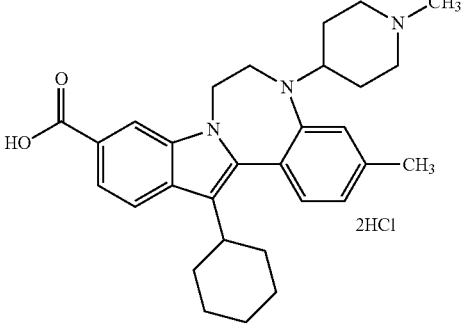 2HCl | 472.3 |
| 1-565 | 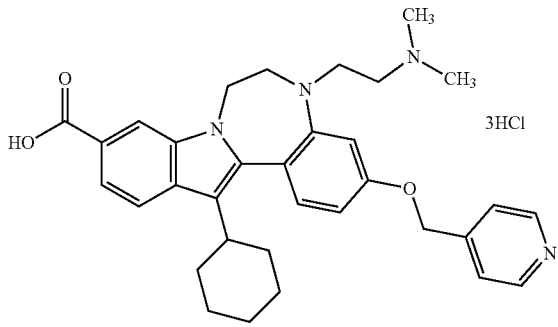 3HCl | 539.3 |
| 1-566 | 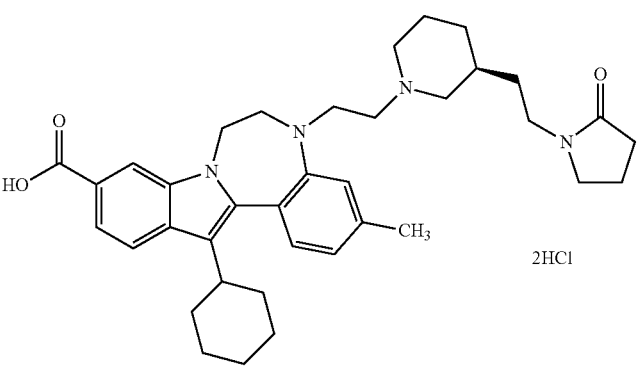 2HCl | 597.4 |
| 1-567 | 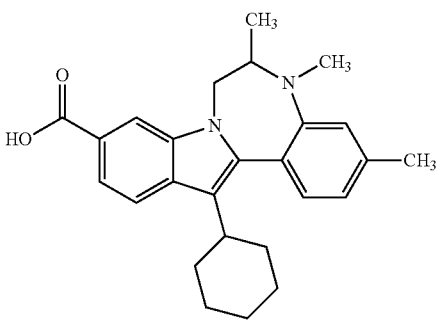 | 403.2 |

TABLE 231
| Ex. | formula | positive MS (M + 1)(free form) |
|---|---|---|
| 1-568 | 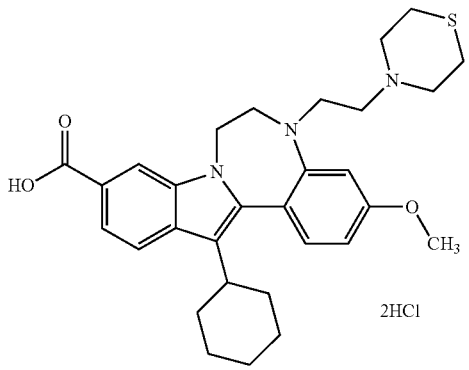 2HCl | 520.3 |
| 1-569 | 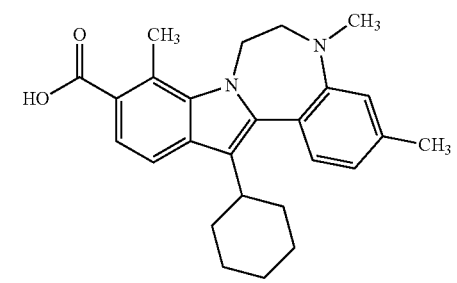 | 403.2 |
| 1-570 | 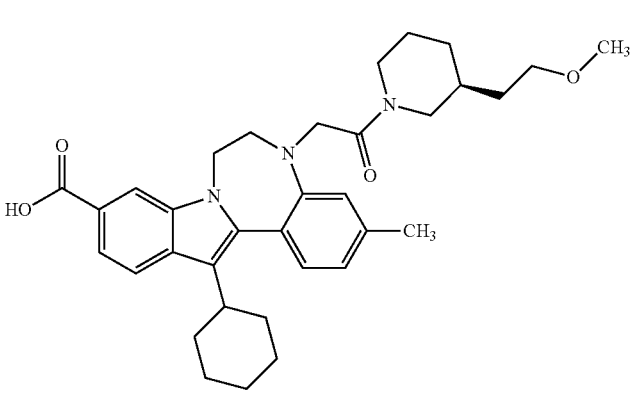 | 558.3 |
| 1-571 | 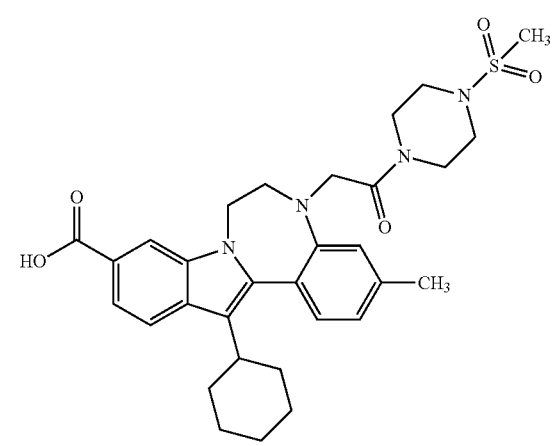 | 579.3 |

TABLE 232

| Ex. | formula | positive MS (M + 1)(free form) |
|---|---|---|
| 1-572 | | 530.3 |
| 1-573 | | 592.3 |
| 1-574 | | 389.2 |
| 1-575 | | 561.3 |

TABLE 233
| Ex. | formula | positive MS (M + 1)(free form) |
|---|---|---|
| 1-576 | 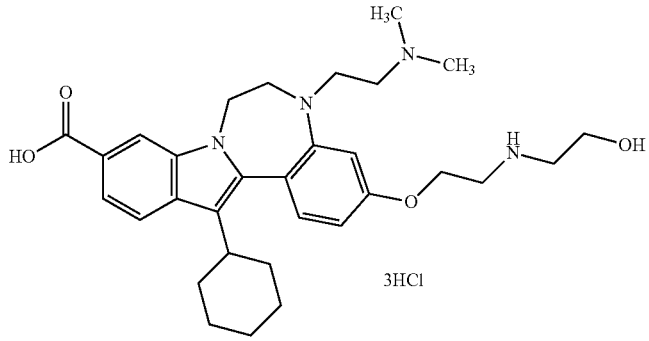 3HCl | 535.3 |
| 1-577 | 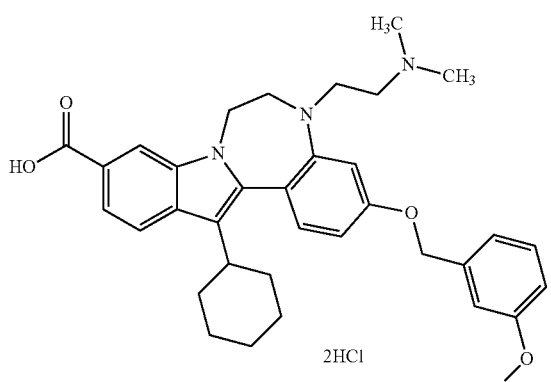 2HCl | 568.3 |
| 1-578 | 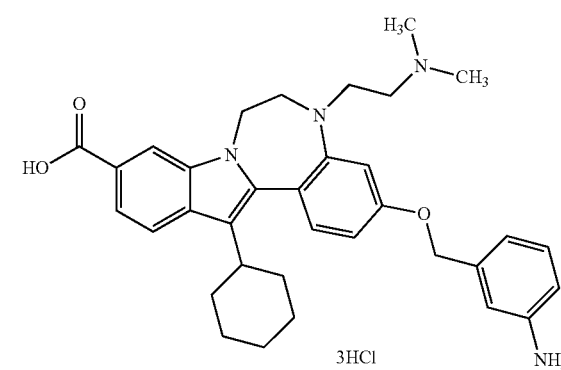 3HCl | 553.3 |
| 1-579 | 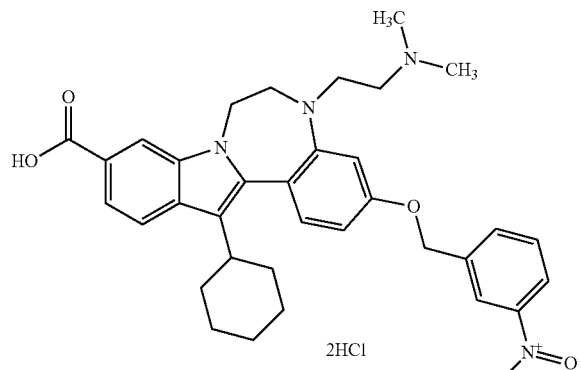 2HCl | 583.3 |

TABLE 234
| Ex. | formula | positive MS (M + 1)(free form) |
|---|---|---|
| 1-580 | 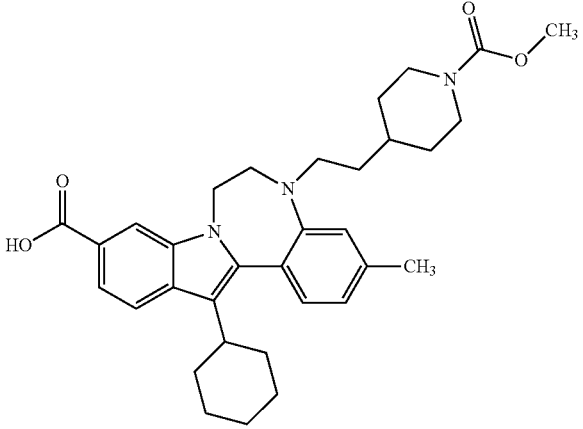 | 564.2 |
| 1-581 | 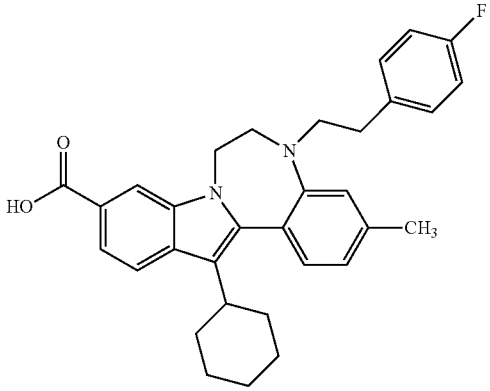 | 497.3 |
| 1-582 | 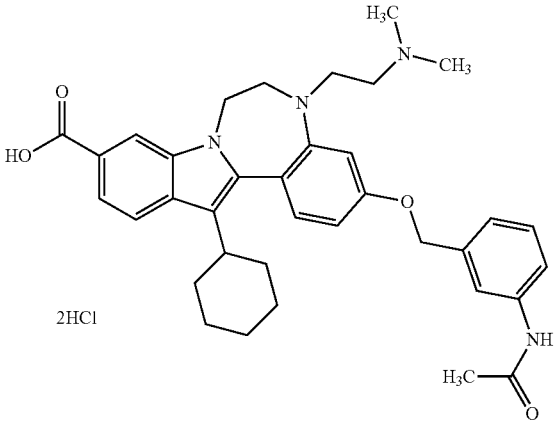 | 595.3 |

TABLE 234-continued
| Ex. | formula | positive MS (M + 1)(free form) |
|---|---|---|
| 1-583 | 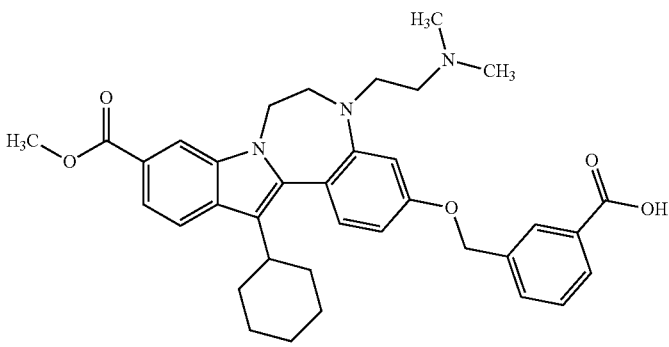 2HCl | 596.3 |
TABLE 235
| Ex. | formula | positive MS (M + 1)(free form) |
|---|---|---|
| 1-584 | 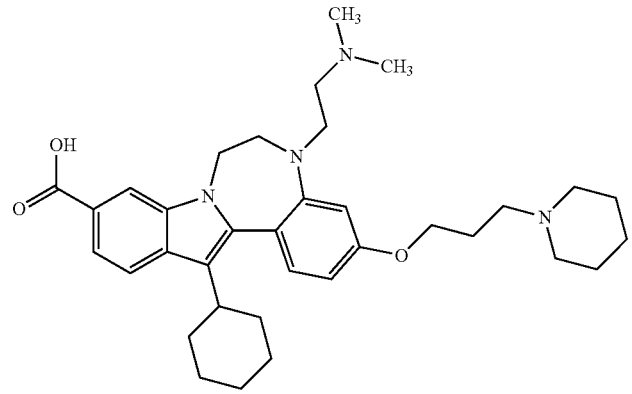 3HCl | 573.5 |
| 1-585 | 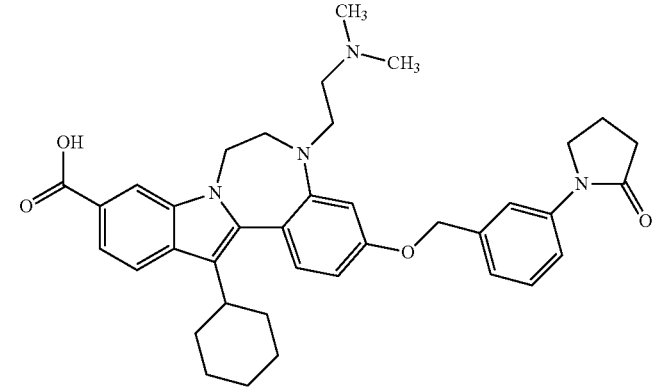 3HCl | 621.4 |

TABLE 235-continued
| Ex. | formula | positive MS (M + 1)(free form) |
|---|---|---|
| 1-586 | 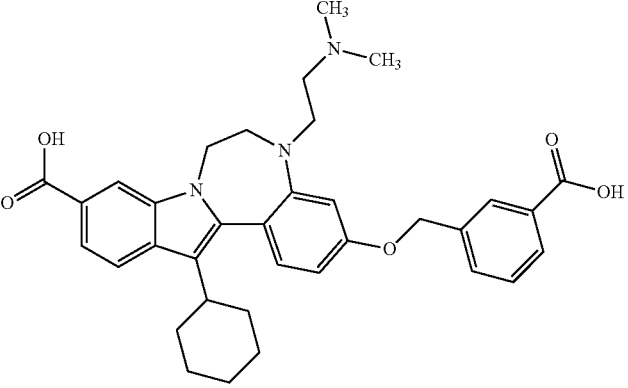 2HCl | 582.3 |
| 1-587 | 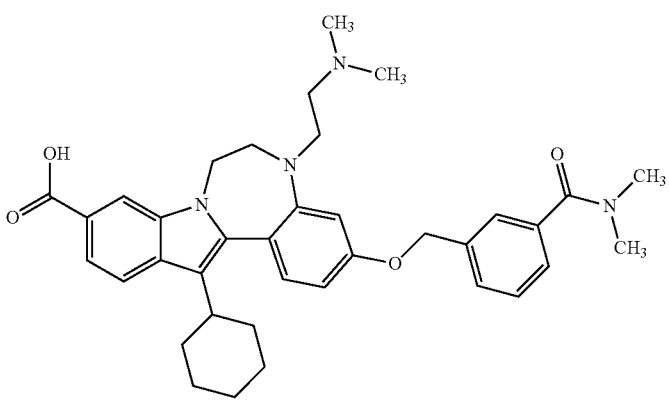 2HCl | 609.4 |
TABLE 236
| Ex. | formula | positive MS (M + 1)(free form) |
|---|---|---|
| 1-588 | 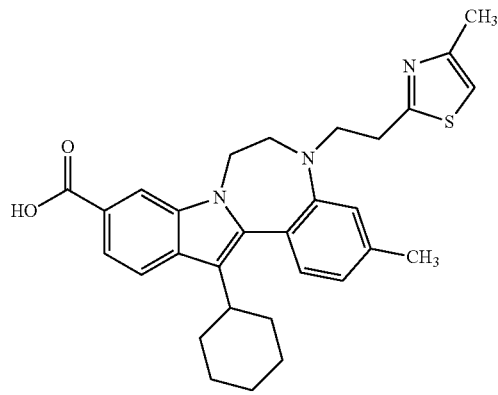 | 500.3 |

TABLE 236-continued
| Ex. | formula | positive MS (M + 1)(free form) |
|---|---|---|
| 1-589 | 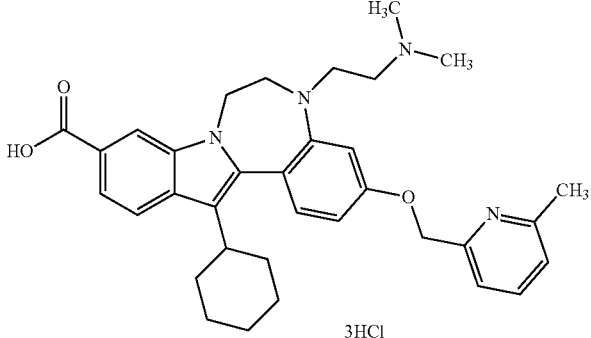 3HCl | 553.3 |
| 1-590 | 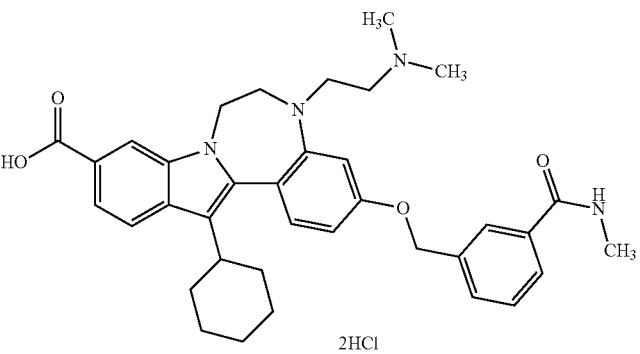 2HCl | 595.4 |
| 1-591 | 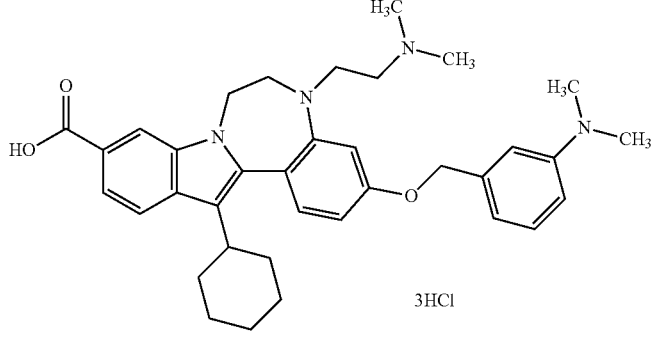 3HCl | 581.3 |
| 1-592 | 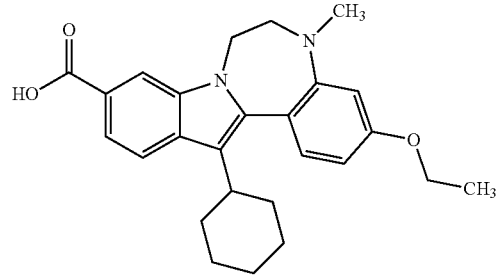 | 419.2 |

TABLE 237

| Ex. | formula | positive MS (M + 1)(free form) |
|---|---|---|
| 1-593 | | 481.2 |
| 1-594 | | 405.1 |
| 1-595 | 3HCl | 579.3 |

TABLE 238

| Ex. | formula | positive MS (M + 1)(free form) |
|---|---|---|
| 1-601 | | 586.2 |

TABLE 238-continued
| Ex. | formula | positive MS (M + 1)(free form) |
|---|---|---|
| 1-602 | 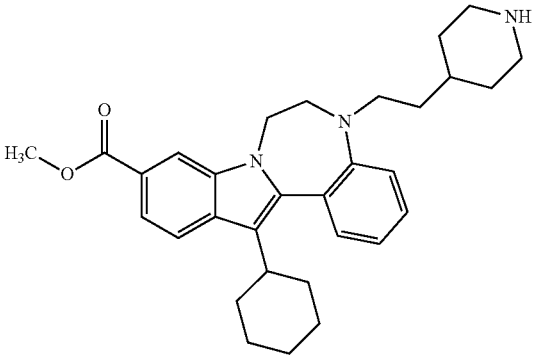 | 468.3 |
| 1-603 | 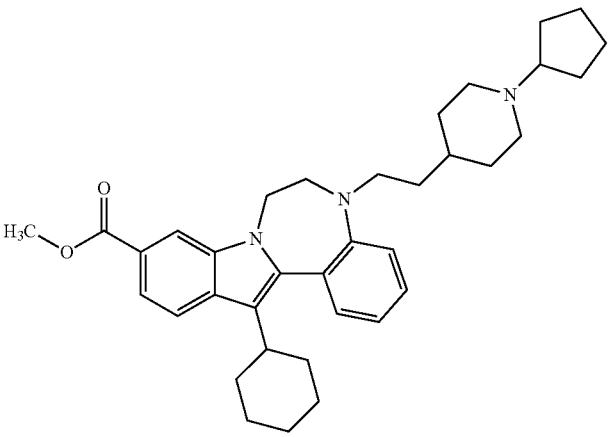 | |
| 1-604 | 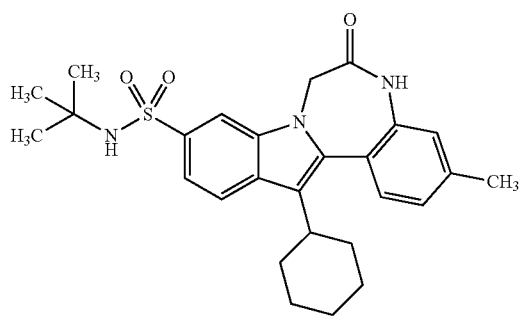 | |

TABLE 239

| Ex. | formula | positive MS (M + 1)(free form) |
|---|---|---|
| 1-605 | | |
| 1-606 | | 577.1 |
| 1-607 | | 521.2 |
| 1-608 | | |

TABLE 239-continued

| Ex. | formula | positive MS (M + 1)(free form) |
|---|---|---|
| 1-609 | | |

TABLE 240

| Ex. | formula | positive MS (M + 1)(free form) |
|---|---|---|
| 1-610 | | |
| 1-611 | | |
| 1-612 | | |

TABLE 240-continued

| Ex. | formula | positive MS (M + 1)(free form) |
|---|---|---|
| 1-613 | | |
| 1-614 | | |

TABLE 241

| Ex. | formula | positive MS (M + 1)(free form) |
|---|---|---|
| 2-456 | (2HCl) | 518.2 |
| 2-457 | | 589.3 |

TABLE 241-continued

| Ex. | formula | positive MS (M + 1)(free form) |
|---|---|---|
| 2-458 | | 489.3 |
| 2-459 | | 503.3 |
| 2-460 | | 503.3 |

TABLE 242

| Ex. | formula | positive MS (M + 1)(free form) |
|---|---|---|
| 2-461 | | 487.3 |

TABLE 242-continued
| Ex. | formula | positive MS (M + 1)(free form) |
|---|---|---|
| 2-462 | 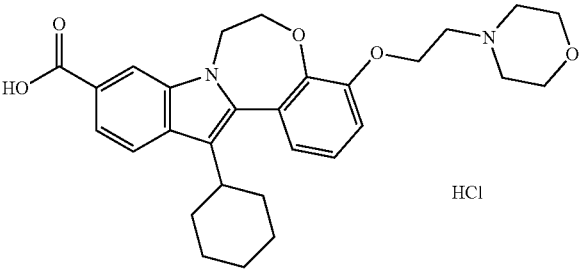 HCl | 491.2 |
| 2-463 | 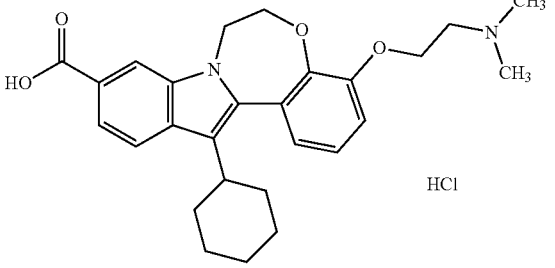 HCl | 449.2 |
| 2-464 | 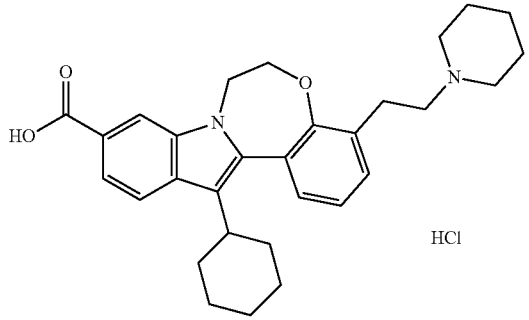 HCl | 473.3 |
| 2-465 | 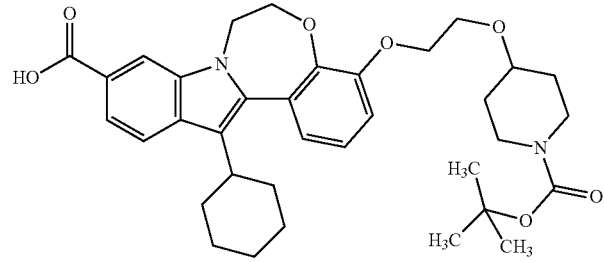 | 605.4 |
TABLE 243
| Ex. | formula | positive MS (M + 1)(free form) |
|---|---|---|
| 2-466 | 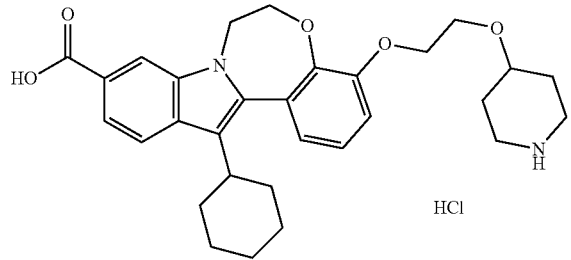 HCl | 505.3 |

TABLE 243-continued
| Ex. | formula | positive MS (M + 1)(free form) |
|---|---|---|
| 2-467 | 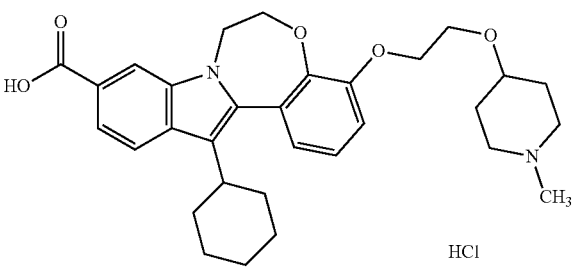 HCl | 519.3 |
| 2-468 | 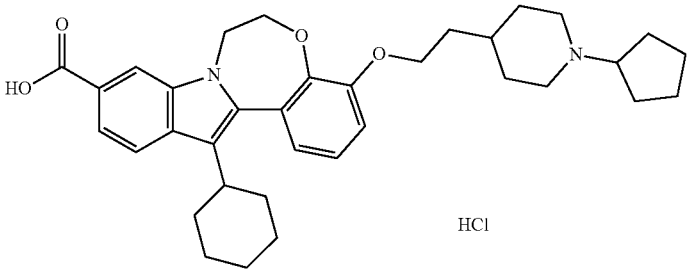 HCl | 557.4 |
| 2-469 | 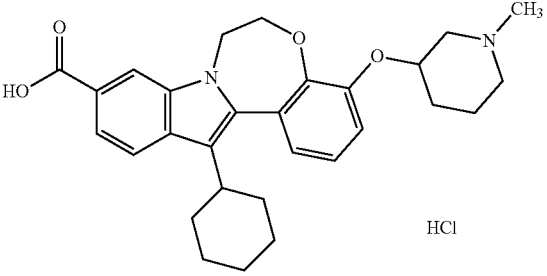 HCl | 475.3 |
| 2-470 | 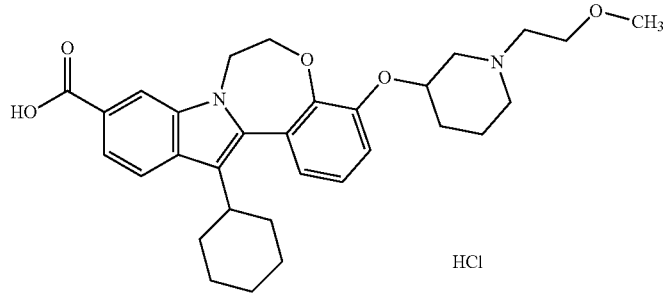 HCl | 519.3 |

TABLE 244
| Ex. | formula | positive MS (M + 1)(free form) |
|---|---|---|
| 2-471 | 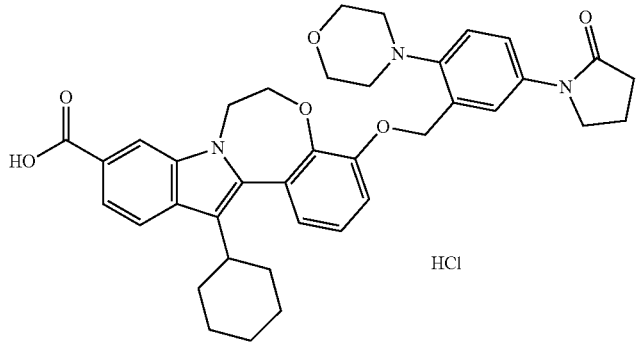 HCl | 636.3 |
| 2-472 | 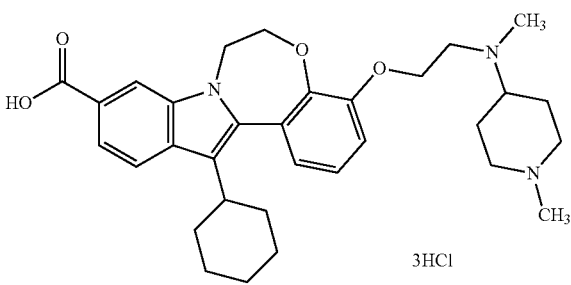 3HCl | 532.3 |
| 2-473 | 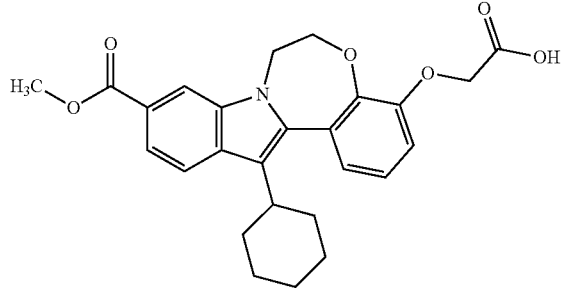 | 450.2 |
| 2-474 | 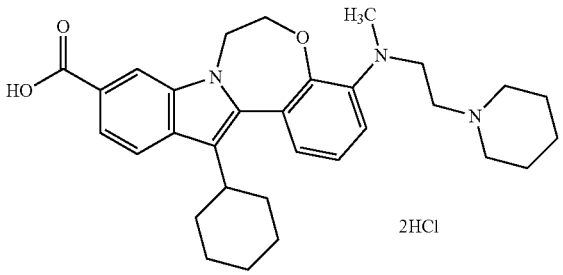 2HCl | 502.3 |
| 2-475 | 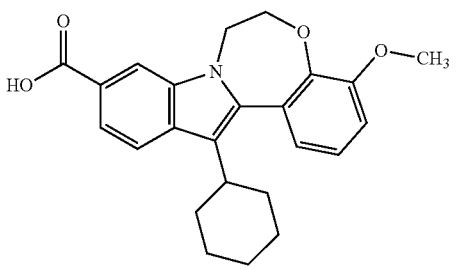 | 392.1 |

TABLE 245
| Ex. | formula | positive MS (M + 1)(free form) |
|---|---|---|
| 2-476 | 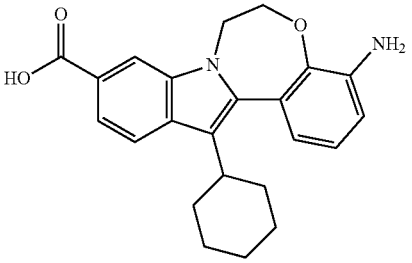 | 377.1 |
| 2-477 | 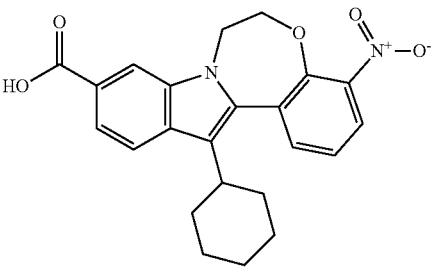 | 407.1 |
| 2-478 | 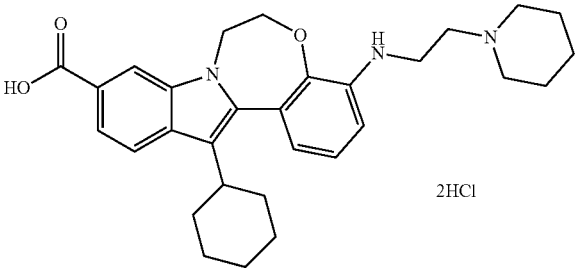 2HCl | 488.3 |
| 2-479 | 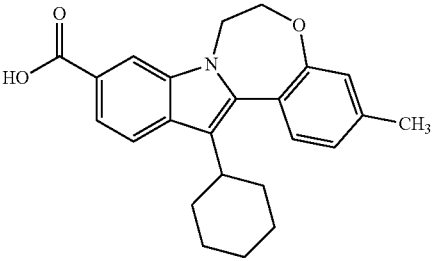 | 376.2 |
| 2-480 | 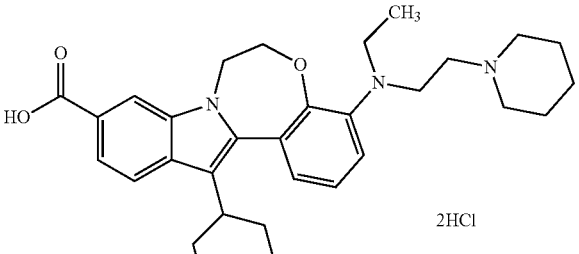 2HCl | 516.4 |

TABLE 246

| Ex. | formula | positive MS (M + 1)(free form) |
|---|---|---|
| 2-481 | | 530.4 |
| 2-482 | | 546.3 |
| 2-483 | | 405.2 |
| 2-484 | | 380.1 |

TABLE 246-continued

| Ex. | formula | positive MS (M + 1)(free form) |
|---|---|---|
| 2-485 | | 530.3 |

TABLE 247

| Ex. | formula | positive MS (M + 1)(free form) |
|---|---|---|
| 2-486 | | 516.3 |

TABLE 248

| Ex. | formula | positive MS (M + 1)(free form) |
|---|---|---|
| 2-501 | | |
| 2-502 | | |

TABLE 248-continued

| Ex. | formula | positive MS (M + 1)(free form) |
|---|---|---|
| 2-503 | | |
| 2-504 | | |

TABLE 249

| Ex. | formula | positive MS (M + 1)(free form) |
|---|---|---|
| 2-505 | | |
| 2-506 | | |
| 2-507 | | |

US 7,977,331 B1
TABLE 249-continued
| Ex. | formula | positive MS (M + 1)(free form) |
|---|---|---|
| 2-508 | 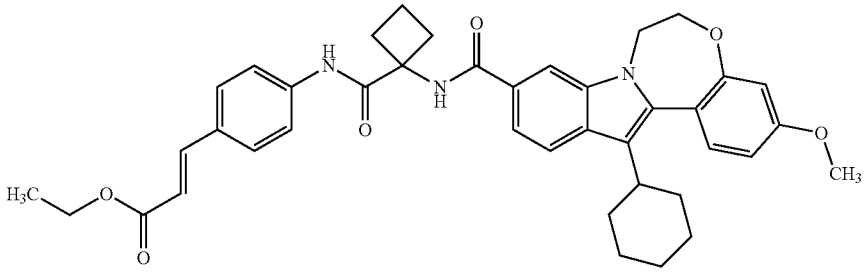 | |
| 2-509 | 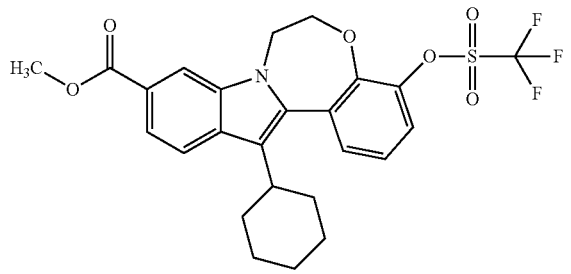 | |
TABLE 250
| Ex. | formula | positive MS (M + 1)(free form) |
|---|---|---|
| 2-510 | 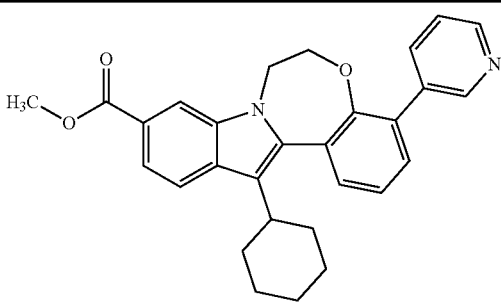 | |
| 2-511 | 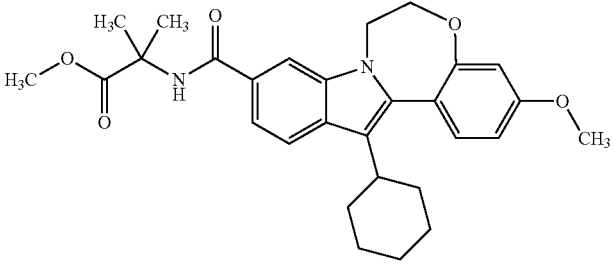 | |
| 2-512 | 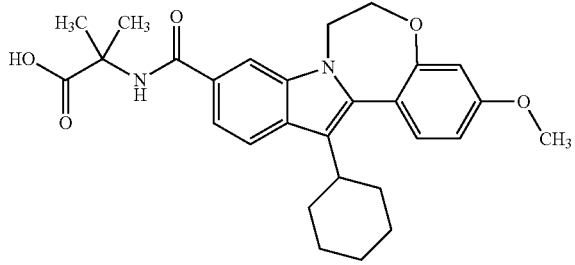 | |

TABLE 250-continued
| Ex. | formula | positive MS (M + 1)(free form) |
|---|---|---|
| 2-513 | 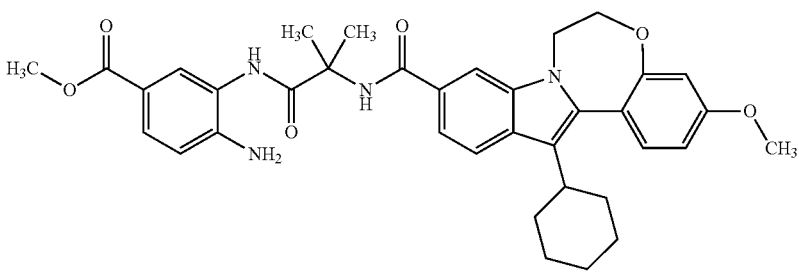 | |
| 2-514 | 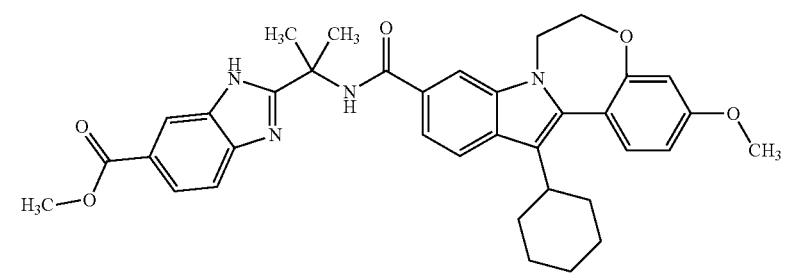 | |
TABLE 251
| Ex. | formula | positive MS (M + 1)(free form) |
|---|---|---|
| 2-515 | 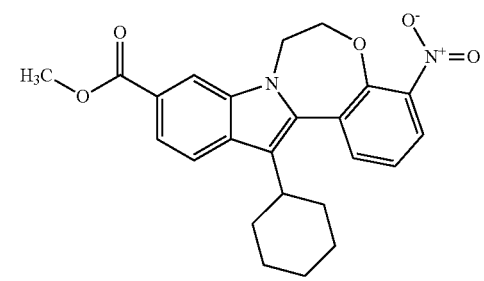 | |
| 2-516 | 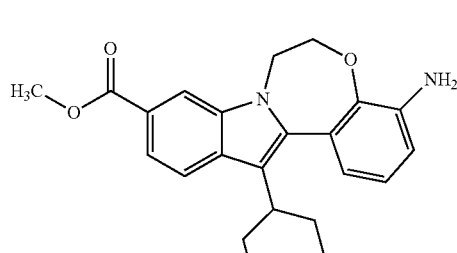 | |

TABLE 251-continued
| Ex. | formula | positive MS (M + 1)(free form) |
|---|---|---|
| 2-517 | 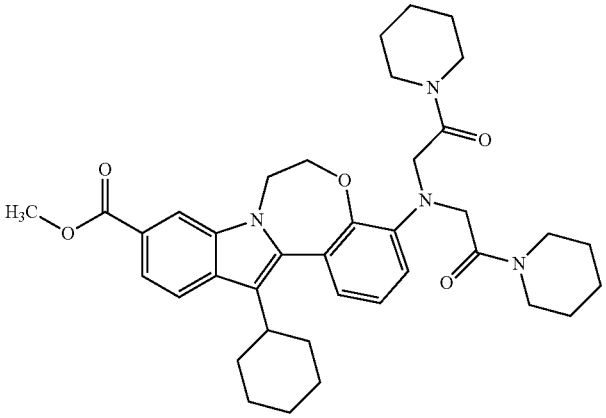 | |
| 2-518 | 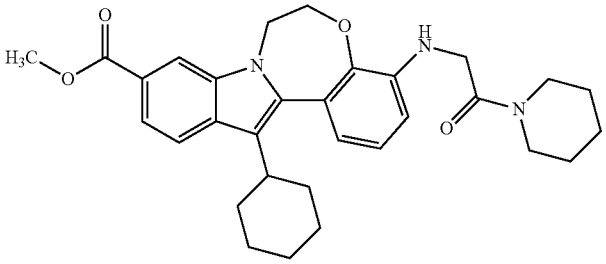 | |
TABLE 252
| Ex. | formula | positive MS (M + 1)(free form) |
|---|---|---|
| 2-519 | 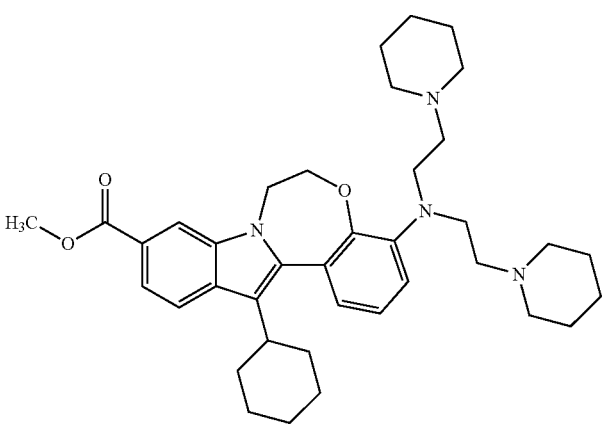 | |

TABLE 252-continued
| Ex. | formula | positive MS (M + 1)(free form) |
|---|---|---|
| 2-520 | 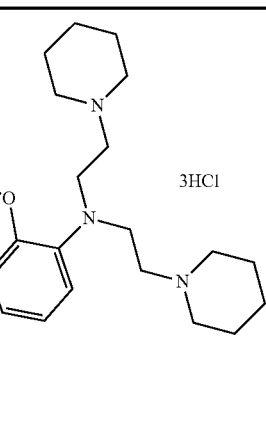 | 599.4 |
| 2-521 | 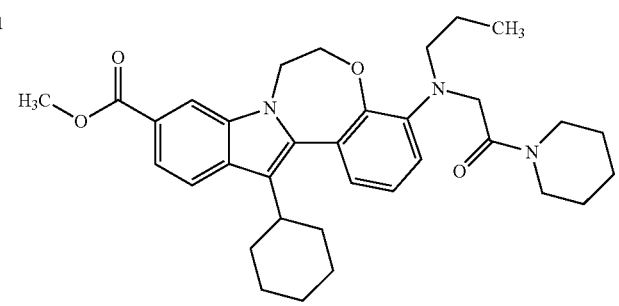 | |
| 2-522 | 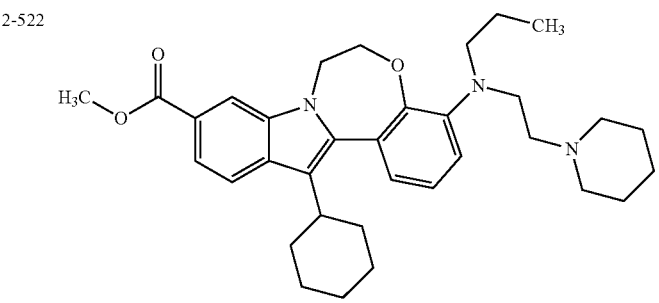 | |
TABLE 253
| Ex. | formula | positive MS (M + 1) (free form) |
|---|---|---|
| 5-4 | 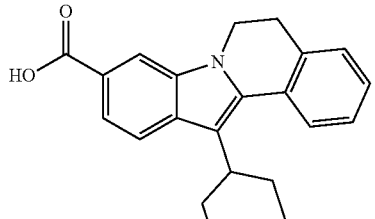 | 346.2 |
TABLE 253-continued
| Ex. | formula | positive MS (M + 1) (free form) |
|---|---|---|
| 5-5 | 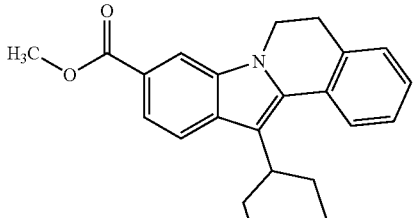 | 360.1 |

TABLE 253-continued

| Ex. | formula | positive MS (M + 1) (free form) |
|---|---|---|
| 5-6 | (structure) | 330.2(M-17) negative MS 346.2(M-1) |
| 5-7 | (structure) | 330.2(M-31) negative MS 360.2(M-1) |

TABLE 254

| Ex. | formula | positive MS (M + 1)(free form) |
|---|---|---|
| 7-9 | (structure) | 393.2 |
| 7-10 | (structure) | 635.3 |

TABLE 255

| Ex. | formula | positive MS (M + 1)(free form) |
|---|---|---|
| 8-8 | (structure) | 390.2 |

TABLE 255-continued

| Ex. | formula | positive MS (M + 1)(free form) |
|---|---|---|
| 8-9 | | 632.4 |

TABLE 256

| Ex. | formula | positive MS (M + 1)(free form) |
|---|---|---|
| 11-1 | | 389.2 |
| 11-2 | | 489.0 |
| 11-3 | | |

TABLE 256-continued
| 11-4 | 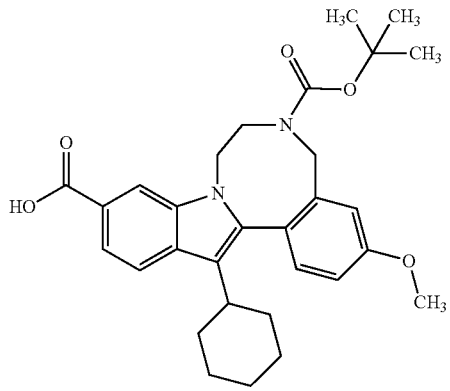 | 505.3 |
| 11-5 | 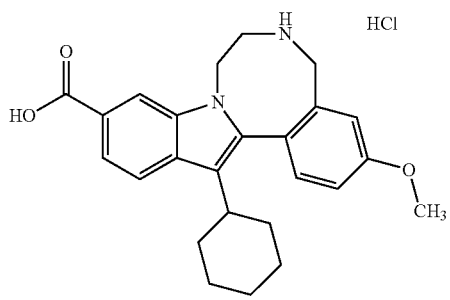 HCl | 405.2 |
TABLE 257
| Ex. | formula | positive MS (M + 1)(free from) |
|---|---|---|
| 11-6 | 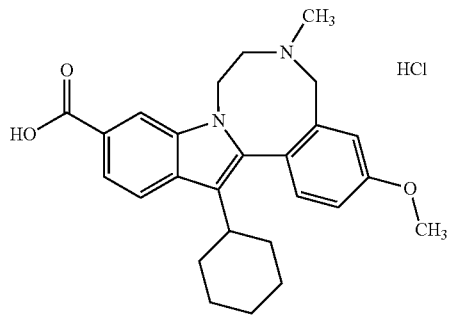 HCl | 419.3 |
| 11-7 | 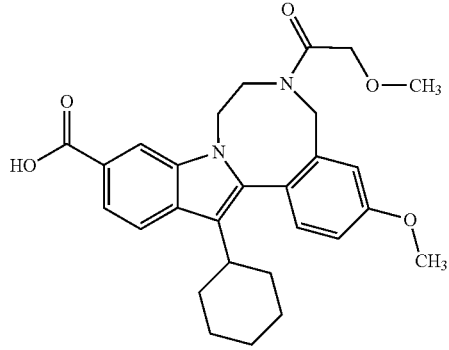 | 477.2 |

TABLE 257-continued
| Ex. | formula | positive MS (M + 1)(free from) |
|---|---|---|
| 11-8 | 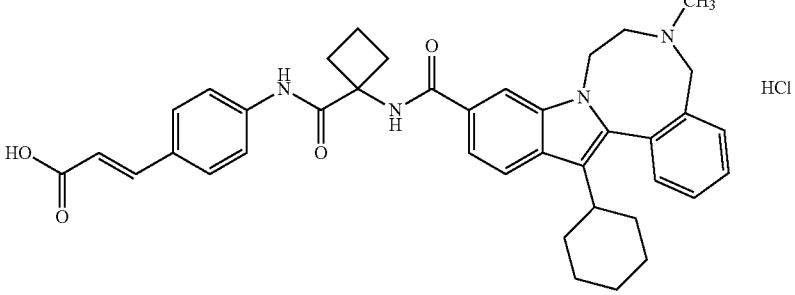 HCl | 631.3 |
TABLE 258
| Ex. | formula | positive MS (M + 1) (free form) |
|---|---|---|
| 12-1 | 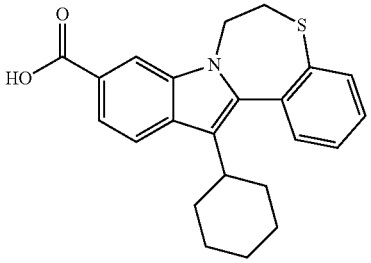 | 378.1 |
| 12-2 | 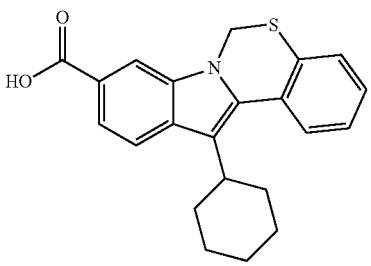 | 364.0 |
TABLE 258-continued
| Ex. | formula | positive MS (M + 1) (free form) |
|---|---|---|
| 12-3 | 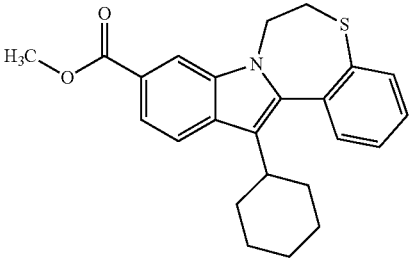 | 392.1 |
| 12-4 | 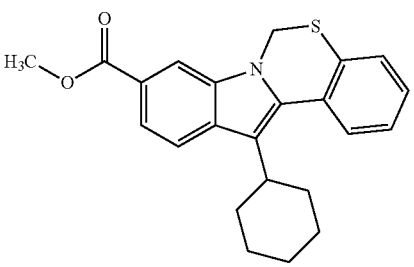 | |
TABLE 259
| Ex. | formula | positive MS (M + 1)(free form) |
|---|---|---|
| 1-615 | 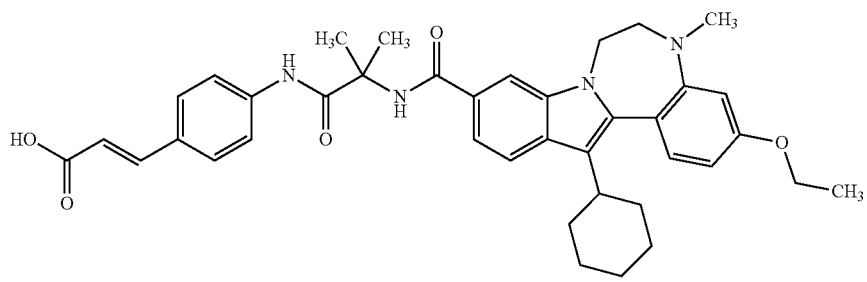 | 649.3 |

TABLE 259-continued
| Ex. | formula | positive MS (M + 1)(free form) |
|---|---|---|
| 1-616 | 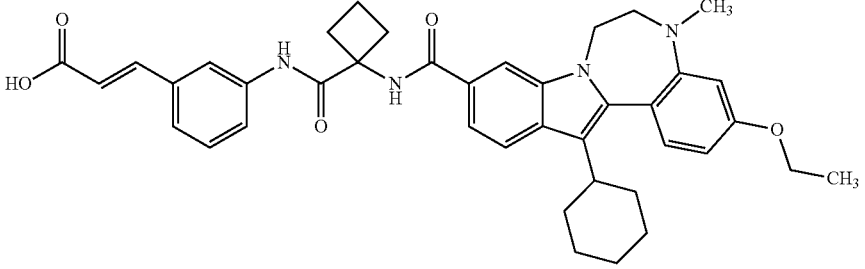 | 661.3 |
| 1-617 | 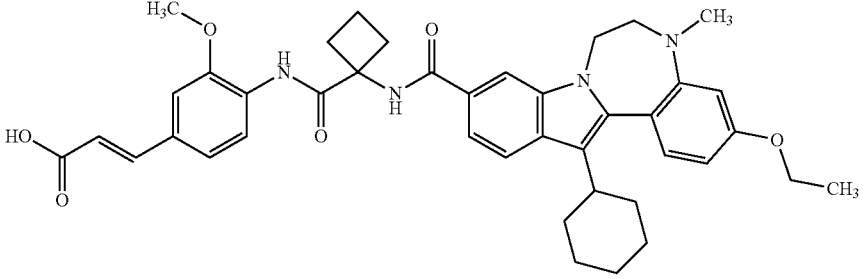 | 691.3 |
| 1-618 | 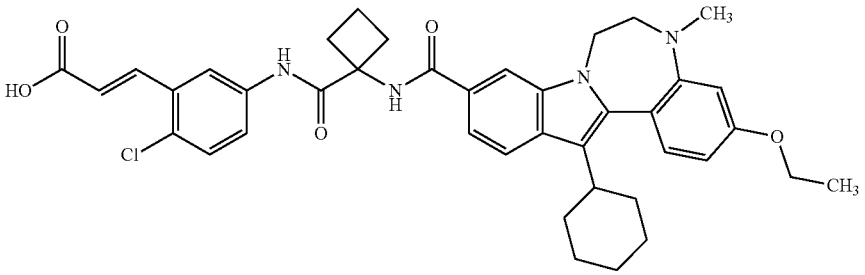 | 695.2 |
| 1-619 | 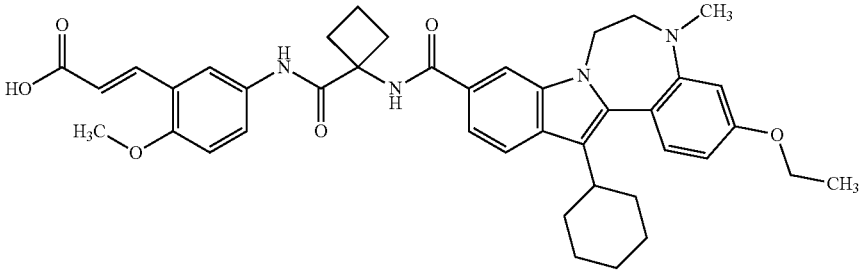 | 691.3 |
| 1-620 | 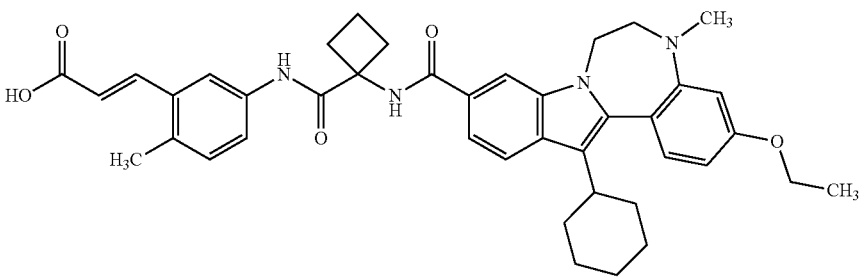 | 675.3 |

TABLE 260
| Ex. | formula | positive MS - (M + 1)(free form) |
|---|---|---|
| 1-621 | 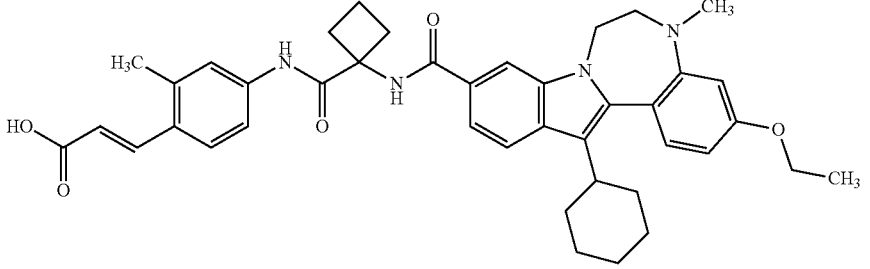 | 675.3 |
| 1-622 | 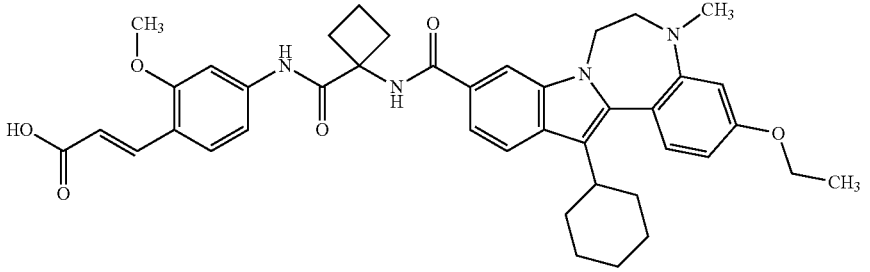 | 691.3 |
| 1-623 | 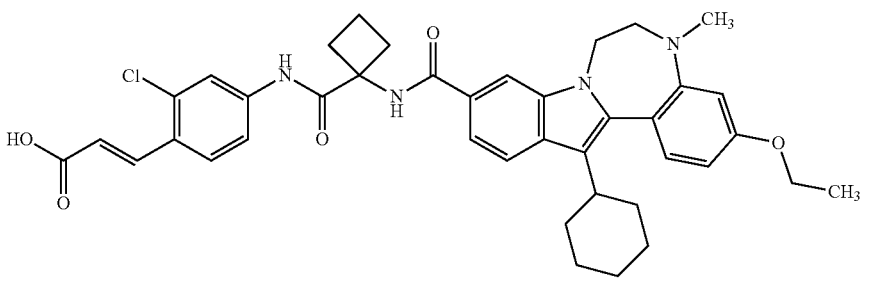 | 695.3 |
TABLE 261
| Ex. | formula | positive MS (M + 1)(free form) |
|---|---|---|
| 2-523 | 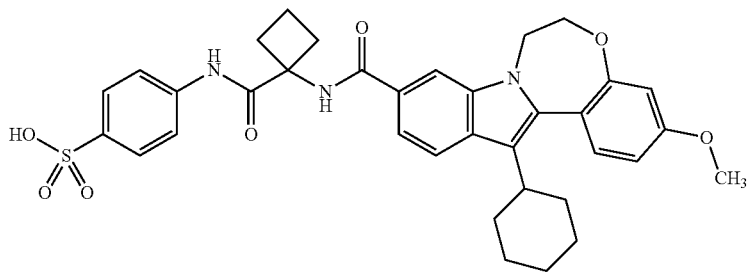 | 644.2 |

TABLE 261-continued

| Ex. | formula | positive MS (M + 1)(free form) |
|---|---|---|
| 2-524 | | 622.3 |
| 2-525 | | 682.3 |
| 2-526 | | 592.3 |

TABLE 262

| Ex. | formula | positive MS (M + 1)(free form) |
|---|---|---|
| 2-527 | | 648.3 |

TABLE 262-continued
| Ex. | formula | positive MS (M + 1)(free form) |
|---|---|---|
| 2-528 | 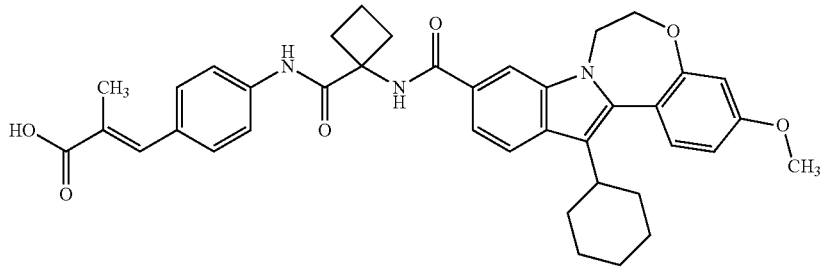 | 648.3 |
| 2-529 | 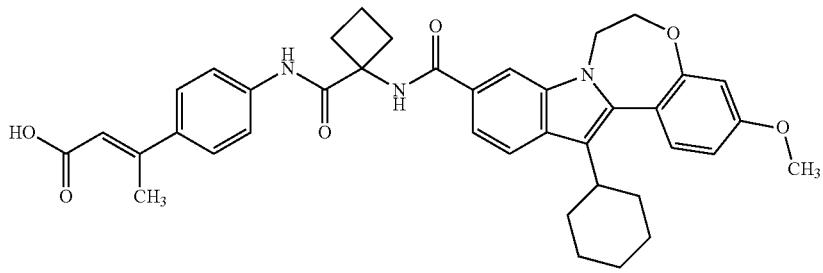 | 648.3 |
| 2-530 | 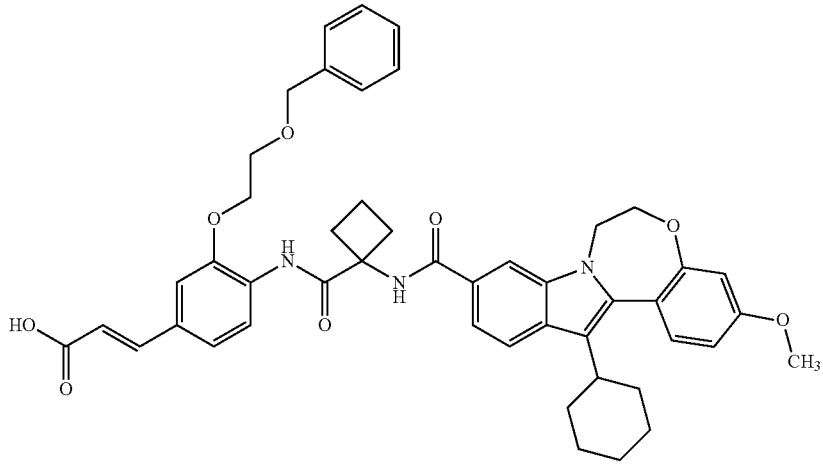 | 784.3 |
| 2-531 | 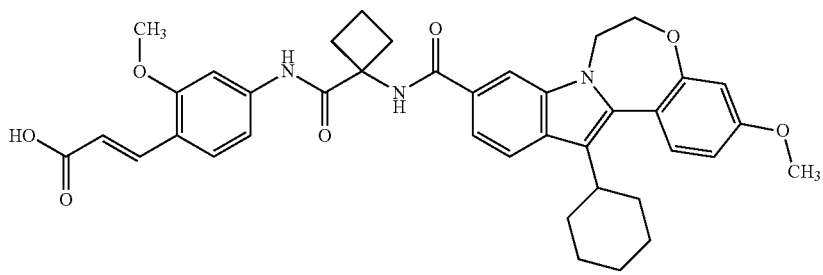 | 664.3 |

TABLE 263

| Ex. | formula | positive MS (M + 1)(free form) |
|---|---|---|
| 2-532 | | 507.3 |
| 2-533 | | 622.3 |
| 2-534 | | 573.5 |
| 2-535 | | 577.3 |

TABLE 264
| Ex. | formula | positive MS (M + 1)(free form) |
|---|---|---|
| 2-536 | 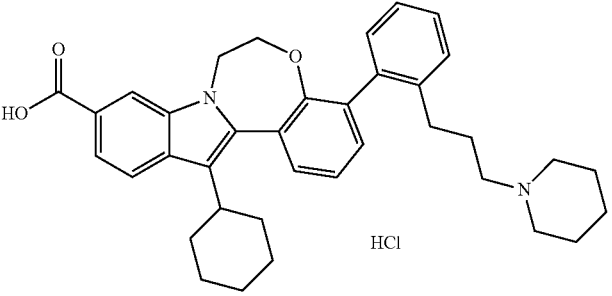 HCl | 563.3 |
| 2-537 | 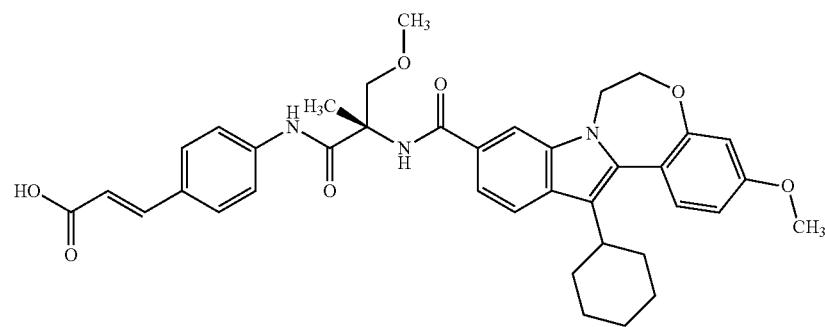 | 652.3 |
| 2-538 | 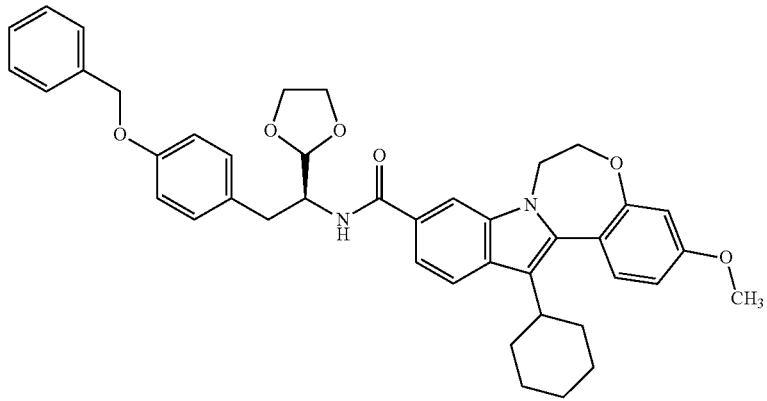 | 673.3 |
| 2-539 | 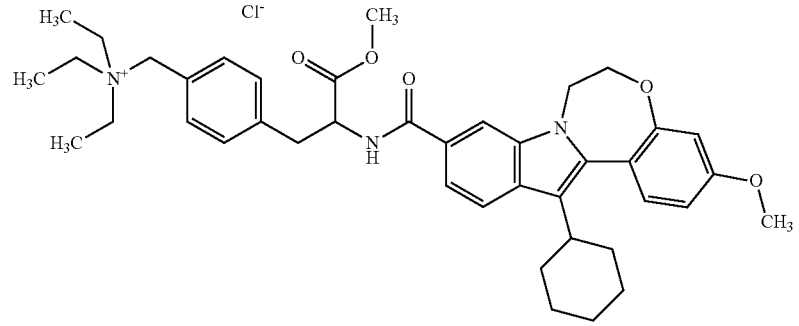 | 666.4 |

TABLE 265

| Ex. | formula | positive MS (M + 1)(free form) |
|---|---|---|
| 2-540 | | 619.3 |
| 2-541 | | 632.3 |
| 2-542 | | 683.3 |
| 2-543 | | 633.3 |
| 2-544 | | 647.3 |

TABLE 266
| Ex. | formula | positive MS (M + 1)(free form) |
|---|---|---|
| 2-545 | 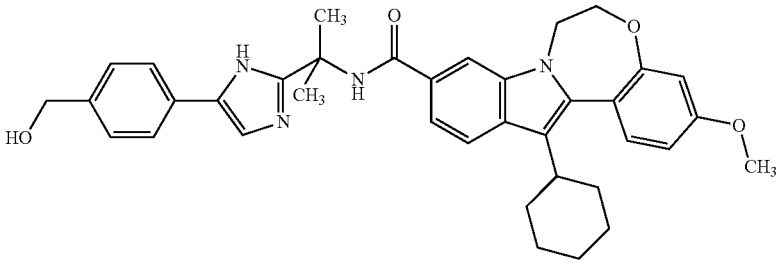 | 605.3 |
| 2-546 | 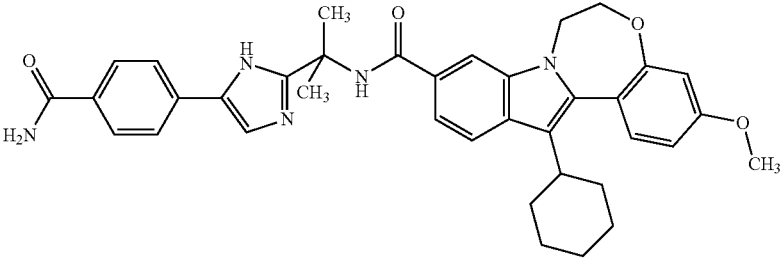 | 618.3 |
| 2-547 | 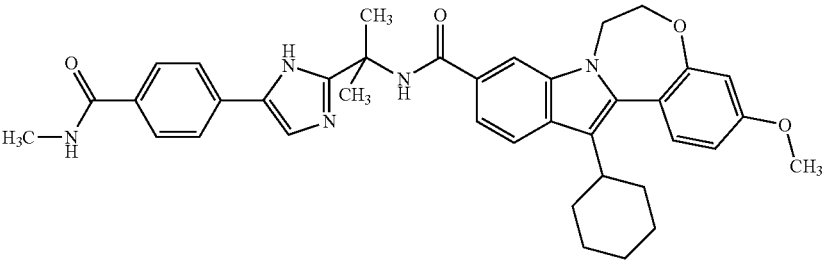 | 632.3 |
| 2-548 | 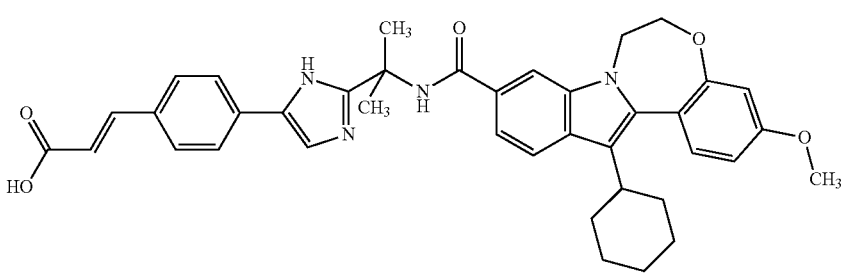 | 645.3 |
| 2-549 | 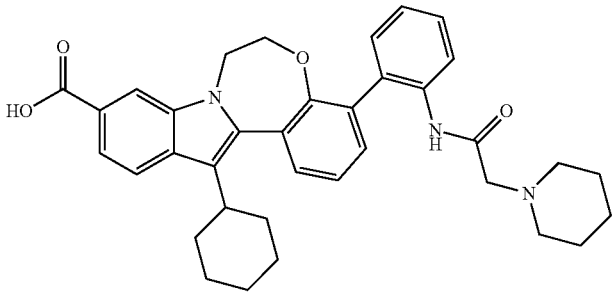 | 578.3 |

TABLE 267

| Ex. | formula | positive MS (M + 1)(free form) |
|---|---|---|
| 2-550 | | 634.3 |
| 2-551 | | 648.3 |
| 2-552 | | 678.3 |
| 2-553 | | 549.3 |
| 2-554 | | 564.3 |

TABLE 268

| Ex. | formula | positive MS (M + 1)(free form) |
|---|---|---|
| 2-555 | 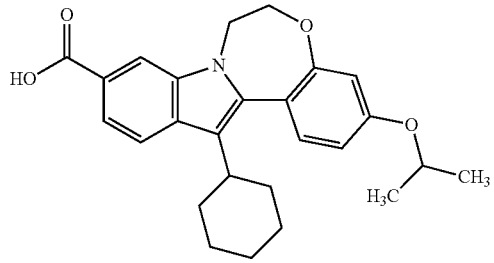 | 420.2 |
| 2-556 | 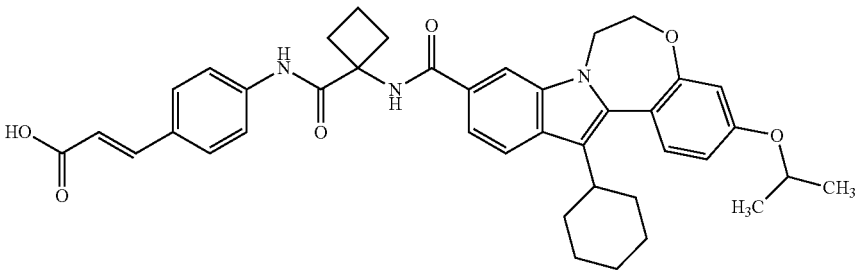 | 662.3 |

The evaluation of the HCV polymerase inhibitory activity of the compound of the present invention is explained in the following. This polymerase is an enzyme coded for by the non-structural protein region called NS5B on the genome RNA of HCV (EMBO J., 15:12-22, 1996).

Experimental Example [I]

i) Preparation of Enzyme (HCV Polymerase)

Using, as a template, a cDNA clone corresponding to the full length genome RNA of HCV BK strain obtained from the blood of a patient with hepatitis C, a region encoding NS5B (J Virol 1991 March, 65(3), 1105-13, 544 amino acids after deletion of 47 amino acids on the C-terminal) was amplified by PCR. The objective gene was prepared by adding a 6 His tag {base pair encoding 6 continuous histidine (His)} to the 3' end thereof and transformed to *Escherichia coli*. The *Escherichia coli* capable of producing the objective protein was cultured. The obtained cells were suspended in a buffer solution and crushed in a microfluidizer. The supernatant was obtained by centrifugation and applied to various column chromatographys {mono-S, Sephacryl S-200 (Pharmacia)}, inclusive of metal chelate chromatography, to give a standard enzyme product.

ii) Synthesis of Substrate RNA

Using a synthetic primer designed based on the sequence of HCV genomic 3' untranslated region, a DNA fragment (148 bp) containing polyU and 3'X sequence was entirely synthesized and cloned into plasmid pBluescript SK II(+) (Stratagene). The cDNA encoding full length NS5B, which was prepared in i) above, was digested with restriction enzyme KpnI to give a cDNA fragment containing the nucleotide sequence of from the restriction enzyme cleavage site to the termination codon. This cDNA fragment was inserted into the upstream of 3' untranslated region of the DNA in pBluescript SK II(+) and ligated. The about 450 bp inserted DNA sequence was used as a template in the preparation of substrate RNA. This plasmid was cleaved immediately after the 3'X sequence, linearized and purified by phenol-chloroform treatment and ethanol precipitation to give DNA.

RNA was synthesized (37° C., 3 hr) by run-off method using this purified DNA as a template, a promoter of pBluescript SK II(+), MEGAscript RNA synthesis kit (Ambion) and T7 RNA polymerase. DNase I was added and the mixture was incubated for 1 hr. The template DNA was removed by decomposition to give a crude RNA product. This crude product was treated with phenol-chloroform and purified by ethanol precipitation to give the objective substrate RNA.

This RNA was applied to formaldehyde denaturation agarose gel electrophoresis to confirm the quality thereof and preserved at −80° C.

iii) Assay of Enzyme (HCV Polymerase) Inhibitory Activity

A test substance (compound of the present invention) and a reaction mixture (30 µl) having the following composition were reacted at 25° C. for 90 min.

10% Trichloroacetic acid at 4° C. and 1% sodium pyrophosphate solution (150 µl) were added to this reaction mixture to stop the reaction. The reaction mixture was left standing in ice for 15 min to insolubilize RNA. This RNA was trapped on a glass filter (Whatman GF/C and the like) upon filtration by suction. This filter was washed with a solution containing 1% trichloroacetic acid and 0.1% sodium pyrophosphate, washed with 90% ethanol and dried. A liquid scintillation cocktail (Packard) was added and the radioactivity of RNA synthesized by the enzyme reaction was measured on a liquid scintillation counter.

The HCV polymerase inhibitory activity ($IC_{50}$) of the compound of the present invention was calculated from the values of radioactivity of the enzyme reaction with and without the test substance.

The results are shown in Tables 269-293.

As the compound of the present invention, preferred is a compound showing less than 1 μM of HCV polymerase inhibitory activity ($IC_{50}$), more preferred is a compound showing less than 0.1 μM of HCV polymerase inhibitory activity ($IC_{50}$), and still more preferred is a compound showing less than 0.01 μM of HCV polymerase inhibitory activity ($IC_{50}$).

Reaction mixture: HCV polymerase (0.5 μg/ml) obtained in 1), substrate RNA (5 μg/ml) obtained in ii), ATP (50 μM), GTP (50 μM), CTP (50 μM), UTP (2 μM), [5,6-$^3$H]UTP (46 Ci/mmol (Armersham), 1 μCi) 20 mM Tris-HCl (pH 7.5), EDTA (1 mM), $MgCl_2$ (5 mM), NaCl (50 mM), DTT (1 mM), BSA (0.01%)

TABLE 269

| Example No. | HCV polymerase inhibitory activity $IC_{50}$ | Example No. | HCV polymerase inhibitory activity $IC_{50}$ |
|---|---|---|---|
| 1-3 | B | 1-7 | B |
| 1-9 | B | 1-14 | B |
| 1-18 | B | 1-19 | A |
| 1-20 | B | 1-21 | B |
| 1-22 | B | 1-23 | B |
| 1-24 | B | 1-25 | B |
| 1-26 | B | 1-27 | B |
| 1-28 | B | 1-29 | B |
| 1-30 | B | 1-31 | A |
| 1-32 | B | 1-33 | B |
| 1-34 | B | 1-35 | B |
| 1-36 | B | 1-37 | B |
| 1-38 | B | 1-39 | B |
| 1-40 | B | 1-41 | B |
| 1-42 | B | 1-43 | B |
| 1-44 | B | 1-45 | B |
| 1-46 | B | 1-47 | B |
| 1-48 | B | 1-49 | B |
| 1-50 | B | 1-51 | B |
| 1-52 | B | 1-53 | B |
| 1-54 | B | 1-55 | B |

TABLE 270

| Example No. | HCV polymerase inhibitory activity $IC_{50}$ | Example No. | HCV polymerase inhibitory activity $IC_{50}$ |
|---|---|---|---|
| 1-56 | B | 1-57 | B |
| 1-60 | B | 1-61 | B |
| 1-62 | B | 1-63 | B |
| 1-64 | B | 1-65 | B |
| 1-66 | B | 1-67 | B |
| 1-68 | B | 1-69 | B |
| 1-70 | B | 1-71 | B |
| 1-72 | B | 1-73 | B |
| 1-74 | B | 1-75 | B |
| 1-76 | B | 1-77 | B |
| 1-78 | B | 1-79 | B |
| 1-80 | B | 1-81 | B |
| 1-82 | B | 1-83 | B |
| 1-84 | B | 1-85 | B |
| 1-86 | A | 1-87 | B |
| 1-88 | B | 1-89 | B |
| 1-90 | B | 1-91 | B |
| 1-92 | B | 1-93 | B |
| 1-94 | B | 1-95 | B |
| 2-3 | B | 2-4 | B |
| 2-5 | B | 2-6 | A |

TABLE 271

| Example No. | HCV polymerase inhibitory activity $IC_{50}$ | Example No. | HCV polymerase inhibitory activity $IC_{50}$ |
|---|---|---|---|
| 2-9 | B | 2-10 | B |
| 2-11 | B | 2-12 | B |
| 2-13 | B | 2-14 | B |
| 2-15 | B | 2-16 | B |
| 2-17 | B | 2-18 | B |
| 2-19 | B | 2-20 | B |
| 2-21 | B | 2-22 | B |
| 2-23 | B | 2-24 | B |
| 2-25 | B | 2-26 | B |
| 2-27 | B | 2-28 | B |
| 2-29 | B | 2-30 | B |
| 2-31 | B | 3-4 | B |
| 4-2 | A | 5-2 | B |
| 5-3 | A | 6-2 | A |
| 7-4 | B | 7-5 | B |
| 7-6 | B | 7-7 | B |
| 8-4 | B | 9-2 | B |
| 9-3 | B | 9-4 | B |

TABLE 272

| Example No. | HCV polymerase inhibitory activity $IC_{50}$ | Example No. | HCV polymerase inhibitory activity $IC_{50}$ |
|---|---|---|---|
| 1-96 | B | 1-97 | B |
| 1-98 | B | 1-99 | B |
| 1-100 | B | 1-101 | B |
| 1-102 | B | 1-103 | B |
| 1-104 | B | 1-105 | B |
| 1-106 | B | 1-107 | B |
| 1-108 | B | 1-109 | B |
| 1-110 | B | 1-111 | B |
| 1-112 | B | 1-113 | B |
| 1-114 | B | 1-115 | B |
| 1-116 | B | 1-117 | B |
| 1-118 | B | 1-119 | B |
| 1-120 | B | 1-121 | B |
| 1-122 | B | 1-123 | B |
| 1-124 | B | 1-125 | B |
| 1-126 | B | 1-129 | B |
| 1-130 | B | 1-131 | B |
| 1-132 | B | 1-133 | B |
| 1-134 | B | 1-135 | B |
| 1-136 | B | 1-137 | B |
| 1-138 | B | 1-139 | B |

Table 273

| Example No. | HCV polymerase inhibitory activity $IC_{50}$ | Example No | HCV polymerase inhibitory activity $IC_{50}$ |
|---|---|---|---|
| 1-140 | B | 1-141 | B |
| 1-142 | B | 1-143 | B |
| 1-144 | B | 1-145 | B |
| 1-146 | B | 1-147 | B |
| 1-148 | B | 1-149 | B |
| 1-150 | B | 1-151 | B |
| 1-152 | B | 1-153 | B |
| 1-154 | B | 1-155 | B |
| 1-156 | B | 1-157 | B |
| 1-158 | A | 1-159 | B |
| 1-160 | B | 1-161 | B |
| 1-162 | B | 1-163 | B |
| 1-164 | B | 1-165 | B |
| 1-166 | B | 1-167 | A |
| 1-168 | B | 1-169 | B |
| 1-170 | B | 1-171 | B |
| 1-172 | B | 1-173 | B |
| 1-174 | B | 1-175 | B |

Table 273-continued

| Example No. | HCV polymerase inhibitory activity IC$_{50}$ | Example No | HCV polymerase inhibitory activity IC$_{50}$ |
|---|---|---|---|
| 1-176 | B | 1-177 | B |
| 1-178 | B | 1-179 | B |
| 1-180 | B | 1-181 | B |

TABLE 274

| Example No. | HCV polymerase inhibitory activity IC$_{50}$ | Example No. | CV polymerase inhibitory activity IC$_{50}$ |
|---|---|---|---|
| 1-182 | B | 1-183 | B |
| 1-184 | B | 1-185 | B |
| 1-186 | B | 1-187 | B |
| 1-188 | B | 1-189 | B |
| 1-190 | B | 1-191 | A |
| 1-192 | B | 1-193 | B |
| 1-194 | B | 1-195 | B |
| 1-196 | B | 1-197 | B |
| 1-198 | B | 1-199 | B |
| 1-200 | B | 1-201 | B |
| 1-202 | B | 1-203 | B |
| 1-204 | B | 1-205 | B |
| 1-206 | B | 1-207 | B |
| 1-208 | B | 1-209 | B |
| 1-210 | B | 1-211 | B |
| 1-212 | B | 1-213 | B |
| 1-214 | B | 1-215 | B |
| 1-216 | B | 1-217 | B |
| 1-218 | B | 1-219 | B |
| 1-220 | B | 1-221 | B |
| 1-222 | B | 1-223 | B |

TABLE 275

| Example No. | HCV polymerase inhibitory activity IC$_{50}$ | Example No. | HCV polymerase inhibitory activity IC$_{50}$ |
|---|---|---|---|
| 1-224 | B | 1-225 | B |
| 1-226 | B | 1-227 | B |
| 1-228 | B | 1-229 | B |
| 1-230 | B | 1-231 | B |
| 1-232 | B | 1-233 | B |
| 1-234 | B | 1-235 | B |
| 1-236 | B | 1-237 | B |
| 1-238 | B | 1-239 | B |
| 1-240 | B | 1-241 | B |
| 1-242 | B | 1-243 | B |
| 1-244 | B | 1-245 | B |
| 1-246 | B | 1-247 | B |
| 1-248 | B | 1-249 | B |
| 1-250 | B | 1-251 | B |
| 1-252 | B | 1-253 | B |
| 1-254 | B | 1-255 | B |
| 1-256 | B | 1-257 | B |
| 1-258 | B | 1-259 | B |
| 1-260 | B | 1-261 | B |
| 1-262 | B | 1-263 | B |
| 1-264 | B | 1-265 | B |

TABLE 276

| Example No. | HCV polymerase inhibitory activity IC$_{50}$ | Example No. | HCV polymerase inhibitory activity IC$_{50}$ |
|---|---|---|---|
| 1-266 | B | 1-267 | B |
| 1-268 | B | 1-269 | B |
| 1-270 | B | 1-271 | B |

TABLE 276-continued

| Example No. | HCV polymerase inhibitory activity IC$_{50}$ | Example No. | HCV polymerase inhibitory activity IC$_{50}$ |
|---|---|---|---|
| 1-272 | B | 1-273 | B |
| 1-274 | B | 1-275 | B |
| 1-276 | B | 1-277 | B |
| 1-278 | B | 1-279 | B |
| 1-280 | B | 1-281 | B |
| 1-282 | B | 1-283 | B |
| 1-284 | B | 1-285 | B |
| 1-286 | B | 1-287 | B |
| 1-288 | B | 1-289 | B |
| 1-290 | B | 1-291 | B |
| 1-292 | B | 1-293 | B |
| 1-294 | B | 1-295 | B |
| 1-296 | B | 1-297 | B |
| 1-298 | B | 1-299 | B |
| 1-300 | B | 1-301 | B |
| 1-302 | B | 1-303 | B |
| 1-304 | B | 1-305 | B |
| 1-306 | B | 1-307 | B |

TABLE 277

| Example No. | HCV polymerase inhibitory activity IC$_{50}$ | Example No. | HCV polymerase inhibitory activity IC$_{50}$ |
|---|---|---|---|
| 1-308 | B | 1-309 | B |
| 1-310 | B | 1-311 | B |
| 1-312 | B | 1-314 | B |
| 1-315 | B | 1-316 | B |
| 1-317 | B | 1-318 | B |
| 1-319 | B | 1-320 | B |
| 1-321 | B | 1-322 | B |
| 1-323 | B | 1-324 | B |
| 1-325 | B | 1-326 | B |
| 1-327 | B | 1-328 | B |
| 1-329 | B | 1-330 | B |
| 1-331 | B | 1-332 | B |
| 1-333 | B | 1-334 | B |
| 1-335 | B | 1-336 | B |
| 1-337 | B | 1-338 | B |
| 1-339 | B | 1-340 | B |
| 1-341 | B | 1-342 | B |
| 1-343 | B | 1-344 | B |
| 1-345 | B | 1-346 | B |
| 1-347 | B | 1-348 | B |
| 1-349 | B | 1-350 | B |

TABLE 278

| Example No. | HCV polymerase inhibitory activity IC$_{50}$ | Example No. | HCV polymerase inhibitory activity IC$_{50}$ |
|---|---|---|---|
| 1-351 | B | 1-352 | B |
| 1-353 | B | 1-354 | B |
| 1-355 | B | 1-356 | B |
| 1-357 | B | 1-358 | B |
| 1-359 | B | 1-360 | B |
| 1-361 | B | 1-362 | B |
| 1-363 | B | 1-364 | B |
| 1-365 | B | 1-366 | B |
| 1-367 | B | 1-368 | B |
| 1-369 | B | 1-370 | B |
| 1-371 | B | 1-372 | B |
| 1-373 | B | 1-374 | B |
| 1-375 | B | 1-376 | B |
| 1-377 | B | 1-378 | B |
| 1-379 | B | 1-380 | B |
| 1-381 | B | 1-382 | B |
| 1-383 | B | 1-384 | B |
| 1-385 | B | 1-386 | B |

TABLE 278-continued

| Example No. | HCV polymerase inhibitory activity IC$_{50}$ | Example No. | HCV polymerase inhibitory activity IC$_{50}$ |
|---|---|---|---|
| 1-387 | B | 1-388 | B |
| 1-389 | B | 1-390 | B |
| 1-391 | B | 1-392 | B |

TABLE 279

| Example No. | HCV polymerase inhibitory activity IC$_{50}$ | Example No. | HCV polymerase inhibitory activity IC$_{50}$ |
|---|---|---|---|
| 1-393 | B | 1-394 | B |
| 1-395 | B | 1-396 | B |
| 1-397 | B | 1-398 | B |
| 1-399 | B | 1-400 | B |
| 1-401 | B | 1-402 | B |
| 1-403 | B | 1-404 | B |
| 1-405 | B | 1-406 | B |
| 1-407 | B | 1-408 | B |
| 1-409 | B | 1-410 | B |
| 1-411 | B | 1-412 | B |
| 1-413 | B | 1-414 | B |
| 1-415 | B | 1-416 | B |
| 1-417 | B | 1-418 | B |
| 1-419 | B | 1-420 | B |
| 1-421 | B | 1-422 | B |
| 1-423 | B | 1-424 | B |
| 1-425 | B | 1-426 | B |
| 1-427 | B | 1-428 | B |
| 1-429 | B | 1-430 | B |
| 1-431 | B | 1-432 | B |
| 1-433 | B | 1-434 | B |

TABLE 280

| Example No. | HCV polymerase inhibitory activity IC$_{50}$ | Example No. | HCV polymerase inhibitory activity IC$_{50}$ |
|---|---|---|---|
| 1-435 | B | 1-436 | B |
| 1-437 | B | 1-438 | B |
| 1-439 | B | 1-440 | B |
| 1-441 | B | 1-442 | B |
| 1-443 | B | 1-444 | B |
| 1-445 | B | | |
| 2-32 | B | 2-33 | B |
| 2-34 | B | 2-35 | B |
| 2-36 | B | 2-37 | B |
| 2-38 | B | 2-39 | B |
| 2-40 | B | 2-41 | B |
| 2-42 | B | 2-43 | B |
| 2-44 | B | 2-45 | B |
| 2-46 | B | 2-47 | B |
| 2-48 | B | 2-49 | B |
| 2-50 | B | 2-51 | B |
| 2-52 | B | 2-53 | B |
| 7-8 | B | 8-5 | B |
| 8-6 | B | 8-7 | B |
| 10-1 | B | 10-2 | A |
| 10-3 | B | 10-4 | A |

TABLE 281

| Example. No. | HCV polymerase inhibitory activity IC$_{50}$ | Example No. | HCV polymerase inhibitory activity IC$_{50}$ |
|---|---|---|---|
| 1-450 | B. | 2-155 | B |
| 1-451 | B | 2-156 | B |
| 1-452 | B | 2-157 | A |

TABLE 281-continued

| Example. No. | HCV polymerase inhibitory activity IC$_{50}$ | Example No. | HCV polymerase inhibitory activity IC$_{50}$ |
|---|---|---|---|
| 1-473 | B | 2-158 | B |
| 1-474 | B | 2-159 | A |
| 1-475 | B | 2-160 | B |
| 1-476 | B | 2-161 | B |
| 1-477 | B | 2-162 | B |
| 1-478 | B | 2-163 | B |
| 1-479 | B | 2-164 | A |
| 1-480 | B | 2-165 | A |
| 1-481 | B | 2-166 | B |
| 1-482 | B | 2-167 | B |
| 1-483 | B | 2-168 | B |
| 1-484 | B | 2-169 | B |
| 2-54 | B | 2-170 | B |
| 2-55 | B | 2-171 | B |
| 2-151 | B | 2-172 | B |
| 2-152 | B | 2-173 | B |
| 2-153 | B | 2-174 | B |
| 2-154 | A | 2-175 | B |

TABLE 282

| Example No. | HCV polymerase inhibitory activity IC50 | Example No. | HCV polymerase inhibitory activity IC50 |
|---|---|---|---|
| 2-176 | B | 2-197 | B |
| 2-177 | B | 2-198 | B |
| 2-178 | B | 2-199 | B |
| 2-179 | A | 2-200 | B |
| 2-180 | B | 2-201 | B |
| 2-181 | B | 2-202 | B |
| 2-182 | B | 2-203 | B |
| 2-183 | B | 2-204 | B |
| 2-184 | B | 2-205 | B |
| 2-185 | A | 2-206 | A |
| 2-186 | A | 2-207 | B |
| 2-187 | A | 2-208 | A |
| 2-188 | A | 2-209 | B |
| 2-189 | A | 2-210 | B |
| 2-190 | B | 2-211 | A |
| 2-191 | B | 2-212 | A |
| 2-192 | B | 2-213 | B |
| 2-193 | B | 2-214 | B |
| 2-194 | B | 2-216 | A |
| 2-195 | B | 2-217 | B |
| 2-196 | B | 2-218 | B |

TABLE 283

| Example No. | HCV polymerase inhibitory activity IC$_{50}$ | Example No. | HCV polymerase inhibitory activity IC$_{50}$ |
|---|---|---|---|
| 2-219 | A | 2-240 | B |
| 2-220 | A | 2-241 | B |
| 2-221 | B | 2-242 | B |
| 2-222 | B | 2-243 | B |
| 2-223 | B | 2-244 | A |
| 2-224 | B | 2-245 | B |
| 2-225 | B | 2-246 | B |
| 2-226 | B | 2-247 | B |
| 2-227 | B | 2-248 | B |
| 2-228 | B | 2-249 | B |
| 2-229 | B | 2-250 | B |
| 2-230 | B | 2-251 | B |
| 2-231 | B | 2-252 | B |
| 2-232 | B | 2-253 | B |
| 2-233 | B | 2-254 | A |
| 2-234 | A | 2-255 | B |
| 2-235 | B | 2-256 | B |
| 2-236 | B | 2-257 | B |

TABLE 283-continued

| Example No. | HCV polymerase inhibitory activity IC$_{50}$ | Example No. | HCV polymerase inhibitory activity IC$_{50}$ |
|---|---|---|---|
| 2-237 | B | 2-258 | B |
| 2-238 | B | 2-259 | B |
| 2-239 | A | 2-260 | B |

TABLE 284

| Example No. | HCV polymerase inhibitory activity IC$_{50}$ | Example No. | HCV polymerase inhibitory activity IC$_{50}$ |
|---|---|---|---|
| 2-261 | B | 2-282 | B |
| 2-262 | B | 2-283 | B |
| 2-263 | B | 2-284 | B |
| 2-264 | B | 2-285 | B |
| 2-265 | A | 2-286 | A |
| 2-266 | A | 2-287 | A |
| 2-267 | A | 2-288 | B |
| 2-268 | A | 2-289 | B |
| 2-269 | B | 2-290 | A |
| 2-270 | B | 2-291 | B |
| 2-271 | B | 2-292 | A |
| 2-272 | B | 2-293 | A |
| 2-273 | B | 2-294 | B |
| 2-274 | B | 2-295 | B |
| 2-275 | B | 2-296 | B |
| 2-276 | B | 2-297 | B |
| 2-277 | B | 2-298 | B |
| 2-278 | B | 2-299 | B |
| 2-279 | B | 2-300 | B |
| 2-280 | B | 2-301 | B |
| 2-281 | A | 2-302 | B |

TABLE 285

| Example No. | HCV polymerase inhibitory activity IC$_{50}$ | Example No. | HCV polymerase inhibitory activity IC$_{50}$ |
|---|---|---|---|
| 2-303 | B | 2-324 | B |
| 2-304 | B | 2-325 | B |
| 2-305 | B | 2-326 | B |
| 2-306 | B | 2-327 | B |
| 2-307 | B | 2-328 | B |
| 2-308 | B | 2-329 | B |
| 2-309 | A | 2-330 | B |
| 2-310 | B | 2-331 | B |
| 2-311 | B | 2-332 | B |
| 2-312 | B | 2-333 | B |
| 2-313 | B | 2-334 | B |
| 2-314 | B | 2-335 | B |
| 2-315 | B | 2-336 | B |
| 2-316 | B | 2-337 | B |
| 2-317 | B | 2-338 | B |
| 2-318 | B | 2-339 | B |
| 2-319 | B | 2-340 | B |
| 2-320 | B | 2-341 | B |
| 2-321 | B | 2-342 | B |
| 2-322 | B | 2-343 | B |
| 2-323 | B | 2-344 | B |

TABLE 286

| Example No. | HCV polymerase inhibitory activity IC$_{50}$ | Example No. | HCV polymerase inhibitory activity IC$_{50}$ |
|---|---|---|---|
| 2-345 | B | 2-366 | B |
| 2-346 | B | 2-367 | B |
| 2-347 | B | 2-368 | B |

TABLE 286-continued

| Example No. | HCV polymerase inhibitory activity IC$_{50}$ | Example No. | HCV polymerase inhibitory activity IC$_{50}$ |
|---|---|---|---|
| 2-348 | B | 2-369 | B |
| 2-349 | B | 2-370 | B |
| 2-350 | B | 2-371 | B |
| 2-351 | B | 2-372 | B |
| 2-352 | B | 2-373 | B |
| 2-353 | B | 2-374 | B |
| 2-354 | B | 2-375 | B |
| 2-355 | B | 2-376 | B |
| 2-356 | B | 2-377 | B |
| 2-357 | B | 2-378 | B |
| 2-358 | B | 2-379 | A |
| 2-359 | B | 2-380 | B |
| 2-360 | B | 2-381 | B |
| 2-361 | B | 2-382 | B |
| 2-362 | B | 2-383 | B |
| 2-363 | B | 2-384 | B |
| 2-364 | B | 2-385 | B |
| 2-365 | B | 2-386 | B |

TABLE 287

| Example No. | HCV polymerase inhibitory activity IC$_{50}$ | Example No. | HCV polymerase inhibitory activity IC$_{50}$ |
|---|---|---|---|
| 2-387 | B | 2-408 | B |
| 2-388 | B | 2-409 | B |
| 2-389 | B | 2-410 | B |
| 2-390 | B | 2-411 | B |
| 2-391 | B | 2-412 | B |
| 2-392 | B | 2-413 | B |
| 2-393 | B | 2-414 | B |
| 2-394 | B | 2-415 | B |
| 2-395 | B | 2-416 | B |
| 2-396 | B | 2-417 | B |
| 2-397 | B | 2-418 | B |
| 2-398 | B | 2-419 | B |
| 2-399 | B | 2-420 | B |
| 2-400 | B | 2-421 | B |
| 2-401 | B | 2-422 | B |
| 2-402 | B | 2-423 | B |
| 2-403 | B | 2-424 | B |
| 2-404 | B | 2-425 | B |
| 2-405 | B | 2-426 | B |
| 2-406 | B | 2-427 | B |
| 2-407 | B | 2-428 | B |

TABLE 288

| Example No. | HCV polymerase inhibitory activity IC$_{50}$ | Example No. | HCV polymerase inhibitory activity IC$_{50}$ |
|---|---|---|---|
| 2-429 | B | 2-443 | B |
| 2-430 | B | 2-444 | B |
| 2-431 | B | 2-445 | B |
| 2-432 | B | 2-446 | B |
| 2-433 | B | 2-447 | B |
| 2-434 | B | 2-448 | B |
| 2-435 | B | 2-449 | B |
| 2-436 | B | 2-450 | B |
| 2-437 | B | 2-451 | B |
| 2-438 | B | 2-452 | B |
| 2-439 | B | 2-453 | B |
| 2-440 | B | 2-454 | B |
| 2-441 | B | 2-455 | B |
| 2-442 | B | | |

TABLE 289

| Example No. | HCV polymerase inhibitory activity IC$_{50}$ | Example No. | HCV polymerase inhibitory activity IC$_{50}$ |
|---|---|---|---|
| 1-485 | B | 1-507 | A |
| 1-486 | B | 1-508 | B |
| 1-487 | B | 1-509 | B |
| 1-488 | B | 1-510 | B |
| 1-489 | B | 1-511 | B |
| 1-490 | B | 1-512 | B |
| 1-491 | B | 1-513 | B |
| 1-492 | B | 1-514 | B |
| 1-493 | B | 1-515 | B |
| 1-494 | B | 1-517 | A |
| 1-495 | B | 1-518 | B |
| 1-496 | B | 1-519 | B |
| 1-497 | B | 1-520 | B |
| 1-498 | B | 1-521 | B |
| 1-499 | B | 1-522 | B |
| 1-500 | B | 1-523 | B |
| 1-501 | B | 1-524 | B |
| 1-502 | B | 1-525 | B |
| 1-503 | B | 1-526 | B |
| 1-504 | B | 1-527 | B |
| 1-506 | A | 1-528 | B |

TABLE 290

| Example No. | HCV polymerase inhibitory activity IC$_{50}$ | Example No. | HCV polymerase inhibitory activity IC$_{50}$ |
|---|---|---|---|
| 1-529 | B | 1-550 | B |
| 1-530 | B | 1-551 | B |
| 1-531 | B | 1-552 | B |
| 1-532 | B | 1-553 | B |
| 1-533 | B | 1-554 | B |
| 1-534 | B | 1-555 | B |
| 1-535 | B | 1-556 | B |
| 1-536 | B | 1-557 | B |
| 1-537 | B | 1-558 | A |
| 1-538 | B | 1-559 | B |
| 1-539 | B | 1-560 | B |
| 1-540 | B | 1-561 | B |
| 1-541 | B | 1-562 | B |
| 1-542 | B | 1-563 | B |
| 1-543 | B | 1-564 | B |
| 1-544 | B | 1-565 | B |
| 1-545 | B | 1-566 | B |
| 1-546 | B | 1-567 | B |
| 1-547 | B | 1-568 | B |
| 1-548 | B | 1-569 | A |
| 1-549 | B | 1-570 | B |

TABLE 291

| Example No. | HCV polymerase inhibitory activity IC$_{50}$ | Example No. | HCV polymerase inhibitory activity IC$_{50}$ |
|---|---|---|---|
| 1-571 | B | 1-592 | B |
| 1-572 | B | 1-593 | B |
| 1-573 | B | 1-594 | B |
| 1-574 | B | 1-595 | B |
| 1-575 | B | 2-456 | B |
| 1-576 | B | 2-457 | B |
| 1-577 | B | 2-458 | B |
| 1-578 | B | 2-459 | B |
| 1-579 | B | 2-460 | B |
| 1-580 | B | 2-461 | B |
| 1-581 | B | 2-462 | B |
| 1-582 | B | 2-463 | B |
| 1-583 | A | 2-464 | B |
| 1-584 | B | 2-465 | B |
| 1-585 | B | 2-466 | B |
| 1-586 | B | 2-467 | B |
| 1-587 | B | 2-468 | B |
| 1-588 | B | 2-469 | B |
| 1-589 | B | 2-470 | B |
| 1-590 | B | 2-471 | B |
| 1-591 | B | 2-472 | B |

TABLE 292

| Example No. | HCV polymerase inhibitory activity IC$_{50}$ | Example No. | HCV polymerase inhibitory activity IC$_{50}$ |
|---|---|---|---|
| 2-473 | A | 12-2 | A |
| 2-474 | B | 1-615 | B |
| 2-475 | B | 1-616 | B |
| 2-476 | B | 1-617 | B |
| 2-477 | B | 1-618 | B |
| 2-478 | B | 1-619 | B |
| 2-479 | B | 1-620 | B |
| 2-480 | B | 1-621 | B |
| 2-481 | B | 1-622 | B |
| 2-482 | B | 1-623 | B |
| 2-483 | B | 2-523 | B |
| 2-484 | B | 2-524 | B |
| 2-485 | B | 2-525 | B |
| 2-486 | B | 2-526 | B |
| 5-4 | A | 2-527 | B |
| 7-9 | B | 2-528 | B |
| 7-10 | B | 2-529 | B |
| 8-8 | A | 2-530 | B |
| 8-9 | B | 2-531 | B |
| 11-1 | B | 2-532 | B |
| 12-1 | B | 2-533 | B |

TABLE 293

| Example No. | HCV polymerase inhibitory activity IC$_{50}$ | Example No. | HCV polymerase inhibitory activity IC$_{50}$ |
|---|---|---|---|
| 2-534 | B | 2-549 | |
| 2-535 | B | 2-550 | B |
| 2-536 | B | 2-551 | B |
| 2-537 | B | 2-552 | B |
| 2-538 | B | 2-553 | B |
| 2-539 | B | 2-554 | B |
| 2-540 | B | 2-555 | B |
| 2-541 | B | 2-556 | |
| 2-542 | B | 5-6 | A |
| 2-543 | B | 11-4 | B |
| 2-544 | B | 11-5 | B |
| 2-545 | B | 11-6 | B |
| 2-546 | B | 11-7 | B |
| 2-547 | B | 11-8 | B |
| 2-548 | B | | |

IC$_{50}$: A not less than 0.1 μM, less than 1 μM
B less than 0.1 μM

Experimental Example [II]

The test compound was dissolved in DMSO (dimethyl sulfoxide; final concentration 0.5%), and adjusted to a 10-fold concentration of the final concentration with a medium.

Replicon cells (Huh-5-2: manufactured by ReBLikon GmbH) were inoculated on a medium at $5 \times 10^3/90$ μl/well in a 96-well plate.

The medium was changed to a 4% HSA (human serum albumin)-containing medium (90 μl) the next day, and 10 μl of the above-mentioned adjusted product at each concentration was added.

At 48 hr later, luciferase activity was measured with Steady-Glo (manufactured by PROMEGA). The inhibitory rate relative to the control group (0.5% DMSO addition group) was calculated and $EC_{50}$ value was determined by proportional calculation, based on the data of two points across 50%, with the concentration of the compound taken as logarithm. Composition of medium: Dulbecco's modified Eagle's medium (DMEM), 10% fetal bovine serum (FBS), 2 mM L-glutamine, 0.1 mM MEM non-essential amino acid, 100 U/ml penicillin, 0.1 mg/ml streptomycin As in the test, one showing high replication inhibitory, or HCV polymerase inhibitory activity in the presence of a protein is one of the preferable embodiments.

As is evident from the above-mentioned results, the compound of the present invention shows a high inhibitory activity against HCV polymerase.

Therefore, the compound of the present invention can provide a pharmaceutical agent effective for the prophylaxis or treatment of hepatitis C, based on the anti-HCV effect afforded by the HCV polymerase inhibitory activity. When used concurrently with a different anti-HCV agent, such as interferon, and/or an anti-inflammatory agent and the like, it can provide a pharmaceutical agent more effective for the prophylaxis or treatment of hepatitis C. Its high inhibitory activity specific to HCV polymerase suggests the possibility of the compound being a pharmaceutical agent with slight side effects, which can be used safely for humans.

Formulation Example is given in the following. This example is merely for the purpose of exemplification and does not limit the invention.

Formulation Example

| | | |
|---|---|---|
| (a) compound of Example 1-9 | 10 g | |
| (b) lactose | 50 g | |
| (c) corn starch | 15 g | |
| (d) sodium carboxymethylcellulose | 44 g | |
| (e) magnesium stearate | 1 g | |

The entire amounts of (a), (b) and (c) and 30 g of (d) are kneaded with water, dried in vacuo and granulated. The obtained granules are mixed with 14 g of (d) and 1 g of (e) and processed into tablets with a tableting machine to give 1000 tablets each containing 10 mg of (a).

This application is based on a patent application Nos. 2004-48815, 2004-169190 and 2004-296390 filed in Japan, the contents of which are hereby incorporated by reference.

The invention claimed is:

1. A compound represented by the following formula [I] or a pharmaceutically acceptable salt thereof:

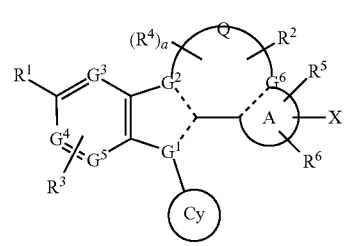

wherein

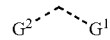

is N—C=C, $G^3$, $G^4$ and $G^5$ are each a carbon atom optionally substituted by $R^3$, Q is —$(CH_2)_c$-$Q^1$-$(CH_2)_d$—

(wherein c and d are each independently 0 or an integer of 1 to 4, $Q^1$ is (1') —O—, (2') —NH—, (3') —S—, (4') —CO—, (5') —SO—, or (6') —$SO_2$—), ring A is benzene, $G^6$ is a carbon atom, a broken line in ring A shows a single bond or a double bond, $R^1$ is (1) a carboxyl group, (2) a carboxylic acid equivalent, (3) —$CONR^{11}R^{12}$ (wherein $R^{11}$ and $R^{12}$ are each independently (1') a hydrogen atom, (2') a $C_{1-6}$ alkyl group optionally substituted by 1 to 3 substituents selected from the following group E, (3') a $C_{2-6}$ alkenyl group optionally substituted by 1 to 3 substituents selected from the following group E, (4') a $C_{6-14}$ aryl group optionally substituted by 1 to 5 substituents selected from the following group E, (5') a heterocyclic group optionally substituted by 1 to 5 substituents selected from the following group E (wherein said heterocyclic group comprises 1 to 4 heteroatoms selected from oxygen atom, nitrogen atom and sulfur atom), or (6') a $C_{3-10}$ cycloalkyl group optionally substituted by 1 to 5 substituents selected from the following group E), or (4) —$COOR^{103}$ (wherein $R^{103}$ is a group selected from the following group C or a glucuronic acid residue), $R^2$ may substitute at a substitutable position on carbon atom or nitrogen atom constituting Q and is (1) a hydrogen atom, (2) a group selected from the following group E, (3) a $C_{1-6}$ alkyl group optionally substituted by 1 to 3 substituents selected from the following group E, (4) a $C_{2-6}$ alkenyl group optionally substituted by 1 to 3 substituents selected from the following group E,

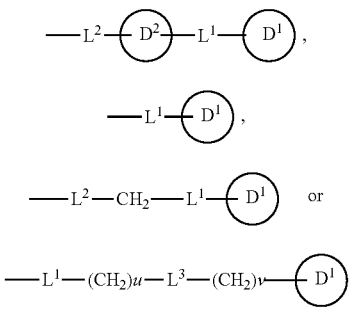

{wherein L¹ and L² are each independently
(1') a bond,
(2') $C_{1-6}$ alkylene,
(3') $C_{2-6}$ alkenylene,
(4') $-(CH_2)_{u1}-O-(CH_2)_{v1}-$,
(5') $-(CH_2)_{u1}-S-(CH_2)_{v1}-$,
(6') $-(CH_2)_{u1}-NR^{L1}-(CH_2)_{v1}-$,
(7') $-(CH_2)_{u1}-CO-(CH_2)_{v1}-$,
(8') $-(CH_2)_{u1}-CONR^{L2}-(CH_2)_{v1}-$,
(9') $-(CH_2)_{u1}-NR^{L2}CO_2-(CH_2)_{v1}-$,
(10') $-(CH_2)_{u1}-NR^{L2}CONR^{L3}-(CH_2)_{v1}-$,
(11') $-(CH_2)_{u1}-NR^{L2}CO-(CH_2)_{v1}-$,
(12') $-(CH_2)_{u1}-NR^{L2}SO_2-(CH_2)_{v1}-$,
(13') $-(CH_2)_{u1}-SO_2-(CH_2)_{v1}-$, or
(14') $-(CH_2)_{u1}-SO_2NR^{L2}-(CH_2)_{v1}-$
(wherein u, v, u1 and v1 are each independently 0 or an integer of 1 to 6,
$R^{L1}$ is
(1'') a hydrogen atom,
(2'') a group selected from the following group C,
(3'') $-COR^{L11}$,
(4'') $-CONR^{L11}R^{L12}$,
(5'') $-COOR^{L11}$ or
(6'') $-SO_2R^{L13}$
(wherein $R^{L11}$ and $R^{L12}$ are each independently a hydrogen atom or a group selected from the following group C, and $R^{L13}$ is a group selected from the following group C),
$R^{L2}$ and $R^{L3}$ are each independently
(1'') a hydrogen atom,
(2'') a group selected from the following group C,
(3'') $-COR^{L11}$ or
(4'') $-SO_2R^{L13}$
(wherein $R^{L11}$ and $R^{L13}$ are as defined above)),
$L^3$ is
(1') $-CHR^{L14}-$ or
(2') $-NR^{L14}-$
(wherein $R^{L14}$ is a group selected from the following group F),
ring $D^1$ and ring $D^2$ are each independently
(1') a $C_{6-14}$ aryl group optionally substituted by 1 to 5 substituents selected from the following group E,
(2') a $C_{3-10}$ cycloalkyl group optionally substituted by 1 to 5 substituents selected from the following group E or
(3') a heterocyclic group optionally substituted by 1 to 5 substituents selected from the following group E
(wherein said heterocyclic group comprises 1 to 4 heteroatoms selected from oxygen atom, nitrogen atom and sulfur atom)},
$R^3$ is
(1) a hydrogen atom,
(2) a halogen atom,
(3) a $C_{1-6}$ alkanoyl group,
(4) a carboxyl group,
(5) a cyano group,
(6) a nitro group,
(7) a $C_{1-6}$ alkyl group optionally substituted by 1 to 3 substituents selected from the following group A,
(8) $-OR^{101}$
(wherein $R^{101}$ is a hydrogen atom or a group selected from the following group C),
(9) $-NR^{102}R^{119}$
(wherein $R^{102}$ and $R^{119}$ are each independently a hydrogen atom, a $C_{1-6}$ alkanoyl group or a $C_{1-6}$ alkylsulfonyl group),
(10) $-COOR^{103}$
(wherein $R^{103}$ is a group selected from the following group C or a glucuronic acid residue),
(11) $-CONR^{104}R^{105}$
(wherein $R^{104}$ and $R^{105}$ are each independently a hydrogen atom, a hydroxyl group, a cyano group, a $C_{1-6}$ alkoxy group or a $C_{1-6}$ alkyl group optionally substituted by 1 to 3 substituents selected from the following group A),
(12) $-SO_2R^{106}$
(wherein $R^{106}$ is a hydroxyl group, an amino group, a $C_{1-6}$ alkyl group or a $C_{1-6}$ alkylamino group),
(13) $-NHCOR^{107}$
(wherein $R^{107}$ is an amino group or a $C_{1-6}$ alkylamino group),
(14) $-C(=NR^{108})-NH_2$
(wherein $R^{108}$ is a hydrogen atom, a $C_{1-6}$ alkyl group optionally substituted by 1 to 3 substituents selected from the following group A, a hydroxyl group or a $C_{1-6}$ alkoxy group),
(15) $-P(=O)(OR^{109})_2$
(wherein $R^{109}$ are each independently a hydrogen atom or a group selected from the following group C),
(16) $-P(=O)(OR^{110})NR^{111}R^{112}$
(wherein $R^{110}$, $R^{111}$ and $R^{112}$ are each independently a hydrogen atom or a group selected from the following group C),
(17) $-CONHCO-R^{113}$
(wherein $R^{113}$ is a group selected from the following group C),
(18) $-CONHSO_2-R^{114}$
(wherein $R^{114}$ is a group selected from the following group C),
(19) $-SO_2NHCO-R^{115}$
(wherein $R^{115}$ is a group selected from the following group C) or
(20) a heterocyclic group optionally substituted by 1 to 5 substituents selected from the following group B (wherein said heterocyclic group comprises 1 to 4 heteroatoms selected from oxygen atom, nitrogen atom and sulfur atom),
$R^4$ may substitute at a substitutable position on carbon atom or nitrogen atom constituting Q and each is independently
(1) a halogen atom,
(2) a $C_{1-6}$ alkyl group optionally substituted by 1 to 3 substituents selected from the following group A,
(3) $-OR^{116}$
(wherein $R^{116}$ is a hydrogen atom or a group selected from the following group C),
(4) $-NR^{117}R^{118}$
(wherein $R^{117}$ and $R^{118}$ are each independently a hydrogen atom, a $C_{1-6}$ alkanoyl group or a group selected from the following group C), (5) a $C_{6-14}$ aryl group optionally substituted by 1 to 5 substituents selected from the following group B or
(6) a heterocyclic group optionally substituted by 1 to 5 substituents selected from the following group B
(wherein said heterocyclic group comprises 1 to 4 heteroatoms selected from oxygen atom, nitrogen atom and sulfur atom),
a is 0, 1 or 2,
$R^5$ and $R^6$ are each independently
(1) a hydrogen atom,
(2) a halogen atom,
(3) a $C_{1-6}$ alkyl group optionally substituted by 1 to 3 substituents selected from the following group A,
(4) —$OR^{120}$
(wherein $R^{120}$ is a hydrogen atom or a group selected from the following group C) or
(5) —$NR^{121}R^{122}$
(wherein $R^{121}$ and $R^{122}$ are each independently a hydrogen atom, a $C_{1-6}$ alkanoyl group or a group selected from the following group C),
ring Cy is
(1) a $C_{3-10}$ cycloalkyl group optionally substituted by 1 to 5 substituents selected from the following group B,
(2) a $C_{3-10}$ cycloalkenyl group optionally substituted by 1 to 5 substituents selected from the following group B or
(3) a heterocyclic group optionally substituted by 1 to 5 substituents selected from the following group B
(wherein said heterocyclic group comprises 1 to 4 heteroatoms selected from oxygen atom, nitrogen atom and sulfur atom),
X is
(1) a group selected from the following group D,
(2) a $C_{2-6}$ alkenyl group optionally substituted by 1 to 3 substituents selected from the following group A or
(3)

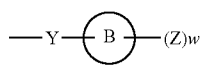

wherein ring B is
(1') a $C_{6-14}$ aryl group,
(2') a $C_{3-10}$ cycloalkyl group or
(3') a heterocyclic group comprising 1 to 4 heteroatoms selected from oxygen atom, nitrogen atom and sulfur atom,
each Z is independently
(1') a group selected from the following group D,
(2') a $C_{6-14}$ aryl group optionally substituted by 1 to 5 substituents selected from the following group D,
(3') a $C_{3-10}$ cycloalkyl group optionally substituted by 1 to 5 substituents selected from the following group D,
(4') a $C_{6-14}$ aryl $C_{1-6}$ alkyl group optionally substituted by 1 to 5 substituents selected from the following group D,
(5') a heterocyclic group optionally substituted by 1 to 5 substituents selected from the following group D
(wherein said heterocyclic group comprises 1 to 4 heteroatoms selected from oxygen atom, nitrogen atom and sulfur atom) or
(6') a heterocycle $C_{1-6}$ alkyl group optionally substituted by 1 to 5 substituents selected from the following group D
(wherein said heterocycle $C_{1-6}$ alkyl group is a $C_{1-6}$ alkyl group substituted by "a heterocyclic group optionally substituted by 1 to 5 substituents selected from group D" as defined above),
w is an integer of 1 to 3, Y is
(a) $C_{1-6}$ alkylene,
(b) $C_{2-6}$ alkenylene or
(c) —$Y^1$—$(CH_2)_m$—$Y^2$—$(CH_2)_n$—
(wherein m and n are each independently 0 or an integer of 1 to 6,
$Y^1$ and $Y^2$ are each independently
(1') a bond,
(2') —O—,
(3') —$NR^{y1}$—,
(4') —S—,
(5') —CO—,
(6') —SO—,
(7') —$SO_2$—,
(8') —$CO_2$—,
(9') —OCO—,
(10') —$CONR^{y2}$—,
(11') —$NR^{y2}CO$—,
(12') —$SO_2NR^{y2}$—,
(13') —$NR^{y2}SO_2$—,
(14') —$NR^{y2}CO_2$—,
(15') —$OCONR^{y2}$—,
(16') —$NR^{y2}CONR^{y3}$—,
(17') —$CR^{y4}R^{y5}$— or
(18') —CH=CH—
(wherein $R^{y1}$ is
(1") a hydrogen atom,
(2") a group selected from the following group C,
(3") —$COOR^{y11}$,
(4") —$CONR^{y11}R^{y12}$,
(5") —$COR^{y11}$ or
(6") —$SO_2R^{y13}$
(wherein $R^{y11}$ and $R^{y12}$ are each independently a hydrogen atom or a group selected from the following group C, and $R^{y13}$ is a group selected from the following group C),
$R^{y2}$ and $R^{y3}$ are each independently
(1") a hydrogen atom,
(2") a group selected from the following group C,
(3") —$COR^{y11}$ or
(4") —$SO_2R^{y13}$ (wherein $R^{y11}$ and $R^{y13}$ are as defined above),
$R^{y4}$ and $R^{y5}$ are each independently
(1") a hydrogen atom,
(2") a carboxyl group,
(3") a group selected from group F,
(4") —$OR^{y14}$ or
(5") —$NHR^{y15}$
(wherein $R^{y14}$ is a group selected from the following group C, $R^{y15}$ is a hydrogen atom, a $C_{1-6}$ alkyl group, a $C_{1-6}$ alkanoyl group or a $C_{6-14}$ aryl $C_{1-6}$ alkyloxycarbonyl group))
group A:
(1) a halogen atom,
(2) a $C_{1-6}$ alkoxy $C_{1-6}$ alkoxy group,
(3) —$OR^{a1}$,
(4) —$SR^{a1}$,
(5) —$NR^{a1}R^{a2}$,
(6) —$COOR^{a1}$,
(7) —$CONR^{a1}R^{a2}$,
(8) —$SO_3H$,
(9) —$SO_2NR^{a1}R^{a2}$,
(10) —$NHCOR^{a1}$ and
(11) —$NHSO_2R^{a3}$
(wherein $R^{a1}$ and $R^{a2}$ are each a hydrogen atom or a $C_{1-6}$ alkyl group, and $R^{a3}$ is a $C_{1-6}$ alkyl group)

group B:
(1) a halogen atom,
(2) a cyano group,
(3) a nitro group,
(4) a $C_{1-6}$ alkyl group,
(5) a halogenated $C_{1-6}$ alkyl group,
(6) —$(CH_2)_r$—$OR^{b1}$,
(7) —$(CH_2)_r$—$SR^{b1}$,
(8) —$(CH_2)_r$—$NR^{b1}R^{b2}$,
(9) —$(CH_2)_r$—$COOR^{b1}$,
(10) —$(CH_2)_r$—$CONR^{b1}R^{b2}$,
(11) —$(CH_2)_r$—$COR^{b1}$,
(12) —$(CH_2)_r$—$NR^{b1}$—$COR^{b2}$,
(13) —$(CH_2)_r$—$NR^{b1}$—$SO_2R^{b3}$,
(14) —$(CH_2)_r$—$SO_2R^{b3}$,
(15) —$(CH_2)_r$—$SO_2NR^{b1}R^{b2}$,
(16) —$(CH_2)_r$—$CONR^{b1}$—$SO_2R^{b3}$,
(17) —$(CH_2)_r$—$SO_2NR^{b1}$—$COR^{b2}$,
(18) —$(CH_2)_r$—$NR^{b1}$—$COOR^{b3}$ and
(19) —$(CH_2)_r$—$NR^{b1}$—$CONR^{b2}R^{b4}$,
(wherein $R^{b1}$, $R^{b2}$ and $R^{b4}$ are each independently a hydrogen atom or a $C_{1-6}$ alkyl group, $R^{b3}$ is a $C_{1-6}$ alkyl group and r is 0 or an integer of 1 to 6)

group C:
(1) a $C_{1-6}$ alkyl group optionally substituted by 1 to 3 substituents selected from the aforementioned group A,
(2) a $C_{6-14}$ aryl group optionally substituted by 1 to 5 substituents selected from the aforementioned group B,
(3) a $C_{6-14}$ aryl $C_{1-6}$ alkyl group optionally substituted by 1 to 5 substituents selected from the aforementioned group B,
(4) a heterocyclic group optionally substituted by 1 to 5 substituents selected from the aforementioned group B and
(5) a heterocycle $C_{1-6}$ alkyl group optionally substituted by 1 to 5 substituents selected from the aforementioned group B group D:
(a) a hydrogen atom,
(b) a halogen atom,
(c) a cyano group,
(d) a nitro group,
(e) a $C_{1-6}$ alkyl group optionally substituted by 1 to 3 substituents selected from the aforementioned group A,
(f) —$(CH_2)_t$—$OR^{d1}$,
wherein $R^{d1}$ is
(1) a hydrogen atom,
(2) a group selected from the following group F,
(3) a $C_{2-6}$ alkenyl group optionally substituted by 1 to 3 substituents selected from the aforementioned group A or
(4) a $C_{2-6}$ alkynyl group optionally substituted by 1 to 3 substituents selected from the aforementioned group A,
hereinafter each t is independently 0 or an integer of 1 to 6,
(g) —$(CH_2)_t$—$S(O)_q$—$R^{d2}$,
wherein $R^{d2}$ is
(1) a hydrogen atom or
(2) a group selected from the following group F,
q is 0, 1, 2 or 3,
(h) —$(CH_2)_t$—$NR^{d3}R^{d4}$,
wherein $R^{d3}$ and $R^{d4}$ are each independently
(1) a hydrogen atom or
(2) a group selected from the following group F,
(i) —$(CH_2)_t$—$COOR^{d5}$, wherein $R^{d5}$ is
(1) a hydrogen atom or
(2) a group selected from the following group F,
(j) —$(CH_2)_t$—$CONR^{d6}R^{d7}$,
wherein $R^{d6}$ and $R^{d7}$ are each independently
(1) a hydrogen atom,
(2) a hydroxyl group,
(3) a group selected from the following group F or
(4) a $C_{1-6}$ alkoxy group,
(k) —$(CH_2)_t$—$COR^{d8}$,
wherein $R^{d8}$ is a group selected from the following group F,
(l) —$(CH_2)_t$—$NR^{d9}CO$—$R^{d10}$,
wherein $R^{d9}$ is
(1) a hydrogen atom,
(2) a $C_{1-6}$ alkyl group optionally substituted by 1 to 3 substituents selected from the aforementioned group A or
(3) a $C_{1-6}$ alkanoyl group,
$R^{d10}$ is
(1) an amino group,
(2) a $C_{1-6}$ alkylamino group or
(3) a group selected from the following group F,
(m) —$(CH_2)_t$—$NR^{d11}SO_2$—$R^{d12}$,
wherein $R^{d11}$ is
(1) a hydrogen atom,
(2) a $C_{1-6}$ alkyl group optionally substituted by 1 to 3 substituents selected from the aforementioned group A or
(3) a $C_{1-6}$ alkanoyl group,
$R^{d12}$ is
(1) a hydrogen atom or
(2) a group selected from the following group F,
(n) —$(CH_2)_t$—$SO_2$—$NR^{d13}R^{d14}$,
wherein $R^{d13}$ and $R^{d14}$ are each independently
(1) a hydrogen atom or
(2) a group selected from the following group F,
(o) —$(CH_2)_t$—$CONR^{d15}$—$SO_2R^{d16}$,
wherein $R^{d15}$ and $R^{d16}$ are each independently
(1) a hydrogen atom or
(2) a group selected from the following group F,
(p) —$(CH_2)_t$—$SO_2NR^{d17}$—$COR^{d18}$,
wherein $R^{d17}$ is
(1) a hydrogen atom or
(2) a group selected from the following group F,
$R^{d18}$ is a group selected from the following group F,
(q) —$(CH_2)_t$—$NR^{d19}$—$COOR^{d20}$,
wherein $R^{d19}$ and $R^{d20}$ are each independently
(1) a hydrogen atom or
(2) a group selected from the following group F,
(r) —$(CH_2)_t$—$NR^{d21}$—$CONR^{d22}R^{d23}$,
wherein $R^{d21}$, $R^{d22}$ and $R^{d23}$ are each independently
(1) a hydrogen atom or
(2) a group selected from the following group F,
(s) —$(CH_2)_t$—$C(=NR^{d24})NH_2$,
wherein $R^{d24}$ is
(1) a hydrogen atom,
(2) a hydroxyl group,
(3) a $C_{1-6}$ alkyl group optionally substituted by 1 to 3 substituents selected from the aforementioned group A or
(4) $C_{1-6}$ alkoxy group,
(t) —$(CH_2)_t$—O—$(CH_2)_p$—$COR^{d25}$, wherein $R^{d25}$ is
(1) an amino group,
(2) a $C_{1-6}$ alkylamino group or
(3) a heterocyclic group optionally substituted by 1 to 5 substituents selected from the aforementioned group B,
p is 0 or an integer of 1 to 6,
and
(u) a heterocyclic group optionally substituted by 1 to 5 substituents selected from the aforementioned group B
(wherein said heterocyclic group comprises 1 to 4 heteroatoms selected from oxygen atom, nitrogen atom and sulfur atom)
group E:
(a) a halogen atom,
(b) a cyano group,
(c) a nitro group,
(d) —$OR^{e1}$,
wherein $R^{e1}$ is
(1) a hydrogen atom,
(2) a group selected from the following group F,
(3) a $C_{2-6}$ alkenyl group optionally substituted by 1 to 3 substituents selected from the aforementioned group A or
(4) a $C_{2-6}$ alkynyl group optionally substituted by 1 to 3 substituents selected from the aforementioned group A,
(e) —$S(O)_q$—$R^{e2}$
wherein $R^{e2}$ is
(1) a hydrogen atom or
(2) a group selected from the following group F,
q is 0, 1, 2 or 3,
(f) —$NR^{e3}R^{e4}$,
wherein $R^{e3}$ and $R^{e4}$ are each independently
(1) a hydrogen atom or
(2) a group selected from the following group F,
(g) —$COOR^{e5}$,
wherein $R^{e5}$ is
(1) a hydrogen atom or
(2) a group selected from the following group F,
(h) —$CONR^{e6}R^{e7}$,
wherein $R^{e6}$ and $R^{e7}$ are each independently
(1) a hydrogen atom,
(2) a hydroxyl group,
(3) a group selected from the following group F or
(4) a $C_{1-6}$ alkoxy group,
(i) —$COR^{e8}$,
wherein $R^{e8}$ is a group selected from the following group F,
(j) —$NR^{e9}CO$—$R^{e10}$,
wherein $R^{e9}$ is
(1) a hydrogen atom,
(2) a $C_{1-6}$ alkyl group or
(3) a $C_{1-6}$ alkanoyl group,
$R^{e10}$ is
(1) an amino group,
(2) a $C_{1-6}$ alkylamino group, or
(3) a group selected from the following group F,
(k) —$NR^{e11}SO_2$—$R^{e12}$,
wherein $R^{e11}$ is
(1) a hydrogen atom,
(2) a $C_{1-6}$ alkyl group or
(3) a $C_{1-6}$ alkanoyl group,
$R^{e12}$ is
(1) a hydrogen atom or
(2) a group selected from the following group F,
(l) —$SO_2$—$NR^{e13}R^{e14}$,
wherein $R^{e13}$ and $R^{e14}$ are each independently
(1) a hydrogen atom or
(2) a group selected from the following group F,
(m) —$CONR^{e15}$—$SO_2R^{e16}$,
wherein $R^{e15}$ and $R^{e16}$ are each independently
(1) a hydrogen atom or
(2) a group selected from the following group F,
(n) —$SO_2NR^{e17}$—$COR^{e18}$,
wherein $R^{e17}$ is
(1) a hydrogen atom or
(2) a group selected from the following group F,
$R^{e18}$ is a group selected from the following group F,
(o) —$NR^{e19}$—$COOR^{e20}$,
wherein $R^{e19}$ and $R^{e20}$ are each independently
(1) a hydrogen atom or
(2) a group selected from the following group F,
(p) —$NR^{e21}$—$CONR^{e22}R^{e23}$,
wherein $R^{e21}$, $R^{e22}$ and $R^{e23}$ are each independently
(1) a hydrogen atom or
(2) a group selected from the following group F,
(q) a $C_{6-14}$ aryl group optionally substituted by 1 to 5 substituents selected from the aforementioned group B,
(r) a heterocyclic group optionally substituted by 1 to 5 substituents selected from the aforementioned group B
(wherein said heterocyclic group comprises 1 to 4 heteroatoms selected from oxygen atom, nitrogen atom and sulfur atom),
(s) a $C_{3-10}$ cycloalkylidene group optionally substituted by 1 to 5 substituents selected from the aforementioned group B, and
(t) a heterocycle ylidene group optionally substituted by 1 to 5 substituents selected from the aforementioned group B
(wherein said heterocycle ylidene group comprises 1 to 4 heteroatoms selected from oxygen atom, nitrogen atom and sulfur atom),
when group E is a substituent on a $C_{6-14}$ aryl group, a $C_{3-10}$ cycloalkyl group or a heterocyclic group, it may be
(u) a $C_{1-6}$ alkyl group optionally substituted by 1 to 3 substituents selected from the aforementioned group A, or
(v) $C_{1-6}$ alkylidene group optionally substituted by 1 to 3 substituents selected from the aforementioned group A
group F:
(1) a $C_{1-6}$ alkyl group optionally substituted by 1 to 3 substituents selected from the aforementioned group A,
(2) a $C_{6-14}$ aryl group optionally substituted by 1 to 5 substituents selected from the aforementioned group B,
(3) a heterocyclic group optionally substituted by 1 to 5 substituents selected from the aforementioned group B
(wherein said heterocyclic group comprises 1 to 4 heteroatoms selected from oxygen atom, nitrogen atom and sulfur atom),
(4) a $C_{3-10}$ cycloalkyl group optionally substituted by 1 to 5 substituents selected from the aforementioned group B,
(5) a $C_{6-14}$ aryl $C_{1-6}$ alkyl group optionally substituted by 1 to 5 substituents selected from the aforementioned group B,
(6) a heterocycle $C_{1-6}$ alkyl group optionally substituted by 1 to 5 substituents selected from the aforementioned group B
(wherein said heterocycle $C_{1-6}$ alkyl group is a $C_{1-6}$ alkyl group substituted by "a heterocyclic group optionally substituted by 1 to 5 substituents selected from group B" as defined above) and
(7) a $C_{3-10}$ cycloalkyl $C_{1-6}$ alkyl group optionally substituted by 1 to 5 substituents selected from the aforementioned group B.

2. The compound of claim 1, wherein ring Cy is a $C_{3-10}$ cycloalkyl group, or a pharmaceutically acceptable salt thereof.

3. The compound of claim 2, wherein ring Cy is a $C_{5-7}$ cycloalkyl group, or a pharmaceutically acceptable salt thereof.

4. The compound of claim 3, wherein ring Cy is cyclohexyl, or a pharmaceutically acceptable salt thereof.

5. The compound of claim 1, wherein $R^2$ is a group selected from the following group E, wherein group E is
 (d) —$OR^{e1}$,
  wherein $R^{e1}$ is
  (1) a hydrogen atom,
  (2) a group selected from group F,
 (g) —$COOR^{e5}$,
  wherein $R^{e5}$ is
  (1) a hydrogen atom or
  (2) a group selected from group F, or
 (h) —$CONR^{e6}R^{e7}$,
  wherein $R^{e6}$ and $R^{e7}$ are each independently
  (1) a hydrogen atom,
  (2) a group selected from group F,
or a pharmaceutically acceptable salt thereof.

6. The compound of claim 1, wherein $R^1$ is
 (1) a carboxyl group,
 (2) —$CONR^{11}R^{12}$
 (wherein $R^{11}$ and $R^{12}$ are each independently
  (1') a hydrogen atom, or
  (2') a $C_{1-6}$ alkyl group optionally substituted by 1 to 3 substituents selected from group E), or
 (3) —$COOR^{103}$
 (wherein $R^{103}$ is a group selected from group C),
or a pharmaceutically acceptable salt thereof.

7. The compound of claim 1, wherein $R^5$, $R^6$, and X are each independently
 (1) a hydrogen atom,
 (2) a halogen atom, or
 (3) —$OR^{120}$
 (wherein $R^{120}$ is a group selected from the group C),
or a pharmaceutically acceptable salt thereof.

8. The compound of claim 7, wherein
 $R^5$ is
 (1) a hydrogen atom,
 (1) a halogen atom, or
 (2) —$OR^{120}$
 (wherein $R^{120}$ is a $C_{1-6}$ alkyl group optionally substituted by 1 to 3 substituents selected from the aforementioned group A),
 and
 $R^6$ and X are each a hydrogen atom,
or a pharmaceutically acceptable salt thereof.

9. The compound of claim 1, wherein Q is a moiety selected from the group consisting of —$(CH_2)_1O$—, —$(CH_2)_2O$—, —$(CH_2)_3O$—, —$(CH_2)_2NH$—, and —$(CH_2)_3NH$—.

10. A method of inhibiting hepatitis C virus polymerase or treating a hepatitis C virus infection, which comprises administering to a human or animal subject suffering from the condition, a therapeutically effective amount of a compound of any of claims 1, 2-8, and 9, or a pharmaceutically acceptable salt thereof.

11. A composition comprising (a) a compound of any of claims 1, 2-8, and 9, or a pharmaceutically acceptable salt thereof, and (b) a pharmaceutically acceptable carrier.

* * * * *